United States Patent
Cee et al.

(10) Patent No.: US 9,394,297 B2
(45) Date of Patent: Jul. 19, 2016

(54) AMIDES AS PIM INHIBITORS

(71) Applicant: AMGEN INC., Thousand Oaks, CA (US)

(72) Inventors: Victor Cee, Thousand Oaks, CA (US); Frank Chavez, Jr., Camarillo, CA (US); Jian J. Chen, Camarillo, CA (US); Essa Hu Harrington, Camarillo, CA (US); Bradley Herberich, Newbury Park, CA (US); Claire L. M. Jackson, San Mateo, CA (US); Brian A. Lanman, Woodland Hills, CA (US); Thomas T. Nguyen, Newbury Park, CA (US); Mark H. Norman, Thousand Oaks, CA (US); Liping H. Pettus, Thousand Oaks, CA (US); Anthony B. Reed, Newbury Park, CA (US); Adrian L. Smith, Simi Valley, CA (US); Nuria A. Tamayo, Newbury Park, CA (US); Andrew Tasker, Simi Valley, CA (US); Hui-Ling Wang, Thousand Oaks, CA (US); Bin Wu, Thousand Oaks, CA (US); Ryan Wurz, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 10 days.

(21) Appl. No.: 14/380,918

(22) PCT Filed: Feb. 27, 2013

(86) PCT No.: PCT/US2013/028087
§ 371 (c)(1),
(2) Date: Aug. 25, 2014

(87) PCT Pub. No.: WO2013/013066
PCT Pub. Date: Sep. 6, 2013

(65) Prior Publication Data
US 2015/0329538 A1 Nov. 19, 2015

Related U.S. Application Data

(60) Provisional application No. 61/720,936, filed on Oct. 31, 2012, provisional application No. 61/604,444, filed on Feb. 28, 2012.

(51) Int. Cl.
*C07D 401/04* (2006.01)
*C07D 471/04* (2006.01)
*C07D 487/04* (2006.01)

(52) U.S. Cl.
CPC ............ *C07D 471/04* (2013.01); *C07D 401/04* (2013.01); *C07D 487/04* (2013.01)

(58) Field of Classification Search
CPC ... C07D 471/04; C07D 401/04; C07D 487/04
See application file for complete search history.

(56) References Cited

FOREIGN PATENT DOCUMENTS

| WO | 01/70743 A1 | 9/2001 |
|---|---|---|
| WO | 2007/110344 A1 | 10/2007 |
| WO | 2009/060197 A1 | 5/2009 |
| WO | 2011/101644 A1 | 8/2011 |
| WO | 2012/078777 A1 | 6/2012 |
| WO | 2012/129338 A1 | 9/2012 |

OTHER PUBLICATIONS

Mullekom et al., Chem. Eur. J. 1998, 4, No. 7, pp. 1235-1243.*
International Search Report for parent PCT Application No. PCT/US2013/028087, mailed on May 3, 2013.
International Preliminary Report on Patentability and Written Opinion for parent PCT Application No. PCT/US2013/028087, dated Sep. 2, 2014.
Morwick, T. "Pim Kinase Inhibitors: A Survey of the Patent Literature", Expert Opinion on Therapeutic Patents, vol. 20(2), pp. 193-212 (2010).

* cited by examiner

*Primary Examiner* — Rebecca Anderson
(74) *Attorney, Agent, or Firm* — Bernard P. Friedrichsen

(57) ABSTRACT

The invention relates to amide-containing compounds of formula (1), and salts thereof. In some embodiments, the invention relates to inhibitors or modulators of Pim-1 and/or Pim-2, and/or Pim-3 protein kinase activity or enzyme function. In still further embodiments, the invention relates to pharmaceutical compositions comprising compounds disclosed herein, and their use in the prevention and treatment of Pim kinase related conditions and diseases, preferably cancer.

20 Claims, No Drawings

AMIDES AS PIM INHIBITORS

CROSS REFERENCES TO RELATED APPLICATIONS

This application is a 371 National Phase Application of PCT/US2013/028087 filed Feb. 27, 2013, which claims the benefit of U.S. Provisional Application No. 61/604,444 filed Feb. 28, 2012 and U.S. Provisional Application No. 61/720,936 filed Oct. 31, 2012.

REFERENCE TO THE SEQUENCE LISTING

The present application is being filed along with a Sequence Listing in electronic format. The Sequence Listing is provided as a file entitled A-1674-US-PCT_ST25.txt, created Aug. 25, 2014, which is 2 KB in size. The information in the electronic format of the Sequence Listing is incorporated herein by reference in its entirety.

FIELD OF THE INVENTION

The present invention relates to certain amide-containing compounds that are Pim inhibitors, pharmaceutical compositions containing such compounds, and processes for preparing such compounds. Provided herein also are methods of treating disorders or diseases treatable by inhibition of Pims, such as cancer, and the like.

BACKGROUND

The role of Pim serine/threonine kinases in the pathogenesis and therapy of hematological malignancies and solid cancers is of interest to the medical community. Pim proteins are constitutively active and are over-expressed in a subset of human cancers, many of hematological origin. Pim kinases also regulate aspects of transformation and drug resistance in hematological malignancies such as DLBCL, MM, and AML where they are overexpressed or mutated. Aberrant expression of Pim-1 or Pim-2 promotes tumor development in mouse models of lymphoma and prostate cancer. Elevated Pim-1 levels correlate with poor prognosis in DLBCL and mantle cell lymphoma. Pims play a role in some solid tumors (e.g. prostate cancer, and head and neck cancer). Whereas elevated levels of Pim-1 and Pim-2 were mostly found in hematological malignancies and prostate cancer, increased Pim-3 expression was observed in different solid tumors. Pim kinases are constitutively active and their activity supports in vitro and in vivo tumour cell growth and survival through modification of an increasing number of common as well as isoform-specific substrates including several cell cycle regulators and apoptosis mediators. Pim-1 mediates homing and migration of normal and malignant hematopoietic cells by regulating chemokine receptor surface expression. Knockdown experiments by RNA interference or dominant-negative acting mutants suggested that Pim kinases are important for maintenance of a transformed phenotype and therefore potential therapeutic targets.

There exists a need for compounds that inhibit the growth of tumors, treat cancer, modulate cell cycle arrest, and/or inhibit molecules such as Pim-1, Pim-2, or Pim-3 and pharmaceutical formulations and medicaments that contain such compounds.

SUMMARY OF THE INVENTION

The present invention comprises a new class of amide compounds useful in the treatment of diseases, such as Pim-mediated diseases, for example cancer. Accordingly, the invention also comprises pharmaceutical compositions comprising the compounds, methods for the treatment of Pim-mediated diseases and other maladies, such as treatment of hematological malignancies and of solid tumors, for example prostate cancer, and head and neck cancer, using the compounds and compositions of the invention, and intermediates and processes useful for the preparation of the compounds of the invention.

The compounds of the invention are represented by the following general structure:

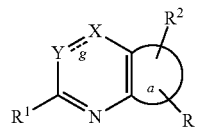

and a pharmaceutically acceptable salt thereof; wherein X; Y; a; g; R; $R^1$; and $R^2$ are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

One aspect of the current invention relates to compounds having the general structure of formula 1:

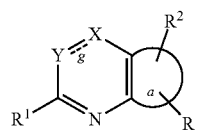

wherein
bond g is a single bond or double bond; provided g is a single bond if Y or X is C=O;
ring a is a ring that together with the 2 carbon atoms to which it attaches, forms a phenyl ring or a 5-6 membered heterocyclic ring;
X is N, $NR^b$, C=O, CH or $CH_2$;
Y is N, $NR^b$, C=O, $CR^a$ or $C(R^a)_2$;
R is an optionally substituted bicyclic amide or

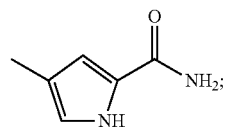

$R^1$ is H, halo, alkyl, amino, alkylamino, alkenylamino, haloalkylamino, alkylsulfonylalkylamino, aminocarbonylalkylamino, aminoalkylamino, hydroxyalkylamino, alkylsulfonylamino, carboxyalkylamino, alkoxycarbonylalkylamino, alkoxyalkylamino, substituted or unsubstituted cycloalkylamino, substituted or unsubstituted cycloalkylalkylamino, substituted or unsubstituted arylamino, substituted or unsubstituted arylalkylamino, substituted or unsubstituted heterocyclylamino, substituted or unsubstituted heterocyclyl $C_{1-6}$ alkylamino, —CONHR$^b$, —NHC=OR$^b$, —OR$^b$, —S(=O)$_n$R$^b$, —COR$^c$, unsubstituted or substituted aryl, unsubstituted or substituted arylalkyl, unsubstituted or substituted arylalkenyl, unsubstituted or substituted cycloalkyl, unsubstituted or substituted cycloalkylalkyl, unsubstituted or substituted heterocyclylalkyl or substituted or unsubstituted heterocyclyl;

R$^2$ is H, or halo;

R$^a$ is H, haloalkyl, hydroxyalkyl, alkyl, alkoxy, HC(=O)—, carboxy, alkoxycarbonyl, or substituted or unsubstituted heterocyclyl;

R$^b$ is H, alkyl, haloalkyl, aminoalkyl, alkoxyalkyl, unsubstituted or substituted cycloalkyl, unsubstituted or substituted aryl, unsubstituted or substituted arylalkyl or unsubstituted or substituted heterocyclyl; and R$^c$ is H, alkyl, alkoxy, alkoxyalkyl, unsubstituted or substituted cycloalkyl, unsubstituted or substituted aryl, unsubstituted or substituted arylalkyl or unsubstituted or substituted heterocyclyl;

and a pharmaceutically acceptable salt thereof.

Another aspect of the current invention relates to compounds having the general structure of Formula 1a, Formula 1b or Formula 1c

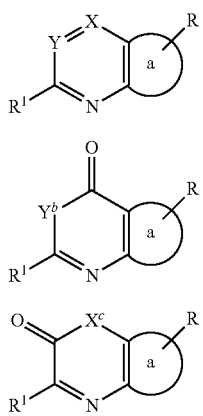

wherein
X is N or CH;
Y is N or CR$^a$;
Y$^b$ is NR$^b$;
X$^c$ is NH or CH$_2$;
ring a is

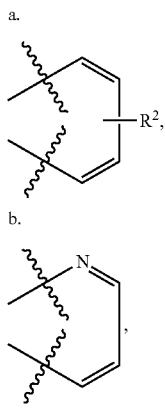

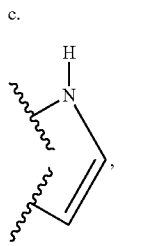

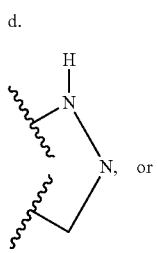

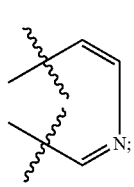

R is an optionally substituted bicyclic amide;

R$^1$ is H, halo, alkyl, amino, alkylamino, alkenylamino, haloalkylamino, alkylsulfonylalkylamino, aminocarbonylalkylamino, aminoalkylamino, hydroxyalkylamino, alkylsulfonylamino, carboxyalkylamino, alkoxycarbonylalkylamino, alkoxyalkylamino, substituted or unsubstituted cycloalkylamino, substituted or unsubstituted cycloalkylalkylamino, substituted or unsubstituted phenylamino, substituted or unsubstituted arylalkylamino, substituted or unsubstituted heterocyclylamino, substituted or unsubstituted heterocyclyl $C_{1-6}$ alkylamino, —CONHR$^b$, —NHC=OR$^b$, —OR$^b$, —S(=O)$_n$R$^b$, —COR$^c$, unsubstituted or substituted aryl, unsubstituted or substituted arylalkyl, unsubstituted or substituted arylalkenyl, unsubstituted or substituted cycloalkyl, unsubstituted or substituted cycloalkylalkyl, unsubstituted or substituted heterocyclylalkyl or substituted or unsubstituted heterocyclyl;

R$^2$ is H, or halo;

R$^a$ is H, amino, haloalkyl, hydroxyalkyl, alkyl, alkoxy, HC(=O)—, carboxy, alkoxycarbonyl, or substituted or unsubstituted heterocyclyl;

R$^b$ is H, alkyl, haloalkyl, aminoalkyl, alkoxy alkyl, unsubstituted or substituted cycloalkyl, unsubstituted or substituted aryl, unsubstituted or substituted aralkyl or unsubstituted or substituted heterocyclyl; and R$^c$ is H, alkyl, alkoxy, alkoxyalkyl, unsubstituted or substituted cycloalkyl, unsubstituted or substituted aryl, unsubstituted or substituted arylalkyl or unsubstituted or substituted heterocyclyl;

and a pharmaceutically acceptable salt thereof.

In another embodiment, the group R is

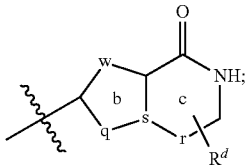

wherein q is NH or CH;
wherein r is CH$_2$ or N;
wherein s is N or C;
wherein w is CH or N;
wherein R$^d$ is one or more substituents selected from H, C$_{1-4}$ alkyl, C$_{1-4}$ hydroxyalkyl, C$_{2-4}$ alkynyl or benzyl; or wherein R$^d$ forms a carbocyclic or heterocyclic ring spiro to ring c;
wherein ring b is unsaturated, or partially saturated; and
wherein ring c is saturated, or partially saturated;
and a pharmaceutically acceptable salt thereof.

In another embodiment, the group R is

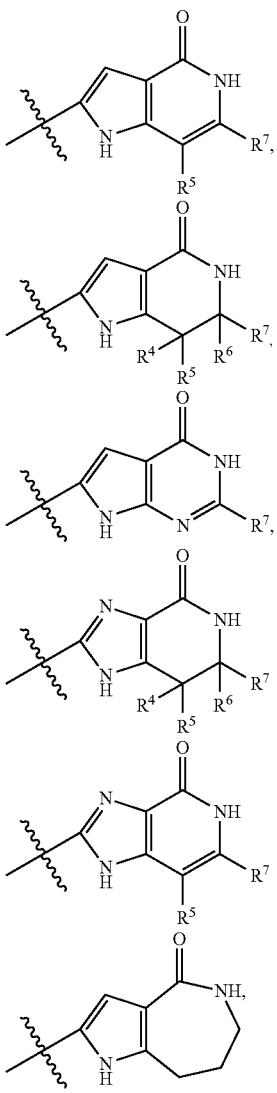

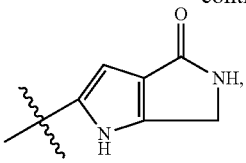

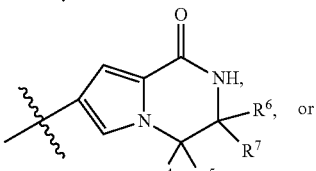

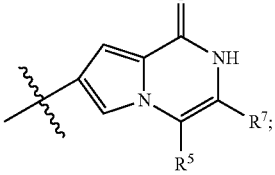

wherein R$^4$ is H or C$_{1-4}$ alkyl;
wherein R$^5$ is H, C$_{1-4}$ alkyl, C$_{1-4}$ hydroxyalkyl, C$_{2-4}$ alkynyl or benzyl; or wherein R$^4$ and R$^5$ together form C$_{3-6}$ cycloalkyl;
wherein R$^6$ is H; and
wherein R$^7$ is H or C$_{1-3}$ alkyl;
and a pharmaceutically acceptable salt thereof.

In another embodiment, R$^4$ is H; R$^5$ is H; R$^6$ is H; and R$^7$ is H; and a pharmaceutically acceptable salt thereof.

In another embodiment, R$^1$ is H, halo, C$_{1-6}$ alkyl, amino, C$_{1-6}$ alkylamino, C$_{2-6}$ alkenylamino, C$_{1-6}$ haloalkylamino, C$_{1-6}$ alkylsulfonyl-C$_{1-6}$ alkylamino, aminocarbonyl-C$_{1-6}$ alkylamino, amino-C$_{1-6}$ alkylamino, hydroxy-C$_{1-6}$ alkylamino, C$_{1-6}$ alkylsulfonylamino, carboxy-C$_{1-6}$ alkylamino, C$_{1-6}$ alkoxycarbonyl-C$_{1-6}$ alkylamino, C$_{1-6}$ alkoxy-C$_{1-6}$ alkylamino, substituted or unsubstituted C$_{3-6}$ cycloalkylamino, substituted or unsubstituted C$_{3-6}$ cycloalkyl-C$_{1-6}$ alkylamino, substituted or unsubstituted phenylamino, substituted or unsubstituted phenyl-C$_{1-3}$ alkylamino, substituted or unsubstituted 3-7-membered heterocyclylamino, substituted or unsubstituted 3-7-membered heterocyclyl-C$_{1-6}$ alkylamino, —CONHR$^b$, —NHC═OR$^b$, —OR$^b$, —S(═O)$_n$R$^b$, —COR$^c$, unsubstituted or substituted aryl, unsubstituted or substituted aryl-C$_{1-6}$ alkyl, unsubstituted or substituted aryl-C$_{2-4}$ alkenyl, unsubstituted or substituted C$_{3-6}$ cycloalkyl, unsubstituted or substituted C$_{3-6}$ cycloalkyl-C$_{1-6}$ alkyl, unsubstituted or substituted 3-7-membered heterocyclyl-C$_{1-6}$ alkyl or substituted or unsubstituted 3-7-membered heterocyclyl; and a pharmaceutically acceptable salt thereof.

In another embodiment, R$^1$ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-trifluoromethylethylamino, methylsulfonyl-(1,1-dimethylethyl)amino, methylsulfonylamino, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-yl amino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 1-azetidinyl, 2,2-dimethyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, or 2-amino-6-fluoro-5-pyridyl; and a pharmaceutically acceptable salt thereof.

In another embodiment, $R^2$ is H or fluoro; and a pharmaceutically acceptable salt thereof.

In another embodiment, ring a is

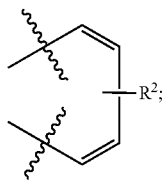

wherein $R^2$ is H or fluoro; and a pharmaceutically acceptable salt thereof.

In another embodiment, ring a is

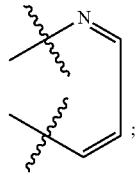 [SMILES: */C=C\C=N/*]

a pharmaceutically acceptable salt thereof.

Another aspect of the current invention relates to compounds having the general structure of Formula 2

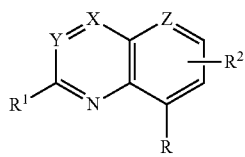

wherein R is

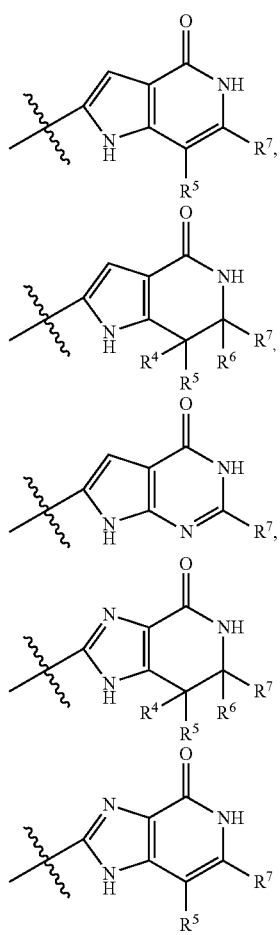

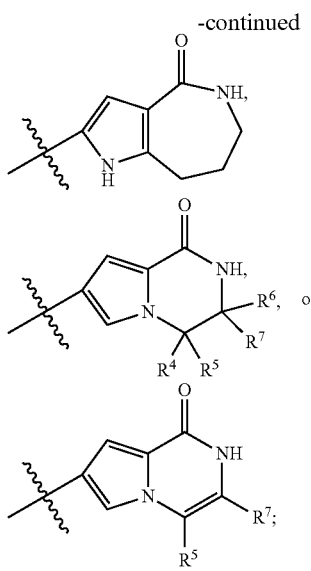

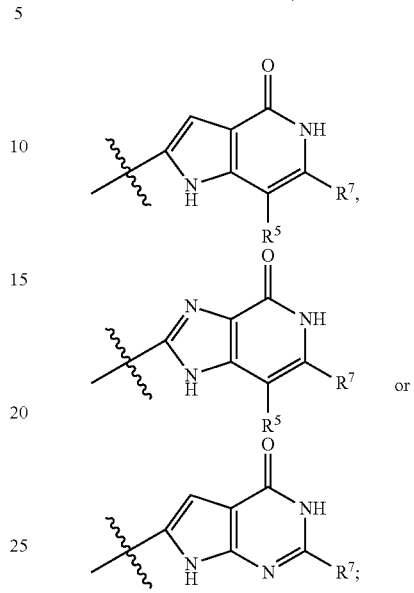

wherein R¹ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, substituted or unsubstituted cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl $C_{1-6}$ alkylamino, —CONHR$^b$, —NHC═OR$^b$, —OR$^b$, —S(═O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;
wherein X is N, NH, CH or CH$_2$;
wherein Y is N, CR$^a$, CHR$^a$ or NR$^b$;
wherein Z is CH or N;
wherein R² is H or halo;
wherein R⁴ is H or $C_{1-4}$ alkyl;
wherein R⁵ is H, $C_{1-4}$ alkyl, $C_{1-4}$ hydroxyalkyl, $C_{2-4}$ alkynyl or benzyl; or wherein R⁴ and R⁵ together form $C_{3-6}$ cycloalkyl;
wherein R⁶ is H;
wherein R⁷ is H, or $C_{1-3}$ alkyl;
wherein R$^a$ is H, amino, $C_{1-2}$ haloalkyl, $C_{1-2}$ hydroxyalkyl, $C_{1-2}$ alkyl, $C_{1-2}$ alkoxy, HC(═O)—, carboxy, alkoxycarbonyl, or substituted or unsubstituted 5-membered N-containing heteroaryl;
wherein R$^b$ is H, $C_{1-6}$ alkyl, $C_{1-6}$ haloalkyl, $C_{1-6}$ aminoalkyl, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-6}$ alkyl or unsubstituted or substituted 5-7 membered heterocyclyl; and
wherein R$^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-6}$ alkyl or unsubstituted or substituted 5-7 membered heterocyclyl; and a pharmaceutically acceptable salt thereof.

In another embodiment, R is

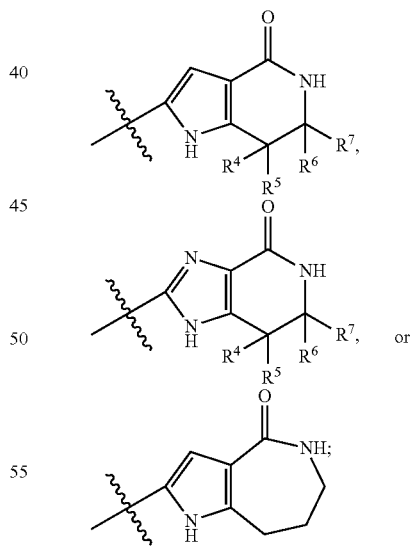

and a pharmaceutically acceptable salt thereof.

In another embodiment, R⁵ is H, methyl, hydroxymethyl, butynyl or benzyl; and R⁷ is H, or methyl; and a pharmaceutically acceptable salt thereof.

In another embodiment, R⁵ is H; and R⁷ is H; and a pharmaceutically acceptable salt thereof.

In another embodiment, R is and a pharmaceutically acceptable salt thereof

In another embodiment, R⁴ is H; R⁵ is H, methyl, hydroxymethyl, butynyl or benzyl; R⁶ is H; and R⁷ is H, or methyl; or wherein R⁴ and R⁵ together form cyclopropyl; and a pharmaceutically acceptable salt thereof.

In another embodiment, R⁴ is H; R⁵ is H; R⁶ is H and R⁷ is H; and a pharmaceutically acceptable salt thereof.

In another embodiment, R is

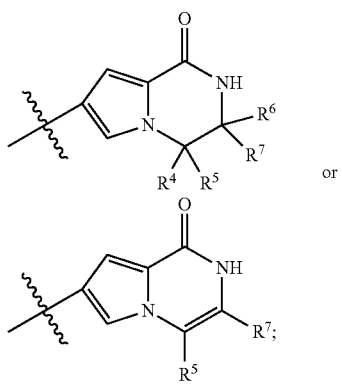

and a pharmaceutically acceptable salt thereof.

In another embodiment, $R^4$ is H; $R^5$ is H, methyl, hydroxymethyl, butynyl or benzyl; $R^6$ is H; and $R^7$ is H, or methyl; or wherein $R^4$ and $R^5$ together form cyclopropyl; and a pharmaceutically acceptable salt thereof.

In another embodiment, $R^4$ is H; $R^5$ is H; $R^6$ is H and $R^7$ is H; and a pharmaceutically acceptable salt thereof.

In another embodiment, $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl; and a pharmaceutically acceptable salt thereof.

In another embodiment, $R^1$ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-trifluoromethylethylamino, methylsulfonyl-(1,1-dimethylethyl)amino, methylsulfonylamino, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-ylamino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 1-azetidinyl, 2,2-dimethyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, or 2-amino-6-fluoro-5-pyridyl; and a pharmaceutically acceptable salt thereof.

In another embodiment, X is CH; Y is CR$^a$ or N; and Z is CH; and a pharmaceutically acceptable salt thereof.

In another embodiment, X is N; Y is CR$^a$; and Z is CH; and a pharmaceutically acceptable salt thereof.

In another embodiment, X is CH; Y is N; and Z is CH; and a pharmaceutically acceptable salt thereof.

In another embodiment, R$^a$ is H, amino, methoxy, trifluoromethyl, HC(=O)— or methyl; and a pharmaceutically acceptable salt thereof.

In another embodiment, R$^a$ is H or methyl; and a pharmaceutically acceptable salt thereof.

In another embodiment, $R^2$ is H or fluoro; and a pharmaceutically acceptable salt thereof.

Another aspect of the current invention relates to compounds having the general structure of Formula 3

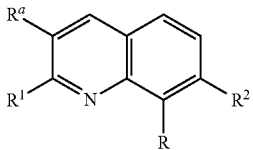

wherein R is

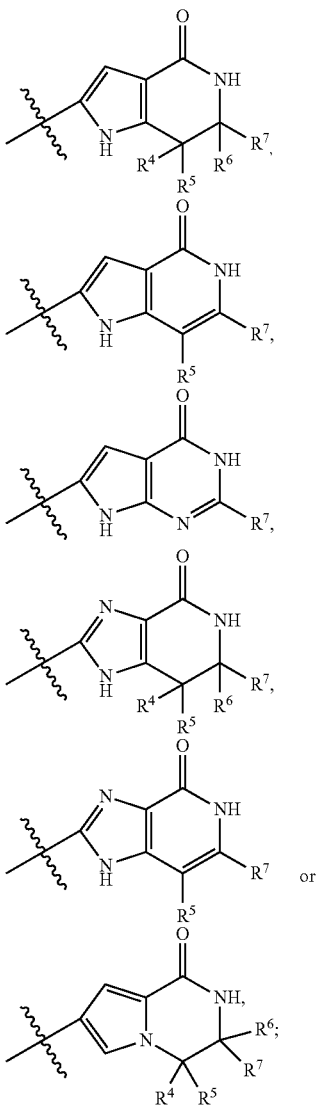

wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein $R^a$ is H, amino, $C_{1-2}$ alkoxy, $C_{1-2}$ haloalkyl, $C_{1-2}$ alkyl or HC(=O)—;

wherein $R^b$ is H, $C_{1-6}$ alkyl, $C_{1-6}$ haloalkyl, $C_{1-6}$ aminoalkyl, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^2$ is H or halo;
wherein $R^4$ is H;
wherein $R^5$ is H, $C_{1-4}$ alkyl, $C_{1-4}$ hydroxyalkyl, $C_{2-4}$ alkynyl, or benzyl; or wherein $R^4$ and $R^5$ together form $C_{3-6}$ cycloalkyl;
wherein $R^6$ is H; and
wherein $R^7$ is H, or $C_{1-3}$ alkyl; and a pharmaceutically acceptable salt thereof.

In another embodiment, $R^1$ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-trifluoromethylethylamino, methylsulfonyl-(1,1-dimethylethyl)amino, methylsulfonylamino, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonylpiperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-ylamino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 1-azetidinyl, 2,2-dimethyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, or 2-amino-6-fluoro-5-pyridyl; and a pharmaceutically acceptable salt thereof.

In another embodiment, $R^5$ is H, methyl, ethyl, 2-methylpropyl, hydroxyethyl, butynyl, or benzyl; and a pharmaceutically acceptable salt thereof.

In another embodiment, $R^7$ is H, or methyl; and a pharmaceutically acceptable salt thereof.

In another embodiment, $R^a$ is amino, H, trifluoromethyl or methyl; and a pharmaceutically acceptable salt thereof;

In another embodiment, $R^5$ is H if $R^7$ is alkyl; further provided $R^7$ is H if $R^5$ is alkyl; and a pharmaceutically acceptable salt thereof.

In another embodiment, R is

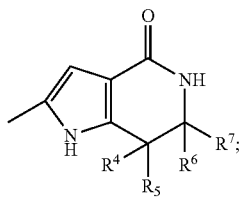

wherein $R^4$ is H; wherein $R^5$ is H; wherein $R^6$ is H; and wherein $R^7$ is H; and a pharmaceutically acceptable salt thereof In another embodiment, $R^2$ is H; and a pharmaceutically acceptable salt thereof.

In another embodiment, $R^a$ is H, amino, methoxy, trifluoromethyl, HC(=O)— or methyl; and a pharmaceutically acceptable salt thereof.

In another embodiment, $R^a$ is H or methyl; and a pharmaceutically acceptable salt thereof.

In another embodiment, $R^4$ is H; $R^5$ is H, $C_{1-2}$ alkyl, $C_{1-2}$ hydroxyalkyl, $C_{2-4}$ alkynyl, or benzyl; or wherein $R^4$ and $R^5$ together form $C_{3-4}$ cycloalkyl; $R^6$ is H; and $R^7$ is H, or $C_{1-2}$ alkyl; and a pharmaceutically acceptable salt thereof.

In another embodiment, $R^b$ is H, $C_{1-6}$ alkyl, $C_{1-2}$ haloalkyl, $C_{1-4}$ aminoalkyl, $C_{1-3}$ alkoxy-$C_{1-3}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl; and a pharmaceutically acceptable salt thereof.

In another embodiment, $R^b$ is an unsubstituted or substituted ring selected from cyclopropyl, cyclobutyl, cyclopentyl, phenyl, pyridyl, piperidinyl, morpholinyl, piperazinyl, pyrrolindinyl, and tetrahydropyranyl; and a pharmaceutically acceptable salt thereof.

In another embodiment, $R^1$ is an unsubstituted or substituted ring selected from phenyl, pyrrolidinyl, azetidinyl, morpholinyl, tetrahydrofuryl, piperidinyl, piperazinyl, pyrazolyl, and pyridyl; and a pharmaceutically acceptable salt thereof.

Another aspect of the current invention relates to compounds having the general structure of Formula 4

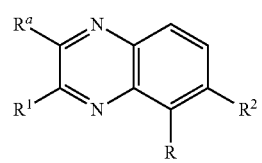

wherein R is

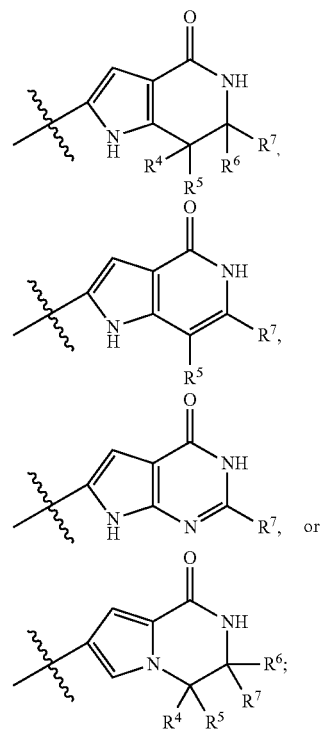

wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, —$CONHR^b$, —$NHC$=$OR^b$, —$OR^b$, —$S(=O)_nR^b$, —$COR^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein $R^a$ is H, amino, $C_{1-2}$ alkoxy, $C_{1-2}$ haloalkyl, $C_{1-2}$ alkyl or HC(=O)—;

wherein $R^b$ is H, $C_{1-6}$ alkyl, $C_{1-6}$ haloalkyl, $C_{1-6}$ aminoalkyl, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^2$ is H or halo;

wherein $R^4$ is H;

wherein $R^5$ is H, $C_{1-4}$ alkyl, $C_{1-4}$ hydroxyalkyl, $C_{2-4}$ alkynyl, or benzyl; or wherein $R^4$ and $R^5$ together form $C_{3-6}$ cycloalkyl;

wherein $R^6$ is H; and wherein $R^7$ is H, or $C_{1-3}$ alkyl; and a pharmaceutically acceptable salt thereof.

In another embodiment, $R^1$ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-trifluoromethylethylamino, methylsulfonyl-(1,1-dimethylethyl)amino, methylsulfonylamino, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-ylamino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 1-azetidinyl, 2,2-dimethyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, or 2-amino-6-fluoro-5-pyridyl; and a pharmaceutically acceptable salt thereof.

In another embodiment, R is

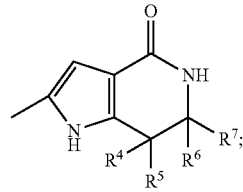

wherein $R^4$ is H; wherein $R^5$ is H; wherein $R^6$ is H; and wherein $R^7$ is H; and a pharmaceutically acceptable salt thereof In another embodiment, $R^2$ is H; and a pharmaceutically acceptable salt thereof.

In another embodiment, $R^a$ is H, amino, methoxy, trifluoromethyl, HC(=O)— or methyl; and a pharmaceutically acceptable salt thereof.

In another embodiment, $R^a$ is amino, H, trifluoromethyl or methyl; and a pharmaceutically acceptable salt thereof.

In another embodiment, $R^a$ is H or methyl; and a pharmaceutically acceptable salt thereof.

In another embodiment, $R^4$ is H; and a pharmaceutically acceptable salt thereof.

In another embodiment, $R^5$ is H, $C_{1-2}$ alkyl, $C_{1-2}$ hydroxyalkyl, $C_{2-4}$ alkynyl, or benzyl; and a pharmaceutically acceptable salt thereof.

In another embodiment, $R^5$ is H, methyl, ethyl, 2-methylpropyl, hydroxyethyl, butynyl, or benzyl; and a pharmaceutically acceptable salt thereof.

In another embodiment, $R^5$ is H if leis alkyl; or $R^7$ is H if $R^5$ is alkyl; and a pharmaceutically acceptable salt thereof.

In another embodiment, $R^4$ and $R^5$ together form $C_{3-4}$ cycloalkyl; and a pharmaceutically acceptable salt thereof.

In another embodiment, $R^6$ is H; and a pharmaceutically acceptable salt thereof.

In another embodiment, $R^7$ is H, or $C_{1-2}$ alkyl; and a pharmaceutically acceptable salt thereof.

In another embodiment, $R^7$ is H, or methyl; and a pharmaceutically acceptable salt thereof.

In another embodiment, $R^b$ is H, $C_{1-6}$ alkyl, $C_{1-2}$ haloalkyl, $C_{1-4}$ aminoalkyl, $C_{1-3}$ alkoxy-$C_{1-3}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl; and a pharmaceutically acceptable salt thereof.

In another embodiment, $R^b$ is an unsubstituted or substituted ring selected from cyclopropyl, cyclobutyl, cyclopentyl, phenyl, pyridyl, piperidinyl, morpholinyl, piperazinyl, pyrrolindinyl, and tetrahydropyranyl; and a pharmaceutically acceptable salt thereof.

In another embodiment, $R^1$ is an unsubstituted or substituted ring selected from phenyl, pyrrolidinyl, azetidinyl, morpholinyl, tetrahydrofuryl, piperidinyl, piperazinyl, pyrazolyl, and pyridyl; and a pharmaceutically acceptable salt thereof.

Another aspect of the current invention relates to compounds having the general structure of Formula 5a and 5b 5a 5b wherein R is

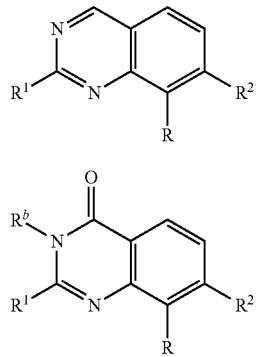

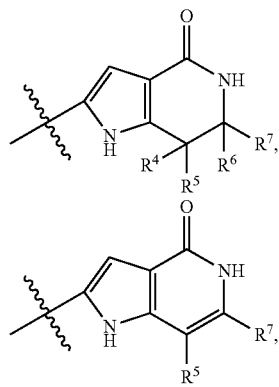

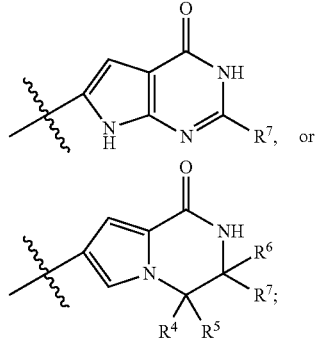

wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein $R^b$ is H, $C_{1-6}$ alkyl, $C_{1-6}$ haloalkyl, $C_{1-6}$ aminoalkyl, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^2$ is H or halo;

wherein $R^4$ is H;

wherein $R^5$ is H, $C_{1-4}$ alkyl, $C_{1-4}$ hydroxyalkyl, $C_{2-4}$ alkynyl, or benzyl; or wherein $R^4$ and $R^5$ together form $C_{3-6}$ cycloalkyl;

wherein $R^6$ is H; and wherein $R^7$ is H, or $C_{1-3}$ alkyl; and a pharmaceutically acceptable salt thereof.

In another embodiment, $R^1$ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-trifluoromethylethylamino, methylsulfonyl-(1,1-dimethylethyl)amino, methylsulfonylamino, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-yl amino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 1-azetidinyl, 2,2-dimethyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, or 2-amino-6-fluoro-5-pyridyl; and a pharmaceutically acceptable salt thereof.

In another embodiment, R is

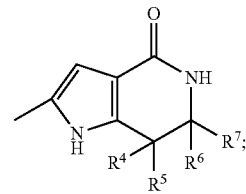

$R^4$ is H; $R^5$ is H; $R^6$ is H; and $R^7$ is H; and a pharmaceutically acceptable salt thereof.

In another embodiment, $R^2$ is H; and a pharmaceutically acceptable salt thereof.

In another embodiment, $R^4$ is H; and a pharmaceutically acceptable salt thereof.

In another embodiment, $R^5$ is H, $C_{1-2}$ alkyl, $C_{1-2}$ hydroxyalkyl, $C_{2-4}$ alkynyl, or benzyl; and a pharmaceutically acceptable salt thereof.

In another embodiment, $R^5$ is H, methyl, ethyl, 2-methylpropyl, hydroxyethyl, butynyl, or benzyl; and a pharmaceutically acceptable salt thereof.

In another embodiment, $R^4$ and $R^5$ together form $C_{3-4}$ cycloalkyl; and a pharmaceutically acceptable salt thereof.

In another embodiment, $R^6$ is H; and a pharmaceutically acceptable salt thereof.

In another embodiment, $R^7$ is H, or $C_{1-2}$ alkyl; and a pharmaceutically acceptable salt thereof.

In another embodiment, $R^7$ is H, or methyl; and a pharmaceutically acceptable salt thereof.

In another embodiment, $R^5$ is H if $R^7$ is alkyl; or $R^7$ is H if $R^5$ is alkyl; and a pharmaceutically acceptable salt thereof.

In another embodiment, $R^b$ is H, $C_{1-6}$ alkyl, $C_{1-2}$ haloalkyl, $C_{1-4}$ aminoalkyl, $C_{1-3}$ alkoxy-$C_{1-3}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocycle; and a pharmaceutically acceptable salt thereof.

In another embodiment, $R^b$ is H, trifluoromethyl or methyl; and a pharmaceutically acceptable salt thereof.

In another embodiment, $R^b$ is an unsubstituted or substituted ring selected from cyclopropyl, cyclobutyl, cyclopentyl, phenyl, pyridyl, piperidinyl, morpholinyl, piperazinyl, pyrrolindinyl, and tetrahydropyranyl; and a pharmaceutically acceptable salt thereof.

In another embodiment, $R^1$ is an unsubstituted or substituted ring selected from phenyl, pyrrolidinyl, azetidinyl, morpholinyl, tetrahydrofuryl, piperidinyl, piperazinyl, pyrazolyl, and pyridyl; and a pharmaceutically acceptable salt thereof.

Another aspect of the current invention relates to compounds having the general structure of Formula 6

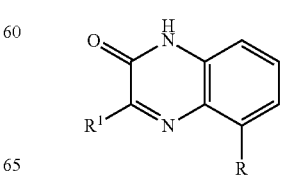

wherein R is

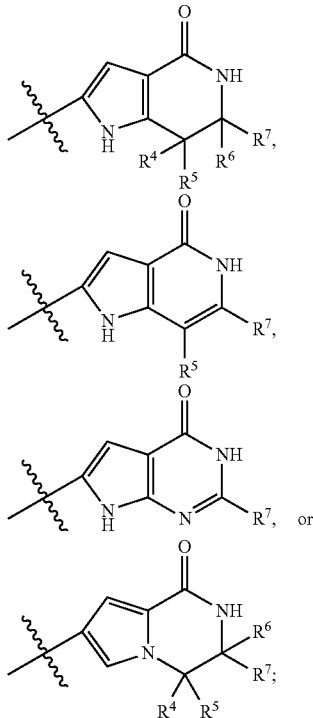

wherein R¹ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, substituted or unsubstituted $C_{3-6}$cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, —CONHR$^b$, —NHC=OR$^b$, —OR$^b$, —S(=O)$_n$R$^b$, —COW, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;
wherein n is 0, 1 or 2;
wherein R$^b$ is H, $C_{1-6}$ alkyl, $C_{1-6}$ haloalkyl, $C_{1-6}$ aminoalkyl, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;
wherein R$^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;
wherein R⁴ is H;
wherein R⁵ is H, $C_{1-4}$ alkyl, $C_{1-4}$ hydroxyalkyl, $C_{2-4}$ alkynyl, or benzyl; or wherein R⁴ and R⁵ together form $C_{3-6}$ cycloalkyl;
wherein R⁶ is H; and
wherein R⁷ is H, or $C_{1-3}$ alkyl;
and a pharmaceutically acceptable salt thereof.
Some particular embodiments of the invention are enumerated here:
1. A compound of Formula 7

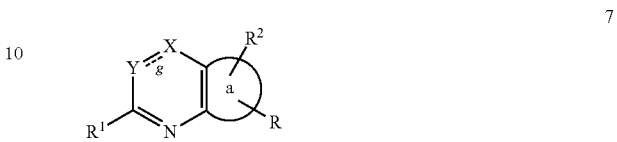

wherein
bond g is a single bond or double bond; provided g is a single bond if Y is C=O or C(R$^a$)$_2$ or X is C=O or CH$_2$;
ring a is a ring that together with the 2 carbon atoms to which it attaches, forms a phenyl ring or a 5-6 membered heterocyclic ring;
X is N, NR$^b$, C=O, CH or CH$_2$;
Y is N, NR$^b$, C=O, CR$^a$ or C(R$^a$)$_2$;
R is an optionally substituted bicyclic amide, optionally substituted bicyclic thioamide, optionally substituted bicyclic oxime,

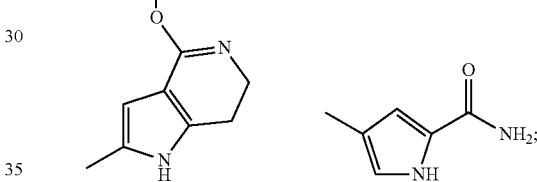

R¹ is H, halo, alkyl, amino, alkylamino, alkenylamino, haloalkylamino, alkylsulfonylalkylamino, aminocarbonylalkylamino, aminoalkylamino, hydroxyalkylamino, alkylsulfonylamino, carboxyalkylamino, alkoxycarbonylalkylamino, alkoxyalkylamino, Boc-aminoalkylamino, alkoxyalkylalkoxyalkylamino, alkylsulfonylalkylaminoalkylamino, substituted or unsubstituted cycloalkylamino, substituted or unsubstituted cycloalkylalkylamino, substituted or unsubstituted arylamino, substituted or unsubstituted arylalkylamino, substituted or unsubstituted heterocyclylamino, substituted or unsubstituted heterocyclyl $C_{1-6}$ alkylamino, —CONHR$^b$, —NHC=OR$^b$, —OR$^b$, —S(=O)$_n$R$^b$, —COR$^c$, unsubstituted or substituted aryl, unsubstituted or substituted arylalkyl, unsubstituted or substituted arylalkenyl, unsubstituted or substituted cycloalkyl, unsubstituted or substituted cycloalkylalkyl, unsubstituted or substituted heterocyclylalkyl or substituted or unsubstituted heterocyclyl;
R² is H, or halo;
R$^a$ is H, halo, haloalkyl, hydroxyalkyl, alkyl, alkynyl, alkoxy, amino, alkylamino, cyano, HC(=O)—, HC(=NOH)—, carboxy, alkoxycarbonyl, or substituted or unsubstituted heterocyclyl;
R$^b$ is H, alkyl, haloalkyl, aminoalkyl, alkoxyalkyl, unsubstituted or substituted cycloalkyl, unsubstituted or substituted aryl, unsubstituted or substituted arylalkyl or unsubstituted or substituted heterocyclyl;
R$^c$ is H, alkyl, alkoxy, alkoxyalkyl, unsubstituted or substituted cycloalkyl, unsubstituted or substituted aryl, unsubstituted or substituted arylalkyl or unsubstituted or substituted heterocyclyl; and $R^d$ is alkyl;

and a pharmaceutically acceptable salt thereof.

2. A compound of embodiment 1 having Formula 7a, Formula 7b or Formula 7c

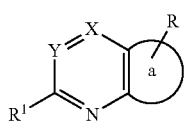

7a

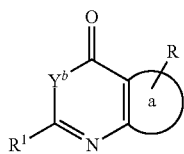

7b

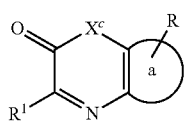

7c wherein

X is N or CH;

Y is N or $CR^a$;

$Y^b$ is $NR^b$;

$X^c$ is NH or $CH_2$;

ring a is a.

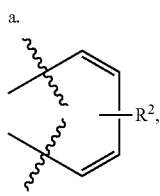

b.

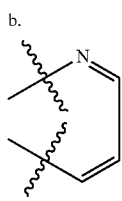

c.

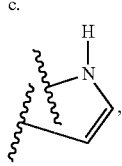

d.

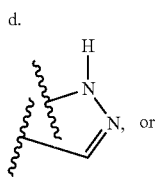, or e.

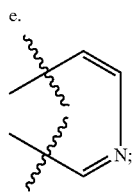

R is an optionally substituted bicyclic amide;

$R^1$ is H, halo, alkyl, amino, alkylamino, alkenylamino, haloalkylamino, alkylsulfonylalkylamino, aminocarbonylalkylamino, aminoalkylamino, hydroxyalkylamino, alkylsulfonylamino, carboxyalkylamino, alkoxycarbonylalkylamino, alkoxyalkylamino, Boc-aminoalkylamino, alkoxyalkoxyalkylamino, alkylsulfonylalkylaminoalkylamino, substituted or unsubstituted cycloalkylamino, substituted or unsubstituted cycloalkylalkylamino, substituted or unsubstituted phenylamino, substituted or unsubstituted arylalkylamino, substituted or unsubstituted heterocyclylamino, substituted or unsubstituted heterocyclyl $C_{1-6}$ alkylamino, —$CONHR^b$, —$NHC$=$OR^b$, —$OR^b$, —$S(=O)_nR^b$, —$COR^c$, unsubstituted or substituted aryl, unsubstituted or substituted arylalkyl, unsubstituted or substituted arylalkenyl, unsubstituted or substituted cycloalkyl, unsubstituted or substituted cycloalkylalkyl, unsubstituted or substituted heterocyclylalkyl or substituted or unsubstituted heterocyclyl;

$R^2$ is H, or halo;

$R^a$ is H, amino, alkylamino, haloalkyl, hydroxyalkyl, alkyl, alkoxy, halo, alkynyl, cyano, $HC(=NOH)$—, $HC(=O)$—, carboxy, alkoxycarbonyl, or substituted or unsubstituted heterocyclyl;

$R^b$ is H, alkyl, haloalkyl, aminoalkyl, alkoxy alkyl, unsubstituted or substituted cycloalkyl, unsubstituted or substituted aryl, unsubstituted or substituted aralkyl or unsubstituted or substituted heterocyclyl;

$R^c$ is H, alkyl, alkoxy, alkoxyalkyl, unsubstituted or substituted cycloalkyl, unsubstituted or substituted aryl, unsubstituted or substituted arylalkyl or unsubstituted or substituted heterocyclyl; and $R^d$ is alkyl;

and a pharmaceutically acceptable salt thereof.

3. Compound of Embodiment 1 wherein R is

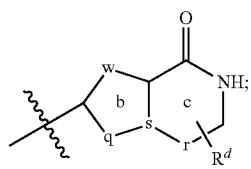

wherein q is NH or CH;

wherein r is $CH_2$ or N;

wherein q is NH or CH;

wherein r is $CH_2$ or N;

wherein s is N or C;

wherein w is $CR^g$ or N;

wherein $R^d$ is one or more substituents selected from H, $C_{1-4}$ alkyl, $C_{1-4}$ hydroxyalkyl, $C_{2-4}$ alkynyl or benzyl; or wherein $R^d$ forms a carbocyclic or heterocyclic ring spiro to ring c;

wherein $R^g$ is H, fluoro or chloro;

wherein ring b is unsaturated, or partially saturated; and wherein ring c is saturated, or partially saturated; and a pharmaceutically acceptable salt thereof.

4. Compound of Embodiment 1 wherein R is

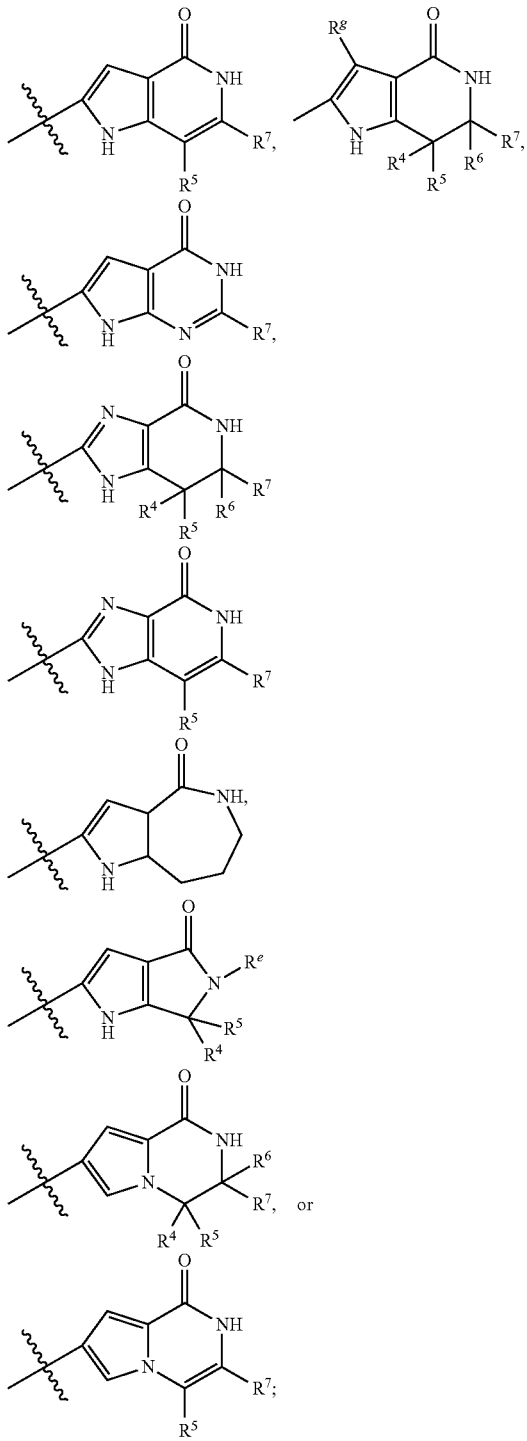

wherein $R^e$ is H or Boc;
wherein $R^g$ is H, fluoro or chloro;
wherein $R^4$ is H or $C_{1-4}$ alkyl;
wherein $R^5$ is H, $C_{1-4}$ alkyl, $C_{1-4}$ hydroxyalkyl, $C_{2-4}$ alkynyl, benzyloxy or benzyl; or wherein $R^4$ and $R^5$ together form $C_{3-6}$ cycloalkyl or 4-6 membered heterocyclyl;
wherein $R^6$ is H; and
wherein $R^7$ is H or $C_{1-3}$ alkyl; and a pharmaceutically acceptable salt thereof.

5. Compound of Embodiment 4 wherein $R^4$ is H; and $R^5$ is H; and a pharmaceutically acceptable salt thereof.

6. Compound of Embodiment 5 wherein $R^6$ is H; and $R^7$ is H; and a pharmaceutically acceptable salt thereof.

7. Compound of Embodiment 4 wherein $R^4$ is H; and $R^5$ is H, methyl, benzyloxymethyl, hydroxymethyl or hydroxyethyl; and a pharmaceutically acceptable salt thereof.

8. Compound of Embodiment 4 wherein together $R^4$ and $R^5$ together form cyclopropyl; and a pharmaceutically acceptable salt thereof.

9. Compound of Embodiment 1 wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, Boc-amino-$C_{1-6}$ alkylamino, $C_{1-6}$ alkoxy-$C_{1-6}$ alkoxy-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl; and a pharmaceutically acceptable salt thereof.

10. Compound of Embodiment 1 wherein $R^1$ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, (2-amino-1,1-dimethylethyl)amino, 2-methyl-2-propen-1-ylamino, 1-methoxycarbonyl-1-ethylamino, 1-methoxycarbonyl-1-methylethylamino, (2-(tert-butoxycarbonylamino)-1,1-dimethylethyl)amino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2,2,2-trifluoroethylamino, 2,2-difluoroethylamino, 2-trifluoromethyl-2-methylethylamino, 2-trifluoromethylethylamino, methylsulfonyl-(1,1-dimethylethyl)amino, (1,1-dimethyl-3-(methylsulfonyl)-propyl)amino, methylsulfonylamino, (1,1-dimethyl-2-(methylsulfonyl)-ethyl)amino, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-ylamino, 2-pyridylamino, 3-pyridylamino, 4-pyridylamino, 5-pyrimidinylamino, benzylamino, 1-phenylethylamino, 2-methyl-3-((1R)-1-(2-pyridinyl)ethyl)amino, 2-methyl-3-((1R)-1-(2-pyrazinyl)ethyl)amino, 2-methyl-3-((1R)-1-(4-pyrimidinyl)ethyl)amino, cyclopropylethylamino, (1-methylcyclopropyl)methylamino, 3-oxetanylmethylamino, 3-methyl-3-oxetanylmethylamino, 2-methoxyethoxy-1,1-dimethylethylamino, ethoxy, isopropoxy, 2,2-dimethylpropoxy, 3-amino-3-methylbutoxy, 2-(trifluoromethyl)ethoxy, 1-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 1-azetidinyl, 2,2-dimethyl-1-azetidinyl, 3-methylsulfonyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, 2-methyl-2-imidazolyl, or 2-amino-6-fluoro-5-pyridyl; and a pharmaceutically acceptable salt thereof.

11. Compound of Embodiment 1 wherein $R^2$ is H or fluoro; and a pharmaceutically acceptable salt thereof.

12. Compound of Embodiment 1 wherein ring a is

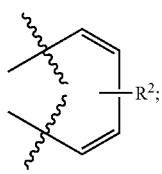

wherein $R^2$ is H or fluoro; and a pharmaceutically acceptable salt thereof.

13. Compound of Embodiment 1 wherein ring a is

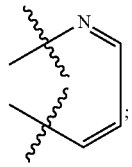

and a pharmaceutically acceptable salt thereof.

14. A compound of Formula 8

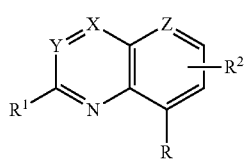

wherein R is

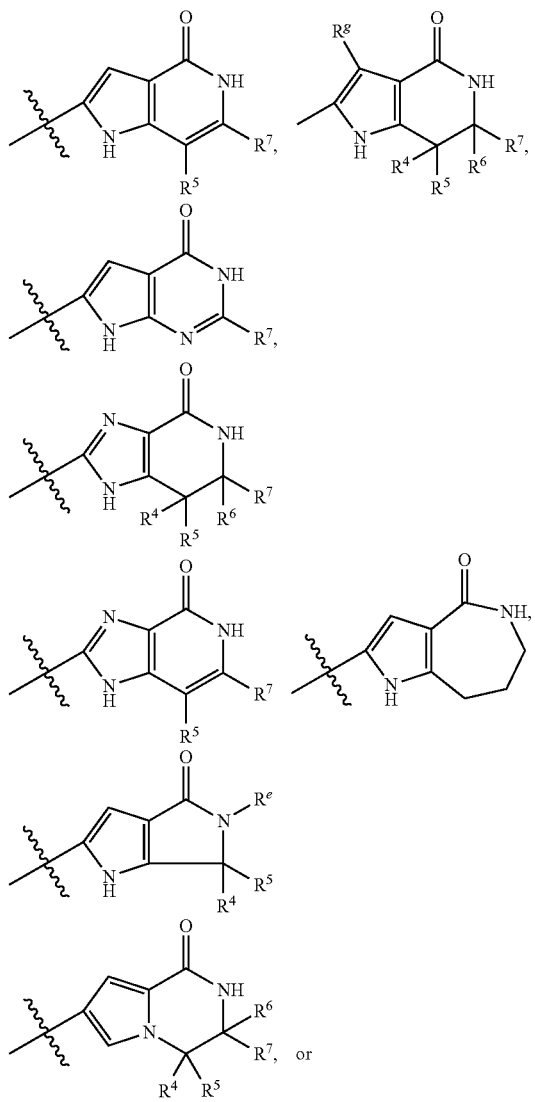

-continued

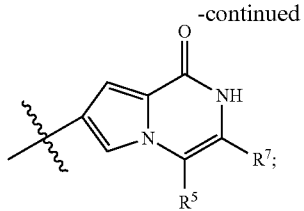

wherein R¹ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, Boc-amino-$C_{1-6}$ alkylamino, $C_{1-6}$ alkoxy-$C_{1-6}$ alkoxy-$C_{1-6}$ alkylamino, $C_{1-6}$ alkylsulfonyl-$C_{1-6}$ alkylamino-$C_{1-6}$ alkylamino, substituted or unsubstituted cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl $C_{1-6}$ alkylamino, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein X is N, NH, CH or $CH_2$;

wherein Y is N, CR$^a$, CHR$^a$ or NR$^b$;

wherein Z is CH or N;

wherein R² is H or halo;

wherein R⁴ is H or $C_{1-4}$ alkyl;

wherein R⁵ is H, $C_{1-4}$ alkyl, $C_{1-4}$ hydroxyalkyl, $C_{2-4}$ alkynyl or benzyl; or wherein R⁴ and R⁵ together form $C_{3-6}$ cycloalkyl or 4-6 membered saturated heterocyclyl;

wherein R⁶ is H;

wherein R⁷ is H, or $C_{1-3}$ alkyl;

wherein R$^a$ is H, amino, halo, $C_{1-2}$ haloalkyl, $C_{1-2}$ hydroxyalkyl, $C_{1-2}$ alkyl, $C_{1-2}$ alkylamino, $C_2$-$C_3$ alkynyl, $C_{1-2}$ alkoxy, cyano, HC(=O)—, HON=CH—, carboxy, alkoxycarbonyl, substituted or unsubstituted 4-membered N-containing heterocyclyl or substituted or unsubstituted 5-membered N-containing heteroaryl;

wherein R$^b$ is H, $C_{1-6}$ alkyl, $C_{1-6}$ haloalkyl, $C_{1-6}$ aminoalkyl, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-6}$ alkyl or unsubstituted or substituted 5-7 membered heterocyclyl;

wherein R$^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-6}$ alkyl or unsubstituted or substituted 5-7 membered heterocyclyl;

wherein R$^e$ is H or Boc; and wherein R$^g$ is H, fluoro or chloro;

and a pharmaceutically acceptable salt thereof.

15. Compound of Embodiment 14 wherein R is

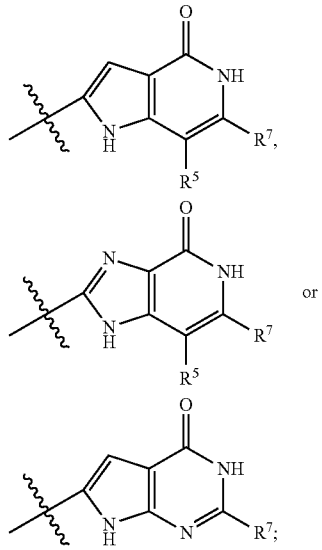

and a pharmaceutically acceptable salt thereof.

16. Compound of Embodiment 15 wherein R⁵ is H, methyl, hydroxymethyl, butynyl or benzyl; and R⁷ is H, or methyl; and a pharmaceutically acceptable salt thereof.

17. Compound of Embodiment 15 wherein R⁵ is H; and R⁷ is H; and a pharmaceutically acceptable salt thereof.

18. Compound of Embodiment 14 wherein R is

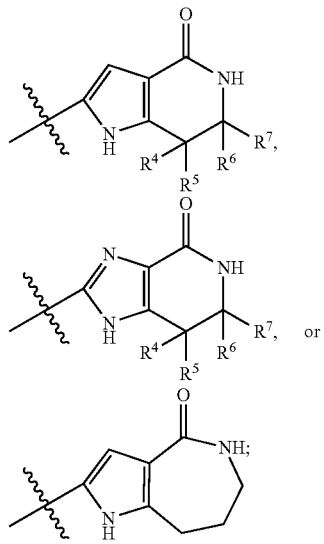

and a pharmaceutically acceptable salt thereof.

19. Compound of Embodiment 18 wherein R⁴ is H; R⁵ is H, methyl, hydroxymethyl, butynyl or benzyl; R⁶ is H; and R⁷ is H, or methyl; or wherein R⁴ and R⁵ together form cyclopropyl; and a pharmaceutically acceptable salt thereof.

20. Compound of Embodiment 18 wherein R⁴ is H; R⁵ is H; R⁶ is H and R⁷ is H; and a pharmaceutically acceptable salt thereof.

21. Compound of Embodiment 14 wherein R is

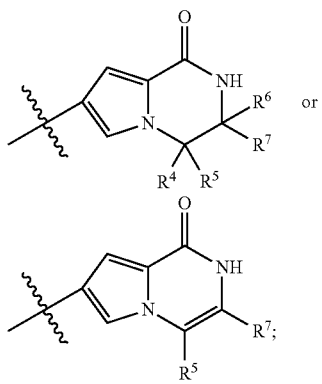

and a pharmaceutically acceptable salt thereof.

22. Compound of Embodiment 21 wherein $R^4$ is H; $R^5$ is H, methyl, hydroxymethyl, butynyl or benzyl; $R^6$ is H; and $R^7$ is H, or methyl; or wherein $R^4$ and $R^5$ together form cyclopropyl; and a pharmaceutically acceptable salt thereof.

23. Compound of Embodiment 21 wherein $R^4$ is H; $R^5$ is H; $R^6$ is H and $R^7$ is H; and a pharmaceutically acceptable salt thereof.

24. Compound of Embodiment 14 wherein $R^1$ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, (2-amino-1,1-dimethylethyl)amino, (2-(tert-butoxycarbonylamino)-1,1-dimethylethyl)amino, 2,2,2-trifluoroethylamino, 2,2-difluoroethylamino, (1,1-dimethyl-3-(methylsulfonyl)-propyl)amino, (1,1-dimethyl-2-(methylsulfonyl)-ethyl)amino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-trifluoromethylethylamino, methylsulfonyl-(1,1-dimethylethyl)amino, methylsulfonylamino, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-yl amino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 2-methyl-3-((1R)-1-(2-pyridinyl)ethyl)amino, 2-methyl-3-((1R)-1-(2-pyrazinyl)ethyl)amino, 2-methyl-3-((1R)-1-(4-pyrimidinyl)ethyl)amino, (1-methylcyclopropyl)methylamino, 2-methoxyethoxy-1,1-dimethylethylamino, ethoxy, isopropoxy, 3-amino-3-methylbutoxy, 2-(trifluoromethyl)ethoxy, 1-(trifluoromethyl)ethoxy, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 1-azetidinyl, 2,2-dimethyl-1-azetidinyl, 3-methylsulfonyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 2-methyl-2-imidazolyl, 1-methyl-4-pyrazolyl, or 2-amino-6-fluoro-5-pyridyl; and a pharmaceutically acceptable salt thereof.

25. Compound of Embodiment 14 wherein X is CH; Y is $CR^a$ or N; and Z is CH; and a pharmaceutically acceptable salt thereof.

26. Compound of Embodiment 14 wherein X is N; Y is $CR^a$; and Z is CH; and a pharmaceutically acceptable salt thereof.

27. Compound of Embodiment 14 wherein X is CH; Y is N; and Z is CH; and a pharmaceutically acceptable salt thereof.

28. Compound of Embodiment 14 wherein $R^a$ is H, chloro, fluoro, bromo, amino, methylamino, hydroxymethyl, HO—N=CH—, methoxy, trifluoromethyl, 1-azetidinyl, 3-hydroxy-1-azetidinyl, 5-methyl-oxadiazol-2-yl, HC(=O)— or methyl; and a pharmaceutically acceptable salt thereof.

28. Compound of Embodiment 14 wherein $R^a$ is H or methyl; and a pharmaceutically acceptable salt thereof.

30. Compound of Embodiment 14 wherein $R^2$ is H or fluoro; and a pharmaceutically acceptable salt thereof.

31. A compound of Formula 9

wherein R is

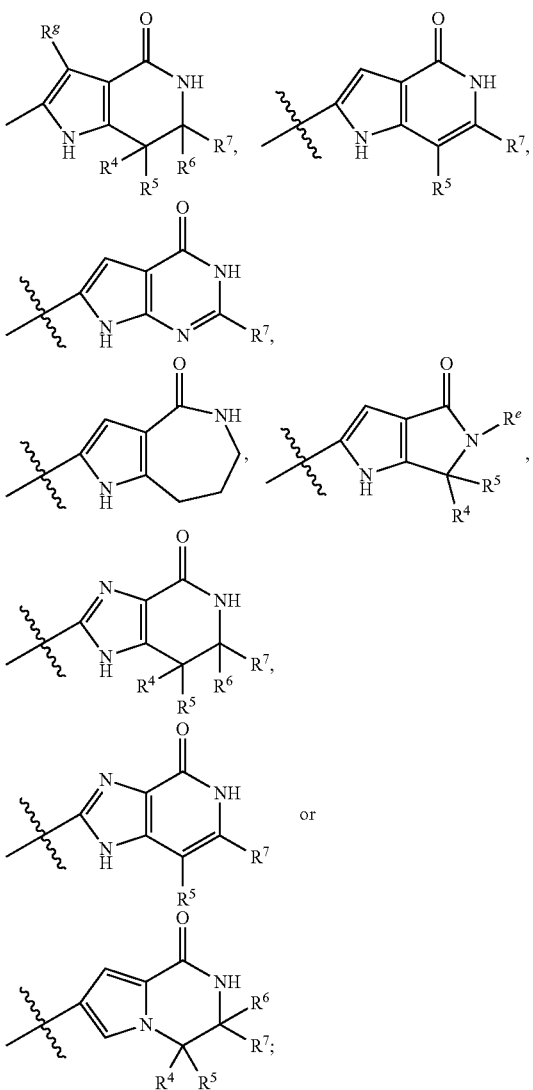

wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkoxycarbonyl-$C_{1-6}$ alkylamino, $C_{1-6}$ alkoxy-$C_{1-6}$ alkylamino, Boc-amino-$C_{1-6}$ alkylamino, $C_{1-6}$ alkoxy-$C_{1-6}$ alkoxy-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein $R^a$ is H, amino, cyano, halo, $C_{1-2}$ alkoxy, $C_{1-2}$ alkylamino, $C_{2-3}$ alkynyl, $C_{1-2}$ haloalkyl, $C_{1-2}$ hydoxyalkyl, $C_{1-2}$ alkyl, HO—N=CH—, HC(=O)— or optionally substituted heterocyclyl;

wherein $R^b$ is H, $C_{1-6}$ alkyl, $C_{1-6}$ haloalkyl, $C_{1-6}$ aminoalkyl, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^e$ is H or Boc;

wherein $R^g$ is H, fluoro or chloro;

wherein $R^2$ is H or halo;

wherein $R^4$ is H;

wherein $R^5$ is H, $C_{1-4}$ alkyl, $C_{1-4}$ hydroxyalkyl, $C_{2-4}$ alkynyl, or benzyl; or wherein $R^4$ and $R^5$ together form $C_{3-6}$ cycloalkyl or 4-6 membered saturated heterocyclyl;

wherein $R^6$ is H; and wherein $R^7$ is H, or $C_{1-3}$ alkyl; and a pharmaceutically acceptable salt thereof.

32. Compound of Embodiment 31 wherein $R^1$ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, (2-amino-1,1-dimethylethyl)amino, (2-(tert-butoxycarbonylamino)-1,1-dimethylethyl)amino, 2,2,2-trifluoroethylamino, 2,2-difluoroethylamino, (1,1-dimethyl-3-(methylsulfonyl)-propyl)amino, (1,1-dimethyl-2-(methylsulfonyl)-ethyl)amino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-(trifluoromethyl)ethylamino, methylsulfonyl-(1,1-dimethylethyl)amino, methylsulfonylamino, 2-methyl-3-((1R)-1-(2-pyridinyl)ethyl)amino, 2-methyl-3-((1R)-1-(2-pyrazinyl)ethyl)amino, 2-methyl-3-((1R)-1-(4-pyrimidinyl)ethyl)amino, (1-methylcyclopropyl)methylamino, 2-methoxyethoxy-1,1-dimethylethylamino, ethoxy, isopropoxy, 3-amino-3-methylbutoxy, 2-(trifluoromethyl)ethoxy, 1-(trifluoromethyl)ethoxy, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, 2-methyl-1-imidazolyl, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-yl amino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 1-(4-pyrimidinyl)ethyl, -(2-pyridyl)ethyl, -(4-pyrazinyl) ethyl, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 3-methylsulfonyl-1-azetidinyl, 2-methyl-2-imidazolyl, 1-azetidinyl, 2,2-dimethyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, or 2-amino-6-fluoro-5-pyridyl; and a pharmaceutically acceptable salt thereof.

33. Compound of Embodiment 31 wherein $R^5$ is H, methyl, ethyl, 2-methylpropyl, hydroxyethyl, butynyl, or benzyl; $R^7$ is H, or methyl; and $R^a$ is amino, H, trifluoromethyl or methyl; provided $R^5$ is H if $R^7$ is alkyl; further provided $R^7$ is H if $R^5$ is alkyl; and a pharmaceutically acceptable salt thereof.

34. Compound of Embodiment 31 wherein R is

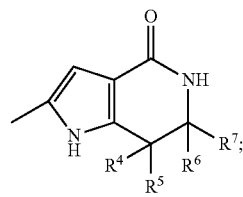

$R^4$ is H; $R^5$ is H; $R^6$ is H; and $R^7$ is H; and a pharmaceutically acceptable salt thereof.

35. Compound of Embodiment 31 wherein $R^2$ is H; and a pharmaceutically acceptable salt thereof.

36. Compound of Embodiment 31 wherein $R^a$ is H, chloro, fluoro, bromo, amino, methylamino, hydroxymethyl, HO—N=CH—, methoxy, trifluoromethyl, 1-azetidinyl, 3-hydroxy-1-azetidinyl, 5-methyl-oxadiazol-2-yl, HC(=O)— or methyl; and a pharmaceutically acceptable salt thereof.

37. Compound of Embodiment 31 wherein $R^a$ is H or methyl; and a pharmaceutically acceptable salt thereof.

38. Compound of Embodiment 31 wherein $R^4$ is H; $R^5$ is H, $C_{1-2}$ alkyl, $C_{1-2}$ hydroxyalkyl, $C_{2-4}$ alkynyl, or benzyl; or wherein $R^4$ and $R^5$ together form $C_{3-4}$ cycloalkyl; $R^6$ is H; and $R^7$ is H, or $C_{1-2}$ alkyl; and a pharmaceutically acceptable salt thereof.

39. Compound of Embodiment 31 wherein $R^b$ is H, $C_{1-6}$ alkyl, $C_{1-2}$ haloalkyl, $C_{1-4}$ aminoalkyl, $C_{1-3}$ alkoxy-$C_{1-3}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl; and a pharmaceutically acceptable salt thereof.

40. Compound of Embodiment 31 wherein $R^b$ is an unsubstituted or substituted ring selected from cyclopropyl, cyclobutyl, cyclopentyl, phenyl, pyridyl, piperidinyl, morpholinyl, piperazinyl, pyrrolindinyl, and tetrahydropyranyl; and a pharmaceutically acceptable salt thereof.

41. Compound of Embodiment 31 wherein $R^1$ is an unsubstituted or substituted ring selected from phenyl, pyrrolidinyl, azetidinyl, morpholinyl, tetrahydrofuryl, piperidinyl, piperazinyl, pyrazolyl, and pyridyl; and a pharmaceutically acceptable salt thereof.

42. A compound of Formula 10

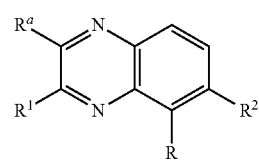

wherein R is

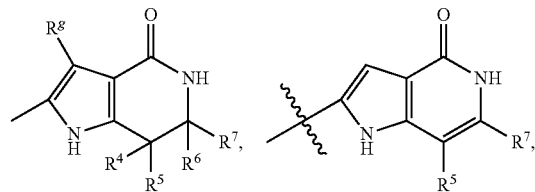

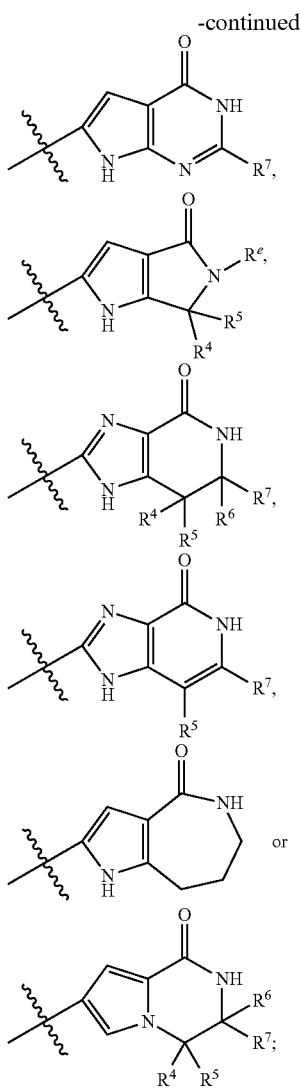

wherein R¹ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, Boc-amino-$C_{1-6}$ alkylamino, $C_{1-6}$ alkoxy-$C_{1-6}$ alkoxy-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, —CONHR$^b$, —NHC═OR$^b$, —OR$^b$, —S(═O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein R$^a$ is H, amino, cyano, halo, $C_{1-2}$ alkoxy, $C_{1-2}$ alkylamino, $C_{2-3}$ alkynyl, $C_{1-2}$ haloalkyl, $C_{1-2}$ hydoxyalkyl, $C_{1-2}$ alkyl, HO—N═CH—, HC(═O)— or optionally substituted heterocyclyl;

wherein R$^b$ is H, $C_{1-6}$ alkyl, $C_{1-6}$ haloalkyl, $C_{1-6}$ aminoalkyl, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein R$^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein R$^e$ is H or Boc;
wherein R$^g$ is H, halo;
wherein R² is H or halo;
wherein R⁴ is H;
wherein R⁵ is H, $C_{1-4}$ alkyl, $C_{1-4}$ hydroxyalkyl, $C_{2-4}$ alkynyl, benzyloxy-$C_{1-4}$ alkyl or benzyl; or wherein R⁴ and R⁵ together form $C_{3-6}$ cycloalkyl or 4-6 membered saturated heterocyclyl;
wherein R⁶ is H; and
wherein R⁷ is H, or $C_{1-3}$ alkyl; and a pharmaceutically acceptable salt thereof.

43. Compound of Embodiment 42 wherein R¹ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, (2-amino-1,1-dimethylethyl)amino, (2-(tert-butoxycarbonylamino)-1,1-dimethylethyl)amino, 2,2,2-trifluoroethylamino, 2,2-difluoroethylamino, (1,1-dimethyl-3-(methylsulfonyl)-propyl)amino, (1,1-dimethyl-2-(methylsulfonyl)-ethyl)amino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-(trifluoromethyl)ethylamino, methylsulfonyl-(1,1-dimethylethyl)amino, methylsulfonylamino, 2-methyl-3-((1R)-1-(2-pyridinyl)ethyl)amino, 2-methyl-3-((1R)-1-(2-pyrazinyl)ethyl)amino, 2-methyl-3-((1R)-1-(4-pyrimidinyl)ethyl)amino, (1-methylcyclopropyl)methylamino, 2-methoxyethoxy-1,1-dimethylethylamino, ethoxy, isopropoxy, 3-amino-3-methylbutoxy, 2-(trifluoromethyl)ethoxy, 1-(trifluoromethyl)ethoxy, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, 2-methyl-1-imidazolyl, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-yl amino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 1-(4-pyrimidinyl)ethyl, -(2-pyridyl)ethyl, -(4-pyrazinyl)ethyl, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 3-methylsulfonyl-1-azetidinyl, 2-methyl-2-imidazolyl, 1-azetidinyl, 2,2-dimethyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, or 2-amino-6-fluoro-5-pyridyl; $R^5$ is H, methyl, ethyl, 2-methylpropyl, hydroxyethyl, butynyl, or benzyl; $R^7$ is H, or methyl; and $R^a$ is amino, H, trifluoromethyl or methyl; and a pharmaceutically acceptable salt thereof; provided $R^5$ is H if $R^7$ is alkyl; further provided $R^7$ is H if $R^5$ is alkyl.

44. Compound of Embodiment 42 wherein R is

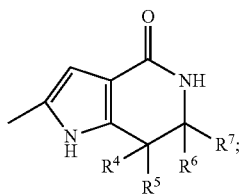

$R^4$ is H; $R^5$ is H; $R^6$ is H; and $R^7$ is H; and a pharmaceutically acceptable salt thereof 45. Compound of Embodiment 42 wherein $R^2$ is H; and a pharmaceutically acceptable salt thereof.

46. Compound of Embodiment 42 wherein $R^a$ is H, chloro, fluoro, bromo, amino, methylamino, hydroxymethyl, HO—N═CH—, methoxy, trifluoromethyl, 1-azetidinyl, 3-hydroxy-1-azetidinyl, 5-methyl-oxadiazol-2-yl, HC(═O)— or methyl; and a pharmaceutically acceptable salt thereof.

47. Compound of Embodiment 42 wherein $R^a$ is H or methyl; and a pharmaceutically acceptable salt thereof.

48. Compound of Embodiment 42 wherein $R^4$ is H; $R^5$ is H, $C_{1-2}$ alkyl, $C_{1-2}$ hydroxyalkyl, $C_{2-4}$ alkynyl, or benzyl; or wherein $R^4$ and $R^5$ together form $C_{3-4}$ cycloalkyl; $R^6$ is H; and $R^7$ is H, or $C_{1-2}$ alkyl; and a pharmaceutically acceptable salt thereof.

49. Compound of Embodiment 42 wherein $R^b$ is H, $C_{1-6}$ alkyl, $C_{1-2}$ haloalkyl, $C_{1-4}$ aminoalkyl, $C_{1-3}$ alkoxy-$C_{1-3}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl; and a pharmaceutically acceptable salt thereof.

50. Compound of Embodiment 42 wherein $R^b$ is an unsubstituted or substituted ring selected from cyclopropyl, cyclobutyl, cyclopentyl, phenyl, pyridyl, piperidinyl, morpholinyl, piperazinyl, pyrrolindinyl, and tetrahydropyranyl; and a pharmaceutically acceptable salt thereof.

51. Compound of Embodiment 42 wherein $R^1$ is an unsubstituted or substituted ring selected from phenyl, pyrrolidinyl, azetidinyl, morpholinyl, tetrahydrofuryl, piperidinyl, piperazinyl, pyrazolyl, and pyridyl; and a pharmaceutically acceptable salt thereof.

52. Compound of Embodiment 42 wherein R is

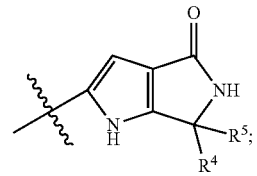

$R^4$ is H; $R^5$ is H, hydroxyethyl, hydroxymethyl or methyl; or wherein $R^4$ and $R^5$ together form cyclopropyl; and a pharmaceutically acceptable salt thereof.

53. A compound of Formula 11a and Formula 11b

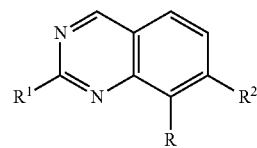

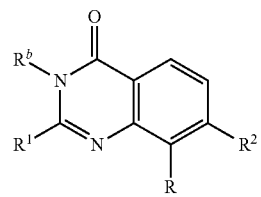

wherein R is

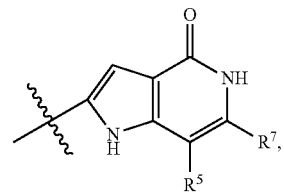

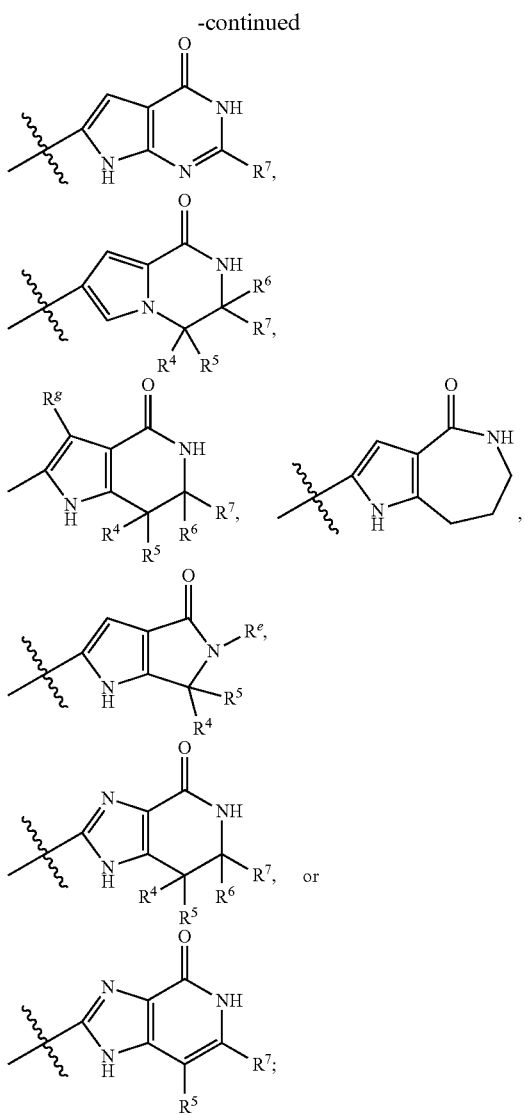

wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, Boc-amino-$C_{1-6}$ alkylamino, $C_{1-6}$ alkoxy-$C_{1-6}$ alkoxy-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, —CONH$R^b$, —NHC=O$R^b$, —O$R^b$, —S(=O)$_n R^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;
wherein n is 0, 1 or 2;
wherein $R^b$ is H, $C_{1-6}$ alkyl, $C_{1-6}$ haloalkyl, $C_{1-6}$ aminoalkyl, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;
wherein $R^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;
wherein $R^e$ is H or Boc;
wherein $R^g$ is H, fluoro or chloro;
wherein $R^2$ is H or halo;
wherein $R^4$ is H;
wherein $R^5$ is H, $C_{1-4}$ alkyl, $C_{1-4}$ hydroxyalkyl, $C_{2-4}$ alkynyl, or benzyl; or wherein $R^4$ and $R^5$ together form $C_{3-6}$ cycloalkyl or 4-6 membered saturated heterocyclyl;
wherein $R^6$ is H; and
wherein $R^7$ is H, or $C_{1-3}$ alkyl; and a pharmaceutically acceptable salt thereof.

54. Compound of Embodiment 53 wherein $R^1$ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, (2-amino-1,1-dimethylethyl)amino, (2-(tert-butoxycarbonylamino)-1,1-dimethylethyl)amino, 2,2,2-trifluoroethylamino, 2,2-difluoroethylamino, (1,1-dimethyl-3-(methylsulfonyl)-propyl)amino, (1,1-dimethyl-2-(methylsulfonyl)-ethyl)amino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-(trifluoromethyl)ethylamino, methylsulfonyl-(1,1-dimethylethyl)amino, methylsulfonylamino, 2-methyl-3-((1R)-1-(2-pyridinyl)ethyl)amino, 2-methyl-3-((1R)-1-(2-pyrazinyl)ethyl)amino, 2-methyl-3-((1R)-1-(4-pyrimidinyl)ethyl)amino, (1-methylcyclopropyl)methylamino, 2-methoxyethoxy-1,1-dimethylethylamino, ethoxy, isopropoxy, 3-amino-3-methylbutoxy, 2-(trifluoromethyl)ethoxy, 1-(trifluoromethyl)ethoxy, cyclopropylamino, I-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, 2-methyl-1-imidazolyl, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOCpiperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-yl amino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 1-(4-pyrimidinyl)ethyl, -(2-pyridyl)ethyl, -(4-pyrazinyl)ethyl, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 3-methylsulfonyl-1-azetidinyl, 2-methyl-2-imidazolyl, 1-azetidinyl, 2,2-dimethyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, or 2-amino-6-fluoro-5-pyridyl; and a pharmaceutically acceptable salt thereof.

55. Compound of Embodiment 53 wherein $R^5$ is H, methyl, ethyl, 2-methylpropyl, hydroxyethyl, butynyl, or benzyl; $R^7$ is H, or methyl; and $R^b$ is H, trifluoromethyl or methyl; and a pharmaceutically acceptable salt thereof; provided $R^5$ is H if $R^7$ is alkyl; further provided $R^7$ is H if $R^5$ is alkyl.

56. Compound of Embodiment 53 wherein R is

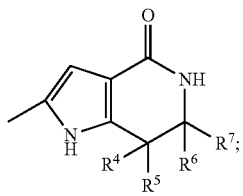

$R^4$ is H; $R^5$ is H; $R^6$ is H; and $R^7$ is H; and a pharmaceutically acceptable salt thereof.

57. Compound of Embodiment 53 wherein $R^2$ is H; and a pharmaceutically acceptable salt thereof.

58. Compound of Embodiment 53 wherein $R^a$ is H, amino, methoxy, trifluoromethyl, HC(=O)— or methyl; and a pharmaceutically acceptable salt thereof.

59. Compound of Embodiment 53 wherein $R^a$ is H or methyl; and a pharmaceutically acceptable salt thereof.

60. Compound of Embodiment 53 wherein $R^4$ is H; $R^5$ is H, $C_{1-2}$ alkyl, $C_{1-2}$ hydroxyalkyl, $C_{2-4}$ alkynyl, or benzyl; or wherein $R^4$ and $R^5$ together form $C_{3-4}$ cycloalkyl; $R^6$ is H; and $R^7$ is H, or $C_{1-2}$ alkyl; and a pharmaceutically acceptable salt thereof.

61. Compound of Embodiment 53 wherein $R^b$ is H, $C_{1-6}$ alkyl, $C_{1-2}$ haloalkyl, $C_{1-4}$ aminoalkyl, $C_{1-3}$ alkoxy-$C_{1-3}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl; and a pharmaceutically acceptable salt thereof.

62. Compound of Embodiment 53 wherein $R^b$ is an unsubstituted or substituted ring selected from cyclopropyl, cyclobutyl, cyclopentyl, phenyl, pyridyl, piperidinyl, morpholinyl, piperazinyl, pyrrolindinyl, and tetrahydropyranyl; and a pharmaceutically acceptable salt thereof.

63. Compound of Embodiment 53 wherein $R^1$ is an unsubstituted or substituted ring selected from phenyl, pyrrolidinyl, azetidinyl, morpholinyl, tetrahydrofuryl, piperidinyl, piperazinyl, pyrazolyl, and pyridyl; and a pharmaceutically acceptable salt thereof.

64. Compound of Embodiment 1 of formula 12

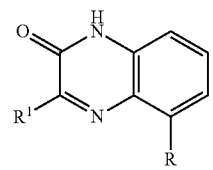

Wherein R is

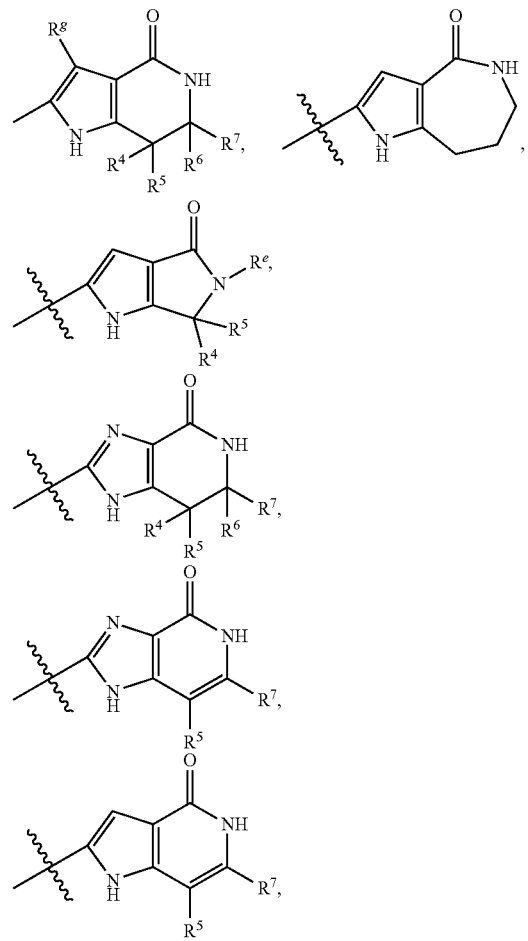

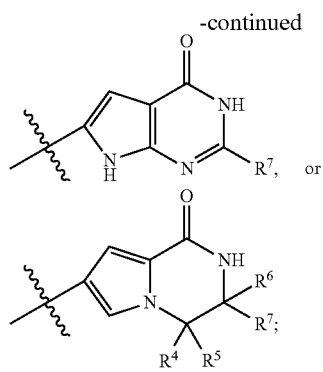

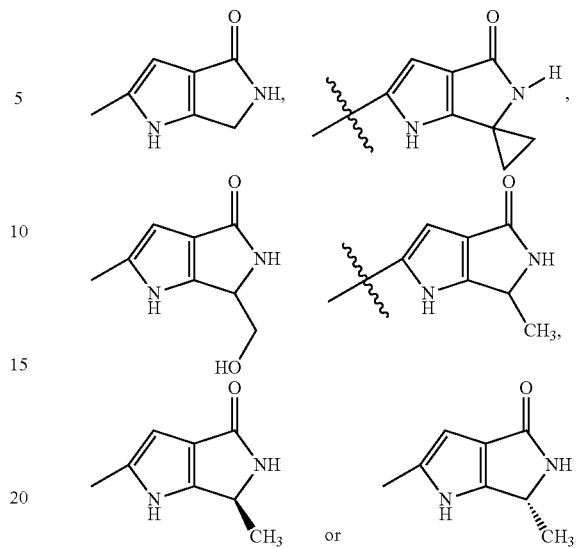

wherein R¹ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, Boc-amino-$C_{1-6}$ alkylamino, $C_{1-6}$ alkoxy-$C_{1-6}$ alkoxy-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein R$^b$ is H, $C_{1-6}$ alkyl, $C_{1-6}$ haloalkyl, $C_{1-6}$ aminoalkyl, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein R$^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein R$^e$ is H or Boc;

wherein R$^g$ is H, fluoro or chloro;

wherein R$^4$ is H;

wherein R$^5$ is H, $C_{1-4}$ alkyl, $C_{1-4}$ hydroxyalkyl, $C_{2-4}$ alkynyl, or benzyl; or wherein R$^4$ and R$^5$ together form $C_{3-6}$ cycloalkyl or 4-6 membered saturated heterocyclyl;

wherein R$^6$ is H; and wherein R$^7$ is H, or $C_{1-3}$ alkyl; and a pharmaceutically acceptable salt thereof.

65. Compound of Embodiment 1 wherein R is an unsubstituted or substituted 8 membered bicyclic amide; and a pharmaceutically acceptable salt thereof.

66. Compound of Embodiment 1 wherein R is an unsubstituted or substituted 9 membered bicyclic amide; and a pharmaceutically acceptable salt thereof.

67. Compound of Embodiment 1 wherein R is selected from and a pharmaceutically acceptable salt thereof.

Some additional embodiments of the invention are enumerated here:

1. A compound of Formula 7

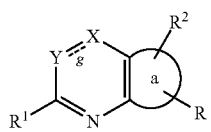

wherein bond g is a single bond or double bond; provided g is a single bond if Y is C=O or C(R$^a$)$_2$ or X is C=O or CH$_2$;

ring a is a ring that together with the 2 carbon atoms to which it attaches, forms a phenyl ring or a 5-6 membered heterocyclic ring;

X is N, NR$^b$, CR$^k$, C=O, or CH$_2$;

Y is N, NR$^b$, C=O, CR$^a$ or C(R$^a$)$_2$;

R is an optionally substituted bicyclic amide, optionally substituted bicyclic thioamide, optionally substituted bicyclic oxime,

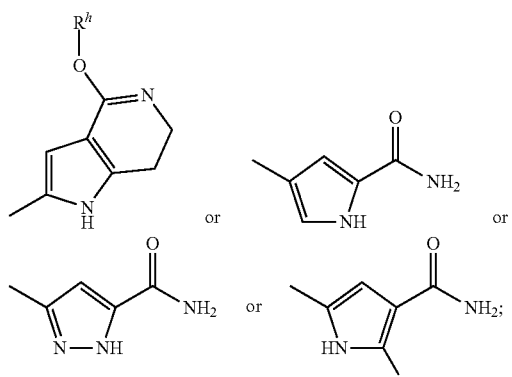

R¹ is H, halo, alkyl, amino, alkylamino, alkenylamino, haloalkylamino, alkylsulfonylalkylamino, aminocarbonylalkylamino, aminoalkylamino, hydroxyalkylamino, alkylsulfonylamino, carboxyalkylamino, alkoxycarbonylalkylamino, alkoxyalkylamino, alkoxycarbonylaminoalkylamino, alkoxyalkoxyalkylamino, alkoxyalkylaminoalkylamino, alkylsulfonylalkylaminoalkylamino, substituted or unsubstituted cycloalkylamino, substituted or unsubstituted cycloalkylalkylamino, substituted or unsubstituted arylamino, substituted or unsubstituted arylalkylamino, substituted or unsubstituted heterocyclylamino, substituted or unsubstituted heterocyclyl $C_{1-6}$ alkylamino, guanidinyl, —CONHR$^b$, —NHC=OR$^b$, —OR$^b$, —S(=O)$_n$R$^b$, —COR$^c$, unsubstituted or substituted aryl, unsubstituted or substituted arylalkyl, unsubstituted or substituted arylalkenyl, unsubstituted or substituted cycloalkyl, unsubstituted or substituted cycloalkylalkyl, unsubstituted or substituted heterocyclylalkyl or substituted or unsubstituted heterocyclyl;

$R^2$ is H, or halo;

$R^a$ is H, halo, haloalkyl, hydroxyalkyl, alkyl, alkynyl, alkoxy, amino, alkylamino, cyano, HC(=O)—, HC(=NOH)—, carboxy, alkoxycarbonyl, or substituted or unsubstituted heterocyclyl;

$R^b$ is H, alkyl, haloalkyl, aminoalkyl, alkoxyalkyl, hydroxyalkyl, unsubstituted or substituted cycloalkyl, unsubstituted or substituted aryl, unsubstituted or substituted arylalkyl or unsubstituted or substituted heterocyclyl;

$R^c$ is H, alkyl, alkoxy, alkoxyalkyl, unsubstituted or substituted cycloalkyl, unsubstituted or substituted aryl, unsubstituted or substituted arylalkyl or unsubstituted or substituted heterocyclyl;

$R^h$ is alkyl;

$R^k$ is H or amino; and $R^m$ is H, alkyl, cycloalkyl or aminoalkyl;

and a pharmaceutically acceptable salt thereof.

2. A compound of Embodiment 1 having Formula 7a, Formula 7b or Formula 7c

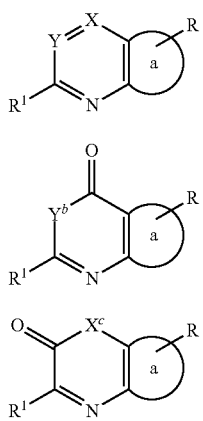

wherein

X is N or CH;

Y is N or CR$^a$;

Y$^b$ is NR$^b$;

X$^c$ is NH or CH$_2$;

ring a is

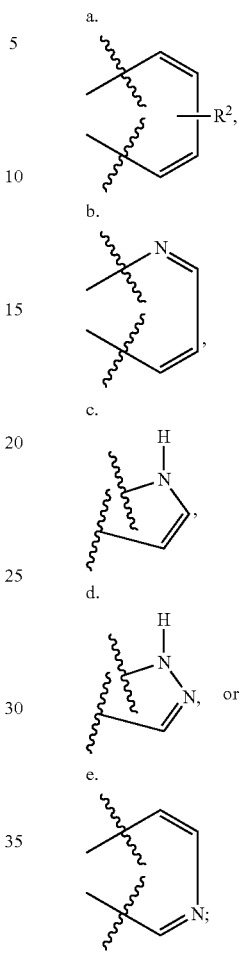

R is an optionally substituted bicyclic amide;

$R^1$ is H, halo, alkyl, amino, alkylamino, alkenylamino, haloalkylamino, alkylsulfonylalkylamino, aminocarbonylalkylamino, aminoalkylamino, hydroxyalkylamino, alkylsulfonylamino, carboxyalkylamino, alkoxycarbonylalkylamino, alkoxyalkylamino, alkoxycarbonylaminoalkylamino, alkoxyalkoxyalkylamino, alkoxyalkylaminoalkylamino, alkylsulfonylalkylaminoalkylamino, substituted or unsubstituted cycloalkylamino, substituted or unsubstituted cycloalkylalkylamino, substituted or unsubstituted arylamino, substituted or unsubstituted arylalkylamino, substituted or unsubstituted heterocyclylamino, substituted or unsubstituted heterocyclyl $C_{1-6}$ alkylamino, guanidinyl, —CONHR$^b$, —NHC=OR$^b$, —OR$^b$, —S(=O)$_n$R$^b$, —COR$^c$, unsubstituted or substituted aryl, unsubstituted or substituted arylalkyl, unsubstituted or substituted arylalkenyl, unsubstituted or substituted cycloalkyl, unsubstituted or substituted cycloalkylalkyl, unsubstituted or substituted heterocyclylalkyl or substituted or unsubstituted heterocyclyl;

$R^2$ is H, or halo;

$R^a$ is H, amino, alkylamino, haloalkyl, hydroxyalkyl, alkyl, alkoxy, halo, alkynyl, cyano, HC(=NOH)—, HC(=O)—, carboxy, alkoxycarbonyl, or substituted or unsubstituted heterocyclyl;

$R^b$ is H, alkyl, haloalkyl, aminoalkyl, alkoxyalkyl, hydroxyalkyl, unsubstituted or substituted cycloalkyl, unsubstituted or substituted aryl, unsubstituted or substituted aralkyl or unsubstituted or substituted heterocyclyl;

$R^c$ is H, alkyl, alkoxy, alkoxyalkyl, unsubstituted or substituted cycloalkyl, unsubstituted or substituted aryl, unsubstituted or substituted arylalkyl or unsubstituted or substituted heterocyclyl; and $R^d$ is alkyl;

and a pharmaceutically acceptable salt thereof.

3. A compound of Formula 8'

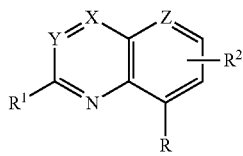

wherein R is

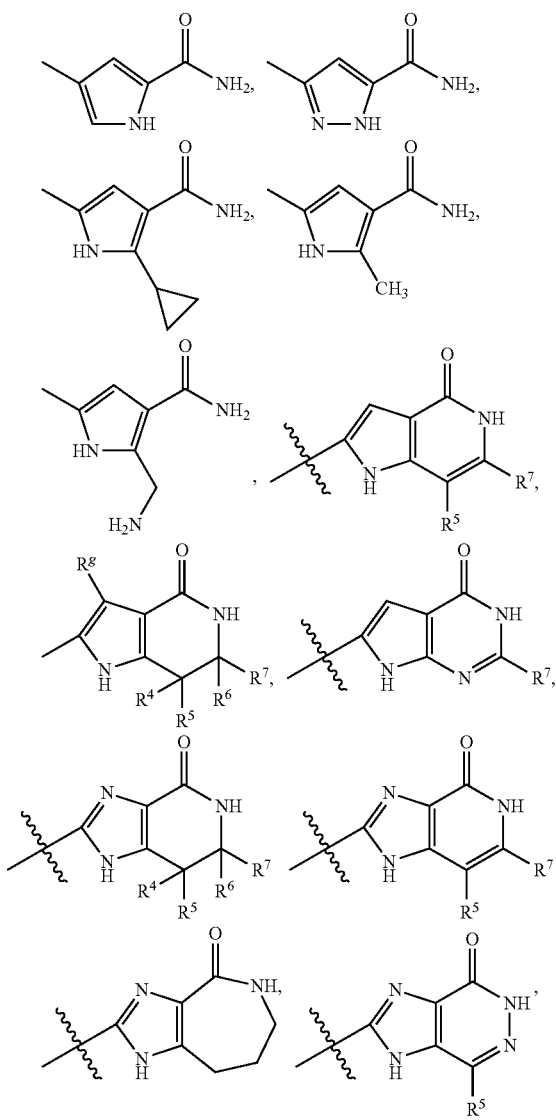

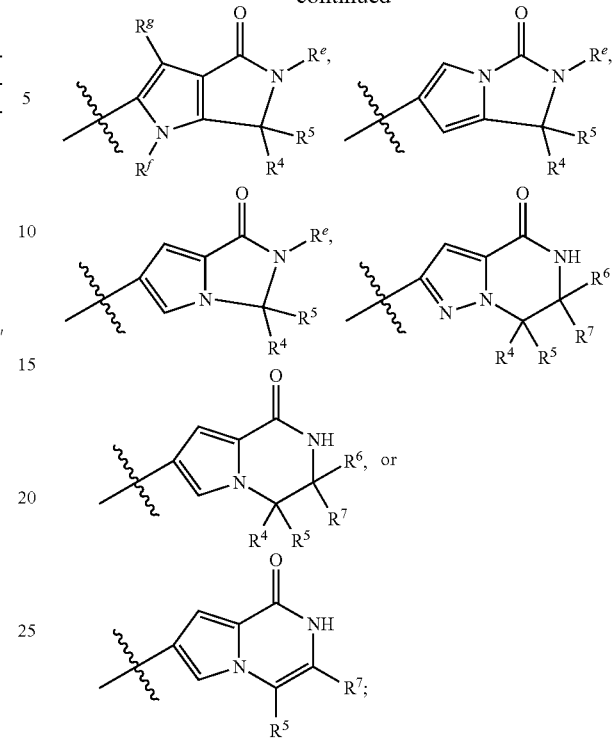

wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, $C_{1-6}$ alkoxycarbonylamino-$C_{1-6}$ alkylamino, $C_{1-6}$ alkoxy-$C_{1-6}$ alkoxy-$C_{1-6}$ alkylamino, $C_{1-6}$ alkoxy-$C_{1-6}$ alkylamino-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, guanidinyl, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein X is N, NH, CH, C=O or CH$_2$;

wherein Y is N, C=O, CR$^a$, CHR$^a$ or NR$^b$; provided X is not N or NH when Y is N or N$^b$;

wherein Z is CH or N;

wherein $R^2$ is H or fluoro;

wherein $R^4$ is H or $C_{1-4}$ alkyl;

wherein $R^5$ is H, $C_{1-4}$ alkyl, $C_{1-4}$ hydroxyalkyl, $C_{1-4}$ aminoalkyl, $C_{2-4}$ alkynyl, $C_{3-6}$ cycloalkyl, $C_{1-4}$ alkoxy-$C_{1-4}$ alkyl, benzyloxy-$C_{1-4}$ alkyl or benzyl; or wherein $R^4$ and $R^5$ together form $C_{3-6}$ cycloalkyl or 4-6 membered saturated heterocyclyl;

wherein R⁶ is H;

wherein R⁷ is H, or $C_{1-3}$ alkyl;

wherein $R^a$ is H, amino, cyano, halo, $C_{1-2}$ alkoxy, $C_{1-2}$ alkylamino, $C_{2-3}$ alkynyl, $C_{1-2}$ haloalkyl, $C_{1-2}$ hydoxyalkyl, $C_{1-2}$ alkyl, HO—N=CH—, HC(=O)—, $C_{1-6}$ alkoxy-$C_{1-6}$ alkyl, $C_{3-6}$ cycloalkyl, aryl, or optionally substituted 3-7-membered heterocyclyl;

wherein $R^b$ is H, $C_{1-6}$ alkyl, $C_{1-6}$ haloalkyl, $C_{1-6}$ aminoalkyl, $C_{1-6}$ alkoxy-$C_{1-6}$ alkyl, $C_{1-6}$ hydroxyalkyl, $C_{1-6}$ alkylsulfonyl-$C_{1-6}$ alkyl, $C_{2-6}$ alkenyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^e$ is H or Boc;

wherein $R^f$ is H or methyl;

wherein $R^g$ is H, or halo;

and a pharmaceutically acceptable salt thereof.

4. A compound of Formula 9'

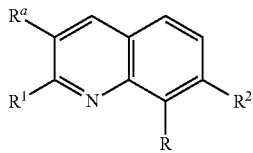

9' wherein R is

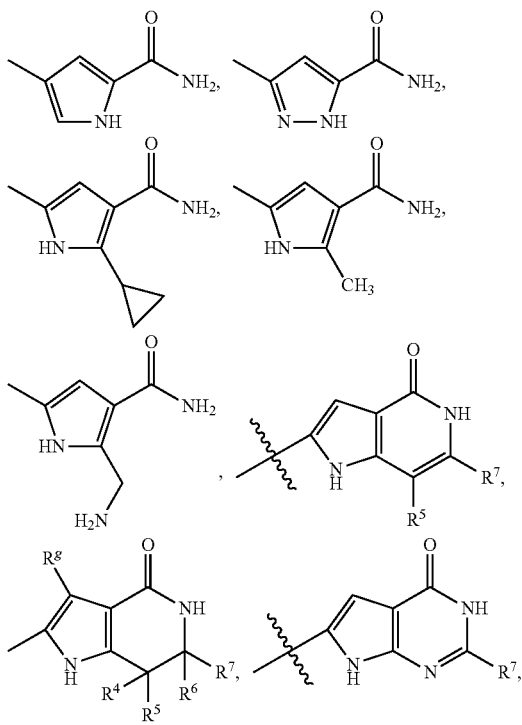

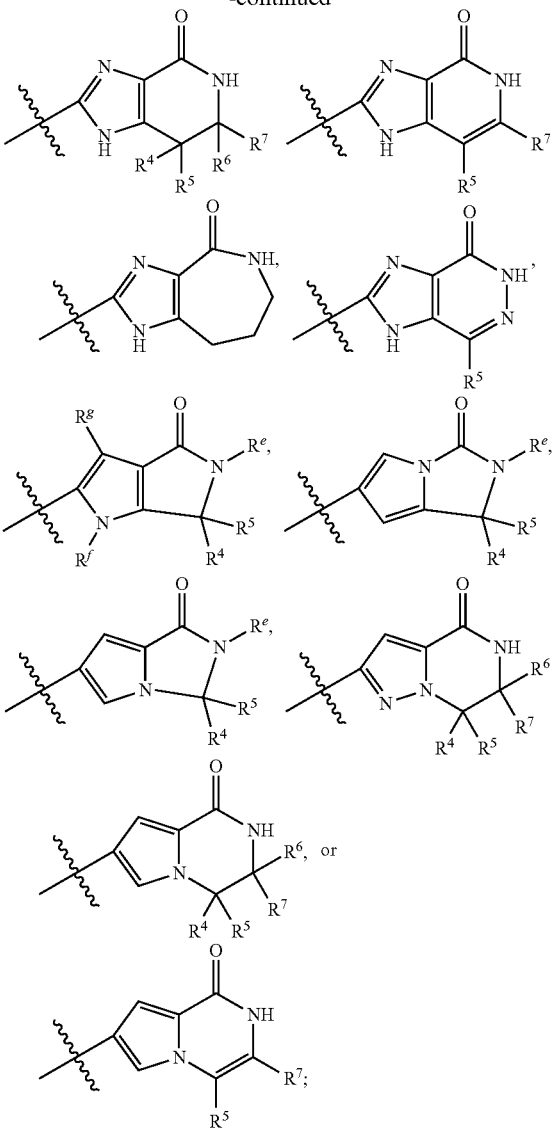

wherein R¹ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, $C_{1-6}$ alkoxycarbonylamino-$C_{1-6}$ alkylamino, $C_{1-6}$ alkoxy-$C_{1-6}$ alkoxy-$C_{1-6}$ alkylamino, $C_{1-6}$ alkoxy-$C_{1-6}$ alkylamino-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, guanidinyl, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein $R^a$ is H, amino, cyano, halo, $C_{1-2}$ alkoxy, $C_{1-2}$ alkylamino, $C_{2-3}$ alkynyl, $C_{1-2}$ haloalkyl, $C_{1-2}$ hydoxyalkyl, $C_{1-2}$ alkyl, HO—N═CH—, HC(═O)—, $C_{1-6}$ alkoxy-$C_{1-6}$ alkoxy-$C_{1-6}$ alkyl, $C_{3-6}$ cycloalkyl, aryl, or optionally substituted 3-7-membered heterocyclyl;

wherein $R^b$ is H, $C_{1-6}$ alkyl, $C_{1-6}$ haloalkyl, $C_{1-6}$ aminoalkyl, $C_{1-6}$ alkoxy-$C_{1-6}$ alkyl, $C_{1-6}$ hydroxyalkyl, $C_{1-6}$ alkylsulfonyl-$C_{1-6}$ alkyl, $C_{2-6}$ alkenyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^e$ is H or Boc;

wherein $R^f$ is H or methyl;

wherein $R^g$ is H, fluoro or chloro;

wherein $R^2$ is H or fluoro;

wherein $R^4$ is H or methyl;

wherein $R^5$ is H, $C_{1-4}$ alkyl, $C_{1-4}$ hydroxyalkyl, $C_{1-4}$ aminoalkyl, $C_{2-4}$ alkynyl, $C_{3-6}$ cycloalkyl, benzyloxy-$C_{1-4}$ alkyl or benzyl; or wherein $R^4$ and $R^5$ together form $C_{3-6}$ cycloalkyl or 4-6 membered saturated heterocyclyl;

wherein $R^6$ is H; and wherein $R^7$ is H, or $C_{1-3}$ alkyl; and a pharmaceutically acceptable salt thereof.

5. A compound of Formula 10'

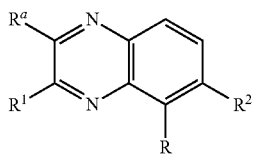

wherein R is

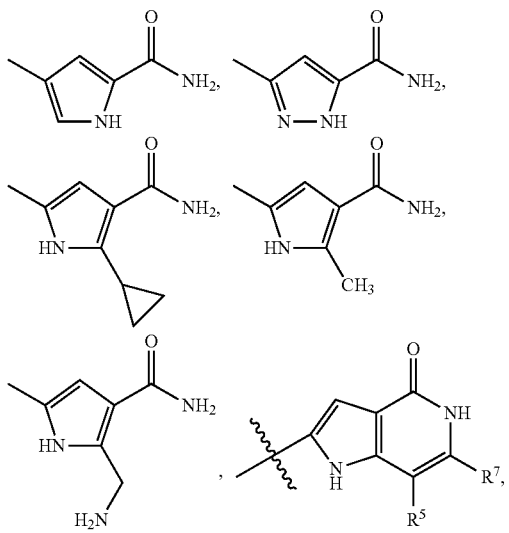

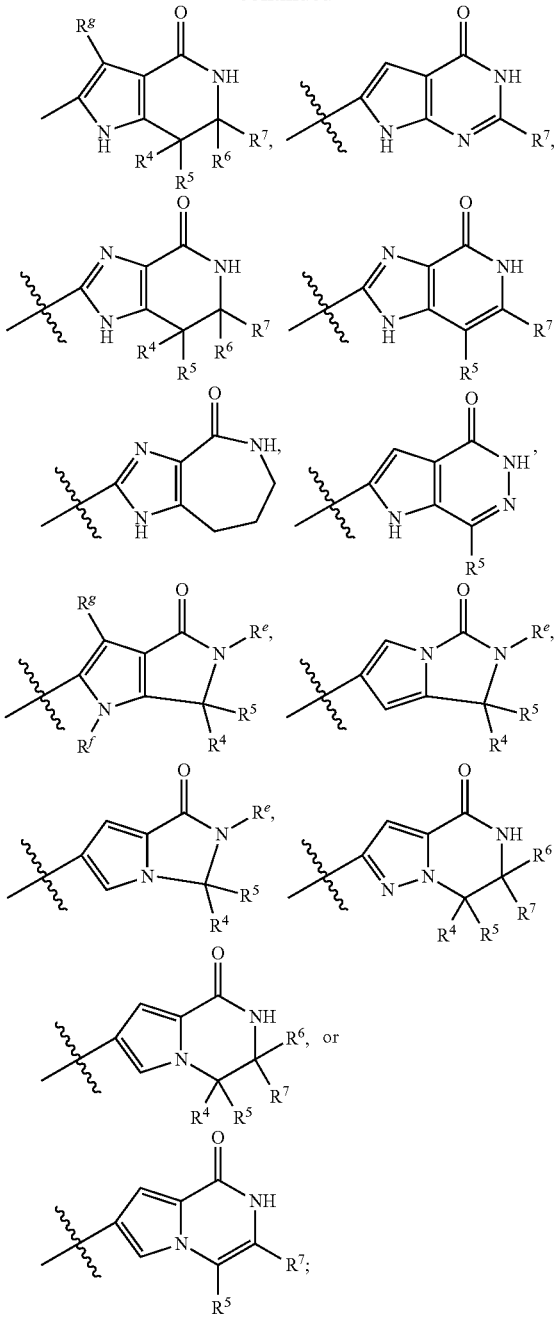

wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, $C_{1-6}$ alkoxycarbonylamino-$C_{1-6}$ alkylamino, $C_{1-6}$ alkoxy-$C_{1-6}$ alkoxy-$C_{1-6}$ alkylamino, $C_{1-6}$ alkoxy-$C_{1-6}$ alkylamino-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, guanidinyl, —CONH$R^b$, —NHC=O$R^b$, —O$R^b$, —S(=O)$_n R^b$, —CO$R^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein $R^a$ is H, amino, cyano, halo, $C_{1-2}$ alkoxy, $C_{1-2}$ alkylamino, $C_{2-3}$ alkynyl, $C_{1-2}$ haloalkyl, $C_{1-2}$ hydoxyalkyl, $C_{1-2}$ alkyl, HO—N=CH—, HC(=O)—, $C_{1-6}$ alkoxy-$C_{1-6}$ alkoxy-$C_{1-6}$ alkyl, $C_{3-6}$ cycloalkyl, aryl, or optionally substituted 3-7-membered heterocyclyl;

wherein $R^b$ is H, $C_{1-6}$ alkyl, $C_{1-6}$ haloalkyl, $C_{1-6}$ aminoalkyl, $C_{1-6}$ alkoxy-$C_{1-6}$ alkyl, $C_{1-6}$ hydroxyalkyl, $C_{1-6}$ alkylsulfonyl-$C_{1-6}$ alkyl, $C_{2-6}$ alkenyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^e$ is H or Boc;

wherein $R^f$ is H or methyl;

wherein $R^g$ is H, fluoro or chloro;

wherein $R^2$ is H or fluoro;

wherein $R^4$ is H or methyl;

wherein $R^5$ is H, $C_{1-4}$ alkyl, $C_{1-4}$ hydroxyalkyl, $C_{1-4}$ aminoalkyl, $C_{2-4}$ alkynyl, $C_{3-6}$ cycloalkyl, benzyloxy-$C_{1-4}$ alkyl or benzyl; or wherein $R^4$ and $R^5$ together form $C_{3-6}$ cycloalkyl or 4-6 membered saturated heterocyclyl;

wherein $R^6$ is H; and wherein $R^7$ is H, or $C_{1-3}$ alkyl; and a pharmaceutically acceptable salt thereof.

6. A compound of Formula 11c and Formula 11d

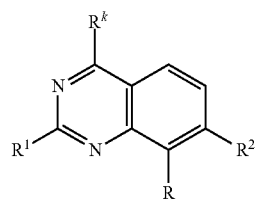

11c

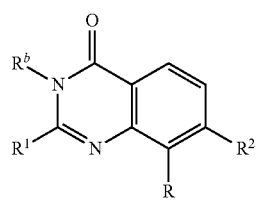

11d wherein R is

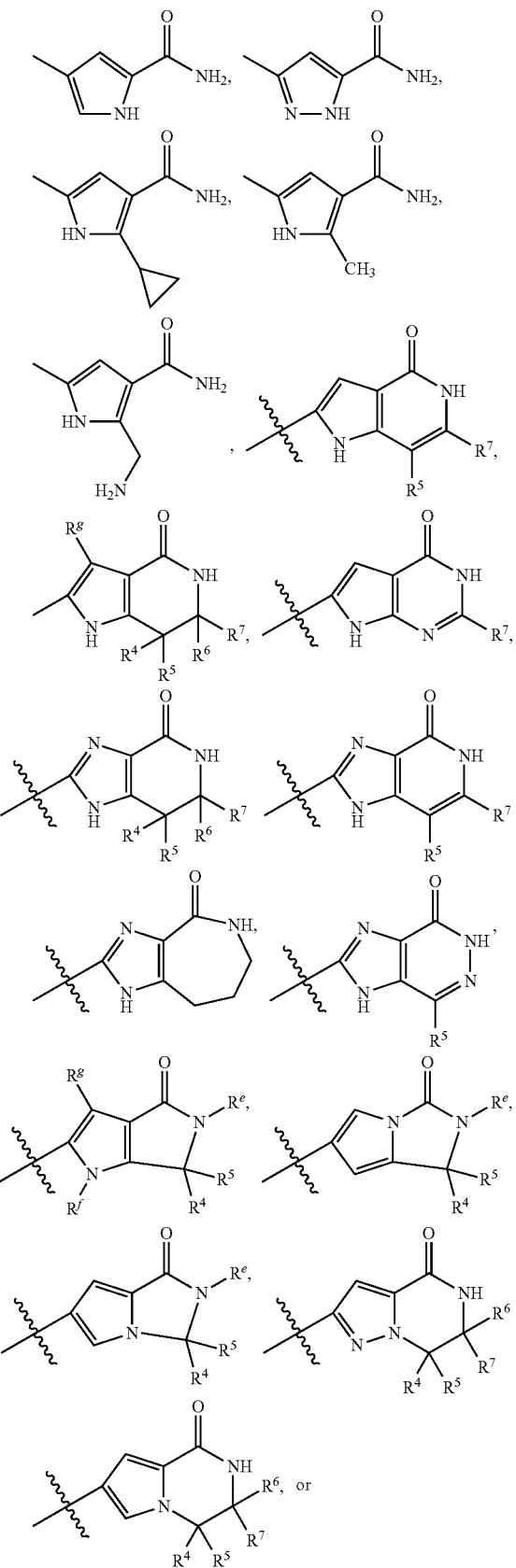

-continued

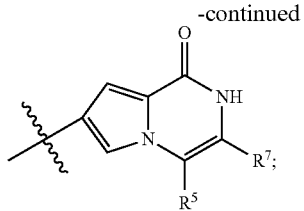

wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, $C_{1-6}$ alkoxycarbonylamino-$C_{1-6}$ alkylamino, $C_{1-6}$ alkoxy-$C_{1-6}$ alkoxy-$C_{1-6}$ alkylamino, $C_{1-6}$ alkoxy-$C_{1-6}$ alkylamino-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, guanidinyl, —CONH$R^b$, —NHC=O$R^b$, —O$R^b$, —S(=O)$_n R^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein $R^b$ is H, $C_{1-6}$ alkyl, $C_{1-6}$ haloalkyl, $C_{1-6}$ aminoalkyl, $C_{1-6}$ alkoxy-$C_{1-6}$ alkyl, $C_{1-6}$ hydroxyalkyl, $C_{1-6}$ alksulfonyl-$C_{1-6}$ alkyl, $C_{2-6}$ alkenyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^e$ is H or Boc;

wherein $R^f$ is H or methyl;

wherein $R^g$ is H, fluoro or chloro;

wherein $R^k$ is H or amino;

wherein $R^2$ is H or fluoro;

wherein $R^4$ is H or methyl;

wherein $R^5$ is H, $C_{1-4}$ alkyl, $C_{3-6}$ cycloalkyl, $C_{1-4}$ aminoalkyl, $C_{1-4}$ hydroxyalkyl, $C_{1-4}$ alkoxy-$C_{1-4}$ alkyl, benzyloxy-$C_{1-4}$ alkyl, $C_{2-4}$ alkynyl, $C_{3-6}$ cycloalkyl or benzyl; or wherein $R^4$ and $R^5$ together form $C_{3-6}$ cycloalkyl or 4-6 membered saturated heterocyclyl;

wherein $R^6$ is H; and wherein $R^7$ is H, or $C_{1-3}$ alkyl; and a pharmaceutically acceptable salt thereof.

7. Compound of Embodiment 1 of formula 12'

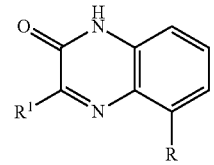

wherein R is

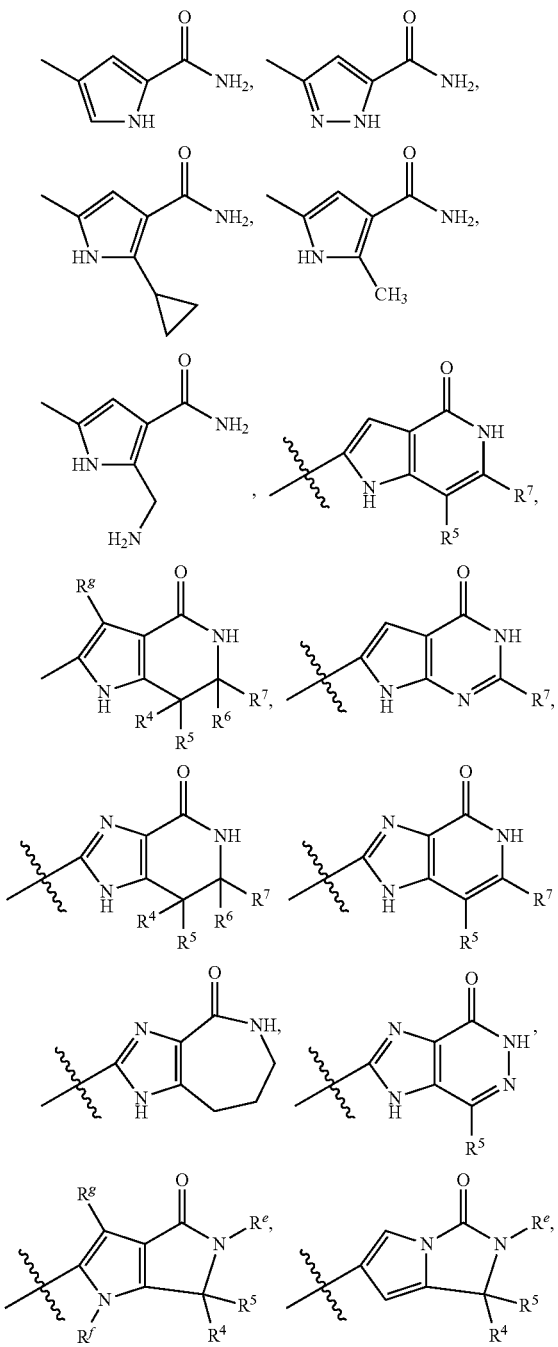

-continued

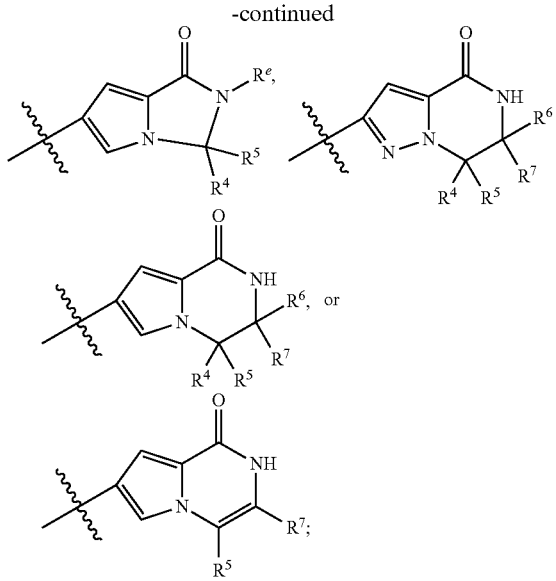

wherein R¹ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, $C_{1-6}$ alkoxycarbonylamino-$C_{1-6}$ alkylamino, $C_{1-6}$ alkoxy-$C_{1-6}$ alkoxy-$C_{1-6}$ alkylamino, $C_{1-6}$ alkoxy-$C_{1-6}$ alkylamino-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, guanidinyl, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein R$^b$ is H, $C_{1-6}$ alkyl, $C_{1-6}$ haloalkyl, $C_{1-6}$ aminoalkyl, $C_{1-6}$ alkoxy-$C_{1-6}$ alkyl, $C_{1-6}$ hydroxyalkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein R$^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein R$^e$ is H or Boc;

wherein R$^f$ is H or methyl;

wherein R$^g$ is H, fluoro or chloro;

wherein R$^4$ is H or methyl;

wherein R$^5$ is H, $C_{1-4}$ alkyl, $C_{1-4}$ hydroxyalkyl, $C_{1-4}$ aminoalkyl, $C_{2-4}$ alkynyl, $C_{3-6}$ cycloalkyl, benzyloxy-$C_{1-4}$ alkyl or benzyl; or wherein R$^4$ and R$^5$ together form $C_{3-6}$ cycloalkyl or 4-6 membered saturated heterocyclyl;

wherein R$^6$ is H; and wherein R$^7$ is H, or $C_{1-3}$ alkyl; and a pharmaceutically acceptable salt thereof.

8. Compound of any one of Embodiments 1-7 wherein R is

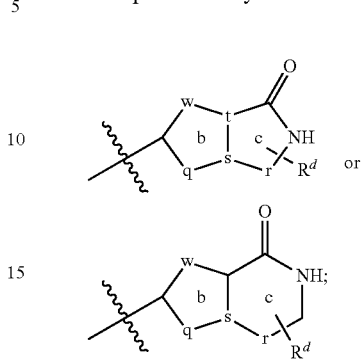

wherein q is NH or CH;

wherein r is CH$_2$ or N;

wherein s is N or C;

wherein w is CR$^g$ or N;

wherein R$^d$ is one or more substituents selected from H, $C_{1-4}$ alkyl, $C_{1-4}$ hydroxyalkyl, $C_{2-4}$ alkynyl or benzyl; or wherein R$^d$ forms a carbocyclic or heterocyclic ring spiro to ring c;

wherein R$^g$ is H, fluoro or chloro;

wherein ring b is unsaturated, or partially saturated; and wherein ring c is saturated, or partially saturated;

and a pharmaceutically acceptable salt thereof.

9. Compound of any one of Embodiments 1-7 wherein R is wherein R is

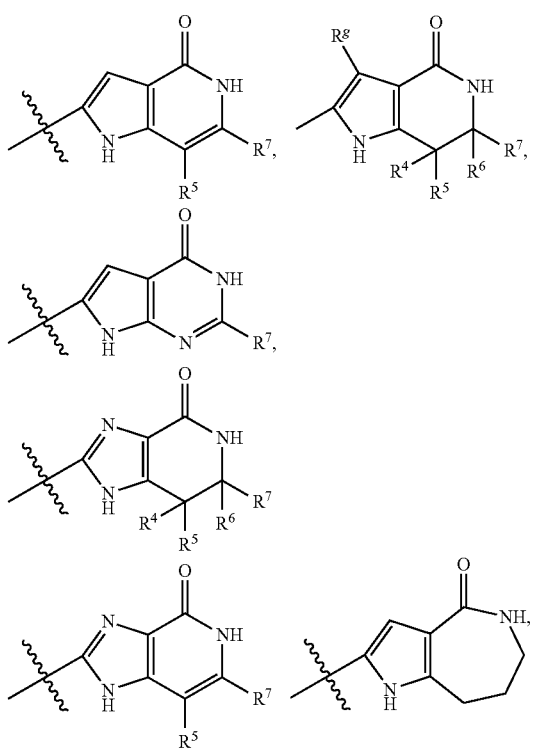

-continued

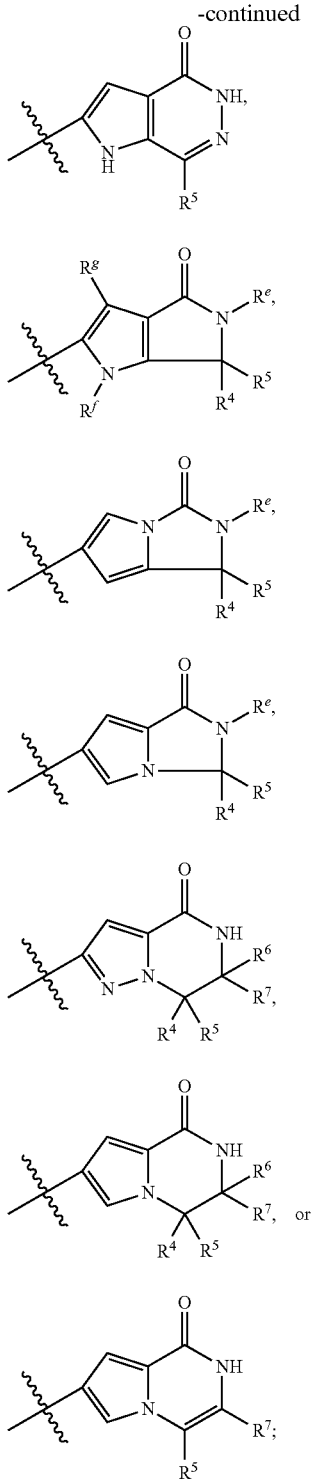

wherein $R^e$ is H or Boc;
wherein $R^f$ is H or methyl;
wherein $R^g$ is H, fluoro or chloro;
wherein $R^4$ is H or $C_{1-4}$ alkyl;
wherein $R^5$ is H, $C_{1-4}$ alkyl, $C_{1-4}$ hydroxyalkyl, benzyloxy-$C_{1-4}$ alkyl, $C_{2-4}$ alkynyl, benzyloxy or benzyl; or wherein $R^4$ and $R^5$ together form $C_{3-6}$ cycloalkyl or 4-6 membered heterocyclyl;
wherein $R^6$ is H; and wherein $R^7$ is H or $C_{1-3}$ alkyl; and a pharmaceutically acceptable salt thereof.

10. Compound of any one of Embodiments 1-7, and a pharmaceutically acceptable salt thereof, wherein R is

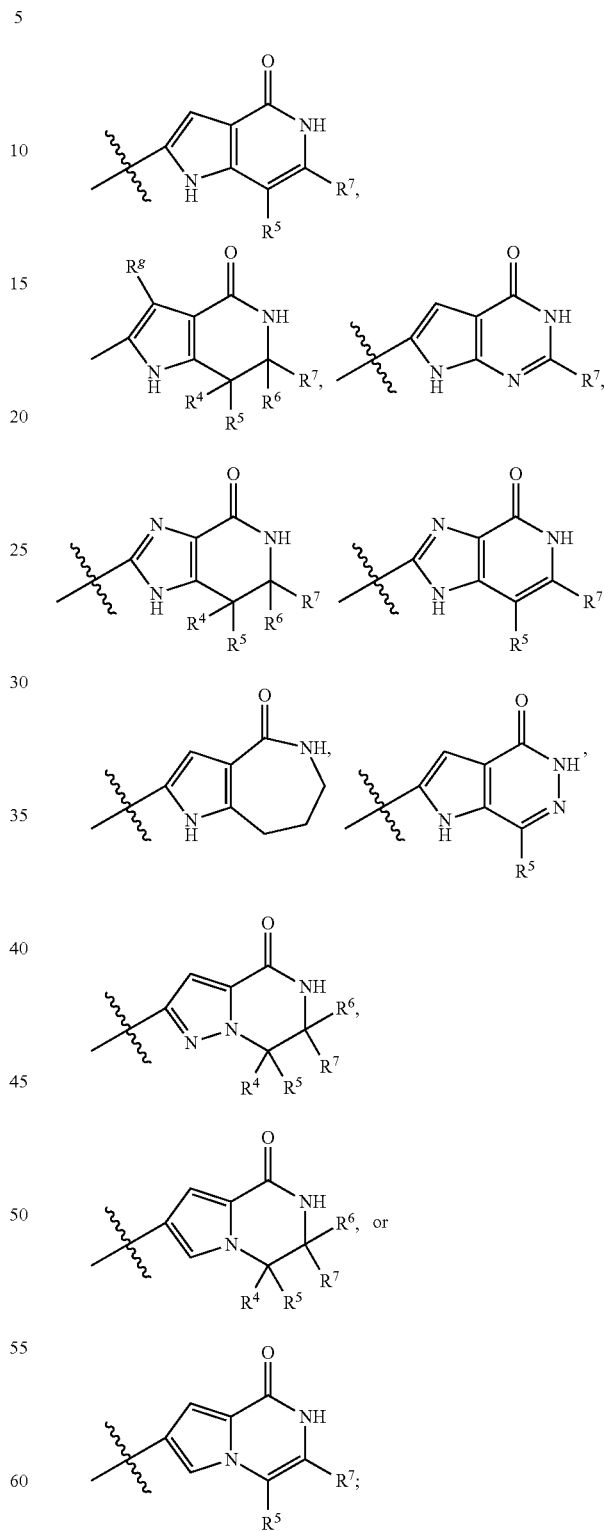

$R^5$ is H, methyl, ethyl, 2-methylpropyl, hydroxyethyl, aminoethyl, cyclopropyl, butynyl, benzyloxymethyl, or benzyl; $R^7$ is H, or methyl; and wherein $R^g$ is H, or chloro; provided $R^5$ is H if $R^7$ is alkyl; further provided $R^7$ is H if $R^5$ is alkyl.

11. Compound of any one of Embodiments 1-7 wherein R is

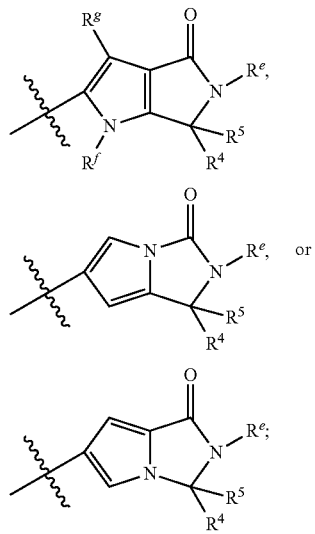

wherein $R^e$ is H or Boc; wherein $R^f$ is H or methyl; wherein $R^g$ is H, or chloro; $R^5$ is H, ethyl, 2-methylpropyl, hydroxyethyl, butynyl, benzyl, aminoethyl, benzyloxymethyl, hydroxymethyl, cyclopropyl or methyl; and $R^4$ is H, or methyl; and a pharmaceutically acceptable salt thereof.

12. Compound of any one of Embodiments 1-7 wherein R is

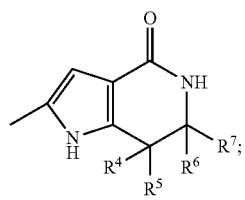

$R^4$ is H; $R^5$ is H; $R^6$ is H; and $R^7$ is H; and a pharmaceutically acceptable salt thereof.

13. Compound of any one of Embodiments 1-7 wherein R is

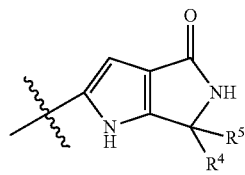

$R^4$ is H; $R^5$ is H, aminoethyl, hydroxyethyl, benzyloxymethyl, hydroxymethyl, cyclopropyl or methyl; or wherein $R^4$ and $R^5$ together form cyclopropyl; and a pharmaceutically acceptable salt thereof.

14. Compound of any one of Embodiments 1-7 wherein R is

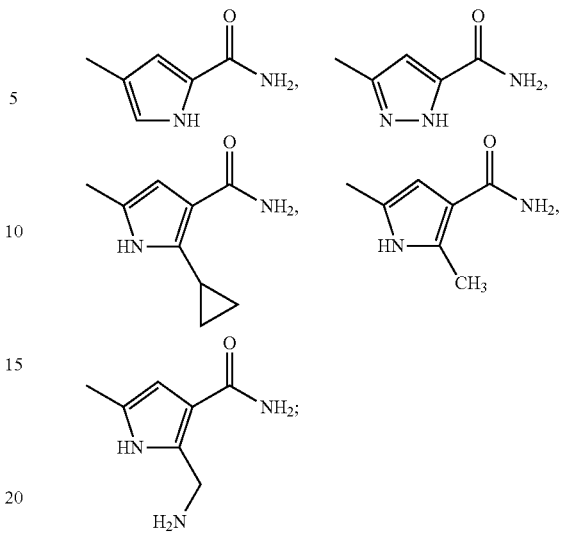

and a pharmaceutically acceptable salt thereof.

15. Compound of any one of Embodiments 1-7 wherein R is selected from

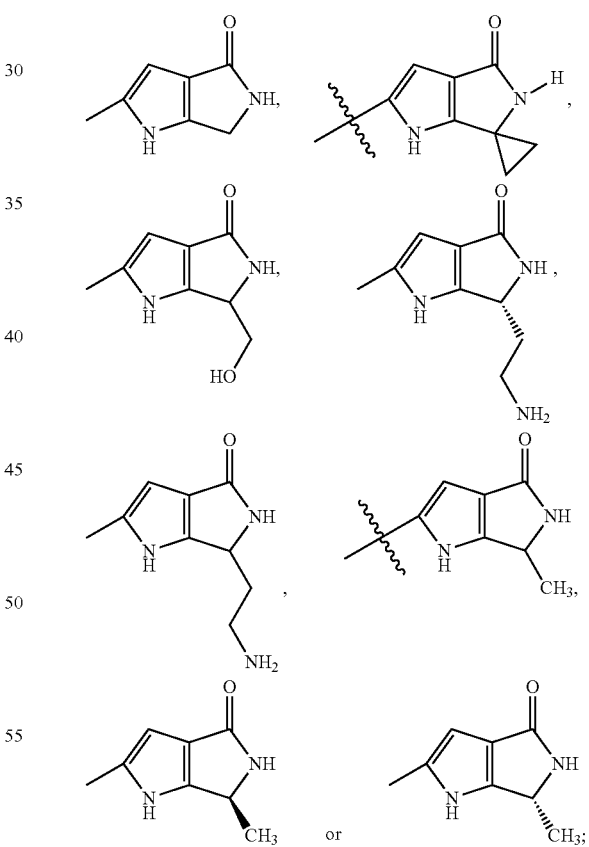

and a pharmaceutically acceptable salt thereof.

16. Compound of any one of Embodiments 1-7 wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, C$_{1-6}$ alkoxy-C$_{1-6}$ alkylamino, C$_{1-6}$ alkoxycarbonylamino-C$_{1-6}$ alkylamino, C$_{1-6}$ alkoxy-C$_{1-6}$ alkoxy-C$_{1-6}$ alkylamino, C$_{1-6}$ alkoxy-C$_{1-6}$ alkylamino-C$_{1-6}$ alkylamino, C$_{1-6}$ alkylsulfonyl-C$_{1-6}$ alkylamino-C$_{1-6}$ alkylamino, substituted or unsubstituted C$_{3-6}$ cycloalkylamino, substituted or unsubstituted C$_{3-6}$ cycloalkyl-C$_{1-6}$ alkylamino, substituted or unsubstituted phenylamino, substituted or unsubstituted phenyl-C$_{1-3}$ alkylamino, substituted or unsubstituted 3-7-membered heterocyclylamino, substituted or unsubstituted 3-7-membered heterocyclyl-C$_{1-6}$ alkylamino, guanidinyl, —CONHR$^b$, —NHC=OR$^b$, —OR$^b$, —S(=O)$_n$R$^b$, —COR$^c$, unsubstituted or substituted aryl, unsubstituted or substituted aryl-C$_{1-6}$ alkyl, unsubstituted or substituted aryl-C$_{2-4}$ alkenyl, unsubstituted or substituted C$_{3-6}$ cycloalkyl, unsubstituted or substituted C$_{3-6}$ cycloalkyl-C$_{1-6}$ alkyl, unsubstituted or substituted 3-7-membered heterocyclyl-C$_{1-6}$ alkyl or substituted or unsubstituted 3-7-membered heterocyclyl; and a pharmaceutically acceptable salt thereof.

17. Compound of any one of Embodiments 1-7 wherein R$^1$ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-ethyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, (2-amino-1,1-dimethylethyl)amino, 3-(bis(2-methoxyethyl)amino)-1,1-dimethylpropyl)amino, (2-(tert-butoxycarbonylamino)-1,1-dimethylethyl)amino, 2,2,2-trifluoroethylamino, 2,2-difluoroethylamino, (1,1-dimethyl-3-(methylsulfonyl)-propyl)amino, (1,1-dimethyl-2-(methylsulfonyl)-ethyl)amino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-(trifluoromethyl)ethylamino, methylsulfonyl-(1,1-dimethylethyl)amino, methylsulfonylamino, 2-methyl-3-((1R)-1-(2-pyridinyl)ethyl)amino, 2-methyl-3-((1R)-1-(2-pyrazinyl)ethyl)amino, 2-methyl-3-((1R)-1-(4-pyrimidinyl)ethyl)amino, (1-methylcyclopropyl)methylamino, 2-methoxyethoxy-1,1-dimethylethylamino, guanidinyl, ethoxy, isopropoxy, 3-amino-3-methylbutoxy, 2-(trifluoromethyl)ethoxy, 1-(trifluoromethyl)ethoxy, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 3-methylcarbonylaminocyclohexylamino, 3-(2,2,2-trifluoroethylamino)cyclohexylamino, 3-methylsulfonylaminocyclohexylamino, 3-(tert-butyl carboxyamino-1-(hydroxyethyl)-carbonylamino)cyclohexylamino, 3-(amino-1-(hydroxyethyl)-carbonylamino)cyclohexylamino, 3-(tert-butylcarboxyamino)-cyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, 2-methyl-1-imidazolyl, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-yl amino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 1-(4-pyrimidinyl)ethyl, 1-(2-pyridyl)ethyl, 1-(2-pyrazinyl)ethyl, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 3-methylsulfonyl-1-azetidinyl, 2-methyl-2-imidazolyl, 1-azetidinyl, 2,2-dimethyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, or 2-amino-6-fluoro-5-pyridyl; and a pharmaceutically acceptable salt thereof.

18. Compound of any one of Embodiments 1-7 wherein R$^1$ is methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, (2-amino-1,1-dimethylethyl)amino, 3-(bis(2-methoxyethyl)amino)-1,1-dimethylpropyl)amino, (2-(tert-butoxycarbonylamino)-1,1-dimethylethyl)amino, 2,2,2-trifluoroethylamino, 2,2-difluoroethylamino, (1,1-dimethyl-3-(methylsulfonyl)-propyl)amino, (1,1-dimethyl-2-(methylsulfonyl)-ethyl)amino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-(trifluoromethyl)ethylamino, methylsulfonyl-(1,1-dimethylethyl)amino, methylsulfonylamino, 2-methyl-3-((1R)-1-(2-pyridinyl)ethyl)amino, 2-methyl-3-((1R)-1-(2-pyrazinyl)ethyl)amino, 2-methyl-3-((1R)-1-(4-pyrimidinyl)ethyl)amino, (1-methylcyclopropyl)methylamino, 2-methoxyethoxy-1,1-dimethylethylamino, guanidinyl, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, 2-methyl-1-imidazolyl, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-yl amino, 2-pyridylamino, 3-pyridylamino, 4-pyridylamino, 5-pyrimidinylamino, benzylamino, 1-phenylethylamino, cyclopropylethylamino, 3-oxetanylmethylamino, or 3-methyl-3-oxetanylmethylamino; and a pharmaceutically acceptable salt thereof.

19. Compound of any one of Embodiments 1-7 wherein $R^1$ is H, chloro, fluoro, 2,2-dimethylpropyl, amino, ethoxy, isopropoxy, 3-amino-3-methylbutoxy, 2-(trifluoromethyl)ethoxy, 1-(trifluoromethyl)ethoxy, 1-(4-pyrimidinyl)ethyl, 1-(2-pyridyl)ethyl, 1-(2-pyrazinyl)ethyl, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, or methoxyethylaminocarbonyl; and a pharmaceutically acceptable salt thereof.

20. Compound of any one of Embodiments 1-7 wherein $R^1$ is an unsubstituted or substituted ring selected from phenyl, pyrrolidinyl, azetidinyl, morpholinyl, tetrahydrofuryl, piperidinyl, piperazinyl, pyrazolyl, and pyridyl; and a pharmaceutically acceptable salt thereof.

21. Compound of Embodiment 1 wherein ring a is

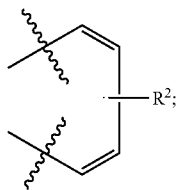

22. Compound of Embodiment 1 wherein ring a is

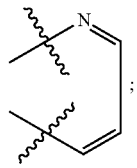

and a pharmaceutically acceptable salt thereof.

23. Compound of Embodiment 1 wherein X is CH; Y is $CR^a$ or N; and Z is CH; and a pharmaceutically acceptable salt thereof.

24. Compound of Embodiment 1 wherein X is N; Y is $CR^a$; and Z is CH; and a pharmaceutically acceptable salt thereof.

25. Compound of Embodiment 1 wherein X is CH; Y is N; and Z is CH; and a pharmaceutically acceptable salt thereof.

26. Compound of Embodiment 1 wherein $R^2$ is H or fluoro; and a pharmaceutically acceptable salt thereof.

27. Compound of any one of Embodiments 1-7 wherein $R^2$ is H; and a pharmaceutically acceptable salt thereof.

28. Compound of any one of Embodiments 1-7 wherein $R^4$ is H; and $R^5$ is H; and a pharmaceutically acceptable salt thereof.

29. Compound of any one of Embodiments 1-7 wherein $R^6$ is H; and $R^7$ is H; and a pharmaceutically acceptable salt thereof.

30. Compound of any one of Embodiments 1-7 wherein $R^4$ is H; and $R^5$ is H, methyl, benzyloxymethyl, hydroxymethyl or hydroxyethyl; and a pharmaceutically acceptable salt thereof.

31. Compound of any one of Embodiments 1-7 wherein together $R^4$ and $R^5$ together form cyclopropyl; and a pharmaceutically acceptable salt thereof.

32. Compound of any one of Embodiments 1-7 wherein $R^5$ is H, $C_{1-2}$ alkyl, $C_{3-4}$ cycloalkyl $C_{1-2}$ aminoalkyl, $C_{1-2}$ hydroxyalkyl, benzyloxy-$C_{1-2}$ alkyl, $C_{2-4}$ alkynyl, or benzyl; or wherein $R^4$ and $R^5$ together form $C_{3-4}$ cycloalkyl; $R^6$ is H; and $R^7$ is H, or $C_{1-2}$ alkyl; and a pharmaceutically acceptable salt thereof.

33. Compound of any one of Embodiments 1-7 wherein $R^5$ is H, methyl, ethyl, 2-methylpropyl, hydroxyethyl, butynyl, or benzyl; $R^7$ is H, or methyl; and $R^a$ is amino, H, trifluoromethyl or methyl; provided $R^5$ is H if $R^7$ is alkyl; further provided $R^7$ is H if $R^5$ is alkyl; and a pharmaceutically acceptable salt thereof.

34. Compound of any one of Embodiments 1-7 $R^a$ is H, halo, $C_{1-4}$ haloalkyl, $C_{1-6}$ hydroxyalkyl, $C_{1-6}$ alkyl, $C_{2-6}$ alkynyl, $C_{1-6}$ alkoxy, amino, $C_{1-6}$ alkylamino, cyano, HC(=O)—, HC(=NOH)—, carboxy, $C_{1-6}$ alkoxycarbonyl, or substituted or unsubstituted 3-6 membered heterocyclyl;

35. Compound of any one of Embodiments 1-7 wherein $R^a$ is H, chloro, fluoro, bromo, amino, methylamino, hydroxymethyl, HO—N=CH—, methoxy, trifluoromethyl, 1-azetidinyl, 3-hydroxy-1-azetidinyl, 5-methyl-oxadiazol-2-yl, HC(=O)— or methyl; and a pharmaceutically acceptable salt thereof.

36. Compound of any one of Embodiments 1-7 wherein $R^a$ is H or methyl; and a pharmaceutically acceptable salt thereof.

37. Compound of any one of Embodiments 1-7 wherein $R^b$ is H, $C_{1-6}$ alkyl, $C_{1-2}$ haloalkyl, $C_{1-4}$ aminoalkyl, $C_{1-3}$ alkoxy-$C_{1-3}$ alkyl, $C_{1-3}$ alkoxy-$C_{1-3}$ alkoxy-$C_{1-3}$ alkyl, $C_{1-3}$ alksulfonyl-C$_{1-4}$alkyl, C$_{2-4}$ alkenyl, unsubstituted or substituted C$_{3-6}$ cycloalkyl, unsubstituted or substituted phenyl, unsubstituted or substituted phenyl-C$_{1-2}$-alkyl or unsubstituted or substituted 4-6 membered heterocyclyl; and a pharmaceutically acceptable salt thereof.

38. Compound of any one of Embodiments 1-7 wherein R$^b$ is an unsubstituted or substituted ring selected from cyclopropyl, cyclobutyl, cyclopentyl, phenyl, pyridyl, piperidinyl, morpholinyl, piperazinyl, pyrrolindinyl, azetidinyl, tetrahydrofuryl and tetrahydropyranyl; and a pharmaceutically acceptable salt thereof.

39. Compound of any one of Embodiments 1-7 wherein R$^b$ is H, methyl, trifluoromethyl, aminomethyl, methoxyethyl, propenyl, methylsulfonylethyl, methylsulfonylpropyl or methoxyethoxyethyl; and a pharmaceutically acceptable salt thereof.

A family of specific compounds of particular interest within Formula 1 consists of compounds and pharmaceutically-acceptable derivatives thereof as follows:

2-(2-methyl-3-((1-methylcyclopropyl)amino)-5-quinoxalinyl)-1,5,6,7-tetrahydro-4H-pyrrolo[3,2-c]pyridin-4-one;
2-(3-((1-methylcyclopropyl)amino)-5-quinoxalinyl)-1,5,6,7-tetrahydro-4H-pyrrolo[3,2-c]pyridin-4-one;
2-(3-(tert-butylamino)-5-quinoxalinyl)-1,5,6,7-tetrahydro-4H-pyrrolo[3,2-c]pyridin-4-one;
2-(3-(cyclopropylamino)-2-methyl-5-quinoxalinyl)-1,5,6,7-tetrahydro-4H-pyrrolo[3,2-c]pyridin-4-one;
2-(3-(tert-butylamino)-2-methyl-5-quinoxalinyl)-1,5,6,7-tetrahydro-4H-pyrrolo[3,2-c]pyridin-4-one;
2-(3-(tert-butyl(ethyl)amino)-5-quinoxalinyl)-1,5,6,7-tetrahydro-4H-pyrrolo[3,2-c]pyridin-4-one;
2-(2-methyl-3-((1-methylcyclobutyl)amino)-5-quinoxalinyl)-1,5,6,7-tetrahydro-4H-pyrrolo[3,2-c]pyridin-4-one;
(±)-2-(3-(cyclopropylamino)-2-methyl-5-quinoxalinyl)-7-methyl-1,5,6,7-tetrahydro-4H-pyrrolo[3,2-c]pyridin-4-one;
(7R)-2-(3-(cyclopropylamino)-2-methyl-5-quinoxalinyl)-7-methyl-1,5,6,7-tetrahydro-4H-pyrrolo[3,2-c]pyridin-4-one;
2-(2-methyl-3-((1-(trifluoromethyl)cyclopropyl)amino)-5-quinoxalinyl)-1,5,6,7-tetrahydro-4H-pyrrolo[3,2-c]pyridin-4-one;
2-(3-((2-hydroxy-1,1-dimethylethyl)amino)-2-methyl-5-quinoxalinyl)-1,5,6,7-tetrahydro-4H-pyrrolo[3,2-c]pyridin-4-one;
2-(3-((2,2-dimethylpropyl)amino)-2-methyl-5-quinoxalinyl)-1,5,6,7-tetrahydro-4H-pyrrolo[3,2-c]pyridin-4-one;
2-(3-(cyclobutylamino)-2-methyl-5-quinoxalinyl)-1,5,6,7-tetrahydro-4H-pyrrolo[3,2-c]pyridin-4-one;
2-(3-(cyclohexylamino)-2-methyl-5-quinoxalinyl)-1,5,6,7-tetrahydro-4H-pyrrolo[3,2-c]pyridin-4-one;
7-(2-methyl-3-((1-methylcyclopropyl)amino)-5-quinoxalinyl)-3,4-dihydropyrrolo[1,2-a]pyrazin-1(2H)-one;
2-(3-(tert-butyl(methyl)amino)-5-quinoxalinyl)-1,5,6,7-tetrahydro-4H-pyrrolo[3,2-c]pyridin-4-one;
1-((3-methyl-8-(4-oxo-4,5,6,7-tetrahydro-1H-pyrrolo[3,2-c]pyridin-2-yl)-2-quinoxalinyl)amino)cyclopropanecarbonitrile;
(7S)-2-(3-(cyclopropylamino)-2-methyl-5-quinoxalinyl)-7-methyl-1,5,6,7-tetrahydro-4H-pyrrolo[3,2-c]pyridin-4-one;
2-(3-((1,1-dimethylpropyl)amino)-2-methyl-5-quinoxalinyl)-1,5,6,7-tetrahydro-4H-pyrrolo[3,2-c]pyridin-4-one;
2-(2-methyl-3-(phenylamino)-5-quinoxalinyl)-1,5,6,7-tetrahydro-4H-pyrrolo[3,2-c]pyridin-4-one;
7-(3-(tert-butylamino)-5-quinoxalinyl)-3,4-dihydropyrrolo[1,2-a]pyrazin-1(2H)-one;
2-(2-(tert-butylamino)-3-methylpyrido[2,3-b]pyrazin-8-yl)-1,5,6,7-tetrahydro-4H-pyrrolo[3,2-c]pyridin-4-one;
2-(3-((1-(hydroxymethyl)cyclopropyl)amino)-2-methyl-5-quinoxalinyl)-1,5,6,7-tetrahydro-4H-pyrrolo[3,2-c]pyridin-4-one;
2-(6-fluoro-2-methyl-3-((1-methylcyclopropyl)amino)-5-quinoxalinyl)-1,5,6,7-tetrahydro-4H-pyrrolo[3,2-c]pyridin-4-one;
2-(3-(tert-butylamino)-6-fluoro-2-methyl-5-quinoxalinyl)-1,5,6,7-tetrahydro-4H-pyrrolo[3,2-c]pyridin-4-one;
2-(2-methyl-3-(((1-methylcyclopropyl)methyl)amino)-5-quinoxalinyl)-1,5,6,7-tetrahydro-4H-pyrrolo[3,2-c]pyridin-4-one; and
2-(2-amino-3-(tert-butylamino)-5-quinoxalinyl)-1,5,6,7-tetrahydro-4H-pyrrolo[3,2-c]pyridin-4-one;
and a pharmaceutically acceptable salt thereof.

A family of specific compounds of particular interest within Formula 7 consists of compounds and pharmaceutically-acceptable salts thereof as follows:

2'-(3-(cyclopropylamino)-6-fluoro-2-methyl-5-quinoxalinyl)-1'H-spiro[cyclopropane-1,6'-pyrrolo[3,4-b]pyrrol]-4'(5'H)-one;
(6R)-2-(3-(cyclopropylamino)-6-fluoro-2-methyl-5-quinoxalinyl)-6-methyl-5,6-dihydropyrrolo[3,4-b]pyrrol-4(1H)-one;
(6S)-2-(3-(cyclopropylamino)-6-fluoro-2-methyl-5-quinoxalinyl)-6-methyl-5,6-dihydropyrrolo[3,4-b]pyrrol-4(1H)-one;
2-(3-(tert-butylamino)-6-fluoro-2-methyl-5-quinoxalinyl)-1,5,6,7-tetrahydro-4H-pyrrolo[3,2-c]pyridin-4-one;
(6R)-6-methyl-2-(2-methyl-3-((1-methylethyl)amino)-5-quinoxalinyl)-5,6-dihydropyrrolo[3,4-b]pyrrol-4(1H)-one;
(6S)-2-(3-(tert-butylamino)-2-methyl-5-quinoxalinyl)-6-methyl-1,5,6,7-tetrahydro-4H-pyrrolo[3,2-c]pyridin-4-one;
(6R)-2-(3-(tert-butylamino)-2-methyl-5-quinoxalinyl)-6-methyl-1,5,6,7-tetrahydro-4H-pyrrolo[3,2-c]pyridin-4-one;
tert-butyl 2-(3-(tert-butylamino)-2-methyl-5-quinoxalinyl)-4-oxo-4,5,6,7-tetrahydro-1H-pyrrolo[3,2-c]pyridine-1-carboxylate;
tert-butyl 2-(3-(tert-butylamino)-2-methyl-5-quinoxalinyl)-4-oxo-1,4,6,7-tetrahydro-5H-pyrrolo[3,2-c]pyridine-5-carboxylate;
2-(3-(tert-butylamino)-2-methyl-5-quinoxalinyl)-1,5,6,7-tetrahydro-4H-pyrrolo[3,2-c]pyridine-4-thione;
(6S)-6-methyl-2-(2-methyl-3-((2,2,2-trifluoroethyl)amino)-5-quinoxalinyl)-5,6-dihydropyrrolo[3,4-b]pyrrol-4(1H)-one;
(6R)-6-methyl-2-(2-methyl-3-((2,2,2-trifluoroethyl)amino)-5-quinoxalinyl)-5,6-dihydropyrrolo[3,4-b]pyrrol-4(1H)-one;
2'-(3-(tert-butylamino)-6-fluoro-2-methyl-5-quinoxalinyl)-1'H-spiro[cyclopropane-1,6'-pyrrolo[3,4-b]pyrrol]-4'(5'H)-one;
2-(3-(tert-butylamino)-6-fluoro-2-methyl-5-quinoxalinyl)-5,6-dihydropyrrolo[3,4-b]pyrrol-4(1H)-one;
(6R)-2-(3-(tert-butylamino)-6-fluoro-2-methyl-5-quinoxalinyl)-6-methyl-5,6-dihydropyrrolo[3,4-b]pyrrol-4(1H)-one;
(6S)-2-(3-(tert-butylamino)-6-fluoro-2-methyl-5-quinoxalinyl)-6-methyl-5,6-dihydropyrrolo[3,4-b]pyrrol-4(1H)-one;
2-(3-(tert-butylamino)-2-methylquinoxalin-5-yl)-5-(hydroxymethyl)-6,7-dihydro-1H-pyrrolo[3,2-c]pyridin-4(5H)-one;

(E/Z)-2-(3-(tert-butylamino)-2-methylquinoxalin-5-yl)-6,7-dihydro-1H-pyrrolo[3,2-c]pyridin-4(5H)-one oxime;
2-(2-methyl-3-((2,2,2-trifluoroethyl)amino)-5-quinoxalinyl)-5,6-dihydropyrrolo[3,4-b]pyrrolo-4(1H)-one;
(6R)-2-(3-((2-hydroxy-1,1-dimethylethyl)amino)-2-methyl-5-quinoxalinyl)-6-methyl-5,6-dihydropyrrolo[3,4-b]pyrrol-4(1H)-one;
2-(3-(tert-butylamino)-2-methyl-5-quinoxalinyl)-1,5,6,7-tetrahydro-4H-indol-4-one;
2-(2-amino-3-(tert-butylamino)-5-quinoxalinyl)-1,5,6,7-tetrahydro-4H-pyrrolo[3,2-c]pyridin-4-one;
2-(3-(tert-butylamino)-2-methyl-5-quinoxalinyl)-5,6,7,8-tetrahydropyrrolo[3,2-c]azepin-4(1H)-one;
2-(3-(tert-butylamino)-2-(hydroxymethyl)-5-quinoxalinyl)-1,5,6,7-tetrahydro-4H-pyrrolo[3,2-c]pyridin-4-one;
2-(3-(tert-butylamino)-2-ethynyl-5-quinoxalinyl)-1,5,6,7-tetrahydro-4H-pyrrolo[3,2-c]pyridin-4-one;
3-(tert-butylamino)-5-(4-oxo-4,5,6,7-tetrahydro-1H-pyrrolo[3,2-c]pyridin-2-yl)-2-quinoxalinecarbaldehyde oxime;
3-(tert-butylamino)-5-(4-oxo-4,5,6,7-tetrahydro-1H-pyrrolo[3,2-c]pyridin-2-yl)-2-quinoxalinecarbonitrile;
2(3-(tert-butylamino)-2-((1S)-1-hydroxyethyl)-5-quinoxalinyl)-1,5,6,7-tetrahydro-4H-pyrrolo[3,2-c]pyridin-4-one;
2(3-(tert-butylamino)-2-((1R)-1-hydroxyethyl)-5-quinoxalinyl)-1,5,6,7-tetrahydro-4H-pyrrolo[3,2-c]pyridin-4-one;
2-(3-(tert-butylamino)-2-ethyl-5-quinoxalinyl)-1,5,6,7-tetrahydro-4H-pyrrolo[3,2-c]pyridin-4-one;
2-(3-(tert-butylamino)-2-methyl-5-quinoxalinyl)-1-methyl-1,5,6,7-tetrahydro-4H-pyrrolo[3,2-c]pyridin-4-one;
5-acetyl-2-(3-(tert-butylamino)-2-methyl-5-quinoxalinyl)-1,5,6,7-tetrahydro-4H-pyrrolo[3,2-c]pyridin-4-one;
tert-butyl (6R)-2-(3-(tert-butylamino)-2-methyl-5-quinoxalinyl)-6-methyl-4-oxo-4,6-dihydropyrrolo[3,4-b]pyrrole-5 (1H)-carboxylate;
2-(3-((2-(2-methoxyethoxy)-1,1-dimethylethyl)amino)-2-methyl-5-quinoxalinyl)-1,5,6,7-tetrahydro-4H-pyrrolo[3,2-c]pyridin-4-one;
2-(2-methyl-3-(3-(methylsulfonyl)-1-azetidinyl)-5-quinoxalinyl)-1,5,6,7-tetrahydro-4H-pyrrolo[3,2-c]pyridin-4-one;
2-(3-(2-methyl-1H-imidazol-1-yl)-5-quinoxalinyl)-1,5,6,7-tetrahydro-4H-pyrrolo[3,2-c]pyridin-4-one;
2-(2-methyl-3-4(1R)-1-(2-pyridinyl)ethyl)amino)-5-quinoxalinyl)-1,5,6,7-tetrahydro-4H-pyrrolo[3,2-c]pyridin-4-one;
2-(2-methyl-3-4(1S)-1-(2-pyridinyl)ethyl)amino)-5-quinoxalinyl)-1,5,6,7-tetrahydro-4H-pyrrolo[3,2-c]pyridin-4-one;
2-(2-methyl-3-(((1R)-1-(2-pyrazinyl)ethyl)amino)-5-quinoxalinyl)-1,5,6,7-tetrahydro-4H-pyrrolo[3,2-c]pyridin-4-one;
2-(2-methyl-3-4(1S)-1-(2-pyrazinyl)ethyl)amino)-5-quinoxalinyl)-1,5,6,7-tetrahydro-4H-pyrrolo[3,2-c]pyridin-4-one;
2-(2-methyl-3-4(1R)-1-(4-pyrimidinyl)ethyl)amino)-5-quinoxalinyl)-1,5,6,7-tetrahydro-4H-pyrrolo[3,2-c]pyridin-4-one;
2-(2-methyl-3-(((1S)-1-(4-pyrimidinyl)ethyl)amino)-5-quinoxalinyl)-1,5,6,7-tetrahydro-4H-pyrrolo[3,2-c]pyridin-4-one;
2'-(3-(tert-butylamino)-2-methyl-5-quinoxalinyl)-1'H-spiro[cyclopropane-1,6'-pyrrolo[3,4-b]pyrrol]-4'(5'H)-one;
2'-(3-(cyclopropylamino)-2-methyl-5-quinoxalinyl)-1'H-spiro[cyclopropane-1,6'-pyrrolo[3,4-b]pyrrol]-4'(5'H)-one;
(6R)-2-(3-(tert-butylamino)-2-methyl-5-quinoxalinyl)-6-methyl-5,6-dihydropyrrolo[3,4-b]pyrrolo-4(1H)-one;
(6S)-2-(3-(tert-butylamino)-2-methyl-5-quinoxalinyl)-6-methyl-5,6-dihydropyrrolo[3,4-b]pyrrol-4(1H)-one;
(6S)-6-methyl-2-(2-methyl-3-((1-methylcyclopropyl)amino)-5-quinoxalinyl)-5,6-dihydropyrrolo[3,4-b]pyrrol-4(1H)-one;
2'-(2-methyl-3-((1-methylcyclopropyl)amino)-5-quinoxalinyl)-1'H-spiro[cyclopropane-1,6'-pyrrolo[3,4-b]pyrrol]-4'(5'H)-one;
2'-(6-fluoro-2-methyl-3-((1-methylethyl)amino)-5-quinoxalinyl)-1'H-spiro[cyclopropane-1,6'-pyrrolo[3,4-b]pyrrol]-4'(5'H)-one;
2'-(3-((2,2-difluoroethyl)amino)-2-methyl-5-quinoxalinyl)-1'H-spiro[cyclopropane-1,6'-pyrrolo[3,4-b]pyrrol]-4'(5'H)-one;
(6R)-2-(3-(tert-butylamino)-2-methyl-5-quinoxalinyl)-6-methyl-5,6-dihydropyrrolo[3,4-b]pyrrole-4(1H)-thione;
(6R)-6-methyl-2-(2-methyl-3-((1-methylcyclopropyl)amino)-5-quinoxalinyl)-5,6-dihydropyrrolo[3,4-b]pyrrol-4(1H)-one;
2-(3-(tert-butylamino)-2-methyl-5-quinoxalinyl)-5,6-dihydropyrrolo[3,4-b]pyrrol-4(1H)-one;
2-(2-methyl-3-(((1-methylcyclopropyl)methyl)amino)-5-quinoxalinyl)-1,5,6,7-tetrahydro-4H-pyrrolo[3,2-c]pyridin-4-one;
2-(2-methyl-3-((2,2,2-trifluoroethyl)amino)-5-quinoxalinyl)-1,5,6,7-tetrahydro-4H-pyrrolo[3,2-c]pyridin-4-one;
2-(3-ethoxy-5-quinoxalinyl)-1,5,6,7-tetrahydro-4H-pyrrolo[3,2-c]pyridin-4-one;
2-(3-((1,1-dimethyl-3-(methylsulfonyl)propyl)amino)-2-methyl-5-quinoxalinyl)-1,5,6,7-tetrahydro-4H-pyrrolo[3,2-c]pyridin-4-one;
tert-butyl (2-methyl-2-((3-methyl-8-(4-oxo-4,5,6,7-tetrahydro-1H-pyrrolo[3,2-c]pyridin-2-yl)-2-quinoxalinyl)amino)propyl)carbamate;
2-(2-(tert-butylamino)-8-quinolinyl)-1,5,6,7-tetrahydro-4H-pyrrolo[3,2-c]pyridin-4-one;
2-(3-((2-amino-1,1-dimethylethyl)amino)-2-methyl-5-quinoxalinyl)-1,5,6,7-tetrahydro-4H-pyrrolo[3,2-c]pyridin-4-one;
2-(3-((1,1-dimethyl-2-((2-(methylsulfonyl)ethyl)amino)ethyl)amino)-2-methyl-5-quinoxalinyl)-1,5,6,7-tetrahydro-4H-pyrrolo[3,2-c]pyridin-4-one;
2-(3-(tert-butylamino)-2-fluoro-5-quinoxalinyl)-1,5,6,7-tetrahydro-4H-pyrrolo[3,2-c]pyridin-4-one;
2-(3-(tert-butylamino)-2-(methylamino)-5-quinoxalinyl)-1,5,6,7-tetrahydro-4H-pyrrolo[3,2-c]pyridin-4-one;
2-(3-(tert-butylamino)-2-chloro-5-quinoxalinyl)-1,5,6,7-tetrahydro-4H-pyrrolo[3,2-c]pyridin-4-one;
2-(3-(tert-butylamino)-2-(3-hydroxy-1-azetidinyl)-5-quinoxalinyl)-1,5,6,7-tetrahydro-4H-pyrrolo[3,2-c]pyridin-4-one;
2-(2-(1-azetidinyl)-3-(tert-butylamino)-5-quinoxalinyl)-1,5,6,7-tetrahydro-4H-pyrrolo[3,2-c]pyridin-4-one;
2-(3-(tert-butylamino)-2-methyl-5-quinoxalinyl)-3-chloro-1,5,6,7-tetrahydro-4H-pyrrolo[3,2-c]pyridin-4-one;
3-bromo-2-(3-(tert-butylamino)-2-methyl-5-quinoxalinyl)-1,5,6,7-tetrahydro-4H-pyrrolo[3,2-c]pyridin-4-one;
2-(3-(tert-butylamino)-2-methyl-5-quinoxalinyl)-3-methyl-1,5,6,7-tetrahydro-4H-pyrrolo[3,2-c]pyridin-4-one;
N-tert-butyl-8-(4-methoxy-6,7-dihydro-1H-pyrrolo[3,2-c]pyridin-2-yl)-3-methyl-2-quinoxalinamine;
(6R)-2-(3-(cyclopropylamino)-6-fluoro-2-methyl-5-quinoxalinyl)-6-((1R)-1-hydroxyethyl)-5,6-dihydropyrrolo[3,4-b]pyrrolo-4(1H)-one;
(6S)-2-(3-(cyclopropylamino)-6-fluoro-2-methyl-5-quinoxalinyl)-6-((1S)-1-hydroxyethyl)-5,6-dihydropyrrolo[3,4-b]pyrrolo-4 (1H)-one;

(6R)-2-(3-(cyclopropylamino)-6-fluoro-2-methyl-5-quinox-
alinyl)-6-((1S)-1-hydroxyethyl)-5,6-dihydropyrrolo[3,4-
b]pyrrolo-4 (1H)-one;
6-((benzyloxy)methyl)-2-(2-methyl-3-((1-methylcyclopro-
pyl)amino)quinoxalin-5-yl)-5,6-dihydropyrrolo[3,4-b]
pyrrolo-4 (1H)-one;
2-(2-methyl-3-((1-methylcyclopropyl)amino)-5-quinoxali-
nyl)-5,6-dihydropyrrolo[3,4-b]pyrrolo-4(1H)-one;
3-chloro-2-(2-methyl-3-((1-methylcyclopropyl)amino)-5-
quinoxalinyl)-5,6-dihydropyrrolo[3,4-b]pyrrol-4(1H)-
one;
(6R)-6-(hydroxymethyl)-2-(2-methyl-3-((1-methylcyclo-
propyl)amino)-5-quinoxalinyl)-5,6-dihydropyrrolo[3,4-
b]pyrrol-4 (1H)-one;
(6S)-6-(hydroxymethyl)-2-(2-methyl-3-((1-methylcyclo-
propyl)amino)-5-quinoxalinyl)-5,6-dihydropyrrolo[3,4-
b]pyrrol-4 (1H)-one;
(6S)-6-(hydroxymethyl)-2-(2-methyl-3-((1-methylcyclo-
propyl)amino)-5-quinoxalinyl)-5,6-dihydropyrrolo[3,4-
b]pyrrol-4 (1H)-one;
(6R)-6-(hydroxymethyl)-2-(2-methyl-3-((1-methylcyclo-
propyl)amino)-5-quinoxalinyl)-5,6-dihydropyrrolo[3,4-
b]pyrrol-4 (1H)-one;
2-(3-(cyclopropylamino)-2-methyl-5-quinoxalinyl)-5,6-di-
hydropyrrolo[3,4-b]pyrrol-4(1H)-one;
6-((benzyloxy)methyl)-2-(3-(cyclopropylamino)-2-meth-
ylquinoxalin-5-yl)-5,6-dihydropyrrolo[3,4-b]pyrrol-4
(1H)-one;
(6R)-2-(3-(cyclopropylamino)-2-methyl-5-quinoxalinyl)-6-
(hydroxymethyl)-5,6-dihydropyrrolo[3,4-b]pyrrol-4(1H)-
one;
(6S)-2-(3-(cyclopropylamino)-2-methyl-5-quinoxalinyl)-6-
(hydroxymethyl)-5,6-dihydropyrrolo[3,4-b]pyrrol-4(1H)-
one;
(6S)-2-(3-(cyclopropylamino)-2-methyl-5-quinoxalinyl)-6-
(hydroxymethyl)-5,6-dihydropyrrolo[3,4-b]pyrrol-4(1H)-
one;
(6R)-2-(3-(cyclopropylamino)-2-methyl-5-quinoxalinyl)-6-
(hydroxymethyl)-5,6-dihydropyrrolo[3,4-b]pyrrol-4(1H)-
one;
2-(3-(tert-butylamino)-2-methylpyrido[3,4-b]pyrazin-5-yl)-
1,5,6,7-tetrahydro-4H-pyrrolo[3,2-c]pyridin-4-one;
2-(6-fluoro-2-methyl-3-((1-methylcyclopropyl)amino)-5-
quinoxalinyl)-1,5,6,7-tetrahydro-4H-pyrrolo[3,2-c]pyri-
din-4-one;
2-(6-fluoro-3-((2-hydroxy-1,1-dimethylethyl)amino)-2-me-
thyl-5-quinoxalinyl)-1,5,6,7-tetrahydro-4H-pyrrolo[3,2-
c]pyridin-4-one;
2-(3-(tert-butylamino)-6-fluoro-2-methyl-5-quinoxalinyl)-
1,5-dihydro-4H-pyrrolo[3,2-c]pyridin-4-one;
2-(3-(tert-butylamino)-2-(5-methyl-1,3,4-oxadiazol-2-yl)-5-
quinoxalinyl)-1,5,6,7-tetrahydro-4H-pyrrolo[3,2-c]pyri-
din-4-one;
2-(6-fluoro-2-methyl-3-((1-methylethyl)amino)-5-quinox-
alinyl)-1,5,6,7-tetrahydro-4H-pyrrolo[3,2-c]pyridin-4-
one;
2-(2-(tert-butylamino)-8-quinazolinyl)-1,5,6,7-tetrahydro-
4H-pyrrolo[3,2-c]pyridin-4-one;
2-(3-((1,1-dimethylpropyl)amino)-6-fluoro-2-methyl-5-qui-
noxalinyl)-1,5,6,7-tetrahydro-4H-pyrrolo[3,2-c]pyridin-
4-one;
2-(6-fluoro-2-methyl-3-((1-methylcyclobutyl)amino)-5-qui-
noxalinyl)-1,5,6,7-tetrahydro-4H-pyrrolo[3,2-c]pyridin-
4-one;
2-(2-(tert-butyl(methyl)amino)-8-quinazolinyl)-1,5,6,7-tet-
rahydro-4H-pyrrolo[3,2-c]pyridin-4-one;

2'-(6-fluoro-2-methyl-3-((1-methylcyclopropyl)amino)-5-
quinoxalinyl)-1'H-spiro[cyclopropane-1,6'-pyrrolo[3,4-b]
pyrrol]-4'(5'H)-one;
(6R)-2-(6-fluoro-2-methyl-3((1-methylcyclopropyl)amino)-
5-quinoxalinyl)-6-methyl-5,6-dihydropyrrolo[3,4-b]pyr-
rol-4 (1H)-one;
(6S)-2-(6-fluoro-2-methyl-3-((1-methylcyclopropyl)amino)-
5-quinoxalinyl)-6-methyl-5,6-dihydropyrrolo[3,4-b]pyr-
rol-4 (1H)-one;
2'-(2-methyl-3-((2,2,2-trifluoroethyl)amino)-5-quinoxali-
nyl)-1'H-spiro[cyclopropane-1,6'-pyrrolo[3,4-b]pyrrol]-4'
(5'H)-one;
(6R)-2-(3-((2,2-difluoroethyl)amino)-2-methyl-5-quinox-
alinyl)-6-methyl-5,6-dihydropyrrolo[3,4-b]pyrrol-4(1H)-
one; and
(6S)-2-(3-((2,2-difluoroethyl)amino)-2-methyl-5-quinoxali-
nyl)-6-methyl-5,6-dihydropyrrolo[3,4-b]pyrrol-4(1H)-
one.

A family of specific compounds of particular interest
within Formula 7 consists of compounds and pharmaceuti-
cally-acceptable salts thereof as follows:
2-(3-(2,6-dimethylphenyl)-5-quinoxalinyl)-1,5,6,7-tetrahy-
dro-4H-pyrrolo[3,2-c]pyridin-4-one;
2-((1-methylethyl)amino)-8-(4-oxo-4,5,6,7-tetrahydro-1H-
pyrrolo[3,2-c]pyridin-2-yl)-3-phenyl-4(3H)-quinazoli-
none;
2-((1-methylethyl)amino)-8-(4-oxo-4,5,6,7-tetrahydro-1H-
pyrrolo[3,2-c]pyridin-2-yl)-3-(3-pyridinyl)-4(3H)-
quinazolinone;
2-(tert-butylamino)-8-(4-oxo-4,5,6,7-tetrahydro-1H-pyrrolo
[3,2-c]pyridin-2-yl)-3-(3-pyridinyl)-4(3H)-quinazoli-
none;
2-(tert-butylamino)-7-fluoro-3-methyl-8-((6R)-6-methyl-4-
oxo-1,4,5,6-tetrahydropyrrolo[3,4-b]pyrrol-2-yl)-4(3H)-
quinazolinone;
2-(tert-butylamino)-3-(1-methylethyl)-8-((6R)-6-methyl-4-
oxo-1,4,5,6-tetrahydropyrrolo[3,4-b]pyrrol-2-yl)-4(3H)-
quinazolinone;
2-(tert-butyl(methyl)amino)-8-((6R)-6-methyl-4-oxo-1,4,5,
6-tetrahydropyrrolo[3,4-b]pyrrol-2-yl)-4(3H)-quinazoli-
none;
2-(tert-butylamino)-8-((6R)-6-methyl-4-oxo-1,4,5,6-tet-
rahydropyrrolo[3,4-b]pyrrol-2-yl)-4(3H)-quinazolinone;
2'-(3-(tert-butylamino)-2-methyl-5-quinoxalinyl)-2,3,5,6-
tetrahydro-1'H-spiro[pyran-4,6'-pyrrolo[3,4-b]pyrrol]-4'
(5'H)-one;
2-(3-(2-chloro-3-pyridinyl)-2-methyl-5-quinoxalinyl)-1,5,6,
7-tetrahydro-4H-pyrrolo[3,2-c]pyridin-4-one;
2-(3-(3-chloro-4-pyridinyl)-2-methyl-5-quinoxalinyl)-1,5,6,
7-tetrahydro-4H-pyrrolo[3,2-c]pyridin-4-one;
2-(3-(4-chloro-3-pyridinyl)-2-methyl-5-quinoxalinyl)-1,5,6,
7-tetrahydro-4H-pyrrolo[3,2-c]pyridin-4-one;
2-(3-(4-amino-2-chlorophenyl)-2-methyl-5-quinoxalinyl)-1,
5,6,7-tetrahydro-4H-pyrrolo[3,2-c]pyridin-4-one;
2-(3-(2-chloro-6-fluorophenyl)-2-methyl-5-quinoxalinyl)-1,
5,6,7-tetrahydro-4H-pyrrolo[3,2-c]pyridin-4-one;
2-((1-methylethyl)amino)-8-(4-oxo-4,5,6,7-tetrahydro-1H-
pyrrolo[3,2-c]pyridin-2-yl)-3-(2-pyridinyl)-4(3H)-
quinazolinone;
2-(3-(tert-butylamino)-2-methyl-5-quinoxalinyl)-7-methyl-
1,5-dihydro-4H-pyrrolo[2,3-d]pyridazin-4-one;
5-(6-fluoro-2-methyl-3-((1-methylcyclopropyl)amino)-5-
quinoxalinyl)-2-methyl-1H-pyrrole-3-carboxamide;
5-(3-(tert-butylamino)-2-methyl-5-quinoxalinyl)-2-cyclo-
propyl-1H-pyrrole-3-carboxamide;
2-(tert-butylamino)-3-methyl-8-(4-oxo-1,4,5,6-tetrahydro-
pyrrolo[3,4-b]pyrrol-2-yl)-4(3H)-quinazolinone;

4-(3-(tert-butylamino)-2-methyl-5-quinoxalinyl)-1H-pyrrole-2-carboxamide;
6-(3-(tert-butylamino)-2-methyl-5-quinoxalinyl)-1,2-dihydro-3H-pyrrolo[1,2-c]imidazol-3-one;
6-(3-(tert-butylamino)-2-methyl-5-quinoxalinyl)-1H-pyrrolo[1,2-c]imidazole-1,3(2H)-dione;
2-(3-(tert-butylamino)-2-methyl-5-quinoxalinyl)-1,5-dihydro-4H-pyrrolo[2,3-d]pyridazin-4-one;
2-(2-methyl-3-phenyl-5-quinoxalinyl)-1,5,6,7-tetrahydro-4H-pyrrolo[3,2-c]pyridin-4-one;
2-(3-chloro-2-methyl-5-quinoxalinyl)-1,5,6,7-tetrahydro-4H-pyrrolo[3,2-c]pyridin-4-one;
2-(2-methyl-3-(2-methylphenyl)-5-quinoxalinyl)-1,5,6,7-tetrahydro-4H-pyrrolo[3,2-c]pyridin-4-one;
2-(3-(2-chlorophenyl)-2-methyl-5-quinoxalinyl)-1,5,6,7-tetrahydro-4H-pyrrolo[3,2-c]pyridin-4-one;
2-(3-(2-fluorophenyl)-2-methyl-5-quinoxalinyl)-1,5,6,7-tetrahydro-4H-pyrrolo[3,2-c]pyridin-4-one;
2-(2-methyl-3-(2-pyridinyl)-5-quinoxalinyl)-1,5,6,7-tetrahydro-4H-pyrrolo[3,2-c]pyridin-4-one;
2-(2-methyl-3-(3-methyl-2-pyridinyl)-5-quinoxalinyl)-1,5,6,7-tetrahydro-4H-pyrrolo[3,2-c]pyridin-4-one;
2-(3-(3-furanyl)-2-methyl-5-quinoxalinyl)-1,5,6,7-tetrahydro-4H-pyrrolo[3,2-c]pyridin-4-one;
2-(2-methyl-3-(1-methyl-1H-imidazol-2-yl)-5-quinoxalinyl)-1,5,6,7-tetrahydro-4H-pyrrolo[3,2-c]pyridin-4-one;
2-(2-methyl-3-(2-methyl-3-furanyl)-5-quinoxalinyl)-1,5,6,7-tetrahydro-4H-pyrrolo[3,2-c]pyridin-4-one;
tert-butyl (cis-3-((3-methyl-8-(4-oxo-4,5,6,7-tetrahydro-1H-pyrrolo[3,2-c]pyridin-2-yl)-2-quinoxalinyl)amino)cyclobutyl)carbamate;
2-(3-((cis-3-aminocyclobutyl)amino)-2-methyl-5-quinoxalinyl)-1,5,6,7-tetrahydro-4H-pyrrolo[3,2-c]pyridin-4-one;
tert-butyl (trans-3-(3-methyl-8-(4-oxo-4,5,6,7-tetrahydro-1H-pyrrolo[3,2-c]pyridin-2-yl)-2-quinoxalinyl)amino)cyclobutyl)carbamate;
2-(3-((trans-3-amino cyclobutyl)amino)-2-methyl-5-quinoxalinyl)-1,5,6,7-tetrahydro-4H-pyrrolo[3,2-c]pyridin-4-one;
2-(3-(tert-butylamino)-2-phenyl-5-quinoxalinyl)-1,5,6,7-tetrahydro-4H-pyrrolo[3,2-c]pyridin-4-one;
2-(3-((cis-3-hydroxycyclobutyl)amino)-2-methyl-5-quinoxalinyl)-1,5,6,7-tetrahydro-4H-pyrrolo[3,2-c]pyridin-4-one;
2-fluoroethyl (cis-3-((3-methyl-8-(4-oxo-4,5,6,7-tetrahydro-1H-pyrrolo[3,2-c]pyridin-2-yl)-2-quinoxalinyl)amino)cyclobutyl)carbamate;
2-(2-methyl-3-((cis-3-((2-(methylsulfonyl)ethyl)amino)cyclobutyl)amino)-5-quinoxalinyl)-1,5,6,7-tetrahydro-4H-pyrrolo[3,2-c]pyridin-4-one;
2-(3-((trans-3-hydroxycyclobutyl)amino)-2-methyl-5-quinoxalinyl)-1,5,6,7-tetrahydro-4H-pyrrolo[3,2-c]pyridin-4-one;
2-(2-methyl-3-((cis-3-(2-oxo-1,3-oxazolidin-3-yl)cyclobutyl)amino)-5-quinoxalinyl)-1,5,6,7-tetrahydro-4H-pyrrolo[3,2-c]pyridin-4-one;
2-(2-methyl-3-((cis-3-((2,2,2-trifluoroethyl)amino)cyclobutyl)amino)-5-quinoxalinyl)-1,5,6,7-tetrahydro-4H-pyrrolo[3,2-c]pyridin-4-one;
N-(3-methyl-8-(4-oxo-4,5,6,7-tetrahydro-1H-pyrrolo[3,2-c]pyridin-2-yl)-2-quinoxalinyl)acetamide;
N-(3-methyl-8-(4-oxo-4,5,6,7-tetrahydro-1H-pyrrolo[3,2-c]pyridin-2-yl)-2-quinoxalinyl)cyclopropanecarboxamide;
1-(3-methyl-8-(4-oxo-4,5,6,7-tetrahydro-1H-pyrrolo[3,2-c]pyridin-2-yl)-2-quinoxalinyl)guanidine;
2-(tert-butylamino)-3-methyl-8-(4-oxo-4,5,6,7-tetrahydro-1H-pyrrolo[3,2-c]pyridin-2-yl)-4(3H)-quinazolinone;
2-(tert-butylamino)-3-methyl-8-(1-oxo-1,2,3,4-tetrahydropyrrolo[1,2-a]pyrazin-7-yl)-4(3H)-quinazolinone;
2-(tert-butylamino)-3-methyl-8-((6R)-6-methyl-4-oxo-1,4,5,6-tetrahydropyrrolo[3,4-b]pyrrol-2-yl)-4(3H)-quinazolinone;
3-methyl-2-((1-methylcyclopropyl)amino)-8-((6R)-6-methyl-4-oxo-1,4,5,6-tetrahydropyrrolo[3,4-b]pyrrol-2-yl)-4(3H)-quinazolinone;
(6R)-6-methyl-2-(2-methyl-3-((1S)-2,2,2-trifluoro-1-methylethoxy)-5-quinoxalinyl)-5,6-dihydropyrrolo[3,4-b]pyrrol-4(1H)-one;
(6R)-6-methyl-2-(2-methyl-3-((1R)-2,2,2-trifluoro-1-methylethoxy)-5-quinoxalinyl)-5,6-dihydropyrrolo[3,4-b]pyrrol-4(1H)-one;
(6R)-3-chloro-6-methyl-2-(2-methyl-3-((1-methylcyclopropyl)amino)-5-quinoxalinyl)-5,6-dihydropyrrolo[3,4-b]pyrrol-4(1H)-one;
(6R)-2-(3-(tert-butylamino)-2-methyl-5-quinoxalinyl)-3-chloro-6-methyl-5,6-dihydropyrrolo[3,4-b]pyrrol-4(1H)-one;
2'-(2-(tert-butylamino)-3-methyl-4-oxo-3,4-dihydro-8-quinazolinyl)-1'H-spiro[cyclopropane-1,6'-pyrrolo[3,4-b]pyrrol]-4'(5'H)-one;
2-(3-((1,1-dimethyl-2-(4-morpholinyl)ethyl)amino)-2-methyl-5-quinoxalinyl)-1,5,6,7-tetrahydro-4H-pyrrolo[3,2-c]pyridin-4-one;
2-(tert-butylamino)-3-(2-methoxyethyl)-8-(4-oxo-1,4,5,6-tetrahydropyrrolo[3,4-b]pyrrol-2-yl)-4(3H)-quinazolinone;
2-(tert-butylamino)-3-(2-methoxy ethyl)-8-((6R)-6-methyl-4-oxo-1,4,5,6-tetrahydropyrrolo[3,4-b]pyrrol-2-yl)-4(3H)-quinazolinone;
3-methyl-2-((1-methylcyclopropyl)oxy)-8-((6R)-6-methyl-4-oxo-1,4,5,6-tetrahydropyrrolo[3,4-b]pyrrol-2-yl)-4(3H)-quinazolinone;
(R)-2-(tert-butylamino)-3-cyclopropyl-7-fluoro-8-(6-methyl-4-oxo-1,4,5,6-tetrahydropyrrolo[3,4-b]pyrrol-2-yl)quinazolin-4(3H)-one;
(6R)-2-(3-(tert-butylamino)-2-methyl-5-quinoxalinyl)-6-(2-hydroxyethyl)-5,6-dihydropyrrolo[3,4-b]pyrrol-4(1H)-one;
(6S)-2-(3-(tert-butylamino)-2-methyl-5-quinoxalinyl)-6-(2-hydroxyethyl)-5,6-dihydropyrrolo[3,4-b]pyrrol-4(1H)-one;
(6R)-6-(2-aminoethyl)-2-(3-(tert-butylamino)-2-methyl-5-quinoxalinyl)-5,6-dihydropyrrolo[3,4-b]pyrrol-4(1H)-one,
(6S)-6-(2-aminoethyl)-2-(3-(tert-butylamino)-2-methyl-5-quinoxalinyl)-5,6-dihydropyrrolo[3,4-b]pyrrol-4(1H)-one;
(R)-2-((1-fluoro-2-methylpropan-2-yl)amino)-3-methyl-8-(6-methyl-4-oxo-1,4,5,6-tetrahydropyrrolo[3,4-b]pyrrol-2-yl)quinazolin-4(3H)-one;
3-methyl-2-((1-methylcyclobutyl)amino)-8-((6R)-6-methyl-4-oxo-1,4,5,6-tetrahydropyrrolo[3,4-b]pyrrol-2-yl)-4(3H)-quinazolinone;
2-(3-(tert-butylamino)-2-methyl-5-quinoxalinyl)-6,6-dimethyl-5,6-dihydropyrrolo[3,4-b]pyrrolo-4(1H)-one;
3-(3-(tert-butylamino)-2-methyl-5-quinoxalinyl)-1H-pyrazole-5-carboxamide;
(6R)-6-((benzyloxy)methyl)-2-(3-(tert-butylamino)-2-methyl-5-quinoxalinyl)-5,6-dihydropyrrolo[3,4-b]pyrrol-4(1H)-one, (6S)-6-((benzyloxy)methyl)-2-(3-(tert-butylamino)-2-methyl-5-quinoxalinyl)-5,6-dihydropyrrolo[3,4-b]pyrrol-4(1H)-one;

(6R)-2-(3-(tert-butylamino)-2-methyl-5-quinoxalinyl)-6-(hydroxymethyl)-5,6-dihydropyrrolo[3,4-b]pyrrol-4(1H)-one, (6S)-2-(3-(tert-butylamino)-2-methyl-5-quinoxalinyl)-6-(hydroxymethyl)-5,6-dihydropyrrolo[3,4-b]pyrrol-4(1H)-one;

(6R)-2-(3-(tert-butylamino)-2-methyl-5-quinoxalinyl)-6-(hydroxymethyl)-1-methyl-5,6-dihydropyrrolo[3,4-b]pyrrol-4(1H)-one, (6S)-2-(3-(tert-butylamino)-2-methyl-5-quinoxalinyl)-6-(hydroxymethyl)-1-methyl-5,6-dihydropyrrolo[3,4-b]pyrrol-4(1H)-one;

2-(3-(tert-butylamino)-2-methyl-5-quinoxalinyl)-6,7-dihydropyrazolo[1,5-a]pyrazin-4(5H)-one;

2-(tert-butylamino)-3-methyl-8-((6S)-6-methyl-4-oxo-1,4,5,6-tetrahydropyrrolo[3,4-b]pyrrol-2-yl)-4(3H)-quinazolinone;

2-((3-(bis(2-methoxyethyl)amino)-1,1-dimethylpropyl)amino)-3-methyl-8-(4-oxo-1,4,5,6-tetrahydropyrrolo[3,4-b]pyrrol-2-yl)-4(3H)-quinazolinone;

2-(tert-butylamino)-3-(2-(2-methoxyethoxy)ethyl)-8-((6R)-6-methyl-4-oxo-1,4,5,6-tetrahydropyrrolo[3,4-b]pyrrol-2-yl)-4(3H)-quinazolinone;

2-(tert-butylamino)-3-cyclopropyl-8-((6R)-6-methyl-4-oxo-1,4,5,6-tetrahydropyrrolo[3,4-b]pyrrol-2-yl)-4(3H)-quinazolinone;

2-(3-((cis-3-(bis(2-fluoroethyl)amino)cyclobutyl)amino)-2-methyl-5-quinoxalinyl)-1,5,6,7-tetrahydro-4H-pyrrolo[3,2-c]pyridin-4-one;

2-(3-((cis-3-((2-fluoroethyl)amino)cyclobutyl)amino)-2-methyl-5-quinoxalinyl)-1,5,6,7-tetrahydro-4H-pyrrolo[3,2-c]pyridin-4-one;

2-(3-((cis-3-((2,2-difluoroethyl)amino)cyclobutyl)amino)-2-methyl-5-quinoxalinyl)-1,5,6,7-tetrahydro-4H-pyrrolo[3,2-c]pyridin-4-one;

2-(3-((cis-3-(dimethylamino)cyclobutyl)amino)-2-methyl-5-quinoxalinyl)-1,5,6,7-tetrahydro-4H-pyrrolo[3,2-c]pyridin-4-one;

2-(2-methyl-3-((cis-3-(4-morpholinyl)cyclobutyl)amino)-5-quinoxalinyl)-1,5,6,7-tetrahydro-4H-pyrrolo[3,2-c]pyridin-4-one; and (R)-2-(tert-butylamino)-3-ethyl-8-(6-methyl-4-oxo-1,4,5,6-tetrahydropyrrolo[3,4-b]pyrrol-2-yl)quinazolin-4(3H)-one.

A family of specific compounds of particular interest within Formula 1 consists of compounds and pharmaceutically-acceptable derivatives thereof as follows:

2-(tert-butylamino)-8-((6R)-6-methyl-4-oxo-1,4,5,6-tetrahydropyrrolo[3,4-b]pyrrol-2-yl)-3-(3-pyridinyl)-4(3H)-quinazolinone;

(6R)-2-(3-(((1S,3R)-3-aminocyclohexyl)amino)-2-methyl-5-quinoxalinyl)-6-methyl-5,6-dihydropyrrolo[3,4-b]pyrrol-4(1H)-one;

(6R)-2-(4-amino-2-(tert-butylamino)-8-quinazolinyl)-6-methyl-5,6-dihydropyrrolo[3,4-b]pyrrolo-4(1H)-one;

2-(tert-butylamino)-8-((6R)-6-(methoxymethyl)-4-oxo-1,4,5,6-tetrahydropyrrolo[3,4-b]pyrrol-2-yl)-3-methyl-4(3H)-quinazolinone, 2-(tert-butylamino)-8-((6S)-6-(methoxymethyl)-4-oxo-1,4,5,6-tetrahydropyrrolo[3,4-b]pyrrol-2-yl)-3-methyl-4(3H)-quinazolinone;

N-((1R,3S)-3-((3-methyl-8-((6R)-6-methyl-4-oxo-1,4,5,6-tetrahydropyrrolo[3,4-b]pyrrolo-2-yl)-2-quinoxalinyl)amino)cyclohexyl)acetamide;

(6R)-6-methyl-2-(2-methyl-3-(((1S,3R)-3-((2,2,2-trifluoroethyl)amino)cyclohexyl)amino)-5-quinoxalinyl)-5,6-dihydropyrrolo[3,4-b]pyrrol-4(1H)-one;

2-(ethyl(1-methylethyl)amino)-8-((6R)-6-methyl-4-oxo-1,4,5,6-tetrahydropyrrolo[3,4-b]pyrrol-2-yl)-4(3H)-quinazolinone;

N-((1R,3S)-3-((3-methyl-8-((6R)-6-methyl-4-oxo-1,4,5,6-tetrahydropyrrolo[3,4-b]pyrrol-2-yl)-2-quinoxalinyl)amino)cyclohexyl)methanesulfonamide;

3-cyclopropyl-7-fluoro-2-((1-methylcyclobutyl)amino)-8-((6R)-6-methyl-4-oxo-1,4,5,6-tetrahydropyrrolo[3,4-b]pyrrol-2-yl)-4(3H)-quinazolinone;

tert-butyl ((1R)-1-(hydroxymethyl)-2-(((1R,3S)-3-((3-methyl-8-((6R)-6-methyl-4-oxo-1,4,5,6-tetrahydropyrrolo[3,4-b]pyrrol-2-yl)-2-quinoxalinyl)amino)cyclohexyl)amino)-2-oxoethyl)carbamate;

3-cyclopropyl-2-((1-methylcyclopropyl)amino)-8-((6R)-6-methyl-4-oxo-1,4,5,6-tetrahydropyrrolo[3,4-b]pyrrol-2-yl)-4(3H)-quinazolinone;

2-(tert-butylamino)-8-((6R)-6-(methoxymethyl)-4-oxo-1,4,5,6-tetrahydropyrrolo[3,4-b]pyrrol-2-yl)-3-methyl-4(3H)-quinazolinone;

2-(tert-butylamino)-8-((6S)-6-(methoxymethyl)-4-oxo-1,4,5,6-tetrahydropyrrolo[3,4-b]pyrrol-2-yl)-3-methyl-4(3H)-quinazolinone;

3-cyclopropyl-7-fluoro-2-((1-methylcyclopropyl)amino)-8-((6R)-6-methyl-4-oxo-1,4,5,6-tetrahydropyrrolo[3,4-b]pyrrol-2-yl)-4(3H)-quinazolinone;

3-cyclopropyl-2-((1-methylcyclobutyl)amino)-8-((6R)-6-methyl-4-oxo-1,4,5,6-tetrahydropyrrolo[3,4-b]pyrrol-2-yl)-4(3H)-quinazolinone;

N-((1R,3S)-3-((3-methyl-8-((6R)-6-methyl-4-oxo-1,4,5,6-tetrahydropyrrolo[3,4-b]pyrrol-2-yl)-2-quinoxalinyl)amino)cyclohexyl)-D-serinamide;

3-cyclopropyl-7-fluoro-2-((1-methylcyclobutyl)amino)-8-((6R)-6-methyl-4-oxo-1,4,5,6-tetrahydropyrrolo[3,4-b]pyrrol-2-yl)-4(3H)-quinazolinone;

(6R)-6-methyl-2-(2-((1-methylcyclopropyl)amino)-8-quinazolinyl)-5,6-dihydropyrrolo[3,4-b]pyrrol-4(1H)-one;

2-(tert-butylamino)-3-(3-hydroxypropyl)-8-((6R)-6-methyl-4-oxo-1,4,5,6-tetrahydropyrrolo[3,4-b]pyrrol-2-yl)-4(3H)-quinazolinone;

2-(tert-butylamino)-8-((6R)-6-methyl-4-oxo-1,4,5,6-tetrahydropyrrolo[3,4-b]pyrrol-2-yl)-3-(2,2,2-trifluoroethyl)-4(3H)-quinazolinone;

7-fluoro-3-methyl-2-((1-methylcyclobutyl)amino)-8-((6R)-6-methyl-4-oxo-1,4,5,6-tetrahydropyrrolo[3,4-b]pyrrol-2-yl)-4(3H)-quinazolinone;

(R)-2-(tert-butylamino)-8-(6-(2-hydroxyethyl)-4-oxo-1,4,5,6-tetrahydropyrrolo[3,4-b]pyrrolo-2-yl)-3-methylquinazolin-4(3H)-one;

(R)-8-(6-(2-aminoethyl)-4-oxo-1,4,5,6-tetrahydropyrrolo[3,4-b]pyrrol-2-yl)-2-(tert-butylamino)-3-methylquinazolin-4(3H)-one;

2-(tert-butylamino)-8-((6R)-6-ethyl-4-oxo-1,4,5,6-tetrahydropyrrolo[3,4-b]pyrrol-2-yl)-3-methyl-4(3H)-quinazolinone;

2-(((1R,3S)-3-aminocyclohexyl)amino)-3-methyl-8-((6R)-6-methyl-4-oxo-1,4,5,6-tetrahydropyrrolo[3,4-b]pyrrol-2-yl)-4(3H)-quinazolinone, 2-(((1S,3R)-3-aminocyclohexyl)amino)-3-methyl-8-((6R)-6-methyl-4-oxo-1,4,5,6-tetrahydropyrrolo[3,4-b]pyrrol-2-yl)-4(3H)-quinazolinone;

2-(tert-butylamino)-3-cyclobutyl-8-((6R)-6-methyl-4-oxo-1,4,5,6-tetrahydropyrrolo[3,4-b]pyrrol-2-yl)-4(3H)-quinazolinone;

(R)-2-(tert-butylamino)-8-(6-methyl-4-oxo-1,4,5,6-tetrahydropyrrolo[3,4-b]pyrrol-2-yl)-3-(3-(methylsulfonyl)propyl)quinazolin-4(3H)-one;

(rac)-tert-butyl ((cis-3-((3-methyl-8-((R)-6-methyl-4-oxo-1,4,5,6-tetrahydropyrrolo[3,4-b]pyrrol-2-yl)-4-oxo-3,4-dihydroquinazolin-2-yl)amino)cyclohexyl)carbamate;

(R)-7-fluoro-3-methyl-8-(6-methyl-4-oxo-1,4,5,6-tetrahydropyrrolo[3,4-b]pyrrol-2-yl)-2-((1-methylcyclopropyl)amino)quinazolin-4(3H)-one;

(R)-2-(tert-butylamino)-3-cyclopropyl-8-(6-ethyl-4-oxo-1,4,5,6-tetrahydropyrrolo[3,4-b]pyrrolo-2-yl)quinazolin-4(3H)-one;

(R)-2-(tert-Butylamino)-3-ethyl-7-fluoro-8-(6-methyl-4-oxo-1,4,5,6-tetrahydropyrrolo[3,4-b]pyrrol-2-yl)quinazolin-4(3H)-one;

(R)-3-Ethyl-7-fluoro-8-(6-methyl-4-oxo-1,4,5,6-tetrahydropyrrolo[3,4-b]pyrrol-2-yl)-2-((1-methylcyclopropyl)amino)quinazolin-4(3H)-one;

R)-2-(tert-butylamino)-8-(6-methyl-4-oxo-1,4,5,6-tetrahydropyrrolo[3,4-b]pyrrolo-2-yl)-3-(2-(methylsulfonyl)ethyl)quinazolin-4(3H)-one; and (R)-2-(tert-butylamino)-8-(6-methyl-4-oxo-1,4,5,6-tetrahydropyrrolo[3,4-b]pyrrol-2-yl)-3-(tetrahydro-2H-pyran-4-yl)quinazolin-4(3H)-one.

Another aspect of the invention relates to a pharmaceutical composition comprising a compound of formula 1-12 and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of cancer.

The compounds of this invention may have in general several asymmetric centers and are typically depicted in the form of racemic mixtures. This invention is intended to encompass racemic mixtures, partially racemic mixtures and separate enantiomers and diasteromers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the present invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and claims:

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" embraces linear or branched radicals having two to about twelve carbon atoms. More preferred alkynyl radicals are "lower alkynyl" radicals having two to about six carbon atoms. Examples of such radicals include ethynyl and the like. Even more preferred are lower alkynyl radicals having two to three carbon atoms.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "alkoxyalkyl" embraces linear or branched alkyl radicals having one to about ten carbon atoms any one of which may be substituted with one or more alkoxyl radicals. More preferred alkoxyalkyl radicals are "lower alkoxyalkyl" radicals having one to six carbon atoms and one or more alkoxyl radicals. Examples of such radicals include methoxymethyl, ethoxyethyl, propoxypropyl and methoxyethyl. Even more preferred are lower alkoxyalkyl radicals having one to three carbon atoms.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S-portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9α-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

"Heterocycle" means a ring comprising at least one carbon atom and at least one other atom selected from N, O and S. Examples of heterocycles that may be found in the claims include, but are not limited to, the following:

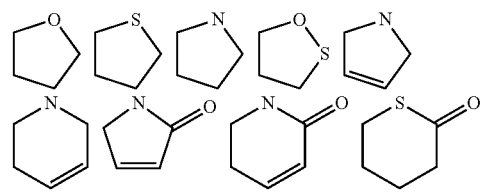

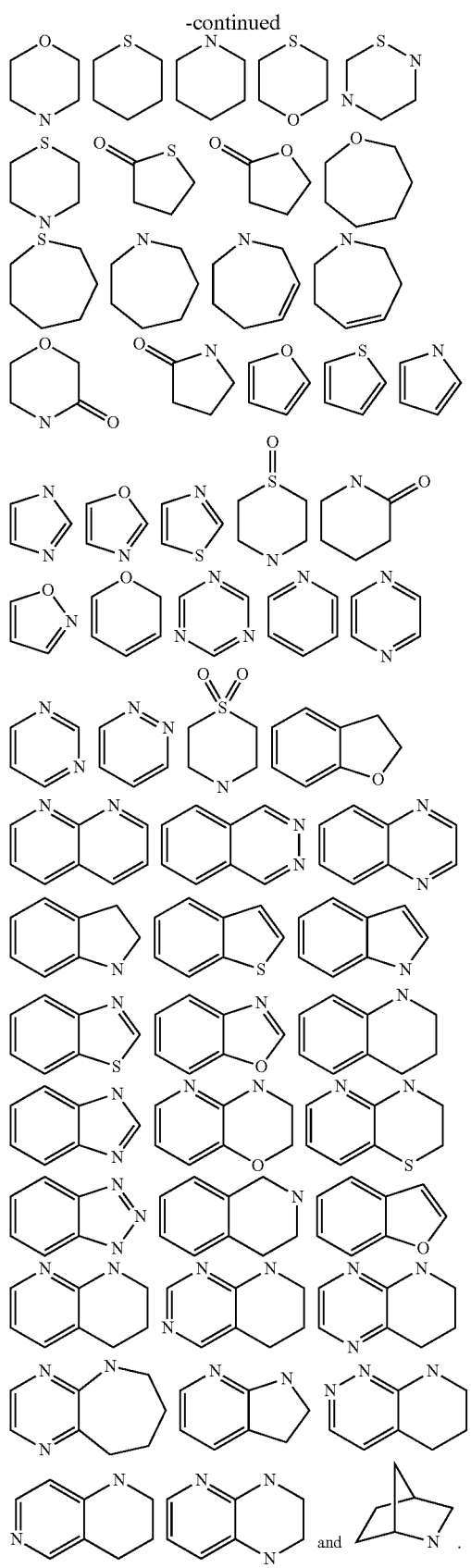

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "alkylcarbonyl" denotes a carbonyl radical substituted with an alkyl group.

The term "alkoxycarbonyl" denotes an ester group, containing an alkoxy substituted carbonyl.

The term "aminocarbonyl" denotes an amide group of the formula —C(=O)NH$_2$.

The terms "aralkyl" or "arylalkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The terms "arylalkenyl" embraces aryl-substituted alkenyl radicals. Preferable aralkyl radicals are "lower arylalkenyl" radicals having aryl radicals attached to alkenyl radicals having two to six carbon atoms. Even more preferred are "phenylalkenyl" where a phenyl ring is attached to alkenyl portions having two to three carbon atoms. The aryl in said arylalkenyl may be additionally substituted with halo, alkyl, alkoxy, halkoalkyl and haloalkoxy.

The terms "cycloalkylalkyl" embraces cycloalkyl-substituted alkyl radicals. Preferable cycloalkylalkyl radicals are "$C_{3-6}$ cycloalkyl-$C_{1-6}$ alkyl" radicals having $C_{3-6}$ cycloalkyl radicals attached to alkyl radicals having one to six carbon atoms. The cycloalkyl in said cycloalkylalkyl may be additionally substituted with halo, alkyl, and the like.

The terms "heterocyclylalkyl" embraces heterocyclyl-substituted alkyl radicals. Preferable heterocyclylalkyl radicals are "3-7 membered heterocyclyl-$C_{1-6}$ alkyl" radicals having 3-7 membered heterocyclyl radicals attached to alkyl radicals having one to six carbon atoms. Other heterocyclylalkyl radicals are "5-7 membered heterocyclyl-$C_{1-3}$ alkyl" radicals having 5-6 membered heterocyclyl radicals attached to alkyl radicals having one to six carbon atoms. The heterocyclyl in said 3-7 membered heterocyclylalkyl may be additionally substituted with halo, alkyl, and the like.

The term "aryloxy" embraces optionally substituted aryl radicals, as defined above, attached to an oxygen atom. Suitable aryloxy radicals may be phenyloxy and the like.

The term "alkylamino" embraces "N-alkylamino" and "N,N-dialkylamino" where amino groups are substituted with one alkyl radical and with two independent alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "alkenylamino" embraces "N-alkenylamino" where amino groups are substituted with one alkenyl radical. More preferred alkenylamino radicals are "lower alkenylamino" radicals having an alkenyl radical of two to six carbon atoms, attached to a nitrogen atom. Even more preferred are lower alkenylamino radicals having two to three carbon atoms.

The term "arylamino" denotes amino groups which have been substituted with one or two aryl radicals, such as N-phenylamino. The arylamino radicals may be further substituted on the aryl ring portion of the radical.

The term "cycloalkylamino" denotes amino groups which have been substituted with one or two cycloalkyl radicals, such as N-cyclohexylamino. The cycloalkylamino radicals may be further substituted on the cycloalkyl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "heterocyclylamino" denotes amino groups which have been substituted with one or two heterocyclyl radicals, such as N-piperidinylamino. The "heterocyclylamino" radicals may be further substituted on the heterocyclyl ring portion of the radical.

The term "aralkylamino" denotes amino groups which have been substituted with one or two aralkyl radicals. More preferred are phenyl-$C_1$-$C_3$-alkylamino radicals, such as N-benzylamino. The aralkylamino radicals may be further substituted on the aryl ring portion.

The term "cycloalkylalkylamino" denotes amino groups which have been substituted with one or two cycloalkylalkyl radicals. More preferred are $C_{1-3}$ cycloalkyl-$C_1$-$C_3$-alkylamino radicals. The cycloalkylalkylamino radicals may be further substituted on the cycloalkyl portion.

The term "heterocyclylalkylamino" denotes amino groups which have been substituted with one or two heterocyclylalkyl radicals. More preferred are 3-7 membered heterocyclyl-$C_1$-$C_6$-alkylamino radicals. Other preferred are 5-6 membered heterocyclyl-$C_1$-$C_3$-alkylamino radicals. The heterocyclylalkylamino radicals may be further substituted on the cycloalkyl portion.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "carboxyalkylamino" embraces amino groups substituted with a carboxyalkyl radical. More preferred carboxyalkylamino radicals are "lower carboxyalkylamino" radicals having one to six carbon atoms. Other preferred carboxyalkylamino groups have alkyl portions with one to three carbon atoms.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "sulfonyl", whether used alone or linked to other terms such as alkylsulfonyl, denotes respectively divalent radicals —$SO_2$—.

The term "alkylsulfonyl" includes sulfonyl radicals substituted with an alkyl radical. More preferred alkylsulfonyl radicals are "lower alkylsulfonyl" radicals having one to six carbon atoms. Even more preferred are lower alkylsulfonyl radicals having one to three carbon atoms. Examples of such lower alkylsulfonyl radicals include methylsulfonyl and ethylsulfonyl.

The term "alkylsulfonylamino" embraces amino groups substituted with an alkylsulfonyl radical. More preferred alkylsulfonylamino radicals are "lower alkylsulfonylamino" radicals having one to six carbon atoms. Other preferred alkylsulfonylamino groups have alkyl portions of one to three carbon atoms.

The term "alkylsulfonylalkylamino" embraces alkylamino groups substituted with an alkylsulfonyl radical. More preferred alkylsulfonylalkylamino radicals are "lower alkylsulfonylalkylamino" radicals having alkyl groups of one to six carbon atoms. Other preferred alkylsulfonylalkylamino groups have alkyl portions of one to three carbon atoms.

The term "alkoxyalkylamino" embraces amino groups substituted with an alkoxyalkyl radical, as previously described. More preferred alkoxyalkylamino radicals are "lower alkoxyalkylamino" radicals having aklyl radicals of one to six carbon atoms. Other preferred alkoxyalkylamino groups have alkyl portions of one to three carbon atoms.

The term "hydroxyalkylamino" embraces amino groups substituted with an hydroxyalkyl radical, as previously described. More preferred hydroxyalkylamino radicals are "lower hydroxyalkylamino" radicals having aklyl radicals of one to six carbon atoms. Other preferred hydroxyalkylamino groups have alkyl portions of one to three carbon atoms.

The term "haloalkylamino" embraces amino groups substituted with a haloalkyl radical, as previously described. More preferred haloalkylamino radicals are "lower haloalkylamino" radicals having aklyl radicals of one to six carbon atoms. Other preferred haloalkylamino groups have alkyl portions of one to three carbon atoms.

The term "aminoalkylamino" embraces alkylamino groups substituted with an amino (—$NH_2$) group. More preferred aminoalkylamino radicals are "lower aminoalkylamino" radicals having alkyl groups of one to six carbon atoms. Other preferred aminoalkylamino groups have alkyl portions of one to three carbon atoms.

The term "aminocarbonylalkylamino" embraces amino groups substituted with an aminocarbonyl radical, as previously described. More preferred aminocarbonylalkylamino radicals are "lower aminocarbonylalkylamino" radicals having aklyl radicals of one to six carbon atoms. Other preferred aminocarbonylalkylamino groups have alkyl portions of one to three carbon atoms.

The term "alkoxycarbonylalkylamino" embraces amino groups substituted with an alkoxycarbonyl radical, as previously described. More preferred alkoxycarbonylalkylamino radicals are "lower alkoxycarbonylalkylamino" radicals having aklyl radicals of one to six carbon atoms. Other preferred alkoxycarbonylalkylamino groups have alkyl portions of one to three carbon atoms.

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The term "oxo" represents the groups =O (as in carbonyl).

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups, and the like, for example as illustrated in the following examples:

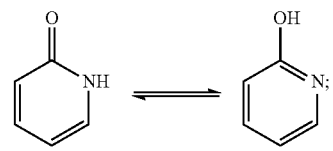 [SMILES: O=c1cccc[nH]1 ; Oc1ccccn1]

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Utility and Methods of Use

An aspect of the present invention is a method for inhibiting Pim kinase activity in a cell, comprising contacting the cell with an effective amount of a compound of Formula 1-12.

Another aspect of the present invention provides a method for treating a condition by modulation of Pim kinase activity comprising administering to a patient in need of such treatment an effective amount of a compound of Formula 1-12.

Another embodiment of the present invention provides a method for treating a cancer disorder in a patient, comprising administering to the patient a composition comprising an amount of a compound of Formula 1-12 effective to inhibit Pim kinase activity in the patient.

Another embodiment of the present invention provides a method for treating a cancer disorder in a patient, wherein the cancer is prostate, head and neck or lymphoma, comprising administering to the patient a composition comprising an amount of a compound of Formula 1-12 effective to inhibit Pim kinase activity in the patient.

Another aspect of the present invention provides the use of any one of the compounds of Formula 1-12 in the manufacture of a medicament for the treatment of cancer.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of formula (1) may range from approximately 0.1-1000 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compounds of the present invention in combination with at least one pharmaceutically acceptable excipient. Acceptable excipients are non-toxic, aid administration, and do not adversely affect the therapeutic benefit of the compounds of the present invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compounds of the present invention based on the total formulation, with the balance being one or more suitable pharmaceutical excipients. Preferably, the compound is present at a level of about 1-80 wt %.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Synthetic Methods

The following abbreviations may be used herein:
Ac$_2$O acetic anhydride
AcOH or HOAc acetic acid
ACN acetonitrile
(A-Phos)$_2$PdCl$_2$ bis[(di-tert-butyl(4-dimethylaminophenyl)-phosphine)]palladium dichloride
aq aqueous ATP adenosine 5'-triphosphate
(BPin)$_2$ bis(pinacolato)diboron
BrettPhos dicyclohexyl(2',4',6'-triisopropoxy-3,6-dimethoxy-[1,1'-biphenyl]-2-yl)phosphine
nBuLi n-butyllithium
t-BuOH tert butyl alcohol
CDCl$_3$ deuterated chloroform
CHCl$_3$ chloroform
Calcd or Calc'd calculated
Conc. concentrated
CuI copper (I) iodide
DCM dichloromethane
DDQ 2,3-dichloro-5,6-dicyano-1,4-benzoquinone
DIPEA, DIEA diisopropylethylamine
DMF N,N-dimethylformamide
DMSO dimethyl sulfoxide
DTT dithiothreitol
EDTA ethylenediamine tetraacetic acid Alternatively, the present compounds may also be used in co-therapies with other agents, such as other kinase inhibitors including CDK inhibitors, mTor inhibitors, Pi3k inhibitors, and Aurora kinase inhibitors.

ESI electrospray ionization
Et$_2$O diethyl ether
Et$_3$N or TEA triethylamine
EtOAc ethyl acetate
EtOH ethyl alcohol
FBS fetal bovine serum
g grams
h hour
HATU O-(7-azobenzotriazol-1-yl)-1,1,3,3-tetramethyluronium hexafluorophosphate
H$_2$ hydrogen
HCl hydrochloric acid
HCO$_2$H formic acid
H$_2$O water
H$_2$O$_2$ hydrogen peroxide
Hex hexanes
HPLC high pressure liquid chromatography
IPA or iPrOH isopropyl alcohol
KF potassium fluoride
KHSO$_4$ potassium bisulfate
KOAc potassium hydroxyacetate
K$_2$CO$_3$ potassium carbonate
K$_3$PO$_4$ potassium phosphate
L liter
LCMS, LC-MS or LC/MS liquid chromatography mass spectroscopy
LDA lithium diisopropylamide
LHMDS or LiHMDS lithium bis(trimethylsilyl)amide
LiOH lithium hydroxide
m/z mass divided by charge
MeI iodomethane
MeOH methyl alcohol
mg milligrams
min minutes
mL milliliters
MgSO$_4$ magnesium sulfate
MS mass spectra
N$_2$ nitrogen
NH$_3$ ammonia
NH$_4$OH ammonium hydroxide
NH$_4$OAc ammonium acetate
NH$_4$Cl ammonium chloride
NaH sodium hydride
NaOH sodium hydroxide
Na$_2$CO$_3$ sodium carbonate
Na$_2$SO$_4$ sodium sulfate
NaHMDS sodium bis(trimethylsilyl)amide
NBS N-bromosuccinimide
NMP 1-methyl-2-pyrrolidinone
NMR nuclear magnetic resonance
Pd(PPh$_3$)$_4$ tetrakis(triphenylphosphine)-palladium (0)
PdCl$_2$(PPh$_3$)$_2$ dichloro bis(triphenylphosphine)-palladium (II)
Pd$_2$dba$_3$ tris(dibenzylideneacetone)dipalladium (0)
Pd(dppf)Cl$_2$ [(1,1-bis(diphenylphosphino)ferrocene]dichloropalladium(II)
Pd(tBu$_3$P)$_2$ bis(tri-tert-butylphosphine)palladium (0)
PdCl$_2$ palladium chloride
P protecting group
POCl$_3$ phosphorus oxychloride
Pos. ion positive ion
rt or RT room temperature
Sat. saturated
TBSOTf tert-butyldimethylsilyl trifluoromethanesulfonate
TFA trifluoroacetic acid
THF tetrahydrofuran
Ts or tosyl para-toluene sulfonyl
wt weight
Xantphos 9,9-dimethyl-4,5-bis(diphenylphosphino)xanthene
Xphos 2-dicyclohexylphosphino-2',4',6'-triisopropylbiphenyl The compounds of the invention can be prepared according to the following procedures of Schemes 1-12, wherein the substituents are as defined for Formulas 1-12 above, except where noted.

Scheme 1

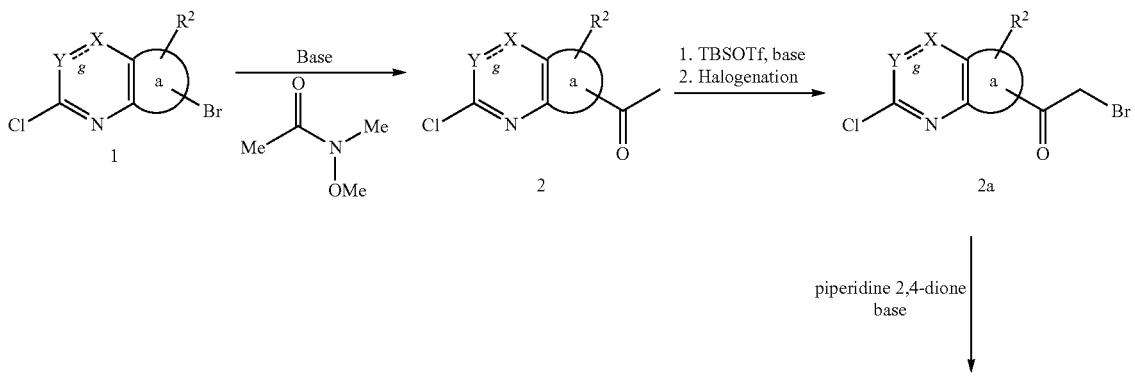

-continued

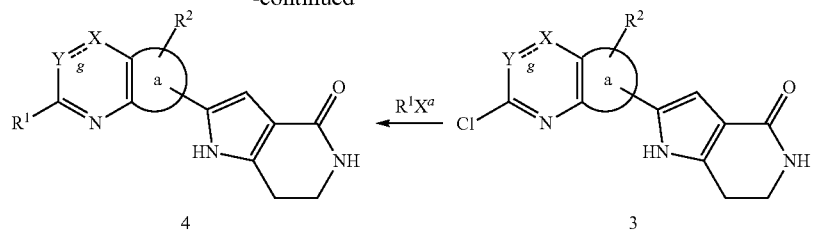

Substituted 6,7-dihydro-1H-pyrrolo[3,2-c]pyridin-4(5H)-ones 4 can be prepared according to the method set out in Scheme 1. A strong alkyl metal, such as an organolithium reagents (e.g. butyllithium) is added to a solution of a dihalobicyclic ring 1 at a temperature below 0° C., preferably below −50° C., even more preferably at about −72° C. Treatment with an acetamide at a temperature below 0° C., preferably below −50° C., even more preferably at about −70° C. yields the acetyl derivative 2. Bromination of the acetyl derivative 2, such as with a base, e.g Et$_3$N, tert-butyldimethylsilyl trifluoromethanesulfonate, and bromination such as with NBS, provides the desired bromoacetyl compound 2a. Treatment of the bromoacetyl compound 2a with an ammonia salt, such as NH$_4$OAc, and piperidine-2,4-dione at a temperature above RT, preferably at about 50° C. affords the 6,7-dihydro-1H-pyrrolo[3,2-c]pyridin-4(5H)-one 3. Substitution of the remaining halo group provides further compounds 4. For example, treatment with arylamines such as aniline, in the presence of a strong non-nucleophilic base, e.g. LHMDS, provides the desired amine derivatives. Alternatively, where the chloro substituent is methyl ester substituent, treatment of compound 1 with a palladium catalyst, such as Pd(PPh$_3$)$_4$ and a tin reagent, such as tributyl(1-ethoxyvinyl)tin, at a temperature higher than RT, preferably above about 50° C., more preferably at about 100° C. provides the corresponding the acetyl derivative 2 [with the ester substitution].

Scheme 2

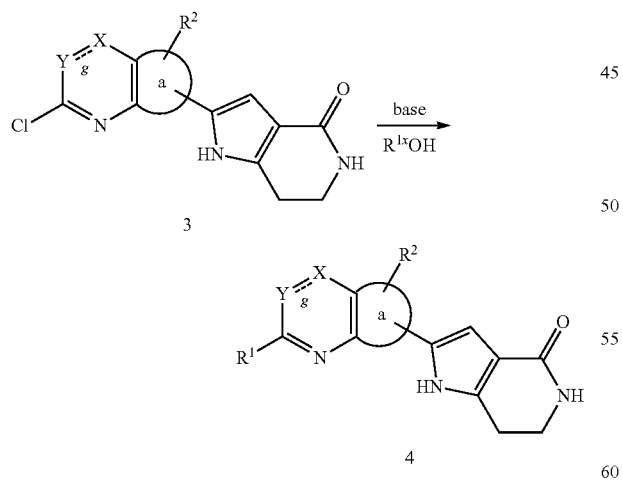

Similarly, ether substituted compounds 4, where R$^1$ is alkoxy, aryloxy and the like, can be prepared according to the method set out in Scheme 2. Alcohols [R$^{1x}$OH] are treated with strong base, such as NaH, then added to the chloro substituted compounds 3 furnished substituted 6,7-dihydro-1H-pyrrolo[3,2-c]pyridin-4(5H)-ones 4.

Scheme 3

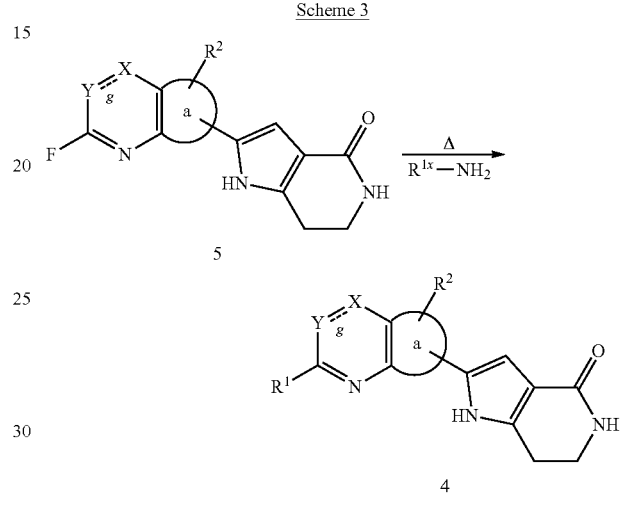

Amino substituted compounds 4, where R$^1$ is alkylamino, arylamino and the like, are prepared by the method described in Scheme 3. Fluoro-substituted compounds 5 and an optionally substituted amine [R$^{1x}$NH$_z$] are heated at a temperature higher than RT, preferably above about 50° C., more preferably at about 80° C. to furnish the desired amines 4.

Scheme 4

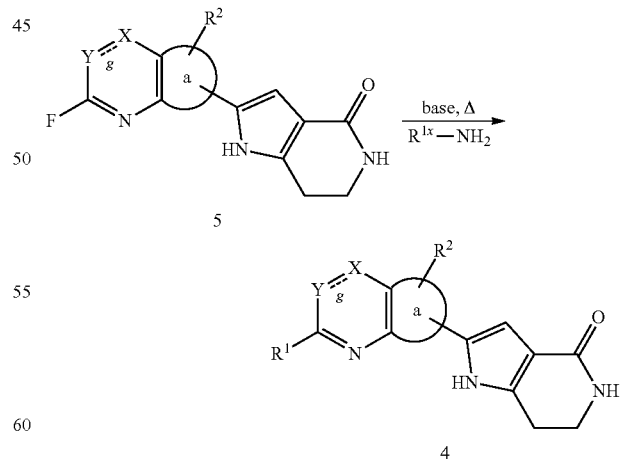

Amino substituted compounds 4, where R$^1$ is heterocyclylamino, and the like, are prepared by the method described in Scheme 4. Fluoro-substituted compound 3 is reacted with a substituted amine salt [R$^{1x}$NH$_2$salt] and base, such as DIPEA, at a temperature higher than RT, preferably above about 50° C., more preferably at about 100° C. to furnish the desired amines 4.

Scheme 5

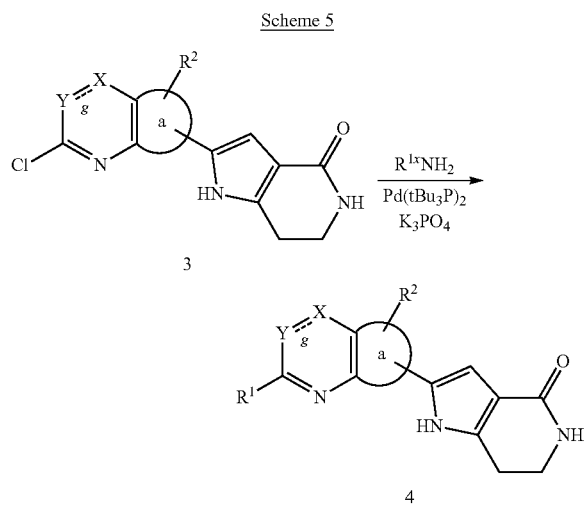

Amino substituted compounds 4, where R¹ is substituted alkylamino, and the like, are prepared by the method described in Scheme 5. Chloro-substituted compound 3 is reacted with a substituted alkylamine [$R^{1x}NH_2$], a catalyst, such as a palladium catalyst, preferably bis(tri-tert-butylphosphine)palladium (0), and a base, such as $K_3PO_4$, at a temperature higher than RT, preferably above about 100° C., more preferably at about 145° C. to furnish the desired amines 4. Alternatively, chloro-substituted compounds 3, is treated with dicyclohexyl(2',4',6'-triisopropoxy-3,6-dimethoxy-[1,1'-biphenyl]-2-yl)phosphine, and BrettPhos precatalyst and a substituted amine, such as a cycloalkylamine [$R^{1x}NH_2$], and a base, such as LiHMDS. The mixture is heated at a temperature higher than RT, preferably above about 50° C., more preferably at about 100° C. to furnish the desired amines 4.

Scheme 6

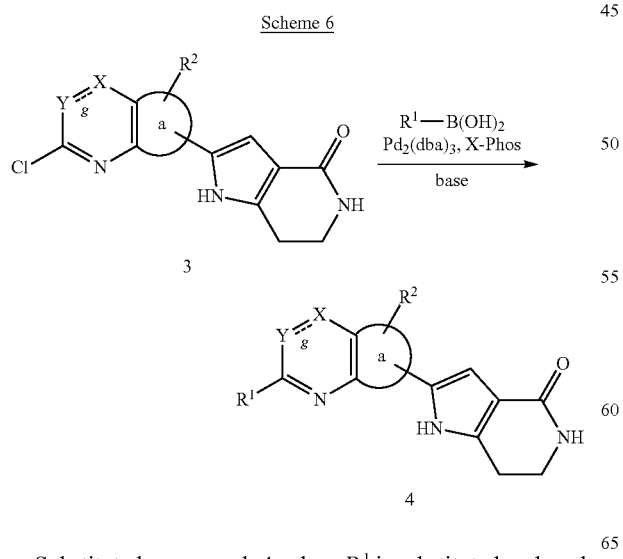

Substituted compounds 4, where R¹ is substituted aryl, and the like, are prepared by the method described in Scheme 6.

Chloro-substituted compound 3 is reacted with a substituted arylboronic acid [$R^1$—$B(OH)_2$], dicyclohexyl(2',4',6'-triisopropyl-[1,1'-biphenyl]-2-yl)phosphine, (X-Phos), a catalyst, such as a palladium catalyst, preferably $Pd_2(dba)_3$, and a base, such as $K_3PO_4$, at a temperature higher than RT, preferably above about 100° C., more preferably at about 130° C. to furnish the desired compounds 4.

Scheme 7

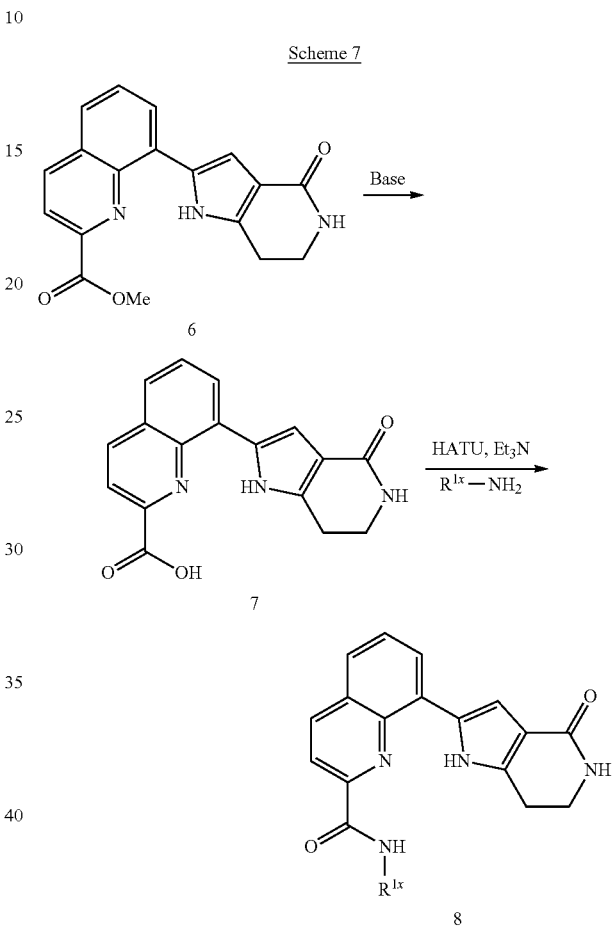

Substituted amides 8, where $R^{1x}$ is alkyl, cycloalkyl, substituted aryl, and the like, are prepared by the method described in Scheme 7. Ester quinolines 6 are converted to the corresponding acids 7 with basification, such as with treatment with NaOH. Treatment with an amine, where $R^{1x}$ is H, alkyl aryl etc., a coupling agent such as HATU, and a base, such as $Et_3N$, at a temperature about RT, affords the desired amides 8.

Scheme 8

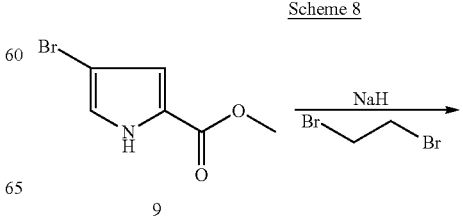

-continued

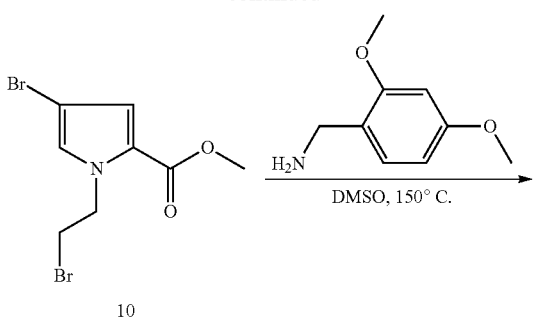

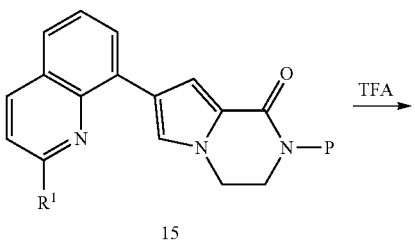

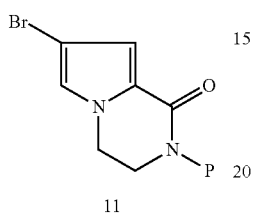

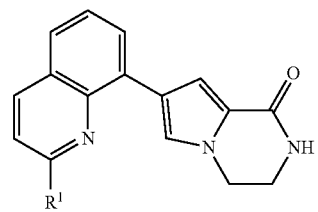

Other cyclic amides can be prepared such as the 3,4-dihydropyrrolo[1,2-a]pyrazin-1(2H)-ones 11 as described in Scheme 8. Methyl 4-bromo-1H-pyrrole-2-carboxylate 9 is reacted with base, such as NaH, and 1,2 dibromoethane at a temperature higher than RT, preferably above about 50° C., more preferably at about at 70° C. to afford the bromoethyl derivative 10. Cyclization, such as with treatment with (2,4-dimethoxyphenyl)methanamine, at a temperature higher than RT, preferably above about 100° C., more preferably at about at 150° C. yields the protected bromo-3,4-dihydropyrrolo[1,2-a]pyrazin-1(2H)-one 11.

Scheme 9

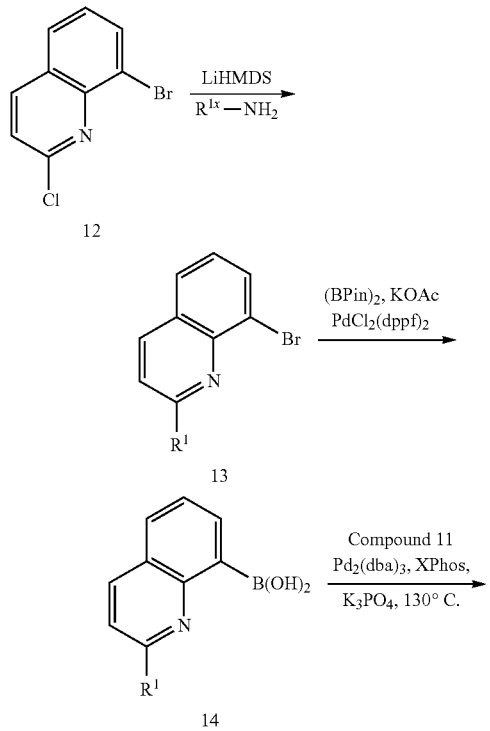

Other cyclic amides of the present invention can be prepared such as the 3,4-dihydropyrrolo[1,2-a]pyrazin-1(2H)-ones 16 as described in Scheme 9. Substituted amines are coupled to the 8-bromo-2-chloroquinoline through treatment with base, such as LiHMDS, at a temperature of about RT, to afford the desired 8-bromoquinolin-2-amine 13. The bromo compound 13 is converted to the boronic acid 14 via treatment with a palladium catalyst, such as Pd(dppf)$_2$Cl$_2$, bis(pinacolato)diboron, and a base such as KOAc, at a temperature higher than RT, preferably above about 75° C., more preferably at about at 115° C. Coupling of the boronic acid 14 with the protected 7-bromo-3,4-dihydropyrrolo[1,2-a]pyrazin-1(2H)-one 11 such as in the presence of a palladium catalyst, such as Pd$_2$(dba)$_3$ or bis(di-tert-butyl(4-dimethylaminophenyl)phosphine)-dichloro-palladium(II), and dicyclohexyl(2',4',6'-triisopropyl-[1,1'-biphenyl]-2-yl)phosphine and a base such as K$_3$PO$_4$, at a temperature higher than RT, preferably above about 75° C., more preferably at about at 130° C., gave the protected 7-(quinolin-8-yl)-3,4-dihydropyrrolo[1,2-a]pyrazin-1(2H)-one 15. Deprotection, such as with acid, at a temperature higher than RT, preferably at about 50° C., affords the desired 7-(quinolin-8-yl)-3,4-dihydropyrrolo[1,2-a]pyrazin-1(2H)-one 16.

Scheme 10

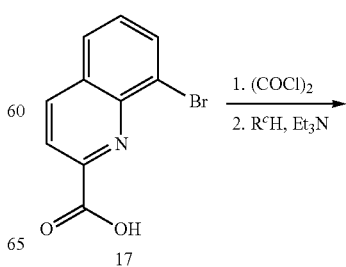

-continued

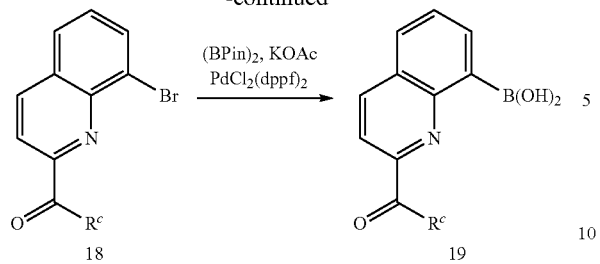

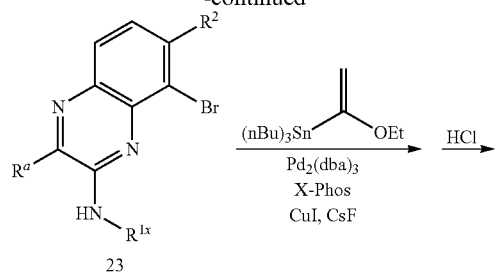

Other boronic acids can be prepared similar to that shown in Scheme 10. Conversion of the carboxylic acid 17 to the acyl derivative 18 is achieved through treatment with oxalyl chloride, at about RT. Substitution with a nitrogen-containing heterocyclic ring, such as $R^c$ is morpholine, piperidine, piperazine or the like, in the presence of base such as $Et_3N$, at about RT, gave the substituted (8-bromoquinolin-2-yl)methanone 18. Conversion to the boronic acid is accomplished following a procedure similar to that described in Scheme 9.

Scheme 11

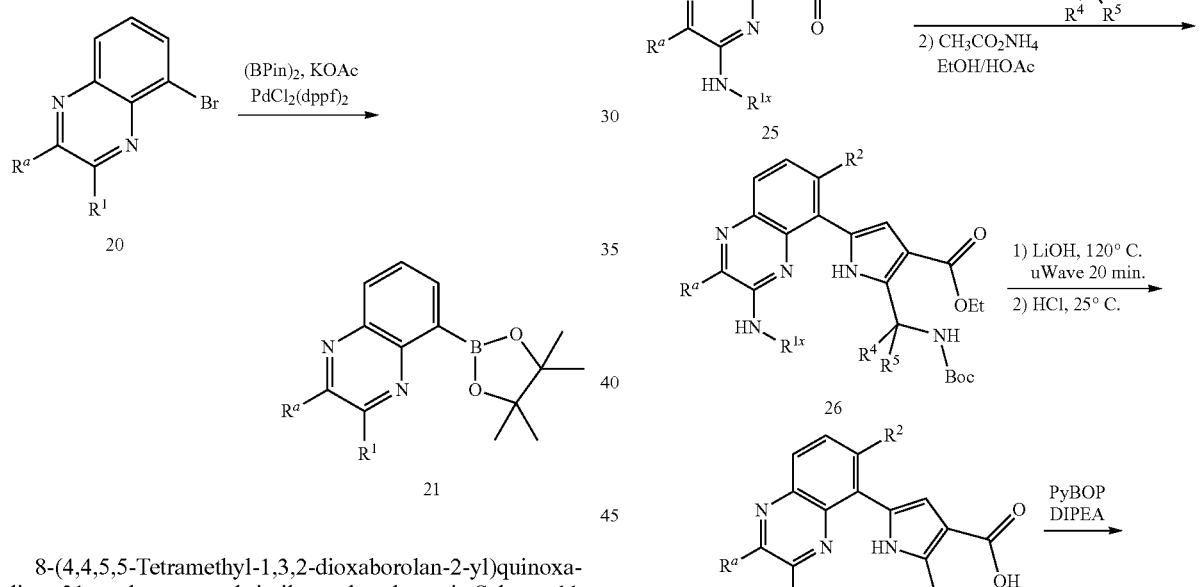

8-(4,4,5,5-Tetramethyl-1,3,2-dioxaborolan-2-yl)quinoxalines 21 can be prepared similar to that shown in Scheme 11. Treatment of the bromo compound 20 with bis(pinacolato)diboron, a palladium catalyst such as $PdCl_2(dppf)_2$, and a base, such as potassium acetate, at a temperature higher than RT, preferably above about 75° C., more preferably at about at 105° C., affords the desired boron derivative 21.

Scheme 12

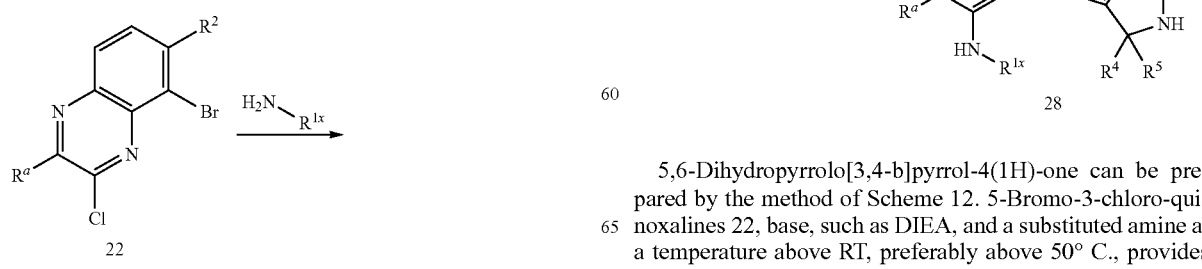

5,6-Dihydropyrrolo[3,4-b]pyrrol-4(1H)-one can be prepared by the method of Scheme 12. 5-Bromo-3-chloro-quinoxalines 22, base, such as DIEA, and a substituted amine at a temperature above RT, preferably above 50° C., provides the 3-aminoquinoxalines 23. Treatment of the 3-aminoquinoxalines 23 with tributyl(1-ethoxyvinyl)tin in the presence of a palladium catalyst such as $Pd_2dba_3$, Xphos, CuI and cesium fluoride at a temperature above RT, preferably above 50° C., provides the ethanones 24. Bromination of the ethanone 24 such as by treatment with tert-butyldimethylsilyl trifluoromethanesulfonate in the presence of base, e.g. TEA, at a temperature below RT, preferably about 0 C, followed by treatment with NBS provides the bromoethanone 25. Formation of ester substituted pyrroles 26 form bromoethanone 25 is accomplished such as by reaction with substituted ethyl 3-(1-(tert-butoxycarbonyl)amino)-3-oxopropanoate. Conversion of the esters 26, such as treatment with LiOH and acid, provides the carboxylic acids 27. Treatment of the carboxylic acids with PyBOP forms the desired 1,6'-pyrrolo[3,4-b]pyrrol]-4'(5'H)-ones 28.

The starting compounds defined in Schemes 1-12 may also be present with functional groups in protected form if necessary and/or in the form of salts, provided a salt-forming group is present and the reaction in salt form is possible. If so desired, one compound of formulas 1-12 can be converted into another compound of formulas 1-12 or a N-oxide thereof; a compound of formulas 1-12 can be converted into a salt; a salt of a compound of formulas 1-12 can be converted into the free compound or another salt; and/or a mixture of isomeric compounds of formulas 1-12 can be separated into the individual isomers.

N-Oxides can be obtained in a known manner by reacting a compound of formulas 1-12 with $H_2O_2$ or a peracid, e.g. 3-chloroperoxy-benzoic acid, in an inert solvent, e.g. dichloromethane, at a temperature between about −10-35° C., such as about 0° C.—RT.

If one or more other functional groups, for example carboxy, hydroxy, amino, or mercapto, are or need to be protected in a compound of formulas 1-12 or in the synthesis of a compound of formulas 1-12, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide and Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formulas 1-12 with a salt-forming group may be prepared in a manner known per se. Acid addition salts of compounds of formulas 1-12 may thus be obtained by treatment with an acid or with a suitable anion exchange reagent. A salt with two acid molecules (for example a dihalogenide of a compound of formulas 1-12) may also be converted into a salt with one acid molecule per compound (for example a monohalogenide); this may be done by heating to a melt, or for example by heating as a solid under a high vacuum at elevated temperature, for example from about 130° C. to about 170° C., one molecule of the acid being expelled per molecule of a compound of formulas 1-12.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., ethyl acetate, ethers, typically aliphatic ethers, e.g., diethylether, or cyclic ethers, e.g., THF, liquid aromatic hydrocarbons, typically benzene or toluene, alcohols, typically MeOH, EtOH or 1-propanol, 2-propanol, nitriles, typically ACN, halogenated hydrocarbons, typically DCM, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formulas 1-12, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maxim/ze the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIPEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); A. Katritzky and A. Pozharski, Handbook of Heterocyclic Chemistry, $2^{nd}$ Ed. (2001); M. Bodanszky, A. Bodanszky: *The practice of Peptide Synthesis* Springer-Verlag, Berlin Heidelberg 1984; J. Seyden-Penne: *Reductions by the Alumino-and Borohydrides in Organic Synthesis*, $2^{nd}$ Ed., Wiley-VCH, 1997; and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas 1-12. These detailed descriptions fall within the scope, and serve to exemplify, the above described General Synthetic Procedures which form part of the invention. These detailed descriptions are presented for illustrative purposes only and are not intended as a restriction on the scope of the invention.

EXPERIMENTAL

Unless otherwise noted, all materials were obtained from commercial suppliers and used without further purification. All parts are by weight and temperatures are in degrees centigrade unless otherwise indicated. All microwave assisted reactions were conducted with a Initiator™ Microwave Synthesizer from Biotage™. All compounds showed NMR spectra consistent with their assigned structures. Melting points were determined on a Buchi apparatus and are uncorrected. MS data was determined by electrospray ionization technique. All examples were purified to >90% purity as determined by high-performance liquid chromatography. Unless otherwise stated, reactions were run at RT.

Analytical Methods:

Unless otherwise indicated, HPLC analyses were run on an Agilent Model 1100 system with an Agilent Technologies Zorbax SB-C$_8$(5μ) reverse phase column (4.6×150 mm) run at 30° C. with a flow rate of about 1.50 mL/min (Agilent Technologies, Santa Clara, Calif.). The mobile phase used solvent A (H$_2$O/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Methods:

Unless otherwise indicated, samples were run on an Agilent model-1100 LC-MSD system with an Agilent Technologies XDB-C$_8$ (3.50 reverse phase column (4.6×75 mm) at 30° C. The flow rate was constant and ranged from about 0.75 mL/min to about 1.0 mL/min. The mobile phase used a mixture of solvent A (H$_2$O/0.1% HCO$_2$H or TFA) and solvent B (ACN/0.1% HCO$_2$H or TFA) with a 5 to for a gradient from 10% to 90% solvent B. The gradient was followed by a 0.5 min period 9 min time period to return to 10% solvent B and a min 10% solvent B re-equilibration (flush) of the column Preparative HPLC Methods:

Where indicated, compounds of the present invention were purified via reverse phase HPLC using a Gilson (Gilson, Middleton, Wis.) or Shimadzu (Columbia, Md.) workstation utilizing one of the following two protocols: (A) Using a 50×100 mm column (Waters, Externa, C$_{18}$, 5μ) (Waters, Milford, Mass.) at 50 mL/min. The mobile phase used was a mixture of solvent A (H$_2$O/10 mM ammonium carbonate at pH about 10, adjusted with conc. NH$_4$OH) and solvent B (85:15 ACN/water, 10 mM ammonium carbonate at pH of about 10 adjusted with conc. NH$_4$OH). Each purification run utilized a ≥10 min gradient from 40% to 100% solvent B followed by a 5 min flow of 100% solvent B. The gradient was followed by a 2 min return to 40% solvent B; or (B) Using a Waters 20×50 mm column at 20 mL/min or Phenomenex Gemini 5μ C$_{18}$ 100×30 mm (Phenomenex, Torrance, Calif.). The mobile phase used was a mixture of solvent A (H$_2$O/0.1% TFA) and solvent B (ACN/0.1% TFA) with a ≥10 min gradient from 5% to 100% solvent B. The gradient is followed by a 2 min return to 5% ACN.

Mass Spectra (MS)

Unless otherwise indicated, all mass spectral data for starting materials, intermediates and/or exemplary compounds are reported as mass/charge (m/z), having an (M+H) or (M−H) molecular ion, depending on the ionization mode (positive or negative). The molecular ion reported was obtained by electrospray detection method. Compounds having an isotopic atom, such as bromine and the like, are reported according to the detected isotopic pattern, as appreciated by those skilled in the art.

Preparation of 2-chloro-8-iodo-3-methylquinazolin-4 (3H)-one (700)

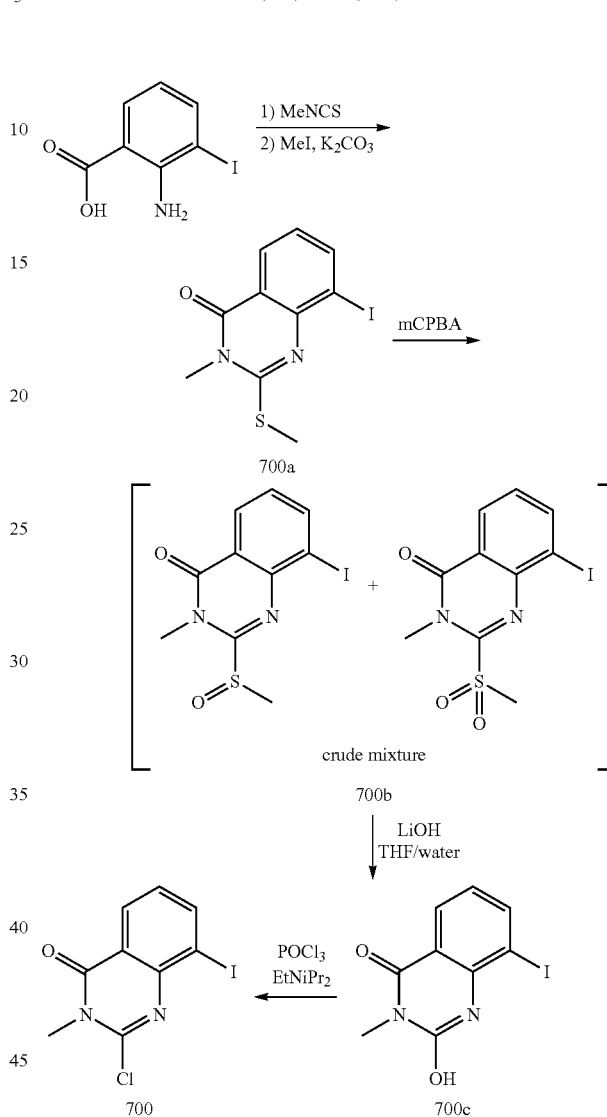

Preparation of 8-iodo-3-methyl-2-(methylthio) quinazolin-4(3H)-one (700a)

A sealable flask was charged with 2-amino-3-iodobenzoic acid (Bosche Scientific; 10 g, 38.0 mmol) and methyl isothiocyanate (5.56 g, 76 mmol) in EtOH (120 mL) followed by TEA (7.93 mL, 57.0 mmol). The flask was sealed and heated in an oil bath at 100° C. for 4 h with a blast shield. The mixture was cooled to RT and the solvent was removed in vacuo. The residue was triturated with Et$_2$O (40 mL) and filtered, dried to give 8-iodo-3-methyl-2-thioxo-2,3-dihydroquinazolin-4 (1H)-one (11.22 g, 35.3 mmol, 93% yield) as an off white solid. Crude material was used in the next step. $^1$H NMR (400 MHz, DMSO-d$_6$) δ ppm 9.97 (1H, br.), 8.23 (1H, d, J=8.4 Hz), 8.00 (1H, d, J=8.0 Hz), 7.15 (1H, t, J=7.5 Hz), 3.65 (3H, s).). m/z (ES, +ve) 318.8 (M+H)$^+$.

At RT, to a mixture of 8-iodo-3-methyl-2-thioxo-2,3-dihydroquinazolin-4(1H)-one (11.2 g g, 35.3 mmol) and K$_2$CO$_3$ (9.76 g, 70.6 mmol) in THF (100 mL) was added MeI (6.58 mL, 106 mmol). The reaction was heated to reflux for 6 h, and then cooled to RT. The mixture was poured into ice/water (300 mL) and stirred for 10 min. The suspension was filtered and the solid was washed with cold water (20 mL) followed by cold ether (20 mL). The solid was dried to give 8-iodo-3-methyl-2-(methylthio)quinazolin-4(3H)-one (700a; 11.4 g, 97% yield) as an off-white solid. Crude material was used in the next step. $^1$H NMR (400 MHz, DMSO-d$_6$) δ ppm 8.31 (1H, dd, J=7.6, 1.4 Hz), 8.08 (1H, dd, J=7.8, 1.4 Hz), 7.19 (1H, t, J=7.7 Hz), 3.51 (3H, s), 2.73 (3H, s). m/z (ES, +ve) 332.9 (M+H)$^+$.

Preparation of 2-chloro-8-iodo-3-methylquinazolin-4(3H)-one (700)

A suspension of 8-iodo-3-methyl-2-(methylthio)quinazolin-4(3H)-one (700a; 15 g, 45.2 mmol) in 400 mL of DCM was set stirring at 0° C. before adding 3-chlorobenzoperoxoic acid (15.59 g of 77% max. Aldrich, 70 mmol) portion wise over 10 min. The ice bath was removed; and the reaction mixture was stirred at RT for 30 min. It was diluted with 200 mL of DCM, washed sequentially with ice cold 2×50 mL of saturated Na$_2$CO$_3$ followed by sat. Na$_2$SO$_3$ solution and 15 mL of brine. The organic solution was dried over Na$_2$SO$_4$, filtered, and concentrated under reduced pressure to give yellow crystalline solid (700b) containing a mixture of 8-iodo-3-methyl-2-(methylsulfinyl)quinazolin-4(3H)-one and 8-iodo-3-methyl-2-(methylsulfonyl)quinazolin-4(3H)-on. The crude material of yellow crystalline solid (700b) in 40 mL of THF and 40 mL of water at RT was treated with LiOH—H$_2$O (6.60 g, 275 mmol). The reaction mixture was stirred in an oil bath at 75° C. for 2.5 h. It was concentrated to half of its volume under reduced pressure. The precipitated solid was filtered, rinsed with 2×5 mL of water followed by 2×5 mL of ether. The off-white crystalline solid was dried in a vacuum oven at 45° C. for 48 h to give 2-hydroxy-8-iodo-3-methylquinazolin-4(3H)-one (700c; 12.79 g, 42.3 mmol, 94% yield). The crude material was used in the next step. m/z (ES, +ve) 302.9 (M+H)$^+$.

At RT, to the off-white solid of 2-hydroxy-8-iodo-3-methylquinazolin-4(3H)-one (700c; 12.79 g, 42.3 mmol) was added POCl$_3$ (46.5 mL, 508 mmol). The resulting white suspension was treated with DIPEA (14.73 mL, 85 mmol) dropwise. The heterogeneous mixture was heated in an oil bath at 105° C. for 26 h. LCMS indicated the reaction was about 60% conversion. It was cooled to RT, and treated with additional POCl$_3$ (12 mL) and DIPEA (14.73 mL, 85 mmol). The resulting dark homogeneous solution was heated at 110° C. in an oil bath for 24 h. LCMS indicated the reaction was about >95% conversion. It was concentrated under reduced pressure. The brown sticky solution was treated with 50 mL of toluene and concentrated under reduced pressure again. The brown residue was cooled with an ice bath, ice was added to the flask, followed by 5 N NaOH solution till pH >9. It was extracted with 3×250 mL of EtOAc. The combined organic solution was washed with 2×25 mL of brine, dried over Na$_2$SO$_4$, filtered and concentrated. The brown residue was purified via silica gel chromatography (25-50% EtOAc in hexanes) to afford 2-chloro-8-iodo-3-methylquinazolin-4(3H)-one (700; 10.51 g, 32.8 mmol, 77% yield) as an off-white crystalline solid. $^1$H NMR (400 MHz, CDCl$_3$) δ ppm 8.21-8.32 (m, 2H), 7.22 (t, J=7.82 Hz, 1H), 3.77 (s, 3H). m/z (ES, +ve) 328.8 (M+H)$^+$.

Preparation of 2-(tert-butylamino)-8-iodo-3-methylquinazolin-4(3H)-one (701)

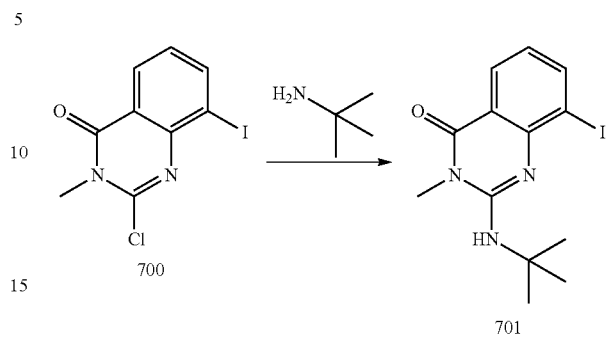

A heterogeneous mixture of tert-butylamine (22.83 mL, 217 mmol) and 2-chloro-8-iodo-3-methylquinazolin-4(3H)-one (700) (4.64 g, 14.48 mmol) in 2 mL of THF in a 100 mL RBF fitted with a reflux condenser was heated in an oil bath at 50° C. for 4 h. The reaction mixture was concentrated under reduced pressure and the brown solid was dissolved in 300 mL of EtOAc, washed sequentially with 10 mL of water, 10 mL of sat. NaHCO$_3$ solution and 10 mL of brine. The organic solution was concentrated. The residue was purified on a silica gel column (25-55% EtOAc in hexanes) to afford 2-(tert-butylamino)-8-iodo-3-methylquinazolin-4(3H)-one (4.64 g, 12.99 mmol, 90% yield) as a yellow crystalline solid. $^1$H NMR (400 MHz, DMSO-d$_6$) δ ppm 8.12 (1H, dd, J=7.5, 1.3 Hz), 7.93 (1H, dd, J=7.8, 1.2 Hz), 6.89 (1H, t, J=7.6 Hz), 6.02 (1H, s), 3.41 (3H, s), 1.60 (9H, s). m/z (ES, +ve) 358.1 (M+H)$^+$.

Preparation of (R)-6-methyl-5,6-dihydropyrrolo[3,4-b]pyrrol-4(1H)-one (702)

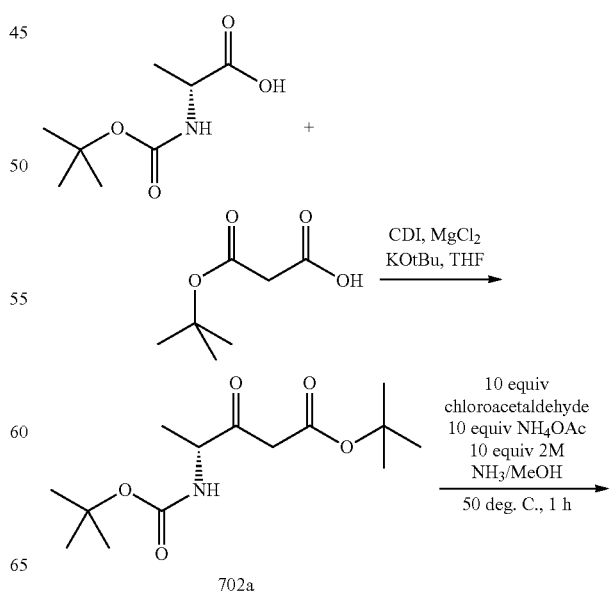

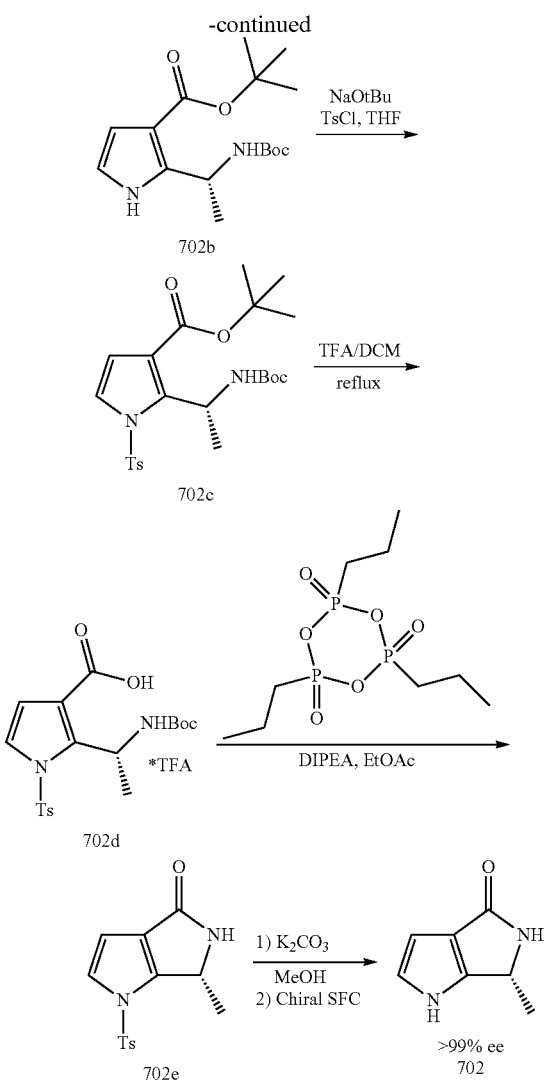

Preparation of (R)-tert-butyl 4-((tert-butoxycarbonyl)amino)-3-oxopentanoate (702a)

Flask A: To a clear solution of mono-tert-butyl malonate (29.3 mL, 190 mmol) and magnesium chloride anhydrous (Aldrich; 18.12 g, 190 mmol) in 400 mL THF in a 3 neck 3000 mL RBF with temperature probe and mechanical stirrer at 2° C. was added potassium tert-butoxide (1.0 M solution in THF, Aldrich; 190 mL, 190 mmol) slowly dropwise via addition funnel such that the temperature did not exceed 10° C. The reaction became cloudy over the addition and was easy to stir. the ice bath was removed, and the reaction was stirred at RT for 3 h. Flask B: To a clear solution of Boc-D-alanine (Chem Impex Intl.; 30.0 g, 159 mmol) in 300 mL THF at RT under $N_2$ (fitted with $N_2$ inlet and gas outlet to bubbler) was added 1,1'-carbonyldiimidazole (Aldrich; 0.926 g, 5.71 mmol) in three portions separated by 5 min. Gas evolution observed. The reaction was stirred 3 h. Then the contents in Flask B were added via funnel to Flask A and the cloudy white reaction was stirred 39 h at RT. The resulting white suspension was cooled in an ice bath and 500 mL 1 N HCl was added at a rate such that the internal temperature did not exceed 20° C. 0.8 L $Et_2O$ was added and the mixture transferred to a separatory funnel. The layers were separated and the organic layer was washed sequentially with 1×200 mL 1 N HCl, 1×200 mL water, 2×200 mL sat'd aq. $NaHCO_3$, 1×200 mL brine, and was dried over anhydrous magnesium sulfate, filtered, and concentrated in vacuo. The resulting clear/colorless oil was treated with small crystals of the desired product and was further concentrated on the rotovap to give a white solid. The material was dried in vacuo for 2 h to give (R)-tert-butyl 4-((tert-butoxycarbonyl)amino)-3-oxopentanoate (34.3 g, 119 mmol, 75% yield) as a white solid. $^1$H NMR (400 MHz, $CDCl_3$) δ ppm 5.15 (1H, br. s.), 4.30-4.51 (1H, m), 3.38-3.58 (2H, m), 1.48 (9H, s), 1.46 (9H, s), 1.37 (3H, d, J=7.2 Hz). m/z (ESI, +ve) 310.1 (M+Na)$^+$.

Preparation of (R)-tert-butyl 2-(1-((tert-butoxycarbonyl)amino)ethyl)-1H-pyrrole-3-carboxylate (702b)

(R)-tert-butyl 4-((tert-butoxycarbonyl)amino)-3-oxopentanoate (702a; 34.3 g, 119 mmol) was treated with $NH_4OAc$ (Fluka; 92 g, 1194 mmol), $NH_3$ (2 M in MeOH; Aldrich; 597 mL, 1194 mmol). To the resulting slurry was added chloroacetaldehyde (50% in water; Aldrich; 154 mL, 1194 mmol) in portions. The temperature of the reaction rose to 42° C. and the reaction was cooled with ice briefly, to 38° C. When no further exotherm was noted, the clear light yellow reaction was placed on a rotovap in a 50° C. water bath. After 40 min, the reaction was dark brown. The reaction was heated for an additional 100 min. The reaction was concentrated in vacuo and treated with DCM and sat'd aq. $NaHCO_3$ with rapid stirring (CAUTION GAS EVOLUTION). The reaction was transferred to a 5 L bottle and solid $NaHCO_3$ was added. When gas evolution was no longer observed and the material was transferred to a separatory funnel. (Noted a lot of chunky material that did not dissolve in DCM, used some MeOH to dissolve.) The water layer was extracted with 3×250 mL of DCM, and the combined organics were dried over anhydrous $Na_2SO_4$, filtered, and concentrated in vacuo. The resulting thick brown oil was dissolved in ~150 mL of DCM, filtered, and purified by silica gel chromatography (1500 g ISCO Redisep gold column) using 0-30% EtOAc/hexanes to elute product. The product-containing fractions were concentrated to afford (R)-tert-butyl 2-(1-((tert-butoxycarbonyl)amino)ethyl)-1H-pyrrole-3-carboxylate (23.41 g, 75 mmol, 63% yield) as a white foam. $^1$H NMR (400 MHz, $CDCl_3$) δ ppm 9.30 (1H, br. s.), 6.53 (2H, dt, J=13.9, 2.8 Hz), 6.10 (1H, br. s.), 5.15 (1H, br. s.), 1.57 (9H, s), 1.53 (3H, d, J=6.8 Hz), 1.43 (9H, s). m/z (ESI, +ve) 333.1 (M+Na)$^+$.

Preparation of (R)-tert-butyl 2-(1-((tert-butoxycarbonyl)amino)ethyl)-1-tosyl-1H-pyrrole-3-carboxylate (702c)

A 1-L 3-necked RBF was charged with (R)-tert-butyl 2-(1-((tert-butoxycarbonyl)amino)ethyl)-1H-pyrrole-3-carboxylate (702b; 20.06 g, 64.6 mmol) and 200 mL THF, fitted with an addition funnel and temperature probe, and cooled in an ice bath to 2° C. Sodium tert-butoxide (2 M in THF; Aldrich; 33.9 mL, 67.9 mmol) was added via addition funnel at such a rate that the temperature of the reaction did not exceed 4° C. After complete addition, the dark brown reaction was stirred for 5 min. A solution of p-toluenesulfonyl chloride (Aldrich; 12.94 g, 67.9 mmol) in 50 mL THF was then added via addition funnel at such a rate that the temperature of the reaction did not exceed 7° C. After complete addition the reaction was stirred 30 min. The reaction was treated with 30 mL water and 100 mL EtOAc and 30 mL sat'd aq. $NaHCO_3$. The layers were separated and the organic washed with brine, dried over anhydrous magnesium sulfate, filtered, and concentrated in vacuo to give 29 g of a tan solid. The material was stirred in 75 mL MeOH for 15 min, and then placed in the freezer. The slurry was filtered rinsing with 2×50 mL ice cold MeOH. The solid was collected and dried in vacuo to give (R)-tert-butyl 2-(1-((tert-butoxycarbonyl)amino)ethyl)-1-tosyl-1H-pyrrole-3-carboxylate (21.0 g, 45.2 mmol, 70% yield) as an off-white solid. $^1$H NMR (400 MHz, CDCl$_3$) δ ppm 7.89 (2H, d, J=7.0 Hz), 7.30 (2H, d, J=8.2 Hz), 7.23 (1H, d, J=3.5 Hz), 6.82 (1H, br. s.), 6.55 (1H, d, J=3.3 Hz), 5.84 (1H, d, J=7.0 Hz), 2.40 (3H, s), 1.55 (9H, s), 1.32-1.44 (12H, m). m/z (ESI, +ve) 487.1 (M+Na)$^+$.

Preparation of (R)-2-(1-aminoethyl)-1-tosyl-1H-pyrrole-3-carboxylic acid compound with TFA (1:1) (702d)

To a solution of (R)-tert-butyl 2-(1-((tert-butoxycarbonyl)amino)ethyl)-1-tosyl-1H-pyrrole-3-carboxylate (702c; 25.11 g, 54.0 mmol) in 120 mL DCM was added TFA (Aldrich; 120 mL, 1621 mmol) slowly in portions (Caution: gas evolution was observed). After complete addition, the dark brown reaction was stirred 5 min, was fitted with a water-cooled reflux condenser and drying tube and was placed in a pre-heated 50° C. oil bath. The reaction was heated at reflux for 3 h; gas evolution was mild. The reaction was cooled and concentrated in vacuo and the solid material was dried in vacuo for 48 h to give (R)-2-(1-aminoethyl)-1-tosyl-1H-pyrrole-3-carboxylic acid compound with 2,2,2-trifluoroacetic acid (1:1) (22.83 g, 54.1 mmol, 100% yield). $^1$H NMR (400 MHz, MeOH-d$_4$) d ppm 7.89 (2H, d, J=8.4 Hz), 7.57 (1H, d, J=3.5 Hz), 7.52 (2H, d, J=8.2 Hz), 6.79 (1H, d, J=3.5 Hz), 5.28 (1H, q, J=6.8 Hz), 2.47 (3H, s), 1.32 (3H, d, J=6.8 Hz). m/z (ESI, +ve) 309.0 (M+H)$^+$.

Preparation of (R)-6-methyl-1-tosyl-5,6-dihydropyrrolo[3,4-b]pyrrol-4(1H)-one (702e)

To a slurry of (R)-2-(1-aminoethyl)-1-tosyl-1H-pyrrole-3-carboxylic acid compound with 2,2,2-trifluoroacetic acid (1:1) (702d; 22.83 g, 54.1 mmol) in 150 mL EtOAc at 0° C. was added DIPEA (28.2 mL, 162 mmol). A portion of the slurry seemed to dissolve. After 10 min, 1-propanephosphonic acid cyclic anhydride (T3P) (50 wt. % solution in EtOAc; Matrix Scientific; 35.0 mL, 59.5 mmol) was added and much of the solid dissolved. After 10 min, the still heterogeneous reaction was warmed to RT. After 4 h, the reaction was dark brown and homogeneous. The reaction was treated with 400 mL sat'd aq. NaHCO$_3$ and transferred to a separatory funnel. The layers were separated and the organic layer was washed with 1× sat'd aq. NaHCO$_3$ then 1× brine, dried over anhydrous Na$_2$SO$_4$, filtered through a glass frit and concentrated in vacuo to give (R)-6-methyl-1-tosyl-5,6-dihydropyrrolo[3,4-b]pyrrol-4(1H)-one (16.5 g, 56.8 mmol, quantitative yield) as a tan foam. $^1$H NMR (400 MHz, CDCl$_3$) δ ppm 7.70-7.77 (2H, m), 7.35 (2H, d, J=8.0 Hz), 7.16 (1H, d, J=3.3 Hz), 6.48 (1H, d, J=3.1 Hz), 5.75 (1H, br. s.), 4.68 (1H, q, J=6.5 Hz), 1.62 (3H, d, J=6.7 Hz). m/z (ESI, +ve) 291.0 (M+H)$^+$.

Preparation of (R)-6-methyl-5,6-dihydropyrrolo[3,4-b]pyrrol-4(1H)-one (702)

To a stirring solution of (R)-6-methyl-1-tosyl-5,6-dihydropyrrolo[3,4-b]pyrrol-4(1H)-one (702e; 15.6 g, 53.7 mmol) in 250 mL MeOH under nitrogen in an ice/water bath was added K$_2$CO$_3$ (14.85 g, 107 mmol). The slurry was stirred and the bath was allowed to slowly expire overnight. The stir bar was removed; 100 g silica gel was added; and the reaction was concentrated in vacuo. A DCM-wetted pad of silica gel (4 cm) was poured in a 15 cm diameter flitted funnel and the dried silica gel/reaction mixture was placed on the silica gel pad and covered with 4 cm sand. 1 L fractions collected: #1—1 L DCM; #2—1 L 10% MeOH/DCM; #3—1 L 10% MeOH/DCM; #4—750 mL 10% MeOH/DCM #5—1 L 10% MeOH/DCM. Fractions 3-5 were combined and concentrated in vacuo to give 7.7 g (74% ee) as a tan solid. The material was further purified by chiral SFC (mobile phase CO$_2$/15% MeOH (20 mM NH$_3$), chiral column ASH (250×30 mm), wave length 256 nm, flow rate 120 mL/min). The second eluting peak was collected and concentrated in vacuo to give (R)-6-methyl-5,6-dihydropyrrolo[3,4-b]pyrrol-4(1H)-one (702) (5.3 g, 39.0 mmol, 73% yield) as an off-white solid. $^1$H NMR (400 MHz, MeOH-d$_4$) δ ppm 6.84 (1H, d, J=2.9 Hz), 6.23 (1H, d, J=2.9 Hz), 4.53 (1H, q, J=6.7 Hz), 1.41 (3H, d, J=6.8 Hz). m/z (ESI, +ve) 137.1 (M+H)$^+$.

Preparation of 5,6-dihydropyrrolo[3,4-b]pyrrol-4(1H)-one (703)

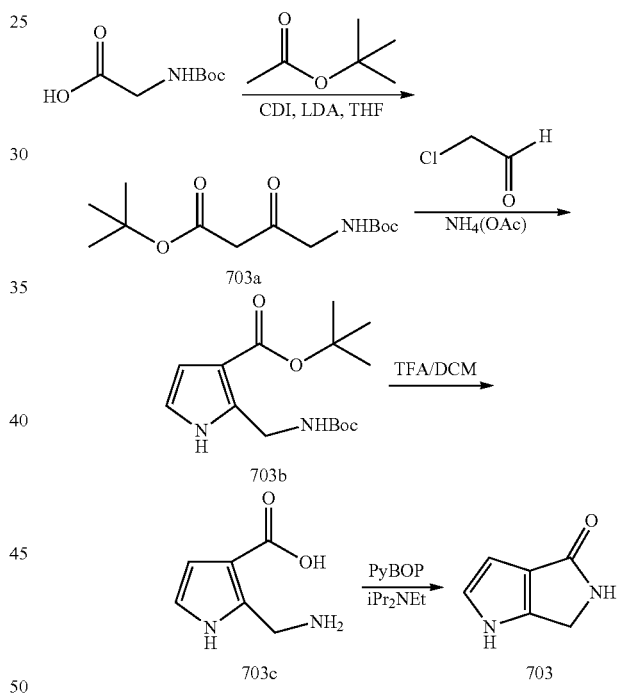

Preparation of tert-butyl 4-((tert-butoxycarbonyl)amino)-3-oxobutanoate (703a)

A 10 L three-necked, round-bottomed flask was charged with diisopropylamine (531 g, 5.25 mol) in THF (3 L) and cooled to −78° C. n-BuLi (2.5M, 2 L, Shangyu hualun-chem, China) was added slowly into the reaction mixture at −78° C. under nitrogen. After the addition was completed, the reaction mixture was warm up to 0° C. slowly and keep at this temperature for 20 min, then cooled to −78° C. and tert-butyl acetate (580 g, 5 mol, Sigma-Aldrich) in THF (1.0 L) was added slowly at −78° C. and stirred at this temperature for 2 h. In a separated 5 L round-bottomed flask, 2-((tert-butoxycarbonyl)amino) acetic acid (280 g, 1.6 mol, Shanghai Chiralchemicals Inc, China) was dissolved in THF (1500 mL), cooled to −30° C., and treated with 1,1'-carbonyldiimidazole (285 g, 1.76 mol). The mixture was stirred for 30 min at −30° C., then this solution was added dropwise to the cooled (−78° C.) above solution previously prepared. After 1 h, the reaction mixture was quenched with aq. 4 N NH$_4$Cl (5 L). Similarly another 5 batches were carried out on 280 g scale. The batches were combined and the solvent was removed in vacuo. The residue was diluted with EtOAc (35 L) and successively washed with water (9 L), brine (9 L) and dried over Na$_2$SO$_4$. The solution was filtered and concentrated in vacuo to give the crude material as a yellow oil (2.38 kg, 90% yield) which was used without further purification.

Preparation of tert-butyl 2-(((tert-butoxycarbonyl)amino)methyl)-1H-pyrrole-3-carboxylate (703b)

Tert-butyl 4-((tert-butoxycarbonyl)amino)-3-oxobutanoate (755 g, 2.76 mol) was treated with ammonia (2 M in MeOH, 7.0 L) and NH$_4$OAc (851 g, 11.04 mol) at RT. The resulting mixture was heated at 40° C. for 1 h, then treated with chloroacetaldehyde, 50% in water (1083 g, 5.52 mol, Sinopharm Chemical Reagent Co., Ltd, China) and stirred at 50° C. for 4 h and cooled to RT. The solvent was removed in vacuo and the crude material was diluted with water and EtOAc (water: EtOAc=1:1,5 L: 5 L). The organic layer was separated, dried (Na$_2$SO$_4$) and concentrated. Similarly another 2 batches were carried out on 755 g scale. The combined residue was purified by flash column chromatography (eluted by 5-20% EtOAc in petroleum ether) to afford tert-butyl 2-(((tert-butoxycarbonyl)amino)methyl)-1H-pyrrole-3-carboxylate (820 g, 32% yield). $^1$H NMR (400 MHz, DMSO-d6) δ 10.96 (s, 1H), 6.91 (s, 1H), 6.58-6.57 (m, 1H), 6.26-6.24 (m, 1H), 4.34-4.33 (m, 2H), 1.44 (s, 9H), 1.36 (s, 9H).

Preparation of 2-(aminomethyl)-1H-pyrrole-3-carboxylic acid (703c)

A 10 L round-bottomed flask was charged with tert-butyl 2-(((tert-butoxycarbonyl)amino)methyl)-1H-pyrrole-3-carboxylate (820 g, 2.8 mol), DCM (2200 mL), and TFA (2200 mL). The reaction mixture was stirred at RT for 10 h and the solvent was removed in vacuo to afford the crude product as TFA salt (1.020 Kg, 100% yield) as an off-white solid and used without further purification. $^1$H NMR (400 MHz, DMSO-d) δ 11.74 (s, 1H), 8.13 (br., 2H), 6.84 (s, 1H), 6.44 (s, 1H), 4.21-4.20 (m, 2H).

Preparation of 5,6-dihydropyrrolo[3,4-b]pyrrol-4(1H)-one (703)

A 5 L round-bottomed flask was charged with 2-(aminomethyl)-1H-pyrrole-3-carboxylic acid TFA salt (1.02 Kg, 2.7 mol), DCM (3.2 L), and DIPEA (2.75 Kg, 21.3 mol). To the reaction mixture was added (benzotriazol-1-yloxy)tripyrrolidinophosphonium hexafluorophosphate (1.55 Kg, 2.97 mol, Accela ChemBio Co. Ltd) and stirred at RT overnight. The solvent was removed in vacuo. The crude material was purified by column chromatography on silica gel (eluting with a gradient of 0% to 5% NH$_3$ (2M in MeOH)/DCM) to give crude product 510 g as sticky oil. The crude product was diluted with EtOAc (4.5 L) and stirred for 1 h. The resulting precipitate was collected by filtration and dried to afford 5,6-dihydropyrrolo[3,4-b]pyrrol-4(1H)-one (104 g, 31% yield) as a white solid. The filtrate was concentrated and re-purified by column chromatography on silica gel to give more product 46.5 g (13.6% yield) as a white solid. Overall 5,6-dihydropyrrolo[3,4-b]pyrrol-4(1H)-one (150.5 g, 44.6% yield) was obtained. MS (ESI, pos. ion) m/z: 123 (M+1); $^1$H NMR (400 MHz, MeOD) δ 6.87 (d, J=3.2 Hz, 1H), 6.27 (d, J=3.2 Hz, 1H), 4.27 (s, 2H).

Preparation of 1'H-spiro[cyclopropane-1,6'-pyrrolo[3,4-b]pyrrol]-4'(5'H)-one (704)

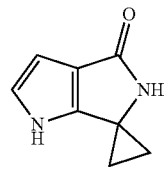

704

This compound was prepared in a manner similar to that described for Intermediate 703, starting from 1-((tert-butoxycarbonyl)amino)cyclopropanecarboxylic acid. $^1$H NMR (400 MHz, DMSO-d$_6$) δ ppm 11.08 (1H, br.), 7.53 (1H, s), 6.82 (1H, s), 6.11 (1H, d, J=2.2 Hz), 1.3 (2H, m), 1.27 (2H, m). m/z (ESI, +ve) 149.0 (M+H)$^+$.

Preparation of (R)-6-methyl-2-(4,4,5,5-tetramethyl-1,3,2-dioxaborolan-2-yl)-5,6-dihydropyrrolo[3,4-b]pyrrol-4(1H)-one (705)

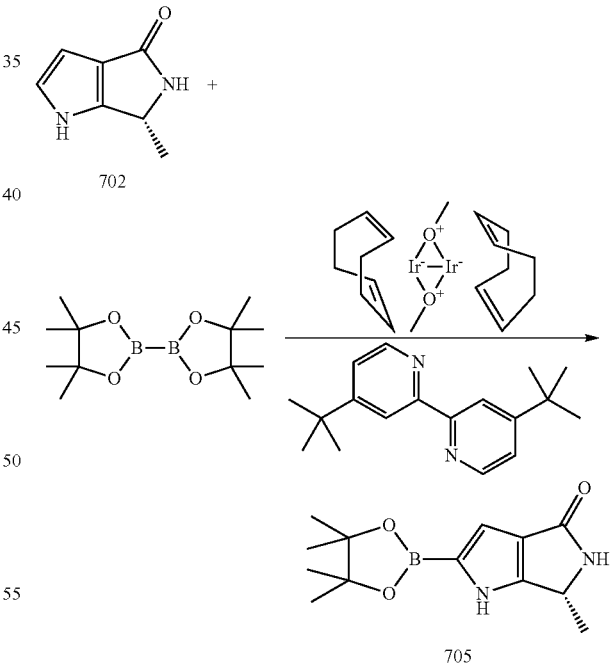

A glass pressure vessel was charged with (R)-6-methyl-5,6-dihydropyrrolo[3,4-b]pyrrol-4(1H)-one (702) (2.50 g, 18.36 mmol), bis(pinacolato)diboron (5.13 g, 20.20 mmol) in MTBE (70 mL) followed by (1,5-cyclooctadiene)(methoxy)iridium(i) dimer (Sigma-Aldrich; 0.36 g, 0.55 mmol) and 4,4'-di-tert-butyl-2,2'-dipyridyl (Sigma-Aldrich; 0.29 g, 1.10 mmol). The mixture was bubbled with Argon for 3 min, then sealed and heated in an oil bath at 55° C. for 2 h. After the reaction mixture was cooled to RT it was filtered through a plug of aluminum oxide (Sigma-Aldrich; neutral, activated, Brockmann I) and washed with DCM (1200 mL) then 5-10% MeOH in DCM (1500 mL). The fractions containing the desired product (as judged by LCMS) were combined and concentrated to give the title compound (5.86 g) as a brown solid. m/z (ESI, +ve ion) 263.0 (M+H)⁺. The crude material was used without further purification. ¹H NMR indicated the desired boronic ester: Starting material: pinacol to be about 1:0.08:0.22. ¹H NMR (400 MHz, DMSO-d₆) δ ppm 11.68 (1H, br.), 7.62 (1H, s), 6.49 (1H, s), 4.40 (1H, m), 1.28 (12, s), 1.17 (3H, d, J=5.9 Hz).

Preparation of 2-(4,4,5,5-tetramethyl-1,3,2-dioxaborolan-2-yl)-5,6-dihydropyrrolo[3,4-b]pyrrol-4(1H)-one (706)

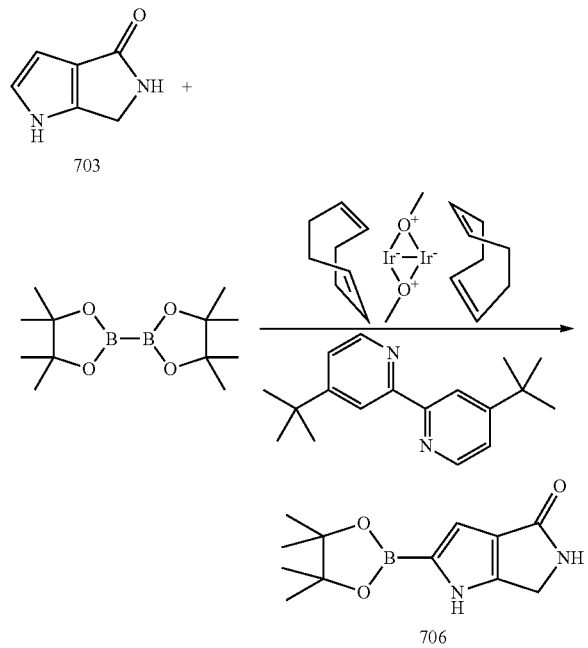

This compound as a brown solid was prepared according to the procedure described for intermediate 705, using 5,6-dihydropyrrolo[3,4-b]pyrrol-4(1H)-one (703) as the starting material. m/z (ESI, +ve) 248.7 (M+H)⁺.

Preparation of 2'-(4,4,5,5-tetramethyl-1,3,2-dioxaborolan-2-yl)-1'H-spiro[cyclopropane-1,6'-pyrrolo[3,4-b]pyrrol]-4'(5'H)-one (707)

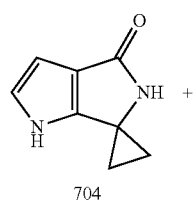

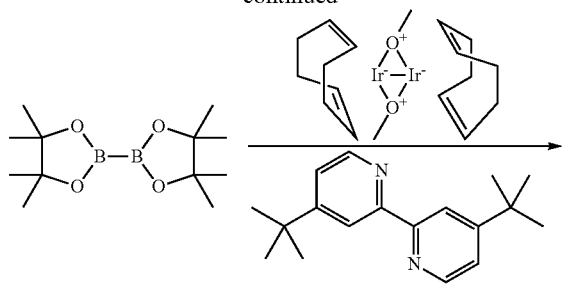

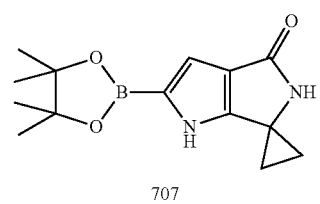

This compound as a brown solid was prepared according to the procedure described for intermediate 705, using 1'H-spiro[cyclopropane-1,6'-pyrrolo[3,4-b]pyrrol]-4'(5'H)-one (704) as the starting material. m/z (ESI, +ve) 275.0 (M+H)⁺.

Preparation of 8-iodo-3-methyl-2-((1-methylcyclobutyl)amino)quinazolin-4(3H)-one (711)

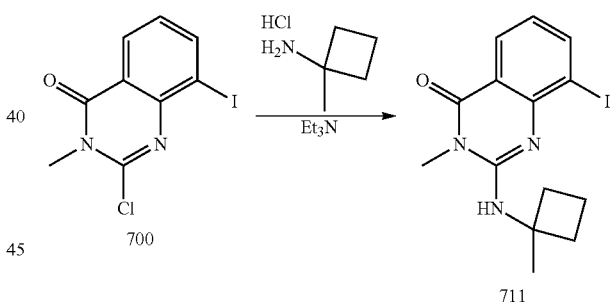

A heterogeneous mixture of 1-methylcyclobutanamine hydrochloride (Oakwood Chemical, cat #041889; 0.69 g, 5.70 mmol) (Oakwood Chemical, cat #041889), 2-chloro-8-iodo-3-methylquinazolin-4(3H)-one (700) (0.96 g, 3.0 mmol) and TEA (2.1 mL, 15.10 mmol) in 2 mL of THF in a sealed glass tube was heated in an oil bath at 80° C. for 4 h. The reaction mixture was diluted with EtOAc, washed with water followed by brine. The organic extract was concentrated and the residue was purified on a silica gel column (25-55% EtOAc in hexanes) to afford 8-iodo-3-methyl-2-((1-methyl-cyclobutyl)amino)quinazolin-4(3H)-one (0.94 g, 2.55 mmol, 85% yield) as a yellow crystalline solid. ¹H NMR (400 MHz, DMSO-d₆) δ ppm 8.11 (1H, dd, J=7.4, 1.4 Hz), 7.92 (1H, dd, J=7.8, 1.4 Hz), 7.03 (1H, s), 6.87 (1H, t, J=7.7 Hz), 3.40 (3H, s), 2.20-2.46 (4H, m), 1.88 (2H, m), 1.72 (3H, s). m/z (ESI, +ve) 370.1 (M+H)⁺.

123

Preparation of 2-((1-fluoro-2-methylpropan-2-yl)amino)-8-iodo-3-methylquinazolin-4(3H)-one (712)

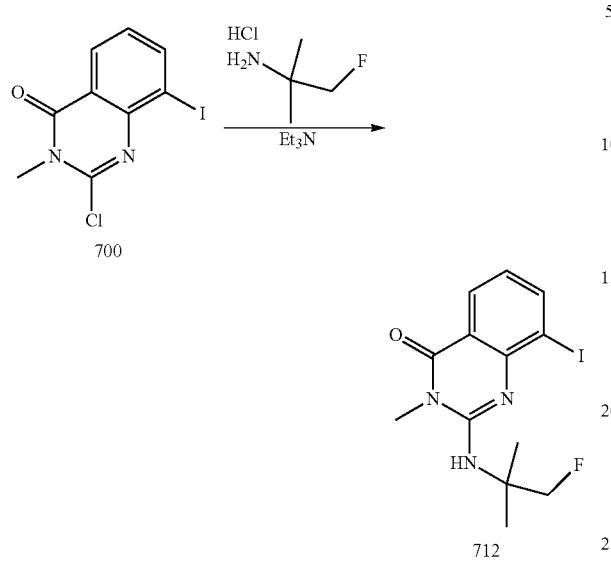

This compound (0.71 g, 63% yield) as a yellow crystalline solid was prepared according to the procedure described for intermediate 711, using 2-chloro-8-iodo-3-methylquinazolin-4(3H)-one (700) (0.96 g, mmol), 2-fluoro-1,1-dimethylethylamine hydrochloride (AmfineCom Inc; 0.69 g, 5.40 mmol) (AmfineCom Inc.) and TEA (2.1 mL, 15.10 mmol) as the starting materials. $^1$H NMR (400 MHz, DMSO-$d_6$) δ ppm 8.16 (1H, d, J=7.2 Hz), 7.96 (1H, d, J=7.4 Hz), 6.95 (1H, t, J=7.6 Hz), 6.16 (1H, br.), 5.04 (1H, s), 4.92 (1H, s), 3.47 (3H, s), 1.58 (6H, s). m/z (ESI, +ve) 375.8 (M+1-1)'.

Preparation of 8-iodo-3-methyl-2-((1-methylcyclopropyl)amino)quinazolin-4(3H)-one (713)

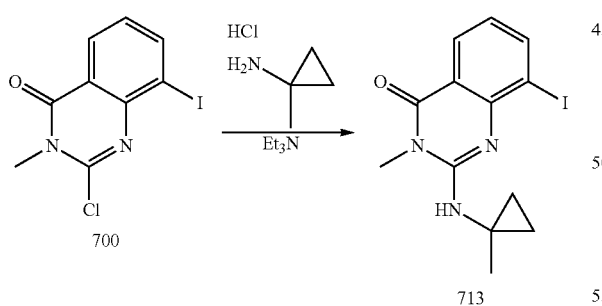

This compound (0.71 g, 80% yield) as a yellow crystalline solid was prepared according to the procedure described for intermediate 711, using 2-chloro-8-iodo-3-methylquinazolin-4(3H)-one (700) (0.80 g, mmol), 1-methylcyclopropanamine hydrochloride (ChemBridge, San Diego, Calif.; 0.471 g, 4.38 mmol), and TEA (2.1 mL, 15.10 mmol) as the starting materials. $^1$H NMR (400 MHz, DMSO-$d_6$) δ ppm 8.14 (1H, dd, J=7.5, 1.3 Hz), 7.93 (1H, dd, J=7.9, 1.3 Hz), 7.49 (1H, s), 6.89 (1H, t, J=7.7 Hz), 3.32 (3H, m), 1.58 (3H, s), 0.84 (2H, m), 0.74 (2H, m). m/z (ESI, +ve) 355.9 (M+H)$^+$.

124

Preparation of (R)-2-bromo-6-methyl-5,6-dihydropyrrolo[3,4-b]pyrrol-4(1H)-one (714)

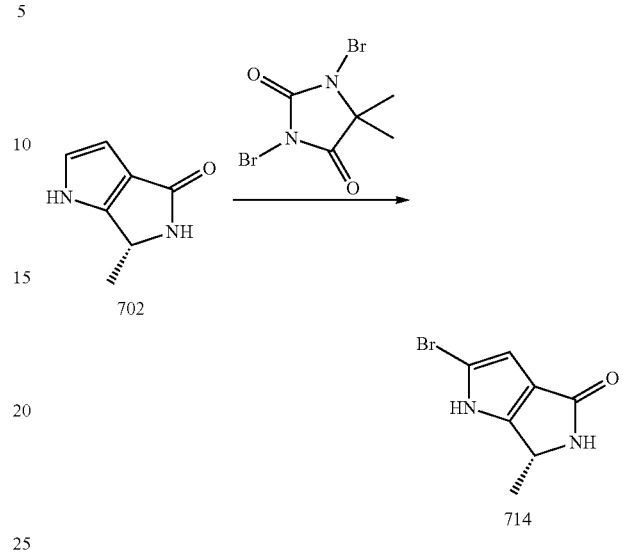

A solution of (R)-6-methyl-5,6-dihydropyrrolo[3,4-b]pyrrolo-4(1H)-one (702) (180 mg, 1.32 mmol) in 5 mL DMF under nitrogen was cooled to −20° C. (acetone bath with periodic addition of dry ice) and treated with 1,3-dibromo-5,5-dimethylhydantoin (Aldrich; 189 mg, 0.66 mmol) in one portion. The resulting mixture was stirred at −20° C. for 30 min, then quenched with water (5 mL), and extracted with EtOAc (2×50 mL). The combined organics were dried over anhydrous $Na_2SO_4$, filtered, and concentrated. The residue was purified on a silica gel column (1-5% MeOH in DCM) to afford (R)-2-bromo-6-methyl-5,6-dihydropyrrolo[3,4-b]pyrrolo-4(1H)-one (714; 266 mg, 94% yield) as a white solid. $^1$H NMR (400 MHz, DMSO-$d_6$) δ ppm 12.13 (1H, br. s.), 7.70 (1H, s), 6.17 (1H, s), 4.30-4.62 (1H, m), 1.27 (3H, d, J=6.7 Hz). m/z (ESI, +ve) 215.0/217.0 (M+H)$^+$.

Preparation of 2-(tert-butylamino)-8-iodo-3-(2-methoxyethyl)quinazolin-4(3H)-one (715)

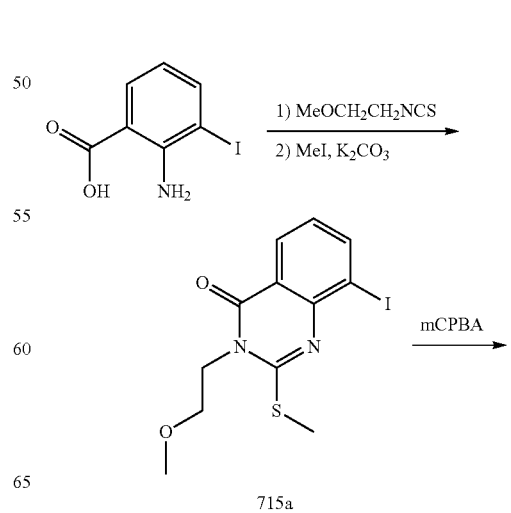

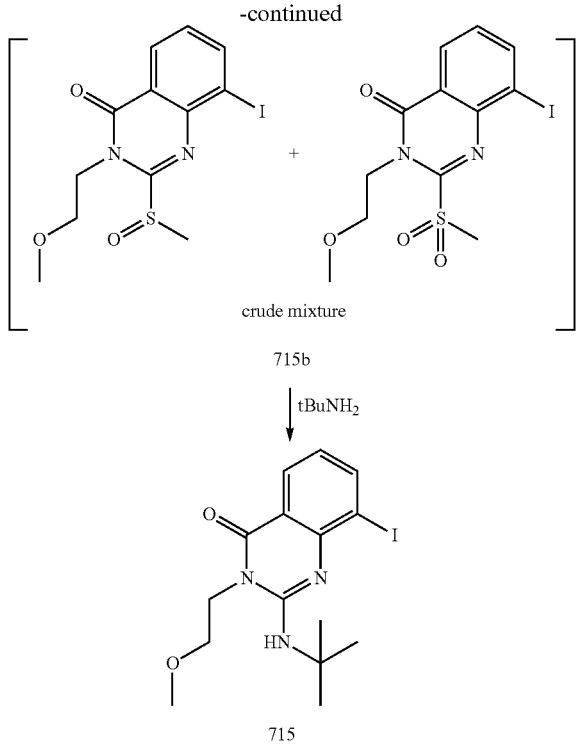

715b crude mixture tBuNH$_2$

715

A sealable flask was charged with 2-amino-3-iodobenzoic acid (5.02 g, 19.09 mmol) and 2-methoxyethyl isothiocyanate (3.35 g, 28.6 mmol) in tBuOH (30 mL) followed by TEA (3.98 mL, 28.6 mmol). The flask was sealed and heated in an oil bath at 100° C. for 4 h with a blast shield. The reaction mixture was cooled to RT and the off white solid was filtered, rinsed with 2×25 mL of ether and dried to give 8-iodo-3-(2-methoxyethyl)-2-thioxo-2,3-dihydroquinazolin-4(1H)-one (6.21 g, 17.15 mmol, 90% yield) as an off white solid. $^1$H NMR (400 MHz, DMSO-d$_6$) δ ppm 9.99 (1H, s), 8.26 (1H, dd, J=7.6, 1.2 Hz), 8.00 (1H, dd, J=7.9, 1.3 Hz), 7.17 (1H, t, J=7.7 Hz), 4.60 (2H, t, J=6.5 Hz), 3.65 (2H, t, J=6.6 Hz), 3.31 (3H, s). m/z (ESI, +ve) 362.8 (M+H)$^+$. To a 500-mL round-bottomed flask was added sequentially 8-iodo-3-(2-methoxyethyl)-2-thioxo-2,3-dihydroquinazolin-4(1H)-one (6.01 g, 16.59 mmol), THF (75 mL K$_2$CO$_3$ (5.73 g, 41.5 mmol), and MeI (2.06 mL, 33.2 mmol). The reaction mixture was heated in an oil bath at 65° C. for 6 h. The mixture was concentrated to half of its volume, poured into ice/water (100 mL) and stirred for 10 min. The suspension was filtered and the solid was washed with cold water (20 mL) and cold ether (20 mL). The off-white solid was dried to give 8-iodo-3-(2-methoxyethyl)-2-(methylthio)quinazolin-4(3H)-one (715a; 4.91 g). The filtrate was extracted with 50 mL of EtOAc. The EtOAc layer was concentrated and the brown solid was stirred in 5 mL of ether and 5 mL of hexanes. The solid was filtered and dried to give 8-iodo-3-(2-methoxyethyl)-2-(methylthio)quinazolin-4(3H)-one (715a; 1.1 g). $^1$H NMR (400 MHz, DMSO-d$_6$) δ ppm 8.34 (1H, dd, J=7.6, 1.4 Hz), 8.09 (1H, dd, J=7.9, 1.3 Hz), 7.22 (1H, t, J=7.7 Hz), 4.25 (2H, t, J=6.2 Hz), 3.65 (2H, t, J=6.2 Hz), 3.30 (3H, s), 2.75 (3H, s). m/z (ESI, +ve) 376.7 (M+H)$^+$.

To a solution of 8-iodo-3-(2-methoxyethyl)-2-(methylthio)quinazolin-4(3H)-one (715a; 1.33 g, 3.54 mmol) in 100 mL of DCM at 0° C. was added 3-chloroperoxybenzoic acid (77% max., 1.47 g, 6.56 mmol) and the resulting mixture was stirred for 1 h at 0° C. It was diluted with 50 mL of DCM, washed with 2×15 mL of sat NaHCO$_3$. The DCM layer was dried over Na$_2$SO$_4$ and concentrated to give a yellow solid as a mixture (715b) of 8-iodo-3-(2-methoxyethyl)-2-(methylsulfonyl)quinazolin-4(3H)-one and 8-iodo-3-(2-methoxyethyl)-2-(methylsulfinyl)quinazolin-4(3H)-one. To the crude mixture (715b) in a sealable glass vessel was added tert-butylamine (3.72 mL, 35.4 mmol) and 5 mL of DMSO. The glass vessel was sealed and heated in an oil bath at 80° C. for 3 h. It was treated with 10 mL of 0.5 N NaOH, and extracted with 2×35 mL of EtOAc. The organic extracts were dried over Na$_2$SO$_4$ and concentrated. The residue was stirred in 25 mL of ether. The insoluble solid was filtered and rinsed with 2×10 mL of ether. The filtrate was concentrated and the residue was purified on a silica gel column (30-80% EtOAc in hexanes) to afford 2-(tert-butylamino)-8-iodo-3-(2-methoxyethyl) quinazolin-4(3H)-one (715) (0.99 g, 2.467 mmol, 70% yield for 2 steps) as a yellow crystalline solid. $^1$H NMR (400 MHz, DMSO-d$_6$) δ ppm 8.16 (1H, dd, J=7.5, 1.5 Hz), 7.94 (1H, dd, J=7.8, 1.4 Hz), 6.92 (1H, t, J=7.7 Hz), 6.46 (1H, s), 4.23 (2H, t, J=4.8 Hz), 3.66 (2H, t, J=4.7 Hz), 3.35 (3H, s), 1.58 (9H, s). m/z (ESI, +ve) 401.9 (M+H)$^+$.

Preparation of 2-(tert-butylamino)-8-iodo-3-(2-(2-methoxyethoxy)ethyl)quinazolin-4(3H)-one (716)

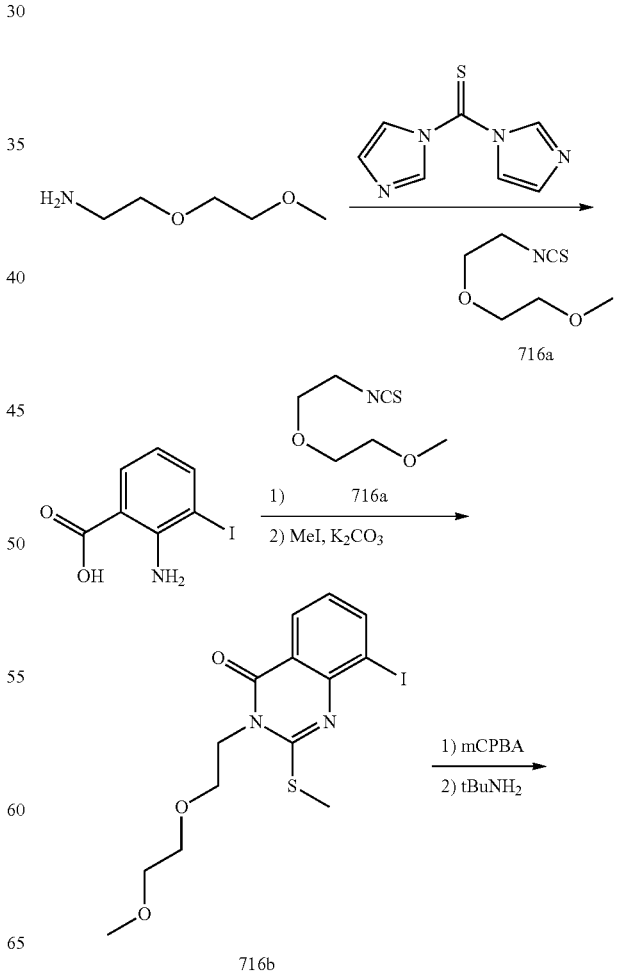

-continued

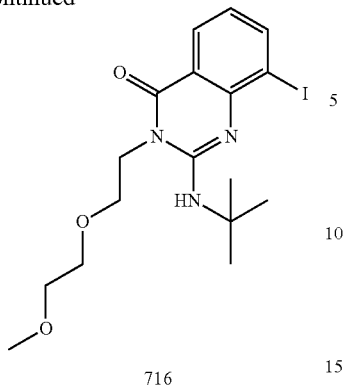

716

Preparation of 1-isothiocyanato-2-(2-methoxyethoxyl)ethane (716a)

To a solution of 2-(2-methoxyethoxyl)ethanamine (0.820 g, 6.88 mmol) in DMF (69 mL) at 0° C. was added dropwise a solution of 1,1'-thiocarbonyldiimidazole (1.349 g, 7.57 mmol) in 21 mL of DMF. The mixture was warmed to RT and stirred for 90 min. The mixture was poured into water (130 mL) and extracted with Et$_2$O (70 mL). The Et$_2$O layer was washed with water, dried over Na$_2$SO$_4$, and filtered. The filtrate was concentrated in vacuo (325 torr, bath temp: 24° C.) to afford 1-isothiocyanato-2-(2-methoxyethoxyl)ethane (0.678 g, 4.21 mmol, 61% yield) as a yellow oil. The crude material was used in next step.

Preparation of 8-iodo-3-(2-(2-methoxyethoxyl)ethyl)-2-(methyl-thio)quinazolin-4(3H)-one (716b)

This compound (0.81 g, 1.92 mmol) was prepared according to the procedures described for Intermediate 715a, starting from 1-isothiocyanato-2-(2-methoxyethoxyl)ethane (716a; 0.67 g, 4.21 mmol). m/z (ESI, +ve ion) 421.0 (M+H)$^+$.

Preparation of 2-(tert-butylamino)-8-iodo-3-(2-(2-methoxy-ethoxy)ethyl)quinazolin-4(3H)-one (716)

This compound (0.33 g, 0.74 mmol) was prepared according to the procedures described for Intermediate 715, starting from 8-iodo-3-(2-(2-methoxyethoxyl)ethyl)-2-(methylthio)quinazolin-4(3H)-one (716b; 0.79 g, 1.87 mmol). $^1$H NMR (400 MHz, CDCl$_3$) δ ppm 8.08 (ddd, J=14.43, 7.68, 1.56 Hz, 2H), 6.84 (t, J=7.73 Hz, 1H), 6.20 (s, 1H), 4.19-4.25 (m, 2H), 3.81-3.86 (m, 2H), 3.60-3.65 (m, 2H), 3.51-3.56 (m, 2H), 3.35 (s, 3H), 1.61 (s, 9H). m/z (ESI, +ve ion) 446.0 (M+H)$^+$.

Preparation of 8-iodo-3-methyl-2-(1-methylcyclopropoxy)quinazolin-4(3H)-one (717)

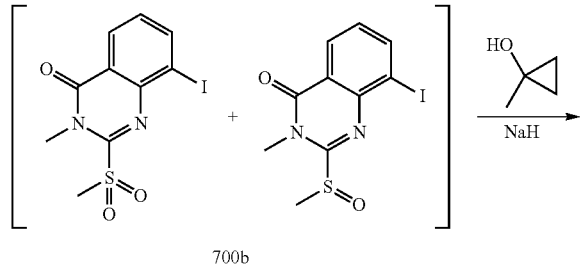

700b

-continued

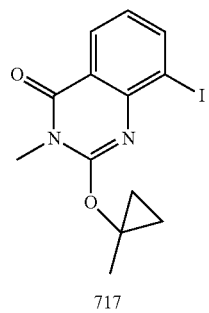

717

At 0° C., to a solution of 1-methylcyclopropanol (0.49 mL, 6.78 mmol) in 20 mL of THF was added NaH (60% wt in mineral oil) (264 mg, 6.61 mmol) and the solution was stirred at RT for 10 min. The resulting white suspension was cooled to 0° C. and crude 700b (590 mg, 1.69 mmol) was added as solid. The reaction mixture was stirred at RT for 1 h. It was treated with 10 mL of ice cold sat NH$_4$Cl, and extracted with 2×35 mL of EtOAc. The organic extracts were dried over Na$_2$SO$_4$ and concentrated. The residue was stirred in 25 mL of EtOAc. The insoluble solid was filtered and discarded. The filtrate was concentrated and purified on a silica gel column (25-55% EtOAc in hexanes) to afford 8-iodo-3-methyl-2-(1-methylcyclopropoxy)quinazolin-4(3H)-one (215 mg, 35% yield) an off white crystalline solid. $^1$H NMR (400 MHz, DMSO-d$_6$) δ ppm 8.28 (1H, dd, J=7.5, 1.5 Hz), 8.05 (1H, dd, J=7.8, 1.4 Hz), 7.14 (1H, m), 3.35 (3H, s), 1.86 (3H, s), 1.10 (2H, m), 0.85 (2H, m). m/z (ESI, +ve ion) 356.9 (M+H)$^+$.

Preparation of 2-(tert-butylamino)-3-cyclopropyl-8-iodoquinazolin-4(3H)-one (718)

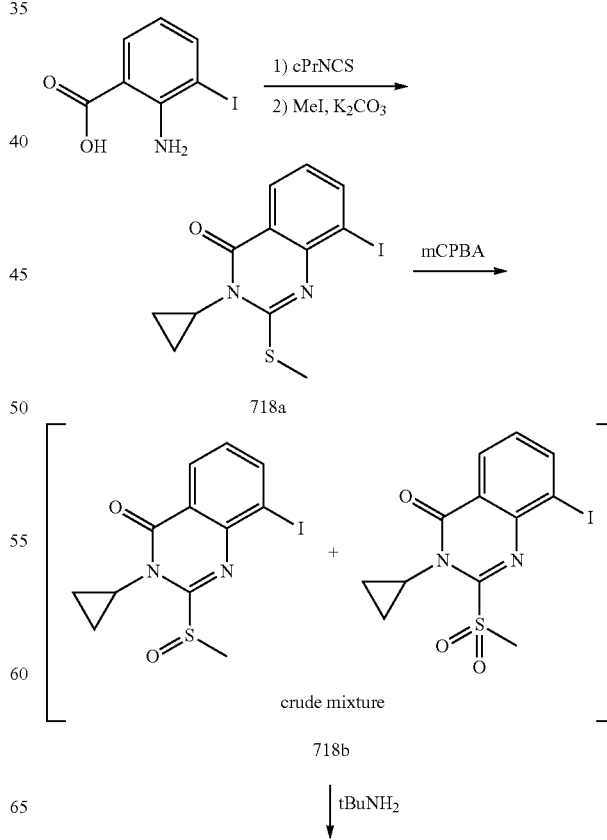

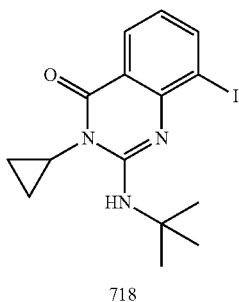

718

This compound was prepared according to the procedures described for Intermediate 715, starting from isothiocyanatocyclopropane. 3-Cyclopropyl-8-iodo-2-(methylthio)quinazolin-4(3H)-one (718a): $^1$H NMR (400 MHz, DMSO-$d_6$) δ ppm 8.28 (1H, dd, J=7.6, 1.4 Hz), 8.04 (1H, dd, J=7.8, 1.4 Hz), 7.17 (1H, t, J=7.7 Hz), 2.85-2.94 (1H, m), 2.65-2.72 (3H, s), 1.16-1.26 (2H, m), 0.93-1.01 (2H, m). m/z (ESI, +ve ion) 358.8 (M+H)$^+$. 2-(tert-Butylamino)-3-cyclopropyl-8-iodoquinazolin-4(3H)-one (718b) as a yellow solid in 53% purity (LCAP). m/z (ESI, +ve ion) 383.9 (M+H)$^+$. $^1$H NMR (400 MHz, CDCl$_3$) δ ppm 8.10 (1H, dd, J=7.6, 1.4 Hz), 8.05 (1H, dd, J=7.9, 1.5 Hz), 6.87 (1H, t, J=7.7 Hz), 5.62 (1H, br. s.), 2.73 (1H, tt, J=6.8, 4.1 Hz), 1.65 (10H, s), 1.30-1.39 (2H, m), 0.88-0.96 (2H, m).

Preparation of 2-amino-3-bromo-4-fluorobenzoic acid (719)

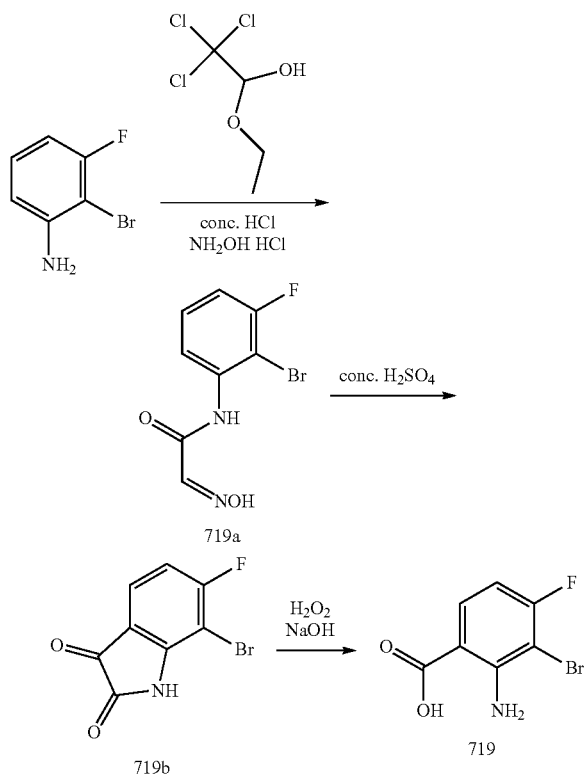

Preparation of N-(2-bromo-3-fluorophenyl)-2-(hydroxyimino)acetamide (719a)

Flask A: A 2 L 3-neck flask with a temperature probe adapter was fixed with a mechanical stirrer, condenser, and temperature probe; the flask was charged with hydroxylamine hydrochloride (Fluka; 12.47 g, 179 mmol), Na$_2$SO$_4$ (51.7 g, 364 mmol), 2,2,2-trichloro-1-ethoxyethanol (15.78 g, 82 mmol), and water (240 ml). This was stirred to 40° C. to affect dissolution. Flask B: A mixture of 2-bromo-3-fluoroaniline (10.33 g, 54.4 mmol) in water (32.0 mL)/conc. HCl (14.95 mL, 179 mmol) was stirred at RT and then at 50° C. to attempt dissolution; EtOH (10 mL) was added as another attempt to dissolve the aniline to no avail. The fine slurry was added to Flask A containing the stirring 2,2,2-trichloro-1-ethoxyethanol solution at 40° C. The reaction was heated to 100° C. and was stirred for 1 h. The reaction was cooled to 5° C. in an ice bath, filtered through a disposable 0.45 micron ZapCap filter (very slow filtration), and washed with water to give N-(2-bromo-3-fluorophenyl)-2-(hydroxyimino)acetamide (12.34 g, 47.3 mmol, 87% yield) as a brown solid after it was dried in a vacuum oven. $^1$H NMR (400 MHz, CDCl$_3$) δ ppm 6.92 (td, J=8.31, 1.37 Hz, 1H), 7.32 (td, J=8.31, 6.26 Hz, 1H), 7.60 (s, 1H), 7.87 (s, 1H), 8.25 (d, J=8.41 Hz, 1H), 8.98 (br. s., 1H). $^{19}$F NMR (377 MHz, CDCl$_3$) δ ppm −104.01 (s, 1F). MS (ESI, pos. ion) m/z: 260.9/262.9 (M+1).

Preparation of 7-bromo-6-fluoroindoline-2,3-dione (719b)

A 2 L 3-neck flask with a temperature probe adapter was fixed with a mechanical stirrer, condenser, and temperature probe. The flask was charged with conc. sulfuric acid (79 mL, 1418 mmol) and was heated to 70° C.; solid N-(2-bromo-3-fluorophenyl)-2-(hydroxyimino)acetamide (719a; 12.34 g, 47.3 mmol) was then slowly added (exotherm) and the temperature raised to 100° C. The brown solution was stirred at 90° C. for 45 min. The heating mantle was replaced with an ice bath to cool the reaction mixture to RT; the brown solution was poured into a beaker containing ice (500 mL), diluted with EtOAc (200 mL), added to a separatory funnel, and extracted with EtOAc (2×150 mL); the combined organics were dried over Na$_2$SO$_4$ and concentrated to give 7-bromo-6-fluoroindoline-2,3-dione (11.53 g, 47.3 mmol, 100% yield) as a reddish solid. $^1$H NMR (400 MHz, CDCl$_3$) δ ppm 6.91 (t, J=8.51 Hz, 1H) 7.63 (dd, J=8.22, 4.89 Hz, 1H) 7.99 (br. s., 1H). $^{19}$F NMR (377 MHz, CDCl$_3$) δ ppm −90.65 (s, 1F). MS (ESI, pos. ion) m/z: 243.9/245.9 (M+1).

Preparation of 2-amino-3-bromo-4-fluorobenzoic acid (719)

A 2 L 3-neck flask with a temperature probe adapter was fixed with a mechanical stirrer, addition funnel, and temperature probe. The flask was charged with 7-bromo-6-fluoroindoline-2,3-dione (719b; 11.53 g, 47.3 mmol) and 1 N NaOH (104 mL, 104 mmol) at RT; 30% hydrogen peroxide (10.62 mL, 104 mmol) was added via addition funnel over 15 min when the temperature of the brown solution raised to 45° C. The reaction mixture was stirred for 1.5 h when mostly product was observed via LCMS. The slurry was acidified to pH 7 with 2 N HCl when a solid was still present; the reaction mixture was diluted with water (100 mL) to effect stirring when it began to bubble. The slurry was then acidified to pH 1.8 with 2 N HCl (no exotherm was observed). After stirring at RT for 30 min, the slurry was filtered, washed with water, and dried in a vacuum oven to give 2-amino-3-bromo-4- fluorobenzoic acid (9.90 g, 42.3 mmol, 90% yield) as a beige solid. ¹H NMR (400 MHz, DMSO-d₆) δ ppm 6.59 (t, J=8.61 Hz, 1H) 7.08 (br. s., 2H) 7.86 (dd, J=8.90, 6.75 Hz, 1H) 13.04 (br. s., 1H). ¹⁹F NMR (377 MHz, DMSO-d₆) δ ppm −97.39 (s, 1F). MS (ESI, pos. ion) m/z: 233.9/235.9 (M+1).

Preparation of 8-bromo-2-chloro-7-fluoro-3-methylquinazolin-4(3H)-one (720)

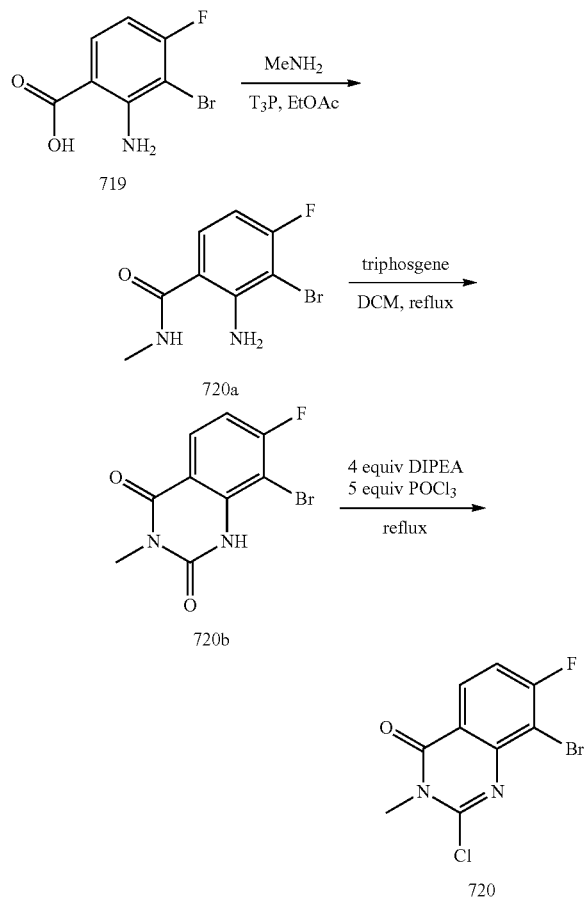

Preparation of 2-amino-3-bromo-4-fluoro-N-methylbenzamide (720a)

To a slurry of 2-amino-3-bromo-4-fluorobenzoic acid (719; 0.690 g, 2.95 mmol) in 5 mL EtOAc was added methanamine (2.0 M in THF; Aldrich, St. Louis, Mo.; 5.90 mL, 11.79 mmol) to give a solution. 1-propanephosphonic acid cyclic anhydride 50 wt % in EtOAc (Matrix Scientific; 1.911 mL, 3.24 mmol) was added. The reaction became warm. The reaction was sealed and stirred rapidly at RT. After 30 min, additional methanamine 2.0 M in THF (Aldrich, St. Louis, Mo.; 5.90 mL, 11.79 mmol) was added. After 1 h, the reaction was partitioned between sat'd NaHCO₃ and EtOAc. The organic layer was washed with sat'd NaHCO₃ once, sat'd NaCl once, and the organics were dried over anhydrous Na₂SO₄, filtered, and concentrated in vacuo to give 2-amino-3-bromo-4-fluoro-N-methylbenzamide (0.57 g, 2.30 mmol, 78% yield). ¹H NMR (400 MHz, DMSO-d₆) δ ppm 8.36 (1H, d, J=3.9 Hz), 7.57 (1H, dd, J=8.8, 6.3 Hz), 6.89 (2H, br. s.), 6.57 (1H, t, J=8.6 Hz), 2.74 (3H, d, J=4.5 Hz). MS (ESI, pos. ion) m/z: 246.9/248.9 (M+1).

Preparation of 8-bromo-7-fluoro-3-methylquinazoline-2,4(1H,3H)-dione (720b)

A mixture of tri-phosgene (Aldrich, St. Louis, Mo.; 0.233 g, 0.784 mmol) and 2-amino-3-bromo-4-fluoro-N-methylbenzamide (720a; 0.57 g, 2.30 mmol) in 23 mL anhydrous DCM was fitted with a water-cooled reflux condenser and drying tube, and heated to reflux overnight. LCMS indicated the reaction was about 85% conversion. Additional triphosgene (0.075 g) was added and heating continued for 5 h. The reaction was cooled and concentrated in vacuo to give 8-bromo-7-fluoro-3-methylquinazoline-2,4(1H,3H)-dione (0.63 g, 2.30 mmol, 100% yield) as a light orange solid. ¹H NMR (400 MHz, DMSO-d₆) δ ppm 10.89 (1H, s), 8.03 (1H, dd, J=8.8, 5.9 Hz), 7.23 (1H, t, J=8.6 Hz), 3.26 (3H, s). MS (ESI, pos. ion) m/z: 272.9/275.0 (M+1).

Preparation of 8-bromo-2-chloro-7-fluoro-3-methylquinazolin-4(3H)-one (720)

A slurry of 8-bromo-7-fluoro-3-methylquinazoline-2,4 (1H,3H)-dione (720b; 0.63 g, 2.30 mmol) in POCl₃ (Aldrich; 2.11 mL, 23.07 mmol) in a 100 mL RBF fitted with a water cooled reflux condenser and drying tube was heated to reflux. After 1 h, no reaction was observed by LCMS. DIPEA (0.80 mL, 4.61 mmol) was added. After 30 min and 1.5 h, LCMS indicated the reaction was about 50% conversion. Additional DIPEA (0.80 mL, 4.61 mmol) was added. After 3 h additional, the reaction reached 100% conversion by LCMS. The reaction was cooled and concentrated in vacuo, then ice was added to the sludge to give a slurry. 10 N NaOH was added until the pH >10, and the mixture was extracted 3×DCM and 1× EtOAc. The combined organics were dried over Na₂SO₄, filtered, and concentrated in vacuo to give 0.76 g of a sticky solid. The material was treated with DCM and purified by silica gel chromatography (40 g column) using 0-30% EtOAc/hexanes. The product-containing fractions were concentrated to afford 8-bromo-2-chloro-7-fluoro-3-methylquinazolin-4(3H)-one (0.54 g, 1.85 mmol, 80% yield) as a white solid. ¹H NMR (400 MHz, CDCl₃) δ ppm 8.24 (1H, dd, J=8.9, 5.8 Hz), 7.24-7.32 (1H, m), 3.78 (3H, s). MS (ESI, pos. ion) m/z: 290.9/292.9 (M+1).

Preparation of 8-bromo-2-chloro-3-cyclopropyl-7-fluoroquinazolin-4(3H)-one (721)

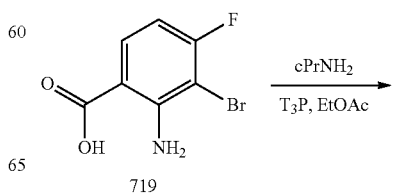

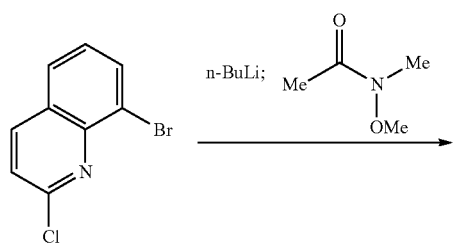

2-Amino-3-bromo-N-cyclopropyl-4-fluorobenzamide (721a) was prepared according to the procedures described for Intermediate 720a. $^1$H NMR (400 MHz, CDCl$_3$) δ ppm 7.22 (1H, dd, J=8.6, 5.9 Hz), 6.42 (1H, dd, J=8.7, 7.9 Hz), 6.07 (1H, br. s.), 2.85 (1H, td, J=6.9, 3.0 Hz), 0.85-0.95 (2H, m), 0.56-0.64 (2H, m). m/z (ESI, +ve ion) (M+H)$^+$ 272.9/ 275.0.

8-Bromo-3-cyclopropyl-7-fluoroquinazoline-2,4(1H, 3H)-dione (721b) was prepared according to the procedures described for Intermediate 720b. $^1$H NMR (400 MHz, DMSO-d$_6$) δ ppm 10.67 (1H, s), 7.99 (1H, dd, J=8.8, 5.9 Hz), 7.19 (1H, t, J=8.6 Hz), 2.60-2.75 (1H, m), 0.97-1.09 (2H, m), 0.68-0.79 (2H, m). m/z (ESI, +ve ion) 289.9/291.9 (M+H)$^+$.

8-Bromo-2-chloro-3-cyclopropyl-7-fluoroquinazolin-4 (3H)-one (721) was prepared according to the procedures described for Intermediate 720. $^1$H NMR (400 MHz, DMSO-d$_6$) δ ppm 8.13 (1H, dd, J=8.9, 6.0 Hz), 7.53 (1H, t, J=8.7 Hz), 2.91-3.10 (1H, m), 1.18-1.23 (2H, m), 0.93-1.01 (2H, m). m/z (ESI, +ve ion) 316.9/319.0 (M+H)$^+$.

Example 1

2-(2-chloroquinolin-8-yl)-6,7-dihydro-1H-pyrrolo[3, 2-c]pyridin-4(5H)-one

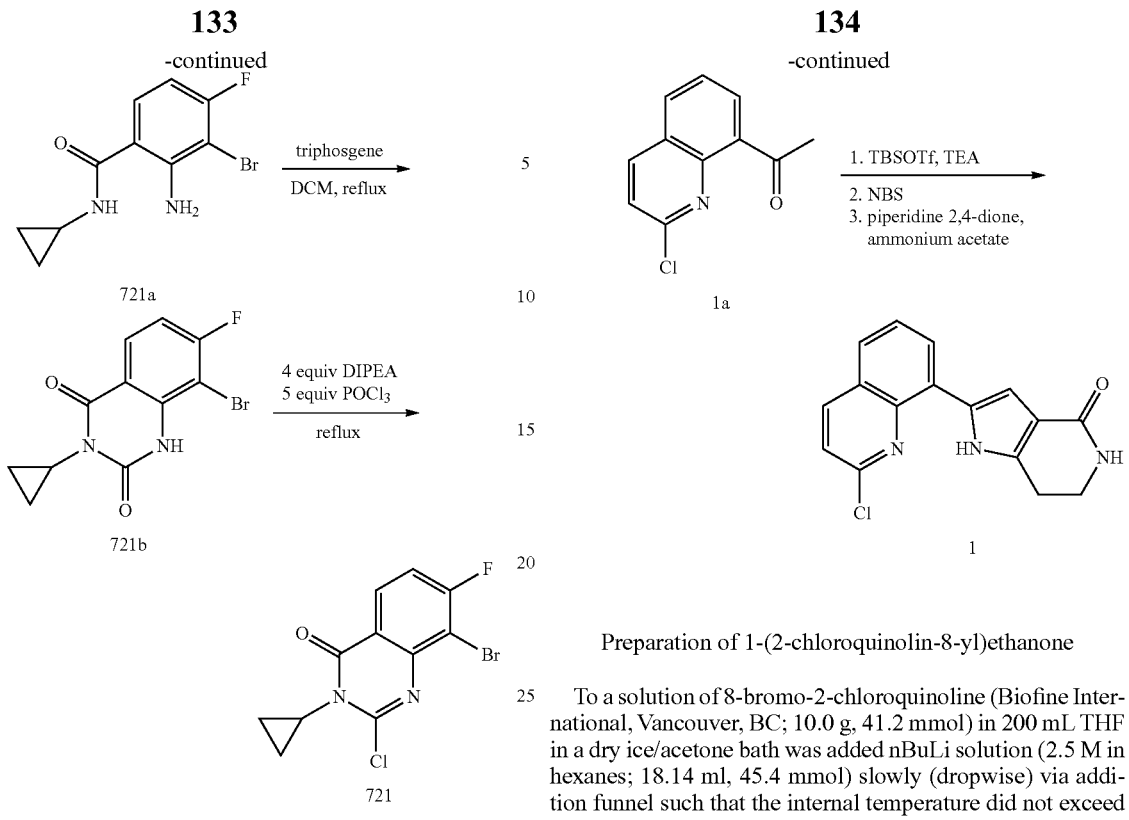

Preparation of 1-(2-chloroquinolin-8-yl)ethanone

To a solution of 8-bromo-2-chloroquinoline (Biofine International, Vancouver, BC; 10.0 g, 41.2 mmol) in 200 mL THF in a dry ice/acetone bath was added nBuLi solution (2.5 M in hexanes; 18.14 ml, 45.4 mmol) slowly (dropwise) via addition funnel such that the internal temperature did not exceed −72° C. After 15 min, N-methoxy-N-methylacetamide (Aldrich; 5.05 ml, 49.5 mmol) was added via syringe such that the internal temperature did not exceed −72° C. The dry ice/acetone bath was removed and the reaction was quenched with 200 mL saturated aq. NH$_4$Cl and diluted with 300 mL Et$_2$O. The organic layer was washed 1× brine, dried over anhydrous MgSO$_4$, filtered, and concentrated in vacuo. The material was treated with DCM and purified by silica gel chromatography (240 g column) using 0-20% EtOAc/hexanes until less polar impurities elute, then 20-40% EtOAc/ hexanes to elute desired material. Fractions were combined and concentrated to give 1-(2-chloroquinolin-8-yl)ethanone (3.63 g, 17.65 mmol, 43% yield) as a peach-colored solid: $^1$H NMR (400 MHz, CDCl$_3$) δ ppm 8.16 (1H, d, J=8.6 Hz), 8.06 (1H, dd, J=7.2, 1.6 Hz), 7.96 (1H, dd, J=8.0, 1.6 Hz), 7.59- 7.66 (1H, m), 7.46 (1H, d, J=8.6 Hz), 2.98 (3H, s). m/z (ESI, +ve) 206.0 (M+H)$^+$.

Preparation of 2-(2-chloroquinolin-8-yl)-6,7-dihydro-1H-pyrrolo[3,2-c]pyridin-4(5H)-one To a solution of 1-(2-chloroquinolin-8-yl)ethanone (3.25 g, 15.80 mmol) in 3 mL DCM at 0° C. was added Et$_3$N (2.86 ml, 20.55 mmol) followed by TBSOTf (3.99 ml, 17.38 mmol), dropwise. The reaction was stirred for 1 h, and then was partitioned between saturated aq. NaHCO$_3$ and DCM. The aq. layer was extracted with DCM 3 times, and the combined organics were dried over anhydrous Na$_2$SO$_4$, filtered, and concentrated in vacuo to give 5.71 g of an orange oil. This oil was taken up in 70 mL THF, treated with water (4.56 ml, 253 mmol) and NBS (2.95 g, 16.59 mmol), and stirred at 25° C. for 15 min. The reaction was then partitioned between water and Et$_2$O. The organic layer was sequentially washed with saturated aq. NaHCO$_3$, water, and saturated aq. NaCl, and the organics layer was dried over anhydrous MgSO$_4$, filtered, and concentrated in vacuo to give 6 g of a yellow solid. This solid was treated with NH$_4$OAc (4.87 g, 63.2 mmol) and piperidine-2,4-dione (see *J Med. Chem.*

2008, 51, 487-501; 2.145 g, 18.97 mmol) and 70 mL EtOH and stirred at RT for 5 min. The resulting yellow slurry was placed in a sealed vial and heated at 50° C. for 4 h, then cooled and concentrated in vacuo. The residue was partitioned between saturated aq. NaHCO$_3$ and DCM. The aq. layer was extracted with DCM (4×), and the combined organics were dried over anhydrous Na$_2$SO$_4$, filtered, and concentrated in vacuo. The material was treated with DCM and purified by silica gel chromatography using 0-65% 90/10 DCM/MeOH in DCM. The product-containing fractions were concentrated to afford 2-(2-chloroquinolin-8-yl)-6,7-dihydro-1H-pyrrolo[3,2-c]pyridin-4(5H)-one (1.86 g, 6.25 mmol, 40% yield) as a orange solid: $^1$H NMR (400 MHz, DMSO-d$_6$) δ ppm 11.71 (1H, br. s), 8.49 (1H, d, J=8.6 Hz), 8.09 (1H, dd, J=7.4, 1.4 Hz), 7.87-7.92 (1H, m), 7.63-7.72 (2H, m), 7.26 (1H, d, J=2.3 Hz), 6.97-7.04 (1H, m), 3.40-3.47 (2H, m), 2.91 (2H, t, J=6.9 Hz). m/z (ESI, +ve) 298.0 (M+H)$^+$.

Example 2

2-(2-(phenylamino)quinolin-8-yl)-6,7-dihydro-1H-pyrrolo[3,2-c]pyridin-4(5H)-one

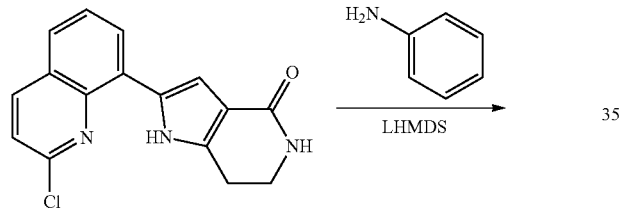

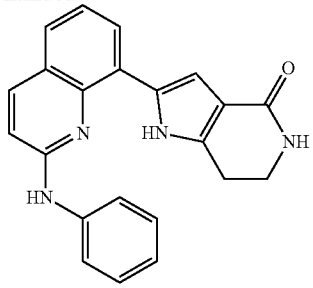

A dark red mixture of aniline (0.077 ml, 0.840 mmol), 2-(2-chloroquinolin-8-yl)-6,7-dihydro-1H-pyrrolo[3,2-c]pyridin-4(5H)-one (Example 1; 0.050 g, 0.168 mmol) and LHMDS (1.0 M solution in THF; 0.840 ml, 0.840 mmol) was sealed and stirred at RT for 1 h. The reaction was then partitioned between saturated aq. NH$_4$Cl and DCM. The aq. layer was extracted with DCM (3×), and the combined organics were dried over anhydrous Na$_2$SO$_4$, filtered, and concentrated in vacuo. The resulting material was suspended in 1 mL MeOH, sonicated for 1 min, filtered, and rinsed 2× MeOH. The solid was dried in vacuo to give 2-(2-(phenylamino)quinolin-8-yl)-6,7-dihydro-1H-pyrrolo[3,2-c]pyridin-4(5H)-one (0.035 g, 0.099 mmol, 59% yield) as a light-yellow solid: $^1$H NMR (400 MHz, DMSO-d$_6$) δ ppm 12.18 (1H, br. s), 9.52 (1H, s), 8.11 (1H, d, J=9.0 Hz), 7.94 (1H, dd, J=7.4, 1.6 Hz), 7.62-7.70 (2H, m), 7.55-7.61 (1H, m), 7.36-7.45 (2H, m), 7.28 (1H, t, J=7.7 Hz), 7.04-7.14 (2H, m), 6.87-6.95 (2H, m), 3.35-3.44 (2H, m), 2.59-2.69 (2H, m). m/z (ESI, +ve) 355.0 (M+H)$^+$.

Example 3

2-(2-benzylquinolin-8-yl)-6,7-dihydro-1H-pyrrolo[3,2-c]pyridin-4(5H)-one

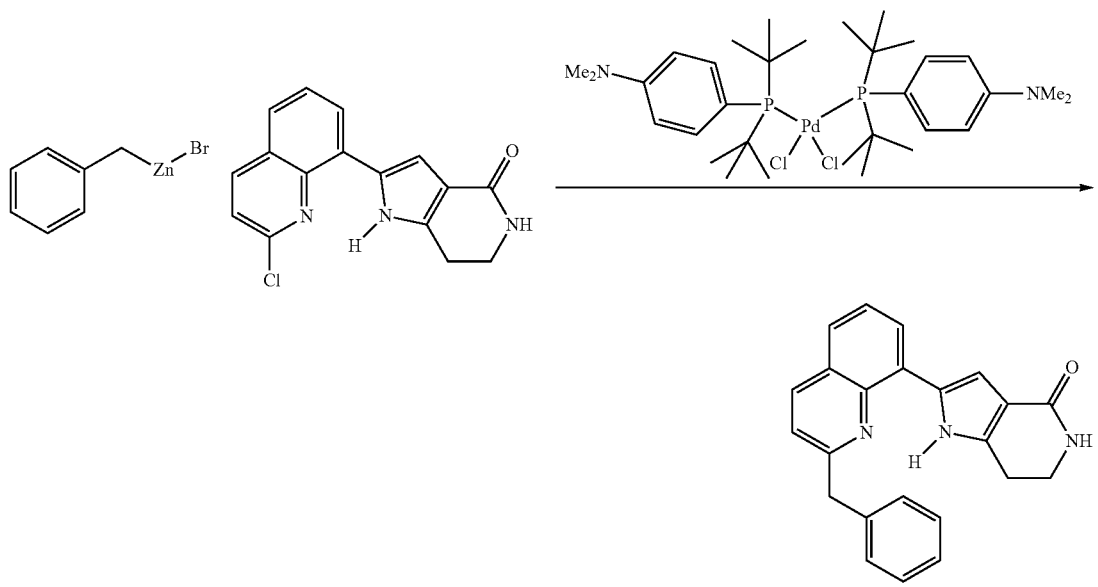

Argon was bubbled through a slurry of bis(4-(di-tert-butylphosphino)-N,N-dimethylbenzenamine)palladium dichloride (Aldrich; 10.23 mg, 0.014 mmol), 2-(2-chloroquinolin-8-yl)-6,7-dihydro-1H-pyrrolo[3,2-c]pyridin-4(5H)-one (Example 1, 0.043 g, 0.144 mmol), and benzylzinc bromide (0.5 M solution in THF; Aldrich; 1.155 ml, 0.578 mmol) in 1.5 mL THF for 2 min. The reaction mixture was sealed and heated to 70° C. After 1 h, the reaction was cooled to RT. The mixture was concentrated, dissolved in DMSO+ 1-2 drops TFA, filtered, and purified by rpHPLC (Phenomenex Gemini 150×30 mm $C_{18}$ column, 15-100% ACN/$H_2O$ with 0.1% TFA); product-containing fractions were concentrated in vacuo and the residue was treated with saturated aq. $NaHCO_3$ and DCM. The aq. layer was extracted 3×DCM and combined organics dried over $Na_2SO_4$, filtered, and concentrated in vacuo to give 2-(2-benzylquinolin-8-yl)-6,7-dihydro-1H-pyrrolo[3,2-c]pyridin-4(5H)-one (0.026 g, 0.074 mmol, 50.9% yield): $^1$H NMR (400 MHz, DMSO-$d_6$) δ ppm 12.17 (1H, br. s), 8.35 (1H, d, J=8.6 Hz), 8.14 (1H, dd, J=7.4, 1.4 Hz), 7.76 (1H, dd, J=8.0, 1.4 Hz), 7.50-7.60 (2H, m), 7.33-7.43 (4H, m), 7.24-7.30 (1H, m), 7.11 (1H, d, J=2.3 Hz), 6.94-7.00 (1H, m), 4.45 (2H, s), 3.38-3.46 (2H, m), 2.80 (2H, t, J=6.9 Hz). m/z (ESI, +ve) 353.9 (M+H)$^+$.

Example 4

2-(2-(methyl(phenyl)amino)quinolin-8-yl)-6,7-dihydro-1H-pyrrolo[3,2-c]pyridin-4(5H)-one

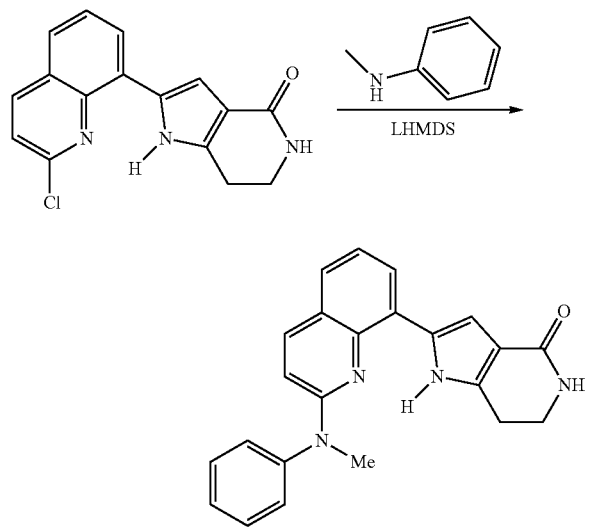

To N-methylaminobenzene (Alfa Aesar, Ward Hill, Mass.; 0.136 ml, 1.259 mmol) and 2-(2-chloroquinolin-8-yl)-6,7-dihydro-1H-pyrrolo[3,2-c]pyridin-4(5H)-one (Example 1; 0.075 g, 0.252 mmol) was added LHMDS (1.0 M solution in THF; 1.259 ml, 1.259 mmol). The resulting mixture was stirred rapidly at RT. After 2 h, the mixture was partitioned between saturated aq. $NH_4Cl$ and DCM. The aq. layer was extracted with DCM (3×), and the combined organics were dried over anhydrous $Na_2SO_4$, filtered, and concentrated in vacuo. The material was treated with DCM and purified by silica gel chromatography (25 g column) using 0-50% 90/10 DCM/MeOH in DCM. The product-containing fractions were concentrated to afford 0.061 g of impure material. The material was dissolved in MeOH and placed in the freezer. The resulting solid was triturated with MeOH (3×1 mL), dried, and the solid collected to give 2-(2-(methyl(phenyl)amino)quinolin-8-yl)-6,7-dihydro-1H-pyrrolo[3,2-c]pyridin-4(5H)-one (0.027 g, 0.073 mmol, 29% yield) as a light-yellow solid: $^1$H NMR (400 MHz, DMSO-$d_6$) δ ppm 12.18 (1H, br. s), 8.05 (1H, d, J=9.2 Hz), 7.99 (1H, dd, J=7.4, 1.6 Hz), 7.50-7.62 (3H, m), 7.34-7.46 (3H, m), 7.28 (1H, t, J=7.6 Hz), 7.03 (1H, d, J=2.2 Hz), 6.89-6.98 (2H, m), 3.59 (3H, s), 3.35-3.45 (2H, m), 2.69 (2H, t, J=6.8 Hz). m/z (ESI, +ve) 369.0 (M+H)$^+$.

Example 5

2-(2-(phenylthio)quinolin-8-yl)-6,7-dihydro-1H-pyrrolo[3,2-c]pyridin-4(5H)-one

To NaH (60 wt % in mineral oil; 0.050 g, 1.259 mmol) in 1 mL NMP was added benzenethiol (0.129 ml, 1.259 mmol). After 10 min, a clear/colorless solution resulted. 2-(2-Chloroquinolin-8-yl)-6,7-dihydro-1H-pyrrolo[3,2-c]pyridin-4(5H)-one (Example 1; 0.075 g, 0.252 mmol) was added as a solid and the reaction became orange. After 1 h, the reaction was sealed and heated to 70° C. for 1 h. The reaction was cooled and was partitioned between saturated aq. $NaHCO_3$ and EtOAc. The organic layer was washed with saturated aq. $NaHCO_3$ (3×) and saturated aq. NaCl (1×), and the organics were dried over anhydrous $Na_2SO_4$, filtered, and concentrated in vacuo. The material was treated with DCM and purified by silica gel chromatography (25 g column) using 0-50% 90/10 DCM/MeOH in DCM. The product-containing fractions were concentrated to afford a yellow solid. The material was treated with 1 mL MeOH, sonicated, and filtered, rinsing with MeOH, to give 2-(2-(phenylthio)quinolin-8-yl)-6,7-dihydro-1H-pyrrolo[3,2-c]pyridin-4(5H)-one (0.042 g, 0.113 mmol, 45% yield) as a yellow solid: $^1$H NMR (400 MHz, DMSO-$d_6$) δ ppm 11.18-11.45 (1H, m), 8.28 (1H, d, J=8.6 Hz), 8.09 (1H, dd, J=7.5, 1.5 Hz), 7.67-7.79 (3H, m), 7.48-7.61 (4H, m), 7.36 (1H, d, J=8.8 Hz), 7.05 (1H, d, J=2.3 Hz), 6.92-6.98 (1H, m), 3.33-3.42 (2H, m), 2.50-2.55 (2H, m). m/z (ESI, +ve) 371.9 (M+H)$^+$.

Example 6

2-(2-((2-fluorophenyl)amino)quinolin-8-yl)-6,7-dihydro-1H-pyrrolo[3,2-c]pyridin-4(5H)-one

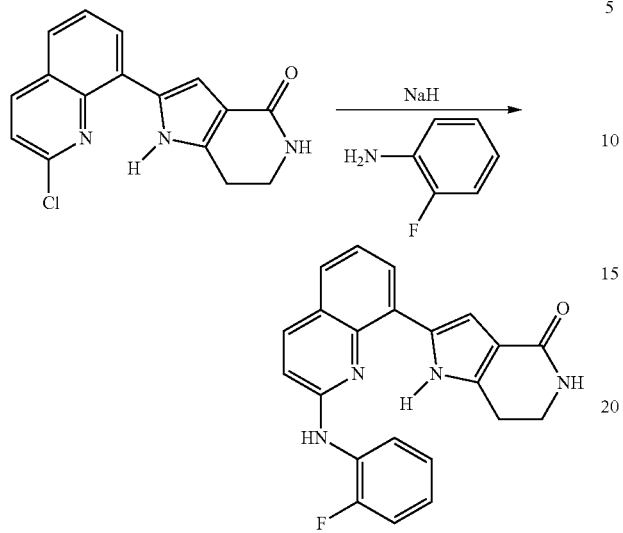

To NaH (60 wt % in mineral oil; 0.071 g, 1.763 mmol) in 1 mL DMF was added 2-fluoroaniline (0.196 g, 1.763 mmol). After 10 min, a clear/colorless solution resulted. 2-(2-Chloroquinolin-8-yl)-6,7-dihydro-1H-pyrrolo[3,2-c]pyridin-4(5H)-one (Example 1; 0.075 g, 0.252 mmol) was added as a solid and the reaction became dark red. After 30 min, the reaction was heated at 70° for 2 h. The reaction mixture was then cooled to RT and partitioned between saturated aq. NH$_4$Cl and EtOAc. The organic layer was washed with saturated aq. NaHCO$_3$ (1×), water (1×), saturated aq. NaCl (1×), and the organics were dried over anhydrous Na$_2$SO$_4$, filtered, and concentrated in vacuo. The material was suspended in DCM and filtered, rinsing 2×DCM, dried in vacuo to give 2-(2-((2-fluorophenyl)amino)quinolin-8-yl)-6,7-dihydro-1H-pyrrolo[3,2-c]pyridin-4(5H)-one (0.021 g, 0.056 mmol, 22% yield) as a dull-yellow solid: $^1$H NMR (400 MHz, DMSO-d$_6$) δ ppm 12.04 (1H, br. s.), 9.32 (1H, s), 8.14 (1H, s), 7.97 (1H, dd, J=7.5, 1.5 Hz), 7.84-7.93 (1H, m), 7.56-7.62 (1H, m), 7.34-7.44 (1H, m), 7.22-7.33 (3H, m), 7.15-7.21 (1H, m), 6.86-6.95 (2H, m), 3.32-3.41 (2H, m), 2.51-2.57 (2H, m). m/z (ESI, +ve) 373.0 (M+H)$^+$.

Example 7

2-(2-((2-chloro-6-fluorophenyl)amino)quinolin-8-yl)-6,7-dihydro-1H-pyrrolo[3,2-c]pyridin-4(5H)-one

Example 12

2-(2-((2-chloro-6-fluorophenyl)amino)quinolin-8-yl)-1H-pyrrolo[3,2-c]pyridin-4(5H)-one

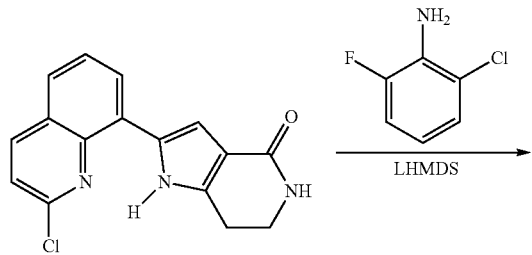

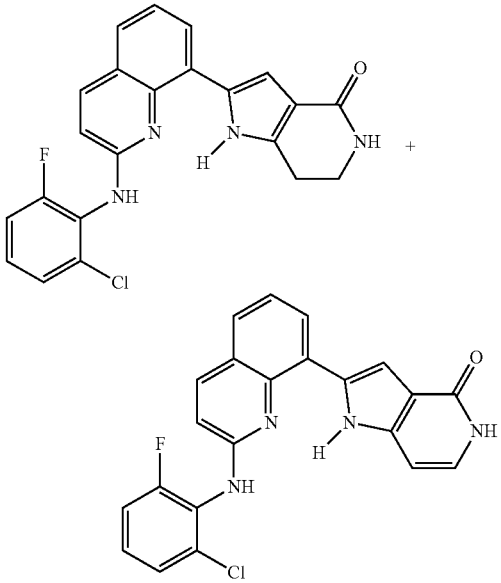

To 2-chloro-6-fluoroaniline (0.183 g, 1.259 mmol) and 2-(2-chloroquinolin-8-yl)-6,7-dihydro-1H-pyrrolo[3,2-c]pyridin-4(5H)-one (Example 1; 0.075 g, 0.252 mmol) was added LHMDS (1.0 M solution in THF; 1.259 ml, 1.259 mmol). The reaction was sealed and stirred 1 h at RT, then for 3 h at 70° C. The reaction was subsequently cooled to RT and stirred overnight. 1.5 mL DMSO and 10 drops TFA were added. The mixture was filtered and purified by rpHPLC (Phenomenex Gemini 150×30 mm C$_{18}$ column, 10-80% ACN/H$_2$O with 0.1% TFA). The product-containing fractions were concentrated in vacuo, and the residue was partitioned between saturated aq. NaHCO$_3$ and DCM. The aq. layer was extracted with DCM (3×), and the combined organic extracts were dried over anhydrous Na$_2$SO$_4$, filtered, and concentrated in vacuo. The material was dissolved in DCM/MeOH, adsorbed onto 0.75 g silica gel, and purified by silica gel chromatography using 0-50% 90/10 MeOH/DCM in DCM. The product-containing fractions were concentrated to separately afford 2-(2-((2-chloro-6-fluorophenyl)amino)quinolin-8-yl)-6,7-dihydro-1H-pyrrolo[3,2-c]pyridin-4(5H)-one (0.022 g, 0.054 mmol, 21% yield) as a light-yellow solid and 2-(2-((2-chloro-6-fluorophenyl)amino)quinolin-8-yl)-1H-pyrrolo[3,2-c]pyridin-4(5H)-one (0.0037 g, 9.14 µmol, 4% yield) as a yellow solid. 2-(2-((2-Chloro-6-fluorophenyl)amino)quinolin-8-yl)-6,7-dihydro-1H-pyrrolo[3,2-c]pyridin-4(5H)-one (7): $^1$H NMR (400 MHz, DMSO-d$_6$) δ ppm 11.82 (1H, br. s), 9.34 (1H, s), 8.16 (1H, d, J=9.0 Hz), 8.01 (1H, dd, J=7.6, 1.6 Hz), 7.55-7.67 (2H, m), 7.41-7.54 (2H, m), 7.28 (1H, t, J=7.7 Hz), 7.13 (1H, d, J=9.0 Hz), 6.83-6.98 (2H, m), 3.32-3.44 (2H, m), 2.43 (2H, t, J=6.8 Hz). m/z (ESI, +ve) 406.9 (M+H)$^+$. 2-(2-((2-Chloro-6-fluorophenyl)amino)quinolin-8-yl)-1H-pyrrolo[3,2-c]pyridin-4(5H)-one (12): $^1$H NMR (400 MHz, DMSO-d$_6$) δ ppm 12.09 (1H, br. s), 10.68 (1H, d, J=6.1 Hz), 9.41 (1H, s), 8.11-8.26 (2H, m), 7.43-7.76 (4H, m), 7.34 (1H, t, J=7.7 Hz), 7.18-7.25 (1H, m), 7.14 (1H, d, J=9.0 Hz), 6.86-7.00 (1H, m), 5.91 (1H, d, J=6.8 Hz). m/z (ESI, +ve) 405.2 (M+H)$^+$.

Example 8

2-(2-((2,4-difluorophenyl)amino)quinolin-8-yl)-6,7-dihydro-1H-pyrrolo[3,2-c]pyridin-4(5H)-one

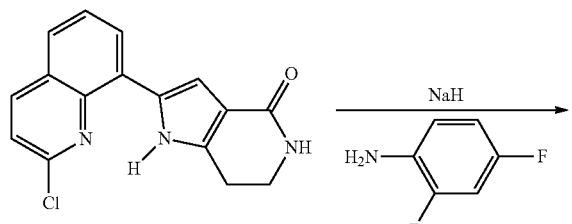

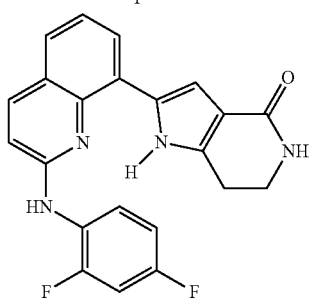

To NaH (60 wt % in mineral oil; 0.071 g, 1.763 mmol) in 1 mL DMF was added 2,4-difluoroaniline (0.178 ml, 1.763 mmol). After 10 min, 2-(2-chloroquinolin-8-yl)-6,7-dihydro-1H-pyrrolo[3,2-c]pyridin-4(5H)-one (Example 1; 0.075 g, 0.252 mmol) was added as a solid and the reaction became dark red. The reaction was heated at 70° C. for 4 h, and then cooled to RT and partitioned between saturated aq. NH₄Cl and EtOAc. The organic layer was separated and sequentially washed with saturated aq. NH₄Cl and saturated aq. NaCl, and the organic layers were dried over anhydrous Na₂SO₄, filtered, and concentrated in vacuo. The material was treated with DCM and purified by silica gel chromatography using 0-50% 90/10 DCM/MeOH in DCM. The product-containing fractions were concentrated to afford 2-(2-((2,4-difluorophenyl)amino)quinolin-8-yl)-6,7-dihydro-1H-pyrrolo[3,2-c]pyridin-4(5H)-one (0.021 g, 0.054 mmol, 21% yield) as a brown solid: $^1$H NMR (400 MHz, DMSO-d₆) δ ppm 11.96 (1H, br. s), 9.27 (1H, s), 8.13 (1H, d, J=9.0 Hz), 7.83-8.00 (2H, m), 7.59 (1H, dt, J=7.6, 0.9 Hz), 7.46 (1H, ddd, J=11.2, 8.8, 2.9 Hz), 7.28 (1H, t, J=7.6 Hz), 7.17-7.24 (1H, m), 7.14 (1H, d, J=9.0 Hz), 6.89-6.96 (2H, m), 3.35-3.41 (2H, m), 2.57 (2H, t, J=6.9 Hz). m/z (ESI, +ve) 391.2 (M+H)⁺.

Example 9

2-(2-(2-chloro-6-fluorophenoxy)quinolin-8-yl)-6,7-dihydro-1H-pyrrolo[3,2-c]pyridin-4(5H)-one

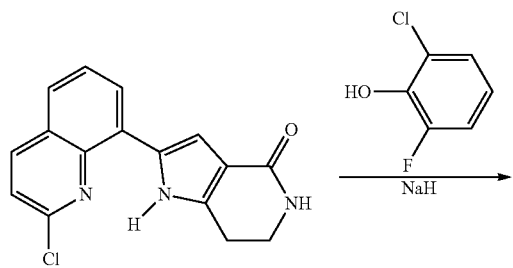

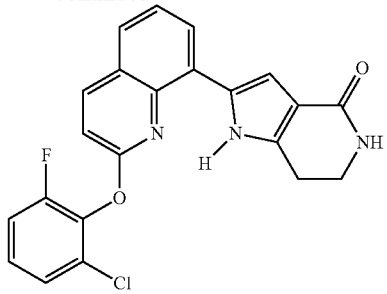

To NaH (60 wt % in mineral oil; 0.071 g, 1.763 mmol) in 1 mL DMF was added 2-chloro-6-fluorophenol (0.258 g, 1.763 mmol). After 10 min, a clear/colorless solution resulted. 2-(2-Chloroquinolin-8-yl)-6,7-dihydro-1H-pyrrolo[3,2-c]pyridin-4(5H)-one (Example 1; 0.075 g, 0.252 mmol) was added and the reaction became dark red. The reaction was heated at 70° C. for 1 h, then at 90° C. for 2 h, then at 110° C. for 14 h. The reaction was cooled to 0° C. and quenched with TFA (0.136 ml, 1.763 mmol), diluted with 1 mL DMSO, filtered, and purified by rpHPLC (Phenomenex Gemini 150×30 mm C₁₈ column, 15-100% ACN/H₂O with 0.1% TFA); product-containing fractions were concentrated in vacuo then treated with saturated aq. NaHCO₃ and DCM. The organic layer was separated and the aq. layer was extracted 3×DCM. The combined organic extracts were then dried over Na₂SO₄, filtered, and concentrated in vacuo to give 2-(2-(2-chloro-6-fluorophenoxy)quinolin-8-yl)-6,7-dihydro-1H-pyrrolo[3,2-c]pyridin-4(5H)-one (0.030 g, 0.074 mmol, 29% yield) as a yellow solid: $^1$H NMR (400 MHz, DMSO-d₆) δ ppm 10.91 (1H, br. s), 8.57 (1H, d, J=8.8 Hz), 8.05-8.15 (1H, m), 7.84 (1H, dt, J=7.7, 0.8 Hz), 7.38-7.69 (5H, m), 6.87-6.91 (1H, m), 6.85 (1H, d, J=2.3 Hz), 3.32-3.38 (2H, m), 2.54-2.50 (2H, m). m/z (ESI, +ve) 408.2 (M+H)⁺.

Example 10

2-(2-(2,4-difluorophenoxy)quinolin-8-yl)-6,7-dihydro-1H-pyrrolo[3,2-c]pyridin-4(5H)-one

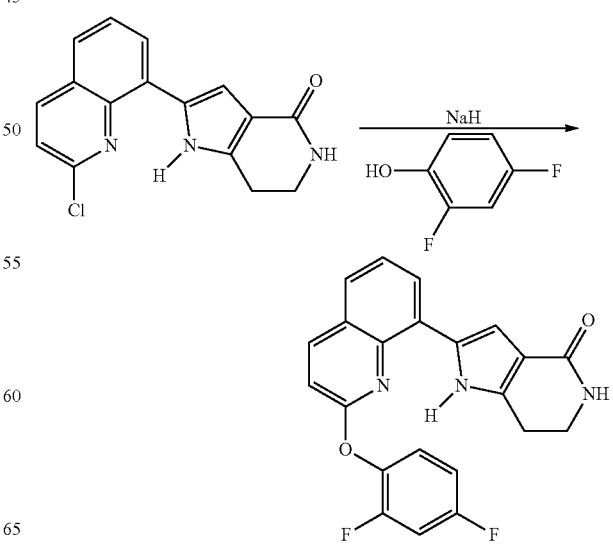

To NaH (60 wt % in mineral oil; 0.071 g, 1.763 mmol) in 1 mL DMF was added 2,4-difluorophenol (0.229 g, 1.76 mmol). After 10 min, a clear/colorless solution resulted. 2-(2-Chloroquinolin-8-yl)-6,7-dihydro-1H-pyrrolo[3,2-c]pyridin-4(5H)-one (Example 1; 0.075 g, 0.252 mmol) was added and the reaction became dark red. The reaction was sealed and heated to 90° C. for 4 h, then cooled to RT and stirred overnight. The reaction was cooled and partitioned between saturated aq. NH$_4$Cl and EtOAc. The organic layer was washed with saturated aq. NaHCO$_3$ (1×), water (1×), saturated aq. NaCl (1×), and the organics were dried over anhydrous Na$_2$SO$_4$, filtered, and concentrated in vacuo. The material was treated with DCM and purified by silica gel chromatography using 0-50% 90/10 DCM/MeOH in DCM. The product-containing fractions were concentrated to afford 2-(2-(2,4-difluorophenoxy)quinolin-8-yl)-6,7-dihydro-1H-pyrrolo[3,2-c]pyridin-4(5H)-one (0.036 g, 0.092 mmol, 37% yield) as a yellow solid: $^1$H NMR (400 MHz, DMSO-d$_6$) δ ppm 10.99 (1H, br. s), 8.52 (1H, d, J=9.0 Hz), 8.09 (1H, dd, J=7.6, 1.4 Hz), 7.79-7.85 (1H, m), 7.55-7.69 (2H, m), 7.51 (1H, t, J=7.7 Hz), 7.47 (1H, d, J=9.0 Hz), 7.30 (1H, dddd, J=9.2, 7.9, 3.1, 1.5 Hz), 6.91-6.94 (1H, m), 6.90 (1H, d, J=2.3 Hz), 3.34-3.40 (2H, m), 2.52-2.57 (2H, m). m/z (ESI, +ve) 392.1 (M+H)$^+$.

Example 11

2-(2-(2-fluorophenoxy)quinolin-8-yl)-6,7-dihydro-1H-pyrrolo[3,2-c]pyridin-4(5H)-one

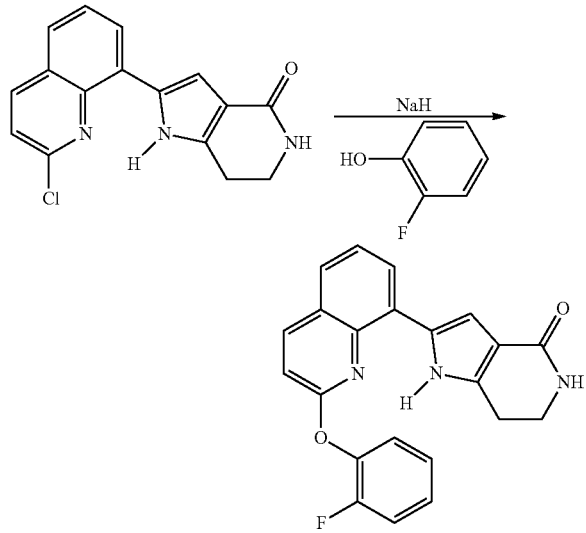

To NaH (60 wt % in mineral oil; 0.071 g, 1.763 mmol) in 1 mL DMF was added 2-fluorophenol (0.163 ml, 1.763 mmol). After 10 min, a clear/colorless solution resulted. 2-(2-Chloroquinolin-8-yl)-6,7-dihydro-1H-pyrrolo[3,2-c]pyridin-4(5H)-one (Example 1; 0.075 g, 0.252 mmol) was added and the reaction became dark red. The reaction was heated to 70° C. After 1 h, the temperature was increased to 90° C. After 4 h, the reaction was cooled to RT and stirred overnight. The reaction was then cooled to 0° C. and quenched with TFA (0.136 ml, 1.763 mmol), diluted with 1 mL DMSO, filtered, and purified by rpHPLC (Phenomenex Gemini 150×30 mm C$_{18}$ column, 15-100% ACN/H$_2$O with 0.1% TFA); product-containing fractions were concentrated in vacuo then treated with saturated aq. NaHCO$_3$ and DCM. The aq. layer was extracted 3×DCM and combined organics dried over Na$_2$SO$_4$, filtered, and concentrated in vacuo to give 2-(2-(2-fluorophenoxy)quinolin-8-yl)-6,7-dihydro-1H-pyrrolo[3,2-c]pyridin-4(5H)-one (0.036 g, 0.096 mmol, 38% yield) as a yellow solid: $^1$H NMR (400 MHz, DMSO-d$_6$) δ ppm 10.91 (1H, br. s), 8.52 (1H, d, J=8.8 Hz), 8.12 (1H, dd, J=7.6, 1.4 Hz), 7.74-7.89 (1H, m), 7.36-7.66 (6H, m), 6.85-6.99 (2H, m), 3.32-3.36 (2H, m), 2.43 (2H, t, J=6.9 Hz). m/z (ESI, +ve) 374.2 (M+H)$^+$.

Example 13

2-(2-(pyrimidin-5-ylamino)quinolin-8-yl)-6,7-dihydro-1H-pyrrolo[3,2-c]pyridin-4(5H)-one

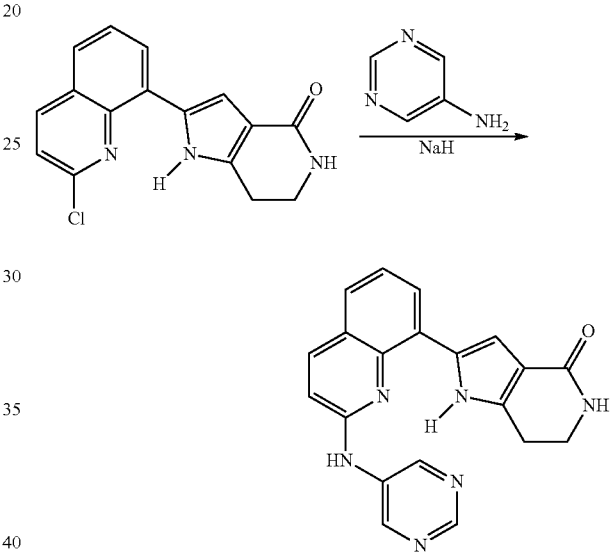

To NaH (60 wt % in mineral oil; 0.071 g, 1.763 mmol) in 1 mL DMF was added 5-aminopyrimidine (AK Scientific, Union City, Calif.; 0.168 g, 1.76 mmol). After 10 min, 2-(2-chloroquinolin-8-yl)-6,7-dihydro-1H-pyrrolo[3,2-c]pyridin-4(5H)-one (Example 1; 0.075 g, 0.252 mmol) was added and the reaction became dark red. After 2 h, the reaction was cooled to 0° C. and TFA (0.136 ml, 1.763 mmol) was added along with 1 mL DMSO. The reaction was filtered, and purified by rpHPLC (Phenomenex Gemini 150×30 mm C$_{18}$ column, 10-60% ACN/H$_2$O with 0.1% TFA); the product-containing fractions were concentrated in vacuo then treated with saturated aq. NaHCO$_3$ and DCM. The organic layer was separated, and the aq. layer was extracted 3×DCM and 1× EtOAc. The combined organic layers were then treated with MeOH until the solid dissolved, dried over anhydrous MgSO$_4$, filtered, and concentrated in vacuo to give 2-(2-(pyrimidin-5-ylamino)quinolin-8-yl)-6,7-dihydro-1H-pyrrolo[3,2-c]pyridin-4(5H)-one (0.039 g, 0.109 mmol, 43% yield) as a yellow solid: $^1$H NMR (400 MHz, DMSO-d$_6$) δ ppm 11.66 (1H, br. s), 9.84 (1H, s), 9.21 (2H, s), 8.82 (1H, s), 8.21 (1H, d, J=8.8 Hz), 7.83 (1H, dd, J=7.2, 1.6 Hz), 7.70 (1H, dd, J=8.0, 1.6 Hz), 7.37 (1H, t, J=7.6 Hz), 7.15 (1H, d, J=8.8 Hz), 6.82-6.95 (1H, m), 6.66 (1H, d, J=2.2 Hz), 3.37-3.54 (2H, m), 2.83 (2H, t, J=6.9 Hz). m/z (ESI, +ve) 357.0 (M+H)$^+$.

Example 14

2-(2-(ethyl(phenyl)amino)quinolin-8-yl)-6,7-dihydro-1H-pyrrolo[3,2-c]pyridin-4(5H)-one

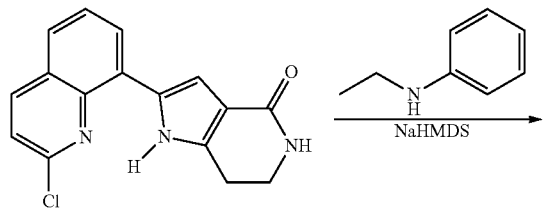

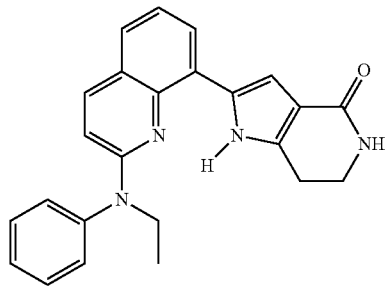

NaHMDS (1.0 M solution in THF; 1.975 ml, 1.975 mmol) was added to N-ethylaniline (0.249 ml, 1.975 mmol) and 2-(2-chloroquinolin-8-yl)-6,7-dihydro-1H-pyrrolo[3,2-c]pyridin-4(5H)-one (Example 1; 0.084 g, 0.282 mmol). The dark red reaction was stirred rapidly at RT. After 2 h, the reaction was quenched with saturated aq. NH₄Cl. The reaction was partitioned between saturated aq. NH₄Cl and DCM. The aq. layer was extracted with DCM (3×), and the combined organics were dried over anhydrous Na₂SO₄, filtered, and concentrated in vacuo. This material was dissolved in DMSO and purified by rpHPLC (Phenomenex Gemini 150× 30 mm C₁₈ column, 10-80% ACN/H₂O with 0.1% TFA); product-containing fractions were treated with saturated aq. NaHCO₃ and DCM. The combined organic layers were then the aq. layer was extracted 3×DCM, the combined organics layers were then dried over Na₂SO₄, filtered, and concentrated in vacuo to give 2-(2-(ethyl(phenyl)amino)quinolin-8-yl)-6,7-dihydro-1H-pyrrolo[3,2-c]pyridin-4(5H)-one (0.044 g, 0.115 mmol, 40.8% yield) as an orange solid: $^1$H NMR (400 MHz, DMSO-$d_6$) δ ppm 12.07-12.29 (1H, m), 7.92-8.19 (2H, m), 7.48-7.63 (3H, m), 7.34-7.47 (3H, m), 7.26 (1H, t, J=7.6 Hz), 6.98-7.07 (1H, m), 6.89-6.98 (1H, m), 6.83 (1H, d, J=9.2 Hz), 4.08 (2H, q, J=7.0 Hz), 3.36-3.44 (2H, m), 2.69 (2H, t, J=6.9 Hz), 1.30 (3H, t, J=7.0 Hz). m/z (ESI, +ve) 383.0 (M+H)⁺.

Example 15

2-(2-((4-chlorophenyl)amino)quinolin-8-yl)-6,7-dihydro-1H-pyrrolo[3,2-c]pyridin-4(5H)-one

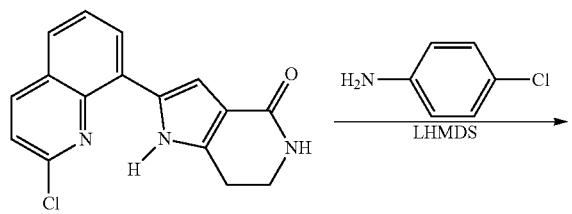

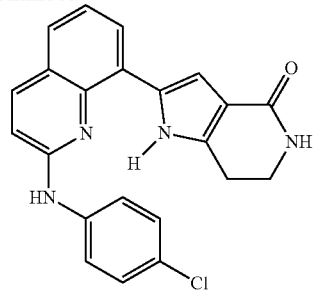

To 4-chloroaniline (Alfa Aesar, Ward Hill, Mass.; 0.225 g, 1.763 mmol) and 2-(2-chloroquinolin-8-yl)-6,7-dihydro-1H-pyrrolo[3,2-c]pyridin-4(5H)-one (Example 1; 0.075 g, 0.252 mmol) was added LHMDS (1.0 M solution in THF; 1.763 ml, 1.763 mmol). After 3 h, the reaction mixture was partitioned between saturated aq. NH₄Cl and DCM. The aq. layer was extracted with DCM (3×), and the combined organics were dried over anhydrous Na₂SO₄, filtered, and concentrated in vacuo. EtOAc was added, the layers were separated, and the organic layer was dried over Na₂SO₄, filtered, and concentrated in vacuo. The solid was suspended in MeOH and filtered, rinsing 1× MeOH to give 2-(2-((4-chlorophenyl)amino)quinolin-8-yl)-6,7-dihydro-1H-pyrrolo[3,2-c]pyridin-4(5H)-one (0.017 g, 0.044 mmol, 17% yield) as a dull-yellow solid: $^1$H NMR (400 MHz, DMSO-$d_6$) δ ppm 11.96 (1H, br. s), 9.62 (1H, s), 8.12 (1H, d, J=9.0 Hz), 7.89 (1H, dt, J=7.2, 0.8 Hz), 7.72-7.81 (2H, m), 7.61 (1H, dt, J=7.8, 0.9 Hz), 7.36-7.46 (2H, m), 7.31 (1H, t, J=7.6 Hz), 7.08 (1H, d, J=9.0 Hz), 6.88-7.00 (2H, m), 3.37-3.52 (2H, m), 2.70 (2H, t, J=6.9 Hz). m/z (ESI, +ve) 389.0 (M+H)⁺.

Example 16

6-(2-(phenylamino)quinolin-8-yl)-3H-pyrrolo[2,3-d]pyrimidin-4(7H)-one

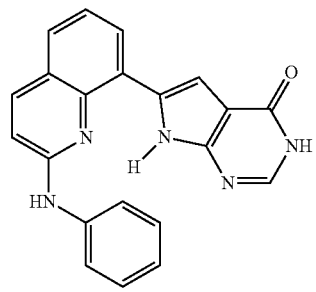

To 6-(2-chloroquinolin-8-yl)-3H-pyrrolo[2,3-d]pyrimidin-4(7H)-one hydrochloride (Example 19b; 0.075 g, 0.225 mmol) and aniline (0.144 ml, 1.576 mmol) was added LHMDS (1.0 M in THF; 1.576 ml, 1.576 mmol). After 1 h the reaction was partitioned between saturated aq. NH₄Cl and EtOAc. The aq. layer was washed with saturated aq. NH₄Cl and 1× brine, dried over Na₂SO₄, and concentrated in vacuo. The solid residue from the separatory funnel was rinsed with 10% DCM/MeOH into an Erlenmeyer flask, dried over anhydrous Na₂SO₄, filtered, and concentrated in vacuo. The resulting solid was suspended in MeOH and filtered. The solid was collected to give 6-(2-(phenylamino)quinolin-8-yl)-3H-pyrrolo[2,3-d]pyrimidin-4(7H)-one (0.012 g, 0.034 mmol, 15% yield) as a dull-yellow solid: $^1$H NMR (400 MHz, DMSO-d₆) δ ppm 12.43 (1H, br. s), 11.80 (1H, br. s.), 9.59 (1H, s), 8.13 (1H, d, J=9.0 Hz), 8.02 (1H, dd, J=7.4, 1.6 Hz), 7.88 (1H, s), 7.78 (2H, dd, J=8.6, 1.2 Hz), 7.67-7.73 (1H, m), 7.28-7.38 (3H, m), 7.09-7.19 (2H, m), 6.97-7.05 (1H, m). m/z (ESI, +ve) 353.9 (M+H)⁺.

Example 17

6-(2-phenoxyquinolin-8-yl)-3H-pyrrolo[2,3-d]pyrimidin-4(7H)-one

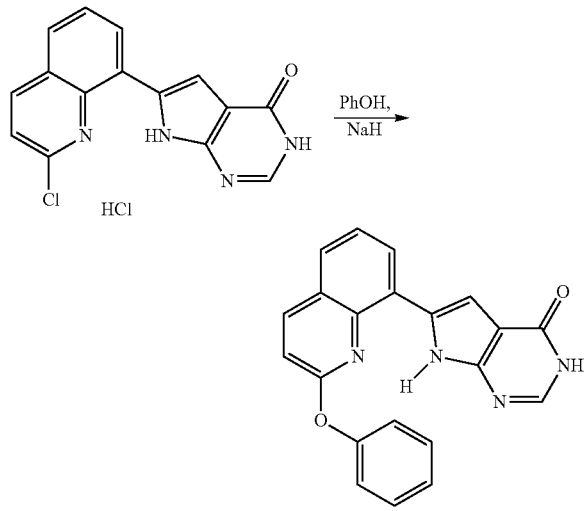

NaH (60% in mineral oil; 0.063 g, 1.576 mmol) was suspended in 1 mL DMF and phenol (0.148 g, 1.576 mmol) was added. After 10 min, 6-(2-chloroquinolin-8-yl)-3H-pyrrolo[2,3-d]pyrimidin-4(7H)-one hydrochloride (Example 19b; 0.075 g, 0.225 mmol) was added, and the reaction was sealed and heated at 70° C. for 2 h, then at 90° C. for 1 h. The reaction was treated with TFA (0.121 ml, 1.576 mmol) and 1 mL DMSO, filtered, and purified by rpHPLC (Phenomenex Gemini 150×30 mm C₁₈ column, 20-100% ACN/H₂O with 0.1% TFA); product-containing fractions were concentrated in vacuo to give 6-(2-phenoxyquinolin-8-yl)-3H-pyrrolo[2,3-d]pyrimidin-4(7H)-one (0.022 g, 0.062 mmol, 28% yield) as a yellow solid: $^1$H NMR (400 MHz, DMSO-d₆) δ ppm 11.72 (1H, br. s), 11.64 (1H, br. s), 8.50 (1H, d, J=8.8 Hz), 8.22 (1H, dd, J=7.5, 1.5 Hz), 7.90 (1H, dd, J=8.0, 1.4 Hz), 7.81 (1H, d, J=3.7 Hz), 7.49-7.58 (3H, m), 7.30-7.42 (4H, m), 7.13 (1H, d, J=2.3 Hz). m/z (ESI, +ve) 355.0 (M+H)⁺.

Example 18

2-(2-(4-chlorophenoxy)quinolin-8-yl)-6,7-dihydro-1H-pyrrolo[3,2-c]pyridin-4(5H)-one

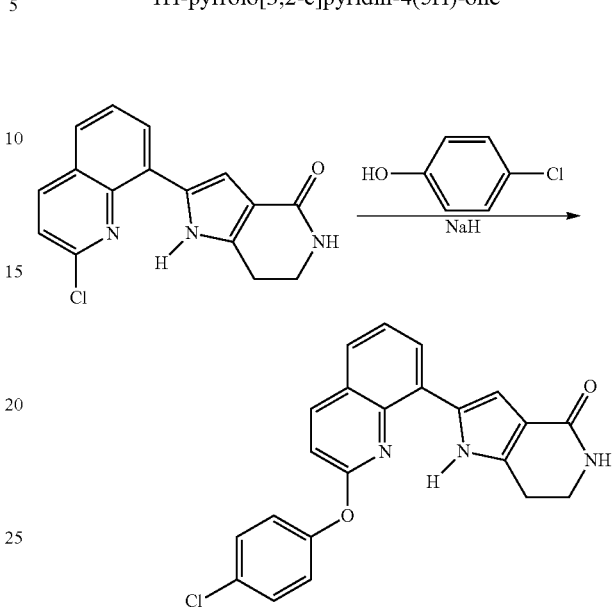

NaH (60% in mineral oil; 0.071 g, 1.763 mmol) was suspended in 1 mL DMF and p-chlorophenol (Aldrich; 0.174 ml, 1.763 mmol) was added. After 10 min, 2-(2-chloroquinolin-8-yl)-6,7-dihydro-1H-pyrrolo[3,2-c]pyridin-4(5H)-one (Example 1; 0.075 g, 0.252 mmol) was added, and the reaction was sealed and heated at 70° C. for 2 h, then at 90° C. for 1 h. The reaction mixture was then treated with TFA (0.136 ml, 1.763 mmol) and 1 mL DMSO, filtered, and purified by rpHPLC (Phenomenex Gemini 150×30 mm C₁₈ column, 20-100% ACN/H₂O with 0.1% TFA); product-containing fractions were concentrated in vacuo to give 2-(2-(4-chlorophenoxy)quinolin-8-yl)-6,7-dihydro-1H-pyrrolo[3,2-c]pyridin-4(5H)-one (0.044 g, 0.113 mmol, 45% yield) as a yellow solid: $^1$H NMR (400 MHz, DMSO-d₆) δ ppm 11.07 (1H, br. s), 8.50 (1H, d, J=9.0 Hz), 8.11 (1H, dt, J=7.6, 0.7 Hz), 7.80 (1H, dt, J=7.9, 0.7 Hz), 7.60-7.71 (2H, m), 7.31-7.55 (4H, m), 6.94 (2H, dd, J=2.0, 0.4 Hz), 3.31-3.42 (2H, m), 2.47-2.51 (2H, m). m/z (ESI, +ve) 389.9 (M+H)⁺.

Example 19

6-(2-chloroquinolin-8-yl)-3H-pyrrolo[2,3-d]pyrimidin-4(7H)-one trifluoroacetate

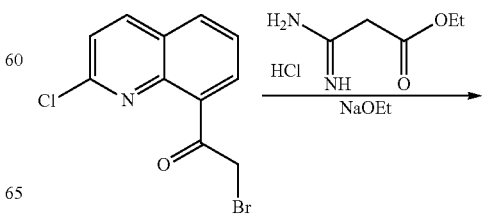

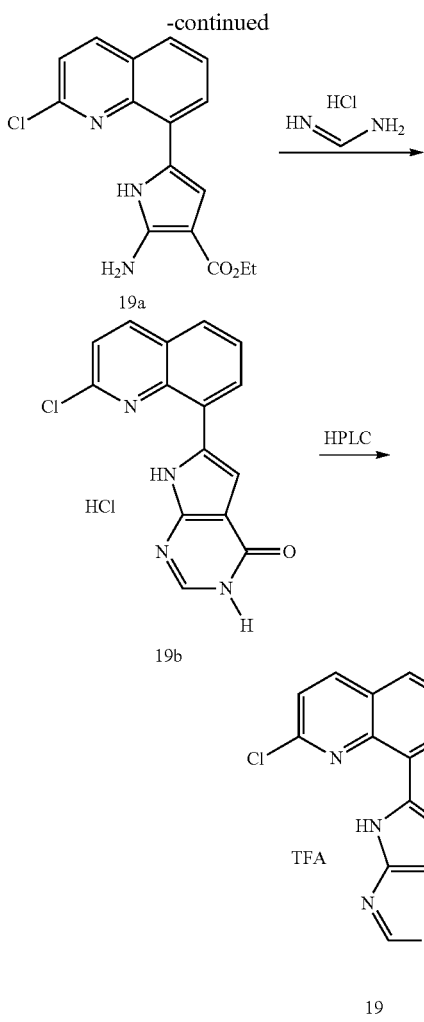

0.7 Hz), 7.48-7.66 (2H, m), 7.07 (1H, dd, J=2.5, 0.4 Hz), 6.10 (2H, s), 4.18 (2H, q, J=7.2 Hz), 1.27 (3H, t, J=7.0 Hz). m/z (ESI, +ve) 316.0 (M+H)$^+$.

Preparation of 6-(2-chloroquinolin-8-yl)-3H-pyrrolo [2,3-d]pyrimidin-4(7H)-one hydrochloride Formamidine hydrochloride (0.296 g, 3.67 mmol) and ethyl 2-amino-5-(2-chloroquinolin-8-yl)-1H-pyrrole-3-carboxylate (0.232 g, 0.735 mmol) were combined in 3 mL IPA, sealed, and heated to 100° C. overnight. An additional 1 mL IPA was added, and the reaction resealed and heated to 110° C. for 24 additional hours. The reaction was cooled, diluted with IPA, and filtered, rinsing 2×IPA. The solid was collected and dried in vacuo to give 6-(2-chloroquinolin-8-yl)-3H-pyrrolo[2,3-d]pyrimidin-4(7H)-one hydrochloride (0.218 g, 0.654 mmol, 89% yield): $^1$H NMR (400 MHz, DMSO-d$_6$) δ ppm 12.34 (1H, br. s.), 8.53 (1H, d, J=8.6 Hz), 8.23-8.30 (1H, m), 8.00 (1H, dd, J=7.9, 1.1 Hz), 7.92 (1H, s), 7.66-7.77 (2H, m), 7.49 (1H, s), 7.01-7.26 (2H, m). m/z (ESI, +ve) 296.9 (M+H)$^+$.

Preparation of 6-(2-chloroquinolin-8-yl)-3H-pyrrolo [2,3-d]pyrimidin-4(7H)-one trifluoroacetate A portion of 6-(2-chloroquinolin-8-yl)-3H-pyrrolo[2,3-d] pyrimidin-4(7H)-one hydrochloride (19b) was dissolved in DMSO and further purified by rpHPLC (Phenomenex Gemini 150×30 mm C$_{18}$ column, 5-70% ACN/H$_2$O with 0.1% TFA); product-containing fraction was concentrated in vacuo to give a pure sample of 6-(2-chloroquinolin-8-yl)-3H-pyrrolo[2,3-d]pyrimidin-4(7H)-one as its trifluoroacetate salt: $^1$H NMR (400 MHz, DMSO-d$_6$) δ ppm 12.33 (1H, br. s), 11.90 (1H, br. s), 8.53 (1H, d, J=8.6 Hz), 8.18-8.32 (1H, m), 8.00 (1H, dd, J=7.8, 0.4 Hz), 7.92 (1H, d, J=3.7 Hz), 7.65-7.78 (2H, m), 7.45-7.53 (1H, m). m/z (ESI, +ve) 296.9 (M+H)$^+$.

Example 20

2-(2-(benzyloxy)quinolin-8-yl)-6,7-dihydro-1H-pyrrolo[3,2-c]pyridin-4(5H)-one

Preparation of ethyl 2-amino-5-(2-chloroquinolin-8-yl)-1H-pyrrole-3-carboxylate

Ethyl 3-amino-3-iminopropanoate hydrochloride (Tyger Scientific, Ewing, N.J.; 1.171 g, 7.03 mmol) was treated with 3 mL EtOH and cooled to 0° C. Sodium ethoxide (21% w/w solution in EtOH; 2.59 ml, 7.03 mmol) was added via syringe and immediate precipitation of a solid was noted. After 10 min, unpurified 2-bromo-1-(2-chloroquinolin-8-yl)ethanone (Example 1, Step 2.2; 1.00 g, 3.51 mmol) was added and the ice/water bath was removed. The reaction was stirred rapidly at RT for 16 h. The reaction was then partitioned between water and DCM. The aq. layer was extracted with DCM (3×), and the combined organics were dried over anhydrous Na$_2$SO$_4$, filtered, and concentrated in vacuo. The resulting slurry was sonicated in 5 mL MeOH and filtered, rinsing 2× MeOH, to give 0.236 g red solid. The filtrate was concentrated in vacuo, and the residue was taken up in DCM, adsorbed onto 4 g silica gel, and purified by silica gel chromatography (40 g column) using 0-30% EtOAc/hexane. The fractions were concentrated to afford 0.387 g of a red solid. The collected solids were combined to provide ethyl 2-amino-5-(2-chloroquinolin-8-yl)-1H-pyrrole-3-carboxylate (0.623 g, 1.973 mmol, 56% yield) as a red solid: $^1$H NMR (400 MHz, DMSO-d$_6$) δ ppm 10.88 (1H, br. s), 8.44 (1H, d, J=8.6 Hz), 8.01 (1H, dt, J=7.6, 0.7 Hz), 7.75 (1H, dt, J=7.9,

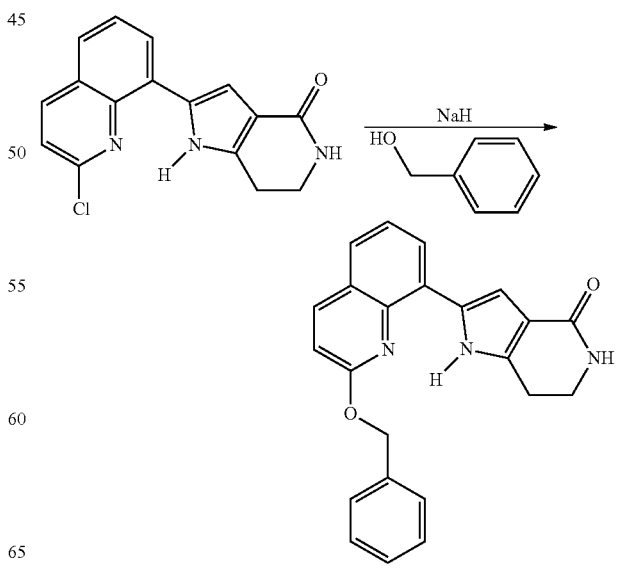

NaH (60% in mineral oil; 0.071 g, 1.763 mmol) was suspended in 1 mL DMF. Phenylmethanol (0.183 ml, 1.763 mmol) was added slowly dropwise. After 10 min, 2-(2-chloroquinolin-8-yl)-6,7-dihydro-1H-pyrrolo[3,2-c]pyridin-4 (5H)-one (Example 1; 0.075 g, 0.252 mmol) was added, and the reaction was heated to 100° C. for 30 min. The mixture was cooled and partitioned between saturated aq. NH$_4$Cl and DCM. The aq. layer was extracted with DCM (3×), and the combined organics were dried over anhydrous Na$_2$SO$_4$, filtered, and concentrated in vacuo. The material was treated with DCM and purified by silica gel chromatography using 0-100% 90/10 DCM/MeOH in DCM The product-containing fractions were concentrated to afford 2-(2-(benzyloxy)quinolin-8-yl)-6,7-dihydro-1H-pyrrolo[3,2-c]pyridin-4(5H)-one (0.018 g, 0.049 mmol, 19% yield) as an orange solid: $^1$H NMR (400 MHz, DMSO-d$_6$) δ ppm 11.76 (1H, br. s), 8.32 (1H, d, J=9.0 Hz), 8.00 (1H, dt, J=7.2, 1.0 Hz), 7.76 (1H, dt, J=7.9, 0.8 Hz), 7.26-7.59 (6H, m), 7.10-7.22 (2H, m), 6.87-6.99 (1H, m), 5.62 (2H, s), 3.36-3.51 (2H, m), 2.86 (2H, t, J=6.9 Hz). m/z (ESI, +ve) 370.0 (M+H)$^+$.

Example 21

2-(2-(benzylamino)quinolin-8-yl)-6,7-dihydro-1H-pyrrolo[3,2-c]pyridin-4(5H)-one

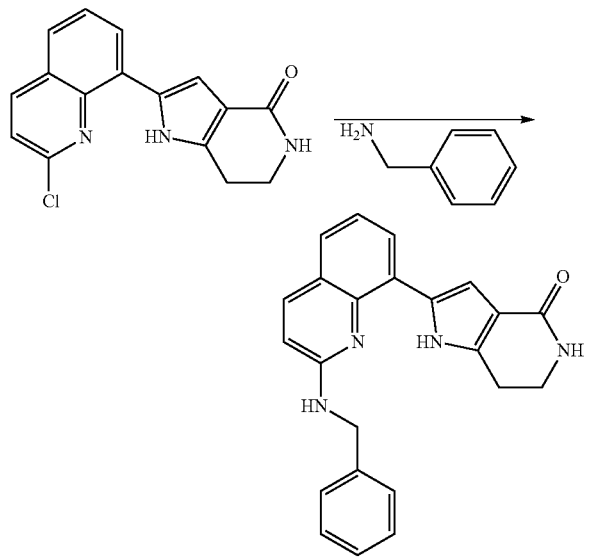

Phenylmethanamine (0.144 g, 1.343 mmol) and 2-(2-chloroquinolin-8-yl)-6,7-dihydro-1H-pyrrolo[3,2-c]pyridin-4 (5H)-one (Example 1; 0.100 g, 0.336 mmol) were combined in 1 mL DMF, sealed, and heated to 100° C. overnight. The mixture was treated with TFA (0.104 ml, 1.343 mmol) and was diluted with 1 mL DMSO, filtered and purified by rpHPLC (Phenomenex Gemini 150×30 mm C$_{18}$ column, 5-60% ACN/H$_2$O with 0.1% TFA); product-containing fractions were treated with saturated aq. NaHCO$_3$ and DCM. The organic layer was separated and the aq. layer was extracted 3×DCM. The combined organic layers were then dried over Na$_2$SO$_4$, filtered, and concentrated in vacuo to give 2-(2-(benzylamino)-quinolin-8-yl)-6,7-dihydro-1H-pyrrolo[3,2-c]pyridin-4(5H)-one (0.011 g, 0.030 mmol, 9% yield) as a light-yellow solid: $^1$H NMR (400 MHz, DMSO-d$_6$) δ ppm 12.45 (1H, br. s), 7.88-8.01 (3H, m), 7.50 (1H, dt, J=7.7, 0.7 Hz), 7.39-7.45 (2H, m), 7.34 (2H, t, J=7.5 Hz), 7.21-7.28 (1H, m), 7.18 (1H, t, J=7.6 Hz), 6.88-7.00 (3H, m), 4.71 (2H, d, J=5.9 Hz), 3.34-3.38 (2H, m), 2.56-2.65 (2H, m). m/z (ESI, +ve) 369.0 (M+H)$^+$.

Example 22 rac-2-(2-chloroquinolin-8-yl)-7-ethyl-6,7-dihydro-1H-pyrrolo[3,2-c]pyridin-4(5H)-one

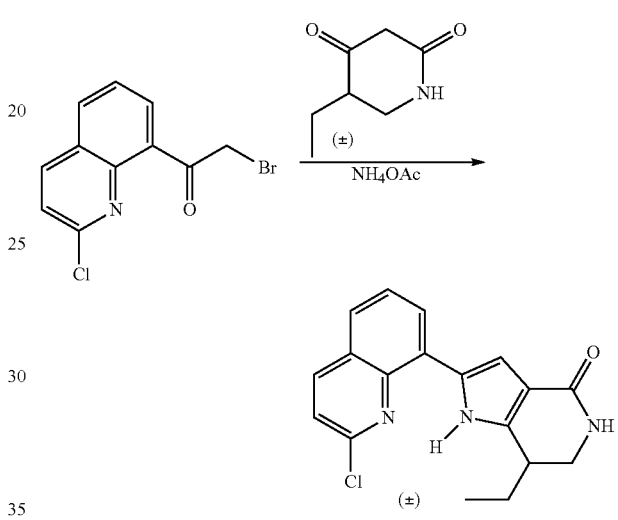

2-Bromo-1-(2-chloroquinolin-8-yl)ethanone (Example 1, step 2.2; 0.500 g, 1.757 mmol), rac-5-ethylpiperidine-2,4-dione (prepared according to *Synthesis* 2007, 3185-3190; 0.335 g, 2.372 mmol), and NH$_4$OAc (0.542 g, 7.03 mmol) were combined in 50 mL EtOH and sealed. The reaction was placed in a 50° C. bath for 4 h, at which point the reaction was cooled to RT and stirred overnight. The reaction was carefully quenched with saturated aq. NaHCO$_3$ (gas evolution) and partitioned between saturated aq. NaHCO$_3$ and DCM. The aq. layer was extracted with DCM (4×), and the combined organics were dried over anhydrous Na$_2$SO$_4$, filtered, and concentrated in vacuo. The material was treated with DCM and purified by silica gel chromatography using 0-100% 90/10 DCM/MeOH in DCM. The product-containing fractions were concentrated to give impure rac-2-(2-chloroquinolin-8-yl)-7-ethyl-6,7-dihydro-1H-pyrrolo[3,2-c]pyridin-4(5H)-one (0.198 g, 0.608 mmol, 35% yield) as a gummy solid. A portion of this material was suspended in MeOH, sonicated, and filtered, rinsing 2× Et$_2$O to give 0.003 mg pure rac-2-(2-chloroquinolin-8-yl)-7-ethyl-6,7-dihydro-1H-pyrrolo[3,2-c]pyridin-4(5H)-one as a yellow solid: $^1$H NMR (400 MHz, DMSO-d$_6$) δ ppm 11.71 (1H, br. s), 8.50 (1H, d, J=8.6 Hz), 8.13 (1H, dt, J=7.4, 0.7 Hz), 7.84-7.94 (1H, m), 7.59-7.73 (2H, m), 7.15-7.25 (1H, m), 6.98 (1H, br. s.), 3.47-3.60 (1H, m), 3.12-3.26 (1H, m), 2.85-2.99 (1H, m), 1.74-1.94 (1H, m), 1.53-1.69 (1H, m), 1.03 (3H, t, J=7.4 Hz). m/z (ESI, +ve) 326.0 (M+H)$^+$.

Example 23 rac-7-ethyl-2-(2-phenoxyquinolin-8-yl)-6,7-dihydro-1H-pyrrolo[3,2-c]pyridin-4(5H)-one

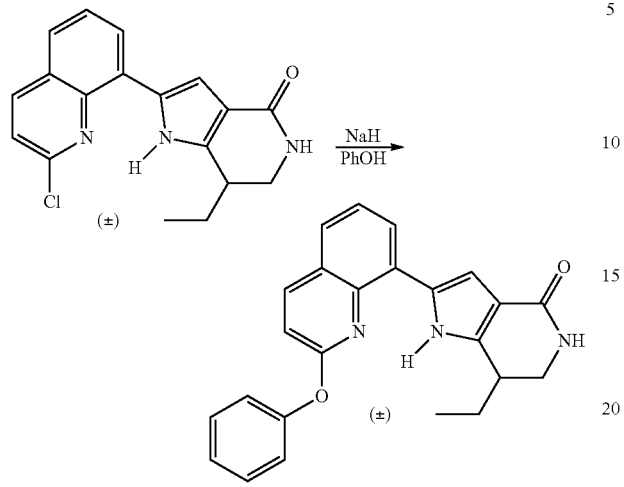

To a slurry of NaH (60% in mineral oil; 0.064 g, 1.611 mmol) in 1 mL DMF was added phenol (0.152 g, 1.611 mmol). After 10 min, rac-2-(2-chloroquinolin-8-yl)-7-ethyl-6,7-dihydro-1H-pyrrolo[3,2-c]pyridin-4(5H)-one (Example 22; 0.075 g, 0.230 mmol) was added, and the reaction was heated to 70° C. After 2 h, the reaction was cooled and treated with TFA (0.124 ml, 1.611 mmol) and 1 mL DMSO, and the solution was filtered and purified by rpHPLC (Phenomenex Gemini 150×30 mm $C_{18}$ column, 15-100% ACN/$H_2O$ with 0.1% TFA); product-containing fraction was treated with saturated aq. $NaHCO_3$ and DCM. The organic layer was separated, and the aq. layer was extracted 3×DCM. The combined organic layers were then dried over $Na_2SO_4$, filtered, and concentrated in vacuo to give rac-7-ethyl-2-(2-phenoxyquinolin-8-yl)-6,7-dihydro-1H-pyrrolo[3,2-c]pyridin-4(5H)-one (0.035 g, 0.091 mmol, 40% yield) as a light-yellow solid: $^1$H NMR (400 MHz, DMSO-$d_6$) δ ppm 11.12 (1H, br. s), 8.50 (1H, d, J=8.8 Hz), 8.14 (1H, dt, J=7.5, 0.7 Hz), 7.80 (1H, dt, J=8.0, 0.7 Hz), 7.35-7.64 (7H, m), 6.90-7.00 (1H, m), 6.82-6.91 (1H, m), 3.38-3.45 (1H, m), 3.12-3.20 (1H, m), 2.24-2.34 (1H, m), 1.13-1.34 (2H, m), 0.82 (3H, t, J=7.3 Hz). m/z (ESI, +ve) 384.0 (M+H)$^+$.

Example 24 rac-7-ethyl-2-(2-(phenylamino)quinolin-8-yl)-6,7-dihydro-1H-pyrrolo[3,2-c]pyridin-4(5H)-one

Example 25

(R)-7-ethyl-2-(2-(phenylamino)quinolin-8-yl)-6,7-dihydro-1H-pyrrolo[3,2-c]pyridin-4(5H)-one, and

Example 239

(S)-7-ethyl-2-(2-(phenylamino)quinolin-8-yl)-6,7-dihydro-1H-pyrrolo[3,2-c]pyridin-4(5H)-one

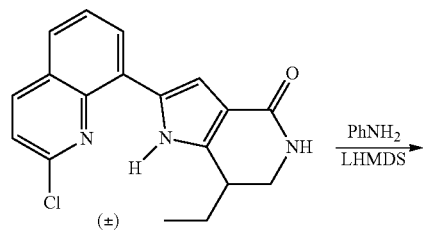

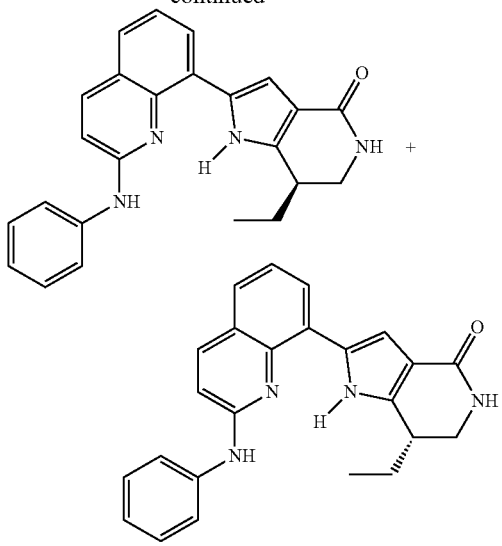

A mixture of 2-(2-chloroquinolin-8-yl)-7-ethyl-6,7-dihydro-1H-pyrrolo[3,2-c]pyridin-4(5H)-one (Example 22; 0.075 g, 0.230 mmol) and aniline (0.105 ml, 1.151 mmol) was treated with LHMDS (1.0 M in THF; 1.151 ml, 1.151 mmol) at RT. After 2 h, the reaction was concentrated, then dissolved in DMSO and treated with TFA (0.089 ml, 1.151 mmol). This material was purified by rpHPLC (Phenomenex Gemini 150×30 mm $C_{18}$ column, 10-70% ACN/$H_2O$ with 0.1% TFA); product-containing fractions were treated with saturated aq. $NaHCO_3$ and DCM. The organic layer was separated, and the aq. layer was extracted 3×DCM. The combined organic layers were then dried over $Na_2SO_4$, filtered, and concentrated in vacuo to give rac-7-ethyl-2-(2-(phenylamino)quinolin-8-yl)-6,7-dihydro-1H-pyrrolo[3,2-c]pyridin-4(5H)-one (0.021 g, 0.055 mmol, 23.85% yield): $^1$H NMR (400 MHz, DMSO-$d_6$) δ ppm 12.24 (1H, br. s), 9.53 (1H, s), 8.12 (1H, d, J=9.0 Hz), 7.96 (1H, dt, J=7.5, 0.6 Hz), 7.53-7.67 (3H, m), 7.39 (2H, t, J=7.8 Hz), 7.29 (1H, t, J=7.6 Hz), 7.03-7.15 (2H, m), 6.86-6.95 (2H, m), 3.46-3.61 (1H, m), 3.06-3.21 (1H, m), 2.58-2.71 (1H, m), 1.15-1.32 (2H, m), 0.66 (3H, t, J=7.3 Hz). m/z (ESI, +ve) 383.0 (M+H)$^+$. A portion of this material was resolved by chiral SFC (Chiralpak IC (21×250 mm, 5 μm); additive in supercritical fluid $CO_2$ was 50% MeOH with 20 mM $NH_3$; 60 mL/min; column temperature 40° C.; outlet pressure 100 bar) to give separated enantiomers (R)-7-ethyl-2-(2-(phenylamino)quinolin-8-yl)-6,7-dihydro-1H-pyrrolo[3,2-c]pyridin-4(5H)-one (Example 25) and (S)-7-ethyl-2-(2-(phenylamino)quinolin-8-yl)-6,7-dihydro-1H-pyrrolo[3,2-c]pyridin-4(5H)-one. (Example 26).

Example 27 rac-2-(2-chloroquinolin-8-yl)-7-methyl-6,7-dihydro-1H-pyrrolo[3,2-c]pyridin-4(5H)-one

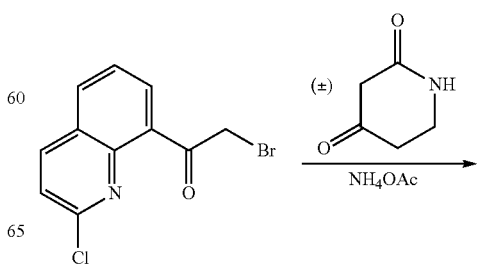

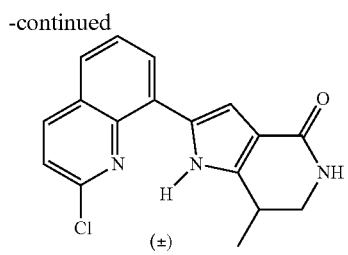

2-Bromo-1-(2-chloroquinolin-8-yl)ethanone (Example 1, step 2.2; 0.550 g, 1.933 mmol), rac-5-methylpiperidine-2,4-dione (prepared according to *J. Med. Chem.* 2009, 52, 293-307; 0.295 g, 2.320 mmol), and NH$_4$OAc (0.596 g, 7.73 mmol) were combined in 5 mL EtOH, sealed, and heated in a 50° C. bath for 4 h. The reaction was partitioned between saturated aq. NaHCO$_3$ and DCM. The aq. layer was extracted with DCM (3×), and the combined organics were dried over anhydrous Na$_2$SO$_4$, filtered, and concentrated in vacuo. The material was treated with DCM and purified by silica gel chromatography using 0-100%-90/10 DCM/MeOH in DCM. The product-containing fractions were concentrated to afford rac-2-(2-chloroquinolin-8-yl)-7-methyl-6,7-dihydro-1H-pyrrolo[3,2-c]pyridin-4(5H)-one (0.182 g, 0.584 mmol, 30% yield) as an orange solid: $^1$H NMR (400 MHz, DMSO-d$_6$) δ ppm 11.68 (1H, br. s), 8.49 (1H, d, J=8.6 Hz), 8.13 (1H, dt, J=7.3, 0.7 Hz), 7.90 (1H, dt, J=8.0, 0.7 Hz), 7.59-7.72 (2H, m), 7.21 (1H, dd, J=2.2, 0.4 Hz), 6.98-7.04 (1H, m), 3.42-3.55 (1H, m), 3.03-3.21 (2H, m), 1.32 (3H, d, J=6.5 Hz). m/z (ESI, +ve) 312.0 (M+H)$^+$.

Example 28 rac-7-methyl-2-(2-phenoxyquinolin-8-yl)-6,7-dihydro-1H-pyrrolo[3,2-c]pyridin-4(5H)-one

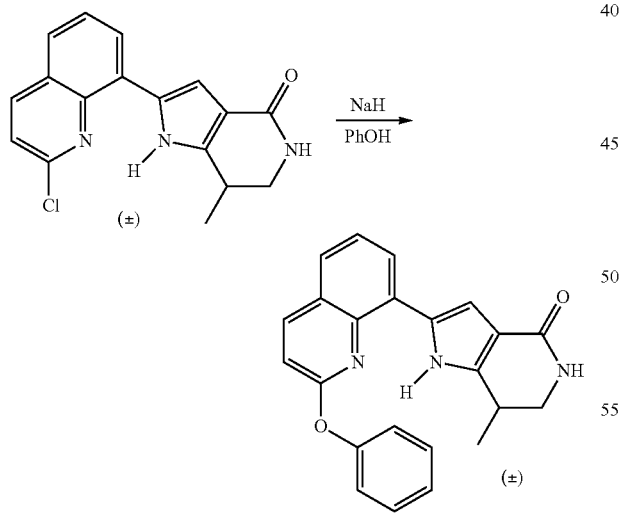

To a slurry of NaH (60% in mineral oil; 0.036 g, 0.898 mmol) in 0.5 mL DMF was added phenol (0.085 g, 0.898 mmol). After 10 min, 2-(2-chloroquinolin-8-yl)-7-methyl-6,7-dihydro-1H-pyrrolo[3,2-c]pyridin-4(5H)-one (Example 27; 0.040 g, 0.128 mmol) was added and the reaction was heated to 80° C. for 2 h. The reaction was cooled, treated with DMSO and TFA (0.069 ml, 0.898 mmol), filtered, and purified by rpHPLC (Phenomenex Gemini 150×30 mm C$_{18}$ column, 15-100% ACN/H$_2$O with 0.1% TFA); product-containing fraction was treated with saturated aq. NaHCO$_3$ and DCM. The organic layer was separated, and the aq. layer was extracted 3×DCM. The combined organic layers were then dried over Na$_2$SO$_4$, filtered, and concentrated in vacuo to give rac-7-methyl-2-(2-phenoxyquinolin-8-yl)-6,7-dihydro-1H-pyrrolo[3,2-c]pyridin-4(5H)-one (0.030 g, 0.081 mmol, 63% yield) as an off-white solid: $^1$H NMR (400 MHz, DMSO-d$_6$) δ ppm 11.10 (1H, br. s), 8.50 (1H, d, J=9.0 Hz), 8.13 (1H, dt, J=7.5, 0.7 Hz), 7.80 (1H, dt, J=7.9, 0.7 Hz), 7.55-7.65 (2H, m), 7.49 (1H, t, J=7.7 Hz), 7.33-7.45 (4H, m), 6.83-6.99 (2H, m), 3.44 (1H, ddt, J=12.3, 5.6, 0.6, 0.6 Hz), 2.92-3.06 (1H, m), 2.55-2.60 (1H, m), 0.90 (3H, d, J=6.8 Hz). m/z (ESI, +ve) 370.1 (M+H)$^+$.

Example 238 rac-7-methyl-2-(2-(phenylamino)quinolin-8-yl)-6,7-dihydro-1H-pyrrolo[3,2-c]pyridin-4(5H)-one Example 29

7-methyl-2-(2-(phenylamino)quinolin-8-yl)-6,7-dihydro-1H-pyrrolo[3,2-c]pyridin-4(5H)-one, (first eluting enantiomer) and Example 30

7-methyl-2-(2-(phenylamino)quinolin-8-yl)-6,7-dihydro-1H-pyrrolo[3,2-c]pyridin-4(5H)-one (second eluting enantiomer)

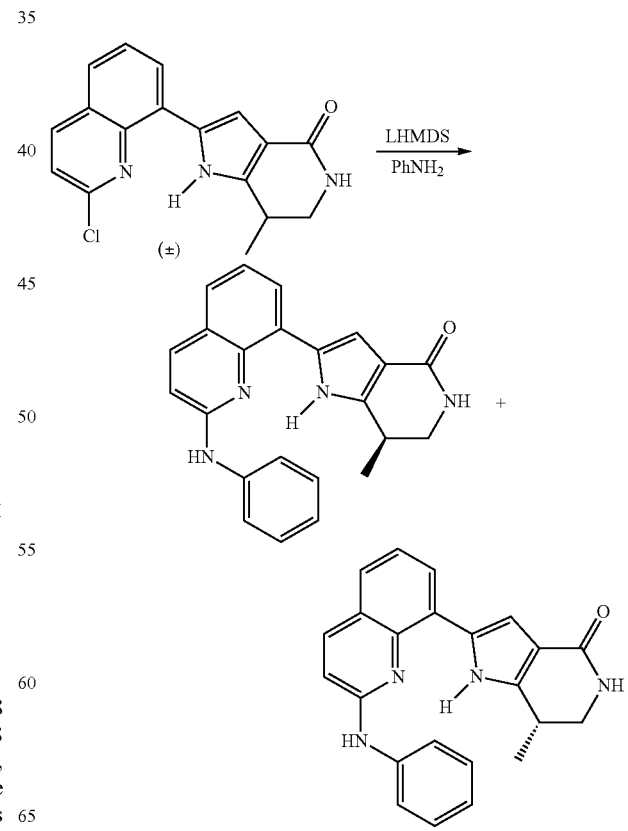

A solution of LHMDS (1.0 M in THF; 2.197 ml, 2.197 mmol), aniline (0.200 ml, 2.197 mmol), and 2-(2-chloroquinolin-8-yl)-7-methyl-6,7-dihydro-1H-pyrrolo[3,2-c]pyridin-4(5H)-one (Example 27; 0.137 g, 0.439 mmol) was stirred at RT for 1.5 h. An additional 2 equiv LHMDS (1.0 M in THF) was added, and the reaction was stirred overnight. The reaction was concentrated under $N_2$, treated with DMSO and TFA (0.474 ml, 6.15 mmol), filtered, and purified by rpHPLC (Phenomenex Gemini 150×30 mm $C_{18}$ column, 10-80% ACN/$H_2O$ with 0.1% TFA); product-containing fractions were treated with saturated aq. $NaHCO_3$ and DCM. The organic layer was separated, and the aq. layer was extracted 3×DCM. The combined organic layers were then dried over $Na_2SO_4$, filtered, and concentrated in vacuo to give rac-7-methyl-2-(2-(phenylamino)quinolin-8-yl)-6,7-dihydro-1H-pyrrolo[3,2-c]pyridin-4(5H)-one (0.065 g, 0.176 mmol, 40% yield, Example 238) as an orange solid: $^1H$ NMR (400 MHz, DMSO-$d_6$) δ ppm 12.11 (1H, br. s), 9.53 (1H, s), 8.12 (1H, d, J=9.0 Hz), 7.93 (1H, dt, J=7.4, 0.8 Hz), 7.56-7.71 (3H, m), 7.34-7.45 (2H, m), 7.29 (1H, t, J=7.6 Hz), 6.99-7.14 (2H, m), 6.85-6.98 (2H, m), 3.38-3.52 (1H, m), 2.86-3.08 (2H, m), 0.84 (3H, d, J=6.7 Hz). m/z (ESI, +ve) 369.1 (M+H)$^+$. A portion of this material was resolved by chiral SFC (ChiralPak AS-H (21×250, 5 μm); additive in supercritical fluid $CO_2$ was 40% MeOH with 20 mM $NH_3$; 60 mL/min; column temperature 40° C.; outlet pressure 100 bar) to give separated enantiomers 7-methyl-2-(2-(phenylamino)quinolin-8-yl)-6,7-dihydro-1H-pyrrolo[3,2-c]pyridin-4(5H)-one (Example 29, first eluting enantiomer) and 7-methyl-2-(2-(phenylamino)quinolin-8-yl)-6,7-dihydro-1H-pyrrolo[3,2-c]pyridin-4(5H)-one (Example 30, second eluting anantiomer).

Example 31 rac-2-(2-chloroquinolin-8-yl)-6-methyl-6,7-dihydro-1H-pyrrolo[3,2-c]pyridin-4(5H)-one

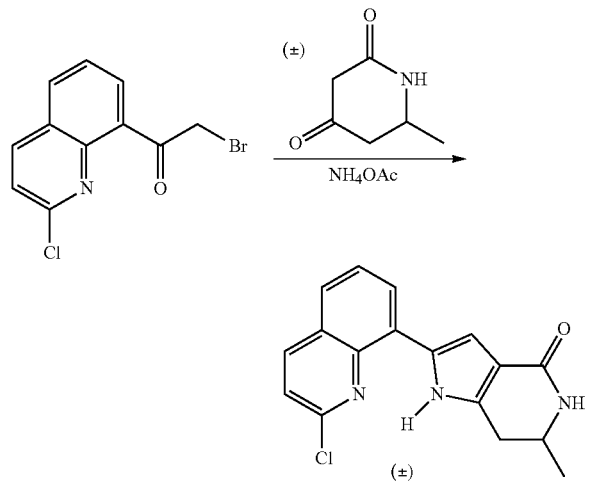

2-Bromo-1-(2-chloroquinolin-8-yl)ethanone (Example 1, step 2.2; 0.500 g, 1.757 mmol), rac-6-methylpiperidine-2,4-dione (prepared according to J. Med. Chem. 2009, 52, 293-307; 0.268 g, 2.109 mmol), and $NH_4OAc$ (0.542 g, 7.03 mmol) were combined in 5 mL EtOH, sealed, and heated in a 50° C. bath for 3 h. The temperature was increased to 70° C. for 1 h. The reaction was cooled and partitioned between saturated aq. $NaHCO_3$ and DCM. The organic layer was separated, and the aq. layer was extracted 3×DCM. The combined organic layers were then dried over $Na_2SO_4$, filtered, and concentrated in vacuo. The material was treated with DCM/MeOH, adsorbed onto 4 g silica gel and dried. The residue was purified by silica gel chromatography using 0-70%-90/10 DCM/MeOH in DCM. The product-containing fractions were concentrated to afford rac-2-(2-chloroquinolin-8-yl)-6-methyl-6,7-dihydro-1H-pyrrolo[3,2-c]pyridin-4(5H)-one (0.100 g, 0.321 mmol, 18% yield) as an orange solid: $^1H$ NMR (400 MHz, CDCl$_3$) δ ppm 12.07 (1H, br. s.), 8.04-8.30 (2H, m), 7.53-7.70 (2H, m), 7.43 (1H, d, J=8.6 Hz), 7.23 (1H, d, J=2.3 Hz), 5.19 (1H, br. s.), 3.94-4.12 (1H, m), 3.05 (1H, dd, J=15.7, 5.0 Hz), 2.85 (1H, dd, J=15.6, 11.3 Hz), 1.41 (3H, d, J=6.5 Hz). m/z (ESI, +ve) 312.0 (M+H)$^+$.

Example 32

2-(2-(ethyl(pyridin-3-yl)amino)quinolin-8-yl)-6,7-dihydro-1H-pyrrolo[3,2-c]pyridin-4(5H)-one

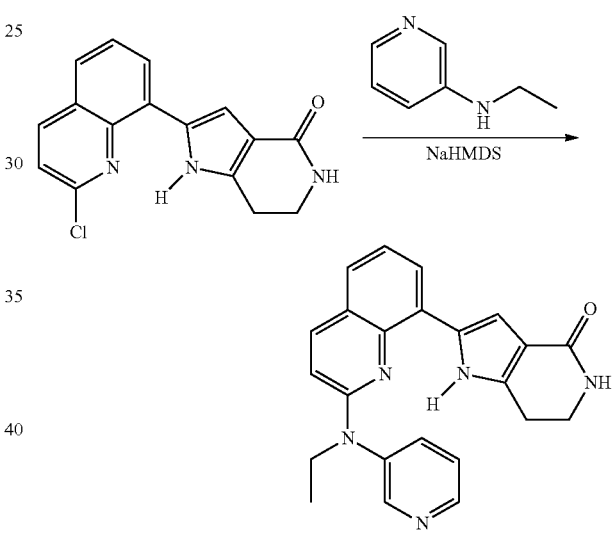

To a mixture of N-ethylpyridin-3-amine (Enamine, Kiev, Ukraine; 0.164 g, 1.343 mmol) and 2-(2-chloroquinolin-8-yl)-6,7-dihydro-1H-pyrrolo[3,2-c]pyridin-4(5H)-one (Example 1; 0.080 g, 0.269 mmol) was added NaHMDS (1.0 M in THF; 1.343 ml, 1.343 mmol). The dark red reaction was stirred for 30 min, then 0.5 mL 1.0 M NaHMDS in THF was added. After 30 min, the reaction was concentrated in vacuo and 2.5 mL DMSO and TFA (0.207 ml, 2.69 mmol) were added. Purified by rpHPLC (Phenomenex Gemini 150×30 mm $C_{18}$ column, 5-60% ACN/$H_2O$ with 0.1% TFA); product-containing fractions were treated with saturated aq. $NaHCO_3$ and DCM. The organic layer was separated, and the aq. layer was extracted 3×DCM. The combined organic layers were then dried over $Na_2SO_4$, filtered, and concentrated in vacuo to give 2-(2-(ethyl(pyridin-3-yl)amino)quinolin-8-yl)-6,7-dihydro-1H-pyrrolo[3,2-c]pyridin-4(5H)-one (0.011 g, 0.029 mmol, 11% yield) as a solid: $^1H$ NMR (400 MHz, DMSO-$d_6$) δ ppm 11.97 (1H, br. s), 8.63-8.69 (1H, m), 8.55-8.62 (1H, m), 8.08 (1H, d, J=9.2 Hz), 7.99 (1H, dt, J=7.5, 0.7 Hz), 7.88 (1H, dt, J=8.2, 2.1 Hz), 7.53-7.63 (2H, m), 7.29 (1H, t, J=7.6 Hz), 6.99-7.07 (1H, m), 6.90-6.97 (2H, m), 4.11 (2H, q, J=7.0 Hz), 3.37-3.45 (2H, m), 2.66 (2H, t, J=6.9 Hz), 1.30 (3H, t, J=7.1 Hz). m/z (ESI, +ve) 384.2 (M+H)+.

Example 237 rac-6-methyl-2-(2-(phenylamino)quinolin-8-yl)-6,7-dihydro-1H-pyrrolo[3,2-c]pyridin-4(5H)-one Examples 33

6-methyl-2-(2-(phenylamino)quinolin-8-yl)-6,7-dihydro-1H-pyrrolo[3,2-c]pyridin-4(5H)-one (first eluting enantiomer), and Examples 34

6-methyl-2-(2-(phenylamino)quinolin-8-yl)-6,7-dihydro-1H-pyrrolo[3,2-c]pyridin-4(5H)-one (second eluting enantiomer)

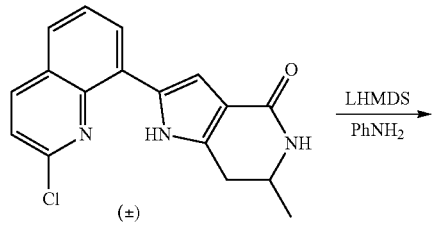

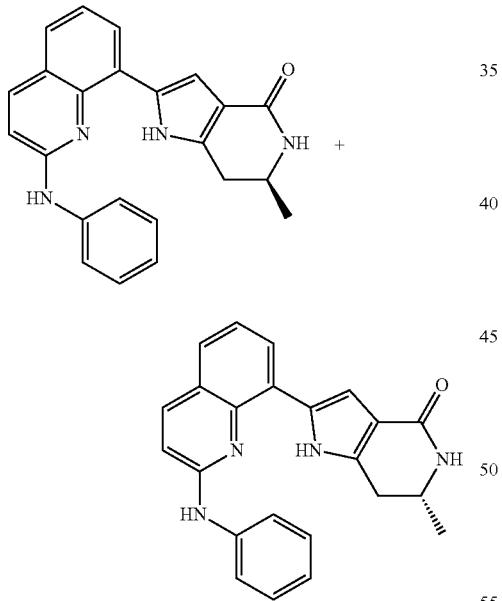

2-(2-Chloroquinolin-8-yl)-6-methyl-6,7-dihydro-1H-pyrrolo[3,2-c]pyridin-4(5H)-one (Example 31; 0.050 g, 0.160 mmol) and aniline (0.073 ml, 0.802 mmol) were treated with LHMDS (1.0 M solution in THF; 1.203 ml, 1.203 mmol). The dark red reaction was stirred for 3 h, at which point it was concentrated then treated with DMSO and TFA (0.185 ml, 2.406 mmol). This material was purified by rpHPLC (Phenomenex Gemini 150×30 mm $C_{18}$ column, 10-80% ACN/$H_2O$ with 0.1% TFA); product-containing fractions were treated with saturated aq. $NaHCO_3$ and DCM. The organic layer was separated, and the aq. layer was extracted 3×DCM. The combined organic layers were then dried over $Na_2SO_4$, filtered, and concentrated in vacuo to give rac-6-methyl-2-(2-(phenylamino)quinolin-8-yl)-6,7-dihydro-1H-pyrrolo[3,2-c]pyridin-4(5H)-one (0.018 g, 0.050 mmol, 31% yield, Example 237) as a yellow solid: $^1$H NMR (400 MHz, DMSO-$d_6$) δ ppm 12.15 (1H, br. s), 9.52 (1H, s), 8.11 (1H, d, J=9.0 Hz), 7.93 (1H, dt, J=7.4, 0.9 Hz), 7.65 (2H, d, J=7.6 Hz), 7.58 (1H, dt, J=7.7, 1.0 Hz), 7.40 (2H, t, J=7.9 Hz), 7.28 (1H, t, J=7.7 Hz), 7.02-7.15 (2H, m), 6.82-6.97 (2H, m), 3.75 (1H, dt, J=11.3, 5.8 Hz), 2.65 (1H, dd, J=15.6, 5.3 Hz), 2.36-2.47 (1H, m), 1.23 (3H, d, J=6.3 Hz). m/z (ESI, +ve) 369.2 (M+H)+. A portion of this material was resolved by chiral SFC (Chiralcel IC-H (150×21 mm, 5 μm); additive in supercritical fluid $CO_2$ was 40% EtOH with 40 mM $NH_3$; 70 mL/min; column temperature 40° C.; outlet pressure 100 bar) to give separated enantiomers 6-methyl-2-(2-(phenylamino)quinolin-8-yl)-6,7-dihydro-1H-pyrrolo[3,2-c]pyridin-4(5H)-one (Example 33, first eluting enantiomer) and 6-methyl-2-(2-(phenylamino)quinolin-8-yl)-6,7-dihydro-1H-pyrrolo[3,2-c]pyridin-4(5H)-one (Example 34, second eluting enantiomer).

Example 36

2-(2-amino-3-phenoxyquinoxalin-5-yl)-6,7-dihydro-1H-pyrrolo[3,2-c]pyridin-4(5H)-one

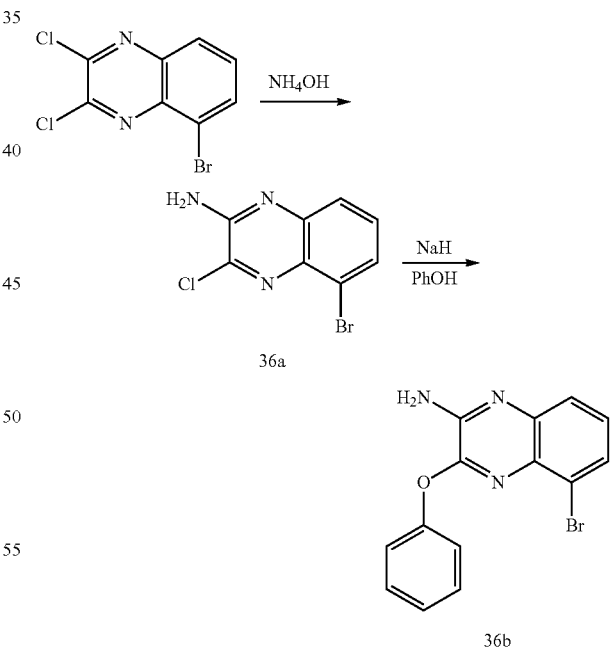

-continued

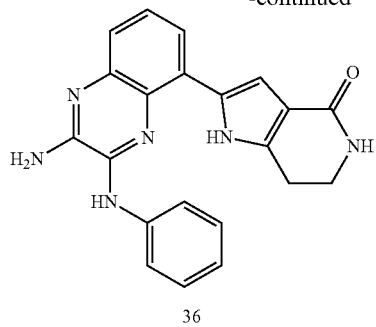

36

Preparation of 5-bromo-3-chloroquinoxalin-2-amine

To a solution of 5-bromo-2,3-dichloroquinoxaline (Leadgen Labs, Orange, Conn.; 2.00 g, 7.20 mmol) in 50 mL DMF at 0° C. was added NH₄OH (30% NH₃ in water; 18.68 ml, 144 mmol) dropwise via syringe. A thick solid formed. 2 mL DMF was added to promote stirring. The thick reaction was sealed and stirred for 2 h at RT. The reaction was diluted with 250 mL water and let stand overnight. In the morning, it was filtered and the solid was air dried, treated with silica gel and DCM, and concentrated in vacuo. The material was purified by silica gel chromatography using 0-50% EtOAc/hexane to separately provide 5-bromo-3-chloroquinoxalin-2-amine (0.510 g, 1.973 mmol, 27% yield) as a peach-colored solid: ¹H NMR (400 MHz, DMSO-d₆) δ ppm 7.69-7.76 (1H, m), 7.43-7.61 (4H, m). m/z (ESI, +ve) 259.9 (M+H)⁺ and 8-bromo-3-chloroquinoxalin-2-amine (0.78 g, 3.02 mmol, 42% yield) as a solid: ¹H NMR (400 MHz, DMSO-d₆) δ ppm 7.94 (1H, dd, J=7.6, 1.4 Hz), 7.73-7.79 (1H, m), 7.61 (2H, br. s.), 7.30 (1H, t, J=7.9 Hz). m/z (ESI, +ve) 259.9 (M+H)⁺.

Preparation of 5-bromo-3-phenoxyquinoxalin-2-amine

To a slurry of NaH (60% dispersion in mineral oil; 0.193 g, 4.84 mmol) in 5 mL DMF at 0° C. under N₂ was added phenol (0.455 g, 4.84 mmol). Gas evolution was observed. The reaction was warmed to RT. After 5 min, 5-bromo-3-chloroquinoxalin-2-amine (0.250 g, 0.967 mmol) was added, and the reaction was sealed and stirred overnight. The reaction was partitioned between saturated aq. NH₄Cl and EtOAc. The organic layer was sequentially washed with water (1×), and saturated aq. NaCl (1×), and then dried over anhydrous Na₂SO₄, filtered, and concentrated in vacuo. The material was treated with DCM and adsorbed onto 2 g silica gel and dried. The material was purified by silica gel chromatography using 0-60% EtOAc/hexane. The product-containing fractions were concentrated to afford 5-bromo-3-phenoxyquinoxalin-2-amine (0.209 g, 0.661 mmol, 68% yield) as a yellow solid: ¹H NMR (400 MHz, DMSO-d₆) δ ppm 7.55 (1H, dt, J=7.6, 0.7 Hz), 7.37-7.51 (7H, m), 7.26-7.35 (2H, m). m/z (ESI, +ve) 316.0 (M+H)⁺.

Preparation of 2-(2-amino-3-phenoxyquinoxalin-5-yl)-6,7-dihydro-1H-pyrrolo[3,2-c]pyridin-4(5H)-one Argon was bubbled through a slurry of tributyl(1-ethoxyvinyl)stannane (0.335 ml, 0.992 mmol), Pd(PPh₃)₄ (0.076 g, 0.066 mmol), and 5-bromo-3-phenoxyquinoxalin-2-amine (0.209 g, 0.661 mmol) in 6 mL toluene for 2 min. The reaction was fitted with a water-cooled reflux condenser, flushed with argon, and heated to reflux. After 3 h, CuI (0.025 g, 0.132 mmol) was added. After 3 h, the reaction was cooled, concentrated in vacuo, and the material was treated with DCM and purified by silica gel chromatography using 0-100% EtOAc/hexane. The resulting yellow oil (0.134 g), containing a mixture of desired product and starting material was used without further purification. This material was dissolved in 5 mL THF and treated with water (0.126 ml, 6.98 mmol). The reaction was cooled to 0° C. and NBS (0.037 ml, 0.436 mmol) was added in one portion. After 20 min the reaction was checked and judged complete. The reaction was partitioned between saturated aq. NaHCO₃ and DCM. The organic layer was separated, and the aq. layer was extracted 3×DCM. The combined organic layers were then dried over Na₂SO₄, filtered, and concentrated in vacuo. The resulting brown foam was treated with piperidine-2,4-dione (0.123 g, 1.090 mmol), NH₄OAc (0.269 g, 3.49 mmol), and 3 mL EtOH, sealed, and placed in a 50° C. oil bath. After 4 h, the reaction was cooled and partitioned between saturated aq. NaHCO₃ and DCM. The aq. layer was extracted with DCM (3×), and the combined organics were dried over anhydrous Na₂SO₄, filtered, and concentrated in vacuo. This material was dissolved in 2.5 mL DMSO, filtered, and purified by rpHPLC (Phenomenex Gemini 150×30 mm C₁₈ column, 10-60% ACN/H₂O with 0.1% TFA); product-containing fractions were treated with saturated aq. NaHCO₃ and DCM. The organic layer was separated, and the aq. layer was extracted 3×DCM. The combined organic layers were then dried over Na₂SO₄, filtered, and concentrated in vacuo to give 2-(2-amino-3-phenoxyquinoxalin-5-yl)-6,7-dihydro-1H-pyrrolo[3,2-c]pyridin-4(5H)-one (0.019 g, 0.051 mmol, 11.73% yield) as a yellow solid: ¹H NMR (400 MHz, DMSO-d₆) δ ppm 10.72 (1H, br. s), 7.57-7.72 (3H, m), 7.26-7.51 (7H, m), 6.87-6.94 (1H, m), 6.83 (1H, dd, J=1.9, 0.5 Hz), 3.30-3.34 (2H, m), 2.37-2.46 (2H, m). m/z (ESI, +ve) 372.0 (M+H)⁺.

Example 37

2-(2-phenoxyquinolin-8-yl)-6,7-dihydro-1H-pyrrolo[3,2-c]pyridin-4(5H)-one

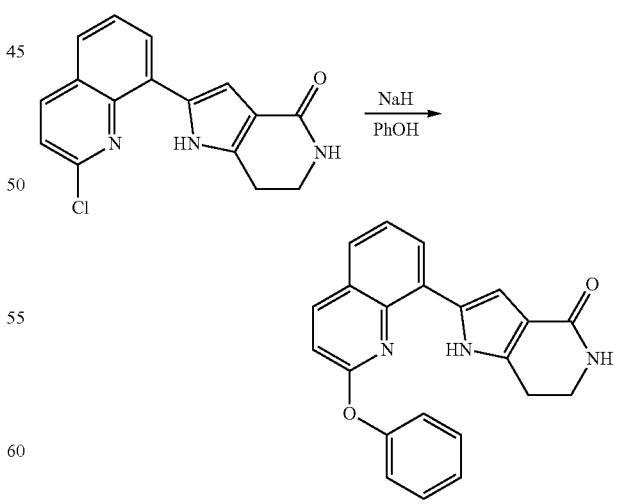

To NaH (60 wt % in mineral oil; 0.047 g, 1.176 mmol) in 1 mL DMF was added phenol (0.111 g, 1.176 mmol). After 10 min, a clear/colorless solution resulted. 2-(2-chloroquinolin-8-yl)-6,7-dihydro-1H-pyrrolo[3,2-c]pyridin-4(5H)-one (Example 1, 0.050 g, 0.168 mmol) was added and the reaction became dark red. After 30 min at RT, the reaction was heated to 70° C. The reaction was judged complete after 5 h at 70° C., and was cooled to RT and quenched with saturated aq. NH₄Cl and EtOAc. The organic layer was sequentially washed with water, and saturated aq. NaCl, then dried over anhydrous Na₂SO₄, filtered, and concentrated in vacuo. The material was treated with DCM and purified by silica gel chromatography using 0-50%-90/10 DCM/MeOH in DCM. The product-containing fractions were concentrated to afford 2-(2-phenoxyquinolin-8-yl)-6,7-dihydro-1H-pyrrolo[3,2-c]pyridin-4(5H)-one (0.048 g, 0.135 mmol, 80% yield) as a light-yellow solid: ¹H NMR (400 MHz, DMSO-d₆) δ ppm 11.04 (1H, br. s), 8.49 (1H, d, J=8.8 Hz), 8.12 (1H, dd, J=7.6, 1.6 Hz), 7.74-7.87 (1H, m), 7.56-7.66 (2H, m), 7.33-7.52 (5H, m), 6.84-7.01 (2H, m), 3.31-3.38 (2H, m), 2.39 (2H, t, J=6.9 Hz). m/z (ESI, +ve) 356.0 (M+H)⁺.

Example 38

2-(2-(3-pyridinylamino)-8-quinolinyl)-1,5,6,7-tetrahydro-4H-pyrrolo[3,2-c]pyridin-4-one

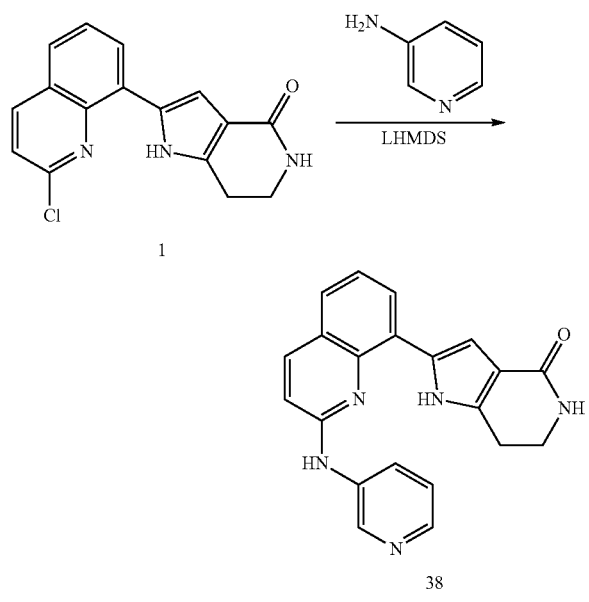

Prepared according to Example 102, using 3-aminopyridine (166 mg, 1.763 mmol, Sigma Aldrich), 2-(2-chloroquinolin-7-yl)-6,7-dihydro-1H-pyrrolo[3,2-c]pyridin-4(5H)-one (Example 1; 105 mg, 0.353 mmol), and 1.0 M LHMDS THF (1763 µl, 1.763 mmol, Sigma Aldrich) and stirring for 2.5 h at 25° C. Purification by washing of the mixture with saturated aq. NH₄Cl provided 2-(2-(3-pyridinylamino)-8-quinolinyl)-1,5,6,7-tetrahydro-4H-pyrrolo[3,2-c]pyridin-4-one (43 mg, 34%). ¹H NMR (400 MHz, DMSO-d₆) δ ppm 11.86-11.91 (1H, m) 9.69-9.72 (1H, m) 8.81-8.85 (1H, m) 8.24-8.32 (2H, m) 8.13-8.19 (1H, m) 7.86-7.91 (1H, m) 7.60-7.66 (1H, m) 7.36-7.41 (1H, m) 7.29-7.36 (1H, m) 7.08-7.15 (1H, m) 6.89-6.95 (1H, m) 6.81-6.86 (1H, m) 3.38-3.46 (2H, m) 2.73 (2H, s). m/z (ESI, +ve) 356.1 (M+H)⁺.

Example 39

2-(2-(3-pyridinyloxy)-8-quinolinyl)-1,5,6,7-tetrahydro-4H-pyrrolo[3,2-c]pyridin-4-one

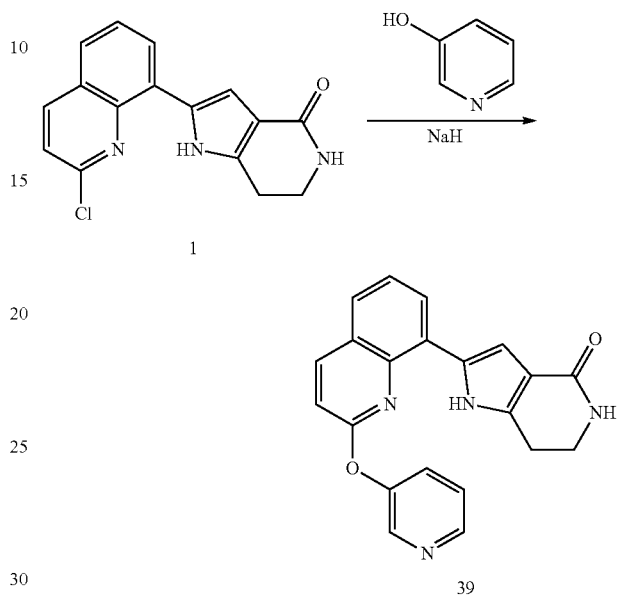

Prepared according to Example 103, using NaH as a 60% dispersion in mineral oil (153 µl, 3.53 mmol, Sigma Aldrich), pyridin-3-ol (335 mg, 3.53 mmol, Sigma Aldrich), and 2-(2-chloroquinolin-8-yl)-6,7-dihydro-1H-pyrrolo[3,2-c]pyridin-4(5H)-one (Example 1; 150 mg, 0.504 mmol) and stirring at 25° C. for 6 h. Purification by column chromatography (silica gel, 0 to 9% MeOH/DCM) followed by trituration with MeOH provided 2-(2-(3-pyridinyloxy)-8-quinolinyl)-1,5,6,7-tetrahydro-4H-pyrrolo[3,2-c]pyridin-4-one (49 mg, 27.3%). ¹H NMR (400 MHz, CDCl₃) δ ppm 11.07-11.15 (1H, m) 8.72-8.76 (2H, m) 8.68 (1H, d, J=1.00 Hz) 8.26 (1H, d, J=1.00 Hz) 8.04-8.09 (1H, m) 7.61-7.70 (2H, m) 7.45-7.57 (2H, m) 7.09-7.14 (1H, m) 5.38 (1H, br. s) 3.52-3.59 (2H, m) 2.54 (2H, t, J=1.00 Hz). m/z (ESI, +ve) 357.0 (M+H)⁺.

Example 40

2-(2-((3-chlorophenyl)amino)-8-quinolinyl)-1,5,6,7-tetrahydro-4H-pyrrolo[3,2-c]pyridin-4-one

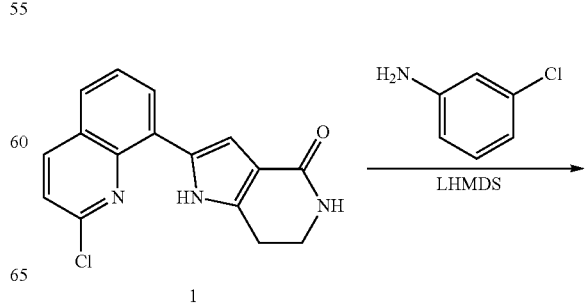

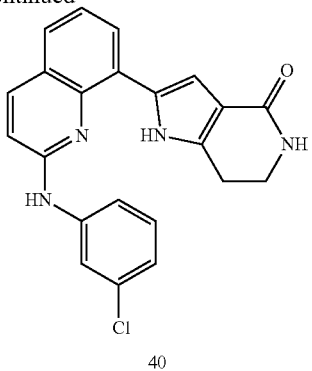

40

Prepared according to Example 102, using 3-chloroaniline (220 μl, 2.099 mmol, Sigma Aldrich), 2-(2-chloroquinolin-8-yl)-6,7-dihydro-1H-pyrrolo[3,2-c]pyridin-4(5H)-one (Example 1; 125 mg, 0.420 mmol). and 1.0 M LHMDS, 1.0M in THF (2099 μl, 2.099 mmol, Sigma Aldrich) and stirring at 25° C. for 30 min. Purification by column chromatography (silica gel 1 to 5% MeOH/DCM) provided 2424(3-chlorophenyl)amino)-8-quinolinyl)-1,5,6,7-tetrahydro-4H-pyrrolo[3,2-c]pyridin-4-one (27 mg, 16.5%). $^1$H NMR (400 MHz, CDCl$_3$) δ ppm 12.09-12.31 (1H, m) 8.03 (2H, d, J=1.00 Hz) 7.57-7.60 (1H, m) 7.50-7.55 (1H, m) 7.33-7.41 (4H, m) 7.17-7.22 (1H, m) 7.12-7.15 (1H, m) 6.88-6.93 (1H, m) 5.23-5.28 (1H, m) 3.55-3.62 (2H, m) 2.67-2.73 (2H, m). m/z (ESI, +ve) 389.1 (M+H)$^+$.

Example 41

2-(2-(3-chlorophenoxy)-8-quinolinyl)-1,5,6,7-tetrahydro-4H-pyrrolo[3,2-c]pyridin-4-one

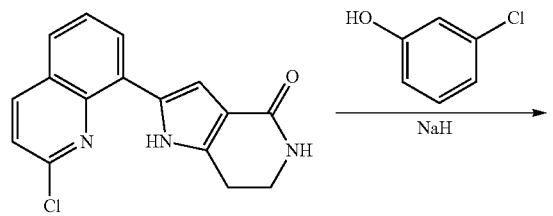

1

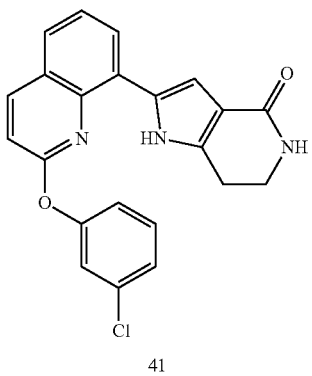

41

Prepared according to Example 103, NaH as a 60% dispersion in mineral oil (143 μl, 3.29 mmol, Sigma Aldrich), 3-chlorophenol (334 μl, 3.29 mmol, Sigma Aldrich), and 2-(2-chloroquinolin-8-yl)-6,7-dihydro-1H-pyrrolo[3,2-c]pyridin-4(5H)-one (Example 1; 140 mg, 0.470 mmol) and stirring at 85° C. for 17 h. Purification by column chromatography (silica gel, 0 to 60% EtOAc/DCM then 5% MeOH/DCM) providing 2-(2-(3-chlorophenoxy)-8-quinolinyl)-1,5,6,7-tetrahydro-4H-pyrrolo[3,2-c]pyridin-4-one (35 mg, 19%). $^1$H NMR (400 MHz, CDCl$_3$) δ ppm 11.28-11.38 (1H, m) 8.23 (1H, d, J=1.00 Hz) 8.04-8.09 (1H, m) 7.61-7.66 (1H, m) 7.48 (2H, q, J=1.00 Hz) 7.36-7.41 (2H, m) 7.19-7.26 (3H, m) 5.84-6.01 (1H, m) 3.58 (2H, t, J=1.00 Hz) 2.55 (2H, t, J=1.00 Hz). m/z (ESI, +ve) 390.0 (M+H)$^+$.

Example 42

2-(2-(3-fluorophenoxy)-8-quinolinyl)-1,5,6,7-tetrahydro-4H-pyrrolo[3,2-c]pyridin-4-one

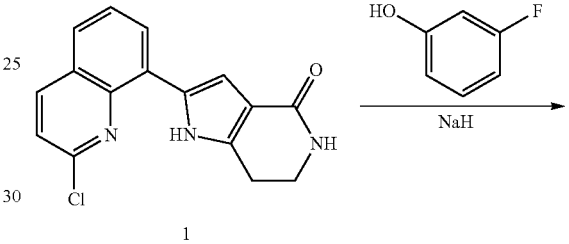

1

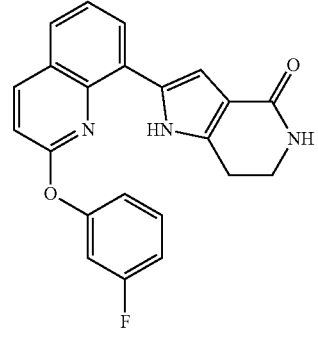

42

Prepared according to Example 103, using NaH as a 60% dispersion in mineral oil (47.0 mg, 1.176 mmol, Sigma Aldrich), 3-fluorophenol (108 μl, 1.176 mmol, Sigma Aldrich), and 2-(2-chloroquinolin-8-yl)-6,7-dihydro-1H-pyrrolo[3,2-c]pyridin-4(5H)-one (Example 1; 50 mg, 0.168 mmol) and heating to 85° C. for 17 h. Purification by reverse-phase HPLC (Phenomenex Gemini column, 10 micron, C$_{18}$, 100 Å, 150×30 mm, 0.1% TFA in ACN/H$_2$O, gradient 5% to 90%) to provide 2-(2-(3-fluorophenoxy)-8-quinolinyl)-1,5,6,7-tetrahydro-4H-pyrrolo[3,2-c]pyridin-4-one (11.2 mg, 11%) as the free base following filtration through a Si-carbonate cartridge (Silicyle) with MeOH. $^1$H NMR (400 MHz, MeOH-d4) δ ppm 7.10 (1H, m) 7.10 (1H, d, J=1.00 Hz) 6.80-6.87 (1H, m) 6.82 (1H, d, J=1.00 Hz) 6.44-6.49 (1H, m) 6.31-6.38 (1H, m) 6.16-6.24 (1H, m) 6.01-6.07 (1H, m) 5.87-5.99 (2H, m) 5.73 (1H, s) 2.23 (2H, t, J=1.00 Hz) 1.26 (2H, t, J=1.00 Hz). m/z (ESI, +ve) 374.1 (M+H)$^+$.

Example 43

2-(2-(3-methylphenoxy)-8-quinolinyl)-1,5,6,7-tetrahydro-4H-pyrrolo[3,2-c]pyridin-4-one

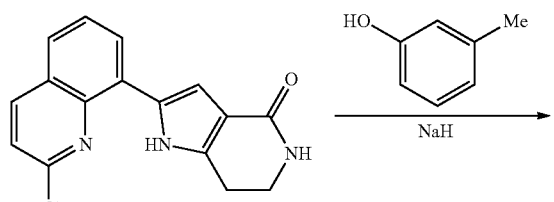

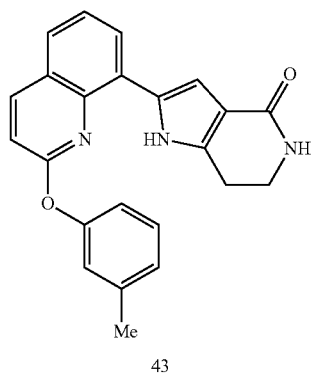

Prepared according to Example 103, using NaH as a 60% dispersion in mineral oil (47.0 mg, 1.176 mmol, Sigma Aldrich) in DMF (1679 µl), m-cresol (123 µl, 1.176 mmol, Sigma Aldrich), and 2-(2-chloroquinolin-8-yl)-6,7-dihydro-1H-pyrrolo[3,2-c]pyridin-4(5H)-one (Example 1; 50 mg, 0.168 mmol) and heating to 85° C. for 16 h. Purification by reverse phase HPLC (Phenomenex Gemini column, 10 micron, $C_{18}$, 100 Å, 150×30 mm, 0.1% TFA in ACN/H$_2$O, gradient 5% to 90%) provided 2-(2-(3-methylphenoxy)-8-quinolinyl)-1,5,6,7-tetrahydro-4H-pyrrolo[3,2-c]pyridin-4-one (5.8 mg, 9.4%) as the free base following filtration through a Si-carbonate cartridge (Silicyle) with MeOH. $^1$H NMR (400 MHz, MeOH-d4) δ ppm 8.37-8.41 (1H, m) 8.10-8.14 (1H, m) 7.73-7.76 (1H, m) 7.46-7.56 (1H, m) 7.28-7.37 (2H, m) 7.14-7.22 (1H, m) 7.04 (3H, s) 3.48-3.55 (2H, m) 3.14-3.19 (2H, m) 2.47 (3H, s). m/z (ESI, +ve) 370.2 (M+H)$^+$.

Example 44

2-(2-((3-methylphenyl)amino)-8-quinolinyl)-1,5,6,7-tetrahydro-4H-pyrrolo[3,2-c]pyridin-4-one

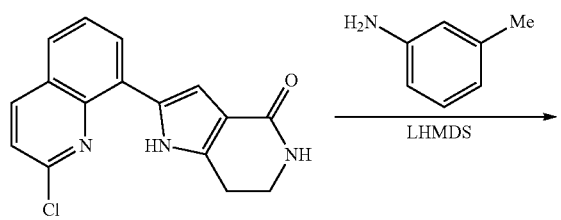

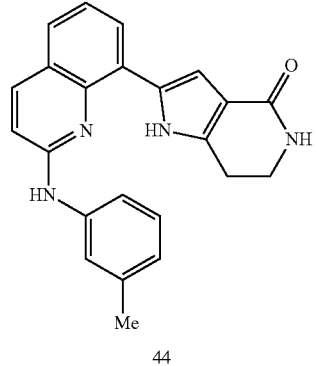

Prepared according to Example 102, using 2-(2-chloroquinolin-8-yl)-6,7-dihydro-1H-pyrrolo[3,2-c]pyridin-4(5H)-one (Example 1; 50 mg, 0.168 mmol), 3-methylaniline (91 µl, 0.840 mmol, Sigma Aldrich), and 1.0 M LHMDS in THF (163 µl, 0.840 mmol, Sigma Aldrich) and stirring at 25° C. for 2.h. Purification by column chromatography (silica gel: 0 to 4% MeOH/DCM) provided 2-(2-((3-methylphenyl)amino)-8-quinolinyl)-1,5,6,7-tetrahydro-4H-pyrrolo[3,2-c]pyridin-4-one (2.5 mg, 4%). $^1$H NMR (400 MHz, MeOH-d4) δ ppm 7.84-7.90 (2H, m) 7.37-7.43 (1H, m) 7.27-7.32 (2H, m) 7.17 (3H, s) 6.88 (2H, m) 3.40 (2H, t, J=1.00 Hz) 2.50 (2H, t, J=1.00 Hz) 2.24 (3H, s). m/z (ESI, +ve) 369.2 (M+H)$^+$.

Example 45

2-(2-((3-fluorophenyl)amino)-8-quinolinyl)-1,5,6,7-tetrahydro-4H-pyrrolo[3,2-c]pyridin-4-one

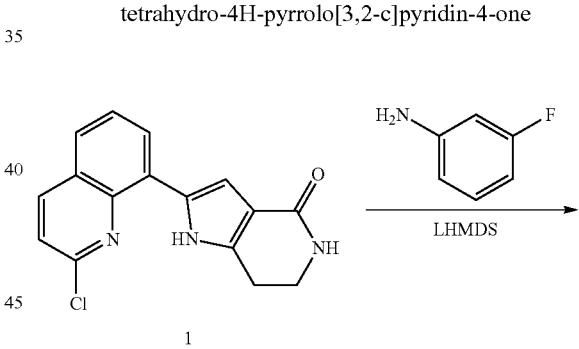

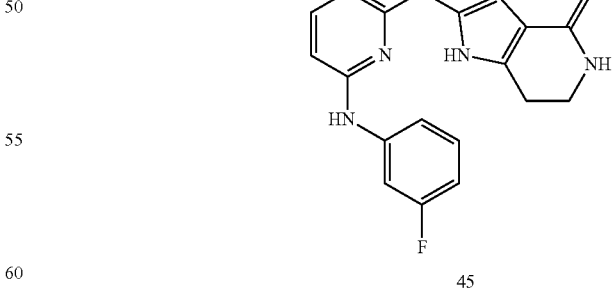

Prepared according to Example 102, using 3-fluoroaniline (230 µl, 2.069 mmol, Sigma Aldrich), 2-(2-chloroquinolin-8-yl)-6,7-dihydro-1H-pyrrolo[3,2-c]pyridin-4(5H)-one (Example 1; 77 mg, 0.259 mmol), and 1.0 M LHMDS, in THF (2069 µl, 2.069 mmol, Sigma Aldrich) and stirring at 25° C.

for 30 min. Purification by column chromatography (silica gel: 0 to 100% EtOAc/hexanes) provided 2424(3-fluorophenyl)amino)-8-quinolinyl)-1,5,6,7-tetrahydro-4H-pyrrolo[3,2-c]pyridin-4-one (43 mg, 44.6%). $^1$H NMR (400 MHz, DMSO-d$_6$) δ ppm 11.91-12.00 (m, 1H) 9.69-9.77 (1H, m) 8.14-8.21 (1H, m) 7.87-7.93 (2H, m) 7.62-7.77 (3H, m) 7.31-7.54 (2H, m) 7.08-7.16 (2H, m) 6.78-6.89 (1H, m) 3.38-3.50 (2H, m) 2.67-2.76 (2H, m). m/z (ESI, +ve) 373.1 (M+H)$^+$.

Example 46

Methyl (8-(4-oxo-4,5,6,7-tetrahydro-1H-pyrrolo[3,2-c]pyridin-2-yl)-2-quinolinyl)phenylcarbamate

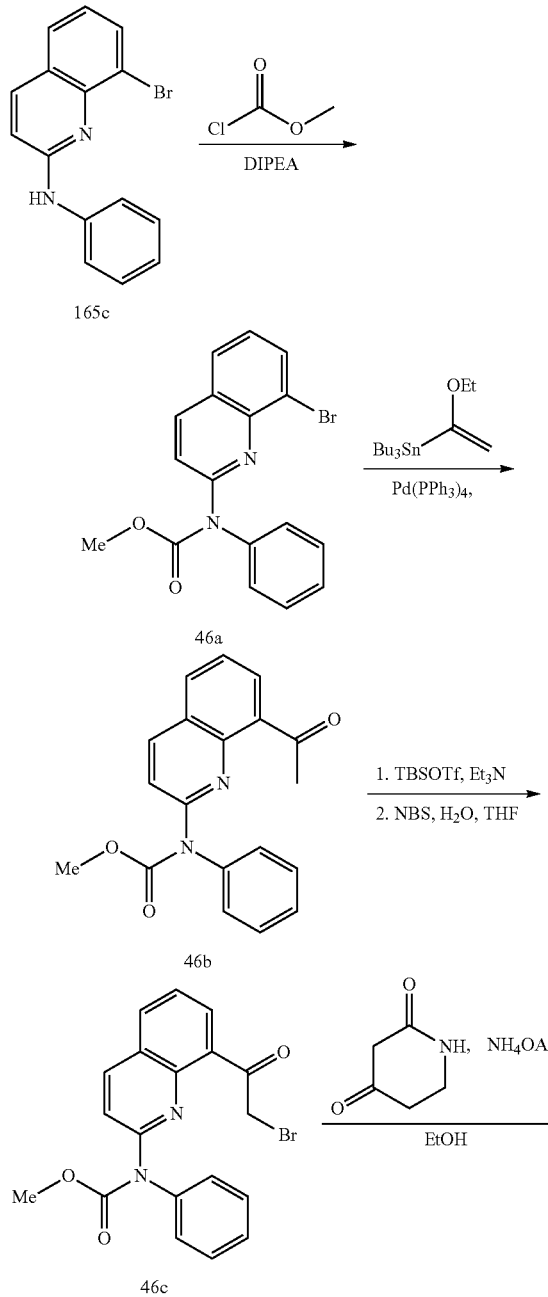

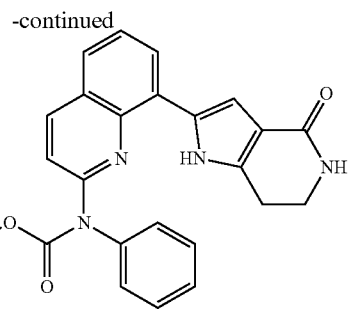

Preparation of methyl (8-acetylquinolin-2-yl)(phenyl)carbamate

Methyl chloroformate (0.155 ml, 2.006 mmol) was added to a solution of 8-bromo-N-phenylquinolin-2-amine (Example 165c; 0.500 g, 1.671 mmol) and DIPEA (0.438 ml, 2.507 mmol) in 5 mL THF and stirred over the weekend. The reaction was then sealed and heated at 70° C. for 6 h. Additional DIPEA (0.438 ml, 2.507 mmol) and methyl chloroformate (0.155 ml, 2.006 mmol) were added and the reaction was stirred overnight at RT. The reaction was heated for several hours at 70° C. The reaction mixture was then quenched with saturated aq. NaHCO$_3$ and diluted with DCM. The organic layer was separated, and the aq. layer was extracted 3×DCM. The combined organic layers were then dried over Na$_2$SO$_4$, filtered, and concentrated in vacuo. The material was treated with DCM and purified by column chromatography (silica gel: 0-10% EtOAc/hexane). The product-containing fractions were concentrated under reduced pressure to afford a mixture of starting material and desired product (0.376 g) that was used in the next step without additional purification.

Preparation of methyl (8-acetylquinolin-2-yl)(phenyl)carbamate

A mixture of Pd(PPh$_3$)$_4$ (60.8 mg, 0.053 mmol, Strem Chemicals, Newburyport, Mass.), tributyl(1-ethoxyvinyl)stannane (391 μl, 1.158 mmol, Sigma Aldrich), methyl (8-bromoquinolin-2-yl)(phenyl)carbamate (Example 46a; 376 mg, 1.053 mmol), and toluene (5.2 mL) were stirred under N$_2$ at 100° C. for 20 h. Purification by column chromatography (silica gel: 0 to 10% EtOAc/hexanes followed by 70% EtOAc/hexanes) provided methyl (8-acetylquinolin-2-yl)(phenyl)carbamate, which was used without further purification in the next step. m/z (ESI, +ve) 349.1 (M+H)$^+$.

Preparation of methyl (8-(2-bromoacetyl)quinolin-2-yl)(phenyl)carbamate

A solution of methyl (8-acetylquinolin-2-yl)(phenyl)carbamate (46b; 790 mg) was set stirring in DCM (2 mL) at 0° C. before adding Et$_3$N (190 μl, 1.368 mmol), and TBSOTf (266 μl, 1.158 mmol) sequentially. An additional 3.0 equivalents of Et$_3$N and TBSOTf were then added sequentially After 5 min., the mixture was diluted with sat. aq. NaHCO$_3$, and extracted with DCM. The organic extract was dried over Na$_2$SO$_4$, filtered and concentrated under reduced pressure. The residue was dissolved in THF (5 mL) before adding water (303 μL, 16.84 mmol) and Br$_2$ (67.4 μl, 1.316 mmol, Sigma Aldrich). The resulting mixture was stirred at RT for 5 min, then diluted with sat. aq. NaHCO$_3$ and extracted with DCM. The organic layer was separated, dried over Na$_2$SO$_4$, filtered, and concentrated under reduced pressure. The brominated product was used without further purification in the subsequent transformation. m/z (ESI, +ve) 399.1 (M+H)$^+$.

Preparation of methyl (8-(4-oxo-4,5,6,7-tetrahydro-1H-pyrrolo[3,2-c]pyridin-2-yl)-2-quinolinyl)phenylcarbamate EtOH (5 mL) was added to a mixture of NH$_4$OAc (406 mg, 5.26 mmol, Sigma Aldrich), piperidine-2,4-dione (179 mg, 1.579 mmol), and methyl (8-(2-bromoacetyl)quinolin-2-yl)(phenyl)carbamate (crude material from the prior step) and the reaction mixture was placed in a sealed vessel and heated at 50° C. for 18 h. The mixture was then concentrated under reduced pressure, diluted with saturated aq. NaHCO$_3$, and extracted with DCM (2×). The combined organic extracts were dried over Na$_2$SO$_4$, filtered, and concentrated under reduced pressure. The residue was purified by column chromatography (silica gel, 0 to 7% MeOH/DCM). An additional purification by reverse phase HPLC (Phenomenex Gemini column, 10 micron, C$_{18}$, 100 Å, 150×30 mm, 0.1% TFA in ACN/H$_2$O, gradient 5% to 90%) provided methyl (8-(4-oxo-4,5,6,7-tetrahydro-1H-pyrrolo[3,2-c]pyridin-2-yl)quinolin-2-yl)(phenyl)carbamate (16 mg, 3.7% over five steps) as the free base following filtration through a Si-carbonate cartridge with MeOH (Silicyle). $^1$H NMR (MeOH-d4) δ: 8.22-8.28 (m, 1H), 7.32-7.72 (m, 10H), 3.81-3.89 (m, 3H), 3.53-3.60 (m, 1H), 3.09-3.13 (m, 2H), 2.81-2.89 (m, 1H). m/z (ESI, +ve) 413.1 (M+H)$^+$.

Example 47 tert-butyl 4-((3-methyl-8-(4-oxo-4,5,6,7-tetrahydro-1H-pyrrolo[3,2-c]pyridin-2-yl)-2-quinoxalinyl)amino)-1-piperidinecarboxylate

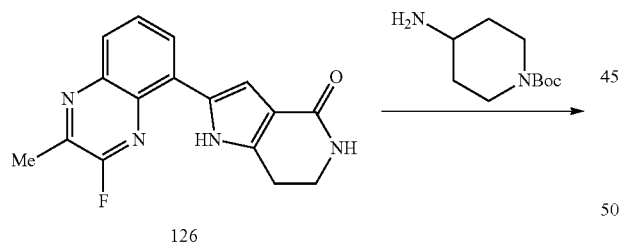

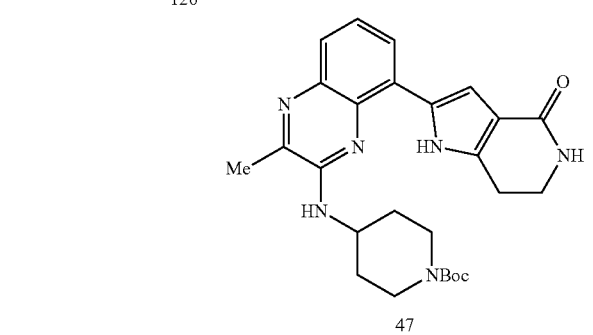

Prepared according to Example 131, using tert-butyl 4-aminopiperidine-1-carboxylate (203 mg, 1.012 mmol, CNH Technologies, Inc., Woburn, Mass.) and 2-(3-fluoro-2-methylquinoxalin-5-yl)-6,7-dihydro-1H-pyrrolo[3,2-c]pyridin-4(5H)-one (Example 126; 100 mg, 0.337 mmol) in DMSO (1.5 mL) and heating to 85° C. for 2 h. Purification by column chromatography (silica gel: 0 to 10% MeOH/DCM) provided tert-butyl 4-(3-methyl-8-(4-oxo-4,5,6,7-tetrahydro-1H-pyrrolo[3,2-c]pyridin-2-yl)quinoxalin-2-yl)amino)piperidine-1-carboxylate (38 mg, 23.6%). $^1$H NMR (400 MHz, MeOH-d4) δ ppm 7.86-7.91 (1H, m) 7.61-7.66 (1H, m) 7.38 (1H, t, J=1.00 Hz) 7.21 (1H, s) 4.28-4.38 (1H, m) 4.15-4.25 (1H, m) 3.64 (1H, t, J=1.00 Hz) 3.37 (2H, s) 2.99-3.05 (2H, m) 2.56 (3H, s) 2.58-2.61 (2H, m) 2.16-2.24 (2H, m) 1.59-1.69 (2H, m) 1.50 (9H, s). m/z (ESI, +ve) 477.2 (M+H)$^+$.

Example 48 tert-butyl (3R)-3-((3-methyl-8-(4-oxo-4,5,6,7-tetrahydro-1H-pyrrolo[3,2-c]pyridin-2-yl)-2-quinoxalinyl)amino)-1-pyrrolidinecarboxylate

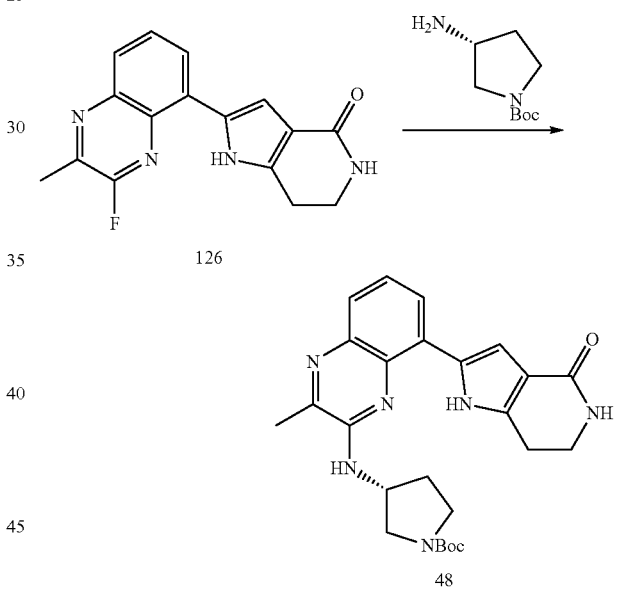

Prepared according to Example 131, using (R)-tert-butyl 3-aminopyrrolidine-1-carboxylate (189 mg, 1.012 mmol, CNH Technologies, Inc., Woburn, Mass.) and 2-(3-fluoro-2-methylquinoxalin-5-yl)-6,7-dihydro-1H-pyrrolo[3,2-c]pyridin-4(5H)-one (Example 126; 100 mg, 0.337 mmol) in DMSO (1.5 mL) and heating at 85° C. for 2 h. Purification by column chromatography (silica gel: 0 to 10% MeOH/DCM) provided (R)-tert-butyl-3-((3-methyl-8-(4-oxo-4,5,6,7-tetrahydro-1H-pyrrolo[3,2-c]pyridin-2-yl)quinoxalin-2-yl)amino)pyrrolidine-1-carboxylate (45 mg, 28.8%). $^1$H NMR (400 MHz, MeOH-d4) δ ppm 7.90-7.96 (1H, m) 7.63-7.69 (1H, m) 7.42 (1H, t, J=1.00 Hz) 7.11 (1H, s) 4.65-4.80 (1H, m) 3.87-4.03 (1H, m) 3.57-3.68 (3H, m) 3.49-3.55 (1H, m) 3.40-3.49 (1H, m) 2.94-3.03 (1H, m) 2.61 (3H, s) 2.35-2.49 (2H, m) 2.19-2.34 (1H, m) 1.45-1.54 (9H, m). m/z (ESI, +ve) 463.2 (M+H)$^+$.

Example 49

(S)-tert-butyl-3-((3-methyl-8-(4-oxo-4,5,6,7-tetrahydro-1H-pyrrolo[3,2-c]pyridin-2-yl)quinoxalin-2-yl)amino)pyrrolidine-1-carboxylate

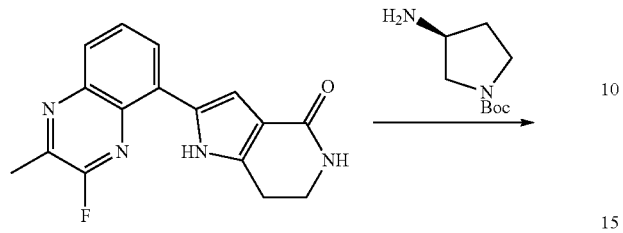

Prepared according to Example 131 using (S)-tert-butyl 3-aminopyrrolidine-1-carboxylate (189 mg, 1.012 mmol) and 2-(3-fluoro-2-methylquinoxalin-5-yl)-6,7-dihydro-1H-pyrrolo[3,2-c]pyridin-4(5H)-one (Example 126; 100 mg, 0.337 mmol) in DMSO (1.5 mL) and heating to 85° C. for 2 h. Purification by column chromatography (silica gel: 0 to 10% MeOH/DCM) provided (S)-tert-butyl-3-((3-methyl-8-(4-oxo-4,5,6,7-tetrahydro-1H-pyrrolo[3,2-c]pyridin-2-yl)quinoxalin-2-yl)amino)pyrrolidine-1-carboxylate (51 mg, 32.8%). $^1$H NMR (400 MHz, MeOH-d4) δ ppm 7.90-7.96 (1H, m) 7.63-7.69 (1H, m) 7.42 (1H, t, J=1.00 Hz) 7.11 (1H, s) 4.65-4.80 (1H, m) 3.87-4.03 (1H, m) 3.57-3.68 (3H, m) 3.49-3.55 (1H, m) 3.40-3.49 (1H, m) 2.94-3.03 (1H, m) 2.61 (3H, s) 2.35-2.49 (2H, m) 2.19-2.34 (1H, m) 1.45-1.54 (9H, m). m/z (ESI, +ve) 463.2 (M+H)$^+$.

Example 50

2-(3-((1-acetyl-4-piperidinyl)amino)-2-methyl-5-quinoxalinyl)-1,5,6,7-tetrahydro-4H-pyrrolo[3,2-c]pyridin-4-one

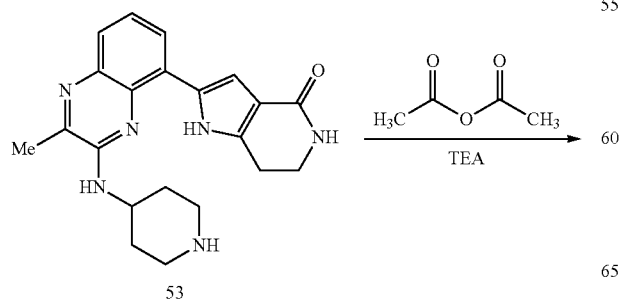

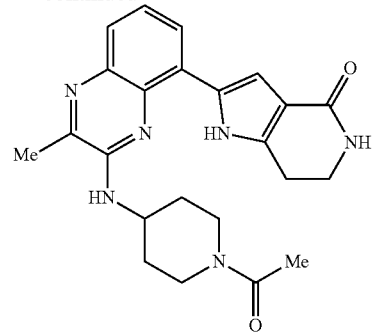

A mixture of 2-(2-methyl-3-(piperidin-4-ylamino)quinoxalin-5-yl)-6,7-dihydro-1H-pyrrolo[3,2-c]pyridin-4(5H)-one (Ex. 53, 55 mg, 0.146 mmol) and DIPEA (76 µl, 0.438 mmol, EMD Biosciences, Rockland, Mass.) in DCM (5.8 mL) was set stirring at 25° C. before adding Ac$_2$O (15.16 µl, 0.161 mmol, Sigma Aldrich) dropwise. The reaction was stirred for 30 min before concentrating under reduced pressure. The residue was taken up in DMSO, and purified by reverse-phase preparative HPLC (Phenomenex Gemini column, 10 micron, C$_{18}$, 100 Å, 150×30 mm, 0.1% TFA in ACN/H$_2$O, gradient 5% to 75%). Product-containing fractions were concentrated under reduced pressure and the residue was loaded onto a pre-washed (MeOH, 1 volume) functionalized Si-carbonate column (Silicyle) and allowed to percolate through to provide 2-(34(1-acetylpiperidin-4-yl)amino)-2-methylquinoxalin-5-yl)-6,7-dihydro-1H-pyrrolo[3,2-c]pyridin-4(5H)-one (12.2 mg, 20.0%). $^1$H NMR (MeOH-d4) δ: 7.84-7.88 (m, 1H), 7.60-7.65 (m, 1H), 7.34-7.40 (m, 1H), 7.23 (s, 1H), 4.55-4.63 (m, 1H), 4.34-4.45 (m, 1H), 3.99-4.07 (m, 1H), 3.58-3.66 (m, 2H), 3.39-3.50 (m, 2H), 2.98-3.04 (m, 1H), 2.58 (s, 3H), 2.27-2.36 (m, 2H), 2.18-2.24 (m, 1H), 2.15 (s, 3H), 1.58-1.69 (m, 2H). m/z (ESI, −ve) 417.1 (M−H)$^-$.

Example 51 tert-butyl (3S)-3-((3-methyl-8-(4-oxo-4,5,6,7-tetrahydro-1H-pyrrolo[3,2-c]pyridin-2-yl)-2-quinoxalinyl)amino)-1-piperidinecarboxylate

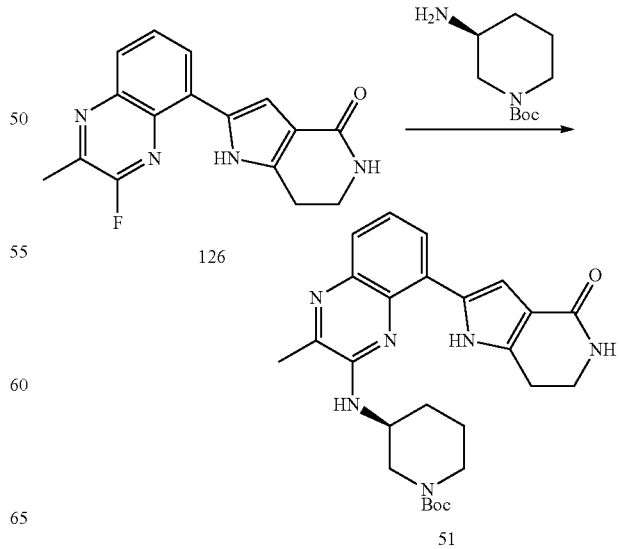

Prepared according to Example 131, (S)-3-amino-1-Boc-piperidine (180 µL, 0.759 mmol, CNH Technologies, Inc., Woburn, Mass.), 2-(3-fluoro-2-methylquinoxalin-5-yl)-6,7-dihydro-1H-pyrrolo[3,2-c]pyridin-4(5H)-one (Example 126; 75 mg, 0.253 mmol), and DMSO (2.5 mL) stirring at 100° C. for 2. Purification by sequential column chromatography (silica gel: 0.5 to 10% MeOH/DCM) and reverse phase chromatography (Phenomenex Gemini column, 10 micron, C$_{18}$, 100 Å, 150×30 mm, 0.1% TFA in ACN/H$_2$O, gradient 5% to 95%) provided tert-butyl (3S)-3-((3-methyl-8-(4-oxo-4,5,6,7-tetrahydro-1H-pyrrolo[3,2-c]pyridin-2-yl)-2-quinoxalinyl)amino)-1-piperidinecarboxylate (5.2 mg, 4.3%) as the free base after washing with saturated aq. NaHCO$_3$, extracting with 10% MeOH/DCM, drying over Na$_2$SO$_4$, and concentrating under reduced pressure. $^1$H NMR (CDCl$_3$) δ: 7.92-7.97 (m, 1H), 7.65-7.71 (m, 1H), 7.37-7.45 (m, 1H), 7.13 (s, 2H), 5.42 (br. s., 1H), 4.12 (s, 1H), 3.62-3.70 (m, 3H), 2.91-2.99 (m, 2H), 2.57 (s, 3H), 1.94-2.07 (m, 1H), 1.89-1.90 (m, 1H), 1.80-1.91 (m, 1H), 1.68 (s, 9H), 1.33-1.55 (m, 5H). m/z (ESI, +ve) 477.2 (M+H)$^+$.

Example 52 tert-butyl (3R)-3-((3-methyl-8-(4-oxo-4,5,6,7-tetrahydro-1H-pyrrolo[3,2-c]pyridin-2-yl)-2-quinoxalinyl)amino)-1-piperidinecarboxylate

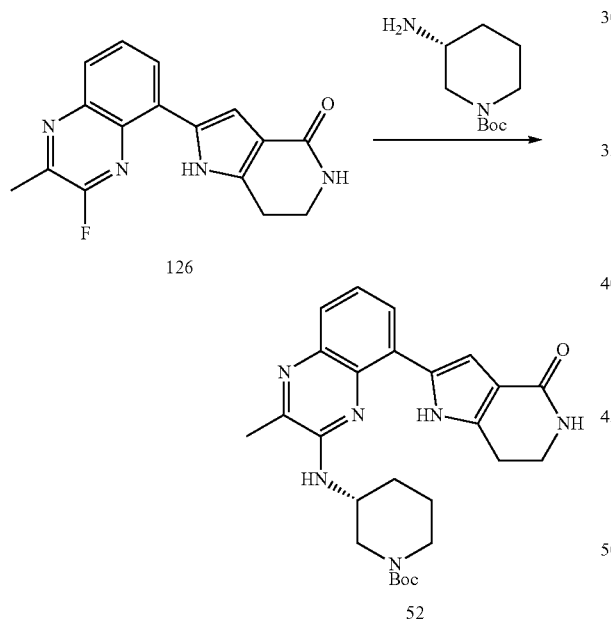

Prepared according to Example 131, using (R)-3-amino-1-boc-piperidine (180 µL, 0.759 mmol, CNH Technologies, Inc., Woburn, Mass.), 2-(3-fluoro-2-methylquinoxalin-5-yl)-6,7-dihydro-1H-pyrrolo[3,2-c]pyridin-4(5H)-one (Example 126; 75 mg, 0.253 mmol), and DMSO (2.5 mL) and stirring at 100° C. for 2 h. Purification by column chromatography (silica gel: 0.5 to 10% MeOH/DCM) and reverse phase chromatography (Phenomenex Gemini column, 10 micron, C$_{18}$, 100 Å, 150×30 mm, 0.1% TFA in ACN/H$_2$O, gradient 5% to 95%) provided tert-butyl (3R)-3-((3-methyl-8-(4-oxo-4,5,6,7-tetrahydro-1H-pyrrolo[3,2-c]pyridin-2-yl)-2-quinoxalinyl)amino)-1-piperidinecarboxylate (1.2 mg, 1.0%) as the free base after washing with saturated aq. NaHCO$_3$, extracting with 10% MeOH/DCM, drying over Na$_2$SO$_4$, and concentrating under reduced pressure. $^1$H NMR (CDCl$_3$) δ: 12.37-12.47 (m, 1H), 7.93-7.98 (m, 1H), 7.66-7.71 (m, 1H), 7.37-7.44 (m, 1H), 7.11-7.16 (m, 1H), 5.43-5.49 (m, 1H), 4.10-4.19 (m, 2H), 3.63-3.70 (m, 4H), 2.93-3.00 (m, 3H), 2.57-2.60 (m, 3H), 2.04-2.06 (m, 2H), 1.78-1.91 (m, 3H), 1.59-1.77 (m, 9H). m/z (ESI, +ve) 477.2 (M+H)$^+$.

Example 53

2-(2-methyl-3-(4-piperidinylamino)-5-quinoxalinyl)-1,5,6,7-tetrahydro-4H-pyrrolo[3,2-c]pyridin-4-one

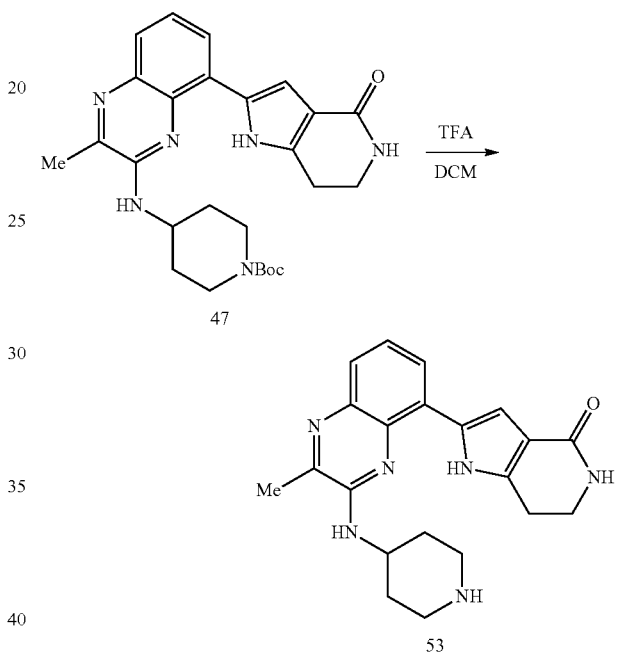

A solution of tert-butyl 4-((3-methyl-8-(4-oxo-4,5,6,7-tetrahydro-1H-pyrrolo[3,2-c]pyridin-2-yl)quinoxalin-2-yl)amino)piperidine-1-carboxylate (Ex. 47, 80 mg, 0.168 mmol) in DCM (1.7 mL) was stirred at 25° C. before adding TFA (12.47 µl, 0.168 mmol, Sigma Aldrich). The resulting solution was stirred for 30 min before carefully adding saturated aq. NaHCO$_3$ (10 mL) and stirring for an additional 30 min. The reaction mixture was then concentrating under reduced pressure, and the residue was taken up in DMSO and purified by reverse-phase preparative HPLC (Phenomenex Gemini column, 10 micron, C$_{18}$, 100 Å, 150×30 mm, 0.1% TFA in ACN/H$_2$O, gradient 5% to 80%). The product-containing fractions were concentrated under reduced pressure, and the residue was loaded onto a pre-washed (MeOH, 1 volume) functionalized Si-carbonate column (Silicyle) and allowed to percolate through, providing 2-(2-methyl-3-(piperidin-4-ylamino)quinoxalin-5-yl)-6,7-dihydro-1H-pyrrolo[3,2-c]pyridin-4(5H)-one (4.3 mg, 6.8%). $^1$H NMR (400 MHz, DMSO-d$_6$) δ ppm 11.92 (1H, s) 7.83-7.91 (1H, m) 7.52-7.58 (2H, m) 7.28-7.35 (1H, m) 7.11-7.16 (1H, m) 3.98-4.11 (3H, m) 3.41-3.49 (2H, m) 2.97-3.06 (2H, m) 2.89 (2H, s) 2.59-2.71 (2H, m) 2.54 (3H, s) 1.93-2.04 (2H, m) 1.43-1.59 (2H, m). m/z (ESI, +ve) 377.1 (M+H)$^+$.

Example 54 rac-2-(3-((cis-2-aminocyclobutyl)amino)-2-methyl-5-quinoxalinyl)-1,5,6,7-tetrahydro-4H-pyrrolo[3,2-c]pyridin-4-one

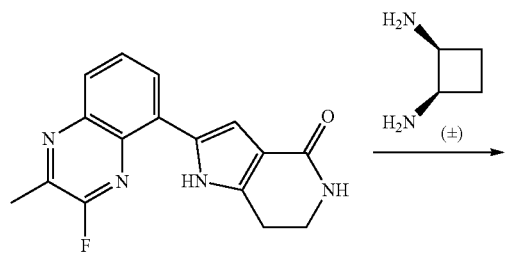

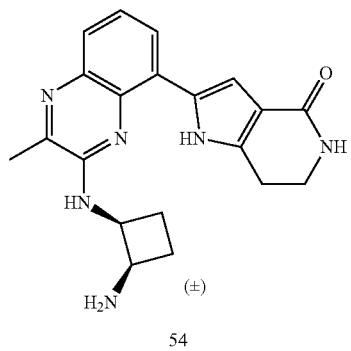

Prepared according to Example 127, using 2-(3-fluoro-2-methylquinoxalin-5-yl)-6,7-dihydro-1H-pyrrolo[3,2-c]pyridin-4(5H)-one (Example 126; 130 mg, 0.439 mmol), cis-cyclobutane-1,2-diamine (Frontier Scientific Services, Newark, Del.; 113 mg, 1.316 mmol), and DMSO (4.4 mL) and stirring at 95° C. for 2 h. Purification by reverse phase HPLC (Phenomenex Gemini column, 10 micron, $C_{18}$, 100 Å, 150×30 mm, 0.1% TFA in ACN/$H_2O$, gradient 5% to 70%) provided rac-2-(3-((cis-2-aminocyclobutyl)amino)-2-methyl-5-quinoxalinyl)-1,5,6,7-tetrahydro-4H-pyrrolo[3,2-c]pyridin-4-one (15 mg, 9.4%). $^1$H NMR (400 MHz, MeOH-d4) δ ppm 7.83-7.88 (1H, m) 7.55-7.61 (1H, m) 7.34 (1H, t, J=1.00 Hz) 7.09 (1H, s) 4.21-4.30 (1H, m) 3.59-3.67 (1H, m) 3.45-3.53 (1H, m) 3.16-3.23 (1H, m) 3.11-3.15 (1H, m) 2.93-3.08 (1H, m) 2.58 (3H, s) 2.34-2.42 (1H, m) 2.19-2.27 (1H, m) 1.56-1.69 (2H, m). m/z (ESI, +ve) 363.2 (M+H)$^+$.

Example 55

2-(2-methyl-3-((3S)-3-pyrrolidinylamino)-5-quinoxalinyl)-1,5,6,7-tetrahydro-4H-pyrrolo[3,2-c]pyridin-4-one

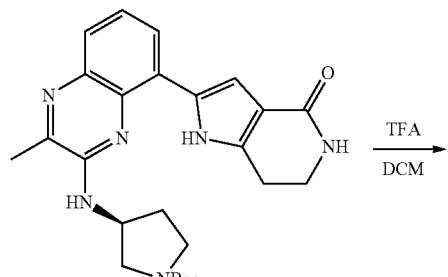

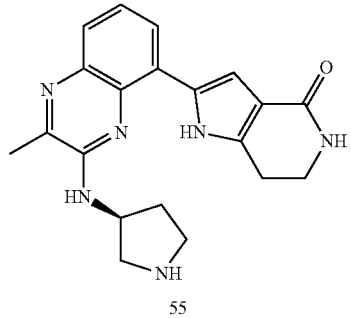

Prepared according to Example 53, using (S)-tert-butyl 34(3-methyl-8-(4-oxo-4,5,6,7-tetrahydro-1H-pyrrolo[3,2-c]pyridin-2-yl)quinoxalin-2-yl)amino)pyrrolidine-1-carboxylate (Ex. 49, 40 mg, 0.086 mmol) in DCM (1 mL) and TFA (6.42 μl, 0.086 mmol) stirring at 25° C. for 30 min. Purification by reverse phase HPLC (Phenomenex Gemini column, 10μ, $C_{18}$, 100 Å, 150×30 mm, 0.1% TFA in ACN/$H_2O$, gradient 5% to 80%) provided 2-(2-methyl-3-((3S)-3-pyrrolidinylamino)-5-quinoxalinyl)-1,5,6,7-tetrahydro-4H-pyrrolo[3,2-c]pyridin-4-one (26 mg, 83.0%) as the free base following filtration through a Si-carbonate cartridge (Silicyle) with MeOH. $^1$H NMR (CDCl$_3$) δ: 12.49-12.59 (m, 1H), 7.94-7.99 (m, 1H), 7.67-7.73 (m, 1H), 7.39-7.46 (m, 1H), 7.13-7.18 (m, 1H), 5.24-5.29 (m, 1H), 5.08-5.15 (m, 1H), 4.50-4.58 (m, 1H), 3.63-3.70 (m, 2H), 3.34-3.42 (m, 1H), 3.15-3.31 (m, 2H), 3.05-3.14 (m, 1H), 2.96-3.03 (m, 2H), 2.62 (s, 3H), 2.35-2.44 (m, 1H), 1.92-2.07 (m, 1H). m/z (ESI, +ve) 363.2 (M+H)$^+$.

Example 56 rac-N-(cis-2-((3-methyl-8-(4-oxo-4,5,6,7-tetrahydro-1H-pyrrolo[3,2-c]pyridin-2-yl)-2-quinoxalinyl)amino)cyclobutyl)acetamide

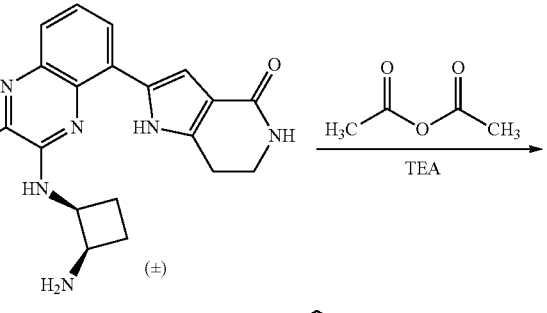

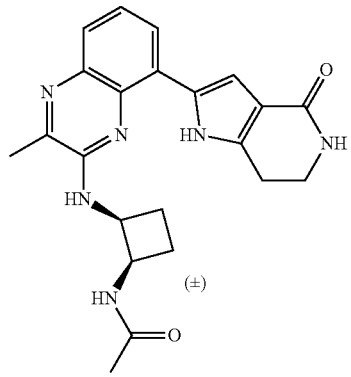

Prepared according to Example 50, using rac-2-(3-((cis-2-aminocyclobutyl)amino)-2-methylquinoxalin-5-yl)-6,7-dihydro-1H-pyrrolo[3,2-c]pyridin-4(5H)-one (Ex. 54, 120 mg, 0.331 mmol) and DIPEA (0.173 ml, 0.993 mmol, and Ac₂O (0.034 ml, 0.364 mmol) in DCM (13.2 mL, and stirring at 25° C. for 2.5 h. Purification by column chromatography (silica gel) provided rac-N-(cis-2-((3-methyl-8-(4-oxo-4,5,6,7-tetrahydro-1H-pyrrolo[3,2-c]pyridin-2-yl)-2-quinoxalinyl)amino)cyclobutyl)acetamide (68.3 mg, 29%). ¹H NMR (400 MHz, DMSO-d6) δ ppm 11.91-11.99 (1H, m) 8.20-8.24 (1H, m) 7.88 (1H, d, J=1.00 Hz) 7.55-7.60 (1H, m) 7.49-7.53 (1H, m) 7.34 (1H, t, J=1.00 Hz) 7.30 (1H, s) 7.03 (1H, s) 4.48-4.59 (2H, m) 3.44-3.51 (2H, m) 2.84-3.02 (3H, m) 2.54 (3H, s) 2.25-2.35 (1H, m) 2.09-2.19 (1H, m) 1.91 (1H, s) 1.70 (1H, s) 1.58-1.67 (1H, m). m/z (ESI, +ve) 405.2 (M+H)⁺.

Example 57

Methyl 2-methyl-N-(3-methyl-8-(4-oxo-4,5,6,7-tetrahydro-1H-pyrrolo[3,2-c]pyridin-2-yl)-2-quinoxalinyl)alaninate

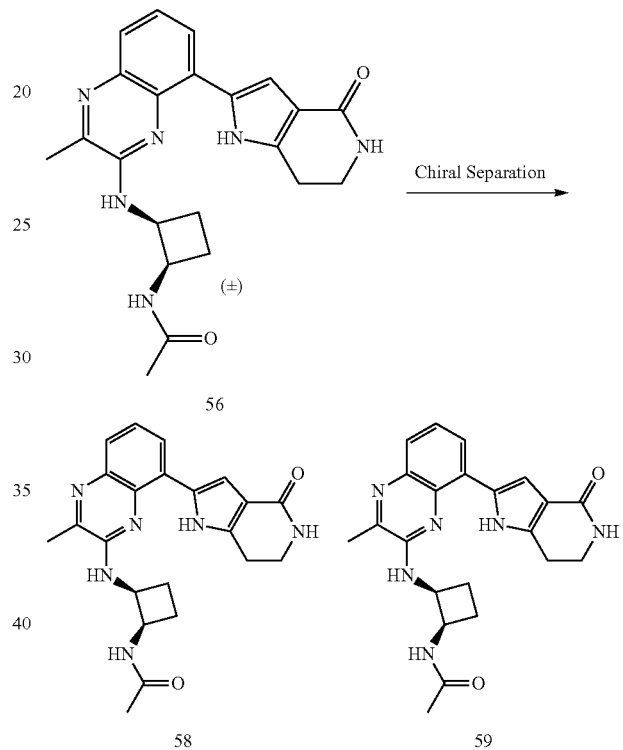

Prepared according to Example 131, using DIPEA (1761 μl, 10.12 mmol), aminoisobutyric acid methyl ester hydrochloride (778 mg, 5.06 mmol, Sigma Aldrich), and 2-(3-fluoro-2-methylquinoxalin-5-yl)-6,7-dihydro-1H-pyrrolo[3,2-c]pyridin-4(5H)-one (Example 126; 500 mg, 1.687 mmol) in DMSO (8437 μl) stirring at 95° C. for 2 h. Purification by column chromatography (silica gel: 0 to 10% MeOH/DCM) provided methyl 2-methyl-2-((3-methyl-8-(4-oxo-4,5,6,7-tetrahydro-1H-pyrrolo[3,2-c]pyridin-2-yl)quinoxalin-2-yl)amino)propanoate (557 mg, 81%). ¹H NMR (CDCl₃) δ: 11.16-11.25 (m, 1H), 7.96-8.01 (m, 1H), 7.69-7.74 (m, 1H), 7.40-7.46 (m, 1H), 7.08-7.12 (m, 1H), 5.56-5.71 (m, 1H), 5.15-5.20 (m, 1H), 3.66-3.73 (m, 2H), 3.56 (s, 3H), 3.25 (s, 2H), 2.65 (s, 3H), 1.79 (s, 6H). m/z (ESI, +ve) 394.1 (M+H)⁺.

Example 58

N-(cis-2-((3-methyl-8-(4-oxo-4,5,6,7-tetrahydro-1H-pyrrolo[3,2-c]pyridin-2-yl)-2-quinoxalinyl)amino)cyclobutyl)acetamide (first-eluting enantiomer)

Example 59

N-(cis-2-((3-methyl-8-(4-oxo-4,5,6,7-tetrahydro-1H-pyrrolo[3,2-c]pyridin-2-yl)-2-quinoxalinyl)amino)cyclobutyl)acetamide (second-eluting enantiomer)

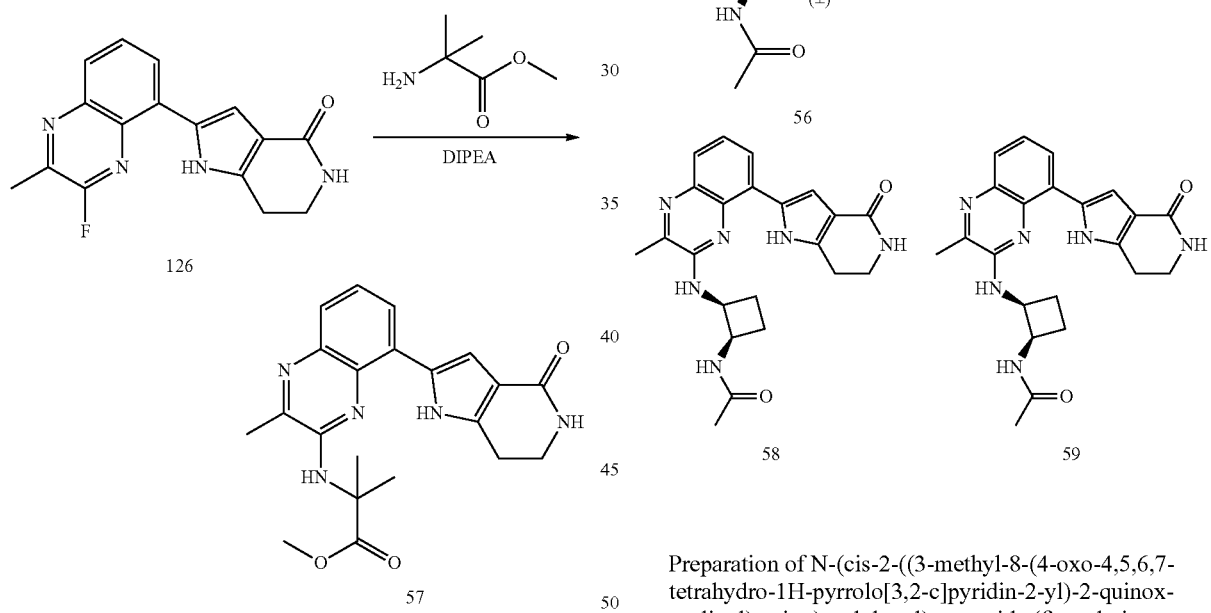

Preparation of N-(cis-2-((3-methyl-8-(4-oxo-4,5,6,7-tetrahydro-1H-pyrrolo[3,2-c]pyridin-2-yl)-2-quinoxalinyl)amino)cyclobutyl)acetamide (first-eluting enantiomer)

A solution of rac-N-(cis-2-((3-methyl-8-(4-oxo-4,5,6,7-tetrahydro-1H-pyrrolo[3,2-c]pyridin-2-yl)-2-quinoxalinyl)amino)cyclobutyl)acetamide (Ex. 56) in 4:1 DCM:MeOH was purified by SFC (IC: 5 urn, 21×25 cm, 60 mL/min, 60% MeOH with 20 mM NH₃ (S/N=2271, detection at 240 nm, T=40° C., BPR=100 bar at 1.2 mL per injection) to provide N-(cis-2-((3-methyl-8-(4-oxo-4,5,6,7-tetrahydro-1H-pyrrolo[3,2-c]pyridin-2-yl)-2-quinoxalinyl)amino)cyclobutyl)acetamide, first-eluting enantiomer (23 mg, 34%): ¹H NMR (MeOH-d4) δ: 7.71-7.79 (m, 1H), 7.47-7.55 (m, 1H), 7.26-7.34 (m, 1H), 7.16 (s, 1H), 4.35-4.52 (m, 2H), 3.63 (s, 2H), 2.92-3.08 (m, 2H), 2.54 (s, 3H), 2.33-2.43 (m, 2H), 2.20-2.33 (m, 1H), 1.82 (s, 3H), 1.65-1.78 (m, 1H). m/z (ESI, +ve) 405.2 (M+H)⁺.

Preparation of N-(cis-2-((3-methyl-8-(4-oxo-4,5,6,7-tetrahydro-1H-pyrrolo[3,2-c]pyridin-2-yl)-2-quinoxalinyl)amino)cyclobutyl)acetamide (second-eluting enantiomer)

A solution of rac-N-(cis-2-((3-methyl-8-(4-oxo-4,5,6,7-tetrahydro-1H-pyrrolo[3,2-c]pyridin-2-yl)-2-quinoxalinyl)amino)cyclobutyl)acetamide in 4:1 DCM:MeOH was purified by SFC (IC: 5 urn, 21×25 cm, 60 mL/min, 60% MeOH with 20 mM NH$_3$ (S/N=2271, detection at 240 nm, T=40° C., BPR=100 bar at 1.2 mL per injection) to provide The second eluting peak provided N-(cis-2-((3-methyl-8-(4-oxo-4,5,6,7-tetrahydro-1H-pyrrolo[3,2-c]pyridin-2-yl)-2-quinoxalinyl)amino)cyclobutyl)-acetamide, second-eluting enantiomer (22 mg, 34%): $^1$H NMR (MeOH-d4) δ: 7.71-7.79 (m, 1H), 7.47-7.55 (m, 1H), 7.26-7.34 (m, 1H), 7.16 (s, 1H), 4.35-4.52 (m, 2H), 3.63 (s, 2H), 2.92-3.08 (m, 2H), 2.54 (s, 3H), 2.33-2.43 (m, 2H), 2.20-2.33 (m, 1H), 1.82 (s, 3H), 1.65-1.78 (m, 1H). m/z (ESI, +ve) 405.2 (M+H)$^+$.

Example 60

2-methyl-N-(3-methyl-8-(4-oxo-4,5,6,7-tetrahydro-1H-pyrrolo[3,2-c]pyridin-2-yl)-2-quinoxalinyl)alanine

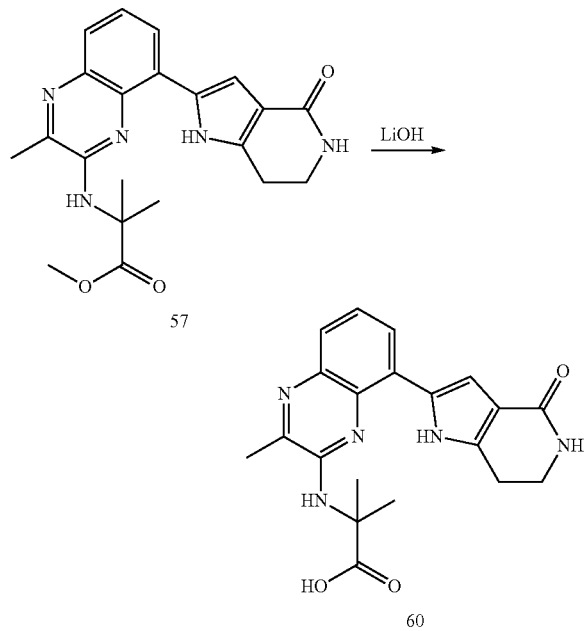

A suspension of methyl 2-methyl-N-(3-methyl-8-(4-oxo-4,5,6,7-tetrahydro-1H-pyrrolo[3,2-c]pyridin-2-yl)-2-quinoxalinyl)alaninate (Ex. 57, 160 mg, 0.407 mmol), LiOH (51.2 mg, 1.220 mmol), and MeOH (2 mL) was stirred at 25° C. for 16 h. The reaction was then diluted with saturated aq. NH$_4$Cl (10 mL) and neutralized to ~pH 6 with 5 N HCl (aq). The resulting solution was extracted with 15% IPA:CHCl$_3$ (3×30 mL) and the combined organic extracts were dried over Na$_2$SO$_4$, filtered, and concentrated under reduced pressure to provide 2-methyl-2-((3-methyl-8-(4-oxo-4,5,6,7-tetrahydro-1H-pyrrolo[3,2-c]pyridin-2-yl)quinoxalin-2-yl)amino)propanoic acid ((145 mg, 94%). $^1$H NMR (MeOH-d4) δ: 7.93-7.98 (m, 1H), 7.58-7.62 (m, 1H), 7.32-7.38 (m, 1H), 6.95 (s, 1H), 3.57-3.62 (m, 2H), 3.17-3.22 (m, 2H), 2.63-2.67 (m, 3H), 1.73-1.76 (m, 6H). m/z (ESI, +ve) 380.1 (M+H)$^+$.

Example 61

2-(2-methyl-3-((3R)-3-pyrrolidinylamino)-5-quinoxalinyl)-1,5,6,7-tetrahydro-4H-pyrrolo[3,2-c]pyridin-4-one

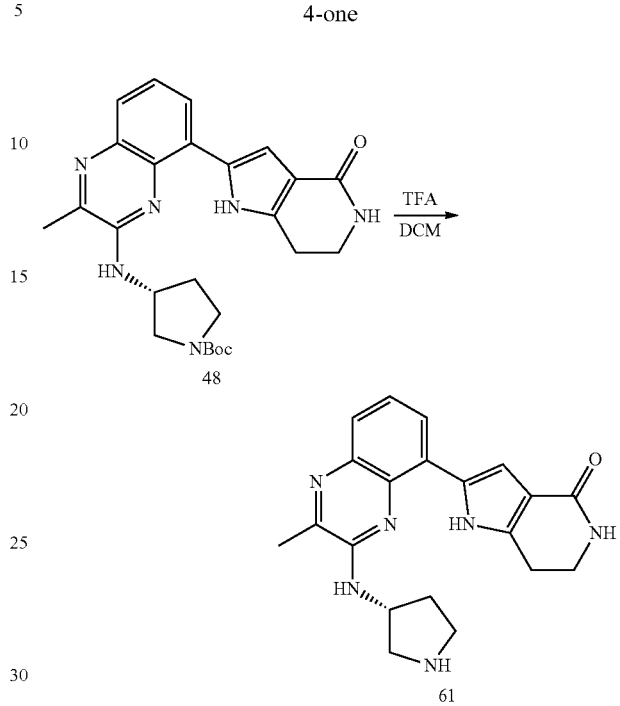

Prepared according to Example 53, using (R)-tert-butyl-3-((3-methyl-8-(4-oxo-4,5,6,7-tetrahydro-1H-pyrrolo[3,2-c]pyridin-2-yl)quinoxalin-2-yl)amino)pyrrolidine-1-carboxylate (Ex. 48, 150 mg, 0.506 mmol), and TFA (940 μl, 12.66 mmol) in DCM (20 mL), stirring at 25° C. for 1.5 h. Purification by column chromatography (silica gel: 0 to 10% MeOH/DCM) provided (R)-2-(2-methyl-3-(pyrrolidin-3-ylamino)quinoxalin-5-yl)-6,7-dihydro-1H-pyrrolo[3,2-c]pyridin-4(5H)-one (140 mg, 76%). $^1$H NMR (DMSO-d$_6$) δ: 12.20 (s, 1H), 7.85-7.92 (m, 1H), 7.54-7.61 (m, 1H), 7.28-7.37 (m, 1H), 7.12 (s, 1H), 6.95 (s, 2H), 4.40-4.52 (m, 1H), 3.40-3.51 (m, 3H), 3.09-3.14 (m, 1H), 2.94-3.07 (m, 2H), 2.88 (s, 3H), 2.58-2.69 (m, 1H), 2.11-2.23 (m, 1H), 1.81-1.95 (m, 1H). m/z (ESI, +ve) 363.2 (M+H)$^+$.

Example 62

2-methyl-N-2-(3-methyl-8-(4-oxo-4,5,6,7-tetrahydro-1H-pyrrolo[3,2-c]pyridin-2-yl)-2-quinoxalinyl)alaninamide

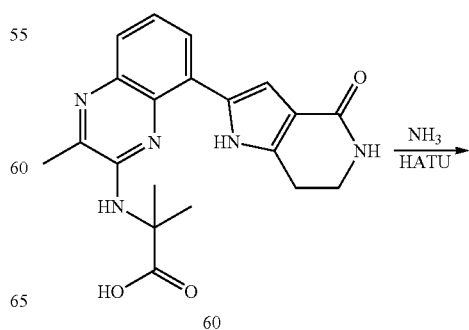

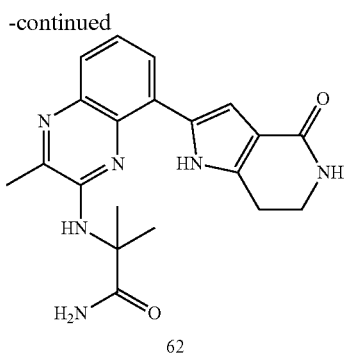

62

A mixture of 2 M NH$_3$ in MeOH (125 μl, 0.250 mmol), DIPEA (43.6 μl, 0.250 mmol), HATU (95 mg, 0.250 mmol, Oakwood Chemical, West Columbia, S.C.), and 2-methyl-2-((3-methyl-8-(4-oxo-4,5,6,7-tetrahydro-1H-pyrrolo[3,2-c]pyridin-2-yl)quinoxalin-2-yl)amino)propanoic acid (Ex. 60, 95 mg, 0.250 mmol) in DMF (2.5 mL) was set stirring at 25° C. for 16 h. The reaction was then diluted with MeOH (3 mL), concentrated, and purified by reverse-phase preparative HPLC using a Phenomenex Gemini column (10 micron, C$_{18}$, 100 Å, 150×30 mm, 0.1% TFA in ACN/H$_2$O, gradient 5% to 70%). The product containing fractions were diluted with saturated aq. NaHCO$_3$ and extracted with 15% MeOH/DCM. The combined extracts were then dried over Na$_2$SO$_4$, filtered, and concentrated in vacuo to provide 2-methyl-N-2-(3-methyl-8-(4-oxo-4,5,6,7-tetrahydro-1H-pyrrolo[3,2-c]pyridin-2-yl)-2-quinoxalinyl)alaninamide (27.6 mg, 29%). $^1$H NMR (DMSO-d$_6$) δ: 7.95-8.00 (m, 1H), 7.54-7.60 (m, 3H), 7.31-7.37 (m, 1H), 7.06-7.11 (m, 1H), 6.93-6.99 (m, 1H), 6.86-6.90 (m, 1H), 6.71-6.75 (m, 1H), 3.39-3.46 (m, 2H), 3.07-3.14 (m, 2H), 2.65 (s, 3H), 1.62 (s, 6H). m/z (ESI, +ve) 379.1 (M+H)$^+$.

Example 63

2-(3-((2-methoxy-1,1-dimethylethyl)amino)-2-methyl-5-quinoxalinyl)-1,5,6,7-tetrahydro-4H-pyrrolo[3,2-c]pyridin-4-one

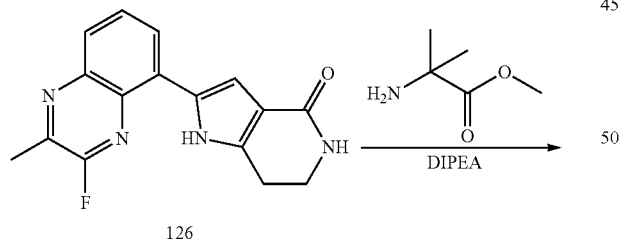

Prepared according to Example 127, using DIPEA (264 μl, 1.519 mmol), (2-methoxy-1,1-dimethylethyl)amine hydrochloride (78 mg, 0.759 mmol, ChemBridge Corp., San Diego, Calif.), 2-(3-fluoro-2-methylquinoxalin-5-yl)-6,7-dihydro-1H-pyrrolo[3,2-c]pyridin-4(5H)-one (Example 126; 75 mg, 0.253 mmol), and DMSO (2.2 mL) and stirring at 100° C. for 3 h. Purification by reverse phase HPLC (Phenomenex Gemini column, 10 micron, C$_{18}$, 100 Å, 150×30 mm, 0.1% TFA in ACN/H$_2$O, gradient 5% to 80%) provided 2-(3-((2-methoxy-1,1-dimethylethyl)amino)-2-methyl-5-quinoxalinyl)-1,5,6,7-tetrahydro-4H-pyrrolo[3,2-c]pyridin-4-one (27 mg, 28.1%). $^1$H NMR (DMSO-d$_6$) δ: 11.83-11.94 (m, 1H), 7.77-7.83 (m, 1H), 7.56-7.62 (m, 1H), 7.31-7.39 (m, 1H), 6.90-6.98 (m, 1H), 5.87-5.92 (m, 1H), 3.62-3.68 (m, 2H), 3.40-3.46 (m, 1H), 3.16-3.20 (m, 2H), 2.81-2.88 (m, 2H), 2.66-2.69 (m, 2H), 2.31-2.36 (m, 3H), 1.50-1.56 (m, 6H). m/z (ESI, +ve) 380.1 (M+H)$^+$.

Example 64

2-(3-(((3R)-1-acetyl-3-pyrrolidinyl)amino)-2-methyl-5-quinoxalinyl)-1,5,6,7-tetrahydro-4H-pyrrolo[3,2-c]pyridin-4-one

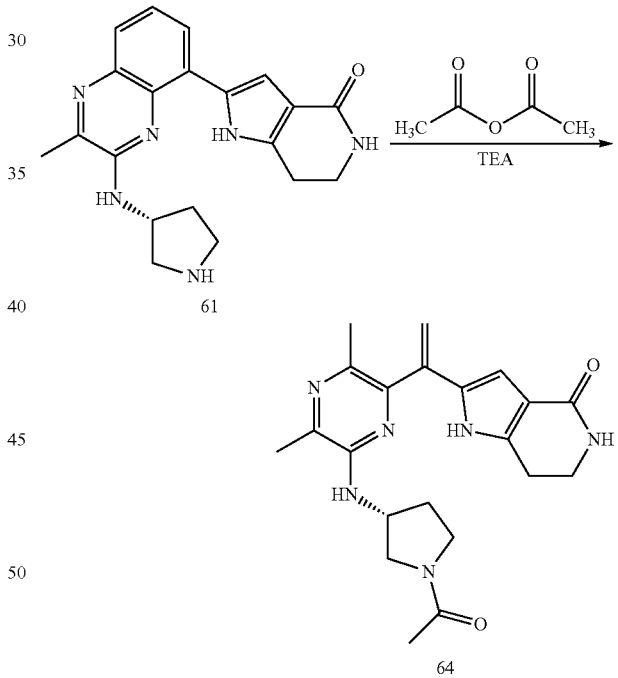

Prepared according to Example 50, using (R)-2-(2-methyl-3-(pyrrolidin-3-ylamino)quinoxalin-5-yl)-6,7-dihydro-1H-pyrrolo[3,2-c]pyridin-4(5H)-one (Ex. 61, 135 mg, 0.372 mmol), Et$_3$N (57.0 μl, 0.410 mmol), and Ac$_2$O (70.3 μl, 0.745 mmol) in DCM (3.7 mL). Purification by trituration with Et$_2$O provided 2-(3-(((3R)-1-acetyl-3-pyrrolidinyl)amino)-2-methyl-5-quinoxalinyl)-1,5,6,7-tetrahydro-4H-pyrrolo[3,2-c]pyridin-4-one (72 mg, 47.8%). $^1$H NMR (DMSO-d$_6$) δ: 7.84-7.91 (m, 1H), 7.57-7.62 (m, 1H), 7.32-7.40 (m, 1H), 7.12-7.21 (m, 2H), 6.91-6.98 (m, 1H), 4.61-4.75 (m, 1H), 3.45-3.98 (m, 3H), 3.38-3.45 (m, 2H), 2.82-2.90 (m, 2H), 2.57 (s, 3H), 2.04-2.44 (m, 2H), 1.98 (s, 3H), 1.12-1.21 (m, 2H). m/z (ESI, +ve) 405.1 (M−H)⁺.

Example 65

(S)-2-(3-((1-acetylpyrrolidin-3-yl)amino)-2-methylquinoxalin-5-yl)-6,7-dihydro-1H-pyrrolo[3,2-c]pyridin-4(5H)-one

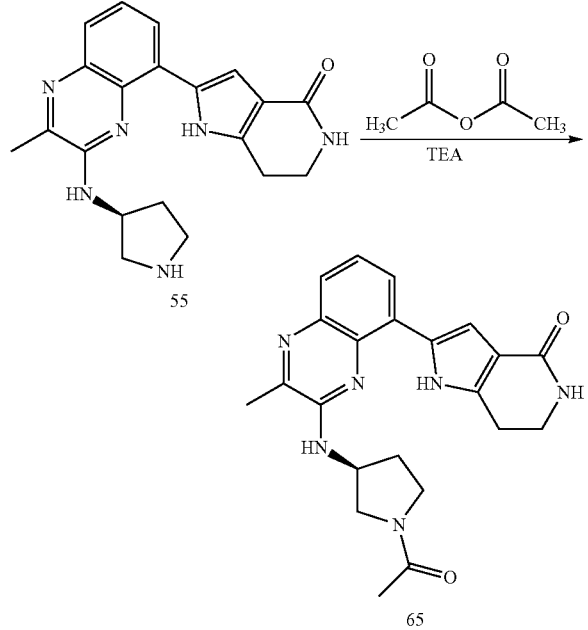

Prepared according to Example 50, using TEA (57.6 µl, 0.414 mmol), (S)-2-(2-methyl-3-(pyrrolidin-3-ylamino)quinoxalin-5-yl)-6,7-dihydro-1H-pyrrolo[3,2-c]pyridin-4(5H)-one (Ex. 55, 125 mg, 0.345 mmol), Ac₂O (65.1 µl, 0.690 mmol), and DCM (3.5 mL) stirring at 25° C. for 1.5 h. Purification by trituration with Et₂O and elution through a Si-carbonate cartridge (Silicycle) provided (S)-2-(3-((1-acetylpyrrolidin-3-yl)amino)-2-methylquinoxalin-5-yl)-6,7-dihydro-1H-pyrrolo[3,2-c]pyridin-4(5H)-one (23 mg, 16.5%). $^1$H NMR (DMSO-$d_6$) δ: 7.84-7.90 (m, 1H), 7.53-7.59 (m, 1H), 7.32-7.40 (m, 1H), 7.13-7.21 (m, 2H), 6.89-6.97 (m, 1H), 4.61-4.75 (m, 1H), 3.45-3.98 (m, 3H), 3.38-3.45 (m, 1H), 2.82-2.90 (m, 2H), 2.57 (s, 3H), 2.04-2.44 (m, 2H), 1.98 (s, 3H), 1.12-1.21 (m, 2H). m/z (ESI, +ve) 405.1 (M+H)⁺.

Example 66

2-(3-((2-methoxy-1,1-dimethylethyl)amino)-2-methyl-5-quinoxalinyl)-1,5,6,7-tetrahydro-4H-pyrrolo[3,2-c]pyridin-4-one

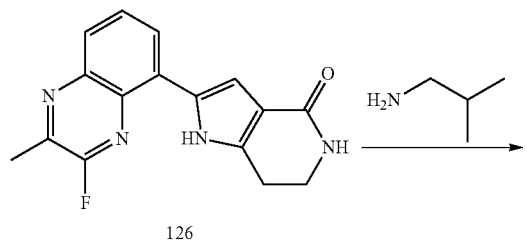

-continued

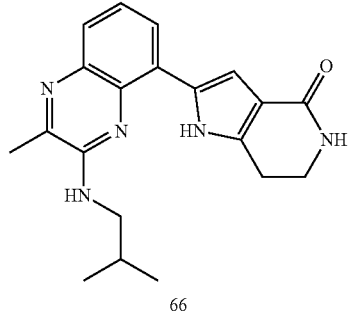

Prepared according to Example 127, using 2-(3-fluoro-2-methylquinoxalin-5-yl)-6,7-dihydro-1H-pyrrolo[3,2-c]pyridin-4(5H)-one (Example 126; 40 mg, 0.135 mmol), 2-methylpropan-1-amine (29.6 mg, 0.405 mmol, Sigma Aldrich), and DMSO (1.4 mL) and stirring at 80° C. for 2 h. Purification by high throughput parallel purification (Rilas Technologies, Woburn, Mass.) provided 2-(3-((2-methoxy-1,1-dimethylethyl)amino)-2-methyl-5-quinoxalinyl)-1,5,6,7-tetrahydro-4H-pyrrolo[3,2-c]pyridin-4-one. $^1$H NMR (DMSO-$d_6$) δ: 12.00 (s, 1H), 7.84-7.88 (m, 1H), 7.51-7.57 (m, 1H), 7.26-7.37 (m, 2H), 7.15 (s, 1H), 6.92 (s, 1H), 3.40-3.47 (m, 2H), 2.84-2.91 (m, 2H), 2.54 (s, 3H), 2.08-2.20 (m, 1H), 0.96-1.01 (m, 6H). m/z (ESI, +ve) 380.1 (M+H)⁺.

Example 67

2-(2-methyl-3-((1-methylcyclopentyl)amino)-5-quinoxalinyl)-1,5,6,7-tetrahydro-4H-pyrrolo[3,2-c]pyridin-4-one

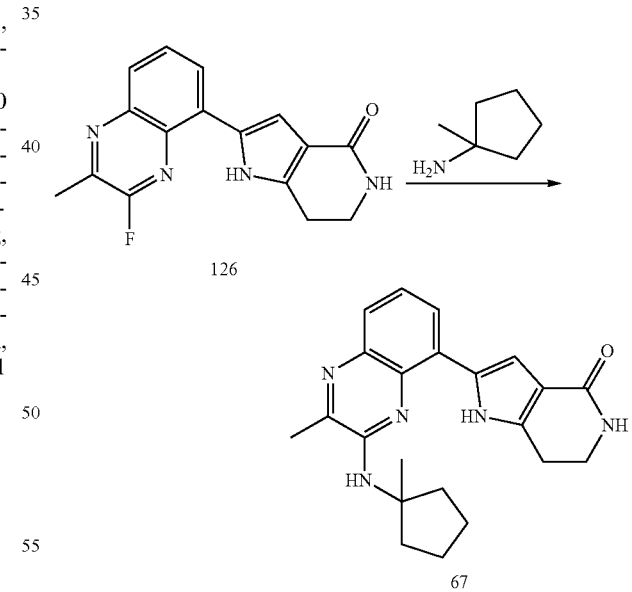

Prepared according to Example 127, using DIPEA (141 µl, 0.803 mmol), 2-(3-fluoro-2-methylquinoxalin-5-yl)-6,7-dihydro-1H-pyrrolo[3,2-c]pyridin-4(5H)-one (Example 126; 40 mg, 0.135 mmol), 1-methylcyclopentanamine (40.2 mg, 0.405 mmol, Sigma Aldrich), and DMSO (1.4 mL) and stirring at 80° C. for 2 h. Purification by high throughput parallel purification (Rilas Technologies, Woburn, Mass.) provided 2-(2-methyl-3-(1-methylcyclopentyl)amino)-5-quinoxalinyl)-1,5,6,7-tetrahydro-4H-pyrrolo[3,2-c]pyridin-4-one. $^1$H NMR (DMSO-d$_6$) δ: 12.21 (s, 1H), 7.83-7.91 (m, 1H), 7.53-7.61 (m, 1H), 7.30-7.39 (m, 1H), 7.07 (s, 1H), 6.95 (s, 1H), 6.18 (s, 1H), 3.40-3.48 (m, 2H), 2.85-2.94 (m, 2H), 2.55 (s, 3H), 2.37-2.48 (m, 2H), 1.67-1.85 (m, 6H), 1.64 (s, 3H). m/z (ESI, +ve) 376.1 (M+H)$^+$.

Example 68

2-(2-methyl-3-(methyl(1-methylethyl)amino)-5-quinoxalinyl)-1,5,6,7-tetrahydro-4H-pyrrolo[3,2-c]pyridin-4-one

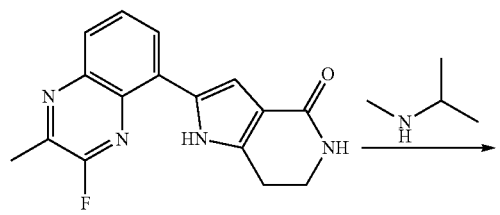

Prepared according to Example 127, using 2-(3-fluoro-2-methylquinoxalin-5-yl)-6,7-dihydro-1H-pyrrolo[3,2-c]pyridin-4(5H)-one (Example 126; 40 mg, 0.135 mmol), N-methylpropan-2-amine (29.6 mg, 0.405 mmol, Sigma Aldrich), and DMSO (1.4 mL) and stirring at 80° C. for 2 h. Purification by high throughput parallel purification (Rilas Technologies, Woburn, Mass.) provided 2-(2-methyl-3-(methyl(1-methylethyl)amino)-5-quinoxalinyl)-1,5,6,7-tetrahydro-4H-pyrrolo[3,2-c]pyridin-4-one. $^1$H NMR (DMSO-d$_6$) δ: 11.87 (br. s, 1H), 7.86-7.93 (m, 1H), 7.59-7.68 (m, 1H), 7.39-7.50 (m, 1H), 7.17 (s, 1H), 6.95 (br. s, 1H), 4.16-4.28 (m, 1H), 3.38-3.46 (m, 2H), 2.82-2.89 (m, 2H), 2.66 (s, 3H), 2.55 (s, 3H), 1.22-1.28 (m, 6H). m/z (ESI, +ve) 350.1 (M+H)$^+$.

Example 69

2-(3-(ethylamino)-2-methyl-5-quinoxalinyl)-1,5,6,7-tetrahydro-4H-pyrrolo[3,2-c]pyridin-4-one

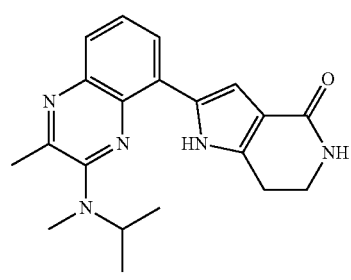

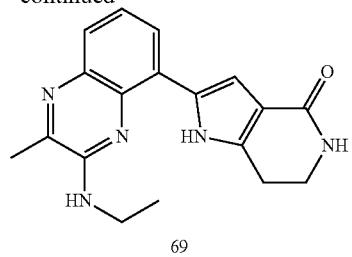

Prepared according to Example 127, using 2-(3-fluoro-2-methylquinoxalin-5-yl)-6,7-dihydro-1H-pyrrolo[3,2-c]pyridin-4(5H)-one (Example 126; 40 mg, 0.135 mmol), 70% v/v ethanamine in water (26.1 mg, 0.405 mmol, Sigma Aldrich), and DMSO (1.4 mL) and stirring at 80° C. for 2 h. Purification by high throughput parallel purification (Rilas Technologies, Woburn, Mass.) provided 2-(3-(ethylamino)-2-methyl-5-quinoxalinyl)-1,5,6,7-tetrahydro-4H-pyrrolo[3,2-c]pyridin-4-one. $^1$H NMR (DMSO-d$_6$) δ: 12.23 (br. s, 1H), 7.84-7.89 (m, 1H), 7.50-7.56 (m, 1H), 7.26-7.33 (m, 2H), 7.06-7.11 (m, 1H), 6.93 (br. s, 1H), 3.48-3.58 (m, 2H), 3.38-3.45 (m, 2H), 2.82-2.89 (m, 2H), 2.50 (s, 3H), 1.30 (t, J=1.0 Hz, 3H). m/z (ESI, +ve) 322.1 (M+H)$^+$.

Example 70

2-(3-((2-amino-2-methylpropyl)amino)-2-methyl-5-quinoxalinyl)-1,5,6,7-tetrahydro-4H-pyrrolo[3,2-c]pyridin-4-one

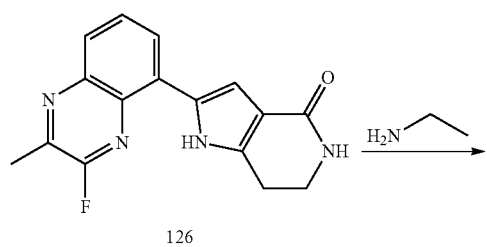

Prepared according to Example 127, using 2-(3-fluoro-2-methylquinoxalin-5-yl)-6,7-dihydro-1H-pyrrolo[3,2-c]pyridin-4(5H)-one (Example 126; 40 mg, 0.135 mmol), 2-methylpropane-1,2-diamine (35.7 mg, 0.405 mmol, Sigma Aldrich), and DMSO (1.4 mL) and stirring at 80° C. for 2 h. Purification by high throughput parallel purification (Rilas Technologies, Woburn, Mass.) provided 2-(34(2-amino-2-methylpropyl)amino)-2-methyl-5-quinoxalinyl)-1,5,6,7-tetrahydro-4H-pyrrolo[3,2-c]pyridin-4-one. $^1$H NMR (DMSO-d$_6$) δ: 12.79-12.88 (m, 1H), 7.82-7.88 (m, 1H), 7.52-7.57 (m, 1H), 7.25-7.32 (m, 1H), 7.11-7.23 (m, 1H), 6.96-7.01 (m, 1H), 6.89-6.95 (m, 1H), 4.31-4.37 (m, 1H), 3.44-3.48 (m, 5H), 2.91-2.97 (m, 2H), 2.54-2.60 (m, 3H), 1.20 (s, 6H). m/z (ESI, +ve) 365.1 (M+H)+.

Example 71

2-(2-methyl-3-((±)-tetrahydro-3-furanylamino)-5-quinoxalinyl)-1,5,6,7-tetrahydro-4H-pyrrolo[3,2-c]pyridin-4-one

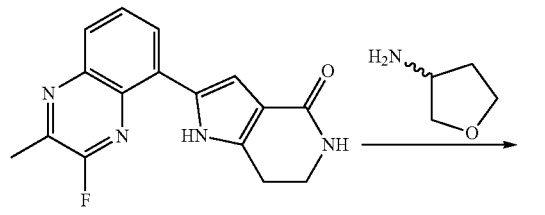

Prepared according to Example 127, using DIPEA (141 µl, 0.803 mmol) 2-(3-fluoro-2-methylquinoxalin-5-yl)-6,7-dihydro-1H-pyrrolo[3,2-c]pyridin-4(5H)-one (Example 126; 40 mg, 0.135 mmol), tetrahydrofuran-3-amine (35.3 mg, 0.405 mmol, Sigma Aldrich), and DMSO (1.4 mL) and stirring at 80° C. for 2 h. Purification by high throughput parallel purification (Rilas Technologies, Woburn, Mass.) by provided 2-(2-methyl-3-((±)-tetrahydro-3-furanylamino)-5-quinoxalinyl)-1,5,6,7-tetrahydro-4H-pyrrolo[3,2-c]pyridin-4-one. $^1$H NMR (DMSO-$d_6$) δ: 11.99 (br. s, 1H), 7.83-7.92 (m, 1H), 7.55-7.61 (m, 1H), 7.31-7.38 (m, 1H), 7.08-7.15 (m, 2H), 6.95 (br. s, 1H), 4.60-4.70 (m, 1H), 4.32-4.38 (m, 2H), 3.99-4.07 (m, 2H), 3.81-3.97 (m, 3H), 2.82-2.92 (m, 1H), 2.54-2.59 (m, 3H), 2.27-2.38 (m, 2H). m/z (ESI, +ve) 364.1 (M+H)+.

Example 72

2-(3-((3-hydroxycyclobutyl)amino)-2-methyl-5-quinoxalinyl)-1,5,6,7-tetrahydro-4H-pyrrolo[3,2-c]pyridin-4-one (mixture of cis- and trans-isomers)

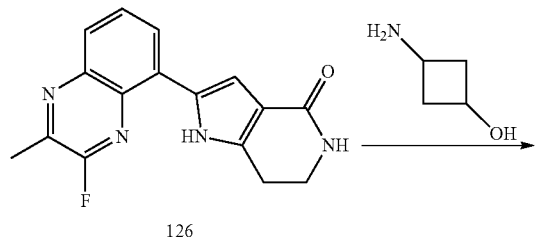

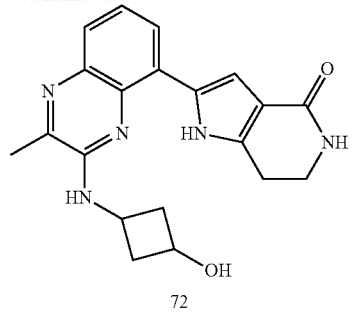

Prepared according to Example 127, using DIPEA (141 µl, 0.803 mmol), 2-(3-fluoro-2-methylquinoxalin-5-yl)-6,7-dihydro-1H-pyrrolo[3,2-c]pyridin-4 (5H)-one (Example 126; 40 mg, 0.135 mmol), 3-aminocyclobutanol (35.3 mg, 0.405 mmol, Sigma Aldrich; mixture of cis- and trans-isomers), and DMSO (1.4 mL) stirring at 80° C. for 2 h. Purification by high throughput parallel purification (Rilas Technologies, Woburn, Mass.) provided 2-(3-((3-hydroxycyclobutyl)amino)-2-methyl-5-quinoxalinyl)-1,5,6,7-tetrahydro-4H-pyrrolo[3,2-c]pyridin-4-one (mixture of cis- and trans-isomers): $^1$H NMR (DMSO-$d_6$) δ: 12.31-12.44 (m, 1H), 7.86-7.95 (m, 1H), 7.51-7.61 (m, 1H), 7.26-7.40 (m, 2H), 7.04-7.11 (m, 1H), 6.91-7.02 (m, 1H), 5.12-5.26 (m, 1H), 4.37-4.53 (m, 1H), 3.86-4.07 (m, 1H), 3.41-3.48 (m, 1H), 2.88-3.01 (m, 2H), 2.75-2.85 (m, 1H), 2.55-2.59 (m, 4H), 2.26-2.48 (m, 2H), 1.94-2.09 (m, 1H). m/z (ESI, +ve) 364.1 (M+H)+.

Example 73

2-(3-4(±)-1,2-dimethylpropyl)amino)-2-methyl-5-quinoxalinyl)-1,5,6,7-tetrahydro-4H-pyrrolo[3,2-c]pyridin-4-one

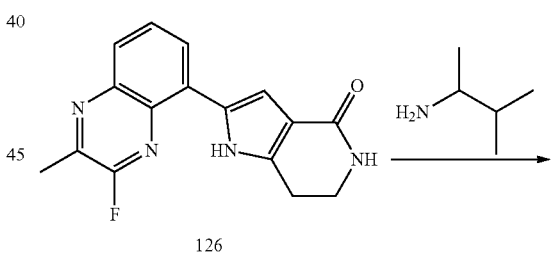

Prepared according to Example 127, using 2-(3-fluoro-2-methylquinoxalin-5-yl)-6,7-dihydro-1H-pyrrolo[3,2-c]pyridin-4(5H)-one (Example 126; 40 mg, 0.135 mmol), rac-3-methylbutan-2-amine (35.3 mg, 0.405 mmol, Sigma Aldrich), and DMSO (1.4 mL) stirring at 80° C. for 2 h.

Purification by high throughput parallel purification (Rilas Technologies, Woburn, Mass.) provided 2-(3-(((±)-1,2-dimethylpropyl)amino)-2-methyl-5-quinoxalinyl)-1,5,6,7-tetrahydro-4H-pyrrolo[3,2-c]pyridin-4-one. $^1$H NMR (DMSO-d$_6$) δ: 11.95-12.11 (m, 1H), 7.81-7.91 (m, 1H), 7.49-7.67 (m, 1H), 7.26-7.37 (m, 1H), 7.08-7.21 (m, 1H), 6.86-7.02 (m, 1H), 6.65-6.84 (m, 1H), 4.01-4.20 (m, 1H), 3.38-3.50 (m, 2H), 2.84-2.96 (m, 2H), 2.58 (s, 3H), 1.98-2.13 (m, 1H), 1.21-1.34 (m, 3H), 0.93-1.12 (m, 6H). m/z (ESI, +ve) 364.1 (M+H)$^+$.

Example 74

2-(3-(((±)-1,1-dioxidotetrahydro-3-thiophenyl)amino)-2-methyl-5-quinoxalinyl)-1,5,6,7-tetrahydro-4H-pyrrolo[3,2-c]pyridin-4-one

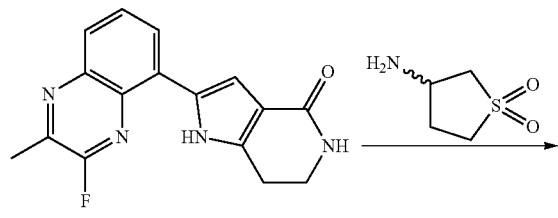

126

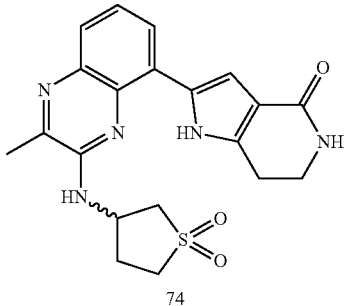

74

Prepared according to Example 127, using DIPEA (141 µl, 0.803 mmol), 2-(3-fluoro-2-methylquinoxalin-5-yl)-6,7-dihydro-1H-pyrrolo[3,2-c]pyridin-4(5H)-one (Example 126; 40 mg, 0.135 mmol), (±) 3-amino-tetrahydrothiophene 1,1-dioxide (54.7 mg, 0.405 mmol, Sigma Aldrich), and DMSO (1.4 mL) and stirring at 80° C. for 2 h. Purification by high throughput parallel purification (Rilas Technologies, Woburn, Mass.) provided 2-(3-(((±)-1,1-dioxidotetrahydro-3-thiophenyl)amino)-2-methyl-5-quinoxalinyl)-1,5,6,7-tetrahydro-4H-pyrrolo[3,2-c]pyridin-4-one. $^1$H NMR (DMSO-d$_6$) δ: 11.52-11.67 (m, 1H), 7.80-7.88 (m, 1H), 7.59-7.69 (m, 1H), 7.34-7.41 (m, 1H), 7.25-7.33 (m, 1H), 6.98-7.07 (m, 1H), 6.85-6.98 (m, 1H), 4.91-5.02 (m, 1H), 3.61-3.72 (m, 2H), 3.39-3.49 (m, 3H), 3.21-3.28 (m, 1H), 2.87-2.97 (m, 2H), 2.65-2.74 (m, 1H), 2.55-2.60 (m, 3H), 2.25-2.40 (m, 1H). m/z (ESI, +ve) 412.1 (M+H)$^+$.

Example 75

2-(2-methyl-3-((3R)-3-piperidinylamino)-5-quinoxalinyl)-1,5,6,7-tetrahydro-4H-pyrrolo[3,2-c]pyridin-4-one

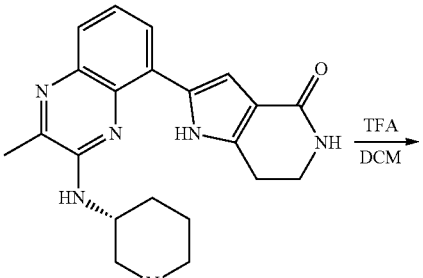

52

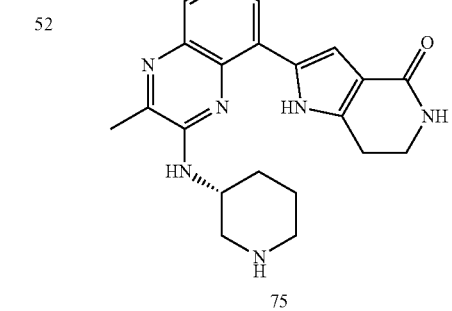

75

Prepared according to Example 53, using tert-butyl (3R)-3-((3-methyl-8-(4-oxo-4,5,6,7-tetrahydro-1H-pyrrolo[3,2-c]pyridin-2-yl)-2-quinoxalinyl)amino)-1-piperidinecarboxylate (Ex. 52) and (2.5:1) DCM:TFA. Purification by reverse-phase preparative HPLC (Phenomenex Gemini column, 10 micron, C$_{18}$, 100 Å, 150×30 mm, 0.1% TFA in ACN/H$_2$O, gradient 5% to 80%) provided 2-(2-methyl-3-((3R)-3-piperidinylamino)-5-quinoxalinyl)-1,5,6,7-tetrahydro-4H-pyrrolo[3,2-c]pyridin-4-one (115 mg, 48%) as the free base after washing with saturated aq. NaHCO$_3$, extracting with 10% MeOH/DCM, drying over Na$_2$SO$_4$, and concentrating under reduced pressure. $^1$H NMR (DMSO-d$_6$) δ: 7.90-7.95 (m, 1H), 7.62-7.70 (m, 1H), 7.30-7.42 (m, 1H), 7.09 (s, 1H), 5.83 (s, 1H), 4.06 (br. s., 1H), 3.61-3.69 (m, 2H), 3.21-3.31 (m, 1H), 2.89-3.09 (m, 5H), 2.66 (s, 3H), 2.15-2.33 (m, 2H), 2.10 (m, 2H), 1.77-1.89 (m, 2H), 1.55-1.70 (m, 1H). m/z (ESI, +ve) 377.2 (M+H)$^+$.

Example 76

2-(2-methyl-3-((3S)-3-piperidinylamino)-5-quinoxalinyl)-1,5,6,7-tetrahydro-4H-pyrrolo[3,2-c]pyridin-4-one

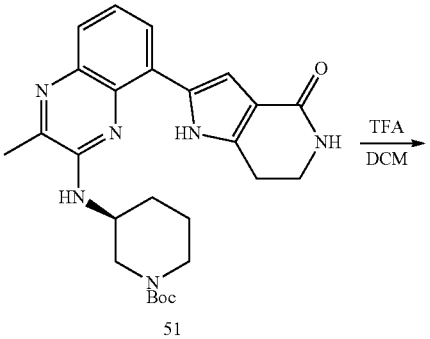

51

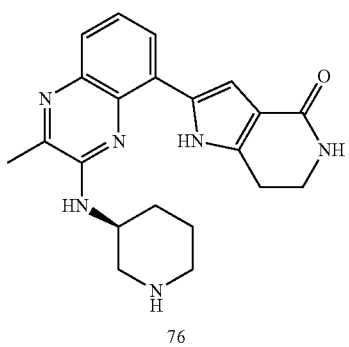

76

Prepared according to Example 53, using tert-butyl (3S)-3-((3-methyl-8-(4-oxo-4,5,6,7-tetrahydro-1H-pyrrolo[3,2-c]pyridin-2-yl)-2-quinoxalinyl)amino)-1-piperidinecarboxylate (Ex. 51) and (2.5:1) DCM:TFA. Purification by reverse-phase preparative HPLC (Phenomenex Gemini column, 10 micron, $C_{18}$, 100 Å, 150×30 mm, 0.1% TFA in ACN/$H_2O$, gradient 5% to 80%) and free-base generation by elution of a solution of the product in MeOH through a pre-washed column of Si-carbonate (SiliaPrep, Silicyle) provided 2-(2-methyl-3-((3S)-3-piperidinylamino)-5-quinoxalinyl)-1,5,6,7-tetrahydro-4H-pyrrolo[3,2-c]pyridin-4-one (105 mg, 44%). $^1$H NMR (CDCl$_3$) δ: 7.87-7.95 (m, 1H), 7.59-7.67 (m, 1H), 7.31-7.42 (m, 1H), 7.09 (s, 1H), 5.29 (s, 1H), 4.06 (br. s., 1H), 3.59-3.66 (m, 2H), 3.20-3.28 (m, 1H), 2.84-3.06 (m, 5H), 2.59 (s, 3H), 2.15-2.33 (m, 2H), 2.03 (m, 2H), 1.73-1.85 (m, 1H), 1.51-1.69 (m, 1H). m/z (ESI, +ve) 377.2 (M+H)$^+$.

Example 77

2'-(3-(cyclopropylamino)-2-methyl-5-quinoxalinyl)-5',6'-dihydrospiro[cyclopropane-1,7'-pyrrolo[3,2-c]pyridin]-4'(1'H)-one

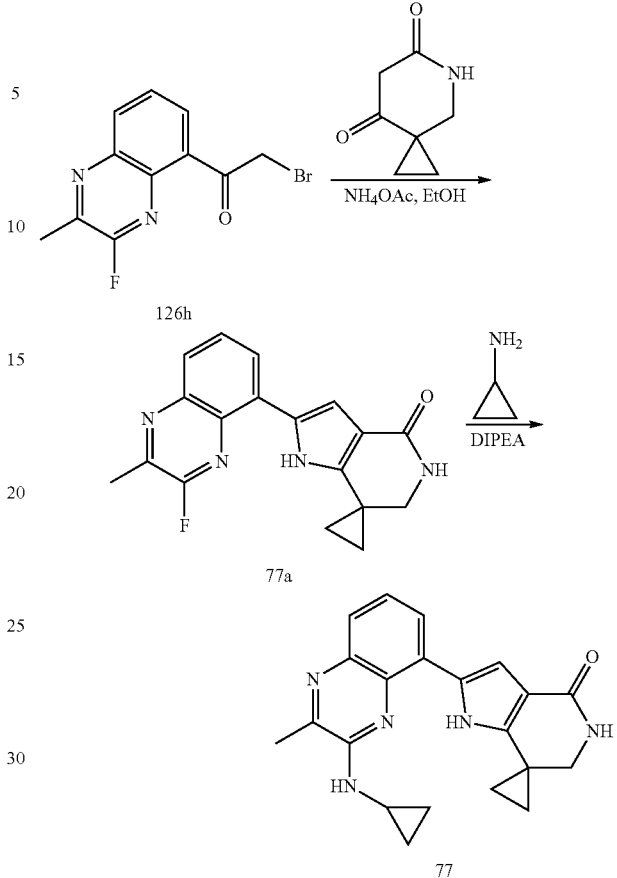

Preparation of ethyl 1-(aminomethyl)cyclopropanecarboxylate

In a 500-mL Parr shaker vessel, Raney nickel (750 mg) was added to MeOH (30 mL). Ethyl 1-cyanocyclopropanecarboxylate (Aldrich; 2.0 g, 14.38 mmol) was added and the resulting mixture was shaken vigorously under an $H_2$ atmosphere (50 psi) for 24 h. The mixture was subsequently filtered through Celite, washing the Celite pad with MeOH (2×20 mL). The combined filtrates were concentrated in vacuo to provide ethyl 1-(aminomethyl)cyclopropanecarboxylate (1.5 g, 10.48 mmol, 73% yield): $^1$H NMR (400 MHz, CDCl$_3$): δ 4.13 (q, 2H, J=7.2 Hz), 3.67 (s, 1H), 3.44 (s, 1H), 2.74 (br s, 2H), 1.27-1.21 (m, 5H), 0.80-0.74 (m, 2H). m/z (ESI, +ve) 144.4 (M+H)$^+$.

Preparation of ethyl 1-((3-ethoxy-3-oxopropanamido)methyl)-cyclopropanecarboxylate Ethyl malonyl chloride (Aldrich; 0.179 mL, 1.398 mmol) was added to a mixture of ethyl 1-(aminomethyl)cyclopropanecarboxylate (200 mg, 1.398 mmol) and Et$_3$N (0.4 mL, 1.538 mmol) in DCM (3 mL) at 0° C. The resulting mixture was warmed to RT and stirred for 4 h. The mixture was partitioned between EtOAc (5 mL) and water (5 mL). The organic layer was separated and sequentially washed with sat. aq. NaHCO$_3$ (3 mL) and 1N aqueous HCl (5 mL), dried over anhydrous Na$_2$SO$_4$, and concentrated in vacuo. Chromatographic purification of the residue (alumina, 30% EtOAc/petroleum ether) provided ethyl 1-((3-ethoxy-3-oxopropanamido)methyl)-cyclopropanecarboxylate (150 mg, 0.583 mmol, 42% yield) as a pale-yellow oil: $^1$H NMR (400 MHz, CDCl$_3$): δ 7.71 (br s, 1H), 4.23-4.11 (m, 3H), 3.70 (s, 1H), 3.45 (s, 1H), 3.44 (s, 1H), 3.30 (s, 2H) 1.30-1.21 (m, 8H), 0.99-0.94 (m, 2H). m/z (ESI, +ve) 258.5 (M+H)$^+$.

Preparation of ethyl 6,8-dioxo-5-azaspiro[2.5]octane-7-carboxylate

To a freshly prepared solution of sodium ethoxide [made from sodium (21 mg, 0.9338 mmol) and EtOH (0.5 mL)] was added a solution of ethyl 1-((3-ethoxy-3-oxopropanamido)methyl)cyclopropanecarboxylate (200 mg, 0.7782 mmol) in toluene (2 mL), and the resulting mixture was heated at reflux for 4 h. The mixture was cooled to RT, diluted with water (5 mL), and extracted with EtOAc (2×5 mL). The combined organic extracts were dried over Na$_2$SO$_4$ and concentrated in vacuo to provide ethyl 6,8-dioxo-5-azaspiro[2.5]octane-7-carboxylate (150 mg, 0.710 mmol, 91% yield): m/z (ESI, +ve) 212.3 (M+H)$^+$.

Preparation of 5-azaspiro[2.5]octane-6,8-dione

Ethyl 6,8-dioxo-5-azaspiro[2.5]octane-7-carboxylate (4.0 g, 18.95 mmol) was taken up in ACN containing 1% v/v water (40 mL) and the resulting solution was heated at 90° C. for 3 h. The mixture was cooled to RT and concentrated in vacuo. The residue was diluted with water (40 mL) and extracted with EtOAc (2×50 mL). The combined organic extracts were dried over Na$_2$SO$_4$, filtered, and concentrated in vacuo. Chromatographic purification of the residue (silica gel, 80% EtOAc/petroleum ether) furnished 5-azaspiro[2.5]octane-6,8-dione (1.2 g, 8.62 mmol, 46% yield) as a pale pink solid: $^1$H NMR (400 MHz, CDCl$_3$): δ 8.24 (br s, 1H), 3.41 (s, 2H), 3.33-3.31 (m, 2H), 1.11-1.05 (m, 2H), 0.98-0.96 (m, 2H). m/z (ESI, +ve) 140.3 (M+H)$^+$.

Preparation of 2'-(3-fluoro-2-methyl-5-quinoxalinyl)-5',6'-dihydrospiro[cyclopropane-1,7'-pyrrolo[3,2-c]pyridin]-4'(1'H)-one In a sealed tube, a mixture of 2-bromo-1-(3-fluoro-2-methylquinoxalin-5-yl)ethanone (126h; 170 mg, 0.60 mmol), 5-azaspiro[2.5]octane-6,8-dione (100 mg, 0.72 mmol) and NH$_4$OAc (0.277 g, 3.59 mmol) in EtOH (6 mL) was stirred at 40° C. for 21 h. 3/1 CHCl$_3$/IPA and saturated NaHCO$_3$ (aq.) were added. The layers were separated and the aq. layer was extracted with 3/1 CHCl$_3$/IPA (2×). The combined organic layers were dried over anhydrous Na$_2$SO$_4$, filtered, and concentrated onto silica gel. Chromatographic purification (silica gel, 0-10% MeOH in DCM) provided 2'-(3-fluoro-2-methyl-5-quinoxalinyl)-5',6'-dihydrospiro[cyclopropane-1,7'-pyrrolo[3,2-c]pyridin]-4'(1'H)-one (77a; 39 mg, 0.12 mmol, 20% yield): $^1$H NMR (400 MHz, CDCl$_3$) δ ppm 8.07 (1H, d, J=7.63 Hz), 7.87 (1H, d, J=8.22 Hz), 7.67-7.75 (1H, m), 7.23 (1H, d, J=2.35 Hz), 5.51 (1H, br. s), 3.48 (2H, d, J=2.35 Hz), 2.78 (3H, d, J=0.98 Hz), 1.17-1.23 (2H, m), 1.10-1.16 (2H, m). $^{19}$F NMR (376 MHz, CDCl$_3$) δ ppm −72.56 (1F, s). m/z (ESI, +ve) 323.1 (M+H)$^+$.

Preparation of 2'-(3-(cyclopropylamino)-2-methyl-5-quinoxalinyl)-5',6'-dihydrospiro[cyclopropane-1,7'-pyrrolo[3,2-c]pyridin]-4'(1'H)-one Prepared according to Example 131 using 2'-(3-fluoro-2-methyl-5-quinoxalinyl)-5',6'-dihydrospiro[cyclopropane-1,7'-pyrrolo[3,2-c]pyridin]-4'(1'H)-one (Ex. 77a; 39 mg, 0.12 mmol), cyclopropylamine (Alfa Aesar, Ward Hill, Mass.; 14 mg, 0.25 mmol) and DIPEA (47 mg, 0.36 mmol) and heating at 100° C. for 1 h. Purification by chromatography (silica gel, 0-100% EtOAc in hexanes followed by 0-10% MeOH in DCM) provided 2'-(3-(cyclopropylamino)-2-methyl-5-quinoxalinyl)-5',6'-dihydrospiro[cyclopropane-1,7'-pyrrolo[3,2-c]pyridin]-4'(1'H)-one (27 mg, 62% yield) as a yellow solid: $^1$H NMR (400 MHz, DMSO-d$_6$) δ ppm 11.53 (1H, br s, D$_2$O exch.), 7.95 (1H, dd, J=7.53, 1.47 Hz), 7.58 (1H, dd, J=8.02, 1.37 Hz), 7.42 (1H, dd, J=2.35, 0.59 Hz), 7.36 (1H, br s, D$_2$O exch.), 7.34 (1H, t, J=7.82 Hz), 7.02 (1H, br s, D$_2$O exch.), 3.29 (2H, d, J=2.35 Hz), 2.91 (1H, tq, J=6.75, 3.52 Hz), 2.51 (3H, s), 1.06-1.12 (2H, m), 0.97-1.02 (2H, m), 0.90-0.97 (2H, m), 0.66-0.74 (2H, m). m/z (ESI, +ve) 360.2 (M+H)$^+$.

Example 78

2-(2-(cyclopentylamino)quinolin-8-yl)-6,7-dihydro-1H-pyrrolo[3,2-c]pyridin-4(5H)-one

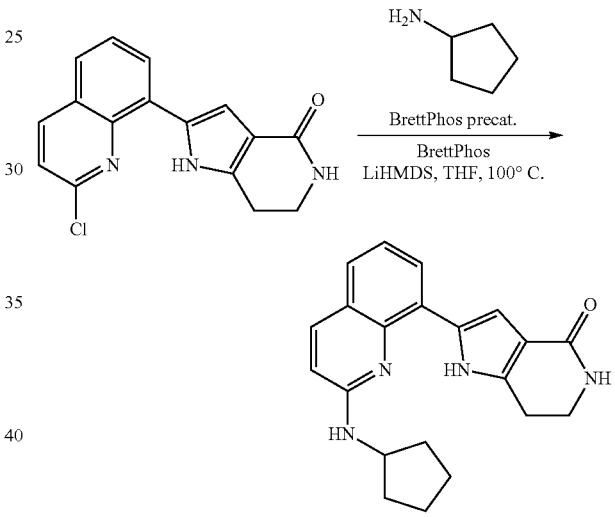

2-(2-Chloroquinolin-8-yl)-6,7-dihydro-1H-pyrrolo[3,2-c]pyridin-4(5H)-one (Example 1; 62 mg, 0.208 mmol), Brettphos (Strem Chemicals, 6.1 mg, 10.4 μmol), and BrettPhos precatalyst (Strem Chemicals, 8.8 mg, 10.4 μmol) were weighed into a 5 mL glass microwave tube, and the tube was purged with argon. The contents were treated with THF (1.5 mL), cyclopentanamine (0.025 mL, 0.250 mmol) and LHMDS 1.0 M in THF (0.458 mL, 0.458 mmol) and the tube was sealed. The mixture was heated at 100° C. for 3 h. The mixture was cooled to RT and partitioned between EtOAc and saturated aq. NH$_4$Cl. The organic layer was washed with water and brine, then concentrated in vacuo. The crude residue was dissolved in DMSO (3.5 mL) and purified by reverse phase using HPLC (Silicycle Silichrome XT C$_{18}$ column; 30×150 mm, 5 μm, 20-95% 0.1% TFA/ACN in 0.1% TFA/water by volume over 10 min), then dried in a Genevac Series II Evaporator affording 2-(2-(cyclopentylamino)quinolin-8-yl)-6,7-dihydro-1H-pyrrolo[3,2-c]pyridin-4(5H)-one 2,2,2-trifluoroacetate (31.3 mg, 0.068 mmol, 32.6% yield) as an amorphous yellow solid: $^1$H NMR (400 MHz, MeOH-d4) δ ppm 8.18-8.66 (m, 1H), 7.86 (dd, J=15.6, 7.3 Hz, 2H), 7.52-7.69 (m, 1H), 6.99-7.49 (m, 1H), 6.87 (br. s., 1H), 4.09-4.41 (m, 1H), 3.65 (t, J=7.0 Hz, 2H), 3.01 (t, J=7.0 Hz, 2H), 2.18

(dd, J=12.0, 5.8 Hz, 2H), 1.62-1.93 (m, 6H). $^{19}$F NMR (376 MHz, MeOH-d4) δ ppm −77.16 (s, 3F). m/z (ESI, +ve ion) 347.1 (M+H)$^+$.

Example 79 rac-2-(2-((1,1,1-trifluoropropan-2-yl)oxy)quinolin-8-yl)-6,7-dihydro-1H-pyrrolo[3,2-c]pyridin-4(5H)-one

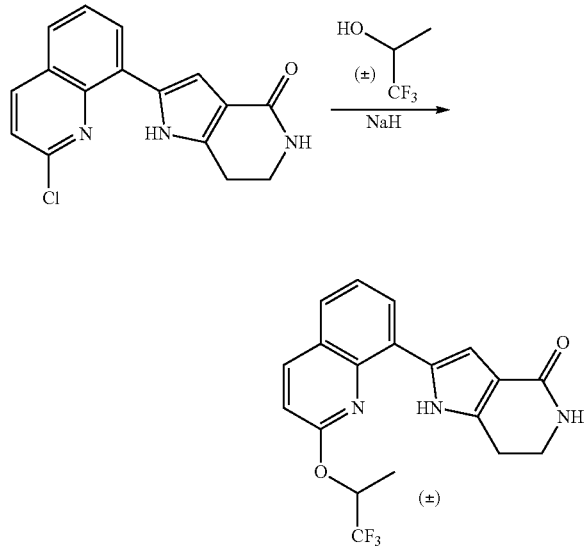

Similar to the procedure described in Example 103, rac-1,1,1,-trifluoro-2-propanol (Aldrich Chemical Company; 0.18 mL, 2.02 mmol) was added to a suspension of NaH (60% w/w in mineral oil) (81 mg, 2.02 mmol) in DMF (2.0 mL) and the resulting light-green solution was stirred at RT for 10 min. 2-(2-chloroquinolin-8-yl)-6,7-dihydro-1H-pyrrolo[3,2-c]pyridin-4(5H)-one (Example 1; 75 mg, 0.25 mmol) was then added and the resulting dark red solution was stirred at RT for 5 min, then heated at 70° C. for 2.5 h. The mixture was cooled to RT and partitioned between EtOAc (70 mL) and saturated aq. NH$_4$Cl (50 mL). The organic layer was separated, sequentially washed with water (20 mL) and brine (20 mL), and then dried over MgSO$_4$, filtered, and concentrated in vacuo. The residue was dissolved in DMSO (2.5 mL) and purified by reverse-phase using HPLC (Silicycle column, 20-95% 0.1% TFA/ACN in 0.1% TFA/water by volume over 10 min), then dried in a Genevac Series II Evaporator. The residue was chromatagraphically purified then (silica gel; 0-10% MeOH in DCM) affording rac-2-(2-((1,1,1-trifluoropropan-2-yl)oxy)quinolin-8-yl)-6,7-dihydro-1H-pyrrolo[3,2-c]pyridin-4(5H)-one (16.0 mg, 0.043 mmol, 16.9% yield) as an amorphous yellow solid: $^1$H NMR (400 MHz, DMSO-d$_6$) δ ppm 11.60 (br. s., 1H), 8.39 (d, J=8.8 Hz, 1H), 7.96 (d, J=6.8 Hz, 1H), 7.82 (d, J=7.2 Hz, 1H), 7.52 (t, J=7.7 Hz, 1H), 7.18 (d, J=8.8 Hz, 1H), 7.01 (d, J=2.2 Hz, 1H), 6.95 (br. s., 1H), 6.09 (dt, J=13.5, 6.8 Hz, 1H), 3.40-3.49 (m, 2H), 2.87 (t, J=6.7 Hz, 2H), 1.57 (d, J=6.7 Hz, 3H). $^{19}$F NMR (376 MHz, DMSO-d$_6$) δ ppm −77.03 (s, 3F). m/z (ESI, +ve ion) 376.0 (M+H)$^+$.

Example 80

2-(2-(cyclopentyloxy)quinolin-8-yl)-6,7-dihydro-1H-pyrrolo[3,2-c]pyridin-4(5H)-one

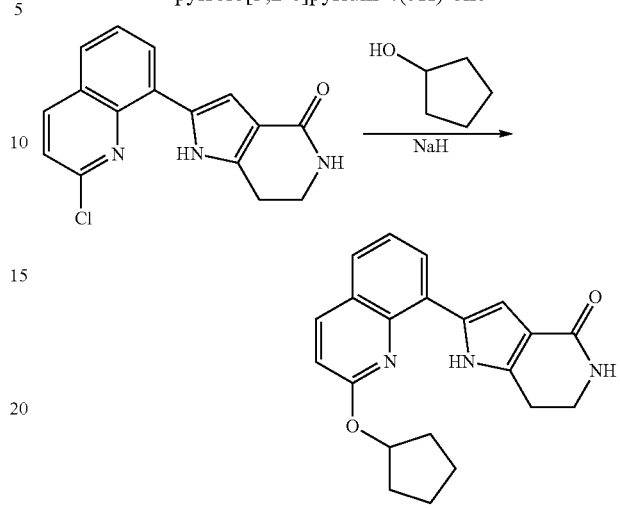

Similar to the method described in Example 103, cyclopentanol (0.18 mL, 2.02 mmol) was added to a suspension of NaH (60% w/w in mineral oil) (81 mg, 2.02 mmol) in DMF (2.0 mL) and the resulting light-yellow solution was stirred at RT for 10 min. 2-(2-Chloroquinolin-8-yl)-6,7-dihydro-1H-pyrrolo[3,2-c]pyridin-4(5H)-one (Example 1; 75 mg, 0.25 mmol) was added and the resulting dark red solution was stirred at RT for 5 min, then heated at 70° C. for 3 h. The mixture was cooled to RT and partitioned between EtOAc (70 mL) and saturated aq. NH$_4$Cl (50 mL). The organic layer was separated, sequentially washed with water (20 mL) and brine (20 mL), and then dried over MgSO$_4$, filtered, and concentrated in vacuo. The crude residue was purified by column chromatography silica gel column, 10-100% EtOAc in hexanes over 25 min. then 100% EtOAc for 10 min.) to give 2-(2-(cyclopentyloxy)quinolin-8-yl)-6,7-dihydro-1H-pyrrolo[3,2-c]pyridin-4(5H)-one (30 mg, 0.09 mmol, 33.8% yield) as an amorphous yellow solid: $^1$H NMR (400 MHz, CDCl$_3$) δ ppm 12.70 (br. s., 1H), 7.95-8.10 (m, 2H), 7.51-7.59 (m, 1H), 7.36-7.45 (m, 1H), 7.17 (d, J=2.0 Hz, 1H), 6.90 (d, J=8.8 Hz, 1H), 5.57 (br. s., 1H), 5.44 (quin, J=4.4 Hz, 1H), 3.68 (t, J=6.7 Hz, 2H), 2.98 (t, J=6.8 Hz, 2H), 2.02-2.16 (m, 4H), 1.84-1.98 (m, 2H), 1.67-1.80 (m, 2H). m/z (ESI, +ve ion) 348.0 (M+H)$^+$.

Example 81

2-(2-(piperidin-4-yloxy)quinolin-8-yl)-6,7-dihydro-1H-pyrrolo[3,2-c]pyridin-4(5H)-one

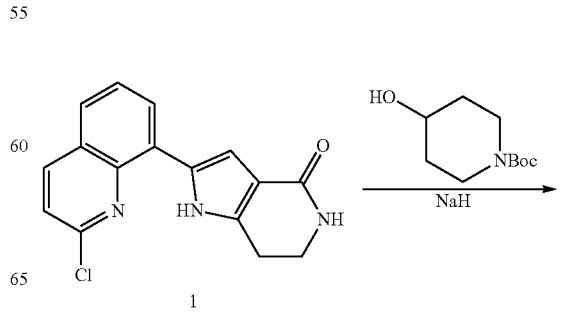

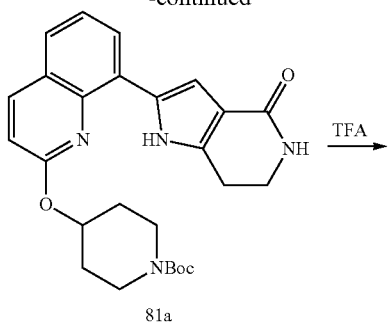

81a

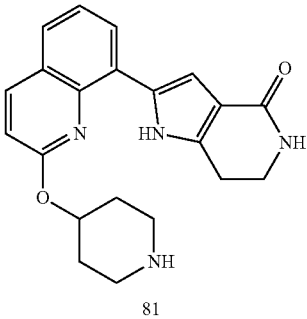

81

Preparation of tert-butyl 4-08-(4-oxo-4,5,6,7-tetrahydro-1H-pyrrolo[3,2-c]pyridin-2-yl)quinolin-2-yl)oxy)piperidine-1-carboxylate Similar to the method described in Example 103, tert-butyl 4-hydroxypiperidine-1-carboxylate (Aldrich; 357 mg, 1.77 mmol) was added to a suspension of NaH (70.9 mg, 1.77 mmol) in DMF (2.0 mL) and the resulting light yellow solution was stirred at RT for 10 min. 2-(2-Chloroquinolin-8-yl)-6,7-dihydro-1H-pyrrolo[3,2-c]pyridin-4(5H)-one (Example 1; 66 mg, 0.22 mmol) was added and the resulting dark red solution was stirred at RT for 5 min, then heated at 70° C. for 2.5 h. The mixture was cooled to RT and partitioned between EtOAc (100 mL) and saturated aq. NH$_4$Cl (50 mL). The organic layer was separated, sequentially washed with water (40 mL) and brine (40 mL), and then dried over MgSO$_4$, filtered, and concentrated in vacuo. Chromatographic purification of the residue (silica gel, 0-10% MeOH in DCM) gave tert-butyl 4-((8-(4-oxo-4,5,6,7-tetrahydro-1H-pyrrolo[3,2-c]pyridin-2-yl)quinolin-2-yl)oxy)piperidine-1-carboxylate as an orange oil. m/z (ESI, +ve ion) 463.3 (M+H)$^+$.

Preparation of 2-(2-(piperidin-4-yloxy)quinolin-8-yl)-6,7-dihydro-1H-pyrrolo[3,2-c]pyridin-4(5H)-one To a solution of tert-butyl 4-((8-(4-oxo-4,5,6,7-tetrahydro-1H-pyrrolo[3,2-c]pyridin-2-yl)quinolin-2-yl)oxy)piperidine-1-carboxylate (0.103 g, 0.22 mmol) in DCM (3.0 mL) at 0° C. was added TFA (0.5 mL, 6.73 mmol). The reaction was stirred at 0° C. for 1 h, then at RT for 40 min. The reaction mixture was then concentrated, the residue was dissolved in DCM, washed with a saturated aq. solution of NaHCO$_3$, dried over MgSO$_4$, filtered and concentrated. The residue was dissolved in DMSO (2.0 mL) and purified by rpHPLC (Silicycle Silichrome XT C$_{18}$ column; 30×150 mm, 5 µm, 5-95% 0.1% TFA/ACN in 0.1% TFA/water by volume over 10 min.), then dried in a Genevac Series II Evaporator to afford 2-(2-(piperidin-4-yloxy)quinolin-8-yl)-6,7-dihydro-1H-pyrrolo[3,2-c]pyridin-4(5H)-one 2,2,2-trifluoroacetate (48.7 mg, 0.094 mmol, 32.4% yield) as an amorphous orange solid: $^1$H NMR (400 MHz, DMSO-d$_6$) δ ppm 11.64 (br. s., 1H), 8.67 (br. s., 1H), 8.47 (br. s., 1H), 8.30 (d, J=9.0 Hz, 1H), 7.96 (d, J=7.2 Hz, 1H), 7.76 (d, J=8.2 Hz, 1H), 7.48 (t, J=7.8 Hz, 1H), 7.35 (d, J=2.0 Hz, 1H), 7.08 (d, J=8.8 Hz, 1H), 6.95 (br. s., 1H), 5.37-5.48 (m, 1H), 3.34-3.50 (m, 4H), 3.18-3.31 (m, 2H), 2.88 (t, J=6.8 Hz, 2H), 2.36 (d, J=14.3 Hz, 2H), 1.87-2.02 (m, 2H). $^{19}$F NMR (376 MHz, DMSO-d$_6$) δ ppm −74.36 (s, 3F). m/z (ESI, +ve ion) 363.0 (M+H)$^+$.

Example 82

2-(2-(((1R,4R)-4-hydroxycyclohexyl)amino)quinolin-8-yl)-6,7-dihydro-1H-pyrrolo[3,2-c]pyridin-4(5H)-one

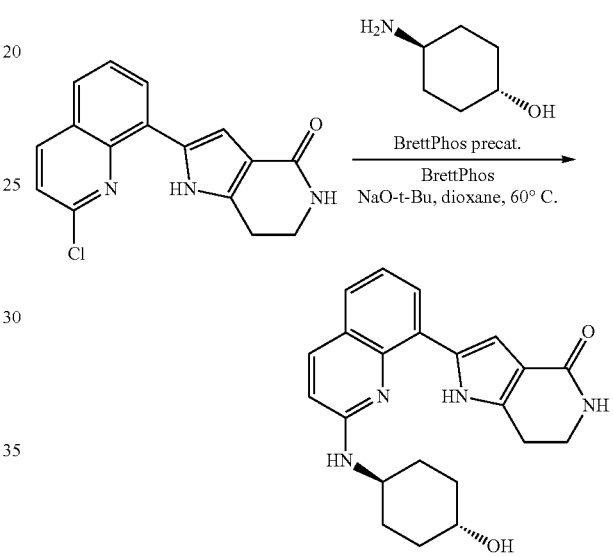

Prepared similar to the method described in Example 78, 2-(2-chloroquinolin-8-yl)-6,7-dihydro-1H-pyrrolo[3,2-c]pyridin-4(5H)-one (Example 1; 78 mg, 0.262 mmol), Brettphos (Strem Chemicals, 7.66 mg, 0.013 mmol), BrettPhos precatalyst (Strem Chemicals, 11 mg, 0.013 mmol), (1R,4R)-4-aminocyclohexanol (Alfa Aesar, Ward Hill, Mass.; 151 mg, 1.31 mmol), and sodium t-butoxide (55 mg, 0.58 mmol) were weighed into a 5 mL glass microwave tube. The tube was purged with argon, then the contents were treated with dioxane (2.5 mL). The mixture was stirred and heated at 60° C. for 2 h, then at RT for 16.5 h. The mixture was partitioned between EtOAc and water and the aq. layer was extracted with EtOAc (3×100 mL). The combined organic layers were washed with brine (50 mL), dried over MgSO$_4$, filtered and concentrated in vacuo. The residue was dissolved in DMSO (4 mL), purified by rpHPLC (Silicycle Silichrome XT C$_{18}$ column; 30×150 mm, 5 µu, 5-95% 0.1% TFA/ACN in 0.1% TFA/water by volume over 10 min.), then dried in a Genevac Personal Evaporator. Two peaks were observed in the LCMS of the combined (formerly) pure factions, corresponding to the desired product (M+1=377.0) and the trifluoromethyl ester (M+1=473.0). This material was dissolved in DCM and sequentially washed with 1N NaOH (2×), and brine, dried over MgSO$_4$, filtered and concentrated to give 2-(2-(((1R,4R)-4-hydroxycyclohexyl)amino)quinolin-8-yl)-6,7-dihydro-1H-pyrrolo[3,2-c]pyridin-4(5H)-one (68.8 mg, 0.183 mmol, 69.8% yield) as an amorphous yellow solid: $^1$H NMR (400 MHz, DMSO-$d_6$) δ ppm 12.71 (br. s., 1H), 7.82-7.98 (m, 2H), 7.46 (d, J=7.0 Hz, 1H), 7.22 (d, J=7.2 Hz, 1H), 7.16 (t, J=7.6 Hz, 1H), 6.96 (s, 2H), 6.82 (d, J=9.0 Hz, 1H), 4.61 (d, J=4.3 Hz, 1H), 3.79 (br. s., 1H), 3.43-3.49 (m, 3H), 2.92 (t, J=6.7 Hz, 2H), 2.10 (d, J=10.0 Hz, 2H), 1.86-1.97 (m, 2H), 1.27-1.44 (m, 4H). m/z (ESI, +ve ion) 377.1 (M+H)$^+$.

Example 83

2-(2-(cyclohexylamino)quinolin-8-yl)-6,7-dihydro-1H-pyrrolo[3,2-c]pyridin-4(5H)-one

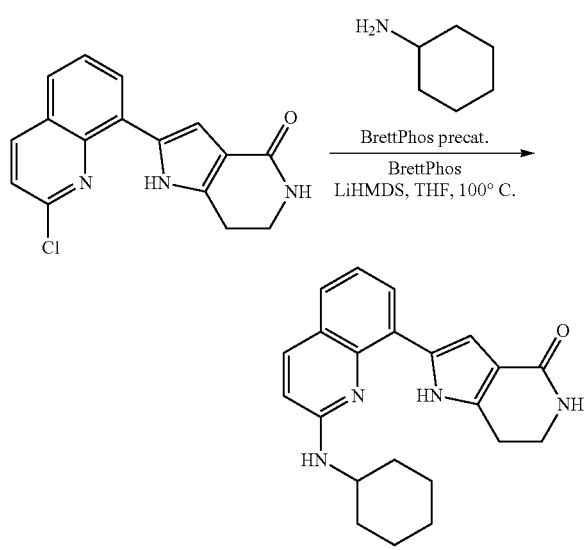

Prepared similar to the method described in Example 78, 2-(2-chloroquinolin-8-yl)-6,7-dihydro-1H-pyrrolo[3,2-c]pyridin-4(5H)-one (Example 1; 106 mg, 0.356 mmol), BrettPhos (Strem Chemicals, 10.4 mg, 0.018 mmol), and BrettPhos precatalyst (Strem Chemicals, 15 mg, 0.018 mmol) were weighed into a 5 mL glass microwave tube, and the tube was purged with argon. The contents were treated with THF (2.0 mL), cyclohexylamine (0.05 mL, 0.43 mmol) and LHMDS 1.0 M in THF (0.78 mL, 0.78 mmol) and the tube was sealed. The mixture was stirred and heated at 100° C. for 2.5 h. The mixture was then cooled to RT and partitioned between EtOAc and saturated aq. NH$_4$Cl. A layer of insoluble material formed and was removed by filtration. The organic layer was washed with water and brine, then concentrated in vacuo. The crude residue was dissolved in DMSO (2.5 mL) and purified by rpHPLC (Silicycle Silichrome XT $C_{18}$ column; 30×150 mm, 5 μm, 20-95% 0.1% TFA/ACN in 0.1% TFA/water by volume over 10 min), then dried in a Genevac Series II Evaporator to afford 2-(2-(cyclohexylamino)quinolin-8-yl)-6,7-dihydro-1H-pyrrolo[3,2-c]pyridin-4(5H)-one 2,2,2-trifluoroacetate (39.6 mg, 0.083 mmol, 23.4% yield) as a dark yellow amorphous solid: $^1$H NMR (400 MHz, MeOH-d4) δ ppm 8.24-8.61 (m, 1H), 7.76-7.97 (m, 2H), 7.53-7.66 (m, 1H), 6.99-7.47 (m, 1H), 6.85 (br. s., 1H), 3.84 (br. s., 1H), 3.65 (t, J=7.0 Hz, 2H), 3.01 (t, J=7.0 Hz, 2H), 2.02-2.18 (m, 2H), 1.80-1.93 (m, 2H), 1.72 (d, J=13.7 Hz, 1H), 1.40-1.61 (m, 4H), 1.26-1.40 (m, 1H). $^{19}$F NMR (376 MHz, MeOH-d4) δ ppm −77.36 (s, 3F). m/z (ESI, +ve ion) 361.2 (M+H)$^+$.

Example 84

2-(2-morpholinoquinolin-8-yl)-6,7-dihydro-1H-pyrrolo[3,2-c]pyridin-4(5H)-one

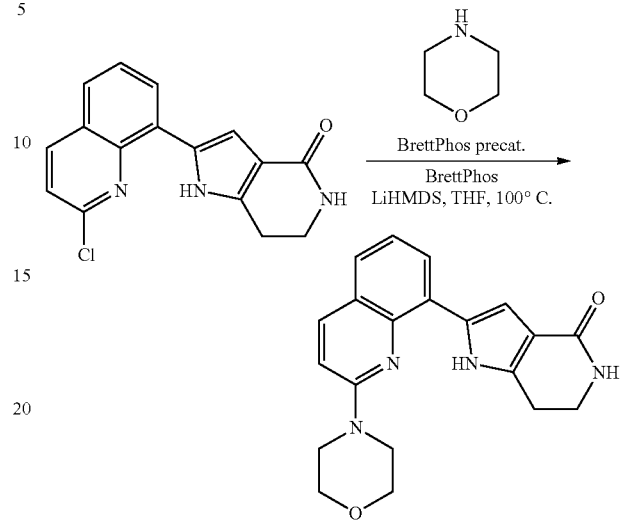

Prepared similar to the method described in Example 78, 2-(2-chloroquinolin-8-yl)-6,7-dihydro-1H-pyrrolo[3,2-c]pyridin-4(5H)-one (Example 1; 107 mg, 0.359 mmol), BrettPhos (Strem Chemicals, 10.5 mg, 0.018 mmol), and BrettPhos precatalyst (Strem Chemicals, 15 mg, 0.018 mmol) were weighed into a 5 mL glass microwave tube, and the tube was purged with argon. The contents were treated with THF (3.0 mL), morpholine (0.04 mL, 0.43 mmol) and LHMDS 1.0 M in THF (0.79 mL, 0.79 mmol) and the tube was sealed. The reaction was stirred and heated at 100° C. for 2.5 h. The mixture was cooled to RT and partitioned between EtOAc and saturated aq. NH$_4$Cl. A layer of insoluble material formed and was removed by filtration. The organic layer was washed with water and brine, then concentrated in vacuo. The crude residue was dissolved in DMSO (2.5 mL) and purified by rpHPLC (Silicycle Silichrome XT $C_{18}$ column; 30×150 mm, 5 μm, 20-95% 0.1% TFA/ACN in 0.1% TFA/water by volume over 10 min), then dried in a Genevac Series II Evaporator affording 2-(2-morpholinoquinolin-8-yl)-6,7-dihydro-1H-pyrrolo[3,2-c]pyridin-4(5H)-one 2,2,2-trifluoroacetate (16.0 mg, 0.035 mmol, 10% yield) as an orange amorphous solid: $^1$H NMR (400 MHz, DMSO-$d_6$) δ ppm 12.14 (br. s., 1H), 8.14 (d, J=9.2 Hz, 1H), 7.91 (d, J=7.2 Hz, 1H), 7.61 (d, J=7.8 Hz, 1H), 7.26-7.38 (m, 2H), 7.00 (1H, br s), 6.98 (d, J=1.8 Hz, 1H), 3.76-3.84 (m, 4H), 3.63-3.71 (m, 4H), 3.43 (t, J=6.8 Hz, 2H), 2.88 (t, J=6.8 Hz, 2H). $^{19}$F NMR (376 MHz, DMSO-$d_6$) δ ppm −75.03 (s, 3F). m/z (ESI, +ve ion) 349.1 (M+H)$^+$.

Example 85

2-(2-((Tetrahydro-2H-pyran-4-yl)amino)quinolin-8-yl)-6,7-dihydro-1H-pyrrolo[3,2-c]pyridin-4(5H)-one

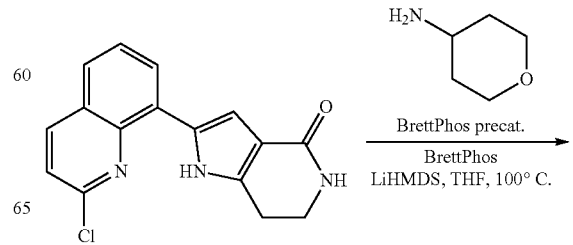

203

-continued

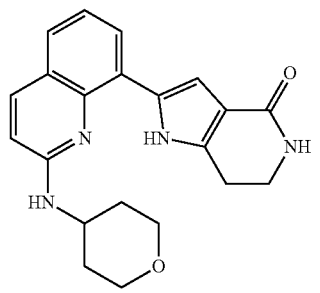

Prepared similar to the method described in Example 78, 2-(2-chloroquinolin-8-yl)-6,7-dihydro-1H-pyrrolo[3,2-c]pyridin-4(5H)-one (Example 1; 117 mg, 0.393 mmol), BrettPhos (Strem Chemicals, 11.5 mg, 0.020 mmol), BrettPhos precatalyst (Strem Chemicals, 16.6 mg, 0.020 mmol) and tetrahydro-2H-pyran-4-amine (Aldrich; 47.7 mg, 0.472 mmol) were weighed into a 5 mL glass microwave tube, and the tube was purged with argon. The contents were treated with THF (3.0 mL), and LHMDS 1.0 M in THF (0.86 mL, 0.86 mmol) and the tube was sealed. The reaction was stirred and heated at 100° C. for 2.5 h. The mixture was cooled to RT and partitioned between EtOAc and saturated aq. NH$_4$Cl. A layer of insoluble material formed and was removed by filtration. The organic layer was washed with water and brine, then concentrated in vacuo. The crude residue was dissolved in DMSO (2.5 mL) and purified by rpHPLC (Silicycle Silichrome XT C$_{18}$ column; 30×150 mm, 5 μm, 5-95% 0.1% TFA/ACN in 0.1% TFA/water by volume over 10 min), then dried in a Genevac Series II Evaporator affording 2-(2-((tetrahydro-2H-pyran-4-yl)amino)quinolin-8-yl)-6,7-dihydro-1H-pyrrolo[3,2-c]pyridin-4(5H)-one 2,2,2-trifluoroacetate (28.3 mg, 0.059 mmol, 15% yield) as an amorphous yellow solid: $^1$H NMR (400 MHz, DMSO-d$_6$) δ ppm 12.41 (br. s., 1H), 7.69-8.10 (m, 2H), 7.33-7.68 (m, 2H), 7.22 (br. s., 1H), 6.50-7.12 (m, 3H), 4.11 (br. s., 1H), 3.93 (d, J=11.5 Hz, 2H), 3.37-3.61 (m, 4H), 2.91 (t, J=6.7 Hz, 2H), 2.02 (br. s., 2H), 1.46-1.66 (m, 2H). $^{19}$F NMR (376 MHz, DMSO-d$_6$) δ ppm −74.91 (s, 3F). m/z (ESI, +ve ion) 363.0 (M+H)$^+$.

Example 86

2-(2-(2-fluoro-4-(methylsulfonyl)phenyl)quinolin-8-yl)-6,7-dihydro-1H-pyrrolo[3,2-c]pyridin-4(5H)-one

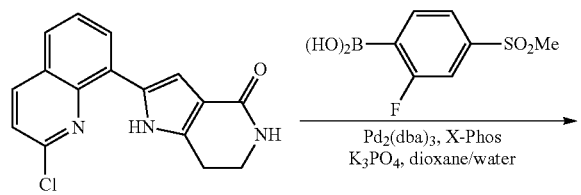

204

-continued

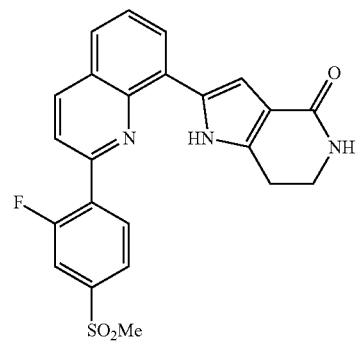

2-(2-Chloroquinolin-8-yl)-6,7-dihydro-1H-pyrrolo[3,2-c]pyridin-4(5H)-one (Example 1; 80 mg, 0.269 mmol), XPhos (7.7 mg, 0.016 mmol; Strem Chemicals), Pd$_2$(dba)$_3$ (7.4 mg, 8.06 μmol), K$_3$PO$_4$ (171 mg, 0.806 mmol) and 2-fluoro-4-(methylsulfonyl)-phenylboronic acid (Combi-Blocks Inc, San Diego, Calif.; 70.3 mg, 0.322 mmol) were weighed into a 5 mL glass microwave tube. The tube was purged with argon and the solids were treated with dioxane (2.0 mL) and water (0.20 mL). The tube was sealed, and the contents were heated an Initiator microwave reactor (Personal Chemistry, Biotage AB, Inc., Upssala, Sweden) at 130° C. for 20 min. The mixture was then treated with water and extracted with EtOAc (3×50 mL). The combined organic extractor were concentrated, then dissolved in DMSO (4 mL). rpHPLC purification of the residue (20-95% 0.1% TFA/ACN in 0.1% TFA/water, Silicycle Silichrome XT C$_{18}$ column; 30×150 mm, 5 μm) followed by drying in a Genevac Series II evaporator afforded 2-(2-(2-fluoro-4-(methylsulfonyl)phenyl)quinolin-8-yl)-6,7-dihydro-1H-pyrrolo[3,2-c]pyridin-4(5H)-one 2,2,2-trifluoroacetate (30.2 mg, 0.055 mmol, 20.5% yield) as an amorphous orange solid: $^1$H NMR (400 MHz, DMSO-d$_6$) δ ppm 12.09 (br. s., 1H), 8.59 (d, J=8.8 Hz, 1H), 8.35 (t, J=7.8 Hz, 1H), 8.13-8.19 (m, 1H), 8.02-8.08 (m, 2H), 7.99 (dd, J=8.2, 1.8 Hz, 1H), 7.88-7.93 (m, 1H), 7.69 (t, J=7.8 Hz, 1H), 7.19 (d, J=2.3 Hz, 1H), 7.00 (br. s., 1H), 3.44 (t, J=6.8 Hz, 2H), 3.38 (s, 3H), 2.91 (t, J=6.8 Hz, 2H). $^{19}$F NMR (377 MHz, DMSO-d$_6$) δ ppm −74.67 (s, 3F), −114.58 (s, 1F). m/z (ESI, +ve ion) 436.0 (M+H)$^+$.

Example 87

2-(2-(6-amino-2-fluoropyridin-3-yl)quinolin-8-yl)-6,7-dihydro-1H-pyrrolo[3,2-c]pyridin-4(5H)-one

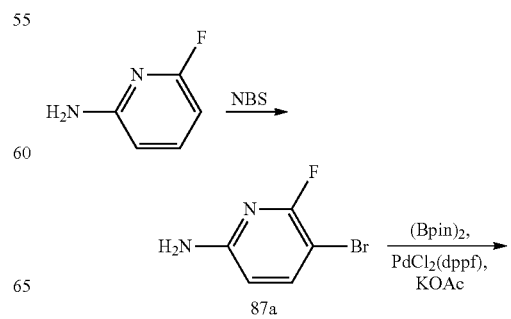

205

-continued

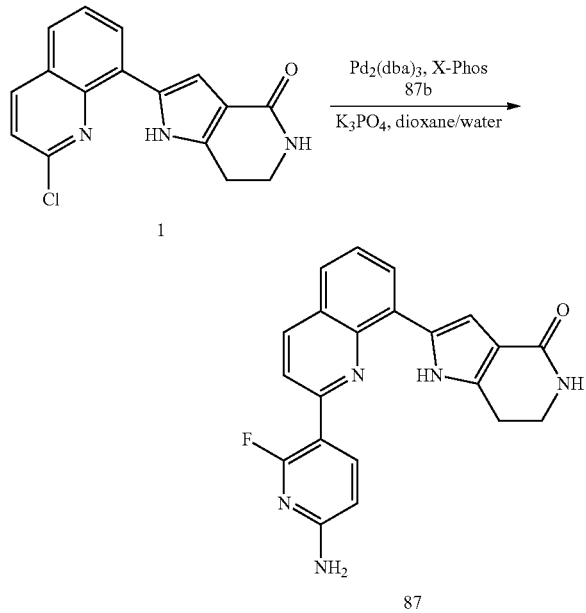

Preparation of 5-bromo-6-fluoropyridin-2-amine

A solution of 6-fluoropyridin-2-amine (Alfa Aesar, Ward Hill, Mass., 5.16 g, 46.0 mmol) in ACN (230 mL) was set stirring at 0° C. before adding NBS (8.19 g, 46.0 mmol) as a solution in ACN (100 mL) by addition funnel over 30 min. After complete addition, the resulting green solution was stirred for an additional 30 min. The reaction mixture was then concentrated under reduced pressure and the residue was dissolved in DCM (20 mL) and adsorbed onto silica. Chromatographic purification (silica gel, 0-75% EtOAc in hexanes) gave 5-bromo-6-fluoropyridin-2-amine (7.6 g, 39.8 mmol, 86% yield) as a white foam. $^1$H NMR (400 MHz, MeOH-d4) δ ppm 7.59 (1H, t, J=8.9 Hz), 6.32 (1H, dd, J=8.5, 1.5 Hz). m/z (ESI, +ve ion) 191.0 (M+H)$^+$.

Preparation of 6-fluoro-5-(4,4,5,5-tetramethyl-1,3,2-dioxaborolan-2-yl)pyridin-2-amine A mixture of KOAc (1.54 g, 15.71 mmol), (BPin)$_2$ (Sigma-Aldrich, 1.99 g, 7.85 mmol), Pd(dppf)Cl$_2$ (Strem Chemicals, 0.428 g, 0.524 mmol), and 5-bromo-6-fluoropyridin-2-amine (1.00 g, 5.24 mmol) was set stirring in dioxane (26.2 mL) at 95° C. After 18 h, the reaction was cooled to RT, and concentrated under reduced pressure. The residue was diluted with DCM (15 mL) and adsorbed onto silica before chromatographic purification (silica gel, 5-40% EtOAc in hexanes, then 15% EtOAc in DCM). Product-containing fractions were concentrated under reduced pressure to give 6-fluoro-5-(4,4,5,5-tetramethyl-1,3,2-dioxaborolan-2-yl)pyridin-2-amine as a purple solid. m/z (ESI, +ve ion) 239.1 (M+H)$^+$.

206

Preparation of 2-(2-(6-amino-2-fluoropyridin-3-yl)quinolin-8-yl)-6,7-dihydro-1H-pyrrolo[3,2-c]pyridin-4(5H)-one 2-(2-Chloroquinolin-8-yl)-6,7-dihydro-1H-pyrrolo[3,2-c]pyridin-4(5H)-one (Example 1; 83 mg, 0.28 mmol), XPhos (8.0 mg, 0.017 mmol; Strem Chemicals), Pd$_2$(dba)$_3$ (7.7 mg, 8.36 μmol), potassium phosphate (178 mg, 0.836 mmol) and 6-fluoro-5-(4,4,5,5-tetramethyl-1,3,2-dioxaborolan-2-yl)pyridin-2-amine (Example 87b; 93 mg, 0.39 mmol) were weighed into a 5 mL glass microwave tube. The tube was purged with argon and the solids were treated with dioxane (2.0 mL) and water (0.20 mL). The tube was sealed, and the contents were heated an Initiator microwave reactor (Personal Chemistry, Biotage AB, Inc., Upssala, Sweden) at 130° C. for 20 min. The mixture was treated with water (10 mL) and extracted with EtOAc (3×50 mL). The combined organic extracts were concentrated, and the residue was taken up in DMSO (6 mL) and purified by rpHPLC (20-95% 0.1% TFA/ACN in 0.1% TFA/water, Silicycle Silichrome XT C$_{18}$ column; 30×150 mm, 5 μm). Product-containing fractions were dried in a Genevac Series II evaporator, affording 2-(2-(6-amino-2-fluoropyridin-3-yl)quinolin-8-yl)-6,7-dihydro-1H-pyrrolo[3,2-c]pyridin-4(5H)-one 2,2,2-trifluoroacetate (1.2 mg, 2.46 μmol, 0.88% yield) as an amorphous orange solid: $^1$H NMR (400 MHz, CDCl$_3$) δ ppm 13.33 (br. s., 1H), 8.26 (d, J=8.6 Hz, 1H), 8.22 (br. s., 1H), 8.04-8.17 (m, 2H), 7.78 (d, J=8.4 Hz, 1H), 7.68 (d, J=7.4 Hz, 1H), 7.56 (t, J=7.8 Hz, 1H), 7.18 (s, 1H), 6.56 (dd, J=8.2, 1.8 Hz, 1H), 3.73 (t, J=6.7 Hz, 2H), 3.09 (t, J=7.2 Hz, 2H). $^{19}$F NMR (376 MHz, CD Cl$_3$) δ ppm −71.34 (s, 1F), −76.17 (s, 3F). m/z (ESI, +ve ion) 374.0 (M+H)$^+$.

Example 88

2-(2-(5-chloro-2-methoxyphenyl)quinolin-8-yl)-6,7-dihydro-1H-pyrrolo[3,2-c]pyridin-4(5H)-one

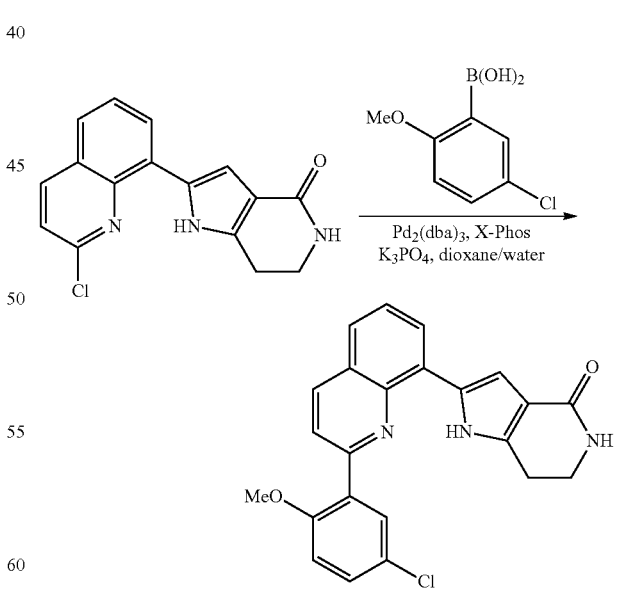

2-(2-Chloroquinolin-8-yl)-6,7-dihydro-1H-pyrrolo[3,2-c]pyridin-4(5H)-one (Example 1; 83 mg, 0.279 mmol), XPhos (Strem Chemicals, 8.0 mg, 0.017 mmol), Pd$_2$(dba)$_3$ (7.7 mg, 8.36 μmol), potassium phosphate (178 mg, 0.836 mmol) and (5-chloro-2-methoxyphenyl)boronic acid (Frontier Scientific, Newark, Del.; 62 mg, 0.34 mmol) were weighed into a 5 mL glass microwave tube. The tube was purged with argon and the solids were treated with dioxane (2.0 mL) and water (0.20 mL). The tube was sealed, and the contents were heated an Initiator microwave reactor (Personal Chemistry, Biotage AB, Inc., Upssala, Sweden) at 110° C. for 15 min. The mixture was treated with water (10 mL) and extracted with EtOAc (3×50 mL). The combined organic extracts were concentrated, then dissolved in DMSO (6 mL). Purification by rpHPLC (20-95% 0.1% TFA/ACN in 0.1% TFA/water, Silicycle Silichrome XT $C_{18}$ column; 30×150 mm, 5 μm) followed by drying in a Genevac Series II evaporator afforded 2-(2-(5-chloro-2-methoxyphenyl)quinolin-8-yl)-6,7-dihydro-1H-pyrrolo[3,2-c]pyridin-4(5H)-one 2,2,2-trifluoroacetate (11.1 mg, 0.021 mmol, 7.7% yield) as an amorphous tan solid: $^1$H NMR (400 MHz, DMSO-$d_6$) δ ppm 12.34 (br. s., 1H), 8.46 (d, J=8.6 Hz, 1H), 8.14 (d, J=7.4 Hz, 1H), 8.02 (d, J=8.8 Hz, 1H), 7.92 (d, J=2.7 Hz, 1H), 7.85 (d, J=8.0 Hz, 1H), 7.63 (t, J=7.7 Hz, 1H), 7.56 (dd, J=8.8, 2.7 Hz, 1H), 7.32 (d, J=9.0 Hz, 1H), 7.11-7.15 (m, 1H), 6.89-7.04 (m, 1H), 3.93 (s, 3H), 3.44 (t, J=6.7 Hz, 2H), 2.90 (t, J=6.8 Hz, 2H). $^{19}$F NMR (376 MHz, DMSO-$d_6$) δ ppm −74.67 (s, 3F). m/z (ESI, +ve ion) 404.0 (M+H)$^+$.

Example 89

(R)-2-(2-(piperidin-3-yloxy)quinolin-8-yl)-6,7-dihydro-1H-pyrrolo[3,2-c]pyridin-4(5H)-one

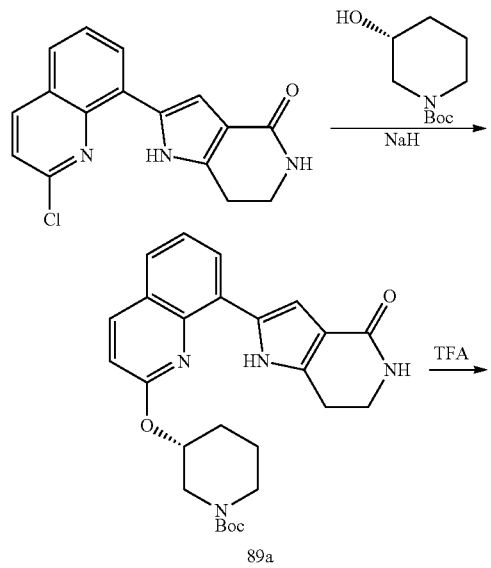

89

Preparation of (R)-tert-butyl 3-((8-(4-oxo-4,5,6,7-tetrahydro-1H-pyrrolo[3,2-c]pyridin-2-yl)quinolin-2-yl)oxy)piperidine-1-carboxylate (R)-tert-Butyl 3-hydroxypiperidine-1-carboxylate (Astatech Inc, Bristol, Pa.; 406 mg, 2.02 mmol) was added to a suspension of NaH (81 mg, 2.02 mmol) in THF (2.5 mL) and the resulting suspension was stirred at RT for 10 min. 2-(2-chloroquinolin-8-yl)-6,7-dihydro-1H-pyrrolo[3,2-c]pyridin-4(5H)-one (Example 1; 75 mg, 0.25 mmol) was added and the resulting suspension was stirred at RT for 5 min, then heated at 70° C. for 5 h. The mixture was cooled to RT and partitioned between EtOAc (60 mL) and saturated aq. NH$_4$Cl (20 mL). The organic layer was separated, sequentially washed with water (20 mL) tand brine (20 mL), then dried over MgSO$_4$, filtered and concentrated in vacuo to give (R)-tert-butyl 3-((8-(4-oxo-4,5,6,7-tetrahydro-1H-pyrrolo[3,2-c]pyridin-2-yl)quinolin-2-yl)oxy)piperidine-1-carboxylate as a light yellow solid. The material was used in the next step without further purification. m/z (ESI, +ve ion) 463.1 (M+H)$^+$.

Preparation of (R)-2-(2-(piperidin-3-yloxy)quinolin-8-yl)-6,7-dihydro-1H-pyrrolo[3,2-c]pyridin-4(5H)-one To a solution of (R)-tert-butyl 3-((8-(4-oxo-4,5,6,7-tetrahydro-1H-pyrrolo[3,2-c]pyridin-2-yl)quinolin-2-yl)oxy)piperidine-1-carboxylate (117 mg, 0.25 mmol) in DCM (3.0 mL) at 0° C. was added TFA (0.5 mL, 6.73 mmol). The reaction was stirred at RT for 20 min. The solution was concentrated, the residue was dissolved in DCM and washed with a saturated aq. solution of NaHCO$_3$. The aq. layer was extracted with DCM (2×). The combined organic layers were dried over MgSO$_4$, filtered and concentrated. The residue was dissolved in DMSO (3.0 mL). Purification by rpHPLC (Silicycle Silichrome XT $C_{18}$ column; 30×150 mm, 5 μm, 5-95% 0.1% TFA/ACN in 0.1% TFA/water by volume over 10 min.), followed by drying in a Genevac Series II Evaporator afforded (R)-2-(2-(piperidin-3-yloxy)quinolin-8-yl)-6,7-dihydro-1H-pyrrolo[3,2-c]pyridin-4(5H)-one 2,2,2-trifluoroacetate (15.7 mg, 0.033 mmol, 13.0% yield) as an amorphous yellow solid: $^1$H NMR (400 MHz, DMSO-$d_6$) δ ppm 11.63 (br. s., 1H), 8.76 (s, 1H), 8.80 (s, 1H), 8.34 (d, J=8.8 Hz, 1H), 7.96 (d, J=7.2 Hz, 1H), 7.79 (d, J=8.0 Hz, 1H), 7.50 (t, J=7.6 Hz, 1H), 7.17 (d, J=2.0 Hz, 1H), 7.10 (d, J=8.8 Hz, 1H), 7.03 (br. s., 1H), 5.52 (br. s., 1H), 3.39-3.55 (m, 4H), 3.15 (br. s., 2H), 2.89 (t, J=6.7 Hz, 2H), 2.13-2.24 (m, 1H), 1.93-2.07 (m, 2H), 1.82-1.92 (m, 1 H). $^{19}$F NMR (376 MHz, DMSO-$d_6$) δ ppm −74.47 (s, 3F). m/z (ESI, +ve ion) 363.0 (M+H)$^+$.

Example 90

2-(2-(cyclohexylamino)-7-fluoroquinolin-8-yl)-6,7-dihydro-1H-pyrrolo[3,2-c]pyridin-4(5H)-one

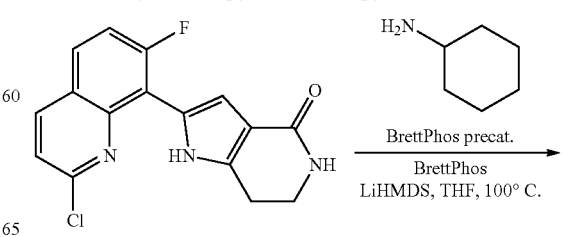

230

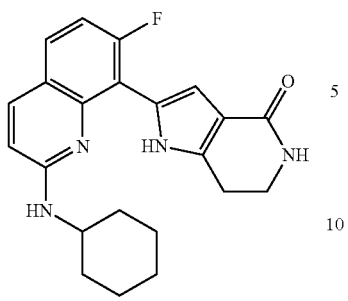

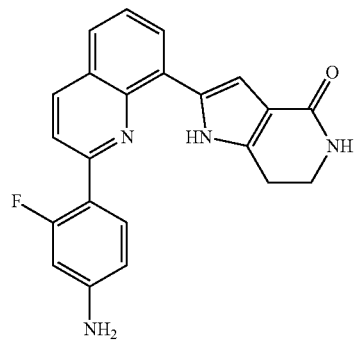

Prepared similarly to the method described in Example 78, 2-(2-chloro-7-fluoroquinolin-8-yl)-6,7-dihydro-1H-pyrrolo[3,2-c]pyridin-4(5H)-one (Example 230; 43.9 mg, 0.139 mmol), BrettPhos (Strem Chemicals, 4.1 mg, 6.95 μmol), and BrettPhos precatalyst (Strem Chemicals, 5.9 mg, 6.95 μmol) were weighed into a 5 mL glass microwave tube, and the tube was purged with argon. The contents were treated with THF (1 mL), cyclohexylamine (0.02 mL, 0.167 mmol) and LHMDS 1.0 M in THF (0.31 mL, 0.31 mmol) and the tube was sealed. The mixture was stirred and heated at 100° C. for 3 h. The mixture was cooled to RT and partitioned between EtOAc and saturated aq. NH$_4$Cl. The organic layer was separated and washed with water and brine, then concentrated in vacuo. The residue was dissolved in DMSO (2 mL) and purified by rpHPLC (Silicycle Silichrome XT C$_{18}$ column; 30×150 mm, 5 μm, 20-95% 0.1% TFA/ACN in 0.1% TFA/water by volume over 10 min), then dried in a Genevac Series II Evaporator affording 2-(2-(cyclohexylamino)-7-fluoroquinolin-8-yl)-6,7-dihydro-1H-pyrrolo[3,2-c]pyridin-4(5H)-one 2,2,2-trifluoroacetate (13.1 mg, 0.027 mmol, 19.1% yield) as an amorphous yellow solid: $^1$H NMR (400 MHz, MeOH-d4) δ ppm 8.17 (d, J=6.3 Hz, 1H), 8.10 (br. s., 1H), 7.71 (d, J=11.3 Hz, 1H), 7.09 (s, 1H), 7.02 (br. s., 1H), 3.93 (br. s., 1H), 3.64 (t, J=7.0 Hz, 2H), 3.03 (t, J=7.1 Hz, 2H), 2.14 (d, J=10.2 Hz, 2H), 1.94 (d, J=13.1 Hz, 2H), 1.80 (d, J=13.1 Hz, 1H), 1.43-1.65 (m, 4H), 1.30-1.42 (m, 1H). $^{19}$F NMR (377 MHz, MeOH-d4) δ ppm −77.12 (s, 3F), −121.66 (br. s., 1F). m/z (ESI, +ve ion) 379.1 (M+H)$^+$.

2-(2-Chloroquinolin-8-yl)-6,7-dihydro-1H-pyrrolo[3,2-c]pyridin-4(5H)-one (Example 1; 90 mg, 0.31 mmol), XPhos (8.7 mg, 0.018 mmol; Strem Chemicals), Pd$_2$(dba)$_3$ (8.3 mg, 9.07 μmol), K$_3$PO$_4$ (192 mg, 0.907 mmol) and 3-fluoro-4-(4,4,5,5-tetramethyl-1,3,2-dioxaborolan-2-yl)aniline (Boron Molecular, Research Triangle, N.C.; 100 mg, 0.42 mmol) were weighed into a 5 mL glass microwave tube. The tube was purged with argon and the solids were treated with dioxane (2.0 mL) and water (0.20 mL). The tube was sealed, and the contents were heated an Initiator microwave reactor (Personal Chemistry, Biotage AB, Inc., Upssala, Sweden) at 100° C. for 20 min. The mixture was treated with water (10 mL) and extracted with EtOAc (3×30 mL). The combined organic extracts were concentrated, then dissolved in DMSO. Purification by rpHPLC (20-95% 0.1% TFA/ACN in 0.1% TFA/water, Silicycle Silichrome XT C$_{18}$ column; 30×150 mm, 5 μm), followed by drying in a Genevac Series II evaporator overnight afforded 2-(2-(4-amino-2-fluorophenyl)quinolin-8-yl)-6,7-dihydro-1H-pyrrolo[3,2-c]pyridin-4(5H)-one bis (2,2,2-trifluoroacetate) (4.4 mg, 7.33 μmol, 2.4% yield) as an amorphous orange film: $^1$H NMR (400 MHz, MeOH-d4) δ ppm 8.53 (d, J=9.0 Hz, 1H), 8.09 (d, J=7.4 Hz, 1H), 8.02 (d, J=8.8 Hz, 1H), 7.85-7.90 (m, 1H), 7.80-7.84 (m, 1H), 7.63-7.70 (m, 1H), 7.09 (s, 1H), 6.73 (dd, J=8.6, 2.0 Hz, 1H), 6.64 (dd, J=15.0, 2.1 Hz, 1H), 3.64 (t, J=7.0 Hz, 2H), 3.02 (t, J=7.0 Hz, 2H). $^{19}$F NMR (376 MHz, MeOH-d4) δ ppm −77.55 (s, 6F), −116.44-115.35 (m, 1F). m/z (ESI, +ve ion) 373.1 (M+H)$^+$.

Example 91

2-(2-(4-amino-2-fluorophenyl)quinolin-8-yl)-6,7-dihydro-1H-pyrrolo[3,2-c]pyridin-4(5H)-one Example 92

(S)-2-(2-(piperidin-3-yloxy)quinolin-8-yl)-6,7-dihydro-1H-pyrrolo[3,2-c]pyridin-4(5H)-one

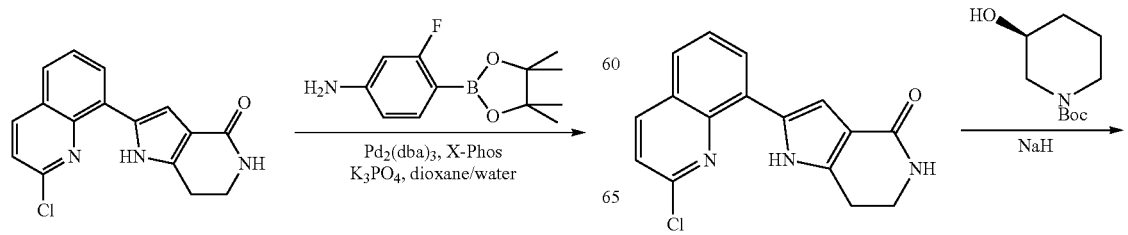

-continued

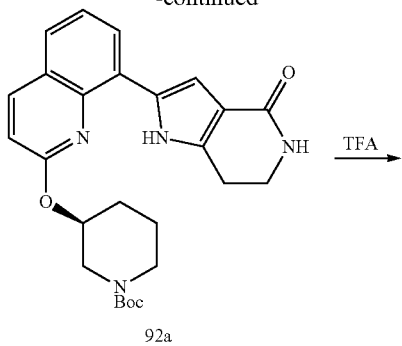

92a

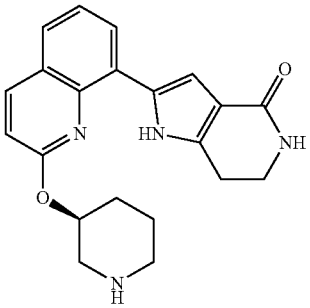

92

Preparation of (S)-tert-butyl 3-((8-(4-oxo-4,5,6,7-tetrahydro-1H-pyrrolo[3,2-c]pyridin-2-yl)quinolin-2-yl)oxy)piperidine-1-carboxylate (S)-tert-Butyl 3-hydroxypiperidine-1-carboxylate (Astatech Inc., Bristol, Pa.; 406 mg, 2.02 mmol) was added to a suspension of NaH (81 mg, 2.02 mmol) in THF (2.5 mL) and the resulting suspension was stirred at RT for 10 min. 2-(2-Chloroquinolin-8-yl)-6,7-dihydro-1H-pyrrolo[3,2-c]pyridin-4(5H)-one (Example 1; 75 mg, 0.25 mmol) was then added and the resulting suspension was stirred at RT for 5 min, then heated at 70° C. for 1.25 h. The mixture was cooled to RT and partitioned between EtOAc (60 mL) and saturated aq. NH₄Cl (20 mL). The organic layer was separated, sequentially washed with water (20 mL) then brine (20 mL), dried over MgSO₄, filtered and concentrated in vacuo to give (S)-tert-butyl 3-((8-(4-oxo-4,5,6,7-tetrahydro-1H-pyrrolo[3,2-c]pyridin-2-yl)quinolin-2-yl)oxy)piperidine-1-carboxylate as a light yellow solid: m/z (ESI, +ve ion) 463.1 (M+H)$^+$. The material was used in the subsequent step without further purification.

Preparation of (S)-2-(2-(piperidin-3-yloxy)quinolin-8-yl)-6,7-dihydro-1H-pyrrolo[3,2-c]pyridin-4(5H)-one 2,2,2-trifluoroacetate To a solution of (S)-tert-butyl 3-((8-(4-oxo-4,5,6,7-tetrahydro-1H-pyrrolo[3,2-c]pyridin-2-yl)quinolin-2-yl)oxy)piperidine-1-carboxylate (117 mg, 0.25 mmol) in DCM (3.0 mL) at 0° C. was added TFA (0.5 mL, 6.73 mmol). The reaction was stirred at 0° C. for 20 min then at RT for 2 h. The solution was concentrated, the residue was dissolved in DCM and washed with a saturated aq. solution of NaHCO₃. The organic layer was separated, and the aq. layer was extracted with DCM (2×). The combined organic layers were then concentrated, and the residue was dissolved in DMSO (3 mL). Purification by rpHPLC (Silicycle Silichrome XT C$_{18}$ column; 30×150 mm, 5 m, 5-95% 0.1% TFA/ACN in 0.1% TFA/water by volume over 10 min.), then drying in a Genevac Series II Evaporator afforded (S)-2-(2-(piperidin-3-yloxy)quinolin-8-yl)-6,7-dihydro-1H-pyrrolo[3,2-c]pyridin-4(5H)-one 2,2,2-trifluoroacetate (27.3 mg, 0.057 mmol, 22.7% yield) as an amorphous brown solid: $^1$H NMR (400 MHz, DMSO-d$_6$) δ ppm 11.62 (br. s., 1H), 8.69-8.85 (m, 2H), 8.33 (d, J=8.8 Hz, 1H), 7.95 (d, J=7.4 Hz, 1H), 7.78 (d, J=7.8 Hz, 1H), 7.49 (t, J=7.7 Hz, 1H), 7.16 (d, J=2.0 Hz, 1H), 7.09 (d, J=8.8 Hz, 1H), 7.02 (br. s., 1H), 5.51 (br. s., 1H), 3.40-3.53 (m, 4H), 3.14 (br. s., 2H), 2.89 (t, J=6.8 Hz, 2H), 2.11-2.23 (m, 1H), 1.94-2.05 (m, 2H), 1.81-1.90 (m, 1H). $^{19}$F NMR (376 MHz, DMSO-d$_6$) δ ppm −74.35 (s, 3F). m/z (ESI, +ve ion) 363.0 (M+H)$^+$.

Example 93

2-(2-(morpholine-4-carbonyl)quinolin-8-yl)-6,7-dihydro-1H-pyrrolo[3,2-c]pyridin-4(5H)-one

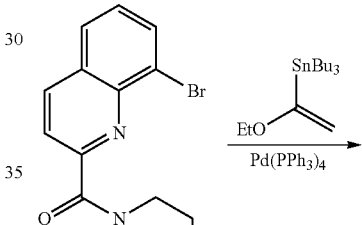

167a

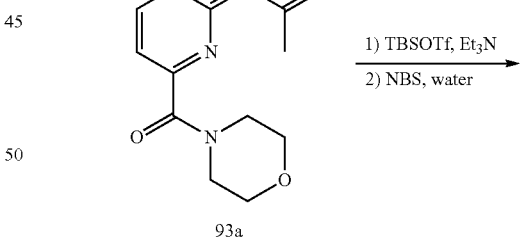

93a

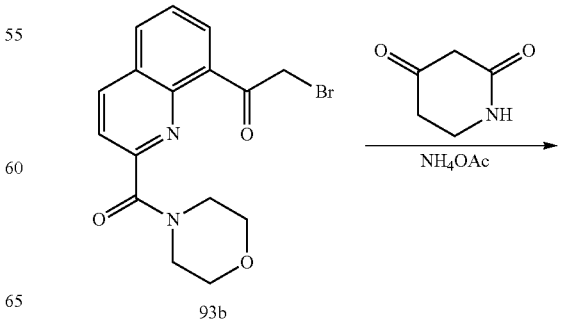

93b

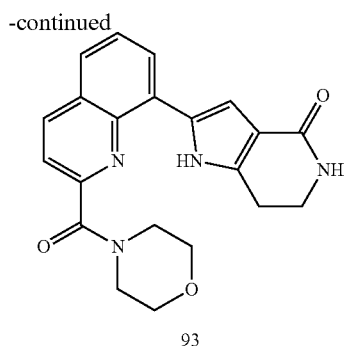

93

Preparation of 1-(2-(morpholine-4-carbonyl)quinolin-8-yl)ethanone

A mixture of Pd(PPh$_3$)$_4$ (18 mg, 0.016 mmol), tributyl(1-ethoxyvinyl)stannane (0.12 mL, 0.34 mmol), (8-bromoquinolin-2-yl)(morpholino)methanone (Example 167a; 100 mg, 0.31 mmol), and toluene (1.5 mL) were stirred in a sealed 5 mL glass microwave tube under argon at 100° C. for 63 h. Formation of both the vinyl ether (M+1=313.1) and the methyl ketone (M+1=285.0) were detected by LCMS. The mixture was concentrated under reduced pressure, and the residue was adsorbed onto silica gel. Chromatographic purification (silica gel, 10-70% EtOAc in hexanes) afforded a mixture of the vinyl ether and the methyl ketone as a colorless oil. The material was dissolved in THF (3 mL), the solution was cooled to 0° C., 2 drops of 1N HCl were added and the solution was stirred at 0° C. for 5 min. EtOAc (25 mL) was added to the reaction mixture and the solution was washed successively with 1N NaOH (5 mL), water (10 mL) and brine (10 mL). The combined aq. washes were extracted with 25% IPA in CHCl$_3$, and all organic layers were then combined, dried over MgSO$_4$, filtered, and concentrated in vacuo to give 1-(2-(morpholine-4-carbonyl)quinolin-8-yl)ethanone (81.4 mg, 0.286 mmol, 92% yield) as a white film: $^1$H NMR (400 MHz, DMSO-d$_6$) δ ppm 8.62 (d, J=8.6 Hz, 1H), 8.18-8.24 (m, 1H), 7.95 (dd, J=7.1, 1.3 Hz, 1H), 7.72-7.83 (m, 2H), 3.72 (s, 4H), 3.56 (d, J=4.7 Hz, 4H), 2.79 (s, 3H). m/z (ESI, +ve ion) 285.0 (M+H)$^+$.

Preparation of 2-bromo-1-(2-(morpholine-4-carbonyl)quinolin-8-yl)ethanone

To a solution of 1-(2-(morpholine-4-carbonyl)quinolin-8-yl)ethanone (0.438 g, 1.54 mmol) in DCM (5 mL) at 0° C. was added TEA (0.28 ml, 2.00 mmol) followed by TBSOTf (0.39 mL, 1.70 mmol). The resulting mixture was stirred at 0° C. for 50 min. The mixture was then partitioned between saturated NaHCO$_3$ and DCM. The organic layer was separated, and the aq. layer was extracted with DCM (3×). The combined organic layers were then dried over anhydrous MgSO$_4$, filtered, and concentrated in vacuo to give a brown oil. The resulting oil was taken up in THF (8 mL) and treated with water (0.44 mL, 24.7 mmol) and NBS (288 mg, 1.62 mmol). The resulting solution was stirred at RT for 20 min. The reaction mixture was then partitioned between water and Et$_2$O, and the organic layer was separated and sequentially washed with saturated NaHCO$_3$, water, and brine, then dried over MgSO$_4$, filtered, and concentrated in vacuo to give a 2-bromo-1-(2-(morpholine-4-carbonyl)quinolin-8-yl)ethanone as a greenish-brown solid. This material was used in the subsequent step without purification, assuming the theoretical yield: $^1$H NMR (400 MHz, DMSO-d$_6$) δ ppm 8.66 (d, J=8.6 Hz, 1H), 8.29 (dd, J=8.1, 1.3 Hz, 1H), 8.11 (dd, J=7.2, 1.4 Hz, 1H), 7.77-7.85 (m, 2H), 3.72 (s, 4H), 3.61-3.62 (m, 2H), 3.57-3.59 (m, 2H), 3.51-3.57 (m, 2H). m/z (ESI, +ve ion) 363.0/365.0 (M+H)$^+$.

Preparation of 2-(2-(morpholine-4-carbonyl)quinolin-8-yl)-6,7-dihydro-1H-pyrrolo[3,2-c]pyridin-4(5H)-one 2-Bromo-1-(2-(morpholine-4-carbonyl)quinolin-8-yl)ethanone (560 mg, 1.54 mmol) in a 25 mL glass microwave tube was suspended in EtOH (5.0 mL). Piperidine-2,4-dione (209 mg, 1.85 mmol) and NH$_4$OAc (475 mg, 6.17 mmol) were added, and the vessel was sealed. The reaction was stirred and heated at 50° C. for 15 h, and the reaction mixture was cooled to RT, carefully quenched with saturated aq. NaHCO$_3$ (gas evolution), and partitioned between saturated aq. NaHCO$_3$ and DCM. The organic layer was separated, and the aq. layer was extracted with DCM (4×). The combined organic layers were then concentrated in vacuo. The residue was dissolved in DMSO (10 mL) and purified by rpHPLC (20-95% 0.1% TFA/ACN in 0.1% TFA/water, Silicycle Silichrome XT C$_{18}$ column; 30×150 mm, 5 μm). The pure fractions were dried in a Genevac Series II evaporator overnight to give 2-(2-(morpholine-4-carbonyl)quinolin-8-yl)-6,7-dihydro-1H-pyrrolo[3,2-c]pyridin-4(5H)-one 2,2,2-trifluoroacetate (85.8 mg, 0.17 mmol, 11.4% yield) as an amorphous brown solid: $^1$H NMR (400 MHz, DMSO-d$_6$) δ ppm 11.89 (br. s., 1H), 8.54 (d, J=8.6 Hz, 1H), 8.13 (d, J=7.4 Hz, 1H), 7.88 (d, J=8.0 Hz, 1H), 7.78 (d, J=8.6 Hz, 1H), 7.69 (t, J=7.8 Hz, 1H), 7.20 (d, J=2.2 Hz, 1H), 6.95-7.04 (m, 1H), 3.75 (d, J=3.5 Hz, 4H), 3.60 (s, 4H), 3.44 (t, J=6.8 Hz, 2H), 2.91 (t, J=6.8 Hz, 2H). $^{19}$F NMR (376 MHz, DMSO-d$_6$) δ ppm −74.71 (s, 3F). m/z (ESI, +ve ion) 377.0 (M+H)$^+$.

Example 94

N-cyclopropyl-8-(4-oxo-4,5,6,7-tetrahydro-1H-pyrrolo[3,2-c]pyridin-2-yl)quinoline-2-carboxamide

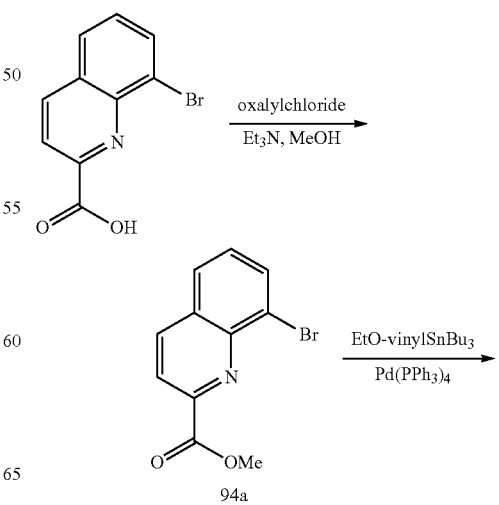

94a

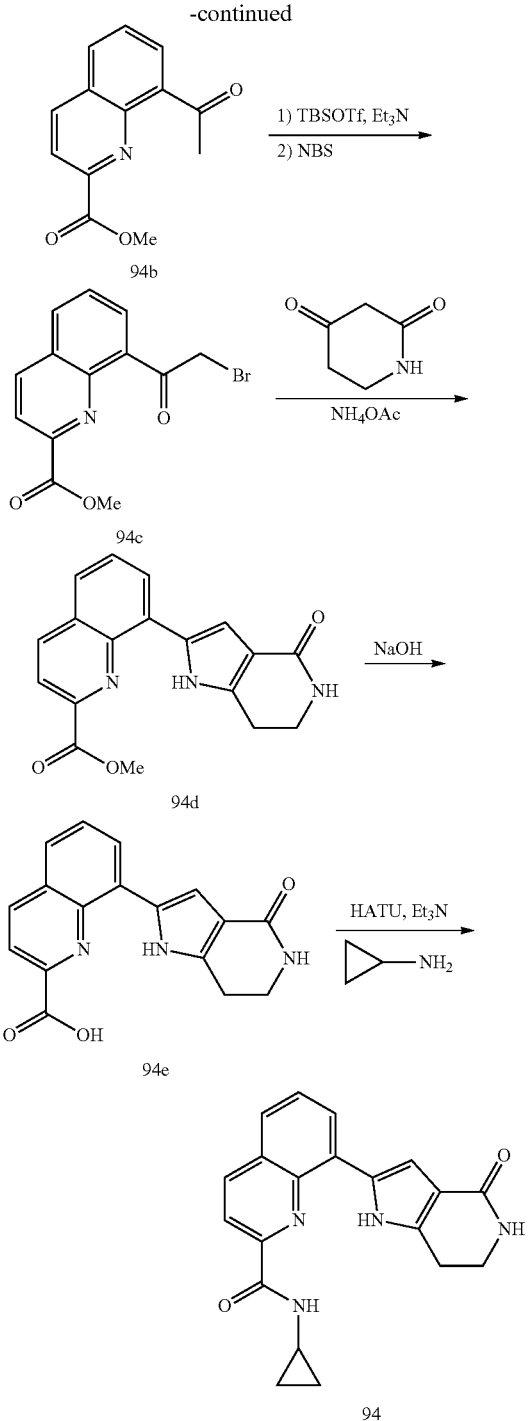

in DCM (50 mL) and cooled to 0° C. MeOH (1.7 mL, 42.1 mmol) and TEA (1.7 mL, 12.6 mmol) were added, the ice bath was removed, and the mixture was stirred at RT for 1 h. The reaction mixture was then diluted with DCM (50 mL), washed sequentially with 0.5 N HCl (25 mL), water (25 mL), 0.5 N NaOH (25 mL) and brine (25 mL), then dried over $MgSO_4$, filtered, and concentrated to give methyl 8-bromoquinoline-2-carboxylate as a brown oil. This material was used without further purification, assuming the theoretical yield: $^1$H NMR (400 MHz, DMSO-$d_6$) δ ppm 8.63 (d, J=8.4 Hz, 1H), 8.24 (d, J=7.4 Hz, 1H), 8.18 (d, J=8.4 Hz, 1H), 8.11 (d, J=8.2 Hz, 1H), 7.64 (t, J=7.8 Hz, 1H), 3.98 (s, 3H). m/z (ESI, +ve ion) 266.0/268.0 (M+H)$^+$.

Preparation of methyl 8-acetylquinoline-2-carboxylate

A mixture of Pd(PPh$_3$)$_4$ (608 mg, 0.53 mmol), tributyl(1-ethoxyvinyl)tin (3.91 mL, 11.57 mmol), methyl 8-bromoquinoline-2-carboxylate (2.80 g, 10.52 mmol), and toluene (50 mL) was heated under argon at 100° C. for 18 h. The mixture was then concentrated under reduced pressure and adsorbed onto silica gel. Column chromatography (silica gel, 10-100% EtOAc in hexanes) afforded a mixture of vinyl ether (M+1=258.0) and the desired acetate. This mixture was dissolved in THF (40 mL), the solution was cooled to 0° C., 10 drops of 1N HCl were added, and the solution was stirred at 0° C. for 5 min. EtOAc (100 mL) was added and the resulting solution was washed successively with 1N NaOH (20 mL), water (40 mL) and brine (40 mL). Significant product remained in the aq. layer and was extracted with 25% IPA in CHCl$_3$. The combined organic layers were dried over MgSO$_4$, filtered, and concentrated to give methyl 8-acetylquinoline-2-carboxylate (1.98 g, 8.64 mmol, 82% yield) as a tan solid: $^1$H NMR (400 MHz, DMSO-d$_6$) δ ppm 8.69 (d, J=8.4 Hz, 1H), 8.27 (dd, J=8.2, 1.4 Hz, 1H), 8.20 (d, J=8.4 Hz, 1H), 8.00 (dd, J=7.2, 1.4 Hz, 1H), 7.79-7.86 (m, 1H), 3.98 (s, 3H), 2.92 (s, 3H). m/z (ESI, +ve ion) 230.0 (M+H)$^+$.

Preparation of methyl 8-(2-bromoacetyl)quinoline-2-carboxylate

To a solution of methyl 8-acetylquinoline-2-carboxylate (1.98 g, 8.64 mmol) in DCM (25 mL) at 0° C. was added TEA (1.56 mL, 11.23 mmol) followed by TBSOTf (1.66 mL, 9.50 mmol). The reaction mixture was stirred at 0° C. for 50 min. The mixture was then partitioned between saturated NaHCO$_3$ and DCM. The organic layer was separated, and the aq. layer was extracted with DCM (2×). The combined organic layers were then dried over anhydrous MgSO$_4$, filtered, and concentrated in vacuo to give methyl 8-(1-((tert-butyldimethylsilyl)oxy)vinyl)quinoline-2-carboxylate as a brown oil: $^1$H NMR (400 MHz, CDCl$_3$) δ ppm 8.29 (d, J=8.4 Hz, 1H), 8.18 (d, J=8.4 Hz, 1H), 8.12 (dd, J=7.3, 1.3 Hz, 1H), 7.80 (dd, J=8.1, 1.3 Hz, 1H), 7.62 (t, J=7.7 Hz, 1H), 6.12 (s, 1H), 4.99 (s, 1H), 4.05 (s, 3H), 1.01 (s, 9H), 0.28 (s, 6H). m/z (ESI, +ve ion) 344.0 (M+H)$^+$. This oil was taken up in THF (10 mL), treated with water (2.5 mL, 138 mmol) and NBS (1.61 g, 9.07 mmol), and stirred at RT for 20 min. The reaction mixture was then partitioned between water and Et$_2$O, and the organic layer was separated and sequentially washed with saturated NaHCO$_3$, water, and brine, then dried over MgSO$_4$, filtered, and concentrated in vacuo to give methyl 8-(2-bromoacetyl)quinoline-2-carboxylate as a greenish-brown solid. This material was used without purification in the subsequent step assuming the theoretical yield: $^1$H NMR (400 MHz, CDCl$_3$)

Preparation of methyl 8-bromoquinoline-2-carboxylate

A suspension of 8-bromoquinoline-2-carboxylic acid (Princeton Biomolecular Research, Monmouth Junction, N.J.; 2.65 g, 10.51 mmol) in DCM (25 mL) at 0° C. was treated with oxalyl chloride, 2.0 M solution in DCM (10.51 mL, 21.0 mmol), followed by 12 drops of DMF. The ice bath was removed, the mixture was stirred at RT for 1 h, becoming completely soluble during that time. The reaction mixture was then concentrated in vacuo and the residue was dissolved δ ppm 8.40 (d, J=8.6 Hz, 1H), 8.30 (d, J=7.0 Hz, 1H), 8.26 (d, J=8.6 Hz, 1H), 8.09 (d, J=8.2 Hz, 1H), 7.76 (t, J=7.6 Hz, 1H), 5.32 (br. s., 2H), 4.08 (s, 3H). m/z (ESI, +ve ion) 308.0/310.1 (M+H)$^+$.

Preparation of methyl 8-(4-oxo-4,5,6,7-tetrahydro-1H-pyrrolo[3,2-c]pyridin-2-yl)quinoline-2-carboxylate Methyl 8-(2-bromoacetyl)quinoline-2-carboxylate (2.66 g, 8.63 mmol) was suspended in MeOH (30 mL). Piperidine-2,4-dione (1.17 g, 10.36 mmol) and NH$_4$OAc (2.66 g, 34.5 mmol) were added, and the resulting mixture was heated at 50° C. for 17 h. The reaction mixture was then carefully quenched with saturated aq. NaHCO$_3$ (gas evolution) and partitioned between saturated aq. NaHCO$_3$ and DCM. The organic layer was separated, and the aq. layer was extracted with DCM (4×). The combined organic layers were washed with brine, dried over MgSO$_4$, filtered, and concentrated in vacuo. Chromatographic purification of the residue (silica gel, 10-20% MeOH in DCM) afforded methyl 8-(4-oxo-4,5,6,7-tetrahydro-1H-pyrrolo[3,2-c]pyridin-2-yl)quinoline-2-carboxylate (841 mg, 2.62 mmol, 30.3% yield) as a brown-black solid: $^1$H NMR (400 MHz, DMSO-d$_6$) δ ppm 12.65 (br. s., 1H), 8.62 (d, J=8.6 Hz, 1H), 8.28 (d, J=7.4 Hz, 1H), 8.17 (d, J=8.6 Hz, 1H), 7.90 (d, J=8.0 Hz, 1H), 7.74 (t, J=7.8 Hz, 1H), 7.32 (d, J=2.2 Hz, 1H), 7.05 (br. s., 1H), 4.03 (s, 3H), 3.47 (td, J=6.8, 2.2 Hz, 2H), 2.94 (t, J=6.8 Hz, 2H). m/z (ESI, +ve ion) 322.0 (M+H)$^+$.

Preparation of 8-(4-oxo-4,5,6,7-tetrahydro-1H-pyrrolo[3,2-c]pyridin-2-yl)quinoline-2-carboxylic acid Methyl 8-(4-oxo-4,5,6,7-tetrahydro-1H-pyrrolo[3,2-c]pyridin-2-yl)quinoline-2-carboxylate (0.84 g, 2.62 mmol) was dissolved in THF (25 mL), NaOH 1.00 N (2.62 mL, 2.62 mmol) was added, and the resulting solution was stirred at RT for 3 h, then at 40° C. for 2 h. The reaction mixture was then concentrated in vacuo the pH was adjusted to <4 using 5 N HCl. A precipitate formed and was isolated by filtration to give 8-(4-oxo-4,5,6,7-tetrahydro-1H-pyrrolo[3,2-c]pyridin-2-yl)quinoline-2-carboxylic acid (647 mg, 2.11 mmol, 80% yield) as a dark-brown solid: $^1$H NMR (400 MHz, DMSO-d$_6$) δ ppm 13.71 (br. s., 1H), 12.72 (br. s., 1H), 8.59 (d, J=8.4 Hz, 1H), 8.26 (d, J=7.4 Hz, 1H), 8.16 (d, J=8.6 Hz, 1H), 7.89 (d, J=8.0 Hz, 1H), 7.72 (t, J=7.7 Hz, 1H), 7.30-7.34 (m, 1H), 7.04 (br. s., 1H), 3.46 (t, J=6.5 Hz, 2H), 2.90 (t, J=6.7 Hz, 2H). m/z (ESI, +ve ion) 308.0 (M+H)$^+$.

Preparation of N-cyclopropyl-8-(4-oxo-4,5,6,7-tetrahydro-1H-pyrrolo[3,2-c]pyridin-2-yl)quinoline-2-carboxamide 2,2,2-trifluoroacetate 8-(4-Oxo-4,5,6,7-tetrahydro-1H-pyrrolo[3,2-c]pyridin-2-yl)quinoline-2-carboxylic acid (59 mg, 0.19 mmol) was dissolved in DMF (1.5 mL), HATU (88 mg, 0.230 mmol), TEA (0.03 mL, 0.23 mmol), and cyclopropylamine (0.03 mL, 0.38 mmol) were added, and the resulting mixture was stirred at RT for 15 min. The mixture was then treated with EtOAc and washed with water. The organic layer was separated, and the aq. layer was extracted with EtOAc (1×), followed by DCM (1×). The combined organic layers were dried over MgSO$_4$, filtered, and concentrated. The residue was dissolved in DMSO (2.8 mL) and purified by rpHPLC (Silicycle Silichrome XT C$_{18}$ column; 30×150 mm, 5 μm, 20-95% 0.1% TFA/ACN in 0.1% TFA/water by volume over 10 min.), then dried in a Genevac Series II Evaporator to afford N-cyclopropyl-8-(4-oxo-4,5,6,7-tetrahydro-1H-pyrrolo[3,2-c]pyridin-2-yl)quinoline-2-carboxamide 2,2,2-trifluoroacetate (9.4 mg, 0.02 mmol, 10.6% yield) as a yellow amorphous solid: $^1$H NMR (400 MHz, MeOH-d4) δ ppm 11.86 (br. s., 1H), 8.50 (d, J=8.6 Hz, 1H), 8.15 (d, J=8.6 Hz, 1H), 8.07 (d, J=7.2 Hz, 1H), 7.87 (d, J=8.2 Hz, 1H), 7.69 (t, J=7.7 Hz, 1H), 7.05-7.09 (m, 1H), 3.65 (t, J=7.0 Hz, 2H), 3.03 (t, J=7.0 Hz, 2H), 2.95-3.00 (m, 1H), 0.88-0.95 (m, 2H), 0.72-0.78 (m, 2H). $^{19}$F NMR (377 MHz, MeOH-d4) δ ppm −77.49 (s, 3F). m/z (ESI, +ve ion) 347.0 (M+H)$^+$.

Example 95

8-(4-oxo-4,5,6,7-tetrahydro-1H-pyrrolo[3,2-c]pyridin-2-yl)-N-phenylquinoline-2-carboxamide

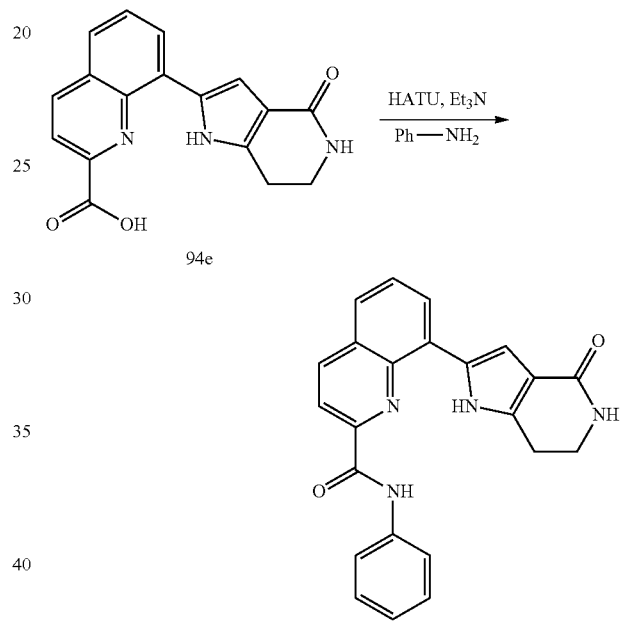

8-(4-Oxo-4,5,6,7-tetrahydro-1H-pyrrolo[3,2-c]pyridin-2-yl)quinoline-2-carboxylic acid (Example 94e; 80 mg, 0.26 mmol) was dissolved in DMF (2.5 mL), HATU (119 mg, 0.31 mmol), Et$_3$N (0.04 mL, 0.31 mmol), and aniline (0.05 mL, 0.52 mmol) were added, and the resulting mixture was stirred at RT for 20 min. The mixture was then treated with EtOAc and washed with water. The organic layer was separated, and the aq. layer was extracted with EtOAc (2×). The combined organic layers were then dried over MgSO$_4$, filtered, and concentrated to in vacuo. DCM was added to the crude material and a precipitate was formed, which contained both the desired product and impurities. Most of the impurities crystallized from hot DCM, and were removed by filtration. The mother liquor was concentrated and the material (desired product and ca. 10% impurity) was suspended in EtOAc. The desired product was recrystallized from hot EtOAc and was isolated by filtration affording 8-(4-oxo-4,5,6,7-tetrahydro-1H-pyrrolo[3,2-c]pyridin-2-yl)-N-phenylquinoline-2-carboxamide (12.9 mg, 0.034 mmol, 13.0% yield) as an amorphous tan solid: $^1$H NMR (400 MHz, DMSO-d$_6$) δ ppm 12.04 (br. s., 1H), 10.55 (s, 1H), 8.68 (d, J=8.4 Hz, 1H), 8.25 (d, J=8.4 Hz, 1H), 8.11 (d, J=7.2 Hz, 1H), 7.99 (d, J=7.6 Hz, 1H), 7.93 (d, J=8.0 Hz, 2H), 7.72-7.81 (m, 1H), 7.44 (t, J=7.7 Hz, 2H), 7.13-7.22 (m, 1H), 7.07 (d, J=10.8 Hz, 2H), 3.44-3.53 (m, 2H), 2.95 (t, J=6.7 Hz, 2H). m/z (ESI, +ve ion) 383.0 (M+H)+.

Example 96

N-(2-methoxyethyl)-8-(4-oxo-4,5,6,7-tetrahydro-1H-pyrrolo[3,2-c]pyridin-2-yl)quinoline-2-carboxamide

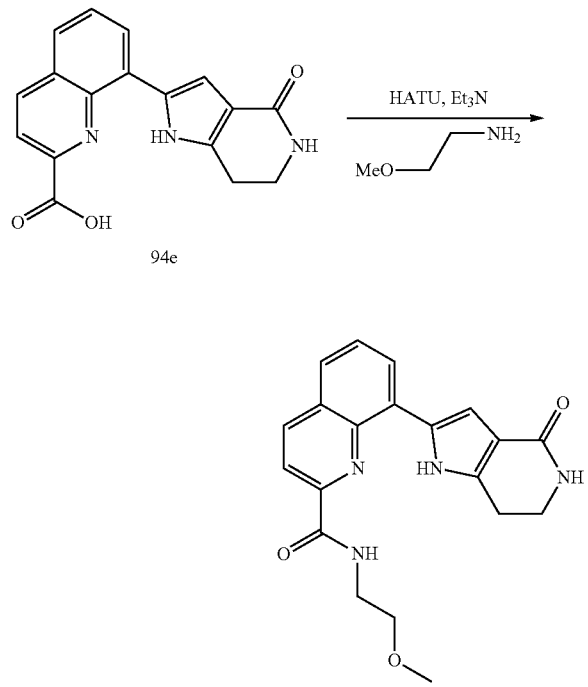

8-(4-Oxo-4,5,6,7-tetrahydro-1H-pyrrolo[3,2-c]pyridin-2-yl)quinoline-2-carboxylic acid (Example 94e; 65 mg, 0.21 mmol) was dissolved in DMF (1.5 mL), HATU (97 mg, 0.254 mmol), TEA (0.04 mL, 0.25 mmol), and 2-methoxyethylamine (0.04 mL, 0.42 mmol) were added, and the resulting mixture was stirred at RT for 15 min. The mixture was then treated with EtOAc and washed with water. The organic layer was separated, and the aq. layer was extracted with EtOAc (2×). The combined organic layers were then dried over MgSO$_4$, filtered, and concentrated. The residue was dissolved in DMSO (2.5 mL) and purified by rpHPLC (Silicycle Silichrome XT C$_{18}$ column; 30×150 mm, 5 μm, 20-95% 0.1% TFA/ACN in 0.1% TFA/water by volume over 10 min.), then dried in a Genevac Series II Evaporator to afford N-(2-methoxyethyl)-8-(4-oxo-4,5,6,7-tetrahydro-1H-pyrrolo[3,2-c]pyridin-2-yl)quinoline-2-carboxamide 2,2,2-trifluoroacetate (19 mg, 0.04 mmol, 18.8% yield) as an amorphous orange solid: $^1$H NMR (400 MHz, DMSO-d$_6$) δ ppm 11.92 (br. s., 1H), 8.70 (br. s., 1H), 8.59 (d, J=8.4 Hz, 1H), 8.07-8.16 (m, 2H), 7.93 (d, J=8.0 Hz, 1H), 7.71 (t, J=7.7 Hz, 1H), 7.01 (br. s., 1H), 6.95 (d, J=1.8 Hz, 1H), 3.58 (s, 4H), 3.46 (t, J=6.7 Hz, 2H), 3.28-3.33 (m, 3H), 2.93 (t, J=6.8 Hz, 2H). $^{19}$F NMR (376 MHz, DMSO-d$_6$) δ ppm −74.70 (s, 3F). m/z (ESI, +ve ion) 365.1 (M+H)+.

Example 97

2-(2-(4-methylpiperazine-1-carbonyl)quinolin-8-yl)-6,7-dihydro-1H-pyrrolo[3,2-c]pyridin-4(5H)-one

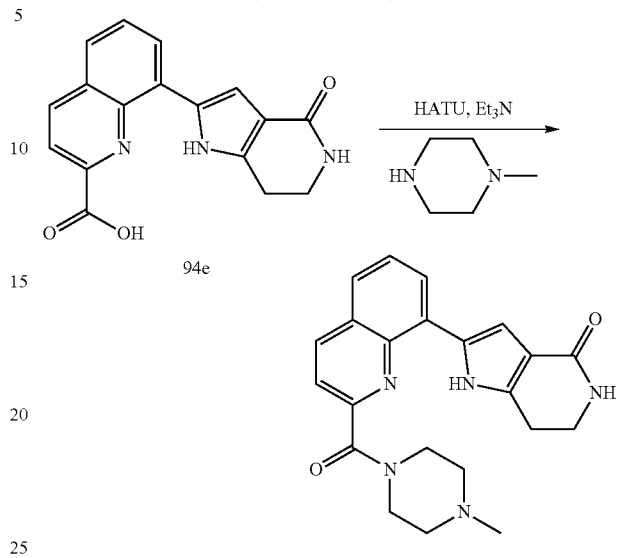

8-(4-Oxo-4,5,6,7-tetrahydro-1H-pyrrolo[3,2-c]pyridin-2-yl)quinoline-2-carboxylic acid (Example 94e; 68 mg, 0.22 mmol) was dissolved in DMF (1.5 mL), HATU (101 mg, 0.27 mmol), Et$_3$N (0.04 mL, 0.27 mmol), and 1-methylpiperazine (0.05 mL, 0.44 mmol) were added, and the resulting mixture was stirred at RT for 15 min. The reaction mixture was then treated with EtOAc and washed with water. The organic layer was separated, and the aq. layer was extracted with EtOAc (2×). The combined organic layers were then dried over MgSO$_4$, filtered, and concentrated. The residue was dissolved in DMSO (2.8 mL) and purified by rpHPLC (Silicycle Silichrome XT C$_{18}$ column; 30×150 mm, 5 μm, 20-95% 0.1% TFA/ACN in 0.1% TFA/water by volume over 10 min.), then dried in a Genevac Series II Evaporator to afford 2-(2-(4-methylpiperazine-1-carbonyl)quinolin-8-yl)-6,7-dihydro-1H-pyrrolo[3,2-c]pyridin-4(5H)-one 2,2,2-trifluoroacetate (26.8 mg, 0.053 mmol, 24.1% yield) as an amorphous tan solid: $^1$H NMR (400 MHz, MeOH-d4) δ ppm 11.67 (br. s., 1H), 8.50 (d, J=8.4 Hz, 1H), 8.04 (d, J=7.2 Hz, 1H), 7.87 (d, J=8.6 Hz, 2H), 7.67-7.75 (m, 1H), 7.40 (d, J=2.0 Hz, 1H), 4.89-4.99 (m, 1H), 4.64-4.75 (m, 1H), 3.67-3.79 (m, 1H), 3.63 (t, J=7.0 Hz, 2H), 3.48-3.59 (m, 1H), 3.33-3.47 (m, 4H), 3.02 (t, J=7.1 Hz, 2H), 2.98 (s, 3H). $^{19}$F NMR (376 MHz, MeOH-d3) δ ppm −77.66 (s, 3F). m/z (ESI, +ve ion) 390.2 (M+H)+.

Example 98

8-(4-oxo-4,5,6,7-tetrahydro-1H-pyrrolo[3,2-c]pyridin-2-yl)-N-(tetrahydro-2H-pyran-4-yl)quinoline-2-carboxamide

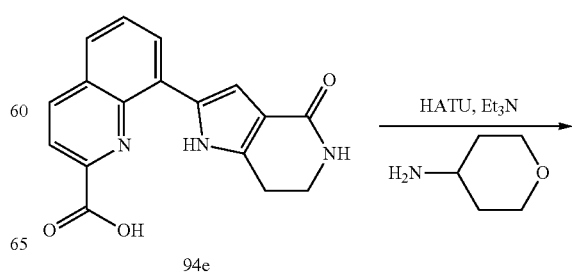

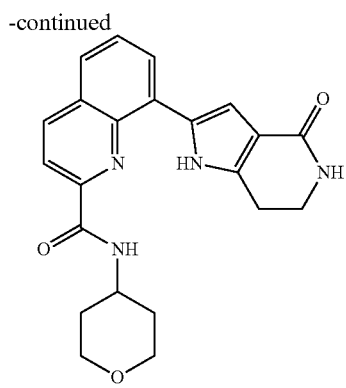

8-(4-Oxo-4,5,6,7-tetrahydro-1H-pyrrolo[3,2-c]pyridin-2-yl)quinoline-2-carboxylic acid (Example 94e; 77 mg, 0.25 mmol) was dissolved in DMF (1.5 mL), HATU (114 mg, 0.30 mmol), Et$_3$N (0.04 mL, 0.30 mmol), and 4-aminotetrahydropyran (Combi-Blocks Inc., San Diego, Calif.; 0.05 mL, 0.50 mmol) were added, and the resulting mixture was stirred at RT for 25 min. The mixture was then treated with EtOAc and washed with water. The organic layer was separated, and the aq. layer was extracted with EtOAc (2×). The combined organic layers were then dried over MgSO$_4$, filtered, and concentrated. The residue was treated with DCM, and a precipitate formed. The DCM was heated, but the precipitate did not dissolve. The suspension was held at RT for 1 h, after which the solid was removed by filtration to give 8-(4-oxo-4,5,6,7-tetrahydro-1H-pyrrolo[3,2-c]pyridin-2-yl)-N-(tetrahydro-2H-pyran-4-yl)quinoline-2-carboxamide (31.2 mg, 0.08 mmol, 32% yield) as a bright yellow amorphous solid: $^1$H NMR (400 MHz, DMSO-d$_6$) δ ppm 12.00 (br. s., 1H), 8.55-8.67 (m, 2H), 8.08-8.16 (m, 2H), 7.93 (d, J=7.8 Hz, 1H), 7.68-7.77 (m, 1H), 6.94-7.05 (m, 2H), 4.00-4.15 (m, 1H), 3.90 (d, J=11.7 Hz, 2H), 3.42-3.52 (m, 4H), 2.91 (t, J=6.7 Hz, 2H), 1.92 (d, J=12.1 Hz, 2H), 1.59-1.74 (m, 2H). m/z (ESI, +ve ion) 391.1 (M+H)$^+$.

Example 99

2-(2-(cyclopropylamino)quinolin-8-yl)-6,7-dihydro-1H-pyrrolo[3,2-c]pyridin-4(5H)-one

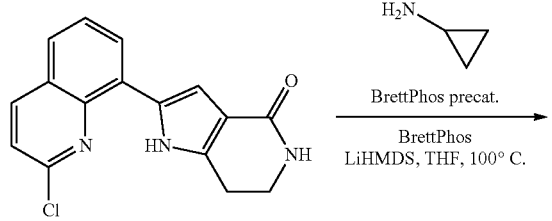

Prepared similarly to the method described in Example 78: 2-(2-chloroquinolin-8-yl)-6,7-dihydro-1H-pyrrolo[3,2-c]pyridin-4(5H)-one (Example 1; 69 mg, 0.232 mmol), Brettphos (Strem Chemicals, 6.8 mg, 0.012 mmol), and BrettPhos precatalyst (Strem Chemicals; 9.8 mg, 0.012 mmol) were weighed into a 5-mL glass microwave tube, and the tube was purged with argon. The contents were treated with THF (1.5 mL), cyclopropanamine (Alfa Aesar, Ward Hill, Mass.; 0.019 mL, 0.278 mmol), and LHMDS (1.0 M in THF; 0.510 mL, 0.510 mmol), and the tube was sealed. The mixture was stirred and heated at 100° C. for 3 h. The reaction mixture was then cooled to RT and partitioned between EtOAc (20 mL) and saturated aq. NH$_4$Cl (10 mL). The organic layer was separated, and the aq. layer was extracted with EtOAc (30 mL). The combined organic layers were concentrated in vacuo. The residue was dissolved in DMSO (2 mL) and purified by rpHPLC (Silicycle Silichrome XT C$_{18}$ column; 30×150 mm, 5 µm, 5-95% 0.1% TFA/ACN in 0.1% TFA/water by volume over 10 min), then dried in a Genevac Series II Evaporator, affording 2-(2-(cyclopropylamino)quinolin-8-yl)-6,7-dihydro-1H-pyrrolo[3,2-c]pyridin-4(5H)-one 2,2,2-trifluoroacetate (15.8 mg, 0.037 mmol, 15.77% yield) as an amorphous yellow solid: $^1$H NMR (400 MHz, MeOH-d4) δ ppm 8.41 (d, J=9.4 Hz, 1H), 7.90 (t, J=8.3 Hz, 2H), 7.54-7.75 (m, 1H), 7.05-7.21 (m, 1H), 7.01 (br. s., 1H), 3.65 (t, J=7.0 Hz, 2H), 3.02 (t, J=7.0 Hz, 2H), 2.91 (tt, J=6.9, 3.6 Hz, 1H), 1.04-1.15 (m, 2H), 0.87 (br. s., 2H). $^{19}$F NMR (376 MHz, MeOH-d4) δ ppm −77.43 (s, 1F). m/z (ESI, +ve ion) 319.2 (M+H)$^+$.

Example 100

7-(2-methyl-3-((1-methylcyclopropyl)amino)quinoxalin-5-yl)-3,4-dihydropyrrolo[1,2-a]pyrazin-1(2H)-one 2,2,2-trifluoroacetate

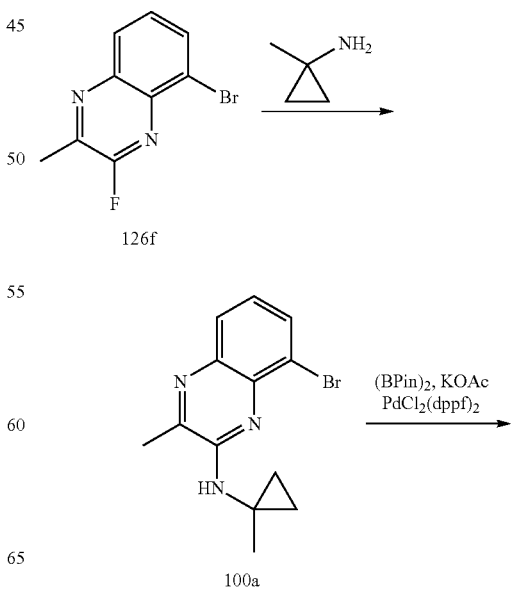

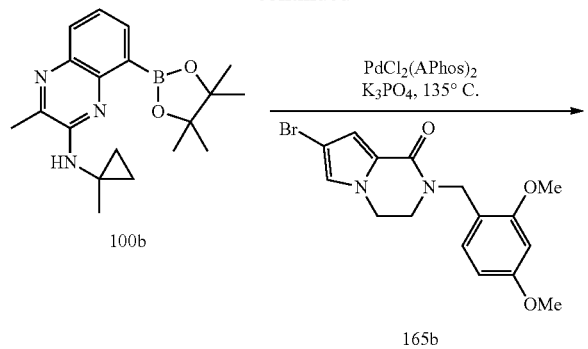

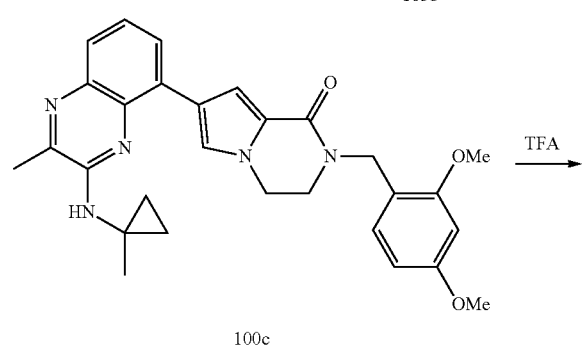

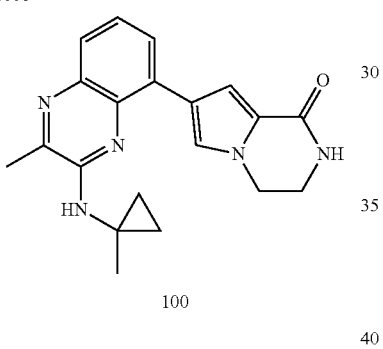

Preparation of 8-bromo-3-methyl-N-(1-methylcyclopropyl)quinoxalin-2-amine

This compound (0.50 g, 45% yield) as a light yellow crystalline solid was prepared according to Example 174, using 5-bromo-3-fluoro-2-methylquinoxaline (126f; 0.96 g, 3.72 mmol), 1-methylcyclopropanamine hydrochloride (ChemBridge, San Diego, Calif.; 0.6 g, 5.58 mmol), and DIPEA (2.59 mL, 14.87 mmol) as starting materials: $^1$H NMR (400 MHz, DMSO-$d_6$) δ ppm 7.83 (dd, J=7.6, 1.2 Hz, 1H), 7.71 (dd, J=8.2, 1.2 Hz, 1H), 7.45-7.51 (m, 1H), 7.22 (t, J=7.8 Hz, 1H), 2.47 (s, 3H), 1.54 (s, 3H), 0.78-0.84 (m, 2H), 0.68-0.75 (m, 2H). m/z (ESI, +ve) 292/294 (M+H)$^+$.

Preparation of 3-methyl-N-(1-methylcyclopropyl)-8-(4,4,5,5-tetramethyl-1,3,2-dioxaborolan-2-yl)quinoxalin-2-amine This compound (350 mg, 60% yield) as a brown amorphous solid was prepared according to Example 174, using 8-bromo-3-methyl-N-(1-methylcyclopropyl)quinoxalin-2-amine (100a; 490 mg, 1.70 mmol) as the starting material. m/z (ESI, +ve ion) 258.2 (M+H)$^+$.

Preparation of 7-(2-methyl-3-((1-methylcyclopropyl)amino)-quinoxalin-5-yl)-3,4-dihydropyrrolo[1,2-a]pyrazin-1(2H)-one 2,2,2-trifluoroacetate This compound was prepared according to Example 174, using 3-methyl-N-(1-methylcyclopropyl)-8-(4,4,5,5-tetramethyl-1,3,2-dioxaborolan-2-yl)quinoxalin-2-amine (100b; 137 mg, 0.41 mmol) as the starting material. Purification by rpHPLC (Silicycle Silichrome XT $C_{18}$ column; 30×150 mm, 5 μm; 20-95% of 0.1% TFA/ACN in 0.1% TFA/water by volume over 10 min), then drying in a Genevac Series II Evaporator afforded 7-(2-methyl-3-((1-methylcyclopropyl)amino)-quinoxalin-5-yl)-3,4-dihydropyrrolo[1,2-a]pyrazin-1(2H)-one 2,2,2-trifluoroacetate (45 mg, 29% yield for 2 steps) as an orange solid. $^1$H NMR (400 MHz, MeOH-d4) δ ppm 8.20 (br. s., 1H), 7.88 (d, J=7.4 Hz, 1H), 7.68 (d, J=7.2 Hz, 1H), 7.55 (br. s., 1H), 7.47 (t, J=7.5 Hz, 1H), 4.22-4.31 (m, 2H), 3.67-3.76 (m, 2H), 2.58 (s, 3H), 1.57 (s, 3H), 0.96-1.02 (m, 2H), 0.89-0.95 (m, 2H). m/z (ESI, +ve ion) 348.1 (M+H)$^+$.

Example 101

2-(2-((2,6-dimethylphenyl)amino)quinolin-8-yl)-6,7-dihydro-1H-pyrrolo[3,2-c]pyridin-4(5H)-one

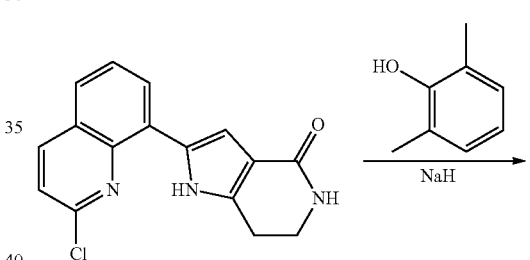

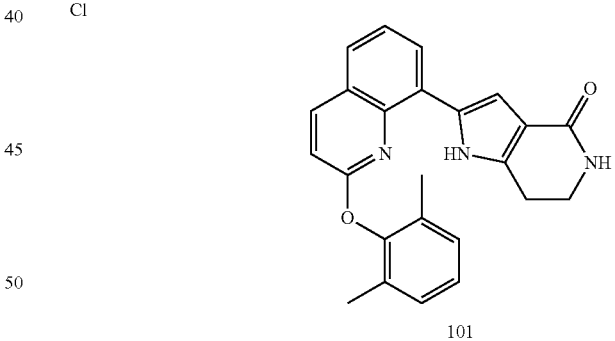

Prepared according to Example 103 using 2,6-dimethylphenol (158 mg, 1.293 mmol) and 2-(2-chloroquinolin-8-yl)-6,7-dihydro-1H-pyrrolo[3,2-c]pyridin-4(5H)-one (Example 1; 50.0 mg, 0.168 mmol), heating at 70° C. for 17 h. Chromatographic purification (silica gel, 0-10% MeOH/DCM) furnished 2-(2-(2,6-dimethylphenoxy)quinolin-8-yl)-6,7-dihydro-1H-pyrrolo[3,2-c]pyridin-4(5H)-one (51.4 mg, 0.134 mmol, 80% yield) as a yellow solid: $^1$H NMR (300 MHz, CDCl$_3$) δ ppm 11.08 (1H, br. s.), 8.21 (1H, d, J=8.8 Hz), 8.03 (1H, dd, J=7.6, 1.3 Hz), 7.61 (1H, dd, J=7.9, 1.3 Hz), 7.42 (1H, t, J=7.8 Hz), 7.29 (1H, s), 7.21 (3H, s), 7.10 (1H, d, J=2.2 Hz), 5.33 (1H, br. s.), 3.51 (2H, td, J=6.8, 1.2 Hz), 2.47 (2H, t, J=6.9 Hz), 2.17 (6H, s). m/z (ESI, +ve) 384.2 (M+H)$^+$.

Example 102

2-(2-((2,6-dimethylphenyl)amino)quinolin-8-yl)-6,7-dihydro-1H-pyrrolo[3,2-c]pyridin-4(5H)-one

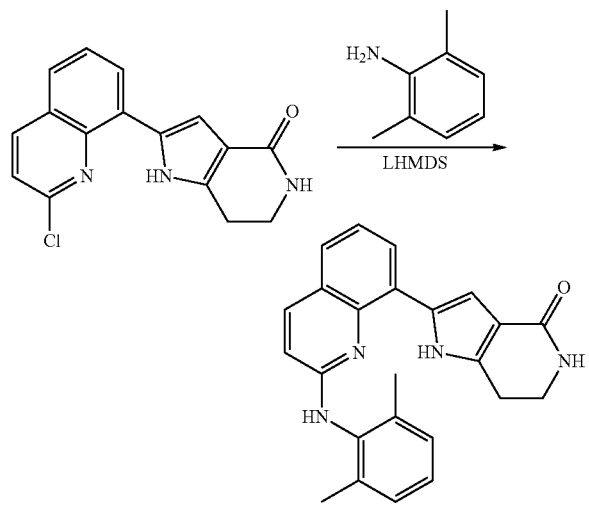

A solution of 2-(2-chloroquinolin-8-yl)-6,7-dihydro-1H-pyrrolo[3,2-c]pyridin-4(5H)-one (Example 1; 51.0 mg, 0.171 mmol), 2,6-dimethylaniline (Aldrich; 106 µl, 0.856 mmol), and LHMDS (1.0 M in THF; 856 µl, 0.856 mmol) was stirred under argon in a sealed flask at 25° C. for 17 h. The mixture was partitioned between DCM (50 mL) and saturated aq. NH₄Cl (30 mL). The organic layer was separated, and the aq. layer was extracted with DCM (2×20 mL). The combined organic extracts were dried over Na₂SO₄, filtered, and concentrated in vacuo. Chromatographic purification of the residue (silica gel, 0-10% MeOH/DCM) followed rpHPLC of the collected material (Phenomenex Gemini $C_{18}$ column (150×30 mm, 10 µm), 35 mL/min, 5-100% ACN/H₂O+0.1% TFA) furnished 2-(2-((2,6-dimethylphenyl)amino)quinolin-8-yl)-6,7-dihydro-1H-pyrrolo[3,2-c]pyridin-4(5H)-one 2,2,2-trifluoroacetate (31.0 mg, 0.062 mmol, 37% yield) as a yellow solid: ¹H NMR (400 MHz, CDCl₃) δ ppm 10.97 (1H, br. s.), 10.32 (1H, br. s.), 8.14 (1H, d, J=9.5 Hz), 7.85 (1H, d, J=7.2 Hz), 7.75 (1H, br. s.), 7.55 (1H, d, J=7.8 Hz), 7.28-7.31 (1H, m), 7.21 (2H, d, J=7.6 Hz), 6.80 (1H, s), 6.51 (1H, d, J=7.2 Hz), 4.72 (1H, br. s), 3.71 (2H, br. s.), 3.04 (2H, br. s.), 2.22 (6H, s). ¹⁹F NMR (377 MHz, CDCl₃) δ ppm −75.96 (3F, s). m/z (ESI, +ve) 383.1 (M+H)⁺.

Example 103

2-(2-(2-chlorophenoxy)quinolin-8-yl)-6,7-dihydro-1H-pyrrolo[3,2-c]pyridin-4(5H)-one

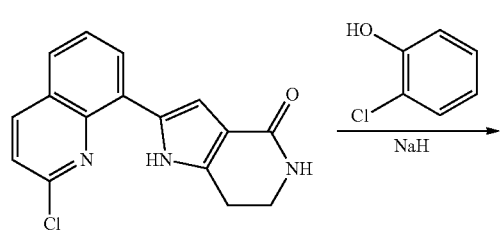

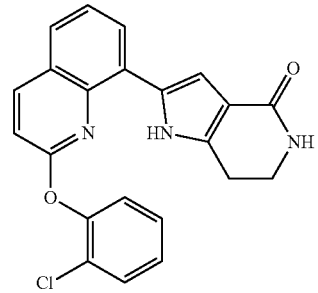

2-Chlorophenol (Aldrich; 0.122 mL, 1.176 mmol) was added to a suspension of NaH (60% w/w in mineral oil; 47.0 mg, 1.176 mmol) in DMF (1.0 mL) and the resulting solution was stirred at 25° C. for 10 min. 2-(2-Chloroquinolin-8-yl)-6,7-dihydro-1H-pyrrolo[3,2-c]pyridin-4(5H)-one (Example 1; 50.0 mg, 0.168 mmol) was added, and the resulting solution was heated at 80° C. for 3 d. The mixture was cooled to RT and partitioned between EtOAc (50 mL) and saturated aq. NH₄Cl (30 mL). The organic layer was separated, sequentially washed with water (2×20 mL) and brine (20 mL), dried over Na₂SO₄, filtered, and concentrated in vacuo. Chromatographic purification of the residue (silica gel, 0-10% MeOH/DCM) followed by rpHPLC of the collected material (Phenomenex Gemini $C_{18}$ column (150×30 mm, 10 µm), 35 mL/min, 5-100% ACN/H₂O+0.1% TFA) furnished 2-(2-(2-chlorophenoxy)quinolin-8-yl)-6,7-dihydro-1H-pyrrolo[3,2-c]pyridin-4(5H)-one 2,2,2-trifluoroacetate (48.0 mg, 0.095 mmol, 57% yield) as a yellow solid: ¹H NMR (400 MHz, CDCl₃) δ ppm 11.28 (1H, br. s.), 8.25 (1H, d, J=8.8 Hz), 8.04 (1H, dd, J=7.5, 0.8 Hz), 7.67 (1H, s), 7.62 (1H, dd, J=7.9, 1.3 Hz), 7.51-7.59 (1H, m), 7.43-7.49 (2H, m), 7.34-7.42 (2H, m), 7.30 (1H, d, J=9.0 Hz), 7.06 (1H, d, J=2.0 Hz), 3.58 (2H, t, J=6.9 Hz), 2.49 (2H, t, J=7.0 Hz). ¹⁹F NMR (377 MHz, CDCl₃) δ ppm −76.32 (3F, s). m/z (ESI, +ve) 390.0 (M+H)⁺.

Example 104

2-(3-methyl-2-phenoxyquinolin-8-yl)-6,7-dihydro-1H-pyrrolo[3,2-c]pyridin-4(5H)-one

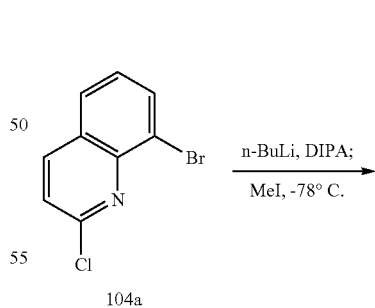

104a

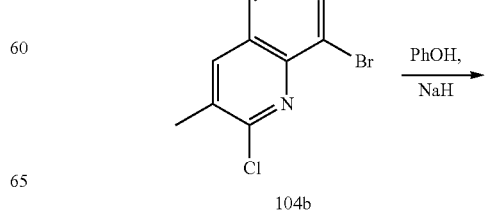

104b

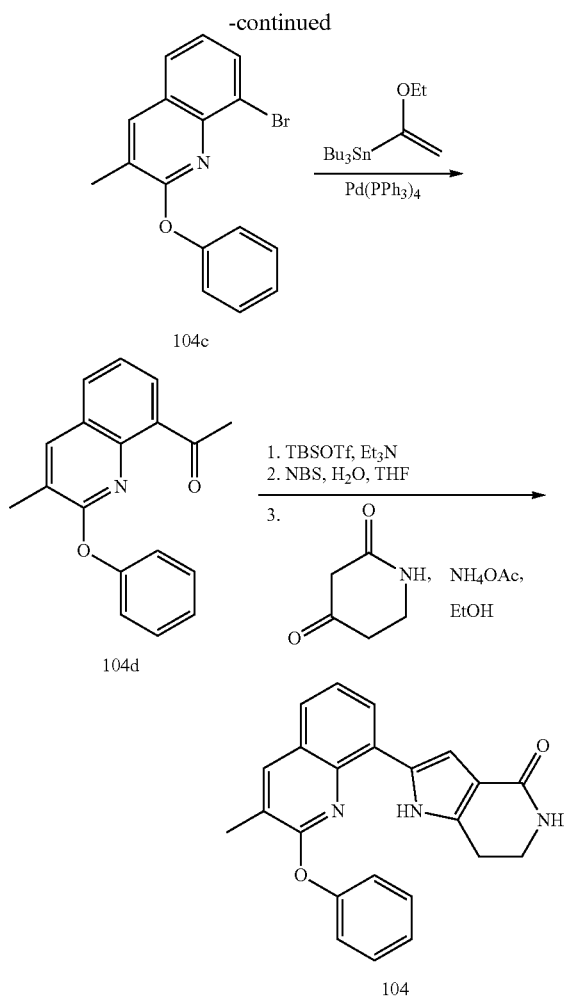

Preparation of 8-bromo-2-chloro-3-methylquinoline nBuLi (1.86 M in hexanes; 6.10 mL, 11.34 mmol) was added to a solution of diisopropylamine (1.600 mL, 11.34 mmol) in THF (20 mL) at 78° C., and the resulting solution was warmed to 0° C., stirred for 5 min, then cooled to 78° C. After 5 min, a solution of 8-bromo-2-chloroquinoline (Biofine International, Vancouver, BC; 2.5 g, 10.31 mmol) in THF (20.0 mL) was added (dropwise over 10 min) The resulting solution was stirred at 78° C. for 50 min and added (dropwise over 10 min) to a solution of MeI (1.925 mL, 30.9 mmol) in THF (20.0 mL) at 78° C. The resulting solution was stirred at 78° C. for 1 h. The mixture was then transferred to an ice bath, and water (1 mL) was added. The resulting mixture was warmed to RT and concentrated onto silica gel. Chromatographic purification (silica gel, 0-25% EtOAc/hexanes) furnished 8-bromo-2-chloro-3-methylquinoline (104b; 1.73 g, 6.74 mmol, 65% yield) as a light-yellow solid (64% pure), which was used without further purification in the subsequent step: m/z (ESI, +ve) 255.9 (M+H)$^+$.

Preparation of 8-bromo-3-methyl-2-phenoxyquinoline

Phenol (954 mg, 10.14 mmol) was added to a suspension of NaH (60% w/w in mineral oil; 406 mg, 10.14 mmol) in DMF (10 mL) at 0° C. and the resulting solution was stirred at 25° C. for 15 min. 8-Bromo-2-chloro-3-methylquinoline (510 mg, 1.988 mmol) was then added, and the resulting solution was heated at 60° C. for 2.5 d. The mixture was cooled to 25° C. and partitioned between EtOAc (100 mL) and saturated aq. NH$_4$Cl (80 mL). The organic layer was separated, sequentially washed with water (2×50 mL) and brine (50 mL), dried over Na$_2$SO$_4$, filtered, and concentrated in vacuo. Chromatographic purification of the residue (silica gel, 0-10% EtOAc/hexanes) furnished 8-bromo-3-methyl-2-phenoxyquinoline (505.5 mg, 1.609 mmol, 81% yield) as a colorless oil, which was used without further purification in the subsequent step: m/z (ESI, +ve) 314.0 (M+H)$^+$.

Preparation of 1-(3-methyl-2-phenoxyquinolin-8-yl)ethanone

A solution of 8-bromo-3-methyl-2-phenoxyquinoline (505.5 mg, 1.609 mmol), tributyl(1-ethoxyvinyl)stannane (Synthonix, Inc., Wake Forest, N.C.; 0.598 mL, 1.770 mmol), and Pd(PPh$_3$)$_4$ (93 mg, 0.080 mmol) in toluene (8.0 mL) was sparged with argon and then stirred under N$_2$ at 100° C. for 16 h. The mixture was cooled to 25° C. and concentrated onto silica gel. Chromatographic purification (silica gel, 0-20% EtOAc/hexanes) furnished 1-(3-methyl-2-phenoxyquinolin-8-yl)ethanone (326.0 mg, 1.176 mmol, 73% yield) as a white solid: $^1$H NMR (400 MHz, CDCl$_3$) δ ppm 7.95 (1H, s), 7.90 (1H, dd, J=7.2, 1.4 Hz), 7.82 (1H, dd, J=8.0, 1.2 Hz), 7.37-7.47 (3H, m), 7.23-7.25 (1H, m), 7.19 (2H, d, J=8.1 Hz), 2.55 (3H, d, J=0.6 Hz), 2.28 (3H, s). m/z (EST, +ve) 278.1 (M+H)$^+$.

Preparation of 2-(3-methyl-2-phenoxyquinolin-8-yl)-6,7-dihydro-1H-pyrrolo[3,2-c]pyridin-4(5H)-one Et$_3$N (0.105 mL, 0.751 mmol) and TBSOTf (0.146 mL, 0.635 mmol) were sequentially added (TBSOTf: dropwise, over 2 min) to a solution of 1-(3-methyl-2-phenoxyquinolin-8-yl)ethanone (160.1 mg, 0.577 mmol) in DCM (3.0 mL) at 0° C., and the resulting was stirred at 0° C. for 30 min. The mixture was partitioned between DCM (50 mL) and saturated aq. NaHCO$_3$ (20 mL). The organic layer was separated, and the aq. layer was extracted with DCM (2×20 mL). The combined organic extracts were then dried over Na$_2$SO$_4$, filtered, and concentrated in vacuo to provide 8-(1-((tert-butyldimethylsilyl)oxy)vinyl)-3-methyl-2-phenoxy quinoline (214.0 mg, 0.547 mmol, 95% yield) as a colorless oil. This material was taken up in THF (3.0 mL), water (0.166 mL, 9.24 mmol) and NBS (103 mg, 0.577 mmol) were sequentially added at 25° C., and the resulting solution was stirred at 25° C. for 15 min. The mixture was partitioned between Et$_2$O (50 mL) and water (30 mL). The organic layer was separated, sequentially washed with saturated aq. NaHCO$_3$ (20 mL), water (20 mL), and brine (20 mL), and then dried over MgSO$_4$, filtered, and concentrated in vacuo to provide 2-bromo-1-(3-methyl-2-phenoxyquinolin-8-yl)ethanone (240 mg) as a light-yellow oil: m/z (ESI, +ve) 356.0 (M+H)$^+$. NH$_4$OAc (178 mg, 2.309 mmol) and piperidine-2,4-dione (78 mg, 0.693 mmol) were added to the resulting oil, and the mixture was taken up in EtOH (3.0 mL) and stirred at 25° C. for 5 min. The reaction vial was sealed under argon and heated at 50° C. for 14.5 h. The mixture was cooled to 25° C. and concentrated in vacuo. The residue was partitioned between DCM (50 mL) and saturated aq. NaHCO$_3$ (30 mL). The aq. layer was extracted with DCM (3×30 mL), and the combined extracts were dried over Na$_2$SO$_4$, filtered, and concentrated in vacuo. Chromatographic purification of the residue (silica gel, 0-10% MeOH/DCM) furnished 2-(3-methyl-2-phenoxyquinolin-8-yl)-6,7- dihydro-1H-pyrrolo[3,2-c]pyridin-4(5H)-one (53.4 mg, 0.145 mmol, 25% yield) as a yellow solid: ¹H NMR (400 MHz, CDCl₃) δ ppm 11.28 (1H, br. s.), 7.92-8.00 (2H, m), 7.50-7.58 (3H, m), 7.34-7.43 (2H, m), 7.29 (2H, d, J=7.8 Hz), 7.08 (1H, d, J=1.8 Hz), 5.36 (1H, br. s.), 3.50 (2H, t, J=6.7 Hz), 2.56 (3H, s), 2.42 (2H, t, J=6.9 Hz). m/z (ESI, +ve) 370.1 (M+H)⁺.

Example 105

2-(3-methyl-2-(phenylamino)quinolin-8-yl)-6,7-dihydro-1H-pyrrolo[3,2-c]pyridin-4(5H)-one Example 106

2-(2-((4-bromophenyl)amino)-3-methylquinolin-8-yl)-6,7-dihydro-1H-pyrrolo[3,2-c]pyridin-4(5H)-one

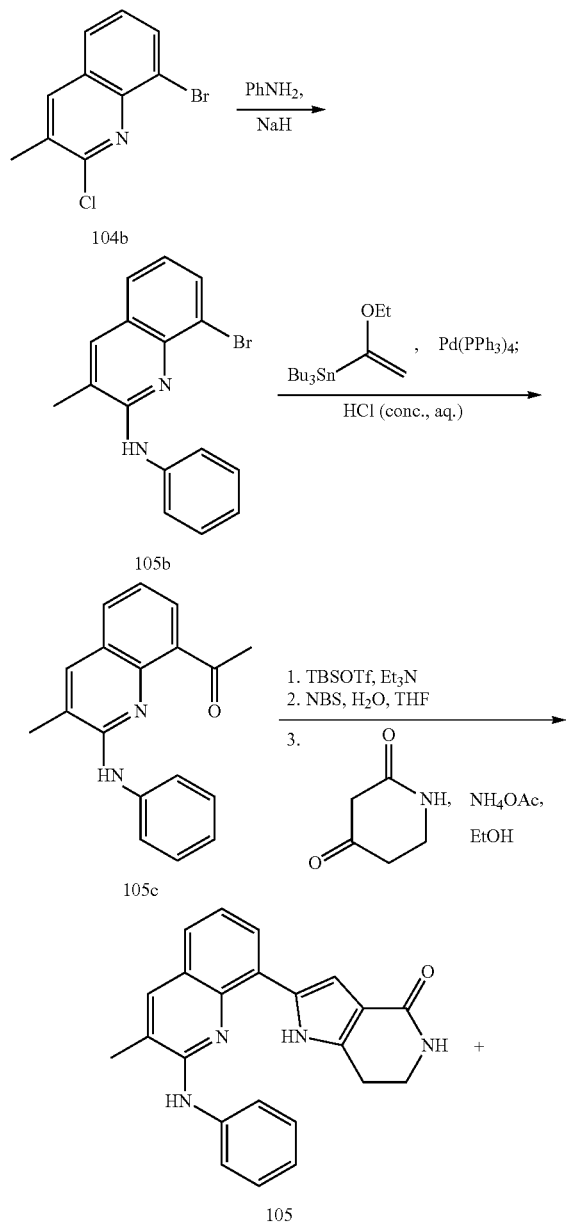

Preparation of 8-bromo-3-methyl-N-phenylquinolin-2-amine

NaH (60% w/w in mineral oil; 390 mg, 9.75 mmol) was added to a solution of aniline (0.888 mL, 9.75 mmol) in DMF (4.0 mL) at 0° C. and the resulting suspension was stirred at 0° C. for 2 min, then warmed to 25° C. and stirred for 5 min. 8-Bromo-2-chloro-3-methylquinoline (Example 104b; 529 mg, 2.062 mmol) was added as a solid, and the resulting solution was stirred at 25° C. for 1.5 h, then at 80° C. bath for 2.5 h. The mixture was cooled to 25° C. and partitioned between EtOAc (100 mL) and saturated aq. NH₄Cl (80 mL). The organic layer was separated and the aq. layer was extracted with EtOAc (2×50 mL). The combined organic extracts were dried over Na₂SO₄, filtered, and concentrated in vacuo. Chromatographic purification of the residue (silica gel, 0-40% EtOAc/hexanes) furnished 8-bromo-3-methyl-N-phenylquinolin-2-amine (182.0 mg, 0.581 mmol, 28% yield) as a brown oil: m/z (ESI, +ve) 313.1 (M+H)⁺.

Preparation of 1-(3-methyl-2-(phenylamino)quinolin-8-yl)ethanone

A solution of 8-bromo-3-methyl-N-phenylquinolin-2-amine (182.0 mg, 0.581 mmol), tributyl(1-ethoxyvinyl)stannane (Synthonix, Inc., Wake Forest, N.C.; 0.216 mL, 0.639 mmol), and Pd(PPh₃)₄ (33.6 mg, 0.029 mmol) in toluene (3.0 mL) was sparged with argon and stirred under argon at 100° C. for 16 h. The mixture was then concentrated in vacuo, and the residue was taken up in THF (3.0 mL). HCl (concentrated, aq.; 0.073 mL, 0.872 mmol) was added, and the resulting mixture was stirred at 60° C. for 15 min. Et₃N (0.243 mL, 1.743 mmol) was added, and the mixture was concentrated onto silica gel. Chromatographic purification (silica gel, 0-50% EtOAc/hexanes) furnished 1-(3-methyl-2-(phenylamino)quinolin-8-yl)ethanone (161 mg, 0.583 mmol, 100% yield) as a yellow oil: ¹H NMR (400 MHz, CD Cl₃) δ ppm 7.79 (1H, s), 7.76 (1H, d, J=7.2 Hz), 7.64-7.72 (3H, m), 7.38 (2H, t, J=7.8 Hz), 7.29 (1H, t, J=7.5 Hz), 7.11 (1H, t, J=7.4 Hz), 6.52 (1H, br. s.), 2.76 (3H, s), 2.44 (3H, s). m/z (ESI, +ve) 277.1 (M+H)⁺.

Preparation of 2-(3-methyl-2-(phenylamino)quinolin-8-yl)-6,7-dihydro-1H-pyrrolo[3,2-c]pyridin-4(5H)-one and 2-(2-((4-bromophenyl)amino)-3-methylquinolin-8-yl)-6,7-dihydro-1H-pyrrolo[3,2-c]pyridin-4(5H)-one Et₃N (0.203 mL, 1.457 mmol) and TBSOTf (0.281 mL, 1.224 mmol, added dropwise, over 2 min) were sequentially added to a solution of 1-(3-methyl-2-(phenylamino)quinolin- 8-yl)ethanone (161 mg, 0.583 mmol) in DCM (3.0 mL) at 0° C., and the resulting solution was stirred at 0° C. for 30 min. The resulting mixture was partitioned between DCM (50 mL) and saturated aq. NaHCO$_3$ (20 mL). The organic layer was separated, and the aq. layer was extracted with DCM (2×20 mL). The combined organic extracts were then dried over Na$_2$SO$_4$, filtered, and concentrated in vacuo to provide 8-(1-((tert-butyldimethylsilyl)oxy)vinyl)-3-methyl-N-phenylquinolin-2-amine as a yellow-orange oil. This material was taken up in THF (3.0 mL), water (0.168 mL, 9.32 mmol) and NBS (104 mg, 0.583 mmol) were sequentially added, and the resulting solution was stirred at 25° C. for 15 min. The mixture was partitioned between Et$_2$O (50 mL) and water (30 mL). The organic layer was separated, sequentially washed with saturated aq. NaHCO$_3$ (20 mL), water (20 mL), and brine (20 mL), and then dried over MgSO$_4$, filtered, and concentrated in vacuo to provide 2-bromo-1-(3-methyl-2-(phenylamino)quinolin-8-yl)ethanone (250 mg) as a yellow-orange solid (containing ca. 30 wt % 2-bromo-1-(2-((4-bromophenyl)amino)-3-methylquinolin-8-yl)ethanone).

NH$_4$OAc (180 mg, 2.331 mmol) and piperidine-2,4-dione (79 mg, 0.699 mmol) were added to this solid, and the mixture was taken up in EtOH (3.0 mL) and stirred at 25° C. for 5 min. The reaction vial was then sealed under argon and heated at 50° C. for 14 h. The mixture was cooled to 25° C. and concentrated in vacuo. The residue was partitioned between DCM (50 mL) and saturated aq. NaHCO$_3$ (30 mL). The aq. layer was extracted with DCM (3×30 mL), and the combined extracts were dried over Na$_2$SO$_4$, filtered, and concentrated in vacuo. Chromatographic purification of the residue (silica gel, 0-10% DCM/MeOH) followed by rpHPLC of the collected solid (Phenomenex Gemini C$_{18}$ column (150×30 mm, 10 µm), 35 mL/min, 5-100% ACN/H$_2$O+0.1% TFA) separately provided 2-(3-methyl-2-(phenylamino)quinolin-8-yl)-6,7-dihydro-1H-pyrrolo[3,2-c]pyridin-4(5H)-one 2,2,2-trifluoroacetate (20.5 mg, 0.042 mmol, 7% yield) as a yellow solid (following trituration of initially obtained oil with Et$_2$O): $^1$H NMR (400 MHz, MeOH-d4) δ ppm 8.30 (1H, br. s.), 7.79 (2H, d, J=7.4 Hz), 7.62 (2H, t, J=7.8 Hz), 7.50-7.57 (3H, m), 7.44 (1H, t, J=7.6 Hz), 6.57 (1H, s), 3.53 (2H, t, J=7.2 Hz), 2.78 (2H, t, J=6.8 Hz), 2.56 (3H, s). $^{19}$F NMR (377 MHz, MeOH-d4) δ ppm −77.49 (3F, s). m/z (ESI, +ve) 369.2 (M+H)$^+$. 2-(2-((4-bromophenyl)amino)-3-methylquinolin-8-yl)-6,7-dihydro-1H-pyrrolo[3,2-c]pyridin-4(5H)-one 2,2,2-trifluoroacetate (6.9 mg, 0.012 mmol, 2% yield) as an orange oil: $^1$H NMR (400 MHz, MeOH-d4) δ ppm 8.14 (1H, br. s.), 7.85 (1H, d, J=7.5 Hz), 7.69 (3H, d, J=8.6 Hz), 7.44-7.50 (2H, m), 7.43 (1H, t, J=7.9 Hz), 6.77 (1H, s), 3.56 (2H, t, J=7.1 Hz), 2.70 (2H, t, J=7.0 Hz), 2.52 (3H, s). $^{19}$F NMR (377 MHz, MeOH-d4) δ ppm −77.51 (3F, br. s.). m/z (ESI, +ve) 447.0 (M+H)$^+$.

Example 107

2-(2-((2-chlorophenyl)amino)quinolin-8-yl)-1H-pyrrolo[3,2-c]pyridin-4(5H)-one

Example 108

2-(2-((2-chlorophenyl)amino)quinolin-8-yl)-6,7-dihydro-1H-pyrrolo[3,2-c]pyridin-4(5H)-one

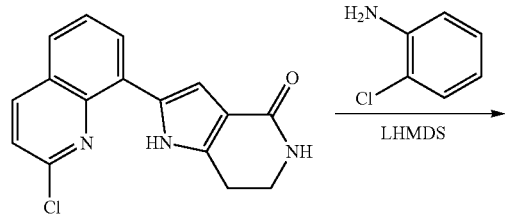

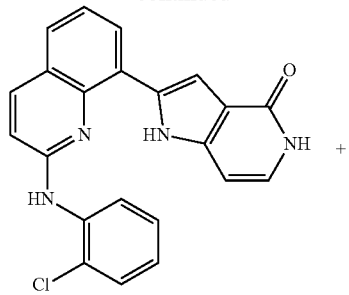

107

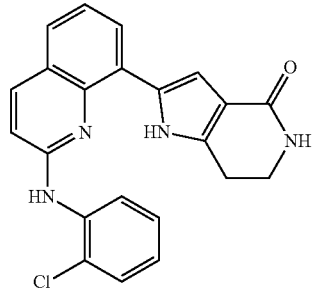

108

A solution of 2-(2-chloroquinolin-8-yl)-6,7-dihydro-1H-pyrrolo[3,2-c]pyridin-4(5H)-one (Example 1; 53.5 mg, 0.180 mmol), 2-chloroaniline (94 µl, 0.898 mmol), and LHMDS (1.0 M in THF; 898 µl, 0.898 mmol) was stirred in a sealed flask at 65° C. for 4 h. The mixture was then partitioned between DCM (50 mL) and saturated aq. NH$_4$Cl (30 mL). The organic layer was separated, and the aq. layer was extracted with DCM (2×20 mL). The combined organic extracts were dried over Na$_2$SO$_4$, filtered, and concentrated in vacuo. Purification of the residue by supercritical-fluid chromatography (Chiralcel OJ-H (250×21 mm, 5 µm), 55% liquid CO$_2$/45% 1:1:1 MeOH:EtOH:IPA (+20 mM aq. NH$_4$OH), 75 mL/min) separately provided 2-(2-((2-chlorophenyl)amino)-quinolin-8-yl)-1H-pyrrolo[3,2-c]pyridin-4(5H)-one (107; 9.7 mg, 0.025 mmol, 14% yield; first-eluting compound) as a yellow solid: $^1$H NMR (400 MHz, CDCl$_3$) δ ppm 12.47 (1H, br. s.), 9.73 (1H, br. s.), 8.17 (2H, t, J=8.9 Hz), 8.06 (1H, d, J=9.0 Hz), 7.59 (2H, t, J=7.6 Hz), 7.39 (3H, quin, J=7.8 Hz), 7.22 (1H, t, J=7.6 Hz), 6.99 (2H, d, J=8.6 Hz), 6.94 (1H, s), 6.08 (1H, d, J=7.0 Hz). m/z (ESI, +ve) 387.0 (M+H)$^+$: and 2-(2-((2-chlorophenyl)amino)quinolin-8-yl)-6,7-dihydro-1H-pyrrolo[3,2-c]pyridin-4(5H)-one (108; 14.0 mg, 0.036 mmol, 20% yield; second-eluting compound) as a yellow solid: $^1$H NMR (400 MHz, CDCl$_3$) δ ppm 12.16 (1H, s), 8.04 (3H, t, J=8.7 Hz), 7.53 (2H, d, J=8.0 Hz), 7.35-7.41 (1H, m), 7.31 (2H, t, J=7.8 Hz), 7.09-7.18 (2H, m), 6.95 (1H, d, J=8.8 Hz), 5.32 (1H, br. s.), 3.53-3.60 (2H, m), 2.68 (2H, br. s.). m/z (ESI, +ve) 389.1 (M+H)$^+$.

Example 109

2-(2-(3-hydroxyphenoxy)quinolin-8-yl)-6,7-dihydro-1H-pyrrolo[3,2-c]pyridin-4(5H)-one

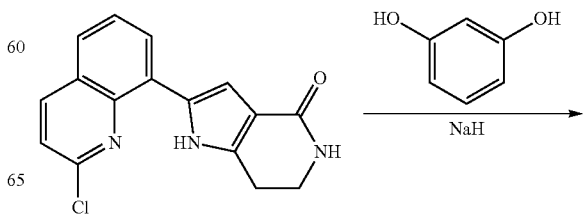

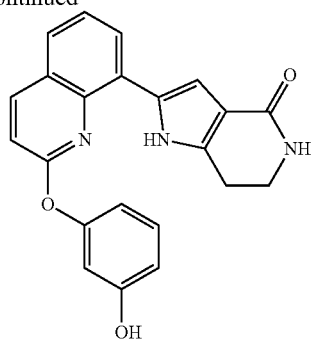

Prepared according to Example 103 using resorcinol (125.5 mg, 1.140 mmol) and 2-(2-chloroquinolin-8-yl)-6,7-dihydro-1H-pyrrolo[3,2-c]pyridin-4(5H)-one (Example 1; 50.0 mg, 0.168 mmol), heating at 90° C. for 18 h. Chromatographic purification (silica gel, 0-10% MeOH/DCM) furnished 2-(2-(3-hydroxyphenoxy)-quinolin-8-yl)-6,7-dihydro-1H-pyrrolo[3,2-c]pyridin-4(5H)-one (48.4 mg, 0.130 mmol, 78% yield) as a light-yellow solid: $^1$H NMR (400 MHz, DMSO-$d_6$) δ ppm 11.20 (1H, br. s.), 9.86 (1H, s), 8.47 (1H, d, J=8.8 Hz), 8.14 (1H, d, J=7.6 Hz), 7.78 (1H, d, J=7.2 Hz), 7.47 (1H, t, J=7.7 Hz), 7.35-7.42 (2H, m), 6.98 (1H, d, J=2.2 Hz), 6.94 (1H, br. s.), 6.83 (1H, m, J=7.8, 1.8 Hz), 6.79 (1H, dd, J=7.9, 1.7 Hz), 6.74 (1H, t, J=2.2 Hz), 3.31-3.37 (2H, m), 2.47-2.49 (2H, obsc. m). m/z (ESI, +ve) 372.0 (M+H)$^+$.

Example 110

2-(2-((3-aminophenyl)amino)quinolin-8-yl)-6,7-dihydro-1H-pyrrolo[3,2-c]pyridin-4(5H)-one

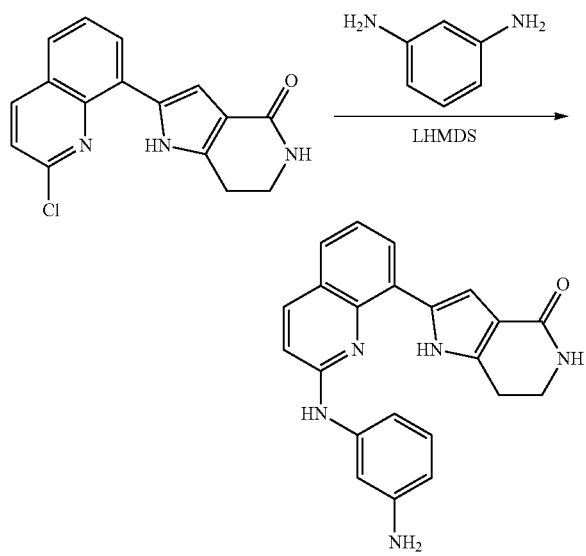

Prepared according to Example 102 using benzene-1,3-diamine (96 mg, 0.888 mmol), 2-(2-chloroquinolin-8-yl)-6,7-dihydro-1H-pyrrolo[3,2-c]pyridin-4(5H)-one (Example 1; 52.9 mg, 0.178 mmol), and LHMDS (1.0 M in THF; 0.888 mL, 0.888 mmol) in THF (1.0 mL), stirring at 25° C. for 3 h. Purification by reversed-phase HPLC (Phenomenex Gemini $C_{18}$ column (150×30 mm, 10 μm), 35 mL/min, 5-100% ACN/$H_2O$+0.1% TFA) furnished 2-(2-((3-aminophenyl)amino)quinolin-8-yl)-6,7-dihydro-1H-pyrrolo[3,2-c]pyridin-4(5H)-one 2,2,2-trifluoroacetate (44.0 mg, 0.091 mmol, 51% yield) as a brown solid: $^1$H NMR (400 MHz, MeOH-d4) δ ppm 8.23 (1H, br. s.), 8.20 (1H, d, J=9.0 Hz), 7.87 (1H, dd, J=7.5, 1.3 Hz), 7.70 (1H, dd, J=8.0, 1.0 Hz), 7.50 (1H, t, J=8.2 Hz), 7.43 (1H, t, J=7.7 Hz), 7.38 (1H, dd, J=8.2, 1.2 Hz), 7.34 (1H, s), 7.13 (1H, d, J=9.0 Hz), 7.07 (1H, dd, J=8.0, 1.4 Hz), 3.61 (2H, t, J=7.1 Hz), 2.92 (2H, t, J=7.1 Hz). $^{19}$F NMR (377 MHz, MeOH-d4) δ ppm −77.59 (3F, s). m/z (ESI, +ve) 370.1 (M+H)$^+$.

Example 111

(R)-2-(2-((1-phenylethyl)amino)quinolin-8-yl)-6,7-dihydro-1H-pyrrolo[3,2-c]pyridin-4(5H)-one

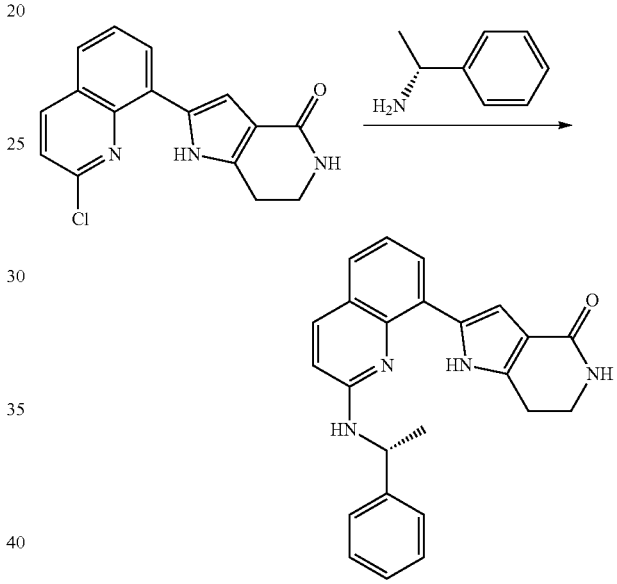

A solution of 2-(2-chloroquinolin-8-yl)-6,7-dihydro-1H-pyrrolo[3,2-c]pyridin-4(5H)-one (Example 1; 68.4 mg, 0.230 mmol) and (R)-(+)-alpha-methylbenzylamine (Aldrich; 0.117 mL, 0.919 mmol) in N-methyl-2-pyrrolidinone (0.2 mL) was stirred at 100° C. for 2.5 d. The mixture was partitioned between DCM (50 mL) and 0.1 N aq. HCl (30 mL). The organic layer was separated, and the aq. layer was extracted with DCM (2×20 mL). The combined organic extracts were sequentially washed with water (30 mL), dried over $Na_2SO_4$, filtered, and concentrated in vacuo. Chromatographic purification of the residue (silica gel, 0-7% MeOH/DCM) followed by rpHPLC (Phenomenex Gemini $C_{18}$ column (150×30 mm, 10 μm), 35 mL/min, 5-100% ACN/$H_2O$+0.1% TFA) provided (R)-2-(2-((1-phenylethyl)amino)quinolin-8-yl)-6,7-dihydro-1H-pyrrolo[3,2-c]pyridin-4(5H)-one 2,2,2-trifluoroacetate (10.5 mg, 0.021 mmol, 9% yield) as a yellow solid: $^1$H NMR (400 MHz, MeOH-d4) δ ppm 8.41 (1H, d, J=9.6 Hz), 7.87 (1H, d, J=7.8 Hz), 7.77 (1H, br. s.), 7.59 (1H, t, J=7.7 Hz), 7.37 (3H, br. s.), 7.27-7.33 (2H, m), 7.23 (1H, br. s.), 6.83 (1H, br. s.), 5.10 (1H, q, J=6.0 Hz), 3.70 (2H, t, J=7.0 Hz), 3.02 (2H, t, J=7.1 Hz), 1.72 (3H, d, J=6.7 Hz). $^{19}$F NMR (377 MHz, MeOH-d4) δ ppm −77.36 (3F, s). m/z (ESI, +ve) 383.1 (M+H)$^+$.

Example 112

(S)-2-(2-((1-phenylethyl)amino)quinolin-8-yl)-6,7-dihydro-1H-pyrrolo[3,2-c]pyridin-4(5H)-one

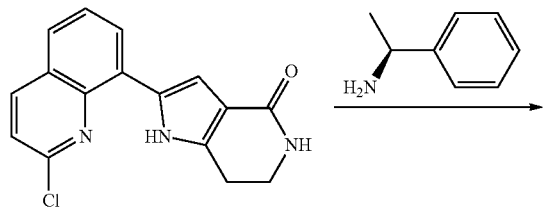

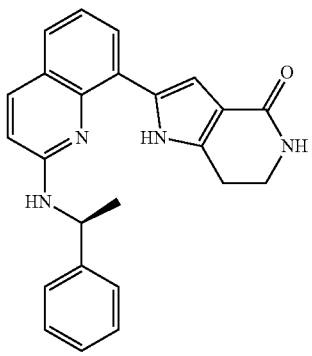

A solution of 2-(2-chloroquinolin-8-yl)-6,7-dihydro-1H-pyrrolo[3,2-c]pyridin-4(5H)-one (Example 1; 77.5 mg, 0.260 mmol) and (S)-1-phenylethanamine (Alfa Aesar, Ward Hill, Mass.; 0.133 mL, 1.041 mmol) in DMSO (0.2 mL) was stirred at 100° C. for 2.5 d. The mixture was partitioned between DCM (50 mL) and 0.1 N aq. HCl (30 mL). The organic layer was separated, and the aq. layer was extracted with DCM (2×20 mL). The combined organic extracts were sequentially washed with water (30 mL), dried over $Na_2SO_4$, filtered, and concentrated in vacuo. Chromatographic purification of the residue (silica gel, 0-7% MeOH/DCM) followed by rpHPLC (Phenomenex Gemini $C_{18}$ column (150×30 mm, 10 μm), 35 mL/min, 5-100% ACN/$H_2O$+0.1% TFA) provided (S)-2-(2-((1-phenylethyl)amino)quinolin-8-yl)-6,7-dihydro-1H-pyrrolo[3,2-c]pyridin-4(5H)-one 2,2,2-trifluoroacetate (26.0 mg, 0.052 mmol, 20% yield) as a yellow solid: $^1$H NMR (400 MHz, MeOH-$d_4$) δ ppm 8.39 (1H, d, J=9.4 Hz), 7.86 (1H, d, J=7.8 Hz), 7.74 (1H, br. s.), 7.57 (1H, t, J=7.2 Hz), 7.31-7.43 (3H, m), 7.27 (2H, br. s.), 7.22 (1H, br. d, J=8.7 Hz), 6.81 (1H, br. s.), 5.07 (1H, q, J=6.1 Hz), 3.68 (2H, t, J=6.9 Hz), 3.00 (2H, t, J=7.1 Hz), 1.69 (3H, d, J=6.8 Hz). $^{19}$F NMR (377 MHz, MeOH-$d_4$) δ ppm −77.42 (3F, s). m/z (ESI, +ve) 383.1 (M+H)$^+$.

Example 113

2-(2-(1-phenylvinyl)quinolin-8-yl)-6,7-dihydro-1H-pyrrolo[3,2-c]pyridin-4(5H)-one

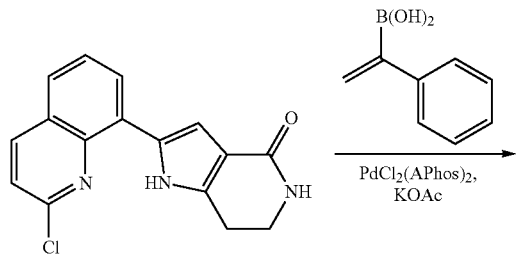

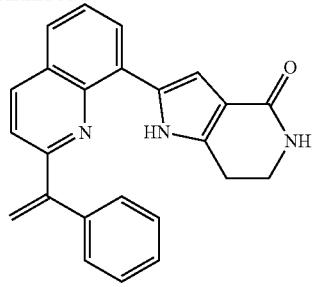

A mixture of 2-(2-chloroquinolin-8-yl)-6,7-dihydro-1H-pyrrolo[3,2-c]pyridin-4(5H)-one (Example 1; 200 mg, 0.672 mmol), (1-phenylvinyl)boronic acid (Aldrich; 139.1 mg, 0.941 mmol), $PdCl_2(APhos)_2$ (23.8 mg, 0.034 mmol), and KOAc (131.8 mg, 1.34 mmol) in EtOH (3.4 mL) was stirred under argon in a sealed tube at 80° C. for 23 h. The mixture was concentrated onto silica gel, and chromatographically purified (silica gel, 0-10% MeOH/DCM) to provide 2-(2-(1-phenylvinyl)quinolin-8-yl)-6,7-dihydro-1H-pyrrolo[3,2-c]pyridin-4(5H)-one (189.2 mg, 0.518 mmol, 77% yield) as an orange solid: $^1$H NMR (400 MHz, CDCl$_3$) δ ppm 12.05 (1H, br. s.), 8.23 (1H, d, J=8.8 Hz), 8.08 (1H, d, J=7.4 Hz), 7.81 (1H, d, J=8.6 Hz), 7.64 (1H, d, J=8.0 Hz), 7.54 (1H, d, J=7.8 Hz), 7.46-7.52 (2H, m), 7.41-7.46 (3H, m), 7.14 (1H, s), 6.01 (1H, s), 5.85 (1H, s), 5.47 (1H, br. s.), 3.47 (2H, td, J=6.9, 1.9 Hz), 2.33 (2H, t, J=6.8 Hz). m/z (ESI, +ve) 366.2 (M+H)$^+$.

Example 114

2-(2-(1-phenylcyclopropyl)quinolin-8-yl)-6,7-dihydro-1H-pyrrolo[3,2-c]pyridin-4(5H)-one

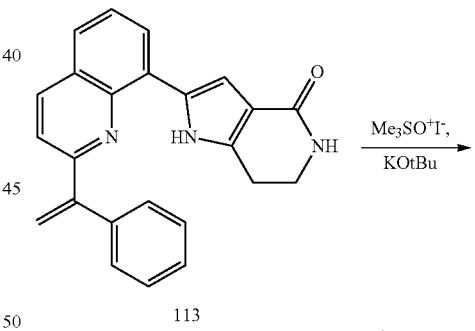

113

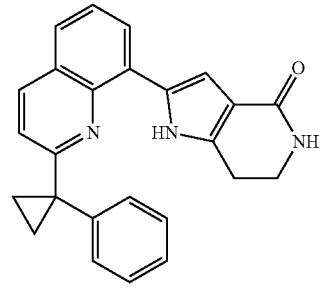

A mixture of potassium tert-butoxide (18.42 mg, 0.164 mmol) and trimethylsulfoxonium iodide (36.1 mg, 0.164 mmol) in anhydrous DMSO (0.5 mL) was stirred under argon at 25° C. for 10 min, providing a colorless solution. A solution of 2-(2-(1-phenylvinyl)quinolin-8-yl)-6,7-dihydro-1H-pyrrolo[3,2-c]pyridin-4(5H)-one (Example 113; 30 mg, 0.082 mmol) in DMSO (1.0 mL) was added (dropwise, over 2 min), and the resulting solution was stirred at 25° C. for 30 min. The reaction solution was diluted with LON aq. HCl (0.1 mL), then partitioned between DCM (50 mL) and water (20 mL). The aq. layer was extracted with additional DCM (20 mL), and the combined organic extracts were dried over Na$_2$SO$_4$, filtered, and concentrated in vacuo. Chromatographic purification of the residue (silica gel, 0-10% MeOH/DCM) furnished 2-(2-(1-phenylcyclopropyl)quinolin-8-yl)-6,7-dihydro-1H-pyrrolo[3,2-c]pyridin-4(5H)-one (18.8 mg, 0.050 mmol, 60% yield) as a yellow solid: $^1$H NMR (400 MHz, CDCl$_3$) δ ppm 12.49 (1H, br. s.), 8.08 (1H, dd, J=7.4, 1.0 Hz), 8.00 (1H, d, J=8.6 Hz), 7.57 (1H, d, J=7.2 Hz), 7.44-7.50 (3H, m), 7.42 (2H, t, J=7.3 Hz), 7.33-7.38 (1H, m), 7.19 (1H, d, J=2.0 Hz), 7.07 (1H, d, J=8.8 Hz), 5.40 (1H, br. s.), 3.63 (2H, td, J=6.8, 2.2 Hz), 2.85 (2H, t, J=6.9 Hz), 1.68-1.72 (2H, m), 1.55-1.60 (2H, m). m/z (ESI, +ve) 380.1 (M+H)$^+$.

Example 245 rac-2-(2-(1-phenylethyl)quinolin-8-yl)-6,7-dihydro-1H-pyrrolo[3,2-c]pyridin-4(5H)-one

Example 115

2-(2-(1-phenylethyl)quinolin-8-yl)-6,7-dihydro-1H-pyrrolo[3,2-c]pyridin-4(5H)-one (first-eluting enantiomer)

Example 116

2-(2-(1-phenylethyl)quinolin-8-yl)-6,7-dihydro-1H-pyrrolo[3,2-c]pyridin-4(5H)-one (second-eluting enantiomer)

A suspension of 2-(2-(1-phenylvinyl)quinolin-8-yl)-6,7-dihydro-1H-pyrrolo[3,2-c]pyridin-4(5H)-one (Example 113; 102.4 mg, 0.280 mmol) and palladium on carbon (10% w/w; 59.6 mg, 0.056 mmol) in MeOH (3.0 mL) was cycled under a H$_2$ gas atmosphere (1 atm; 3 evacuation/H2 back-fill cycles) and then stirred at 25° C. for 1 d. The mixture was filtered through Celite, washing the filter cake with MeOH (10 mL). The combined filtrates were concentrated in vacuo to provide rac-2-(2-(1-phenylethyl)quinolin-8-yl)-6,7-dihydro-1H-pyrrolo[3,2-c]pyridin-4(5H)-one (81.0 mg, 0.220 mmol, 79% yield) as a yellow-orange solid: $^1$H NMR (400 MHz, CDCl$_3$) δ ppm 12.91 (1H, br. s.), 8.07-8.13 (2H, m), 7.60 (1H, dd, J=8.0, 1.0 Hz), 7.48-7.54 (1H, m), 7.35 (1H, d, J=6.8 Hz), 7.32-7.34 (2H, m), 7.29 (3H, d, J=6.8 Hz), 7.21 (1H, d, J=2.0 Hz), 5.38 (1H, br. s.), 4.54 (1H, q, J=7.0 Hz), 3.64 (2H, td, J=6.8, 2.5 Hz), 2.87-2.93 (2H, m), 1.87 (3H, d, J=7.0 Hz). m/z (ESI, +ve) 368.3 (M+H)$^+$. Separation of this material by supercritical-fluid chromatography (Chiralcel OJ (250×21 mm, 10 μm), 50% liquid CO$_2$/50% MeOH (+40 mM NH3), 50 mL/min) separately afforded 2-(2-(1-phenylethyl)quinolin-8-yl)-6,7-dihydro-1H-pyrrolo[3,2-c]pyridin-4(5H)-one, first-eluting enantiomer (115; 30.5 mg, 0.083 mmol) and 2-(2-(1-phenylethyl)quinolin-8-yl)-6,7-dihydro-1H-pyrrolo[3,2-c]pyridin-4(5H)-one, second eluting enantiomer (116; 27.6 mg, 0.075 mmol).

Example 250 rac-7-ethyl-2-(3-methyl-2-(phenylamino)quinolin-8-yl)-6,7-dihydro-1H-pyrrolo[3,2-c]pyridin-4(5H)-one

Example 117

7-ethyl-2-(3-methyl-2-(phenylamino)quinolin-8-yl)-6,7-dihydro-1H-pyrrolo[3,2-c]pyridin-4(5H)-one (first-eluting enantiomer)

Example 118

7-ethyl-2-(3-methyl-2-(phenylamino)quinolin-8-yl)-6,7-dihydro-1H-pyrrolo[3,2-c]pyridin-4(5H)-one (second-eluting enantiomer)

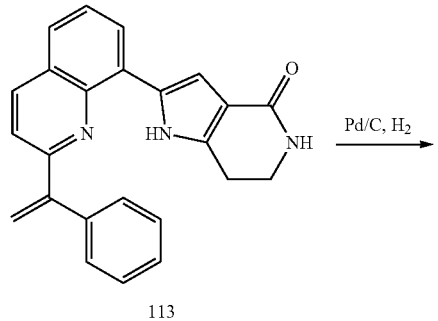

113

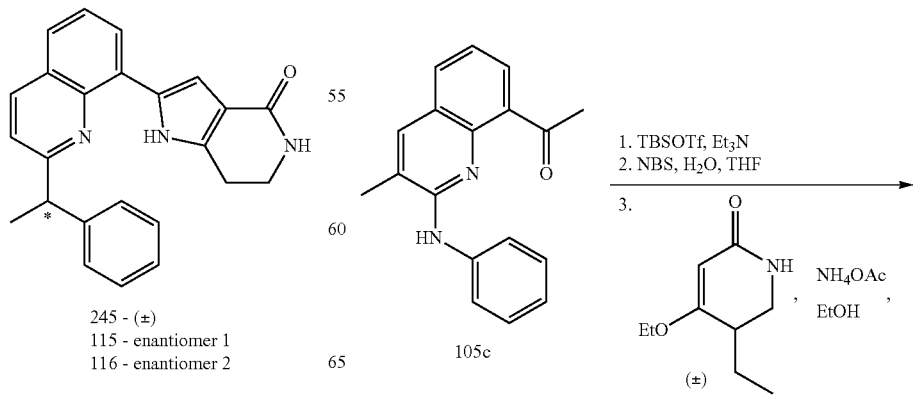

245 - (±)
115 - enantiomer 1
116 - enantiomer 2

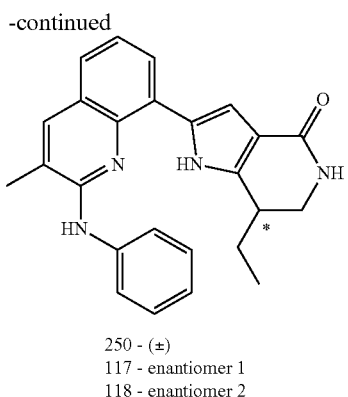

250 - (±)
117 - enantiomer 1
118 - enantiomer 2

Et₃N (0.241 mL, 1.728 mmol) and TBSOTf (0.318 mL, 1.383 mmol, added dropwise, over 2 min) were sequentially added to a solution of 1-(3-methyl-2-(phenylamino)quinolin-8-yl)ethanone (Example 105c; 308.1 mg, 0.691 mmol) in DCM (3.5 mL) at 0° C., and the resulting solution was stirred at 0° C. for 30 min. The mixture was then partitioned between DCM (50 mL) and saturated aq. NaHCO₃ (20 mL). The organic layer was separated, and the aq. layer was extracted with DCM (2×20 mL). The combined organic extracts were dried over Na₂SO₄, filtered, and concentrated in vacuo to provide crude 8-(1-((tert-butyldimethylsilyl)oxy)vinyl)-3-methyl-N-phenylquinolin-2-amine (450.0 mg) as a yellow-orange solid. This material was taken up in THF (3.50 mL), water (0.199 mL, 11.06 mmol) and NBS (123 mg, 0.691 mmol) were sequentially added at 0° C., and the resulting solution was stirred at 0° C. for 2 min. The mixture was partitioned between Et₂O (50 mL) and water (30 mL). The organic layer was separated, sequentially washed with saturated aq. NaHCO₃ (20 mL), water (20 mL), and brine (20 mL), and then dried over Na₂SO₄, filtered, and concentrated in vacuo to provide crude 2-bromo-1-(3-methyl-2-(phenylamino)quinolin-8-yl)ethanone (404.1 mg) as a yellow-orange solid. NH₄OAc (213 mg, 2.77 mmol) and 4-ethoxy-5-ethyl-5,6-dihydropyridin-2(1H)-one (prepared according to *Synthesis* 2007, 3185-3190; 140 mg, 0.830 mmol) were added to the resulting solid. The mixture was taken up in EtOH (3.5 mL) and heated in a sealed flask under argon at 50° C. for 16 h. The mixture was then cooled to 25° C. and concentrated in vacuo. The residue was partitioned between DCM (50 mL) and sat. aq. NaHCO₃ (30 mL). The aq. layer was extracted with DCM (3×30 mL), and the combined extracts were dried over Na₂SO₄, filtered, and concentrated in vacuo. Chromatographic purification of the residue (silica gel, 0-100% EtOAc/hexanes, then 0-10% MeOH/DCM) furnished rac-7-ethyl-2-(3-methyl-2-(phenylamino)quinolin-8-yl)-6,7-dihydro-1H-pyrrolo[3,2-c]pyridin-4(5H)-one (80.6 mg, 0.203 mmol, 29% yield) as a yellow solid: ¹H NMR (400 MHz, CD Cl₃) δ ppm 12.34 (1H, br. s.), 7.96 (1H, dd, J=7.5, 1.1 Hz), 7.83 (1H, s), 7.52 (2H, d, J=7.6 Hz), 7.45 (1H, dd, J=7.8, 1.0 Hz), 7.41 (2H, t, J=7.8 Hz), 7.30 (1H, t, J=7.7 Hz), 7.21 (1H, t, J=7.5 Hz), 7.10 (1H, d, J=2.2 Hz), 6.44 (1H, br. s.), 5.22 (1H, br. s.), 3.63 (1H, ddd, J=12.0, 5.5, 2.1 Hz), 3.23 (1H, ddd, J=12.0, 6.2, 3.1 Hz), 2.46-2.54 (1H, m), 2.45 (3H, s), 1.14-1.23 (1H, m), 1.02-1.12 (1H, m), 0.65 (3H, t, J=7.4 Hz). m/z (ESI, +ve) 397.2 (M+H)⁺. Separation of this material by supercritical-fluid chromatography (Chiralcel AD-H (250×21 mm, 5 µm), 55% liquid CO₂/45% MeOH (+20 mM NH3), 60 mL/min) separately afforded 7-ethyl-2-(3-methyl-2-(phenylamino)quinolin-8-yl)-6,7-dihydro-1H-pyrrolo[3, 2-c]pyridin-4(5H)-one, first-eluting enantiomer (117; 27.0 mg, 0.068 mmol) and 7-ethyl-2-(3-methyl-2-(phenylamino)quinolin-8-yl)-6,7-dihydro-1H-pyrrolo[3,2-c]pyridin-4 (5H)-one, second eluting enantiomer (118; 27.8 mg, 0.070 mmol).

Example 119 rac-7-benzyl-2-(quinolin-8-yl)-6,7-dihydro-1H-pyrrolo[3,2-c]pyridin-4(5H)-one

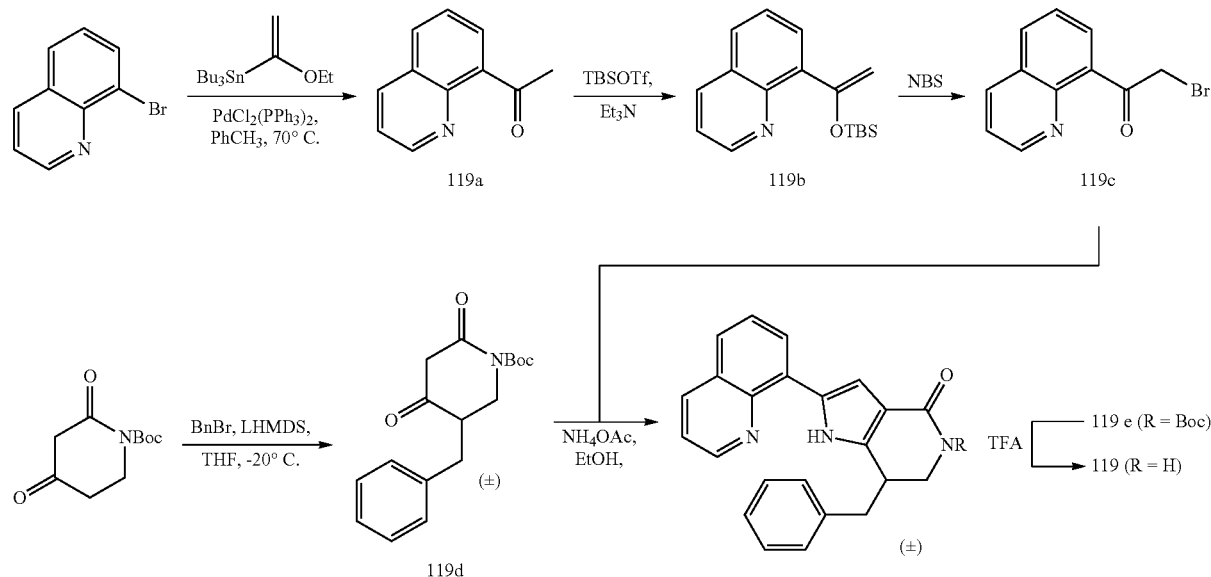

Preparation of 1-(quinolin-8-yl)ethanone

A mixture of 8-bromoquinoline (2.0 g, 9.661 mmol), tributyl(1-ethoxyvinyl)stannane (4.19 g, 11.59 mmol), and Pd(PPh₃)₄ (557 mg, 0.483 mmol) in toluene (50 mL) was heated under argon at 70° C. for 24 h. The mixture was cooled to RT and extracted with EtOAc (2×25 mL). The combined extracts were dried over Na$_2$SO$_4$, filtered, and concentrated in vacuo. Chromatographic purification of the residue (silica gel, 30% EtOAc/petroleum ether) furnished 1-(quinolin-8-yl)ethanone (1.2 g, 7.01 mmol, 73% yield) as an off-white solid: $^1$H NMR (400 MHz, DMSO-d$_6$) δ 8.99 (1H, dd, J=2 Hz & 2.4 Hz), 8.22 (1H, dd, J=2 Hz & 6.4 Hz), 7.95 (2H, d, J=7.6 Hz), 7.59 (1H, t, J=8 Hz), 7.48 (1H, dd, J=4 Hz), 2.95 (3H, s). m/z (ESI, +ve) 172.0 (M+H)$^+$.

Preparation of
8-(1-((tert-butyldimethylsilyl)oxy)vinyl)quinoline

To a solution of 1-(quinolin-8-yl)ethanone (200 mg, 1.169 mmol) and TEA (0.2 mL, 1.520 mmol) in DCM (2 mL) at 0° C. was added TBSOTf (339 mg, 1.286 mmol), and the resulting mixture was stirred at 0° C. for 1 h. The mixture was diluted with sat. aq. NaHCO$_3$ and extracted with EtOAc (2×5 mL). The combined extracts were dried over Na$_2$SO$_4$, filtered, and concentrated in vacuo to yield crude 8-(1-((tert-butyldimethylsilyl)oxy)vinyl)quinoline (300 mg) as a black solid (used without further purification): $^1$H NMR (400 MHz, DMSO-d$_6$): δ 9.07 (1H, dd, J=1.6 Hz & 2.4 Hz), 8.23 (1H, dd, J=2 Hz & 6.4 Hz), 8.00 (1H, dd, J=1.6 Hz & 5.6 Hz), 7.84 (1H, dd, J=1.6 Hz & 6.8 Hz), 7.59 (1H, t, J=7.6 Hz), 7.49 (1H, dd, J=4 Hz & 4.4 Hz), 5.43 (1H, s), 5.02 (1H, s), 1.01 (9H, s), 0.20 (6H, s). m/z (ESI, +ve) 285.9 (M+H)$^+$.

Preparation of 2-bromo-1-(quinolin-8-yl)ethanone

To a solution of 8-(1-((tert-butyldimethylsilyl)oxy)vinyl) quinoline (300 mg, 1.045 mmol) in THF (5 mL) and water (1 mL) was added NBS (203 mg, 1.149 mmol), and the resulting mixture was stirred at 25° C. for 30 min. The mixture was diluted with water (5 mL) and extracted in to EtOAc (2×5 mL). The combined extracts were dried over Na$_2$SO$_4$, filtered, and concentrated in vacuo to yield crude 2-bromo-1-(quinolin-8-yl)ethanone (200 mg) (used without further purification in subsequent transformations): $^1$H NMR (400 MHz, DMSO-d$_6$) δ 8.99-8.98 (1H, m), 8.27-8.23 (1H, m), 8.17-8.15 (1H, m), 7.67-7.63 (1H, m), 5.18 (1H, s), 5.02 (1H, s), 2.78 (2H, s). m/z (ESI, +ve) 249.9 (M+H)$^+$.

Preparation of rac-tert-butyl
5-benzyl-2,4-dioxopiperidine-1-carboxylate

To a solution of tert-butyl 2,4-dioxopiperidine-1-carboxylate (Ark Pharm, Inc., Libertyville, Ill.; 2.0 g, 9.389 mmol) in THF (1 L) at 20° C. was added LHMDS (1.0M in THF; 23.47 mL, 23.47 mmol) (dropwise), and the resulting mixture was stirred at 20° C. for 30 min. Benzyl bromide (3.1 g, 18.77 mmol) was added, and the resulting mixture was stirred at 20° C. for 1 h. The mixture was neutralized with 10M aq. KHSO$_4$ solution and extracted with EtOAc. The organic extract was dried over Na$_2$SO$_4$, filtered, and concentrated in vacuo to provide crude rac-tert-butyl 5-benzyl-2,4-dioxopiperidine-1-carboxylate (1.0 g) (used without further purification in subsequent transformations): m/z (ESI, +ve) 204.0 [(M+H)-100]$^+$.

Preparation of rac-tert-butyl 7-benzyl-4-oxo-2-(quinolin-8-yl)-6,7-dihydro-1H-pyrrolo[3,2-c]pyridine-5(4H)-carboxylate A mixture of 2-bromo-1-(quinolin-8-yl)ethanone (Ex. 119c; 400 mg, 1.606 mmol), rac-tert-butyl 5-benzyl-2,4-dioxopiperidine-1-carboxylate (548 mg, 1.927 mmol), and NH$_4$OAc (494 mg, 1.927 mmol) in EtOH (4 mL) was stirred at 25° C. for 15 h. EtOH was removed in vacuo, and the residue was suspended in 2N aq. HCl (5 mL) and washed with EtOAc (2×5 mL). The aq. layer was neutralized with sat. aq. NaHCO$_3$ (15 mL) and extracted with EtOAc (2×10 mL). The combined extracts were dried over Na$_2$SO$_4$, filtered, and concentrated in vacuo. Chromatographic purification of the residue (basic alumina, 50% EtOAc/petroleum ether) furnished rac-tert-butyl 7-benzyl-4-oxo-2-(quinolin-8-yl)-6,7-dihydro-1H-pyrrolo[3,2-c]pyridine-5(4H)-carboxylate (200 mg, 0.441 mmol, 27% yield) as a light-yellow solid: m/z (ESI, +ve) 353.9 [(M+H)-100]$^+$.

Preparation of rac-7-benzyl-2-(quinolin-8-yl)-6,7-dihydro-1H-pyrrolo[3,2-c]pyridin-4(5H)-one A mixture of rac-tert-butyl 7-benzyl-4-oxo-2-(quinolin-8-yl)-6,7-dihydro-1H-pyrrolo[3,2-c]pyridine-5(4H)-carboxylate (200 mg, 0.441 mmol), DCM (10 mL), and TFA (2 mL) was stirred at RT for 2 h. The mixture was concentrated in vacuo, and the residue was suspended in 1N aq. HCl (10 mL) and washed with EtOAc (5 mL). The aq. layer was neutralized with sat. aq. NaHCO$_3$ (5 mL) and extracted with EtOAc (2×10 mL). The combined extracts were dried over Na$_2$SO$_4$, filtered, and concentrated in vacuo. Purification of the residue by preparative TLC (80% EtOAc/petroleum ether) afforded rac-7-benzyl-2-(quinolin-8-yl)-6,7-dihydro-1H-pyrrolo[3,2-c]pyridin-4(5H)-one (30 mg, 0.085 mmol, 19% yield) as a pale green solid: $^1$H NMR (400 MHz, DMSO-d$_6$) δ 12.29 (1H, br s), 8.92 (1H, dd, J=1.6 Hz & 2.8 Hz), 8.47 (1H, dd, J=1.6 Hz & 6.8 Hz), 8.21 (1H, d, J=7.2 Hz), 7.86 (1H, d, J=8 Hz), 7.67-7.62 (2H, m), 7.43-7.40 (4H, m), 7.33-7.30 (1H, m), 7.18 (1H, d, J=2 Hz), 7.06 (1H, br s), 3.48-3.40 (1H, m), 3.20-3.10 (2H, m), 2.92-2.86 (2H, m). m/z (ESI, +ve) 353.9 (M+H)$^+$.

Example 120 rac-2-(2-((trans-3-aminocyclohexyl)amino)quinolin-8-yl)-6,7-dihydro-1H-pyrrolo[3,2-c]pyridin-4(5H)-one Example 121

2-(2-((cis-3-aminocyclohexyl)amino)quinolin-8-yl)-6,7-dihydro-1H-pyrrolo[3,2-c]pyridin-4(5H)-one
(first-eluting enantiomer)

Example 122

2-(2-((cis-3-aminocyclohexyl)amino)quinolin-8-yl)-6,7-dihydro-1H-pyrrolo[3,2-c]pyridin-4(5H)-one
(second-eluting enantiomer)

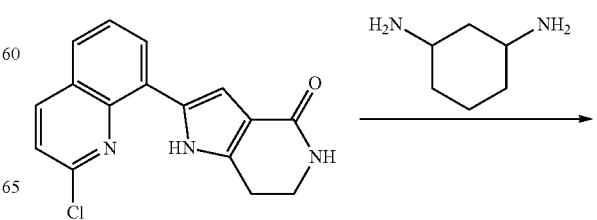

-continued

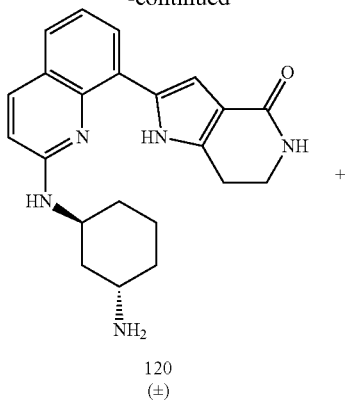

120 (±)

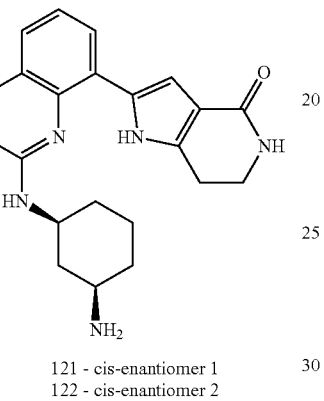

121 - cis-enantiomer 1
122 - cis-enantiomer 2

A solution of 2-(2-chloroquinolin-8-yl)-6,7-dihydro-1H-pyrrolo[3,2-c]pyridin-4(5H)-one (Example 1; 101 mg, 0.339 mmol) and cyclohexane-1,3-diamine (Aldich; 0.204 mL, 1.696 mmol) in DMSO (0.6 mL) was stirred under argon at 100° C. for 1 d. The mixture was cooled to 25° C., diluted with DMSO (1.8 mL), and purified by revered-phase HPLC (Phenomenex Gemini $C_{18}$ column (150×30 mm, 10 μm), 35 mL/min, 5-100% ACN/$H_2O$+0.1% TFA) to provide 2-(2-((3-aminocyclohexyl)amino)-quinolin-8-yl)-6,7-dihydro-1H-pyrrolo[3,2-c]pyridin-4(5H)-one 2,2,2-trifluoroacetate (159.8 mg, 0.326 mmol, 96% yield) as a yellow-brown solid: m/z (ESI, +ve) 376.3 (M+H)$^+$. Separation of this material by supercritical-fluid chromatography (Chiralcel OD-H (150× 21 mm, 5 μm), 60% liquid $CO_2$/40% MeOH (+0.2% diethylamine), 75 mL/min, followed by repurification of 122 by Princeton Chromatography pyridine amide column (250×21 mm, 5 μm), 70% liquid $CO_2$/30% MeOH (+0.2% diethylamine), 75 mL/min) separately afforded rac-2-(2-((trans-3-aminocyclohexyl)amino)quinolin-8-yl)-6,7-dihydro-1H-pyrrolo[3,2-c]pyridin-4(5H)-one (120; 4.5 mg, 0.012 mmol) as a light-yellow solid: $^1$H NMR (400 MHz, MeOH-d4) δ ppm 7.94 (1H, dd, J=7.5, 1.1 Hz), 7.84 (1H, d, J=9.0 Hz), 7.46 (1H, dd, J=7.7, 0.9 Hz), 7.20 (1H, t, J=7.6 Hz), 7.03 (1H, s), 6.87 (1H, d, J=9.0 Hz), 4.39 (1H, br. s.), 3.62 (2H, t, J=7.0 Hz), 3.14 (1H, t, J=9.9 Hz), 3.02 (2H, td, J=7.0, 2.6 Hz), 2.34 (1H, d, J=13.7 Hz), 1.89-2.01 (2H, m), 1.74-1.85 (3H, m), 1.58-1.68 (1H, m), 1.31-1.41 (1H, m). m/z (ESI, +ve) 376.3 (M+H)$^+$:
and 2-(2-((cis-3-aminocyclohexyl)amino)quinolin-8-yl)-6,7-dihydro-1H-pyrrolo[3,2-c]pyridin-4(5H)-one, first-eluting enantiomer (121; 20.0 mg, 0.053 mmol) as a light-yellow solid: $^1$H NMR (400 MHz, MeOH-d4 δ ppm 7.93 (1H, d, J=7.4 Hz), 7.83 (1H, d, J=9.0 Hz), 7.46 (1H, d, J=7.4 Hz), 7.19 (1H, t, J=7.7 Hz), 7.07 (1H, s), 6.77 (1H, d, J=8.8 Hz), 3.96 (1H, t, J=11.4 Hz), 3.64 (2H, t, J=6.9 Hz), 3.35-3.42 (1H, m), 3.03 (2H, td, J=6.9, 1.3 Hz), 2.96 (1H, t, J=11.4 Hz), 2.47 (1H, d, J=11.0 Hz), 2.21 (1H, d, J=11.3 Hz), 1.88-2.05 (2H, m), 1.47-1.65 (1H, m), 1.22-1.37 (2H, m). m/z (ESI, +ve) 376.3 (M+H); and 2-(2-((cis-3-aminocyclohexyl)amino) quinolin-8-yl)-6,7-dihydro-1H-pyrrolo[3,2-c]pyridin-4 (5H)-one, second-eluting enantiomer (122; 18.0 mg, 0.048 mmol) as a light-yellow solid: $^1$H NMR (400 MHz, MeOH-d4 δ ppm 7.92 (1H, dd, J=7.6, 1.2 Hz), 7.81 (1H, d, J=9.0 Hz), 7.44 (1H, d, J=7.8 Hz), 7.18 (1H, t, J=7.6 Hz), 7.05 (1H, s), 6.75 (1H, d, J=9.0 Hz), 3.93 (1H, tt, J=11.5, 3.5 Hz), 3.63 (2H, t, J=7.0 Hz), 3.33-3.40 (1H, m), 3.02 (2H, td, J=7.0, 2.1 Hz), 2.92 (1H, tt, J=11.3, 3.7 Hz), 2.44 (1H, d, J=12.1 Hz), 2.20 (1H, d, J=13.1 Hz), 1.88-2.02 (2H, m), 1.54 (1H, qt, J=13.4, 3.7 Hz), 1.20-1.33 (2H, m). m/z (ESI, +ve) 376.3 (M+H)$^+$.

Example 123

(S)-2-(2-(piperidin-3-ylamino)quinolin-8-yl)-6,7-dihydro-1H-pyrrolo[3,2-c]pyridin-4(5H)-one

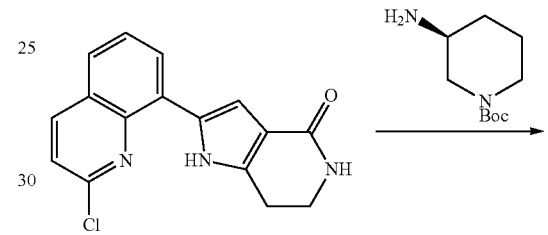

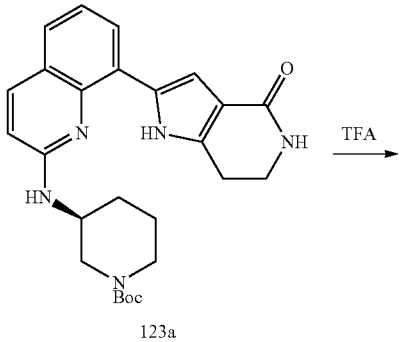

123a

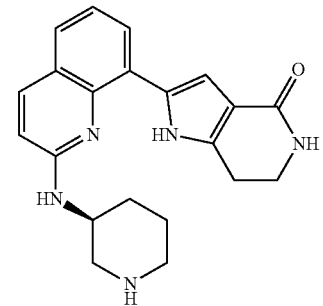

123

Preparation of (S)-tert-butyl 3-((8-(4-oxo-4,5,6,7-tetrahydro-1H-pyrrolo[3,2-c]pyridin-2-yl)quinolin-2-yl)amino)piperidine-1-carboxylate A solution of 2-(2-chloroquinolin-8-yl)-6,7-dihydro-1H-pyrrolo[3,2-c]pyridin-4(5H)-one (Example 1; 50 mg, 0.168 mmol) and (S)-tert-butyl 3-aminopiperidine-1-carboxylate (Chem-Impex International, Wood Dale, Ill.; 168 mg, 0.840 mmol) in DMSO (0.5 mL) was stirred under argon at 100° C. for 19 h, then at 130° C. for 5 h, then at 150° C. for 17 h. The mixture was cooled to 25° C. and partitioned between DCM (30 mL) and water (20 mL). The organic layer was separated, and the aq. layer was extracted with DCM (2×20 mL). The combined organic extracts were dried over $Na_2SO_4$, filtered, and concentrated in vacuo to provide crude (S)-tert-butyl 3-((8-(4-oxo-4,5,6,7-tetrahydro-1H-pyrrolo[3,2-c]pyridin-2-yl)quinolin-2-yl)amino)piperidine-1-carboxylate (193.5 mg) as a brown solid (used without further purification in the subsequent transformation): m/z (ESI, +ve) 462.4 (M+H)$^+$.

Preparation of (S)-2-(2-(piperidin-3-ylamino)quinolin-8-yl)-6,7-dihydro-1H-pyrrolo[3,2-c]pyridin-4(5H)-one A mixture of (S)-tert-butyl 3-((8-(4-oxo-4,5,6,7-tetrahydro-1H-pyrrolo[3,2-c]pyridin-2-yl)quinolin-2-yl)amino)piperidine-1-carboxylate (78.0 mg, 0.169 mmol) and TFA (0.30 mL, 3.894 mmol) in DCM (1.5 mL) was stirred at 25° C. for 1 h. The mixture was concentrated in vacuo, and the residue was taken up in DMSO (2.0 mL) and purified by reversed-phase HPLC (Phenomenex Gemini $C_{18}$ column (150×30 mm, 10 μm), 35 mL/min, 5-100% ACN/$H_2O$+0.1% TFA) to provide (S)-2-(2-(piperidin-3-ylamino)quinolin-8-yl)-6,7-dihydro-1H-pyrrolo[3,2-c]pyridin-4(5H)-one 2,2,2-trifluoroacetate (41.1 mg, 0.086 mmol, 51% yield) as a yellow-orange solid: $^1$H NMR (400 MHz, MeOH-d4) δ ppm 8.16 (1H, br. s.), 7.84 (1H, dd, J=7.5, 1.1 Hz), 7.69 (1H, d, J=7.6 Hz), 7.35-7.46 (1H, m), 7.25-7.34 (1H, m), 6.97-7.09 (1H, m), 4.33-4.45 (1H, m), 3.74 (1H, dd, J=12.3, 3.3 Hz), 3.64 (2H, t, J=7.1 Hz), 3.41 (1H, dt, J=12.7, 3.8 Hz), 3.04-3.16 (2H, m), 3.01 (2H, t, J=7.0 Hz), 2.26-2.35 (1H, m), 2.08-2.19 (1H, m), 1.90-2.04 (1H, m), 1.70-1.84 (1H, m). $^{19}$F NMR (377 MHz, MeOH-d4) δ ppm −77.49 (3F, s). m/z (ESI, +ve) 362.3 (M+H)$^+$.

Example 124

(R)-2-(2-(piperidin-3-ylamino)quinolin-8-yl)-6,7-dihydro-1H-pyrrolo[3,2-c]pyridin-4(5H)-one

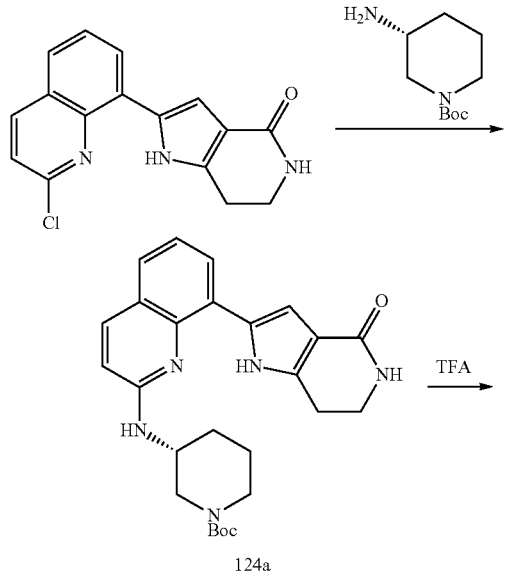

124a

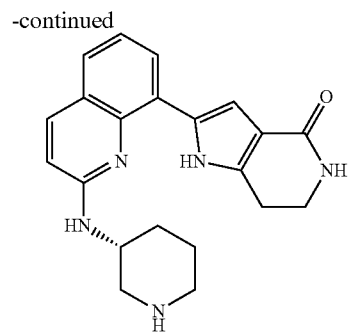

124

Preparation of (R)-tert-butyl 3-((8-(4-oxo-4,5,6,7-tetrahydro-1H-pyrrolo[3,2-c]pyridin-2-yl)quinolin-2-yl)amino)piperidine-1-carboxylate A solution of 2-(2-chloroquinolin-8-yl)-6,7-dihydro-1H-pyrrolo[3,2-c]pyridin-4(5H)-one (Example 1; 50 mg, 0.168 mmol) and (R)-tert-butyl 3-aminopiperidine-1-carboxylate (Small Molecules, Inc., Hoboken, N.J.; 168 mg, 0.840 mmol) in DMSO (0.5 mL) was stirred under argon at 100° C. for 19 h, then 130° C. for 5 h, then 150° C. for 17 h. The mixture was cooled to 25° C. and partitioned between DCM (30 mL) and water (20 mL). The organic layer was separated, and the aq. layer was extracted with DCM (2×20 mL). The combined organic extracts were sequentially washed with water (20 mL), dried over $Na_2SO_4$, filtered, and concentrated in vacuo to provide crude (R)-tert-butyl 3-((8-(4-oxo-4,5,6,7-tetrahydro-1H-pyrrolo[3,2-c]pyridin-2-yl)quinolin-2-yl)amino)piperidine-1-carboxylate (179.7 mg) as a brown foam (used without further purification in the subsequent transformation): m/z (ESI, +ve) 462.4 (M+H)$^+$.

Preparation of (R)-2-(2-(piperidin-3-ylamino)quinolin-8-yl)-6,7-dihydro-1H-pyrrolo[3,2-c]pyridin-4(5H)-one A mixture of (R)-tert-butyl 3-((8-(4-oxo-4,5,6,7-tetrahydro-1H-pyrrolo[3,2-c]pyridin-2-yl)quinolin-2-yl)amino)piperidine-1-carboxylate (78.0 mg, 0.169 mmol) and TFA (0.45 mL, 5.84 mmol) in DCM (1.5 mL) was stirred at 0° C. for 10 min, then at 25° C. for 1 h. The mixture was concentrated in vacuo, and the residue was taken up in DMSO (2.0 mL) and purified by reversed-phase HPLC (Phenomenex Gemini $C_{18}$ column (150×30 mm, 10 μm), 35 mL/min, 5-100% ACN/$H_2O$+0.1% TFA) to provide (R)-2-(2-(piperidin-3-ylamino)quinolin-8-yl)-6,7-dihydro-1H-pyrrolo[3,2-c]pyridin-4(5H)-one 2,2,2-trifluoroacetate (30.7 mg, 0.065 mmol, 38% yield) as a yellowish-brown solid: $^1$H NMR (400 MHz, MeOH-d4) δ ppm 8.08 (1H, dd, J=9.6, 4.1 Hz), 7.85 (1H, dd, J=7.5, 1.3 Hz), 7.65 (1H, d, J=7.4 Hz), 7.43 (1H, br. s.), 7.37 (1H, t, J=7.5 Hz), 6.96 (1H, d, J=7.2 Hz), 4.40-4.50 (1H, m), 3.79 (1H, dd, J=11.7, 2.3 Hz), 3.66 (2H, t, J=7.0 Hz), 3.43 (1H, dt, J=12.8, 4.3 Hz), 3.06-3.18 (2H, m), 3.03 (2H, t, J=7.1 Hz), 2.27-2.38 (1H, m), 2.10-2.22 (1H, m), 1.93-2.07 (1H, m), 1.72-1.85 (1H, m). $^{19}$F NMR (377 MHz, MeOH-d4) δ ppm −77.29 (3F, s). m/z (ESI, +ve) 362.1 (M+H)$^+$.

Example 125 rac-7-isobutyl-2-(quinolin-8-yl)-6,7-dihydro-1H-pyrrolo[3,2-c]pyridin-4(5H)-one

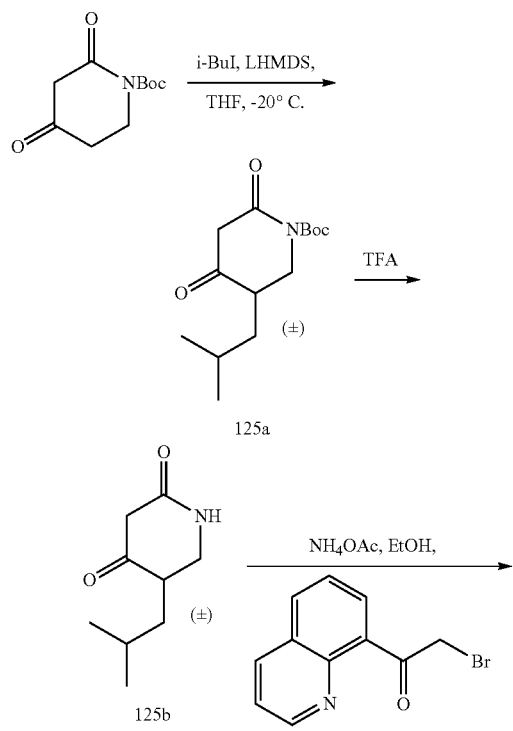

Preparation of rac-tert-butyl 5-isobutyl-2,4-dioxopiperidine-1-carboxylate

To a solution of tert-butyl 2,4-dioxopiperidine-1-carboxylate (Ark Pharm, Inc., Libertyville, Ill.; 2.0 g, 9.389 mmol) in THF (1 L) at 20° C. was added LHMDS (1.0M in THF; 23.47 mL, 23.47 mmol) (dropwise), and the resulting mixture was stirred at 20° C. for 30 min. Isobutyl iodide (6.9 g, 37.55 mmol) was added, and the resulting mixture was stirred at 20° C. for 1 h. The mixture was neutralized with 10M aq. KHSO₄ solution and extracted with EtOAc. The organic extract was dried over Na₂SO₄, filtered, and concentrated in vacuo to provide crude rac-tert-butyl 5-isobutyl-2,4-dioxopiperidine-1-carboxylate (0.75 g) (used without further purification in subsequent transformations): m/z (ESI, +ve) 170.0 [(M+H)-100]⁺.

Preparation of rac-5-isobutylpiperidine-2,4-dione

A mixture of rac-tert-butyl 5-isobutyl-2,4-dioxopiperidine-1-carboxylate (300 mg, 1.115 mmol), DCM (1 mL), and TFA (0.1 mL) was stirred at 25° C. for 2 h. The mixture was concentrated in vacuo and chromatographically purified (basic alumina, 40% EtOAc/petroleum ether) to afford rac-5-isobutylpiperidine-2,4-dione (85 mg, 45% yield) as a pale yellow solid: m/z (ESI, +ve) 170 (M+H)⁺.

Preparation of rac-7-isobutyl-2-(quinolin-8-yl)-6,7-dihydro-1H-pyrrolo[3,2-c]pyridin-4(5H)-one A mixture of 2-bromo-1-(quinolin-8-yl)ethanone (Example 119c; 1.0 g, 4.016 mmol), rac-5-isobutylpiperidine-2,4-dione (890 mg, 4.819 mmol), and NH₄OAc (1.2 g, 16.0 mmol) in EtOH (10 mL) was stirred at 25° C. for 15 h. EtOH was removed in vacuo, and the residue was suspended in 2N aq. HCl (10 mL) and washed with EtOAc (2×20 mL). The aq. layer was neutralized with sat. aq. NaHCO₃ (25 mL) and extracted with EtOAc (2×25 mL). The combined extracts were dried over Na₂SO₄, filtered, and concentrated in vacuo. Purification of the residue by preparative TLC (40% EtOAc/petroleum ether) furnished rac-7-isobutyl-2-(quinolin-8-yl)-6,7-dihydro-1H-pyrrolo[3,2-c]pyridin-4(5H)-one (20 mg, 0.063 mmol, 2% yield) as a dark-green solid: ¹H NMR (400 MHz, DMSO-d₆) δ 12.42 (1H, br s), 9.01 (1H, dd, J=1.6 Hz & 2.4 Hz), 8.45 (1H, dd, J=2 Hz & 6.4 Hz), 8.17 (1H, dd, J=1.2 Hz & 6.4 Hz), 7.84 (1H, dd, J=1.2 Hz & 6.8 Hz), 7.64-7.60 (2H, m), 7.15 (1H, d, J=2.4 Hz), 6.98 (1H, br s), 3.54-3.50 (1H, m), 3.19-3.10 (2H, m), 1.72-1.59 (2H, m), 1.50-1.45 (1H, m), 1.02 (3H, d, J=6.4 Hz), 0.97 (3H, d, J=6.4 Hz). m/z (ESI, +ve) 319.9 (M+H)⁺.

Example 126

2-(3-Fluoro-2-methylquinoxalin-5-yl)-6,7-dihydro-1H-pyrrolo[3,2-c]pyridin-4(5H)-one

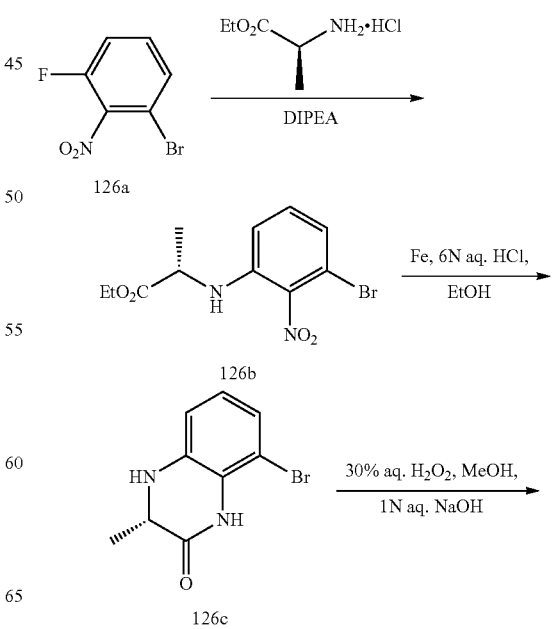

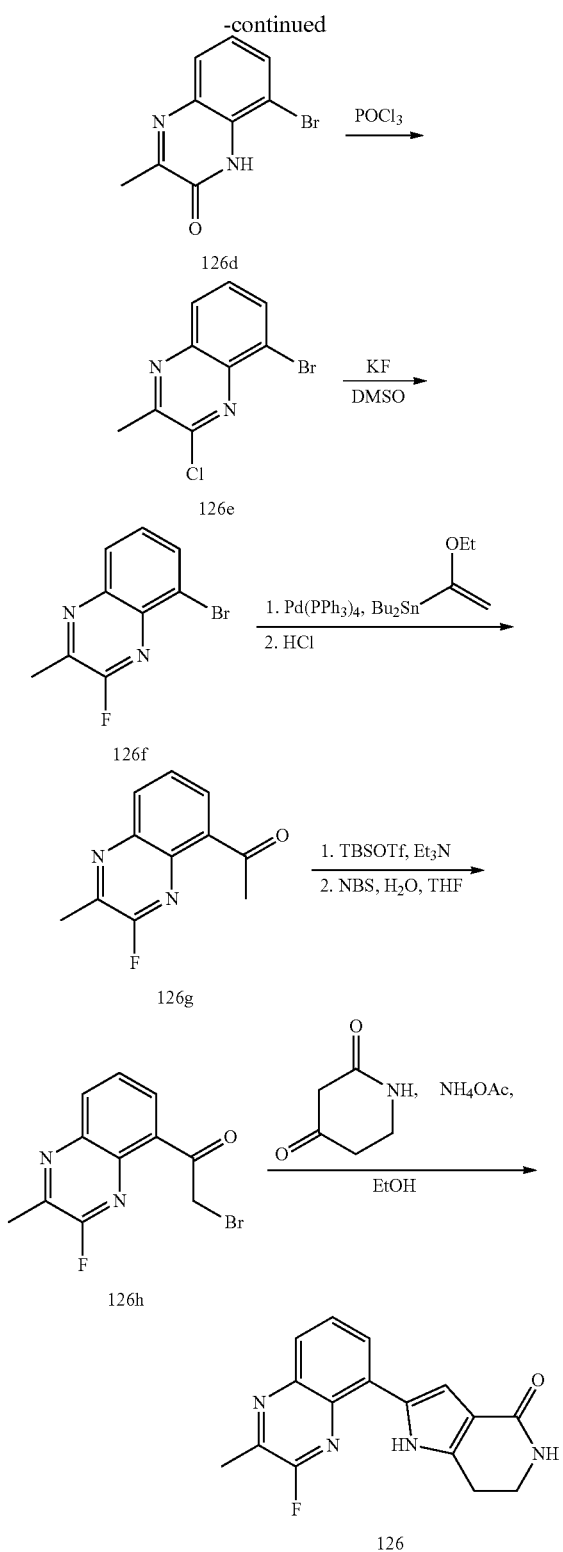

Preparation of (S)-ethyl 2-((3-bromo-2-nitrophenyl)amino)propanoate

DIPEA (45.1 mL, 259 mmol) was added to a stirred solution of L-alanine ethyl ester hydrochloride (Aldrich; 34.1 g, 222 mmol) and 1-bromo-3-fluoro-2-nitrobenzene (126a; Ark Pharm, Inc., Libertyville, Ill.; 16.29 g, 74.0 mmol) in N,N-dimethylacetamide (15 mL) and the resulting yellow solution was stirred at RT for 15 min. A water-cooled reflux condenser was attached to the flask, and the resulting mixture was heated at 80° C. for 18 h. The reaction was cooled to RT, diluted with saturated aq. NH$_4$Cl (100 mL), and extracted with EtOAc (4×75 mL). The combined organic extracts were dried over Na$_2$SO$_4$, filtered, and concentrated in vacuo to provide (S)-ethyl 2-((3-bromo-2-nitrophenyl)amino)propanoate (126b; 24.1 g) as a brown residue (contains 10% starting material by LCMS and $^1$H NMR), which was used directly in the subsequent step: $^1$H NMR (400 MHz, CDCl$_3$) δ ppm 7.13 (1H, t, J=8.2 Hz), 7.00 (1H, d, J=8.0 Hz), 6.64 (1H, d, J=8.4 Hz), 5.89 (1H, d, J=6.8 Hz), 4.22 (2H, m, J=7.0, 7.0, 7.0 Hz), 4.14 (1H, quin, J=7.1 Hz), 1.51 (3H, d, J=7.0 Hz), 1.27 (3H, t, J=7.1 Hz). m/z (ESI, +ve) 317.0 (M+H)$^+$.

Preparation of (S)-8-bromo-3-methyl-3,4-dihydroquinoxalin-2(1H)-one

To a 2-L, 3-necked round-bottomed flask equipped with a mechanical stirrer, nitrogen gas inlet, and temperature probe was sequentially added (S)-ethyl 2-((3-bromo-2-nitrophenyl)amino)-propanoate (50 g, 158 mmol), EtOH (750 mL), and iron powder (325 mesh, Aldrich; 39.6 g, 709 mmol). The resulting slurry was cooled to 0-5° C. on an ice water bath, and HCl (6.0 N, aq.; 342 mL, 2050 mmol) was added, dropwise, such that the internal reaction temperature did not exceed 5° C. After 1 h, brine (500 mL) and EtOAc (1500 mL) were added, such that the internal reaction temperature was kept below 10° C. The resulting mixture was vacuum filtered, and the collected solid was washed with EtOAc. The organic phase of the filtrate was separated and sequentially washed with brine (300 mL), saturated aq. NaHCO$_3$ (500 mL; repeated until aq. layer pH ≥7), and EDTA trisodium salt solution (1 N, aq.; 300 mL). The organic layer was then concentrated in vacuo to provide (S)-8-bromo-3-methyl-3,4-dihydroquinoxalin-2(1H)-one (126c; 40.0 g, 165.9 mmol, 105% yield) as a light-brown oil, which was used without further purification in the subsequent step: m/z (ESI, +ve) 241.0 (M+H)$^+$.

Preparation of 8-bromo-3-methylquinoxalin-2(1H)-one

A solution of (S)-8-bromo-3-methyl-3,4-dihydroquinoxalin-2(1H)-one (17 g, 70.5 mmol), MeOH (141 mL), and 1.0 N aq. NaOH (141 mL, 141 mmol) was stirred at 85° C. in a three-necked round-bottom flask fitted with a septum, reflux condenser, and addition funnel. A mixture of H$_2$O$_2$ (30% in water; 25.2 mL, 247 mmol) and deionized water (10 mL) was then added, dropwise via the addition funnel, over 45 min, and the resulting mixture was heated at 85° C. for 17 h. The mixture was cooled to RT, 5 N aq. HCl (36 mL) was added, and the resulting slurry was extracted with 10% MeOH/DCM (3×150 mL). The combined extracts were dried over Na$_2$SO$_4$, filtered, and concentrated in vacuo to give 8-bromo-3-methylquinoxalin-2(1H)-one (126d; 13.16 g, 55.1 mmol, 78% yield) as a tan solid, which was used without further purification in the subsequent step: $^1$H NMR (400 MHz, CDCl$_3$) δ ppm 9.03 (1H, s), 7.77 (1H, d, J=8.2 Hz), 7.67 (1H, d, J=7.6 Hz), 7.22 (1H, t, J=7.8 Hz), 2.61 (3H, s). m/z (ESI, +ve) 239.0 (M+H)$^+$.

Preparation of 5-bromo-3-chloro-2-methylquinoxaline

A slurry of 8-bromo-3-methylquinoxalin-2(1H)-one (6.33 g, 26.5 mmol) in phosphorus oxychloride (20 mL, 219 mmol)

was heated at reflux for 1.5 h in a round-bottomed flask fitted with a water-cooled reflux condenser and drying tube. Excess POCl₃ was removed in vacuo (16 Torr, 36° C.), and the residue was taken up in DCM (50 mL), transferred to an Erlenmeyer flask, cooled to 0° C., and saturated aq. NaHCO₃ (ca. 80 mL) was added (cautiously, with rapid stirring). The resulting biphasic mixture was stirred rapidly for 5 min. Upon cessation of gas evolution, the mixture was extracted with DCM (3×200 mL), and the combined extracts were dried over Na₂SO₄, filtered, and concentrated onto silica gel. Chromatographic purification of the residue (silica gel, 0-30% EtOAc/hexanes) furnished 5-bromo-3-chloro-2-methylquinoxaline (126e; 5.12 g, 19.85 mmol, 75% yield) as a light-yellow solid: ¹H NMR (400 MHz, CDCl₃) δ ppm 8.02 (1H, d, J=7.6 Hz), 8.00 (1H, dd, J=8.4, 1.2 Hz), 7.60 (1H, t, J=7.9 Hz), 2.87 (3H, s). m/z (ESI, +ve) 256.9 (M+H)⁺.

Preparation 5-bromo-3-fluoro-2-methylquinoxaline

A 1-L, three-necked round-bottomed flask equipped with a mechanical stirrer, a nitrogen gas inlet, and a temperature probe was charged 5-bromo-3-chloro-2-methylquinoxaline (21.5 g, 83 mmol), DMSO (215 mL) and KF (4.85 mL, 209 mmol), and the resulting mixture was heated at 90° C. for 2.5 h. The mixture was cooled to RT and ice/water (430 mL) was added. The precipitated solid was collected by vacuum filtration and then washed with water (100 mL) and dried in vacuo to afford 5-bromo-3-fluoro-2-methylquinoxaline (126f; 21 g) as a brown solid, which was used without further purification in the subsequent step: ¹H NMR (400 MHz, CDCl3) δ ppm 8.03 (1H, d, J=2.2 Hz), 8.01 (1H, d, J=1.2 Hz), 7.59 (1H, t, J=7.9 Hz), 2.79 (3H, d, J=1.4 Hz). ¹⁹F NMR (377 MHz, CDCl₃) δ ppm −70.61 (1F, br. s.). m/z (ESI, +ve) 240.9 (M+H)⁺.

Preparation of 1-(3-fluoro-2-methylquinoxalin-5-yl)ethanone

A 1-L, three-necked round-bottomed flask equipped with a mechanical stirrer, reflux condenser, nitrogen gas inlet, and a temperature probe was charged with 5-bromo-3-fluoro-2-methylquinoxaline (30 g, 124 mmol), Pd(PPh₃)₄ (4.31 g, 3.73 mmol), toluene (300 mL), and tributyl(1-ethoxyvinyl)tin (Synthonix, Wake Forest, N.C.; 46.2 mL, 137 mmol), and the resulting mixture was heated under N₂ atmosphere at 90° C. for 18 hours. The mixture was cooled to RT, HCl (6.0 N, aq.; 12.45 mL, 74.7 mmol) was added, and the resulting mixture was stirred at RT for 10 min. The mixture was extracted with EtOAc (500 mL). The organic layer was separated and sequentially washed with brine (2×200 mL) and saturated aq. NaHCO₃ (100 mL) and then concentrated in vacuo. Chromatographic purification of the residue (silica gel, 0-100% DCM/heptane followed by repurification with silica gel, 0-75% EtOAc/heptane) furnished 1-(3-fluoro-2-methylquinoxalin-5-yl)ethanone (126 g; 16.0 g, 78.4 mmol, 63% yield) as an orange solid: ¹H NMR (400 MHz, CDCl₃) δ ppm 8.20 (1H, dd, J=8.3, 1.3 Hz), 8.10 (1H, dd, J=7.3, 1.1 Hz), 7.77 (1H, t, J=7.8 Hz), 2.92 (3H, s), 2.79 (3H, d, J=1.6 Hz). ¹⁹F NMR (377 MHz, CDCl₃) δ ppm −69.81 (1F, s). m/z (ESI, +ve) 205.1 (M+H)⁺.

Preparation of 2-bromo-1-(3-fluoro-2-methylquinoxalin-5-yl)ethanone

TBSOTf (2.92 mL, 12.73 mmol) was added (dropwise, over 3 min) to a mixture 1-(3-fluoro-2-methylquinoxalin-5-yl)ethanone (2.00 g, 9.79 mmol) and TEA (2.05 mL, 14.7 mmol) in DCM (100 mL) at 0° C., and the resulting solution was stirred at 0° C. for 30 min. The mixture was diluted with DCM (50 mL), washed with saturated aq. NaHCO₃ (2×100 mL), dried over Na₂SO₄, filtered, and concentrated in vacuo to provide 5-(1-(((tert-butyldimethylsilyl)oxy)vinyl)-3-fluoro-2-methylquinoxaline (3.451 g) as an orange-brown oil. This oil was taken up in THF (100 mL) and cooled to 0° C., water (2.82 mL, 157 mmol) and NBS (1.743 g, 9.79 mmol) were sequentially added, and the resulting solution was stirred at 0° C. for 2 min. The mixture was diluted with Et₂O (100 mL) and sequentially washed with water (80 mL), saturated aq. NaHCO₃ (80 mL), water (80 mL), and brine (80 mL). The resulting solution was dried over Na₂SO₄, filtered, and concentrated onto silica gel. Chromatographic purification (silica gel, 0-20% EtOAc/hexanes) provided 2-bromo-1-(3-fluoro-2-methylquinoxalin-5-yl)ethanone (2.77 g, 9.78 mmol, 100% yield) as a yellow solid: ¹H NMR (400 MHz, CDCl₃) δ ppm 8.27 (1H, d, J=5.3 Hz), 8.25 (1H, d, J=4.3 Hz), 7.82 (1H, t, J=7.8 Hz), 5.02 (2H, s), 2.80 (3H, d, J=1.4 Hz). ¹⁹F NMR (376 MHz, CDCl₃) δ ppm −69.34 (1F, s). m/z (ESI, +ve) 283.0 (M+H)⁺.

Preparation of 2-(3-fluoro-2-methylquinoxalin-5-yl)-6,7-dihydro-1H-pyrrolo[3,2-c]pyridin-4(5H)-one A mixture of 2-bromo-1-(3-fluoro-2-methylquinoxalin-5-yl)ethanone (5.69 g, 20.10 mmol), piperidine-2,4-dione (4.55 g, 40.2 mmol), and NH₄OAc (7.75 g, 100 mmol) in EtOH (200 ml) was stirred in a sealed flask at 40° C. for 16 h. The mixture was cooled to RT and concentrated in vacuo. The residue was sonicated in MeOH (100 ml), and the suspended solid was collected by vacuum filtration to provide 2-(3-fluoro-2-methylquinoxalin-5-yl)-6,7-dihydro-1H-pyrrolo[3,2-c]pyridin-4(5H)-one (1.91 g, 6.44 mmol, 32% yield) as a brown solid: ¹H NMR (400 MHz, DMSO-d₆) δ ppm 11.69 (1H, br. s.), 8.04 (1H, d, J=7.4 Hz), 7.89 (1H, d, J=8.0 Hz), 7.80 (1H, t, J=7.8 Hz), 7.22 (1H, d, J=2.0 Hz), 7.01 (1H, br. s.), 3.43 (2H, td, J=6.5, 2.0 Hz), 2.89 (2H, t, J=6.8 Hz), 2.71 (3H, s). ¹⁹F NMR (376 MHz, DMSO-d₆) δ ppm −71.83 (1F, s). m/z (ESI, +ve) 297.0 (M+H)⁺.

Example 127

2-(2-methyl-3-((tetrahydro-2H-pyran-4-yl)amino)quinoxalin-5-yl)-6,7-dihydro-1H-pyrrolo[3,2-c]pyridin-4(5H)-one

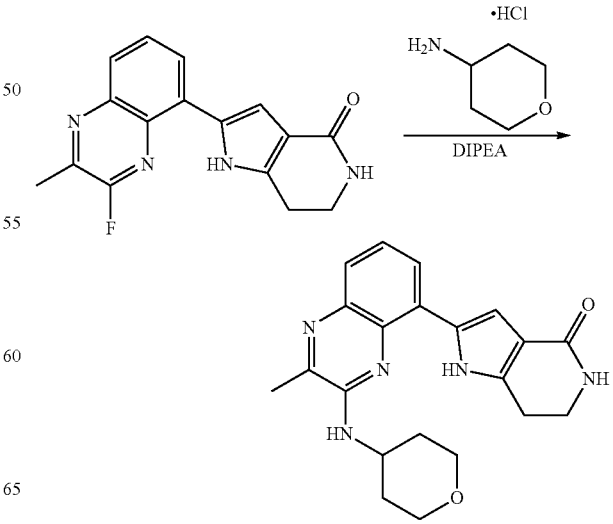

A solution of 2-(3-fluoro-2-methylquinoxalin-5-yl)-6,7-dihydro-1H-pyrrolo[3,2-c]pyridin-4(5H)-one (Example 126; 19.6 mg, 0.066 mmol), tetrahydro-2H-pyran-4-amine hydrochloride (Aldrich; 33.1 mg, 0.241 mmol), and DIPEA (0.063 mL, 0.364 mmol) in DMSO (0.8 mL) was stirred under argon at 100° C. for 2 h. The mixture was diluted with DMSO (1.2 mL) and purified by rpHPLC (Phenomenex Gemini C18 column (150×30 mm, 10 μm), 35 mL/min, 5-100% ACN/H$_2$O+0.1% TFA) to provide 2-(2-methyl-3-((tetrahydro-2H-pyran-4-yl)amino)quinoxalin-5-yl)-6,7-dihydro-1H-pyrrolo[3,2-c]pyridin-4(5H)-one 2,2,2-trifluoroacetate (28.1 mg, 0.057 mmol, 86% yield) as a red-orange solid: $^1$H NMR (400 MHz, MeOH-d$_4$) δ ppm 7.90 (1H, dd, J=7.5, 0.7 Hz), 7.63 (1H, dd, J=8.0, 0.8 Hz), 7.40 (1H, t, J=7.8 Hz), 7.18 (1H, s), 4.35 (1H, tt, J=11.0, 3.9 Hz), 4.08 (2H, dt, J=10.2, 2.0 Hz), 3.69 (2H, dd, J=11.8, 1.8 Hz), 3.64 (2H, t, J=7.0 Hz), 3.03 (2H, t, J=7.0 Hz), 2.62 (3H, s), 2.12-2.20 (2H, m), 1.79-1.85 (1H, m), 1.73-1.79 (1H, m). $^{19}$F NMR (377 MHz, MeOH-d$_4$) δ ppm −77.63 (3F, s). m/z (ESI, +ve) 378.2 (M+H)$^+$.

Example 128

(R)-2-((3-methyl-8-(4-oxo-4,5,6,7-tetrahydro-1H-pyrrolo[3,2-c]pyridin-2-yl)quinoxalin-2-yl)amino)propanamide

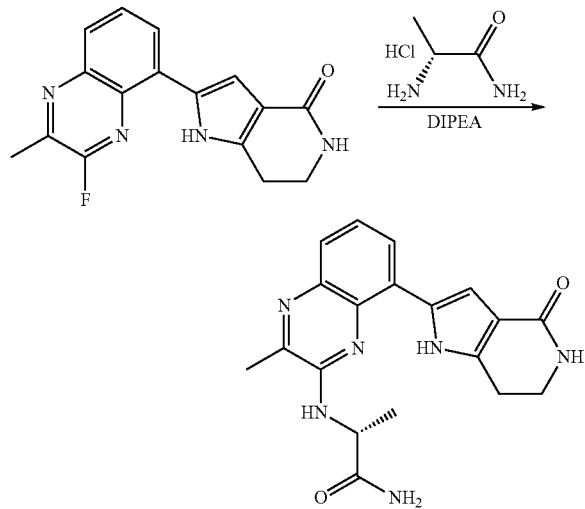

Prepared according to Example 127 using 2-(3-fluoro-2-methylquinoxalin-5-yl)-6,7-dihydro-1H-pyrrolo[3,2-c]pyridin-4(5H)-one (Example 126; 40.4 mg, 0.095 mmol), D-alaninamide hydrochloride (Advanced ChemTech, Louisville, Ky.; 47.6 mg, 0.382 mmol), and DIPEA (0.133 mL, 0.764 mmol) in DMSO (0.8 mL), heating at 100° C. for 1 h. Purified by reversed-phase HPLC (Phenomenex Gemini C$_{18}$ column (150×30 mm, 10 μm), 35 mL/min, 5-100% ACN/H$_2$O+0.1% TFA) to provide (R)-2-((3-methyl-8-(4-oxo-4,5,6,7-tetrahydro-1H-pyrrolo[3,2-c]pyridin-2-yl)quinoxalin-2-yl)amino)propanamide 2,2,2-trifluoroacetate (28.4 mg, 0.059 mmol, 62% yield) as a red-brown oil: $^1$H NMR (400 MHz, MeOH-d$_4$) δ ppm 11.67 (1H, br. s.), 7.96 (1H, d, J=7.6 Hz), 7.64 (1H, dd, J=8.0, 1.0 Hz), 7.41 (1H, t, J=7.9 Hz), 7.06 (1H, s), 4.43 (1H, q, J=7.4 Hz), 3.61 (2H, t, J=7.1 Hz), 3.06-3.23 (2H, m), 2.69 (3H, s), 1.69 (3H, d, J=7.2 Hz). $^{19}$F NMR (376 MHz, MeOH-d$_4$) δ ppm −77.65 (3F, s). m/z (ESI, +ve) 365.1 (M+H)$^+$.

Example 129

(S)-2-((3-methyl-8-(4-oxo-4,5,6,7-tetrahydro-1H-pyrrolo[3,2-c]pyridin-2-yl)quinoxalin-2-yl)amino)propanamide

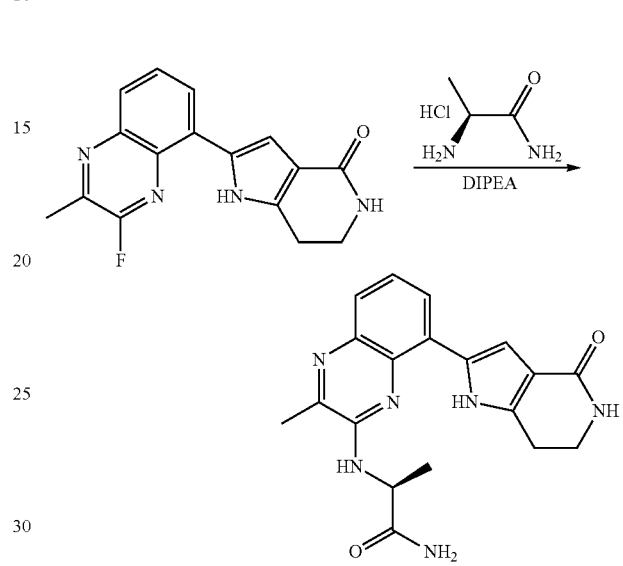

Prepared according to Example 127 using 2-(3-fluoro-2-methylquinoxalin-5-yl)-6,7-dihydro-1H-pyrrolo[3,2-c]pyridin-4(5H)-one (Example 126; 38.4 mg, 0.091 mmol), L-alaninamide hydrochloride (Aldrich; 45.2 mg, 0.363 mmol), and DIPEA (0.126 mL, 0.726 mmol) in DMSO (0.8 mL), heating at 100° C. for 1 h. Purified by reversed-phase HPLC (Phenomenex Gemini C$_{18}$ column (150×30 mm, 10 μm), 35 mL/min, 5-100% ACN/H$_2$O+0.1% TFA) to provide (S)-2-((3-methyl-8-(4-oxo-4,5,6,7-tetrahydro-1H-pyrrolo[3,2-c]pyridin-2-yl)quinoxalin-2-yl)amino)propanamide 2,2,2-trifluoroacetate (33.7 mg, 0.070 mmol, 78% yield) as a reddish-brown solid: $^1$H NMR (400 MHz, MeOH-d$_4$) δ ppm 11.68 (1H, br. s.), 7.96 (1H, dd, J=7.5, 1.1 Hz), 7.64 (1H, dd, J=8.0, 1.2 Hz), 7.41 (1H, t, J=7.9 Hz), 7.06 (1H, s), 4.44 (1H, q, J=7.2 Hz), 3.61 (2H, t, J=7.1 Hz), 3.06-3.23 (2H, m), 2.70 (3H, s), 1.69 (3H, d, J=7.2 Hz). $^{19}$F NMR (377 MHz, MeOH-d$_4$) δ ppm −77.66 (3F, s). m/z (ESI, +ve) 365.1 (M+H)$^+$.

Example 130

2-(3-(cyclopentylamino)-2-methylquinoxalin-5-yl)-6,7-dihydro-1H-pyrrolo[3,2-c]pyridin-4(5H)-one

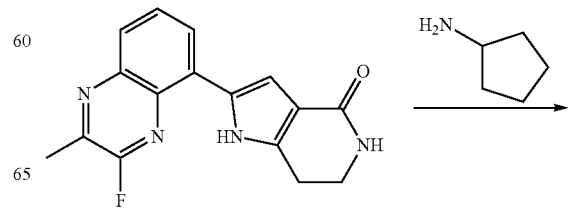

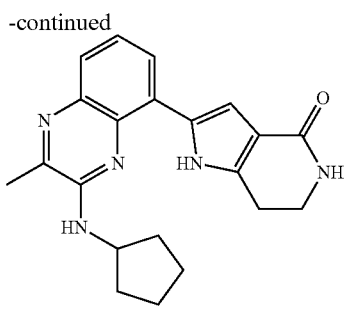

Prepared according to Example 127 using 2-(3-fluoro-2-methylquinoxalin-5-yl)-6,7-dihydro-1H-pyrrolo[3,2-c]pyridin-4(5H)-one (Example 126; 39.8 mg, 0.094 mmol) and cyclopentanamine (0.028 mL, 0.282 mmol) in DMSO (0.8 mL), heating at 100° C. for 50 min. Purification by reversed-phase HPLC (Phenomenex Gemini C18 column (150×30 mm, 10 μm), 35 mL/min, 5-100% ACN/H$_2$O+0.1% TFA) followed by chromatographic purification (silica gel, 0-100% EtOAc/hexanes, then 0-3% MeOH/DCM) furnished 2-(3-(cyclopentylamino)-2-methylquinoxalin-5-yl)-6,7-dihydro-1H-pyrrolo[3,2-c]pyridin-4(5H)-one (6.8 mg, 0.019 mmol, 20% yield) as a yellow solid: $^1$H NMR (400 MHz, DMSO-d$_6$) δ ppm 12.27 (1H, br. s.), 7.89 (1H, d, J=7.4 Hz), 7.56 (1H, d, J=7.6 Hz), 7.32 (1H, t, J=7.8 Hz), 7.12 (1H, s), 6.94 (1H, d, J=5.9 Hz), 4.34-4.42 (1H, m), 4.03 (1H, s), 3.43 (2H, t, J=6.9 Hz), 2.87 (2H, t, J=6.8 Hz), 2.55 (3H, s), 2.04-2.17 (2H, m), 1.69-1.83 (4H, m), 1.66 (2H, d, J=7.6 Hz). m/z (ESI, +ve) 362.1 (M+H)$^+$.

Example 131

2-(3-(cyclobutylamino)-2-methylquinoxalin-5-yl)-6,7-dihydro-1H-pyrrolo[3,2-c]pyridin-4(5H)-one

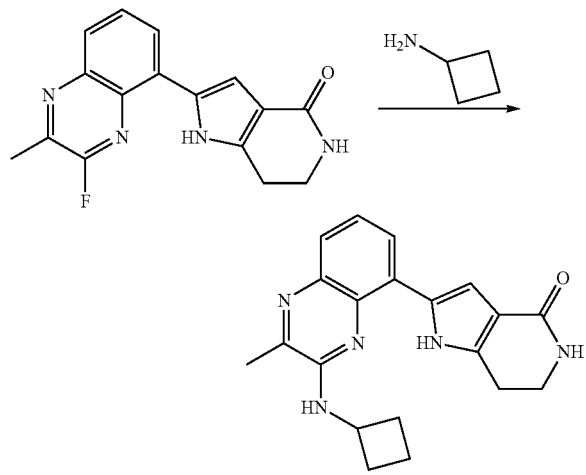

A solution of 2-(3-fluoro-2-methylquinoxalin-5-yl)-6,7-dihydro-1H-pyrrolo[3,2-c]pyridin-4(5H)-one (Example 126; 84.7 mg, 0.200 mmol) and cyclobutanamine (0.051 mL, 0.600 mmol) in DMSO (1.5 mL) was stirred under argon at 80° C. for 35 min. The mixture was cooled to 25° C. and diluted with water (40 mL). The resulting mixture was extracted with 5% MeOH/DCM (2×50 mL), and the combined extracts were sequentially washed with water (2×50 mL), dried over Na$_2$SO$_4$, filtered, and concentrated onto silica gel. Chromatographic purification (silica gel, 0-100% EtOAc/hexanes, then 0-10% MeOH/DCM) furnished 2-(3-(cyclobutylamino)-2-methylquinoxalin-5-yl)-6,7-dihydro-1H-pyrrolo[3,2-c]pyridin-4(5H)-one (44.7 mg, 0.129 mmol, 64% yield) as a yellow solid: $^1$H NMR (400 MHz, DMSO-d$_6$) δ ppm 12.37 (1H, br. s.), 7.90 (1H, dd, J=7.6, 1.2 Hz), 7.56 (1H, dd, J=8.0, 1.2 Hz), 7.39 (1H, d, J=6.3 Hz), 7.32 (1H, t, J=7.8 Hz), 7.10 (1H, d, J=2.0 Hz), 6.96 (1H, br. s.), 4.52 (1H, dq, J=15.2, 7.6 Hz), 3.45 (2H, td, J=6.8, 2.4 Hz), 2.92 (2H, t, J=6.8 Hz), 2.55 (3H, s), 2.42-2.48 (2H, m), 2.10-2.24 (2H, m), 1.78-1.91 (2H, m). m/z (ESI, +ve) 348.2 (M+H)$^+$.

Example 132

2-(3-(cyclohexylamino)-2-methylquinoxalin-5-yl)-6,7-dihydro-1H-pyrrolo[3,2-c]pyridin-4(5H)-one

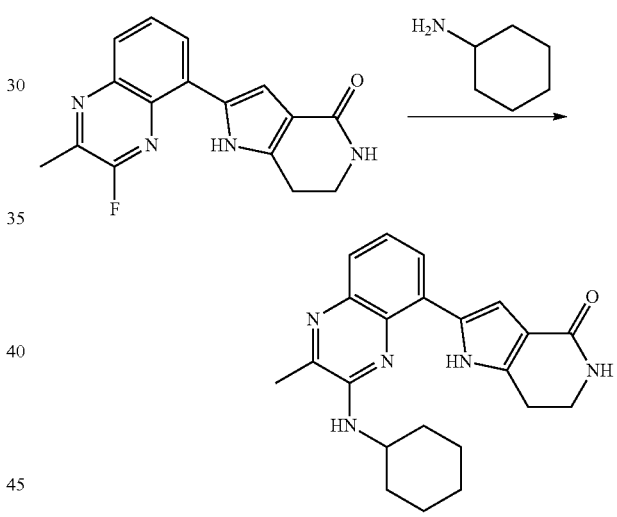

Prepared according to Example 127 using 2-(3-fluoro-2-methylquinoxalin-5-yl)-6,7-dihydro-1H-pyrrolo[3,2-c]pyridin-4(5H)-one (Example 126; 43.2 mg, 0.102 mmol) and cyclohexanamine (0.035 mL, 0.306 mmol) in DMSO (0.8 mL), heating at 100° C. for 50 min. Purification by reversed-phase HPLC (Phenomenex Gemini C$_{18}$ column (150×30 mm, 10 μm), 35 mL/min, 5-100% ACN/H$_2$O+0.1% TFA) furnished 2-(3-(cyclohexylamino)-2-methylquinoxalin-5-yl)-6,7-dihydro-1H-pyrrolo[3,2-c]pyridin-4(5H)-one 2,2,2-trifluoroacetate (17.1 mg, 0.035 mmol, 34% yield) as a red solid: $^1$H NMR (400 MHz, MeOH-d$_4$) δ ppm 7.92 (1H, d, J=7.4 Hz), 7.60 (1H, d, J=7.8 Hz), 7.37 (1H, t, J=7.9 Hz), 7.10 (1H, s), 3.96-4.05 (1H, m), 3.63 (2H, t, J=7.0 Hz), 3.01 (2H, t, J=7.0 Hz), 2.59 (3H, s), 2.20 (2H, d, J=9.8 Hz), 1.87-1.95 (2H, m), 1.78 (1H, d, J=12.9 Hz), 1.41-1.60 (4H, m), 1.34 (1H, t, J=12.4 Hz). $^{19}$F NMR (376 MHz, MeOH-d$_4$) δ ppm −77.54 (3F, br. s.). m/z (ESI, +ve) 376.3 (M+H)$^+$.

Example 133

2-(2-methyl-3-morpholinoquinoxalin-5-yl)-6,7-dihydro-1H-pyrrolo[3,2-c]pyridin-4(5H)-one

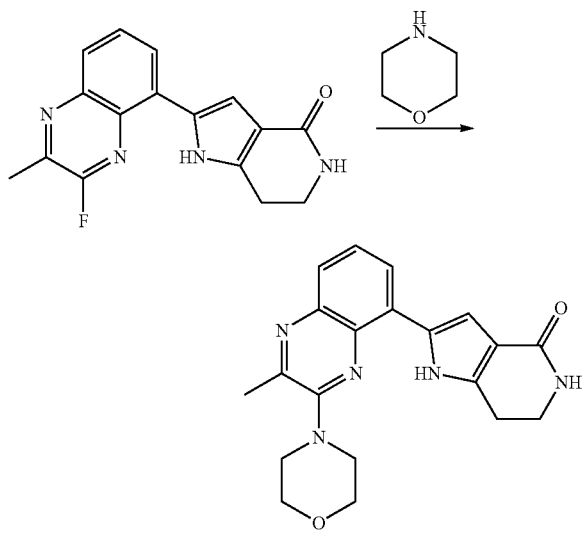

Prepared according to Example 127 using 2-(3-fluoro-2-methylquinoxalin-5-yl)-6,7-dihydro-1H-pyrrolo[3,2-c]pyridin-4(5H)-one (Example 126; 42.5 mg, 0.100 mmol) and morpholine (0.026 mL, 0.301 mmol) in DMSO (0.8 mL), heating at 100° C. for 40 min. Purification by reversed-phase HPLC (Phenomenex Gemini $C_{18}$ column (150×30 mm, 10 μm), 35 mL/min, 5-100% ACN/$H_2O$+0.1% TFA) furnished 2-(2-methyl-3-morpholinoquinoxalin-5-yl)-6,7-dihydro-1H-pyrrolo[3,2-c]pyridin-4(5H)-one 2,2,2-trifluoroacetate (27.5 mg, 0.058 mmol, 57% yield) as a yellow-orange solid: $^1$H NMR (400 MHz, DMSO-$d_6$) δ ppm 11.78 (1H, br. s.), 7.95 (1H, d, J=7.6 Hz), 7.71 (1H, d, J=8.0 Hz), 7.57 (1H, t, J=7.8 Hz), 7.16 (1H, d, J=2.2 Hz), 6.99 (1H, br. s.), 3.80-3.89 (4H, m), 3.42 (6H, d, J=7.4 Hz), 2.89 (2H, t, J=6.8 Hz), 2.68 (3H, s). $^{19}$F NMR (376 MHz, DMSO-$d_6$) δ ppm −74.46 (3F, s). m/z (ESI, +ve) 364.1 (M+H)$^+$.

Example 134

2-(3-(cycloheptylamino)-2-methylquinoxalin-5-yl)-6,7-dihydro-1H-pyrrolo[3,2-c]pyridin-4(5H)-one

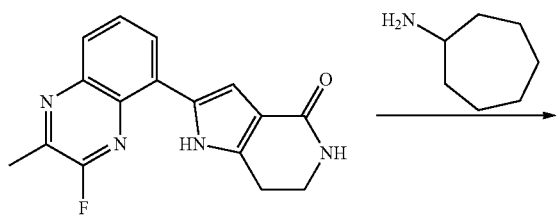

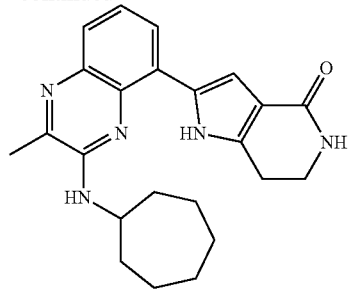

Prepared similar to that described in Example 131 using 2-(3-fluoro-2-methylquinoxalin-5-yl)-6,7-dihydro-1H-pyrrolo[3,2-c]pyridin-4(5H)-one (Example 126; 38.7 mg, 0.091 mmol) and cycloheptanamine (TCI America, Portland, Oreg.; 0.035 mL, 0.274 mmol) in DMSO (0.8 mL), heating at 100° C. for 40 min. Chromatographic purification (silica gel, 0-100% EtOAc/hexanes, then 0-10% MeOH/DCM) furnished 2-(3-(cycloheptylamino)-2-methylquinoxalin-5-yl)-6,7-dihydro-1H-pyrrolo[3,2-c]pyridin-4(5H)-one (29.8 mg, 0.077 mmol, 84% yield) as a yellow solid: $^1$H NMR (400 MHz, DMSO-$d_6$) δ ppm 11.95 (1H, br. s.), 7.86 (1H, d, J=7.6 Hz), 7.55 (1H, d, J=7.8 Hz), 7.30 (1H, t, J=7.8 Hz), 7.11 (1H, d, J=2.0 Hz), 6.92 (1H, br. s.), 6.79 (1H, d, J=7.4 Hz), 4.14-4.29 (1H, m), 3.44 (2H, td, J=6.8, 2.2 Hz), 2.88 (2H, t, J=6.7 Hz), 2.53 (3H, br. s.), 1.97-2.10 (2H, m), 1.62-1.79 (6H, m), 1.49-1.61 (4H, m). m/z (ESI, +ve) 390.2 (M+H)$^+$.

Example 135

2-(2-methyl-3-((2-methylallyl)amino)quinoxalin-5-yl)-6,7-dihydro-1H-pyrrolo[3,2-c]pyridin-4(5H)-one

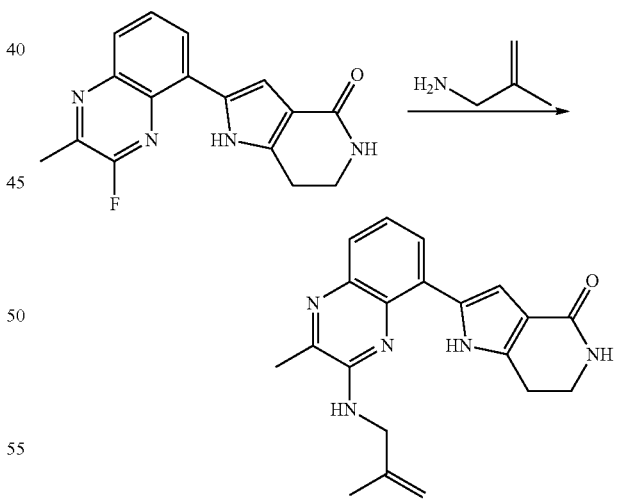

Prepared similar to that described in Example 131 using 2-(3-fluoro-2-methylquinoxalin-5-yl)-6,7-dihydro-1H-pyrrolo[3,2-c]pyridin-4(5H)-one (Example 126; 45.5 mg, 0.107 mmol) and 2-methylallylamine (Matrix Scientific, Columbia, S.C.; 0.039 mL, 0.430 mmol) in DMSO (0.8 mL), heating at 80° C. for 30 min. Chromatographic purification (silica gel, 0-100% EtOAc/hexanes, then 0-10% MeOH/DCM) furnished 2-(2-methyl-3-((2-methylallyl)amino)quinoxalin-5-yl)-6,7-dihydro-1H-pyrrolo[3,2-c]pyridin-4(5H)-one (22.0 mg, 0.063 mmol, 59% yield) as a yellow solid: $^1$H NMR (400 MHz, DMSO-d$_6$) δ ppm 11.83 (1H, br. s.), 7.87 (1H, dd, J=7.6, 1.2 Hz), 7.59 (1H, t, J=5.6 Hz), 7.56 (1H, m, J=8.0, 1.2 Hz), 7.31 (1H, t, J=7.8 Hz), 7.10 (1H, d, J=2.2 Hz), 6.93 (1H, s), 4.86 (1H, s), 4.83 (1H, s), 4.05 (2H, d, J=5.7 Hz), 3.42 (2H, td, J=6.8, 2.3 Hz), 2.86 (2H, t, J=6.8 Hz), 2.57 (3H, s), 1.85 (3H, s). m/z (ESI, +ve) 348.2 (M+H)$^+$.

Example 136

(S)-methyl 2-((3-methyl-8-(4-oxo-4,5,6,7-tetrahydro-1H-pyrrolo[3,2-c]pyridin-2-yl)quinoxalin-2-yl)amino)propanoate

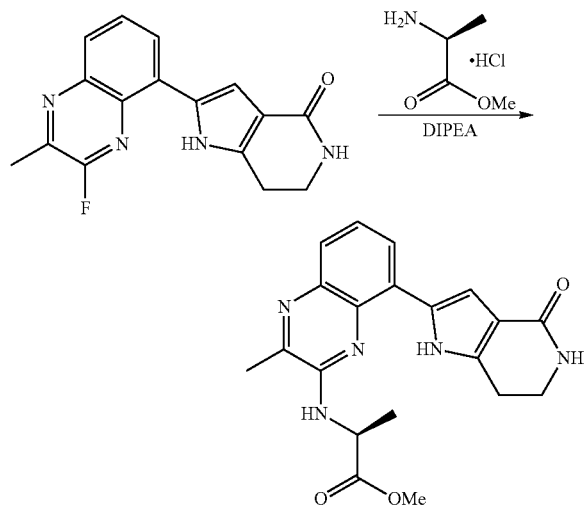

Prepared similar to that described in Example 131 using 2-(3-fluoro-2-methylquinoxalin-5-yl)-6,7-dihydro-1H-pyrrolo[3,2-c]pyridin-4(5H)-one (Example 126; 48.0 mg, 0.113 mmol), L-alanine methyl ester hydrochloride (Aldrich; 47.5 mg, 0.340 mmol), and DIPEA (0.119 mL, 0.680 mmol) in DMSO (0.8 mL), heating at 100° C. for 30 min. Chromatographic purification (silica gel, 0-100% EtOAc/hexanes, then 0-10% MeOH/DCM) furnished (S)-methyl 24(3-methyl-8-(4-oxo-4,5,6,7-tetrahydro-1H-pyrrolo[3,2-c]pyridin-2-yl)quinoxalin-2-yl)amino)propanoate (24.9 mg, 0.066 mmol, 58% yield) as a yellow-orange solid: $^1$H NMR (400 MHz, DMSO-d$_6$) δ ppm 11.60 (1H, br. s.), 7.90 (1H, dd, J=7.4, 1.2 Hz), 7.61 (1H, dd, J=8.0, 1.2 Hz), 7.47 (1H, d, J=6.8 Hz), 7.37 (1H, t, J=7.8 Hz), 6.97 (1H, s), 6.92 (1H, d, J=2.2 Hz), 4.76 (1H, quin, J=7.2 Hz), 3.54 (3H, s), 3.45 (2H, td, J=6.8, 2.4 Hz), 2.94 (2H, td, J=6.8, 2.9 Hz), 2.62 (3H, s), 1.60 (3H, d, J=7.2 Hz). m/z (ESI, +ve) 380.1 (M+H)$^+$.

Example 137

(R)-methyl 2-((3-methyl-8-(4-oxo-4,5,6,7-tetrahydro-1H-pyrrolo[3,2-c]pyridin-2-yl)quinoxalin-2-yl)amino)propanoate

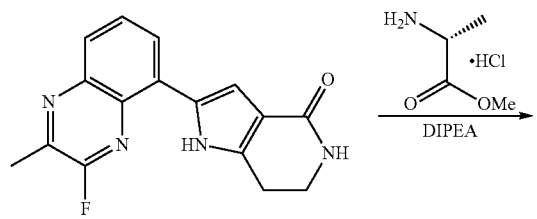

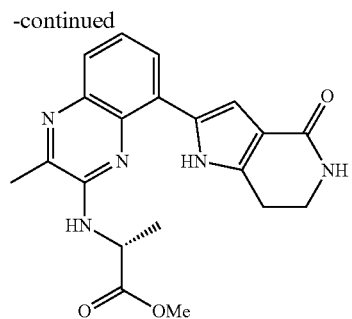

Prepared similar to that described in Example 131 using 2-(3-fluoro-2-methylquinoxalin-5-yl)-6,7-dihydro-1H-pyrrolo[3,2-c]pyridin-4(5H)-one (Example 126; 37.7 mg, 0.089 mmol), D-alanine methyl ester hydrochloride (Aldrich; 37.3 mg, 0.267 mmol), and DIPEA (0.093 mL, 0.534 mmol) in DMSO (0.8 mL), heating at 100° C. for 30 min. Chromatographic purification (silica gel, 0-100% EtOAc/hexanes, then 0-10% MeOH/DCM) furnished (R)-methyl 2-((3-methyl-8-(4-oxo-4,5,6,7-tetrahydro-1H-pyrrolo[3,2-c]pyridin-2-yl)quinoxalin-2-yl)amino)propanoate (21.3 mg, 0.056 mmol, 63% yield) as a yellow-orange solid: $^1$H NMR (400 MHz, DMSO-d$_6$) δ ppm 11.57 (1H, br. s.), 7.87 (1H, dd, J=7.5, 1.1 Hz), 7.58 (1H, dd, J=7.9, 1.1 Hz), 7.44 (1H, d, J=6.7 Hz), 7.34 (1H, t, J=7.8 Hz), 6.94 (1H, s), 6.89 (1H, d, J=2.2 Hz), 4.72 (1H, quin, J=7.1 Hz), 3.50 (3H, s), 3.42 (2H, td, J=6.7, 2.2 Hz), 2.91 (2H, td, J=6.8, 2.8 Hz), 2.59 (3H, s), 1.57 (3H, d, J=7.2 Hz). m/z (ESI, +ve) 380.3 (M+H)$^+$.

Example 138

2-(2-methyl-3-(pyrrolidin-1-yl)quinoxalin-5-yl)-6,7-dihydro-1H-pyrrolo[3,2-c]pyridin-4(5H)-one

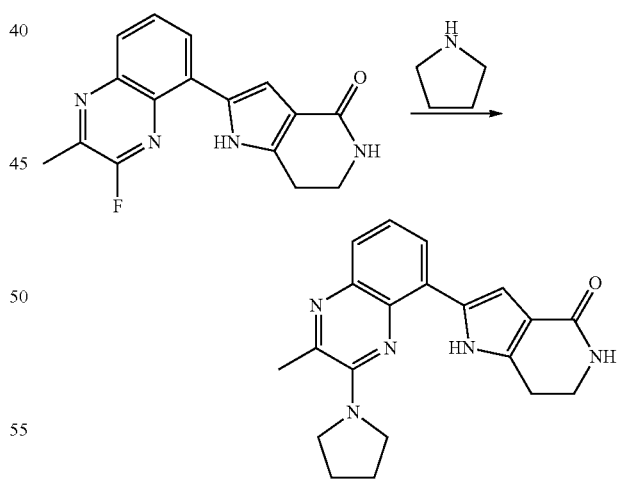

Prepared similar to that described in Example 131 using 2-(3-fluoro-2-methylquinoxalin-5-yl)-6,7-dihydro-1H-pyrrolo[3,2-c]pyridin-4(5H)-one (Example 126; 41.3 mg, 0.098 mmol) and pyrrolidine (0.024 mL, 0.293 mmol) in DMSO (0.8 mL), heating at 85° C. for 40 min. Chromatographic purification (silica gel, 0-100% EtOAc/hexanes, then 0-10% MeOH/DCM) furnished 2-(2-methyl-3-(pyrrolidin-1-yl)quinoxalin-5-yl)-6,7-dihydro-1H-pyrrolo[3,2-c]pyridin-4(5H)-one (21.0 mg, 0.060 mmol, 62% yield) as a yellow solid: $^1$H NMR (400 MHz, DMSO-$d_6$) δ ppm 12.08 (1H, br. s.), 7.90 (1H, dd, J=7.4, 1.2 Hz), 7.58 (1H, dd, J=7.9, 1.1 Hz), 7.34 (1H, t, J=7.8 Hz), 7.11 (1H, d, J=2.2 Hz), 6.96 (1H, s), 3.71-3.85 (4H, m), 3.42 (2H, td, J=6.8, 2.3 Hz), 2.86 (2H, t, J=6.8 Hz), 2.79 (3H, s), 1.94-2.05 (4H, m). m/z (ESI, +ve) 348.2 (M+H)$^+$.

Example 139

2-(3-(azetidin-1-yl)-2-methylquinoxalin-5-yl)-6,7-dihydro-1H-pyrrolo[3,2-c]pyridin-4(5H)-one

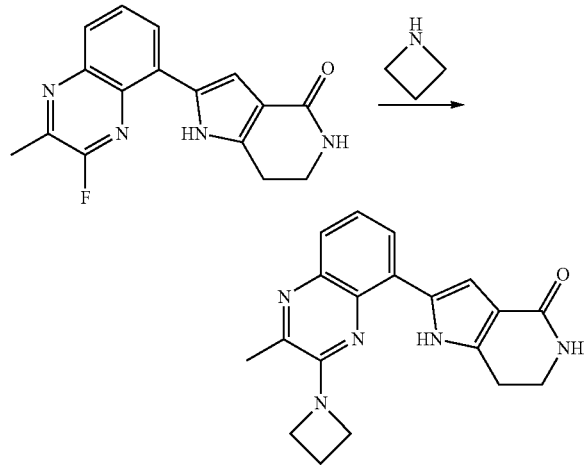

Prepared similar to that described in Example 131 using 2-(3-fluoro-2-methylquinoxalin-5-yl)-6,7-dihydro-1H-pyrrolo[3,2-c]pyridin-4(5H)-one (Example 126; 38.0 mg, 0.090 mmol) and azetidine (Aldrich; 0.018 mL, 0.269 mmol) in DMSO (0.8 mL), heating at 60° C. for 40 min. Chromatographic purification (silica gel, 0-100% EtOAc/hexanes, then 0-10% MeOH/DCM) furnished 2-(3-(azetidin-1-yl)-2-methylquinoxalin-5-yl)-6,7-dihydro-1H-pyrrolo[3,2-c]pyridin-4(5H)-one (13.3 mg, 0.040 mmol, 44% yield) as a yellow solid: $^1$H NMR (400 MHz, DMSO-$d_6$) δ ppm 12.05 (1H, br. s.), 7.91 (1H, dd, J=7.5, 1.1 Hz), 7.59 (1H, dd, J=7.8, 1.0 Hz), 7.36 (1H, t, J=7.7 Hz), 7.14 (1H, d, J=2.2 Hz), 6.96 (1H, s), 4.41 (4H, t, J=7.6 Hz), 3.42 (2H, td, J=6.6, 2.1 Hz), 2.87 (2H, t, J=7.0 Hz), 2.60 (3H, s), 2.35-2.45 (2H, m). m/z (ESI, +ve) 334.1 (M+H)$^+$.

Example 140

2-(3-((cis-3-aminocyclohexyl)amino)-2-methylquinoxalin-5-yl)-6,7-dihydro-1H-pyrrolo[3,2-c]pyridin-4(5H)-one (first-eluting enantiomer)

Example 141

2-(3-((cis-3-aminocyclohexyl)amino)-2-methylquinoxalin-5-yl)-6,7-dihydro-1H-pyrrolo[3,2-c]pyridin-4(5H)-one (second-eluting enantiomer)

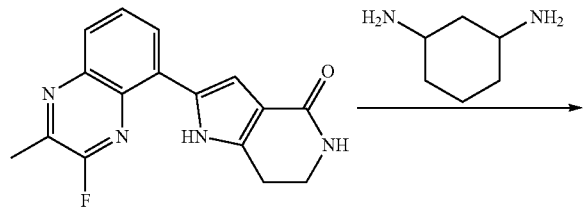

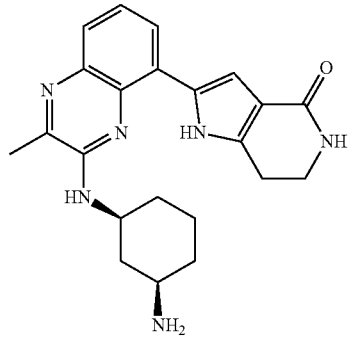

140 - cis-enantiomer 1
141 - cis-enantiomer 2

Prepared similar to that described in Example 127 using 2-(3-fluoro-2-methylquinoxalin-5-yl)-6,7-dihydro-1H-pyrrolo[3,2-c]pyridin-4(5H)-one (Example 126; 68.2 mg, 0.161 mmol) and cyclohexane-1,3-diamine (TCI America, Portland, Oreg.; 0.097 mL, 0.806 mmol) in DMSO (1.0 mL), heating at 100° C. for 1 h. Purification by reversed-phase HPLC (Phenomenex Gemini $C_{18}$ column (150×30 mm, 10 μm), 35 mL/min, 5-100% ACN/H$_2$O+0.1% TFA) provided 2-(34(3-aminocyclohexyl)amino)-2-methylquinoxalin-5-yl)-6,7-dihydro-1H-pyrrolo[3,2-c]pyridin-4(5H)-one 2,2,2-trifluoroacetate (mixture of isomers; 69.6 mg, 0.138 mmol, 86% yield) as a red-orange oil: m/z (ESI, +ve) 391.1 (M+H)$^+$. Separation of this material by supercritical-fluid chromatography (Chiralcel OD-H (250×21 mm, 5 μm), 55% liquid CO$_2$/45% EtOH (+40 mM NH$_3$), 55 mL/min, followed by repurification of 140 by Chiralcel AD-H (250×21 mm, 5 μm), 65% liquid CO$_2$/35% EtOH (+40 mM NH$_3$), 63 mL/min) separately afforded: 2-(3-((cis-3-aminocyclohexyl)amino)-2-methylquinoxalin-5-yl)-6,7-dihydro-1H-pyrrolo[3,2-c]pyridin-4(5H)-one, first-eluting enantiomer (140; 8.3 mg, 0.021 mmol) as a yellow-brown solid: $^1$H NMR (400 MHz, MeOD) δ ppm 7.77 (1H, dd, J=7.4, 0.8 Hz), 7.50 (1H, dd, J=8.0, 1.0 Hz), 7.25 (1H, t, J=7.8 Hz), 7.05 (1H, s), 3.95-4.05 (1H, m), 3.52 (2H, t, J=6.9 Hz), 2.89 (2H, td, J=7.0, 1.6 Hz), 2.43-2.47 (3H, m), 2.35 (1H, d, J=11.7 Hz), 2.06 (1H, d, J=11.0 Hz), 1.80-1.93 (2H, m), 1.40-1.55 (2H, m), 1.28-1.38 (1H, m), 1.17-1.26 (2H, m). m/z (ESI, +ve) 391.2 (M+H)$^+$; and 2-(3-((cis-3-aminocyclohexyl)amino)-2-methylquinoxalin-5-yl)-6,7-dihydro-1H-pyrrolo[3,2-c]pyridin-4(5H)-one, second-eluting enantiomer (141; 8.5 mg, 0.022 mmol) as a yellow-brown solid: $^1$H NMR (400 MHz, MeOD) δ ppm 7.86 (1H, dd, J=7.4, 1.2 Hz), 7.59 (1H, dd, J=8.1, 1.1 Hz), 7.34 (1H, t, J=7.8 Hz), 7.15 (1H, s), 4.04-4.14 (1H, m), 3.62 (2H, t, J=7.0 Hz), 2.98 (2H, td, J=7.0, 1.4 Hz), 2.52-2.56 (3H, m), 2.45 (1H, d, J=11.5 Hz), 2.16 (1H, d, J=10.8 Hz), 1.90-2.03 (2H, m), 1.49-1.64 (2H, m), 1.38-1.47 (1H, m), 1.28-1.38 (2H, m). m/z (ESI, +ve) 391.2 (M+H)$^+$.

Example 142

2-(3-((cis-3-aminocyclopentyl)amino)-2-methylquinoxalin-5-yl)-6,7-dihydro-1H-pyrrolo[3,2-c]pyridin-4(5H)-one (first-eluting enantiomer)

Example 143

2-(3-((cis-3-aminocyclopentyl)amino)-2-methylquinoxalin-5-yl)-6,7-dihydro-1H-pyrrolo[3,2-c]pyridin-4(5H)-one (second-eluting enantiomer)

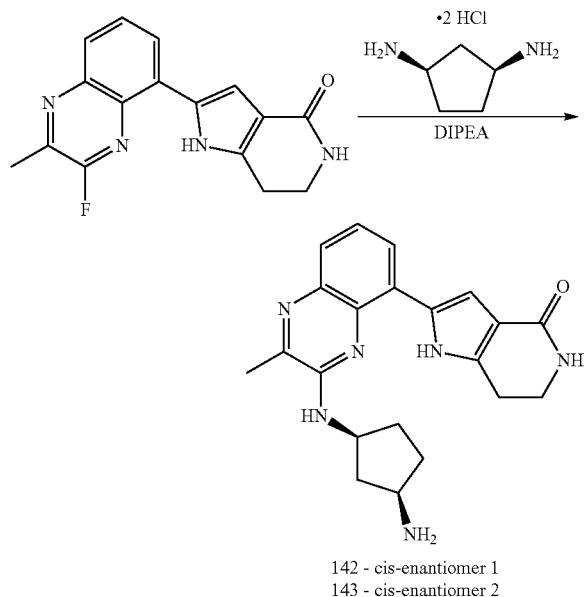

142 - cis-enantiomer 1
143 - cis-enantiomer 2

Prepared similar to that described in Example 127 using 2-(3-fluoro-2-methylquinoxalin-5-yl)-6,7-dihydro-1H-pyrrolo[3,2-c]pyridin-4(5H)-one (Example 126; 50 mg, 0.118 mmol), cyclopentane-1,3-diamine dihydrochloride (Chemgenx, LLC, Rocky Hill, N.J.; 102 mg, 0.591 mmol), and DIPEA (0.206 mL, 1.181 mmol) in DMSO (0.8 mL), heating at 100° C. for 1 h. Purification by reversed-phase HPLC (Phenomenex Gemini $C_{18}$ column (150×30 mm, 10 µm), 35 mL/min, 5-100% ACN/$H_2O$+0.1% TFA) provided 2-(3-((3-aminocyclopentyl)amino)-2-methylquinoxalin-5-yl)-6,7-dihydro-1H-pyrrolo[3,2-c]pyridin-4(5H)-one 2,2,2-trifluoroacetate (37.5 mg, 0.076 mmol, 65% yield) as a red-orange solid: m/z (ESI, +ve) 377.1 (M+H)$^+$. Separation of this material by supercritical-fluid chromatography (Chiralcel AD-H (250×21 mm, 5 µm column in series with 150×21 mm, 5 µm column), 70% liquid $CO_2$/30% EtOH (+0.5% isopropylamine), 60 mL/min) separately afforded: 2-(3-((cis-3-aminocyclopentyl)amino)-2-methylquinoxalin-5-yl)-6,7-dihydro-1H-pyrrolo[3,2-c]pyridin-4(5H)-one, first-eluting enantiomer (142; 4.7 mg, 0.012 mmol) as a yellow solid: $^1$H NMR (400 MHz, MeOH-d4) δ ppm 7.89 (1H, dd, J=7.5, 0.9 Hz), 7.59 (1H, dd, J=8.1, 0.9 Hz), 7.35 (1H, t, J=7.8 Hz), 7.10 (1H, s), 4.42 (1H, quin, J=6.9 Hz), 3.61 (2H, t, J=7.0 Hz), 3.47-3.55 (1H, m), 2.96 (2H, td, J=7.0, 1.6 Hz), 2.58-2.66 (1H, m), 2.57 (3H, s), 2.17-2.28 (1H, m), 2.08 (1H, td, J=13.3, 7.2 Hz), 1.90-2.01 (1H, m), 1.64-1.75 (1H, m), 1.56-1.61 (1H, m). m/z (ESI, +ve) 377.3 (M+H)$^+$; and 2-(3-((cis-3-aminocyclopentyl)amino)-2-methylquinoxalin-5-yl)-6,7-dihydro-1H-pyrrolo[3,2-c]pyridin-4(5H)-one, second-eluting enantiomer (143; 5.1 mg, 0.014 mmol) as a yellow solid: $^1$H NMR (400 MHz, MeOH-d4) δ ppm 7.90 (1H, dd, J=7.4, 0.8 Hz), 7.60 (1H, dd, J=8.0, 1.0 Hz), 7.35 (1H, t, J=7.8 Hz), 7.11 (1H, s), 4.45 (1H, quin, J=7.1 Hz), 3.62 (2H, t, J=7.0 Hz), 3.46-3.55 (1H, m), 2.97 (2H, td, J=7.0, 1.2 Hz), 2.59-2.67 (1H, m), 2.57 (3H, s), 2.18-2.29 (1H, m), 2.02-2.14 (1H, m), 1.91-2.02 (1H, m), 1.64-1.75 (1H, m), 1.56-1.62 (1H, m). m/z (ESI, +ve) 377.1 (M+H)$^+$.

Example 144

2-(2-methyl-3-((1-methylcyclobutyl)amino)quinoxalin-5-yl)-6,7-dihydro-1H-pyrrolo[3,2-c]pyridin-4(5H)-one

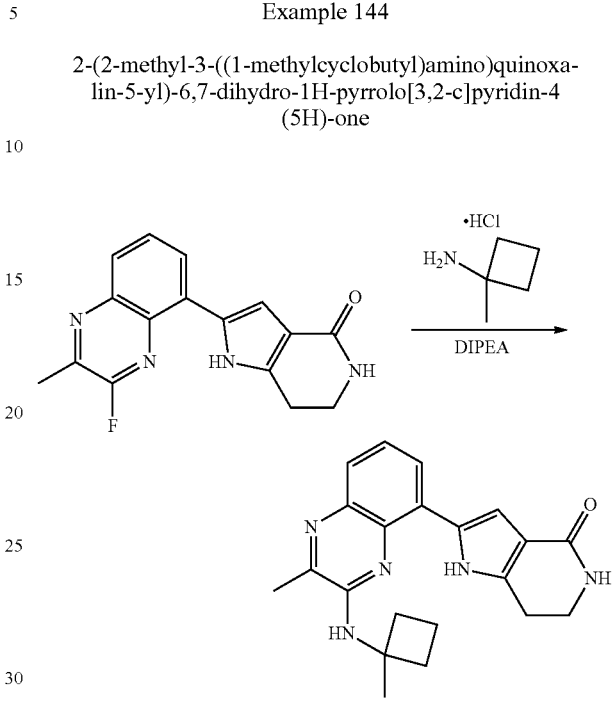

Prepared similar to that described in Example 131 using 2-(3-fluoro-2-methylquinoxalin-5-yl)-6,7-dihydro-1H-pyrrolo[3,2-c]pyridin-4(5H)-one (Example 126; 41.6 mg, 0.094 mmol), 1-methylcyclobutanamine hydrochloride (ChemBridge, San Diego, Calif.; 34.3 mg, 0.282 mmol), and DIPEA (0.098 mL, 0.564 mmol) in DMSO (0.8 mL), heating at 90° C. for 19 h. Chromatographic purification (silica gel, 0-100% EtOAc/hexanes, then 0-10% MeOH/DCM) furnished 2-(2-methyl-3-((1-methylcyclobutyl)amino)quinoxalin-5-yl)-6,7-dihydro-1H-pyrrolo[3,2-c]pyridin-4(5H)-one (26.4 mg, 0.073 mmol, 78% yield) as a yellow solid: $^1$H NMR (400 MHz, DMSO-d$_6$) δ ppm 12.29 (1H, br. s.), 7.89 (1H, d, J=6.8 Hz), 7.56 (1H, d, J=7.2 Hz), 7.32 (1H, t, J=7.8 Hz), 7.04 (1H, d, J=1.8 Hz), 7.01 (1H, s), 6.98 (1H, br. s.), 3.45 (2H, td, J=6.8, 2.2 Hz), 2.92 (2H, t, J=6.7 Hz), 2.56 (3H, s), 2.42-2.49 (2H, m), 2.21-2.30 (2H, m), 1.86-2.00 (2H, m), 1.69 (3H, s). m/z (ESI, +ve) 362.3 (M+H)$^+$.

Example 145

2-(3-((3,3-difluorocyclobutyl)amino)-2-methylquinoxalin-5-yl)-6,7-dihydro-1H-pyrrolo[3,2-c]pyridin-4(5H)-one

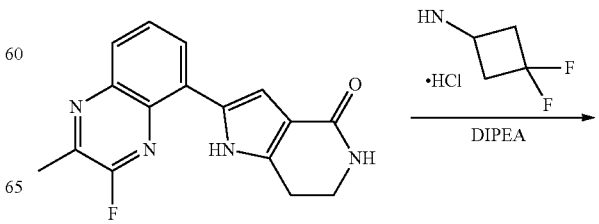

-continued

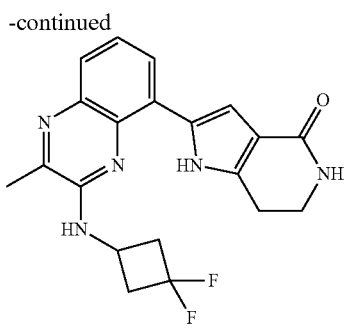

Prepared similar to that described in Example 131 using 2-(3-fluoro-2-methylquinoxalin-5-yl)-6,7-dihydro-1H-pyrrolo[3,2-c]pyridin-4(5H)-one (Example 126; 46.7 mg, 0.106 mmol), 3,3-difluorocyclobutanamine hydrochloride (PharmaStone, Lexington, Mass.; 45.5 mg, 0.317 mmol), and DIPEA (0.110 mL, 0.634 mmol) in DMSO (0.8 mL), heating at 80° C. for 1.5 h. Chromatographic purification (silica gel, 0-100% EtOAc/hexanes, then 0-10% MeOH/DCM) furnished 2434(3,3-difluorocyclobutyl)amino)-2-methylquinoxalin-5-yl)-6,7-dihydro-1H-pyrrolo[3,2-c]pyridin-4(5H)-one (26.5 mg, 0.069 mmol, 66% yield) as a yellow solid: $^1$H NMR (400 MHz, DMSO-$d_6$) δ ppm 11.97 (1H, br. s.), 7.88 (1H, dd, J=7.6, 1.2 Hz), 7.60 (1H, dd, J=8.0, 1.0 Hz), 7.51 (1H, d, J=5.5 Hz), 7.37 (1H, t, J=7.8 Hz), 7.06 (1H, d, J=2.2 Hz), 6.94 (1H, br. s.), 4.39-4.51 (1H, m), 3.45 (2H, td, J=6.7, 2.5 Hz), 3.04-3.15 (2H, m), 2.88 (2H, t, J=6.7 Hz), 2.86-2.92 (2H, m), 2.57 (3H, s). $^{19}$F NMR (377 MHz, DMSO-$d_6$) δ ppm -82.16 to -81.43 (1F, m), -95.87 to -95.05 (1F, m). m/z (ESI, +ve) 384.2 (M+H)$^+$.

Example 146

2-(3-(((1-(hydroxymethyl)cyclobutyl)amino)-2-methylquinoxalin-5-yl)-6,7-dihydro-1H-pyrrolo[3,2-c]pyridin-4(5H)-one

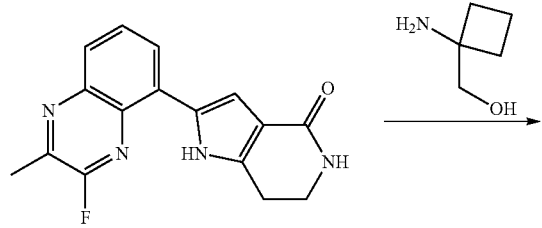

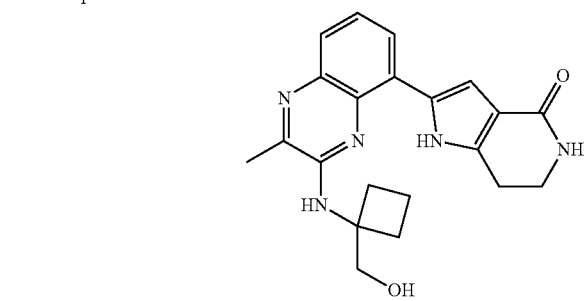

Prepared similar to that described in Example 127 using 2-(3-fluoro-2-methylquinoxalin-5-yl)-6,7-dihydro-1H-pyrrolo[3,2-c]pyridin-4(5H)-one (Example 126; 40 mg, 0.090 mmol) and (1-aminocyclobutyl)methanol (J&W Pharmlab, Levittown, Pa.; 27.4 mg, 0.271 mmol) in DMSO (0.8 mL), heating at 100° C. for 2 h. Purification by reversed-phase HPLC (Phenomenex Gemini $C_{18}$ column (150×30 mm, 10 μm), 35 mL/min, 5-100% ACN/H$_2$O+0.1% TFA) provided 2-(3-(((1-(hydroxymethyl)cyclobutyl)amino)-2-methylquinoxalin-5-yl)-6,7-dihydro-1H-pyrrolo[3,2-c]pyridin-4(5H)-one 2,2,2-trifluoroacetate (20.9 mg, 0.043 mmol, 47% yield) as a red solid: $^1$H NMR (400 MHz, DMSO-$d_6$) δ ppm 12.25 (1H, br. s.), 7.86 (1H, dd, J=7.5, 1.3 Hz), 7.54 (1H, dd, J=8.0, 1.2 Hz), 7.30 (1H, t, J=7.8 Hz), 6.98 (1H, d, J=2.0 Hz), 6.95 (1H, br. s.), 6.83 (1H, s), 3.86 (2H, s), 3.44 (2H, t, J=6.8 Hz), 2.91 (2H, t, J=6.8 Hz), 2.56 (3H, s), 2.30-2.40 (4H, m), 1.78-1.98 (2H, m). $^{19}$F NMR (377 MHz, DMSO-$d_6$) δ ppm -74.58 (3F, s). m/z (ESI, +ve) 378.2 (M+H)$^+$.

Example 147

2-(2-methyl-3-(neopentylamino)quinoxalin-5-yl)-6,7-dihydro-1H-pyrrolo[3,2-c]pyridin-4(5H)-one

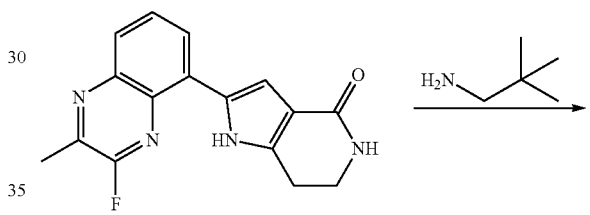

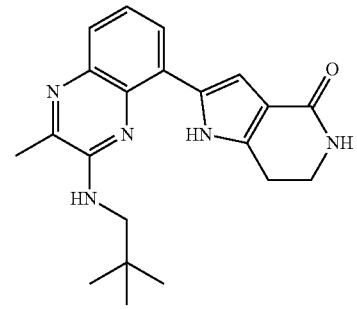

Prepared similar to that described in Example 131 using 2-(3-fluoro-2-methylquinoxalin-5-yl)-6,7-dihydro-1H-pyrrolo[3,2-c]pyridin-4(5H)-one (Example 126; 40 mg, 0.090 mmol) and 2,2-dimethylpropan-1-amine (TCI America, Portland, Oreg.; 0.032 mL, 0.271 mmol) in DMSO (0.8 mL), heating at 80° C. for 2 h. Chromatographic purification (silica gel, 0-100% EtOAc/hexanes, then 0-10% MeOH/DCM) furnished 2-(2-methyl-3-(neopentylamino)quinoxalin-5-yl)-6,7-dihydro-1H-pyrrolo[3,2-c]pyridin-4(5H)-one (31.4 mg, 0.086 mmol, 96% yield) as a yellow solid: $^1$H NMR (400 MHz, DMSO-$d_6$) δ ppm 12.05 (1H, br. s.), 7.85 (1H, dd, J=7.7, 0.8 Hz), 7.55 (1H, dd, J=8.0, 0.9 Hz), 7.30 (1H, t, J=7.7 Hz), 7.21 (1H, d, J=2.2 Hz), 7.02 (1H, t, J=6.4 Hz), 6.92 (1H, br. s.), 3.41-3.48 (4H, m), 2.88 (2H, t, J=6.8 Hz), 2.57 (3H, s), 0.99 (9H, s). m/z (ESI, +ve) 364.2 (M+H)$^+$.

Example 148

2-(3-((2-hydroxy-2-methylpropyl)amino)-2-methylquinoxalin-5-yl)-6,7-dihydro-1H-pyrrolo[3,2-c]pyridin-4(5H)-one

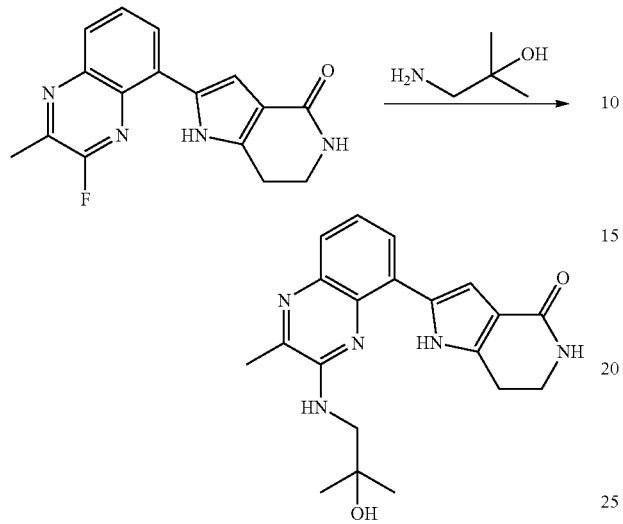

Prepared similar to that described in Example 131 using 2-(3-fluoro-2-methylquinoxalin-5-yl)-6,7-dihydro-1H-pyrrolo[3,2-c]pyridin-4(5H)-one (Example 126; 41.8 mg, 0.095 mmol) and 1-amino-2-methylpropan-2-ol (Tyger Scientific, Ewing, N.J.; 0.027 mL, 0.284 mmol) in DMSO (0.8 mL), heating at 100° C. for 30 min. Chromatographic purification (silica gel, 0-100% EtOAc/hexanes, then 0-10% MeOH/DCM) furnished 2-(3-((2-hydroxy-2-methylpropyl)amino)-2-methylquinoxalin-5-0-6,7-dihydro-1H-pyrrolo[3,2-c]pyridin-4(5H)-one (4.50 mg, 0.012 mmol, 13% yield) as a yellow solid, following trituration with Et$_2$O (2×2 mL): $^1$H NMR (400 MHz, DMSO-d$_6$) δ ppm 12.40 (1H, br. s.), 7.86 (1H, d, J=7.4 Hz), 7.55 (1H, d, J=8.0 Hz), 7.29 (1H, t, J=7.8 Hz), 7.13 (1H, t, J=5.9 Hz), 6.97 (1H, s), 6.93 (1H, s), 4.86 (1H, s), 3.51 (2H, d, J=5.5 Hz), 3.42 (2H, t, J=6.7 Hz), 2.90 (2H, t, J=6.7 Hz), 2.56 (3H, s), 1.27 (6H, s). m/z (ESI, +ve) 366.2 (M+H)$^+$.

Example 149 tert-butyl 3-((3-methyl-8-(4-oxo-4,5,6,7-tetrahydro-1H-pyrrolo[3,2-c]pyridin-2-yl)quinoxalin-2-yl)amino)azetidine-1-carboxylate

Example 150

2-(3-(azetidin-3-ylamino)-2-methylquinoxalin-5-yl)-6,7-dihydro-1H-pyrrolo[3,2-c]pyridin-4(5H)-one

Example 153

2-(3-((1-acetylazetidin-3-yl)amino)-2-methylquinoxalin-5-yl)-6,7-dihydro-1H-pyrrolo[3,2-c]pyridin-4(5H)-one

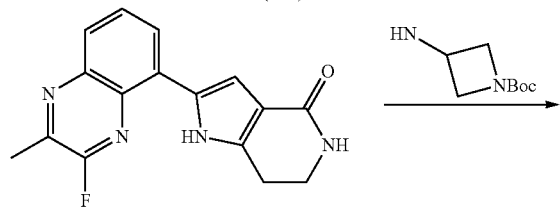

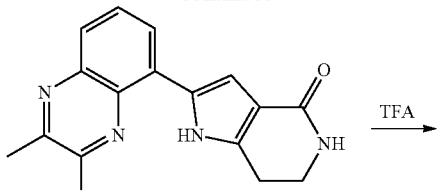

149

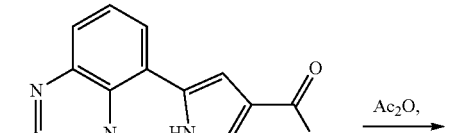

150

[structure] 153

Preparation of tert-butyl 3-((3-methyl-8-(4-oxo-4,5,6,7-tetrahydro-1H-pyrrolo[3,2-c]pyridin-2-yl)quinoxalin-2-yl)amino)azetidine-1-carboxylate Prepared similar to that described in Example 131 using 2-(3-fluoro-2-methylquinoxalin-5-yl)-6,7-dihydro-1H-pyrrolo[3,2-c]pyridin-4(5H)-one (Example 126; 170.6 mg, 0.386 mmol) and tert-butyl 3-amino)azetidine-1-carboxylate (Astatech, Inc., Guelph, ON, Canada; 0.151 mL, 0.964 mmol) in DMSO (3.0 mL), heating at 100° C. for 1 h. Chromatographic purification (silica gel, 0-100% EtOAc/hexanes, then 0-10% MeOH/DCM) furnished tert-butyl 3-((3-methyl-8-(4-oxo-4,5,6,7-tetrahydro-1H-pyrrolo[3,2-c]pyridin-2-yl)quinoxalin-2-yl)amino)azetidine-1-carboxylate (104.0 mg, 0.232 mmol, 60% yield) as a yellow solid: $^1$H NMR (400 MHz, DMSO-d$_6$) δ ppm 11.75 (1H, br. s.), 7.85 (1H, dd, J=7.5, 0.9 Hz), 7.60 (1H, dd, J=8.0, 1.0 Hz), 7.58 (1H, d, J=5.3 Hz), 7.37 (1H, t, J=7.8 Hz), 7.12 (1H, d, J=1.4 Hz), 6.95 (1H, br. s.), 4.70-4.82 (1H, m), 4.28 (2H, br. s.), 3.97 (2H, dd, J=8.8, 5.1 Hz), 3.44 (2H, t, J=6.7 Hz), 2.91 (2H, t, J=6.8 Hz), 2.58 (3H, s), 1.40 (9H, s). m/z (ESI, +ve) 449.0 (M+H)$^+$.

Preparation of 2-(3-(azetidin-3-ylamino)-2-methylquinoxalin-5-yl)-6,7-dihydro-1H-pyrrolo[3,2-c]pyridin-4(5H)-one A solution of tert-butyl 3-((3-methyl-8-(4-oxo-4,5,6,7-tetrahydro-1H-pyrrolo[3,2-c]pyridin-2-yl)quinoxalin-2-yl)amino)azetidine-1-carboxylate (98.0 mg, 0.218 mmol) and TFA (1.0 mL, 12.98 mmol) in DCM (2.0 mL) was stirred at 25° C. for 1 h. MeOH (2 mL) was added, and the mixture was concentrated in vacuo. The residue was partitioned between 5% MeOH/DCM (80 mL) and saturated aq. NaHCO$_3$ (50 mL). The aq. layer was separated and concentrated in vacuo. Sonication of the residue with 5% MeOH/DCM (80 mL, then 2×40 mL) and concentration of the combined organic layers provided a yellow-orange oil. This oil was triturated with Et$_2$O, the supernatant was drawn off, and the precipitated residue was taken up in 5% MeOH/DCM, filtered, and dried in vacuo to provide a yellow foam. Purification of this foam by reversed-phase HPLC (Phenomenex Gemini C$_{18}$ column (150×30 mm, 10 μm), 35 mL/min, 5-100% ACN/H$_2$O+0.1% TFA) furnished 2-(3-(azetidin-3-ylamino)-2-methylquinoxalin-5-yl)-6,7-dihydro-1H-pyrrolo[3,2-c]pyridin-4(5H)-one 2,2,2-trifluoroacetate (41.0 mg, 0.089 mmol, 41% yield) as a red-brown solid: $^1$H NMR (400 MHz, MeOH-d$_4$) δ ppm 11.47 (1H, br. s.), 7.78 (1H, d, J=7.2 Hz), 7.69 (1H, d, J=8.0 Hz), 7.45 (1H, t, J=8.0 Hz), 7.34 (1H, d, J=2.0 Hz), 5.21 (1H, quin, J=7.5 Hz), 4.43-4.51 (2H, m), 4.18-4.28 (2H, m), 3.63 (2H, t, J=7.0 Hz), 3.01 (2H, t, J=7.0 Hz), 2.64 (3H, s). $^{19}$F NMR (376 MHz, MeOH-d$_4$) δ ppm −77.58 (3F, s). m/z (ESI, +ve) 349.1 (M+H)$^+$.

Preparation of 2-(3-((1-acetylazetidin-3-yl)amino)-2-methylquinoxalin-5-yl)-6,7-dihydro-1H-pyrrolo[3,2-c]pyridin-4(5H)-one Ac$_2$O (4.49 μl, 0.048 mmol) was added to a mixture of 2-(3-(azetidin-3-ylamino)-2-methylquinoxalin-5-yl)-6,7-dihydro-1H-pyrrolo[3,2-c]pyridin-4(5H)-one 2,2,2-trifluoroacetate (20.0 mg, 0.043 mmol) and DIPEA (0.023 mL, 0.130 mmol) in DCM (1.0 mL), and the resulting yellow suspension was stirred at 25° C. for 10 min. The mixture was concentrated in vacuo, and the residue was taken up in in DMSO (2.0 mL) and purified by reversed-phase HPLC (Phenomenex Gemini C$_{18}$ column (150×30 mm, 10 μm), 35 mL/min, 5-100% ACN/H$_2$O+0.1% TFA) to provide 2-(3-((1-acetylazetidin-3-yl)amino)-2-methylquinoxalin-5-yl)-6,7-dihydro-1H-pyrrolo[3,2-c]pyridin-4(5H)-one 2,2,2-trifluoroacetate (19.0 mg, 0.038 mmol, 87% yield) as a red solid: $^1$H NMR (400 MHz, MeOH-d$_4$) δ ppm 7.86 (1H, d, J=7.4 Hz), 7.66 (1H, d, J=7.4 Hz), 7.44 (1H, t, J=7.8 Hz), 7.18 (1H, s), 4.89-4.97 (1H, m), 4.69 (1H, t, J=8.3 Hz), 4.46 (1H, dd, J=9.9, 8.1 Hz), 4.23 (1H, dd, J=9.2, 5.1 Hz), 4.05 (1H, dd, J=10.4, 5.1 Hz), 3.64 (2H, t, J=7.1 Hz), 3.04 (2H, t, J=7.0 Hz), 2.66 (3H, s), 1.91 (3H, s). $^{19}$F NMR (376 MHz, MeOH-d$_4$) δ ppm −77.73 (3F, s). m/z (ESI, +ve) 391.1 (M+H)$^+$.

Example 151

2-(3-cyclobutoxy-2-methylquinoxalin-5-yl)-6,7-dihydro-1H-pyrrolo[3,2-c]pyridin-4(5H)-on

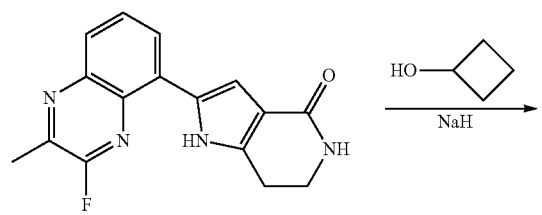

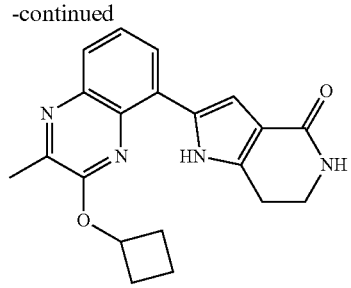

NaH (60% w/w in mineral oil; 37.8 mg, 0.945 mmol) was added to a solution of of cyclobutanol (Aldrich; 0.074 mL, 0.945 mmol) in DMF (1.0 mL) and the resulting suspension was stirred at 25° C. for 10 min. 2-(3-Fluoro-2-methylquinoxalin-5-yl)-6,7-dihydro-1H-pyrrolo[3,2-c]pyridin-4(5H)-one (Example 126; 40 mg, 0.135 mmol) was added, and the resulting solution was heated at 60° C. for 3 h. The mixture was cooled to 25° C., diluted with half-saturated aq. NH$_4$Cl (30 mL), and extracted with DCM (2×40 mL). The combined organic extracts were washed with water (40 mL), dried over Na$_2$SO$_4$, filtered, and concentrated in vacuo. Chromatographic purification of the residue (silica gel, 0-100% EtOAc/hexanes, then 0-10% MeOH/DCM) furnished 2-(3-cyclobutoxy-2-methylquinoxalin-5-yl)-6,7-dihydro-1H-pyrrolo[3,2-c]pyridin-4(5H)-one (17.8 mg, 0.051 mmol, 38% yield) as a yellow solid: $^1$H NMR (400 MHz, CDCl$_3$) δ ppm 12.07 (1H, br. s.), 7.99 (1H, d, J=7.6 Hz), 7.78 (1H, d, J=7.2 Hz), 7.55 (1H, t, J=7.8 Hz), 7.18 (1H, d, J=2.0 Hz), 5.46 (1H, br. s.), 5.28 (1H, quin, J=7.4 Hz), 3.70 (2H, t, J=6.7 Hz), 3.02 (2H, t, J=6.8 Hz), 2.68 (3H, s), 2.59-2.67 (2H, m), 2.33-2.45 (2H, m), 2.01-2.13 (1H, m), 1.77-1.92 (1H, m). m/z (ESI, +ve) 349.2 (M+H)$^+$.

Example 152

2-(2-methyl-3-(neopentyloxy)quinoxalin-5-yl)-6,7-dihydro-1H-pyrrolo[3,2-c]pyridin-4(5H)-one

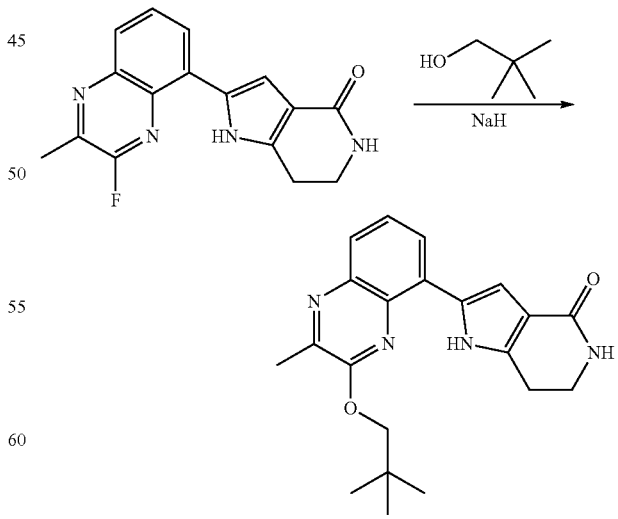

NaH (60% w/w in mineral oil; 37.8 mg, 0.945 mmol) was added to a solution of neopentyl alcohol (Aldrich; 0.103 mL, 0.945 mmol) in DMF (1.0 mL), and the resulting suspension was stirred at 25° C. for 10 min. 2-(3-Fluoro-2-methylquinoxalin-5-yl)-6,7-dihydro-1H-pyrrolo[3,2-c]pyridin-4(5H)-one (Example 126; 40 mg, 0.135 mmol) was added, and the resulting solution was heated at 100° C. for 17 h. The mixture was cooled to 25° C., diluted with half-saturated aq. NH₄Cl (30 mL), and extracted with DCM (2×40 mL). The combined organic extracts were washed with water (40 mL), dried over Na₂SO4, filtered, and concentrated in vacuo. Chromatographic purification of the residue (silica gel, 0-100% EtOAc/hexanes, then 0-10% MeOH/DCM) furnished 2-(2-methyl-3-(neopentyloxy)quinoxalin-5-yl)-6,7-dihydro-1H-pyrrolo[3,2-c]pyridin-4(5H)-one (15.3 mg, 0.042 mmol, 31% yield) as a yellow solid: $^1$H NMR (400 MHz, CDCl₃) δ ppm 12.03 (1H, br. s.), 8.00 (1H, d, J=7.6 Hz), 7.79 (1H, d, J=8.0 Hz), 7.56 (1H, t, J=7.8 Hz), 7.18 (1H, d, J=2.0 Hz), 5.43 (1H, br. s.), 4.12 (2H, s), 3.68 (2H, td, J=6.5, 1.4 Hz), 2.96 (2H, t, J=6.8 Hz), 2.71 (3H, s), 1.18 (9H, s). m/z (ESI, +ve) 365.1 (M+H)⁺.

Example 154

2-(2-methyl-3-(tert-pentylamino)quinoxalin-5-yl)-6,7-dihydro-1H-pyrrolo[3,2-c]pyridin-4(5H)-one

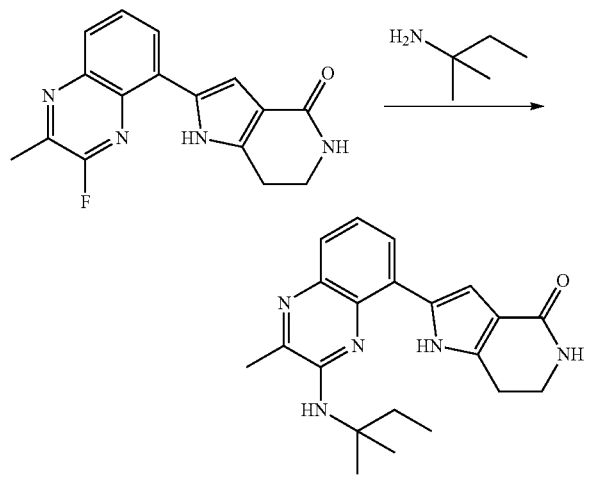

Prepared similar to that described in Example 131 using 2-(3-fluoro-2-methylquinoxalin-5-yl)-6,7-dihydro-1H-pyrrolo[3,2-c]pyridin-4(5H)-one (Example 126; 48.0 mg, 0.162 mmol) and 2-methylbutan-2-amine (Aldrich; 0.047 mL, 0.405 mmol) in DMSO (1.0 mL), heating 70° C. for 9 h. Chromatographic purification (silica gel, 0-100% EtOAc/hexanes, then 0-10% MeOH/DCM) furnished 2-(2-methyl-3-(tert-pentylamino)quinoxalin-5-yl)-6,7-dihydro-1H-pyrrolo[3,2-c]pyridin-4(5H)-one (30.5 mg, 0.084 mmol, 52% yield) as a yellow solid: $^1$H NMR (400 MHz, CDCl₃) δ ppm 12.51 (1H, br. s.), 7.94 (1H, dd, J=7.5, 0.8 Hz), 7.65 (1H, dd, J=8.1, 0.7 Hz), 7.38 (1H, t, J=7.8 Hz), 7.11 (1H, d, J=2.0 Hz), 5.38 (1H, br. s.), 4.77 (1H, s), 3.66 (2H, td, J=6.8, 1.9 Hz), 2.99 (2H, t, J=6.8 Hz), 2.57 (3H, s), 2.03 (2H, q, J=7.4 Hz), 1.61 (6H, s), 0.97 (3H, t, J=7.4 Hz). m/z (ESI, +ve) 364.2 (M+H)⁺.

Example 155

2-(2-methyl-3-((1-methylcyclohexyl)amino)quinoxalin-5-yl)-6,7-dihydro-1H-pyrrolo[3,2-c]pyridin-4(5H)-one

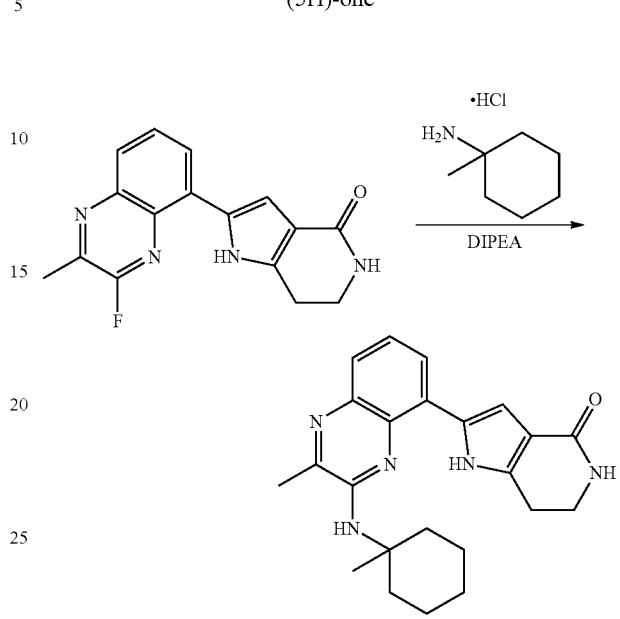

A solution of 2-(3-fluoro-2-methylquinoxalin-5-yl)-6,7-dihydro-1H-pyrrolo[3,2-c]pyridin-4(5H)-one (Example 126; 49.3 mg, 0.166 mmol), 1-methylcyclohexanamine hydrochloride (ChemBridge, San Diego, Calif.; 74.7 mg, 0.499 mmol), and DIPEA (0.174 mL, 0.998 mmol) in DMSO (1.0 mL) was heated at 100° C. for 2 h, then at 120° C. for 5 h, then at 80° C. for 5 d. Additional 1-methylcyclohexanamine hydrochloride (74.7 mg, 0.499 mmol) and DIPEA (0.174 mL, 0.998 mmol) were added, and the resulting mixture was heated at 120° C. for 20 h. The mixture was cooled to 25° C. and diluted with water (40 mL). The resulting mixture was extracted with DCM (2×40 mL), and the combined extracts were sequentially washed with water (40 mL), dried over Na₂SO₄, filtered, and concentrated onto silica gel. Chromatographic purification (silica gel, 0-100% EtOAc/hexanes, then 0-10% MeOH/DCM) followed by reversed-phase HPLC (Phenomenex Gemini C₁₈ column (150×30 mm, 10 μm), 35 mL/min, 5-100% ACN/H₂O+0.1% TFA) yielded 2-(2-methyl-3-((1-methylcyclohexyl)amino)quinoxalin-5-yl)-6,7-dihydro-1H-pyrrolo[3,2-c]pyridin-4(5H)-one 2,2,2-trifluoroacetate (10.0 mg, 0.020 mmol, 12% yield) as a red solid: $^1$H NMR (400 MHz, MeOH-d₄) δ ppm 7.90 (1H, dd, J=7.5, 0.7 Hz), 7.62 (1H, d, J=7.4 Hz), 7.38 (1H, t, J=7.8 Hz), 7.00 (1H, s), 3.62 (2H, t, J=7.1 Hz), 2.99 (2H, t, J=7.0 Hz), 2.64 (3H, s), 2.37 (2H, d, J=13.3 Hz), 1.69-1.78 (2H, m), 1.65-1.68 (3H, m), 1.60 (5H, br. s.), 1.37-1.49 (1H, m). $^{19}$F NMR (376 MHz, MeOH-d₄) δ ppm −77.57 (3F, s). m/z (ESI, +ve) 390.2 (M+H)⁺.

Example 156 rac-2-(3-fluoro-2-methylquinoxalin-5-yl)-7-methyl-6,7-dihydro-1H-pyrrolo[3,2-c]pyridin-4(5H)-one Example 160

2-(3-fluoro-2-methylquinoxalin-5-yl)-7-methyl-6,7-dihydro-1H-pyrrolo[3,2-c]pyridin-4(5H)-one enantiomers (first-eluting enantiomer)

Example 161

2-(3-fluoro-2-methylquinoxalin-5-yl)-7-methyl-6,7-dihydro-1H-pyrrolo[3,2-c]pyridin-4(5H)-one enantiomers (second-eluting enantiomer)

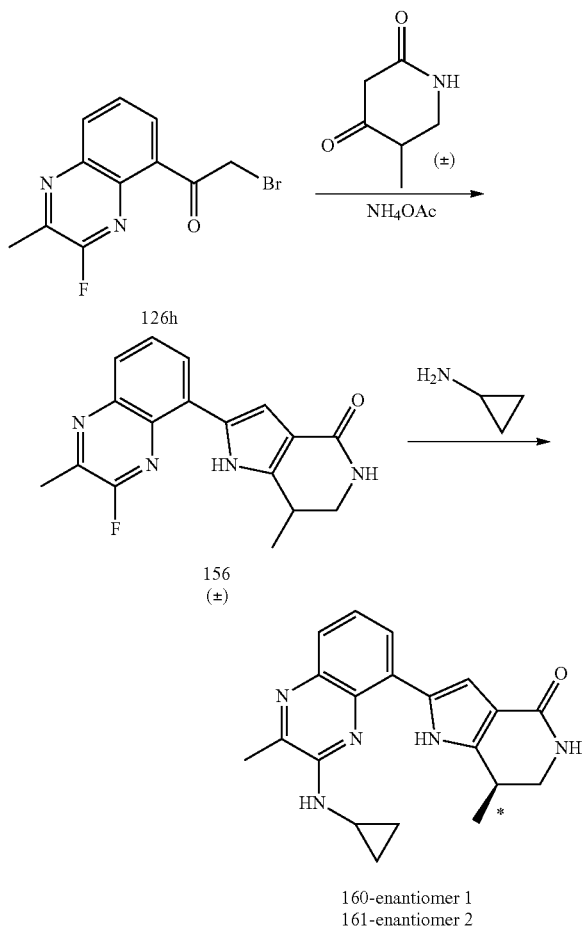

160-enantiomer 1
161-enantiomer 2

Preparation of 156: rac-2-(3-fluoro-2-methylquinoxalin-5-yl)-7-methyl-6,7-dihydro-1H-pyrrolo[3,2-c]pyridin-4(5H)-one A mixture of 2-bromo-1-(3-fluoro-2-methylquinoxalin-5-yl)ethanone (Example 126h; 735.7 mg, 2.60 mmol), 5-methylpiperidine-2,4-dione (prepared according to J. Med. Chem. 2009, 52, 293-307; 396 mg, 3.12 mmol), and NH$_4$OAc (801 mg, 10.40 mmol) in EtOH (7.0 mL) was stirred under argon in a sealed flask at 40° C. for 17 h. The reaction was cooled to 25° C. and concentrated in vacuo. The residue was partitioned between 5% MeOH/DCM (80 mL) and water (80 mL), and the organic layer was separated. The aq. layer was extracted with 5% MeOH/DCM (2×60 mL), and the combined organic layers were washed with brine (80 mL), dried over Na$_2$SO$_4$, filtered, and concentrated onto silica gel. Chromatographic purification (silica gel, 0-10% MeOH/DCM) furnished rac-2-(3-fluoro-2-methylquinoxalin-5-yl)-7-methyl-6,7-dihydro-1H-pyrrolo[3,2-c]pyridin-4(5H)-one (237.1 mg, 0.764 mmol, 29% yield) as an orange solid: $^1$H NMR (400 MHz, DMSO-d$_6$) δ ppm 11.55 (1H, br. s.), 8.07 (1H, d, J=7.6 Hz), 7.91 (1H, d, J=8.2 Hz), 7.82 (1H, t, J=8.0 Hz), 7.20 (1H, d, J=2.2 Hz), 7.01 (1H, br. s.), 3.43-3.54 (1H, m), 3.05-3.19 (2H, m), 2.71 (3H, s), 1.30 (3H, d, J=6.3 Hz). $^{19}$F NMR (376 MHz, DMSO-d$_6$) δ ppm −71.86 (1F, s). m/z (ESI, +ve) 311.1 (M+H)$^+$.

Preparation of 2-(3-fluoro-2-methylquinoxalin-5-yl)-7-methyl-6,7-dihydro-1H-pyrrolo[3,2-c]pyridin-4(5H)-one enantiomers Prepared similar to that described in Example 131 using rac-2-(3-fluoro-2-methylquinoxalin-5-yl)-7-methyl-6,7-dihydro-1H-pyrrolo[3,2-c]pyridin-4(5H)-one (Example 156; 62.4 mg, 0.201 mmol) and cyclopropanamine (Alfa Aesar, Ward Hill, Mass.; 0.042 mL, 0.603 mmol) in DMSO (1.0 mL), heating at 100° C. for 1.5 h. Chromatographic purification (silica gel, 0-100% EtOAc/hexanes, then 0-10% MeOH/DCM) furnished rac-2-(3-(cyclopropylamino)-2-methylquinoxalin-5-yl)-7-methyl-6,7-dihydro-1H-pyrrolo[3,2-c]pyridin-4(5H)-one (58.8 mg, 0.169 mmol, 84% yield) as a yellow solid: $^1$H NMR (400 MHz, DMSO-d$_6$) δ ppm 12.51 (1H, br. s.), 7.99 (1H, d, J=7.4 Hz), 7.53-7.64 (2H, m), 7.36 (1H, t, J=7.7 Hz), 7.18 (1H, d, J=1.8 Hz), 6.98 (1H, br. s.), 3.46-3.58 (1H, m), 3.05-3.20 (2H, m), 2.88-2.98 (1H, m), 2.51 (3H, br. s.), 1.24 (3H, d, J=6.5 Hz), 0.88-1.00 (2H, m), 0.68-0.78 (2H, m). m/z (ESI, +ve) 348.2 (M+H)$^+$. Separation of this material by supercritical-fluid chromatography (Chiralpak AS-H (250×21 mm, 5 μn), 60% liquid CO$_2$/40% MeOH (+20 mM NH$_3$), 70 mL/min) separately afforded: 2-(3-(cyclopropylamino)-2-methylquinoxalin-5-yl)-7-methyl-6,7-dihydro-1H-pyrrolo[3,2-c]pyridin-4(5H)-one, first-eluting enantiomer (160; 19.6 mg, 0.056 mmol) as a yellow solid; and 2-(3-(cyclopropylamino)-2-methylquinoxalin-5-yl)-7-methyl-6,7-dihydro-1H-pyrrolo[3,2-c]pyridin-4(5H)-one, second-eluting enantiomer (161; 19.2 mg, 0.055 mmol) as a yellow solid.

Example 159

2-(3-(butylamino)-2-methylquinoxalin-5-yl)-6,7-dihydro-1H-pyrrolo[3,2-c]pyridin-4(5H)-one

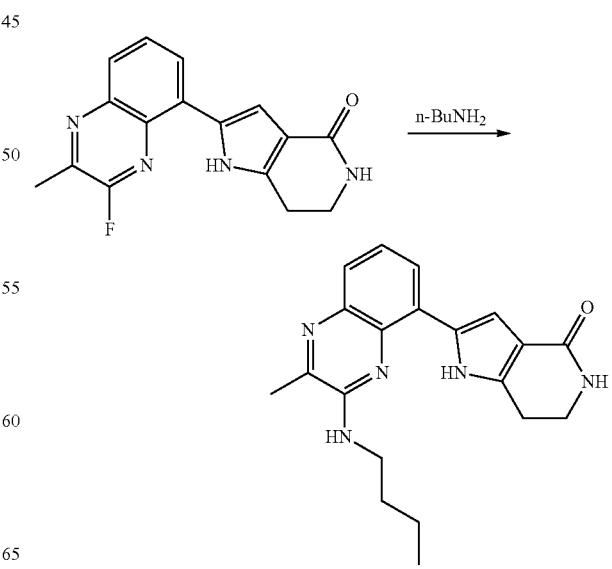

Prepared similar to that described in Example 131 using 2-(3-fluoro-2-methylquinoxalin-5-yl)-6,7-dihydro-1H-pyrrolo[3,2-c]pyridin-4(5H)-one (Example 126; 41.5 mg, 0.140 mmol) and butan-1-amine (0.042 mL, 0.420 mmol) in DMSO (1.0 mL), heating at 75° C. for 45 min. Chromatographic purification (silica gel, 0-100% EtOAc/hexanes, then 0-10% MeOH/DCM) furnished 2-(3-(butylamino)-2-methylquinoxalin-5-yl)-6,7-dihydro-1H-pyrrolo[3,2-c]pyridin-4(5H)-one (6.28 mg, 0.018 mmol, 13% yield) as a yellow solid: $^1$H NMR (400 MHz, DMSO-$d_6$) δ ppm 12.15 (1H, br. s.), 7.88 (1H, d, J=7.4 Hz), 7.56 (1H, d, J=8.0 Hz), 7.27-7.36 (2H, m), 7.13 (1H, d, J=1.6 Hz), 6.94 (1H, br. s.), 3.52 (2H, q, J=6.7 Hz), 3.44 (2H, td, J=6.7, 2.0 Hz), 2.87 (2H, t, J=6.7 Hz), 2.53 (3H, s), 1.72 (2H, quin, J=7.4 Hz), 1.47 (2H, sxt, J=7.3 Hz), 0.94 (3H, t, J=7.3 Hz). m/z (ESI, +ve) 350.1 (M+H)$^+$.

Example 162

2-(3-(tert-butylamino)-2-methylquinoxalin-5-yl)-7-methyl-6,7-dihydro-1H-pyrrolo[3,2-c]pyridin-4(5H)-one (first-eluting enantiomer)

Example 163

2-(3-(tert-butylamino)-2-methylquinoxalin-5-yl)-7-methyl-6,7-dihydro-1H-pyrrolo[3,2-c]pyridin-4(5H)-one (second-eluting enantiomer)

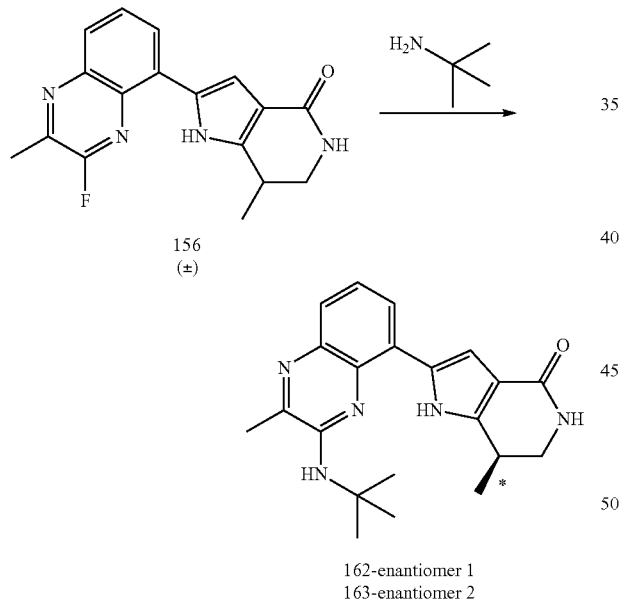

156
(±)

162-enantiomer 1
163-enantiomer 2

2-(3-(tert-Butylamino)-2-methylquinoxalin-5-yl)-7-methyl-6,7-dihydro-1H-pyrrolo[3,2-c]pyridin-4(5H)-one enantiomers were prepared similar to that described in Example 131 using rac-2-(3-fluoro-2-methylquinoxalin-5-yl)-7-methyl-6,7-dihydro-1H-pyrrolo[3,2-c]pyridin-4(5H)-one (Example 156; 69.4 mg, 0.224 mmol) and 2-methylpropan-2-amine (TCI America, Portland, Oreg.; 0.071 mL, 0.671 mmol) in DMSO (1.0 mL), heating 100° C. for 1.5 h. Chromatographic purification (silica gel, 0-100% EtOAc/hexanes, then 0-10% MeOH/DCM) furnished rac-2-(3-(tert-butylamino)-2-methylquinoxalin-5-yl)-7-methyl-6,7-dihydro-1H-pyrrolo[3,2-c]pyridin-4(5H)-one (43.6 mg, 0.120 mmol, 54% yield) as a yellow solid: $^1$H NMR (400 MHz, DMSO-$d_6$) δ ppm 11.60 (1H, br. s.), 7.79 (1H, d, J=7.4 Hz), 7.59 (1H, d, J=8.2 Hz), 7.33 (1H, t, J=7.8 Hz), 6.95 (1H, s), 6.92 (1H, br. s.), 5.97 (1H, s), 3.45-3.55 (1H, m), 3.01-3.14 (2H, m), 2.55 (3H, s), 1.54 (9H, s), 1.27 (3H, d, J=6.3 Hz). m/z (ESI, +ve) 364.2 (M+H)$^+$. Separation of this material by supercritical-fluid chromatography (Chiralpak AS-H (250×21 mm, 5 µm), 70% liquid $CO_2$/30% MeOH (+20 mM $NH_3$), 70 mL/min) separately afforded: 2-(3-(tert-butylamino)-2-methylquinoxalin-5-yl)-7-methyl-6,7-dihydro-1H-pyrrolo[3,2-c]pyridin-4(5H)-one, first-eluting enantiomer (162; 17.4 mg, 0.048 mmol) as a yellow solid; and 2-(3-(tert-butylamino)-2-methylquinoxalin-5-yl)-7-methyl-6,7-dihydro-1H-pyrrolo[3,2-c]pyridin-4(5H)-one, second-eluting enantiomer (163; 16.4 mg, 0.045 mmol) as a yellow solid.

Example 164

1-methyl-4-(2-(phenylamino)quinolin-8-yl)-1H-pyrrole-2-carboxamide

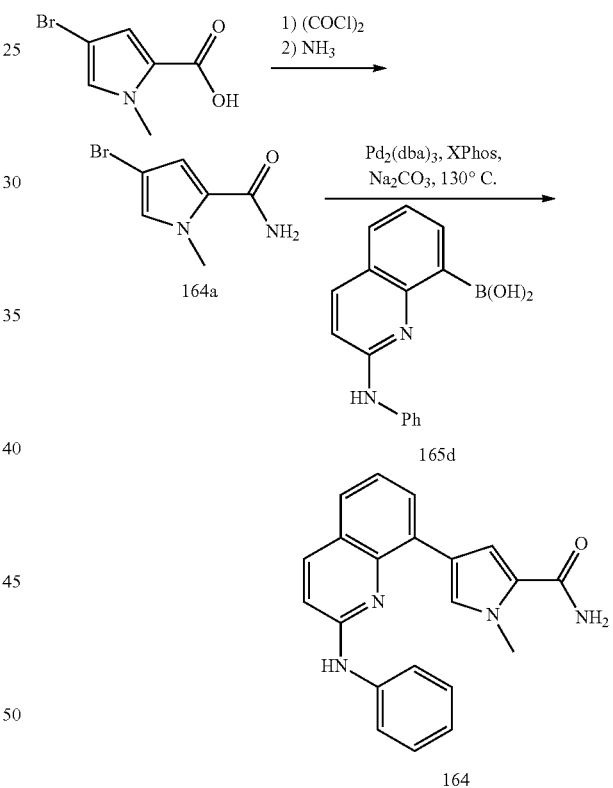

Preparation of
4-bromo-1-methyl-1H-pyrrole-2-carboxamide

To a suspension of 4-bromo-1-methyl-1H-pyrrole-2-carboxylic acid (Matrix Scientific, Columbia, S.C.; 390 mg, 1.91 mmol) in 5 mL of DCM at RT was added oxalyl chloride (2.0 M solution in DCM, 1.912 mL, 3.82 mmol) followed by 3 drops of DMF. After stirring at RT for 30 min, the mixture was concentrated under reduced pressure. The remaining off white solid was cooled with an ice bath, $NH_3$ (0.5 M solution in 1,4-dioxane, 15.3 mL, 7.65 mmol) was added. After stirring at RT for 30 min, the mixture was diluted with 50 mL of EtOAc and washed with 2×15 mL of water. The organic layer was dried over Na$_2$SO$_4$ and concentrated to give 4-bromo-1-methyl-1H-pyrrole-2-carboxamide (329 mg, 85% yield) as a brown crystalline solid that was used without further purification. $^1$H NMR (400 MHz, DMSO-d$_6$) δ ppm 7.51 (1H, br.), 7.08 (1H, d, J=1.8 Hz), 7.01 (1H, br.), 6.86 (1H, d, J=1.8 Hz), 3.80 (3H, s). m/z (ESI, +ve) 202.9/204.9 (M+H)$^+$.

Preparation of 1-methyl-4-(2-(phenylamino)quinolin-8-yl)-1H-pyrrole-2-carboxamide A mixture of 4-bromo-1-methyl-1H-pyrrole-2-carboxamide (164a; 40 mg, 0.20 mmol), (2-(phenylamino)quinolin-8-yl)boronic acid (Example 165d; 68 mg, 0.26 mmol), XPhos (10 mg) and Pd$_2$(dba)$_3$ (10 mg) in 2 mL of dioxane and 0.5 mL of 2 N Na$_2$CO$_3$ was heated in a microwave at 130° C. for 20 min. The mixture was partitioned between 20 mL of EtOAc and 5 mL of 0.5 N NaOH. The organic layer was concentrated, and purified on silica gel column (25-85% EtOAc in hexanes) to give 1-methyl-4-(2-(phenylamino)quinolin-8-yl)-1H-pyrrole-2-carboxamide (19 mg, 27% yield) as an off-white crystalline solid. $^1$H NMR (400 MHz, DMSO-d$_6$) δ ppm 9.35 (1H, s), 8.06 (1H, d, J=8.8 Hz), 7.90 (2H, m), 7.84 (1H, d, J=1.8 Hz), 7.68 (1H, dd, J=7.3, 1.5 Hz), 7.56 (1H, dd, J=7.8, 1.4 Hz), 7.48 (1H, br.), 7.37 (1H, d, J=2.0 Hz), 7.35-7.24 (3H, m), 7.06 (1H, d, J=8.8 Hz), 7.00 (1H, t, J=7.3 Hz), 6.82 (1H, br.), 3.87 (3H, s). m/z (ESI, +ve) 343.1 (M+H)$^+$.

Example 165

7-(2-(phenylamino)quinolin-8-yl)-3,4-dihydropyrrolo[1,2-a]pyrazin-1(2H)-one

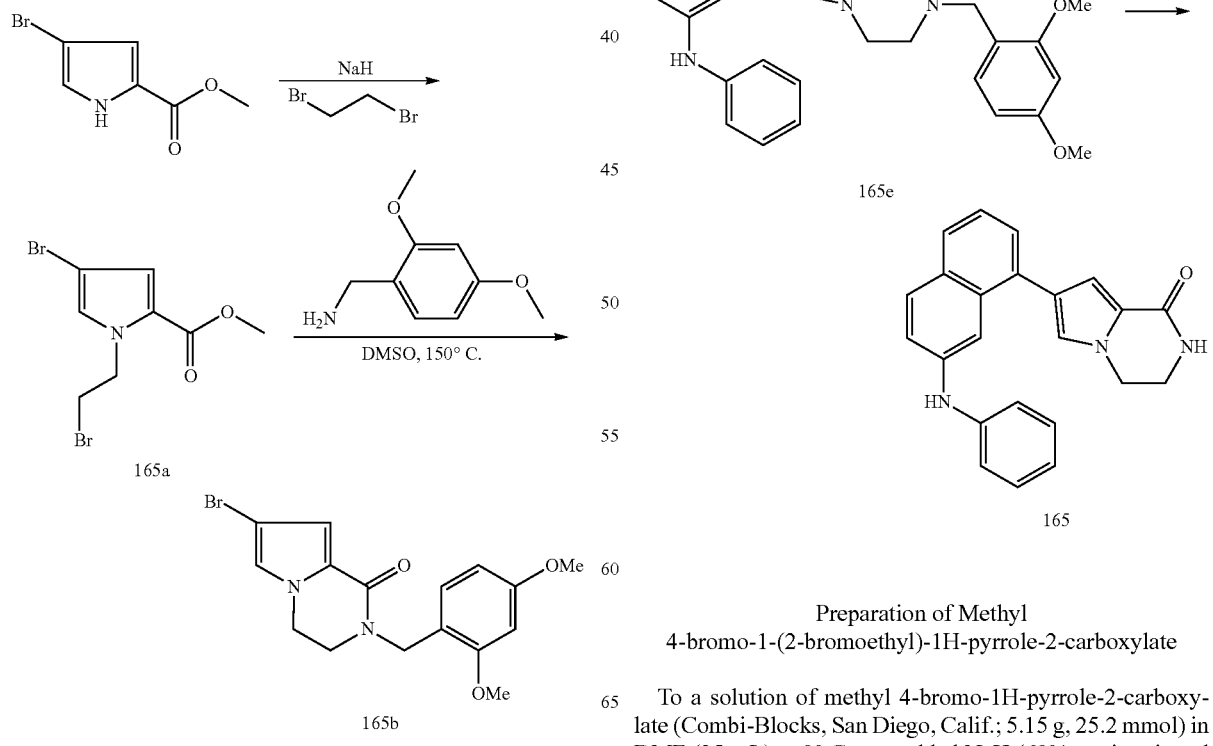

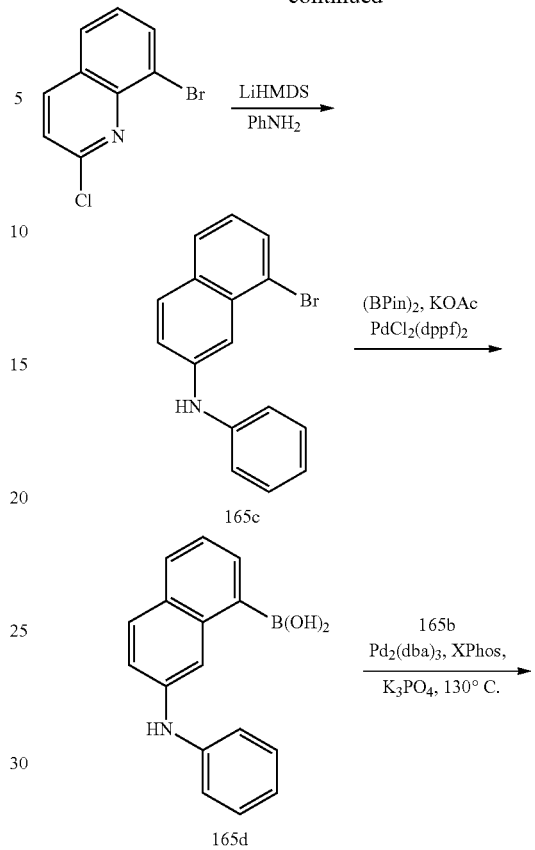

Preparation of Methyl 4-bromo-1-(2-bromoethyl)-1H-pyrrole-2-carboxylate

To a solution of methyl 4-bromo-1H-pyrrole-2-carboxylate (Combi-Blocks, San Diego, Calif.; 5.15 g, 25.2 mmol) in DMF (25 mL) at 0° C. was added NaH (60% wt. in mineral oil, 1.81 g, 45.4 mmol) and the resulting mixture was stirred at 0° C. for 15 min. 1,2dibromoethane (4.79 ml, 55.5 mmol) was added and the reaction was stirred at RT for 10 min, then heated in an oil bath at 70° C. for 2 h. After cooling to RT, it was treated with ice cold NH$_4$Cl solution (10 mL), extracted with 2×75 mL of EtOAc. The combined organic layers were washed with brine, dried over Na$_2$SO$_4$ and concentrated. Purification on a silica gel column (15-35% EtOAc in hexanes) furnished methyl 4-bromo-1-(2-bromoethyl)-1H-pyrrole-2-carboxylate (3.60 g, 11.58 mmol, 46% yield) as an off-white amorphous solid. $^1$H NMR (400 MHz, DMSO-d$_6$) δ ppm 7.41 (1H, d, J=2.0 Hz), 6.92 (1H, d, J=1.8 Hz), 4.65 (2H, t, J=6.5 Hz), 3.75 (5H, m). m/z (ESI, +ve) 311.9 (M+H)$^+$.

Preparation of 7-Bromo-2-(2,4-dimethoxybenzyl)-3,4-dihydropyrrolo[1,2-a]pyrazin-1(2H)-one (2,4-Dimethoxyphenyl)methanamine (Aldrich; 4.36 mL, 28.9 mmol) was added to a stirred solution of methyl 4-bromo-1-(2-bromoethyl)-1H-pyrrole-2-carboxylate (Example 165a; 3.60 g, 11.58 mmol) in DMSO (15 mL) at RT. The reaction was heated at 150° C. in an oil bath for 5 h. After it was cooled to RT, the brown mixture was partitioned between 10 mL of 2.0 N aq. HCl and 200 mL of EtOAc. The layers were separated; the organic solution was washed with 2.0 N aq. HCl (5 mL) followed by brine (5 mL), dried (Na$_2$SO$_4$), and concentrated. Purification on a silica gel column (25-75% EtOAc in Hexanes) gave 7-bromo-2-(2,4-dimethoxybenzyl)-3,4-dihydropyrrolo[1,2-a]pyrazin-1(2H)-one (3.61 g, 9.88 mmol, 85% yield) as an off-white crystalline solid. $^1$H NMR (400 MHz, DMSO-d$_6$) δ ppm 7.15 (1H, d, J=1.8 Hz), 7.11 (1H, d, J=8.2 Hz), 6.68 (1H, d, J=1.8 Hz), 6.59 (1H, d, J=2.3 Hz), 6.50 (1H, dd, J=8.3, 2.4 Hz), 4.53 (2H, s), 4.12 (2H, dd, J=6.7, 5.2 Hz), 3.81 (3H, s), 3.76 (3H, s), 3.57 (2H, dd, J=6.7, 5.0 Hz). m/z (ESI, +ve) 365/367 (M+H)$^+$.

Preparation of 8-bromo-N-phenylquinolin-2-amine

To a solution of aniline (0.76 g, 8.16 mmol) and 8-bromo-2-chloroquinoline (Biofine International, Vancouver, BC; 1.1 g, 4.54 mmol) in THF (7 mL) at 0° C. was added LiHMDS (1.0 M solution in THF, 13.61 mL, 13.61 mmol) drop wise via a syringe. The resulting brown mixture was stirred at RT for 1 h, and then quenched with sat. NH$_4$Cl solution (15 mL) and extracted with EtOAc (2×50 mL). The combined organic solution was concentrated and the residue was purified on a silica gel column (25-45% EtOAc in hexanes) to afford 8-bromo-N-phenylquinolin-2-amine (Ex. 165c, 1.03 g, 3.44 mmol, 76% yield) as a brown crystalline solid. $^1$H NMR (400 MHz, DMSO-d$_6$) δ ppm 9.69 (1H, s), 8.21 (2H, d, J=7.8 Hz), 8.10 (1H, d, J=8.8 Hz), 7.94 (1H, m), 7.77 (1H, d, J=7.0 Hz), 7.35 (2H, t, J=7.8 Hz), 7.21 (1H, t, J=7.7 Hz), 7.13 (1H, d, J=9.0 Hz), 6.98 (1H, t, J=7.3 Hz). m/z (ESI, +ve) 299/301 (M+H)$^+$.

Preparation of (2-(phenylamino)quinolin-8-yl)boronic acid

A mixture of 8-bromo-N-phenylquinolin-2-amine (Example 165c; 160 mg, 0.535 mmol), bis(pinacolato)diboron (272 mg, 1.07 mmol), KOAc (210 mg, 2.14 mmol) and Pd(dppf)Cl$_2$ (Strem Chemicals; 21.8 mg, 0.027 mmol) in DMF (2 mL) was heated in a microwave at 115° C. for 25 min. The resulting heterogeneous mixture was diluted with 25 mL of EtOAc and filtered through a pad of Celite. The filtrate was washed with 2×10 mL water. The organic layer was dried over Na$_2$SO$_4$ and concentrated to give a mixture of 2 products, N-phenylquinolin-2-amine (m/z (ESI, +ve) 221.0 (M+H)$^+$ in about 20%) and (2-(phenylamino)quinolin-8-yl)boronic acid (m/z (ESI, +ve) 265.0 (M+H)$^+$ in about 80%, Ex. 165d), which was used in the next step without further purification.

Preparation of 2-(2,4-dimethoxybenzyl)-7-(2-(phenylamino)quinolin-8-yl)-3,4-dihydropyrrolo[1,2-a]pyrazin-1(2H)-one A mixture of the above-obtained crude (2-(phenylamino)quinolin-8-yl)boronic acid (Example 165d), 7-bromo-2-(2,4-dimethoxybenzyl)-3,4-dihydropyrrolo[1,2-a]pyrazin-1(2H)-one (Example 165b; 150 mg, 0.41 mmol), potassium phosphate (262 mg, 1.23 mmol), Pd$_2$(dba)$_3$ (15 mg, 0.016 mmol) and XPhos (Strem Chemicals; 15 mg, 0.033 mmol) in 2 mL of dioxane and 0.5 mL of water was heated in a microwave at 130° C. for 25 min. It was cooled to RT and treated with additional 7-bromo-2-(2,4-dimethoxybenzyl)-3,4-dihydropyrrolo[1,2-a]pyrazin-1(2H)-one (88 mg, 0.23 mmol) and (A-Phos)$_2$PdCl$_2$ (20 mg). The mixture was heated in a microwave at 130° C. for 25 min. It was cooled to RT, partitioned between 20 mL of EtOAc and 5 mL of 0.5 N NaOH. The organic layer was concentrated. Purification on silica gel column (25-85% EtOAc in hexanes) gave 2-(2,4-dimethoxybenzyl)-7-(2-(phenylamino)quinolin-8-yl)-3,4-dihydropyrrolo[1,2-a]pyrazin-1(2H)-one (m/z (ESI, +ve) 505.1 (M+H)$^+$ in about 55% pure) as a brown solid, which was used in the next step without further purification.

Preparation of 165

7-(2-(phenylamino)quinolin-8-yl)-3,4-dihydropyrrolo[1,2-a]pyrazin-1(2H)-one. The above obtained 2-(2,4-dimethoxybenzyl)-7-(2-(phenylamino)quinolin-8-yl)-3,4-dihydropyrrolo[1,2-a]pyrazin-1(2H)-one in 1 mL of TFA and 1 mL of DCE was heated in an oil bath at 50° C. for 2 h. It was concentrated under reduced pressure. The orange residue was partitioned between 50 mL of EtOAc and 5 mL of 2 N NaOH. The EtOAc layer was separated, washed with 10 mL of brine, and concentrated. Purification on a silica gel column (1-5% MeOH in EtOAc) gave 7-(2-(phenylamino)quinolin-8-yl)-3,4-dihydropyrrolo[1,2-a]pyrazin-1(2H)-one (56 mg, 0.158 mmol, 35% yield for 3 steps) as an off-white crystalline solid. $^1$H NMR (400 MHz, DMSO-d$_6$) δ ppm 9.36 (1H, br.), 8.07 (1H, d, J=8.8 Hz), 7.91 (3H, dd, J=4.7, 2.9 Hz), 7.77 (1H, dd, J=7.3, 1.3 Hz), 7.69 (1H, br.), 7.59 (1H, dd, J=7.8, 1.2 Hz), 7.35 (2H, t, J=7.8 Hz), 7.28 (1H, t, J=7.6 Hz), 7.21 (1H, d, J=1.6 Hz), 7.07 (1H, d, J=9.0 Hz), 7.00 (1H, t, J=7.3 Hz), 4.12 (2H, m), 3.59 (2H, t, J=7.0 Hz). m/z (ESI, +ve) 355.1 (M+H)$^+$.

Example 166

7-(2-(pyridin-3-ylamino)quinolin-8-yl)-3,4-dihydropyrrolo[1,2-a]pyrazin-1(2H)-one

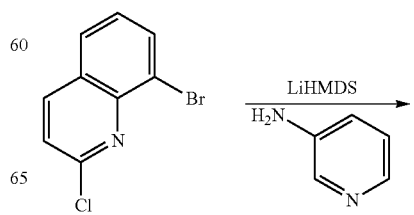

281
-continued

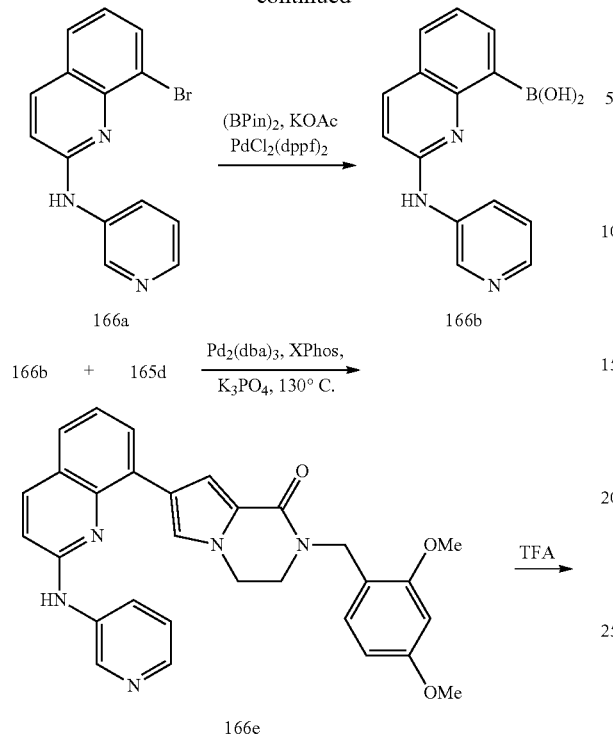

Preparation of
8-bromo-N-(pyridin-3-yl)quinolin-2-amine

This compound (1.03 g, 57% yield) as a tan crystalline solid was prepared similarly to that described in the preparation of 165c, using 8-bromo-2-chloroquinoline (Biofine International, Vancouver, BC; 1.46 g, 6.02 mmol), pyridin-3-amine (Aldrich; 0.68 g, 7.22 mmol), and LiHMDS (1.0 M solution in THF; 15.05 mL, 15.05 mmol) as starting materials. $^1$H NMR (400 MHz, DMSO-D$_6$) δ ppm 9.93 (1H, s), 9.20 (1H, d, J=2.3 Hz), 8.84 (1H, d, J=8.4 Hz), 8.24-8.13 (2H, m), 7.99 (1H, d, J=7.6 Hz), 7.82 (1H, d, J=7.6 Hz), 7.39 (1H, dd, J=8.4, 4.7 Hz), 7.26 (1H, t, J=7.7 Hz), 7.18 (1H, d, J=8.8 Hz). m/z (ESI, +ve) 300/302 (M+H)$^+$.

Preparation of 7-(2-(pyridin-3-ylamino)quinolin-8-yl)-3,4-dihydropyrrolo[1,2-a]pyrazin-1(2H)-one This compound (33 mg, 17% yield, for 3 steps) as an off-white crystalline solid was prepared similarly to Example 165, using 8-bromo-N-(pyridin-3-yl)quinolin-2-amine (Example 166a) as a starting material. $^1$H NMR (400 MHz, DMSO-d$_6$) δ ppm 9.68 (1H, br.), 8.95 (1H, br.), 8.61 (1H, d, J=7.8 Hz), 8.22 (1H, m), 8.14 (1H, d, J=9.0 Hz), 7.80-7.66 (3H, m), 7.62 (1H, d, J=7.4 Hz), 7.42 (1H, m), 7.32 (1H, t, J=7.5 Hz), 7.16 (1H, s), 7.10 (1H, d, J=8.8 Hz), 4.13 (2H, t, J=5.6 Hz), 3.58 (2H, m). m/z (ESI, +ve) 356.1 (M+H)$^+$.

282

Example 167

7-(2-(morpholine-4-carbonyl)quinolin-8-yl)-3,4-dihydropyrrolo[1,2-a]pyrazin-1(2H)-one

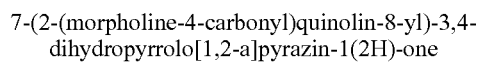
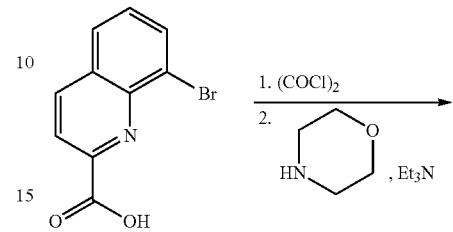
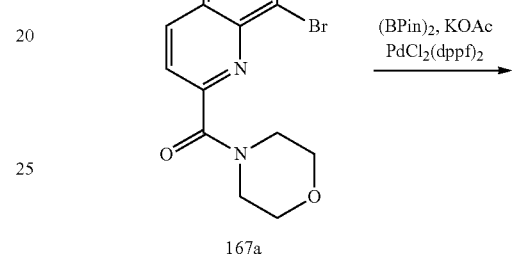
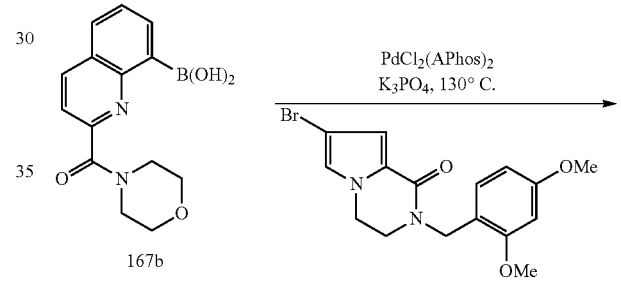
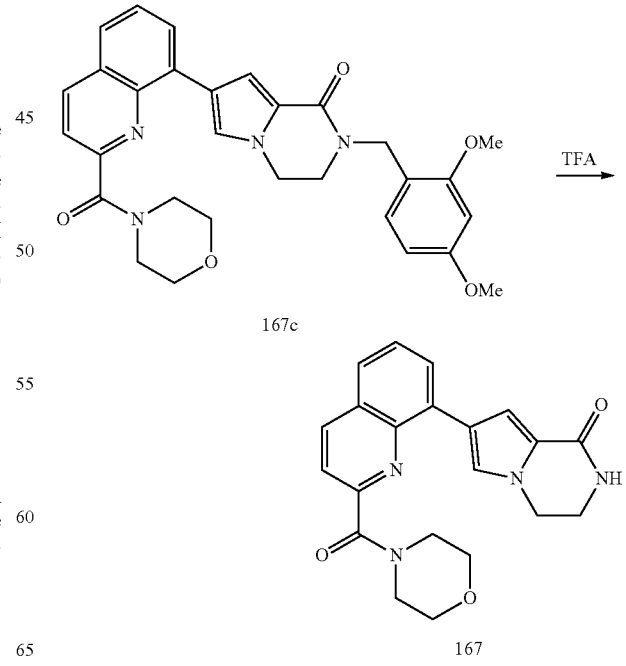

Preparation of 167a (8-bromoquinolin-2-yl)(morpholino)methanone. At 0° C., oxalyl chloride (2.0 M solution in DCM, 2.73 mL, 5.47 mmol) was added to a suspension of 8-bromoquinoline-2-carboxylic acid (Princeton BioMolecular Research, Monmouth Junction, N.J.; 690 mg, 2.74 mmol) in 5 mL of DCM followed by 3 drops of DMF. The heterogeneous mixture was stirred at RT for 1 h, and it became homogeneous. The volatiles were removed in vacuo, and the residual brown solid was dissolved in 10 mL of DCM and cooled with an ice bath. Morpholine (0.29 mL, 3.28 mmol) and Et$_3$N (0.46 mL, 3.28 mmol) were added. The reaction was stirred at RT for 1 h. The mixture was then diluted with 50 mL of DCM, washed sequentially with 5 mL of 0.5 N HCl, 5 mL of water, 5 mL of 0.5 N NaOH and 5 mL of brine. The DCM solution was dried over Na$_2$SO$_4$ and concentrated to give a brown oil. Re-crystallization from ether/hexanes gave (8-bromoquinolin-2-yl)(morpholino)methanone (855 mg, 97% yield) as a tan crystalline solid. $^1$H NMR (400 MHz, DMSO-d$_6$) δ ppm 8.60 (1H, d, J=8.6 Hz), 8.22 (1H, m), 8.10 (1H, d, J=8.0 Hz), 7.86 (1H, d, J=8.4 Hz), 7.61 (1H, t, J=7.8 Hz), 3.79 (4H, br.), 3.69 (4H, br). m/z (ESI, +ve) 321/323 (M+H)$^+$.

Preparation of 167b: (2-(morpholine-4-carbonyl)quinolin-8-yl)boronic acid

A mixture of (8-bromoquinolin-2-yl)(morpholino)methanone (Example 167a; 240 mg, 0.74 mmol), KOAc (293 mg, 2.99 mmol) and Pd(dppf)Cl$_2$ (30 mg, 0.037 mmol) in 1.5 mL of DMF was heated in an oil bath at 100° C. for 80 min. The mixture was then cooled to RT, diluted with 50 mL of EtOAc, and washed with 2×10 mL of water. The organic layer was dried over Na$_2$SO$_4$ and concentrated to give a brown residue containing (2-(morpholine-4-carbonyl)quinolin-8-yl)boronic acid. m/z (ESI, +ve) 287.1 (M+H)$^+$.

Preparation of 2-(2,4-dimethoxybenzyl)-7-(2-(morpholine-4-carbonyl)quinolin-8-yl)-3,4-dihydropyrrolo[1,2-a]pyrazin-1(2H)-one A mixture of the above-obtained crude (2-(morpholine-4-carbonyl)quinolin-8-yl)boronic acid, 7-bromo-2-(2,4-dimethoxybenzyl)-3,4-dihydropyrrolo[1,2-a]pyrazin-1(2H)-one (Example 165b; 0.248 g, 0.68 mmol), K$_3$PO$_4$ (0.433 g, 2.04 mmol) and (A-Phos)$_2$PdCl$_2$ (24 mg, 0.034 mmol) in 2 mL of dioxane and 0.5 mL of water was heated in a microwave at 130° C. for 25 min. The mixture was partitioned between 10 mL of EtOAc and 2 mL of 0.5 N NaOH. The organic layer was concentrated and purified on a silica gel column (100% EtOAc) to give 2-(2,4-dimethoxybenzyl)-7-(2-(morpholine-4-carbonyl)quinolin-8-yl)-3,4-dihydropyrrolo[1,2-a]pyrazin-1(2H)-one as a brown solid in about 90% pure. m/z (ESI, +ve) 527.0 (M+H)$^+$.

Preparation of 7-(2-(morpholine-4-carbonyl)quinolin-8-yl)-3,4-dihydropyrrolo[1,2-a]pyrazin-1(2H)-one The above-obtained brown solid 2-(2,4-dimethoxybenzyl)-7-(2-(morpholine-4-carbonyl)quinolin-8-yl)-3,4-dihydropyrrolo[1,2-a]pyrazin-1(2H)-one (Example 167c) in 1 mL of TFA and 1 mL of DCM was heated in an oil bath at 50° C. for 1 h. The mixture was concentrated under reduced pressure. The orange residue was partitioned between 50 mL of EtOAc and 5 mL of 2 N NaOH. The EtOAc layer was washed with 10 mL of brine and concentrated. Purification of the brown residue on a silica gel column (1-10% MeOH in EtOAc) gave 7-(2-(morpholine-4-carbonyl)quinolin-8-yl)-3,4-dihydropyrrolo[1,2-a]pyrazin-1(2H)-one (80 mg, 0.213 mmol, 31% yield for 3 steps) as a tan crystalline solid. $^1$H NMR (400 MHz, DMSO-d$_6$) δ ppm 8.51 (1H, d, J=8.6 Hz), 8.07 (1H, dd, J=7.3, 1.3 Hz), 7.94 (1H, d, J=1.6 Hz), 7.86 (1H, m), 7.75 (2H, d, J=8.4 Hz), 7.67 (1H, t, J=7.7 Hz), 7.36 (1H, d, J=1.8 Hz), 4.23 (2H, m), 3.75 (4H, m), 3.64 (4H, m), 3.57 (2H, m). m/z (ESI, +ve) 377.0 (M+H)$^+$.

Example 168

7-(2-(pyrrolidine-1-carbonyl)quinolin-8-yl)-3,4-dihydropyrrolo[1,2-a]pyrazin-1(2H)-one

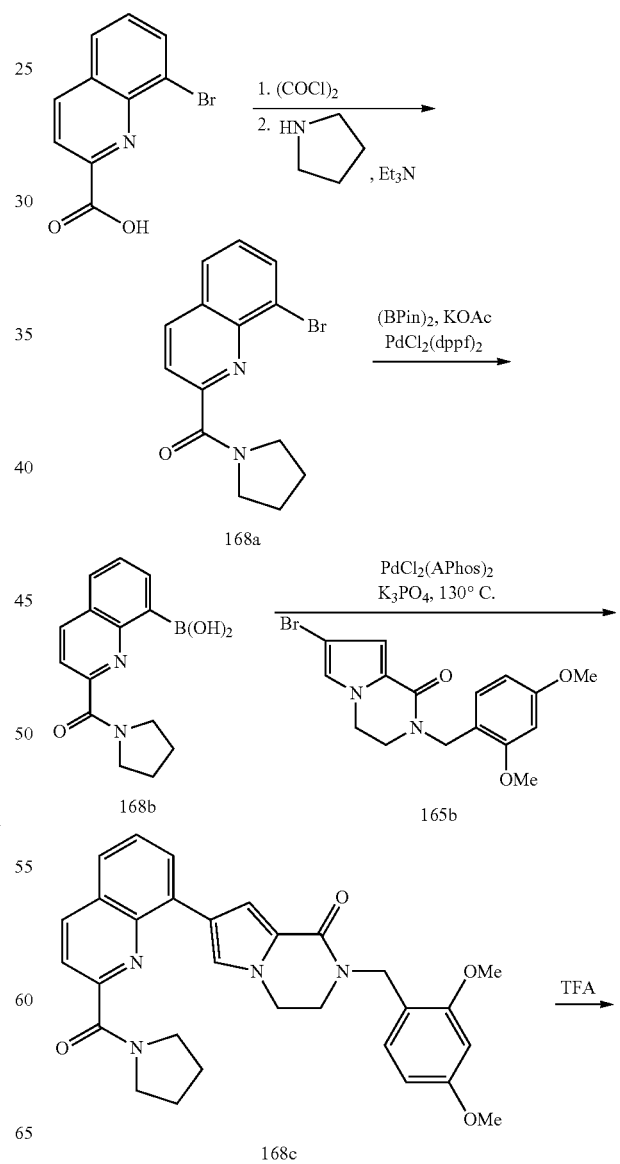

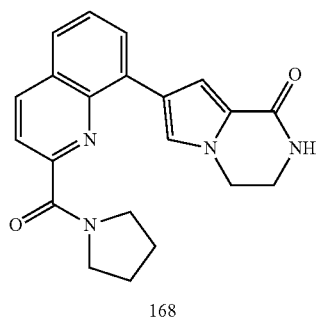

168

Preparation of (8-bromoquinolin-2-yl)(pyrrolidin-1-yl)methanone

This compound (365 mg, 94% yield) as a tan crystalline solid was prepared similarly to that described in Example 167a, using 8-bromoquinoline-2-carboxylic acid (Princeton BioMolecular Research, Monmouth Junction, N.J.; 320 mg, 1.27 mmol), oxalyl chloride (2.54 mmol), and pyrrolidine (0.10 mL, 1.27 mmol) as starting materials. $^1$H NMR (400 MHz, DMSO-$d_6$) δ ppm 8.59 (1H, d, J=8.4 Hz), 8.23 (1H, dd, J=7.6, 1.2 Hz), 8.11 (1H, dd, J=8.2, 1.0 Hz), 8.01 (1H, d, J=8.6 Hz), 7.63 (1H, t, J=7.8 Hz), 3.98 (2H, t, J=6.5 Hz), 3.61 (2H, t, J=6.5 Hz), 1.95 (4H, m). m/z (ESI, +ve) 307/307 (M+H)$^+$.

Preparation of 168: 7-(2-(pyrrolidine-1-carbonyl)quinolin-8-yl)-3,4-dihydropyrrolo[1,2-a]pyrazin-1(2H)-one This compound (48 mg, 20% yield for 3 steps) as a tan crystalline solid was prepared similarly to that described in Example 167, using (8-bromoquinolin-2-yl)(pyrrolidin-1-yl)methanone (Example 168a; 210 mg, 0.69 mmol) as starting material. $^1$H NMR (400 MHz, DMSO-$d_6$) δ ppm 8.47 (1H, d, J=8.6 Hz), 8.02 (1H, d, J=7.2 Hz), 7.89 (2H, m), 7.81 (1H, d, J=8.6 Hz), 7.65 (2H, m), 7.32 (1H, d, J=1.6 Hz), 4.16 (2H, m), 3.70 (2H, t, J=6.4 Hz), 3.53 (4H, m), 1.79 (4H, m). m/z (ESI, +ve) 361.1 (M+H)$^+$.

Example 173

7-(3-(tert-butylamino)quinoxalin-5-yl)-3,4-dihydropyrrolo[1,2-a]pyrazin-1(2H)-one

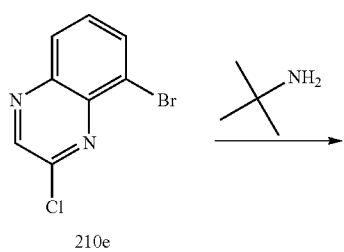

210e

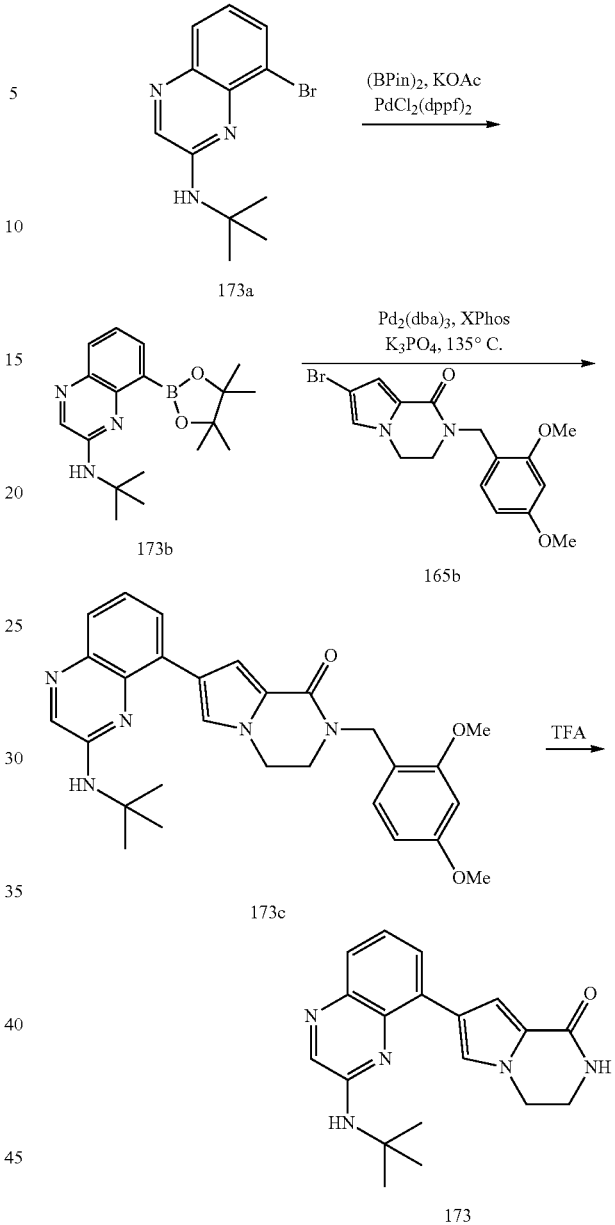

Preparation of 173a: 8-bromo-N-(tert-butyl)quinoxalin-2-amine

A solution of 8-bromo-2-chloroquinoxaline (Example 210e; 1.53 g, 6.28 mmol) and tert-butylamine (Aldrich; 3.30 mL, 31.4 mmol) in DMSO (15 mL) was stirred at 100° C. for 2 h. The mixture was treated with DCM (100 mL), and washed with saturated aq. NaHCO$_3$ (2×50 mL) and brine (50 mL). The organic layer was dried over MgSO$_4$, filtered, and concentrated. The crude material was purified on a silica gel column (23-32% EtOAc in hexanes) affording 8-bromo-N-(tert-butyl)quinoxalin-2-amine (1.75 g, 97% yield) as a yellow viscous oil which crystallized upon standing. $^1$H NMR (400 MHz, CDCl$_3$) δ ppm 8.05 (1H, s), 7.85 (1H, d, J=7.6 Hz), 7.78 (1H, d, J=7.8 Hz), 7.19 (1H, t, J=7.9 Hz), 4.89 (1H, br. s.), 1.61 (9H, s). m/z (ESI, +ve) 280/282 (M+H)$^+$.

Preparation of 173b: N-(tert-butyl)-8-(4,4,5,5-tetramethyl-1,3,2-dioxaborolan-2-yl)quinoxalin-2-amine A mixture of 8-bromo-N-(tert-butyl)quinoxalin-2-amine (Example 173a; 1.00 g, 3.57 mmol), (BPin)₂ (1.81 g, 7.14 mmol), KOAc (1.40 g, 14.28 mmol) and Pd(dppf)Cl₂ (Stem Chemicals; 146 mg, 0.18 mmol) in DMF (10.0 mL) was heated in an oil bath at 105° C. for 2 h. The resulting mixture was then diluted with 50 mL of EtOAc, and washed with water (3×15 mL). The organic layer was then dried over MgSO₄ and concentrated. The brown residue was purified on a silica gel column (35-70% EtOAc in hexanes) affording N-(tert-butyl)-8-(4,4,5,5-tetramethyl-1,3,2-dioxaborolan-2-yl)quinoxalin-2-amine (1.2 G, in about 80% purity) as a yellow viscous oil. ¹H NMR (400 MHz, MeOH-d₄) δ ppm 8.24 (1H, s), 7.77 (1H, d, J=8.0 Hz), 7.71 (1H, br. s.), 7.39 (1H, dd, J=7.9, 7.1 Hz), 1.59 (9H, s), 1.30 (6H, s), 1.26 (6H, s). m/z (ESI, +ve) 246.2 (M+H)⁺.

Preparation of 7-(3-(tert-butylamino)quinoxalin-5-yl)-3,4-dihydropyrrolo[1,2-a]pyrazin-1(2H)-one This compound (50 mg, 46% for 2 step) as a yellow crystalline solid was prepared similarly to that described in Example 174, using N-(tert-butyl)-8-(4,4,5,5-tetramethyl-1,3,2-dioxaborolan-2-yl)quinoxalin-2-amine (Example 173b; 142 mg of the 80% pure material, 0.31 mmol) as the starting material. ¹H ¹H NMR (400 MHz, DMSO-d₆) δ ppm 8.31 (1H, s), 7.86 (1H, d, J=1.6 Hz), 7.77 (1H, dd, J=7.4, 1.4 Hz), 7.67 (1H, br.), 7.58 (1H, dd, J=8.0, 1.4 Hz), 7.20-7.41 (3H, m), 4.15 (2H, m), 3.55 (2H, t, J=7.0 Hz), 1.51 (9H, s). m/z (ESI, +ve ion) 336.2 (M+H)⁺.

Example 174

7-(2-(pyrrolidine-1-carbonyl)quinolin-8-yl)-3,4-dihydropyrrolo[1,2-a]pyrazin-1(2H)-one

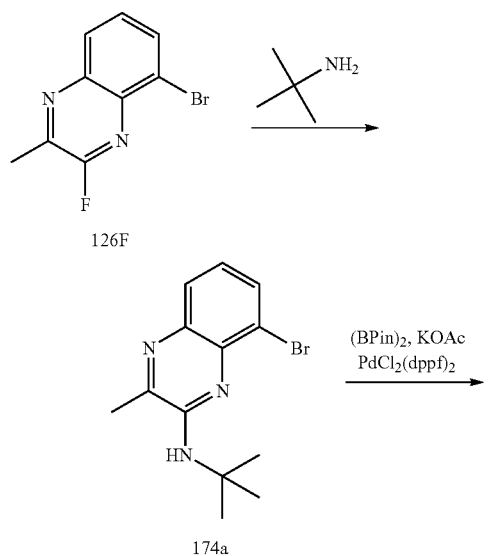

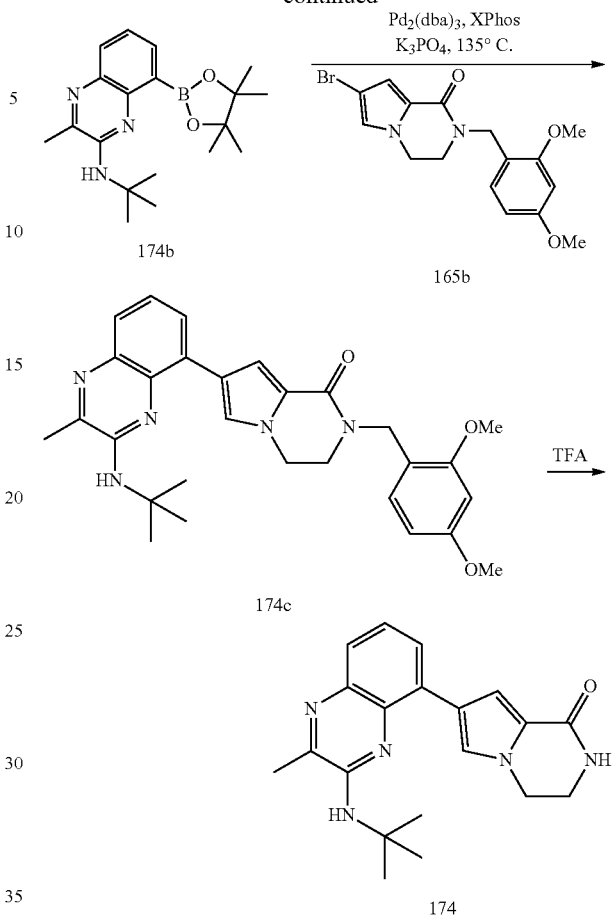

Preparation of 8-bromo-N-(tert-butyl)quinoxalin-2-amine

A solution of 5-bromo-3-fluoro-2-methylquinoxaline (Example 126f; 1.5 g, 6.22 mmol) and tert-butylamine (Aldrich; 3.27 mL, 31.1 mmol) in DMSO (15 mL) was stirred at 100° C. for 2.5 h. The mixture was subsequently diluted with DCM (150 mL), and washed with saturated aq. NaHCO₃ (3×15 mL). The organic layer was separated, dried over MgSO₄, filtered, and concentrated. The crude material was purified on a silica gel column (18-25% EtOAc in hexanes) to give 8-bromo-N-(tert-butyl)-3-methylquinoxalin-2-amine (1.58 g, 86% yield) as an amorphous pink solid. ¹H NMR (400 MHz, DMSO-d₆) δ ppm 7.79-7.86 (m, 1H), 7.71 (dd, J=8.1, 1.1 Hz, 1H), 7.22 (t, J=7.9 Hz, 1H), 6.17 (s, 1H), 2.55 (s, 3H), 1.58 (s, 9H). m/z (ESI, +ve ion) 294.0/296.0 (M+H)⁺.

Preparation of N-(tert-butyl)-3-methyl-8-(4,4,5,5-tetramethyl-1,3,2-dioxaborolan-2-yl)quinoxalin-2-amine A mixture of 8-bromo-N-(tert-butyl)-3-methylquinoxalin-2-amine (Example 174a; 1.28 g, 4.35 mmol) (BPin)₂ (2.21 g, 8.71 mmol), KOAc (1.71 g, 17.42 mmol,) and Pd(dppf)Cl₂ (0.18 g, 0.22 mmol) in DMF (10.89 mL) was heated at 105° C. in an oil bath for 3 h. The dark mixture was then diluted with 50 mL of EtOAc, and washed with water (3×5 mL). The organic layer was separated, dried over MgSO₄ and concentrated. The crude residue was purified on a silica gel column (15-50% EtOAc in hexanes) to provide N-(tert-butyl)-3-methyl-8-(4,4,5,5-tetramethyl-1,3,2-dioxaborolan-2-yl)quinoxalin-2-amine (0.85 g, 57% yield). $^1$H NMR (400 MHz, DMSO-d$_6$) δ ppm 8.02 (br., 1H), 7.70-7.78 (m, 2H), 7.28 (dd, J=7.8, 7.2 Hz, 1H), 3.31 (s, 3H), 1.57 (s, 9H), 1.33 (s, 12H). m/z (ESI, +ve ion) 260.1 (M+H)$^+$.

Preparation of 7-(3-(tert-butylamino)-2-methylquinoxalin-5-yl)-2-(2,4-dimethoxybenzyl)-3,4-dihydropyrrolo[1,2-a]pyrazin-1(2H)-one A mixture of N-(tert-butyl)-3-methyl-8-(4,4,5,5-tetramethyl-1,3,2-dioxaborolan-2-yl)quinoxalin-2-amine (Example 174b; 187 mg, 0.55 mmol), XPhos (Strem, Newburyport, Mass.; 13 mg, 0.027 mmol), Pd$_2$(dba)$_3$ (12 mg, 0.014 mmol), 7-bromo-2-(2,4-dimethoxybenzyl)-3,4-dihydropyrrolo[1,2-a]pyrazin-1(2H)-one (Example 165b; 167 mg, 0.46 mmol) and potassium phosphate (291 mg, 1.37 mmol) in 2 mL of dioxane and 0.5 mL of water was heated in a microwave at 135° C. for 45 min. The mixture was then treated with 2 mL of 1 N NaOH, and extracted with EtOAc (2×5 mL). The organic extracts were concentrated. Purification of the brown residue on a silica gel column (eluted with 25-75% EtOAc in hexanes) afforded 7-(3-(tert-butylamino)-2-methylquinoxalin-5-yl)-2-(2,4-dimethoxybenzyl)-3,4-dihydropyrrolo[1,2-a]pyrazin-1(2H)-one (60 mg) as a brown amorphous solid. m/z (ESI, +ve) 500.1 (M+H)$^+$.

Preparation of 7-(3-(tert-butylamino)-2-methylquinoxalin-5-yl)-3,4-dihydropyrrolo[1,2-a]pyrazin-1(2H)-one The brown amorphous solid (Example 174c) in 0.5 mL of TFA and 0.5 mL of DCM was heated in an oil bath at 60° C. for 30 min. The resulting dark red mixture was concentrated and the residue was partitioned between 5 mL of 1 N NaOH and 50 mL of EtOAc. The organic layer was washed with 5 mL of brine, and concentrated. The residue was purified on a silica gel column (1-5% MeOH in EtOAc) to give 7-(3-(tert-butylamino)-2-methylquinoxalin-5-yl)-3,4-dihydropyrrolo[1,2-a]pyrazin-1(2H)-one (35 mg, 22% yield) as a yellow crystalline solid. $^1$H NMR (400 MHz, DMSO-d$_6$) δ ppm 7.81 (1H, d, J=1.4 Hz), 7.70 (1H, m), 7.65 (1H, br), 7.56 (1H, m), 7.30 (1H, t, J=7.7 Hz), 7.26 (1H, d, J=1.6 Hz), 5.83 (1H, s), 4.15 (2H, m), 3.55 (2H, m), 2.54 (3H, s), 1.55 (9H, s). m/z (ESI, +ve) 350.1 (M+H)$^+$.

Example 175

2-(2-((2,6-difluorophenyl)amino)quinolin-8-yl)-6,7-dihydro-1H-pyrrolo[3,2-c]pyridin-4(5H)-one

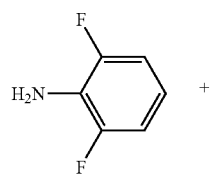

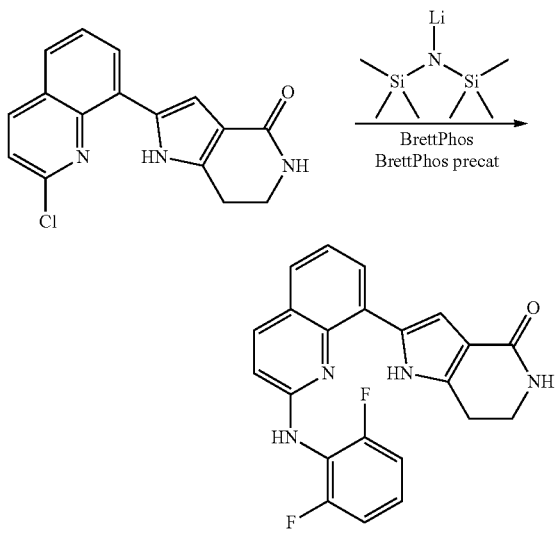

Prepared similarly to Example 82 using 2-(2-chloroquinolin-8-yl)-6,7-dihydro-1H-pyrrolo[3,2-c]pyridin-4(5H)-one (Example 1; 51 mg, 0.171 mmol), 2,6-difluoroaniline (26.5 mg, 0.206 mmol, Aldrich), BrettPhos (Strem, Newburyport, Mass.; 5.0 mg, 8.56 μmol), and BrettPhos precat (Strem, Newburyport, Mass.; 7.3 mg, 8.56 μmol), heating at 100° C. for 3 h. Purification by silica gel (100% DCM to 20% MeOH/DCM) provided 2-(2-((2,6-difluorophenyl)amino)quinolin-8-yl)-6,7-dihydro-1H-pyrrolo[3,2-c]pyridin-4(5H)-one (22% yield). $^1$H NMR (400 MHz, DMSO-d$_6$) δ ppm 2.47 (t, J=6.75 Hz, 2H) 3.33-3.39 (m, 2H) 6.91-6.95 (m, 2H) 7.14 (d, J=9.00 Hz, 1H) 7.28-7.32 (m, 1H) 7.33 (d, J=4.50 Hz, 1H) 7.35-7.40 (m, 1H) 7.44-7.54 (m, 1H) 7.62 (d, J=6.85 Hz, 1H) 8.01-8.06 (m, 1H) 8.18 (d, J=9.00 Hz, 1H) 9.31 (s, 1H) 11.90 (br. s., 1H). $^{19}$F NMR (376 MHz, DMSO-d$_6$) δ ppm −117.35 (2F, s). MS (ESI, pos. ion) m/z: 391.2 (M+1).

Example 176

2-(2-(2,6-difluorophenoxy)quinolin-8-yl)-6,7-dihydro-1H-pyrrolo[3,2-c]pyridin-4(5H)-one

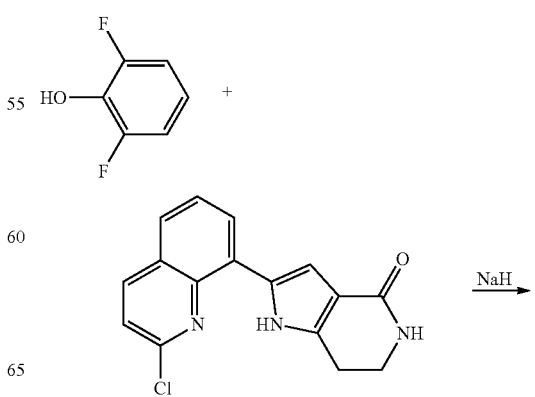

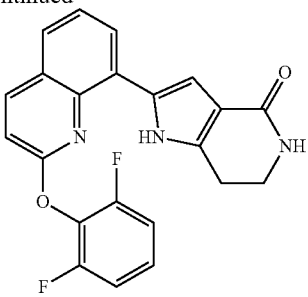

Prepared in a manner similar to that described in Example 79 using 2-(2-chloroquinolin-8-yl)-6,7-dihydro-1H-pyrrolo[3,2-c]pyridin-4(5H)-one (Example 1; 61 mg, 0.205 mmol) and 2,6-difluorophenol (133 mg, 1.024 mmol, Aldrich) and heating at 120° C. for 5 min in a microwave (Biotage Initiator). Purification by silica gel (100% DCM to 20% MeOH/DCM) provided 2-(2-(2,6-difluorophenoxy)quinolin-8-yl)-6,7-dihydro-1H-pyrrolo[3,2-c]pyridin-4(5H)-one (54% yield). $^1$H NMR (400 MHz, DMSO-$d_6$) δ ppm 2.51-2.57 (m, 2H) 3.34-3.39 (m, 2H) 6.86 (d, J=2.35 Hz, 1H) 6.91 (br. s., 1H) 7.40-7.47 (m, 2H) 7.48-7.54 (m, 1H) 7.55 (d, J=1.96 Hz, 1H) 7.57 (s, 1H) 7.87 (dd, J=8.02, 0.98 Hz, 1H) 8.11 (dd, J=7.43, 1.17 Hz, 1H) 8.58 (d, J=9.00 Hz, 1H) 10.96 (br. s., 1H). $^{19}$F NMR (376 MHz, DMSO-$d_6$) δ ppm −126.54 (2F, s). MS (ESI, pos. ion) m/z: 392.1 (M+1).

Example 177

2-(3-phenoxyquinoxalin-5-yl)-6,7-dihydro-1H-pyrrolo[3,2-c]pyridin-4(5H)-one

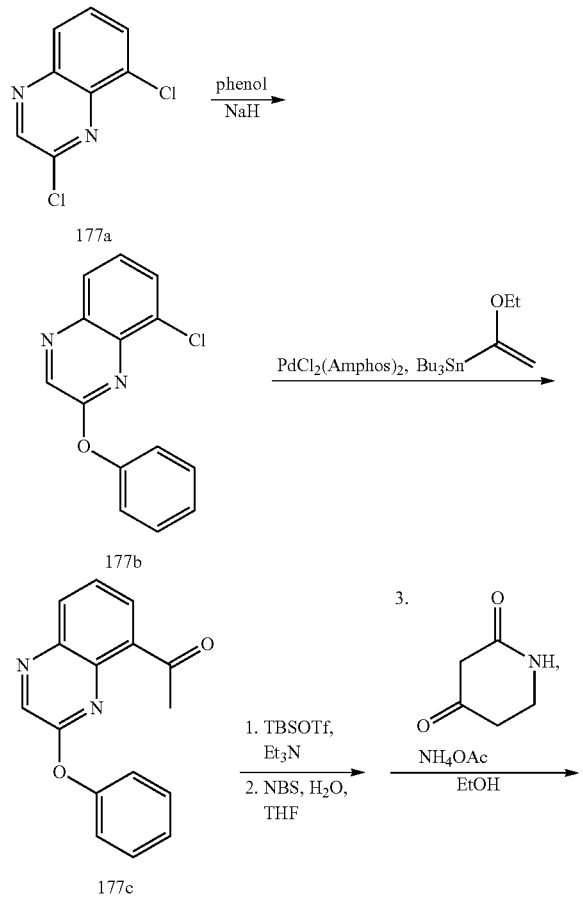

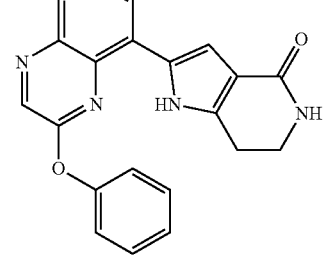

Preparation of 8-chloro-2-phenoxyquinoxaline

NaH (60% w/w in mineral oil; 269 mg, 6.72 mmol) was added to a solution of phenol (633 mg, 6.72 mmol) in THF (4.5 ml) at 0° C.; the resulting mixture was stirred for 15 min before 2,8-dichloroquinoxaline (177a, 892 mg, 4.48 mmol, Pharmabridge, Inc., Doylestown, Pa.) in THF (10 ml) was added at 0° C. The mixture was slowly warmed to RT and stirred for 16 h. The crude material was quenched with MeOH and was purified by silica gel (100% hexanes to 20% EtOAc/hexanes) to provide 8-chloro-2-phenoxyquinoxaline (61% yield) as a yellow solid. MS (ESI, pos. ion) m/z: 257.2 (M+1).

Preparation of 1-(3-phenoxyquinoxalin-5-yl)ethanone

A solution of 8-chloro-2-phenoxyquinoxaline (253 mg, 0.986 mmol), tributyl(1-ethoxyvinyl)stannane (499 μl, 1.478 mmol, Aldrich), and PdCl$_2$(Amphos)$_2$ (34.9 mg, 0.049 mmol) in toluene (9.9 ml) was stirred at 110° C. in a sealed tube for 16 h. Purification by silica gel (100% hexanes to 10% EtOAc/hexanes) provided 1-(3-phenoxyquinoxalin-5-yl)ethanone as a white solid. MS (ESI, pos. ion) m/z: 365.2 (M+1).

Preparation of 2-(3-phenoxyquinoxalin-5-yl)-6,7-dihydro-1H-pyrrolo[3,2-c]pyridin-4(5H)-one A solution of 1-(3-phenoxyquinoxalin-5-yl)ethanone (130 mg, 0.492 mmol), TEA (89 μl, 0.639 mmol), and TBSOTf (124 μl, 0.541 mmol) in DCM (3279 μl) was stirred at 0° C. for 30 min. The mixture was then diluted with DCM (100 ml), added to a separatory funnel, and washed with saturated aq. NaHCO$_3$ (2×75 ml) before the organic layer was separated, dried over Na$_2$SO$_4$, and concentrated to give the silyl enol ether as a yellow oil. A solution of the resulting oil, water (142 μl, 7.87 mmol), and NBS (88 mg, 0.492 mmol) in THF (3279 μl) was stirred at RT for 15 min. The mixture was diluted with Et$_2$O (100 ml), added to a separatory funnel, and washed with saturated aq. NaHCO$_3$ (2×75 ml) before the organic layer was separated, dried over Na$_2$SO$_4$, and concentrated to give the alpha-bromoacetic acid. MS (ESI, pos. ion) m/z: 342.8/345 (M+1). A solution of the resulting yellow oil, piperidine-2,4-dione (66.8 mg, 0.590 mmol), and NH$_4$OAc (152 mg, 1.968 mmol) in EtOH (3279 μl) was stirred at 50° C. for 16 h. Purification by rpHPLC (Phenomenex Gemini C$_{18}$, 10 μm, 150×30 mm; 10-100% ACN/water with 0.1% TFA) provided 2-(3-phenoxyquinoxalin-5-yl)-6,7-dihydro-1H-pyrrolo[3,2-c]pyridin-4(5H)-one (6% yield) as a yellow solid. $^1$H NMR (400 MHz, CDCl$_3$) δ ppm 2.48 (t, J=6.94 Hz, 2H) 3.49-3.55 (m, 2H) 5.29 (br. s., 1H) 7.11 (d, J=2.15 Hz, 1H) 7.30-7.34 (m, 2H) 7.43 (t, J=7.4 Hz, 1H) 7.55-7.65 (m, 3H) 7.91 (dd, J=8.22, 0.98 Hz, 1H) 8.04 (dd, J=7.63, 1.17 Hz, 1H) 8.83 (s, 1H) 10.81 (br. s., 1H). MS (ESI, pos. ion) m/z: 357.2 (M+1).

Example 178

2-(2-phenoxyquinolin-8-yl)-1H-imidazo[4,5-c]pyridin-4(5H)-one

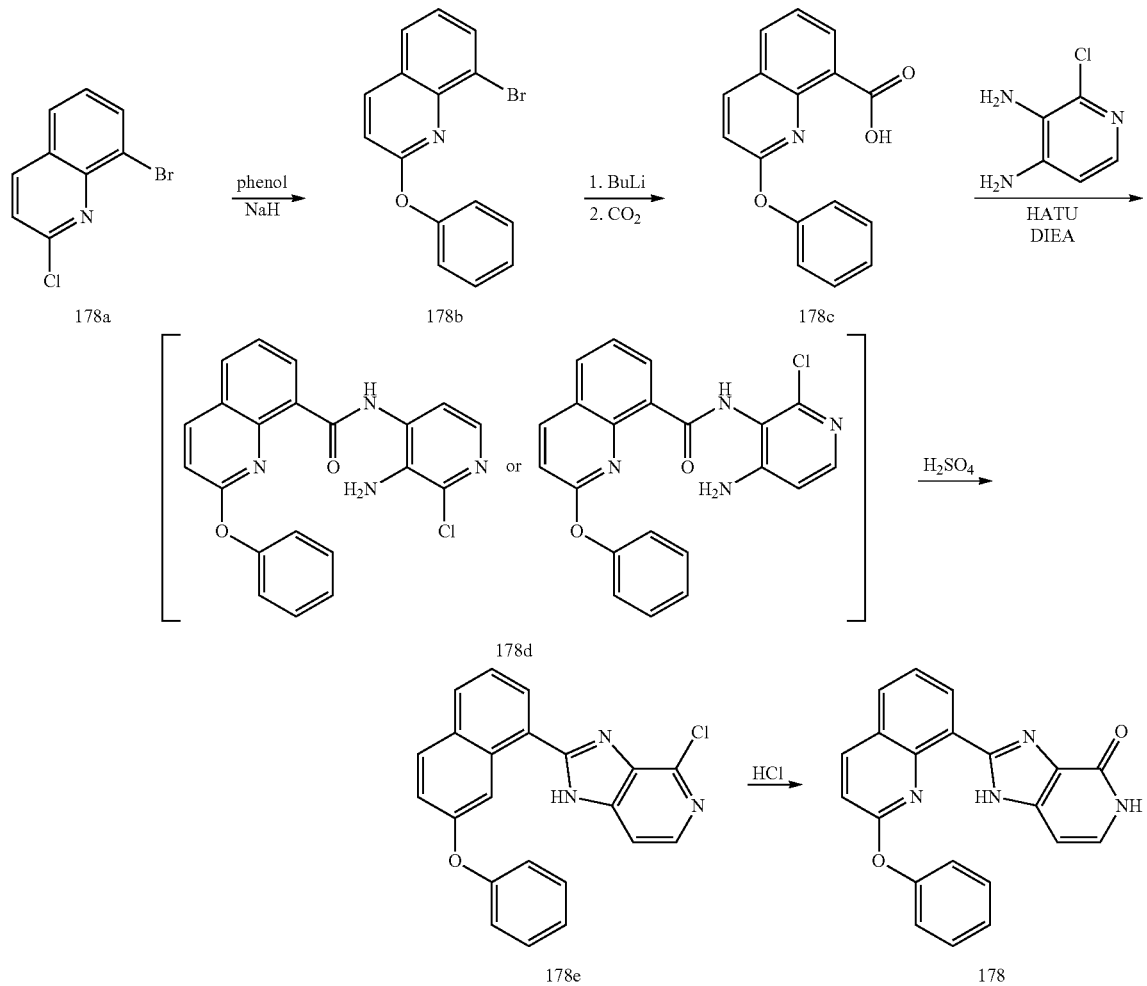

Preparation of 8-bromo-2-phenoxyquinoline

NaH (60% w/w in mineral oil; 1.311 g, 32.8 mmol) was added to a solution of phenol (3.09 g, 32.8 mmol, Aldrich) in THF (219 ml) at 0° C.; the resulting mixture was stirred for 10 min before 8-bromo-2-chloroquinoline (178a, 5.30 g, 21.86 mmol, Biofine International, Inc., Vancouver, BC) in THF (100 ml) was added. The reaction was stirred at 0° C. for 1 h before it was warmed to RT and stirred for 3 h, then heated at reflux for 24 h. Purification by silica gel chromatography (100% hexanes to 10% EtOAc/hexanes) provided 8-bromo-2-phenoxyquinoline (178b, 41% yield) as a light yellow oil. MS (ESI, pos. ion) m/z: 300.0/302 (M+1).

Preparation of 2-phenoxyquinoline-8-carboxylic acid nBuLi (2.5M in hexanes; 3.58 ml, 8.95 mmol) was added to a solution of 8-bromo-2-phenoxyquinoline (1.79 g, 5.96 mmol) in THF (59.6 ml) at −78° C. and the resulting mixture was stirred for 15 min before it was quenched by the addition of a few pieces of dry ice. The mixture was taken out of the dry ice/acetone bath, and the resulting carboxylate was quenched with 1 N HCl after stirring for 15 min. The mixture was then partitioned between Et$_2$O (100 mL) and 1 N NaOH. The organic layer was separated, and the aq. layer was acidified to ~pH 5 with 5 N HCl and extracted 3 times with 100 ml of Et$_2$O. All organic layers were then combined, dried over Na$_2$SO$_4$, and concentrated via rotovap to provide 2-phenoxyquinoline-8-carboxylic acid (178c, 63% yield). MS (ESI, pos. ion) m/z: 266.2 (M+1).

Preparation of N-(3-amino-2-chloropyridin-4-yl)-2-phenoxyquinoline-8-carboxamide (or N-(4-amino-2-chloropyridin-3-yl)-2-phenoxyquinoline-8-carboxamide)

A mixture of 2-phenoxyquinoline-8-carboxylic acid (119 mg, 0.449 mmol), 2-chloropyridine-3,4-diamine (97 mg, 0.673 mmol, Waterstone Technology, Carmel, Ind.), HATU (341 mg, 0.897 mmol), and DIPEA (235 µl, 1.346 mmol) in DMF (449 µl) was stirred at RT for 2 h. The mixture was diluted with EtOAc (100 ml), added to a separatory funnel, and washed with saturated aq. NaHCO$_3$ (3×75 ml) before the organic layer was separated, dried over Na$_2$SO$_4$, and concentrated. Purification by silica chromatography (100% DCM to 5% MeOH/DCM) provided N-(3-amino-2-chloropyridin-4-yl)-2-phenoxyquinoline-8-carboxamide (or N-(4-amino-2- chloropyridin-3-yl)-2-phenoxyquinoline-8-carboxamide; regioisomer not determined; 178d, 49% yield). MS (ESI, pos. ion) m/z: 391.2 (M+1).

Preparation of 8-(4-chloro-1H-imidazo[4,5-c]pyridin-2-yl)-2-phenoxyquinoline

A solution of the material from Example 178d (68 mg, 0.174 mmol) in $H_2SO_4$ (1933 µl, 17.40 mmol) (note: dissolution is exothermic) was stirred at RT for 15 min. The reaction was quenched with ice and then diluted with EtOAc (100 ml), added to a separatory funnel, and washed with water (75 ml) before the organic layer was separated, dried over $Na_2SO_4$, and concentrated. Purification by silica gel chromatography (100% DCM to 2% MeOH/DCM) provided 8-(4-chloro-1H-imidazo[4,5-c]pyridin-2-yl)-2-phenoxyquinoline (178e, 6% yield) as a white solid. MS (ESI, pos. ion) m/z: 373.0 (M+1).

Preparation of 2-(2-phenoxyquinolin-8-yl)-1H-imidazo[4,5-c]pyridin-4(5H)-one

A mixture of 8-(4-chloro-1H-imidazo[4,5-c]pyridin-2-yl)-2-phenoxyquinoline (60 mg, 0.161 mmol) in HCl (3219 µl, 16.09 mmol) was heated in a microwave (Biotage Initiator) for 10 min at 120° C. Purification by rpHPLC (Phenomenex Gemini $C_{18}$, 10 µm, 150×30 mm; 10-100% ACN/water with 0.1% TFA) provided 2-(2-phenoxyquinolin-8-yl)-1H-imidazo[4,5-c]pyridin-4(5H)-one (178, 0.7% yield) as an off-white solid. $^1$H NMR (400 MHz, MeOH-$d_4$) δ ppm 6.37 (d, J=7.04 Hz, 1H) 7.34 (d, J=7.04 Hz, 1H) 7.41-7.45 (m, 2H) 7.48 (d, J=8.80 Hz, 1H) 7.55-7.60 (m, 1H) 7.66-7.74 (m, 3H) 8.17 (d, J=7.82 Hz, 1H) 8.55 (d, J=9.00 Hz, 1H) 8.76 (d, J=7.43 Hz, 1H). MS (ESI, pos. ion) m/z: 355.0 (M+1).

Example 179

2-(2-phenoxyquinolin-8-yl)oxazolo[4,5-c]pyridin-4(5H)-one

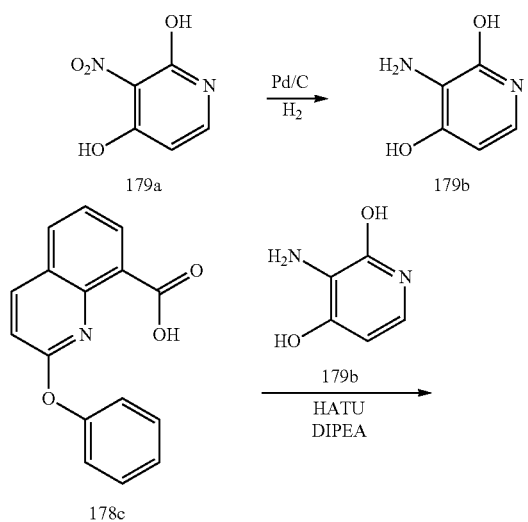

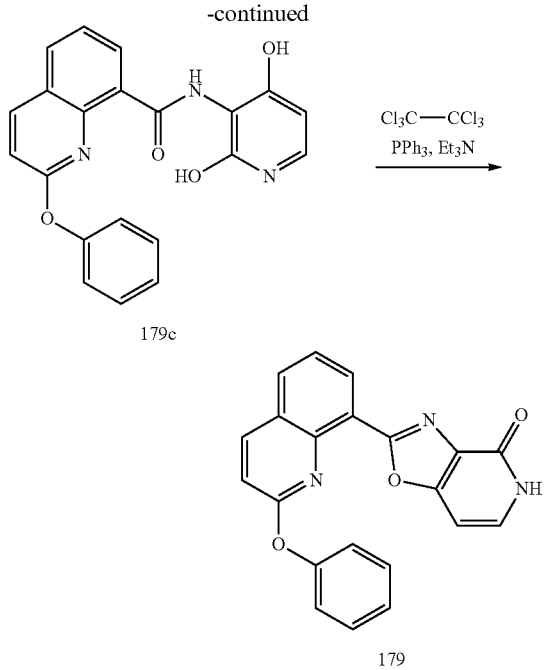

Preparation of 3-aminopyridine-2,4-diol

A mixture of 3-nitropyridine-2,4-diol (1.63 g, 10.44 mmol, Alfa Aesar, Ward Hills, Mass.) and palladium on carbon (10%, wet; 1.2 g, 10 mmol) in EtOAc (52.2 ml) was stirred at RT under $H_2$ (50 psi) for 22 h. The mixture was filtered through a pad of Celite and was washed with MeOH to give 3-aminopyridine-2,4-diol (179b, 44% yield) as a brown, amorphous solid. MS (ESI, pos. ion) m/z: 127.2 (M+1).

Preparation of N-(2,4-dihydroxypyridin-3-yl)-2-phenoxyquinoline-8-carboxamide

A mixture of 2-phenoxyquinoline-8-carboxylic acid (178c 217 mg, 0.818 mmol), 3-aminopyridine-2,4-diol (155 mg, 1.227 mmol), HATU (622 mg, 1.636 mmol), and DIPEA (438 µl, 2.454 mmol) in DMF (1636 µl) was stirred at RT for 1 h. Purification by silica gel (100% DCM to 5% MeOH/DCM) provided N-(2,4-dihydroxypyridin-3-yl)-2-phenoxyquinoline-8-carboxamide (179c) as a yellow solid. MS (ESI, pos. ion) m/z: 374.2 (M+1).

Preparation of 179: 2-(2-phenoxyquinolin-8-yl)oxazolo[4,5-c]pyridin-4(5H)-one

A solution of triphenylphosphine (421 mg, 1.607 mmol), $Et_3N$ (597 µl, 4.29 mmol), and perchloroethane (317 mg, 1.339 mmol) in DCM (5357 µl) was stirred at RT for 5 min before a slurry of N-(2,4-dihydroxypyridin-3-yl)-2-phenoxyquinoline-8-carboxamide (200 mg, 0.536 mmol) in DCM (3 ml) was added to make a light yellow solution; this was stirred for 1 h at RT. The reaction mixture was then concentrated onto silica gel and chromatographically purified (silica gel, 100% DCM to 4% MeOH/DCM) to provide 2-(2-phenoxyquinolin-8-yl)oxazolo[4,5-c]pyridin-4(5H)-one (179, 38% yield over two steps) as a white solid. $^1$H NMR (400 MHz, CDCl$_3$) δ ppm 6.46 (d, J=7.04 Hz, 1H) 7.22-7.30 (m, 2H) 7.36-7.47 (m, 5H) 7.55 (t, J=7.73 Hz, 1H) 7.95 (d, J=7.24 Hz, 1H) 8.22 (d, J=8.80 Hz, 1H) 8.64 (d, J=6.26 Hz, 1H) 12.51 (br. s., 1H). MS (ESI, pos. ion) m/z: 356.1 (M+1).

Example 180

2-(3-(phenylamino)quinoxalin-5-yl)-6,7-dihydro-1H-pyrrolo[3,2-c]pyridin-4(5H)-one

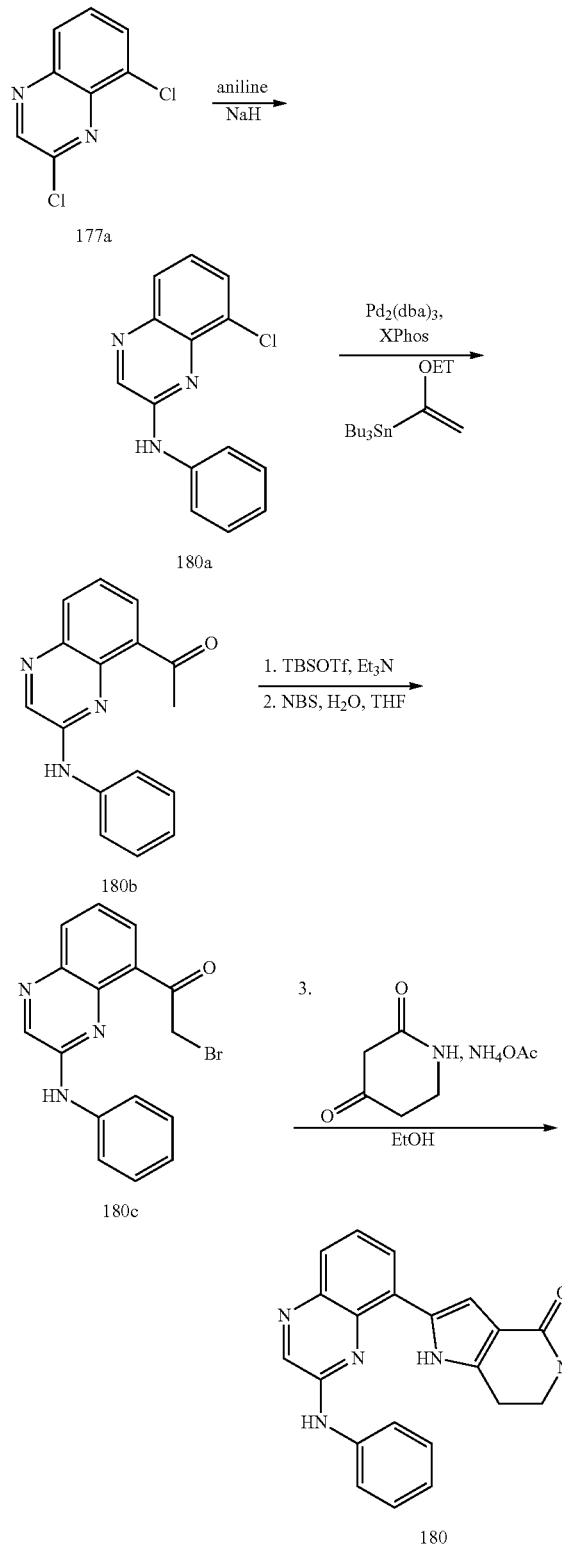

Preparation of 8-chloro-N-phenylquinoxalin-2-amine

Aniline (0.810 ml, 8.89 mmol) was added to a mixture of NaH (60% w/w in mineral oil; 0.356 g, 8.89 mmol) in THF (59.3 ml) at 0° C.; the resulting mixture was stirred for 15 min before 2,8-dichloroquinoxaline (177a, 1.18 g, 5.93 mmol, Pharmabridge, Inc., Doylestown, Pa.) was added; the reaction mixture was stirred at 50° C. for 16 h. Purification by silica gel (100% hexanes to 40% EtOAc/hexanes) provided 8-chloro-N-phenylquinoxalin-2-amine (180a, 43% yield) as a yellow solid. MS (ESI, pos. ion) m/z: 256.2 (M+1).

Preparation of 1-(3-(phenylamino)quinoxalin-5-yl)ethanone

A mixture of 8-chloro-N-phenylquinoxalin-2-amine (0.65 g, 2.54 mmol), tributyl(1-ethoxyvinyl)stannane (1.288 ml, 3.81 mmol, Aldrich), $Pd_2(dba)_3$ (0.582 g, 0.636 mmol), XPhos (Strem, Newburyport, Mass.; 0.303 g, 0.636 mmol), copper(I) iodide (0.097 g, 0.508 mmol), and cesium fluoride (0.772 g, 5.08 mmol) in dioxane (12.71 ml) was heated in a microwave (Biotage Initiator) for 20 min at 160° C. Purification by silica gel (100% hexanes to 30% EtOAc/hexanes) provided 1-(3-(phenylamino)quinoxalin-5-yl)ethanone (180b, 78% yield) as a yellow oil. MS (ESI, pos. ion) m/z: 264.2 (M+1).

Preparation of 2-bromo-1-(3-(phenylamino)quinoxalin-5-yl)ethanone

A solution of 1-(3-(phenylamino)quinoxalin-5-yl)ethanone (180 mg, 0.684 mmol), TBSOTf (157 µl, 0.684 mmol), and $Et_3N$ (124 µl, 0.889 mmol) in DCM (4558 µl) at 0° C. was stirred for 30 min. The mixture was diluted with $Et_2O$ (100 ml), added to a separatory funnel, and washed with saturated aq. $NaHCO_3$ (2×75 ml) before the organic layer was separated, dried over $Na_2SO_4$, and concentrated to provide the silyl enol ether. NBS (6836 µl, 0.684 mmol) was added portionwise to a solution of the resulting enol ether and water (0.2 ml) in THF (4558 µl) at 0° C. The mixture was diluted with $Et_2O$ (100 ml), added to a separatory funnel, and washed with saturated aq. $NaHCO_3$ (3×75 ml) before the organic layer was separated, dried over $Na_2SO_4$, and concentrated to give 2-bromo-1-(3-(phenylamino)quinoxalin-5-yl)ethanone as a yellow oil. MS (ESI, pos. ion) m/z: 342.0/344.0 (M+1).

Preparation of 2-(3-(phenylamino)quinoxalin-5-yl)-6,7-dihydro-1H-pyrrolo[3,2-c]pyridin-4(5H)-one A mixture of 2-bromo-1-(3-(phenylamino)quinoxalin-5-yl)ethanone, $NH_4OAc$ (211 mg, 2.73 mmol), and piperidine-2,4-dione (93 mg, 0.820 mmol) in EtOH (4558 µl) was heated to 50° C. for 16 h. The mixture was diluted with $Et_2O$ (150 ml), added to a separatory funnel, and washed with saturated aq. brine (3×100 ml) before the organic layer was separated, dried over $Na_2SO_4$, and concentrated. Purification by silica gel (100% DCM to 4% MeOH/DCM) provided 2-(3-(phenylamino)quinoxalin-5-yl)-6,7-dihydro-1H-pyrrolo[3,2-c]pyridin-4(5H)-one (180, 6% yield) as a yellow-brown solid. $^1$H NMR (400 MHz, DMSO-$d_6$) δ ppm 2.77 (t, J=6.55 Hz, 2H) 3.43 (t, J=5.67 Hz, 2H) 6.94 (br. s., 1H) 6.99 (s, 1H) 7.11 (t, J=7.24 Hz, 1H) 7.38-7.50 (m, 3H) 7.71 (d, J=8.22 Hz, 1H)

7.82 (d, J=7.82 Hz, 2H) 7.92 (d, J=7.24 Hz, 1H) 8.59 (s, 1H) 10.02 (s, 1H) 11.75 (br. s., 1H). MS (ESI, pos. ion) m/z: 356.1 (M+1).

Example 181

2-(2-chloroquinolin-8-yl)oxazolo[4,5-c]pyridin-4(5H)-one

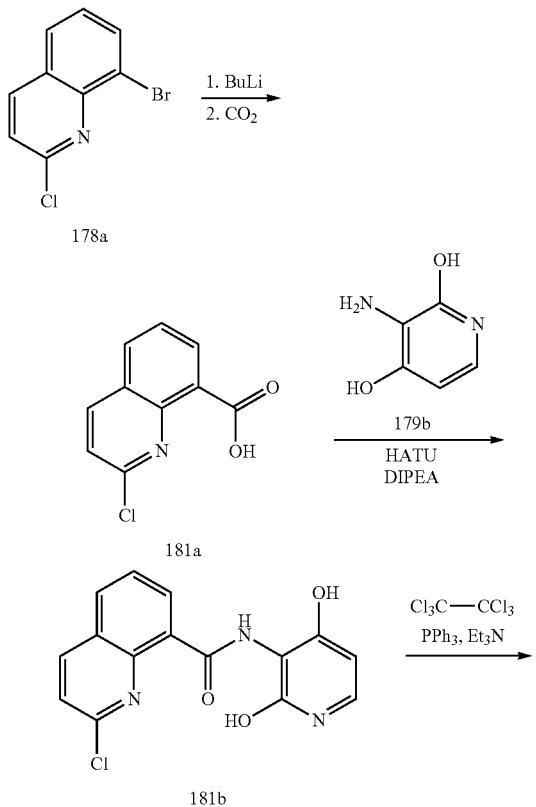

Preparation of 2-chloroquinoline-8-carboxylic acid nBuLi (2.2M in hexanes; 7.50 ml, 16.49 mmol) was added dropwise over 2 min to a solution of 8-bromo-2-chloroquinoline (4.00 g, 16.49 mmol, Biofine International, Inc., Vancouver, BC) in THF (82 ml) at −78° C. The resulting mixture was stirred at −78° C. for 20 min before $CO_2$ was bubbled into the solution for 5 min at −78° C. The mixture was quenched with 2 N HCl (10 ml). The resulting mixture was partitioned between 100 ml of $Et_2O$ and 1 N NaOH. The organic layer was separated, and the aq. layer was acidified to ~pH 2 with 5 N HCl and extracted 3 times with 150 ml $Et_2O$. The combined organic extracts were dried over $Na_2SO_4$ and concentrated to provide 2-chloroquinoline-8-carboxylic acid (181a, >99% yield) as a light brown solid. MS (ESI, pos. ion) m/z: 208.2 (M+1).

Preparation of 2-chloro-N-(2,4-dihydroxypyridin-3-yl)quinoline-8-carboxamide A mixture of 2-chloroquinoline-8-carboxylic acid (0.42 g, 2.023 mmol), 3-aminopyridine-2,4-diol (Example 179b, 0.383 g, 3.03 mmol), HATU (1.154 g, 3.03 mmol), and N-ethyl-N-isopropylpropan-2-amine (1.083 ml, 6.07 mmol) in DMF (2.023 ml) was stirred at RT for 16 h. The mixture was diluted with EtOAc (200 ml), added to a separatory funnel, and washed with water (3×100 ml) before the organic layer was separated, dried over $Na_2SO_4$, and concentrated. Purification by silica gel (100% DCM to 4% MeOH/DCM) provided 2-chloro-N-(2,4-dihydroxypyridin-3-yl)quinoline-8-carboxamide (181b, 24% yield as a yellow solid). MS (ESI, pos. ion) m/z: 316.2 (M+1).

Preparation of 2-(2-chloroquinolin-8-yl)oxazolo[4,5-c]pyridin-4(5H)-one

A solution of triphenylphosphine (381 mg, 1.454 mmol), perchloroethane (287 mg, 1.212 mmol), and $Et_3N$ (540 µl, 3.88 mmol) in DCM (4846 µl) was stirred at RT for 1 h. The yellow solution was transferred to a flask containing solid 2-chloro-N-(2,4-dihydroxypyridin-3-yl)quinoline-8-carboxamide (153 mg, 0.485 mmol); this was stirred at RT for 1 h. Purification by silica gel (100% DCM to 4% MeOH/DCM) provided 2-(2-chloroquinolin-8-yl)oxazolo[4,5-c]pyridin-4(5H)-one (181, >99% yield) as an off-white solid. $^1$H NMR (400 MHz, DMSO-$d_6$) δ ppm 6.92 (d, J=7.04 Hz, 1H) 7.53 (t, J=6.65 Hz, 1H) 7.77 (d, J=8.61 Hz, 1H) 7.84-7.90 (m, 1H) 8.35 (dd, J=8.22, 1.37 Hz, 1H) 8.43 (dd, J=7.24, 1.37 Hz, 1H) 8.64 (d, J=8.61 Hz, 1H) 11.89 (br. s., 1H). MS (ESI, pos. ion) m/z: 298.1 (M+1).

Example 182

2-(2-(phenylamino)quinolin-8-yl)oxazolo[4,5-c]pyridin-4(5H)-one

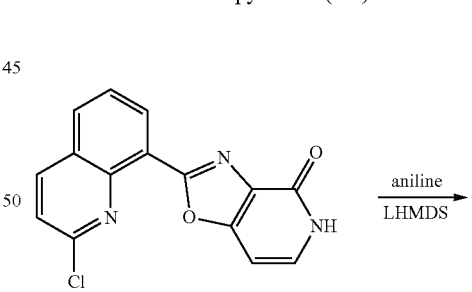

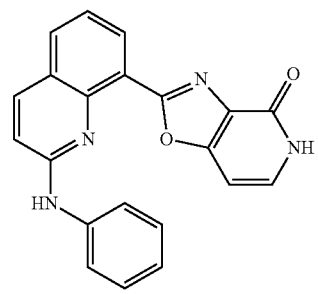

LHMDS (1.0M in THF; 2015 μl, 2.015 mmol) was added to a solution of 2-(2-chloroquinolin-8-yl)oxazolo[4,5-c]pyridin-4(5H)-one (Example 181; 120 mg, 0.403 mmol) and aniline (184 μl, 2.015 mmol) in dioxane (4031 μl) at RT; and the resulting mixture was stirred at RT for 30 min. The mixture was diluted with EtOAc (150 ml), added to a separatory funnel, and washed with saturated aq. NH$_4$Cl (2×100 ml) before the organic layer was separated, dried over Na$_2$SO$_4$, and concentrated. Purification by silica gel (100% DCM to 5% MeOH/DCM) provided 2-(2-(phenylamino)quinolin-8-yl)oxazolo[4,5-c]pyridin-4(5H)-one (14% yield) as a dark orange solid. $^1$H NMR (400 MHz, DMSO-d$_6$) δ ppm 6.87-6.94 (m, 2H) 7.16 (d, J=9.00 Hz, 1H) 7.27 (t, J=7.82 Hz, 2H) 7.45 (t, J=7.63 Hz, 1H) 7.55 (t, J=6.55 Hz, 1H) 7.98 (d, J=6.85 Hz, 1H) 8.10 (d, J=7.83 Hz, 2H) 8.15-8.20 (m, 2H) 9.69 (s, 1H) 11.87 (br. s., 1H). MS (ESI, pos. ion) m/z: 355.1 (M+1).

Example 183

2-(2-methyl-3-(phenylamino)quinoxalin-5-yl)-6,7-dihydro-1H-pyrrolo[3,2-c]pyridin-4(5H)-one

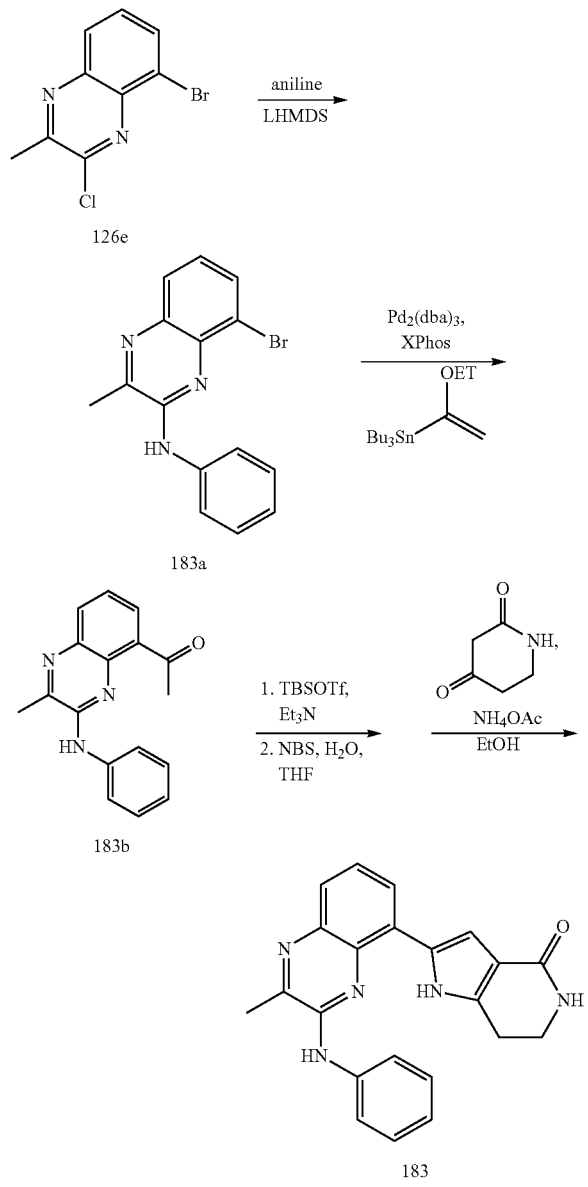

Preparation of 8-bromo-3-methyl-N-phenylquinoxalin-2-amine

LHMDS (1.0M in THF; 14.37 ml, 14.37 mmol) was added to a solution of 5-bromo-3-chloro-2-methylquinoxaline (126e, 0.74 g, 2.87 mmol) and aniline (1.309 ml, 14.37 mmol, Alfa Aesar, Ward Hill, Mass.) in dioxane (28.7 ml) at RT, and the resulting mixture was stirred at RT for 30 min. The mixture was diluted with EtOAc (200 ml), added to a separatory funnel, and washed with saturated aq. NH$_4$Cl (2×150 ml) before the organic layer was separated, dried over Na$_2$SO$_4$, and concentrated. Purification by silica gel (100% hexanes to 20% EtOAc/hexanes) provided 8-bromo-3-methyl-N-phenylquinoxalin-2-amine (183a, 71% yield) as a brown oil. MS (ESI, pos. ion) m/z: 314.2/316.2 (M+1).

Preparation of 1-(2-methyl-3-(phenylamino)quinoxalin-5-yl)ethanone

A mixture of 8-bromo-3-methyl-N-phenylquinoxalin-2-amine (0.64 g, 2.037 mmol), tributyl(1-ethoxyvinyl)stannane (1.032 ml, 3.06 mmol; Aldrich), Pd$_2$(dba)$_3$ (0.187 g, 0.204 mmol), XPhos (Strem, Newburyport, Mass.; 0.097 g, 0.204 mmol), CuI (0.078 g, 0.407 mmol), and cesium fluoride (0.928 g, 6.11 mmol) in dioxane (10.19 ml) was heated in a microwave reactor (Biotage Initiator) for 20 min at 160° C. The mixture was diluted with EtOAc (200 ml), added to a separatory funnel, and washed with saturated aq. NH$_4$Cl (3×150 ml) before the organic layer was separated, dried over Na$_2$SO$_4$, and concentrated. Purification by silica gel (100% hexanes to 30% EtOAc/hexanes) provided 1-(2-methyl-3-(phenylamino)quinoxalin-5-yl)ethanone (183b, 21% yield) as a brown, amorphous solid. MS (ESI, pos. ion) m/z: 278.2 (M+1).

Preparation of 2-(2-methyl-3-(phenylamino)quinoxalin-5-yl)-6,7-dihydro-1H-pyrrolo[3,2-c]pyridin-4(5H)-one TBSOTF (269 μl, 1.172 mmol) was added to a solution of 1-(2-methyl-3-(phenylamino)quinoxalin-5-yl)ethanone (130 mg, 0.469 mmol) and Et$_3$N (85 μl, 0.609 mmol) in DCM (1953 μl) at 0° C. The reaction was stirred for 30 min and then diluted with Et$_2$O (150 ml), added to a separatory funnel, and washed with saturated aq. NaHCO$_3$ (2×75 ml). The organic layer was separated, dried over Na$_2$SO$_4$, and concentrated in vacuo to provide the silyl enol ether as a yellow oil. 1-Bromopyrrolidine-2,5-dione in THF (4688 μl, 0.469 mmol) was added (in three portions) to a solution of the resulting yellow oil in a mixture of water (135 μl, 7.50 mmol) and THF (1953 μl) at 0° C. After 20 min, the mixture was diluted with Et$_2$O (100 ml), added to a separatory funnel, and washed with saturated aq. NaHCO$_3$ (2×75 ml) before the organic layer was separated, dried over Na$_2$SO$_4$, and concentrated to give the intermediate alpha-bromoketone. A solution of the resulting alpha-bromoketone, NH$_4$OAc (145 mg, 1.875 mmol), and piperidine-2,4-dione (63.6 mg, 0.563 mmol) in EtOH (1953 μl) was stirred at 50° C. for 16 h. The reaction mixture was diluted with Et$_2$O (100 ml), added to a separatory funnel, and washed with saturated aq. NaHCO$_3$ (2×75 ml) before the organic layer was separated, dried over Na$_2$SO$_4$, and concentrated. Purification by silica gel (100% DCM to 3% MeOH/DCM) provided 2-(2-methyl-3-(phenylamino)quinoxalin-5-yl)-6,7-dihydro-1H-pyrrolo[3,2-c]pyridin-4(5H)-one (183, 5% yield) as a yellow-brown solid. $^1$H NMR (400 MHz, DMSO-d$_6$) δ ppm 2.55 (t, J=7.24 Hz, 2H) 2.75 (s, 3H) 3.38 (td, J=6.80, 2.45 Hz, 2H) 6.93-6.97 (m, 2H) 7.23-7.28 (m, 1H) 7.42 (t, J=7.82 Hz, 1 H) 7.51 (t, J=7.82 Hz, 2H) 7.64-7.67 (m, 1H) 7.69 (d, J=7.63 Hz, 2H) 7.93-7.96 (m, 1H) 8.97 (s, 1H) 11.71 (br. s., 1H). MS (ESI, pos. ion) m/z: 370.2 (M+1).

Example 184

2-(2-(pyridin-4-ylamino)quinolin-8-yl)-6,7-dihydro-1H-pyrrolo[3,2-c]pyridin-4(5H)-one

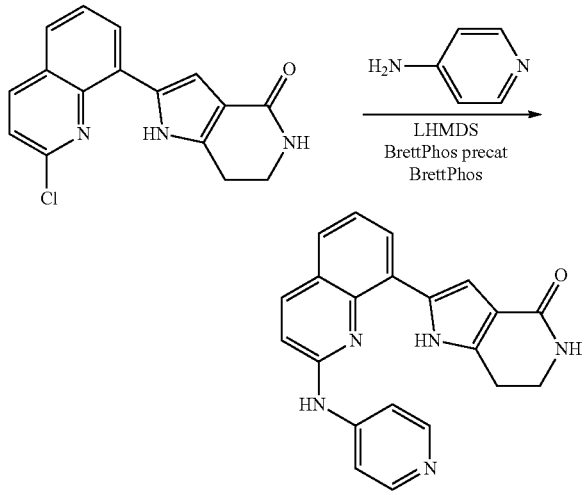

Prepared similarly to that described in Example 82 using 2-(2-chloroquinolin-8-yl)-6,7-dihydro-1H-pyrrolo[3,2-c]pyridin-4(5H)-one (Example 1; 58 mg, 0.195 mmol), pyridin-4-amine (22.00 mg, 0.234 mmol, Aldrich), BrettPhos precat (Strem, Newburyport, Mass.; 8.25 mg, 9.74 μmmol), Brettphos (Strem, Newburyport, Mass.; 5.70 mg, 9.74 μmmol), and LHMDS (1.0M in THF; 429 μl, 0.429 mmol), heating at 150° C. for 40 min in a microwave (Biotage Initiator). Purification by silica gel chromatography (100% DCM to 10% MeOH/DCM) provided 2-(2-(pyridin-4-ylamino)quinolin-8-yl)-6,7-dihydro-1H-pyrrolo[3,2-c]pyridin-4(5H)-one (13% yield). ¹H NMR (400 MHz, MeOH-d₄) δ ppm 2.85 (t, J=7.04 Hz, 2H) 3.62 (t, J=7.04 Hz, 2H) 6.99 (s, 1H) 7.11 (d, J=9.00 Hz, 1H) 7.39 (t, J=7.73 Hz, 1H) 7.64 (dd, J=8.02, 1.17 Hz, 1H) 7.75 (d, J=6.46 Hz, 2H) 7.94 (dd, J=7.43, 1.17 Hz, 1H) 8.14 (d, J=8.80 Hz, 1H) 8.33 (d, J=6.26 Hz, 2H). MS (ESI, pos. ion) m/z: 356.3 (M+1).

Example 185

2-(2-(pyridin-2-ylamino)quinolin-8-yl)-6,7-dihydro-1H-pyrrolo[3,2-c]pyridin-4(5H)-one

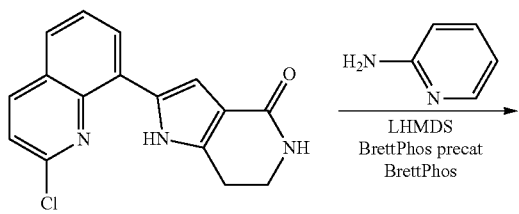

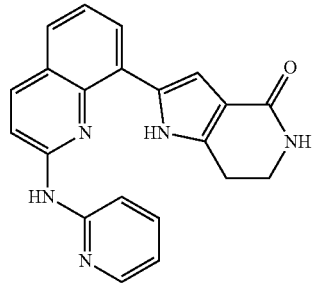

Prepared similarly to that described in Example 82 using 2-(2-chloroquinolin-8-yl)-6,7-dihydro-1H-pyrrolo[3,2-c]pyridin-4(5H)-one (Example 1; 154 mg, 0.517 mmol), pyridin-2-amine (58.4 mg, 0.621 mmol, Aldrich), BrettPhos precat (Strem, Newburyport, Mass.; 21.90 mg, 0.026 mmol), Brettphos (Strem, Newburyport, Mass.; 15.12 mg, 0.026 mmol), and LHMDS (1.0M in THF; 1138 μl, 1.138 mmol), heating at 150° C. for 30 min in a microwave reactor (Biotage Initiator). Purification by silica gel (100% DCM to 5% MeOH/DCM) provided 2-(2-(pyridin-2-ylamino)quinolin-8-yl)-6,7-dihydro-1H-pyrrolo[3,2-c]pyridin-4(5H)-one (29% yield). ¹H NMR (400 MHz, DMSO-d₆) δ ppm 2.92 (t, J=6.75 Hz, 2H) 3.45 (td, J=6.80, 2.25 Hz, 2H) 6.96 (br. s., 1H) 6.99 (d, J=2.15 Hz, 1H) 7.02 (dd, J=6.85, 5.48 Hz, 1H) 7.36 (t, J=7.73 Hz, 1H) 7.54 (d, J=8.80 Hz, 1H) 7.58 (d, J=8.22 Hz, 1H) 7.63 (d, J=7.24 Hz, 1H) 7.76 (td, J=6.85, 1.96 Hz, 1H) 8.02 (dd, J=6.46, 0.98 Hz, 1H) 8.20 (d, J=9.00 Hz, 1H) 8.41 (dd, J=4.89, 1.37 Hz, 1H) 10.16 (s, 1H) 12.72 (br. s., 1H). MS (ESI, pos. ion) m/z: 356.1 (M+1).

Example 186

2-(3-(ethyl(phenyl)amino)quinoxalin-5-yl)-6,7-dihydro-1H-pyrrolo[3,2-c]pyridin-4(5H)-one

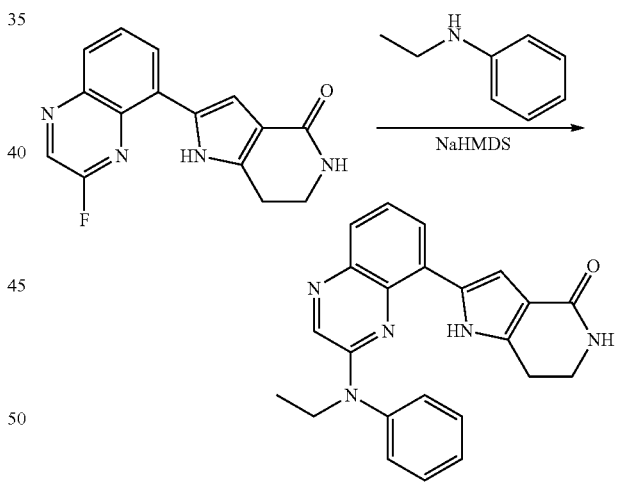

Prepared similarly to that described in Example 210 using 2-(3-fluoroquinoxalin-5-yl)-6,7-dihydro-1H-pyrrolo[3,2-c]pyridin-4(5H)-one (Example 210i; 24 mg, 0.085 mmol), N-ethylaniline (75 μl, 0.595 mmol, Alfa Aesar, Ward Hill, Mass.), and NaHMDS (1.0M in THF; 595 μl, 0.595 mmol) and heating at 22° C. for 30 min. Purification by silica gel (100% DCM to 4% MeOH/DCM) provided 2-(3-(ethyl(phenyl)amino)quinoxalin-5-yl)-6,7-dihydro-1H-pyrrolo[3,2-c]pyridin-4(5H)-one (40% yield). ¹H NMR (400 MHz, CDCl₃) δ ppm 1.46 (t, J=7.14 Hz, 3H) 2.80 (t, J=6.85 Hz, 2H) 3.61 (td, J=6.90, 2.45 Hz, 2H) 4.10 (q, J=7.24 Hz, 2H) 5.35 (br. s., 1H) 7.14 (d, J=2.15 Hz, 1H) 7.33-7.37 (m, 2H) 7.39-7.45 (m, 2H) 7.51-7.56 (m, 2H) 7.72 (dd, J=8.02, 1.17 Hz, 1H) 7.99 (dd, J=7.63, 1.37 Hz, 1H) 8.35 (s, 1H) 12.12 (br. s., 1H). MS (ESI, pos. ion) m/z: 384.4 (M+1).

Example 187 rac-7-methyl-2-(3-(phenylamino)quinoxalin-5-yl)-6,7-dihydro-1H-pyrrolo[3,2-c]pyridin-4(5H)-one

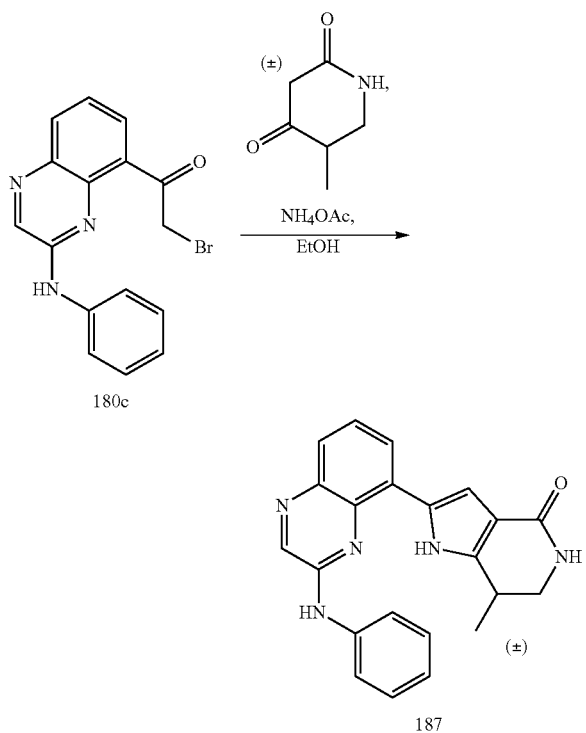

A mixture of 2-bromo-1-(3-(phenylamino)quinoxalin-5-yl)ethanone (180c, 62 mg, 0.18 mmol), rac-5-methylpiperidine-2,4-dione (prepared according to J. Med. Chem. 2009, 52, 293-307; 27.8 mg, 0.219 mmol), and NH₄OAc (56.2 mg, 0.729 mmol) in EtOH (1215 µl) was stirred at 50° C. for 16 h. The mixture was diluted with EtOAc (150 ml), added to a separatory funnel, and washed with saturated aq. NaHCO₃ (2×75 ml) before the organic layer was separated, dried over Na₂SO₄, and concentrated. Purification by silica gel (100% DCM to 4% MeOH/DCM) then by rpHPLC (Phenomenex Gemini C$_{18}$, 10 µm, 150×30 mm; 10-100% ACN/water with 0.1% TFA) provided rac-7-methyl-2-(3-(phenylamino)quinoxalin-5-yl)-6,7-dihydro-1H-pyrrolo[3,2-c]pyridin-4 (5H)-one (5% yield) as a yellow solid. $^1$H NMR (400 MHz, MeOH-d$_4$) δ ppm 0.95 (d, J=6.85 Hz, 3H) 3.02 (sxt, J=6.69 Hz, 1H) 3.21 (dd, J=12.32, 7.43 Hz, 1H) 3.61 (dd, J=12.42, 5.58 Hz, 1H) 7.01 (s, 1H) 7.21 (t, J=7.43 1H) 7.40-7.49 (m, 3H) 7.65 (s, 1H) 7.66 (s, 1H) 7.72 (dd, J=8.02, 1.17 Hz, 1H) 7.99 (dd, J=7.53, 1.27 Hz, 1H) 8.48 (s, 1H). MS (ESI, pos. ion) m/z: 370.1 (M+1).

Example 188

2-(3-(methyl(phenyl)amino)quinoxalin-5-yl)-6,7-dihydro-1H-pyrrolo[3,2-c]pyridin-4(5H)-one

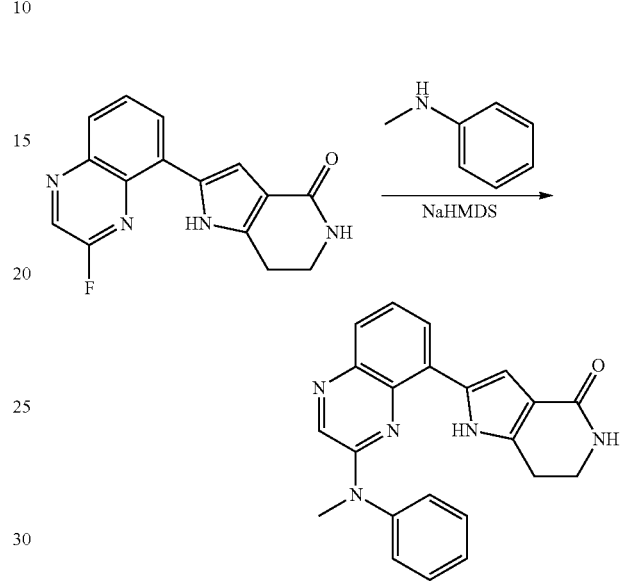

Prepared similarly to that described in Example 210 using 2-(3-fluoroquinoxalin-5-yl)-6,7-dihydro-1H-pyrrolo[3,2-c]pyridin-4(5H)-one (Example 210i; 56 mg, 0.198 mmol), N-methylaniline (150 µl, 1.389 mmol, Alfa Aesar, Ward Hill, Mass.), and NaHMDS (1.0M in THF; 1389 µl, 1.389 mmol) and heating at 0° C. for 1 h. Purification by silica gel (100% DCM to 3% MeOH/DCM) provided 2-(3-(methyl(phenyl)amino)quinoxalin-5-yl)-6,7-dihydro-1H-pyrrolo[3,2-c]pyridin-4(5H)-one (46% yield). $^1$H NMR (400 MHz, DMSO-d$_6$) δ ppm 2.76 (t, J=6.94 Hz, 2H) 3.33 (s, 3H) 3.42 (td, J=6.80, 2.45 Hz, 2H) 6.97 (br. s., 1H) 7.15 (d, J=2.15 Hz, 1H) 7.41-7.49 (m, 2H) 7.50-7.55 (m, 2H) 7.56-7.62 (m, 2H) 7.70 (dd, J=8.02, 1.17 Hz, 1H) 8.01 (dd, J=7.53, 1.27 Hz, 1H) 8.45 (s, 1H) 11.70 (br. s., 1H). MS (ESI, pos. ion) m/z: 370.2 (M+1).

Example 189

2-(2-(phenylamino)quinolin-8-yl)-1H-imidazo[4,5-c]pyridin-4(5H)-one 2,2,2-trifluoroacetate

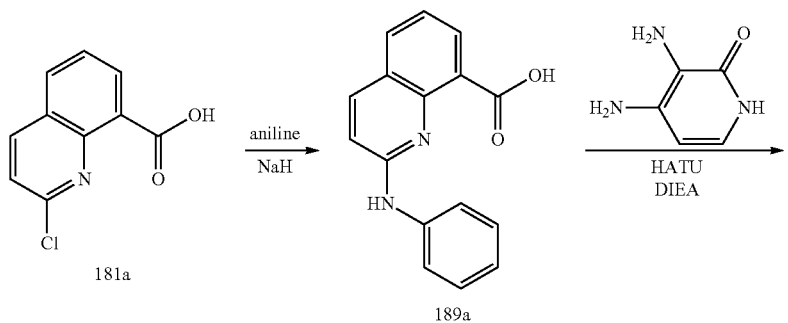

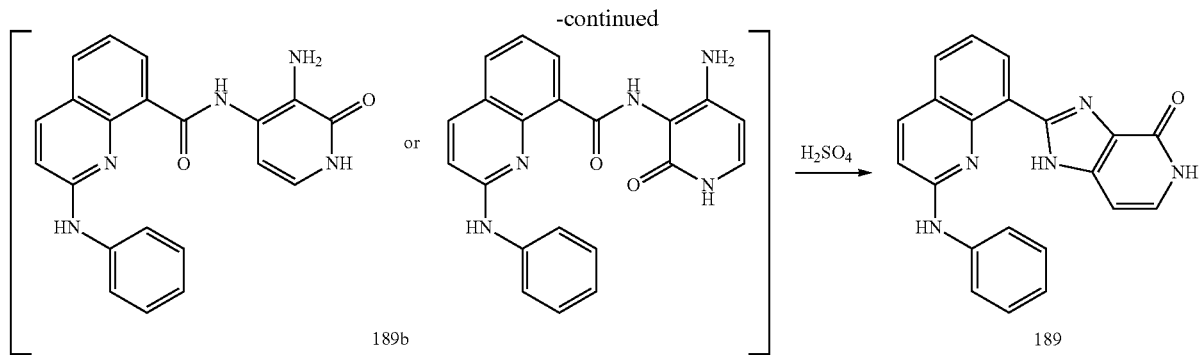

Preparation of 189a: 2-(phenylamino)quinoline-8-carboxylic acid

NaH (60% w/w in mineral oil; 0.549 g, 13.73 mmol) was added to a mixture of 2-chloroquinoline-8-carboxylic acid (181a, 0.95 g, 4.58 mmol) and aniline (0.834 ml, 9.15 mmol) in THF (11 ml) at 0° C.; the reaction was heated to 50° C. for 2 h. The mixture was diluted with 75 ml of $Et_2O$ and washed with 1 N NaOH. The organic layer was separated, and the aq. layer was acidified to ~pH 1 with 5 N HCl and extracted 4 times with 75 ml of EtOAc. All organic extracts were then combined dried over $Na_2SO_4$, and concentrated to give 2-(phenylamino)quinoline-8-carboxylic acid (35% yield) as a light-brown solid. MS (ESI, pos. ion) m/z: 265.2 (M+1).

Preparation of N-(3-amino-2-oxo-1,2-dihydropyridin-4-yl)-2-(phenylamino)quinoline-8-carboxamide (or N-(4-amino-2-oxo-1,2-dihydropyridin-3-yl)-2-(phenylamino)quinoline-8-carboxamide)

A mixture of 2-(phenylamino)quinoline-8-carboxylic acid (0.42 g, 1.589 mmol), 3,4-diaminopyridin-2(1H)-one (0.199 g, 1.589 mmol, Sphinx Scientific Laboratory LLC, Sycamore, Ill.), 2-(3H-[1,2,3]triazolo[4,5-b]pyridin-3-yl)-1,1,3,3-tetramethylisouronium hexafluorophosphate (V) (0.604 g, 1.589 mmol), and N-ethyl-N-isopropylpropan-2-amine (0.277 ml, 1.589 mmol) in DMF (1.589 ml) was stirred at RT for 2 h. The reaction was diluted with (3:2) $CHCl_3$/IPA (200 ml), added to a separatory funnel, and washed with water (2×50 ml) before the organic layer was separated, dried over $Na_2SO_4$, and concentrated to give N-(3-amino-2-oxo-1,2-dihydropyridin-4-yl)-2-(phenylamino)quinoline-8-carboxamide (or N-(4-amino-2-oxo-1,2-dihydropyridin-3-yl)-2-(phenylamino)quinoline-8-carboxamide; regiochemistry not established) as a brown amorphous solid. MS (ESI, pos. ion) m/z: 372.2 (M+1).

Preparation of 2-(2-(phenylamino)quinolin-8-yl)-1H-imidazo[4,5-c]pyridin-4(5H)-one 2,2,2-trifluoroacetate A solution of the material from Example 189b (0.59 g, 1.589 mmol) in 9 M sulfuric acid (17.65 ml, 159 mmol) was heated in a microwave reactor (Biotage Initiator) at 140° C. for 30 min. The reaction mixture was dumped into a beaker of ice and 10 N NaOH (16 ml), resulting in the precipitation of a solid. This precipitate was collected by vacuum filtration and washed with MeOH to give a brown solid. Purification by rpHPLC (Phenomenex Gemini $C_{18}$, 10 μm, 150×30 mm; 10-100% ACN/water with 0.1% TFA) provided 2-(2-(phenylamino)quinolin-8-yl)-1H-imidazo[4,5-c]pyridin-4(5H)-one 2,2,2-trifluoroacetate (5% yield) as a brown solid. $^1$H NMR (400 MHz, DMSO-$d_6$) δ ppm 6.32 (br. s., 1H) 7.13-7.22 (m, 4H) 7.45 (d, J=15.45 Hz, 3H) 7.67 (d, J=7.82 Hz, 2H) 7.88 (dd, J=7.82, 1.17 Hz, 1H) 8.23 (d, J=9.00 Hz, 1H) 8.53 (d, J=7.24 Hz, 1H) 9.75 (s, 1H) 11.15 (br. s., 1H). MS (ESI, pos. ion) m/z: 354.2 (M+1).

Example 190

2-(2-methyl-3-(pyridin-2-ylamino)quinoxalin-5-yl)-6,7-dihydro-1H-pyrrolo[3,2-c]pyridin-4(5H)-one

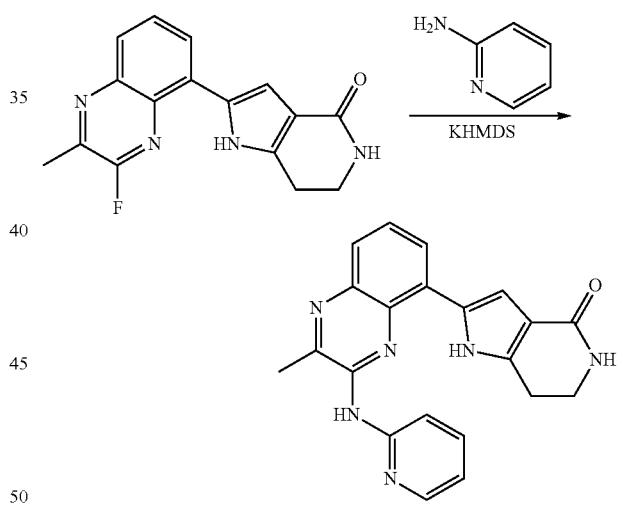

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 61 mg, 0.206 mmol), pyridin-2-amine (97 mg, 1.029 mmol, Aldrich), and KHMDS in toluene (2059 μl, 1.029 mmol) stirring at 22° C. for 1 h. Purification by silica gel (100% DCM to 8% MeOH/DCM) provided 2-(2-methyl-3-(pyridin-2-ylamino)quinoxalin-5-yl)-6,7-dihydro-1H-pyrrolo[3,2-c]pyridin-4(5H)-one (9% yield). $^1$H NMR (400 MHz, DMSO-$d_6$) δ ppm 2.80 (s, 3H) 2.85 (t, J=6.75 Hz, 2H) 3.44 (dt, J=6.85, 3.42 Hz, 2H) 5.86 (br. s., 1H) 6.99 (br. s., 1H) 7.06 (s, 1H) 7.15 (t, J=5.97 Hz, 1H) 7.53 (t, J=7.82 Hz, 1H) 7.70 (d, J=8.22 Hz, 1H) 7.78-7.83 (m, 1H) 7.86 (dd, J=7.04, 1.76 Hz, 1H) 8.02 (d, J=7.24 Hz, 1H) 8.52 (d, J=3.52 Hz, 1H) 9.32 (s, 1H). MS (ESI, pos. ion) m/z: 371.1 (M+1).

Example 191

2-(2-methyl-3-(propylamino)-5-quinoxalinyl)-1,5,6,7-tetrahydro-4H-pyrrolo[3,2-c]pyridin-4-one

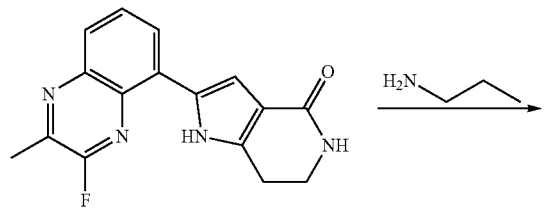

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 50 mg, 0.169 mmol) and propan-1-amine (41.6 μl, 0.506 mmol, Aldrich), heating at 100° C. for 2 h. Purification by silica gel (100% DCM to 5% MeOH/DCM) provided 2-(2-methyl-3-(propylamino)quinoxalin-5-yl)-6,7-dihydro-1H-pyrrolo[3,2-c]pyridin-4(5H)-one (57% yield). $^1$H NMR (400 MHz, DMSO-$d_6$) δ ppm 1.07 (t, J=7.34 Hz, 3H) 1.80 (sxt, J=7.39 Hz, 2H) 2.58 (s, 3H) 2.93 (t, J=6.85 Hz, 2H) 3.46-3.57 (m, 4H) 6.98 (br. s., 1H) 7.20 (d, J=2.35 Hz, 1H) 7.34-7.43 (m, 2H) 7.61 (dd, J=8.02, 1.17 Hz, 1H) 7.93 (d, J=7.63 Hz, 1H) 12.19 (br. s., 1H). MS (ESI, pos. ion) m/z: 336.2 (M+1).

Example 192

2-(3-(isopropylamino)-2-methylquinoxalin-5-yl)-6,7-dihydro-1H-pyrrolo[3,2-c]pyridin-4(5H)-one

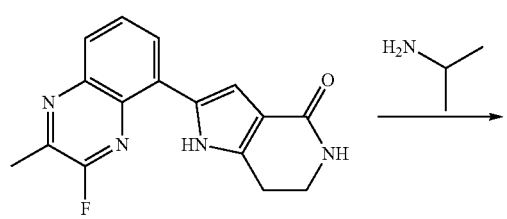

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 45 mg, 0.152 mmol) and propan-2-amine (38.8 μl, 0.456 mmol, Aldrich), heating at 100° C. for 30 min. Purification by silica gel (100% DCM to 3% MeOH/DCM) provided 2-(3-(isopropylamino)-2-methylquinoxalin-5-yl)-6,7-dihydro-1H-pyrrolo[3,2-c]pyridin-4 (5H)-one (47% yield). $^1$H NMR (400 MHz, DMSO-$d_6$) δ ppm 1.38 (d, J=6.46 Hz, 6H) 2.56 (s, 3H) 2.90 (t, J=6.85 Hz, 2H) 3.45 (td, J=6.80, 2.25 Hz, 2H) 4.30 (dq, J=13.23, 6.48 Hz, 1H) 6.88 (d, J=7.04 Hz, 1H) 6.96 (br. s., 1H) 7.12 (s, 1H) 7.33 (t, J=7.82 Hz, 1H) 7.57 (dd, J=7.92, 1.27 Hz, 1H) 7.90 (dd, J=7.63, 1.17 Hz, 1H) 12.23 (br. s., 1H). MS (ESI, pos. ion) m/z: 336.0 (M+1).

Example 193

2-(3-(tert-butylamino)-2-methylquinoxalin-5-yl)-6,7-dihydro-1H-pyrrolo[3,2-c]pyridin-4(5H)-one

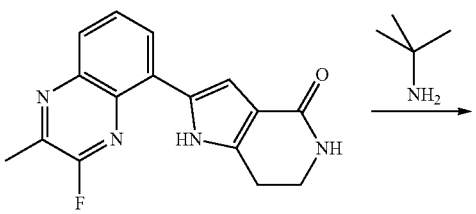

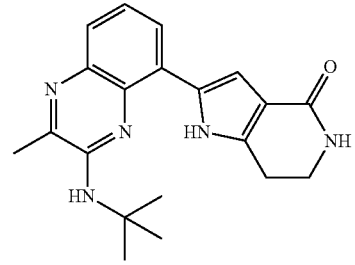

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 63 mg, 0.213 mmol) and 2-methylpropan-2-amine (44.9 μl, 0.425 mmol, Aldrich), heating at 100° C. for 3 h. Purification by silica gel (100% DCM to 4% MeOH/DCM) provided 2-(3-(tert-butylamino)-2-methylquinoxalin-5-yl)-6,7-dihydro-1H-pyrrolo[3,2-c]pyridin-4(5H)-one (32% yield). $^1$H NMR (400 MHz, DMSO-$d_6$) δ ppm 1.58 (s, 9H) 2.57 (s, 3H) 2.88 (t, J=6.94 Hz, 2H) 3.45 (td, J=6.80, 2.45 Hz, 2H) 6.03 (s, 1H) 6.95 (br. s., 1H) 7.04 (d, J=2.15 Hz, 1H) 7.35 (t, J=7.82 Hz, 1H) 7.59 (dd, J=8.02, 1.37 Hz, 1H) 7.84 (dd, J=7.53, 1.27 Hz, 1H) 12.01 (br. s., 1H). MS (ESI, pos. ion) m/z: 350.3 (M+1).

Example 194

2-(3-(cyclopropylamino)-2-methylquinoxalin-5-yl)-6,7-dihydro-1H-pyrrolo[3,2-c]pyridin-4(5H)-one

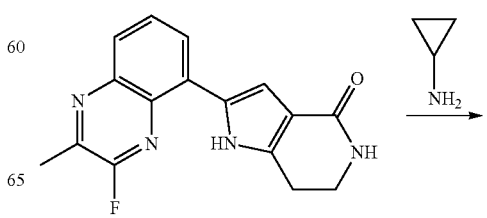

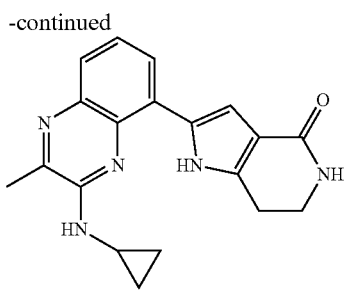

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 55 mg, 0.186 mmol) and cyclopropanamine (25.7 μl, 0.371 mmol, Aldrich), heating at 100° C. for 30 min. Purification by silica gel (100% DCM to 4% MeOH/DCM) provided 2-(3-(cyclopropylamino)-2-methylquinoxalin-5-yl)-6,7-dihydro-1H-pyrrolo[3,2-c]pyridin-4(5H)-one (78% yield). ¹H NMR (400 MHz, DMSO-d₆) δ ppm 0.70-0.75 (m, 2H) 0.96 (dd, J=6.65, 1.96 Hz, 2H) 2.56 (s, 3H) 2.86-2.96 (m, 3H) 3.44 (td, J=6.80, 2.25 Hz, 2H) 6.98 (br. s., 1H) 7.16 (d, J=2.15 Hz, 1H) 7.37 (t, J=7.82 Hz, 1H) 7.58 (d, J=1.17 Hz, 2H) 7.99 (dd, J=7.63, 1.17 Hz, 1H) 12.83 (br. s., 1H). MS (ESI, pos. ion) m/z: 334.2 (M+1).

Example 195 rac-2-(2-methyl-3-((1-methyl-6-oxopiperidin-3-yl)amino)quinoxalin-5-yl)-6,7-dihydro-1H-pyrrolo[3,2-c]pyridin-4(5H)-one 2,2,2-trifluoroacetate

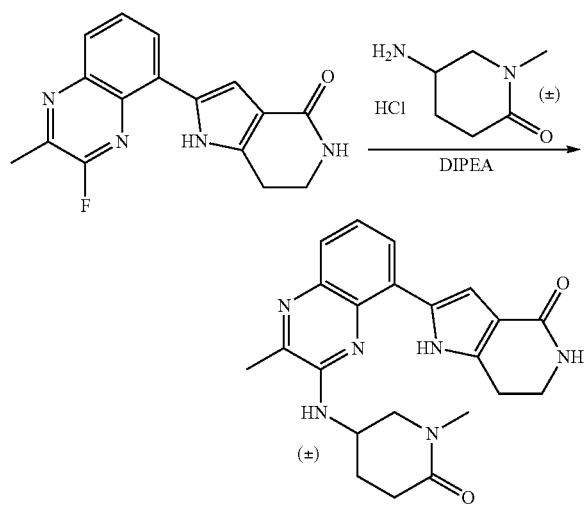

Prepared similarly to that described in Example 127 using 2-(3-fluoro-2-methylquinoxalin-5-yl)-6,7-dihydro-1H-pyrrolo[3,2-c]pyridin-4 (5H)-one (Example 126; 42 mg, 0.142 mmol), rac-5-amino-1-methylpiperidin-2-one hydrochloride (46.7 mg, 0.283 mmol, Advanced ChemBlocks, Inc.), and DIPEA (123 μl, 0.709 mmol), heating at 100° C. for 4 h. Purification by rpHPLC (Phenomenex Gemini C18, 10 μm, 150×30 mm; 10-100% ACN/water with 0.1% TFA) provided rac-2-(2-methyl-3-((1-methyl-6-oxopiperidin-3-yl)amino)quinoxalin-5-yl)-6,7-dihydro-1H-pyrrolo[3,2-c]pyridin-4 (5H)-one 2,2,2-trifluoroacetate (44% yield). ¹H NMR (400 MHz, DMSO-d₆) δ ppm 1.93-2.06 (m, 1H) 2.17 (br. s., 1H) 2.35-2.45 (m, 1H) 2.55 (s, 1H) 2.57 (s, 3H) 2.76-2.89 (m, 5H) 3.36-3.47 (m, 3H) 3.64 (dd, J=11.64, 4.99 Hz, 1H) 4.56 (d, J=3.13 Hz, 1H) 6.94 (br. s., 1H) 7.04 (d, J=6.85 Hz, 1H) 7.11 (d, J=2.15 Hz, 1H) 7.36 (t, J=7.73 Hz, 1H) 7.60 (dd, J=8.12, 1.08 Hz, 1H) 7.86 (dd, J=7.53, 1.08 Hz, 1H) 11.81 (br. s., 1H). MS (ESI, pos. ion) m/z: 405.2 (M+1).

Example 196

2-(2-methyl-3-(oxetan-3-ylamino)quinoxalin-5-yl)-6,7-dihydro-1H-pyrrolo[3,2-c]pyridin-4(5H)-one

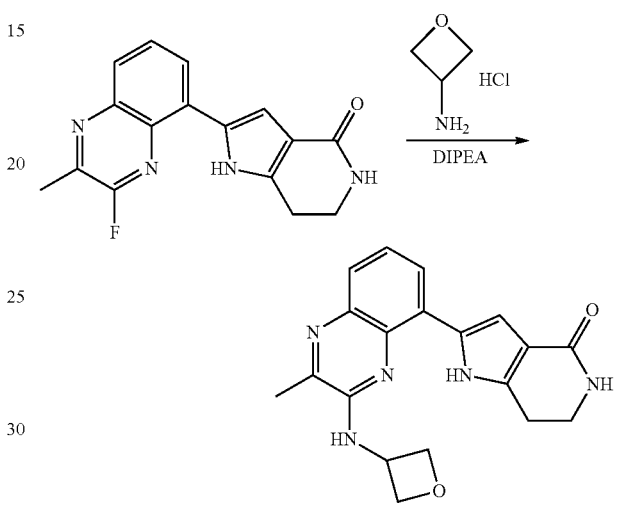

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 41 mg, 0.138 mmol), oxetan-3-amine hydrochloride (30.3 mg, 0.277 mmol, Frontier Scientific), and DIPEA (121 μl, 0.692 mmol), heating at 100° C. for 30 min. Purification by silica gel (100% DCM to 8% MeOH/DCM) provided 2-(2-methyl-3-(oxetan-3-ylamino)quinoxalin-5-yl)-6,7-dihydro-1H-pyrrolo[3,2-c]pyridin-4(5H)-one (66% yield). ¹H NMR (400 MHz, DMSO-d₆) δ ppm 2.60 (s, 3H) 2.92 (t, J=6.85 Hz, 2H) 3.45 (td, J=6.85, 2.35 Hz, 2H) 4.74 (t, J=6.16 Hz, 2H) 4.98 (t, J=6.16 Hz, 2H) 5.04-5.15 (m, 1H) 6.98 (br. s., 1H) 7.10 (d, J=2.15 Hz, 1H) 7.37 (t, J=7.73 Hz, 1H) 7.60 (dd, J=8.02, 1.17 Hz, 1H) 7.70 (d, J=4.69 Hz, 1H) 7.85 (dd, J=7.63, 1.17 Hz, 1H) 11.80 (br. s., 1H). MS (ESI, pos. ion) m/z: 350.1 (M+1).

Example 197

2-(2-methyl-3-((3-methyloxetan-3-yl)amino)quinoxalin-5-yl)-6,7-dihydro-1H-pyrrolo[3,2-c]pyridin-4(5H)-one

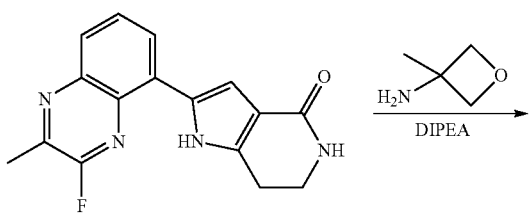

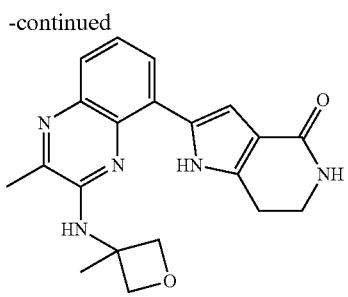

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 47 mg, 0.159 mmol), 3-methyloxetan-3-amine (27.6 mg, 0.317 mmol; Synthonix, Wake Forest, N.C.), and DIPEA (83 µl, 0.476 mmol), heating at 100° C. for 2.5 h. Purification by silica gel (100% DCM to 6% MeOH/DCM) provided 2-(2-methyl-3-((3-methyloxetan-3-yl)amino)quinoxalin-5-yl)-6,7-dihydro-1H-pyrrolo[3,2-c]pyridin-4(5H)-one (38% yield). $^1$H NMR (400 MHz, DMSO-d$_6$) δ ppm 1.80 (s, 3H) 2.57 (s, 3H) 2.89 (t, J=6.85 Hz, 2H) 3.45 (td, J=6.85, 2.35 Hz, 2H) 4.60 (d, J=6.26 Hz, 2H) 4.87 (d, J=6.26 Hz, 2H) 6.95 (br. s., 1H) 7.06 (d, J=2.35 Hz, 1H) 7.34-7.41 (m, 2H) 7.61 (dd, J=8.02, 1.37 Hz, 1H) 7.82 (dd, J=7.63, 1.37 Hz, 1H) 11.66 (br. s., 1H). MS (ESI, pos. ion) m/z: 364.2 (M+1).

Example 198 rac-2-(2-methyl-3-((tetrahydro-2H-pyran-3-yl)amino)quinoxalin-5-yl)-6,7-dihydro-1H-pyrrolo[3,2-c]pyridin-4(5H)-one

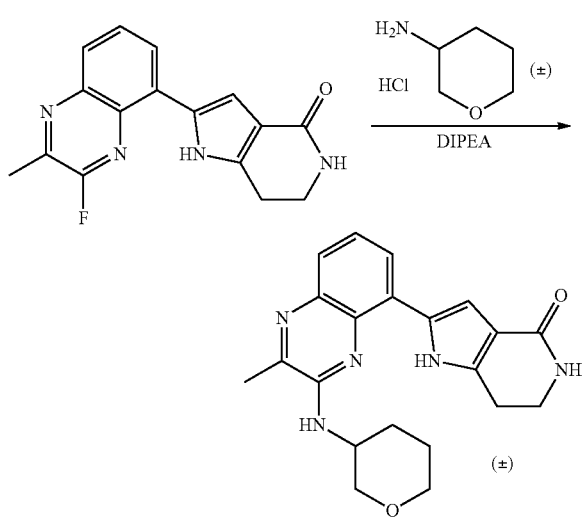

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 44 mg, 0.148 mmol), rac-tetrahydro-2H-pyran-3-amine hydrochloride (40.9 mg, 0.297 mmol, Matrix Scientific, Columbia, S.C.), and DIPEA (129 µl, 0.742 mmol), heating at 100° C. for 1 h. Purification by silica gel (100% DCM to 6% MeOH/DCM) provided rac-2-(2-methyl-3-((tetrahydro-2H-pyran-3-yl)amino)quinoxalin-5-yl)-6,7-dihydro-1H-pyrrolo[3,2-c]pyridin-4(5H)-one (75% yield). $^1$H NMR (400 MHz, DMSO-d$_6$) δ ppm 1.72-1.83 (m, 3H) 2.13-2.21 (m, 1H) 2.56 (s, 3H) 2.91 (t, J=6.85 Hz, 2H) 3.35-3.42 (m, 2H) 3.45 (td, J=6.85, 2.35 Hz, 2H) 3.87 (d, J=10.76 Hz, 1H) 4.01-4.08 (m, 1H) 4.12-4.20 (m, 1H) 6.86 (d, J=7.24 Hz, 1H) 6.94 (br. s., 1H) 7.08 (d, J=2.15 Hz, 1H) 7.35 (t, J=7.82 Hz, 1H) 7.59 (dd, J=8.12, 1.27 Hz, 1H) 7.91 (dd, J=7.53, 1.27 Hz, 1H) 12.07 (br. s., 1H). MS (ESI, pos. ion) m/z: 378.2 (M+1). Chiral purification [SFC: Chiralpak OH-J (30×150 mm), A: liquid CO$_2$, B: 20 mM NH$_3$ in MeOH/EtOH/isopropanol (1:1:1), isocratic: 70:30 (A:B), 70 mL/min] separately afforded 2-(2-methyl-3-((tetrahydro-2H-pyran-3-yl)amino)quinoxalin-5-yl)-6,7-dihydro-1H-pyrrolo[3,2-c]pyridin-4(5H)-one (first eluting enantiomer, 208) and 2-(2-methyl-3-((tetrahydro-2H-pyran-3-yl)amino)quinoxalin-5-yl)-6,7-dihydro-1H-pyrrolo[3,2-c]pyridin-4(5H)-one (second eluting enantiomer, 209).

Example 199 rac-2-(2-methyl-3-((6-oxopiperidin-3-yl)amino)quinoxalin-5-yl)-6,7-dihydro-1H-pyrrolo[3,2-c]pyridin-4(5H)-one

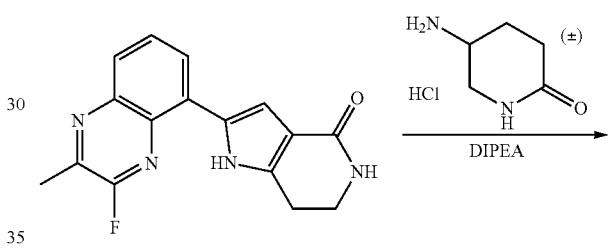

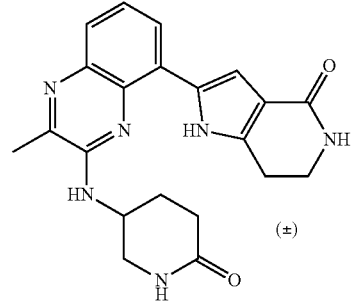

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 48 mg, 0.162 mmol), rac-5-aminopiperidin-2-one hydrochloride (48.8 mg, 0.324 mmol, Advanced ChemBlocks, Inc., Burlingame, Calif.), and DIPEA (141 µl, 0.810 mmol), heating at 100° C. for 1.5 h. Purification by silica gel (100% DCM to 20% MeOH/DCM) provided rac-2-(2-methyl-3-((6-oxopiperidin-3-yl)amino)quinoxalin-5-yl)-6,7-dihydro-1H-pyrrolo[3,2-c]pyridin-4(5H)-one (33% yield). $^1$H NMR (400 MHz, DMSO-d$_6$) δ ppm 1.93-2.07 (m, 1H) 2.14-2.23 (m, 1H) 2.31-2.41 (m, 1H) 2.58 (s, 3H) 2.83-2.90 (m, 2H) 3.23-3.29 (m, 1H) 3.44 (td, J=6.85, 2.15 Hz, 2H) 3.51-3.59 (m, 1H) 4.39-4.51 (m, 1H) 6.94 (br. s., 1H) 7.00 (d, J=6.65 Hz, 1H) 7.13 (s, 1H) 7.37 (t, J=7.82 Hz, 1H) 7.50 (d, J=2.15 Hz, 1H) 7.61 (d, J=7.04 Hz, 1H) 7.89 (d, J=7.63 Hz, 1H) 11.90 (br. s., 1H). MS (ESI, pos. ion) m/z: 391.3 (M+1).

Example 200 rac-2-(2-methyl-3-((2-oxopiperidin-3-yl)amino)quinoxalin-5-yl)-6,7-dihydro-1H-pyrrolo[3,2-c]pyridin-4(5H)-one

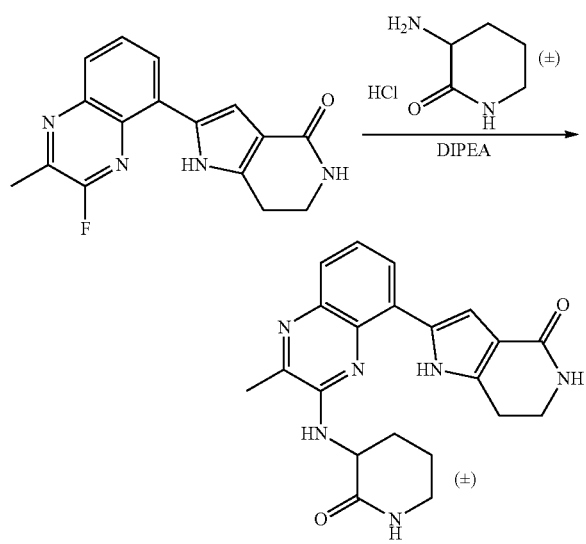

Prepared similar to that described in Example 131 using 2-(3-fluoro-2-methylquinoxalin-5-yl)-6,7-dihydro-1H-pyrrolo[3,2-c]pyridin-4(5H)-one (Example 126; 42 mg, 0.142 mmol), rac-aminopiperidin-2-one hydrochloride (42.7 mg, 0.283 mmol, Matrix Scientific, Inc., Columbia, S.C.), and DIPEA (123 µl, 0.709 mmol), heating at 100° C. for 1.5 h. Purification by rpHPLC (Phenomenex Gemini C18, 10 µm, 150×30 mm; 10-100% ACN/water with 0.1% TFA) and silica gel (100% DCM to 10% MeOH/DCM) provided rac-2-(2-methyl-3-((2-oxopiperidin-3-yl)amino)quinoxalin-5-yl)-6,7-dihydro-1H-pyrrolo[3,2-c]pyridin-4(5H)-one (33% yield). $^1$H NMR (400 MHz, DMSO-$d_6$) δ ppm 1.82-2.01 (m, 3H) 2.27-2.37 (m, 1H) 2.57 (s, 3H) 2.83-2.91 (m, 2H) 3.21-3.29 (m, 2H) 3.45 (td, J=6.94, 2.35 Hz, 2H) 4.63-4.72 (m, 1H) 6.94 (s, 1H) 7.05-7.13 (m, 2H) 7.36 (t, J=7.82 Hz, 1H) 7.60 (dd, J=8.02, 1.17 Hz, 1H) 7.82-7.89 (m, 2H) 11.85 (br. s., 1H). MS (ESI, pos. ion) m/z: 391.1 (M+1).

Example 201

2-(3-((1-hydroxy-2-methylpropan-2-yl)amino)-2-methylquinoxalin-5-yl)-6,7-dihydro-1H-pyrrolo[3,2-c]pyridin-4(5H)-one

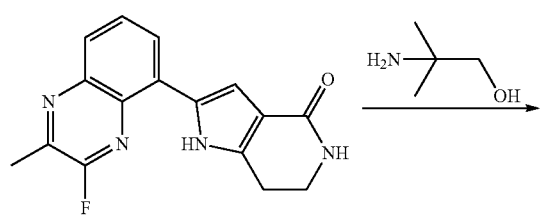

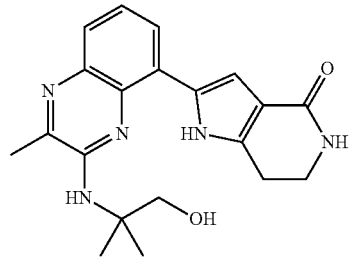

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 48 mg, 0.162 mmol) and 2-amino-2-methylpropan-1-ol (31.1 µl, 0.324 mmol, Sigma-Aldrich), heating at 100° C. for 1.5 h. Purification by silica gel (100% DCM to 6% MeOH/DCM) provided 2-(3-((1-hydroxy-2-methylpropan-2-yl)amino)-2-methylquinoxalin-5-yl)-6,7-dihydro-1H-pyrrolo[3,2-c]pyridin-4(5H)-one (17% yield). $^1$H NMR (400 MHz, DMSO-$d_6$) δ ppm 1.52 (s, 6H) 2.56 (s, 3H) 2.88 (t, J=6.94 Hz, 2H) 3.45 (td, J=6.80, 2.45 Hz, 2H) 3.66 (d, J=5.28 Hz, 2H) 5.15 (t, J=5.58 Hz, 1H) 5.87 (s, 1H) 6.96 (br. s., 1H) 7.03 (d, J=2.15 Hz, 1H) 7.35 (t, J=7.82 Hz, 1H) 7.59 (dd, J=8.02, 1.37 Hz, 1H) 7.84 (dd, J=7.43, 1.37 Hz, 1H) 12.03 (br. s., 1H). MS (ESI, pos. ion) m/z: 366.0 (M+1).

Example 202

2-(2-methyl-3-((1-methylcyclopropyl)amino)quinoxalin-5-yl)-6,7-dihydro-1H-pyrrolo[3,2-c]pyridin-4(5H)-one

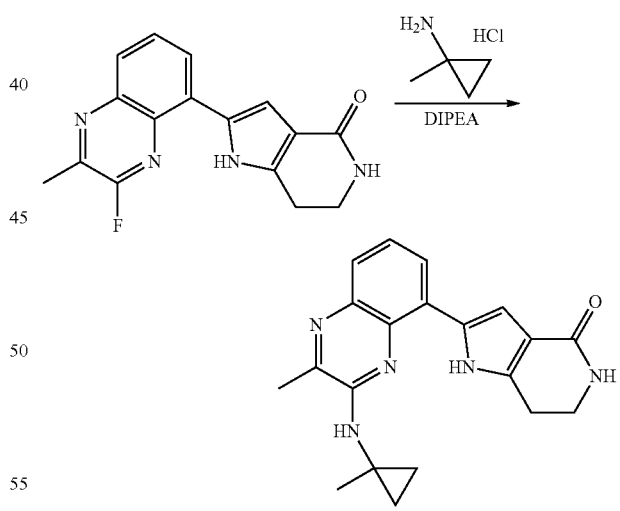

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 48 mg, 0.162 mmol), 1-methylcyclopropanamine hydrochloride (34.9 mg, 0.324 mmol, ChemBridge, San Diego, Calif.), and DIPEA (141 µl, 0.810 mmol), heating at 100° C. for 2 h. Purification by silica gel (100% DCM to 6% MeOH/DCM) provided 2-(2-methyl-3-((1-methylcyclopropyl)amino)quinoxalin-5-yl)-6,7-dihydro-1H-pyrrolo[3,2-c]pyridin-4(5H)-one (25% yield). $^1$H NMR (400 MHz, MeOH-$d_4$) δ ppm 0.93-1.00 (m, 2H) 1.01-1.07 (m, 2H) 1.66 (s, 3H) 2.53 (s, 3H) 3.03 (t, J=7.04 Hz, 2H) 3.64 (t, J=7.04 Hz, 2H) 7.11 (s, 1H) 7.39 (t, J=7.92 Hz, 1H) 7.61 (d, J=8.02 Hz, 1H) 8.00 (d, J=7.63 Hz, 1H). MS (ESI, pos. ion) m/z: 348.2 (M+1).

Example 203

2-(2-methyl-3-((4-methyltetrahydro-2H-pyran-4-yl)amino)quinoxalin-5-yl)-6,7-dihydro-1H-pyrrolo[3,2-c]pyridin-4(5H)-one

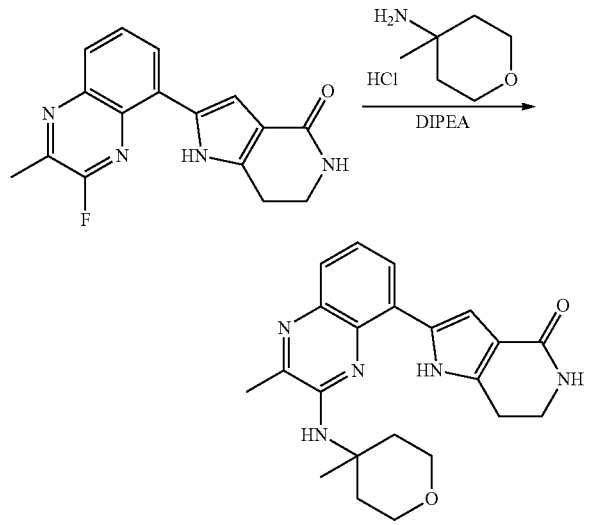

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 48 mg, 0.162 mmol), 4-methyltetrahydro-2H-pyran-4-amine hydrochloride (49.1 mg, 0.324 mmol, Biofine International, Blaine, Wash.), and DIPEA (141 µl, 0.810 mmol), heating at 100° C. for 20 h. Purification by silica gel (100% DCM to 5% MeOH/DCM) provided 2-(2-methyl-3-((4-methyltetrahydro-2H-pyran-4-yl)amino)quinoxalin-5-yl)-6,7-dihydro-1H-pyrrolo[3,2-c]pyridin-4(5H)-one (6% yield). ¹H NMR (400 MHz, MeOD) δ ppm 1.73 (s, 3H) 1.85-1.95 (m, 2H) 2.53 (d, J=13.50 Hz, 2H) 2.67 (s, 3H) 3.01 (t, J=7.14 Hz, 2H) 3.64 (t, J=7.14 Hz, 2H) 3.76-3.82 (m, 4H) 7.00 (s, 1H) 7.40 (t, J=7.82 Hz, 1H) 7.65 (dd, J=8.12, 1.27 Hz, 1H) 7.88 (dd, J=7.53, 1.27 Hz, 1H). MS (ESI, pos. ion) m/z: 392.1 (M+1).

Example 204

2-(3-((3-hydroxycyclohexyl)amino)-2-methylquinoxalin-5-yl)-6,7-dihydro-1H-pyrrolo[3,2-c]pyridin-4(5H)-one (mixture of racemic cis- and trans-isomers)

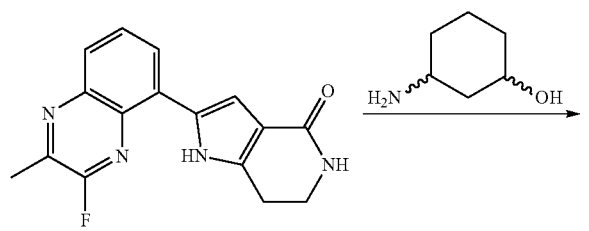

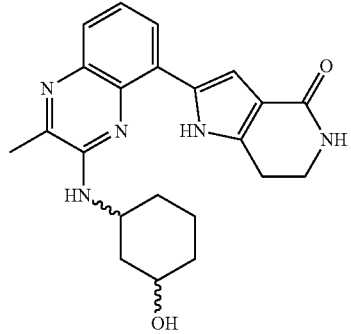

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 48 mg, 0.162 mmol) and 3-aminocyclohexanol (37.0 mg, 0.324 mmol, AB Chem, Inc., Dorval, Canada; mixture of racemic cis- and trans-isomers) and heating at 100° C. for 2 h. Purification by silica gel (100% DCM to 8% MeOH/DCM) provided 2-(3-((3-hydroxycyclohexyl)amino)-2-methylquinoxalin-5-yl)-6,7-dihydro-1H-pyrrolo[3,2-c]pyridin-4(5H)-one (17% yield; mixture of racemic cis- and trans-isomers). ¹H NMR (400 MHz, DMSO-d₆) δ ppm 1.12-1.27 (m, 1H) 1.32-1.51 (m, 3H) 1.55-1.69 (m, 1H) 1.70-1.83 (m, 1H) 1.87 (d, J=12.72 Hz, 1H) 2.00 (br. s., 2H) 2.27 (d, J=11.93 Hz, 1H) 2.55 (d, J=4.11 Hz, 3H) 2.86-3.05 (m, 3H) 3.41-3.72 (m, 4H) 4.02-4.48 (m, 2H) 4.69-4.83 (m, 1H) 6.73-7.02 (m, 2H) 7.07-7.18 (m, 1H) 7.32 (td, J=7.82, 2.15 Hz, 1H) 7.53-7.60 (m, 1H) 7.85-7.96 (m, 1H) 11.86-12.16 (m, 1H). MS (ESI, pos. ion) m/z: 392 (M+1).

Example 205

2-(3-((2-hydroxycyclohexyl)amino)-2-methylquinoxalin-5-yl)-6,7-dihydro-1H-pyrrolo[3,2-c]pyridin-4(5H)-one (mixture of racemic cis- and trans-isomers)

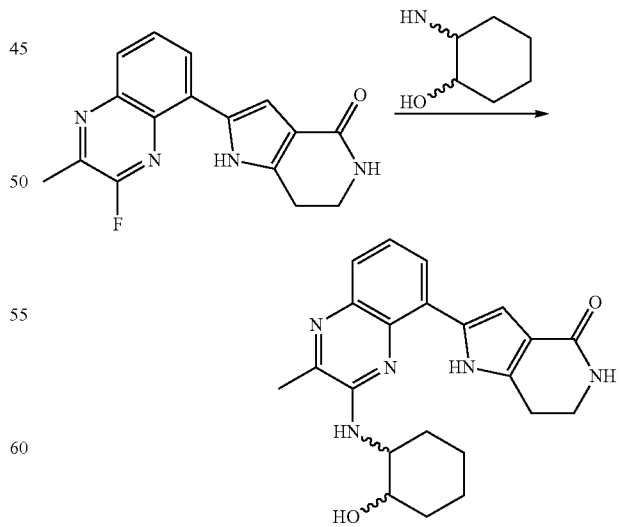

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 48 mg, 0.162

319 mmol) and 2-aminocyclohexanol (37.0 mg, 0.324 mmol, TCI America, Portland, Oreg.; mixture of racemic cis- and trans-isomers) and heating at 100° C. for 2 h. Purification by silica gel (100% DCM to 8% MeOH/DCM) provided 2434(2-hydroxycyclohexyl)amino)-2-methylquinoxalin-5-yl)-6,7-dihydro-1H-pyrrolo[3,2-c]pyridin-4(5H)-one (24% yield; mixture of racemic cis- and trans-isomers). $^1$H NMR (400 MHz, DMSO-d$_6$) δ ppm 1.37-1.50 (m, 2H) 1.54-1.86 (m, 6H) 2.56 (s, 3H) 2.88 (t, J=6.85 Hz, 2H) 3.44 (td, J=6.75, 2.15 Hz, 2H) 4.08 (br. s., 2H) 4.84 (br. s., 1H) 6.23 (d, J=7.04 Hz, 1H) 6.89 (br. s., 1H) 7.14 (d, J=2.15 Hz, 1H) 7.32 (t, J=7.82 Hz, 1H) 7.56 (d, J=6.85 Hz, 1H) 7.86 (d, J=6.26 Hz, 1H) 11.86 (br. s., 1H). MS (ESI, pos. ion) m/z: 392.3 (M+1).

Example 206

2-(3-((trans-4-hydroxycyclohexyl)amino)-2-methylquinoxalin-5-yl)-6,7-dihydro-1H-pyrrolo[3,2-c]pyridin-4(5H)-one

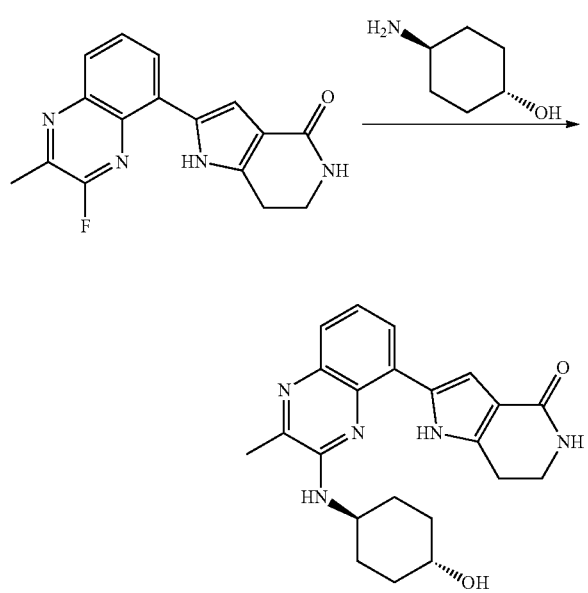

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 48 mg, 0.162 mmol) and trans-4-aminocyclohexanol (32.7 mg, 0.283 mmol; Alfa Aesar, Ward Hill, Mass.), heating at 100° C. for 1 h. Purification by silica gel (100% DCM to 10% MeOH/DCM) provided 2-(3-((trans-4-hydroxycyclohexyl)amino)-2-methylquinoxalin-5-yl)-6,7-dihydro-1H-pyrrolo[3,2-c]pyridin-4(5H)-one (54% yield). $^1$H NMR (400 MHz, DMSO-d$_6$) δ ppm 1.34-1.57 (m, 4H) 1.93 (d, J=11.54 Hz, 2H) 2.09 (d, J=12.32 Hz, 2H) 2.54 (s, 3H) 2.92 (t, J=6.85 Hz, 2H) 3.42-3.54 (m, 3H) 3.91-4.04 (m, 1H) 4.60 (br. s., 1H) 6.75 (d, J=7.43 Hz, 1H) 6.94 (s, 1H) 7.08 (d, J=2.15 Hz, 1H) 7.32 (t, J=7.82 Hz, 1H) 7.57 (dd, J=8.02, 1.37 Hz, 1H) 7.89 (dd, J=7.53, 1.27 Hz, 1H) 11.96 (br. s., 1H). MS (ESI, pos. ion) m/z: 392.3 (M+1).

320

Example 207

2-(3-((cis-4-hydroxycyclohexyl)amino)-2-methylquinoxalin-5-yl)-6,7-dihydro-1H-pyrrolo[3,2-c]pyridin-4(5H)-one

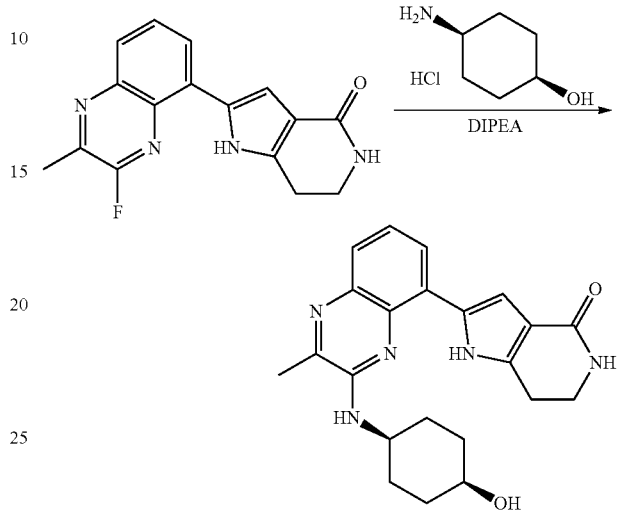

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 41 mg, 0.138 mmol), cis-4-aminocyclohexanol (42.0 mg, 0.277 mmol, J&W Pharmlab, Levittown, Pa.), and DIPEA (121 μl, 0.692 mmol), heating at 100° C. for 1 h. Purification by silica gel (100% DCM to 10% MeOH/DCM) provided 2-(3-((cis-4-hydroxycyclohexyl)amino)-2-methylquinoxalin-5-yl)-6,7-dihydro-1H-pyrrolo[3,2-c]pyridin-4(5H)-one (26% yield). $^1$H NMR (400 MHz, DMSO-d$_6$) δ ppm 1.61-1.71 (m, 2H) 1.72-1.83 (m, 4H) 1.83-1.96 (m, 2H) 2.56 (s, 3H) 2.89 (t, J=6.85 Hz, 2H) 3.41-3.48 (m, 2H) 3.88 (br. s., 1H) 3.97-4.07 (m, 1H) 4.42 (br. s., 1H) 6.77 (d, J=7.04 Hz, 1H) 6.91 (br. s., 1H) 7.18 (d, J=1.76 Hz, 1H) 7.31 (t, J=7.82 Hz, 1H) 7.55 (d, J=7.82 Hz, 1H) 7.87 (d, J=7.63 Hz, 1H) 11.94 (br. s., 1H). MS (ESI, pos. ion) m/z: 392.1 (M+1).

Example 210

2-(3-(tert-butylamino)quinoxalin-5-yl)-6,7-dihydro-1H-pyrrolo[3,2-c]pyridin-4(5H)-one

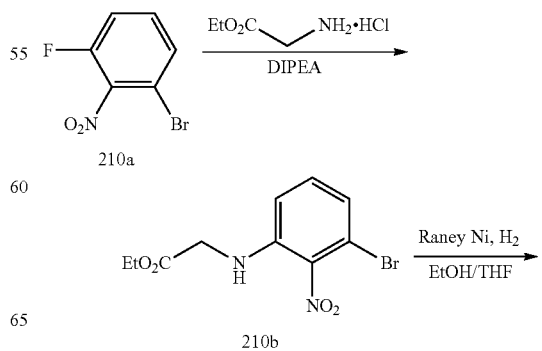

-continued

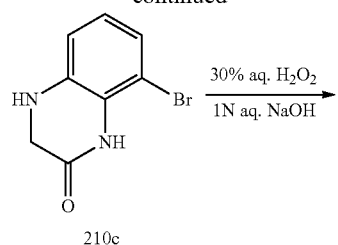
210c

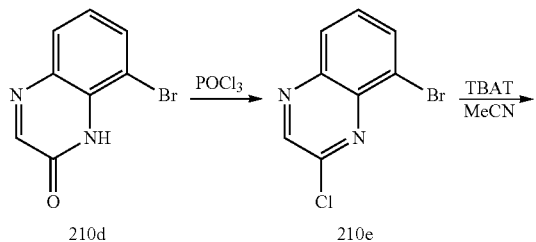
210d  210e

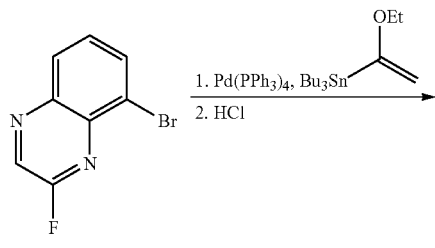
210f

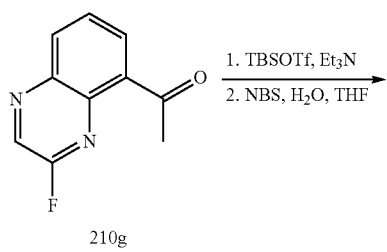
210g

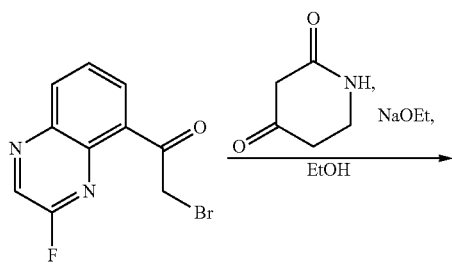
210h

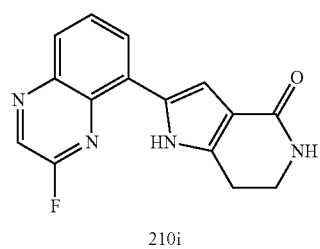
210i

-continued

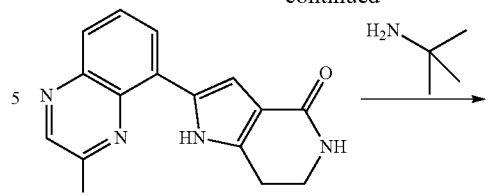

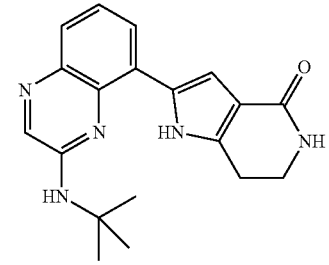

Preparation of ethyl
2-((3-bromo-2-nitrophenyl)amino)acetate

A mixture of 1-bromo-3-fluoro-2-nitrobenzene (10.25 g, 46.6 mmol; Ark Pharm, Inc., Libertyville, Ill.), ethyl 2-aminoacetate hydrochloride (6.50 g, 46.6 mmol; Aldrich), and N-ethyl-N-isopropylpropan-2-amine (24.35 ml, 140 mmol) in DMA (116 ml) was heated to 80° C. for 5 h. The mixture was diluted with DCM (400 ml), added to a separatory funnel, and washed with water (4×200 ml) before the organic layer was separated, dried over $Na_2SO_4$, and concentrated to give ethyl 2-((3-bromo-2-nitrophenyl)amino)acetate (210b, >99% yield) as a yellow oil (contaminated with DMA). MS (ESI, pos. ion) m/z: 303.0/305.0 (M+1).

Preparation of ethyl
2-((2-amino-3-bromophenyl)amino)acetate

Raney 2800 nickel, in water (Aldrich; 8 mL) was added to a solution of ethyl 2-((3-bromo-2-nitrophenyl)amino)acetate (14.12 g, 46.6 mmol) in EtOH (290 ml) and THF (290 ml); the mixture was placed under an atmosphere of $H_2$ and was stirred at RT for 20 h. The mixture was filtered through a pad of wet Celite, topped with sand, and washed with DCM to give ethyl 2-((2-amino-3-bromophenyl)amino)acetate (210c) as a brown liquid. MS (ESI, pos. ion) m/z: 273.0/275.0 (M+1).

Preparation of 8-bromoquinoxalin-2(1H)-one

30% $H_2O_2$ (14.27 ml, 466 mmol) was added to a mixture of ethyl 2-((2-amino-3-bromophenyl)amino)acetate (12.72 g, 46.6 mmol) in 1 N aq. NaOH (58.2 ml, 58.2 mmol) before it was heated to 95° C. for 2 h in a sealed tube behind a blast shield. After cooling the reaction, 1 N HCl (58 ml) was added, and the precipitated solid was filtered, washed with water, and dried in a vacuum oven (50° C., over the 3 d) to give 8-bromoquinoxalin-2(1H)-one (210d, 38% yield over two steps) as a brown solid. MS (ESI, pos. ion) m/z: 225.0/227.0 (M+1).

Preparation of 8-bromo-2-chloroquinoxaline

A mixture of 8-bromoquinoxalin-2(1H)-one (483 mg, 2.146 mmol) in phosphoryl trichloride (100 mL) was heated to 50° C. for 2 h. The crude material was concentrated to remove the $POCl_3$, diluted with EtOAc (150 ml), added to a separatory funnel, and washed with water (2×100 ml) and saturated aq. NaHCO₃ (100 ml) before the organic layer was separated, dried over Na₂SO₄, and concentrated. The mixture and was adsorbed onto silica and was purified via automated flash chromatography (silica gel) with 100% hexanes to 5% EtOAc/hexanes to give 8-bromo-2-chloroquinoxaline (210e, 55% yield) as an off-white solid. MS (ESI, pos. ion) m/z: 243.0/245 (M+1).

Preparation of 8-bromo-2-fluoroquinoxaline

A solution of 8-bromo-2-chloroquinoxaline (2.57 g, 10.55 mmol) and tetrabutylammonium difluorotriphenylsilicate (IV) (12.54 g, 23.22 mmol; Aldrich) in ACN (53 ml) was stirred at 80° C. for 16 h. The mixture was concentrated, diluted with EtOAc, and filtered. The crude material was adsorbed onto silica and was purified via automated flash chromatography (silica gel) with 100% hexanes to 60% DCM in hexanes to give 8-bromo-2-fluoroquinoxaline (210f, 92% yield) as a white. MS (ESI, pos. ion) m/z: 227.0/229.0 (M+1).

Preparation of 1-(3-fluoroquinoxalin-5-yl)ethanone

A solution of 8-bromo-2-fluoroquinoxaline (2.36 g, 10.39 mmol), tributyl(1-ethoxyvinyl)stannane (3.86 ml, 11.43 mmol; Aldrich), and Pd(PPh₃)₄ (0.360 g, 0.312 mmol) in toluene (74 ml) and THF (29 ml) was heated to reflux for 1.5 h. The reaction mixture was cooled to RT before conc. HCl (1.083 ml, 12.99 mmol) was added to convert the silyl enol ether to the methyl ketone. After stirring for 5 min, Et₃N (3.62 ml, 26.0 mmol) was added to quench the HCl. The crude material was concentrated, taken up in DCM, adsorbed onto silica, and purified via automated flash chromatography (silica gel) with 100% hexanes to 60% DCM in hexanes to give 1-(3-fluoroquinoxalin-5-yl)ethanone (210 g, 87% yield) as a pale yellow solid. MS (ESI, pos. ion) m/z: 191.0 (M+1).

Preparation of 2-bromo-1-(3-fluoroquinoxalin-5-yl)ethanone

A solution of 1-(3-fluoroquinoxalin-5-yl)ethanone (1.71 g, 8.99 mmol), triethylamine (3.76 ml, 27.0 mmol), and TBSOTf (4.13 ml, 17.98 mmol) in DCM (90 ml) was stirred at 0° C. for 30 min. The reaction mixture was diluted with DCM (200 ml), added to a separatory funnel, and washed with saturated aq. NaHCO₃ (2×100 ml) before the organic layer was separated, dried over Na₂SO₄, and concentrated to give the intermediate silyl enol ether. MS (ESI, pos. ion) m/z: 305.1 (M+1). A solution of the resulting oil, 1-bromopyrrolidine-2,5-dione (1.600 g, 8.99 mmol), and water (2.59 ml, 144 mmol) in THF (90 ml) was stirred at 0° C. for 30 min. The mixture was diluted with DCM (200 ml), added to a separatory funnel, and washed with saturated aq. NaHCO₃ (2×100 ml) before the organic layer was separated, dried over Na₂SO₄, and concentrated. The crude was adsorbed onto silica and was purified via automated flash chromatography (silica gel) with 100% hexanes to 20% EtOAc in hexanes to give 2-bromo-1-(3-fluoroquinoxalin-5-yl)ethanone (210h, 62% yield) as a light-yellow solid. MS (ESI, pos. ion) m/z: 269.0/271.0 (M+1).

Preparation of 2-(3-fluoroquinoxalin-5-yl)-6,7-dihydro-1H-pyrrolo[3,2-c]pyridin-4(5H)-one A solution of piperidine-2,4-dione (0.767 g, 6.78 mmol) and sodium ethanolate in EtOH (2.080 ml, 5.65 mmol) in EtOH (56.5 ml) was stirred for 40 min at RT before it was added to 2-bromo-1-(3-fluoroquinoxalin-5-yl)ethanone (1.52 g, 5.65 mmol) in EtOH (20 ml); this was stirred at RT for 3.5 h when a yellow solution was observed. MS (ESI, pos. ion) m/z: 302.0 (M+1). NH₄OAc (2.177 g, 28.2 mmol) was added, and the resulting mixture was stirred overnight at RT to give a yellow heterogeneous mixture. The mixture was diluted with (3:2) CHCl₃/IPA (200 ml), added to a separatory funnel, and washed with saturated aq. NaHCO₃ (2×100 ml) before the organic layer was separated, dried over Na₂SO₄, and concentrated. The crude material was adsorbed onto silica and was purified via automated flash chromatography (silica gel) with 100% DCM to 3% MeOH in DCM to give 2-(3-fluoroquinoxalin-5-yl)-6,7-dihydro-1H-pyrrolo[3,2-c]pyridin-4(5H)-one (210i, 36% yield) as a yellow solid. MS (ESI, pos. ion) m/z: 283.0 (M+1).

Preparation of 2-(3-(tert-butylamino)quinoxalin-5-yl)-6,7-dihydro-1H-pyrrolo[3,2-c]pyridin-4(5H)-one A solution of 2-(3-fluoroquinoxalin-5-yl)-6,7-dihydro-1H-pyrrolo[3,2-c]pyridin-4(5H)-one (210i, 75 mg, 0.266 mmol) and 2-methylpropan-2-amine (56.1 μl, 0.531 mmol; Aldrich) in DMSO (2.6 ml) was stirred at 100° C. for 1 h. The mixture was diluted with DCM (150 ml), added to a separatory funnel, and washed with saturated aq. NaHCO₃ (2×100 ml) before the organic layer was separated, dried over Na₂SO₄, and concentrated. The impure material was dissolved in DMSO (~20 mg/ml) and injected (4×1.0 ml) onto a Shimadzu preparatory LC (rpHPLC: Phenomenex Gemini C₁₈, 10 μm, 150×30 mm; 10-100% MeCN/water with 0.1% TFA) before the pure fractions were combined, basicified with NaHCO₃ (saturated, aq.), extracted with DCM, separated, dried over Na₂SO₄, and concentrated via rotary evaporation to give 2-(3-(tert-butylamino)quinoxalin-5-yl)-6,7-dihydro-1H-pyrrolo[3,2-c]pyridin-4(5H)-one (210, 25% yield) as a yellow solid. $^1$H NMR (400 MHz, DMSO-d₆) δ ppm 1.54 (s, 9H) 2.87 (t, J=6.85 Hz, 2H) 3.45 (td, J=6.85, 2.35 Hz, 2H) 6.95 (br. s., 1H) 7.07 (d, J=2.15 Hz, 1H) 7.34 (t, J=7.82 Hz, 1H) 7.58 (s, 1H) 7.61 (dd, J=7.92, 1.27 Hz, 1H) 7.90 (dd, J=7.53, 1.27 Hz, 1H) 8.38 (s, 1H) 12.13 (br. s., 1H). MS (ESI, pos. ion) m/z: 336.2 (M+1).

Example 211

2-(3-((1-methylcyclopropyl)amino)quinoxalin-5-yl)-6,7-dihydro-1H-pyrrolo[3,2-c]pyridin-4(5H)-one

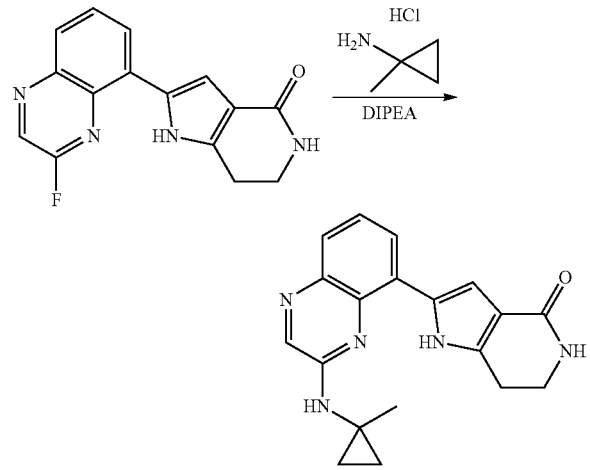

325

Prepared similarly to that described in Example 210 using 2-(3-fluoroquinoxalin-5-yl)-6,7-dihydro-1H-pyrrolo[3,2-c]pyridin-4(5H)-one (Example 210i; 72 mg, 0.255 mmol), 1-methylcyclopropanamine hydrochloride (54.9 mg, 0.510 mmol, ChemBridge, San Diego, Calif.), and DIPEA (223 μl, 1.275 mmol), heating at 100° C. for 1 h. Purification by silica gel (100% DCM to 4% MeOH/DCM) provided 2434(1-methylcyclopropyl)amino)-quinoxalin-5-yl)-6,7-dihydro-1H-pyrrolo[3,2-c]pyridin-4(5H)-one (21% yield). $^1$H NMR (400 MHz, DMSO-d$_6$) δ ppm 0.89 (s, 4H) 1.54 (s, 3H) 2.93 (t, J=6.85 Hz, 2H) 3.46 (td, J=6.85, 2.35 Hz, 2H) 6.99 (br. s., 1H) 7.15 (d, J=1.56 Hz, 1H) 7.37 (t, J=7.82 Hz, 1H) 7.63 (dd, J=8.02, 0.98 Hz, 1H) 8.05 (dd, J=7.63, 1.17 Hz, 1H) 8.33 (s, 2H) 12.89 (br. s., 1H). MS (ESI, pos. ion) m/z: 334.1 (M+1).

Example 212

2-(3-(2,2-dimethylpiperidin-1-yl)quinoxalin-5-yl)-6,7-dihydro-1H-pyrrolo[3,2-c]pyridin-4(5H)-one

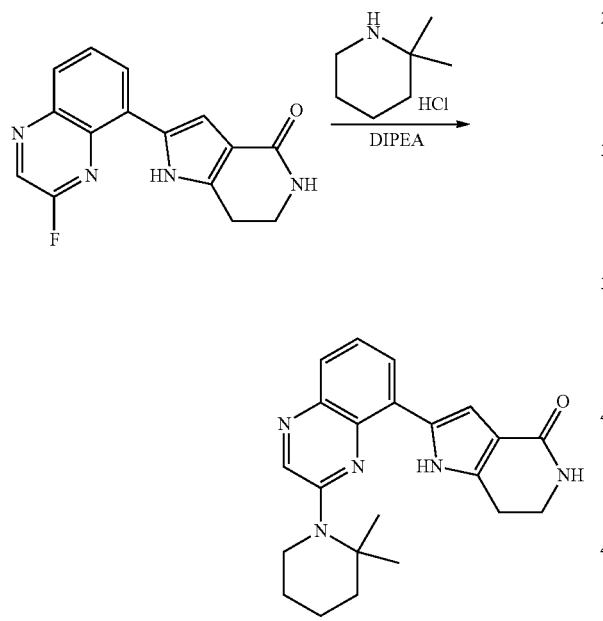

Prepared similarly to that described in Example 210 using 2-(3-fluoroquinoxalin-5-yl)-6,7-dihydro-1H-pyrrolo[3,2-c]pyridin-4(5H)-one (Example 210i; 110 mg, 0.390 mmol), 2,2-dimethylpiperidine hydrochloride (117 mg, 0.779 mmol, Anichem, North Brunswick, N.J.), and DIPEA (339 μl, 1.948 mmol), heating at 120° C. for 5 h. Purification by rpHPLC (Phenomenex Gemini C$_{18}$, 10 μm, 150×30 mm; 10-100% ACN/water with 0.1% TFA) provided 2-(3-(2,2-dimethylpiperidin-1-yl)quinoxalin-5-yl)-6,7-dihydro-1H-pyrrolo[3,2-c]pyridin-4(5H)-one (14% yield). $^1$H NMR (400 MHz, DMSO-d$_6$) δ ppm 1.48 (s, 6H) 1.61-1.82 (m, 6H) 2.87 (t, J=6.85 Hz, 2H) 3.45 (td, J=6.80, 2.45 Hz, 2H) 3.61-3.66 (m, 2H) 6.96 (br. s., 1H) 7.09 (d, J=2.35 Hz, 1H) 7.52 (t, J=7.82 Hz, 1H) 7.73 (dd, J=8.12, 1.27 Hz, 1H) 7.93 (dd, J=7.43, 1.37 Hz, 1H) 8.78 (s, 1H) 11.76 (br. s., 1H). MS (ESI, pos. ion) m/z: 376.3 (M+1).

Example 213

2-(3-(3,3-dimethylmorpholino)quinoxalin-5-yl)-6,7-dihydro-1H-pyrrolo[3,2-c]pyridin-4(5H)-one

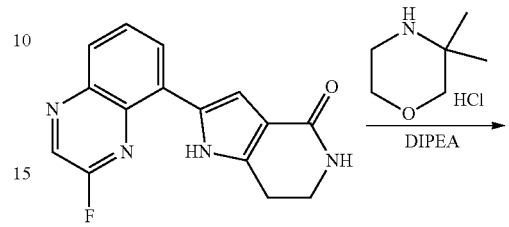

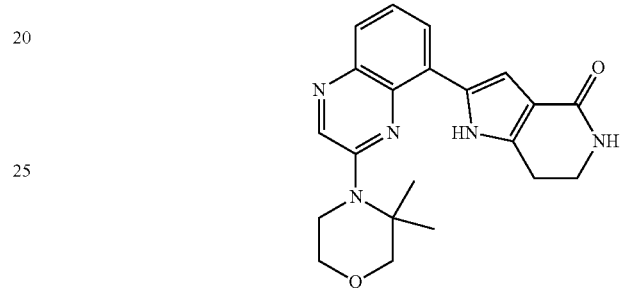

Prepared similarly to that described in Example 210 using 2-(3-fluoroquinoxalin-5-yl)-6,7-dihydro-1H-pyrrolo[3,2-c]pyridin-4(5H)-one (Example 210i; 65 mg, 0.230 mmol), 3,3-dimethylmorpholine hydrochloride (69.8 mg, 0.461 mmol, Tyger Scientific, Ewing, N.J.), and DIPEA (201 μl, 1.151 mmol), heating at 100° C. for 3 h. Purification by silica gel (100% DCM to 4% MeOH/DCM) provided 2-(3-(3,3-dimethylmorpholino)quinoxalin-5-yl)-6,7-dihydro-1H-pyrrolo[3,2-c]pyridin-4(5H)-one (12% yield). $^1$H NMR (400 MHz, DMSO-d$_6$) δ ppm 1.50 (s, 6H) 2.92 (t, J=6.85 Hz, 2H) 3.46-3.50 (m, 2H) 3.51 (s, 2H) 3.74-3.79 (m, 2H) 3.90-3.94 (m, 2H) 7.00 (br. s., 1H) 7.12 (d, J=2.15 Hz, 1H) 7.59 (t, J=7.82 Hz, 1H) 7.81 (dd, J=8.12, 1.27 Hz, 1H) 7.96 (dd, J=7.53, 1.27 Hz, 1H) 8.91 (s, 1H) 11.69 (br. s., 1H). MS (ESI, pos. ion) m/z: 378.0 (M+1).

Example 214

2-(3-(3,3-dimethylpiperazin-1-yl)quinoxalin-5-yl)-6,7-dihydro-1H-pyrrolo[3,2-c]pyridin-4(5H)-one

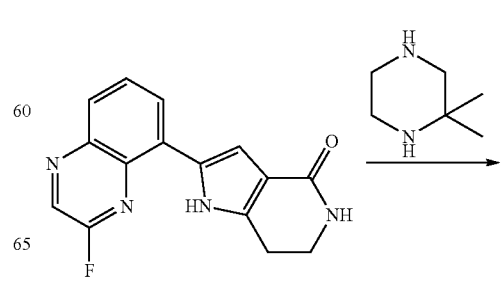

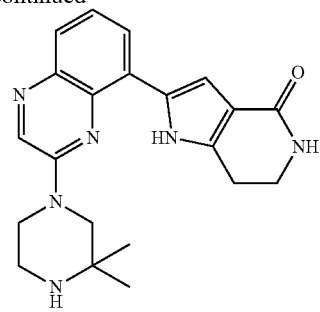

Prepared similarly to that described in Example 210 using 2-(3-fluoroquinoxalin-5-yl)-6,7-dihydro-1H-pyrrolo[3,2-c]pyridin-4(5H)-one (Example 210i; 57 mg, 0.202 mmol) and 2,2-dimethylpiperazine (46.1 mg, 0.404 mmol, Chem-Impex International, Wood Dale, Ill.), heating at 60° C. for 1 h. Purification by filtration provided 2-(3-(3,3-dimethylpiperazin-1-yl)quinoxalin-5-yl)-6,7-dihydro-1H-pyrrolo[3,2-c]pyridin-4(5H)-one (67% yield). $^1$H NMR (400 MHz, DMSO-$d_6$) δ ppm 1.13 (s, 6H) 2.87 (t, J=6.85 Hz, 2H) 2.92-2.99 (m, 2H) 3.44 (td, J=6.85, 2.15 Hz, 2H) 3.61 (s, 2H) 3.74 (t, J=4.69 Hz, 2H) 6.94 (br. s., 1H) 7.14 (d, J=2.15 Hz, 1H) 7.39 (t, J=7.82 Hz, 1H) 7.66 (d, J=6.85 Hz, 1H) 7.89 (d, J=6.46 Hz, 1H) 8.87 (s, 1H) 11.77 (br. s., 1H). MS (ESI, pos. ion) m/z: 377.1 (M+1).

Example 215

2-(3-(tert-butyl(methyl)amino)quinoxalin-5-yl)-6,7-dihydro-1H-pyrrolo[3,2-c]pyridin-4(5H)-one

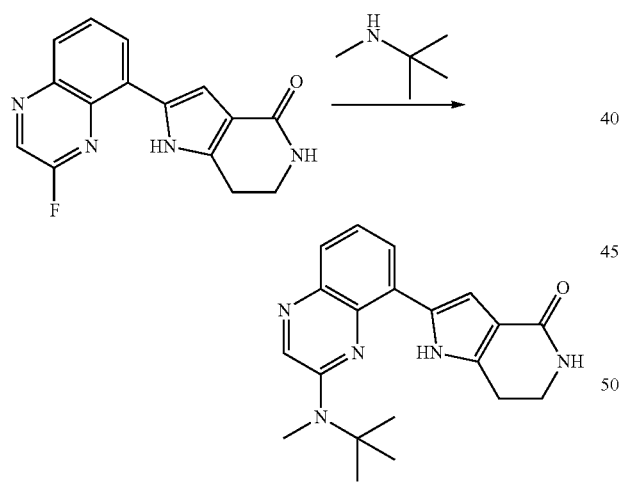

Prepared similarly to that described in Example 210 using 2-(3-fluoroquinoxalin-5-yl)-6,7-dihydro-1H-pyrrolo[3,2-c]pyridin-4(5H)-one (Example 210i; 73 mg, 0.259 mmol) and N,2-dimethylpropan-2-amine (93 µl, 0.776 mmol, Fluka) and heating at 120° C. for 7 h. Purification by silica gel (100% DCM to 4% MeOH/DCM) provided 2-(3-(tert-butyl(methyl)amino)quinoxalin-5-yl)-6,7-dihydro-1H-pyrrolo[3,2-c]pyridin-4(5H)-one (72% yield). $^1$H NMR (400 MHz, DMSO-$d_6$) δ ppm 1.56 (s, 9H) 2.87 (t, J=6.94 Hz, 2H) 3.26 (s, 3H) 3.44 (td, J=6.80, 2.45 Hz, 2H) 6.95 (br. s., 1H) 7.07 (d, J=2.35 Hz, 1 H) 7.44 (t, J=7.82 Hz, 1H) 7.70 (dd, J=8.02, 1.17 Hz, 1H) 7.90 (dd, J=7.43, 1.37 Hz, 1H) 8.75 (s, 1H) 11.78 (br. s., 1H). MS (ESI, pos. ion) m/z: 350.1 (M+1).

Example 216

2-(3-(diethylamino)quinoxalin-5-yl)-6,7-dihydro-1H-pyrrolo[3,2-c]pyridin-4(5H)-one

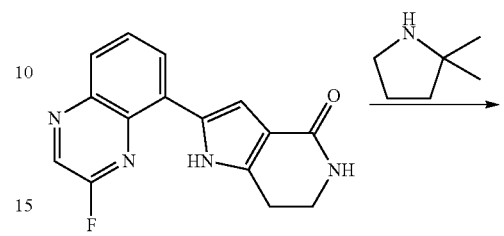

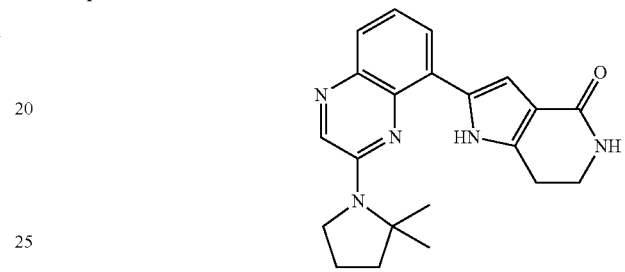

Prepared similarly to that described in Example 210 using 2-(3-fluoroquinoxalin-5-yl)-6,7-dihydro-1H-pyrrolo[3,2-c]pyridin-4(5H)-one (Example 210i; 82 mg, 0.290 mmol) and 2,2-dimethylpyrrolidine (57.6 mg, 0.581 mmol; Chem-Bridge, San Diego, Calif.) and heating at 100° C. for 16 h. Purification by rpHPLC (Phenomenex Gemini C18, 10 µm, 150×30 mm; 10-100% ACN/water with 0.1% TFA) provided 2-(3-(diethylamino)quinoxalin-5-yl)-6,7-dihydro-1H-pyrrolo[3,2-c]pyridin-4(5H)-one (50% yield). $^1$H NMR (400 MHz, DMSO-$d_6$) δ ppm 1.61 (s, 6H) 1.96-2.06 (m, 4H) 2.87 (t, J=6.94 Hz, 2H) 3.43 (td, J=6.85, 2.35 Hz, 2H) 3.78 (t, J=6.16 Hz, 2H) 6.95 (br. s., 1H) 7.07 (d, J=2.15 Hz, 1H) 7.36 (t, J=7.73 Hz, 1H) 7.66 (dd, J=8.02, 1.17 Hz, 1H) 7.89-7.94 (m, 1H) 8.62 (s, 1H) 11.99 (br. s., 1H). MS (ESI, pos. ion) m/z: 362.1 (M+1).

Example 217

2-(3-(2,2-dimethylpiperazin-1-yl)quinoxalin-5-yl)-6,7-dihydro-1H-pyrrolo[3,2-c]pyridin-4(5H)-one

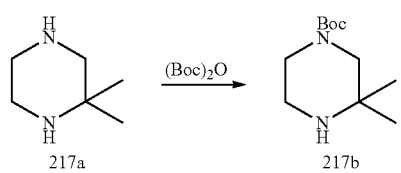

329

-continued

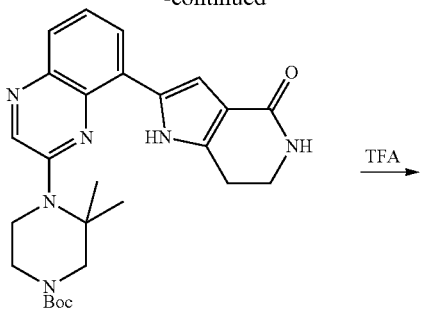

217c

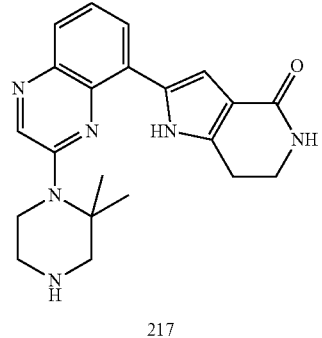

217

Preparation of 217b: tert-butyl 3,3-dimethylpiperazine-1-carboxylate

Di-tert-butyl dicarbonate (719 mg, 3.29 mmol) was added to a solution of 2,2-dimethylpiperazine (376 mg, 3.29 mmol, Chem-Impex International, Wood Dale, Ill.) in DCM (20 mL) and the resulting mixture was stirred at 0° C. for 5 h. The mixture was diluted with DCM (100 ml), added to a separatory funnel, and washed with saturated aq. brine (2×75 ml) before the organic layer was separated, dried over $Na_2SO_4$, and concentrated to give tert-butyl 3,3-dimethylpiperazine-1-carboxylate (86% yield) as a clear oil. MS (ESI, pos. ion) m/z: 215.2 (M+1).

Preparation of 217c: tert-butyl 3,3-dimethyl-4-(8-(4-oxo-4,5,6,7-tetrahydro-1H-pyrrolo[3,2-c]pyridin-2-yl)quinoxalin-2-yl)piperazine-1-carboxylate Prepared similarly to that described in Example 210 using 2-(3-fluoroquinoxalin-5-yl)-6,7-dihydro-1H-pyrrolo[3,2-c]pyridin-4(5H)-one (Example 210i; 100 mg, 0.354 mmol) and tert-butyl 3,3-dimethylpiperazine-1-carboxylate (152 mg, 0.709 mmol), heating at 120° C. for 1 d. Purification by rpHPLC (Phenomenex Gemini $C_{18}$, 10 μm, 150×30 mm; 10-100% ACN/water with 0.1% TFA) provided tert-butyl 3,3-dimethyl-4-(8-(4-oxo-4,5,6,7-tetrahydro-1H-pyrrolo[3,2-c]pyridin-2-yl)quinoxalin-2-yl)piperazine-1-carboxylate (16% yield). MS (ESI, pos. ion) m/z: 477.2 (M+1).

Preparation of 217: 2-(3-(2,2-dimethylpiperazin-1-yl)quinoxalin-5-yl)-6,7-dihydro-1H-pyrrolo[3,2-c]pyridin-4(5H)-one A solution of tert-butyl 3,3-dimethyl-4-(8-(4-oxo-4,5,6,7-tetrahydro-1H-pyrrolo[3,2-c]pyridin-2-yl)quinoxalin-2-yl)piperazine-1-carboxylate (27 mg, 0.057 mmol) and TFA (4.36 μl, 0.057 mmol) in DCM (567 μl) was stirred at RT for

330

20 min. Purification by silica gel (100% DCM to 8% [2 M $NH_3$ in MeOH]/DCM) provided 2-(3-(2,2-dimethylpiperazin-1-yl)quinoxalin-5-yl)-6,7-dihydro-1H-pyrrolo[3,2-c]pyridin-4(5H)-one (19% yield) as a yellow solid. $^1$H NMR (400 MHz, DMSO-$d_6$) δ ppm 1.45 (s, 6H) 2.32-2.35 (m, 1H) 2.66-2.71 (m, 2H) 2.86 (t, J=6.94 Hz, 2H) 2.95-2.99 (m, 1H) 3.44 (td, J=6.75, 2.35 Hz, 2H) 3.60 (t, J=4.9 Hz, 2H) 6.96 (s, 1H) 7.09 (d, J=2.15 Hz, 1H) 7.52 (t, J=7.63 Hz, 1H) 7.73 (d, J=7.04 Hz, 1H) 7.92 (d, J=7.43 Hz, 1H) 8.81 (s, 1H) 11.71 (s, 1H). MS (ESI, pos. ion) m/z: 377.1 (M+1).

Example 218

2-(3-amino-2-methylquinoxalin-5-yl)-6,7-dihydro-1H-pyrrolo[3,2-c]pyridin-4(5H)-one

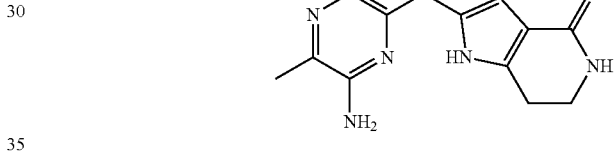

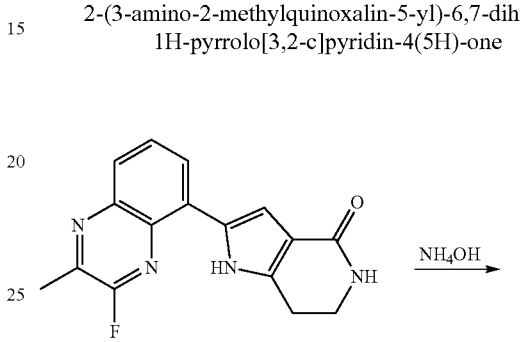

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 51 mg, 0.172 mmol) and $NH_4OH$ (670 μl, 17.21 mmol) in propan-2-ol (1.7 ml) and heating in a microwave reactor (Biotage Initiator) at 120° C. for 10 min. Purification by silica gel (100% DCM to 5% MeOH/DCM) provided 2-(3-amino-2-methylquinoxalin-5-yl)-6,7-dihydro-1H-pyrrolo[3,2-c]pyridin-4(5H)-one (61% yield). $^1$H NMR (400 MHz, DMSO-$d_6$) δ ppm 2.52 (s, 3H) 2.94 (t, J=6.85 Hz, 2H) 3.44 (td, J=6.80, 2.25 Hz, 2H) 6.94 (br. s., 1H) 6.98 (d, J=2.15 Hz, 1H) 7.15 (br. s., 2H) 7.29 (t, J=7.82 Hz, 1H) 7.54 (dd, J=8.02, 0.98 Hz, 1H) 7.91 (dd, J=7.53, 1.08 Hz, 1H) 12.45 (br. s., 1H). MS (ESI, pos. ion) m/z: 294.0 (M+1).

Example 219

2-(2-methyl-3-(methylamino)quinoxalin-5-yl)-6,7-dihydro-1H-pyrrolo[3,2-c]pyridin-4(5H)-one

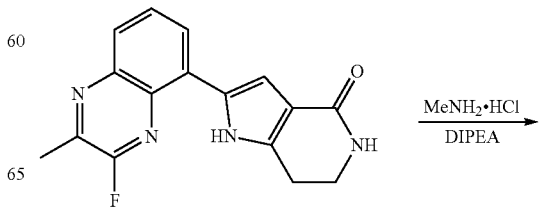

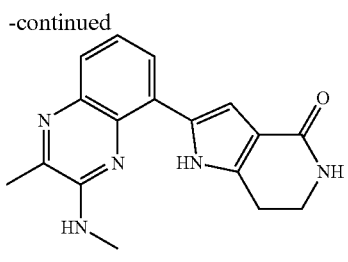

Prepared similarly to that described in Example 131 using 2-(3-fluoro-2-methylquinoxalin-5-yl)-6,7-dihydro-1H-pyrrolo[3,2-c]pyridin-4(5H)-one (Example 126; 67 mg, 0.226 mmol), methanamine hydrochloride (30.5 mg, 0.452 mmol; Sigma-Aldrich), and DIPEA (197 µl, 1.131 mmol), heating at 100° C. for 3 h. Purification by silica gel (100% DCM to 5% 2 M NH₃ in MeOH/DCM) provided 2-(2-methyl-3-(methylamino)quinoxalin-5-yl)-6,7-dihydro-1H-pyrrolo[3,2-c]pyridin-4(5H)-one (16% yield). ¹H NMR (400 MHz, DMSO-d₆) δ ppm 2.53 (s, 3H) 2.88 (t, J=6.85 Hz, 2H) 3.05 (d, J=4.50 Hz, 3H) 3.43 (td, J=6.80, 2.25 Hz, 2H) 6.94-6.98 (m, 1H) 7.13 (d, J=1.96 Hz, 1H) 7.32 (t, J=7.73 Hz, 1H) 7.37-7.43 (m, 1H) 7.58 (d, J=6.85 Hz, 1H) 7.90 (d, J=6.46 Hz, 1H) 12.24 (br. s., 1H). MS (ESI, pos. ion) m/z: 308.1 (M+1).

Example 220

2-(3-(tert-butyl(ethyl)amino)quinoxalin-5-yl)-6,7-dihydro-1H-pyrrolo[3,2-c]pyridin-4(5H)-one

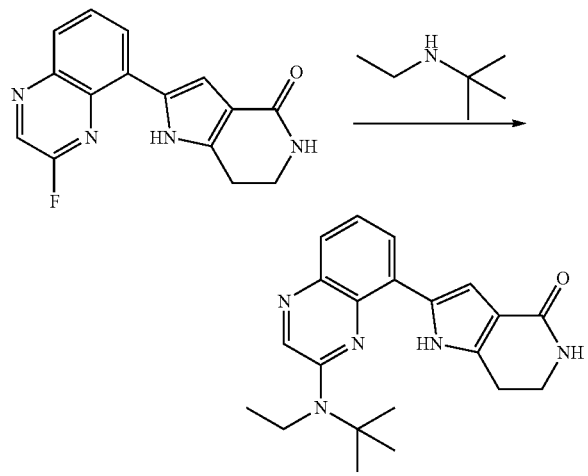

Prepared similarly to that described in Example 210 using 2-(3-fluoroquinoxalin-5-yl)-6,7-dihydro-1H-pyrrolo[3,2-c]pyridin-4(5H)-one (Example 210i; 79 mg, 0.280 mmol) and N-ethyl-2-methylpropan-2-amine (142 mg, 1.399 mmol, TCI International, Portland, Oreg.), heating at 120° C. for 16 h. Purification by rpHPLC (Phenomenex Gemini C18, 10 µm, 150×30 mm; 10100% ACN/water with 0.1% TFA) provided 2-(3-(tert-butyl(ethyl)amino)quinoxalin-5-yl)-6,7-dihydro-1H-pyrrolo[3,2-c]pyridin-4(5H)-one (16% yield). ¹H NMR (400 MHz, DMSO-d₆) δ ppm 1.28 (t, J=6.94 Hz, 3H) 1.60 (s, 9H) 2.85 (t, J=6.94 Hz, 2H) 3.43 (td, J=6.80, 2.25 Hz, 2H) 3.80 (q, J=6.91 Hz, 2H) 6.94 (br. s., 1H) 7.03 (d, J=2.15 Hz, 1H) 7.41 (t, J=7.73 Hz, 1H) 7.69 (d, J=8.22 Hz, 1H) 7.87 (d, J=7.43 Hz, 1H) 8.71 (s, 1H) 11.69 (br. s., 1H). MS (ESI, pos. ion) m/z: 364.1 (M+1).

Example 221

2-(3-(tert-butylthio)-2-methylquinoxalin-5-yl)-6,7-dihydro-1H-pyrrolo[3,2-c]pyridin-4(5H)-one Prepared similarly to that described in Example 127 using 2-(3-fluoro-2-methylquinoxalin-5-yl)-6,7-dihydro-1H-pyrrolo[3,2-c]pyridin-4(5H)-one (Example 210i; 74 mg, 0.250 mmol) and 2-methylpropane-2-thiol (67.6 mg, 0.749 mmol; Acros, Geel, Belgium), heating at 100° C. for 7 h. Purification by rpHPLC (Phenomenex Gemini C₁₈, 10 µm, 150×30 mm; 10-100% ACN/water with 0.1% TFA) provided 2-(3-(tert-butylthio)-2-methylquinoxalin-5-yl)-6,7-dihydro-1H-pyrrolo[3,2-c]pyridin-4(5H)-one (26% yield). ¹H NMR (400 MHz, DMSO-d₆) δ ppm 1.62 (s, 9H) 2.59 (s, 3H) 2.83 (t, J=6.85 Hz, 2H) 3.43 (td, J=6.80, 2.25 Hz, 2H) 6.93 (d, J=2.15 Hz, 2H) 7.63 (t, J=7.63 Hz, 1H) 7.80-7.88 (m, 2H) 11.50 (br. s., 1H). MS (ESI, pos. ion) m/z: 367.1 (M+1).

Example 222

2-(3-(tert-butyl(methyl)amino)-2-methylquinoxalin-5-yl)-6,7-dihydro-1H-pyrrolo[3,2-c]pyridin-4(5H)-one

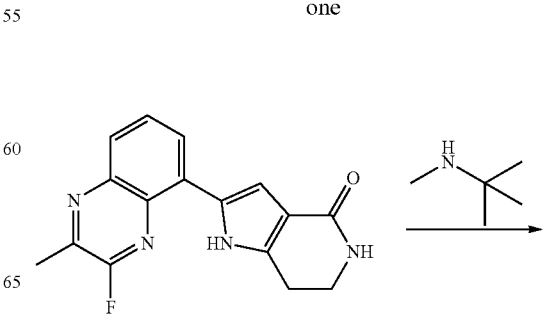

333

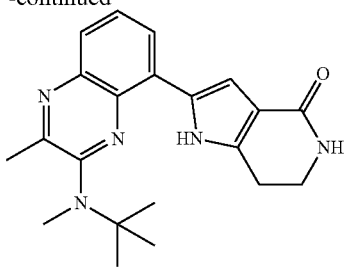

Prepared similarly to that described in Example 127 using 2-(3-fluoro-2-methylquinoxalin-5-yl)-6,7-dihydro-1H-pyrrolo[3,2-c]pyridin-4(5H)-one (Example 126; 75 mg, 0.253 mmol) and N-2-dimethylpropan-2-amine (110 mg, 1.266 mmol; Fluka) and heating at 120° C. for 16 h. Purification by rpHPLC (Phenomenex Gemini $C_{18}$, 10 µm, 150×30 mm; 10-100% ACN/water with 0.1% TFA) provided 2-(3-(tert-butyl(methyl)amino)-2-methylquinoxalin-5-yl)-6,7-dihydro-1H-pyrrolo[3,2-c]pyridin-4(5H)-one (3% yield). $^1$H NMR (400 MHz, CDCl$_3$) δ ppm 1.46 (s, 9H) 2.75 (s, 3H) 2.89 (s, 3H) 2.98 (t, J=6.85 Hz, 2H) 3.66 (td, J=6.85, 2.54 Hz, 2H) 5.33 (br. s., 1H) 7.18 (d, J=2.15 Hz, 1H) 7.59 (t, J=7.82 Hz, 1H) 7.76 (d, J=7.43 Hz, 1H) 8.00 (d, J=7.43 Hz, 1H) 12.23 (br. s., 1H). MS (ESI, pos. ion) m/z: 364.1 (M+1).

Example 223

2-(3-(2,2-dimethylazetidin-1-yl)quinoxalin-5-yl)-6,7-dihydro-1H-pyrrolo[3,2-c]pyridin-4(5H)-one

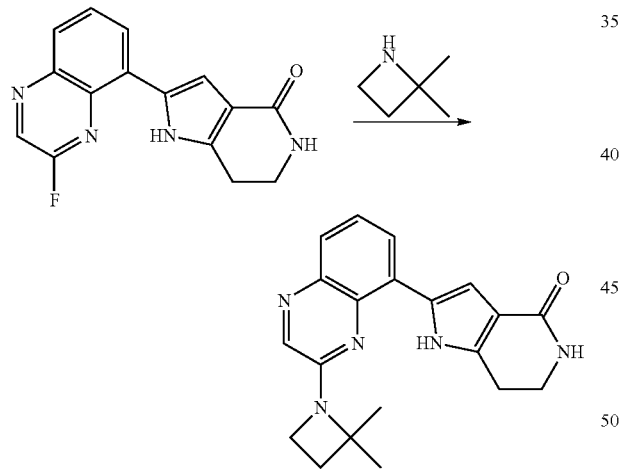

Prepared similarly to that described in Example 210 using 2-(3-fluoroquinoxalin-5-yl)-6,7-dihydro-1H-pyrrolo[3,2-c]pyridin-4(5H)-one (Example 210i; 93 mg, 0.329 mmol) and 2,2-dimethylazetidine (84 mg, 0.988 mmol; FCH Group, Chernigov, Ukraine), heating at 100° C. for 4 h. Purification by silica gel (100% DCM to 4% MeOH/DCM) provided 2-(3-(2,2-dimethylazetidin-1-yl)quinoxalin-5-yl)-6,7-dihydro-1H-pyrrolo[3,2-c]pyridin-4(5H)-one (59% yield). $^1$H NMR (400 MHz, DMSO-d$_6$) δ ppm 1.66 (s, 6H) 2.27 (t, J=7.53 Hz, 2H) 2.87 (t, J=6.85 Hz, 2H) 3.42 (td, J=6.75, 2.15 Hz, 2H) 4.14 (br. s., 2H) 6.95 (br. s., 1H) 7.12 (d, J=2.15 Hz, 1H) 7.36 (t, J=7.73 Hz, 1H) 7.64 (d, J=8.02 Hz, 1H) 7.95 (d, J=7.43 Hz, 1H) 8.35 (br. s., 1H) 12.09 (br. s., 1H). MS (ESI, pos. ion) m/z: 364.1 (M+1).

334

Example 224

2-(3-(tert-butylamino)-2-(trifluoromethyl)quinoxalin-5-yl)-6,7-dihydro-1H-pyrrolo[3,2-c]pyridin-4(5H)-one

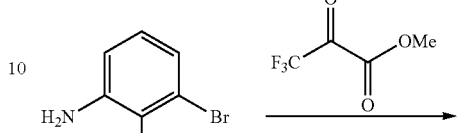

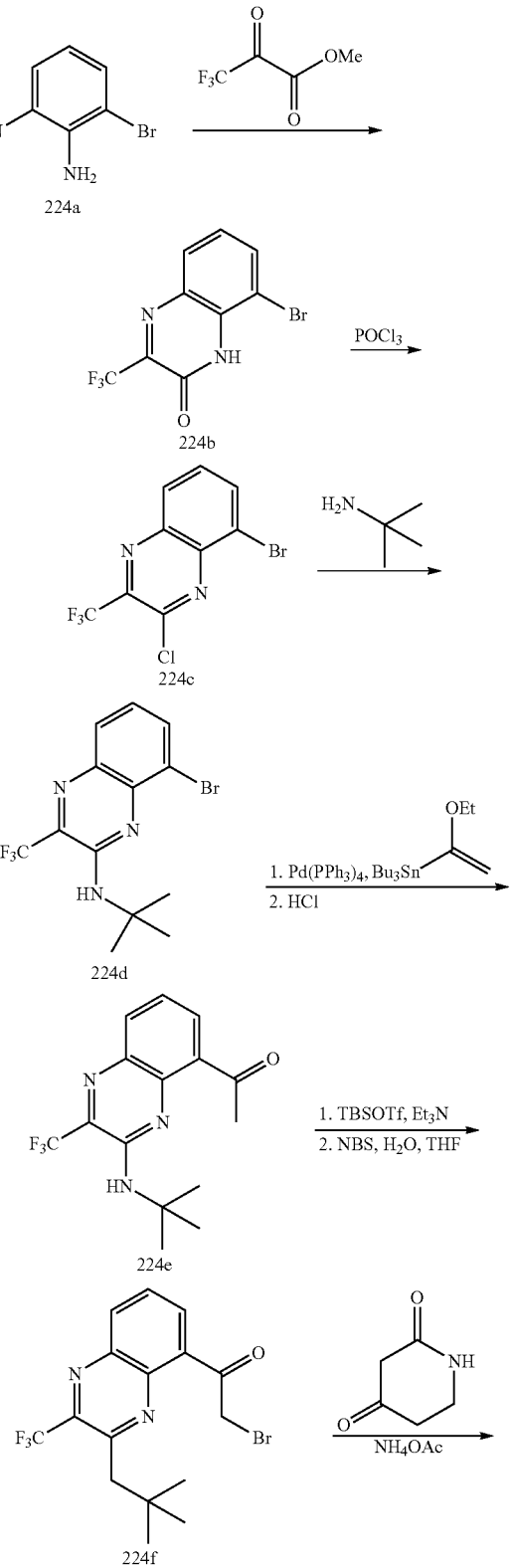

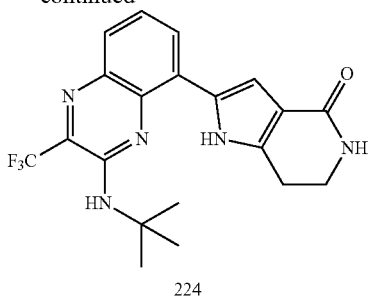

224

Preparation of 224b: 8-bromo-3-(trifluoromethyl)quinoxalin-2(1H)-one

A solution of 3-bromobenzene-1,2-diamine (1.00 g, 5.35 mmol, CombiBlocks, Inc., San Diego, Calif.) and methyl 3,3,3-trifluoro-2-oxopropanoate (0.655 mL, 6.42 mmol; Alfa Aesar, Ward Hill, Mass.) in EtOH (15 mL) was stirred at reflux under argon for 17 h. The mixture was concentrated in vacuo. Purification by silica gel (0-70% EtOAc/Hexanes) provided 8-bromo-3-(trifluoromethyl)quinoxalin-2(1H)-one (224b, 29% yield) as a tan solid. $^1$H NMR (400 MHz, DMSO-$d_6$) δ ppm 12.43 (1H, br. s.), 8.04 (1H, d, J=7.8 Hz), 7.95 (1H, d, J=8.2 Hz), 7.38 (1H, t, J=7.9 Hz). $^{19}$F NMR (377 MHz, DMSO-$d_6$) δ ppm −68.44 (3F, br. s.). MS (ESI, pos. ion) m/z: 293.0 (M+1).

Preparation of 224c: 5-bromo-3-chloro-2-(trifluoromethyl)quinoxaline

A solution of 8-bromo-3-(trifluoromethyl)quinoxalin-2 (1H)-one (432.0 mg, 1.474 mmol) in POCl$_3$ (5.0 mL) was heated at reflux for 10 h then at 100° C. for 2.5 d, then at 140° C. for 10 h. Excess POCl$_3$ was removed in vacuo, and the residue was taken up in DCM (60 mL) and transferred to an Erlenmeyer flask before saturated aq. NaHCO$_3$ (40 mL) was added cautiously (over 5 min) with rapid stirring. The resulting biphasic mixture was stirred rapidly for 5 min (some gas evolution), and the organic layer was separated. The aq. layer was extracted with DCM (3×20 mL), and all organic layers were combined, dried over Na$_2$SO$_4$, filtered, and concentrated in vacuo to provide 5-bromo-3-chloro-2-(trifluoromethyl)quinoxaline (224c, 52%). MS (ESI, pos. ion) m/z: 310.9 (M+1).

Preparation of 224d: 8-bromo-N-(tert-butyl)-3-(trifluoromethyl)quinoxalin-2-amine A solution of 5-bromo-3-chloro-2-(trifluoromethyl)quinoxaline (239 mg, 0.767 mmol) and 2-methylpropan-2-amine (243 μl, 2.302 mmol; Aldrich) in DMSO (7.6 ml) was stirred at 100° C. for 7 h (more 2-methylpropan-2-amine (243 μl, 2.302 mmol) was added after 3 h). The mixture was then diluted with DCM (150 ml), added to a separatory funnel, and washed with saturated aq. NaHCO$_3$ (2×100 ml) before the organic layer was separated, dried over Na$_2$SO$_4$, and concentrated. Purification by silica gel (100% hexanes to 20% EtOAc in hexanes) provided 8-bromo-N-(tert-butyl)-3-(trifluoromethyl)quinoxalin-2-amine (224d, 77% yield) as a light yellow solid. MS (ESI, pos. ion) m/z: 348.0/350.2 (M+1).

Preparation of 224e: provided 1-(3-(tert-butylamino)-2-(trifluoromethyl)quinoxalin-5-yl)ethanone A mixture of 8-bromo-N-(tert-butyl)-3-(trifluoromethyl) quinoxalin-2-amine (206 mg, 0.592 mmol), tributyl(1-ethoxyvinyl)stannane (300 μl, 0.888 mmol; Aldrich), and Pd(PPh$_3$)$_4$ (0) (68.4 mg, 0.059 mmol) in toluene (5.9 ml) was heated to 100° C. for 8 h; more Pd(PPh$_3$)$_4$ (0) (68.4 mg, 0.059 mmol) and tributyl(1-ethoxyvinyl)stannane (300 μl, 0.888 mmol) were added and the reaction was stirred at 100° C. for another 16 h. Concentrated HCl (61.6 μl, 0.740 mmol) was then added, and the resulting mixture was concentrated onto silica gel. Chromatographic purification (silica gel, 100% hexanes to 10% EtOAc in hexanes) provided 1-(3-(tert-butylamino)-2-(trifluoromethyl)quinoxalin-5-yl)ethanone (224e, >99% yield) as a light yellow solid. MS (ESI, pos. ion) m/z: 312.2 (M+1).

Preparation of 224f: 2-bromo-1-(3-(tert-butylamino)-2-(trifluoromethyl)quinoxalin-5-yl)ethanone A solution of 1-(3-(tert-butylamino)-2-(trifluoromethyl) quinoxalin-5-yl)ethanone (185 mg, 0.594 mmol), TBSOTf (205 μl, 0.891 mmol), and Et$_3$N (248 μl, 1.783 mmol) in DCM (5943 μl) was stirred at 0° C. for 30 min. The mixture was diluted with DCM (100 ml), added to a separatory funnel, and washed with saturated aq. NaHCO$_3$ (2×75 ml). The organic layer was separated, dried over Na$_2$SO$_4$, and concentrated to provide the silyl enol ether. MS (ESI, pos. ion) m/z: 426.2 (M+1). A solution of the resulting oil, 1-bromopyrrolidine-2,5-dione (106 mg, 0.594 mmol), and water (171 μl, 9.51 mmol) in THF (5943 μl) at 0° C. was stirred for 1 h. The mixture was diluted with DCM (100 ml), added to a separatory funnel, and washed with saturated aq. NaHCO$_3$ (2×75 ml). The organic layer was separated, dried over Na$_2$SO$_4$, and concentrated. Purification by silica gel (100% hexanes to 10% EtOAc in hexanes) provided 2-bromo-1-(3-(tert-butylamino)-2-(trifluoromethyl)quinoxalin-5-yl)ethanone (224f, 60% yield) as a yellow solid. MS (ESI, pos. ion) m/z: 390.2 (M+1).

Preparation of 224: 2-(3-(tert-butylamino)-2-(trifluoromethyl)quinoxalin-5-yl)-6,7-dihydro-1H-pyrrolo[3,2-c]pyridin-4(5H)-one A solution of 2-bromo-1-(3-(tert-butylamino)-2-(trifluoromethyl)quinoxalin-5-yl)ethanone (140 mg, 0.359 mmol), piperidine-2,4-dione (60.9 mg, 0.538 mmol), and NH$_4$OAc (138 mg, 1.794 mmol) in EtOH (3.6 ml) was stirred at 50° C. for 16 h. The mixture was diluted with DCM (100 ml), added to a separatory funnel, and washed with saturated aq. NaHCO$_3$ (2×75 ml). The organic layer was separated, dried over Na$_2$SO$_4$, and concentrated. Purification by silica gel (100% DCM to 4% 2 M NH$_3$ in MeOH/DCM) provided 2-(3-(tert-butylamino)-2-(trifluoromethyl)quinoxalin-5-yl)-6,7-dihydro-1H-pyrrolo[3,2-c]pyridin-4(5H)-one (224, 24% yield) as a yellow solid. $^1$H NMR (400 MHz, CDCl$_3$) δ ppm 1.67 (s, 9H) 2.99 (t, J=6.85 Hz, 2H) 3.67 (td, J=6.85, 2.54 Hz, 2H) 5.36 (br. s., 1H) 5.44 (br. s., 1H) 7.14 (d, J=2.15 Hz, 1H) 7.48 (t, J=7.92 Hz, 1H) 7.79 (dd, J=8.22, 1.17 Hz, 1H) 8.08 (dd, J=7.63, 1.17 Hz, 1H) 12.06 (br. s., 1H). $^{19}$F NMR (376 MHz, DMSO-$d_6$) δ ppm −67.46 (3F, s). MS (ESI, pos. ion) m/z: 404.1 (M+1).

Example 225

2-(2-phenoxyquinolin-8-yl)-1H-pyrrolo[3,2-c]pyridin-4(5H)-one

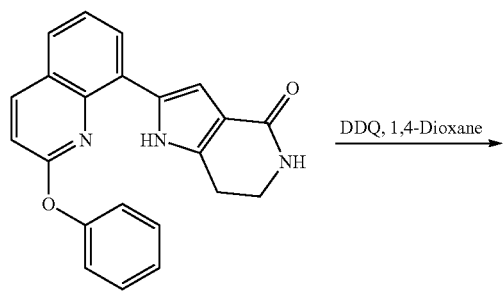

To a solution of 2-(2-phenoxyquinolin-8-yl)-6,7-dihydro-1H-pyrrolo[3,2-c]pyridin-4(5H)-one (Example 37; 0.07 g, 0.197 mmol) in 1,4-dioxane (20 mL) was added DDQ (0.134 g, 0.591 mmol), and the reaction was stirred at RT for 2.5 h. The mixture was diluted with ice water (50 mL) and extracted with EtOAc (50 mL). The organic layer was separated, dried, filtered and concentrated. The residue was purified with preparative HPLC (Phenomenex Gemini $C_{18}$ column (100×50 mm, 10 μm), 90 mL/min, 30-90% ACN in water with 0.1% TFA) to give 2-(2-phenoxyquinolin-8-yl)-1H-pyrrolo[3,2-c]pyridin-4(5H)-one (0.034 g, 49%) as a pale brown solid. MS (ESI, pos. ion) m/z: 354.1 (M+1); $^1$H NMR (400 MHz, DMSO-$d_6$): δ 11.28 (s, 1H), 10.73 (d, 1H, J=5.2 Hz), 8.54 (d, 1H, J=8.9 Hz), 8.31 (d, 1H, J=7.1 Hz), 7.89 (d, 1H, J=7.6 Hz), 7.67 (t, J=7.8 Hz, 2H), 7.54 (t, J=7.6 Hz, 2H), 7.44-7.47 (m, 3H), 7.24 (d, 1H, J=1.3 Hz), 6.90-7.03 (m, 1H), 5.87 (d, 1H, J=7.0 Hz).

Example 226

2-(2-phenylquinolin-8-yl)-6,7-dihydro-1H-pyrrolo[3,2-c]pyridin-4(5H)-one

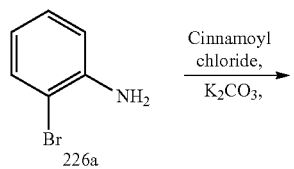

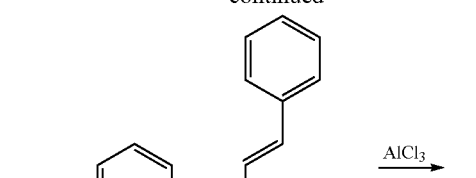

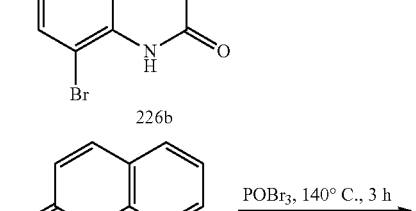

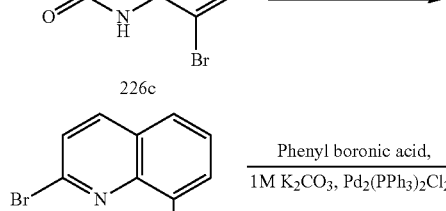

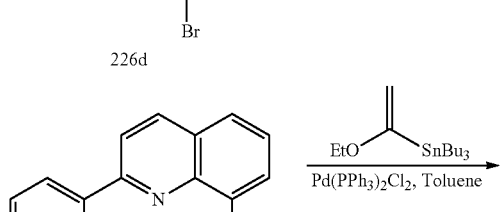

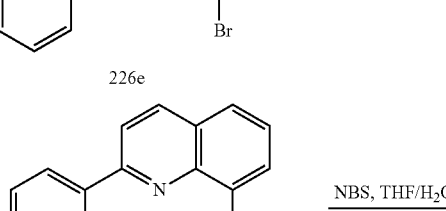

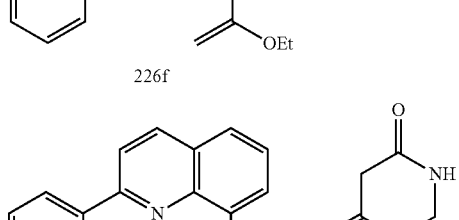

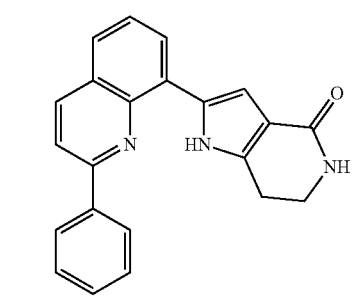

Preparation of 226b: N-(2-bromophenyl)cinnamamide

To a mixture of 2-bromoaniline (0.976 g, 5.81 mmol, Sigma-Aldrich) and $K_2CO_3$ (1.16 g, 8.71 mmol) in water (5.5 mL) and acetone (4.5 mL) was added cinnamoyl chloride (1 g, 5.81 mmol, Sigma-Aldrich) and the reaction was stirred for 2 h at 0° C. The mixture was treated with ice cold water (25 mL) to obtain a brownish precipitate. The precipitate was filtered and dried under vacuum. The crude material was further treated with petroleum ether to give N-(2-bromophenyl)cinnamamide (1.1 g, 64%) as off-white solid. MS (ESI, pos. ion) m/z: 303.2 (M+1).

Preparation of 226c: 8-bromoquinolin-2(1H)-one

Aluminum chloride (2.6 g, 19.92 mmol) was added to a solution of N-(2-bromophenyl)cinnamamide (1.0 g, 3.32 mmol) in chlorobenzene, and the resulting mixture was heated at 125° C. for 2 h. The reaction mixture was then cooled to 50° C. and treated with ice-cold water (25 mL) to provide a brown precipitate. The precipitate was collected by vacuum filtration and dried in vacuo, then triturated with EtOH to provide 8-bromoquinolin-2(1H)-one (0.5 g, 67% yield) as an off-white solid. m/z (ESI, +ve) 226.2 $(M+H)^+$

Preparation of 226d: 2,8-dibromoquinoline

A mixture of phosphorus oxybromide (1.59 g, 5.55 mmol) and 8-bromo-2(1H)-quinolinone (0.250 g, 1.11 mmol) was heated at 125° C. for 2 h before being poured onto ice. The resulting precipitate was filtered and crystallized from MeOH to give 2,8-dibromo-quinoline (0.2 g, 64%) as colorless prisms. MS (ESI, pos. ion) m/z: 287.8 (M+1).

Preparation of 226e: 8-bromo-2-phenylquinoline

To a mixture of 2,8-dibromoquinoline (1.0 g, 3.49 mmol), $Pd(PPh_3)_4$ (0.2 g, 0.174 mmol) in toluene:EtOH:$H_2O$ (10 mL:1 mL:1 mL) under argon atmosphere was added $Na_2CO_3$ (0.44 g, 4.18 mmol) and phenyl boronic acid (0.507 g, 4.18 mmol) and the reaction was heated to reflux for 24 h. The mixture was cooled to RT and diluted with EtOAc (50 mL), washed with water and brine (50 mL). The organic layer was dried, filtered and concentrated. The residue was purified by column chromatography (10:1 hexane:EtOAc) to give 8-bromo-2-phenylquinoline (0.75 g, 76%) as pale brown oil. MS (ESI, pos. ion) m/z: 284.0 (M+1).

Preparation of 8-(1-ethoxyvinyl)-2-phenylquinoline

In a sealed tube, to the suspension of 8-bromo-2-phenylquinoline (0.1 g, 0.352 mmol) in toluene (5 mL) was added $PdCl_2(PPh_3)_2$ (0.012 g, 0.017 mmol) and tributyl (1-ethoxyvinyl)stannane (0.15 g, 0.422 mmol) under $N_2$. The reaction was heated at 80° C. for 12 h, then cooled to RT. The solvent was removed and the crude material was used in the next step without further purification.

Preparation of 2-bromo-1-(2-phenylquinolin-8-yl)ethanone

To a solution of 8-(1-ethoxyvinyl)-2-phenoxyquinoline (0.1 g, 0.307 mmol) in THF (7 mL) was added NBS (0.065 g, 0.368 mmol) and water (3 mL). The mixture was stirred at RT for 1 h, then the solvent was removed in vacuo. The residue was stirred in water for 5-10 min, filtered, and the solid was washed with water and dried under vacuum to give the crude material (0.1 g) as a pale brown solid, which was used in the next step without further purification.

Preparation of 2-(2-phenylquinolin-8-yl)-6,7-dihydro-1H-pyrrolo[3,2-c]pyridin-4(5H)-one To a solution of 2-bromo-1-(2-phenylquinolin-8-yl)ethanone (0.5 g, 1.53 mmol) in EtOH (10 mL) was added $NH_4OAc$ (0.2 g, 1.83 mmol) and piperidine-2,4-dione (0.592 g, 7.65 mmol) under $N_2$, and the reaction was stirred at RT for 2 days. The mixture was diluted with excess of ice water and the resulting suspension was filtered and washed with water to give the crude material. This crude material was triturated with $Et_2O$ (3×30 mL) and further purified by preparative HPLC (Phenomenex Gemini $C_{18}$ column (100×50 mm, 10 μm), 90 mL/min, 40-90% ACN in water with 0.1% TFA) to give 2-(2-phenylquinolin-8-yl)-6,7-dihydro-1H-pyrrolo[3,2-c]pyridin-4(5H)-one (0.015 g, 2%) as pale brown solid. MS (ESI, pos. ion) m/z: 340.2 (M+1); $^1H$ NMR (400 MHz, MeOH-$d_4$): δ 8.39 (d, 1H, J=8.7 Hz), 8.14 (dd, 3H, J=5.3, 3.8 Hz), 8.02 (d, 1H, J=8.7 Hz), 7.72-7.80 (m, 1H), 7.46-7.65 (m, 4H), 7.17 (s, 1H), 3.62 (t, 2H, J=7.1 Hz), 3.00 (t, 2H, J=7.1 Hz).

Example 227

2-(7-fluoro-2-(phenylamino)quinolin-8-yl)-6,7-dihydro-1H-pyrrolo[3,2-c]pyridin-4(5H)-one

Example 230

2-(2-chloro-7-fluoroquinolin-8-yl)-6,7-dihydro-1H-pyrrolo[3,2-c]pyridin-4(5H)-one

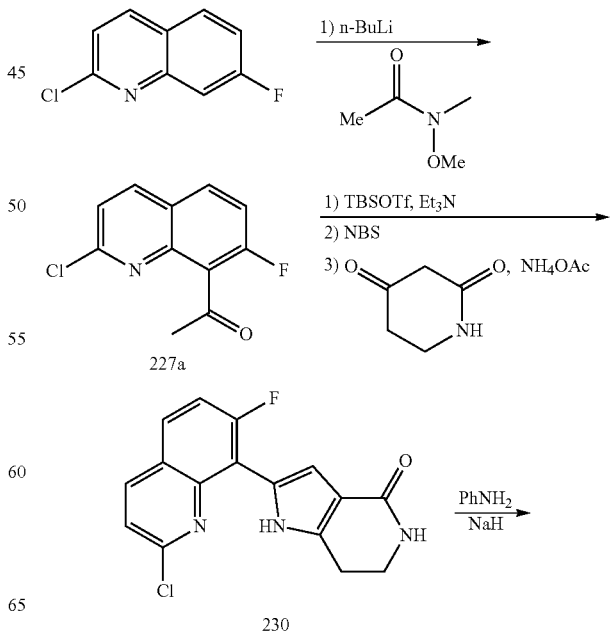

230

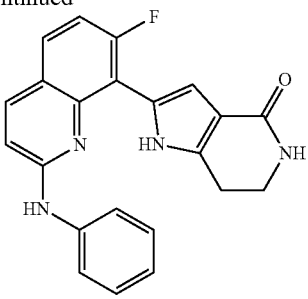

227

Preparation of 1-(2-chloro-7-fluoroquinolin-8-yl)ethanone

To a solution of 2-chloro-7-fluoroquinoline (ECA International Corp, Palatine, Ill.; 300 mg, 1.652 mmol) in THF (5.0 mL) at −78° C. was added nBuLi, 1.6 M in hexanes (1.24 mL, 1.98 mmol) slowly dropwise. The solution was stirred at −78° C. for 30 min. A solution of N-methoxy-N-methylacetamide (0.25 mL, 2.48 mmol) in THF (0.5 mL) was added slowly dropwise via syringe. After 10 min, the reaction was warmed to RT. After 15 min, the reaction was quenched by addition of saturated aq. NH$_4$Cl. The reaction was partitioned between saturated NH$_4$Cl and EtOAc. The organic layer was washed with brine, dried over MgSO$_4$, filtered and concentrated. The crude material was purified by silica gel chromatography, using 0-50% EtOAc/hexane. The pure fractions were combined and concentrated in vacuo to give 1-(2-chloro-7-fluoroquinolin-8-yl)ethanone (56 mg, 0.250 mmol, 15.16% yield): $^1$H NMR (400 MHz, DMSO-d$_6$) δ ppm 8.57 (d, J=8.6 Hz, 1H), 8.25 (dd, J=9.1, 6.2 Hz, 1H), 7.65-7.74 (m, 2H), 2.68 (s, 3H). m/z (ESI, +ve ion) 224.0 (M+H)$^+$.

Preparation of 230: 2-(2-chloro-7-fluoroquinolin-8-yl)-6,7-dihydro-1H-pyrrolo[3,2-c]pyridin-4(5H)-one To a solution of 1-(2-chloro-7-fluoroquinolin-8-yl)ethanone (237 mg, 1.060 mmol) in 3 mL DCM at 0° C. was added Et$_3$N (0.19 mL, 1.38 mmol) followed by TBSOTf (0.27 mL, 1.17 mmol dropwise). The reaction was stirred for 1 h, and was partitioned between saturated NaHCO$_3$ and CH$_2$Cl$_2$. The aq. layer was extracted with CH$_2$Cl$_2$ (3×), and the crude material was concentrated to a yellow oil. The resulting oil was taken up in THF (6 mL), treated with water (0.31 mL, 16.9 mmol) and NBS (198 mg, 1.113 mmol). After 35 min, the mixture was partitioned between water and Et$_2$O. The organic layer was sequentially washed with saturated NaHCO$_3$, water, and saturated and NaCl, and then dried over anhydrous MgSO$_4$, filtered, and concentrated in vacuo to give a yellow, viscous oil. This oil was treated with ammonium acetate (327 mg, 4.24 mmol) and piperidine-2,4-dione (144 mg, 1.272 mmol) and EtOH (6.0 mL) and stirred at RT for 5 min. The resulting yellow slurry was placed in a 50° C. bath for 16 h, cooled, and concentrated in vacuo. The crude residue was purified by silica gel chromatography (0-20% MeOH in DCM), affording 2-(2-chloro-7-fluoroquinolin-8-yl)-6,7-dihydro-1H-pyrrolo[3,2-c]pyridin-4(5H)-one (84.8 mg, 0.269 mmol, 25.3% yield) as an orange solid: $^1$H NMR (400 MHz, MeOH-d4) δ ppm 8.29 (1H, d, J=8.6 Hz), 8.16 (1H, d, J=7.4 Hz), 7.75 (1H, d, J=11.7 Hz), 7.49 (1H, d, J=8.6 Hz), 7.15 (1H, d, J=3.7 Hz), 3.64 (2H, t, J=7.0 Hz), 3.03 (2H, t, J=7.0 Hz). $^{19}$F NMR (377 MHz, MeOH-d4) δ ppm −113.85 (1F, s). m/z (ESI, +ve ion) 316.1 (M+H)$^+$. m/z (ESI, +ve ion) 316.1 (M+H)$^+$.

Preparation of 227: 2-(7-fluoro-2-(phenylamino)quinolin-8-yl)-6,7-dihydro-1H-pyrrolo[3,2-c]pyridin-4(5H)-one bis(2,2,2-trifluoroacetate)

Aniline (173 mg, 1.86 mmol) was added to a mixture of 2-(2-chloro-7-fluoroquinolin-8-yl)-6,7-dihydro-1H-pyrrolo[3,2-c]pyridin-4(5H)-one (84 mg, 0.266 mmol) and NaH 60 wt % in mineral oil (74.5 mg, 1.862 mmol) in DMF (1.5 mL), and the resulting mixture was heated to 70° C. for 4.5 h then quenched with sat'd aq NH$_4$Cl. The reaction mixture was then cooled and partitioned between saturated NH$_4$Cl and EtOAc. The organic layer was sequentially washed with saturated NaHCO$_3$, water, and saturated NaCl, then dried over anhydrous Na$_2$SO$_4$, filtered, and concentrated in vacuo. Chromatographic purification (silica gel, 0-20% MeOH in DCM) afforded enriched material which was repurified by rpHPLC (20-95% 0.1% TFA/ACN in 0.1% TFA/water, Silicycle Silichrome XT C$_{18}$ column; 30×150 mm, 5 μm) affording 2-(7-fluoro-2-(phenylamino)quinolin-8-yl)-6,7-dihydro-1H-pyrrolo[3,2-c]pyridin-4(5H)-one bis(2,2,2-trifluoroacetate) (9.4 mg, 0.016 mmol, 5.88% yield) as a yellow/orange amorphous solid after drying under vacuum overnight: $^1$H NMR (400 MHz, MeOH-d$_4$) δ ppm 8.24 (1H, d, J=9.2 Hz), 7.77 (1H, dd, J=8.6, 5.9 Hz), 7.47-7.54 (4H, m), 7.27-7.36 (2H, m), 7.10 (1H, d, J=9.2 Hz), 6.95 (1H, d, J=1.8 Hz), 3.55 (2H, t, J=7.0 Hz), 2.77 (2H, t, J=7.0 Hz). m/z (ESI, +ve ion) 373.1 (M+H)$^+$.

Example 228

2-(7-fluoro-2-(pyridin-3-ylamino)quinolin-8-yl)-6,7-dihydro-1H-pyrrolo[3,2-c]pyridin-4(5H)-one

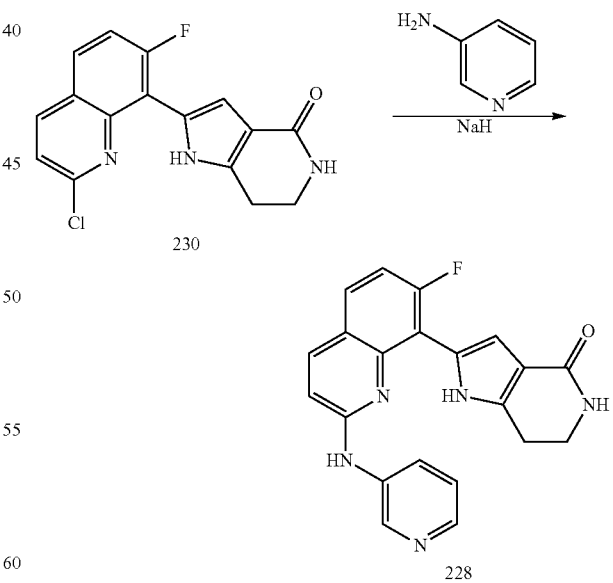

228

A mixture of 2-(2-chloro-7-fluoroquinolin-8-yl)-6,7-dihydro-1H-pyrrolo[3,2-c]pyridin-4(5H)-one (Example 230; 60 mg, 0.190 mmol), NaH 60 wt % in mineral oil (53.2 mg, 1.330 mmol), and pyridin-3-amine (Aldrich, St. Louis, Mass.; 125 mg, 1.330 mmol) in DMF (1.5 mL) was heated at 70° C. for 4.5 h. The reaction mixture was then cooled to RT and extracted with EtOAc (2×25 mL) and washed with saturated NaCl. The combined organic layers were concentrated and purified by rpHPLC (20-95% 0.1% TFA/ACN in 0.1% TFA/water, Silicycle Silichrome XT C18 column; 30×150 mm, 5 μm) to afford 2-(7-fluoro-2-(pyridin-3-ylamino)quinolin-8-yl)-6,7-dihydro-1H-pyrrolo[3,2-c]pyridin-4(5H)-one bis(2,2,2-trifluoroacetate) (9.6 mg, 0.016 mmol, 8.40% yield) as a tan amorphous solid after drying under vacuum overnight: $^1$H NMR (400 MHz, MeOH-d4) δ ppm 10.10 (1H, d, J=2.3 Hz), 8.63-8.70 (1H, m), 8.40 (1H, d, J=5.5 Hz), 8.26 (1H, d, J=8.8 Hz), 7.94 (1H, dd, J=8.7, 5.6 Hz), 7.83 (1H, dd, J=9.0, 6.1 Hz), 7.37 (1H, dd, J=10.4, 9.0 Hz), 7.09-7.18 (2H, m), 3.69 (2H, t, J=7.0 Hz), 2.97 (2H, t, J=7.0 Hz). $^{19}$F NMR (377 MHz, MeOH-d4) δ ppm −111.51 (1F, s). m/z (ESI, +ve ion) 374.1 (M+H)$^+$.

Example 229

2-(7-fluoro-2-(1-methyl-1H-pyrazol-4-yl)quinolin-8-yl)-6,7-dihydro-1H-pyrrolo[3,2-c]pyridin-4(5H)-one

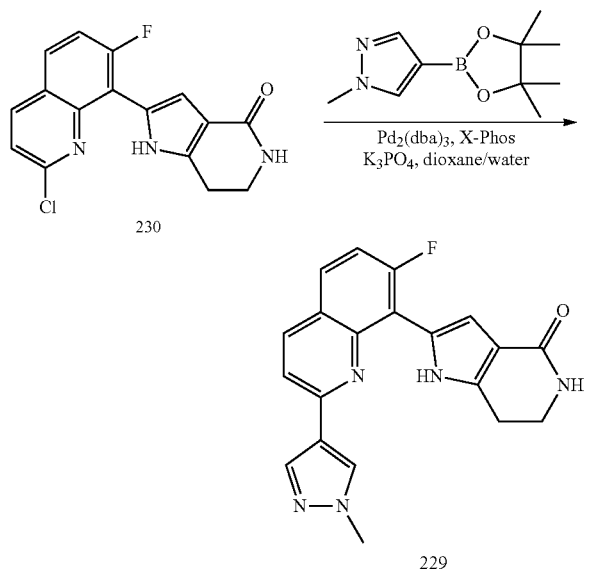

In a 5-mL glass microwave tube 2-(2-chloro-7-fluoroquinolin-8-yl)-6,7-dihydro-1H-pyrrolo[3,2-c]pyridin-4(5H)-one (Example 230; 64 mg, 0.20 mmoles), XPhos (Strem, 5.80 mg, 0.012 mmol), Pd$_2$(dba)$_3$ (5.57 mg, 6.08 μmol), K$_3$PO$_4$ (129 mg, 0.608 mmol) and 1-methyl-4-(4,4,5,5-tetramethyl-1,3,2-dioxaborolan-2-yl)-1H-pyrazole (Boron Molecular, Research Triangle, N.C.; 50.6 mg, 0.24 mmol) were purged with argon, treated with dioxane (3 mL) and water (0.60 mL) and heated at 130° C. for 30 min. The mixture was treated with water, extracted with DCM, washed with brine and concentrated. Purification by rpHPLC (20-95% 0.1% TFA/ACN in 0.1% TFA/water, Silicycle Silichrome XT C$_{18}$ column; 30×150 mm, 5 μm) afforded 2-(7-fluoro-2-(1-methyl-1H-pyrazol-4-yl)quinolin-8-yl)-6,7-dihydro-1H-pyrrolo[3,2-c]pyridin-4(5H)-one (1.3 mg, 3.60 μmol, 1.8% yield) as an orange amorphous solid: $^1$H NMR (400 MHz, MeOH-d4) δ ppm 8.60 (1H, d, J=8.8 Hz), 8.57 (1H, s), 8.35 (1H, s), 8.27 (1H, d, J=6.7 Hz), 8.01 (1H, d, J=8.8 Hz), 7.88 (1H, d, J=11.7 Hz), 7.19 (1H, s), 4.05 (3H, s), 3.62 (2H, t, J=6.9 Hz), 3.02 (2H, t, J=6.9 Hz). $^{19}$F NMR (376 MHz, MeOH-d4) δ ppm −77.32 (1F, s). m/z (ESI, +ve ion) 362.1 (M+H)$^+$.

Example 231

2-(2-(2,6-difluorophenyl)quinolin-8-yl)-6,7-dihydro-1H-pyrrolo[3,2-c]pyridin-4(5H)-one

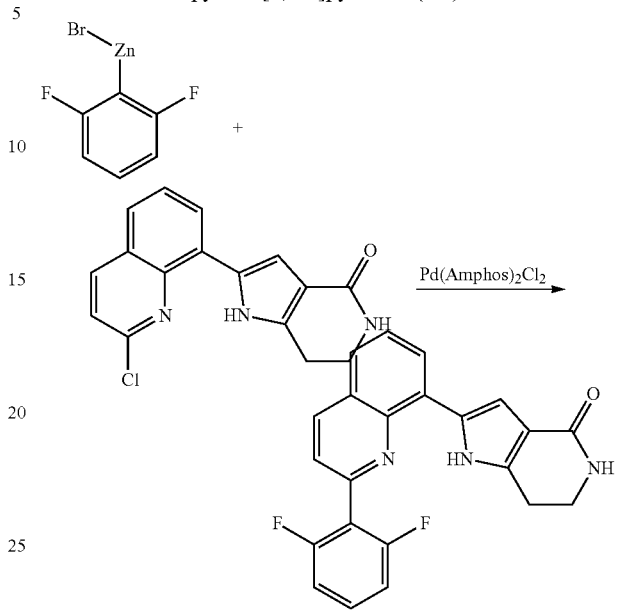

In a 5 mL glass microwave tube 2-(2-chloroquinolin-8-yl)-6,7-dihydro-1H-pyrrolo[3,2-c]pyridin-4(5H)-one (Example 1; 59 mg, 0.198 mmol) and Pd(Amphos)$_2$Cl$_2$ (14 mg, 0.02 mmol) were treated with (2,6-difluorophenyl)zinc(II) bromide 0.5 M in THF (Rieke Metals, Lincoln, Nebr.; 0.59 mL, 0.30 mmol) and heated to 90° C. for 20 min. The mixture was treated with 1N NaOH (5 mL) and the resulting solution was extracted with EtOAc (3×15 mL). The combined extracts were concentrated and purified by rpHPLC (20-95% 0.1% TFA/ACN in 0.1% TFA/water, Silicycle Silichrome XT C$_{18}$ column; 30×150 mm, 5 μm) affording 2-(2-(2,6-difluorophenyl)quinolin-8-yl)-6,7-dihydro-1H-pyrrolo[3,2-c]pyridin-4(5H)-one 2,2,2-trifluoroacetate (5.7 mg, 0.012 mmol, 5.9% yield) as a yellow amorphous solid after drying in the genevac overnight: $^1$H NMR (400 MHz, DMSO-d$_6$) δ ppm 12.17 (1H, br. s.), 8.60 (1H, d, J=8.6 Hz), 8.23 (1H, d, J=7.0 Hz), 7.93 (1H, d, J=7.8 Hz), 7.87 (1H, d, J=8.6 Hz), 7.64-7.77 (2H, m), 7.41 (2H, t, J=8.3 Hz), 7.30 (1H, d, J=2.2 Hz), 7.04 (1H, br. s.), 3.45 (2H, t, J=6.7 Hz), 2.89 (2H, t, J=6.8 Hz). $^{19}$F NMR (376 MHz, DMSO-d$_6$) δ ppm −74.49 (3F, s), −115.54 (2F, s). m/z (ESI, +ve ion) 376.1 (M+H)$^+$.

Example 232

4-methyl-3-(8-(4-oxo-4,5,6,7-tetrahydro-1H-pyrrolo[3,2-c]pyridin-2-yl)-2-quinolinyl)benzamide

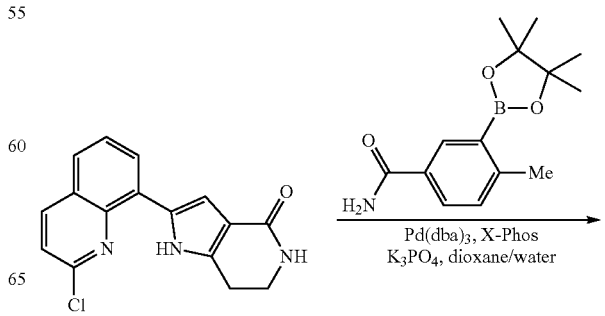

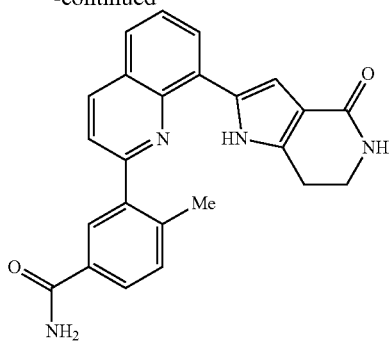

In a 5-mL glass microwave tube 4-methyl-3-(4,4,5,5-tetramethyl-1,3,2-dioxaborolan-2-yl)benzamide (prepared according to WO/2008050808; 70.4 mg, 0.27 mmol), XPhos (7.0 mg, 0.015 mmol), Pd$_2$(dba)$_3$ (6.7 mg, 7.36 μmol), potassium phosphate (156 mg, 0.74 mmol) and 2-(2-chloroquinolin-8-yl)-6,7-dihydro-1H-pyrrolo[3,2-c]pyridin-4(5H)-one (Example 1; 73 mg, 0.25 mmol) were purged with argon treated with dioxane (3.0 mL) and water (0.60 mL) and heated in the microwave at 130° C. for 20 min. The mixture was treated with water and extracted with EtOAc (2×25 mL). The combined extracts were concentrated and purified by rpHPLC (20-95% 0.1% TFA/ACN in 0.1% TFA/water, Silicycle Silichrome XT C$_{18}$ column; 30×150 mm, 5 μm) to afford 4-methyl-3-(8-(4-oxo-4,5,6,7-tetrahydro-1H-pyrrolo[3,2-c]pyridin-2-yl)quinolin-2-yl)benzamide bis(2,2,2-trifluoroacetate) (7.9 mg, 0.013 mmol, 5.2% yield) as a yellow amorphous solid after drying under vacuum overnight: $^1$H NMR (400 MHz, MeOH-d4) δ ppm 8.41 (1H, d, J=8.6 Hz), 8.16-8.23 (2H, m), 7.93 (1H, d, J=8.6 Hz), 7.81 (1H, d, J=7.2 Hz), 7.75 (1H, s), 7.63 (1H, t, J=7.7 Hz), 7.51 (1H, d, J=8.0 Hz), 7.14-7.20 (1H, m), 3.59 (2H, t, J=7.0 Hz), 2.92 (2H, t, J=7.1 Hz), 2.54 (3H, s). m/z (ESI, +ve ion) 397.1 (M+H)$^+$.

Example 233

7-(3-(cyclopropylamino)-2-methylquinoxalin-5-yl)-3,4-dihydropyrrolo[1,2-a]pyrazin-1(2H)-one 2,2,2-trifluoroacetate

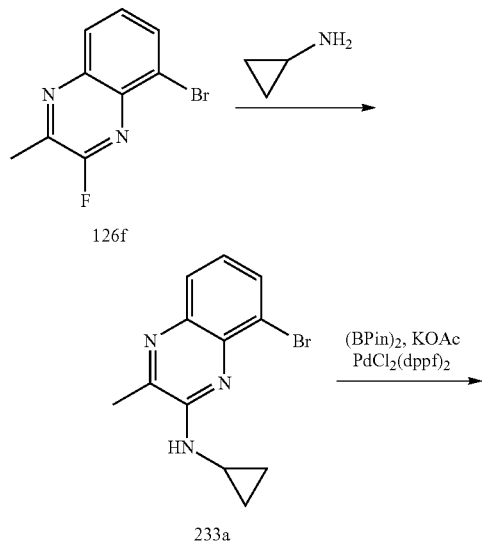

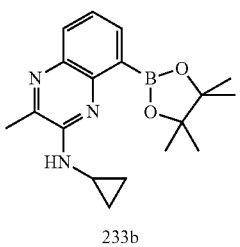

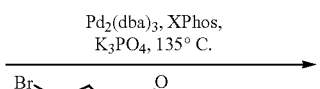

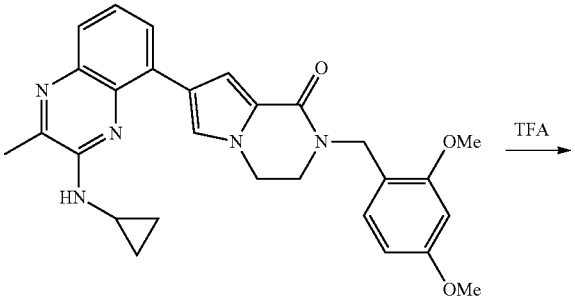

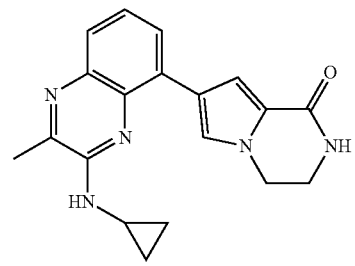

Preparation of 233a:
8-bromo-N-cyclopropyl-3-methylquinoxalin-2-amine

This compound (1.06 g, 83% yield) as a light yellow crystalline solid was prepared similarly to that described in the preparation of Example 174a, using 5-bromo-3-fluoro-2-methylquinoxaline (Example 126f; 1.11 g, 4.60 mmol) and cyclopropanamine (Aldrich; 1.50 mL, 21.65 mmol) as starting materials. $^1$H NMR (400 MHz, CDCl$_3$) δ ppm 7.84 (1H, dd, J=7.6, 1.2 Hz), 7.78 (1H, dd, J=8.2, 1.2 Hz), 7.19-7.26 (1H, m), 5.12 (1H, br. s.), 3.04-3.14 (1H, m), 2.47-2.55 (3H, m), 0.93-1.01 (2H, m), 0.60-0.68 (2H, m). m/z (ESI, +ve) 278/280 (M+H)$^+$.

Preparation of 233b. 3-methyl-N-(1-methylcyclopropyl)-8-(4,4,5,5-tetramethyl-1,3,2-dioxaborolan-2-yl)quinoxalin-2-amine This compound (215 mg, 33% yield) as a brown amorphous solid was prepared similarly to that described in the preparation of Example 174b, using 8-bromo-N-cyclopropyl-3-methylquinoxalin-2-amine (Example 233a; 550 mg, 1.98 mmol) as the starting material. $^1$H NMR (400 MHz, MeOH-d4) δ ppm 7.92 (1H, d, J=6.8 Hz), 7.78 (1H, dd, J=8.1, 1.3 Hz), 7.40-7.48 (1H, m), 2.84 (1H, dt, J=6.9, 3.4 Hz), 2.55-2.59 (3H, m), 1.21 (12H, s), 1.03-1.10 (2H, m), 0.74-0.81 (2H, m) m/z (ESI, +ve ion) 244.1 (M+H)$^+$.

Preparation of 233: 7-(3-(cyclopropylamino)-2-methylquinoxalin-5-yl)-3,4-dihydropyrrolo[1,2-a]pyrazin-1(2H)-one 2,2,2-trifluoroacetate This compound was prepared similarly to that described in Example 174, using N-cyclopropyl-3-methyl-8-(4,4,5,5-tetramethyl-1,3,2-dioxaborolan-2-yl)quinoxalin-2-amine (Example 233b; 113 mg, 0.34 mmol) as the starting material. Purification by rpHPLC (Silicycle Silichrome XT $C_{18}$ column; 30×150 mm, 5 μm; 20-95% of 0.1% TFA/ACN in 0.1% TFA/water by volume over 10 min), then drying in a Genevac Series II Evaporator afforded 7-(2-methyl-3-((1-methylcyclopropyl)amino)quinoxalin-5-yl)-3,4-dihydropyrrolo[1,2-a]pyrazin-1(2H)-one 2,2,2-trifluoroacetate (10 mg, 7% yield for 2 steps) as an orange solid. $^1$H NMR (400 MHz, DMSO-$d_6$) δ ppm 8.36 (1H, d, J=1.6 Hz), 7.82-7.89 (1H, m), 7.65 (1H, br. s.), 7.56 (1H, dd, J=8.1, 1.3 Hz), 7.51 (1H, d, J=1.8 Hz), 7.32 (1H, t, J=7.7 Hz), 7.26 (1H, br. s.), 4.12-4.19 (2H, m), 3.83 (1H, br.), 3.54 (2H, m), 2.55 (3H, s), 2.85 (1H, m), 0.89-0.96 (2H, m), 0.61-0.69 (2H, m). m/z (ESI, +ve ion) 334.2 (M+H)$^+$.

Example 235

(±)-7-(3-(tert-butylamino)-2-methyl-5-quinoxalinyl)-4-(2-hydroxyethyl)-3,4-dihydropyrrolo[1,2-a]pyrazin-1(2H)-one

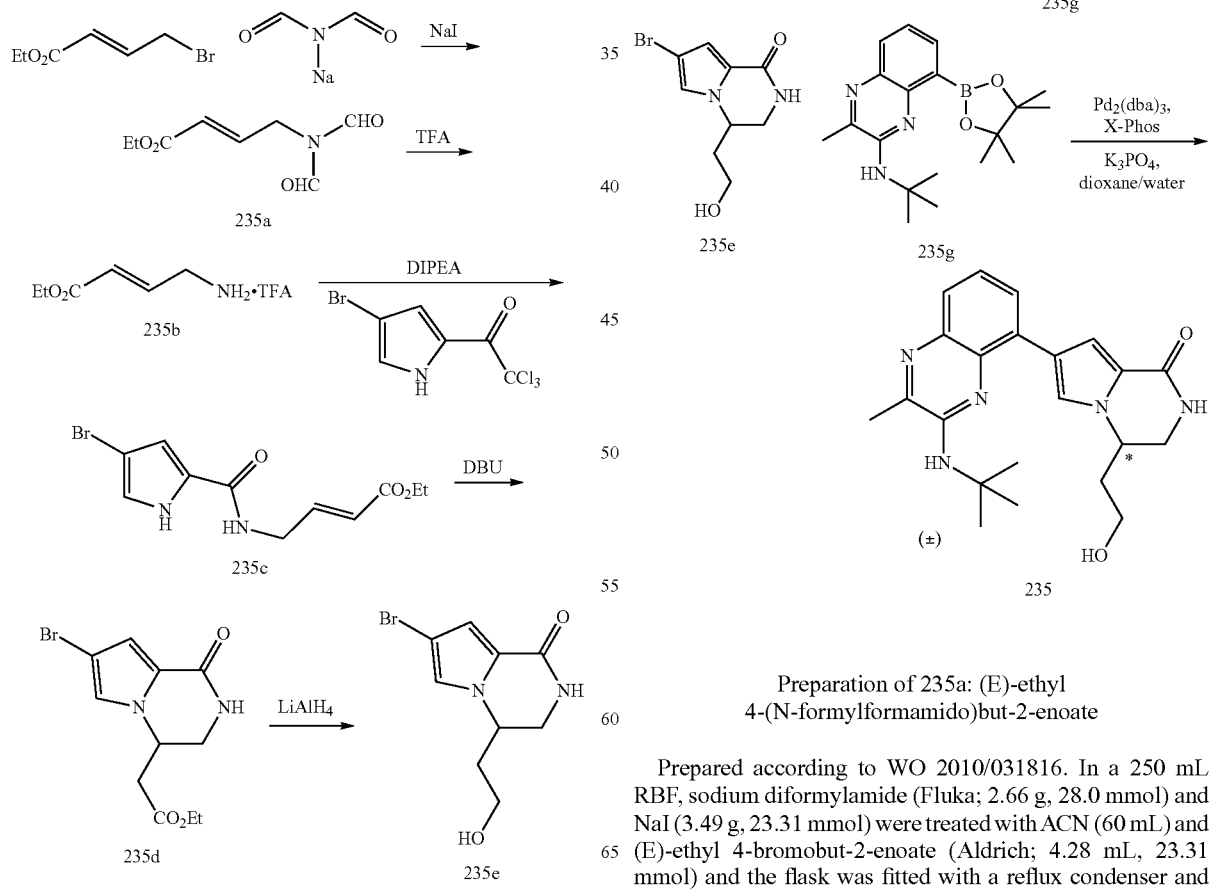

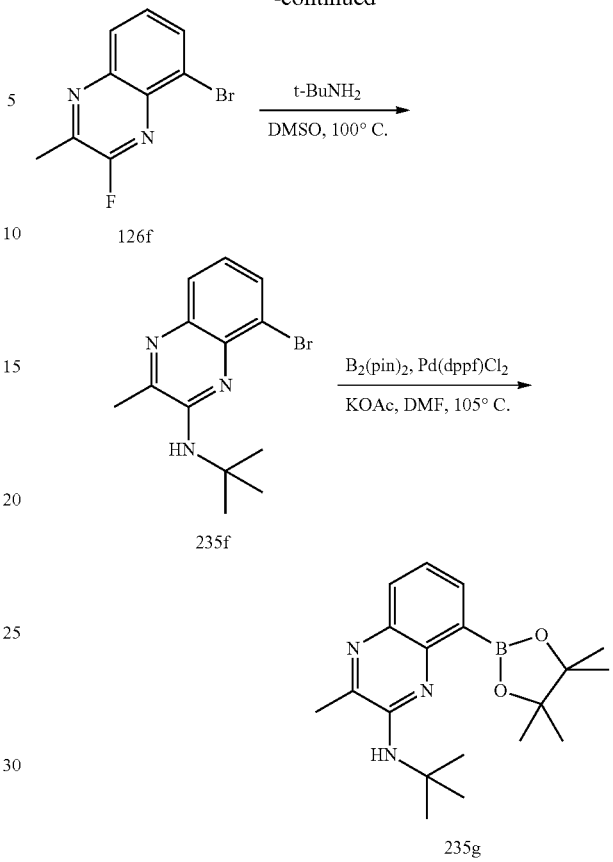

Preparation of 235a: (E)-ethyl 4-(N-formylformamido)but-2-enoate

Prepared according to WO 2010/031816. In a 250 mL RBF, sodium diformylamide (Fluka; 2.66 g, 28.0 mmol) and NaI (3.49 g, 23.31 mmol) were treated with ACN (60 mL) and (E)-ethyl 4-bromobut-2-enoate (Aldrich; 4.28 mL, 23.31 mmol) and the flask was fitted with a reflux condenser and heated at reflux overnight (16 h). The mixture was concentrated in vacuo and the crude residue was treated with water and extracted with EtOAc (100 mL). The organic extract was washed with brine, then dried over MgSO$_4$, filtered, and concentrated. The resulting light-brown solid was suspended in Et$_2$O (ca. 10 mL), filtered, and washed with Et$_2$O (5 mL), then dried by drawing air through the filtercake for 2 min to afford (E)-ethyl 4-(N-formylformamido)but-2-enoate (3.66 g, 19.76 mmol, 85% yield) as a brown amorphous solid: $^1$H NMR (400 MHz, CDCl$_3$) δ ppm 8.91 (2H, br. s.), 6.74-6.84 (1H, m), 5.90 (1H, dt, J=15.8, 1.6 Hz), 4.40 (2H, d, J=4.5 Hz), 4.13-4.24 (2H, m), 1.20-1.33 (3H, m). m/z (ESI, +ve ion) 186.1 (M+H)$^+$. The crude material was used in the subsequent step without further purification.

Preparation of 235b: (E)-ethyl 4-aminobut-2-enoate 2,2,2-trifluoroacetate. Prepared according to WO 2010/031816

(E)-Ethyl 4-(N-formylformamido)but-2-enoate (3.04 g, 16.43 mmol) was treated with EtOH (20 mL) and TFA (10.0 mL, 130 mmol), fitted with a reflux condenser and heated to 80° C. for 21 h. The mixture was concentrated on the rotovap and dried under high vacuum affording crude (E)-ethyl 4-aminobut-2-enoate 2,2,2-trifluoroacetate as a light yellow viscous liquid: m/z (ESI, +ve ion) 130.1 (M+H)$^+$. The crude material was used in the next step without further purification.

Preparation of 235c: (E)-ethyl 4-(4-bromo-1H-pyrrole-2-carboxamido)but-2-enoate

Prepared according to WO 2010/031816. A 250 mL RBF containing 1-(4-bromo-1H-pyrrol-2-yl)-2,2,2-trichloroethanone (Combi-Blocks Inc. San Diego, Calif., 2.40 g, 8.24 mmol) was treated with DCM (80 mL) followed by DIPEA (10 mL, 57.7 mmol). To this stirring solution at RT was slowly added (E)-ethyl 4-aminobut-2-enoate 2,2,2-trifluoroacetate (4.01 g, 16.47 mmol) in DCM (20 mL), and the resulting solution was stirred at RT for 6 h. The reaction mixture was then concentrated in vacuo, and the residue was purified by silica gel chromatography (40-70% EtOAc in hexanes) to provide (E)-ethyl 4-(4-bromo-1H-pyrrole-2-carboxamido)but-2-enoate (2.35 g, 7.80 mmol, 95% yield) as a light yellow crystalline solid: $^1$H NMR (400 MHz, CDCl$_3$) δ ppm 9.48 (1H, br. s.), 6.89-7.01 (2H, m), 6.58 (1H, dd, J=2.7, 1.4 Hz), 5.89-6.02 (2H, m), 4.16-4.24 (4H, m), 1.23-1.32 (3H, m). m/z (ESI, +ve ion) 301.0/302.9 (M+H)$^+$.

Preparation of 235d: Ethyl 2-(7-bromo-1-oxo-1,2,3,4-tetrahydropyrrolo[1,2-a]pyrazin-4-yl)acetate (E)-Ethyl 4-(4-bromo-1H-pyrrole-2-carboxamido)but-2-enoate (2.35 g, 7.80 mmol) was treated with ACN (30 mL) and DBU (0.27 mL, 1.80 mmol) and stirred at RT for 2 h. The mixture was then concentrated in vacuo. Chromatographic purification of the residue (silica gel, 30-50% EtOAc in hexanes) afforded ethyl 2-(7-bromo-1-oxo-1,2,3,4-tetrahydropyrrolo[1,2-a]pyrazin-4-yl)acetate (1.24 g, 4.12 mmol, 52.8% yield) as a colorless viscous oil which crystallized to a white solid: $^1$H NMR (400 MHz, CDCl$_3$) δ ppm 6.93 (1H, d, J=1.6 Hz), 6.84 (1H, d, J=1.8 Hz), 5.87 (1H, br. s.), 4.65 (1H, tt, J=6.8, 3.4 Hz), 4.11-4.24 (2H, m), 3.92 (1H, dd, J=12.8, 4.0 Hz), 3.46-3.54 (1H, m), 2.74-2.90 (2H, m), 1.26 (3H, t, J=7.1 Hz). m/z (ESI, +ve ion) 301.0/303.0 (M+H)$^+$.

Preparation of 235e: 7-bromo-4-(2-hydroxyethyl)-3,4-dihydropyrrolo[1,2-a]pyrazin-1(2H)-one Ethyl 2-(7-bromo-1-oxo-1,2,3,4-tetrahydropyrrolo[1,2-a]pyrazin-4-yl)acetate (1.23 g, 4.1 mmol) was treated with THF (30 mL), cooled to 0° C. and treated with LiAlH$_4$, 1.0 M solution in THF (4.1 mL, 4.1 mmol) and stirred at 0° C. for 30 min. The reaction was quenched by slow dropwise addition of an aq. solution of sodium potassium tartrate and stirred at RT for 30 min. The resulting mixture was extracted with EtOAc (3×25 mL), washed with brine and dried over MgSO$_4$, filtered and concentrated in vacuo to afford crude 7-bromo-4-(2-hydroxyethyl)-3,4-dihydropyrrolo[1,2-a]pyrazin-1(2H)-one (987 mg, 3.81 mmol, 93% yield) as a white crystalline solid: $^1$H NMR (400 MHz, MeOH-d4) δ ppm 7.10 (1H, s), 6.83 (1H, s), 4.47 (1H, tt, J=7.1, 3.7 Hz), 3.85 (1H, dd, J=13.2, 4.2 Hz), 3.68 (1H, dt, J=11.2, 5.6 Hz), 3.46-3.56 (2H, m), 1.91-2.07 (2H, m). m/z (ESI, +ve ion) 259.0/261.0 (M+H)$^+$.

Preparation of 235f: 8-bromo-N-(tert-butyl)-3-methylquinoxalin-2-amine

A solution of 5-bromo-3-fluoro-2-methylquinoxaline (Example 126f; 1.05 g, 4.36 mmol) and tert-butylamine (2.29 mL, 21.8 mmol) in DMSO (10 mL) was stirred at 100° C. for 2.5 h. The mixture was then diluted with DCM (150 mL) and washed with saturated aq. NaHCO$_3$ (3×100 mL). The organic layer was separated, dried over MgSO$_4$, filtered, and concentrated. The crude material was adsorbed onto silica and chromatographically purified (silica gel; 0-4% MeOH in DCM) to give 8-bromo-N-(tert-butyl)-3-methylquinoxalin-2-amine as an amorphous pink solid: $^1$H NMR (400 MHz, DMSO-d$_6$) δ ppm 7.82 (d, J=7.6 Hz, 1H), 7.68-7.74 (m, 1H), 7.22 (t, J=7.9 Hz, 1H), 6.17 (s, 1H), 2.55 (s, 3H), 1.58 (s, 9H). m/z (ESI, +ve ion) 294.0/296.0 (M+H)$^+$.

Preparation of 235g: N-(tert-butyl)-3-methyl-8-(4,4,5,5-tetramethyl-1,3,2-dioxaborolan-2-yl)quinoxalin-2-amine A mixture of 8-bromo-N-(tert-butyl)-3-methylquinoxalin-2-amine (1.28 g, 4.35 mmol) bis(pinacolato)diboron (2.21 g, 8.71 mmol), KOAc (1.71 g, 17.42 mmol) and PdCl$_2$(PPh$_3$)$_2$ (178 mg, 0.218 mmol) in DMF (11 mL) was heated at 105° C. for 3 h. The suspension was then diluted with 50 mL of EtOAc and washed with water (3×25 mL). The organic layer was dried over MgSO$_4$ and concentrated. The crude residue was chromatographically purified (silica gel, 0-50% EtOAc in hexanes), affording N-(tert-butyl)-3-methyl-8-(4,4,5,5-tetramethyl-1,3,2-dioxaborolan-2-yl)quinoxalin-2-amine (856 mg, 2.51 mmol, 57.6% yield): $^1$H NMR (400 MHz, MeOH-d$_4$) δ ppm 7.70-7.78 (m, 2H), 7.28 (dd, J=7.8, 7.2 Hz, 1H), 3.31 (s, 3H), 1.57 (s, 9H), 1.33 (s, 12H). m/z (ESI, +ve ion) 260.1 (M+H)$^+$.

Preparation of 235: (±)-7-(3-(tert-butylamino)-2-methyl-5-quinoxalinyl)-4-(2-hydroxyethyl)-3,4-dihydropyrrolo[1,2-a]pyrazin-1(2H)-one In a 5 mL glass microwave vial 7-bromo-4-(2-hydroxyethyl)-3,4-dihydropyrrolo[1,2-a]pyrazin-1(2H)-one (47 mg, 0.181 mmol), dicyclohexyl(2',4',6'-triisopropyl-[1,1'-biphenyl]-2-yl)phosphine (5.2 mg, 10.88 μmol), Pd$_2$(dba)$_3$ (5.0 mg, 5.44 μmol), K$_2$PO$_4$ (116 mg, 0.544 mmol) and N-(tert-butyl)-3-methyl-8-(4,4,5,5-tetramethyl-1,3,2-dioxaborolan-2-yl)quinoxalin-2-amine (74.3 mg, 0.22 mmol) were purged with argon and treated with dioxane (2.5 mL) and water (0.83 mL), then heated in the microwave at 130° C. for 20 min. The resulting mixture was treated with water and extracted with EtOAc, and the organic extracts was washed with brine and concentrated. rpHPLC purification of the residue (20-95% 0.1% TFA/ACN in 0.1% TFA/water, Silicycle Silichrome XT $C_{18}$ column; 30×150 mm, 5 pan) afforded (R)-7-(3-(tert-butylamino)-2-methylquinoxalin-5-yl)-4-(2-hydroxyethyl)-3,4-dihydropyrrolo[1,2-a]pyrazin-1(2H)-one 2,2,2-trifluoroacetate (21.3 mg, 0.042 mmol, 46.2% yield) and (S)-7-(3-(tert-butylamino)-2-methylquinoxalin-5-yl)-4-(2-hydroxyethyl)-3,4-dihydropyrrolo[1,2-a]pyrazin-1(2H)-one 2,2,2-trifluoroacetate (21.3 mg, 0.042 mmol, 46.2% yield) as a racemic mixture as a bright yellow amorphous solid after drying in the genevac overnight: $^1$H NMR (400 MHz, DMSO-$d_6$) δ ppm 7.89 (1H, d, J=1.6 Hz), 7.69-7.74 (1H, m), 7.62 (1H, br. s.), 7.53-7.58 (1H, m), 7.30 (1H, t, J=7.7 Hz), 7.22 (1H, d, J=1.6 Hz), 5.83 (1H, br. s.), 4.33-4.42 (1H, m), 3.45-3.58 (3H, m), 3.38 (1H, dt, J=13.0, 4.1 Hz), 2.54 (3H, s), 2.02 (1H, dd, J=13.4, 6.4 Hz), 1.90 (1H, dd, J=13.8, 7.3 Hz), 1.49-1.59 (9H, m). m/z (ESI, +ve ion) 394.1 (M+H)$^+$.

Example 236

2-(2-phenoxyquinazolin-8-yl)-6,7-dihydro-1H-pyrrolo[3,2-c]pyridin-4(5H)-one 2,2,2-trifluoroacetate

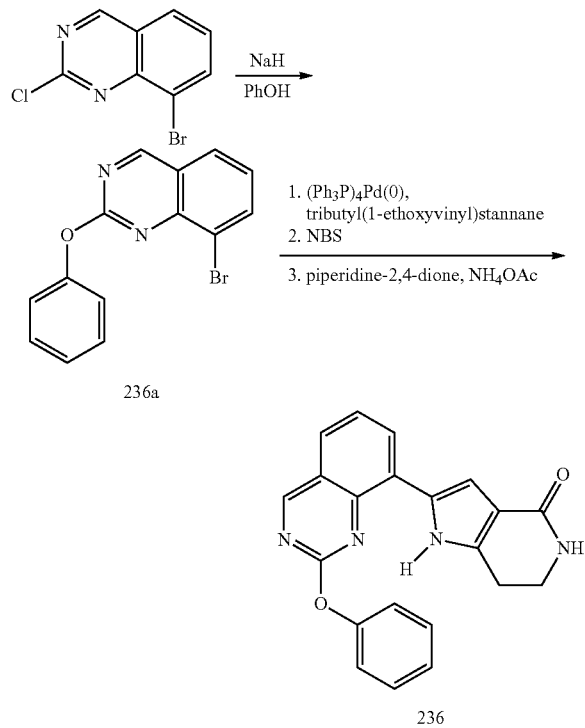

236a

236

Preparation of 236a: 8-bromo-2-phenoxyquinazoline

A mixture of 8-bromo-2-chloroquinazoline (Ark Pharm Inc, Libertyville Ill.; 0.550 g, 2.259 mmol), cesium carbonate (0.883 g, 2.71 mmol), and phenol (0.234 g, 2.485 mmol) in 3 mL DMSO was sealed and heated to 120° C. for 2 h. The reaction was then partitioned between water and EtOAc. The organic layer was sequentially washed with water (2×), and saturated aq. NaCl (1×), then dried over anhydrous Na$_2$SO$_4$, filtered, and concentrated in vacuo. The material was treated with DCM and purified by silica gel chromatography using 0-20% EtOAc/hexane. The material-containing fractions were concentrated to afford 8-bromo-2-phenoxyquinazoline (0.486 g, 1.614 mmol, 71% yield) as a yellow solid: $^1$H NMR (400 MHz, CDCl$_3$) δ ppm 9.25 (1H, s), 8.15 (1H, dd, J=7.6, 1.4 Hz), 7.87 (1H, dd, J=8.0, 1.4 Hz), 7.34-7.50 (5H, m), 7.26-7.31 (1H, m). m/z (ESI, +ve) 302.9 (M+H)$^+$.

Preparation of 236: 2-(2-phenoxyquinazolin-8-yl)-6,7-dihydro-1H-pyrrolo[3,2-c]pyridin-4(5H)-one 2,2,2-trifluoroacetate Argon was bubbled through a mixture of tributyl(1-ethoxyvinyl)stannane (0.874 g, 2.421 mmol), 8-bromo-2-phenoxyquinazoline (0.486 g, 1.614 mmol), and Pd(PPh$_3$)$_4$ (0.093 g, 0.081 mmol) in 5 mL toluene for 2 min. The reaction flask was then sealed and placed in a 70° C. bath overnight, then heated at 100° C. for 3 h. The reaction mixture was then cooled to RT and concentrated in vacuo. The residue was chromatographically purified (silica gel, 0-50% EtOAc/hexane), and the major material was collected (0.314 g) and treated with 5 mL THF, water (0.310 ml, 17.19 mmol), and NBS (0.201 g, 1.128 mmol). After 30 min, the reaction was concentrated to a small volume and partitioned between water and EtOAc. The organic layer was separated and washed with water (3×), then dried over anhydrous Na$_2$SO$_4$, filtered, and concentrated in vacuo to give 0.358 g yellow solid. This material was taken up in 5 mL EtOH and treated with piperidine-2,4-dione (0.146 g, 1.289 mmol) and NH4OAc (0.331 g, 4.30 mmol). The slurry was stirred at RT for 30 min. The reaction was then sealed and heated to 70° C. After 1 h, the mixture was partitioned between water and EtOAc. The organic layer was separated and sequentially washed with water (2×), half-saturated sodium bisulfite (1×), saturated aq. NaCl (1×), then dried over anhydrous Na$_2$SO$_4$, filtered, and concentrated in vacuo. The material was treated with DCM and purified by silica gel chromatography using 0-100% 90/10 DCM/MeOH in DCM. The product-containing fractions were concentrated to afford the desired product with some impurities (0.065 g). The material was sonicated in MeOH and filtered, rinsing with MeOH, to give 0.040 g orange solid. This material was dissolved in DMSO and purified by rpHPLC (Phenomenex Gemini 150× 30 mm $C_{18}$ column, 10-80% ACN/H$_2$O with 0.1% TFA); product-containing fractions were concentrated in vacuo to give 2-(2-phenoxyquinazolin-8-yl)-6,7-dihydro-1H-pyrrolo[3,2-c]pyridin-4(5H)-one 2,2,2-trifluoroacetate (0.020 g, 0.043 mmol, 4% yield) as an orange solid: $^1$H NMR (400 MHz, CDCl$_3$) d ppm 11.10 (1H, br. s), 9.40 (1H, s), 8.15-8.26 (1H, m), 7.76 (1H, dt, J=7.9, 0.7 Hz), 7.31-7.64 (6H, m), 7.12 (1H, d, J=2.2 Hz), 5.84 (1H, br. s), 3.55 (2H, tt, J=7.0, 1.0 Hz), 2.52 (2H, t, J=6.9 Hz). m/z (ESI, +ve) 357.2 (M+H)$^+$.

Example 240

N-(3-methyl-8-(4-oxo-4,5,6,7-tetrahydro-1H-pyrrolo[3,2-c]pyridin-2-yl)quinoxalin-2-yl)methanesulfonamide 2,2,2-trifluoroacetate

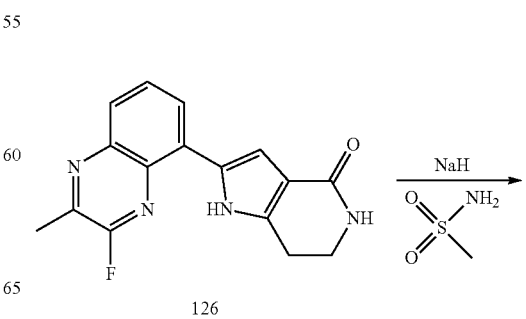

126

-continued

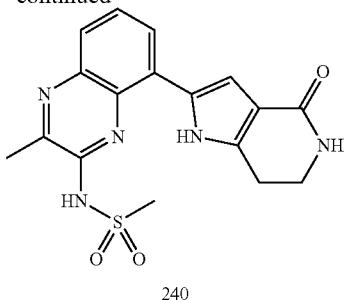

240

To a slurry of NaH (60% in mineral oil; 0.064 g, 1.606 mmol) in 1 mL DMF at 0° C. was added methanesulfonamide (TCI America, Portland, Oreg.; 0.153 g, 1.606 mmol) in portions. The ice/water bath was removed and the reaction warmed to RT. 2-(3-fluoro-2-methylquinoxalin-5-yl)-6,7-dihydro-1H-pyrrolo[3,2-c]pyridin-4(5H)-one (Example 126; 0.068 g, 0.229 mmol) was added. After 30 min, the reaction was cooled to 0° C., TFA (0.177 ml, 2.295 mmol) was added (dropwise via syringe), and 1 mL DMSO was added. The solution was filtered through a 0.45 micron syringe filter and purified by rpHPLC (Phenomenex Gemini 150×30 mm C$_{18}$ column, 10-70% ACN/H$_2$O with 0.1% TFA); product-containing fractions were concentrated in vacuo, to give N-(3-methyl-8-(4-oxo-4,5,6,7-tetrahydro-1H-pyrrolo[3,2-c]pyridin-2-yl)quinoxalin-2-yl)methanesulfonamide 2,2,2-trifluoroacetate (0.020 g, 0.041 mmol, 18% yield) as a brown solid: $^1$H NMR (400 MHz, DMSO-d$_6$) δ ppm 12.09 (1H, br. s.), 10.98 (1H, br. s), 8.11 (1H, d, J=7.6 Hz), 7.74 (1H, dt, J=8.0, 0.8 Hz), 7.54-7.66 (1H, m), 7.05-7.15 (1H, m), 7.01 (1H, br. s.), 3.44 (2H, t, J=7.0 Hz), 3.39 (3H, s), 2.91 (2H, t, J=6.9 Hz), 2.68 (3H, s). m/z (ESI, +ve) 372.0 (M+H)$^+$.

Example 241

2-(3-(((3R)-1-acetyl-3-piperidinyl)amino)-2-methyl-5-quinoxalinyl)-1,5,6,7-tetrahydro-4H-pyrrolo[3,2-c]pyridin-4-one

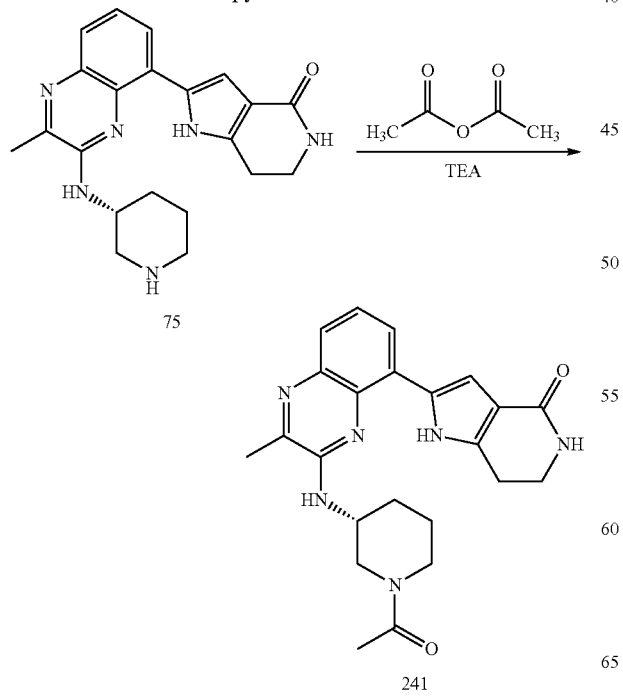

Prepared according to Example 50, using TEA (39.9 μl, 0.287 mmol), 2-(2-methyl-3-((3R)-3-piperidinylamino)-5-quinoxalinyl)-1,5,6,7-tetrahydro-4H-pyrrolo[3,2-c]pyridin-4-one (Ex. 75, 90 mg, 0.239 mmol), Ac$_2$O (45.1 μl, 0.478 mmol), and DCM (2.4 mL) and stirring at 25° C. for 1 h. Isolation of the free base from the mixture by addition of saturated aq. NaHCO$_3$ and extraction with 10% MeOH/DCM, followed by drying of the organic extract over Na$_2$SO$_4$, filtration, and concentration under reduced pressure afforded 2-(3-(((3R)-1-acetyl-3-piperidinyl)amino)-2-methyl-5-quinoxalinyl)-1,5,6,7-tetrahydro-4H-pyrrolo[3,2-c]pyridin-4-one (34 mg, 30%). $^1$H NMR (DMSO-d$_6$) δ: 7.85-7.91 (m, 1H), 7.77-7.83 (m, 1H), 7.54-7.63 (m, 2H), 7.30-7.40 (m, 2H), 7.05-7.11 (m, 1H), 4.45-4.55 (m, 1H), 4.27-4.39 (m, 1H), 4.13-4.27 (m, 1H), 3.96-4.10 (m, 1H), 3.86-3.95 (m, 1H), 3.76-3.86 (m, 1H), 3.39-3.46 (m, 3H), 2.87-2.97 (m, 1H), 2.07 (s, 3H), 1.59 (s, 3H), 1.10-1.22 (m, 3H). m/z (ESI, +ve) 419.1 (M+H)$^+$.

Example 242

2-(3-(((3S)-1-acetyl-3-piperidinyl)amino)-2-methyl-5-quinoxalinyl)-1,5,6,7-tetrahydro-4H-pyrrolo[3,2-c]pyridin-4-one

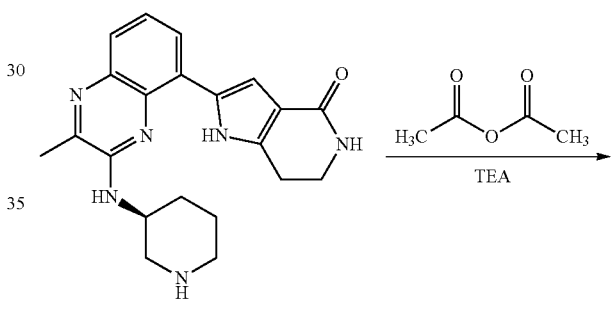

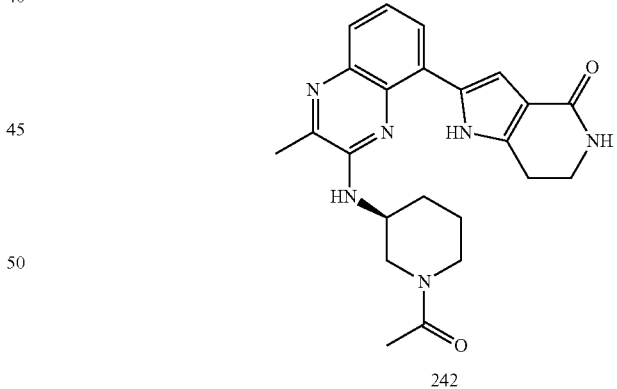

Prepared according to Example 50, using TEA (37.7 μl, 0.271 mmol, Sigma Aldrich), (S)-2-(2-methyl-3-(piperidin-3-ylamino)quinoxalin-5-yl)-6,7-dihydro-1H-pyrrolo[3,2-c]pyridin-4(5H)-one (Ex. 76, 85 mg, 0.226 mmol), Ac$_2$O (42.6 μl, 0.452 mmol), and DCM (2.3 mL) and stirring at 25° C. for 1 h. Purification by concentration of the reaction solution, solubilization in MeOH, and filtration through a pre-washed column of Si-carbonate (SiliaPrep, Silicyle) provided 2-(3-(((3S)-1-acetyl-3-piperidinyl)amino)-2-methyl-5-quinoxalinyl)-1,5,6,7-tetrahydro-4H-pyrrolo[3,2-c]pyridin-4-one (28 mg, 30%). $^1$H NMR (DMSO-d$_6$) δ: 7.85-7.91 (m, 1H), 7.77-

7.83 (m, 1H), 7.54-7.63 (m, 2H), 7.30-7.40 (m, 2H), 7.05-7.11 (m, 1H), 4.45-4.55 (m, 1H), 4.27-4.39 (m, 1H), 4.13-4.27 (m, 1H), 3.96-4.10 (m, 1H), 3.86-3.95 (m, 1H), 3.76-3.86 (m, 1H), 3.39-3.46 (m, 3H), 2.87-2.97 (m, 1H), 2.01-2.07 (m, 3H), 1.59 (s, 3H), 1.10-1.22 (m, 3H). m/z (ESI, +ve) 419.1 (M+H)⁺.

Example 243

2-(2-methyl-3-((1-methyl-3-azetidinyl)amino)-5-quinoxalinyl)-1,5,6,7-tetrahydro-4H-pyrrolo[3,2-c]pyridin-4-one

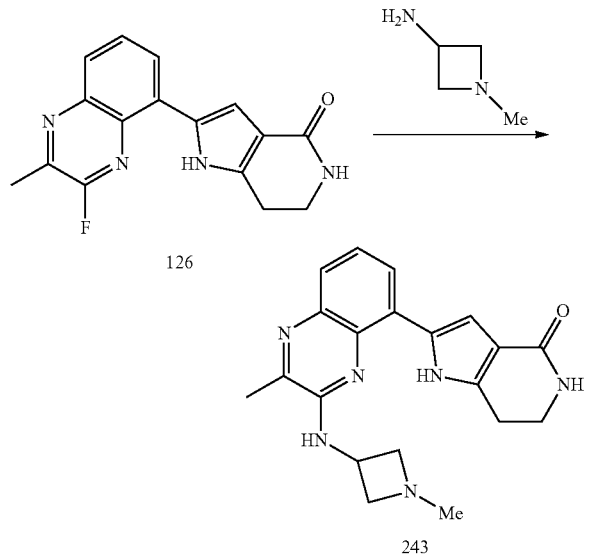

Prepared similarly to that described in Example 127, using 2-(3-fluoro-2-methylquinoxalin-5-yl)-6,7-dihydro-1H-pyrrolo[3,2-c]pyridin-4(5H)-one (Example 126; 75 mg, 0.135 mmol), 1-methylazetidin-3-amine (87 mg, 0.405 mmol), and DMSO (1.4 mL) and stirring at 80° C. for 2 h. Purification by high-throughput parallel purification (Rilas Technologies, Woburn, Mass.) provided 2-(2-methyl-3-((1-methyl-3-azetidinyl)amino)-5-quinoxalinyl)-1,5,6,7-tetrahydro-4H-pyrrolo[3,2-c]pyridin-4-one. ¹H NMR (MeOH-d4) δ: 7.80-7.85 (m, 1H), 7.63-7.68 (m, 1H), 7.36-7.42 (m, 1H), 6.93 (s, 1H), 3.59-3.65 (m, 2H), 3.22-3.26 (m, 2H), 3.11-3.14 (m, 1H), 2.97-3.04 (m, 2H), 2.59 (s, 3H), 2.01 (s, 3H). m/z (ESI, +ve) 363.2 (M+H)⁺.

Example 244

2-(2-(1-phenylcyclopropyl)quinazolin-8-yl)-6,7-dihydro-1H-pyrrolo[3,2-c]pyridin-4(5H)-one

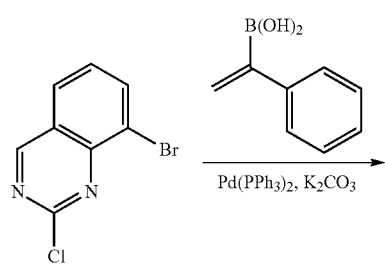

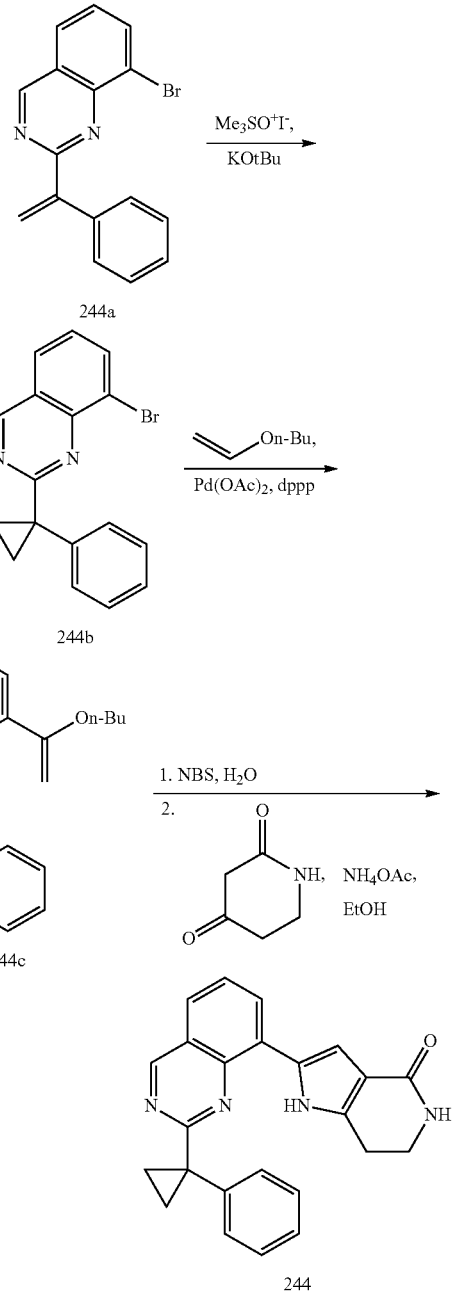

Preparation of 244a:
8-bromo-2-(1-phenylvinyl)quinazoline

A suspension of 8-bromo-2-chloroquinazoline (Ark Pharm, Inc., Libertyville, Ill.; 2.00 g, 8.21 mmol), (1-phenylvinyl)boronic acid (Aldrich; 1.215 g, 8.21 mmol), potassium carbonate (2.384 g, 17.25 mmol), and Pd(PPh₃)₄ (0.190 g, 0.164 mmol) in toluene (75 mL) was stirred under argon at 90° C. for 2.5 d. The reaction was cooled to 25° C. and partitioned between EtOAc (200 mL) and water (100 mL). The organic layer was separated, sequentially washed with water (2×80 mL) and brine (80 mL), dried over Na₂SO₄, filtered, and concentrated in vacuo. Chromatographic purification of the residue (silica gel, 0-100% hexanes/DCM) furnished 8-bromo-2-(1-phenylvinyl)quinazoline (380 mg, 1.221 mmol, 15% yield) as a yellow solid: $^1$H NMR (400 MHz, CDCl$_3$) δ ppm 9.36 (1H, s), 8.20 (1H, s), 7.88 (1H, d, J=8.0 Hz), 7.58-7.65 (2H, m), 7.44-7.51 (2H, m), 7.40-7.44 (2H, m), 6.84 (1H, s), 5.99 (1H, s). m/z (ESI, +ve) 311.0 (M+H)$^+$.

Preparation of 244b:
8-bromo-2-(1-phenylcyclopropyl)quinazoline

A mixture of potassium tert-butoxide (284 mg, 2.532 mmol) and trimethylsulfoxonium iodide (Aldrich; 557 mg, 2.532 mmol) in anhydrous DMSO (6.5 mL) was stirred under argon at 25° C. for 10 min. A solution of 8-bromo-2-(1-phenylvinyl)quinazoline (393.9 mg, 1.266 mmol) in DMSO (10.0 mL) was added (dropwise, over 8 min), and the resulting brown solution was stirred at 25° C. for 30 min. The reaction was diluted with water (20 mL) and 1.0N aq. HCl (1.2 mL), then partitioned between DCM (120 mL) and water (70 mL). The aq. layer was extracted with additional DCM (70 mL), and the combined organic extracts were dried over Na$_2$SO$_4$, filtered, and concentrated in vacuo. Chromatographic purification of the residue (silica gel, 0-40% EtOAc/hexanes) provided 8-bromo-2-(1-phenylcyclopropyl)quinazoline (153.8 mg, 0.473 mmol, 37% yield) as a light-yellow solid: $^1$H NMR (400 MHz, CDCl$_3$) δ ppm 9.18 (1H, s), 8.11 (1H, d, J=7.4 Hz), 7.78 (1H, d, J=8.0 Hz), 7.50 (2H, d, J=7.6 Hz), 7.38 (3H, td, J=7.6, 2.6 Hz), 7.30 (1H, t, J=7.4 Hz), 1.92-1.98 (2H, m), 1.51-1.55 (2H, m). m/z (ESI, +ve) 325.1 (M+H)$^+$.

Preparation of 244c: 8-(1-butoxyvinyl)-2-(1-phenyl-cyclopropyl)quinazoline

A solution of 8-bromo-2-(1-phenylcyclopropyl)quinazoline (153.8 mg, 0.473 mmol), diacetoxypalladium (10.62 mg, 0.047 mmol), potassium carbonate (131 mg, 0.946 mmol), 1,3-bis(diphenylphosphino)propane (42.9 mg, 0.104 mmol), and 1-(vinyloxy)butane (0.067 mL, 0.520 mmol) in a mixture of DMF (2.0 mL) and water (0.400 mL) was stirred under argon in a sealed tube at 70° C. for 3 d. The mixture was adsorbed onto silica gel (DMF was removed in vacuo). Chromatographic purification (silica gel, 0-30% EtOAc/hexanes) furnished 8-(1-butoxyvinyl)-2-(1-phenylcyclopropyl)quinazoline (100.0 mg, 0.290 mmol, 61% yield) as a colorless oil: $^1$H NMR (400 MHz, CDCl$_3$) δ ppm 9.21 (1H, s), 8.16 (1H, dd, J=7.4, 1.4 Hz), 7.73 (1H, dd, J=8.0, 1.4 Hz), 7.43-7.52 (2H, m), 7.32-7.40 (2H, m), 7.26-7.31 (2H, m), 5.32 (1H, d, J=2.0 Hz), 4.41 (1H, d, J=2.0 Hz), 3.81 (2H, t, J=6.5 Hz), 1.82-1.94 (4H, m), 1.69-1.80 (2H, m), 1.47-1.51 (2H, m), 0.93-1.03 (3H, m). m/z (ESI, +ve) 345.2 (M+H)$^+$.

Preparation of 244: 2-(2-(1-phenylcyclopropyl)quinazolin-8-yl)-6,7-dihydro-1H-pyrrolo[3,2-c]pyridin-4(5H)-one NBS (51.7 mg, 0.290 mmol) was added to a solution 8-(1-butoxyvinyl)-2-(1-phenylcyclopropyl)quinazoline (100.0 mg, 0.290 mmol) in THF (2.2 mL) and water (0.084 mL, 4.65 mmol) at 0° C. and the resulting solution was stirred at 0° C. for 2 min. The mixture was partitioned between Et$_2$O (50 mL) and water (30 mL). The organic layer was separated, sequentially washed with saturated aq. NaHCO$_3$ (20 mL), water (20 mL), and brine (20 mL), dried over Na$_2$SO$_4$, filtered, and concentrated in vacuo to provide crude 2-bromo-1-(2-(1-phenylcyclopropyl)quinazolin-8-yl)ethanone (124.8 mg) as a light-yellow oil. NH$_4$OAc (90 mg, 1.161 mmol) and piperi-dine-2,4-dione (39.4 mg, 0.348 mmol) were added to the resulting oil, and the mixture was taken up in EtOH (2.2 mL) and stirred under argon in a sealed flask at 50° C. for 15.5 h. The reaction was cooled to 25° C. and concentrated in vacuo. The residue was partitioned between DCM (50 mL) and saturated aq. NaHCO$_3$ (30 mL). The aq. layer was extracted with DCM (2×30 mL), and the combined organic extracts were dried over Na$_2$SO$_4$, filtered, and concentrated in vacuo. Chromatographic purification of the residue (silica gel, 0-10% MeOH/DCM) furnished 2-(2-(1-phenylcyclopropyl)quinazolin-8-yl)-6,7-dihydro-1H-pyrrolo[3,2-c]pyridin-4(5H)-one (35.3 mg, 0.093 mmol, 32% yield) as a yellow-orange solid: $^1$H NMR (400 MHz, CDCl$_3$) δ ppm 11.24 (1H, br. s.), 9.28 (1H, s), 8.16 (1H, d, J=7.6 Hz), 7.66 (1H, d, J=7.8 Hz), 7.52-7.58 (3H, m), 7.46 (2H, t, J=7.3 Hz), 7.39 (1H, t, J=7.2 Hz), 7.11 (1H, d, J=2.2 Hz), 5.45 (1H, br. s.), 3.51 (2H, td, J=7.0, 2.1 Hz), 2.49 (2H, t, J=6.9 Hz), 1.95 (2H, q, J=3.6 Hz), 1.51 (2H, q, J=3.6 Hz). m/z (ESI, +ve) 381.2 (M+H)$^+$.

Example 249 rac-2-(3-(isopropylamino)-2-methylquinoxalin-5-yl)-7-methyl-6,7-dihydro-1H-pyrrolo[3,2-c]pyridin-4(5H)-one

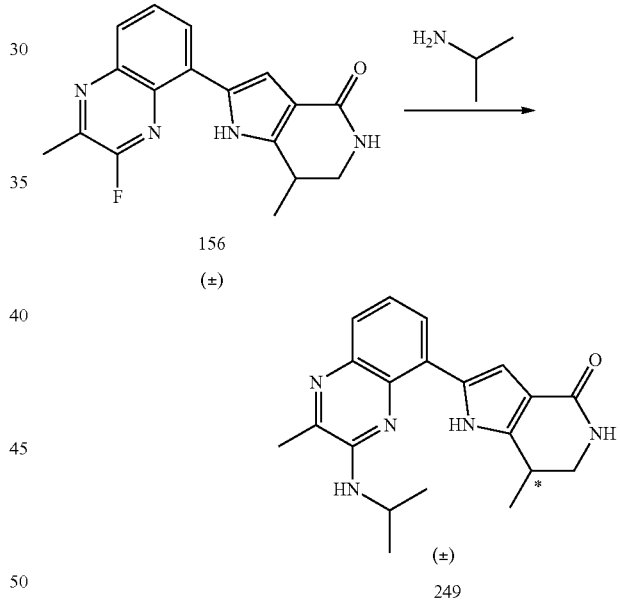

A solution of rac-2-(3-fluoro-2-methylquinoxalin-5-yl)-7-methyl-6,7-dihydro-1H-pyrrolo[3,2-c]pyridin-4(5H)-one (Example 156; 27.8 mg, 0.090 mmol) and isopropylamine (0.023 mL, 0.269 mmol) in DMSO (0.8 mL) was heated under argon in a sealed flask at 60° C. for 1 h. The reaction was cooled to 25° C. and diluted with water (10 mL). The precipitated solid was collected by vacuum filtration, washed with water (2×5 mL), and dried in vacuo to provide rac-2-(3-(isopropylamino)-2-methylquinoxalin-5-yl)-7-methyl-6,7-dihydro-1H-pyrrolo[3,2-c]pyridin-4(5H)-one (19.6 mg, 0.056 mmol, 63% yield) as a yellow solid: $^1$H NMR (400 MHz, DMSO-d$_6$) δ ppm 12.02 (1H, br. s.), 7.90 (1H, d, J=7.2 Hz), 7.56 (1H, d, J=7.4 Hz), 7.31 (1H, t, J=7.8 Hz), 7.03 (1H, d, J=1.8 Hz), 6.97 (1H, br. s.), 6.89 (1H, d, J=7.2 Hz), 4.35 (1H, dq, J=13.3, 6.4 Hz), 3.46 (1H, dt, J=10.0, 3.4 Hz), 3.05-3.19 (2H, m), 2.54 (3H, s), 1.36 (3H, d, J=6.5 Hz), 1.32 (3H, d, J=6.5 Hz), 1.29 (3H, d, J=6.3 Hz). m/z (ESI, +ve) 350.1 (M+H)+.

Example 251

2-(2-(phenylamino)quinazolin-8-yl)-6,7-dihydro-1H-pyrrolo[3,2-c]pyridin-4(5H)-one

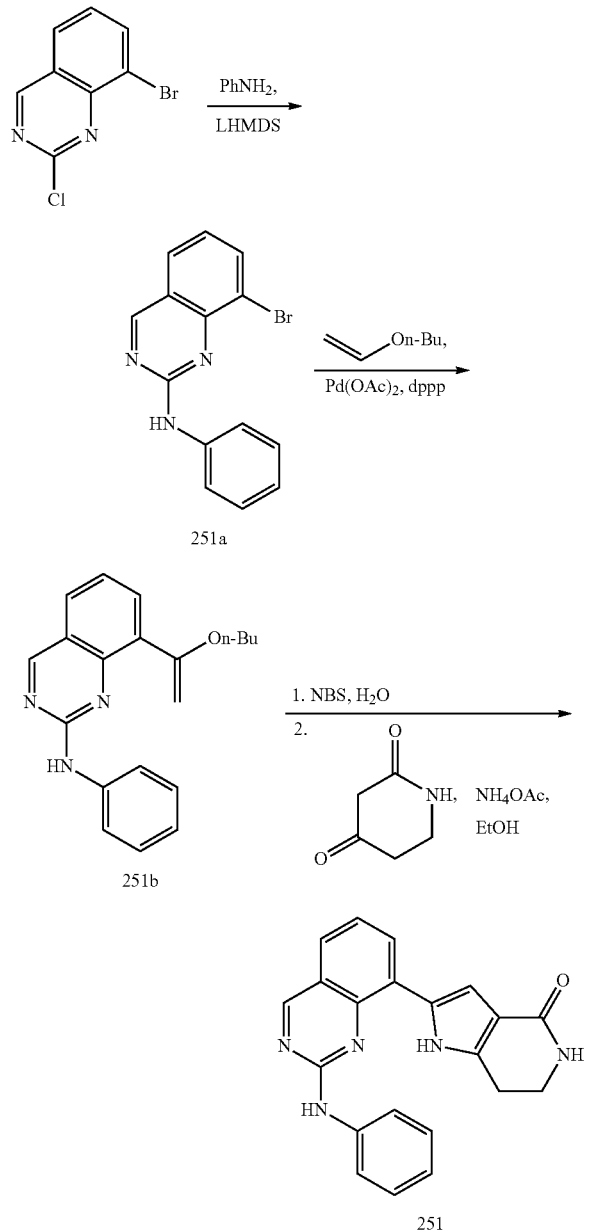

Preparation of 251a:
8-bromo-N-phenylquinazolin-2-amine

LHMDS (1.0M in THF; 4.11 mL, 4.11 mmol) was added to a solution of 8-bromo-2-chloroquinazoline (Ark Pharm, Inc., Libertyville, Ill.; 500 mg, 2.053 mmol) and aniline (0.337 mL, 3.70 mmol) in THF (10 mL) at 0° C., and the resulting solution was stirred at 0° C. for 10 min. Saturated aq. NH4Cl (10 mL) was added, and the resulting mixture was partitioned between EtOAc (50 mL) and additional saturated aq. NH4Cl (30 mL). The organic layer was separated, washed with brine (30 mL), dried over Na2SO4, filtered and concentrated in vacuo. Chromatographic purification of the residue (silica gel, 0-10% MeOH/DCM) furnished 8-bromo-N-phenylquinazolin-2-amine (616 mg, 2.052 mmol, 100% yield) as a yellow solid: m/z (ESI, +ve) 300.0 (M+H)+.

Preparation of 251b:
8-(1-butoxyvinyl)-N-phenylquinazolin-2-amine

A solution of 8-bromo-N-phenylquinazolin-2-amine (310.3 mg, 1.034 mmol), diacetoxypalladium (23.21 mg, 0.103 mmol), potassium carbonate (286 mg, 2.068 mmol), 1,3-bis(diphenylphosphino)propane (94 mg, 0.227 mmol), and 1-(vinyloxy)butane (0.147 mL, 1.137 mmol) in a mixture of DMF (4.0 mL) and water (0.800 mL) was stirred under argon in a sealed tube at 70° C. for 3 d. The mixture was adsorbed onto silica gel (DMF was removed in vacuo). Chromatographic purification (silica gel, 0-50% EtOAc/hexanes, 20 min, 254 nm) furnished 8-(1-butoxyvinyl)-N-phenylquinazolin-2-amine (220 mg, 0.689 mmol, 67% yield) as a yellow solid: $^1$H NMR (400 MHz, CDCl$_3$) δ ppm 9.06 (1H, s), 7.95 (1H, s), 7.90 (2H, d, J=8.2 Hz), 7.68 (1H, d, J=8.0 Hz), 7.34-7.37 (2H, m), 7.33 (1H, br. d, J=3.8 Hz), 7.31 (1H, d, J=7.8 Hz), 7.05 (1H, t, J=7.3 Hz), 4.99 (1H, d, J=1.0 Hz), 4.64 (1H, s), 3.99 (2H, t, J=6.7 Hz), 1.81 (2H, quin, J=7.1 Hz), 1.50 (2H, sxt, J=7.5 Hz), 0.96 (3H, t, J=7.4 Hz). m/z (ESI, +ve) 320.1 (M+H)+.

Preparation of 251: 2-(2-(phenylamino)quinazolin-8-yl)-6,7-dihydro-1H-pyrrolo[3,2-c]pyridin-4(5H)-one NBS (58.2 mg, 0.327 mmol) was added to a solution 8-(1-butoxyvinyl)-N-phenylquinazolin-2-amine (104.5 mg, 0.327 mmol) in THF (2.4 mL) and water (0.094 mL, 5.23 mmol) at 0° C. and the resulting mixture was stirred at 0° C. for 2 min. The mixture was partitioned between Et2O (50 mL) and water (30 mL). The organic layer was separated, sequentially washed with saturated aq. NaHCO3 (20 mL), water (20 mL), and brine (20 mL), dried over Na2SO4, filtered, and concentrated in vacuo to provide crude 2-bromo-1-(2-(phenylamino)quinazolin-8-yl)ethanone (140 mg) as a yellow-orange oil. NH4OAc (101 mg, 1.309 mmol) and piperidine-2,4-dione (44.4 mg, 0.393 mmol) were added to the resulting oil, and the mixture was taken up in EtOH (2.4 mL) and stirred under argon in a sealed flask at 50° C. for 15.5 h. The reaction was cooled to 25° C. and concentrated in vacuo. The residue was partitioned between DCM (50 mL) and saturated aq. NaHCO3 (30 mL). The aq. layer was extracted with DCM (3×30 mL), and the combined extracts were dried over Na2SO4, filtered, and concentrated in vacuo. Chromatographic purification of the residue (silica gel, 0-10% MeOH/DCM) furnished 2-(2-(phenylamino)quinazolin-8-yl)-6,7-dihydro-1H-pyrrolo[3,2-c]pyridin-4(5H)-one (21.3 mg, 0.060 mmol, 18% yield) as a yellow-orange solid: $^1$H NMR (400 MHz, DMSO-d$_6$) δ ppm 11.99 (1H, br. s.), 9.97 (1H, s), 9.35 (1H, s), 8.14 (1H, d, J=7.6 Hz), 7.78 (3H, t, J=7.4 Hz), 7.34-7.45 (4H, m), 7.10 (1H, t, J=7.0 Hz), 7.03-7.07 (1H, m), 3.43 (2H, t, J=6.9 Hz), 2.79 (2H, t, J=6.6 Hz). m/z (ESI, +ve) 356.3 (M+H)+.

Example 252 rac-7-methyl-2-(2-methyl-3-(methylamino)quinoxa-lin-5-yl)-6,7-dihydro-1H-pyrrolo[3,2-c]pyridin-4(5H)-one

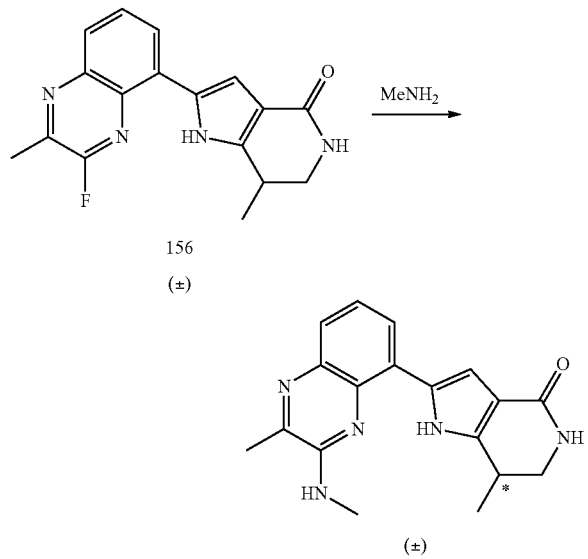

156
(±)

A solution of rac-2-(3-fluoro-2-methylquinoxalin-5-yl)-7-methyl-6,7-dihydro-1H-pyrrolo[3,2-c]pyridin-4(5H)-one (Example 156; 32.7 mg, 0.105 mmol) and methylamine (2.0M in THF; 0.158 mL, 0.316 mmol) in DMSO (0.8 mL) was stirred under argon in a sealed flask at 25° C. for 10 min, then at 60° C. for 1 h. The reaction was cooled to 25° C. and diluted with water (10 mL). The precipitated solid was collected by vacuum filtration, washed with water (2×5 mL), and dried in vacuo to provide rac-7-methyl-2-(2-methyl-3-(methylamino)quinoxalin-5-yl)-6,7-dihydro-1H-pyrrolo[3,2-c]pyridin-4(5H)-one (21.0 mg, 0.065 mmol, 62% yield) as a yellow solid: $^1$H NMR (400 MHz, DMSO-$d_6$) δ ppm 12.24 (1H, br. s.), 7.93 (1H, d, J=7.4 Hz), 7.57 (1H, d, J=7.8 Hz), 7.45 (1H, d, J=4.3 Hz), 7.32 (1H, t, J=7.8 Hz), 7.04 (1H, s), 6.99 (1H, br. s.), 3.43 (1H, dt, J=11.0, 4.0 Hz), 3.09-3.21 (2H, m), 3.07 (3H, s), 2.52 (3H, s), 1.30 (3H, d, J=6.5 Hz). m/z (ESI, +ve) 322.1 (M+H)$^+$.

Example 253 rac-2-(3-(dimethylamino)-2-methylquinoxalin-5-yl)-7-methyl-6,7-dihydro-1H-pyrrolo[3,2-c]pyridin-4(5H)-one

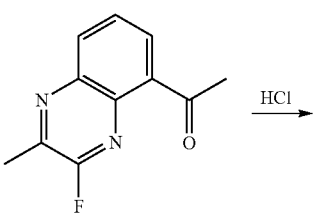

156
(±)

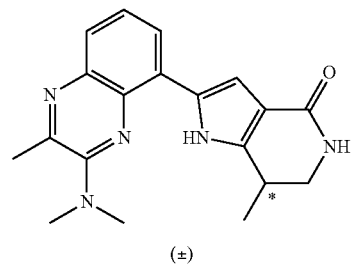

(±)

A solution of rac-2-(3-fluoro-2-methylquinoxalin-5-yl)-7-methyl-6,7-dihydro-1H-pyrrolo[3,2-c]pyridin-4(5H)-one (Example 156; 32.0 mg, 0.103 mmol) and dimethylamine (2.0M in THF; 0.155 mL, 0.309 mmol) in DMSO (0.8 mL) was stirred under argon in a sealed microwave flask at 25° C. for 10 min, then at 60° C. for 18 h. Additional dimethylamine (2.0M in THF; 0.155 mL, 0.309 mmol) was added, and the resulting mixture was stirred under argon in a sealed microwave flask at 60° C. for 4.5 h. The reaction was cooled to 25° C. and diluted with water (10 mL). The precipitated solid was collected by vacuum filtration, washed with water (2×5 mL), and dried in vacuo to provide rac-2-(3-(dimethylamino)-2-methylquinoxalin-5-yl)-7-methyl-6,7-dihydro-1H-pyrrolo[3,2-c]pyridin-4(5H)-one (22.7 mg, 0.068 mmol, 66% yield) as a yellow-orange solid: $^1$H NMR (400 MHz, DMSO-$d_6$) δ ppm 11.81 (1H, br. s.), 7.96 (1H, dd, J=7.5, 1.1 Hz), 7.66 (1H, dd, J=8.1, 0.9 Hz), 7.47 (1H, t, J=7.8 Hz), 7.08 (1H, d, J=2.2 Hz), 6.99 (1H, br. s.), 3.40-3.49 (1H, m), 3.13-3.15 (6H, m), 3.06-3.18 (2H, m), 2.71 (3H, s), 1.30 (3H, d, J=6.5 Hz). m/z (ESI, +ve) 336.2 (M+H)$^+$.

Example 254

2-(2-methyl-3-((1,1,1-trifluoro-2-methylpropan-2-yl)amino)quinoxalin-5-yl)-6,7-dihydro-1H-pyrrolo[3,2-c]pyridin-4(5H)-one

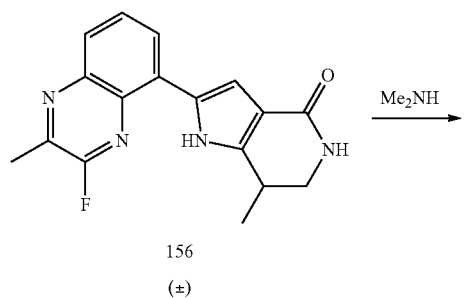

126g

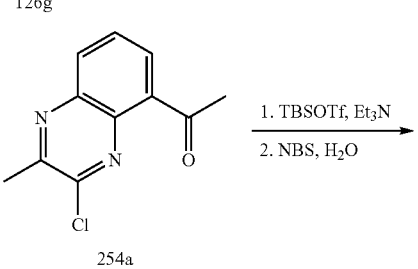

254a

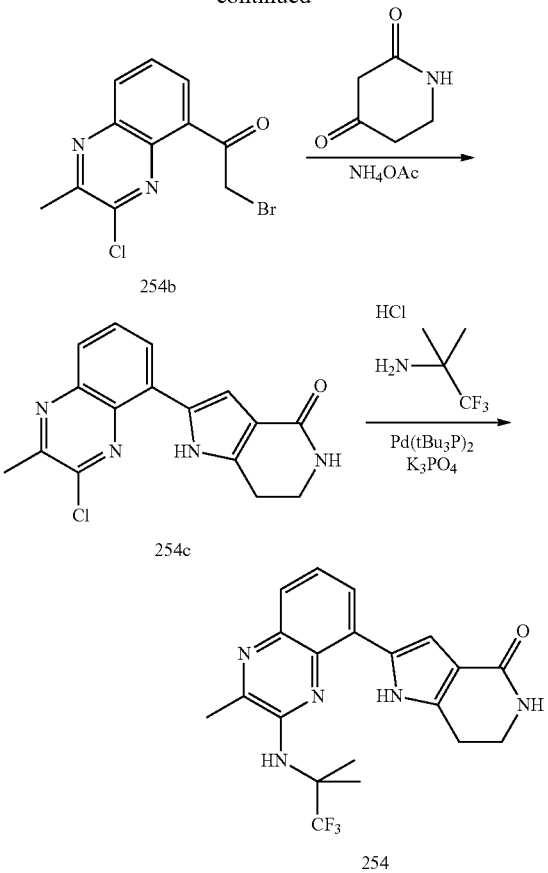

Preparation of 254a: 1-(3-chloro-2-methylquinoxalin-5-yl)ethanone 1-(3-Fluoro-2-methylquinoxalin-5-yl)ethanone (126g, 2.00 g, 9.79 mmol) was treated with HCl (4.0 M solution in 1,4-dioxane; 24.49 ml, 98 mmol), and the homogeneous reaction was fitted with a drying tube. After 6 h the reaction was concentrated in vacuo, and the solid was taken up in DCM. Solid $NaHCO_3$ was added cautiously with rapid stirring; and saturated aq. $NaHCO_3$ was sequentially added cautiously with rapid stirring. The mixture was partitioned between saturated $NaHCO_3$ and DCM. The aq. layer was extracted with DCM (2×), and the combined organics were dried over anhydrous $Na_2SO_4$, filtered, and concentrated in vacuo to give 1-(3-chloro-2-methylquinoxalin-5-yl)ethanone (254a, 99% yield) as an orange-brown solid. MS (ESI, pos. ion) m/z: 221.0 (M+1).

Preparation of 254b: 2-bromo-1-(3-chloro-2-methylquinoxalin-5-yl)ethanone

A solution of 1-(3-chloro-2-methylquinoxalin-5-yl)ethanone (2.13 g, 9.65 mmol), $Et_3N$ (4.04 ml, 29.0 mmol), and TBSOTf (3.33 ml, 14.48 mmol) in DCM (97 ml) at 0° C. was stirred for 30 min. The mixture was diluted with DCM (100 ml), and washed with saturated aq. $NaHCO_3$ (2×75 ml) before the organic layer was separated, dried over $Na_2SO_4$, and concentrated to provide the silyl enol ether as an oil. MS (ESI, pos. ion) m/z: 335.1 (M+1). A solution of the resulting oil, 1-bromopyrrolidine-2,5-dione (1.718 g, 9.65 mmol), and water (2.78 ml, 154 mmol) in THF (97 ml) was stirred at 0° C. for 30. The mixture was diluted with DCM (100 ml), added to a separatory funnel, and washed with saturated aq. $NaHCO_3$ (2×75 ml) before the organic layer was separated, and dried over $Na_2SO_4$. Purification by silica gel (100% hexanes to 3% EtOAc in hexanes) provided 2-bromo-1-(3-chloro-2-methylquinoxalin-5-yl)ethanone (254b, 54% yield) as a light yellow solid. MS (ESI, pos. ion) m/z: 299.0 (M+1).

Preparation of 254c: 2-(3-chloro-2-methylquinoxalin-5-yl)-6,7-dihydro-1H-pyrrolo[3,2-c]pyridin-4(5H)-one A mixture of 2-bromo-1-(3-chloro-2-methylquinoxalin-5-yl)ethanone (1.57 g, 5.24 mmol), piperidine-2,4-dione (0.889 g, 7.86 mmol), and $NH_4OAc$ (2.020 g, 26.2 mmol) in EtOH (52 ml) was stirred at 50° C. for 2.5 d. The mixture was concentrated and was diluted with DCM (200 ml), added to a separatory funnel, and washed with saturated aq. $NaHCO_3$ (2×100 ml) before the organic layer was separated, dried over $Na_2SO_4$, and concentrated. Purification by silica gel (100% DCM to 4% 2 M $NH_3$ in MeOH/DCM) provided 2-(3-chloro-2-methylquinoxalin-5-yl)-6,7-dihydro-1H-pyrrolo[3,2-c]pyridin-4(5H)-one (254c, 26% yield) as a yellow solid. MS (ESI, pos. ion) m/z: 313.2 (M+1).

Preparation of 254: 2-(2-methyl-3-((1,1,1-trifluoro-2-methylpropan-2-yl)amino)quinoxalin-5-yl)-6,7-dihydro-1H-pyrrolo[3,2-c]pyridin-4(5H)-one A mixture of 2-(3-chloro-2-methylquinoxalin-5-yl)-6,7-dihydro-1H-pyrrolo[3,2-c]pyridin-4(5H)-one (254c, 85 mg, 0.272 mmol), 1,1,1-trifluoro-2-methylpropan-2-amine hydrochloride (178 mg, 1.087 mmol, Oakwood Products, West Columbia, S.C.), $Pd(tBu_3P)_2$ (Strem, Newburyport, Mass.; 13.89 mg, 0.027 mmol), and $K_2PO_4$ (346 mg, 1.631 mmol) in DMA (2718 µl) was stirred at 120° C. for 5 h; the reaction was then heated to 145° C. for 2.5 d. The mixture was diluted with DCM (100 ml), and washed with saturated aq. $NaHCO_3$ (2×75 ml) before the organic layer was separated, dried over $Na_2SO_4$, and concentrated. Purification by silica gel (100% DCM to 5% 2 M $NH_3$ in MeOH/DCM) then by rpHPLC (Phenomenex Gemini $C_{18}$, 10 µm, 150×30 mm; 10-100% ACN/water with 0.1% TFA) provided 2-(2-methyl-3-((1,1,1-trifluoro-2-methylpropan-2-yl)amino)quinoxalin-5-yl)-6,7-dihydro-1H-pyrrolo[3,2-c]pyridin-4(5H)-one (254, 2% yield) as a yellow solid. MS (ESI, pos. ion) m/z: 404.1 (M+1). $^1$H NMR (400 MHz, $CDCl_3$) δ ppm 1.81 (s, 6H) 2.63 (s, 3H) 2.97 (t, J=6.94 Hz, 2H) 3.66 (td, J=6.85, 2.54 Hz, 2H) 4.77 (s, 1H) 5.29 (br. s., 1H) 7.10 (d, J=2.15 Hz, 1H) 7.46 (t, J=7.92 Hz, 1H) 7.70 (dd, J=8.12, 1.27 Hz, 1H) 7.95 (dd, J=7.63, 1.37 Hz, 1H) 11.79 (br. s., 1H). $^{19}$F NMR (376 MHz, DMSO-$d_6$) δ ppm −78.37 (3F, s).

Example 255

(S)-2-(2-methyl-3-((1,1,1-trifluoropropan-2-yl)amino)quinoxalin-5-yl)-6,7-dihydro-1H-pyrrolo[3,2-c]pyridin-4(5H)-one

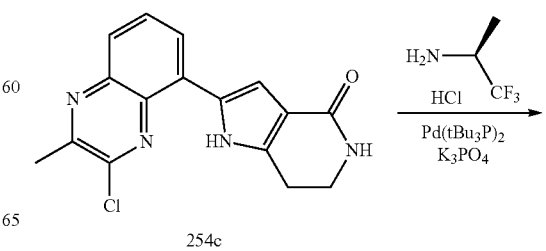

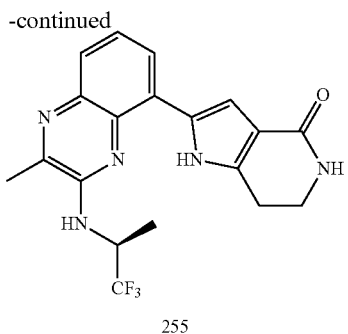

255

Prepared similarly to that described in Example 254 using 2-(3-chloro-2-methylquinoxalin-5-yl)-6,7-dihydro-1H-pyrrolo[3,2-c]pyridin-4(5H)-one (Example 254c; 34 mg, 0.109 mmol), (S)-1,1,1-trifluoropropan-2-amine hydrochloride (32.5 mg, 0.217 mmol, SynQuest Laboratories, Alachua, Fla.), Pd(tBu$_3$P)$_2$ (Strem, Newburyport, Mass.; 5.56 mg, 10.87 µmol), and K$_3$PO$_4$ (92 mg, 0.435 mmol), heating at 100° C. for 2 h. Purification by silica gel (100% DCM to 4% 2 M NH$_3$ in MeOH/DCM) then by rpHPLC (Phenomenex Gemini C$_{18}$, 10 pan, 150×30 mm; 10-100% ACN/water with 0.1% TFA) provided (S)-2-(2-methyl-3-((1,1,1-trifluoropropan-2-yl)amino)quinoxalin-5-yl)-6,7-dihydro-1H-pyrrolo[3,2-c]pyridin-4(5H)-one (16% yield). MS (ESI, pos. ion) m/z: 390.2 (M+1). $^1$H NMR (400 MHz, CDCl$_3$) δ ppm 1.61 (d, J=6.85 Hz, 3H) 2.66 (s, 3H) 2.96 (t, J=6.85 Hz, 2H) 3.66 (td, J=6.85, 2.54 Hz, 2H) 4.85 (s, 1H) 4.86-4.96 (m, 1H) 5.35 (br. s., 1H) 7.12 (d, J=2.35 Hz, 1H) 7.47 (t, J=7.82 Hz, 1H) 7.73 (dd, J=8.12, 1.27 Hz, 1H) 7.94 (dd, J=7.63, 1.17 Hz, 1H) 11.60 (br. s., 1H). $^{19}$F NMR (376 MHz, DMSO-d$_6$) δ ppm -76.30 (3F, s).

Example 256

(R)-2-(2-methyl-3-((1,1,1-trifluoropropan-2-yl)amino)quinoxalin-5-yl)-6,7-dihydro-1H-pyrrolo[3,2-c]pyridin-4(5H)-one

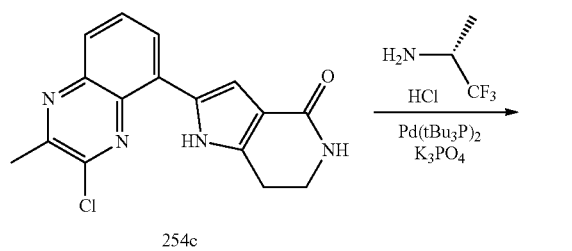

254c

256

Prepared similarly to that described in Example 254 using 2-(3-chloro-2-methylquinoxalin-5-yl)-6,7-dihydro-1H-pyrrolo[3,2-c]pyridin-4(5H)-one (Example 254c; 47 mg, 0.150 mmol), (R)-1,1,1-trifluoropropan-2-amine hydrochloride (44.9 mg, 0.301 mmol, SynQuest Laboratories, Alachua, Fla.), Pd(tBu$_3$P)$_2$ (Strem, Newburyport, Mass.; 7.68 mg, 0.015 mmol), and K$_3$PO$_4$ (128 mg, 0.601 mmol), heating at 100° C. for 18 h. Purification by silica gel (100% DCM to 4% 2 M NH$_3$ in MeOH/DCM) then by rpHPLC (Phenomenex Gemini C18, 10 µm, 150×30 mm; 10-100% ACN/water with 0.1% TFA) provided (R)-2-(2-methyl-3-((1,1,1-trifluoropropan-2-yl)amino)quinoxalin-5-yl)-6,7-dihydro-1H-pyrrolo[3,2-c]pyridin-4(5H)-one (10% yield). MS (ESI, pos. ion) m/z: 390.2 (M+1). $^1$H NMR (400 MHz, CDCl$_3$) δ ppm 1.61 (br. s., 3H) 2.66 (s, 3H) 2.96 (t, J=6.85 Hz, 2H) 3.66 (td, J=6.90, 2.45 Hz, 2H) 4.81 (s, 1H) 4.91 (dq, J=14.04, 6.93 Hz, 1H) 5.29 (br. s., 1H) 7.12 (d, J=2.15 Hz, 1H) 7.48 (t, J=7.82 Hz, 1H) 7.73 (d, J=7.04 Hz, 1H) 7.95 (dd, J=7.63, 1.17 Hz, 1H) 11.59 (br. s., 1H). $^{19}$F NMR (376 MHz, DMSO-d$_6$) δ ppm -76.30 (3F, s).

Example 257

2-(2-methylquinoxalin-5-yl)-6,7-dihydro-1H-pyrrolo[3,2-c]pyridin-4(5H)-one

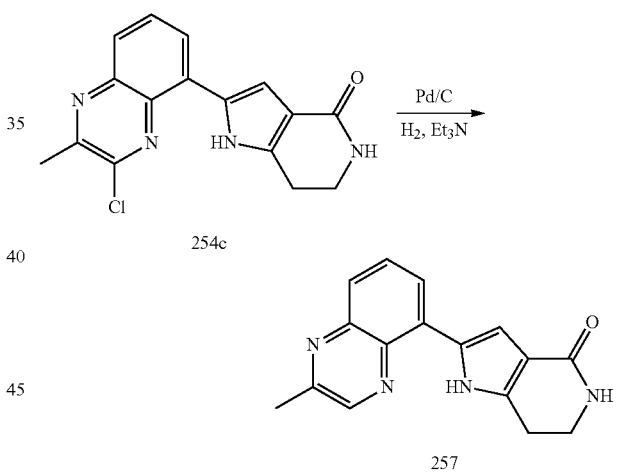

254c

257

A mixture of 2-(3-chloro-2-methylquinoxalin-5-yl)-6,7-dihydro-1H-pyrrolo[3,2-c]pyridin-4(5H)-one (23 mg, 0.074 mmol), Et$_3$N (20.50 µl, 0.147 mmol), and 10% Pd/C (wet; 8.71 mg, 0.074 mmol) in EtOH (735 µl) was stirred at RT under H$_2$ gas (10 psi). After stirring for 1.5 h, the mixture was filtered and washed with MeOH. The solution was stirred open to air for 16 h. Purification by silica gel (100% DCM to 4% [2 M NH$_3$ in MeOH]/DCM) then by rpHPLC (Phenomenex Gemini C$_{18}$, 10 µm, 150×30 mm; 10-100% ACN/water with 0.1% TFA) provided 2-(2-methylquinoxalin-5-yl)-6,7-dihydro-1H-pyrrolo[3,2-c]pyridin-4(5H)-one (39% yield) as a yellow solid. MS (ESI, pos. ion) m/z: 279.0 (M+1). $^1$H NMR (400 MHz, CDCl$_3$) δ ppm 2.81 (s, 3H) 3.05 (t, J=6.94 Hz, 2H) 3.67 (td, J=6.94, 2.54 Hz, 2H) 5.36 (br. s., 1H) 7.25-7.26 (m, 1H) 7.74 (t, J=8.02 Hz, 1H) 7.84 (dd, J=8.41, 1.17 Hz, 1H) 8.08 (dd, J=7.63, 1.17 Hz, 1H) 8.72 (s, 1H) 12.09 (br. s., 1H).

Example 258

2-(2-methyl-3-((1-(trifluoromethyl)cyclopropyl)amino)quinoxalin-5-yl)-6,7-dihydro-1H-pyrrolo[3,2-c]pyridin-4(5H)-one

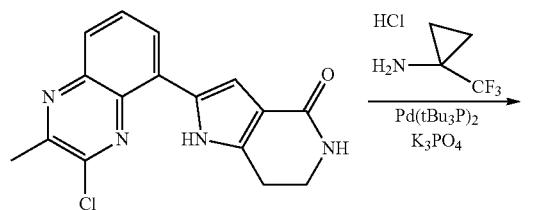

254c

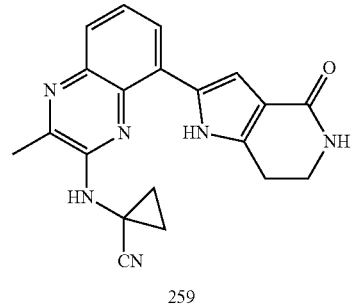

258

Prepared similarly to that described in Example 254 using 2-(3-chloro-2-methylquinoxalin-5-yl)-6,7-dihydro-1H-pyrrolo[3,2-c]pyridin-4(5H)-one (Example 254c; 23 mg, 0.074 mmol), 1-(trifluoromethyl)cyclopropanamine hydrochloride (47.5 mg, 0.294 mmol, Astatech, Inc., Bristol, Pa.), Pd(tBu₃P)₂ (Strem, Newburyport, Mass.; 3.76 mg, 7.35 µmol), and K₃PO₄ (94 mg, 0.441 mmol), heating at 120° C. for 16 h. Purification by silica gel (100% DCM to 3% 2 M NH₃ in MeOH/DCM) then by rpHPLC (Phenomenex Gemini C₁₈, 10 µm, 150×30 mm; 10-100% ACN/water with 0.1% TFA) provided 2-(2-methyl-3-((1-(trifluoromethyl)cyclopropyl)amino)quinoxalin-5-yl)-6,7-dihydro-1H-pyrrolo[3,2-c]pyridin-4(5H)-one (14% yield). MS (ESI, pos. ion) m/z: 402.2 (M+1). ¹H NMR (400 MHz, CDCl₃) δ ppm 1.29-1.33 (m, 2H) 1.58-1.62 (m, 2H) 2.62 (s, 3H) 2.95 (t, J=6.85 Hz, 2H) 3.66 (td, J=6.85, 2.54 Hz, 2H) 5.31 (br. s., 1H) 5.45 (s, 1H) 7.17 (d, J=2.15 Hz, 1H) 7.48 (t, J=7.63, 1 H) 7.71 (dd, J=8.12, 1.27 Hz, 1H) 7.99 (dd, J=7.53, 1.27 Hz, 1H) 12.47 (br. s., 1H). ¹⁹F NMR (376 MHz, DMSO-d₆) δ ppm −72.08 (3F, s).

Example 259

1-((3-methyl-8-(4-oxo-4,5,6,7-tetrahydro-1H-pyrrolo[3,2-c]pyridin-2-yl)quinoxalin-2-yl)amino)cyclopropanecarbonitrile

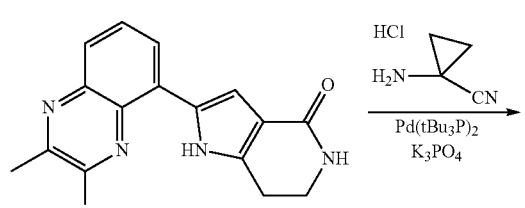

254c

Prepared similarly to that described in Example 254 using 2-(3-chloro-2-methylquinoxalin-5-yl)-6,7-dihydro-1H-pyrrolo[3,2-c]pyridin-4(5H)-one (Example 254c; 65 mg, 0.208 mmol), 1-aminocyclopropanecarbonitrile hydrochloride (99 mg, 0.831 mmol; Alfa Aesar, Ward Hill, Mass.), Pd(tBu₃P)₂ (Strem, Newburyport, Mass.; 10.62 mg, 0.021 mmol), and K₃PO₄ (265 mg, 1.247 mmol), heating at 120° C. for 16 h. Purification by silica gel (100% DCM to 5% 2 M NH₃ in MeOH/DCM) provided 14(3-methyl-8-(4-oxo-4,5,6,7-tetrahydro-1H-pyrrolo[3,2-c]pyridin-2-yl)quinoxalin-2-yl)amino)cyclopropanecarbonitrile (23% yield). MS (ESI, pos. ion) m/z: 359.1 (M+1). ¹H NMR (400 MHz, CDCl₃) δ ppm 1.42-1.46 (m, 2H) 1.71-1.76 (m, 2H) 2.60 (s, 3H) 3.07 (t, J=6.85 Hz, 2H) 3.65 (td, J=6.85, 2.54 Hz, 2H) 5.28 (br. s., 1H) 5.62 (br. s., 1H) 7.17 (d, J=2.15 Hz, 1H) 7.53 (t, J=7.92 Hz, 1H) 7.75 (d, J=8.02 Hz, 1H) 8.02 (d, J=7.63 Hz, 1H) 12.10 (br. s., 1H).

Example 260

6-(3-(cyclobutylamino)-2-methylquinoxalin-5-yl)-3H-pyrrolo[2,3-d]pyrimidin-4(7H)-one

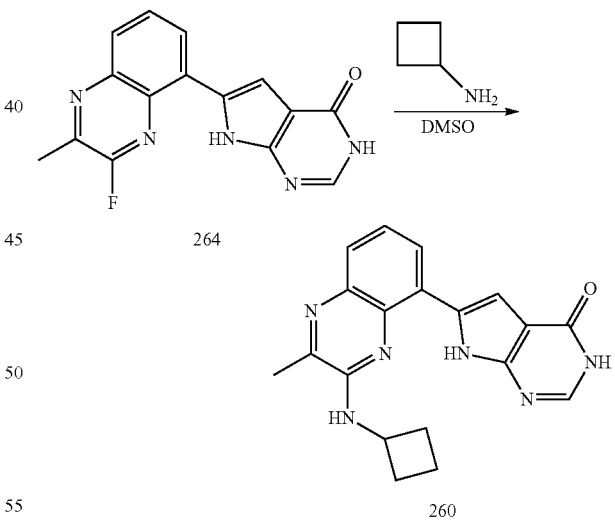

A glass microwave reaction vessel was charged with 6-(3-fluoro-2-methylquinoxalin-5-yl)-3H-pyrrolo[2,3-d]pyrimidin-4(7H)-one (Example 264; 60 mg, 0.203 mmol) and cyclobutylamine (0.173 mL, 2.032 mmol) in DMSO (0.6 mL). The reaction was heated in an oil bath at 50° C. for 15 min. The mixture was purified by rpHPLC (Phenomenex Gemini C₁₈ column (100×50 mm, 10 µm), 90 mL/min, 5-40% ACN in water with 0.1% TFA). Product-containing fractions were combined and ACN was removed in vacuo. The residual mixture was neutralized with saturated aq. NaHCO₃, and the suspension was filtered and dried to give 6-(3-(cyclobutylamino)-2-methylquinoxalin-5-yl)-3H-pyrrolo[2,3-d]pyrimidin-4(7H)-one (15 mg, 0.043 mmol, 21% yield) as a yellow solid. MS (ESI, pos. ion) m/z: 347.1 (M+1); ¹H NMR (400 MHz, DMSO-d₆) δ ppm 12.69 (brs, 1H), 11.97 (brs, 1H), 8.10 (1H, d, J=7.2 Hz), 7.90 (1H, br. s.), 7.66 (1H, d, J=7.0 Hz), 7.47 (1H, br. s.), 7.37 (2H, br. s.), 4.50 (1H, br. s.), 2.58 (3H, br. s.), 2.16-2.28 (2H, m), 1.83-1.97 (2H, m).

Example 261

6-(3-(tert-butylamino)-2-methylquinoxalin-5-yl)-3H-pyrrolo[2,3-d]pyrimidin-4(7H)-one

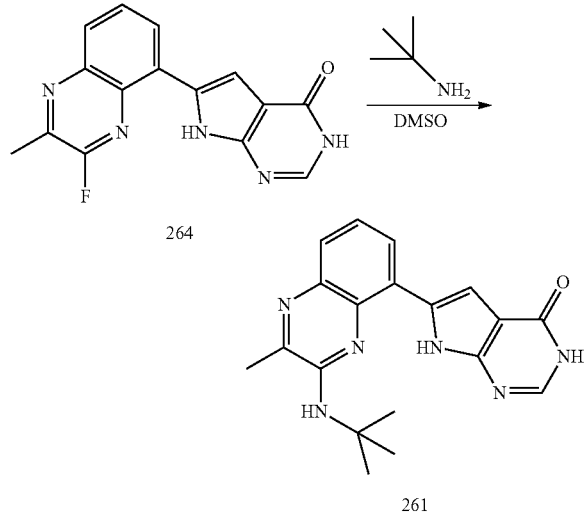

Prepared similarly to that described in Example 260 using 6-(3-fluoro-2-methylquinoxalin-5-yl)-3H-pyrrolo[2,3-d]pyrimidin-4(7H)-one (Example 264; 60 mg, 0.203 mmol) and tert-butylamine (0.214 mL, 2.032 mmol) in DMSO (2 mL) at RT for 30 min. The mixture was purified with rpHPLC (Phenomenex Gemini C₁₈ column (100×50 mm, 10 μm), 90 mL/min, 5-40% ACN in water with 0.1% TFA) to give 6-(3-(tert-butylamino)-2-methylquinoxalin-5-yl)-3H-pyrrolo[2,3-d]pyrimidin-4(7H)-one (13.0 mg, 0.037 mmol, 18% yield) as a yellow solid. MS (ESI, pos. ion) m/z: 349.1 (M+1); ¹H NMR (400 MHz, DMSO-d₆) δ ppm 12.34 (brs, 1H), 11.87 (brs, 1H); 7.99 (1H, d, J=6.8 Hz), 7.87 (1H, s), 7.66 (1H, d, J=7.0 Hz), 7.38 (1H, t, J=7.8 Hz), 7.27 (1H, s), 6.08 (1H, s), 2.57 (3H, s), 1.58 (9H, s).

Example 263

6-(3-((1-hydroxy-2-methylpropan-2-yl)amino)-2-methylquinoxalin-5-yl)-3H-pyrrolo[2,3-d]pyrimidin-4(7H)-one

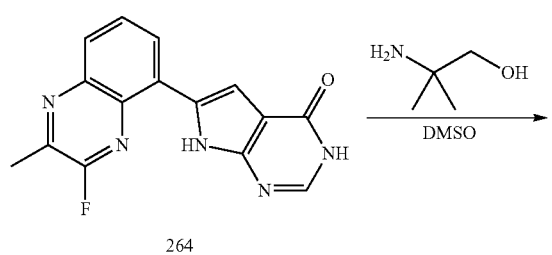

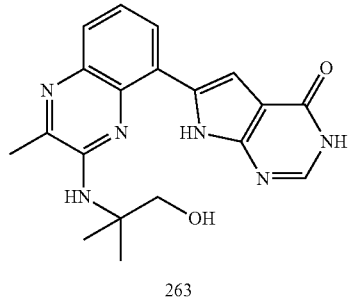

263

Prepared similarly to that described in Example 260 using 6-(3-fluoro-2-methylquinoxalin-5-yl)-3H-pyrrolo[2,3-d]pyrimidin-4(7H)-one (Example 264; 60 mg, 0.203 mmol) and 2-amino-2-methylpropanol (81 μl, 0.847 mmol, Sigma-Aldrich) in DMSO (2 mL) at 50° C. for 20 min. The mixture was purified by rpHPLC (Phenomenex Gemini C₁₈ column (100× 50 mm, 10 μm), 90 mL/min, 5-30% ACN in water with 0.1% TFA) to give 6-(3-((1-hydroxy-2-methylpropan-2-yl)amino)-2-methylquinoxalin-5-yl)-3H-pyrrolo[2,3-d]pyrimidin-4(7H)-one (8.0 mg, 0.022 mmol, 13% yield) as a yellow solid. MS (ESI, pos. ion) m/z: 365.1 (M+1); ¹H NMR (400 MHz, DMSO-d₆) δ ppm 12.44 (1H, s), 11.86 (1H, br. s.), 8.00 (1H, dd, J=7.5, 1.3 Hz), 7.90 (1H, d, J=3.7 Hz), 7.70 (1H, d, J=8.0 Hz), 7.41 (1H, t, J=7.8 Hz), 7.28 (1H, d, J=2.2 Hz), 5.94 (1H, s), 5.12 (1H, t, J=5.9 Hz), 3.65 (2H, d, J=5.7 Hz), 2.57 (3H, s), 1.54 (6H, s)

Example 262

6-(3-amino-2-methylquinoxalin-5-yl)-3H-pyrrolo[2,3-d]pyrimidin-4(7H)-one

Example 264

6-(3-fluoro-2-methylquinoxalin-5-yl)-3H-pyrrolo[2,3-d]pyrimidin-4(7H)-one

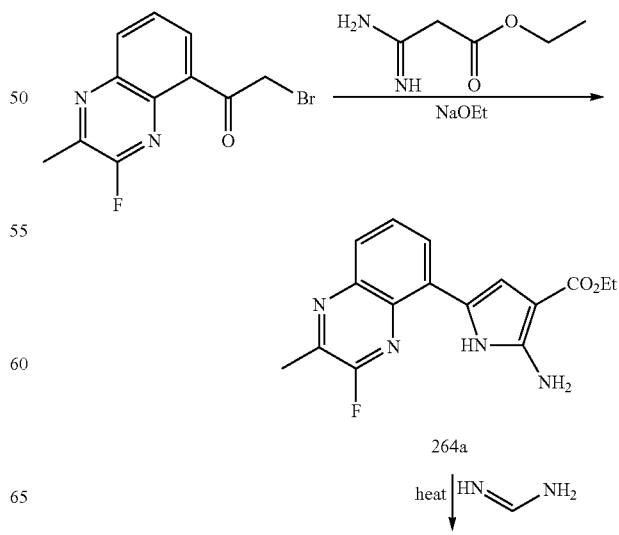

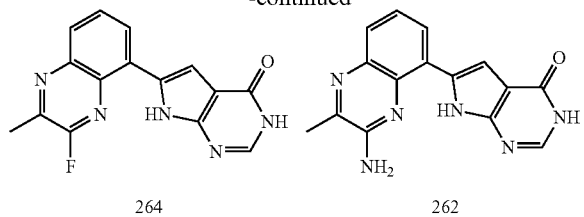

264

262

Preparation of 264a: Ethyl 2-amino-5-(3-fluoro-2-methylquinoxalin-5-yl)-1H-pyrrole-3-carboxylate A glass microwave reaction vessel was charged with ethyl 3-amino-3-iminopropanoate hydrochloride (1.248 g, 7.49 mmol, Tyger Scientific, Inc., Ewing, N.J.) in EtOH (5 mL) and the solution was cooled to 0° C. Sodium ethoxide (21% w/w solution in EtOH; 2.80 mL, 7.49 mmol) was added dropwise and a precipitate was formed. After 10 min, 2-bromo-1-(3-fluoro-2-methylquinoxalin-5-yl)ethanone (Example 126h; 1.06 g, 3.74 mmol) was added, and the reaction was stirred at RT for 3 h. The reaction was quenched with water and extracted with DCM. The combined organic layers were dried (MgSO$_4$), filtered and concentrated. The residue was purified with silica gel chromatography (10-25% EtOAc in Hexanes) to give ethyl 2-amino-5-(3-fluoro-2-methylquinoxalin-5-yl)-1H-pyrrole-3-carboxylate (615 mg, 1.957 mmol, 52% yield) as an orange solid. MS (ESI, pos. ion) m/z: 315.0 (M+1).

Preparation of 264: 6-(3-fluoro-2-methylquinoxalin-5-yl)-3H-pyrrolo[2,3-d]pyrimidin-4(7H)-one A glass microwave reaction vessel was charged with ethyl 2-amino-5-(3-fluoro-2-methylquinoxalin-5-yl)-1H-pyrrole-3-carboxylate (615 mg, 1.957 mmol) and formamidine hydrochloride (788 mg, 9.78 mmol, Sigma-Aldrich) in 2-propanol (9 mL). The reaction was stirred and heated in an oil bath at 120° C. for 30 h. The mixture was cooled to RT and filtered. The solid was washed with iPrOH and dried to give the product. MS (ESI, pos. ion) m/z: 296.0 (M+1). $^1$H NMR (400 MHz, DMSO-d6) d ppm 12.10 (brs, 1H), 8.24 (1H, d, J=8.0 Hz), 8.01 (1H, d, J=8.4 Hz), 7.94 (1H, s), 7.83-7.90 (1H, m), 7.45 (1H, s), 2.74 (3H, s). Compound 262: 6-(3-amino-2-methylquinoxalin-5-yl)-3H-pyrrolo[2,3-d]pyrimidin-4(7H)-one was also isolated from the above mixture through preparative rpHPLC (Phenomenex Gemini C$_{18}$ column (100×50 mm, 10 μm), 90 mL/min, 5-40% ACN in water with 0.1% TFA): MS (ESI, pos. ion) m/z: 293.1 (M+1); $^1$H NMR (400 MHz, DMSO-d$_6$) δ ppm 12.69 (1H, br. s.), 11.85 (1H, br. s.), 8.12 (1H, d, J=6.7 Hz), 7.92 (1H, s), 7.66 (1H, d, J=7.0 Hz), 7.26-7.40 (4H, m), 2.54 (3H, br. s.).

Example 265

3-methyl-2-(methylthio)-8-(4-oxo-4,5,6,7-tetrahydro-1H-pyrrolo[3,2-c]pyridin-2-yl)quinazolin-4(3H)-one Example 266

3-methyl-8-(4-oxo-4,5,6,7-tetrahydro-1H-pyrrolo[3,2-c]pyridin-2-yl)-2-(phenylamino)quinazolin-4(3H)-one

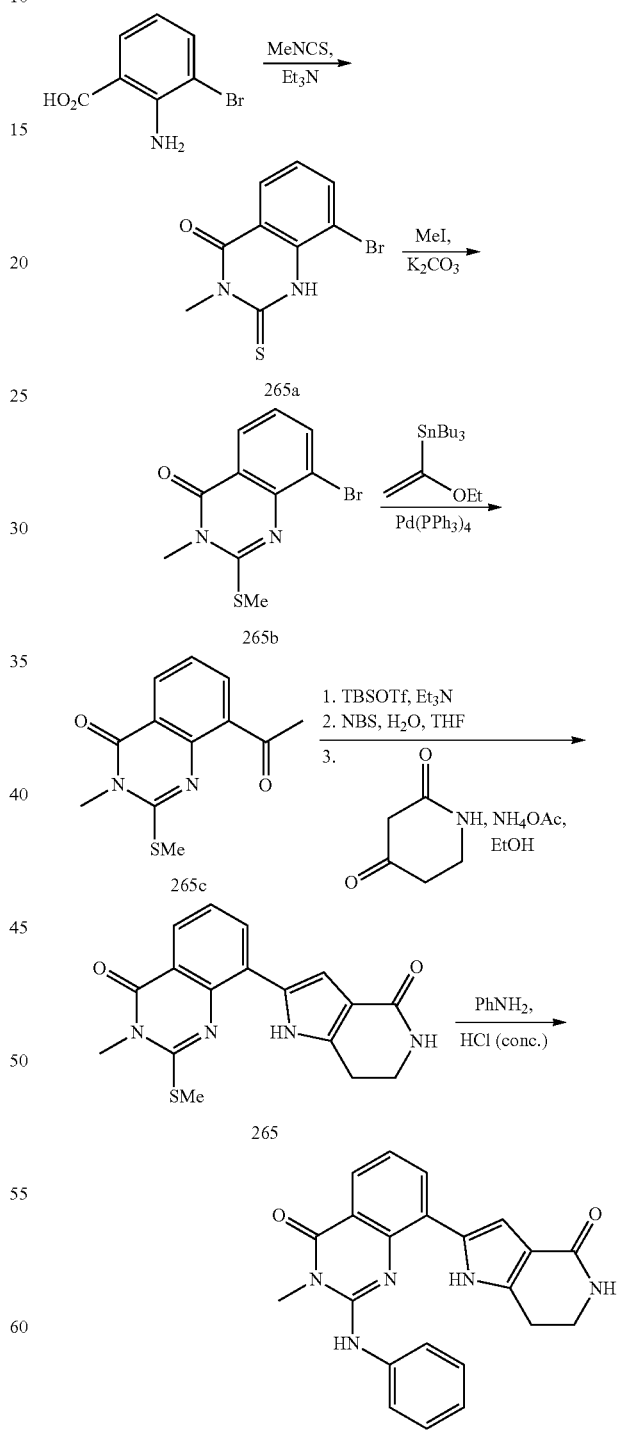

265a

265b

265c

265

266

Preparation of 265a: 8-bromo-3-methyl-2-thioxo-2,3-dihydroquinazolin-4(1H)-one A solution of 2-amino-3-bromobenzoic acid (Maybridge, Trevillett, UK; 3.03 g, 14.02 mmol) and isothiocyanatomethane (Aldrich; 1.151 mL, 16.82 mmol) in EtOH (28 mL) was stirred at 75° C. for 3.5 d. Additional isothiocyanatomethane (2.302 mL, 33.64 mmol) and Et$_3$N (2.74 mL, 19.63 mmol) were added, and the resulting mixture was stirred at 75° C. for 1 d. The mixture was concentrated in vacuo and the residue was triturated with Et$_2$O (40 mL) to provide 8-bromo-3-methyl-2-thioxo-2,3-dihydroquinazolin-4(1H)-one (2.90 g, 10.70 mmol, 76% yield) as a yellow-orange solid: $^1$H NMR (400 MHz, CDCl$_3$) δ ppm 9.52 (1H, br. s.), 8.11 (1H, d, J=8.0 Hz), 7.85 (1H, dd, J=7.9, 1.3 Hz), 7.20 (1H, t, J=7.9 Hz), 3.83 (3H, s). m/z (ESI, +ve) 271.0 (M+H)$^+$.

Preparation of 265b: 8-bromo-3-methyl-2-(methylthio)quinazolin-4(3H)-one

A suspension of 8-bromo-3-methyl-2-thioxo-2,3-dihydroquinazolin-4(1H)-one (1.00 g, 3.69 mmol), potassium carbonate (0.510 g, 3.69 mmol), and MeI (0.344 mL, 5.53 mmol) in THF (7.0 mL) was stirred at 25° C. for 3d. The mixture was vacuum filtered, and the filtrate was concentrated in vacuo to provide 8-bromo-3-methyl-2-(methylthio)quinazolin-4(3H)-one (1.052 g, 3.69 mmol, 100% yield) as an off-white solid: $^1$H NMR (400 MHz, CDCl$_3$) δ ppm 8.18 (1H, dd, J=7.9, 1.1 Hz), 7.96 (1H, dd, J=7.6, 1.2 Hz), 7.22 (1H, t, J=7.8 Hz), 3.62 (3H, s), 2.75 (3H, s). m/z (ESI, +ve) 284.9 (M+H)$^+$.

Preparation of 265c: 8-acetyl-3-methyl-2-(methylthio)quinazolin-4(3H)-one

A solution of 8-bromo-3-methyl-2-(methylthio)quinazolin-4(3H)-one (500 mg, 1.753 mmol), tributyl(1-ethoxyvinyl)stannane (Synthonix, Wake Forest, N.C.; 0.652 mL, 1.929 mmol), and Pd(PPh$_3$)$_4$ (81 mg, 0.070 mmol) in toluene (9.0 mL) was stirred under argon at 100° C. for 19 h, then at 110° C. for 1 d. The reaction was cooled to 25° C. and concentrated onto silica gel. Chromatographic purification (silica gel, 0-50% EtOAc/Hexanes) furnished 8-acetyl-3-methyl-2-(methylthio)quinazolin-4(3H)-one (128.7 mg, 0.518 mmol, 30% yield) as a white solid: m/z (ESI, +ve) 249.2 (M+H)$^+$. 8-(1-ethoxyvinyl)-3-methyl-2-(methylthio)quinazolin-4(3H)-one (35.5 mg, 0.128 mmol, 7% yield) as a colorless oil: m/z (ESI, +ve) 277.1 (M+H)$^+$.

Preparation of 265: 3-methyl-2-(methylthio)-8-(4-oxo-4,5,6,7-tetrahydro-1H-pyrrolo[3,2-c]pyridin-2-yl)quinazolin-4(3H)-one Et$_3$N (0.094 mL, 0.674 mmol) and TBSOTf (0.131 mL, 0.570 mmol) were sequentially added to a yellow solution of 8-acetyl-3-methyl-2-(methylthio)quinazolin-4(3H)-one (128.7 mg, 0.518 mmol) in DCM (2.7 mL) at 0° C., and the resulting light-yellow solution was stirred at 0° C. for 30 min. The mixture was partitioned between DCM (50 mL) and saturated aq. NaHCO$_3$ (20 mL). The organic layer was separated, and the aq. layer was extracted with DCM (30 mL). The combined organic extracts were dried over Na$_2$SO$_4$, filtered, and concentrated in vacuo to provide crude 8-(1-((tert-butyldimethylsilyl)oxy)vinyl)-3-methyl-2-(methylthio)quinazolin-4(3H)-one as a peach-colored solid. This material was combined with 8-(1-ethoxyvinyl)-3-methyl-2-(methylthio)quinazolin-4(3H)-one (35.5 mg, 0.128 mmol), and the resulting mixture was taken up in THF (2.70 mL). Water (0.149 mL, 8.29 mmol) and NBS (115 mg, 0.648 mmol) were sequentially added at 25° C., and the resulting solution was stirred at 25° C. for 30 min. The mixture was partitioned between Et$_2$O (50 mL) and water (30 mL). The organic layer was separated, sequentially washed with saturated aq. NaHCO$_3$ (20 mL), water (20 mL), and brine (20 mL), then dried over Na$_2$SO$_4$, filtered, and concentrated in vacuo to provide crude 8-(2-bromoacetyl)-3-methyl-2-(methylthio)quinazolin-4(3H)-one as an off-white solid. NH4OAc (200 mg, 2.59 mmol) and piperidine-2,4-dione (88 mg, 0.777 mmol) were added to this solid, and the resulting mixture was taken up in EtOH (2.70 mL) and heated under argon in a sealed flask at 40° C. for 16 h. The reaction suspension was vacuum filtered, and the collected solid was washed with MeOH (20 mL) and dried in vacuo. The residue was triturated with DMSO (2.0 mL), and the resulting suspension was vacuum filtered. The collected solid was sequentially washed with MeOH (5 mL) and DCM (5 mL) and dried in vacuo to provide 3-methyl-2-(methylthio)-8-(4-oxo-4,5,6,7-tetrahydro-1H-pyrrolo[3,2-c]pyridin-2-yl)quinazolin-4(3H)-one (57.1 mg, 0.168 mmol, 26% yield) as a yellow solid: $^1$H NMR (400 MHz, DMSO-d$_6$) δ ppm 11.67 (1H, br. s.), 8.05 (1H, dd, J=7.6, 1.2 Hz), 7.95 (1H, dd, J=7.8, 1.0 Hz), 7.44 (1H, t, J=7.8 Hz), 7.03 (1H, d, J=2.3 Hz), 6.96 (1H, br. s.), 3.56 (3H, s), 3.41 (2H, td, J=6.8, 2.2 Hz), 2.85 (2H, t, J=6.9 Hz), 2.74 (3H, s). m/z (ESI, +ve) 341.1 (M+H)$^+$.

Preparation of 266: 3-methyl-8-(4-oxo-4,5,6,7-tetrahydro-1H-pyrrolo[3,2-c]pyridin-2-yl)-2-(phenylamino)quinazolin-4(3H)-one A suspension of 3-methyl-2-(methylthio)-8-(4-oxo-4,5,6,7-tetrahydro-1H-pyrrolo[3,2-c]pyridin-2-yl)quinazolin-4(3H)-one (34.0 mg, 0.100 mmol), aniline (0.5 mL, 5.49 mmol), and HCl (conc.) (20 μl, 0.240 mmol) was heated by microwave in a sealed flask at 150° C. for 10 min. The mixture was diluted with Et$_2$O (5 mL) and the precipitated solid was collected by vacuum filtration, washed with Et$_2$O (5 mL), and dried in vacuo. Purification of the residue by revered-phase HPLC (Phenomenex Gemini C$_{18}$ column (150×30 mm, 10 μm), 35 mL/min, 5-100% ACN/H$_2$O+0.1% TFA) followed by supercritical-fluid chromatography (Chiralcel OD-H (250× 21 mm, 5 μm), 50% liquid CO$_2$/50% MeOH, 55 mL/min) afforded 3-methyl-8-(4-oxo-4,5,6,7-tetrahydro-1H-pyrrolo[3,2-c]pyridin-2-yl)-2-(phenylamino)quinazolin-4(3H)-one (1.6 mg, 4.15 μmol) as a white solid: $^1$H NMR (400 MHz, DMSO-d$_6$) δ ppm 8.98-9.15 (1H, m), 7.95-8.04 (1H, m), 7.81 (1H, d, J=7.6 Hz), 7.41-7.53 (5H, m), 7.23-7.33 (1H, m), 7.08-7.18 (1H, m), 6.89 (1H, s), 6.82 (1H, s), 3.61 (3H, s), 3.28 (2H, obsc. m), 2.33 (2H, m). m/z (ESI, +ve) 386.1 (M+H)$^+$.

The following compounds in Table 1 can be prepared via procedures similar to that described for Examples 286 and 369:

TABLE 1

| Example # | Name |
| --- | --- |
| 269 | 2-(3-(3-amino-3-methylbutoxy)-2-methyl-5-quinoxalinyl)-1,5,6,7-tetrahydro-4H-pyrrolo[3,2-c]pyridin-4-one |
| 270 | 2-(3-(((1S)-1-cyclopropylethyl)amino)-2-methyl-5-quinoxalinyl)-1,5,6,7-tetrahydro-4H-pyrrolo[3,2-c]pyridin-4-one |
| 271 | 2-(3-(((1R)-1-cyclopropylethyl)amino)-2-methyl-5-quinoxalinyl)-1,5,6,7-tetrahydro-4H-pyrrolo[3,2-c]pyridin-4-one |

TABLE 1-continued

| Example # | Name |
|---|---|
| 272 | 2-(3-(2,2-dimethylpropyl)-2-methyl-5-quinoxalinyl)-1,5,6,7-tetrahydro-4H-pyrrolo[3,2-c]pyridin-4-one |
| 273 | rac-2-(3-amino-2-methyl-5-quinoxalinyl)-7-(4-chlorobenzyl)-1,5,6,7-tetrahydro-4H-pyrrolo[3,2-c]pyridin-4-one |
| 274 | 2-(3-((1,1-dimethyl-2-(methylsulfonyl)ethyl)amino)-2-methyl-5-quinoxalinyl)-1,5,6,7-tetrahydro-4H-pyrrolo[3,2-c]pyridin-4-one |
| 275 | 2-(2-methyl-3-((3-oxetanylmethyl)amino)-5-quinoxalinyl)-1,5,6,7-tetrahydro-4H-pyrrolo[3,2-c]pyridin-4-one |
| 276 | 2-(3-(tert-butylamino)-2-methoxy-5-quinoxalinyl)-1,5,6,7-tetrahydro-4H-pyrrolo[3,2-c]pyridin-4-one |
| 277 | 2-(3-((1-(hydroxymethyl)cyclopropyl)amino)-2-methyl-5-quinoxalinyl)-1,5,6,7-tetrahydro-4H-pyrrolo[3,2-c]pyridin-4-one |
| 278 | rac-2-(3-(tert-butylamino)-2-methyl-5-quinoxalinyl)-7-(2-butyn-1-yl)-1,5,6,7-tetrahydro-4H-pyrrolo[3,2-c]pyridin-4-one |
| 279 | 2-(3-((3-hydroxy-1,1-dimethylpropyl)amino)-2-methyl-5-quinoxalinyl)-1,5,6,7-tetrahydro-4H-pyrrolo[3,2-c]pyridin-4-one |
| 280 | rac-7-(2-butyn-1-yl)-2-(3-fluoro-2-methyl-5-quinoxalinyl)-1,5,6,7-tetrahydro-4H-pyrrolo[3,2-c]pyridin-4-one |
| 281 | 2-(2-methyl-3-(((3-methyl-3-oxetanyl)methyl)amino)-5-quinoxalinyl)-1,5,6,7-tetrahydro-4H-pyrrolo[3,2-c]pyridin-4-one |
| 282 | 3-(tert-butylamino)-5-(4-oxo-4,5,6,7-tetrahydro-1H-pyrrolo[3,2-c]pyridin-2-yl)-2-quinoxalinecarbaldehyde |
| 283 | 2-(2-(tert-butylamino)-3-methylpyrido[2,3-b]pyrazin-8-yl)-1,5,6,7-tetrahydro-4H-pyrrolo[3,2-c]pyridin-4-one |
| 284 | 3-(tert-butylamino)-5-(4-oxo-4,5,6,7-tetrahydro-1H-pyrrolo[3,2-c]pyridin-2-yl)-2(1H)-quinoxalinone |
| 285 | 2-(2-methyl-3-(((1-methylcyclopropyl)methyl)amino)-5-quinoxalinyl)-1,5,6,7-tetrahydro-4H-pyrrolo[3,2-c]pyridin-4-one |
| 286 | 2-(2-amino-3-(tert-butylamino)-5-quinoxalinyl)-1,5,6,7-tetrahydro-4H-pyrrolo[3,2-c]pyridin-4-one |

Preparation of 5-bromo-3-chloro-6-fluoro-2-methylquinoxaline (600)

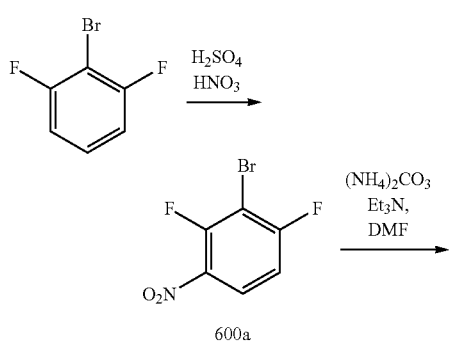

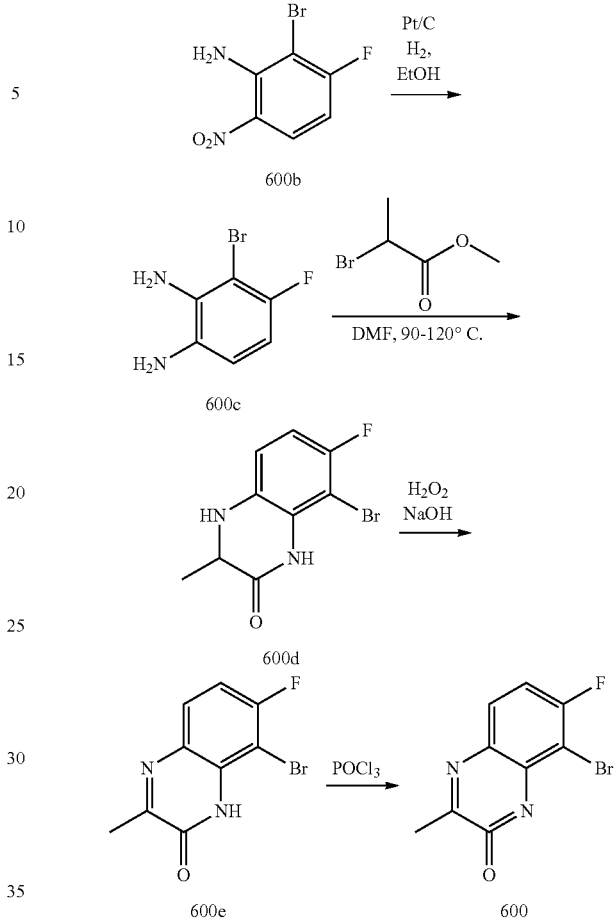

Preparation of 2-bromo-1,3-difluoro-4-nitrobenzene (600a)

1-Bromo-2,6-difluorobenzene (Oakwood Products Inc., West Columbia, S.C.) (15.4 mL, 104 mmol) was treated with $H_2SO_4$ (77 mL of 95-98% pure, 1445 mmol) and cooled in an ice bath. It was treated with $HNO_3$ (68 mL of 69-70% pure, 1050 mmol) slowly dropwise via a dropping funnel and stirred for and additional 30 min. The mixture was poured onto ice (500 mL) and stirred vigorously for 3 min. The resulting suspension was extracted with DCM (4×100 mL), washed with brine (500 mL) and dried over $Na_2SO_4$, filtered and concentrated affording crude 2-bromo-1,3-difluoro-4-nitrobenzene (32.55 g, 137 mmol) as a bright yellow crystalline solid. $^1H$ NMR (400 MHz, $CDCl_3$) δ ppm 8.13 (1H, ddd, J=9.1, 8.1, 5.5 Hz), 7.13 (1H, ddd, J=9.3, 7.1, 2.0 Hz). $^{19}F$ NMR (376 MHz, $CDCl_3$) δ ppm −92.06 (1F, s), −104.31 (1F, s). m/z (ESI, +ve ion) 259.1/261.1 (M+Na)$^+$.

Preparation of 2-bromo-3-fluoro-6-nitroaniline (600b)

Prepared according to WO 2010/046388. 2-Bromo-1,3-difluoro-4-nitrobenzene (600a) (27.15 g, 114 mmol) was treated with ammonium carbonate (Sigma Aldrich, 10.96 g, 114 mmol) and DMF (200 mL) followed by $Et_3N$ (47.7 mL, 342 mmol) and stirred at RT for 48 h. The mixture was treated with water and extracted with DCM (300 mL). The DCM layer was washed with water (3×200 mL) and brine (3×200 mL), dried over MgSO$_4$, filtered and concentrated affording crude 2-bromo-3-fluoro-6-nitroaniline (25.99 g, 111 mmol, 97% yield) as a bright yellow amorphous solid. $^1$H NMR (400 MHz, CDCl$_3$) δ ppm 8.22 (1H, dd, J=9.6, 5.9 Hz), 6.81 (2H, br. s.), 6.56 (2H, dd, J=9.6, 7.2 Hz). $^{19}$F NMR (376 MHz, CDCl$_3$) δ ppm −90.92 (1F, s). m/z (ESI, +ve ion) 234.9/236.9 (M+H)$^+$.

Preparation of 3-bromo-4-fluorobenzene-1,2-diamine (600c)

A 500 mL round-bottomed flask containing Pt/C (5%, 6.00 g, 1.54 mmol) and 2-bromo-3-fluoro-6-nitroaniline (600b) (20.85 g, 89 mmol) were treated with EtOH (250 mL) and stirred under an atmosphere of H$_2$ (balloon) for 22 h. LC-MS indicated ca. 35% conversion to the desired material (M+1=204.9/206.9). Another balloon of H$_2$ was added and it was stirred for another 16 h resulting in >90% conversion to the desired product (M+1=204.9/207.1) by LC-MS. The suspension was filtered through a plug of Celite washing with EtOH and concentrated affording crude 3-bromo-4-fluorobenzene-1,2-diamine (18 g, 88 mmol, 99% yield) as a black/purple viscous oil. $^1$H NMR (400 MHz, CDCl$_3$) δ ppm 6.60 (1H, dd, J=8.5, 5.2 Hz), 6.42-6.50 (1H, m). $^{19}$F NMR (376 MHz, CDCl$_3$) δ ppm −116.48 (1F, s). m/z (ESI, +ve ion) 204.9/206.9 (M+H)$^+$.

Preparation of 8-bromo-7-fluoro-3-methyl-3,4-dihydroquinoxalin-2(1H)-one (600d)

A 500 mL round-bottomed flask charged with 3-bromo-4-fluorobenzene-1,2-diamine (600c) (18 g, 88 mmol), DMF (100 mL), ethyl 2-bromopropionate (Sigma Aldrich, 11.54 mL, 89 mmol) and NaHCO$_3$ (7.60 g powder, 90 mmol) was heated to 90° C. with a reflux condenser for 30 min, then at 120° C. for 15 h. The reaction mixture was cooled to RT, treated with brine and extracted with EtOAc (2×200 mL), washed with brine (3×) and dried over Na$_2$SO$_4$, filtered and concentrated affording crude 8-bromo-7-fluoro-3-methyl-3,4-dihydroquinoxalin-2(1H)-one (21.75 g, 84 mmol, 96% yield) as an orange-brown viscous oil. The material was used in the subsequent step without further purification. $^1$H NMR (400 MHz, DMSO-d$_6$) δ ppm 9.67 (s, 1H) 6.78-6.89 (m, 1H) 6.48-6.78 (m, 1H) 6.07-6.35 (m, 1H) 1.25 (d, J=6.46 Hz, 3H). $^{19}$F NMR (377 MHz, DMSO-d$_6$) δ ppm −120.49 (1F, s). m/z (ESI, +ve ion) 259.0/261.0 (M+H)$^+$.

Preparation of 8-bromo-7-fluoro-3-methylquinoxalin-2(1H)-one (600e)

A mixture of water (14 mL) and 30% H$_2$O$_2$ (30.0 mL, 294 mmol) was added slowly dropwise to a solution of 8-bromo-7-fluoro-3-methyl-3,4-dihydroquinoxalin-2(1H)-one (600e) (21.7 g, 84 mmol) in 1 N NaOH (168 mL, 168 mmol) and MeOH (140 mL). The flask was fitted with a reflux condenser and heated at 85° C. for 3 h. LC-MS indicated ca. 87% conversion to the desired product (M+1=257.0/259.0). The reaction mixture was cooled to RT and acidified with 2 N HCl to ca. pH 6 and was diluted with CHCl$_3$/IPA(4:1) (100 mL), added to a separatory funnel. The resulting suspension was filtered through a sintered glass frit, washing with water and dried affording 8-bromo-7-fluoro-3-methylquinoxalin-2(1H)-one (5.83 g, 22 mmol, 22% yield) as a light brown solid. m/z (ESI, +ve ion) 257.0/259.0 (M+H)$^+$. $^1$H NMR (400 MHz, DMSO-d$_6$) δ ppm 11.83 (1H, br. s.), 7.67-7.88 (1H, m), 7.34 (1H, t, J=8.4 Hz), 2.43 (3H, s). $^{19}$F NMR (377 MHz, DMSO-d$_6$) δ ppm −104.13 (1F, s). The aq. solution was extracted with CHCl$_3$:i-PrOH 9:1 (6×100 mL), dried over MgSO$_4$, filtered and concentrated affording additional 8-bromo-7-fluoro-3-methylquinoxalin-2(1H)-one (12.51 g, 49 mmol, 58% yield) as a dark brown amorphous solid (ca. 80% purity). The material was used in the subsequent step without further purification.

Preparation of 5-bromo-3-chloro-6-fluoro-2-methylquinoxaline (600)

In a 500-mL round-bottomed flask, a mixture of 8-bromo-7-fluoro-3-methylquinoxalin-2(1H)-one (600) (3.57 g, 13.89 mmol) and POCl$_3$ (20.0 mL, 215 mmol) was heated at 90° C. for 1.5 h with a reflux condenser. The reaction mixture was cooled to RT and most of the excess POCl$_3$ was removed under reduced pressure (rotary evaporator). The mixture was treated with EtOAc (100 mL), cooled in an ice bath, treated with ice chips and 1 N NaOH slowly. After phase separation, the organic layer was washed with brine (50 mL), dried over MgSO$_4$, filtered and concentrated to afford the crude product as a brown solid. The crude residue was purified by chromatography on the ISCO Combiflash Rf (80 g Redisep column, using a gradient of 0-100% DCM in hexanes (eluted with ca. 35-60% DCM)) affording 5-bromo-3-chloro-6-fluoro-2-methylquinoxaline (1.88 g, 6.82 mmol, 49% yield) as a light orange crystalline solid. m/z (ESI, +ve ion) 275.0/277.0 (M+H)$^+$. $^1$H NMR (400 MHz, CDCl$_3$) δ ppm 8.01 (1H, dd, J=9.3, 5.4 Hz), 7.58 (1H, dd, J=9.1, 8.1 Hz), 2.86 (3H, s). $^{19}$F NMR (376 MHz, CDCl$_3$) δ ppm −99.07 (1F, s).

Preparation of ethyl 4-((tert-butoxycarbonyl)amino)-3-oxobutanoate (601)

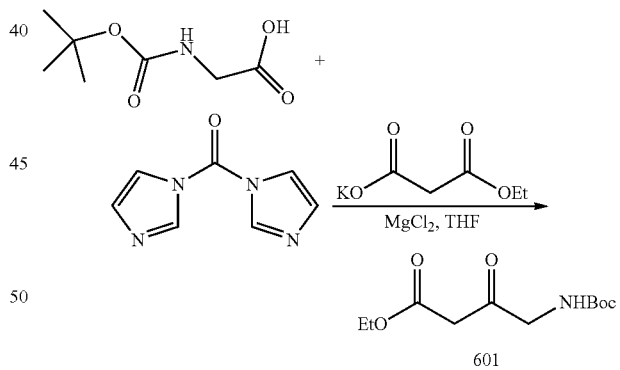

601

Referenced: *J. Med. Chem.* 2008, 51 (3), 487-501. At RT, 1,1'-carbonyldiimidazole (13.88 g, 86 mmol) was added to a solution of N-Boc-glycine (Sigma-Aldrich Chemical Company, Inc.) (10.00 g, 57.1 mmol) in THF (200 mL) and the mixture was stirred for 3 h. Magnesium chloride (10.87 g, 114 mmol) and potassium ethyl malonate (Sigma-Aldrich Chemical Company, Inc.) (19.43 g, 114 mmol) were added and the resulting suspension was heated in an oil bath at 50° C. for 18 h. The reaction mixture was concentrated under reduced pressure. The off-white residue was treated with EtOAc (300 mL), then washed sequentially with 5% sodium bisulfate (2×25 mL), saturated NaHCO$_3$ (2×50 mL), and brine (25 mL). The organic layer was dried over anhydrous Na$_2$SO$_4$, filtered and concentrated. The crude material was purified by chromatography through a Thomson Single Step pre-packed silica gel column (160 g, eluted with a gradient of 0-75% EtOAc in hexanes) to provide ethyl 4-((tert-butoxycarbonyl)amino)-3-oxobutanoate (10.33 g, 42.1 mmol, 74% yield) as a colorless viscous oil after drying under vacuum overnight. $^1$H NMR (400 MHz, CDCl$_3$) δ ppm 5.16 (1H, d, J=5.7 Hz), 4.21 (2H, m), 4.08-4.16 (2H, m), 3.48 (2H, s), 1.45 (9H, s), 1.29 (3H, m). m/z (ESI, +ve) 268.0 (M+Na)$^+$.

Preparation of (R)-ethyl 4-((tert-butoxycarbonyl)amino)-3-oxopentanoate (602)

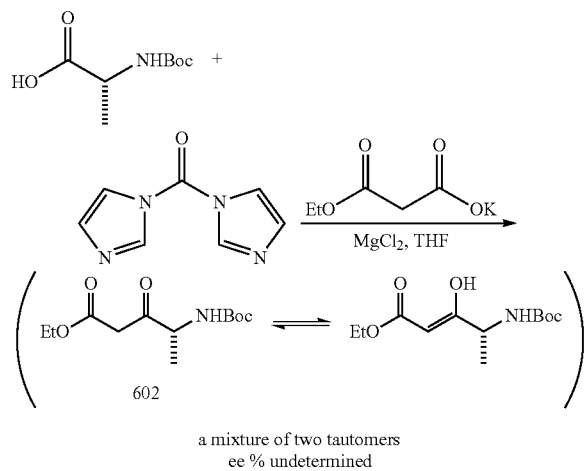

a mixture of two tautomers
ee % undetermined

A tautomeric mixture of (R)-ethyl 4-((tert-butoxycarbonyl)amino)-3-oxopentanoate and (R,Z)-ethyl 4-((tert-butoxycarbonyl)amino)-3-hydroxypent-2-enoate (21.4 g, 83 mmol, 78% yield) as white solid was prepared according the procedures described for Intermediate 603 (see below), using potassium ethyl malonate (36.0 g, 211 mmol) as the reagent. ee % was not determined m/z (ESI, +ve) 282.0 (M+23)$^+$.

Preparation of (R)-methyl 4-((tert-butoxycarbonyl)amino)-3-oxopentanoate (603)

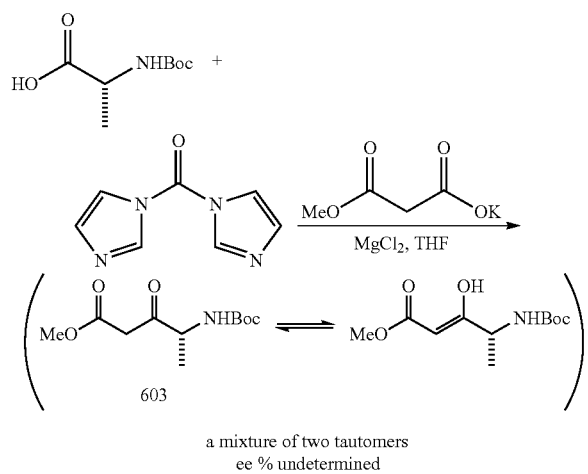

a mixture of two tautomers
ee % undetermined

To a 1-L 3-neck round-bottomed flask, connected to a mechanical stirrer, was added N-Boc-D-alanine (20.00 g, 106 mmol) followed by THF (529 mL). Then 1,1'-carbonyldiimidazole (25.7 g, 159 mmol) was slowly added into the reaction mixture (note: gas evolution was observed). The mixture was stirred under inert atmosphere for 3 h. Then magnesium chloride (20.13 g, 211 mmol), followed by potassium methyl malonate (33.0 g, 211 mmol) were added into the reaction mixture. The reaction mixture was heated at 50° C. in an oil bath for 16 h. It was cooled to RT, diluted with EtOAc (1 L) and filtered through a pad of celite. The filtrate was concentrated in-vacuo. The organic residue was diluted with CHCl$_3$ (400 mL) and washed with sat. aq. NaHCO$_3$ (300 mL). The aq. layer was extracted with CHCl$_3$ (2×300 mL). The combined organic extracts were dried over Na$_2$SO$_4$, filtered and concentrated in-vacuo. The crude material was purified by chromatography through two Interchim puriFlash UP (25 micron) pre-packed silica-gel column (300 gram), eluting with a gradient of 0-18% EtOAc in hexane. The mixed fractions were combined and purified by chromatography through an Interchim puriFlash UP (15 micron) pre-packed silica-gel column (120 grams), eluting with a gradient of 0-18% EtOAc in hexane. The fractions with desired material were combined and concentrated in-vacuo, to provide a mixture of (R)-methyl 4-((tert-butoxycarbonyl)amino)-3-oxopentanoate and (R,Z)-methyl 4-((tert-butoxycarbonyl)amino)-3-hydroxypent-2-enoate (21.03 g, 86 mmol, 81% yield) as white solid. ee % was not determined. m/z (ESI, +ve) 268.0 (M+23)'.

Preparation of ethyl 3-(1-((tert-butoxycarbonyl)amino)cyclopropyl)-3-oxopropanoate (604)

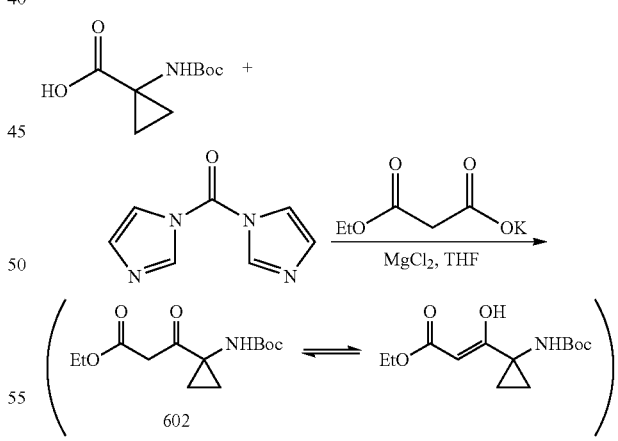

A tautomeric mixture of ethyl 3-(1-((tert-butoxycarbonyl)amino)cyclopropyl)-3-oxopropanoate and (Z)-ethyl 3-(1-((tert-butoxycarbonyl)amino)cyclopropyl)-3-hydroxyacrylate (3.15 g, 11.61 mmol, 90% yield) as an off white solid was prepared according the procedures described for Intermediate 601, using 1-(Boc-amino)cyclopropanecarboxylic acid (Chem-Impex International, Inc., cat #04052) (2.59 g, 12.87 mmol) as the reagent. m/z (ESI, +ve) 294.2 (M+23)+.

Preparation of 2-bromo-1-(3-(tert-butylamino)-6-fluoro-2-methylquinoxalin-5-yl)ethanone (605)

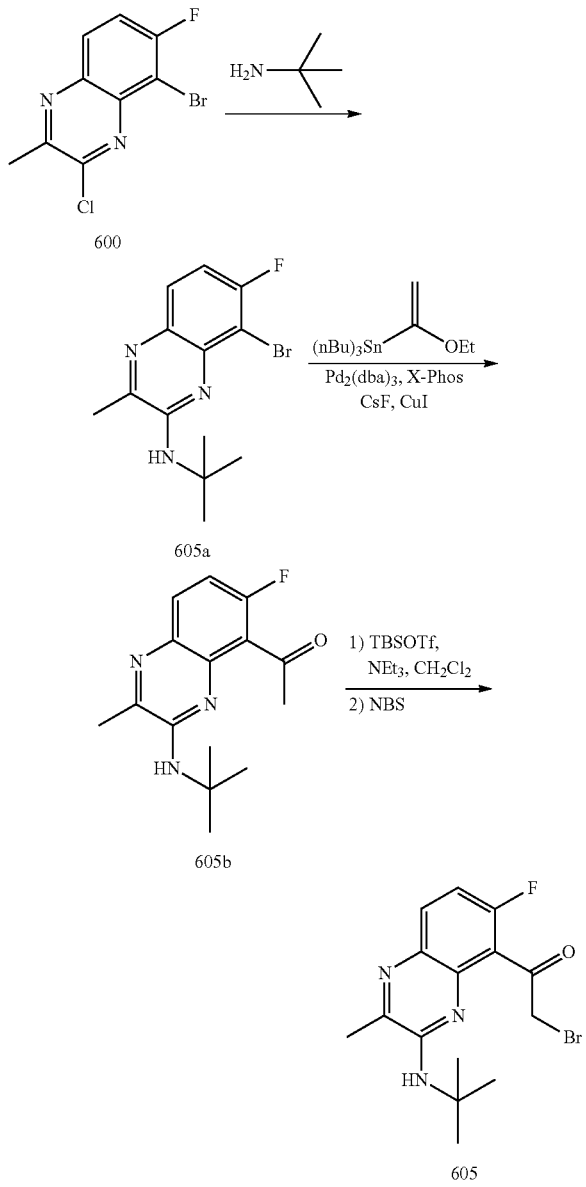

A mixture of 5-bromo-3-chloro-6-fluoro-2-methylquinoxaline (600) (5.00 g, 18.15 mmol) and tert-butylamine (Alfa-Aesar, Ward Hill, Ma) (9.62 mL, 91 mmol) in DMSO (50 mL) in a sealed tube was heated at 100° C. for 2 h. After cooling to RT, the mixture was diluted with EtOAc and saturated NaHCO$_3$ (aq.). The layers were separated and the aq. layer was extracted with EtOAc (3×). The combined organic layers were washed with water and brine and dried over anhydrous Na$_2$SO$_4$, filtered and concentrated. The crude material was absorbed onto a plug of silica gel and purified by silica gel chromatography (0-20% EtOAc in hexanes) to provide 8-bromo-N-(tert-butyl)-7-fluoro-3-methylquinoxalin-2-amine (605a) (4.70 g, 15.06 mmol, 83% yield) as an orange solid. $^1$H NMR (400 MHz, CDCl$_3$) δ ppm 7.71 (1H, dd, J=9.0, 5.7 Hz), 7.14 (1H, t, J=8.6 Hz), 4.82 (1H, br. s.), 2.51 (3H, s), 1.64 (9H, s). $^{19}$F NMR (376 MHz, CDCl$_3$) δ ppm −103.85 (s, 1F). m/z (ESI, +ve) 312.0, 314.0 (M+H)$^+$.

A round bottomed flask was charged with 8-bromo-N-(tert-butyl)-7-fluoro-3-methylquinoxalin-2-amine (605a) (4.70 g, 15.06 mmol), tributyl(1-ethoxyvinyl)tin (Sigma-Aldrich) (7.63 mL, 22.58 mmol), Pd$_2$dba$_3$ (Strem Chemicals Inc., 1.38 g, 1.51 mmol), Xphos (Strem Chemicals Inc.) (718 mg, 1.51 mmol), CuI (Strem Chemicals Inc.) (573 mg, 3.01 mmol) and CsF (Sigma-Aldrich) (6.86 g, 45.2 mmol) in dioxane (75 mL). The tube was sealed and heated to 80° C. in an oil bath overnight. LCMS shows enol ether as major product (m/z (ESI, +ve) 304.0 (M+H)$^+$). The reaction mixture was cooled to RT. Concentrated HCl (aq.) (3.14 mL, 37.6 mmol) was added and the mixture stirred at RT for 30 min. The mixture was filtered through Celite and the filter cake was washed with EtOAc and water. The layers were separated and the aq. layer was extracted with EtOAc (2×). The combined organic layers were dried over anhydrous Na$_2$SO$_4$, filtered and concentrated. The crude material was absorbed onto a plug of silica gel and purified by silica gel chromatography (0-50% EtOAc in hexanes) to provide 1-(3-(tert-butylamino)-6-fluoro-2-methylquinoxalin-5-yl)ethanone (605b) (3.76 g, 13.64 mmol, 91% yield) as a light orange solid. $^1$H NMR (400 MHz, CDCl$_3$) δ ppm 7.77 (dd, J=9.00, 5.87 Hz, 1H), 7.08 (t, J=9.00 Hz, 1H), 2.70 (s, 3H), 2.49 (s, 3H), 1.52 (s, 9H). $^{19}$F NMR (376 MHz, CDCl$_3$) δ ppm −115.38 (s, 1F). m/z (ESI, +ve) 276.1 (M+H)$^+$.

NEt$_3$ (2.84 mL, 20.50 mmol) and TBSOTf (Sigma-Aldrich) (3.45 mL, 15.00 mmol) were added to a solution of 1-(3-(tert-butylamino)-6-fluoro-2-methylquinoxalin-5-yl)ethanone (605b) (3.76 g, 13.64 mmol) in CH$_2$Cl$_2$ (68 mL) at 0° C. The mixture was stirred for 1 h at 0° C. and then sat. NaHCO$_3$ (aq.) was added and the layers were separated. The aq. layer was extracted with CH$_2$Cl$_2$ (2×). The combined organic layers were dried over anhydrous Na$_2$SO$_4$, filtered and concentrated to give the silyl enol ether. m/z (ESI, +ve) 319.1 (M+H)$^+$. THF (68 mL) and water (3.93 mL, 218 mmol) were added and the mixture was cooled to 0° C. NBS (Alfa-Aesar, Ward Hill, Ma) (2.43 g, 13.64 mmol) was added and the mixture was stirred at 0° C. for 30 min. EtOAc and saturated NaHCO$_3$ (aq.) were added and the layers were separated. The aq. layer was extracted with EtOAc (2×). The combined organic layers were dried over anhydrous Na$_2$SO$_4$, filtered and concentrated. The crude material was absorbed onto a plug of silica gel and purified by silica gel chromatography (0-50% EtOAc in hexanes) to provide the title compound (605) (2.19 g, 6.18 mmol, 45% yield) as a light-yellow solid. $^1$H NMR (400 MHz, CDCl$_3$) δ ppm 7.83 (dd, J=9.10, 5.97 Hz, 1H), 7.11 (t, J=9.00 Hz, 1H), 4.86 (br. s., 1H), 4.59 (s, 2H), 2.50 (s, 3H), 1.54 (br. s., 9H). $^{19}$F NMR (377 MHz, CDCl$_3$) δ ppm −112.97 (s, 1F). m/z (ESI, +ve) 354.0, 356.0 (M+H)$^+$.

Preparation of 2-bromo-1-(3-(tert-butylamino)-2-methylquinoxalin-5-yl)ethanone (606)

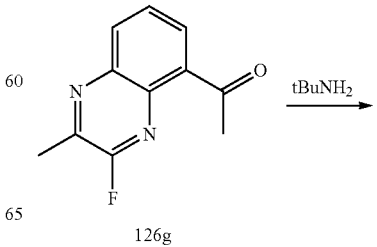

383
-continued

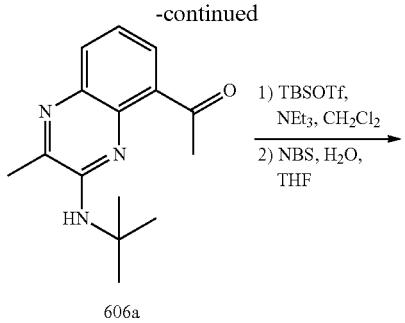

To a stirred solution of 1-(3-fluoro-2-methylquinoxalin-5-yl)ethanone (126g) (13 g, 63.7 mmol) in DMSO (100 mL) was added t-BuNH$_2$ (33.7 mL, 318 mmol). The reaction mixture was heated in an oil bath at 65° C. for 4 h. It was cooled to RT, treated with 100 mL of ice cold water. The precipitated light orange solid was collected, washed with water (2×15 mL), dried in a vacuum oven at 35° C. for 18 h to give 1-(3-(tert-butylamino)-2-methylquinoxalin-5-yl)ethanone (606a) (14.96 g, 91% yield) which was used in the next step without further purification. $^1$H NMR (400 MHz, CDCl$_3$) δ ppm 7.90 (dd, J=8.12, 1.66 Hz, 1H), 7.76 (dd, J=7.34, 1.66 Hz, 1H), 7.35 (t, J=7.73 Hz, 1H), 4.81 (br., 1H), 2.88 (s, 3H), 2.53 (s, 3H), 1.57 (s, 9H). m/z (ESI, +ve) 258.2 (M+H)$^+$.

To a stirred solution of 1-(3-(tert-butylamino)-2-methylquinoxalin-5-yl)ethanone (606a) (14.96 g, 58.1 mmol) and TEA (12.15 mL, 87 mmol) in DCM (100 mL) at 0° C. was added tert-butyldimethylsilyl trifluoromethanesulfonate (13.18 mL, 57.4 mmol) dropwise. After the addition, the reaction mixture was stirred at RT for 3 h. It was cooled with an ice bath and quenched with 50 mL of saturated NaHCO$_3$. The layers were separated. The aq. layer was extracted with DCM (2×50 mL). The combined DCM extracts were dried over Na$_2$SO$_4$ and concentrated. The remaining light brown oil was dissolved in THF (100 mL) and H$_2$O (10 mL), cooled with an ice bath, and treated with NBS (10.35 g, 58.1 mmol) in a single portion. The resulting mixture was stirred at 0° C. for 2 h, quenched with 50 mL of saturated NaHCO$_3$, and extracted with EtOAc (3×100 mL). The organic extracts were combined, washed with 20 mL of brine, dried over MgSO$_4$ and concentrated. The resulting yellow solid was treated with 100 mL of MeOH and stirred for 10 min. The yellow solid was filtered, rinsed with MeOH (2×5 mL), collected and dried in a vacuum oven at RT for 18 h to give 2-bromo-1-(3-(tert-butylamino)-2-methylquinoxalin-5-yl)ethanone (606) (15.5 g, 79% yield). $^1$H NMR (400 MHz, DMSO-d$_6$) δ ppm 7.91 (1H, dd, J=8.0, 1.6 Hz), 7.75 (1H, dd, J=7.3, 1.5 Hz), 7.41 (1H, t, J=7.6 Hz), 6.18 (1H, s), 5.15 (2H, s), 2.58 (3H, s), 1.52 (9H, s). m/z (ESI, +ve) 336/338 (M+H)$^+$.

384

Preparation of 2-bromo-6,7-dihydro-1H-pyrrolo[3,2-c]pyridin-4(5H)-one (607)

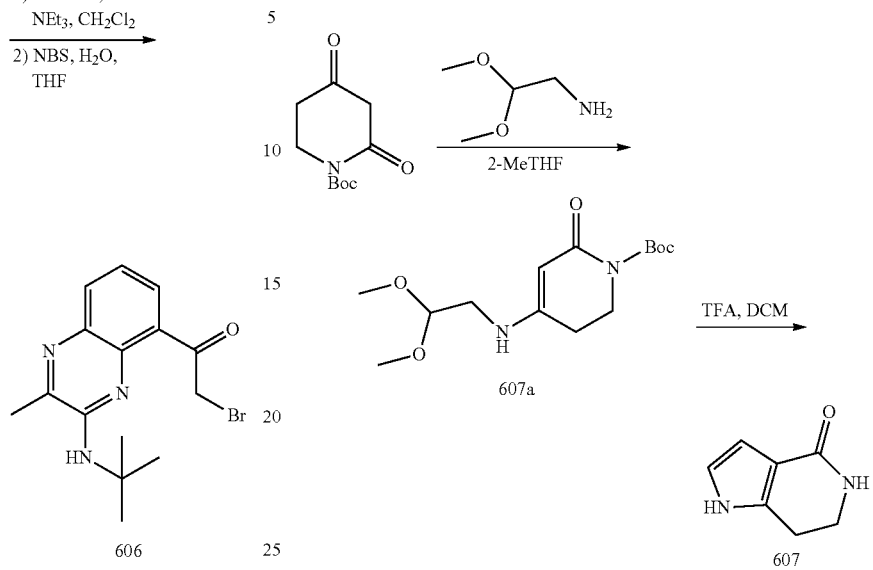

A solution of tert-butyl 2,4-dioxopiperidine-1-carboxylate (85.2 g, 0.4 mol) (WuxiApptec, China) and aminoacetaldehyde dimethyl acetal (84 g, 0.8 mmol) (Sigma Aldrich) in 2-Me-THF (0.6 L) was heated in an oil bath at 75° C. refluxed for 24 h. The solvent was then removed and the residue was diluted with water (25 mL) and extracted with DCM (0.4 L×3). The combined organic layers were dried (Na$_2$SO$_4$), filtered and concentrated to give the crude product (607a) (107.8 g, 90%) which was used in the next step without further purification. MS (ESI, pos. ion) m/z: 301.0 (M+1).

To a 3 L round-bottomed flask was added tert-butyl 4-((2,2-dimethoxyethyl)amino)-2-oxo-5,6-dihydropyridine-1(2H)-carboxylate (607a) (107.8 g, 359 mmol) and TFA (550 mL, 3.6 mol) in DCM (1.6 L). The reaction mixture was stirred at RT for 28 h; then the solvent was removed. The residue was purified by silica gel chromatography (eluted with 8% EtOH in EtOAc) to give 6,7-dihydro-1H-pyrrolo[3,2-c]pyridin-4(5H)-one (607) (16 g, 33%) as a white crystalline solid. MS (ESI, pos. ion) m/z: 137.2 (M+1). $^1$H NMR (400 MHz, MeOD) δ 6.65 (d, J=3.2 Hz, 1H), 6.40 (d, J=2.8 Hz, 1H), 3.50 (t, J=7.2 Hz, 2H), 2.82 (t, J=6.8 Hz, 2H).

Preparation of 2-(4,4,5,5-tetramethyl-1,3,2-dioxaborolan-2-yl)-6,7-dihydro-1H-pyrrolo[3,2-c]pyridin-4(5H)-one (608)

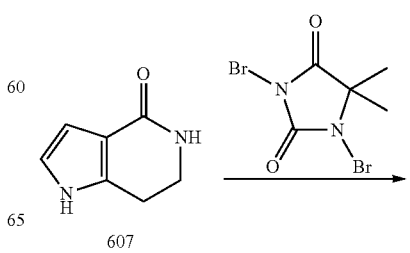

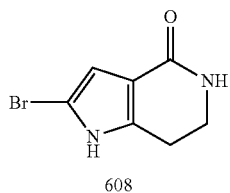

To a 100-mL round-bottomed flask was added 1,5,6,7-tetrahydro-pyrrolo[3,2-c]pyridin-4-one (607) (500 mg, 3.67 mmol) in DMF (10 mL). The solution was cooled to −60° C. and 1,3-dibromo-5,5-dimethyl-2,4-imidazolidinedione (525 mg, 1.83 mmol) (Sigma Aldrich) was added. The reaction mixture was stirred at −60° C. for 20 min, then poured into ice/water (20 mL). The mixture was extracted with CHCl$_3$/iPrOH (4:1) and the combined organic layers were dried, filtered and concentrated. The residue was purified with silica gel chromatography (eluted with 1-5% MeOH in DCM) to give the title compound (350 mg, 44% yield) as a white solid. MS (ESI, pos. ion) m/z: 215.0 (M+1). $^1$H NMR (400 MHz, DMSO-d6) δ ppm 11.81 (1H, br.), 6.95 (1H, br.), 6.21 (1H, s), 3.34 (2H, td, J=6.9, 2.5 Hz), 2.69 (2H, t, J=6.8 Hz).

Preparation of 2-bromo-6,7-dihydro-1H-pyrrolo[3,2-c]pyridin-4(5H)-one (609)

ture was diluted with DCM (50 mL) and filtered through a large pad of aluminum oxide (basic alumina) (150 mesh, Sigma-Aldrich). The mixture was first rinsed with DCM (800 mL) and the desired boronic ester was eluted with 10% MeOH in DCM (500 mL) affording crude boronic ester (609) (3.70 g, 14.10 mmol, 96% yield) as a dark brown oil. This material was used in next step of synthesis, without further purification. m/z (ESI, +ve) 263.1 (M+H).

Method-Y:

A glass microwave reaction vessel was charged with 2-bromo-6,7-dihydro-1H-pyrrolo[3,2-c]pyridin-4(5H)-one (608) (300 mg, 1.39 mmol), (BPin)$_2$ (709 mg, 2.79 mmol), THF (4 mL), Pd(dppf)Cl$_2$ (57.0 mg, 0.07 mmol) and KOAc (548 mg, 5.58 mmol). The reaction mixture was stirred and heated in an Initiator microwave reactor (Personal Chemistry, Biotage AB, Inc., Upssala, Sweden) at 100° C. for 160 min. The solvent was removed and the mixture was filtered through a plug of basic alumina and eluted first with 40% EtOAc in Hexanes then 2% MeOH in DCM. The filtrate from DCM/MeOH elution was concentrated to give the crude boronic ester (609) (200 mg) as a dark amorphous solid, which was used in the next reaction without further purification. MS (ESI, pos. ion) m/z: 263.1 (M+1).

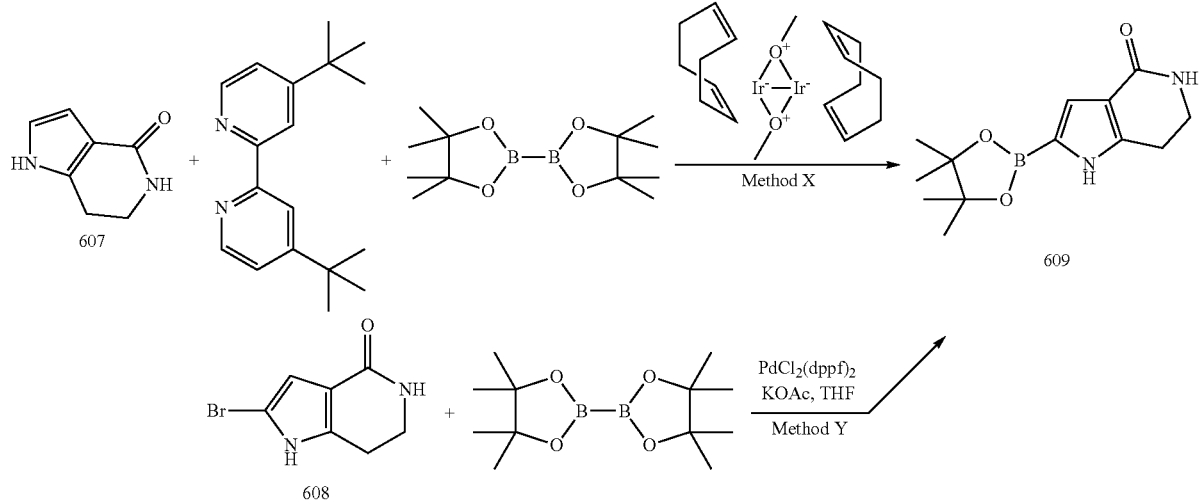

Method-X:

A glass reaction vessel was charged with 6,7-dihydro-1H-pyrrolo[3,2-c]pyridin-4(5H)-one (607) (2.00 g, 14.69 mmol), (BPin)$_2$ (Aldrich) (5.60 g, 22.03 mmol), 4,4-di-tert-butyl-2,2-dipyridyl (Sigma-Aldrich) (0.237 g, 0.88 mmol) and bis(1,5-cyclooctadiene)di-mu-methoxydiiridium(i) (Aldrich) (0.292 g, 0.441 mmol) in methyl tert-butyl ether (Sigma-Aldrich) (21 mL). The mixture was purged with argon for 5 min. The reaction vessel was sealed with QianCap™ and secured behind a blast shield. The vessel was placed into a pre-heated (50° C.) oil bath and stirred 1 h. The progress of the reaction was monitored by LC/MS, which showed around >99% conversion to desired boronic ester. The reaction mix- Preparation of 2-bromo-1-(6-fluoro-2-methyl-3-((1-methylcyclopropyl)amino)quinoxalin-5-yl)ethanone (610)

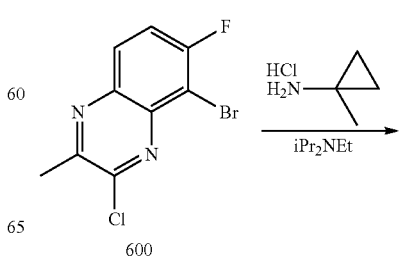

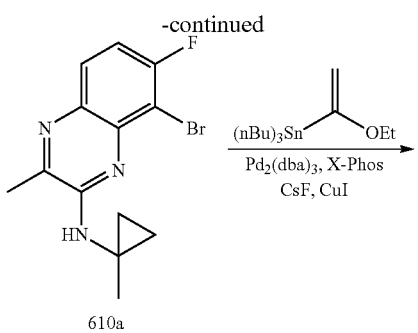

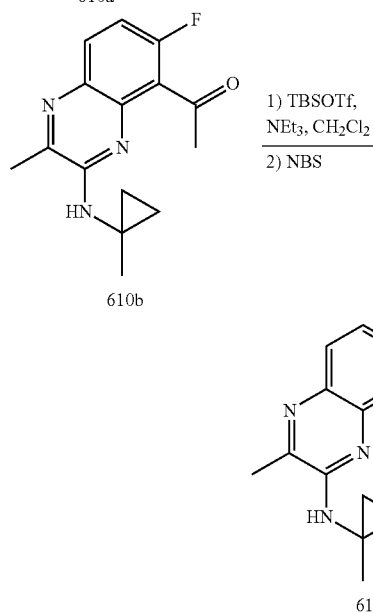

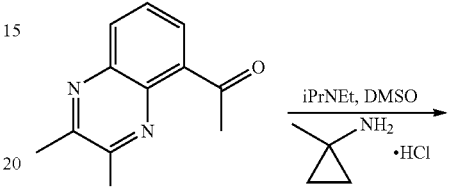

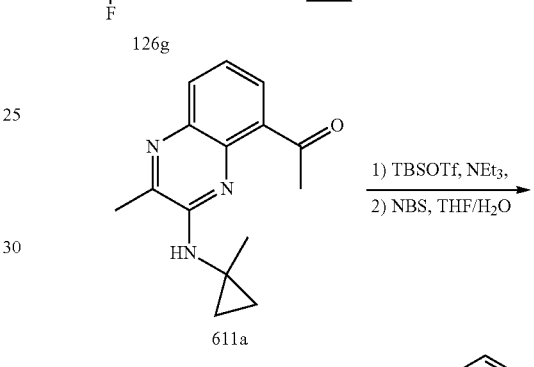

To a 15-mL glass reaction vial was added 5-bromo-3-chloro-6-fluoro-2-methylquinoxaline (600) (2.02 g, 7.33 mmol), 1-methylcyclopropanamine hydrochloride (ChemBridge, San Diego, Calif.) (1.420 g, 13.20 mmol) and DIEA (5.10 mL, 29.3 mmol) in DMSO (6 mL). The reaction mixture was stirred at 100° C. for 5 h. The reaction mixture was cooled to RT and poured over ice water. The precipitated orange solid was filtered, washed with water (2×5 mL), ether (2×5 mL). The orange solid was dried overnight to afford 1.77 g of 8-bromo-7-fluoro-3-methyl-N-(1-methylcyclopropyl)quinoxalin-2-amine (610a). The filtrate was extracted with EtOAc (2×10 mL). The organic extracts were washed with water and dried over Na$_2$SO$_4$, and concentrated in vacuo to give the crude material as an orange solid. The crude material was absorbed onto a plug of silica gel and purified by chromatography (with a gradient of 0-20% EtOAc in hexanes) to provide 8-bromo-7-fluoro-3-methyl-N-(1-methylcyclopropyl)quinoxalin-2-amine (610a) (474 mg) as an orange solid. $^1$H NMR (400 MHz, CDCl$_3$) δ ppm 7.74 (1H, dd, J=9.1, 5.8 Hz), 7.17 (1H, t, J=8.7 Hz), 5.29 (1H, br. s.), 2.49 (3H, s), 1.61 (3H, s), 0.86 (3H, d, J=4.7 Hz). $^{19}$F NMR (376 MHz, CDCl$_3$) δ ppm −103.55 (1F, s). m/z (ESI, +ve ion) 310.0/312.0 (M+H)$^+$.

1-(6-Fluoro-2-methyl-3-((1-methylcyclopropyl)amino)quinoxalin-5-yl)ethanone (610b) (740 mg, 60% yield) as a light yellow solid was prepared according to the procedure described for Intermediate 605b, using 8-bromo-7-fluoro-3-methyl-N-(1-methylcyclopropyl)quinoxalin-2-amine (610a) (1.39 g, 4.49 mmol) as the starting material. m/z (ESI, +ve ion) 274.2 (M+H)$^+$.

2-Bromo-1-(6-fluoro-2-methyl-3-((1-methylcyclopropyl)amino)quinoxalin-5-yl)ethanone (610) (846 mg, 56% yield) as a light yellow solid was prepared according to the procedure described for Intermediate 605, using 1-(6-fluoro-2-methyl-3-((1-methylcyclopropyl)amino)quinoxalin-5-yl)ethanone (610b) (1.18 g, 4.31 mmol) as the starting material. m/z (ESI, +ve ion) 352.1/354.1 (M+H)$^+$.

Preparation of 2-bromo-1-(2-methyl-3-((1-methylcyclopropyl)amino)-5-quinoxalinyl)ethanone (611)

To a 250 mL round-bottomed flask was added 1-(3-fluoro-2-methylquinoxalin-5-yl)ethanone (126g) (14.5 g, 71 mmol), DMSO (100 mL), DIEA (27 mL, 156 mmol) and finally 1-methylcyclopropanamine hydrochloride (8.02 g, 92 mmol) (ChemBridge Corporation, San Diego, Calif.). The solution was heated at 85° C. for 7 h. After cooling to RT, the solution was poured into sat NaHCO$_3$ (250 mL) and extracted with EtOAc (3×250 mL). The combined extracts were washed with H$_2$O (3×250 mL) and brine and then dried (Na$_2$SO$_4$) and concentrated to afford 1-(2-methyl-3-((1-methylcyclopropyl)amino)-5-quinoxalinyl)ethanone (611a) as a purple solid, which was used directly in the subsequent step. m/z (ESI, +ve) 256.1 (M+H)$^+$.

To a 1000 mL round bottomed flask was added the above obtained purple solid, 1-(2-methyl-3-((1-methylcyclopropyl)amino)quinoxalin-5-yl)ethanone (18.1 g, 70.9 mmol), DCM (500 mL), and TEA (12.9 mL, 92 mmol). The solution was cooled to 0° C. and tert-butyldimethylsilyl trifluoromethanesulfonate (17.9 mL, 78 mmol) (Sigma-Aldrich) was added over 5 min. The solution was warmed to RT and stir for 30 min. The solution was diluted with DCM and then washed with sat NaHCO$_3$ (2×), dried (Na$_2$SO$_4$) and concentrated to afford a red oil.

A solution of the red oil in THF (350 mL) and water (35 mL) was cooled to 0° C. and treated with NBS (12.6 g, 70.9 mmol, Sigma-Aldrich) in portions. The mixture was stirred at 0° C. for 1.5 h and then treated with sat NaHCO$_3$ (200 mL). The solution was diluted with EtOAc (300 mL) and then was partially concentrated. The solution was extracted with EtOAc (3×250 mL) and the combined extracts were washed with brine and then dried (Na$_2$SO$_4$) and concentrated onto silica. Purification by silica gel chromatography (0.0 to 45% EtOAc/hexane) afforded 2-bromo-1-(2-methyl-3-((1-methylcyclopropyl)amino)-5-quinoxalinyl)ethanone (14.6 g, 43.7 mmol, 62% yield over 3 steps) as a red solid. $^1$H NMR (400 MHz, DMSO-d$_6$) δ ppm 7.96 (dd, J=7.9, 1.5 Hz, 1H), 7.92 (dd, J=7.5, 1.5 Hz, 1H), 7.76 (br s, 1H), 7.42 (t, J=7.7 Hz, 1H), 5.52 (s, 2H), 2.48 (s, 3H), 1.45 (s, 3H), 0.83-0.90 (m, 2H), 0.71-0.78 (m, 2H). m/z (ESI, +ve) 334.0/336.0 (M+H)$^+$.

Preparation of (R)-ethyl 5-(benzyloxy)-4-((tert-butoxycarbonyl)amino)-3-oxopentanoate (612)

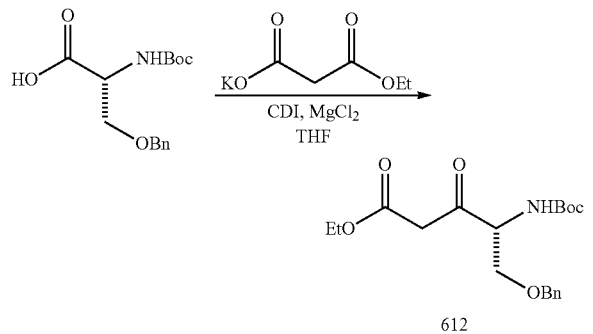

612

To a 250-mL round-bottomed flask was added (R)-3-(benzyloxy)-2-((tert-butoxycarbonyl)amino)propanoic acid (5.68 g, 19.2 mmol) (Sigma-Aldrich), 1,1'-carbonyldiimidazole (4.68 g, 28.8 mmol), and THF (100 mL). The reaction mixture was stirred at RT for 4 h. The reaction mixture was treated with magnesium chloride (3.66 g, 38.4 mmol) (Strem Chem.) followed by ethyl potassium malonate (6.54 g, 38.4 mmol) (Sigma-Aldrich) and heated at 50° C. for 18 h. The solvents were removed under vacuum and the residue was dissolved EtOAc (200 mL), washed sequentially with 10% sodium bisulfate (10 mL), sat NaHCO$_3$ (2×10 mL), brine, dried over Na$_2$SO$_4$, and concentrated. The crude material was absorbed onto a plug of silica gel and purified by chromatography through a Redi-Sep pre-packed silica gel column (40 g), eluted with a gradient of 0-30% EtOAc in hexanes, to provide the title compound (5.73 g, 82% yield) as a white solid. ee % was not determined m/z (ESI, +ve) 388.2 (M+Na)$^+$.

Preparation of 2-bromo-1-(3-(cyclopropylamino)-2-methylquinoxalin-5-yl)ethanone (613)

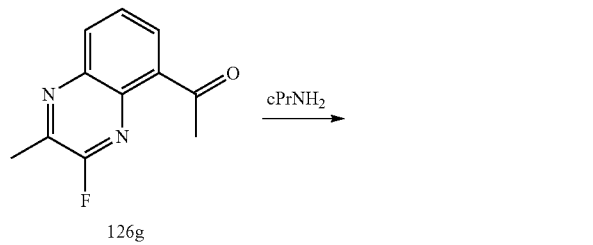

126g

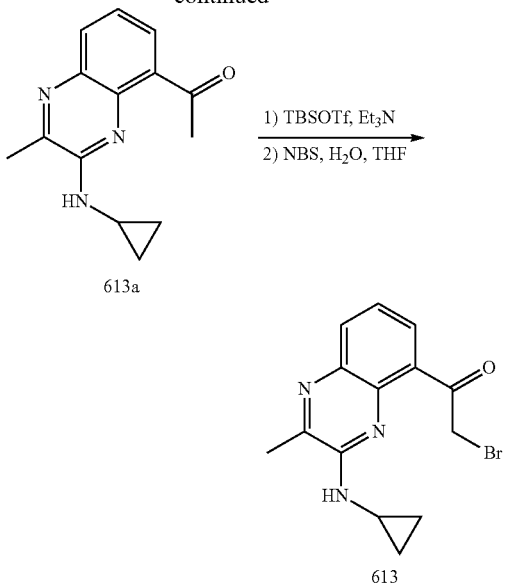

613a

613

This compound was prepared according the procedures described for Intermediate 606, in a 2-step fashion. m/z (ESI, +ve) 320/322 (M+H)$^+$. $^1$H NMR (400 MHz, DMSO-d$_6$) δ 7.96 (dd, J=1.56, 8.02 Hz, 1H), 7.92 (dd, J=1.57, 7.43 Hz, 1H), 7.73 (s, 1H), 7.42 (t, J=7.73 Hz, 1H), 5.51 (s, 2H), 2.48 (s, 3H), 1.46 (s, 3H), 0.84-0.90 (m, 2H), 0.72-0.77 (m, 2H).

Example 352

Preparation of (4S,5R)-ethyl 4-((tert-butoxycarbonyl)amino)-5-((tert-butyldimethylsilyl)oxy)-3-oxohexanoate (614)

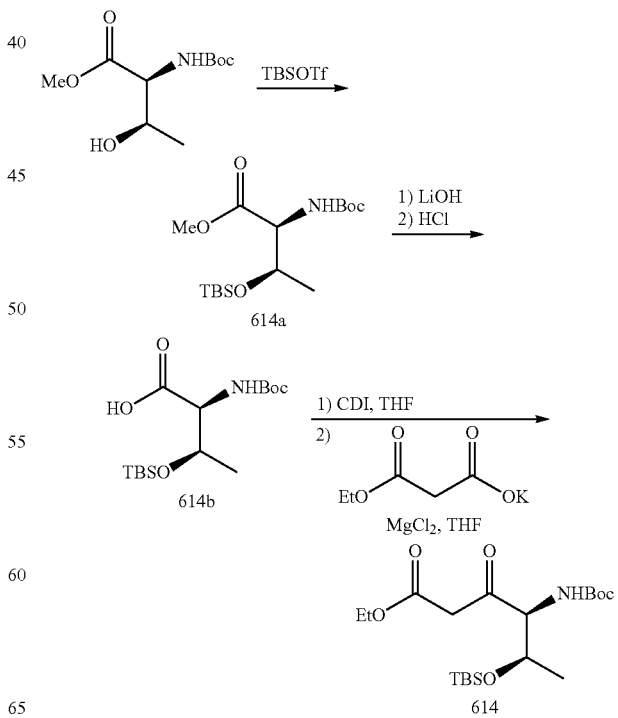

614

A solution of N-(tert-butoxycarbonyl)-L-threonine methyl ester (Aldrich) (717 mg, 3.07 mmol) in DCM (10 mL) was cooled in an ice-water bath and treated with 2,6-dimethylpyridine (Aldrich) (1.07 mL, 9.22 mmol) followed by tert-butyldimethylsilyl trifluoromethanesulfonate (Fluka) (0.85 mL, 3.69 mmol). The solution was stirred for 16 h, poured into 1 M aq. HCl (100 mL), and extracted with DCM (2×50 mL). The organic extracts were washed with saturated aq. NaHCO₃ (100 mL), dried (MgSO₄), filtered, and concentrated to give (2S,3R)-methyl 2-((tert-butoxycarbonyl)amino)-3-((tert-butyldimethylsilyl)oxy)butanoate (614a) (1.07 g, 3.08 mmol, 100% yield) as a colorless oil.

A solution of (2S,3R)-methyl 2-((tert-butoxycarbonyl)amino)-3-((tert-butyldimethylsilyl)oxy)butanoate (614a) (1.07 g, 3.08 mmol) in THF (25 mL) was treated with 1.0 M aq. LiOH (6.16 mL, 6.16 mmol) and the mixture was stirred for 72 h. The mixture was diluted with saturated aq. brine (100 mL) containing 1.0 M aq. HCl (10 mL), and extracted into EtOAc (2×100 mL). The combined organic extracts were dried (MgSO₄) and concentrated to give (2S,3R)-2-((tert-butoxycarbonyl)amino)-3-((tert-butyldimethylsilyl)oxy)butanoic acid (614b) (1.03 g, 3.09 mmol, 100% yield) as a viscous colorless oil that crystallized upon standing. LC-MS m/z 356.1, [M+Na]⁺.

A solution of (2S,3R)-2-((tert-butoxycarbonyl)amino)-3-((tert-butyldimethylsilyl)oxy)butanoic acid (614b) (1.01 g, 3.03 mmol) in THF (10 mL) was treated with 1,1'-carbonyldiimidazole (Aldrich) (0.59 g, 3.63 mmol) and heated at 60° C. for 2 h. A mixture of potassium ethyl malonate (Aldrich) (1.03 g, 6.06 mmol) and magnesium chloride (Aldrich) (0.58 g, 6.06 mmol) was added to the solution and heating was continued at 50° C. for 6 d. The suspension was extracted into EtOAc (2×100 mL) from saturated brine (100 mL) containing 1.0 M aq. HCl (25 mL). The combined organic extracts were washed with saturated aq. NaHCO₃ (100 mL), back-extracting with EtOAc (100 mL). The organic extracts were dried (MgSO₄) and concentrated to give (4S,5R)-ethyl 4-((tert-butoxycarbonyl)amino)-5-((tert-butyldimethylsilyl)oxy)-3-oxohexanoate (614) (995 mg, 2.46 mmol, 81% yield) as a pale yellow oil. LC-MS m/z 426.0, [M+Na]⁺.

Preparation of (4R,5S)-ethyl 4-((tert-butoxycarbonyl)amino)-5-((tert-butyldimethylsilyl)oxy)-3-oxohexanoate (615)

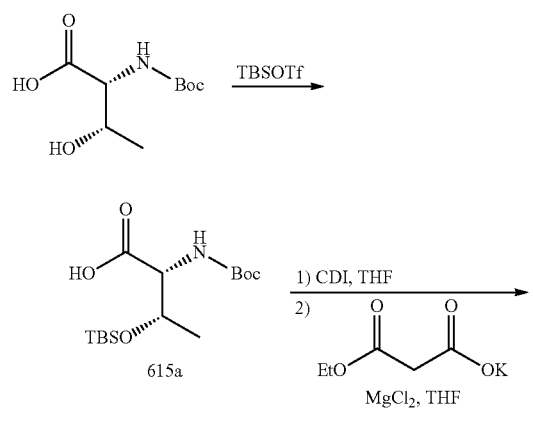

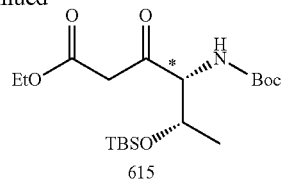

615

*partial racemization possible

A solution of (2R,3S)-2-((tert-butoxycarbonyl)amino)-3-hydroxybutanoic acid (Frontier Scientific, Utah) (9.94 g, 45.3 mmol) in DCM (100 mL) was treated with 2,6-dimethylpyridine (Fluka) (15.79 mL, 136 mmol). A solution of tert-butyldimethylsilyl trifluoromethanesulfonate (Fluka) (22.9 mL, 100 mmol) in DCM (50 mL) was added dropwise over 1 h. The mixture was stirred for an additional 2 h, after which time the reaction was complete by LC-MS analysis. The mixture was diluted with saturated brine (100 mL) and acidified with a slight excess of 1.0 M aq. HCl. The mixture was stirred for 30 min, the layers were separated, and the aq. layer was extracted with DCM (100 mL). The combined organic extracts were dried (MgSO₄) and concentrated to give crude product as a white semi-solid (26 g). The crude product was dissolved in MeOH (25 mL) and a solution of anhydrous Na₂CO₃ (4.80 g, 45.3 mmol) in water (25 mL) was added dropwise. The solution was stirred for 15 min and then concentrated to remove the MeOH. The resulting oily solution was diluted with water (175 mL) and hexane (200 mL) and stirred for 15 min. The aq. layer was separated and washed with a further 200 mL of hexane. The aq. layer was separated, diluted with DCM (200 mL), and 1.0 M aq. HCl was added dropwise to the stirred mixture. The mixture was separated and the aq. layer extracted with DCM (100 mL). The combined organic layers were dried (MgSO₄) and concentrated to give (2R,3S)-2-((tert-butoxycarbonyl)amino)-3-((tert-butyldimethylsilyl)oxy)butanoic acid (615a) (14.52 g, 43.5 mmol, 96% yield) as a colorless viscous oil. LC-MS m/z 356.1 [M+Na]¹.

A solution of (2R,3S)-2-((tert-butoxycarbonyl)amino)-3-((tert-butyldimethylsilyl)oxy)butanoic acid (615a) (14.52 g, 43.5 mmol) in THF (100 mL) was treated with 1,1'-carbonyldiimidazole (7.41 g, 45.7 mmol) and stirred at RT for 30 min and then at 60° C. for 2 h. The mixture was cooled to RT and then potassium ethyl malonate (Aldrich) (14.82 g, 87 mmol) and magnesium chloride (Aldrich) (8.29 g, 87 mmol) were added. The resulting suspension was stirred at 50° C. for 20 h. The suspension was concentrated and then extracted into EtOAc (2×100 mL) from saturated aq. brine (500 mL) containing 5 M aq. HCl (40 mL, 200 mmol). The combined organic extracts were washed with saturated aq. NaHCO₃ (2×100 mL), dried (Na₂SO₄), and concentrated to give a pale yellow gum. The crude product was purified by flash chromatography on silica gel (160 g) eluting with DCM to give (4R,5S)-ethyl 4-((tert-butoxycarbonyl)amino)-5-((tert-butyldimethylsilyl)oxy)-3-oxohexanoate (165) (11.49 g, 28.5 mmol, 65% yield) as a colorless oil. LC-MS m/z 426.0, [M+Na]⁺.

Preparation of 2-bromo-1-(2-methyl-3-((2,2,2-trifluoroethyl)amino)quinoxalin-5-yl)ethanone (616)

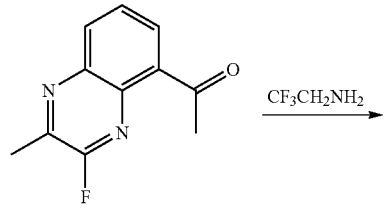

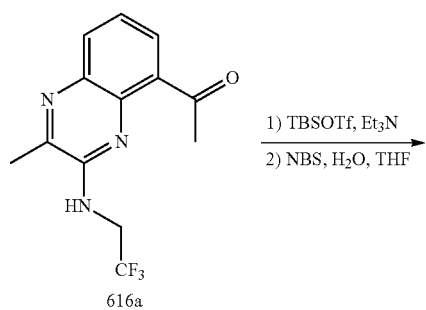

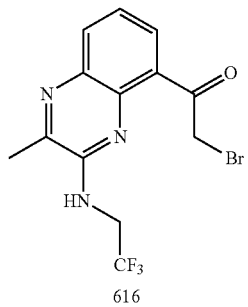

This compound was prepared according the procedures described for Intermediate 606, in a 2-step fashion. m/z (ESI, +ve) 362/364 (M+H)$^+$. $^1$H NMR (400 MHz, CDCl$_3$) δ ppm 8.07 (2H, dt, J=4.7, 3.3 Hz), 7.52 (1H, t, J=7.8 Hz), 5.20 (1H, br. s.), 4.94 (2H, s), 4.37 (2H, qd, J=8.9, 6.6 Hz), 2.66 (3H, s). $^{19}$F NMR (377 MHz, CDCl$_3$) δ ppm −71.88 (1F, s).

Preparation of 2-bromo-1-(3-((2,2-difluoroethyl)amino)-2-methylquinoxalin-5-yl)ethanone (617)

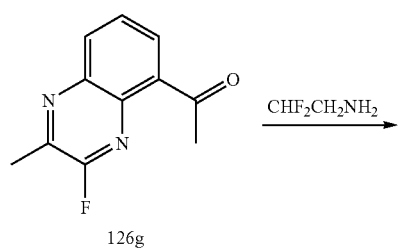

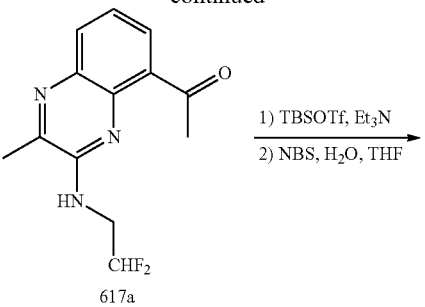

This compound was prepared according the procedures described for Intermediate 606, in a 2-step fashion. m/z (ESI, +ve) 344/346 (M+H)$^+$. $^1$H NMR (400 MHz, DMSO-d$_6$) δ ppm 8.04 (1H, dd, J=8.0, 1.6 Hz), 7.98 (1H, dd, J=7.4, 1.6 Hz), 7.88 (1H, t, J=5.9 Hz), 7.51 (1H, t, J=7.7 Hz), 6.47 (0.25 H, m), 6.33 (0.5; H, t, J=4.2 Hz), 6.18 (0.25; H, m), 3.96 (2H, m), 2.61 (3H, s). $^{19}$F NMR (377 MHz, DMSO-d$_6$) δ ppm −120.84 and −120.98.

Preparation of 3-fluoro-2-methyl-5-(4,4,5,5-tetramethyl-1,3,2-dioxaborolan-2-yl)quinoxaline (618)

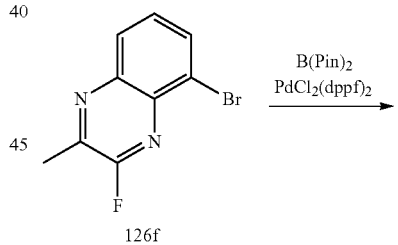

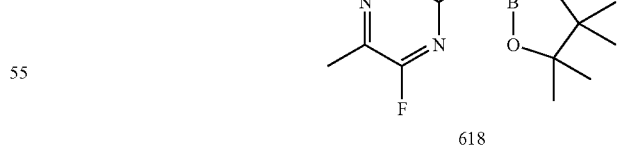

A mixture of 5-bromo-3-fluoro-2-methylquinoxaline (1261) (1.04 g, 4.31 mmol) (BPin)$_2$ (Aldrich) (2.19 g, 8.63 mmol), KOAc (1.69 g, 17.26 mmol) and Pd(dppf)Cl$_2$ (Strem) (176 mg, 0.21 mmol) in THF (10.0 mL) was heated at 100° C. for 1 h. LC-MS indicated the presence of 3-fluoro-2-methylquinoxalin-5-yl)boronic acid (m/z (ESI, +ve) 207.1 (M+H)$^+$) with no hydrolysis of the fluoride. The reaction mixture was cooled to RT, diluted with EtOAc (150 mL), washed with water (30 mL) followed by brine (30 mL), dried over MgSO$_4$, filtered and concentrated. Purification of the residue on a silica gel column (eluted with 20-50% EtOAc in hexanes) afforded 3-fluoro-2-methyl-5-(4,4,5,5-tetramethyl-1,3,2-dioxaborolan-2-yl)quinoxaline (1.65g, >100% yield) as a light yellow crystalline solid. $^1$H NMR (400 MHz, MeOH-d4) δ ppm 8.10-8.17 (2H, m), 7.79 (1H, dd, J=8.0, 7.2 Hz), 2.76 (3H, d, J=1.6 Hz), 1.46 (12H, s). A small amount of 2,3-dimethylbutane-2,3-diol was present $^1$H NMR, which may be accounted for the >100% yield. This material was used without further purification. $^{19}$F NMR (377 MHz, MeOH-d4) δ ppm −73.49 (1F, s).

Preparation of 2-bromo-1-(6-fluoro-3-(isopropylamino)-2-methylquinoxalin-5-yl)ethanone (619)

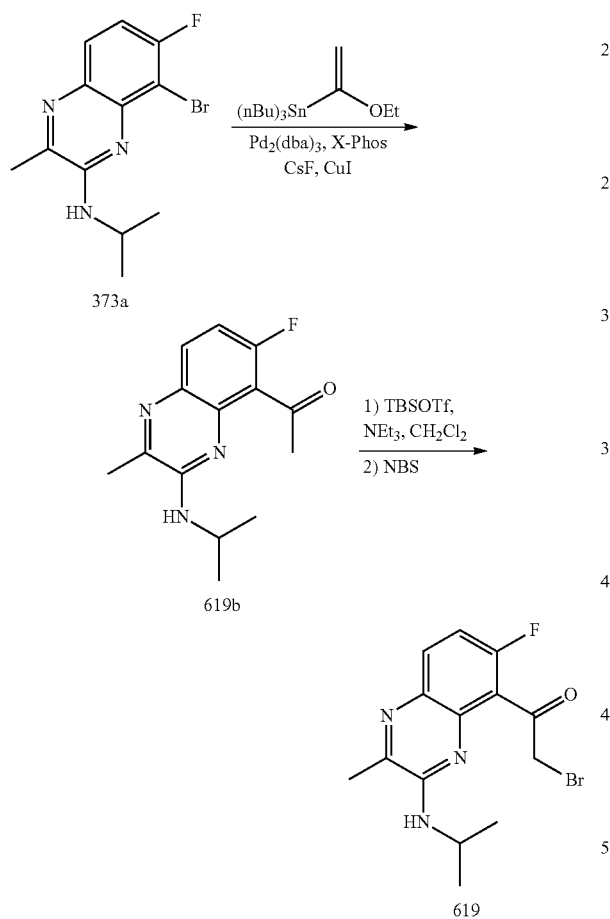

1-(6-Fluoro-3-(isopropylamino)-2-methylquinoxalin-5-yl)ethanone (619b) (3.58 g, 90% yield) as an orange solid was prepared according to the procedures described for Intermediate 610b, using 8-bromo-7-fluoro-N-isopropyl-3-methylquinoxalin-2-amine (373a) (2.00 g, 6.70 mmol) as the starting material. $^{19}$F NMR (377 MHz, DMSO-d$_6$) δ ppm −116.42. $^1$H NMR (400 MHz, DMSO-d$_6$) δ ppm 7.80 (1H, dd, J=9.0, 6.1 Hz), 7.20 (1H, t, J=9.2 Hz), 7.01 (1H, d, J=7.4 Hz), 4.23 (1H, m), 2.66 (3H, s), 2.52 (3H, s), 1.26 (6H, d, J=6.7 Hz). m/z (ESI, +ve) 262.1 (M+H)$^+$.

2-Bromo-1-(6-fluoro-3-(isopropylamino)-2-methylquinoxalin-5-yl)ethanone (619) (1.47 g, 4.32 mmol, 84% yield) as a yellow waxy solid was prepared according to the procedures described for Intermediate 610, using 1-(6-fluoro-3-(isopropylamino)-2-methylquinoxalin-5-yl)ethanone (619b) (1.34 g, 5.13 mmol) as the starting material. m/z (ESI, +ve) 340/342 (M+H)$^+$.

Preparation of 8-bromo-2-chloro-3-methylquinazolin-4(3H)-one (722)

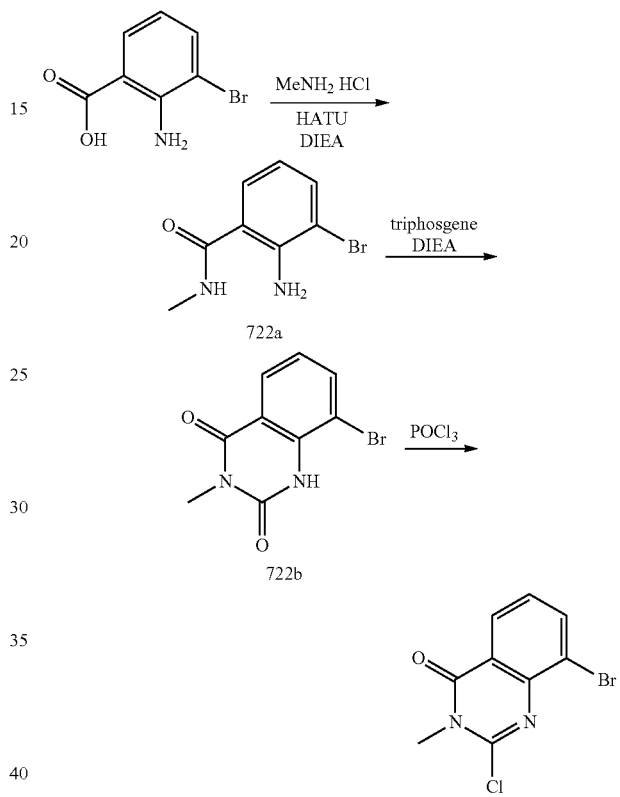

Preparation of 2-amino-3-bromo-N-methylbenzamide (722a)

A yellow mixture of 2-amino-3-bromobenzoic acid (Oakwood Products, Inc., West Columbia, S.C., 2.07 g, 9.58 mmol), methanamine hydrochloride (0.712 g, 10.54 mmol), 2-(3H-[1,2,3]triazolo[4,5-b]pyridin-3-yl)-1,1,3,3-tetramethylisouronium hexafluorophosphate (V) (4.37 g, 11.50 mmol), and Et$_3$N (3.07 mL, 22.04 mmol) in DMF (19.16 mL) was stirred at RT for 1 h. The reaction mixture was diluted with EtOAc (200 mL), added to a separatory funnel, and washed with saturated aqueous NaHCO$_3$ (2×100 mL); the organic layer was separated, dried over Na$_2$SO$_4$, and concentrated. The crude product in DCM was loaded onto the column and was purified via automated flash chromatography (silica gel) with 0-40% EtOAc in hexanes to give 2-amino-3-bromo-N-methylbenzamide (722a, 1.09 g, 4.76 mmol, 50% yield) as a white solid. $^1$H NMR (400 MHz, CDCl$_3$) δ ppm 2.97 (d, J=4.89 Hz, 3H) 6.06 (br. s., 3H) 6.52 (t, J=7.92 Hz, 1H) 7.26 (dd, J=7.82, 1.17 Hz, 1H) 7.50 (dd, J=7.92, 1.27 Hz, 1H). MS (ESI, pos. ion) m/z: 228.9/230.9 (M+1).

Preparation of 8-bromo-3-methylquinazoline-2,4(1H,3H)-dione (722b)

A solution of 2-amino-3-bromo-N-methylbenzamide (722a, 1.09 g, 4.76 mmol), N-ethyl-N-isopropylpropan-2-amine (0.829 ml, 4.76 mmol), and triphosgene (0.494 g, 1.66 mmol) in DCM (47.6 mL) was stirred at reflux for 19 h. More triphosgene (0.212 g, 0.714 mmol) was added, and the reaction mixture was refluxed for 1 h; mostly product was observed via LCMS. The crude product was adsorbed onto silica and was purified via automated flash chromatography (silica gel) with 0-100% EtOAc in hexanes to give 8-bromo-3-methylquinazoline-2,4(1H,3H)-dione (722b, 1.19 g, 4.67 mmol, 98% yield) as a white solid. $^1$H NMR (400 MHz, CDCl$_3$) δ ppm 3.46 (s, 3H) 7.13 (t, J=7.92 Hz, 1H) 7.81 (dd, J=7.92, 1.27 Hz, 1H) 8.12 (dd, J=8.02, 0.59 Hz, 1H) 8.20 (br. s., 1H). MS (ESI, pos. ion) m/z: 254.9/257 (M+1).

Preparation of 8-bromo-2-chloro-3-methylquinazolin-4(3H)-one (722)

A slurry of 8-bromo-3-methylquinazoline-2,4(1H,3H)-dione (722b, 1.14 g, 4.47 mmol), phosphoryl trichloride (4.09 mL, 44.7 mmol), and N-ethyl-N-isopropylpropan-2-amine (3.11 mL, 17.88 mmol) was stirred at reflux for 19 h. The reaction mixture was concentrated, diluted with ice, basicified with 10 N NaOH to ~pH 10, filtered, and washed with water to give brown solid. The solid was transferred to an Erlenmeyer flask and dissolved in DCM when a small aqueous layer formed; this was partitioned in a separatory funnel. The organic layer was partially concentrated, loaded onto the column and was purified via automated flash chromatography (silica gel) with 0-40% EtOAc in hexanes to give 8-bromo-2-chloro-3-methylquinazolin-4(3H)-one (722) (1.03 g, 3.77 mmol, 84% yield) as a light yellow solid. $^1$H NMR (400 MHz, CHLOROFORM-d) δ ppm 3.77 (s, 3H) 7.35 (t, J=7.92 Hz, 1H) 8.02 (dd, J=7.82, 1.37 Hz, 1H) 8.21 (dd, J=8.02, 1.37 Hz, 1H). MS (ESI, pos. ion) m/z: 273.9/275.9 (M+1).

Preparation of 8-bromo-2-chloro-3-cyclopropylquinazolin-4(3H)-one (723)

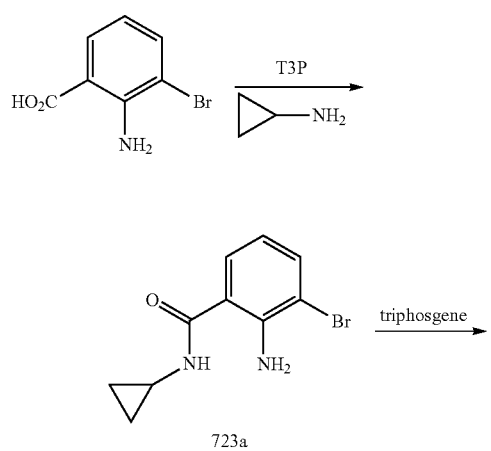

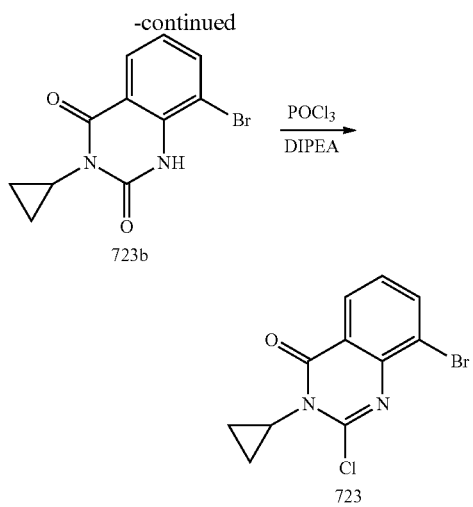

Preparation of 2-amino-3-bromo-N-cyclopropylbenzamide (723a)

To a heterogenous mixture of 2-amino-3-bromobenzoic acid (Sigma-Aldrich; 8.00 g, 37.0 mmol) in EtOAc (80 mL) at 0° C. was added 1-propanephosphonic acid cyclic anhydride (T3P) (Alfa-Aesar; 50 wt. % solution in EtOAc, 24.00 mL, 40.7 mmol) followed by cyclopropylamine (2.57 mL, 37.0 mmol). The ice bath was removed and the reaction was stirred at RT for 1 h. Saturated NaHCO$_3$ (aq.) was added and the mixture was stirred for 5 minutes. The layers were separated and the organic layer was washed with saturated NaHCO$_3$ (aq.) and brine. The aqueous layer was extracted with EtOAc (3×). The combined organic layers were dried over anhydrous Na$_2$SO$_4$, filtered and concentrated to afford 2-amino-3-bromo-N-cyclopropylbenzamide (723a; 6.00 g, 23.52 mmol, 64% yield) as a white solid. $^1$H NMR (400 MHz, CDCl$_3$) δ ppm 7.50 (dd, J=7.82, 1.37 Hz, 1H), 7.20 (dd, J=7.92, 1.27 Hz, 1H), 6.50 (t, J=7.82 Hz, 1H), 6.13 (br. s., 2H), 2.85 (tq, J=7.02, 3.54 Hz, 1H), 0.83-0.91 (m, 2H), 0.57-0.64 (m, 2H). m/z (ES, +ve) 255.1, 257.0 (M+H)$^+$.

Preparation of 8-bromo-3-cyclopropylquinazoline-2,4(1H,3H)-dione (723b)

Triphosgene (Sigma-Aldrich; 2.79 g, 9.41 mmol) was added to a solution of 2-amino-3-bromo-N-cyclopropylbenzamide (723a; 6.00 g, 23.52 mmol) in DCM (235 mL) at RT. The mixture was heated to reflux and stirred overnight (17 h). The mixture turned cloudy upon heating. The next morning the reaction mixture was cooled and concentrated to afford 8-bromo-3-cyclopropylquinazoline-2,4(1H,3H)-dione (723b; 6.61 g, 23.51 mmol, 100% yield) as a pale yellow solid. $^1$H NMR (400 MHz, CDCl$_3$) δ ppm 8.09 (d, J=8.02 Hz, 1H), 8.06 (br. s., 1H), 7.78 (dd, J=7.82, 1.17 Hz, 1H), 7.10 (t, J=7.92 Hz, 1H), 2.74-2.84 (m, 1H), 1.21 (q, J=7.04 Hz, 2H), 0.83-0.91 (m, 2H). m/z (ES, +ve) 281.0, 283.0 (M+H)$^+$.

Preparation of 8-bromo-2-chloro-3-cyclopropylquinazolin-4(3H)-one (723)

A mixture of 8-bromo-3-cyclopropylquinazoline-2,4(1H,3H)-dione (723b; 5.00 g, 17.79 mmol), POCl$_3$ (8.29 mL, 89.0 mmol) and DIPEA (12.38 mL, 71.1 mmol) was stirred at reflux overnight. The reaction was then cooled and concentrated. The brown syrup was cooled in an ice bath and then ice was added to the reaction mixture. The brown sludge was added to 100 mL of 10 M NaOH (aq.) and ice and stirred for 20 min. The mixture was filtered and the brown solid was washed with water and then put into solution with CH$_2$Cl$_2$ and filtered. The filtrate was collected and dried over Na$_2$SO$_4$, filtered and concentrated to afford 8-bromo-2-chloro-3-cyclopropylquinazolin-4(3H)-one (723) (4.54 g, 15.16 mmol, 85% yield) as a brown solid. $^1$H NMR (400 MHz, CDCl$_3$) δ ppm 8.17 (dd, J=8.02, 1.56 Hz, 1H), 7.99 (dd, J=7.82, 1.56 Hz, 1H), 7.32 (t, J=7.92 Hz, 1H), 3.02 (tt, J=7.12, 4.03 Hz, 1H), 1.33-1.43 (m, 2H), 0.94-1.04 (m, 2H). m/z (ES, +ve) 298.9, 301.0 (M+H)$^+$.

Preparation of (R)-6-(2-(benzyloxy)ethyl)-5,6-dihydropyrrolo[3,4-b]pyrrol-4(1H)-one (724)

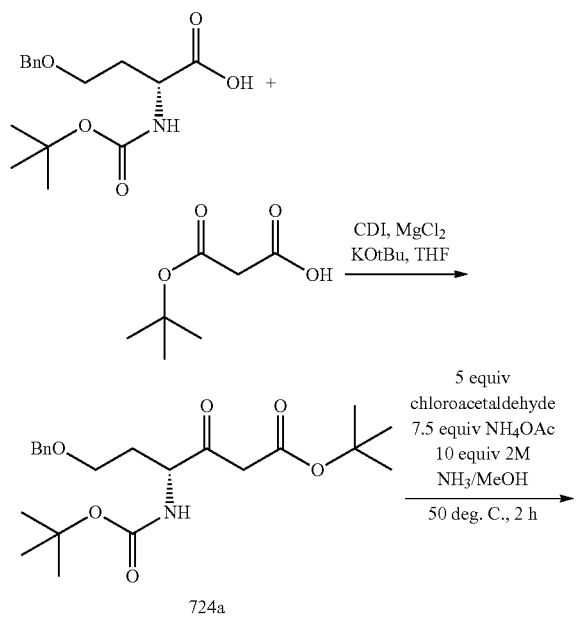

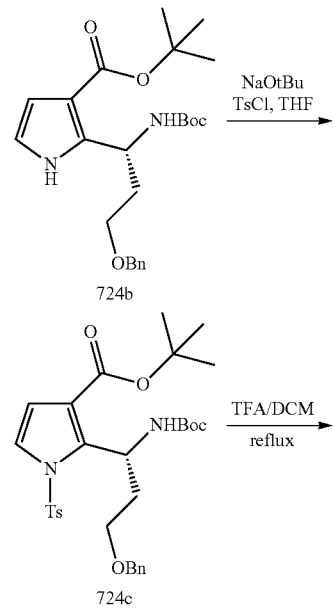

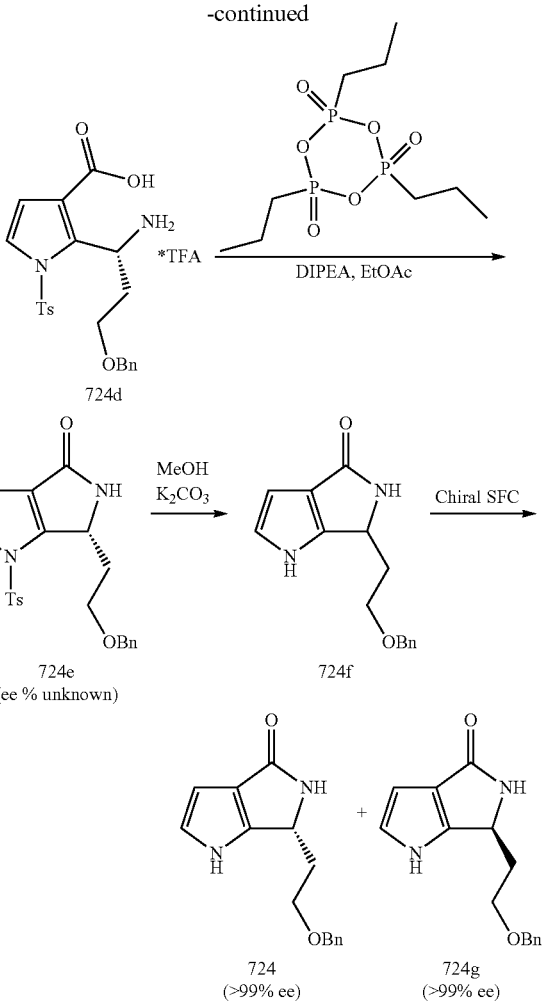

Preparation of (R)-tert-butyl-6-(benzyloxy)-4-((tert-butoxycarbonyl)amino)-3-oxohexanoate (724a)

Flask A: To a clear solution of (R)-4-(benzyloxy)-2-((tert-butoxycarbonyl)amino)butanoic acid (Combi-Blocks Inc, 5.01 g, 16.19 mmol) in THF (40 mL) at RT under nitrogen was added 1,1'-carbonyldiimidazole (3.94 g, 24.29 mmol) in one portion. Gas evolution observed and the reaction mixture was stirred 3 h. Flask B: To a cloudy mixture of mono-tert-butyl malonate (Sigma Aldrich, 4.99 mL, 32.4 mmol) and anhydrous magnesium chloride (Sigma Aldrich, 3.08 g, 32.4 mmol) in THF (60 mL) in a 3-necked 500 mL round-bottomed flask with a temperature probe at 2° C. was added potassium tert-butoxide (1.0M solution in THF, 32.4 mL, 32.4 mmol) slowly dropwise via addition funnel such that the temperature did not exceed 8° C. The resulting white suspension was stirred at RT for 2 h. The contents of Flask A was added to Flask B and the reaction mixture heated at 50° C. with stirring overnight (16 h). The reaction mixture was cooled to RT. The resulting white suspension was treated with 1N HCl (15 mL) to pH=7 and Et$_2$O (60 mL) and washed with brine (30 mL), dried over anhydrous MgSO$_4$, filtered, and concentrated affording crude (R)-tert-butyl 6-(benzyloxy)-4-((tert-butoxycarbonyl)amino)-3-oxohexanoate and (R,Z)-tert-butyl 6-(benzyloxy)-4-((tert-butoxycarbonyl)amino)-3-hydroxyhex-2-enoate (724a) as a viscous light yellow oil. m/z (ESI, +ve) 430.2 (M+Na)$^+$.

Preparation of (R)-tert-butyl-2-(3-(benzyloxy)-1-((tert-butoxycarbonyl)amino)propyl)-1H-pyrrole-3-carboxylate (724b)

(R)-tert-Butyl 6-(benzyloxy)-4-((tert-butoxycarbonyl)amino)-3-oxohexanoate (724a, 6.60 g, 16.20 mmol) was treated with $NH_3$ (2 M in MeOH, 81 mL, 162 mmol) and ammonium acetate (9.36 g, 121 mmol) at RT. The resulting mixture was stirred for at 50° C. for 30 min, then treated with chloroacetaldehyde (50 wt % in water, 10.42 mL, 81 mmol) and stirred at 50° C. for 2 h. The reaction mixture was stirred at RT overnight (16 h). The reaction mixture was concentrated to remove most of MeOH and partitioned between sat'd $NaHCO_3$ (100 mL) and EtOAc (100 mL). The aqueous layer was extracted with EtOAc (2×50 mL), and the combined organic extracts were washed with water and brine, dried over anhydrous $MgSO_4$, filtered, and concentrated under reduced pressure (rotary evaporator) to afford the crude product as a brown oil. The crude residue was purified on an ISCO Combiflash RF (160 g Thomson SingleStep column, using a gradient of 0-10% EtOAc in DCM) affording (R)-tert-butyl 2-(3-(benzyloxy)-1-((tert-butoxycarbonyl)amino)propyl)-1H-pyrrole-3-carboxylate (724b, 4.31 g, 10.01 mmol, 61.8% yield) as a light yellow viscous oil upon concentration of the product containing fractions. m/z (ESI, +ve) 453.2 $(M+Na)^+$.

Preparation of (R)-tert-butyl 2-(3-(benzyloxy)-1-((tert-butoxycarbonyl)amino)propyl)-1-tosyl-1H-pyrrole-3-carboxylate (724c)

(R)-tert-Butyl 2-(3-(benzyloxy)-1-((tert-butoxycarbonyl)amino)propyl)-1H-pyrrole-3-carboxylate (724b, 4.31 g, 10.01 mmol) was dissolved in THF (40 mL) under nitrogen and cooled in an ice bath. Sodium tert-butoxide (1M in THF, 10.01 mL, 10.01 mmol) was added and the mixture stirred for 5 min. Toluene-4-sulfonyl chloride (1.91 g, 10.01 mmol) was added to the solution and the mixture was stirred at 0° C. for 30 min. Water (50 mL) and EtOAc (50 mL) were added to the reaction mixture and the organic layer was washed with brine and dried over $MgSO_4$, filtered and concentrated affording crude (R)-tert-butyl-2-(1-amino-3-(benzyloxy)propyl)-1-tosyl-1H-pyrrole-3-carboxylate (724c) as an orange viscous oil. m/z (ESI, +ve) 607.2 $(M+Na)^+$.

Preparation of (R)-2-(1-amino-3-(benzyloxy)propyl)-1-tosyl-1H-pyrrole-3-carboxylic acid compound with 2,2,2-trifluoroacetic acid (1:1) (724d)

An orange solution of (R)-tert-butyl 2-(3-(benzyloxy)-1-((tert-butoxycarbonyl)amino)propyl)-1-tosyl-1H-pyrrole-3-carboxylate (504c, 5.85 g, 10.00 mmol) in DCM (15 mL) was treated with TFA (15 mL, 202 mmol) and heated at 40° C. for 2 h. The TFA and DCM was removed in vacuo affording (R)-2-(1-amino-3-(benzyloxy)propyl)-1-tosyl-1H-pyrrole-3-carboxylic acid compound with 2,2,2-trifluoroacetic acid (1:1) (724d) as a dark orange viscous oil which was used for the next step without purification. m/z (ESI, +ve) 429.2 $(M+1)'$.

Preparation of (R)-6-(2-(benzyloxy)ethyl)-1-tosyl-5,6-dihydropyrrolo[3,4-b]pyrrol-4(1H)-one (724e)

To a solution of (R)-2-(1-amino-3-(benzyloxy)propyl)-1-tosyl-1H-pyrrole-3-carboxylic acid compound with TFA (1:1) (504d, 5.43 g, 10.01 mmol) and DIEA (5.22 mL, 30.0 mmol) in EtOAc (50 mL) was added 1-propanephosphonic acid cyclic anhydride (50 wt. % in EtOAc, 5.96 mL, 10.01 mmol) dropwise via syringe. All solids dissolved to give a light brown solution. After 1 h, the reaction was partitioned between sat'd $NaHCO_3$ and EtOAc. The organic layer was washed with sat'd $NaHCO_3$ once, sat'd NaCl once, and the organics were dried over anhydrous $MgSO_4$, filtered, and concentrated in vacuo to give (R)-6-(2-(benzyloxy)ethyl)-1-tosyl-5,6-dihydropyrrolo[3,4-b]pyrrol-4(1H)-one (724e) (3.51 g, 8.55 mmol, 85% yield) as a light brown foam. m/z (ESI, +ve) 411.1 $(M+Na)^+$.

Preparation of (R)-6-(2-(benzyloxy)ethyl)-5,6-dihydropyrrolo[3,4-b]pyrrol-4(1H)-one (724)

To a solution of (R)-6-(2-(benzyloxy)ethyl)-1-tosyl-5,6-dihydropyrrolo[3,4-b]pyrrol-4(1H)-one (724e, 3.51 g, 8.55 mmol) in MeOH (50 mL) in an ice bath was added $K_2CO_3$ (2.36 g, 17.10 mmol) in one portion. The resulting white suspension was stirred in an ice bath for 1 h and at RT for 1 h. The resulting suspension was filtered through a pad of Celite washing with MeOH. 10 g silica gel was added to the filtrate and concentrated in vacuo. The resulting solid was purified using an ISCO Combiflash RF (40 g Grace Reverlis column, using a gradient of 0-10% 2 M $NH_3$/MeOH in DCM) affording (R)-6-(2-(benzyloxy)ethyl)-5,6-dihydropyrrolo[3,4-b]pyrrol-4(1H)-one (724f; 1.84 g, 7.17 mmol, 84% yield) as an orange-brown viscous oil. m/z (ESI, +ve) 257.1 $(M+1)^+$. The material (724f) was further purified by chiral SFC (mobile phase $CO_2$/30% MeOH (20 mM $NH_3$), chiral column AS (250×30 mm), wave length 245 nm, flow rate 120 mL/min) The first eluting peak was collected and concentrated in vacuo to give (S)-6-(2-(benzyloxy)ethyl)-5,6-dihydropyrrolo[3,4-b]pyrrol-4(1H)-one (724g) (537 mg, 3.04 mmol, 24% yield, >99% ee) as an orange tar. The second eluting peak was collected and concentrated in vacuo to give (R)-6-(2-(benzyloxy)ethyl)-5,6-dihydropyrrolo[3,4-b]pyrrol-4(1H)-one (724) (780 mg, 3.04 mmol, 35% yield, >99% ee) as an orange tar. $^1H$ NMR (400 MHz, $CDCl_3$) δ ppm 8.46 (1H, br. s.), 7.33-7.44 (5H, m), 6.58 (1H, t, J=2.3 Hz), 6.32 (1H, dd, J=2.8, 1.9 Hz), 5.70 (1H, br. s.), 4.56 (2H, s), 4.52 (1H, dd, J=8.4, 4.7 Hz), 3.77 (2H, dd, J=6.7, 4.3 Hz), 1.90-2.07 (2H, m). m/z (ESI, +ve) 257.1 $(M+1)^+$.

Example 283

2'-(3-(cyclopropylamino)-6-fluoro-2-methylquinoxalin-5-yl)-1'H-spiro[cyclopropane-1,6'-pyrrolo[3,4-b]pyrrol]-4'(5'H)-one

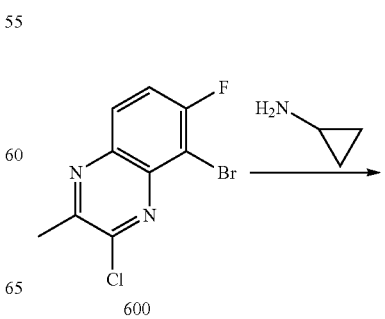

600

403

-continued

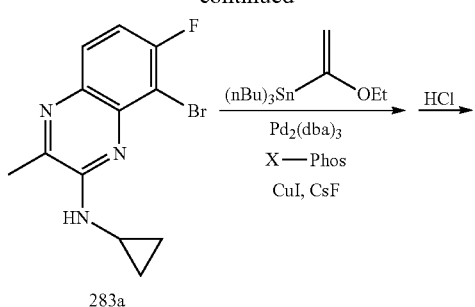

283a

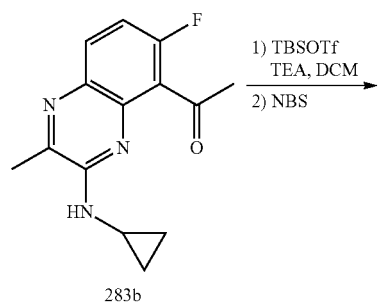

283b

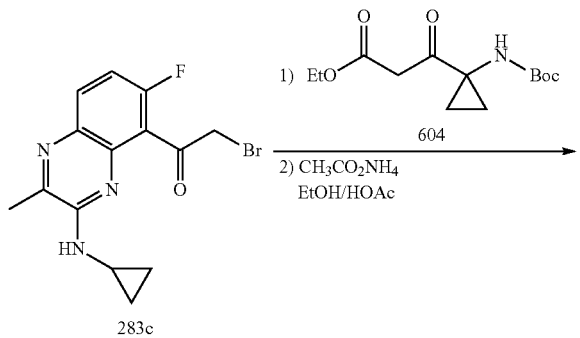

283c

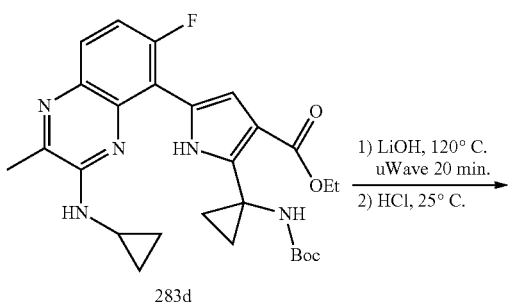

283d

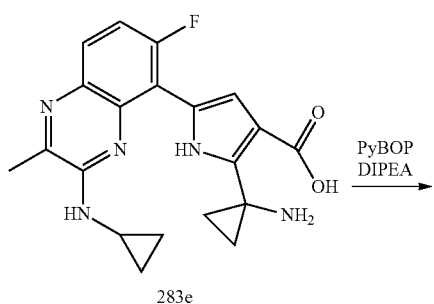

283e

404

-continued

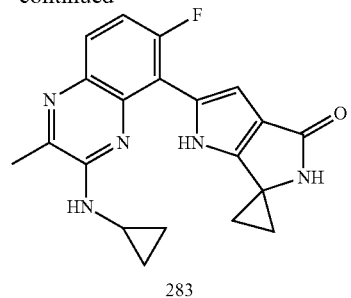

283

Preparation of 8-bromo-N-cyclopropyl-7-fluoro-3-methylquinoxalin-2-amine (283a)

A mixture of 5-bromo-3-chloro-6-fluoro-2-methylquinoxaline (600) (4.0 g, 14.52 mmol), DIEA (5.07 mL, 29.0 mmol) and cyclopropanamine (2.01 mL, 29.0 mmol) in DMSO (10 mL) in a sealed glass tube was heated in an oil bath at 85° C. for 3 h. The reaction mixture was poured onto 50 g of ice; the insoluble yellow solid was filtered, washed with 2×25 mL of water followed by 2×15 mL of hexanes. The yellow solid was collected and dried in a vacuum oven at 45° C. for 1 h to afford 3.1 g of the title compound. The filtrate was extracted with 2×50 mL of EtOAc. The combined organic extract was dried over MgSO$_4$, filtered and concentrated. The crude residue was purified on a silica gel column (20-50% EtOAc in hexanes) affording 0.9 g of the title compound as a light orange crystalline solid. $^1$H NMR (400 MHz, DMSO-d$_6$) δ ppm 7.77 (1H, dd, J=9.0, 6.1 Hz), 7.47 (1H, br.), 7.33 (1H, t, J=8.8 Hz), 3.06 (1H, m), 2.47 (3H, s), 0.81 (2H, m), 0.67 (2H, m). $^{19}$F NMR (377 MHz, DMSO-d$_6$) δ ppm −104.62. m/z (ESI, +ve) 296/298 (M+H).

Preparation of 1-(3-(cyclopropylamino)-6-fluoro-2-methylquinoxalin-5-yl)ethanone (283b)

A 150-mL round bottomed flask was charged with 8-bromo-N-cyclopropyl-7-fluoro-3-methylquinoxalin-2-amine (283a) (1.60 g, 5.40 mmol), tributyl(1-ethoxyvinyl)tin (Sigma-Aldrich) (2.74 mL, 8.10 mmol), Pd$_2$dba$_3$ (Strem Chemicals) (0.15 g, 0.16 mmol), Xphos (Strem Chemicals) (0.15 g, 0.32 mmol), CuI (Strem Chemicals) (0.21 g, 1.08 mmol) and cesium fluoride (Sigma-Aldrich) (2.46 g, 16.21 mmol) in dioxane (27.0 mL). The flask was purged with argon for 3 min, placed into a pre-heated (80° C.) bath and stirred 2.5 h while under inert atmosphere. The progress of the reaction was monitored by LCMS, which showed desired material. The mixture was removed from the heat bath and cooled to RT. The mixture was treated with 1 N HCl (20 mL) and stirred at RT 30 min. The mixture was filtered through AW Standard Super-Celt NF (Sigma-Aldrich). The filter cake was washed with EtOAc and water. The aq. layer was extracted with EtOAc (3×). The combined organic extracts were dried over Na$_2$SO$_4$, filtered and concentrated in vacuo. The crude material was purified by chromatography through a SiliCycle SiliaSep HP pre-packed silica-gel column (SiliCycle, Quebec City, Canada; 40 gram), eluting with a gradient of 0-20% EtOAc in DCM, to provide 1-(3-(cyclopropylamino)-6-fluoro-2-methylquinoxalin-5-yl)ethanone (283b) (1.22 g, 4.72 mmol, 87% yield) as a light yellow solid. $^1$H NMR (400 MHz, DMSO-d$_6$) δ ppm 7.82 (dd, J=9.00, 6.06 Hz, 1H), 7.51 (dd, J=2.74, 0.39 Hz, 1H), 7.23 (t, J=9.29 Hz, 1H), 2.78-2.97 (m, 1H), 2.76 (s, 3H), 2.46 (s, 3H), 0.70-0.83 (m, 2H), 0.52-0.70 (m, 2H). m/z (ESI, +ve) 260 (M+H).

Preparation of 2-bromo-1-(3-(cyclopropylamino)-6-fluoro-2-methylquinoxalin-5-yl)ethanone (283c)

To a stirred solution of 1-(3-(cyclopropylamino)-6-fluoro-2-methylquinoxalin-5-yl)ethanone (283b) (1.44 g, 5.55 mmol) in DCM (13.88 mL) at 0° C. was added TEA (0.91 mL, 6.54 mmol) and tert-butyldimethylsilyl trifluoromethanesulfonate (Sigma-Aldrich) (1.40 mL, 6.11 mmol). The overall mixture was stirred at 0° C. for 1 h, while under inert atmosphere. The reaction mixture was treated with saturated NaHCO$_3$ (20 mL) and the layers were separated. The aq. layer was extracted with DCM (3×). The combined organic extracts were dried over Na$_2$SO$_4$, filtered and concentrated in vacuo. m/z (ESI, +ve) 374 (M+H). The residue was treated with THF (13.88 mL) and water (1.6 mL). The resulting mixture was chilled to 0° C. in an ice/water bath. NBS (Alfa Aesar, Ward Hill, Mass.) (0.99 g, 5.55 mmol) was added into the mixture and the overall mixture was stirred at 0° C. for 30 min. The mixture was diluted with DCM (40 mL) and saturated NaHCO$_3$ (10 mL). The layers were separated and the aq. layer was extracted with DCM (3×). The organic extracts were combined, dried over Na$_2$SO$_4$, filtered and concentrated in vacuo. The crude material was purified by chromatography through a SiliCycle SiliaSep pre-packed silica-gel column (120 gram), eluting with a gradient of 0-25% EtOAc in DCM, to provide 2-bromo-1-(3-(cyclopropylamino)-6-fluoro-2-methylquinoxalin-5-yl)ethanone (283c) (1.19 g, 3.52 mmol, 63% yield) as light yellow solid. $^1$H NMR (400 MHz, DMSO-d$_6$) δ ppm 7.94 (dd, J=9.00, 5.87 Hz, 1H), 7.65-7.84 (m, 1H), 7.32 (t, J=9.39 Hz, 1H), 5.18 (s, 2H), 2.69-2.91 (m, 1H), 2.51 (s, 3H), 0.76-0.95 (m, 2H), 0.60-0.76 (m, 2H). m/z (ESI, +ve) 338/341 (M+H).

Preparation of ethyl 2-(1-((tert-butoxycarbonyl) amino)cyclopropyl)-5-(3-(cyclopropylamino)-6-fluoro-2-methylquinoxalin-5-yl)-1H-pyrrole-3-carboxylate (283d)

At RT, to a mixture of 2-bromo-1-(3-(cyclopropylamino)-6-fluoro-2-methylquinoxalin-5-yl)ethanone (283c) (1.18 g, 3.49 mmol) and ethyl 3-(1-((tert-butoxycarbonyl)amino)cyclopropyl)-3-oxopropanoate (604) (1.14 g, 4.19 mmol) dissolved in DMF (10.26 mL) was added K$_2$CO$_3$ (1.21 g, 8.72 mmol). The overall mixture was stirred overnight. The mixture was diluted with saturated NaHCO$_3$ (100 mL) and CHCl$_3$ (100 mL). The layers were separated and the aq. layer was extracted with CHCl$_3$ (3×). The combined organic extracts were dried over Na$_2$SO$_4$, filtered and concentrated in vacuo. The crude material was purified by chromatography through an Interchim puriFlash UP (25 micron) pre-packed silica-gel column (80 grams), eluting with a gradient of 0-30% EtOAc in DCM, to provide ethyl 2-(1-((tert-butoxycarbonyl)amino) cyclopropanecarbonyl)-4-(3-(cyclopropylamino)-6-fluoro-2-methylquinoxalin-5-yl)-4-oxobutanoate (0.69 g, 1.30 mmol, 37% yield) as a yellow oil. The yellow oil was put into a sealed tube with 2:1 mixture of EtOH/AcOH (3 mL) and NH$_4$OAc (Sigma) (0.80 g, 10.5 mmol) was added and the mixture was stirred at 60° C. overnight. The precipitate solid was filtered and washed with Et$_2$O (3×2 mL) to give ethyl 2-(1-((tert-butoxycarbonyl)amino)cyclopropyl)-5-(3-(cyclopropylamino)-6-fluoro-2-methylquinoxalin-5-yl)-1H-pyrrole-3-carboxylate (0.41 g, 23% yield) as a yellow solid. m/z (ESI, +ve) 510 (M+H).

Preparation of 2-(1-aminocyclopropyl)-5-(3-(cyclopropylamino)-6-fluoro-2-methylquinoxalin-5-yl)-1H-pyrrole-3-carboxylic acid (283e)

A glass microwave reaction vessel was charged with ethyl 2-(1-((tert-butoxycarbonyl)amino)cyclopropyl)-5-(3-(cyclopropylamino)-6-fluoro-2-methylquinoxalin-5-yl)-1H-pyrrole-3-carboxylate (283d) (0.38 g, 0.76 mmol) and LiOH monohydrate (Fluka/Aldrich) (191 mg, 4.56 mmol) in 1,4-Dioxane (7 mL)/Water (3.5 mL). The reaction mixture was stirred and heated in a Discover model microwave reactor (CEM, Matthews, N.C.) at 120° C. for 20 min (100 watts, Powermax feature off). This material was transferred to a 150-mL round-bottomed flask and added 4 M HCl in 1,4-dioxane (Aldrich) until pH 2-3. The mixture was stirred at RT for 2 h. The mixture was neutralized with 5 N NaOH (pH 7), then concentrated under reduced pressure to half of its volume. The residue was diluted with hexanes and placed into a sonicator for 30 sec. The precipitated solid was collected by filtration and washed with hexanes. This gave 2-(1-aminocyclopropyl)-5-(3-(cyclopropylamino)-6-fluoro-2-methylquinoxalin-5-yl)-1H-pyrrole-3-carboxylic acid hydrochloride (283e) (0.30 g, 0.718 mmol, 95% yield) as a tan solid. $^1$H NMR (400 MHz, MeOH-d4) δ ppm 7.86 (m, 1H), 7.44 (m, 1H), 7.34 (s, 1H), 2.68 (s, 3H), 1.56 (m, 4H), 1.14 (d, 2H), 0.91 (s, 2H). m/z (ESI, +ve) 383 (M+H).

Preparation of 2'-(3-(cyclopropylamino)-6-fluoro-2-methylquinoxalin-5-yl)-1'H-spiro[cyclopropane-1,6'-pyrrolo[3,4-b]pyrrol]-4'(5'H)-one (283)

To a 50-mL round-bottomed flask was added 2-(1-aminocyclopropyl)-5-(3-(cyclopropylamino)-6-fluoro-2-methylquinoxalin-5-yl)-1H-pyrrole-3-carboxylic acid hydrochloride (283e; 0.30 g, 0.718 mmol), DIEA (Aldrich) (0.75 mL, 4.31 mmol) in DMF (1.8 mL) and DCM (1.8 mL). Then 1H-benzotriazol-1-yl-oxytripyrrolidinophosphonium hexafluorophosphate (PyBOP) (Matrix innovation, Quebec City, Canada) (0.45 g, 0.86 mmol) was added into the reaction mixture. The overall mixture was stirred under inert atmosphere 40 min. The mixture was partially concentrated (removed DCM) in vacuo, then diluted with water and stirred 10 min. The precipitate was collected by filtration. The solids were triturated from hot EtOH in a sealed tube. The solids were collected by filtration, washed with Et$_2$O, and dried in a reduced pressure oven (40° C.) overnight. This gave 2'-(3-(cyclopropylamino)-6-fluoro-2-methylquinoxalin-5-yl)-1'H-spiro[cyclopropane-1,6'-pyrrolo[3,4-b]pyrrol]-4'(5'H)-one (283) (0.13 g, 0.36 mmol, 50% yield) as a light yellow solid. $^1$H NMR (400 MHz, DMSO-d$_6$) δ ppm 12.61 (br. S, 1H), 7.74 (br. s, 1H), 7.62-7.70 (m, 2H), 6.92 (br. s, 1H), 1.38-1.45 (m, 2H), 1.35 (br. s, 3H), 0.75-0.84 (m, 2H), 0.72 (br. s, 4H). m/z (ESI, +ve) 364 (M+H).

Example 284

(R)-2-(3-(cyclopropylamino)-6-fluoro-2-methylquinoxalin-5-yl)-6-methyl-5,6-dihydropyrrolo[3,4-b]pyrrol-4(1H)-one & Example 285: (S)-2-(3-(cyclopropylamino)-6-fluoro-2-methylquinoxalin-5-yl)-6-methyl-5,6-dihydropyrrolo[3,4-b]pyrrol-4(1H)-one

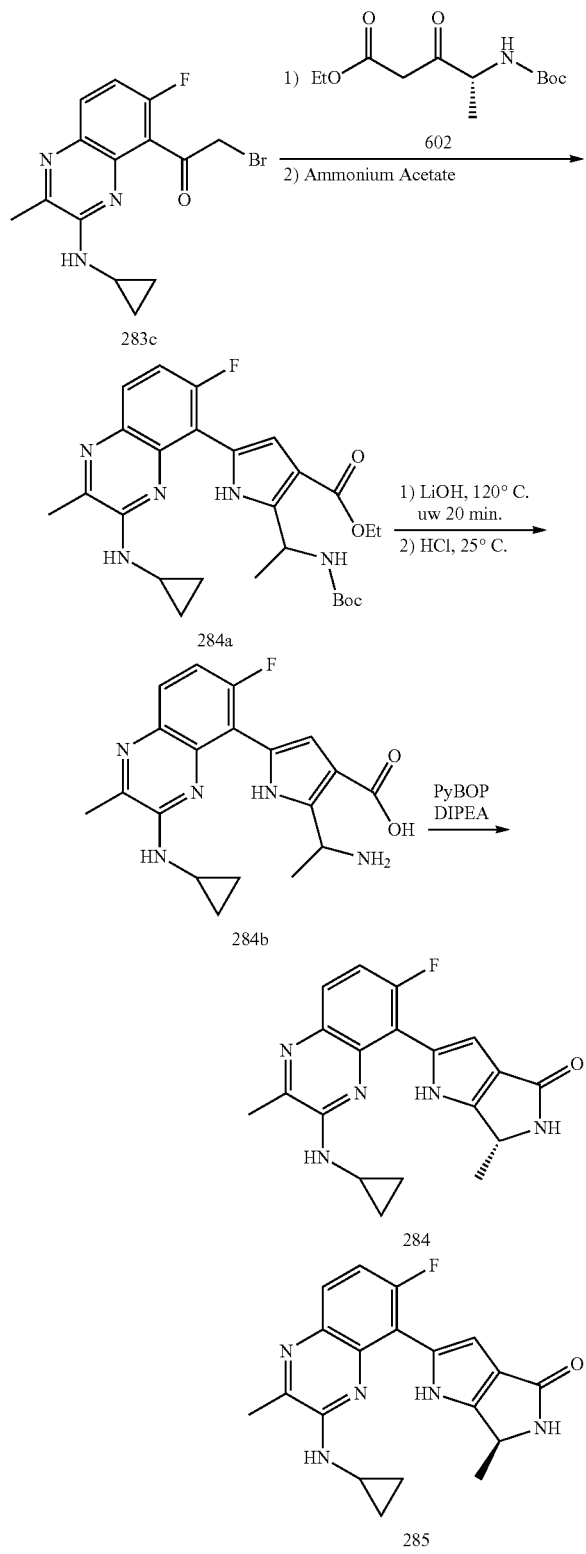

Preparation of ethyl 2-(1-((tert-butoxycarbonyl)amino)ethyl)-5-(3-(cyclopropylamino)-6-fluoro-2-methylquinoxalin-5-yl)-1H-pyrrole-3-carboxylate (284a)

A mixture of 2-bromo-1-(3-(cyclopropylamino)-6-fluoro-2-methylquinoxalin-5-yl)ethanone (293c) (0.81 g, 2.38 mmol) and (R)-ethyl 4-((tert-butoxycarbonyl)amino)-3-oxopentanoate (602) (0.74 g, 2.86 mmol) was dissolved in DMF (7.00 mL). Then $K_2CO_3$ (Acros Organics, New Jersey) (0.82 g, 5.95 mmol) was added into the reaction mixture. The overall mixture was stirred under inert atmosphere overnight. The mixture was diluted with saturated $NaHCO_3$ (10 mL) and $CHCl_3$ (20 mL). The layers were separated and the aq. layer was extracted with $CHCl_3$ (3×). The combined organic extracts were dried over $Na_2SO_4$, filtered and concentrated in vacuo. The crude material was purified by chromatography through an Interchim PuriFlash UP (25 micron) pre-packed silica-gel column (40 gram), eluting with a gradient of 0-30% EtOAc in DCM, to provide ethyl 4-((tert-butoxycarbonyl)amino)-2-(2-(3-(cyclopropylamino)-6-fluoro-2-methylquinoxalin-5-yl)-2-oxoethyl)-3-oxopentanoate (1.20 g, 2.32 mmol, 98% yield) as a yellow oil.

The diketone intermediate (1.20 g, step 1) was put into a sealed tube with EtOH (3 mL) and AcOH (2 mL). Then $NH_4OAc$ (Sigma-Aldrich) (1.47 g, 19.04 mmol) was added and the mixture was stirred at 60° C. overnight. The precipitate was collected by filtration and the solids were washed with $Et_2O$ (3×). This gave ethyl 2-(1-((tert-butoxycarbonyl)amino)ethyl)-5-(3-(cyclopropylamino)-6-fluoro-2-methylquinoxalin-5-yl)-1H-pyrrole-3-carboxylate (284a) (0.42 g, 0.844 mmol, 35% yield) as a yellow solid. m/z (ESI, +ve) 498 (M+H).

Preparation of 2-(1-aminoethyl)-5-(3-(cyclopropylamino)-6-fluoro-2-methylquinoxalin-5-yl)-1H-pyrrole-3-carboxylic acid (284b)

A glass microwave reaction vessel (80 mL) was charged with ethyl 2-(1-((tert-butoxycarbonyl)amino)ethyl)-5-(3-(cyclopropylamino)-6-fluoro-2-methylquinoxalin-5-yl)-1H-pyrrole-3-carboxylate (284a) (0.41 g, 0.81 mmol) and LiOH monohydrate (Sigma-Aldrich) (342 mg, 8.16 mmol) in 1,4-Dioxane (12 mL) and water (10 mL). The reaction mixture was stirred and heated in a CEM Voyager Microwave (Large-Scale Unit) at 120° C. for 35 min (100 watts, Powermax feature off). This material was transferred to a 150-mL round-bottomed flask for next step in the reaction. m/z (ESI, +ve) 470 (M+H). To the mixture from step 1, was added 4 M HCl/1,4-dioxane (Sigma-Aldrich) until pH 2-3. The mixture was stirred at RT for 4 h. The mixture was neutralized with 5 N NaOH (pH 7). The precipitate was collected by filtration and the solids were washed with hexanes. This gave 2-(1-aminoethyl)-5-(3-(cyclopropylamino)-6-fluoro-2-methylquinoxalin-5-yl)-1H-pyrrole-3-carboxylic acid (284b; 285 mg, 0.77 mmol, 95% yield) as light yellow solid. m/z (ESI, +ve) 353 (M-NH₂)'.

Preparation of (R)-2-(3-(cyclopropylamino)-6-fluoro-2-methylquinoxalin-5-yl)-6-methyl-5,6-dihydropyrrolo[3,4-b]pyrrol-4(1H)-one & (S)-2-(3-(cyclopropylamino)-6-fluoro-2-methylquinoxalin-5-yl)-6-methyl-5,6-dihydropyrrolo[3,4-b]pyrrol-4(1H)-one To a 50-mL round-bottomed flask was added 2-(1-aminoethyl)-5-(3-(cyclopropylamino)-6-fluoro-2-methylquinoxalin-5-yl)-1H-pyrrole-3-carboxylic acid (284b) (0.270 g, 0.731 mmol), DIEA (0.76 mL, 4.39 mmol) in DMF (1.83 mL) and DCM (1.85 mL). Then 1H-benzotriazol-1-yl-oxytripyr-rolidinophosphonium hexafluorophosphate (PyBOP) (Matrix innovation, Quebec City, Canada) (0.76 g, 1.46 mmol) was added into the reaction mixture. The overall mixture was stirred under inert atmosphere 2 h. The mixture was partially concentrated to remove DCM, then diluted with water and stirred 10 min. The precipitate was collected by filtration. The solids were triturated from warm EtOH in a sealed tube. The solids were collected by filtration and the solids were washed with $Et_2O$. The solids were dried in a reduced pressure oven overnight. Chiral separation of this material was by supercritical-fluid chromatography (Chiralpak IC (250×21 mm, 5 um column) Mobile Phase: 63:37 (A:B); A: liquid $CO_2$; B: MeOH (20 mM $NH_3$); 75 mL/min; oven temperature: 40° C.); Inlet Pressure: 100 bar; Wavelength: 230 nm) to give example 284 (first eluting product) & example 285 (second eluting product). Example 284: (R)-2-(3-(cyclopropylamino)-6-fluoro-2-methylquinoxalin-5-yl)-6-methyl-5,6-dihydropyr-rolo[3,4-b]pyrrol-4(1H)-one (284) (50 mg, 19% yield; >99% ee) as a light yellow solid. $^1$H NMR (400 MHz, DMSO-$d_6$) δ ppm 13.37-13.45 (m, 1H), 7.80-7.86 (m, 1H), 7.78 (br. s, 1H), 7.62-7.72 (m, 1H), 7.31-7.42 (m, 1H), 6.88 (br. s, 1H), 4.69 (q, J=6.98 Hz, 1H), 2.91-3.02 (m, 1H), 2.55-2.60 (m, 3H), 1.39 (d, J=6.46 Hz, 3H), 0.96-1.02 (m, 1H), 0.95 (br. s, 1H), 0.79 (dd, J=7.92, 3.62 Hz, 2H). m/z (ESI, +ve) 352 (M+H). Example 285: (S)-2-(3-(cyclopropylamino)-6-fluoro-2-methylquinoxalin-5-yl)-6-methyl-5,6-dihydropyrrolo[3,4-b]pyrrol-4(1H)-one (285) (65 mg, 25% yield; >99% ee) as a light yellow solid. $^1$H NMR (400 MHz, DMSO-$d_6$) δ ppm 13.37 (br. s, 1H), 7.76-7.82 (m, 1H), 7.73 (br. s, 1H), 7.63-7.71 (m, 1H), 7.31-7.40 (m, 1H), 6.83-6.89 (m, 1H), 4.62-4.71 (m, 1H), 2.95 (br. s, 1H), 2.52 (br. s, 3H), 1.36 (d, J=6.65 Hz, 3H), 0.89-0.97 (m, 2H), 0.76 (dd, J=7.82, 3.33 Hz, 2H). m/z (ESI, +ve) 352 (M+H).

Example 286

2-(3-(tert-butylamino)-6-fluoro-2-methylquinoxalin-5-yl)-6,7-dihydro-1H-pyrrolo[3,2-c]pyridin-4(5H)-one

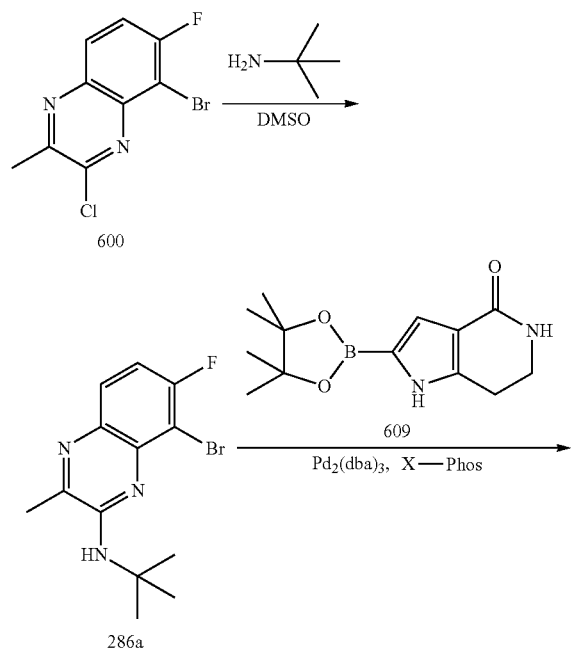

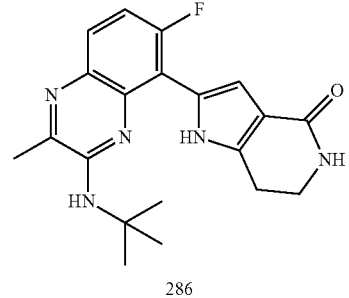

Preparation of 8-bromo-N-(tert-butyl)-7-fluoro-3-methylquinoxalin-2-amine (286a)

A glass reaction vessel was charged with 5-bromo-3-chloro-6-fluoro-2-methylquinoxaline (600) (9.705 g, 35.2 mmol) in DMSO (58.7 mL). Then tert-butylamine (Alfa Aesar; Ward Hill, Mass.) (18.51 mL, 176 mmol) was added into the mixture. The vial was sealed, then placed into a pre-heated (100° C.) oil bath and stirred 2 h. The vessel was removed from the heat source and cooled to RT. The mixture was poured into water (1100 mL) sat undisturbed 30 min, then stirred. The precipitate was collected by filtration (through a medium fritted-funnel) and the solids were washed with water. The solids were dried in a reduced-pressure oven overnight, to provide 8-bromo-N-(tert-butyl)-7-fluoro-3-methylquinoxalin-2-amine (286a) (8.27 g, 75% yield) as a tan solid. $^1$H NMR (400 MHz, DMSO-$d_6$) δ ppm 7.75 (dd, J=9.00, 5.87 Hz, 1H) 7.33 (t, J=8.80 Hz, 1H) 6.30 (s, 1H) 2.54 (s, 3H) 1.59 (s, 9H). m/z (ESI, +ve) 311.9 (M+H).

Preparation of 2-(3-(tert-butylamino)-6-fluoro-2-methylquinoxalin-5-yl)-6,7-dihydro-1H-pyrrolo[3,2-c]pyridin-4(5H)-one (286)

A glass microwave reaction vessel (80 mL) was charged with 8-bromo-N-(tert-butyl)-7-fluoro-3-methylquinoxalin-2-amine (286a) (1.20 g, 3.84 mmol) and 2-(4,4,5,5-tetramethyl-1,3,2-dioxaborolan-2-yl)-6,7-dihydro-1H-pyrrolo[3,2-c]pyridin-4(5H)-one (609; 1.81 g, 6.92 mmol) in 1,4-dioxane (15 mL)/water (4.8 mL). Then $Pd_2(dba)_3$ (Strem Chemicals,) (0.176 g, 0.19 mmol), Xphos (Strem Chemicals,) (181 mg, 0.38 mmol) and potassium phosphate tribasic (Fisher Scientific, Fair Lawn, N.J.) (2.45 g, 11.53 mmol) were added into the reaction mixture. The glass vessel was sealed and heated in a CEM Voyager Microwave (Matthews, N.C.; large-scale unit) at 110° C. for 20 min (50 watts, Powermax feature off). The mixture was diluted with DCM (50 mL) and filtered through AW Standard Super-Celt NF (Sigma-Aldrich). The filtrate was concentrated in-vacuo and the crude residue was diluted with DCM, then filtered through a fine-fritted funnel. The crude material was purified by chromatography through an Interchim PuriFlash UP pre-packed silica-gel column (Interchim INC, San Pedro, Calif.; 200 gram), eluted with a gradient of 0-8% EtOAc in $CH_2Cl_2$ (for recovery of the starting material, 8-bromo-N-(tert-butyl)-7-fluoro-3-methylquinoxalin-2-amine), then with a gradient of 0-5% MeOH in DCM, to provide 2-(3-(tert-butylamino)-6-fluoro-2-methylquinoxalin-5-yl)-6,7-dihydro-1H-pyrrolo[3,2-c]pyridin-4 (5H)-one (286) (0.55 g, 1.50 mmol, 39% yield) as a tan solid. $^1$H NMR (400 MHz, DMSO-$d_6$) δ ppm 12.09 (br., 1H), 7.65 (dd, J=9.00, 5.87 Hz, 1H), 7.26-7.34 (m, 1H), 6.95-7.01 (m, 1H), 6.73-6.77 (m, 1H), 6.15 (s, 1H), 3.41-3.48 (m, 2H), 2.86 (t, J,=,6.85 Hz, 2H), 2.55 (s, 3H), 1.51 (s, 9H). m/z (ESI, +ve) 368 (M+H).

Example 287

(6R)-6-methyl-2-(2-methyl-3-((1-methylethyl)amino)-5-quinoxalinyl)-5,6-dihydropyrrolo[3,4-b]pyrrol-4(1H)-one

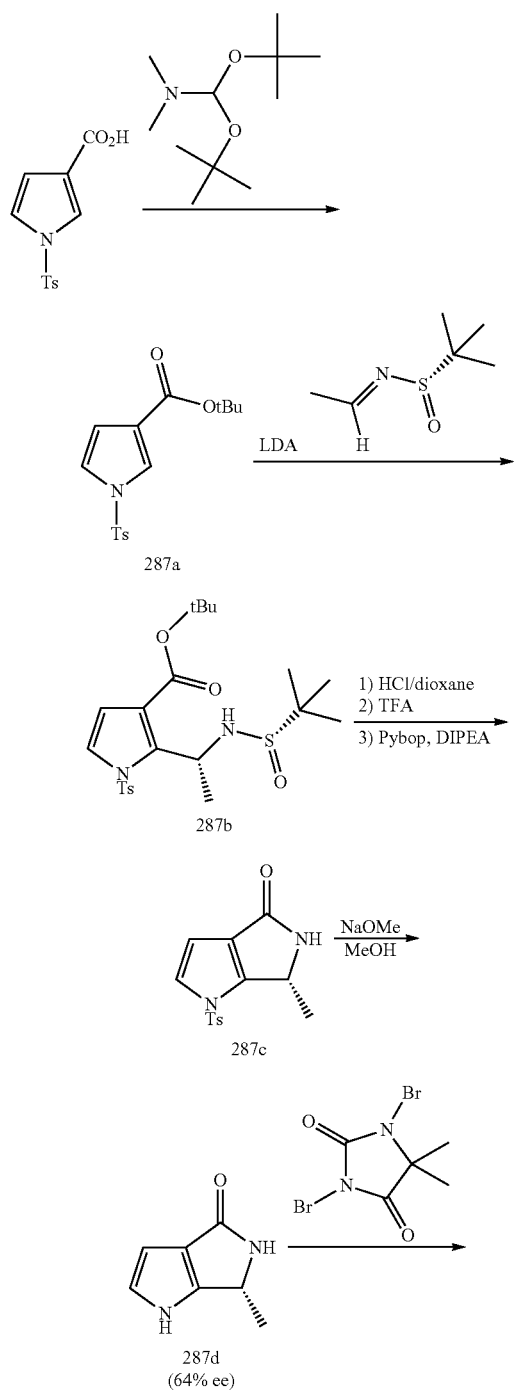

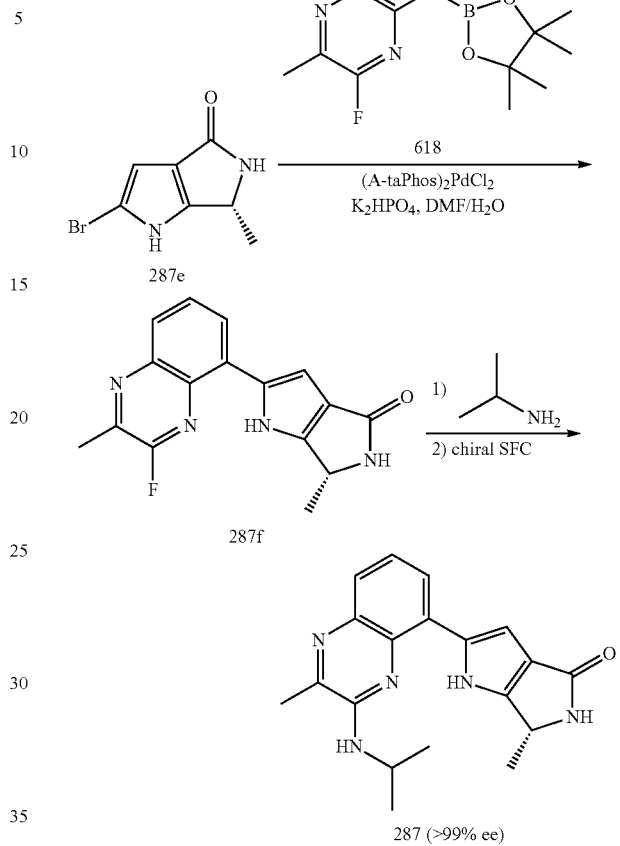

Preparation of tert-butyl 1-tosyl-1H-pyrrole-3-carboxylate (287a)

A 3-neck RBF was charged with 1-tosyl-1H-pyrrole-3-carboxylic acid (Astatech, Bristol, Pa.; 2.00 g, 7.54 mmol) and 20 mL anhydrous toluene, and was fitted with a water cooled reflux condenser and heated to reflux under $N_2$. N,N-dimethylformamide di-tert-butyl acetal (Aldrich; 14.46 mL, 60.4 mmol) was added slowly dropwise via addition funnel. The reaction mixture was stirred for 1 h, then the oil bath was turned off, and the reaction mixture was cooled to RT over the weekend. It was partitioned between saturated aq. $NaHCO_3$ and $Et_2O$. The organic layer was washed with saturated aq. $NaHCO_3$ once, saturated aq. NaCl once, and the organics were dried over anhydrous $Na_2SO_4$, filtered, and concentrated in vacuo. The material was treated with DCM and purified by silica gel chromatography (80 g column) using 0-20% EtOAc/hexanes. The product-containing fractions were concentrated to afford tert-butyl 1-tosyl-1H-pyrrole-3-carboxylate (287a; 2.22 g, 6.91 mmol, 92% yield) as a white solid. $^1$H NMR (400 MHz, CDCl$_3$) δ ppm 7.80 (2H, d, J=8.4 Hz), 7.63-7.70 (1H, m), 7.33 (2H, d, J=8.2 Hz), 7.09 (1H, dd, J=3.3, 2.3 Hz), 6.61 (1H, dd, J=3.3, 1.6 Hz), 2.43 (3H, s), 1.53 (9H, s). m/z (ESI, +ve) 266.0 (M+H)$^+$.

Preparation of tert-butyl 2-((R)-14(S)-1,1-dimethyl-ethylsulfinamido)ethyl)-1-tosyl-1H-pyrrole-3-carboxylate (287b)

To a solution of tert-butyl 1-tosyl-1H-pyrrole-3-carboxylate (,287a 1.67 g, 5.20 mmol) in 40 mL of THF at −78° C. was added LDA(Aldrich) (1.7 M solution in heptane/THF/ethylbenzene, 3.67 mL, 6.24 mmol) slowly dropwise. After 45 min, a solution of (S,E)-N-ethylidene-2-methylpropane-2-sulfinamide (Prepared according to PCT Int. Appl., WO2005103020; 0.765 g, 5.20 mmol) in THF was added slowly dropwise via syringe over several min. After 15 min, the acetone/dry ice bath was removed and the reaction was quenched by dropwise addition of saturated aq. NH$_4$Cl and Et$_2$O. The organic layer was washed with saturated aq. NH$_4$Cl once, saturated aq. NaCl once and the organics were dried over anhydrous MgSO$_4$, filtered, and concentrated in vacuo. The material was treated with DCM and purified by silica gel chromatography (80 g ISCO redisep gold column) using 0-50% EtOAc/hexanes. The product-containing fractions were concentrated to afford tert-butyl 2-((R)-1-((S)-1,1-dimethylethylsulfinamido)ethyl)-1-tosyl-1H-pyrrole-3-carboxylate (287b; 1.05 g, 2.24 mmol, 43% yield) as a white solid. $^1$H NMR (400 MHz, CDCl$_3$) δ ppm 7.73 (2H, d, J=8.2 Hz), 7.28-7.34 (3H, m), 6.58 (1H, d, J=3.3 Hz), 5.95 (1H, d, J=9.2 Hz), 5.14 (1H, br. s.), 2.43 (3H, s), 1.50-1.54 (12H, m), 0.96 (9H, s). m/z (ESI, +ve) 469.1 (MA-1)[11].

Preparation of (R)-6-methyl-1-tosyl-5,6-dihydropyrrolo[3,4-b]pyrrol-4(1H)-one (287c)

To tert-butyl 2-((R)-1-((S)-1,1-dimethylethylsulfinamido)ethyl)-1-tosyl-1H-pyrrole-3-carboxylate (287b, 0.55 g, 1.17 mmol) in 4 mL of dioxane under N$_2$ was added hydrogen chloride (Aldrich, St. Louis, Mo.; 4.40 ml of 4.0 M solution in 1,4-dioxane, 17.60 mmol). The homogeneous reaction was sealed and allowed to stir overnight. The reaction was concentrated in vacuo to give a foam. This material was treated with 3 mL DCM and TFA (Aldrich, St. Louis, Mo.; 2.62 mL, 35.2 mmol) and fitted with a drying tube. After 5 h, the stir bar was removed and the reaction was concentrated in vacuo and placed on hood pump overnight, to give a light yellow solid. The solid was treated with 5 mL DCM and 5 mL DMF and cooled to 0° C. DIEA (Aldrich, 1.23 mL, 7.04 mmol) was added dropwise via syringe to give a solution, and PyBoP (Aldrich, 0.73 g, 1.41 mmol) was added in one portion. The ice bath was removed and the reaction warmed to RT. After 1 h, the reaction was treated with ice and saturated aq. NaHCO$_3$. The reaction was partitioned between saturated aq. NaHCO$_3$ and Et$_2$O (slightly cloudy). The aq. layer was extracted 1× Et$_2$O, and the combined organic layers were washed with water 2 times, saturated aq. NaCl once, and the organics (rinsed some undissolved solid into organics from sep funnel with DCM) were dried over anhydrous MgSO$_4$, filtered, and concentrated in vacuo. The material was treated with DCM and purified by silica gel chromatography (40 g ISCO gold column) using 0-100% EtOAc/hexanes. The product-containing fractions were concentrated to afford (R)-6-methyl-1-tosyl-5,6-dihydropyrrolo[3,4-b]pyrrol-4(1H)-one (287c; 0.194 g, 0.67 mmol, 57% yield) as a white foam. $^1$H NMR (400 MHz, CDCl$_3$) δ ppm 7.74 (2H, d, J=8.4 Hz), 7.35 (2H, d, J=8.2 Hz), 7.16 (1H, d, J=3.1 Hz), 6.48 (1H, d, J=3.1 Hz), 5.76 (1H, br. s.), 4.68 (1H, q, J=6.6 Hz), 2.45 (3H, s), 1.62 (3H, d, J=6.7 Hz). m/z (ESI, +ve) 291.0 (M+H)$^+$.

Preparation of (R)-6-methyl-5,6-dihydropyrrolo[3,4-b]pyrrol-4(1H)-one (287d)

To a slurry of (R)-6-methyl-1-tosyl-5,6-dihydropyrrolo[3,4-b]pyrrol-4(1H)-one (287c, 0.194 g, 0.67 mmol) in 3 mL of anhydrous MeOH under N$_2$ was added sodium methoxide (Aldrich; 2.67 mL of 0.5 M in MeOH, 1.34 mmol). The slurry was stirred rapidly for 1 h at which point the reaction was checked and judged complete. The reaction was treated with DCM to give a solution, and was adsorbed onto 2 g silica gel, dried, and purified by silica gel chromatography (24 g ISCO gold column) using 0-100% of 90/10 DCM/MeOH in DCM. The product-containing fractions were concentrated to afford (R)-6-methyl-5,6-dihydropyrrolo[3,4-b]pyrrolo-4(1H)-one (287d; 0.068 g, 0.50 mmol, 75% yield) as a waxy white solid. The material was determined to be 64% ee enriched in the indicated enantiomer by chiral SFC chromatography: Analytical SFC method: Column: Chiralpak AS-H (150×4.6 mm, 5 micron); Mobile Phase: 85:15 (A:B) A: Liquid CO$_2$. B: MeOH (20 mM NH$_3$); Flow Rate: 4.0 mL/min; Oven/Column Temp.: 40 deg. C.; Outlet Pressure: 100 bar; Peak 1 (2.14 min) is (S)-6-methyl-5,6-dihydropyrrolo[3,4-b]pyrrol-4(1H)-one; Peak 2 (2.56 min) is (R)-6-methyl-5,6-dihydropyrrolo[3,4-b]pyrrol-4(1H)-one. Analytical data: $^1$H NMR (400 MHz, DMSO-d$_6$) δ ppm 11.31 (1H, br. s.), 7.51 (1H, s), 6.83 (1H, t, J=2.2 Hz), 6.06 (1H, dd, J=2.7, 1.6 Hz), 4.42 (1H, q, J=6.5 Hz), 1.29 (3H, d, J=6.7 Hz). m/z (ESI, +ve) 137.1 (M+H)$^+$.

Preparation of (R)-2-bromo-6-methyl-5,6-dihydropyrrolo[3,4-b]pyrrol-4(1H)-one

A solution of (R)-6-methyl-5,6-dihydropyrrolo[3,4-b]pyrrolo-4(1H)-one (287d, 0.068 g, 0.50 mmol) in 5 mL DMF under N$_2$ was cooled to −55° C. (acetone bath with periodic addition of dry ice). 1,3-dibromo-5,5-dimethylhydantoin (Aldrich; 0.071 g, 0.250 mmol) was added in one portion and the resulting cloudy reaction was stirred at −55° C. for 5 min. After 5 additional min, the reaction was clear and light yellow. The reaction was diluted with water the reaction was partitioned between saturated aq. NaHCO$_3$ and DCM. The aq. layer was extracted with DCM 3 times, and the combined organics were dried over anhydrous Na$_2$SO$_4$, filtered, and concentrated in vacuo. DMF was removed by rotovap for 15 min with hood pump and bath at 45° C. The aq. layer was extracted a further 4×DCM, dried over anhydrous Na$_2$SO$_4$, filtered, combined with first extraction materials, and concentrated in vacuo. The material was treated with 20% MeOH in DCM and adsorbed onto 1.0 g silica gel and purified by silica gel chromatography (12 g ISCO gold column) using 0-100% 90/10 DCM/MeOH The product-containing fractions were concentrated to afford (R)-2-bromo-6-methyl-5,6-dihydropyrrolo[3,4-b]pyrrol-4(1H)-one (287e; 0.058 g, 0.27 mmol, 54% yield) as a white solid. $^1$H NMR (400 MHz, DMSO-d$_6$) δ ppm 12.13 (1H, br. s.), 7.70 (1H, s), 6.17 (1H, s), 4.30-4.62 (1H, m), 1.27 (3H, d, J=6.7 Hz) m/z (ESI, +ve) 215.0/217.0 (M+H)$^+$.

Preparation of (R)-2-(3-fluoro-2-methylquinoxalin-5-yl)-6-methyl-5,6-dihydropyrrolo[3,4-b]pyrrol-4(1H)-one (287l)

Argon was bubbled into a slurry of potassium phosphate dibasic (Aldrich; 0.164 g, 0.944 mmol), 1,1-bis[(di-t-butyl-p-methylaminophenyl]palladium(ii) chloride (Aldrich; 0.019 g, 0.027 mmol), 3-fluoro-2-methyl-5-(4,4,5,5-tetramethyl-1,3,2-dioxaborolan-2-yl)quinoxaline (618) (0.155 g, 0.539 mmol), (R)-2-bromo-6-methyl-5,6-dihydropyrrolo[3,4-b]pyrrol-4(1H)-one (287) (0.058 g, 0.270 mmol) in 1.5 mL DMF and 0.5 mL water for 1 min. The reaction was sealed and placed in a 70° C. oil bath for 45 min. Additional 1 equiv boronic ester and 5 mg catalyst added, and the reaction was heated 30 min additional. The reaction was partitioned between water and EtOAc. The aq. layer was extracted 1× EtOAc, and the combined organic layers were washed with water 2 times, saturated aq. NaCl once, and the organics were dried over anhydrous Na₂SO₄, filtered, and concentrated in vacuo. The material was treated with DCM and purified by silica gel chromatography (24 g column) using 0-100% 90/10 DCM/MeOH in DCM. The product-containing fractions were concentrated to afford (R)-2-(3-fluoro-2-methylquinoxalin-5-yl)-6-methyl-5,6-dihydropyrrolo[3,4-b]pyrrol-4 (1H)-one (287f; 0.034 g, 0.115 mmol, 42% yield) as a orange solid. ¹H NMR (400 MHz, DMSO-d₆) δ ppm 11.90 (1H, s), 8.07 (1H, d, J=7.6 Hz), 7.94 (1H, d, J=8.2 Hz), 7.78-7.88 (1H, m), 7.69 (1H, s), 7.01 (1H, d, J=1.6 Hz), 4.58 (1H, q, J=6.7 Hz), 2.71 (3H, s), 1.41 (3H, d, J=6.7 Hz). m/z (ESI, +ve) 297.0 (M+H)⁺.

Preparation of (R)-2-(3-(isopropylamino)-2-methylquinoxalin-5-yl)-6-methyl-5,6-dihydropyrrolo[3,4-b]pyrrol-4(1H)-one (287)

(R)-2-(3-fluoro-2-methylquinoxalin-5-yl)-6-methyl-5,6-dihydropyrrolo[3,4-b]pyrrolo-4(1H)-one (0.029 g, 0.098 mmol) propan-2-amine (Aldrich; 0.125 ml, 1.468 mmol) and 0.5 mL of DMSO were combined in a sealable tube and heated to 60° C. for 1 h. The reaction was concentrated and placed on hood pump vacuum overnight. The material was purified by preparative SFC: OD-H (Sum, 21 mm×25 cm, S/N=1203) with 30% organic modifier modifier: 70% carbon dioxide; Organic modifier: MeOH with 20 mM NH₃; F=60 mL/min, T=40 C, BPR=100 bar, P=158 bar, 278 nm. Concentration of fractions containing the major peak (peak 2) gave (R)-2-(3-(isopropylamino)-2-methylquinoxalin-5-yl)-6-methyl-5,6-dihydropyrrolo[3,4-b]pyrrol-4(1H)-one (287; >99% ee, 15 mg, 0.045 mmol, 46% yield): ¹H NMR (400 MHz, DMSO-d₆) δ ppm 12.24 (1H, s), 7.88 (1H, dd, J=7.6, 1.2 Hz), 7.52-7.70 (2H, m), 7.33 (1H, t, J=7.8 Hz), 6.95 (1H, d, J=1.6 Hz), 6.86 (1H, d, J=7.2 Hz), 4.58 (1H, q, J=6.7 Hz), 4.33 (1H, dq, J=13.4, 6.6 Hz), 2.54 (3H, s), 1.37 (6H, t, J=6.8 Hz), 1.32 (3H, d, J=6.5 Hz). m/z (ESI, +ve) 336.2 (M+H)⁺.

Examples 288

(6S)-2-(3-(tert-butylamino)-2-methyl-5-quinoxalinyl)-6-methyl-1,5,6,7-tetrahydro-4H-pyrrolo[3,2-c]pyridin-4-one, and 289: (6R)-2-(3-(tert-butylamino)-2-methyl-5-quinoxalinyl)-6-methyl-1,5,6,7-tetrahydro-4H-pyrrolo[3,2-c]pyridin-4-one

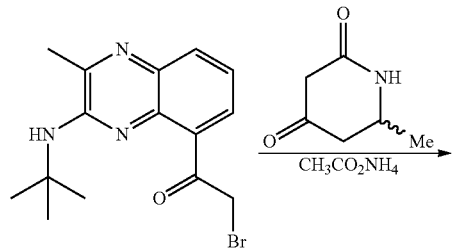

606

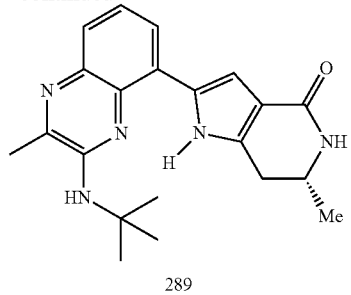

289

A slurry of NH₄OAc (Fisher Chemical, Fair Lawn, N.J.; 668 mg, 8.66 mmol), 2-bromo-1-(3-(tert-butylamino)-2-methylquinoxalin-5-yl)ethanone (Example 606; 364 mg, 1.08 mmol), 6-methylpiperidine-2,4-dione (prepared according to J. Med. Chem. 2009, 52, 293-307; 275 mg, 2.16 mmol) in 5 mL of EtOH was sealed in a glass tube and heated to 60° C. in an oil bath. After 1 h, the reaction was checked by LCMS and additional NH₄OAc (668 mg, 8.66 mmol) and 2-bromo-1-(3-(tert-butylamino)-2-methylquinoxalin-5-yl)ethanone (364 mg, 1.08 mmol) was added. Heating was continued for 2 h, and the reaction was stirred over the weekend at RT. A yellow precipitate was collected by filtration, rinsed with (2×) Et₂O, and dried in vacuo to give 0.272 g yellow solid. A portion of this material (0.232 g) was purified by chiral SFC (Chiralpak ASH 250×20, 5 micron, 20% MeOH containing 20 mM NH₃, 70 mL/min, 278-nm, 93/165 Bar) to give: first eluting peak, (6S)-2-(3-(tert-butylamino)-2-methyl-5-quinoxalinyl)-6-methyl-1,5,6,7-tetrahydro-4H-pyrrolo[3,2-c]pyridin-4-one (288) (51 mg, 13% yield) and second eluting peak, (6R)-2-(3-(tert-butylamino)-2-methyl-5-quinoxalinyl)-6-methyl-1,5,6,7-tetrahydro-4H-pyrrolo[3,2-c]pyridin-4-one (289) (42 mg, 11% yield). ¹H NMR (400 MHz, DMSO-d₆) δ ppm 11.94 (1H, br. s.), 7.82 (1H, dd, J=7.4, 1.4 Hz), 7.57 (1H, dd, J=8.0, 1.2 Hz), 7.33 (1H, t, J=7.8 Hz), 6.99 (1H, d, J=2.2 Hz), 6.88 (1H, s), 6.01 (1H, s), 3.80 (1H, dt, J=11.2, 5.9 Hz), 2.91 (1H, dd, J=15.8, 5.1 Hz), 2.57-2.72 (1H, m), 2.57 (3H, br. s.), 1.56 (9H, s), 1.25 (3H, d, J=6.3 Hz). m/z (ESI, +ve) 364.1 (M+H)⁺.

Example 290 tert-butyl 2-(3-(tert-butylamino)-2-methylquinoxalin-5-yl)-4-oxo-4,5,6,7-tetrahydro-1H-pyrrolo[3,2-c]pyridine-1-carboxylate

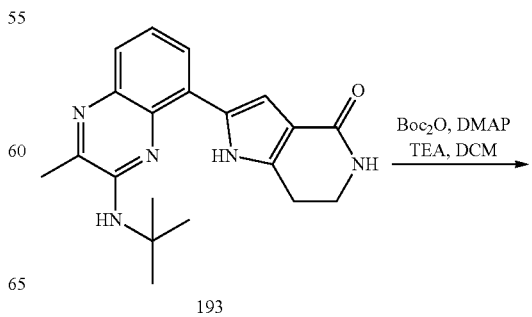

193

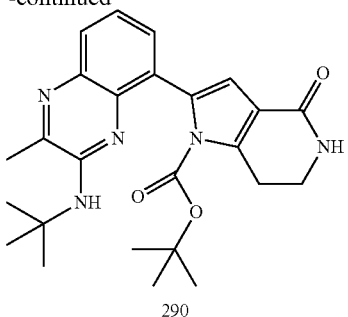

290

To a suspension of 2-(3-(tert-butylamino)-2-methylquinoxalin-5-yl)-6,7-dihydro-1H-pyrrolo[3,2-c]pyridin-4(5H)-one (193) (0.05 g, 0.143 mmol), 4-(dimethylamino)pyridine (1.7 mg, 0.014 mmol), TEA (0.024 mL, 0.17 mmol) in DCM (0.3 mL) was added di-tert-butyl dicarbonate (Sigma-Aldrich) (0.034 mL, 0.157 mmol). An additional 0.34 mL of di-tert-butyl dicarbonate was added after 1 h stirring at RT. After a total of 2 h of stirring at RT, the reaction mixture was diluted with DCM and washed with saturated NaHCO$_3$ solution. The organic layer was concentrated. The residue was purified on a silica gel column (10-100% EtOAc/hexanes followed by 1-10% MeOH/DCM) to provide tert-butyl 2-(3-(tert-butylamino)-2-methylquinoxalin-5-yl)-4-oxo-4,5,6,7-tetrahydro-1H-pyrrolo[3,2-c]pyridine-1-carboxylate (290) (28 mg, 43% yield). $^1$H NMR (300 MHz, CDCl$_3$) δ ppm 0.84 (s, 9H), 1.32 (s, 9H), 2.50 (s, 3H), 3.23-3.36 (m, 2H), 3.58-3.69 (m, 2H), 4.54-4.62 (m, 1H), 5.54-5.66 (m, 1H), 6.52-6.61 (m, 1H), 7.30-7.39 (m, 1H), 7.45-7.54 (m, 1H), 7.75-7.84 (m, 1H), 7.75-7.83 (m, 1H). m/z (ES, +ve) 450.1 (M+H)$^+$.

Example 291 tert-butyl 2-(3-(tert-butylamino)-2-methylquinoxalin-5-yl)-4-oxo-6,7-dihydro-1H-pyrrolo[3,2-c]pyridine-5(4H)-carboxylate

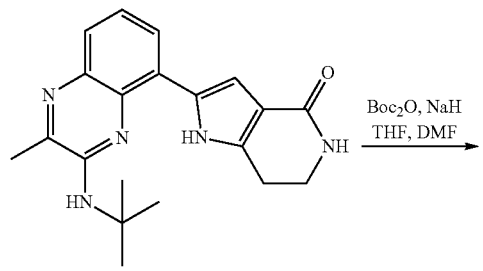

193

Boc$_2$O, NaH
THF, DMF

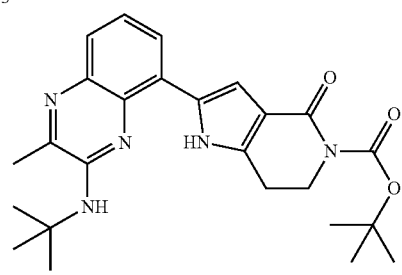

291

To a mixture of 2-(3-(tert-butylamino)-2-methylquinoxalin-5-yl)-6,7-dihydro-1H-pyrrolo[3,2-c]pyridin-4(5H)-one (193) (50 mg, 0.14 mmol) in DMF (0.14 mL) and THF (0.14 mL) was added NaH (13 mg, 0.33 mmol). After stirring for 5 min, di-tert-butyl dicarbonate (0.03 mL, 0.14 mmol) was added and the resulting mixture was stir at RT overnight. Reaction mixture was quenched with water and extracted with DCM. The DCM layer was concentrated and the residue was purified on a silica gel column (1-3% MeOH in DCM) to produce title compound (291) (11 mg, 0.024 mmol, 17% yield). $^1$H NMR (300 MHz, CDCl$_3$) δ ppm 1.58 (s, 14H), 1.66 (s, 9H), 2.56 (s, 3H), 2.92-3.05 (m, 3H), 4.07-4.22 (m, 2H), 4.77-4.92 (m, 1H), 7.05-7.18 (m, 1H), 7.32-7.44 (m, 1H), 7.61-7.72 (m, 1H), 7.88-7.97 (m, 1H), 12.59-12.72 (m, 1H). m/z (ES, +ve) 450.1 (M+H)$^+$.

Example 292

2-(3-(tert-butylamino)-2-methylquinoxalin-5-yl)-6,7-dihydro-1H-pyrrolo[3,2-c]pyridine-4(5H)-thione

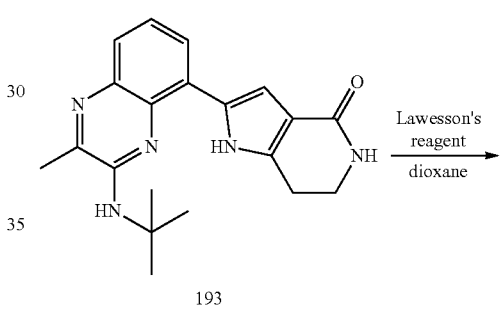

193

Lawesson's reagent
dioxane

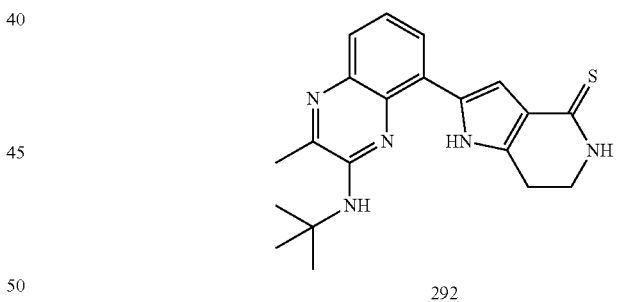

292

A mixture of 2-(3-(tert-butylamino)-2-methylquinoxalin-5-yl)-6,7-dihydro-1H-pyrrolo[3,2-c]pyridin-4(5H)-one (193) (0.02 g, 0.057 mmol), Lawesson's reagent (Sigma-Aldrich) (0.028 g, 0.069 mmol), Dioxane (0.88 mL) was heated to 75° C. overnight. Reaction mixture was directly loaded onto prep-plate TLC. Purification (3% MeOH/DCM) provided 2-(3-(tert-butylamino)-2-methylquinoxalin-5-yl)-6,7-dihydro-1H-pyrrolo[3,2-c]pyridine-4(5H)-thione (292) (8 mg, 36% yield). $^1$H NMR (300 MHz, CDCl$_3$) δ ppm 1.54-1.60 (m, 4H), 1.66 (s, 9H), 2.56 (s, 3H), 2.95-3.08 (m, 2H), 3.62-3.76 (m, 2H), 4.78-4.93 (m, 1H), 7.28-7.31 (m, 1H), 7.34-7.45 (m, 1H), 7.62-7.72 (m, 1H), 7.95-8.04 (m, 1H), 12.69-12.74 (m, 1H). m/z (ES, +ve) 366.3 (M+H)$^+$.

Examples 293

(6S)-6-methyl-2-(2-methyl-3-((2,2,2-trifluoroethyl)amino)-5-quinoxalinyl)-5,6-dihydropyrrolo[3,4-b]pyrrol-4(1H)-one; and 294: (6R)-6-methyl-2-(2-methyl-3-((2,2,2-trifluoroethyl)amino)-5-quinoxalinyl)-5,6-dihydropyrrolo[3,4-b]pyrrol-4(1H)-one

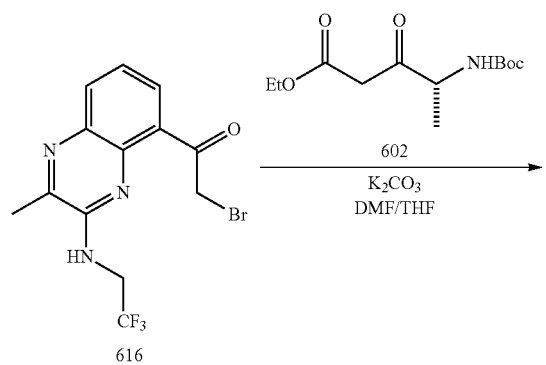

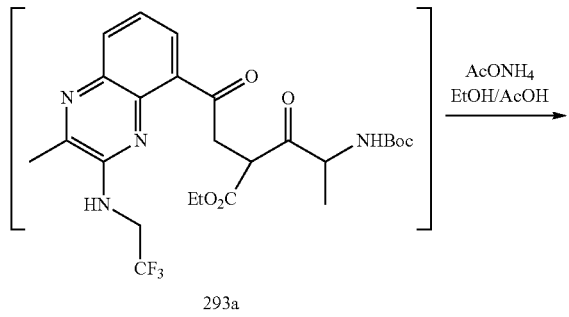

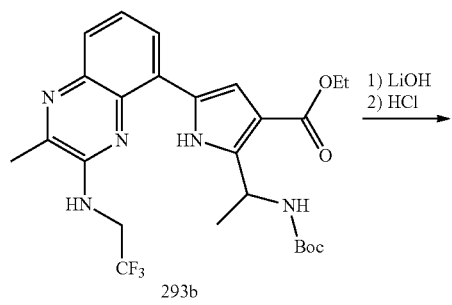

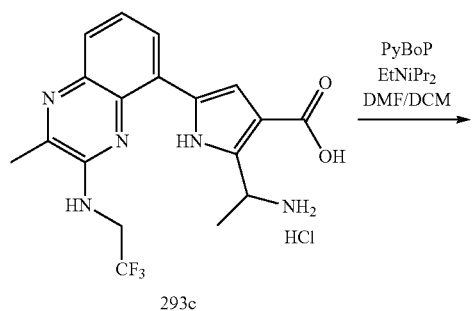

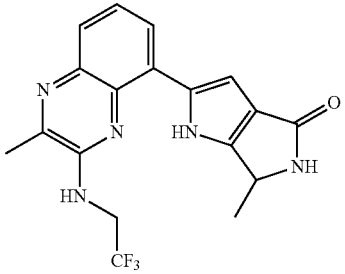

Preparation of ethyl 2-(1-((tert-butoxycarbonyl)amino)ethyl)-5-(2-methyl-3-((2,2,2-trifluoroethyl)amino)quinoxalin-5-yl)-1H-pyrrole-3-carboxylate (293b)

A mixture of 2-bromo-1-(2-methyl-3-((2,2,2-trifluoroethyl)amino)quinoxalin-5-yl)ethanone (616) (300 mg, 0.83 mmol), ethyl 4-((tert-butoxycarbonyl)amino)-3-oxopentanoate (602) (258 mg, 0.99 mmol) and K$_2$CO$_3$ (286 mg, 2.07 mmol) in DMF (2.75 mL) was stirred at RT for 1 h. The reaction mixture was concentrated. Saturated NH$_4$Cl (aq.) and EtOAc was added and the layers were separated. The aq. layer was extracted with EtOAc (2×). The combined organic layers were dried over anhydrous Na$_2$SO$_4$, filtered and concentrated. The crude material was purified by silica gel chromatography (0-50% EtOAc in hexanes) to provide ethyl 4-((tert-butoxycarbonyl)amino)-2-(2-(2-methyl-3-((2,2,2-trifluoroethyl)amino)quinoxalin-5-yl)-2-oxoethyl)-3-oxopentanoate (293a) (285 mg, 64% yield). m/z (ESI, +ve) 541.1 (M+H)$^+$. This material was put into a sealed tube with 2 mL of EtOH. AcOH (1 mL) and NH$_4$OAc (511 mg, 6.63 mmol) were added and the mixture was stirred at 60° C. overnight (21 h). The reaction mixture was concentrated. The residue was put into solution with EtOAc and water. The layers were separated and the organic layer was washed with water, 1 M NaOH (aq.) and brine. The organic layer was dried over anhydrous Na$_2$SO$_4$, filtered and concentrated. The crude material was purified by silica gel chromatography (0-50% EtOAc in hexanes) to provide ethyl 2-(1-((tert-butoxycarbonyl)amino)ethyl)-5-(2-methyl-3-((2,2,2-trifluoroethyl)amino)quinoxalin-5-yl)-1H-pyrrole-3-carboxylate (293b) (215 mg, 0.41 mmol, 50% yield) as a yellow foam. $^1$H NMR (400 MHz, CDCl$_3$) δ ppm 7.87 (dt, J=7.53, 0.73 Hz, 1H), 7.29-7.44 (m, 2H), 7.12 (d, J=2.54 Hz, 1H), 5.00 (br. s., 1H), 4.25-4.53 (m, 4H), 2.14-2.30 (m, 2H), 1.64 (s, 3H), 1.58 (d, J=7.24 Hz, 3H), 1.36-1.48 (m, 12H). $^{19}$F NMR (377 MHz, CDCl$_3$) δ ppm −70.80. m/z (ESI, +ve) 522.2 (M+H)$^+$.

421

Preparation of 2-(1-aminoethyl)-5-(2-methyl-3-((2,2,2-trifluoroethyl)amino)-quinoxalin-5-yl)-1H-pyrrole-3-carboxylic acid hydrochloride (293c)

A glass microwave reaction vessel was charged with ethyl 2-(1-((tert-butoxycarbonyl)amino)ethyl)-5-(2-methyl-3-((2,2,2-trifluoroethyl)amino)quinoxalin-5-yl)-1H-pyrrole-3-carboxylate (293b) (380 mg, 0.73 mmol) and LiOH monohydrate (153 mg, 3.64 mmol) in dioxane (4 mL) and water (2 mL). The reaction mixture was stirred and heated in at 110° C. for 3 h. After cooling to RT, the reaction mixture was diluted with Et$_2$O and water and the layers were separated. The organic layer was acidified with 2 M HCl and extracted with EtOAc (3×). The combined organic layers were dried over anhydrous Na$_2$SO$_4$, filtered and concentrated to give 338 mg of an orange solid. m/z (ESI, +ve) 494.1 (M+H)$^+$. This material was dissolved in 4 mL of dioxane and treated with a 4 M solution HCl in 1,4-dioxane (Sigma-Aldrich) (4.55 mL, 18.22 mmol) at RT for 2 h. The reaction mixture was concentrated and the solid was suspended with 1/1 Et$_2$O/hexanes and collected by filtration to give 2-(1-aminoethyl)-5-(2-methyl-3-((2,2,2-trifluoroethyl)amino)quinoxalin-5-yl)-1H-pyrrole-3-carboxylic acid hydrochloride (293c) (274 mg, 0.64 mmol, 87% yield) as a red solid. m/z (ESI, +ve) 377.0 (M−NH$_2$)$^+$.

Preparation of Examples 293 and 294

Benzotriazol-1-yloxytripyrrolidinophosphonium hexafluorophosphate (PyBOP) (AK Scientific, Inc., Union City, Calif.) (431 mg, 0.83 mmol) was added to a solution of 2-(1-aminoethyl)-5-(2-methyl-3-((2,2,2-trifluoroethyl)amino)quinoxalin-5-yl)-1H-pyrrole-3-carboxylic acid hydrochloride (293c) (274 mg, 0.64 mmol) and DIPEA (0.44 mL, 2.55 mmol) in CH$_2$Cl$_2$ (16 mL) and DMF (16 mL) at RT. After 30 min the reaction mixture was concentrated. The residue was diluted with EtOAc and washed sequentially with water, saturated NaHCO$_3$ (aq.) and brine. The organic layer was dried over anhydrous Na$_2$SO$_4$, filtered and concentrated. The crude material was absorbed onto a plug of silica gel and purified by silica gel chromatography (0-5% MeOH in CH$_2$Cl$_2$), to provide rac-6-methyl-2-(2-methyl-3-((2,2,2-trifluoroethyl)amino)quinoxalin-5-yl)-5,6-dihydropyrrolo[3,4-b]pyrrol-4(1H)-one (293d) (100 mg, 0.27 mmol, 42% yield) as a yellow solid. The mixture of enantiomers was subjected to chiral SFC (ChiralPak AS-H (21×250, 5 μm); additive in supercritical fluid CO$_2$ was 25% MeOH with 20 mM NH$_3$; 75 mL/min; column temperature 40° C.; outlet pressure 100 bar) to give separated enantiomers. Example 293 (first eluting peak): (S)-6-methyl-2-(2-methyl-3-((2,2,2-trifluoroethyl)amino)quinoxalin-5-yl)-5,6-dihydropyrrolo[3,4-b]pyrrol-4(1H)-one (3 mg, 7.99 μmol, 1% yield, >99% ee) as a yellow solid. $^1$H NMR (400 MHz, DMSO-d$_6$) δ ppm 11.83-11.95 (m, 1H), 7.86-7.93 (m, 1H), 7.74 (t, J=6.26 Hz, 1H), 7.68 (dd, J=8.12, 1.47 Hz, 1H), 7.64 (d, J=0.39 Hz, 1H), 7.44 (t, J=7.82 Hz, 1H), 6.85-6.92 (m, 1H), 4.52-4.66 (m, 1H), 4.16-4.33 (m, 1H), 4.09 (q, J=5.15 Hz, 1H), 2.60 (s, 3H), 1.39 (d, J=6.65 Hz, 3H). $^{19}$F NMR (376 MHz, DMSO-d$_6$) δ ppm −69.51 (s, 3F). m/z (ESI, +ve) 376.1 (M+H); and Example 294 (second eluting peak): (R)-6-methyl-2-(2-methyl-3-((2,2,2-trifluoroethyl)amino)quinoxalin-5-yl)-5,6-dihydropyrrolo[3,4-b]pyrrol-4(1H)-one (44 mg, 0.12 mmol, 18% yield, >99% ee). m/z (ESI, +ve) 376.1 (M+H)$^+$.

422

Example 295

2'-(3-(tert-butylamino)-6-fluoro-2-methylquinoxalin-5-yl)-1'H-spiro[cyclopropane-1,6'-pyrrolo[3,4-b]pyrrol]-4'(5'H)-one

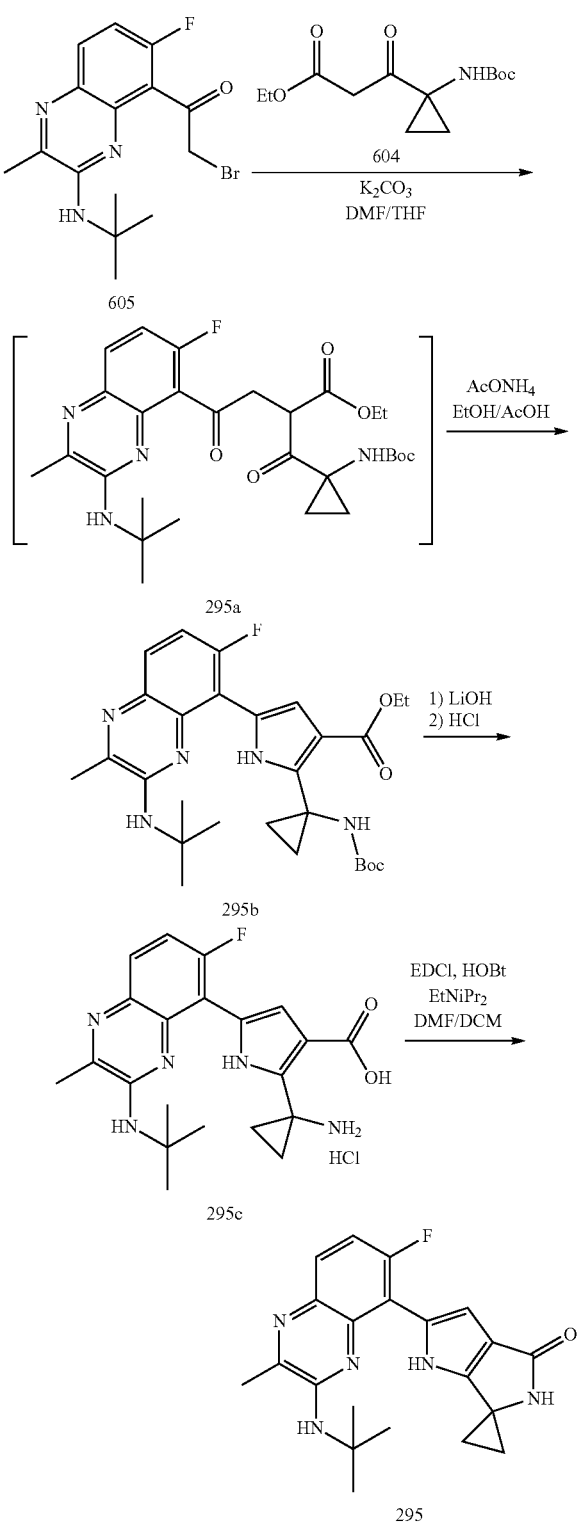

Preparation of ethyl 2-(1-((tert-butoxycarbonyl)amino)cyclopropyl)-5-(3-(tert-butylamino)-6-fluoro-2-methylquinoxalin-5-yl)-1H-pyrrole-3-carboxylate (295b)

This compound (230 mg, 0.44 mmol, 58% yield) as a yellow foam was prepared according to the procedures described for Intermediate 293b, using 2-bromo-1-(3-(tert-butylamino)-6-fluoro-2-methylquinoxalin-5-yl)ethanone (605) (268 mg, 0.76 mmol), ethyl 3-(1-((tert-butoxycarbonyl)amino)cyclopropyl)-3-oxopropanoate (604) (619 mg, 2.28 mmol) and K$_2$CO$_3$ (525 mg, 3.80 mmol) in EtOH (2 mL) and THF (2 mL) was stirred at RT for 2 days, followed by subsequent treatment of the resulting 295a (light-yellow oil, m/z (ESI, +ve) 545.2 (M+H)$^+$) with NH$_4$OAc (469 mg, 6.08 mmol) in EtOH (5 mL) and HOAc (3 mL) at 60° C. for 18 h. $^1$H NMR (400 MHz, CDCl$_3$) δ ppm 7.64 (dd, J=8.90, 5.97 Hz, 1H), 7.17 (dd, J=11.74, 9.00 Hz, 1H), 4.86 (s, 1H), 4.34 (q, J=7.04 Hz, 2H), 2.52 (s, 3H), 1.64 (s, 9H), 1.40 (t, J=7.14 Hz, 3H), 1.36 (s, 9H), 1.20-1.33 (m, 4H). $^{19}$F NMR (376 MHz, CDCl$_3$) δ ppm −109.93 (s, 1F). m/z (ESI, +ve) 526.2 (M+H)$^+$.

Preparation of 2-(1-aminocyclopropyl)-5-(3-(tert-butylamino)-6-fluoro-2-methylquinoxalin-5-yl)-1H-pyrrole-3-carboxylic acid hydrochloride (295c)

A glass microwave reaction vessel was charged with ethyl 2-(1-((tert-butoxycarbonyl)amino)cyclopropyl)-5-(3-(tert-butylamino)-6-fluoro-2-methylquinoxalin-5-yl)-1H-pyrrole-3-carboxylate (295b) (230 mg, 0.44 mmol) and LiOH monohydrate (Sigma-Aldrich) (184 mg, 4.38 mmol) in dioxane (1.5 mL) and water (0.75 mL). The reaction mixture was heated at 110° C. for 17 h. After cooling to RT, the reaction mixture was diluted with Et$_2$O and water and the layers were separated. The Et$_2$O layer was discarded. The aq. layer was acidified with 2 M HCl and extracted with EtOAc (3×). The combined EtOAc layers were dried over anhydrous Na$_2$SO$_4$, filtered and concentrated to give a light yellow solid. m/z (ESI, +ve) 498.2 (M+H)$^+$. The light yellow solid was dissolved in 1 mL of dioxane and treated with 4.0 M HCl in 1,4-dioxane (Sigma-Aldrich) (5 mL, 20.00 mmol) at RT. After 24 h, the reaction mixture was concentrated and the orange solid was collected by filtration to give 2-(1-aminocyclopropyl)-5-(3-(tert-butylamino)-6-fluoro-2-methylquinoxalin-5-yl)-1H-pyrrole-3-carboxylic acid hydrochloride (295c) (180 mg, 0.42 mmol, 95% yield). m/z (ESI, +ve) 381.1 (M−NH$_2$)$^+$.

Preparation of Example 295

To a suspension of 2-(1-aminocyclopropyl)-5-(3-(tert-butylamino)-6-fluoro-2-methylquinoxalin-5-yl)-1H-pyrrole-3-carboxylic acid hydrochloride (295c) (140 mg, 0.32 mmol) in 8 mL of DMF and 8 mL of DCM at RT was sequentially added 1-hydroxybenzotriazole (AK Scientific, Inc., Union City, Calif.) (65 mg, 0.48 mmol), 1-(3-dimethylaminopropyl)-3-ethylcarbodiimide hydrochloride (Sigma-Aldrich) (93 mg, 0.48 mmol) and DIPEA (Sigma-Aldrich) (0.34 mL, 1.94 mmol). The reaction mixture was stirred at RT for 16 h and was then concentrated. The yellow oil was dissolved in CH$_2$Cl$_2$ and washed with water, 1 M NaOH (aq.) and brine. The organic layer was dried over anhydrous Na$_2$SO$_4$, filtered and concentrated. The crude material was absorbed onto a plug of silica gel and purified by silica gel chromatography (0-5% MeOH in CH$_2$Cl$_2$) to provide 2'-(3-(tert-butylamino)-6-fluoro-2-methylquinoxalin-5-yl)-1'H-spiro[cyclopropane-1,6'-pyrrolo[3,4-b]pyrrol]-4'(5'H)-one (295) (50 mg, 0.13 mmol, 41% yield) as a light yellow solid. $^1$H NMR (400 MHz, DMSO-d$_6$) δ ppm 11.52 (s, 1H), 7.70 (dd, J=9.00, 5.87 Hz, 1H), 7.63 (s, 1H), 7.30 (dd, J=10.47, 8.90 Hz, 1H), 6.49-6.55 (m, 1H), 6.07 (s, 1H), 2.54 (s, 3H), 1.43 (s, 9H), 1.37-1.41 (m, 2H), 1.29-1.35 (m, 2H). $^{19}$F NMR (376 MHz, DMSO-d$_6$) δ ppm −111.61 (s, 1F). m/z (ESI, +ve) 380.1 (M+H)$^+$.

Example 296

2-(3-(tert-butylamino)-6-fluoro-2-methyl-5-quinoxalinyl)-5,6-dihydropyrrolo[3,4-b]pyrrol-4(1H)-one

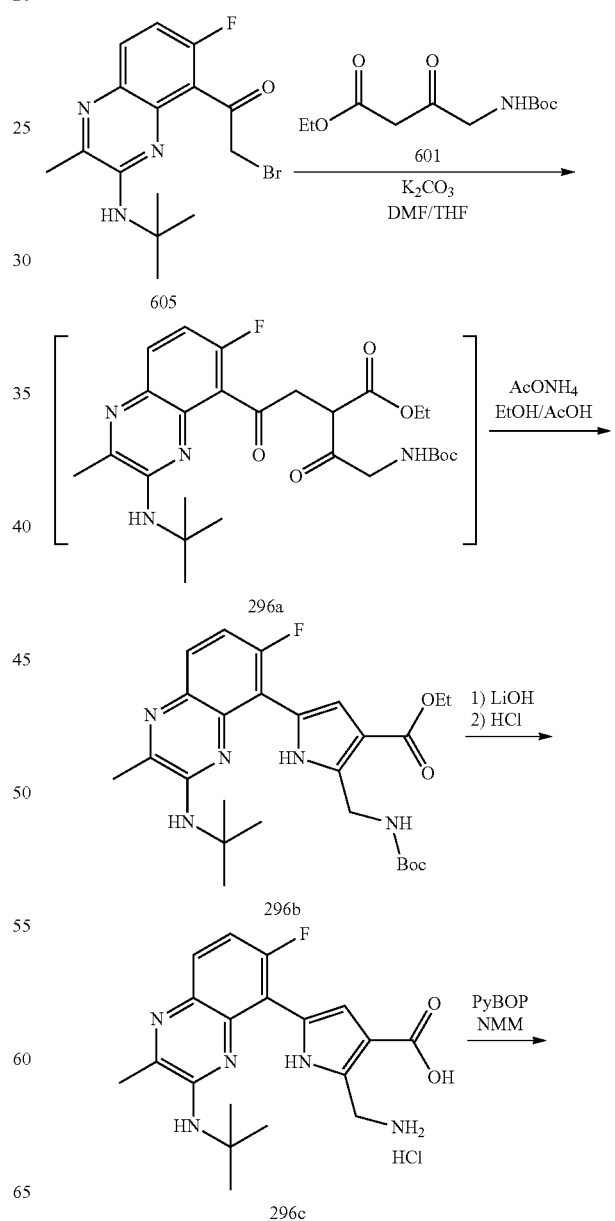

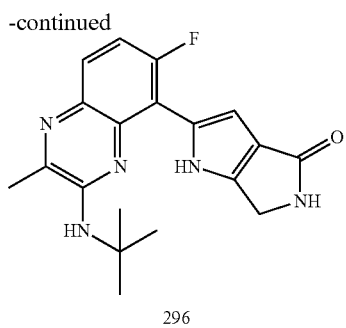

296

Preparation of ethyl 2-(((tert-butoxycarbonyl)amino)methyl)-5-(3-(tert-butylamino)-6-fluoro-2-methylquinoxalin-5-yl)-1H-pyrrole-3-carboxylate (296b)

This compound (873 mg, 34% yield) as a yellow foam was prepared according to the procedure described for intermediate 293b, using 2-bromo-1-(3-(tert-butylamino)-6-fluoro-2-methylquinoxalin-5-yl)ethanone (605) (1.81 g, 5.11 mmol), ethyl 4-((tert-butoxycarbonyl)amino)-3-oxobutanoate (601) (1.50 g, 6.13 mmol) and $K_2CO_3$ (1.77 g, 12.77 mmol) in DMF (17 mL) was stirred at RT for 6 h, followed by the subsequent treatment of the resulting ethyl 4-((tert-butoxycarbonyl)amino)-2-(2-(3-(tert-butylamino)-6-fluoro-2-methylquinoxalin-5-yl)-2-oxoethyl)-3-oxobutanoate (296a) (1.43 g, 2.76 mmol, 54% yield, m/z (ESI, +ve) 519.2 (M+H)$^+$) with $NH_4$Oac (3.15 g, 40.9 mmol) in 12 mL of EtOH and AcOH (6 mL). $^1$H NMR (400 MHz, CDCl$_3$) δ ppm 7.63 (dd, J=8.80, 5.67 Hz, 1H), 7.34 (dd, J=4.60, 2.45 Hz, 1H), 7.21 (dd, J=11.64, 8.90 Hz, 1H), 4.94 (s, 1H), 4.62 (d, J=5.87 Hz, 2H), 4.34 (q, J=7.24 Hz, 2H), 2.54 (s, 3H), 1.69 (s, 9H), 1.43 (s, 9H), 1.38-1.42 (m, 3H). $^{19}$F NMR (376 MHz, CDCl$_3$) δ ppm −107.37 (s, 1F). m/z (ESI, +ve) 500.1 (M+H)$^+$.

Preparation of 2-(aminomethyl)-5-(3-(tert-butylamino)-6-fluoro-2-methylquinoxalin-5-yl)-1H-pyrrole-3-carboxylic acid hydrochloride (296c)

A mixture of ethyl 24(tert-butoxycarbonyl)amino)methyl)-5-(3-(tert-butylamino)-6-fluoro-2-methylquinoxalin-5-yl)-1H-pyrrole-3-carboxylate (295b) (873 mg, 1.75 mmol) and LiOH monohydrate (0.24 mL, 8.74 mmol) in dioxane (12 mL) and water (6 mL). The reaction was stirred at reflux for 4 h. After cooling to RT, the reaction mixture was diluted with Et$_2$O and water and the layers were separated. The Et$_2$O layer was discarded. The organic layer was acidified with 2 M HCl (aq.) and extracted with EtOAc (3×). The combined EtOAc layers were dried over anhydrous Na$_2$SO$_4$, filtered and concentrated to give 765 mg of an orange solid. m/z (ESI, +ve) 472.1 (M+H)$^+$. The orange solid was dissolved in 7 mL of dioxane and treated with a 4.0 M solution of HCl in 1,4-dioxane (Sigma-Aldrich) (10.9 mL, 43.7 mmol) at RT for 3 h. The reaction mixture was concentrated and the solid was suspended in 1/1 Et$_2$O/hexanes and collected by filtration to give 2-(aminomethyl)-5-(3-(tert-butylamino)-6-fluoro-2-methylquinoxalin-5-yl)-1H-pyrrole-3-carboxylic acid hydrochloride (296c) (655 mg, 1.61 mmol, 92% yield) as an orange solid. m/z (ESI, +ve) 355.1 (M-NH$_2$)$^+$.

Preparation of Example 296

Benzotriazol-1-yloxytripyrrolidinophosphonium hexafluorophosphate (AK Scientific, Inc., Union City, Calif.) (879 mg, 1.69 mmol) was added to a solution of 2-(aminomethyl)-5-(3-(tert-butylamino)-6-fluoro-2-methylquinoxalin-5-yl)-1H-pyrrole-3-carboxylic acid hydrochloride (296c) (530 mg, 1.30 mmol) and 4-methylmorpholine (Sigma-Aldrich) (0.43 mL, 3.90 mmol) in CH$_2$Cl$_2$ (6.5 mL) and DMF (6.5 mL) at 0° C. After 30 min the reaction mixture was concentrated. The residue was put into solution with EtOAc and the organic layer was washed with water, saturated NaHCO$_3$ (aq.) and brine, dried over anhydrous Na$_2$SO$_4$, filtered and concentrated. The crude material was absorbed onto a plug of silica gel and purified by silica gel chromatography (0-5% MeOH in CH$_2$Cl$_2$). The purified material was suspended in Et$_2$O and collected by filtration and washed with Et$_2$O to provide 2-(3-(tert-butylamino)-6-fluoro-2-methylquinoxalin-5-yl)-5,6-dihydropyrrolo[3,4-b]pyrrolo-4(1H)-one (72 mg, 0.20 mmol, 16% yield) as a light yellow solid. $^1$H NMR (400 MHz, DMSO-d$_6$) δ ppm 12.00 (s, 1H), 7.71 (dd, J=9.00, 5.87 Hz, 1H), 7.53 (s, 1H), 7.31 (dd, J=10.56, 9.00 Hz, 1H), 6.57 (t, J=1.76 Hz, 1H), 6.12 (s, 1H), 4.24-4.30 (m, 2H), 2.55 (s, 3H), 1.46 (s, 9H). $^{19}$F NMR (377 MHz, DMSO-d6) δ ppm −111.59 (s, 1F). m/z (ESI, +ve) 354.0 (M+H)$^+$.

Examples 297

(6R)-2-(3-(tert-butylamino)-6-fluoro-2-methyl-5-quinoxalinyl)-6-methyl-5,6-dihydropyrrolo[3,4-b]pyrrol-4(1H)-one; and 298: (6S)-2-(3-(tert-butylamino)-6-fluoro-2-methyl-5-quinoxalinyl)-6-methyl-5,6-dihydropyrrolo[3,4-b]pyrrol-4(1H)-one

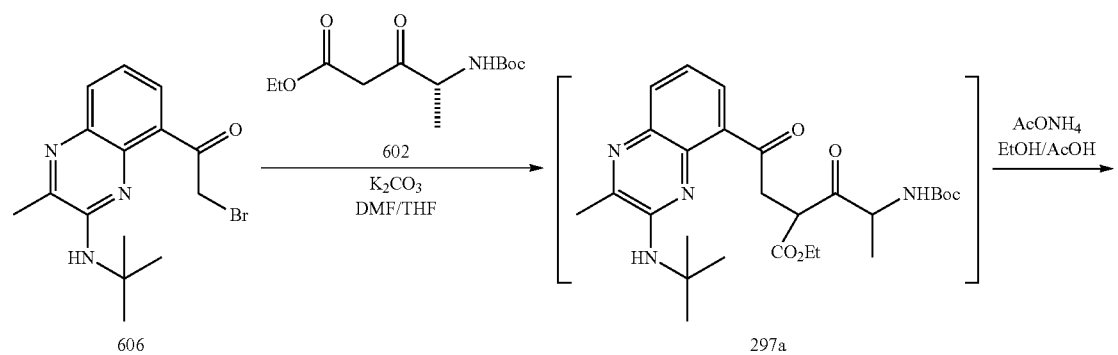

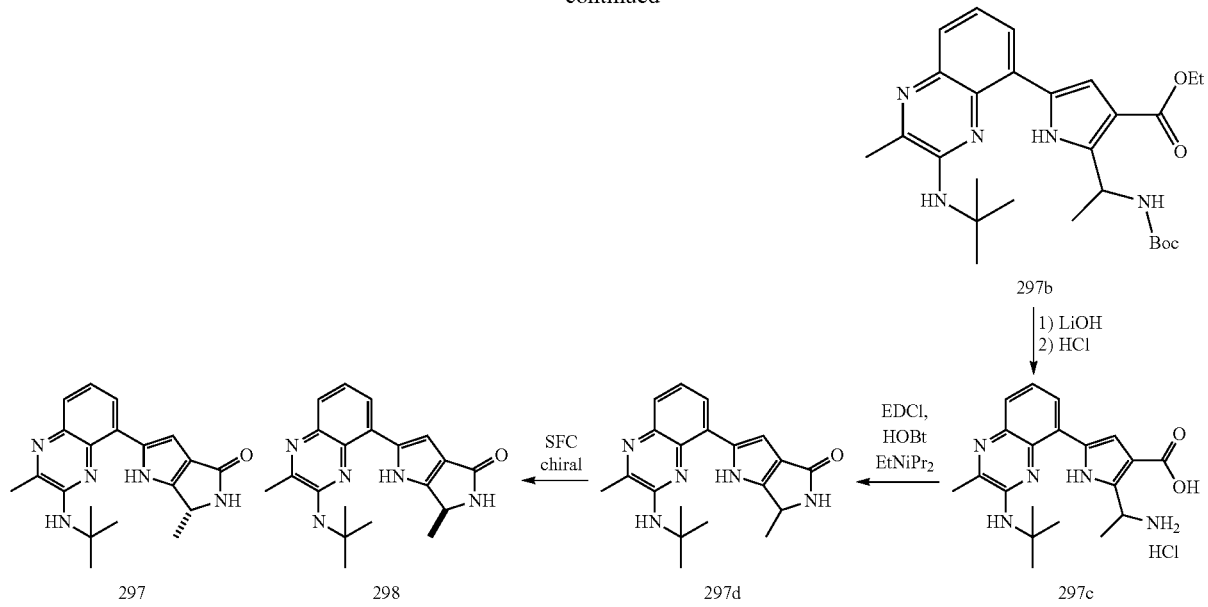

Preparation of ethyl 2-(1-((tert-butoxycarbonyl)amino)ethyl)-5-(3-(tert-butylamino)-6-fluoro-2-methylquinoxalin-5-yl)-1H-pyrrole-3-carboxylate (297b)

This compound (245 mg, 46% yield) as a yellow foam was prepared according to the procedures described for 293b, using 2-bromo-1-(3-(tert-butylamino)-6-fluoro-2-methylquinoxalin-5-yl)ethanone (605) (366 mg, 1.03 mmol), (R)-ethyl 4-((tert-butoxycarbonyl)amino)-3-oxopentanoate (602) (322 mg, 1.24 mmol) and $K_2CO_3$ (357 mg, 2.58 mmol) in DMF (3.5 mL), followed by the subsequent treatment of the resulting ethyl 4-((tert-butoxycarbonyl)amino)-2-(2-(3-(tert-butylamino)-6-fluoro-2-methylquinoxalin-5-yl)-2-oxoethyl)-3-oxopentanoate (297a) (360 mg, 0.68 mmol, 65% yield, m/z 533.2 (ESI, +ve) (M+H)$^+$) with $NH_4OAc$ (637 mg, 8.27 mmol) in 2 mL of EtOH and AcOH (1 mL). $^1$H NMR (400 MHz, $CDCl_3$) δ ppm 7.61 (dd, J=9.00, 5.67 Hz, 1H), 7.32-7.36 (m, 1H), 7.20 (dd, J=11.54, 9.00 Hz, 1H), 6.97 (d, J=9.98 Hz, 1H), 5.09-5.21 (m, 1H), 4.96 (s, 1H), 4.36 (qd, J=7.14, 2.05 Hz, 2H), 2.54 (s, 3H), 1.72 (s, 9H), 1.53 (d, J=6.85 Hz, 3H), 1.36-1.46 (m, 12H). $^{19}$F NMR (376 MHz, $CDCl_3$) δ ppm −107.07 (s, 1F). m/z 514.2 (ESI, +ve) (M+H)$^+$.

Preparation of 2-(1-aminoethyl)-5-(3-(tert-butylamino)-6-fluoro-2-methylquinoxalin-5-yl)-1H-pyrrole-3-carboxylic acid hydrochloride (297c)

A glass microwave reaction vessel was charged with ethyl 2-(1-((tert-butoxycarbonyl)amino)ethyl)-5-(3-(tert-butylamino)-6-fluoro-2-methylquinoxalin-5-yl)-1H-pyrrole-3-carboxylate (297b) (245 mg, 0.48 mmol) and LiOH monohydrate (100 mg, 2.39 mmol) in dioxane (3 mL) and water (1.5 mL). The reaction mixture was stirred and heated in a microwave reactor at 110° C. for 1 h. After cooling to RT, the reaction mixture was diluted with $Et_2O$ and water and the layers were separated. The $Et_2O$ layer was discarded. The organic layer was acidified with 2 M HCl and extracted with EtOAc (3×). The combined organic layers were dried over anhydrous $Na_2SO_4$, filtered and concentrated to give 215 mg of a light yellow solid. m/z (ESI, +ve) 486.2 (M+H)$^+$. The light yellow solid (215 mg) was dissolved in 2 mL of dioxane and treated with a 4.0 M solution of HCl in 1,4-dioxane (Sigma-Aldrich) (2.98 mL, 11.93 mmol) at RT overnight. The reaction mixture was concentrated and the solid was suspended with 1/1 $Et_2O$/hexanes and collected by filtration to give 2-(1-aminoethyl)-5-(3-(tert-butylamino)-6-fluoro-2-methylquinoxalin-5-yl)-1H-pyrrole-3-carboxylic acid hydrochloride (297c) (194 mg, 0.46 mmol, 96% yield) as an orange solid. m/z (ESI, +ve) 369.2 (M-$NH_2$)'.

Preparation of Examples 297 and 298

To a suspension of 2-(1-aminoethyl)-5-(3-(tert-butylamino)-6-fluoro-2-methylquinoxalin-5-yl)-1H-pyrrole-3-carboxylic acid hydrochloride (297c) (194 mg, 0.46 mmol) in 9 mL of DMF and 9 ml of DCM at RT was sequentially added 1-hydroxybenzotriazole (AK Scientific, Inc., Union City, Calif.) (93 mg, 0.69 mmol), N-(3-dimethylaminopropyl)-N'-ethylcarbodiimide hydrochloride (Sigma-Aldrich) (132 mg, 0.69 mmol) and DIPEA (0.48 mL, 2.76 mmol). The reaction mixture was stirred at RT for 23 h and then concentrated. The yellow oil was dissolved in $CH_2Cl_2$ and washed with water, 1 M NaOH (aq.) and brine. The organic layer was dried over anhydrous $Na_2SO_4$, filtered and concentrated. The crude material was purified by silica gel chromatography (0-5% MeOH in $CH_2Cl_2$) to provide 120 mg of 297d. m/z (ESI, +ve) 368.1 (M+H)$^+$. The mixture of enantiomers was subjected to chiral SFC (ChiralPak AS-H (21×250, 5 μm); additive in supercritical fluid $CO_2$ was 20% MeOH with 20 mM $NH_3$; 70 mL/min; column temperature 40° C.; outlet pressure 100 bar) to give separated enantiomers. Example 297 (first eluting peak): (R)-2-(3-(tert-butylamino)-6-fluoro-2-methylquinoxalin-5-yl)-6-methyl-5,6-dihydropyrrolo[3,4-b]pyrrolo-4(1H)-one (37 mg, 0.10 mmol, 22% yield, >99% ee) as a yellow solid. $^1$H NMR (400 MHz, $CDCl_3$) δ ppm 12.95 (br. s., 1H), 7.64 (dd, J=8.80, 5.67 Hz, 1H), 7.19-7.25 (m, 1H), 7.17 (dd, J=4.50, 1.56 Hz, 1H), 5.77 (s, 2H), 4.96 (s, 2H), 4.69 (q, J=6.46 Hz, 2H), 2.56 (s, 3H), 1.67 (s, 9H), 1.55 (d, J=6.65 Hz, 3H). $^{19}$F NMR (377 MHz, $CDCl_3$) δ ppm −105.51 (s, 1F). m/z (ESI, +ve) 368.1 (M+H); and Example 298 (second eluting peak): (S)-2-(3-(tert-butylamino)-6-fluoro-2-methylquinoxalin-5-yl)-6-methyl-5,6-dihydropyrrolo[3,4-b]pyrrol-4(1H)-one (5 mg, 0.0.1 mmol, 3% yield, 92% ee) as a yellow solid. m/z (ESI, +ve) 368.1 (M+H)$^+$.

Example 299

2-(3-(tert-butylamino)-2-methylquinoxalin-5-yl)-5-(hydroxymethyl)-6,7-dihydro-1H-pyrrolo[3,2-c]pyridin-4(5H)-one

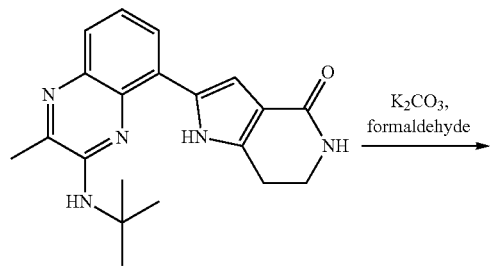

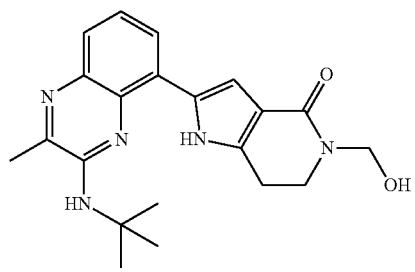

A mixture of 2-(3-(tert-butylamino)-2-methylquinoxalin-5-yl)-6,7-dihydro-1H-pyrrolo[3,2-c]pyridin-4(5H)-one (193) (0.2 g, 0.57 mmol), K₂CO₃ (0.16 g, 1.14 mmol), and formaldehyde (Sigma-Aldrich) (0.46 mL of 37% wt. in water, 5.72 mmol) in THF (5.72 mL) were combined and stirred at 50° C. overnight. The reaction mixture was directly loaded onto a biotage and purified three times (0-100% EtOAc:EtOH (3:1)/hexane; 0-40% then 40% EtOAc:EtOH (3:1)/hexanes; then 0-20% then 20% EtOAc:EtOH (3:1)/hexanes) to yield the title compound (6 mg, 3% yield). ¹H NMR (300 MHz, CDCl₃) d ppm 1.49-1.75 (m, 23H) 2.56 (s, 3H) 2.95-3.10 (m, 2H) 3.20-3.34 (m, 1H) 3.74-3.91 (m, 2H) 4.79-4.92 (m, 1H) 4.98-5.08 (m, 2H) 7.01-7.14 (m, 1H) 7.31-7.46 (m, 1H) 7.59-7.72 (m, 1H) 7.89-8.03 (m, 1H) 12.51-12.65 (m, 1H). m/z (ES, +ve) 380.1 (M+H)⁺.

Example 300

(E/Z)-2-(3-(tert-butylamino)-2-methylquinoxalin-5-yl)-6,7-dihydro-1H-pyrrolo[3,2-c]pyridin-4(5H)-one oxime

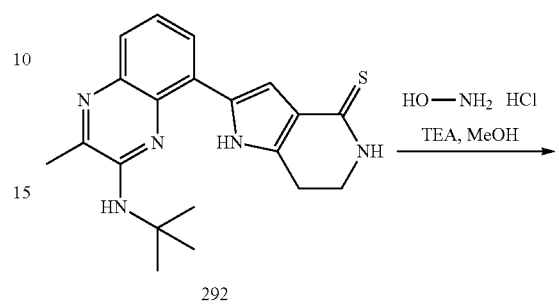

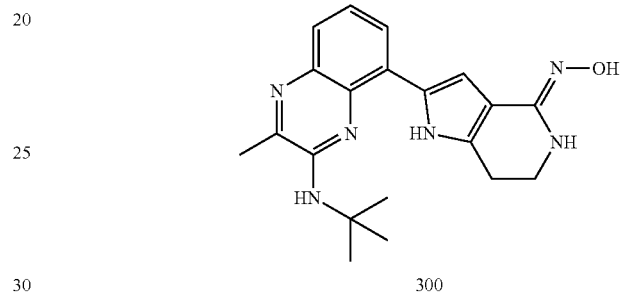

A mixture of 2-(3-(tert-butylamino)-2-methylquinoxalin-5-yl)-6,7-dihydro-1H-pyrrolo[3,2-c]pyridine-4(5H)-thione (292) (0.21 g, 0.57 mmol), hydroxyammonium chloride (80 mg, 1.14 mmol), TEA (0.16 mL, 1.14 mmol) in MeOH (4 mL) was stirred at RT overnight then heated to 50° C. for 4 h. Reaction mixture was directly loaded onto Biotage samplet. Purification (0-100% EtOAc:EtOH(3:1)/hexanes) provided title compound (26 mg, 12% yield). ¹H NMR (300 MHz, MeOH-d4) δ ppm 1.62 (s, 9H), 1.81-1.90 (m, 1H), 2.59 (s, 3H), 3.04-3.18 (m, 2H), 3.71-3.82 (m, 2H), 7.34-7.45 (m, 1H), 7.63-7.73 (m, 1H), 7.80-7.90 (m, 1H). m/z (ES, +ve) 365.0 (M+H)⁺.

Example 301

2-(2-methyl-3-((2,2,2-trifluoroethyl)amino)-5-quinoxalinyl)-5,6-dihydropyrrolo[3,4-b]pyrrol-4(1H)-one

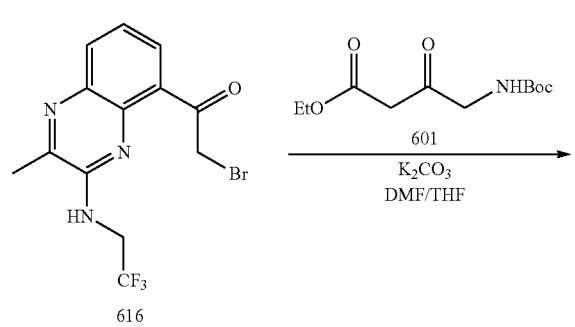

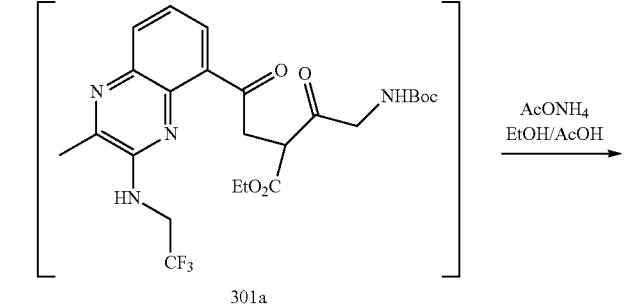

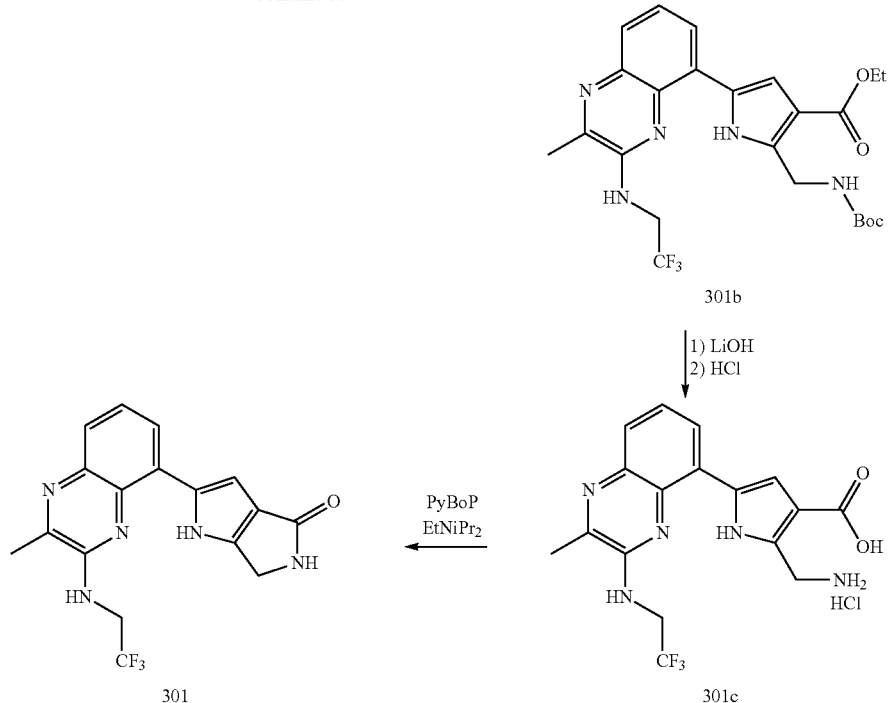

Preparation of ethyl 2-(((tert-butoxycarbonyl)amino)methyl)-5-(2-methyl-3-((2,2,2-trifluoroethyl)amino)quinoxalin-5-yl)-1H-pyrrole-3-carboxylate (301b)

This compound (380 mg, 0.75 mmol, 55% yield) as a yellow solid was prepared according to the procedure described for 293b, using 2-bromo-1-(2-methyl-3-((2,2,2-trifluoroethyl)amino)quinoxalin-5-yl)ethanone (616) (492 mg, 1.36 mmol), ethyl 4-((tert-butoxycarbonyl)amino)-3-oxobutanoate (601) (400 mg, 1.63 mmol) and $K_2CO_3$ (0.21 mL, 3.40 mmol) in DMF (2.75 mL), followed by subsequent treatment of the resulting ethyl 4-((tert-butoxycarbonyl)amino)-2-(2-(2-methyl-3-((2,2,2-trifluoroethyl)amino)quinoxalin-5-yl)-2-oxoethyl)-3-oxobutanoate (301a) (530 mg, m/z (ESI, +ve) 527.2 (M+H)$^+$) with $NH_4OAc$ (838 mg, 10.87 mmol) in 2 mL of EtOH and AcOH (1 mL) at 60° C. overnight. $^1$H NMR (400 MHz, CDCl$_3$) δ ppm 7.92-7.98 (m, 1H), 7.68-7.74 (m, 1H), 7.44 (t, J=7.92 Hz, 1H), 7.11 (d, J=2.74 Hz, 1H), 5.44 (br. s., 1H), 5.18 (t, J=6.26 Hz, 1H), 4.56-4.65 (m, 2H), 4.54 (d, J=6.46 Hz, 2H), 4.33 (q, J=7.17 Hz, 2H), 2.63 (s, 3H), 1.35-1.43 (m, 12H). $^{19}$F NMR (376 MHz, CDCl$_3$) δ ppm −70.89 (s, 3F). m/z (ESI, +ve) 508.1 (M+H)$^+$.

Preparation of 2-(aminomethyl)-5-(2-methyl-3-((2,2,2-trifluoroethyl)amino)quinoxalin-5-yl)-1H-pyrrole-3-carboxylic acid hydrochloride (301c)

A glass microwave reaction vessel was charged with ethyl 2-(((tert-butoxycarbonyl)amino)methyl)-5-(2-methyl-3-((2,2,2-trifluoroethyl)amino)quinoxalin-5-yl)-1H-pyrrole-3-carboxylate (301b) (380 mg, 0.75 mmol) and LiOH monohydrate (157 mg, 3.74 mmol) in dioxane (5 mL) and water (2.5 mL). The tube was sealed and the reaction mixture was stirred and heated at 110° C. for 3 h. After cooling to RT, the reaction mixture was diluted with Et$_2$O and water and the layers were separated. The Et$_2$O layer was discarded. The aq. layer was acidified with 2 M HCl (aq.) and extracted with EtOAc (3×). The combined organic layers were dried over anhydrous Na$_2$SO$_4$, filtered and concentrated to give 2-(((tert-butoxycarbonyl)amino)methyl)-5-(2-methyl-3-((2,2,2-trifluoroethyl)amino)quinoxalin-5-yl)-1H-pyrrole-3-carboxylic acid (308 mg, 0.64 mmol) as an orange solid. m/z (ESI, +ve) 480.2 (M+H)$^+$. The orange solid (308 mg) was dissolved in 4 mL of dioxane and treated with a 4 M solution of HCl in 1,4-dioxane (4.68 mL, 18.72 mmol) at RT. The reaction mixture was stirred at RT overnight and was then concentrated. The solid was suspended with 1/1 Et$_2$O/hexanes and collected by filtration to give 2-(aminomethyl)-5-(2-methyl-3-((2,2,2-trifluoroethyl)amino)quinoxalin-5-yl)-1H-pyrrole-3-carboxylic acid hydrochloride (301c) (255 mg, 0.61 mmol, 82% yield) as a red solid. $^1$H NMR (400 MHz, DMSO-d$_6$) δ ppm 12.30 (br. s., 1H), 8.37 (t, J=5.77 Hz, 2H), 7.95 (dt, J=7.48, 0.76 Hz, 1H), 7.77 (t, J=6.16 Hz, 1H), 7.71 (dt, J=7.97, 0.81 Hz, 1H), 7.46 (t, J=7.82 Hz, 1H), 7.42 (dd, J=2.35, 0.39 Hz, 1H), 4.38-4.49 (m, 2H), 4.34 (q, J=5.35 Hz, 2H), 2.60 (s, 3H). $^{19}$F NMR (377 MHz, DMSO-d$_6$) δ ppm −69.61 (s, 3F). m/z (ESI, +ve) 363.0 (M-NH$_2$)'.

Preparation of Example 301

Benzotriazol-1-yloxytripyrrolidinophosphonium hexafluorophosphate (AK Scientific, Inc., Union City, Calif.) (415 mg, 0.80 mmol) was added to a solution of 2-(aminomethyl)-5-(2-methyl-3-((2,2,2-trifluoroethyl)amino)quinoxalin-5-yl)-1H-pyrrole-3-carboxylic acid hydrochloride (301c) (255 mg, 0.61 mmol) and DIPEA (Sigma-Aldrich) (0.43 mL, 2.45 mmol) in CH$_2$Cl$_2$ (15 mL) and DMF (15 mL) at RT. After 30 min the reaction mixture was concentrated. EtOAc and H$_2$O were added and the layers were separated. The aq. layer was extracted with EtOAc (2×). The combined organic layers were dried over anhydrous Na$_2$SO$_4$, filtered and concentrated. The crude material was absorbed onto a plug of silica gel and purified by silica gel chromatography (0-5% MeOH in CH$_2$Cl$_2$), to provide a yellow solid. The combined fractions were triturated with CH₂Cl₂ and the solid was collected by filtration and washed with CH₂Cl₂ and Et₂O to provide 2-(2-methyl-3-((2,2,2-trifluoroethyl)amino)quinoxalin-5-yl)-5,6-dihydropyrrolo[3,4-b]pyrrol-4(1H)-one (301) (48 mg, 0.13 mmol, 22% yield) as a yellow solid. $^1$H NMR (400 MHz, DMSO-d₆) δ ppm 11.97 (br. s., 1H), 7.89 (d, J=7.04 Hz, 1H), 7.74 (t, J=6.55 Hz, 1H), 7.67 (d, J=8.22 Hz, 1H), 7.52 (br. s., 1H), 7.39-7.47 (m, 1H), 6.97 (s, 1H), 4.33-4.46 (m, 2H), 4.25 (br. s., 2H), 2.59 (s, 3H). $^{19}$F NMR (376 MHz, DMSO-d₆) δ ppm −69.44 (s, 3F). m/z (ESI, +ve) 362.0 (M+H)⁺.

Examples 302

(6R)-2-(3-((2-hydroxy-1,1-dimethylethyl)amino)-2-methyl-5-quinoxalinyl)-6-methyl-5,6-dihydropyrrolo[3,4-b]pyrrol-4(1H)-one material was purified by chromatography (0-50% EtOAc in hexanes) to provide ethyl 3-((tert-butoxycarbonyl)amino)-2-(3-fluoro-2-methylquinoxaline-5-carbonyl)butanoate (302a) (520 mg, 1.24 mmol). This material (520 mg, 1.24 mmol) was transferred into a sealed tube with 6 mL of EtOH and AcOH (3 mL) and NH₄OAc (1.09 g, 14.13 mmol) were added and the mixture was stirred at RT for 21 h. The reaction mixture was concentrated. The residue was put into solution with EtOAc and water. The layers were separated and the organic layer was washed with water, saturated NaHCO₃ (aq.) and brine. The organic layer was dried over anhydrous Na₂SO₄, filtered and concentrated. The crude material was purified by silica gel chromatography (0-50% EtOAc in hexanes) to provide ethyl 2-(1-((tert-butoxycarbonyl)amino)ethyl)-5-(3-fluoro-2-methylquinoxalin-5-yl)-1H-pyrrole-3-carboxylate (302b) (250 mg, 0.57 mmol, 32% yield) as a yellow foam. $^1$H NMR (400 MHz, CDCl₃) δ ppm 8.07 (dt, J=7.53, 0.73 Hz,

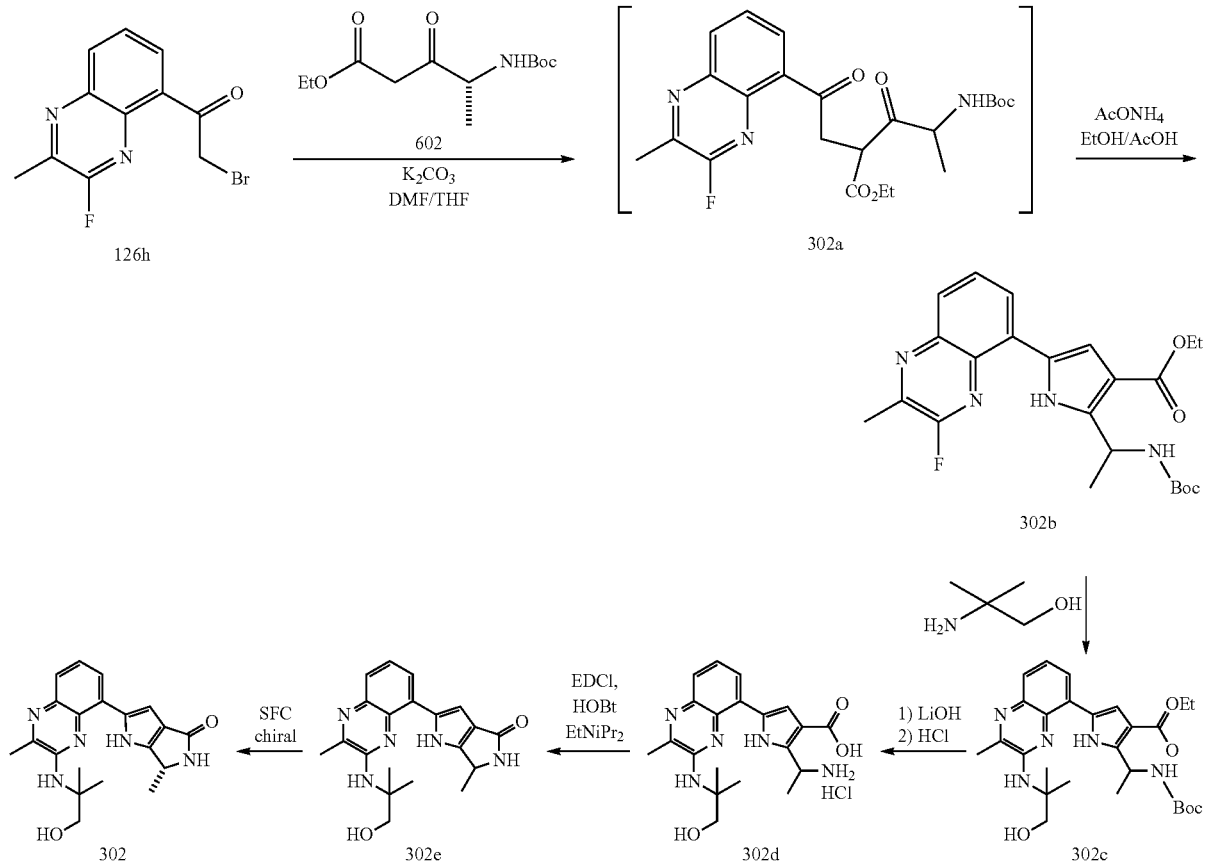

Preparation of ethyl 2-(1-((tert-butoxycarbonyl)amino)ethyl)-5-(3-fluoro-2-methylquinoxalin-5-yl)-1H-pyrrole-3-carboxylate (302b)

A mixture of 2-bromo-1-(3-fluoro-2-methylquinoxalin-5-yl)ethanone (126h) (500 mg, 1.77 mmol), ethyl 4-((tert-butoxycarbonyl)amino)-3-oxopentanoate (602) (550 mg, 2.12 mmol) and K₂CO₃ (610 mg, 4.42 mmol) in DMF (2.4 mL) was stirred at RT for 1 h. The reaction mixture was concentrated. Saturated NH₄Cl (aq.) and EtOAc was added and the layers were separated. The aq. layer was extracted with EtOAc (2×). The combined organic layers were dried over anhydrous Na₂SO₄, filtered and concentrated. The crude 1H), 7.88 (dt, J=7.92, 0.83 Hz, 1H), 7.67-7.73 (m, 1H), 7.22 (d, J=2.74 Hz, 1H), 5.25 (quin, J=7.29 Hz, 1H), 4.29-4.39 (m, 2H), 2.79 (d, J=1.37 Hz, 3H), 1.59 (d, J=7.04 Hz, 3H), 1.44 (br. s., 9H), 1.38-1.42 (m, 3H). $^{19}$F NMR (377 MHz, CDCl₃) δ ppm −71.82 (s, 1F). m/z (ESI, +ve) 443.1 (M+H)⁺.

Preparation of ethyl 2-(1-((tert-butoxycarbonyl)amino)ethyl)-5-(3-((1-hydroxy-2-methylpropan-2-yl)amino)-2-methylquinoxalin-5-yl)-1H-pyrrole-3-carboxylate (302c)

A mixture of ethyl 2-(1-((tert-butoxycarbonyl)amino)ethyl)-5-(3-fluoro-2-methylquinoxalin-5-yl)-1H-pyrrole-3-carboxylate (302b) (250 mg, 0.57 mmol) and 2-amino-2- methyl-1-propanol (Sigma-Aldrich) (0.11 mL, 1.13 mmol) in DMSO (2 mL) was heated at 70° C. for 18 h. The reaction mixture was cooled to RT and water and EtOAc was added. The layers were separated and the aq. layer was extracted with EtOAc (2×). The combined organic layers were washed with water and brine and dried over anhydrous $Na_2SO_4$, filtered and concentrated. The crude material was purified by chromatography (0-100% EtOAc in hexanes) to provide ethyl 2-(1-((tert-butoxycarbonyl)amino)ethyl)-5-(34(1-hydroxy-2-methylpropan-2-yl)amino)-2-methylquinoxalin-5-yl)-1H-pyrrole-3-carboxylate (302c) (208 mg, 0.41 mmol, 72% yield) as a yellow oil. m/z (ESI, +ve) 512.2 (M+H)⁺.

Preparation of 2-(1-aminoethyl)-5-(3-((1-hydroxy-2-methylpropan-2-yl)amino)-2-methylquinoxalin-5-yl)-1H-pyrrole-3-carboxylic acid hydrochloride (302d)

A glass microwave reaction vessel was charged with ethyl 2-(1-((tert-butoxycarbonyl)amino)ethyl)-5-(3-((1-hydroxy-2-methylpropan-2-yl)amino)-2-methylquinoxalin-5-yl)-1H-pyrrole-3-carboxylate (302c) (208 mg, 0.41 mmol) and LiOH monohydrate (85 mg, 2.03 mmol) in dioxane (2.7 mL) and water (1.3 mL). The reaction mixture was stirred and heated in microwave at 110° C. for 1 h and 20 min. After cooling to RT, the reaction mixture was diluted with $Et_2O$ and water and the layers were separated. The $Et_2O$ layer was discarded. The aq. layer was acidified with 2 M HCl (aq.) and extracted with EtOAc (3×). The combined EtOAc layers were dried over anhydrous $Na_2SO_4$, filtered and concentrated to give 160 mg of a light yellow solid. m/z (ESI, +ve) 484.1 (M+H)⁺. The light yellow solid (160 mg) was dissolved in 2 mL of dioxane and treated with a 4 M solution of HCl in 1,4-dioxane (2.54 mL, 10.2 mmol) at RT. The reaction mixture was stirred overnight and was then concentrated. The solid was suspended with 1/1 $Et_2O$/hexanes and collected by filtration to give 2-(1-aminoethyl)-5-(3-((1-hydroxy-2-methylpropan-2-yl)amino)-2-methylquinoxalin-5-yl)-1H-pyrrole-3-carboxylic acid hydrochloride (302d) (140 mg, 0.33 mmol, 82% yield) as an orange solid. m/z (ESI, +ve) 367.1 (M-$NH_2$)⁺.

Preparation of example 302

Benzotriazol-1-yloxytripyrrolidinophosphonium hexafluorophosphate (AK Scientific, Inc., Union City, Calif.) (226 mg, 0.43 mmol) was added to a solution of 2-(1-aminoethyl)-5-(3-((1-hydroxy-2-methylpropan-2-yl)amino)-2-methylquinoxalin-5-yl)-1H-pyrrole-3-carboxylic acid hydrochloride (302d) (140 mg, 0.33 mmol) and DIPEA (0.23 mL, 1.33 mmol) in $CH_2Cl_2$ (8 mL) and DMF (8 mL) at RT. After 30 min the reaction mixture was concentrated. The residue was put into solution with EtOAc and the organic layer was washed with water, saturated $NaHCO_3$ (aq.) and brine. The organic layer was dried over anhydrous $Na_2SO_4$, filtered and concentrated. The crude material was absorbed onto a plug of silica gel and purified by silica gel chromatography (0-5% MeOH in $CH_2Cl_2$) to provide 2-(3-((1-hydroxy-2-methylpropan-2-yl)amino)-2-methylquinoxalin-5-yl)-6-methyl-5,6-dihydropyrrolo[3,4-b]pyrrol-4(1H)-one (302e) (35 mg, 0.096 mmol, 28% yield) as a yellow foam. The mixture of enantiomers was separated by chiral SFC (Chiralcel OJ (Sepax) (21×250, 5 µm); additive in supercritical fluid $CO_2$ was 15% MeOH with 20 mM $NH_3$; 75 mL/min; column temperature 40° C.; outlet pressure 100 bar) to give Example 302: (R)-2-(34(1-hydroxy-2-methylpropan-2-yl)amino)-2-methylquinoxalin-5-yl)-6-methyl-5,6-dihydropyrrolo[3,4-b]pyrrol-4(1H)-one (22 mg, 0.06 mmol, 18% yield, >99% ee).

¹H NMR (400 MHz, CDCl₃) δ ppm 7.92 (dd, J=7.63, 1.56 Hz, 1H), 7.69 (dd, J=8.02, 1.56 Hz, 1H), 7.39 (t, J=7.82 Hz, 1H), 6.87 (d, J=1.56 Hz, 1H), 4.60-4.69 (m, 1H), 3.80-3.91 (m, 2H), 2.59 (s, 3H), 1.63-1.64 (m, 3H), 1.61-1.62 (m, 3H), 1.53 (d, J=6.65 Hz, 3H). m/z (ESI, +ve) 366.2 (M+H)⁺.

Example 303

2-(3-(tert-butylamino)-2-methylquinoxalin-5-yl)-6,7-dihydro-1H-indol-4(5H)-one

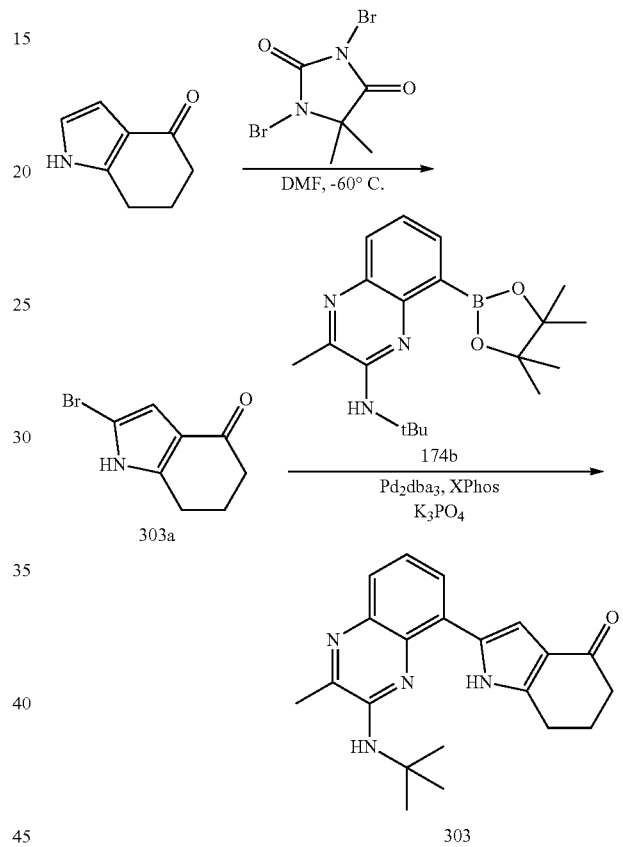

Preparation of 2-bromo-6,7-dihydro-1H-indol-4(5H)-one (303a)

1,3-Dibromo-5,5-dimethylhydantoin (Fluka, St. Louis, Mo.) (532 mg, 1.86 mmol) was added to a solution of 6,7-dihydro-1H-indol-4(5H)-one (Aldrich) (503.0 mg, 3.72 mmol) in DMF (13 mL) at 60° C. and the resulting mixture was stirred at 60° C. for 10 min. The mixture was then concentrated in vacuo (65° C., 24 Torr), and the residual oil was chromatographically purified (silica gel, 0-80% EtOAc/hexanes). The isolated product was taken up in EtOAc (100 mL) and sequentially washed with saturated aq. $NaHCO_3$ (3×40 mL) and brine (40 mL). The organic layer was dried over $Na_2SO_4$, filtered, and concentrated in vacuo to provide 2-bromo-6,7-dihydro-1H-indol-4(5H)-one (664 mg, 3.10 mmol, 83% yield) as a white solid: ¹H NMR (400 MHz, CDCl₃) δ ppm 8.43 (1H, br. s.), 6.51 (1H, d, J=2.3 Hz), 2.79 (2H, t, J=6.2 Hz), 2.48 (2H, t, J=6.6 Hz), 2.15 (2H, quin, J=6.3 Hz). m/z (ESI, +ve) 214.1/216.1 (M+H)⁺.

Preparation of 2-(3-(tert-butylamino)-2-methylquinoxalin-5-yl)-6,7-dihydro-1H-indol-4(5H)-one (303)

A mixture of N-(tert-butyl)-3-methyl-8-(4,4,5,5-tetramethyl-1,3,2-dioxaborolan-2-yl)quinoxalin-2-amine (174b) (222.6 mg, 0.652 mmol), 2-bromo-6,7-dihydro-1H-indol-4(5H)-one (303a; 209 mg, 0.978 mmol), $K_2PO_4$ (415 mg, 1.957 mmol), (Strem Chemicals, Inc., 31.1 mg, 0.065 mmol), and $Pd_2dba_3$ (Aldrich, 29.9 mg, 0.033 mmol) in a mixture of dioxane (4.5 mL) and water (0.900 mL) was heated under argon at 105° C. for 1 h. The reaction mixture was subsequently cooled to RT and diluted with water (30 mL). The resulting mixture was extracted with 5% MeOH/DCM (3×30 mL), and the combined extracts were dried over $Na_2SO_4$, filtered, and concentrated onto silica gel. Chromatographic purification (silica gel, 0-100% EtOAc/hexanes) furnished 2-(3-(tert-butylamino)-2-methylquinoxalin-5-yl)-6,7-dihydro-1H-indol-4(5H)-one (175 mg, 0.502 mmol, 77% yield) as a yellow solid: $^1$H NMR (400 MHz, $CDCl_3$) δ ppm 12.52 (1H, br. s.), 7.96 (1H, dd, J=7.6, 1.0 Hz), 7.73 (1H, d, J=7.8 Hz), 7.40 (1H, t, J=7.8 Hz), 7.08 (1H, d, J=2.0 Hz), 4.89 (1H, s), 2.93 (2H, t, J=6.2 Hz), 2.60 (3H, s), 2.51-2.57 (2H, m), 2.23 (2H, quin, J=6.3 Hz), 1.68 (9H, s). m/z (ESI, +ve) 349.2 (M+H)$^+$.

Example 304

2-(2-amino-3-(tert-butylamino)quinoxalin-5-yl)-6,7-dihydro-1H-pyrrolo[3,2-c]pyridin-4(5H)-one

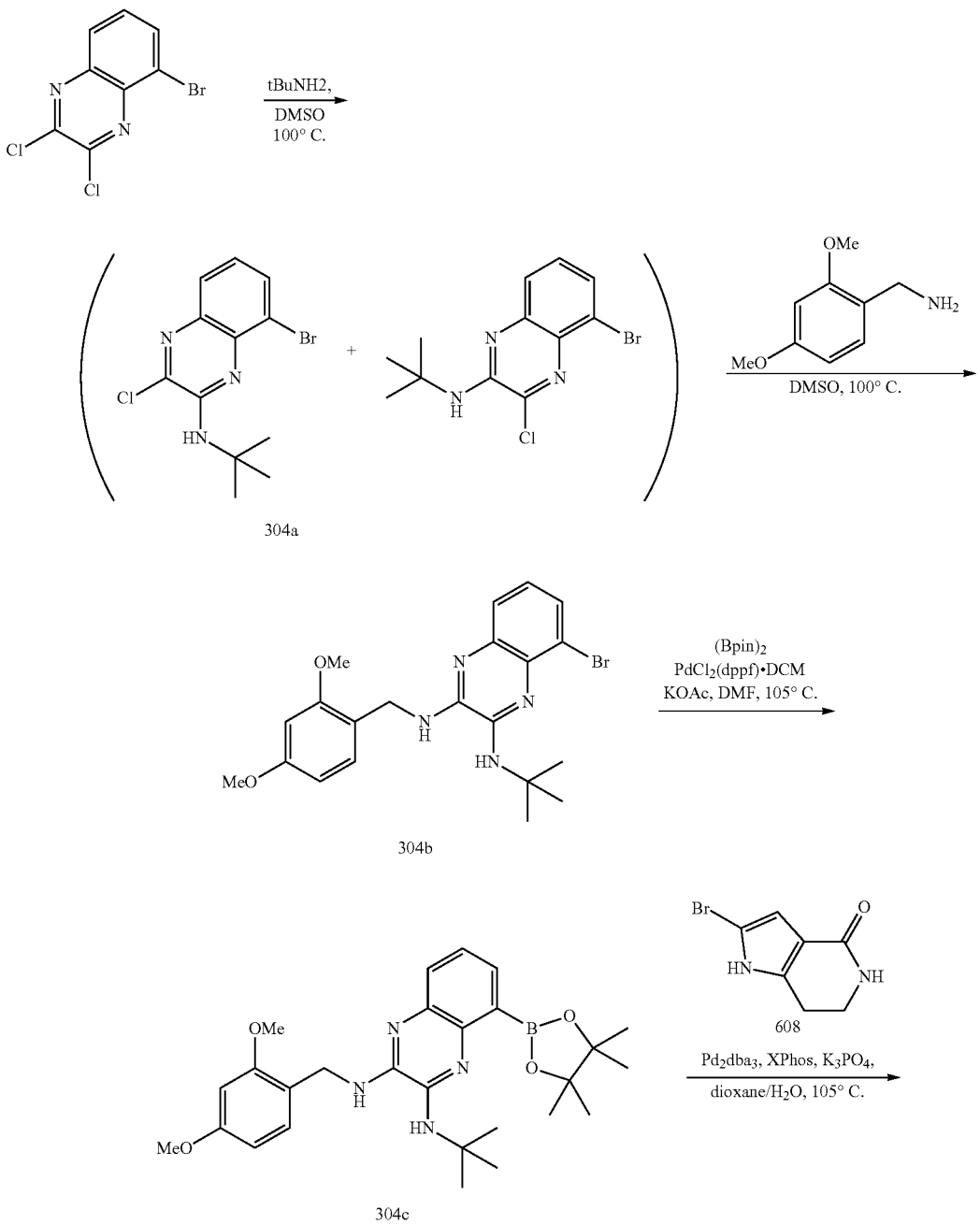

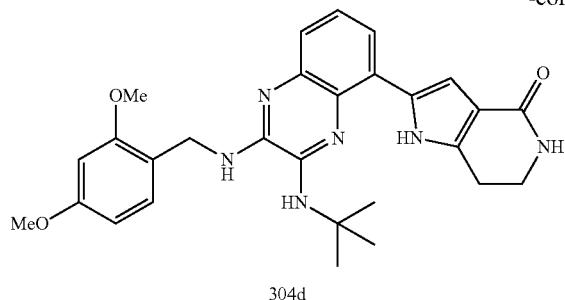 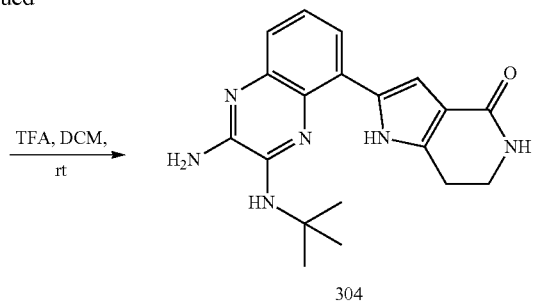

304d → 304

Preparation of 8-bromo-N-(tert-butyl)-3-chloroquinoxalin-2-amine (304a)

A solution of 5-bromo-2,3-dichloroquinoxaline (LeadGen Labs, LLC, Orange, Conn.) (305 mg, 1.10 mmol) and 2-methylpropan-2-amine (Aldrich) (0.12 mL, 1.10 mmol) in DMSO (5.0 mL) was stirred under argon at 65° C. for 17 h (water-cooled reflux condenser attached to flask). Additional 2-methylpropan-2-amine (0.06 mL, 0.57 mmol) was added, and the resulting solution was stirred at 100° C. for 5 h. The reaction mixture was subsequently cooled to 25° C. and diluted with half-saturated aq. NaHCO$_3$ (80 mL). The resulting mixture was extracted with DCM (2×80 mL), and the combined extracts were sequentially washed with water (2×50 mL), dried over Na$_2$SO$_4$, filtered, and concentrated onto silica gel. Chromatographic purification (silica gel, 0-10% EtOAc/hexanes) furnished a ~2.5:1 mixture of 8-bromo-N-(tert-butyl)-3-chloroquinoxalin-2-amine and 5-bromo-N-(tert-butyl)-3-chloroquinoxalin-2-amine (224 mg, 0.71 mmol, 65% yield) as an off-white solid: 8-bromo-N-(tert-butyl)-3-chloroquinoxalin-2-amine: $^1$H NMR (400 MHz, CDCl$_3$) δ ppm 7.86 (1H, dd, J=7.6, 1.0 Hz), 7.72 (1H, dd, J=8.2, 1.0 Hz), 7.21 (1H, t, J=7.9 Hz), 5.63 (1H, br. s.), 1.63 (9H, s). m/z (ESI, +ve) 314.0 (M+H)$^+$. 5-bromo-N-(tert-butyl)-3-chloroquinoxalin-2-amine: $^1$H NMR (400 MHz, CDCl$_3$) δ ppm 7.65 (1H, d, J=3.7 Hz), 7.63 (1H, d, J=3.3 Hz), 7.39 (1H, t, J=8.0 Hz), 5.60 (1H, br. s.), 1.57 (9H, s). m/z (ESI, +ve) 314.0 (M+H)$^+$.

Preparation of 5-bromo-N$^3$-(tert-butyl)-N$^2$-(2,4-dimethoxybenzyl)quinoxaline-2,3-diamine (304b)

A solution of 8-bromo-N-(tert-butyl)-3-chloroquinoxalin-2-amine (304a) (2.5:1 mixture with 5-bromo-N-(tert-butyl)-3-chloroquinoxalin-2-amine, 169 mg, 0.54 mmol) and (2,4-dimethoxyphenyl)methanamine (Aldrich) (0.16 mL, 1.07 mmol) in DMSO (1.0 mL) was stirred under argon at 100° C. for 2.5 h. The reaction mixture was subsequently cooled to 25° C. and diluted with water (15 mL). The precipitated solid was collected by vacuum filtration and chromatographically purified (silica gel, 5-100% DCM/hexanes). The isolated material was then taken up in DMSO (2.0 mL) and purified by rpHPLC (Phenomenex Gemini C18 column (150×30 mm, 10 mm), 35 mL/min, 10-100% CH$_3$CN/H$_2$O+0.1% TFA) to provide 5-bromo-N$^3$-(tert-butyl)-N$^2$-(2,4-dimethoxybenzyl)quinoxaline-2,3-diamine 2,2,2-trifluoroacetate (116 mg, 0.21 mmol, 39% yield) as a white solid (first compound eluted from column): $^1$H NMR (400 MHz, MeOH-d4) δ ppm 7.70 (1H, dd, J=7.8, 0.8 Hz), 7.67 (1H, dd, J=8.2, 1.0 Hz), 7.32 (1H, d, J=8.4 Hz), 7.24 (1H, t, J=8.0 Hz), 6.65 (1H, d, J=2.3 Hz), 6.59 (1H, dd, J=8.4, 2.3 Hz), 4.74 (2H, s), 3.86 (3H, s), 3.83 (3H, s), 1.63 (9H, s). $^{19}$F NMR (376 MHz, MeOH-d4) δ ppm −77.08 (3F, s). m/z (ESI, +ve) 445.1/447.1 (M+H)$^+$.

Preparation of N$^3$-(tert-butyl)-N$^2$-(2,4-dimethoxybenzyl)-5-(4,4,5,5-tetramethyl-1,3,2-dioxaborolan-2-yl)quinoxaline-2,3-diamine (304c)

A solution of 5-bromo-N$^3$-(tert-butyl)-N$^2$-(2,4-dimethoxybenzyl)quinoxaline-2,3-diamine 2,2,2-trifluoroacetate (304b; 116.6 mg, 0.21 mmol), (BPin)$_2$ (106 mg, 0.42 mmol), Pd(dppf)Cl$_2$CH$_2$Cl$_2$ (Strem Chemicals, Inc., 8.51 mg, 10.42 µmol), and KOAc (102 mg, 1.04 mmol) in DMF (0.5 mL) was stirred under argon at 105° C. for 6 h. Additional KOAc (102 mg, 1.04 mmol), (BPin)$_2$ (106 mg, 0.42 mmol), and Pd(dppf)Cl$_2$CH$_2$Cl$_2$ (8.51 mg, 10.42 µmol) were then added, and the resulting mixture was stirred under argon at 105° C. for 2 h. The reaction mixture was subsequently cooled to RT, diluted with EtOAc (50 mL), washed with water (3×25 mL), dried over Na$_2$SO$_4$, filtered, and concentrated onto silica gel. Chromatographic purification of the residue (silica gel, 0-70% EtOAc/hexanes) furnished N$^3$-(tert-butyl)-N$^2$-(2,4-dimethoxybenzyl)-5-(4,4,5,5-tetramethyl-1,3,2-dioxaborolan-2-yl)quinoxaline-2,3-diamine (109 mg) as a yellow solid: $^1$H NMR (400 MHz, CDCl$_3$) δ ppm 7.71 (2H, d, J=6.1 Hz), 7.28-7.37 (2H, m), 6.50 (1H, br. s.), 6.46 (1H, d, J=7.8 Hz), 4.68 (1H, br. s.), 4.64 (2H, br. s.), 4.18 (1H, br. s.), 3.86 (3H, br. s.), 3.81 (3H, br. s.), 1.59 (9H, br. s.), 1.39 (12H, br. s.). m/z (ESI, +ve) 411.2 (M+H$^+$; as boronic acid)+493.2 (M+H$^+$).

Preparation of 2-(3-(tert-butylamino)-2-((2,4-dimethoxybenzyl)amino)quinoxalin-5-yl)-6,7-dihydro-1H-pyrrolo[3,2-c]pyridin-4(5H)-one (304d)

A mixture of N$^3$-(tert-butyl)-N$^2$-(2,4-dimethoxybenzyl)-5-(4,4,5,5-tetramethyl-1,3,2-dioxaborolan-2-yl)quinoxaline-2,3-diamine (304c; 109.6 mg, 0.09 mmol), 2-bromo-6,7-dihydro-1H-pyrrolo[3,2-c]pyridin-4(5H)-one (608) (80 mg, 0.37 mmol), K$_2$PO$_4$ (59 mg, 0.28 mmol), X-Phos (Strem Chemicals, Inc.) (4.46 mg, 9.35 µmol), and Pd$_2$dba$_3$ (Aldrich) (4.28 mg, 4.67 µmol) in a mixture of dioxane (1.0 mL) and water (0.20 mL) was stirred under argon at 105° C. for 3 h. Additional Pd$_2$dba$_3$ (4.28 mg, 4.67 µmol) and dicyclohexyl (2',4',6'-triisopropyl-[1,1'-biphenyl]-2-yl)phosphine (4.46 mg, 9.35 µmol) were added, and the resulting mixture was stirred under argon at 105° C. for 15 h. The reaction mixture was subsequently diluted with DCM (10 mL) and concentrated onto silica gel. Chromatographic purification (silica gel, 0-100% EtOAc/hexanes, then 0-10% MeOH/DCM) furnished 2-(3-(tert-butylamino)-2-((2,4-dimethoxybenzyl)amino)quinoxalin-5-yl)-6,7-dihydro-1H-pyrrolo[3,2-c]pyridin-4(5H)-one (56.3 mg) as a yellow solid: m/z (ESI, +ve) 501.2 (M+H)$^+$.

Preparation of 2-(2-amino-3-(tert-butylamino)quinoxalin-5-yl)-6,7-dihydro-1H-pyrrolo[3,2-c]pyridin-4(5H)-one (304)

A solution of 2-(3-(tert-butylamino)-2-((2,4-dimethoxybenzyl)amino)quinoxalin-5-yl)-6,7-dihydro-1H-pyrrolo[3,2-c]pyridin-4(5H)-one (304d) (40 mg, 0.08 mmol) and TFA (1.0 mL, 12.98 mmol) in DCM (1.0 mL) was stirred at 25° C. for 1 h. The reaction mixture was subsequently heated at 40° C. for 1 h. The reaction mixture was then concentrated in vacuo, and the residue was partitioned between EtOAc (50 mL) and saturated aq. NaHCO₃ (30 mL). The organic layer was separated, washed with brine (20 mL), dried over Na₂SO₄, filtered, and concentrated in vacuo. Chromatographic purification of the residue (silica gel, 0-10% MeOH/DCM) furnished 2-(2-amino-3-(tert-butylamino)quinoxalin-5-yl)-6,7-dihydro-1H-pyrrolo[3,2-c]pyridin-4(5H)-one (6.4 mg, 0.018 mmol, 23% yield) as a light-yellow solid: ¹H NMR (400 MHz, DMSO-d₆) δ ppm 12.12 (1H, br. s.), 7.53 (1H, dd, J=7.0, 1.8 Hz), 7.19-7.22 (1H, m), 7.14-7.19 (1H, m), 6.92 (1H, br. s.), 6.90 (1H, d, J=2.0 Hz), 6.86 (2H, s), 6.33 (1H, s), 3.43 (2H, td, J=6.9, 2.2 Hz), 2.86 (2H, t, J=6.7 Hz), 1.56 (9H, s). m/z (ESI, +ve) 351.2 (M+H)⁺.

Example 305

2-(3-(tert-butylamino)-2-methylquinoxalin-5-yl)-5,6,7,8-tetrahydropyrrolo[3,2-c]azepin-4(1H)-one

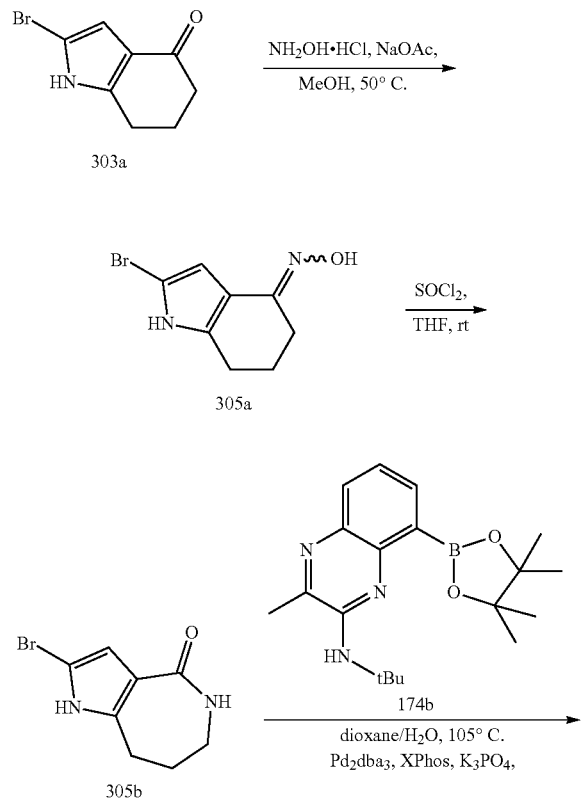

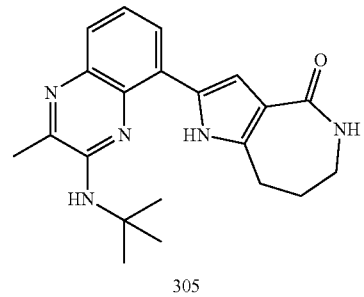

305

Preparation of 2-bromo-6,7-dihydro-1H-indol-4(5H)-one oxime (305a)

A solution of 2-bromo-6,7-dihydro-1H-indol-4(5H)-one (303a) (222 mg, 1.04 mmol), hydroxylamine hydrochloride (80 mg, 1.14 mmol), and sodium acetate (94 mg, 1.14 mmol) in MeOH (28 mL) was stirred under argon at 50° C. for 22 h. The reaction mixture was then concentrated in vacuo, and the residue was partitioned between saturated aq. NaHCO₃ (40 mL) and EtOAc (60 mL). The organic layer was separated, and the aq. layer was extracted with EtOAc (60 mL). The combined extracts were dried over Na₂SO₄, filtered, and concentrated in vacuo to provide 2-bromo-6,7-dihydro-1H-indol-4(5H)-one oxime (273 mg) as an off-white solid. ¹H NMR (400 MHz, CDCl₃) δ ppm: (~2:1 mixture of oxime isomers) Major isomer: 7.99 (1H, br. s.), 6.36 (1H, br. s.), 2.71 (2H, br. s.), 2.63 (2H, br. s.), 1.89-1.98 (2H, m). Minor isomer: ¹H NMR (400 MHz, CDCl₃) δ ppm 8.14 (1H, br. s.), 6.97 (1H, br. s.), 2.67-2.75 (2H, m), 2.47 (2H, br. s.), 1.99 (2H, br. s.). m/z (ESI, +ve) 228.9/231.1 (M+H)⁺.

Preparation of 2-bromo-5,6,7,8-tetrahydropyrrolo[3,2-c]azepin-4(1H)-one (305b)

Thionyl chloride (0.06 mL, 0.90 mmol) was added to a solution of 2-bromo-6,7-dihydro-1H-indol-4(5H)-one oxime (305a) (186 mg, 0.81 mmol) in THF (8.0 mL) at 25° C., and the resulting solution was stirred at 25° C. for 18 h. The reaction mixture was then diluted with EtOAc (40 mL), sequentially washed with saturated aq. NaHCO₃ (2×30 mL) and brine (20 mL), dried over Na₂SO₄, filtered, and concentrated in vacuo. Chromatographic purification of the residue (silica gel, 0-10% MeOH/DCM) furnished 2-bromo-5,6,7,8-tetrahydropyrrolo[3,2-c]azepin-4(1H)-one (102 mg, 0.44 mmol, 55% yield) as a light-brown solid. ¹H NMR (400 MHz, DMSO-d₆) δ ppm 11.59 (1H, br. s.), 7.36 (1H, t, J=4.5 Hz), 6.27 (1H, d, J=2.7 Hz), 3.09-3.16 (2H, m), 2.82 (2H, t, J=6.6 Hz), 1.82-1.91 (2H, m). m/z (ESI, +ve) 228.9/231.1 (M+H)⁺.

Preparation of 2-(3-(tert-butylamino)-2-methylquinoxalin-5-yl)-5,6,7,8-tetrahydropyrrolo[3,2-c]azepin-4(1H)-one (305)

A mixture of N-(tert-butyl)-3-methyl-8-(4,4,5,5-tetramethyl-1,3,2-dioxaborolan-2-yl)quinoxalin-2-amine (174b) (341 mg, 0.66 mmol), 2-bromo-5,6,7,8-tetrahydropyrrolo[3,2-c]azepin-4(1H)-one (305b) (84.0 mg, 0.37 mmol), K₂PO₄ (420 mg, 1.98 mmol), X-Phos (Strem Chemicals, Inc., 17.5 mg, 0.037 mmol), and Pd₂dba₃ (Aldrich, 16.8 mg, 0.018 mmol) in a mixture of dioxane (3.0 mL) and water (0.60 mL) was stirred under argon at 105° C. for 1.5 h. The reaction mixture was subsequently diluted with DCM (10 mL) and concentrated onto silica gel. Chromatographic purification (silica gel, 0-100% EtOAc/hexanes, then 0-10% MeOH/DCM) furnished 2-(3-(tert-butylamino)-2-methylquinoxalin-5-yl)-5,6,7,8-tetrahydropyrrolo[3,2-c]azepin-4(1H)-one (128 mg, 0.35 mmol, 96% yield) as a yellow solid: $^1$H NMR (400 MHz, DMSO-$d_6$) δ ppm 11.77 (1H, br. s.), 7.83 (1H, dd, J=7.4, 1.0 Hz), 7.56 (1H, dd, J=7.8, 1.0 Hz), 7.32 (2H, t, J=7.7 Hz), 7.09 (1H, d, J=2.7 Hz), 6.01 (1H, s), 3.21 (2H, dd, J=8.5, 4.6 Hz), 3.02 (2H, t, J=6.5 Hz), 2.55 (3H, s), 1.92-2.01 (2H, m), 1.58 (9H, s). m/z (ESI, +ve) 364.2 (M+H)$^+$.

Example 306

2-(3-(tert-butylamino)-2-(hydroxymethyl)quinoxalin-5-yl)-6,7-dihydro-1H-pyrrolo[3,2-c]pyridin-4(5H)-one

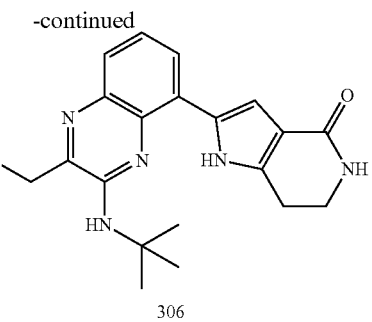

306

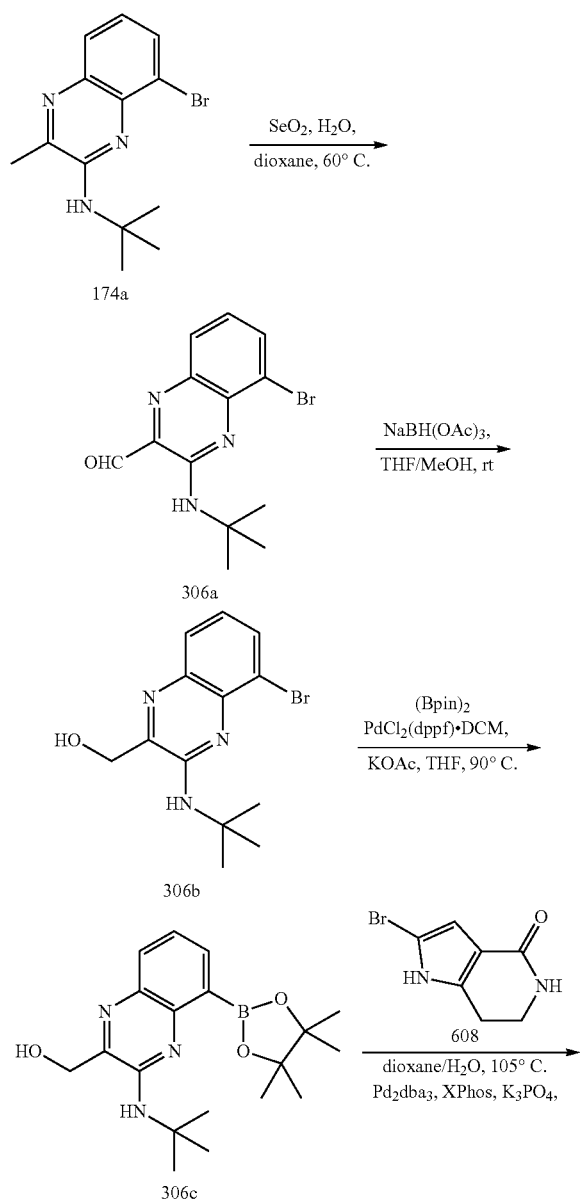

Preparation of 5-bromo-3-(tert-butylamino)quinoxaline-2-carbaldehyde (306a)

A solution of 8-bromo-N-(tert-butyl)-3-methylquinoxalin-2-amine (174a) (137 mg, 0.47 mmol), selenium dioxide (Aldrich; 57.0 mg, 0.51 mmol), and water (0.084 mL, 4.67 mmol) in 1,4-dioxane (5.0 mL) was stirred under argon at 60° C. for 19 h. The reaction mixture was then cooled to RT, diluted with DCM (5 mL), and adsorbed onto silica gel. Chromatographic purification (silica gel, 0-10% EtOAc/hexanes) furnished 5-bromo-3-(tert-butylamino)quinoxaline-2-carbaldehyde (132. mg, 0.43 mmol, 92% yield) as a yellow-orange solid. $^1$H NMR (400 MHz, CDCl$_3$) δ ppm 10.14 (1H, s), 8.03 (1H, br. s.), 7.99 (1H, d, J=7.4 Hz), 7.88 (1H, d, J=8.4 Hz), 7.22-7.25 (1H, m), 1.64 (9H, s). m/z (ESI, +ve) 308.0/310.1 (M+H)$^+$.

Preparation of 5-bromo-3-(tert-butylamino)quinoxalin-2-yl)methanol (306b)

A solution of 5-bromo-3-(tert-butylamino)quinoxaline-2-carbaldehyde (306a) (113 mg, 0.37 mmol) and sodium triacetoxyhydroborate (78 mg, 0.37 mmol) in THF (7.5 mL) was stirred at 25° C. for 10 min. MeOH (1.0 mL) was added, and the resulting mixture was stirred at 25° C. for 10 min. Additional sodium triacetoxyhydroborate (78 mg, 0.37 mmol) was added, and the resulting mixture was stirred at 25° C. for 10 min. Further sodium triacetoxyhydroborate (78 mg, 0.37 mmol) was added, and the resulting mixture was stirred at 25° C. for 10 min. Saturated aq. NaHCO$_3$ (10 mL) was then added, and the resulting mixture was partitioned between EtOAc (70 mL) and half-saturated aq. NaHCO$_3$ solution (50 mL). The organic layer was separated, and the aq. layer was extracted with EtOAc (30 mL). The combined organic extracts were washed with brine (40 mL), dried over Na$_2$SO$_4$, filtered, and concentrated in vacuo to provide (5-bromo-3-(tert-butylamino)quinoxalin-2-yl)methanol (114 mg, 0.37 mmol, 100% yield) as a yellow-brown solid. $^1$H NMR (400 MHz, CDCl$_3$) δ ppm 7.84 (1H, d, J=7.6 Hz), 7.76 (1H, d, J=8.0 Hz), 7.20 (1H, t, J=7.9 Hz), 5.10 (1H, br. s.), 4.72 (2H, s), 3.92 (1H, br. s.), 1.62 (9H, s). m/z (ESI, +ve) 310.0/312.0 (M+H)$^+$.

Preparation of (3-(tert-butylamino)-5-(4,4,5,5-tetramethyl-1,3,2-dioxaborolan-2-yl)quinoxalin-2-yl)methanol (306c)

A solution of (5-bromo-3-(tert-butylamino)quinoxalin-2-yl)methanol (306b) (114 mg, 0.37 mmol), (BPin)$_2$ (188 mg, 0.74 mmol), Pd(dppf)Cl$_2$CH$_2$Cl$_2$ (Strem Chemicals, Inc., 15.10 mg, 0.018 mmol), and KOAc (145 mg, 1.48 mmol) in THF (3.5 mL) was stirred under argon in a sealed vial at 90° C. for 16 h. The reaction mixture was subsequently cooled to RT and concentrated onto silica gel. Chromatographic purification (silica gel, 0-80% EtOAc/hexanes) furnished (3-(tert-butylamino)-5-(4,4,5,5-tetramethyl-1,3,2-dioxaborolan-2-yl)quinoxalin-2-yl)methanol (150 mg) as an orange oil. $^1$H NMR (400 MHz, CDCl$_3$) δ ppm 7.97 (1H, dd, J=6.7, 1.0 Hz), 7.90 (1H, dd, J=7.9, 1.3 Hz), 7.32-7.39 (1H, m), 4.73 (1H, br. s.), 4.67 (2H, s), 3.92-4.04 (1H, m), 1.63 (9H, s), 1.41 (12H, s). m/z (ESI, +ve) 276.2 (M+H$^{11}$; as boronic acid).

Preparation of 2-(3-(tert-butylamino)-2-(hydroxymethyl)quinoxalin-5-yl)-6,7-dihydro-1H-pyrrolo[3,2-c]pyridin-4(5H)-one (306)

A mixture of (3-(tert-butylamino)-5-(4,4,5,5-tetramethyl-1,3,2-dioxaborolan-2-yl)quinoxalin-2-yl)methanol (306c) (150 mg, 0.21 mmol), 2-bromo-6,7-dihydro-1H-pyrrolo[3,2-c]pyridin-4(5H)-one (608) (133 mg, 0.62 mmol), K$_2$PO$_4$ (262 mg, 1.24 mmol), X-Phos (Strem Chemicals, Inc., 9.8 mg, 0.02 mmol), and Pd$_2$dba$_3$ (Aldrich, 9.43 mg, 10.30 μmol) in a mixture of dioxane (2.5 mL) and water (0.50 mL) was stirred under argon in a sealed flask at 105° C. for 28 h. The reaction mixture was subsequently diluted with DCM (10 mL) and concentrated onto silica gel. Chromatographic purification (silica gel, 0-100% EtOAc/hexanes, then 0-10% MeOH/DCM) followed by rpHPLC (Phenomenex Gemini C18 column (150×30 mm, 10 mm), 35 mL/min, 5-100% CH$_3$CN/H$_2$O+0.1% TFA) afforded a TFA salt, which partitioned between 5% MeOH/DCM (30 mL) and saturated aq. NaHCO$_3$ (40 mL). The organic layer was separated, and the aq. layer was extracted with 5% MeOH/DCM (0 mL). The combined extracts were then dried over Na$_2$SO$_4$, filtered, and concentrated in vacuo to provide 2-(3-(tert-butylamino)-2-(hydroxymethyl)quinoxalin-5-yl)-6,7-dihydro-1H-pyrrolo[3,2-c]pyridin-4(5H)-one (9.3 mg, 0.025 mmol, 12% yield) as a yellow solid. $^1$H NMR (400 MHz, DMSO-d$_6$) δ ppm 12.00 (1H, br. s.), 7.87 (1H, dd, J=7.6, 1.4 Hz), 7.60 (1H, dd, J=8.0, 1.4 Hz), 7.35 (1H, t, J=7.8 Hz), 7.07 (1H, d, J=2.2 Hz), 6.97 (1H, br. s.), 6.96 (1H, br. s.), 6.12 (1H, br. s.), 4.72 (2H, br. s.), 3.43 (2H, td, J=6.7, 2.2 Hz), 2.86 (2H, t, J=6.8 Hz), 1.55 (9H, s). m/z (ESI, +ve) 366.2 (M+H)$^+$.

Example 307

2-(3-(tert-butylamino)-2-ethynylquinoxalin-5-yl)-6,7-dihydro-1H-pyrrolo[3,2-c]pyridin-4(5H)-one

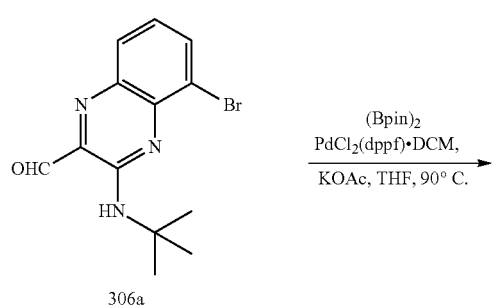

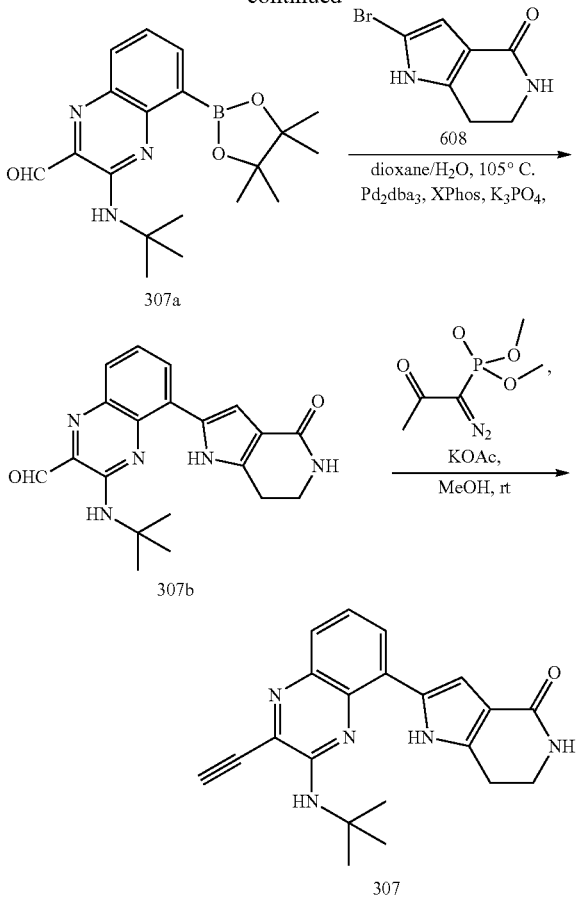

Preparation of 3-(tert-butylamino)-5-(4,4,5,5-tetramethyl-1,3,2-dioxaborolan-2-yl)quinoxaline-2-carbaldehyde (307a)

A solution of 5-bromo-3-(tert-butylamino)quinoxaline-2-carbaldehyde (306a) (491 mg, 1.59 mmol), (BPin)$_2$ (810 mg, 3.19 mmol), Pd(dppf)Cl$_2$CH$_2$Cl$_2$ (Strem Chemicals, Inc., 65 mg, 0.08 mmol), and KOAc (626 mg, 6.38 mmol) in THF (15.0 mL) was stirred under argon in a sealed flask at 90° C. for 16.5 h. The reaction mixture was subsequently cooled to RT and concentrated onto silica gel. Chromatographic purification (silica gel, 0-40% EtOAc/hexanes) furnished 3-(tert-butylamino)-5-(4,4,5,5-tetramethyl-1,3,2-dioxaborolan-2-yl)quinoxaline-2-carbaldehyde (600 mg) as a yellow-orange solid: m/z (ESI, +ve) 274.1 (M+H$^+$; as boronic acid).

Preparation of 3-(tert-butylamino)-5-(4-oxo-4,5,6,7-tetrahydro-1H-pyrrolo[3,2-c]pyridin-2-yl)quinoxaline-2-carbaldehyde (307b)

A mixture of 3-(tert-butylamino)-5-(4,4,5,5-tetramethyl-1,3,2-dioxaborolan-2-yl)quinoxaline-2-carbaldehyde (307a) (600.0 mg, 1.18 mmol), 2-bromo-6,7-dihydro-1H-pyrrolo[3,2-c]pyridin-4(5H)-one (608) (407 mg, 1.89 mmol), K$_2$PO$_4$ (753 mg, 3.55 mmol), X-Phos (Strem Chemicals, Inc., 56.4 mg, 0.12 mmol), and Pd$_2$dba$_3$ (Aldrich, 54.1 mg, 0.06 mmol) in a mixture of 1,4-dioxane (10 mL) and water (2.0 mL) was heated under argon at 105° C. for 1 h. The reaction mixture was cooled to RT, diluted with water (30 mL), and extracted with 5% MeOH/DCM (3×30 mL). The combined extracts were dried over Na$_2$SO$_4$, filtered, and concentrated onto silica gel. Chromatographic purification (silica gel, 0-100% EtOAc/hexanes, then 0-10% MeOH/DCM) furnished 3-(tert-butylamino)-5-(4-oxo-4,5,6,7-tetrahydro-1H-pyrrolo[3,2-c]pyridin-2-yl)quinoxaline-2-carbaldehyde (79.0 mg, 0.22 mmol, 18% yield) as a dark-red solid: m/z (ESI, +ve) 364.2 (M+H)$^+$.

Preparation of 2-(3-(tert-butylamino)-2-ethynylquinoxalin-5-yl)-6,7-dihydro-1H-pyrrolo[3,2-c]pyridin-4(5H)-one (307)

Dimethyl(1-diazo-2-oxopropyl)phosphonate (Anichem, Inc., North Brunswick, N.J.; 8.63 µl, 0.06 mmol) was added to a suspension of 3-(tert-butylamino)-5-(4-oxo-4,5,6,7-tetrahydro-1H-pyrrolo[3,2-c]pyridin-2-yl)quinoxaline-2-carbaldehyde (307b) (19.0 mg, 0.05 mmol) and K$_2$CO$_3$ (28.9 mg, 0.21 mmol) in MeOH (1.0 mL) and the resulting mixture was stirred at 23° C. for 16 h. Additional dimethyl(1-diazo-2-oxopropyl)phosphonate (20 µl, 0.13 mmol) was added, and the resulting mixture was stirred at 23° C. for 17 h. The reaction mixture was subsequently concentrated onto silica gel and chromatographically purified (silica gel, 0-100% EtOAc/hexanes, then 0-10% MeOH/DCM) to provide 2-(3-(tert-butylamino)-2-ethynylquinoxalin-5-yl)-6,7-dihydro-1H-pyrrolo[3,2-c]pyridin-4(5H)-one (2.8 mg, 7.79 µmol, 15% yield) as a yellow solid (following trituration with Et$_2$O (0.5 mL)): $^1$H NMR (400 MHz, CDCl$_3$) δ ppm 12.39 (1H, br. s.), 8.14 (1H, d, J=7.4 Hz), 8.10 (1H, d, J=8.0 Hz), 8.04 (1H, d, J=3.9 Hz), 7.72 (1H, t, J=7.8 Hz), 6.82 (1H, d, J=3.7 Hz), 5.49 (1H, br. s.), 3.81-3.86 (1H, m), 3.68-3.75 (2H, m), 3.06 (2H, t, J=6.9 Hz), 1.96 (9H, s). m/z (ESI, +ve) 360.2 (M+H)$^+$.

Example 308

(E)-3-(tert-butylamino)-5-(4-oxo-4,5,6,7-tetrahydro-1H-pyrrolo[3,2-c]pyridin-2-yl)quinoxaline-2-carbaldehyde oxime

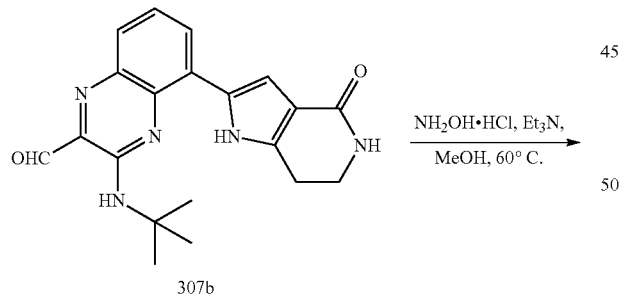

307b

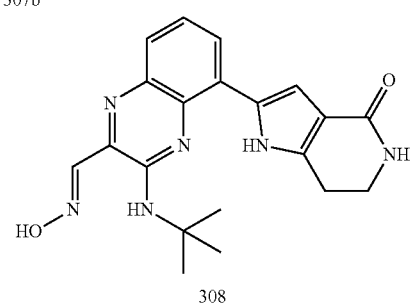

308

A solution of 3-(tert-butylamino)-5-(4-oxo-4,5,6,7-tetrahydro-1H-pyrrolo[3,2-c]pyridin-2-yl)quinoxaline-2-carbaldehyde (307b) (44.0 mg, 0.12 mmol), hydroxylamine hydrochloride (11.7 mg, 0.17 mmol), and TEA (0.024 mL, 0.17 mmol) in MeOH (5.0 mL) was stirred at 60° C. for 1.5 h. The reaction mixture was subsequently cooled to RT, diluted with saturated aq. NaHCO$_3$ (20 mL), and extracted with 5% MeOH/DCM (2×30 mL). The combined extracts were sequentially washed with water (30 mL) and brine (20 mL), dried over Na$_2$SO$_4$, filtered, and concentrated onto silica gel. Chromatographic purification (silica gel, 0-100% EtOAc/hexanes, then 0-10% MeOH/DCM) furnished (E)-3-(tert-butylamino)-5-(4-oxo-4,5,6,7-tetrahydro-1H-pyrrolo[3,2-c]pyridin-2-yl)quinoxaline-2-carbaldehyde oxime (31.0 mg, 0.082 mmol, 68% yield) as an orange solid: $^1$H NMR (400 MHz, DMSO-d$_6$) δ ppm 12.34 (1H, br. s.), 11.86 (1H, br. s.), 8.34 (1H, s), 8.31 (1H, s), 7.91 (1H, dd, J=7.3, 1.1 Hz), 7.67 (1H, dd, J=8.0, 1.0 Hz), 7.40 (1H, t, J=7.8 Hz), 7.09 (1H, d, J=2.2 Hz), 6.95 (1H, br. s.), 3.43 (2H, td, J=6.8, 2.2 Hz), 2.86 (2H, t, J=6.8 Hz), 1.57 (9H, s). m/z (ESI, +ve) 379.1 (M+H)$^+$.

Example 309

3-(tert-butylamino)-5-(4-oxo-4,5,6,7-tetrahydro-1H-pyrrolo[3,2-c]pyridin-2-yl)quinoxaline-2-carbonitrile

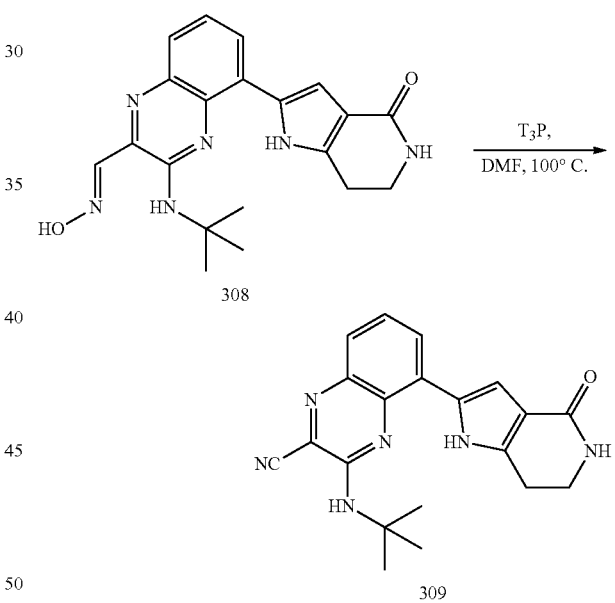

A solution of (E)-3-(tert-butylamino)-5-(4-oxo-4,5,6,7-tetrahydro-1H-pyrrolo[3,2-c]pyridin-2-yl)quinoxaline-2-carbaldehyde oxime (308) (26.3 mg, 0.069 mmol) and 1-propanephosphonic acid cyclic anhydride (Alfa Aesar, Ward Hill, Mass.; 50 wt % solution in EtOAc; 0.16 mL, 0.28 mmol) in DMF (2.0 mL) was stirred at 100° C. for 3.5 h. The reaction mixture was then cooled to RT, diluted with saturated aq. NaHCO$_3$ (30 mL), and extracted with 5% MeOH/DCM (2×30 mL). The combined extracts were sequentially washed with water (2×20 mL) and brine (20 mL), dried over Na$_2$SO$_4$, filtered, and concentrated in vacuo. The residue was taken up in DMSO (2.0 mL) and purified by rpHPLC (Phenomenex Gemini C18 column (150×30 mm, 10 mm), 35 mL/min, 5-100% CH$_3$CN/H$_2$O+0.1% TFA). Product-containing fractions were combined and neutralized with saturated aq.

NaHCO₃ (30 mL). The resulting mixture was extracted with 5% MeOH/DCM (2×30 mL), and the combined extracts were dried over Na₂SO₄, filtered, and concentrated in vacuo to provide 3-(tert-butylamino)-5-(4-oxo-4,5,6,7-tetrahydro-1H-pyrrolo[3,2-c]pyridin-2-yl)quinoxaline-2-carbonitrile (8.9 mg, 0.025 mmol, 36% yield) as a red-orange solid. ¹H NMR (400 MHz, DMSO-d₆) δ ppm 11.61 (1H, br. s.), 7.98 (1H, dd, J=7.4, 1.2 Hz), 7.73 (1H, dd, J=8.2, 1.2 Hz), 7.52 (1H, t, J=7.8 Hz), 7.12 (1H, d, J=2.3 Hz), 6.95 (1H, br. s.), 6.60 (1H, s), 3.42 (2H, td, J=6.8, 2.2 Hz), 2.84 (2H, t, J=6.8 Hz), 1.53 (9H, s). m/z (ESI, +ve) 361.1 (M+H)⁺.

Examples 310

(S)-2-(3-(tert-butylamino)-2-(1-hydroxyethyl)quinoxalin-5-yl)-6,7-dihydro-1H-pyrrolo[3,2-c]pyridin-4(5H)-one; and 311: (R)-2-(3-(tert-butylamino)-2-(1-hydroxyethyl)quinoxalin-5-yl)-6,7-dihydro-1H-pyrrolo[3,2-c]pyridin-4(5H)-one

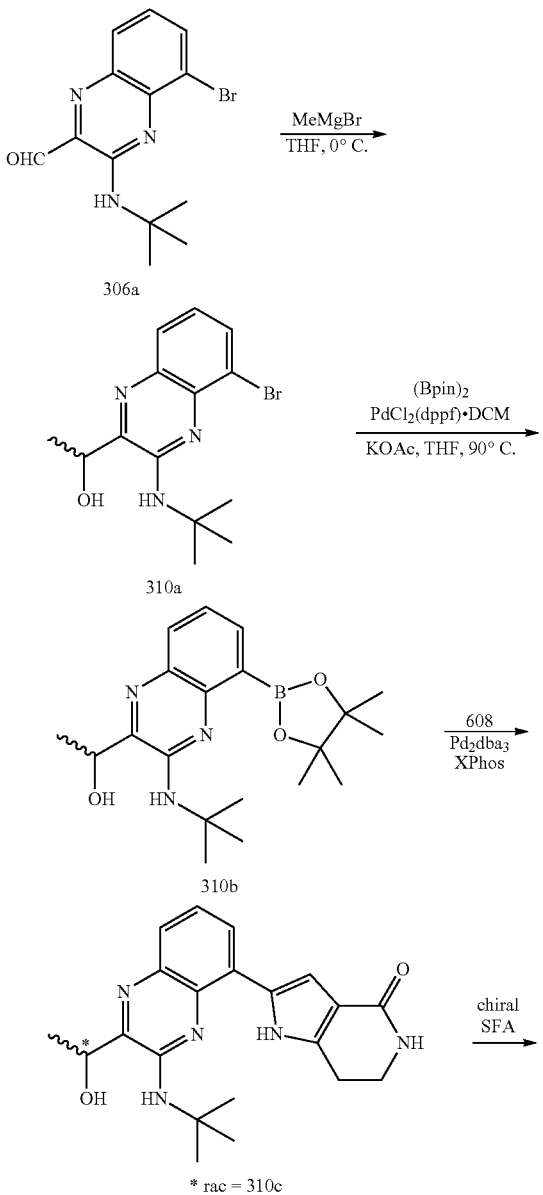

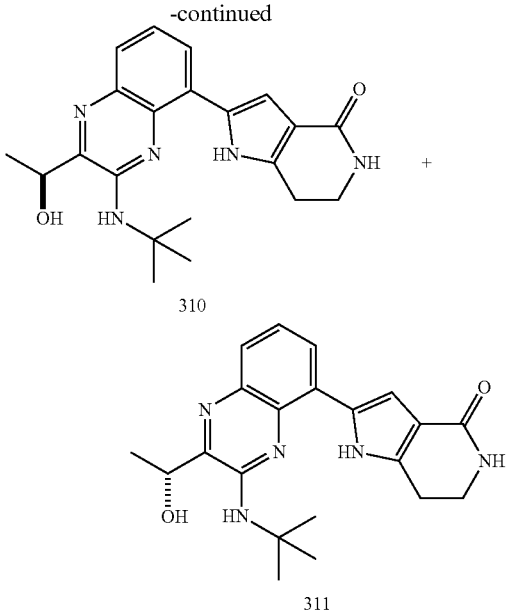

Preparation of 1-(5-bromo-3-(tert-butylamino)quinoxalin-2-yl)ethanol (310a)

Methylmagnesium bromide (Aldrich) (3.0M in Et₂O; 2.23 mL, 6.70 mmol) was added to a solution of 5-bromo-3-(tert-butylamino)quinoxaline-2-carbaldehyde (306a) (983.0 mg, 3.19 mmol) in THF (15.0 mL) at 0° C., and the resulting solution was stirred at 0° C. for 5 min. Water (5 mL) was added, and the resulting mixture was partitioned between saturated aq. NaHCO₃ (80 mL) and EtOAc (120 mL). The organic layer was separated and sequentially washed with brine (60 mL), dried over Na₂SO₄, filtered, and concentrated in vacuo. Chromatographic purification of the residue (silica gel, 0-40% EtOAc/hexanes) furnished 1-(5-bromo-3-(tert-butylamino)quinoxalin-2-yl)ethanol (952 mg, 2.94 mmol, 92% yield) as a light-yellow solid (following trituration with hexanes). ¹H NMR (400 MHz, CDCl₃) δ ppm 7.83 (1H, dd, J=7.6, 1.4 Hz), 7.75 (1H, dd, J=8.2, 1.4 Hz), 7.19 (1H, t, J=7.9 Hz), 5.74 (1H, br. s.), 5.01 (1H, q, J=6.7 Hz), 3.55 (1H, br. s.), 1.63 (9H, s), 1.59 (3H, d, J=6.7 Hz). m/z (EST, +ve) 324.1/326.1 (M+H)⁺.

Preparation of 1-(3-(tert-butylamino)-5-(4,4,5,5-tetramethyl-1,3,2-dioxaborolan-2-yl)quinoxalin-2-yl)ethanol (310b)

A solution of 1-(5-bromo-3-(tert-butylamino)quinoxalin-2-yl)ethanol (310a) (731 mg, 2.25 mmol), (BPin)₂ (1145 mg, 4.51 mmol), Pd(dppf)Cl₂·CH₂Cl₂ (Strem Chemicals, Inc., 92 mg, 0.11 mmol), and KOAc (885 mg, 9.02 mmol) in THF (20 mL) was stirred under argon in a sealed flask at 90° C. for 1 d. The reaction mixture was subsequently cooled to RT and concentrated onto silica gel. Chromatographic purification (silica gel, 0-60% EtOAc/hexanes) furnished 1-(3-(tert-butylamino)-5-(4,4,5,5-tetramethyl-1,3,2-dioxaborolan-2-yl)quinoxalin-2-yl)ethanol (960 mg) as a yellow oil. ¹H NMR (400 MHz, CDCl₃) δ ppm 7.96 (1H, dd, J=6.8, 1.6 Hz), 7.86 (1H, dd, J=8.0, 1.6 Hz), 7.34 (1H, dd, J=8.0, 7.0 Hz), 5.35 (1H, br. s.), 4.94 (1H, q, J=6.7 Hz), 1.63 (9H, s), 1.55 (3H, d, J=6.7 Hz), 1.41 (12H, s). m/z (ESI, +ve) 290.2 (M+H+; as boronic acid).

Preparation of Examples 310 and 311

A mixture of 1-(3-(tert-butylamino)-5-(4,4,5,5-tetramethyl-1,3,2-dioxaborolan-2-yl)quinoxalin-2-yl)ethanol (310b; 960 mg, 1.732 mmol), 2-bromo-6,7-dihydro-1H-pyrrolo[3,2-c]pyridin-4(5H)-one (608) (596 mg, 2.77 mmol), $K_2PO_4$ (1177 mg, 5.54 mmol), X-Phos (Strem Chemicals, Inc., 83 mg, 0.173 mmol), and $Pd_2dba_3$ (Aldrich) (79 mg, 0.087 mmol) in a mixture of 1,4-dioxane (15 mL) and water (3.00 mL) was heated under argon at 105° C. for 1.5 h. The reaction mixture was then cooled to RT, diluted with water (100 mL), and extracted with 5% MeOH/DCM (3×100 mL). The combined extracts were dried over $Na_2SO_4$, filtered, and concentrated onto silica gel. Chromatographic purification (silica gel, 0-100% EtOAc/hexanes, then 0-10% MeOH/DCM) followed by trituration of the collected solid with $Et_2O$ (10 mL) furnished 2-(3-(tert-butylamino)-2-(1-hydroxyethyl)quinoxalin-5-yl)-6,7-dihydro-1H-pyrrolo[3,2-c]pyridin-4(5H)-one (310) (172 mg, 0.45 mmol, 26% yield) as a light-yellow solid. $^1$H NMR (400 MHz, DMSO-$d_6$) δ ppm 11.99 (1H, br. s.), 7.85 (1H, dd, J=7.5, 1.3 Hz), 7.58 (1H, dd, J=8.0, 1.2 Hz), 7.47 (1H, s), 7.34 (1H, t, J=7.8 Hz), 7.04 (1H, d, J=2.2 Hz), 6.93 (1H, s), 6.43 (1H, br. s.), 4.96 (1H, q, J=6.8 Hz), 3.43 (2H, td, J=6.8, 2.5 Hz), 2.86 (2H, t, J=6.8 Hz), 1.54 (9H, s), 1.50 (3H, d, J=6.7 Hz). m/z (ESI, +ve) 380.1 (M+H)$^+$. Separation of this material (310c) by supercritical-fluid chromatography (Chiralpak IC (150×30 mm, 10 μm), 70% liquid $CO_2$/30% MeOH (+20 mM $NH_4OH$, 70 mL/min) separately afforded: first-eluting peak, (S)-2-(3-(tert-butylamino)-2-(1-hydroxyethyl)quinoxalin-5-yl)-6,7-dihydro-1H-pyrrolo[3,2-c]pyridin-4(5H)-one, (310; 35.0 mg, 0.092 mmol, m/z (ESI, +ve) 380.1 (M+H)$^+$); and second-eluting peak, (R)-2-(3-(tert-butylamino)-2-(1-hydroxyethyl)quinoxalin-5-yl)-6,7-dihydro-1H-pyrrolo[3,2-c]pyridin-4(5H)-one (311; 39.0 mg, 0.103 mmol, m/z (ESI, +ve) 380.1 (M+H)$^+$).

Example 312

2-(3-(tert-butylamino)-2-ethylquinoxalin-5-yl)-6,7-dihydro-1H-pyrrolo[3,2-c]pyridin-4(5H)-one

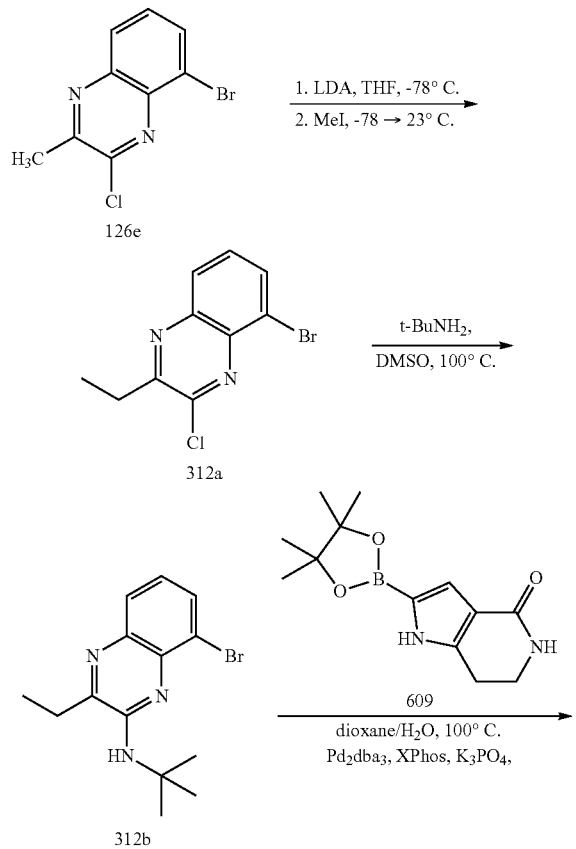

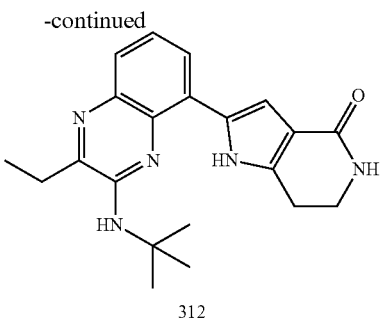

Preparation of 5-bromo-3-chloro-2-ethylquinoxaline (312a)

LDA(Aldrich) (1.7M in heptane/THF/ethylbenzene; 0.60 mL, 1.01 mmol) was added (dropwise, over 1 min) to a solution of 5-bromo-3-chloro-2-methylquinoxaline (126e) (238 mg, 0.92 mmol) in THF (8.0 mL) in an oven-dried flask under argon at –78° C., and the resulting solution was stirred at –78° C. for 7 min. Methyl iodide (0.12 mL, 1.85 mmol) was then added, and the resulting solution was stirred at –78° C. for 15 min, then warmed to 23° C. and stir at 23° C. for 16 h. The reaction mixture was subsequently cooled to 0° C., water (0.5 mL) was added, and the reaction mixture was concentrated onto silica gel and chromatographically purified (silica gel, 0-15% EtOAc/hexanes) to provide 5-bromo-3-chloro-2-ethylquinoxaline (136 mg, 0.50 mmol, 54% yield) as a light-orange solid. $^1$H NMR (400 MHz, $CDCl_3$) δ ppm 8.04 (1H, d, J=3.1 Hz), 8.02 (1H, d, J=2.3 Hz), 7.60 (1H, t, J=8.0 Hz), 3.20 (2H, q, J=7.4 Hz), 1.44 (3H, t, J=7.4 Hz). m/z (ESI, +ve) 271.0/272.9 (M+H)$^+$.

Preparation of 8-bromo-N-(tert-butyl)-3-ethylquinoxalin-2-amine (312b)

A solution of 5-bromo-3-chloro-2-ethylquinoxaline (312a) (131 mg, 0.48 mmol) and t-butylamine (Aldrich) (0.25 mL, 2.41 mmol) in DMSO (1.0 mL) was stirred under argon in a sealed flask at 100° C. for 17 h. The reaction mixture was then cooled to RT and partitioned between $Et_2O$ (80 mL) and saturated aq. $NaHCO_3$ (80 mL). The organic layer was separated and sequentially washed with water (50 mL) and brine (40 mL), then dried over $Na_2SO_4$, filtered, and concentrated in vacuo to provide 8-bromo-N-(tert-butyl)-3-ethylquinoxalin-2-amine (136 mg, 0.44 mmol, 92% yield) as a yellow-orange solid. $^1$H NMR (400 MHz, $CDCl_3$) δ ppm 7.86 (1H, d, J=8.2 Hz), 7.82 (1H, dd, J=7.6, 1.2 Hz), 7.20 (1H, t, J=7.9 Hz), 4.87 (1H, br. s.), 2.84 (2H, q, J=7.4 Hz), 1.64 (9H, s), 1.42 (3H, t, J=7.4 Hz). m/z (ESI, +ve) 308.3/310.3 (M+H)$^+$.

Preparation of 2-(3-(tert-butylamino)-2-ethylquinoxalin-5-yl)-6,7-dihydro-1H-pyrrolo[3,2-c]pyridin-4(5H)-one (312)

A mixture of 8-bromo-N-(tert-butyl)-3-ethylquinoxalin-2-amine (312b; 134.8 mg, 0.437 mmol), 2-(4,4,5,5-tetramethyl-1,3,2-dioxaborolan-2-yl)-6,7-dihydro-1H-pyrrolo[3,2-c]pyridin-4(5H)-one (609) (345 mg, 0.90 mmol), $K_2PO_4$ (279 mg, 1.31 mmol), X-Phos (Strem Chemicals, Inc.) (20 mg, 0.04 mmol), and $Pd_2dba_3$ (Aldrich, 20 mg, 0.022 mmol) in a mixture of 1,4-dioxane (5.0 mL) and water (1.00 mL) was stirred under argon at 100° C. for 1 h. The reaction mixture was then concentrated onto silica gel and chromatographically purified (silica gel, 0-100% EtOAc/hexanes, then 0-10% MeOH/DCM) to provide 2-(3-(tert-butylamino)-2-ethylquinoxalin-5-yl)-6,7-dihydro-1H-pyrrolo[3,2-c]pyridin-4(5H)-one (6.7 mg, 0.018 mmol, 4% yield) as a yellow-orange solid. ¹H NMR (400 MHz, DMSO-d₆) δ ppm 12.00 (1H, br. s.), 7.82 (1H, dd, J=7.4, 1.2 Hz), 7.60 (1H, dd, J=8.1, 1.3 Hz), 7.33 (1H, t, J=7.8 Hz), 7.02 (1H, d, J=2.0 Hz), 6.96 (1H, br. s.), 6.04 (1H, s), 3.42 (2H, td, J=6.9, 2.2 Hz), 2.90 (2H, q, J=7.2 Hz), 2.85 (2H, t, J=7.0 Hz), 1.56 (9H, s), 1.29 (3H, t, J=7.2 Hz). m/z (ESI, +ve) 364.1 (M+H)⁺.

Example 314

2-(3-(tert-butylamino)-2-methylquinoxalin-5-yl)-1-methyl-6,7-dihydro-1H-pyrrolo[3,2-c]pyridin-4(5H)-one

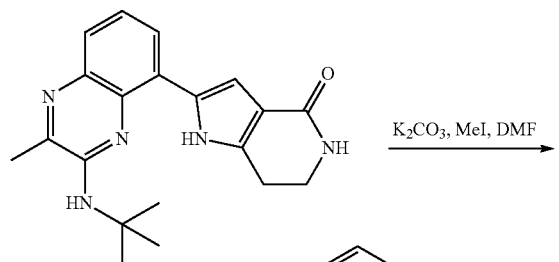

A mixture of 2-(3-(tert-butylamino)-2-methylquinoxalin-5-yl)-6,7-dihydro-1H-pyrrolo[3,2-c]pyridin-4(5H)-one (193) (0.10 g, 0.28 mmol), K₂CO₃ (0.13 g, 0.92 mmol), and MeI (0.027 mL, 0.43 mmol) in DMF (4 mL) was stirred at 50° C. in 24 h. The reaction mixture was cooled, added H₂O, the solid was filtered, dried and purified by ISCO (0-30% EtOAc/DCM) to give the title compound (35 mg, 34% yield). ¹H NMR (400 MHz, DMSO-d₆) δ ppm 7.71-7.78 (1H, m), 7.40-7.50 (1H, m), 7.35 (1H, t, J=7.6 Hz), 6.86 (1H, br. s.), 6.22 (1H, s), 5.87 (1H, s), 3.39-3.50 (3H, m), 3.11-3.21 (2H, m), 2.77 (2H, t, J=6.8 Hz), 2.51 (3H, s), 1.28 (9H, s). m/z (ESI, +ve) 364.0 (M+H)⁺.

Example 315

5-acetyl-2-(3-(tert-butylamino)-2-methylquinoxalin-5-yl)-6,7-dihydro-1H-pyrrolo[3,2-c]pyridin-4(5H)-one

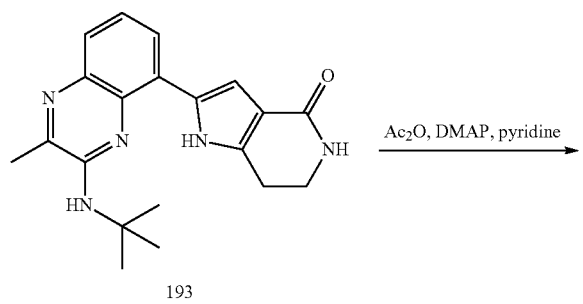

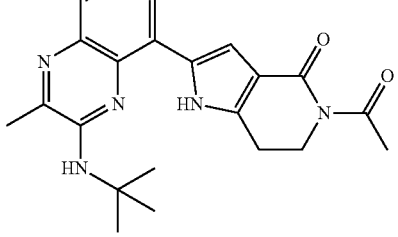

A mixture of 2-(3-(tert-butylamino)-2-methylquinoxalin-5-yl)-6,7-dihydro-1H-pyrrolo[3,2-c]pyridin-4(5H)-one (193) (0.13 g, 0.37 mmol), DMAP (0.45 g, 3.75 mmol), and Ac₂O (0.35 mL, 3.75 mmol) in pyridine (2 mL) was stirred at 50° C. in 24h. The reaction mixture was cooled, concentrated to dryness, purified by ISCO (0-30% EtOAc/DCM) to give the title compound (33 mg, 22%). ¹H NMR (400 MHz, DMSO-d₆) δ ppm 12.11 (1H, br. s.), 7.75-7.88 (1H, m), 7.54-7.67 (1H, m), 7.35 (1H, t, J=7.8 Hz), 7.30 (1H, d, J=2.2 Hz), 6.01 (1H, s), 4.14 (2H, t, J=6.3 Hz), 2.94 (2H, t, J=6.4 Hz), 2.55 (3H, s), 2.44 (3H, s), 1.56 (9H, s). m/z (ESI, +ve) 392.0 (M+H)⁺.

Example 316 tert-butyl 2-(3-(tert-butylamino)-2-methylquinoxalin-5-yl)-6-methyl-4-oxo-4,6-dihydropyrrolo[3,4-b]pyrrole-5(1H)-carboxylate

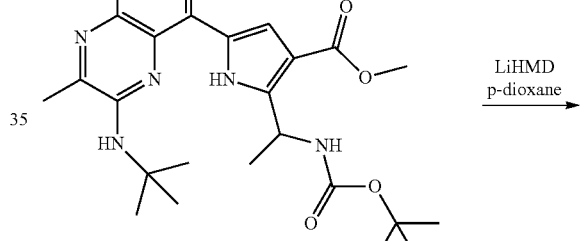

To a stirred solution of methyl 2-(1-((tert-butoxycarbonyl)amino)ethyl)-5-(3-(tert-butylamino)-2-methylquinoxalin-5-yl)-1H-pyrrole-3-carboxylate (326b) (0.13 g, 0.27 mmol) in p-dioxane (2 mL) was added LiHMDS (1.64 mL, 1.64 mmol) dropwise. After the addition, the mixture was stirred at RT in overnight, then heated at 60° C. in 1 h, cooled to RT, and quenched with saturated aq. NH₄Cl, extracted with EtOAc (3×). The extracts were dried over MgSO₄, filtered, concentrated and purified by ISCO (0-70% EtOAc/Hexanes) to give the title compound (43 mg, 35%). ¹H NMR (400 MHz, DMSO-d₆) δ ppm 12.09 (1H, s), 7.78 (1H, dd, J=7.4, 1.4 Hz), 7.67 (1H, dd, J=8.2, 1.4 Hz), 7.38 (1H, t, J=7.7 Hz), 6.94 (1H, s), 6.00 (1H, s), 4.99 (1H, q, J=6.5 Hz), 2.56 (3H, s), 1.59 (3H, d, J=6.5 Hz), 1.52 (9H, s), 1.51 (9H, s). m/z (ESI, +ve) 450.0 (M+H)⁺.

Example 317

2-(3-((2-(2-methoxyethoxy)-1,1-dimethylethyl)
amino)-2-methyl-5-quinoxalinyl)-1,5,6,7-tetrahydro-
4H-pyrrolo[3,2-c]pyridin-4-one

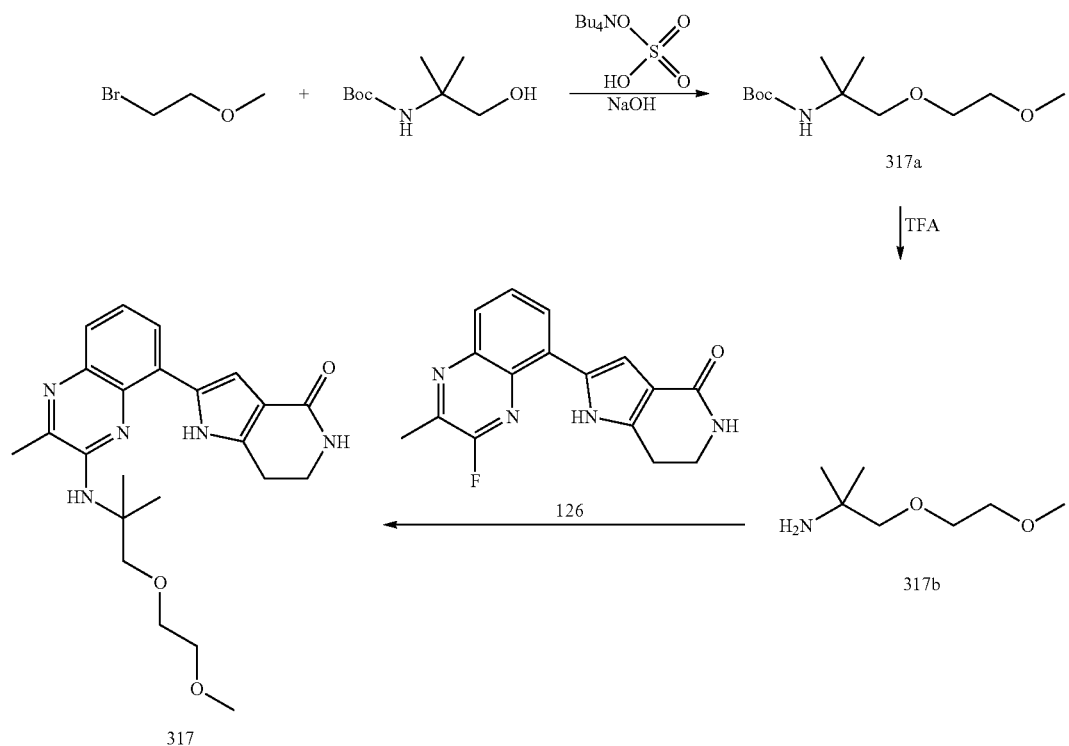

In a glass tube, a mixture of 2-(boc-amino)-2-methyl-1-propanol (Sigma-Aldrich Chemical Company, Inc.) (1.50 g, 7.93 mmol) and tetrabutylammonium hydrogen sulfate (0.27 g, 0.79 mmol) in toluene (10 mL) was treated with 2-bromoethyl methyl ether (Sigma-Aldrich Chemical Company, Inc.) (0.89 mL, 9.51 mmol) followed by NaOH (3.96 mL of 5 N solution, 19.81 mmol). The glass tube was sealed and heated at 40° C. in an oil bath for 4 d. The reaction mixture was diluted with 50 mL of EtOAc. The aq. layer was separated and discarded. The organic layer was washed with 2×5 mL of brine, concentrated and the residue was purified on a silica gel column (25-45% EtOAc in hexanes) to give 0.53 g of an off-white crystalline solid as a 1:1 mixture of tert-butyl (1-(2-methoxyethoxy)-2-methylpropan-2-yl)carbamate (317a) [m/z (ESI, +ve) 270 (M+H)$^+$] and the starting material, 2-(boc-amino)-2-methyl-1-propanol [m/z (ESI, +ve) 212.1 (M+Na)$^+$]. This material was used without further purification.

A solution of the above obtained 0.53 g of 1:1 mixture of tert-butyl (1-hydroxy-2-methylpropan-2-yl)carbamate and tert-butyl (1-(2-methoxyethoxy)-2-methylpropan-2-yl)carbamate in 10 mL of DCM and TFA (1.4 mL, 19.60 mmol) was stirred at RT for 2 h. It was concentrated under reduced pressure. The residue was treated with 10 mL of 1 N NaOH, and extracted with 3×30 mL of EtOAc. The combined organic layers were washed with 5 mL of brine, dried over Na$_2$SO$_4$ and concentrated to give an off-white amorphous solid containing a 1:1 mixture of tert-butyl (1-(2-methoxyethoxy)-2-methylpropan-2-yl)carbamate (317b) [m/z (ESI, +ve) 148.0 (M+H)$^+$] and 2-amino-2-methylpropan-1-ol [m/z (ESI, +ve) 90.0 (M+H)$^+$]. This material was used without further purification. A solution of the above obtained off-white amorphous solid containing a 1:1 mixture of tert-butyl (1-(2-methoxyethoxy)-2-methylpropan-2-yl)carbamate (317b) [m/z (ESI, +ve) 148.0 (M+H)$^+$] and 2-amino-2-methylpropan-1-ol [m/z (ESI, +ve) 90.0 (M+H)$^+$], and 2-(3-fluoro-2-methylquinoxalin-5-yl)-6,7-dihydro-1H-pyrrolo[3,2-c]pyridin-4(5H)-one (126) (135 mg, 0.45 mmol), and TEA (0.13 mL, 0.91 mmol) in 1.5 mL of DMSO in a sealed glass tube was heated in a microwave at 150° C. for 0.5 h. The reaction mixture was diluted with 75 mL of EtOAc, washed with 5 mL of water followed by 5 mL of brine. The organic layer was dried over Na$_2$SO$_4$ and concentrated. The residue was purified on a silica gel column (1-5% MeOH in DCM) to give 2-(3-((1-(2-methoxyethoxy)-2-methylpropan-2-yl)amino)-2-methylquinoxalin-5-yl)-6,7-dihydro-1H-pyrrolo[3,2-c]pyridin-4(5H)-one (40 mg, 20% yield) in 92% pure as a yellow crystalline solid. $^1$H NMR (400 MHz, DMSO-d$_6$) δ ppm 11.87 (1H, br.), 7.82 (1H, d, J=7.6 Hz), 7.61 (1H, d, J=8.0 Hz), 7.36 (1H, t, J=7.7 Hz), 7.00 (2H, m), 5.92 (1H, br.), 3.71 (2H, s), 3.59 (2H, m), 3.44 (2H, m), 3.20 (3H, s), 3.18 (2H, m), 2.87 (2H, m), 2.55 (3H, s.), 1.54 (6H, s). m/z (ESI, +ve) 424.0 (M+H)$^+$.

Example 318

2-(2-methyl-3-(3-(methylsulfonyl)-1-azetidinyl)-5-quinoxalinyl)-1,5,6,7-tetrahydro-4H-pyrrolo[3,2-c]pyridin-4-one

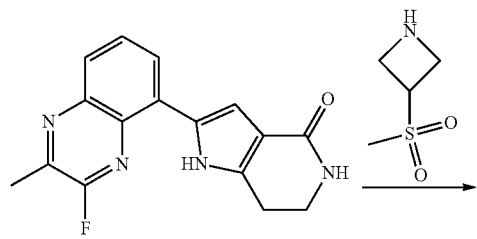

126

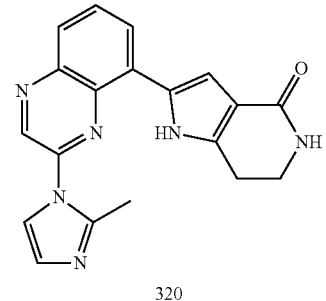

320

A solution of 2-(3-fluoroquinoxalin-5-yl)-6,7-dihydro-1H-pyrrolo[3,2-c]pyridin-4(5H)-one (210i) (40 mg, 0.14 mmol) and 2-methylimidazole (Sigma-Aldrich Corporation) (35 mg, 0.42 mmol) in 0.5 mL of NMP was heated in a microwave at 125° C. for 30 min. Purification of the crude reaction mixture on a silica gel column (1-6% MeOH in DCM) gave the title compound (30 mg, 61% yield) as a yellow crystalline solid. $^1$H NMR (400 MHz, DMSO-$d_6$) δ ppm 11.75 (1H, br.), 9.32 (1H, s), 8.13 (1H, dd, J=7.4, 1.2 Hz), 8.03 (1H, dd, J=8.2, 1.2 Hz), 7.98 (1H, d, J=1.6 Hz), 7.85-7.95 (1H, m), 7.14 (1H, d, J=2.2 Hz), 7.08 (1H, d, J=1.6 Hz), 7.04 (1H, br.), 3.45 (2H, td, J=6.8, 2.3 Hz), 2.90 (2H, t, J=6.8 Hz), 2.64 (3H, s). m/z (ESI, +ve) 345.2 (M+H)$^+$.

318

A solution of 3-methanesulfonyl-azetidine (10.95 mg, 0.08 mmol) (Pharmablock Co. Ltd, cat# PBJH0053), 2-(3-fluoro-2-methylquinoxalin-5-yl)-6,7-dihydro-1H-pyrrolo[3,2-c]pyridin-4(5H)-one (126) (24 mg, 0.081 mmol) and DIEA (15.50 µL, 0.09 mmol) in 0.5 mL of NMP was heated in a microwave at 125° C. for 30 min. Purification of the crude reaction mixture on a silica gel column (1-6% MeOH in DCM) gave 2-(2-methyl-3-(3-(methylsulfonyl)azetidin-1-yl)quinoxalin-5-yl)-6,7-dihydro-1H-pyrrolo[3,2-c]pyridin-4(5H)-one (16 mg, 48% yield) as a yellow crystalline solid. $^1$H NMR (400 MHz, DMSO-$d_6$) δ ppm 11.83 (1H, br.), 7.93 (1H, m, 7.65 (1H, m), 7.44 (1H, m), 7.14 (1H, s), 6.99 (1H, br.), 4.72 (2H, m), 4.60 (2H, m), 4.48 (1H, m), 3.43 (2H, m), 3.15 (3H, s), 2.89 (2H, m), 2.63 (3H, s). m/z (ESI, +ve) 12.1 (M+H)$^+$.

Example 321

2-(2-methyl-3-((1-(pyridin-2-yl)ethyl)amino)quinoxalin-5-yl)-6,7-dihydro-1H-pyrrolo[3,2-c]pyridin-4(5H)-one

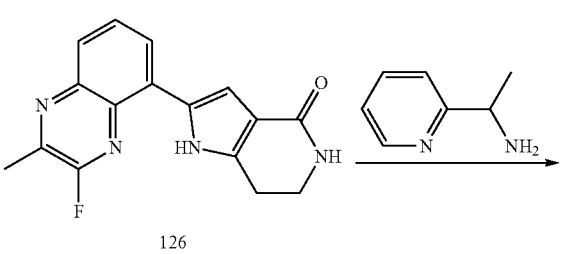

126

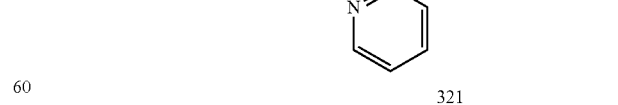

321

This compound (16 mg, 44% yield) as a yellow crystalline solid was prepared according the procedures described for Example 318, using 2-(3-fluoro-2-methylquinoxalin-5-yl)-6,7-dihydro-1H-pyrrolo[3,2-c]pyridin-4(5H)-one (126) (27 mg, 0.09 mmol), 1-(2-pyridyl)ethylamine (16.7 mg, 0.14

Example 320

2-(2-methyl-3-(3-(methylsulfonyl)-1-azetidinyl)-5-quinoxalinyl)-1,5,6,7-tetrahydro-4H-pyrrolo[3,2-c]pyridin-4-one

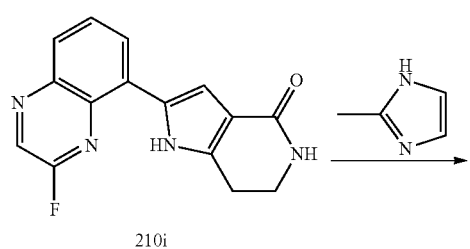

210i mmol) [Matrix Scientific, cat# 012223] and DIEA (24 µL, 0.13 mmol) in 2 mL of NMP (heated in a microwave at 150° C. for 30 min) $^1$H NMR (400 MHz, DMSO-$d_6$) δ ppm 12.08 (1H, br.), 8.51 (1H, d, J=4.5 Hz), 7.89 (1H, d, J=7.4 Hz), 7.77 (1H, m), 7.62 (2H, m), 7.55 (1H, d, J=7.8 Hz), 7.33 (1H, m), 7.21 (1H, m), 7.00 (1H, br.), 6.90 (1H, d, J=2.0 Hz), 5.31 (1H, t, J=7.1 Hz), 3.47 (2H, m), 3.11 (2H, m), 2.70 (3H, s), 1.69 (3H, d, J=7.0 Hz). m/z (EST, +ve) 399.0 (M+H)$^+$.

Example 322

2-(2-methyl-3-((1-(pyrazin-2-yl)ethyl)amino)quinoxalin-5-yl)-6,7-dihydro-1H-pyrrolo[3,2-c]pyridin-4(5H)-one

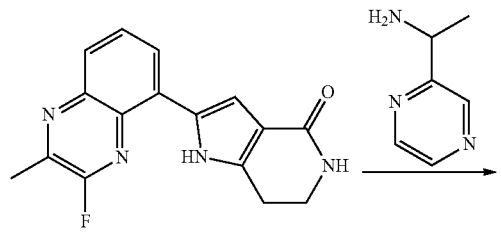

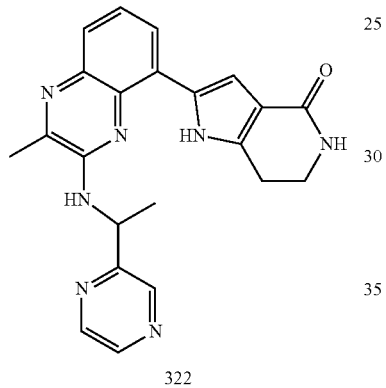

322

This compound (40 mg, 55% yield) as a yellow crystalline solid was prepared according the procedures described for Example 318, using 2-(3-fluoro-2-methylquinoxalin-5-yl)-6,7-dihydro-1H-pyrrolo[3,2-c]pyridin-4(5H)-one (126) (54 mg, 0.18 mmol), 1-(pyrazin-2-yl)ethanamine (45 mg, 0.36 mmol) (Essen Scientific LLC, cat # ES10-0543) and DIEA (64 µL, 0.36 mmol) in 2 mL of DMSO (heated in a microwave at 165° C. for 45 min). $^1$H NMR (400 MHz, DMSO-$d_6$) δ ppm 11.81 (1H, br.), 8.87 (1H, m), 8.59 (1H, m), 8.50 (1H, d, J=2.5 Hz), 7.87 (1H, d, J=7.2 Hz), 7.67 (1H, d, J=7.0 Hz), 7.57 (1H, d, J=7.4 Hz), 7.32 (1H, t, J=7.8 Hz), 6.99 (1H, br.), 6.90 (1H, d, J=2.2 Hz), 5.41 (1H, m), 3.48 (2H, m), 3.03 (2H, m), 2.68 (3H, s), 1.74 (3H, d, J=7.0 Hz). m/z (ESI, +ve) 400.1 (M+H)$^+$.

Example 323

2-(2-methyl-3-((1-(pyrimidin-4-yl)ethyl)amino)quinoxalin-5-yl)-6,7-dihydro-1H-pyrrolo[3,2-c]pyridin-4(5H)-one

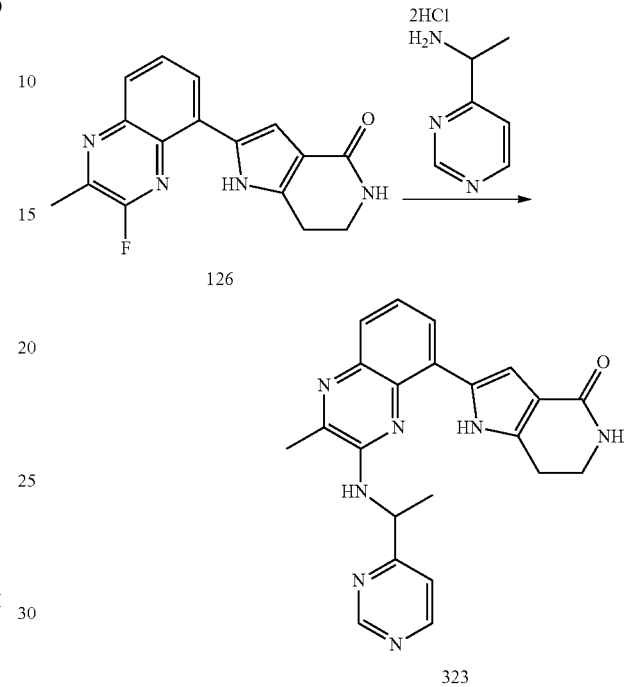

This compound (41 mg, 56% yield) as a yellow crystalline solid was prepared according the procedures described for Example 318, using 2-(3-fluoro-2-methylquinoxalin-5-yl)-6,7-dihydro-1H-pyrrolo[3,2-c]pyridin-4(5H)-one (126) (55 mg, 0.19 mmol), (1-(pyrimidin-4-yl)ethanamine dihydrochloride (73 mg, 0.37 mmol) (ChemBridge Corporation) and DIEA (0.26 mL, 1.48 mmol) in 2 mL of DMSO (heated in a microwave at 160° C. for 30 min) $^1$H NMR (400 MHz, DMSO-$d_6$) δ ppm 11.73 (1H, br.), 9.15 (1H, s), 8.69 (1H, d, J=5.1 Hz), 7.87 (1H, d, J=7.2 Hz), 7.67 (2H, d, J=4.3 Hz), 7.57 (1H, d, J=8.0 Hz), 7.32 (1H, t, J=7.7 Hz), 6.99 (1H, br.), 6.87 (1H, s), 5.27 (1H, m), 3.48 (2H, m), 3.06 (2H, m), 2.69 (3H, s), 1.69 (3H, d, J=6.8 Hz). m/z (ESI, +ve) 400.1 (M+H)$^+$.

Example 324

2'-(3-(tert-butylamino)-2-methyl-5-quinoxalinyl)-1'H-spiro[cyclopropane-1,6'-pyrrolo[3,4-b]pyrrol]-4'(5'H)-one

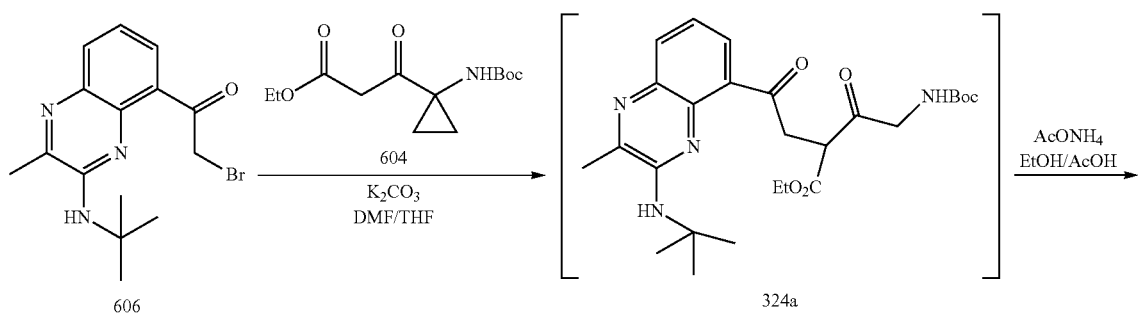

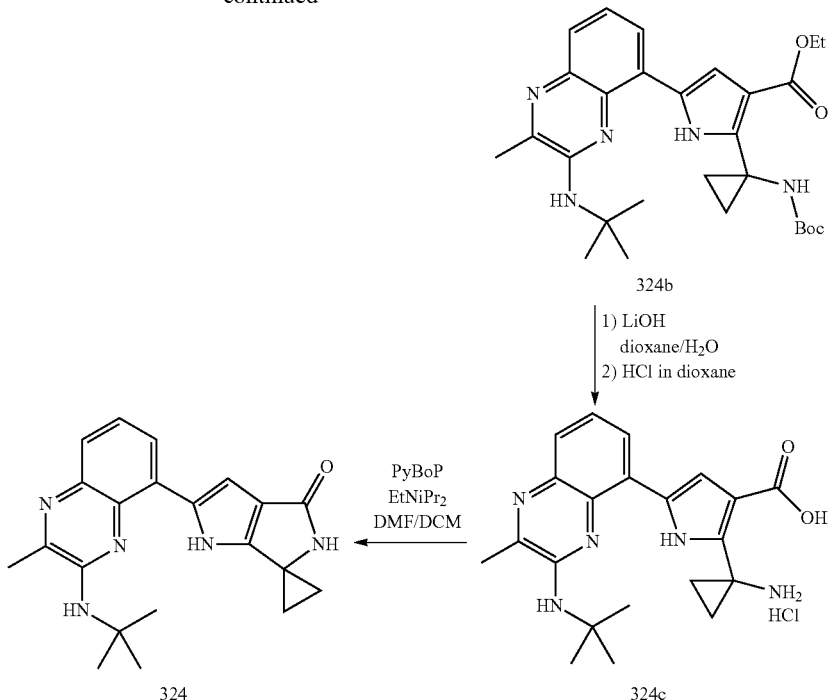

Preparation of ethyl 2-(1-((tert-butoxycarbonyl)amino)cyclopropyl)-5-(3-(tert-butylamino)-2-methylquinoxalin-5-yl)-1H-pyrrole-3-carboxylate (324b)

At RT, a mixture of 2-bromo-1-(3-(tert-butylamino)-2-methylquinoxalin-5-yl)ethanone (606) (1.01 g, 3.00 mmol) and ethyl 3-(1-((tert-butoxycarbonyl)amino)cyclopropyl)-3-oxopropanoate (604) (0.978 g, 3.60 mmol) in 5 mL of THF and 5 mL of DMF was treated with K$_2$CO$_3$ (1.04 g, 7.51 mmol). After the reaction mixture was stirred at RT for 18 h, it was diluted with 100 mL of EtOAc and filtered. The filtrate was washed with sat. NH$_4$Cl (2×15 mL) followed by brine (10 mL), and concentrated. The crude material was purified by silica gel chromatography (25-50% EtOAc in hexanes) to afford ethyl 2-(1-((tert-butoxycarbonyl)amino)cyclopropanecarbonyl)-4-(3-(tert-butylamino)-2-methylquinoxalin-5-yl)-4-oxobutanoate as a yellow amorphous solid (324a). m/z (ESI, +ve) 527.3 (M+H)$^+$. In a glass tube, a solution of ethyl 2-(1-((tert-butoxycarbonyl)amino)cyclopropanecarbonyl)-4-(3-(tert-butylamino)-2-methylquinoxalin-5-yl)-4-oxobutanoate as a yellow amorphous solid (324a) in 5 mL of EtOH and 2.5 mL of AcOH was treated with NH$_4$OAc (1.39 g, 18.02 mmol). The glass tube was sealed, and heated in an oil bath at 55° C. for 8 h. The reaction mixture was concentrated to half of its volume. The residue was diluted with 150 mL of EtOAc and washed sequentially with 15 mL of water, 10 mL of 0.5 N NaOH and 10 mL of brine. The organic layer was dried over anhydrous Na$_2$SO$_4$, filtered and concentrated. The crude material was purified by silica gel chromatography (25-50% EtOAc in hexanes) to provide ethyl 2-(1-((tert-butoxycarbonyl)amino)cyclopropyl)-5-(3-(tert-butylamino)-2-methylquinoxalin-5-yl)-1H-pyrrole-3-carboxylate (1.4 g, 2.76 mmol, 92% yield) as a yellow amorphous solid. $^1$H NMR (400 MHz, DMSO-d$_6$) δ ppm 11.21 (1H, br.), 7.87 (1H, d, J=7.2 Hz), 7.61 (1H, dd, J=8.0, 1.4 Hz), 7.40 (1H, d, J=2.7 Hz), 7.35 (1H, t, J=7.8 Hz), 6.92 (1H, br.), 5.90 (1H, s), 4.25 (2H, q, J=7.1 Hz), 2.56 (3H, s), 1.58 (9H, s), 1.26-1.39 (14H, m), 1.13 (2H, m). m/z (ESI, +ve) 508.3 (M+H)$^+$.

Preparation of Example 324

A solution of ethyl 2-(1-((tert-butoxycarbonyl)amino)cyclopropyl)-5-(3-(tert-butylamino)-2-methylquinoxalin-5-yl)-1H-pyrrole-3-carboxylate (324b) (1.1 g, 2.16 mmol) in 8 mL of dioxane and 8 mL of water was added LiOH monohydrate (0.45 g, 10.83 mmol) and heated in an oil bath at 110° C. for 18 h. It was concentrated under reduced pressure to half of its volume. The remaining mixture was lyophilized for 24 h to give a yellow solid. m/z (ESI, +ve) 480.2 (M+H)$^+$. To the yellow solid suspended in 5 mL of dioxane at 0° C. was treated with 10 mL of 4 N HCl in dioxane. The resulting orange mixture was stirred at RT for 3 h. The mixture was concentrated to half of its volume. The insoluble solid was filtered, rinsed with 2×5 mL of ether. The filtrate was discarded. The orange solid was dried in a vacuum oven at 40° C. for 1 h to give 2-(1-aminocyclopropyl)-5-(3-(tert-butylamino)-2-methylquinoxalin-5-yl)-1H-pyrrole-3-carboxylic acid hydrochloride (324c), which was used as crude material and based on theoretical yield. m/z (ESI, +ve) 380.2 (M+H)$^+$. A suspension of the above obtained 2-(1-aminocyclopropyl)-5-(3-(tert-butylamino)-2-methylquinoxalin-5-yl)-1H-pyrrole-3-carboxylic acid hydrochloride (324c) in 12 mL of DMF and 12 mL of DCM was treated with DIEA (2.25 mL, 12.93 mmol) followed by (benzotriazol-1-yloxy)tripyrrolidinophosphonium hexafluorophosphate (1.40 g, 2.70 mmol). The resulting homogeneous solution was stirred at RT for 2 h. It was diluted with 200 mL of DCM, washed sequentially with 25 mL of water, 25 mL of 1 N NaOH and 25 mL of brine. The organic solution was concentrated and the residue was purified on a silica gel column (50% EtOAc in hexanes followed by 1-3% MeOH in EtOAc) to give 2'-(3-(tert-butylamino)-2-methylquinoxalin-5-yl)-1'H-spiro[cyclopropane-1,6'-pyrrolo[3,4-b]pyrrol]-4'(5'H)-one (324) (540 mg, 1.494 mmol, 69% yield) as a yellow crystalline solid. $^1$H NMR (400 MHz, DMSO-d$_6$) δ ppm 11.64 (1H, br.), 7.78 (1H, d, J=6.5 Hz), 7.67 (1H, s), 7.60 (1H, m), 7.35 (1H, t, J=7.8 Hz), 6.90 (1H, m), 6.00 (1H, s), 2.56 (3H, s), 1.52 (9H, s), 1.42 (2H, m), 1.33 (2H, m). m/z (ESI, +ve) 362.1 (M+H)$^+$.

Example 325

2'-(3-(cyclopropylamino)-2-methyl-5-quinoxalinyl)-1'H-spiro[cyclopropane-1,6'-pyrrolo[3,4-b]pyrrol]-4'(5'H)-one

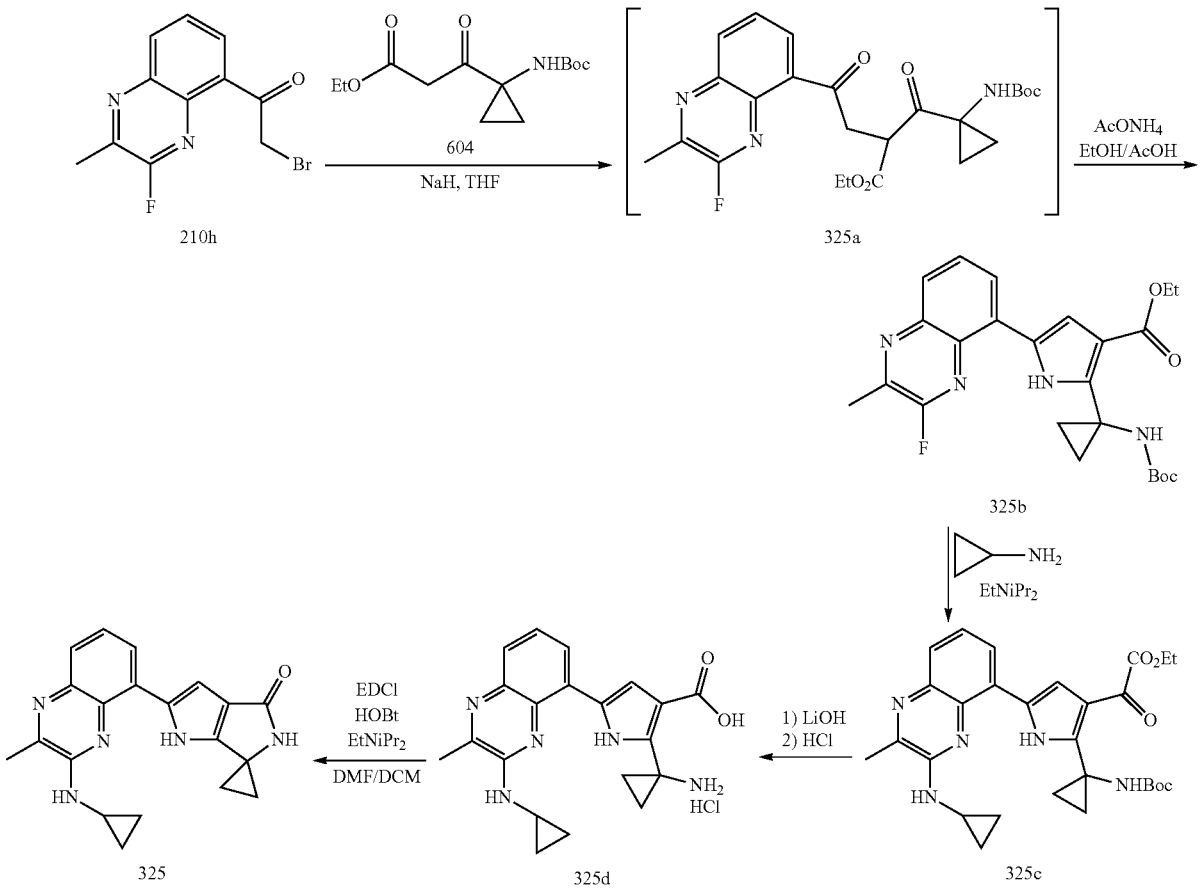

Preparation of ethyl 2-(1-((tert-butoxycarbonyl)amino)cyclopropyl)-5-(3-fluoro-2-methylquinoxalin-5-yl)-1H-pyrrole-3-carboxylate (325b)

At 0° C., a solution of ethyl 3-(1-((tert-butoxycarbonyl)amino)cyclopropyl)-3-oxopropanoate (604; 1.53 g, 5.64 mmol) in 20 mL of THF was treated with NaH (60% dispersion in mineral oil, 0.56 g, 14.10 mmol) and stirred at 0° C. for 1 h. A solution of 2-bromo-1-(3-fluoro-2-methylquinoxalin-5-yl)ethanone (210h; 1.75 g, 6.20 mmol) in 10 mL of THF was added drop wise and the mixture stirred at 0° C. for 4 h. The solvents were removed under reduced pressure. The brown residue (325a: m/z (ESI, +ve) 496.5 (M+Na)$^+$) was cooled in an ice bath and dissolved in EtOH/AcOH (1:1, 30 mL), and NH$_4$OAc (1.91 g, 24.81 mmol) was added. Ice bath was removed and the mixture was stirred at RT for 18 h. It was concentrated to half of its volume. The yellow residue was treated with 20 mL of water and extracted with 3×50 mL of EtOAc. The organic extracts were washed with 10 mL of sat NaHCO$_3$ and 10 mL of brine, dried and concentrated. LCMS indicated a mixture of 60% of m/z (ESI, +ve) 496.5 (M+Na)$^+$; and 40% of the desired m/z (ESI, +ve) 455.1 (M+H)$^+$. The brown residue was purified on a silica gel column (25-45% EtOAc in hexanes) to give: first eluting compound, ethyl 2-(1-((tert-butoxycarbonyl)amino)cyclopropyl)-5-(3-fluoro-2-methylquinoxalin-5-yl)-1H-pyrrole-3-carboxylate (325b) (870 mg, 1.91 mmol, 34% yield) as a yellow amorphous solid, m/z (ESI, +ve) 455.1 (M+H)$^+$; and second eluting compound, ethyl 2-(1-((tert-butoxycarbonyl)amino)cyclopropanecarbonyl)-4-(3-fluoro-2-methylquinoxalin-5-yl)-4-oxobutanoate (325a, 1.06 g) as a yellow amorphous solid, m/z (ESI, +ve) 496.5 (M+Na)$^+$. To a solution ethyl 2-(1-((tert-butoxycarbonyl)amino)cyclopropanecarbonyl)-4-(3-fluoro-2-methylquinoxalin-5-yl)-4-oxobutanoate (325a, 1.06 g, 2.2 mmol) in 5 mL of EtOH and HOAc (0.3 mL, 5.1 mmol) in a glass tube at RT was added NH$_4$OAc (1.02 g, 13.2 mmol). The glass tube was sealed and stirred at RT for 2 h. Additional NH$_4$OAc (500 mg, 6.6 mmol) was added to the mixture and stirring was continued for 18 h. The insoluble solid was filtered, rinsed with 2×25 mL of EtOAc. The filtrate was concentrated. The yellow residue was treated with 20 mL of water and extracted with 3×50 mL of EtOAc. The organic extracts were washed with 10 mL of sat NaHCO$_3$ and 10 mL of brine, dried and concentrated. The residue was purified on a silica gel column (25-45% EtOAc in hexanes) to give ethyl 2-(1-((tert-butoxycarbonyl)amino)cyclopropyl)-5-(3-fluoro-2-methylquinoxalin-5-yl)-1H-pyrrole-3-carboxylate (325b) (218 mg) as a yellow amorphous solid, m/z (ESI, +ve) 455.1 (M+H)$^+$.

Preparation of ethyl 2-(1-((tert-butoxycarbonyl)
amino)cyclopropyl)-5-(3-(cyclopropylamino)-2-me-
thylquinoxalin-5-yl)-1H-pyrrole-3-carboxylate
(325c)

A solution of ethyl 2-(1-((tert-butoxycarbonyl)amino)cyclopropyl)-5-(3-fluoro-2-methylquinoxalin-5-yl)-1H-pyrrole-3-carboxylate (325b) (218 mg, 0.480 mmol), cyclopropanamine (82 mg, 1.44 mmol) and DIEA (0.17 mL, 0.96 mmol) in 3 mL of DMSO was heated in an oil bath at 80° C. for 5 h. It was diluted with 50 mL of EtOAc, washed with 5 mL of water. The organic solution was concentrated and the residue was stirred in 5 mL of ether. The insoluble yellow solid was filtered, rinsed with 2×2 mL of ether to give 133 mg of ethyl 2-(1-((tert-butoxycarbonyl)amino)cyclopropyl)-5-(3-(cyclopropylamino)-2-methylquinoxalin-5-yl)-1H-pyrrole-3-carboxylate, as a yellow crystalline solid. The filtrate was concentrated and the residue was purified on a silica gel column (25-70% EtOAc in Hexanes) to give 67 mg ethyl 2-(1-((tert-butoxycarbonyl)amino)cyclopropyl)-5-(3-(cyclopropylamino)-2-methylquinoxalin-5-yl)-1H-pyrrole-3-carboxylate. $^1$H NMR (400 MHz, DMSO-d$_6$) δ ppm 12.31 (1H, br.), 8.05 (1H, m), 7.61 (1H, dd, J=8.0, 1.2 Hz), 7.42 (1H, d, J=3.5 Hz), 7.35 (1H, t, J=7.8 Hz), 7.26 (1H, br.), 7.02 (2H, br.), 4.28 (2H, q, J=7.0 Hz), 2.56 (3H, s), 1.35 (4H, m), 1.32 (9H, s), 1.03-1.19 (5H, m), 0.63-0.78 (2H, m). m/z (ESI, +ve) 492.2 (M+H)$^+$.

Preparation of Example 325

A solution of ethyl 2-(1-((tert-butoxycarbonyl)amino)cyclopropyl)-5-(3-(cyclopropylamino)-2-methylquinoxalin-5-yl)-1H-pyrrole-3-carboxylate (325c; 190 mg, 0.39 mmol) in 2 mL of dioxane and 1.5 mL of water was added LiOH hydrate (81 mg, 1.93 mmol) and heated in a microwave at 110° C. for 80 min. It was lyophilized to give a yellow solid. m/z (ESI, +ve) 464.1 (M+H)$^+$. To the yellow solid suspended in 3 mL of dioxane was added 3 mL of 4 N HCl in dioxane and stirred at RT for 1.5 h. The reaction mixture was concentrated to half of its volume. The insoluble solid was filtered, rinsed with 2×3 mL of hexanes/ether in 1/1 ratio. The filtrate was discarded. The orange solid was dried in a vacuum oven at RT for 18 h to 2-(1-aminocyclopropyl)-5-(3-(cyclopropylamino)-2-methylquinoxalin-5-yl)-1H-pyrrole-3-carboxylic acid hydrochloride (325d). m/z (ESI, +ve) 364.1 (M+H)$^+$. This material was used as crude. At 0° C., a suspension of 2-(1-aminocyclopropyl)-5-(3-(cyclopropylamino)-2-methylquinoxalin-5-yl)-1H-pyrrole-3-carboxylic acid hydrochloride (325d) in 8 mL of DMF and 8 mL of DCM was sequentially treated with 1-(3-dimethylaminopropyl)-3-ethylcarbodiimide hydrochloride (146 mg, 0.76 mmol), 1-hydroxybenzotriazole (103 mg, 0.76 mmol) and DIEA (0.40 mL, 2.28 mmol). The homogeneous reaction mixture was stirred at RT for 18 h. It was diluted with 100 mL of DCM, washed sequentially with 5 mL of water, 5 mL of 1 N NaOH, and 5 mL of brine, dried over Na$_2$SO$_4$, and concentrated. The residue was purified by silica gel chromatography (50-100% EtOAc in DCM followed by 1-5% MeOH in DCM) to give 2'-(3-(cyclopropylamino)-2-methylquinoxalin-5-yl)-1'H-spiro[cyclopropane-1,6'-pyrrolo[3,4-b]pyrrol]-4'(5'H)-one (325) (86 mg, 60% yield) as a yellow crystalline solid. $^1$H NMR (400 MHz, DMSO-d$_6$) δ ppm 12.31 (1H, br.), 7.97 (1H, dd, J=7.5, 1.3 Hz), 7.69 (1H, s), 7.62 (1H, dd, J=8.0, 1.2 Hz), 7.51 (1H, d, J=2.2 Hz), 7.38 (1H, t, J=7.8 Hz), 7.19 (1H, d, J=1.4 Hz), 2.94 (1H, dd, J=6.5, 3.7 Hz), 2.53 (3H, s), 1.45 (2H, m), 1.35 (2H, m), 0.817 (2H, m), 0.68 (2H, m). m/z (ESI, +ve) 346.1 (M+H)$^+$.

Examples 326

(6R)-2-(3-(tert-butylamino)-2-methyl-5-quinoxalinyl)-6-methyl-5,6-dihydropyrrolo[3,4-b]pyrrol-4(1H)-one; and 327: (6S)-2-(3-(tert-butylamino)-2-methyl-5-quinoxalinyl)-6-methyl-5,6-dihydropyrrolo[3,4-b]pyrrol-4(1H)-one

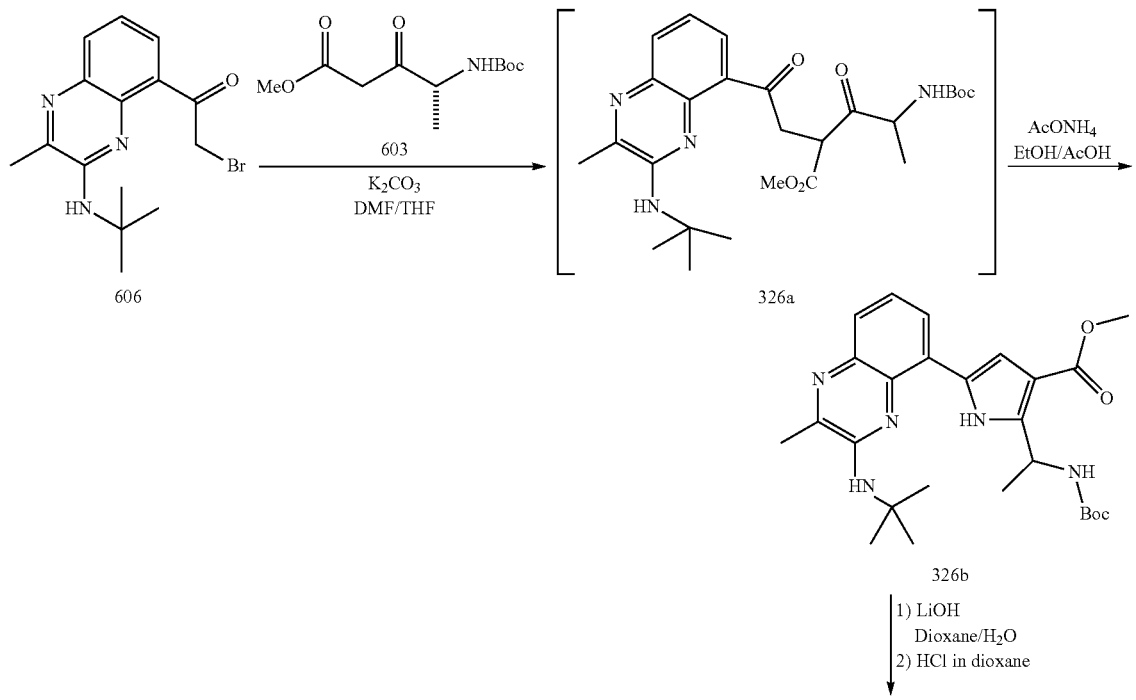

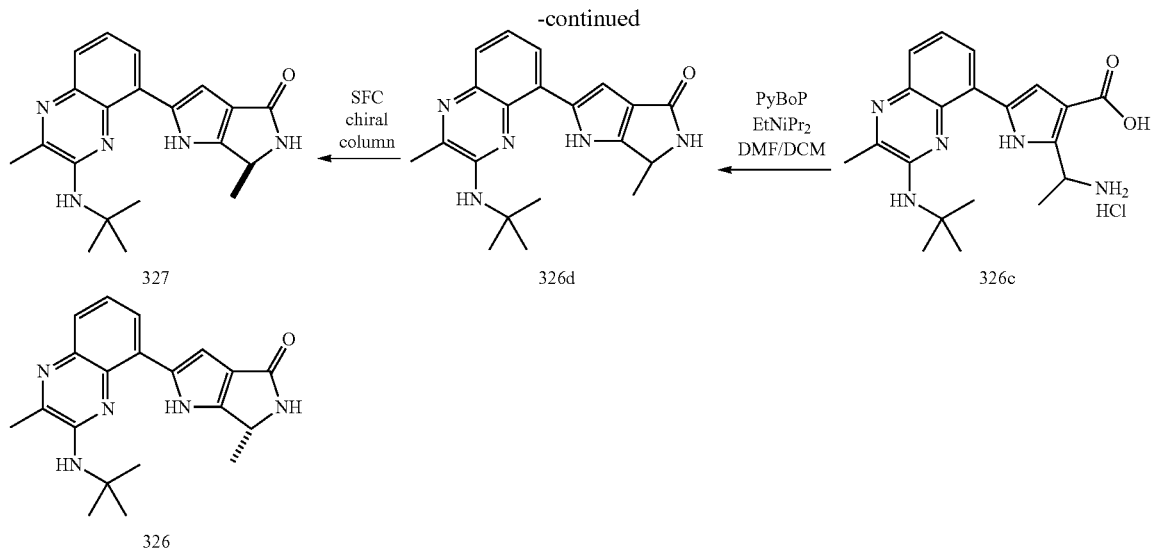

Preparation of methyl 2-(1-((tert-butoxycarbonyl)amino)ethyl)-5-(3-(tert-butylamino)-2-methylquinoxalin-5-yl)-1H-pyrrole-3-carboxylate (326b)

At RT, a solution of (R)-methyl 4-((tert-butoxycarbonyl)amino)-3-oxopentanoate (603) (5.38 g, 21.95 mmol) in 20 mL of THF and 20 mL of DMF was treated with 2-bromo-1-(3-(tert-butylamino)-2-methylquinoxalin-5-yl)ethanone (606) (5.44 g, 16.18 mmol) and $K_2CO_3$ (5.59 g, 40.4 mmol) and stirred at RT for 6 h. It was diluted with 250 mL of EtOAc, filtered through a flitted funnel, rinsed with 2×15 mL of EtOAc. The filtrate was washed with sat $NH_4Cl$ (2×25 mL) followed by brine (15 mL). The organic solution was dried over $Na_2SO_4$ and concentrated. The residue was passed through a short column (35-75% EtOAc in hexanes) to get rid of the solvent front peaks and the base line peaks. Fractions with m/z (ESI, +ve) 501.2 (M+H)[1] were collected and concentrated to give methyl 4-((tert-butoxycarbonyl)amino)-2-(2-(3-(tert-butylamino)-2-methylquinoxalin-5-yl)-2-oxoethyl)-3-oxopentanoate (326a) as a brown residue. To the brown residue in a glass tube in 25 mL of EtOH and 10 mL of HOAc was added $NH_4OAc$ (8.46 g, 110 mmol). The tube was sealed and heated in an oil bath at 50° C. for 8 h. The mixture was concentrated to half of its volume, diluted with 250 mL of EtOAc, washed sequentially with 15 mL of water, 15 mL of 1 N NaOH and 5 mL of brine. The organic solution was concentrated and the residue was purified on a silica gel column (eluted with a gradient of 35-65% EtOAc in hexanes) to give methyl 2-(1-((tert-butoxycarbonyl)amino)ethyl)-5-(3-(tert-butylamino)-2-methylquinoxalin-5-yl)-1H-pyrrole-3-carboxylate (326b) (6.3 g, 71% yield) as a yellow amorphous. $^1H$ NMR (400 MHz, DMSO-$d_6$) δ ppm 11.42 (1H, br.), 7.76 (1H, dd, J=7.4, 1.2 Hz), 7.63 (1H, dd, J=8.0, 1.2 Hz), 7.38 (2H, m), 7.03 (1H, d, J=7.8 Hz), 5.94 (1H, s), 5.44 (1H, m), 3.77 (3H, s), 2.56 (3H, s), 1.58 (9H, s), 1.40 (12H, m). m/z (ESI, +ve) 482.1 (M+H)$^+$.

Preparation of 2-(1-aminoethyl)-5-(3-(tert-butylamino)-2-methylquinoxalin-5-yl)-1H-pyrrole-3-carboxylic acid hydrochloride (326c)

A mixture of ethyl 2-(1-((tert-butoxycarbonyl)amino)ethyl)-5-(3-(tert-butylamino)-2-methylquinoxalin-5-yl)-1H-pyrrole-3-carboxylate (326b) (6.30 g, 12.71 mmol) and LiOH hydrated (2.67 g, 63.6 mmol) in dioxane (24 mL) and water (24 mL) was heated in an oil bath at 100° C. for 10 h. The reaction mixture was concentrated to half of its volume. The remaining mixture was lyophilized for 24 h to give a yellow solid. The yellow solid suspended in 15 mL of dioxane at 0° C. was treated with 35 mL of 4 N HCl in dioxane. The resulting orange mixture was stirred at RT for 2 h. The mixture was concentrated to half of its volume. The insoluble solid was filtered, rinsed with 2×10 mL of ether. The filtrate was discarded. The orange solid was dried in a vacuum oven at 40° C. for 1 h to give 2-(1-aminoethyl)-5-(3-(tert-butylamino)-2-methylquinoxalin-5-yl)-1H-pyrrole-3-carboxylic acid hydrochloride (326c), which was used as crude material and based on theoretical yield. m/z (ESI, +ve) 368.1 (M+H)$^+$.

Preparation of Examples 326 and 327

To a mixture of 2-(1-aminoethyl)-5-(3-(tert-butylamino)-2-methylquinoxalin-5-yl)-1H-pyrrole-3-carboxylic acid hydrochloride (326c) (⅔ of the crude material from previous step, estimated to be 9.4 mmol) in 30 mL of DMF and 25 mL of DCM at 0° C. was added DIEA (0.98 mL, 56.4 mmol) and (benzotriazol-1-yloxy)tripyrrolidinophosphonium hexafluorophosphate (Sigma-Aldrich Chemical Company, Inc.) (6.11 g, 11.75 mmol). The resulting homogeneous solution was stirred at RT for 8 h. It was diluted with 300 mL of DCM, washed sequentially with 15 mL of water, 2×10 mL of 1 N NaOH, and 10 mL of brine. The organic solution was concentrated and the residue was purified on a silica gel column (eluted with a gradient of 1-5% MeOH in DCM) to provide a brown amorphous solid containing 2-(3-(tert-butylamino)-2-methylquinoxalin-5-yl)-6-methyl-5,6-dihydropyrrolo[3,4-b]pyrrolo-4(1H)-one (326d), m/z (ESI, +ve) 350.0 (M+H)$^+$; and a significant amount of undesired side product, tri(pyrrolidin-1-yl)phosphine oxide, m/z (ESI, +ve) 258.0 (M+H)$^+$. The individual enantiomers of Example 326d were obtained by chiral SFC (Column: Chiralcel OJH (250×20 mm, 5µ); Mobile Phase: 85:15 (A:B); A: Liquid $CO_2$; B: MeOH (20 mM $NH_3$); Flow Rate: 70 mL/min; Oven Temp: 40° C.; Inlet Pressure: 100 bar; Wavelength: 278 nm) to give Example 326 (first eluting product) and Example 327 (second eluting product). Example 326: (6R)-2-(3-(tert-butylamino)-2-methyl-5- quinoxalinyl)-6-methyl-5,6-dihydropyrrolo[3,4-b]pyrrol-4 (1H)-one (810 mg, 25% yield, >99% ee) as a yellow crystalline solid was obtained. $^1$H NMR (400 MHz, DMSO-$d_6$) δ ppm 12.00 (1H, br.), 7.83 (1H, dd, J=7.4, 1.2 Hz), 7.64 (2H, m), 7.37 (1H, t, J=7.7 Hz), 6.85 (1H, d, J=1.4 Hz), 6.02 (1H, s), 4.57 (1H, q, J=6.6 Hz), 2.58 (3H, s), 1.56 (9H, s), 1.40 (3H, d, J=6.7 Hz). m/z (ESI, +ve) 350.0 (M+H)$^+$. Example 327: (6S)-2-(3-(tert-butylamino)-2-methyl-5-quinoxalinyl)-6-methyl-5,6-dihydropyrrolo[3,4-b]pyrrol-4(1H)-one (85 mg, 2.6% yield, >99% ee) as a brown crystalline solid was obtained. m/z (ESI, +ve) 350.0 (M+H)$^+$.

Example 329

2'-(2-methyl-3-((1-methylcyclopropyl)amino)-5-quinoxalinyl)-1'H-spiro[cyclopropane-1,6'-pyrrolo[3,4-b]pyrrol]-4'(5'H)-one cedures described for Intermediate 324b, using 2-bromo-1-(2-methyl-3-((1-methylcyclopropyl)amino)quinoxalin-5-yl) ethanone (611) (810 mg, 2.42 mmol), ethyl 3-(1-((tert-butoxycarbonyl)amino)cyclopropyl)-3-oxopropanoate (604) (789 mg, 2.91 mmol) as the starting materials, followed by the subsequent treatment of the resulting 329a (m/z (ESI, +ve) 525.2 (M+H)$^+$) with NH$_4$OAc (1.12 g, 14.54 mmol) in 3 mL of EtOH and 1.5 mL of HOAc at 50° C. for 4 h. m/z (ESI, +ve) 506.1 (M+H)$^+$.

Preparation of Example 329

Ethyl 2-(1-((tert-butoxycarbonyl)amino)cyclopropyl)-5-(2-methyl-3-((1-methylcyclopropyl)amino)quinoxalin-5-yl)-1H-pyrrole-3-carboxylate (329b) (925 mg, 1.829 mmol) was converted to 2-(1-aminocyclopropyl)-5-(2-methyl-3-((1-methylcyclopropyl)amino)quinoxalin-5-yl)-1H-pyrrole-3-carboxylic acid hydrochloride (329c: m/z (ESI, +ve) 378.1

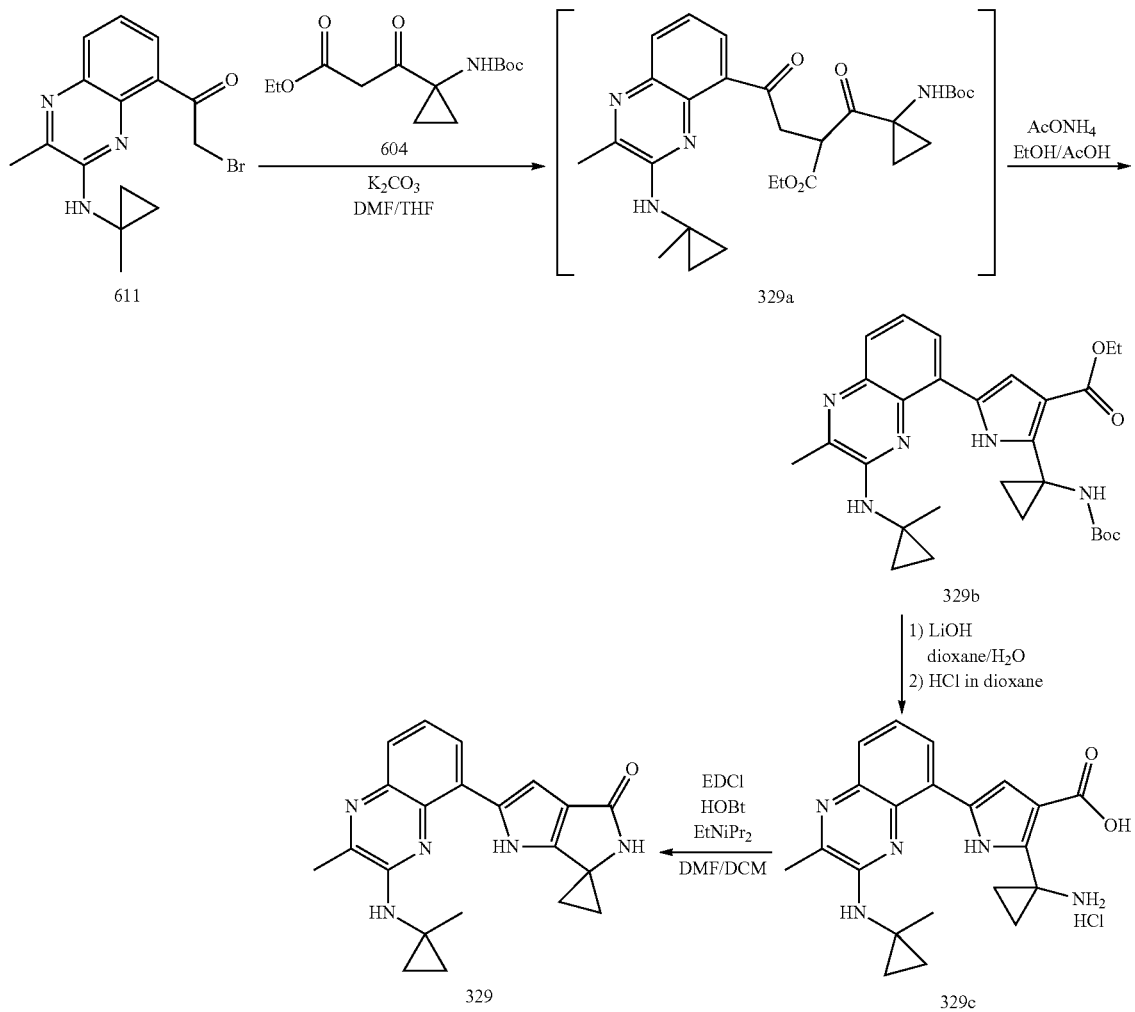

Preparation of ethyl 2-(1-((tert-butoxycarbonyl) amino)cyclopropyl)-5-(2-methyl-3-((1-methylcyclopropyl)amino)quinoxalin-5-yl)-1H-pyrrole-3-carboxylate (329b)

This compound (930 mg, 1.84 mmol, 76% yield) as a yellow amorphous solid was prepared according to the pro- (M+H)+) in a fashion similar to that described for Intermediate 324c. This material was used as crude. At RT, to a suspension of 2-(1-aminocyclopropyl)-5-(2-methyl-3-((1-methylcyclopropyl)amino)-quinoxalin-5-yl)-1H-pyrrole-3-carboxylic acid hydrochloride (329c) in 10 mL of DMF and 10 mL of DCM was sequentially added 1-(3-dimethylaminopropyl)-3-ethylcarbodiimide hydrochloride (619 mg, 3.23 mmol), 1-hydroxybenzotriazole (436 mg, 3.23 mmol) and DIEA (1.77 mL, 10.20 mmol). The homogeneous reaction mixture was stirred at RT for 18 h. It was diluted with 80 mL of DCM, washed sequentially with 5 mL of water, 5 mL of 1 N NaOH and 5 mL of brine, dried over $Na_2SO_4$, and concentrated. The residue was purified by silica gel chromatography (50-100% EtOAc in DCM followed by 1-5% MeOH in DCM) twice to give 2'-(2-methyl-3-((1-methylcyclopropyl)amino)quinoxalin-5-yl)-1'H-spiro[cyclopropane-1,6'-pyrrolo[3,4-b]pyrrol]-4'(5'H)-one (329) (192 mg, 30% yield) as a yellow crystalline solid. $^1$H NMR (400 MHz, DMSO-$d_6$) δ ppm 12.28 (1H, br.), 8.00 (1H, d, J=7.4 Hz), 7.73 (1H, s), 7.54-7.68 (2H, m), 7.36 (1H, t, J=7.8 Hz), 7.22 (1H, s), 2.52 (3H, s), 1.50 (3H, s), 1.48 (2H, m), 1.31 (2H, m), 0.94 (2H, m), 0.74 (2H, m). m/z (ESI, +ve) 360.2 $(M+H)^+$.

Example 330

2'-(6-Fluoro-3-(isopropylamino)-2-methylquinoxalin-5-yl)-1'H-spiro[cyclopropane-1,6'-pyrrolo[3,4-b]pyrrol]-4'(5'H)-one Preparation of ethyl 2-(1-((tert-butoxycarbonyl)amino)cyclopropyl)-5-(6-fluoro-3-(isopropylamino)-2-methylquinoxalin-5-yl)-1H-pyrrole-3-carboxylate (330b)

This compound (1.07 g, 85% yield) as a yellow amorphous solid was prepared according to the procedures described for Intermediate 324b, using 2-bromo-1-(6-fluoro-3-(isopropylamino)-2-methylquinoxalin-5-yl)ethanone (619) (840 mg, 2.47 mmol), ethyl 3-(1-((tert-butoxycarbonyl)amino)cyclopropyl)-3-oxopropanoate (604) (804 mg, 2.96 mmol) as the starting materials, followed by the subsequent treatment of the resulting 330a (m/z (ESI, +ve) 531.2 $(M+H)^+$) with $NH_4OAc$ (952 mg, 12.35 mmol) in 3 mL of EtOH and 1.5 mL of HOAc at 50° C. for 4 h. m/z (ESI, +ve) 512.2 $(M+H)^+$.

Preparation of Example 330

Ethyl 2-(1-((tert-butoxycarbonyl)amino)cyclopropyl)-5-(6-fluoro-3-(isopropylamino)-2-methylquinoxalin-5-yl)-1H-pyrrole-3-carboxylate (330b) (1.0 g, 1.95 mmol) was converted to 2-(1-aminocyclopropyl)-5-(6-fluoro-3-(isopro-

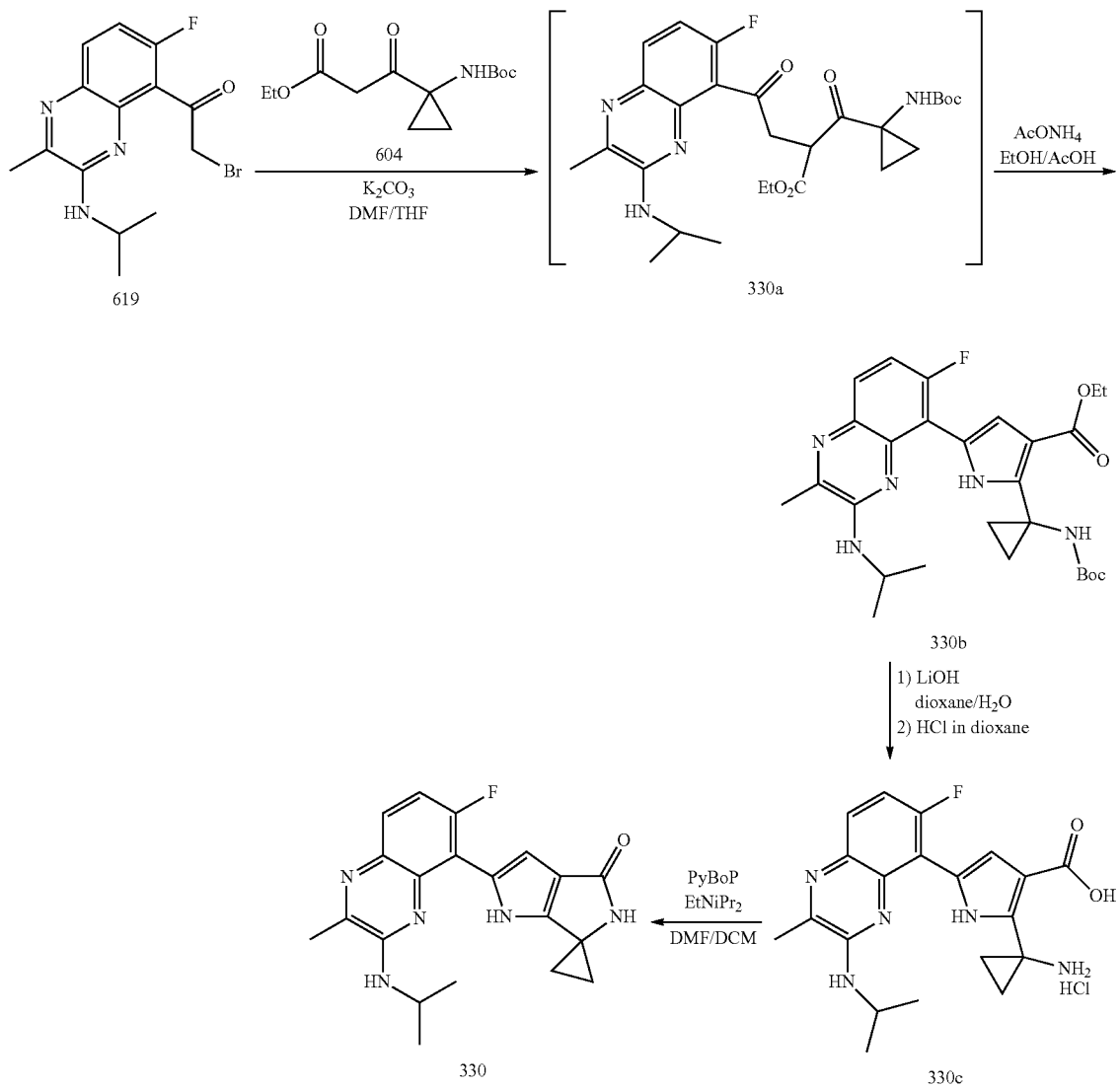

pylamino)-2-methylquinoxalin-5-yl)-1H-pyrrole-3-carboxylic acid hydrochloride (330c: m/z (ESI, +ve) 384.1 (M+H)$^+$) in a fashion similar to that described for Intermediate 324c. This material was used as crude. A suspension of 2-(1-aminocyclopropyl)-5-(6-fluoro-3-(isopropylamino)-2-methylquinoxalin-5-yl)-1H-pyrrole-3-carboxylic acid hydrochloride (330c) (798 mg, 1.9 mmol) in DMF (10 mL) and DCM (10 mL) at 0° C. was treated with DIEA (1.98 mL, 11.40 mmol) followed by (benzotriazol-1-yloxy)tripyrrolidinophosphonium hexafluorophosphate (1.29 g, 2.47 mmol). The ice bath was removed and the resulting mixture was stirred at RT for 1 h. The mixture was poured onto 150 G of ice. The insoluble brown solid was filtered, rinsed with 2×5 mL of water followed by 3×10 mL of DCM. The solid was collected, dried in a vacuum oven at 45° C. for 1 h to give 425 mg of 2'-(6-fluoro-3-(isopropylamino)-2-methylquinoxalin-5-yl)-1'H-spiro[cyclopropane-1,6'-pyrrolo[3,4-b]pyrrol]-4'(5'H)-one (330) as a yellow crystalline solid. The filtrate was transferred to a separatory funnel, extracted with 50 mL of DCM. The organic layer was washed with 10 mL of 1 N NaOH followed by 10 mL of brine, dried over Na$_2$SO$_4$ and concentrated. The residue was stirred in 50 mL of EtOAc for 30 min. The insoluble yellow crystalline solid was filtered to give additional 165 mg of 2'-(6-fluoro-3-(isopropylamino)-2-methylquinoxalin-5-yl)-1'H-spiro[cyclopropane-1,6'-pyrrolo[3,4-b]pyrrol]-4'(5'H)-one (330). $^1$H NMR (400 MHz, DMSO-d$_6$) δ ppm 12.12 (1H, br.), 7.68 (2H, m), 7.29 (1H, m), 7.02 (1H, br.), 6.73 (1H, s), 4.26 (1H, m), 2.52 (3H, s) 11.40 (4H, m), 1.29 (6H, m). $^{19}$F NMR (377 MHz, DMSO-d$_6$) δ ppm −110.86. m/z (ESI, +ve) 366.2 (M+H)$^+$.

Example 331

2'-(3-((2,2-difluoroethyl)amino)-2-methylquinoxalin-5-yl)-1'H-spiro[cyclopropane-1,6'-pyrrolo[3,4-b]pyrrol]-4'(5'H)-one

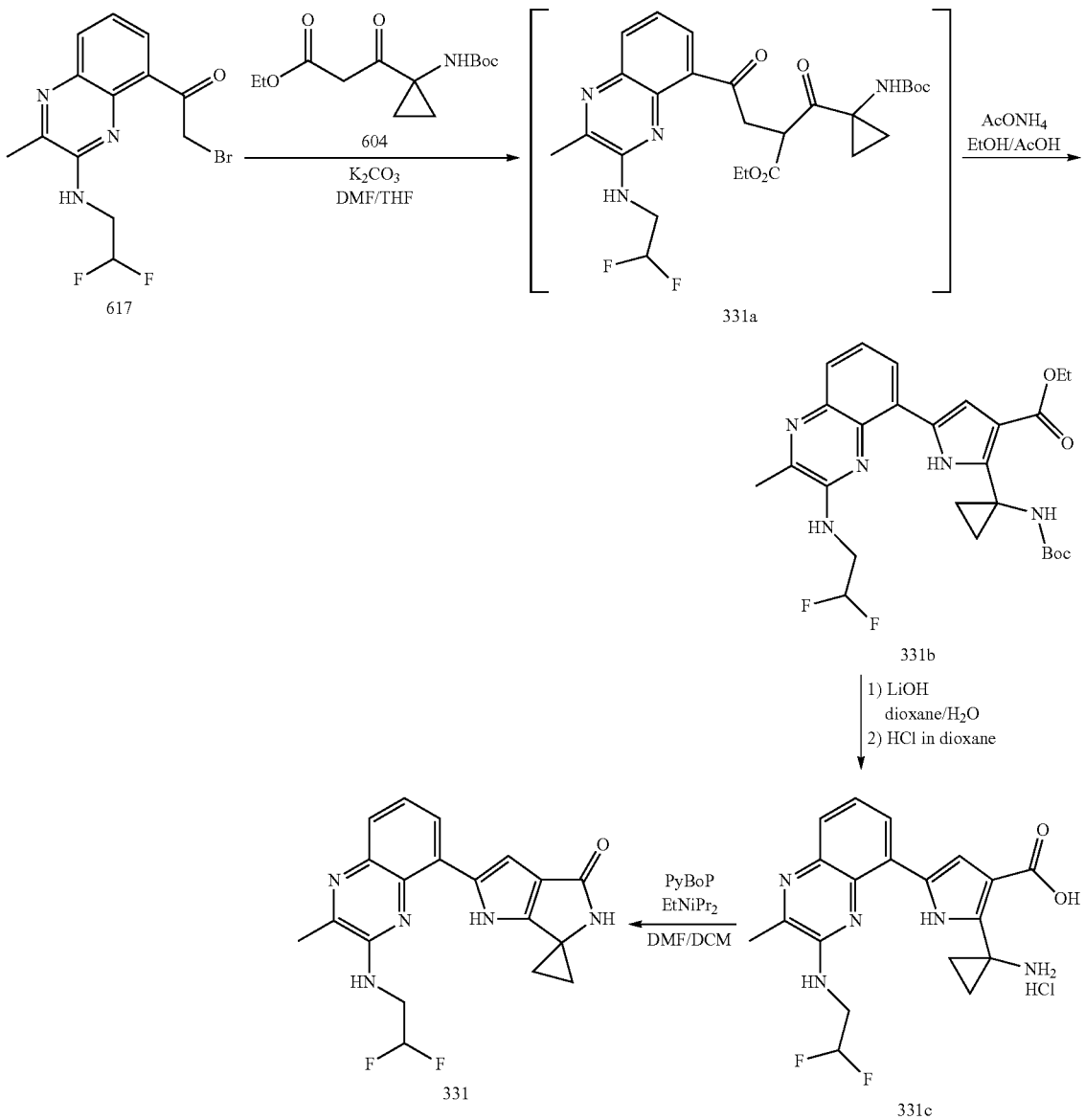

Preparation of ethyl 2-(1-((tert-butoxycarbonyl) amino)cyclopropyl)-5-(3-((2,2-difluoroethyl)amino)-2-methylquinoxalin-5-yl)-1H-pyrrole-3-carboxylate (331b)

This compound (0.40 g, 41% yield) as a yellow amorphous solid was prepared according to the procedures described for Intermediate 324b, using 2-bromo-1-(34(2,2-difluoroethyl)amino)-2-methylquinoxalin-5-yl)ethanone (617) (583 mg, 2.26 mmol), ethyl 3-(1-((tert-butoxycarbonyl)amino)cyclopropyl)-3-oxopropanoate (604) (650 mg, 1.89 mmol) as the starting materials, followed by the subsequent treatment of the resulting 331a (m/z (ESI, +ve) 535.2 (M+H)$^+$) with NH$_4$OAc (728 mg, 9.44 mmol) in 3 mL of EtOH and 1.5 mL of HOAc at 50° C. for 4 h. m/z (ESI, +ve) 516.2 (M+H)$^+$.

Preparation of Example 331

Ethyl 2-(1-((tert-butoxycarbonyl)amino)cyclopropyl)-5-(34(2,2-difluoroethyl)amino)-2-methylquinoxalin-5-yl)-1H-pyrrole-3-carboxylate (331b) (378 mg, 0.73 mmol) was converted to 2-(1-aminocyclopropyl)-5-(3-((2,2-difluoroethyl)amino)-2-methylquinoxalin-5-yl)-1H-pyrrole-3-carboxylic acid hydrochloride (331c: m/z (ESI, +ve) 388.1 (M+H)$^+$) in a fashion similar to that described for Intermediate 324c. This material was used as crude. A suspension of 2-(1-aminocyclopropyl)-5-(3-((2,2-difluoroethyl)amino)-2-methylquinoxalin-5-yl)-1H-pyrrole-3-carboxylic acid hydrochloride (331c) in DMF (5 mL) and DCM (5 mL) at 0° C. was treated with DIEA (0.76 mL, 4.38 mmol) followed by (benzotriazol-1-yloxy)tripyrrolidinophosphonium hexafluorophosphate (456 mg, 0.87 mmol). The ice bath was removed and the resulting mixture was stirred at RT for 18 h. It was treated with 20 G of ice, the yellow solid was filtered, washed sequentially with 5 mL of water, 5 mL of 0.5 N NaOH, 5 mL of water and 2×5 mL of DCM. The yellow solid was dried in a vacuum oven at 45° C. for 5 h to give 2'-(3-((2,2-difluoroethyl)amino)-2-methylquinoxalin-5-yl)-1'H-spiro[cyclopropane-1,6'-pyrrolo[3,4-b]pyrrol]-4'(5'H)-one (331) (179 mg, 0.48 mmol, 66% yield). $^1$H NMR (400 MHz, DMSO-d$_6$) δ ppm 11.59 (1H, br.), 7.83 (1H, d, J=8.0 Hz), 7.65 (2H, m), 7.58 (1H, br.), 7.40 (1H, t, J=7.5 Hz), 6.85 (1H, s), 6.43 (0.25; H, m), 6.29 (0.5; H, m), 6.14 (0.25; H, m), 3.92 (2H, m), 2.57 (3H, s), 1.42 (2H, m), 1.38 (2H, m). $^{19}$F NMR (376 MHz, DMSO-d$_6$) δ ppm −120.48. m/z (ESI, +ve) 370.1 (M+H)$^+$.

Example 332

(6R)-2-(3-(tert-butylamino)-2-methyl-5-quinoxalinyl)-6-methyl-5,6-dihydropyrrolo[3,4-b]pyrrole-4(1H)-thione A mixture of (R)-2-(3-(tert-butylamino)-2-methylquinoxalin-5-yl)-6-methyl-5,6-dihydropyrrolo[3,4-b]pyrrolo-4(1H)-one (326) (25 mg, 0.072 mmol), Lawesson's reagent (35 mg, 0.086 mmol) in dioxane (2 mL) was heated at 90° C. in a microwave for 60 min. The reaction mixture was directly loaded onto a silica gel column and eluted with 100% EtOAc to give a brown amorphous solid that contained about 92% pure of m/z (ESI, +ve) 366.2 (M+H)$^+$. The brown amorphous solid was stirred in 2 mL of ether and 2 mL of hexanes. The precipitated solid was filtered and dried in a vacuum oven at 45° C. for 1 h to give the title compound (16 mg, 61% yield) as a brown crystalline solid. $^1$H NMR (400 MHz, DMSO-d$_6$) δ ppm 12.09 (1H, br.), 9.84 (1H, s), 7.83 (1H, dd, J=7.5, 1.3 Hz), 7.64 (1H, m), 7.37 (1H, t, J=7.7 Hz), 6.98 (1H, d, J=1.6 Hz), 6.02 (1H, s), 4.79 (1H, q, J=7.0 Hz), 2.58 (3H, s), 1.56 (9H, s), 1.45 (3H, d, J=6.8 Hz). m/z (ESI, +ve) 366.2 (M+H)$^+$.

Examples 333

(6R)-6-methyl-2-(2-methyl-3-((1-methylcyclopropyl)amino)-5-quinoxalinyl)-5,6-dihydropyrrolo[3,4-b]pyrrol-4(1H)-one; and 328: (6S)-6-methyl-2-(2-methyl-3-((1-methylcyclopropyl)amino)-5-quinoxalinyl)-5,6-dihydropyrrolo[3,4-b]pyrrol-4(1H)-one

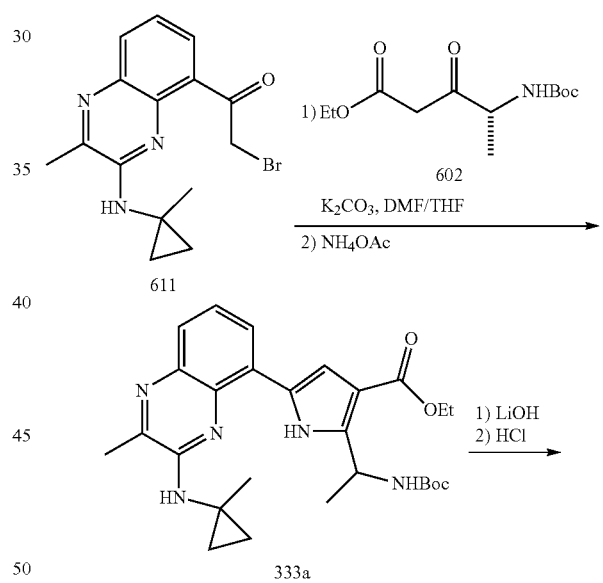

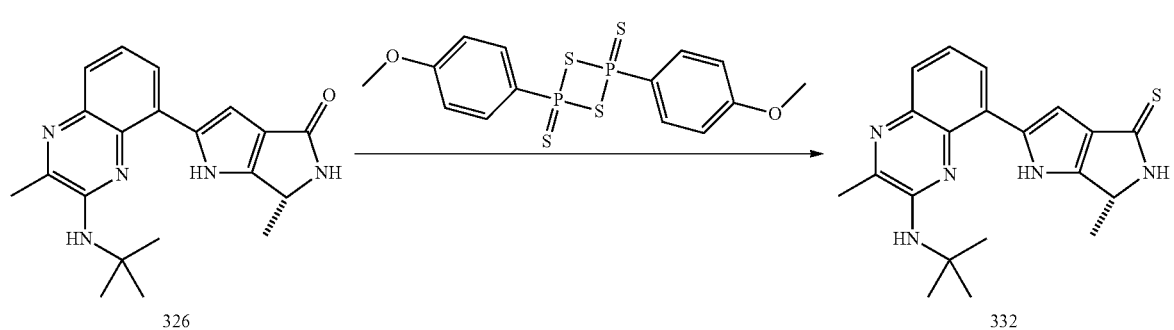

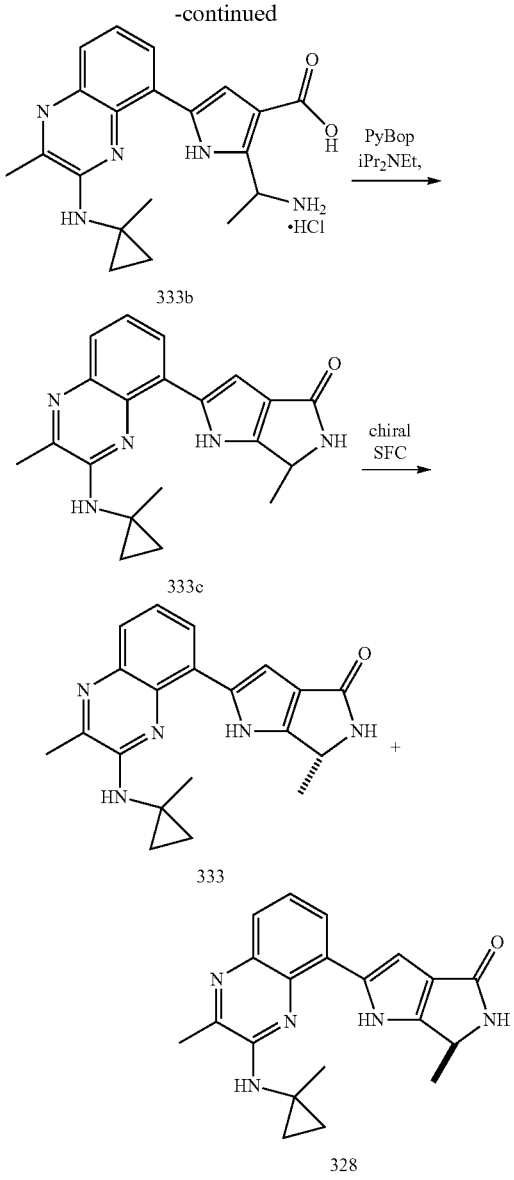

Preparation of ethyl 2-(1-((tert-butoxycarbonyl)amino)ethyl)-5-(2-methyl-3-((1-methylcyclopropyl)amino)-5-quinoxalinyl)-1H-pyrrole-3-carboxylate (333a)

To a 1000 mL round bottomed flask was added 2-bromo-1-(2-methyl-3-((1-methylcyclopropyl)amino)-5-quinoxalinyl)ethanone (611) (14.6 g, 43.7 mmol), DMF (35 mL), THF (35 mL), ethyl (4R)-4-((tert-butoxycarbonyl)amino)-3-oxopentanoate (602) (13.7 g, 52.7 mmol) and $K_2CO_3$ (15.1 g, 109 mmol). The mixture was stirred at RT. After 4 h, the mixture was diluted with sat $NaHCO_3$ and extracted with EtOAc (3×100 mL). The combined extracts were washed with water (2×100 mL) and brine (100 mL) and then dried ($Na_2SO_4$) and concentrated to afford ethyl (4S)-4-((tert-butoxycarbonyl)amino)-2-(2-(2-methyl-3-((1-methylcyclopropyl)amino)-5-quinoxalinyl)-2-oxoethyl)-3-oxopentanoate as a brown amorphous solid which was used without further purification. m/z (ESI, +ve) 513.2 (M+H)$^+$. The brown amorphous solid was treated with EtOH (80 mL), AcOH (8.0 mL), and finally $NH_4OAc$ (10.1 g, 131 mmol). The mixture was stirred at RT for 12 h. The solution was partially concentrated and then was diluted with sat $NaHCO_3$ and EtOAc. The phases were separated and the organic phase was washed with water, dried ($Na_2SO_4$) and concentrated onto silica. Purification by silica gel chromatography (half of the material was purified on a Redisep Gold 330 g column, 0-50% EtOAc/hexanes and the other half on an Interchim 300 g column, 25 micron, 10 to 35% isocratic at 35% EtOAc/Hex) afforded ethyl 2-(1-((tert-butoxycarbonyl)amino)ethyl)-5-(2-methyl-3-((1-methylcyclopropyl)amino)-5-quinoxalinyl)-1H-pyrrole-3-carboxylate (6.96 g, 14.1 mmol, 32% yield) as a yellow solid. $^1$H NMR (400 MHz, DMSO-d$_6$) δ ppm 11.72 (br s., 1H), 7.87-7.96 (m, 2H), 7.59 (dd, J=8.0, 1.2 Hz, 1H), 7.47 (s, 1H), 7.33-7.40 (m, 1H), 7.06 (d, J=7.0 Hz, 1H), 5.32-5.45 (m, 1H), 4.17-4.28 (m, 2H), 2.47 (s, 3H), 1.57 (s, 3H), 1.32-1.44 (m, 12H), 1.28 (t, J=7.0 Hz, 3H), 0.91-1.05 (m, 2H), 0.80-0.91 (m, 2H). m/z (ESI, +ve) 494.1 (M+H)$^+$.

Preparation of Example 333

(6R)-6-methyl-2-(2-methyl-3-((1-methylcyclopropyl)amino)-5-quinoxalinyl)-5,6-dihydropyrrolo[3,4-b]pyrrol-4(1H)-one; and Example 328: (6S)-6-methyl-2-(2-methyl-3-((1-methylcyclopropyl)amino)-5-quinoxalinyl)-5,6-dihydropyrrolo[3,4-b]pyrrol-4(1H)-one To a 250 mL round bottomed flask was added ethyl 2-((1S)-1-(((tert-butoxycarbonyl)amino)ethyl)-5-(2-methyl-3-((1-methylcyclopropyl)amino)-5-quinoxalinyl)-1H-pyrrole-3-carboxylate (333a) (6.96 g, 14.1 mmol), dioxane (40 mL), water (40 mL) and LiOH (1.69 g, 70.5 mmol). The mixture was stirred and heated at 110° C. for 19 h. The solution was cooled to RT and then concentrated on the rotovap to afford 2-(1-((tert-butoxycarbonyl)amino)ethyl)-5-(2-methyl-3-((1-methylcyclopropyl)amino)-5-quinoxalinyl)-1H-pyrrole-3-carboxylic acid a tan solid which was used in the next step without further purification. m/z (ESI, +ve) 466.2 (M+H)$^+$. The resulting material was treated with 1,4-dioxane (30 mL) and hydrogen chloride (4 M in 1,4-dioxane, 80 mL, 320 mmol) (Sigma-Aldrich). The solution was stirred at rt for 30 min and then concentrated on the rotovap to afford 2-(1-aminoethyl)-5-(2-methyl-3-((1-methylcyclopropyl)amino)-5-quinoxalinyl)-1H-pyrrole-3-carboxylic acid (333b) which was used in the next step without further purification. m/z (ESI, +ve) 349.1 (M-NH$_2$)$^+$. To the 2-(1-aminoethyl)-5-(2-methyl-3-((1-methylcyclopropyl)amino)-5-quinoxalinyl)-1H-pyrrole-3-carboxylic acid (333b) in a 250 mL round-bottomed flask was added DCM (40 mL), DMF (40 mL), and DIEA (7.80 mL, 44.9 mmol). The mixture was cooled to 0° C. and benzotriazol-1-yloxytripyrrolidinophosphonium hexafluorophosphate (PyBop, 8.56 g, 16.5 mmol) (Matrix Innovation) was added. The solution was stirred at 0° C. for 40 min and then poured into sat $NaHCO_3$ (200 mL) and extracted with EtOAc (3×200 mL). The combined extracts were washed with water (3×200 mL), and brine (100 mL) and then dried ($Na_2SO_4$) and concentrated onto silica. Purification by silica gel chromatography (0-4% MeOH in $CH_2Cl_2$) afforded 6-methyl-2-(2-methyl-3-((1-methylcyclopropyl)amino)-5-quinoxalinyl)-5,6-dihydropyrrolo[3,4-b]pyrrol-4(1H)-one (333c) as a yellow solid. m/z (ESI, +ve) 348.0 (M+H)$^+$. The yellow solid (333c) was subjected to chiral preparative SFC purification (Column: Chiral Technologies, Inc., Chiralpak, AD-H (5 μm, 21 mm×25 cm). Eluent: 70% carbon dioxide and 30% organic modifier (MeOH with 20 mM NH$_3$). Flow=60 mL/min, temperature=40° C., pressure=100 bar, detection wavelength=278 nm. Sample was dissolved in 45 mL DCM/MeOH (1:1), 0.8 mL per injection). Two peaks were collected: Peak 1: ee of peak 1 >99.5%, Peak 2: ee of peak 2 >99.5%. Peak 1 was concentrated to afford (6R)-6-methyl-2-(2-methyl-3-((1-methylcyclopropyl) amino)-5-quinoxalinyl)-5,6-dihydropyrrolo[3,4-b]pyrrol-4 (1H)-one (333) (1.26 g, 3.63 mmol, 24% yield) as a yellow solid. $^1$H NMR (400 MHz, DMSO-$d_6$) δ ppm 13.04 (s, 1H), 8.03 (dd, J=7.6, 1.2 Hz, 1H), 7.73 (br s, 2H), 7.59 (dd, J=8.0, 1.2 Hz, 1H), 7.35 (t, J=7.8 Hz, 1H), 7.05 (d, J=1.2 Hz, 1H), 4.66 (q, J=6.5 Hz, 1H), 2.49 (s, 3H) 1.54 (s, 3H), 1.38 (d, J=6.7 Hz, 3H), 0.92-1.02 (m, 2H), 0.84-0.92 (m, 2H). m/z (ESI, +ve) 348.0 (M+H)$^+$. Peak 2 was concentrated to afford (6R)-6-methyl-2-(2-methyl-3((1-methylcyclopropyl) amino)-5-quinoxalinyl)-5,6-dihydropyrrolo[3,4-b]pyrrolo-4 (1H)-one (328) (105 mg, 0.30 mmol, 2% yield) as a yellow solid. $^1$H NMR (400 MHz, DMSO-$d_6$) δ ppm 13.04 (s, 1H), 8.03 (dd, J=7.6, 1.2 Hz, 1H), 7.73 (br s, 2H), 7.59 (dd, J=8.0, 1.2 Hz, 1H), 7.35 (t, J=7.8 Hz, 1H), 7.05 (d, J=1.2 Hz, 1H), 4.66 (q, J=6.5 Hz, 1H), 2.49 (s, 3H) 1.54 (s, 3H), 1.38 (d, J=6.7 Hz, 3H), 0.92-1.02 (m, 2H), 0.84-0.92 (m, 2H). m/z (ESI, +ve) 348.0 (M+H)$^+$.

Example 334

2-(3-(tert-Butylamino)-2-methyl-5-quinoxalinyl)-5,6-dihydropyrrolo[3,4-b]pyrrol-4(1H)-one Preparation of ethyl 2-(((tert-butoxycarbonyl)amino) methyl)-5-(3-(tert-butylamino)-2-methylquinoxalin-5-yl)-1H-pyrrole-3-carboxylate (334b)

To a 25-mL round-bottomed flask was added ethyl 4-((tert-butoxycarbonyl)amino)-3-oxobutanoate (601) (0.47 g, 1.91 mmol), $K_2CO_3$ (0.41 g, 2.97 mmol), 2-bromo-1-(3-(tert-butylamino)-2-methylquinoxalin-5-yl)ethanone (606) (0.40 g, 1.19 mmol), THF (3 mL), and EtOH (3 mL). The reaction mixture was stirred at RT for 16 h. The reaction mixture was diluted with sat $NH_4Cl$ (5 mL) and extracted with EtOAc (10 mL). The organic extract was washed with water (5 mL), dried over $Na_2SO_4$ and concentrated. Ethyl 4-((tert-butoxycarbonyl)amino)-2-(2-(3-(tert-butylamino)-2-methylquinoxalin-5-yl)-2-oxoethyl)-3-oxobutanoate (334a) was obtained as a light yellow oil and used without further purification. m/z (ESI, +ve) 501.3 (M+H)$^+$. To a 15-mL glass tube was added ethyl 4-((tert-butoxycarbonyl)amino)-2-(2-(3-(tert-butylamino)-2-methylquinoxalin-5-yl)-2-oxoethyl)-3-oxobutanoate (334a), crude from previous step, $NH_4OAc$ (0.36 g, 4.71 mmol), EtOH (2 mL), and AcOH (1 mL). The tube was sealed and heated at 50° C. for 3 h. The reaction mixture was cooled to RT and was concentrated to half of its

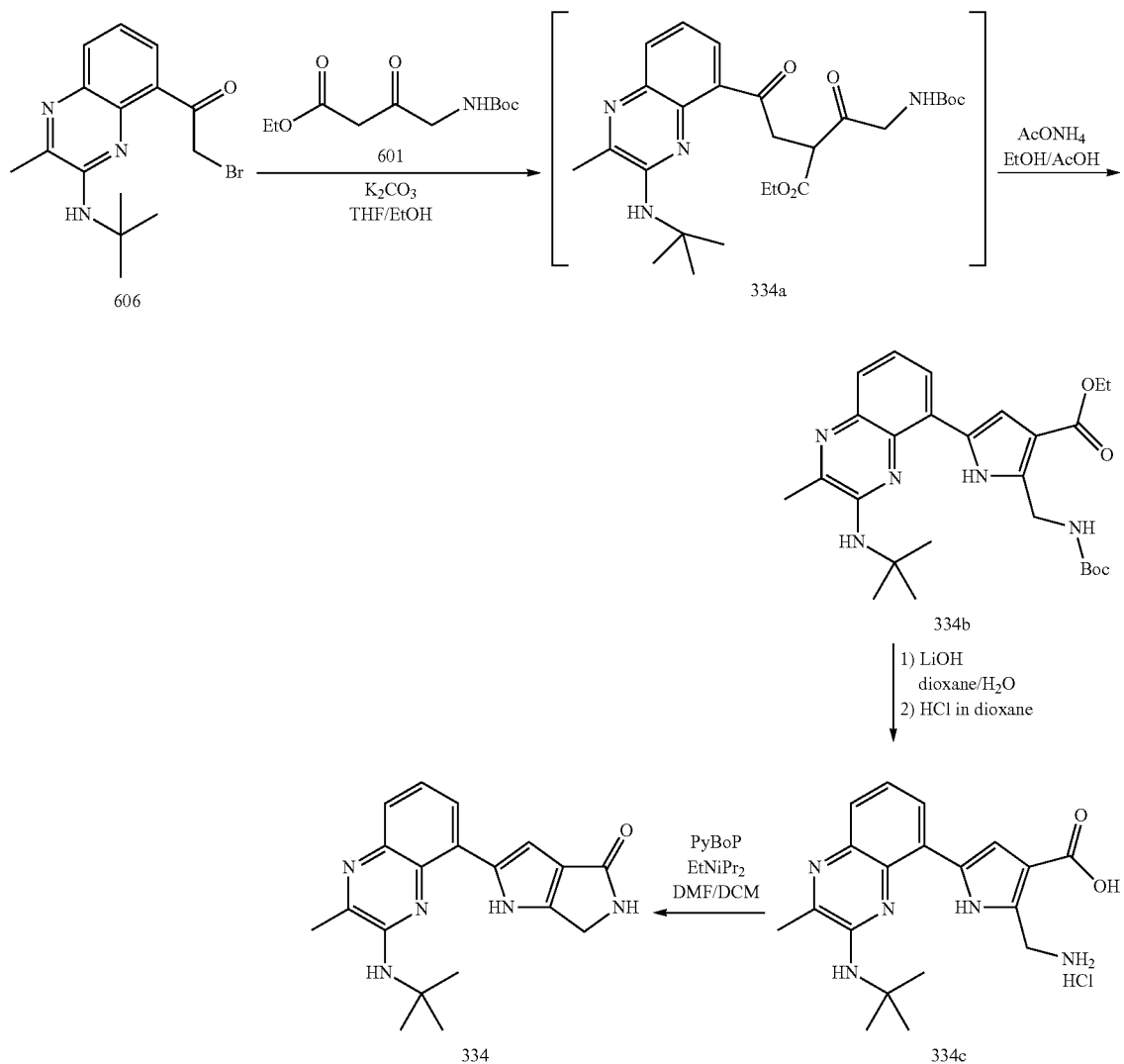

volume. The mixture was diluted with EtOAc (10 mL) and water (5 mL). The organic extract was washed with NaOH (1N, 5 mL), water (5 mL), brine (5 mL), dried over $Na_2SO_4$, and concentrated. The crude material was absorbed onto a plug of silica gel and purified by chromatography through a Redi-Sep pre-packed silica gel column (24 g), eluting with a gradient of 0% to 30% EtOAc in hexanes to give ethyl 2-(((tert-butoxycarbonyl)amino)methyl)-5-(3-(tert-butylamino)-2-methylquinoxalin-5-yl)-1H-pyrrole-3-carboxylate (334b) (0.33 g, 59% yield) as a yellow solid. $^1$H NMR (400 MHz, DMSO-$d_6$) δ 11.64 (br. s., 1H), 7.82 (dd, J=1.17, 7.43 Hz, 1H), 7.58-7.64 (m, 1H), 7.41 (d, J=2.74 Hz, 1H), 7.35 (s, 1H), 6.94 (br. s., 1H), 4.53 (d, J=5.28 Hz, 2H), 4.21 (q, J=7.04 Hz, 2H), 2.56 (s, 3H), 1.58 (s, 9H), 1.39 (s, 9H), 1.30 (t, J=7.10 Hz, 3H). m/z (ESI, +ve) 482.2 (M+H)$^+$.

Preparation of 2-(aminomethyl)-5-(3-(tert-butylamino)-2-methylquinoxalin-5-yl)-1H-pyrrole-3-carboxylic acid hydrochloride (334c)

A glass microwave reaction vessel was charged with ethyl 2-(((tert-butoxycarbonyl)amino)methyl)-5-(3-(tert-butylamino)-2-methylquinoxalin-5-yl)-1H-pyrrole-3-carboxylate (334b) (0.27 g, 0.56 mmol), LiOH hydrated (0.12 g, 2.82 mmol), dioxane (3 mL), and water (1 mL). The reaction mixture was stirred and heated in an Initiator microwave reactor (Personal Chemistry, Biotage AB, Inc., Uppsala, Sweden) at 110° C. for 3 h. The reaction mixture was acidified with HCl (1 N, 5 mL) and the orange solid obtained was filtered, washed with water, ether, and dried in a vacuum oven at 50° C. for 3 h. The orange solid was suspended in dioxane (2 mL), treated with HCl (2 mL of 4 N in dioxane), and stirred at RT for 4 h. The mixture was concentrated to half of its volume and the orange solid obtained was filtered, washed with ether and dried to give 2-(aminomethyl)-5-(3-(tert-butylamino)-2-methylquinoxalin-5-yl)-1H-pyrrole-3-carboxylic acid hydrochloride (334c), which was used as crude material and based on theoretical yield.

Preparation 2-(3-(tert-butylamino)-2-methylquinoxalin-5-yl)-5,6-dihydropyrrolo[3,4-b]pyrrol-4(1H)-one (334). To a 100-mL round-bottomed flask was added 2-(aminomethyl)-5-(3-(tert-butylamino)-2-methylquinoxalin-5-yl)-1H-pyrrole-3-carboxylic acid hydrochloride (334c) (0.21 g, 0.55 mmol), DCM (10 mL), DMF (10 mL), DIEA (0.29 mL, 1.65 mmol), and (benzotriazol-1-yloxy)tripyrrolidinophosphonium hexafluorophosphate (0.34 g, 0.66 mmol) (Sigma-Aldrich Chemical Company, Inc.). The reaction mixture was stirred at RT for 30 min, concentrated to half of its volume, and diluted with EtOAc (10 mL). The organic extract was washed with sat $NaHCO_3$ (5 mL), dried over $Na_2SO_4$, and concentrated. The crude material was absorbed onto a plug of silica gel and purified by chromatography through a Redi-Sep pre-packed silica gel column (12 g), eluted first with 30% EtOAc in hexanes, and then with a gradient of 0-4% 2 M $NH_3$/MeOH in DCM to provide 2-(3-(tert-butylamino)-2-methylquinoxalin-5-yl)-5,6-dihydropyrrolo[3,4-b]pyrrol-4 (1H)-one (334) (97 mg, 52% yield) as a yellow solid. $^1$H NMR (400 MHz, DMSO-$d_6$) δ 12.08 (br. s., 1H), 7.82 (d, J=7.24 Hz, 1H), 7.63 (d, J=8.02 Hz, 1H), 7.53 (s, 1H), 7.37 (t, J=7.73 Hz, 1H), 6.94 (s, 1H), 6.02 (s, 1H), 4.29 (s, 2H), 2.58 (s, 3H), 1.55 (s, 9H). m/z (ESI, +ve) 336.2 (M+H)$^+$.

Example 335

2-(2-Methyl-3-(((1-methylcyclopropyl)methyl)amino)-5-quinoxalinyl)-1,5,6,7-tetrahydro-4H-pyrrolo[3,2-c]pyridin-4-one

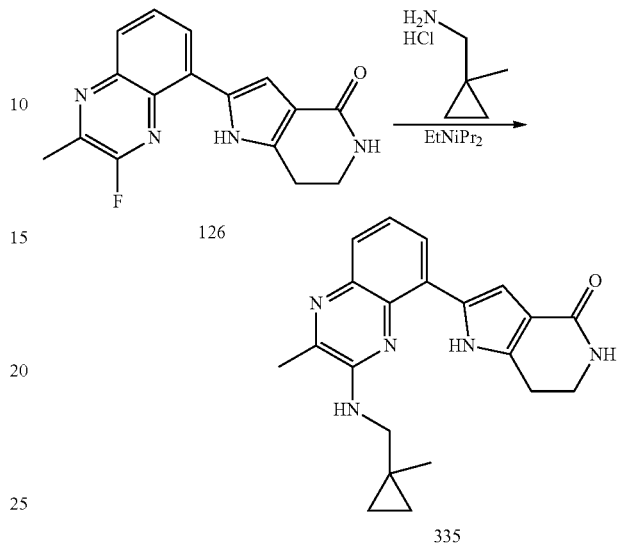

A solution of 2-(3-fluoro-2-methylquinoxalin-5-yl)-6,7-dihydro-1H-pyrrolo[3,2-c]pyridin-4(5H)-one (126) (46 mg, 0.16 mmol), (1-methylcyclopropyl)methanamine hydrochloride (37.8 mg, 0.310 mmol) (Princeton Bio, Princeton, N.J.), and DIEA (136 μL, 0.776 mmol) in DMSO (1.5 mL) was heated at 100° C. for 1.5 h. The crude product was diluted in DMSO (~20 mg/mL) and injected (3×1.0 mL) onto the Shimadzu preparatory LC (Phenomenex Gemini C18, 10 μm, 150×30 mm; 10-100% MeCN/water with 0.1% TFA); the pure fractions were combined, basicified with $NaHCO_3$ (saturated, aq.), extracted with DCM, separated, dried over $Na_2SO_4$, and concentrated via rotary evaporation to give 2-(2-methyl-3-(((1-methylcyclopropyl)methyl)amino)quinoxalin-5-yl)-6,7-dihydro-1H-pyrrolo[3,2-c]pyridin-4(5H)-one (335) (5 mg, 0.014 mmol, 9% yield). $^1$H NMR (400 MHz, DMSO-$d_6$) δ ppm 0.25-0.29 (m, 2H) 0.57-0.62 (m, 2H) 1.20 (s, 3H) 2.56 (s, 3H) 2.89 (t, J=6.75 Hz, 2H) 3.45 (td, J=6.75, 2.35 Hz, 2H) 3.57 (d, J=5.87 Hz, 2H) 6.97 (br. s., 1H) 7.14 (d, J=1.96 Hz, 1H) 7.19 (t, J=5.87 Hz, 1H) 7.32 (t, J=7.82 Hz, 1H) 7.57 (dd, J=8.02, 1.17 Hz, 1H) 7.87 (dd, J=7.53, 1.08 Hz, 1H) 12.04 (br. s., 1H). MS (ESI, pos. ion) m/z: 362.1 (M+1).

Example 336

2-(2-methyl-3-((2,2,2-trifluoroethyl)amino)-5-quinoxalinyl)-1,5,6,7-tetrahydro-4H-pyrrolo[3,2-c]pyridin-4-one

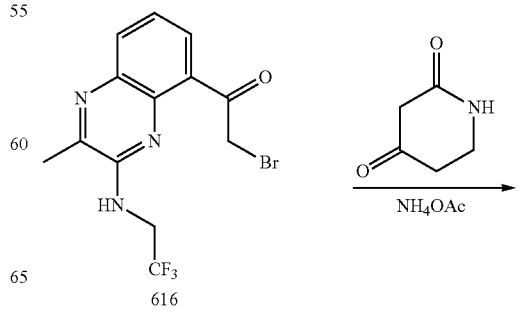

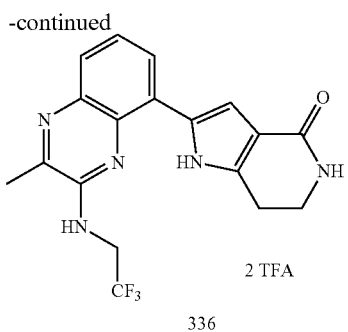

336

A solution of 2-bromo-1-(2-methyl-3-((2,2,2-trifluoroethyl)amino)quinoxalin-5-yl)ethanone (616) (40 mg, 0.11 mmol), piperidine-2,4-dione (Inogent, Hyderabad, India) (24.99 mg, 0.22 mmol), and NH₄OAc (42.6 mg, 0.55 mmol) in EtOH (1.1 mL) was stirred at 40° C. for 2.5 d. The crude product was adsorbed onto silica and was purified via automated flash chromatography (silica gel) with 100% DCM to 4% 2 M NH₃ in MeOH/DCM to give impure product. The crude product was dissolved in DMSO (~20 mg/mL) and injected (1×1.0 mL) onto the Shimadzu preparatory LC (Phenomenex Gemini C18, 10 μm, 150×30 mm; 10-100% MeCN/water with 0.1% TFA); the pure fraction was concentrated via rotary evaporation to give 2-(2-methyl-3-((2,2,2-trifluoroethyl)amino)quinoxalin-5-yl)-6,7-dihydro-1H-pyrrolo[3,2-c]pyridin-4(5H)-one (336) (4 mg, 6% yield) as a brick red solid. ¹H NMR (400 MHz, MeOH) δ ppm 2.66 (s, 3H) 2.99 (t, J=7.04 Hz, 2H) 3.65 (t, J=7.24 Hz, 2H) 4.38 (q, J=9.52 Hz, 2H) 7.09 (s, 1H) 7.48 (t, J=7.82 Hz, 1H) 7.70 (d, J=8.02 Hz, 1H) 7.98 (d, J=7.24 Hz, 1H) 11.98 (br. s., 1H). ¹⁹F NMR (377 MHz, MeOH) δ ppm −77.59 (br. s., 6F) −72.18 (s, 3F). MS (ESI, pos. ion) m/z: 376.1 (M+1).

Example 337

2-(3-ethoxy-5-quinoxalinyl)-1,5,6,7-tetrahydro-4H-pyrrolo[3,2-c]pyridin-4-one

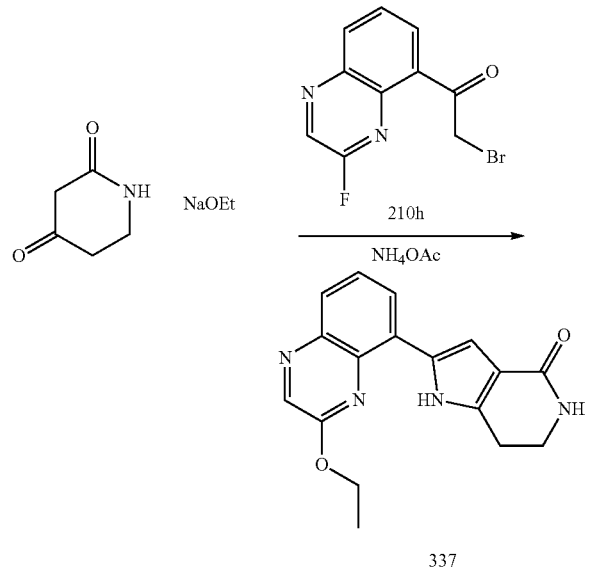

Sodium ethanolate in EtOH (6.88 mL of 21% wt., 18.68 mmol) was added to a solution of piperidine-2,4-dione (Inogent, Hyderabad, India) (2.50 g, 22.08 mmol) in EtOH (100 mL) at RT. The reaction mixture was stirred for 1 h; it was added to a mixture of 2-bromo-1-(3-fluoroquinoxalin-5-yl)ethanone (210h, 4.57 g, 16.98 mmol) in EtOH (100 mL) at RT. The reaction mixture was stirred at RT for 4 h when mostly the alkylated dione was observed; NH₄OAc (6.55 g, 85 mmol) was then added and stirred at rt for 16 h. The reaction mixture was diluted with CHCl₃/IPA(3:2) (200 mL), added to a separatory funnel, and washed with saturated aq. NaHCO₃ (2×100 mL); the organic layer was separated, dried over Na₂SO₄, and concentrated. The crude product was adsorbed onto silica and was purified via automated flash chromatography (silica gel) with 100% hexanes to 100% EtOAc in hexanes then 100% DCM to 6% MeOH in DCM to give 2-(3-ethoxyquinoxalin-5-yl)-6,7-dihydro-1H-pyrrolo[3,2-c]pyridin-4(5H)-one (337) (85 mg, 0.276 mmol, 2% yield) as a yellow solid. ¹H NMR (400 MHz, DMSO-d₆) δ ppm 1.47 (t, J=7.04 Hz, 2H) 2.88 (t, J=6.94 Hz, 2H) 3.43 (td, J=6.80, 2.45 Hz, 2H) 4.58 (q, J=7.04 Hz, 1H) 7.00 (br. S., 1H) 7.21 (d, J=2.35 Hz, 1H) 7.64 (t, J=7.82 Hz, 1H) 7.85 (dd, J=8.02, 1.17 Hz, 1H) 8.02 (dd, J=7.63, 1.17 Hz, 1H) 8.64 (s, 1H). MS (ESI, pos. ion) m/z: 309.2 (M+1).

Example 338

2-(3-((1,1-dimethyl-3-(methylsulfonyl)propyl)amino)-2-methyl-5-quinoxalinyl)-1,5,6,7-tetrahydro-4H-pyrrolo[3,2-c]pyridin-4-one

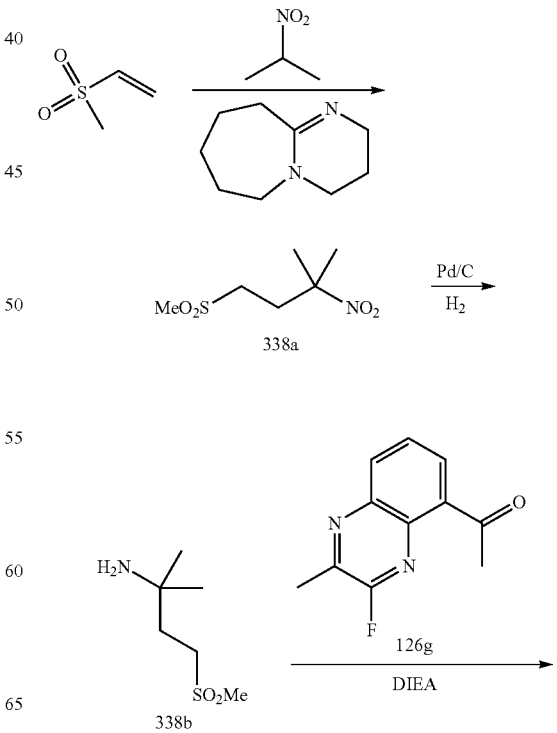

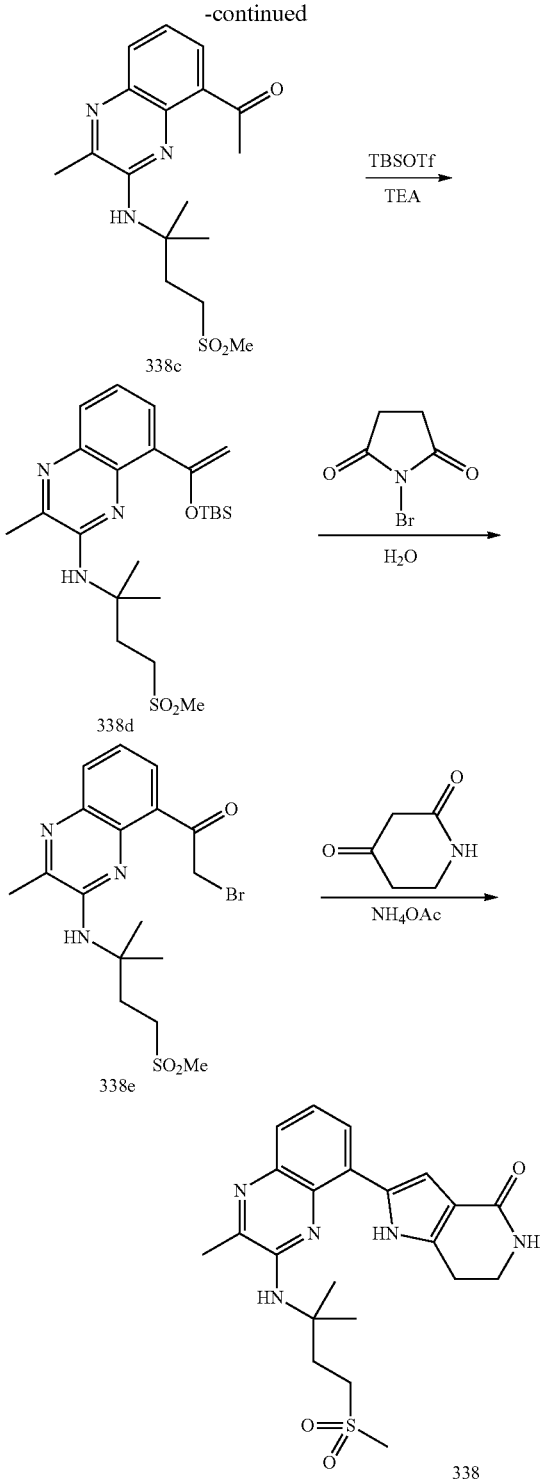

3-methyl-1-(methylsulfonyl)-3-nitrobutane (338a, 2.45 g, 12.55 mmol, 73% yield) as a white solid. ¹H NMR (400 MHz, DEUTERIUM OXIDE) δ ppm 1.31 (s, 6H) 2.08 (d, J=17.02 Hz, 1H) 2.08 (dd, J=4.30, 3.52 Hz, 1H) 3.05 (s, 3H) 3.33 (d, J=17.02 Hz, 1H) 3.33 (t, J=3.91 Hz, 1H).

Preparation of
2-methyl-4-(methylsulfonyl)butan-2-amine (338b)

At RT, Pd/C (1.262 g of 10% wt., 10.65 mmol) was added to a solution of 3-methyl-1-(methylsulfonyl)-3-nitrobutane (338a, 2.08 g, 10.65 mmol) in EtOH (53.3 mL) and DCM (53.3 mL). The reaction mixture was placed under hydrogen (46 psi) in a carbonate jacketed reaction vessel at RT for 16 h when the pressure had reduced to ambient pressure. The reaction vessel was pressurized again to 50 psi hydrogen for 3 d when the pressure had reduced to 40 psi. The mixture was filtered through a pad of Celite, covered with sand, and washed with DCM then MeOH. The filtrate was distilled to first remove the DCM and MeOH before a white solid was observed; this was filtered, washed with DCM, and dried in vacuo to give 2-methyl-4-(methylsulfonyl)butan-2-amine (338b, 1.62 g, 9.80 mmol, 92% yield) as a crystalline white solid. ¹H NMR (400 MHz, DMSO-d₆) δ ppm 1.27 (s, 6H) 2.00 (d, J=17.21 Hz, 1H) 2.00 (t, J=4.11 Hz, 1H) 3.02 (s, 3H) 3.29 (d, J=17.21 Hz, 1H) 3.29 (t, J=4.50 Hz, 1H) 8.20 (br. s., 2H). MS (ESI, pos. ion) m/z: 166.2 (M+1).

Preparation of 1-(2-methyl-3-((2-methyl-4-(methyl-sulfonyl)butan-2-yl)amino)quinoxalin-5-yl)ethanone (338c)

A solution of 1-(3-fluoro-2-methylquinoxalin-5-yl)etha-none (126g, 300 mg, 1.469 mmol), 2-methyl-4-(methylsul-fonyl)butan-2-amine (338b, 486 mg, 2.94 mmol), and N-ethyl-N-isopropylpropan-2-amine (1.02 mL, 5.88 mmol) in NMP (2.94 mL) was stirred at 120° C. for 16 h when product and a small amount of hydrolysis were observed via lcms. The reaction mixture was diluted with DCM (150 mL), added to a separatory funnel, and washed with saturated aq. NaHCO₃ (3×100 mL); the organic layer was separated, dried over Na₂SO₄, and concentrated. The crude product was adsorbed onto silica and was purified via automated flash chromatography (silica gel) with 100% DCM to 2% 2 M NH₃ in MeOH/DCM to give 1-(2-methyl-3-((2-methyl-4-(methylsulfonyl)butan-2-yl)amino)quinoxalin-5-yl)ethanone (338c, 513 mg, 1.47 mmol, 100% yield) as a red oil contaminated with NMP. ¹H NMR (400 MHz, CDCl₃) δ ppm 1.56 (s, 6H) 2.56 (s, 3H) 2.62-2.68 (m, 2H) 2.78 (s, 3H) 2.83 (s, 3H) 2.94-3.01 (m, 2H) 4.82 (s, 1H) 7.40 (dd, J=8.12, 7.34 Hz, 1H) 7.70 (dd, J=7.34, 1.47 Hz, 1H) 7.92 (dd, J=8.12, 1.47 Hz, 1H). MS (ESI, pos. ion) m/z: 350.2 (M+1).

Preparation of 8-(1-(((tert-butyldimethylsilyl)oxy) vinyl)-3-methyl-N-(2-methyl-4-(methylsulfonyl) butan-2-yl)quinoxalin-2-amine (338d)

A solution of 1-(2-methyl-3-((2-methyl-4-(methylsulfo-nyl)butan-2-yl)amino)quinoxalin-5-yl)ethanone (338c, 0.51 g, 1.46 mmol), tert-butyldimethylsilyl trifluoromethane-sulfonate (0.50 mL, 2.20 mmol), and TEA (0.61 mL, 4.40 mmol) in DCM (14.68 mL) was stirred at 0° C. for 30 min when silyl enol ether was observed via lcms. The reaction mixture was diluted with DCM (150 mL), added to a separatory funnel, and washed with saturated aq. NaHCO₃ (75 mL) before the organic layer was separated, dried over Na₂SO₄, and concentrated to give 8-(1-(((tert-butyldimethylsilyl)oxy)

Preparation of
3-methyl-1-(methylsulfonyl)-3-nitrobutane (338a)

A solution of (methylsulfonyl)ethene (1.51 mL, 17.24 mmol, Sigma-Aldrich) and 2,3,4,6,7,8,9,10-octahydropy-rimido[1,2-a]azepine (3.86 ml, 25.9 mmol) in 2-nitropropane (72.8 mL, 810 mmol, Sigma-Aldrich) was stirred at RT for 2 d. The crude product was adsorbed onto silica and was purified via automated flash chromatography (silica gel) with 100% DCM followed by 1% 2 M NH₃ in MeOH/DCM to give vinyl)-3-methyl-N-(2-methyl-4-(methylsulfonyl)butan-2-yl)quinoxalin-2-amine (338d) as a yellow oil. MS (ESI, pos. ion) m/z: 464.2 (M+1).

Preparation of 2-bromo-1-(2-methyl-3-((2-methyl-4-(methylsulfonyl)butan-2-yl)amino)quinoxalin-5-yl)ethanone (338e)

A solution of 8-(1-((tert-butyldimethylsilyl)oxy)vinyl)-3-methyl-N-(2-methyl-4-(methylsulfonyl)butan-2-yl)quinoxalin-2-amine (338d), 1-bromopyrrolidine-2,5-dione (0.26 g, 1.46 mmol), and water (0.42 mL, 23.49 mmol) in THF (14.68 mL) was stirred at 0° C. for 15 min before it was warmed to RT and stir for 2 h when product was observed via lcms. The reaction mixture was diluted with DCM (150 mL), added to a separatory funnel, and washed with saturated aq. NaHCO₃ (75 mL) before the organic layer was separated, dried over Na₂SO₄, and concentrated. The crude product was adsorbed onto silica and was purified via automated flash chromatography (silica gel) with 100% DCM followed by 3% 2 M NH₃ in MeOH/DCM to give 2-bromo-1-(2-methyl-3-((2-methyl-4-(methylsulfonyl)butan-2-yl)amino)quinoxalin-5-yl)ethanone (338e, 306 mg, 0.71 mmol, 49% yield) as a red oil. MS (ESI, pos. ion) m/z: 428.2/430.2 (M+1).

Preparation of 2-(2-methyl-3-((2-methyl-4-(methylsulfonyl)butan-2-yl)amino)quinoxalin-5-yl)-6,7-dihydro-1H-pyrrolo[3,2-c]pyridin-4(5H)-one (338)

A mixture of 2-bromo-1-(2-methyl-3-((2-methyl-4-(methylsulfonyl)butan-2-yl)amino)quinoxalin-5-yl)ethanone (338e, 306 mg, 0.71 mmol), piperidine-2,4-dione (Inogent, Hyderabad, India) (121 mg, 1.07 mmol), NH₄OAc (220 mg, 2.86 mmol) in EtOH (7.15 mL) was stirred at 50° C. for 16 h. The reaction mixture was diluted with DCM (100 mL), added to a separatory funnel, and washed with saturated aq. NaHCO₃ (2×75 mL) before the organic layer was separated, dried over Na₂SO₄, and concentrated. The crude product was adsorbed onto silica and was purified via automated flash chromatography (silica gel) with 100% DCM to 3% 2 M NH₃ in MeOH/DCM to give 2-(2-methyl-3-((2-methyl-4-(methylsulfonyl)butan-2-yl)amino)quinoxalin-5-yl)-6,7-dihydro-1H-pyrrolo[3,2-c]pyridin-4(5H)-one (338) (30 mg, 0.07 mmol, 10% yield) as a yellow solid. ¹H NMR (400 MHz, CDCl₃) δ ppm 1.57 (s, 6H) 2.58 (s, 3H) 2.65 (d, J=16.43 Hz, 1H) 2.65 (dd, J=4.11, 3.13 Hz, 1H) 2.70 (s, 3H) 3.01 (t, J=6.94 Hz, 2H) 3.05 (d, J=16.63 Hz, 1H) 3.05 (dd, J=3.91, 2.93 Hz, 1H) 3.64 (td, J=6.80, 2.45 Hz, 2H) 4.76 (s, 1H) 5.45 (br. s., 1H) 6.94 (d, J=1.96 Hz, 1H) 7.41 (t, J=7.73 Hz, 1H) 7.72 (d, J=7.24 Hz, 1H) 7.81 (d, J=7.43 Hz, 1H) 11.05 (br. s., 1H). MS (ESI, pos. ion) m/z: 442.1 (M+1).

Example 339 tert-butyl (2-methyl-2-((3-methyl-8-(4-oxo-4,5,6,7-tetrahydro-1H-pyrrolo[3,2-c]pyridin-2-yl)-2-quinoxalinyl)amino)propyl)carbamate

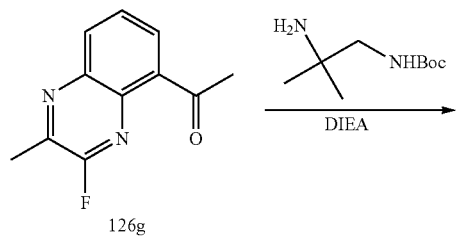

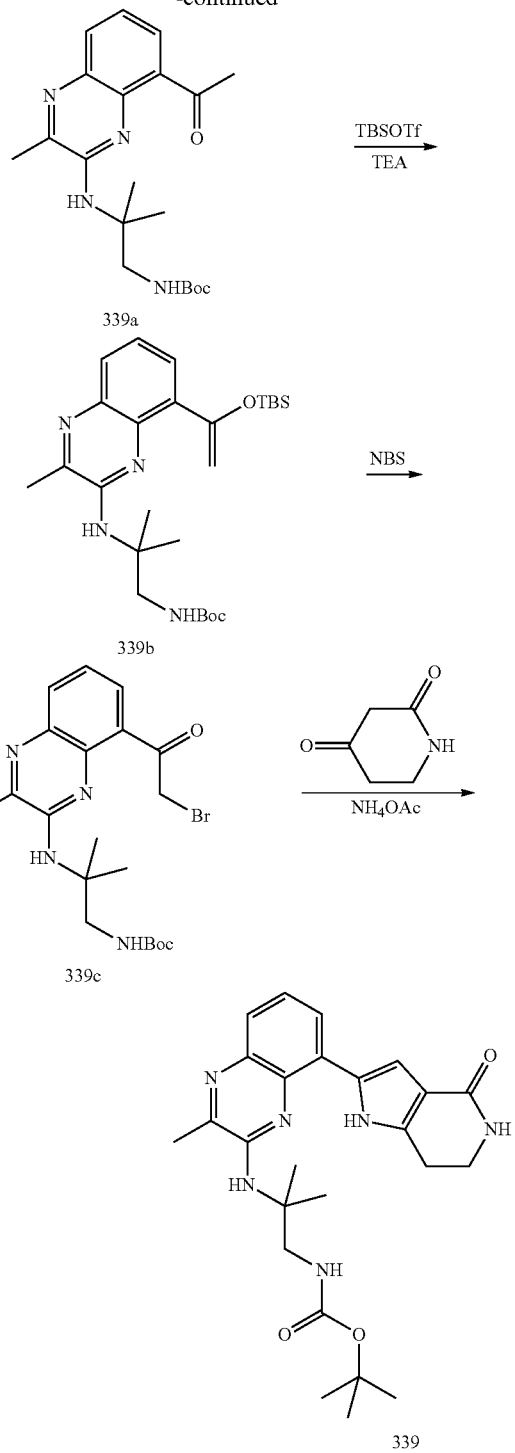

Preparation of tert-butyl (2-((8-acetyl-3-methylquinoxalin-2-yl)amino)-2-methylpropyl)carbamate (339a)

A solution of 1-(3-fluoro-2-methylquinoxalin-5-yl)ethanone (126g) (0.65 g, 3.19 mmol), tert-butyl (2-amino-2-methylpropyl)carbamate (1.20 g, 6.37 mmol), and DIEA (2.22 mL, 12.75 mmol) in NMP (6.37 mL) was stirred at 170° C. for 1.5 h when mostly product was observed via lcms. The reaction mixture was diluted with DCM (100 mL), added to a separatory funnel, and washed with saturated aq. brine (4×100 mL); the organic layer was separated, dried over Na$_2$SO$_4$, and concentrated. The crude product was adsorbed onto silica and was purified via automated flash chromatography (silica gel) with 10-40% EtOAc in hexanes to give tert-butyl (2-((8-acetyl-3-methylquinoxalin-2-yl)amino)-2-methylpropyl)carbamate (339a) (0.78 g, 2.09 mmol, 65% yield) as a honey colored solid. $^1$H NMR (400 MHz, CDCl$_3$) δ ppm 1.48 (s, 9H) 1.57 (s, 6H) 2.55 (s, 3H) 2.87 (s, 3H) 3.33 (d, J=6.85 Hz, 2H) 5.25 (t, J=6.55 Hz, 1H) 6.53 (s, 1H) 7.32 (t, J=7.73 Hz, 1H) 7.73 (dd, J=7.34, 1.47 Hz, 1H) 7.88 (dd, J=8.02, 1.37 Hz, 1H). MS (ESI, pos. ion) m/z: 373.2 (M+1).

Preparation of tert-butyl (2-((8-(1-(((tert-butyldimethylsilyl)oxy)vinyl)-3-methylquinoxalin-2-yl)amino)-2-methylpropyl)carbamate (339b)

A solution of tert-butyl (2-((8-acetyl-3-methylquinoxalin-2-yl)amino)-2-methylpropyl)carbamate (339a, 0.78 g, 2.094 mmol), tert-butyldimethylsilyl trifluoromethanesulfonate (0.72 mL, 3.14 mmol), and TEA (0.88 mL, 6.28 mmol) in DCM (21 mL) was stirred at 0° C. for 20 min when the silyl enol ether was observed via lcms. The reaction mixture was diluted with DCM (100 mL), added to a separatory funnel, and washed with saturated aq. NaHCO$_3$ (100 mL) before the organic layer was separated, dried over Na$_2$SO$_4$, and concentrated to give tert-butyl (2-((8-(1-(((tert-butyldimethylsilyl)oxy)vinyl)-3-methylquinoxalin-2-yl)amino)-2-methylpropyl)carbamate (339b) as a yellow oil. MS (ESI, pos. ion) m/z: 487.3 (M+1).

Preparation of tert-butyl (2-08-(2-bromoacetyl)-3-methylquinoxalin-2-yl)amino)-2-methylpropyl)carbamate (339c)

A solution of tert-butyl (2-((8-(1-(((tert-butyldimethylsilyl)oxy)vinyl)-3-methylquinoxalin-2-yl)amino)-2-methylpropyl)carbamate (339b), 1-bromopyrrolidine-2,5-dione (0.41 g, 2.30 mmol), and water (0.60 mL, 33.5 mmol) in THF (21 mL) was stirred at 0° C. and warmed to RT and stir for 30 min when product was observed via lcms. The reaction mixture was diluted with DCM (100 mL), added to a separatory funnel, and washed with saturated aq. NaHCO$_3$ (100 mL); the organic layer was separated, dried over Na$_2$SO$_4$, and concentrated. The crude product was adsorbed onto silica and was purified via automated flash chromatography (silica gel) with 10-40% EtOAc in hexanes to give tert-butyl (2-((8-(2-bromoacetyl)-3-methylquinoxalin-2-yl)amino)-2-methylpropyl)carbamate (339c) (0.49 g, 1.08 mmol, 52% yield) as a yellow amorphous solid. $^1$H NMR (400 MHz, CDCl$_3$) δ ppm 1.48 (s, 9H) 1.57 (s, 6H) 2.55 (s, 3H) 3.32 (d, J=6.85 Hz, 2H) 5.00 (s, 2H) 5.11 (dd, J=7.63, 5.09 Hz, 1H) 6.73 (s, 1H) 7.36 (t, J=7.73 Hz, 1H) 7.85 (d, J=7.24 Hz, 1H) 7.93 (d, J=8.02 Hz, 1H). MS (ESI, pos. ion) m/z: 451.2/453.2 (M+1).

Preparation of tert-butyl (2-methyl-2-((3-methyl-8-(4-oxo-4,5,6,7-tetrahydro-1H-pyrrolo[3,2-c]pyridin-2-yl)quinoxalin-2-yl)amino)propyl)carbamate (339)

A solution of tert-butyl (2-((8-(2-bromoacetyl)-3-methylquinoxalin-2-yl)amino)-2-methylpropyl)carbamate (339c) (0.49 g, 1.09 mmol), piperidine-2,4-dione (Inogent, Hyderabad, India, 184 mg, 1.63 mmol), and NH$_4$OAc (335 mg, 4.34 mmol) in EtOH (10.86 mL) was stirred at 50° C. for 16 h when product was observed via lcms. The reaction mixture was diluted with DCM (100 mL), added to a separatory funnel, and washed with saturated aq. NaHCO$_3$ (2×75 mL) before the organic layer was separated, dried over Na$_2$SO$_4$, and concentrated. The crude product was adsorbed onto silica and was purified via automated flash chromatography (silica gel) with 1-6% of 2 M NH$_3$ in MeOH/DCM to give tert-butyl (2-methyl-2-((3-methyl-8-(4-oxo-4,5,6,7-tetrahydro-1H-pyrrolo[3,2-c]pyridin-2-yl)quinoxalin-2-yl)amino)propyl)carbamate (339) (0.12 g, 0.26 mmol, 24% yield) as a yellow solid. $^1$H NMR (400 MHz, CDCl$_3$) δ ppm 1.48 (s, 9H) 1.64 (s, 6H) 2.56 (s, 3H) 2.94 (t, J=6.94 Hz, 2H) 3.36 (d, J=6.65 Hz, 2H) 3.63 (td, J=6.80, 2.25 Hz, 2H) 5.60 (t, J=6.55 Hz, 1H) 6.05 (br. s., 1H) 6.70 (s, 1H) 7.06 (d, J=1.96 Hz, 1H) 7.32 (t, J=7.73 Hz, 1H) 7.61 (dd, J=7.92, 1.08 Hz, 1H) 7.87 (dd, J=7.63, 1.17 Hz, 1H) 12.60 (br. s., 1H). MS (ESI, pos. ion) m/z: 465.2 (M+1).

Example 340

2-(2-(tert-butylamino)-8-quinolinyl)-1,5,6,7-tetrahydro-4H-pyrrolo[3,2-c]pyridin-4-one

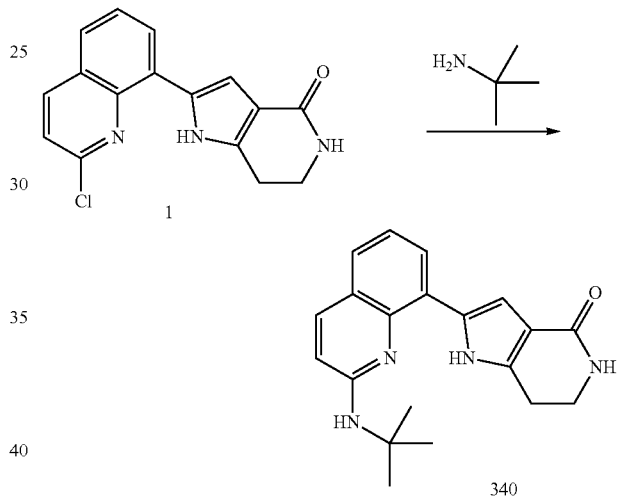

A solution of 2-(2-chloroquinolin-8-yl)-6,7-dihydro-1H-pyrrolo[3,2-c]pyridin-4(5H)-one (1) (125 mg, 0.42 mmol) and 2-methylpropan-2-amine (154 mg, 2.10 mmol) (Sigma-Aldrich) in NMP (0.84 mL) was heated in a sealed tube at 165° C. for 2.5 d. The reaction mixture was diluted with DCM (100 mL), added to a separatory funnel, and washed with saturated aq. brine (4×100 mL) before the organic layer was separated, dried over Na$_2$SO$_4$, and concentrated. The crude product was adsorbed onto silica and was purified via automated flash chromatography (silica gel) with 1-4% of 2 M NH$_3$ in MeOH/DCM to give 2-(2-(tert-butylamino)quinolin-8-yl)-6,7-dihydro-1H-pyrrolo[3,2-c]pyridin-4(5H)-one (30 mg) (0.09 mmol, 21% yield) as a yellow oil which was slightly impure. This material was dissolved in MeOH (~20 mg/mL) and injected (2×1.0 mL) onto the Shimadzu preparatory LC (Phenomenex Gemini C18, 10 µm, 150×30 mm; 10-100% MeCN/water with 0.1% TFA); the pure fractions were combined, basicified with NaHCO$_3$ (saturated, aq.), extracted with CHCl$_3$/IPA(3:2), separated, dried over Na$_2$SO$_4$, and concentrated via rotary evaporation to give 2-(2-(tert-butylamino)quinolin-8-yl)-6,7-dihydro-1H-pyrrolo[3,2-c]pyridin-4(5H)-one (340) (19 mg, 0.08 mmol, 14% yield) as a light yellow solid. $^1$H NMR (400 MHz, CDCl$_3$) δ ppm 1.62 (s, 9H) 2.99 (t, J=6.94 Hz, 2H) 3.65 (td, J=6.85, 2.35 Hz, 2H) 4.84 (s, 1H) 5.71 (br. s., 1H) 6.56 (d, J=9.00 Hz, 1H) 7.10 (d, J=1.76 Hz, 1H) 7.21 (t, J=7.73 Hz, 1H) 7.38 (d, J=7.63 Hz, 1H) 7.75 (d, J=9.00 Hz, 1H) 7.96 (d, J=7.63 Hz, 1H) 13.24 (br. s., 1H). MS (ESI, pos. ion) m/z: 353.3 (M+1).

Example 341

2-(3-((2-amino-1,1-dimethylethyl)amino)-2-methyl-5-quinoxalinyl)-1,5,6,7-tetrahydro-4H-pyrrolo[3,2-c]pyridin-4-one

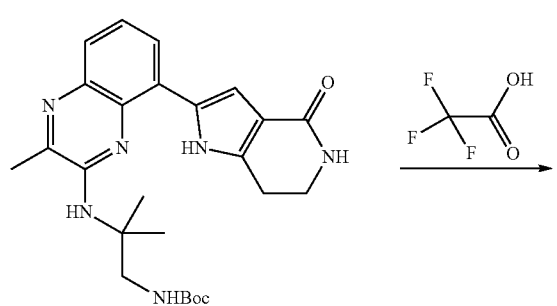

339

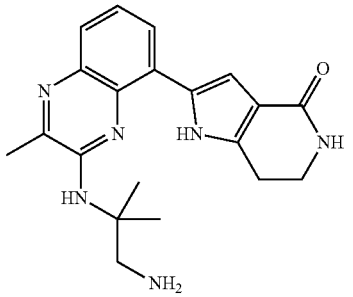

341

A solution of tert-butyl (2-methyl-2-((3-methyl-8-(4-oxo-4,5,6,7-tetrahydro-1H-pyrrolo[3,2-c]pyridin-2-yl)quinoxalin-2-yl)amino)propyl)carbamate (339) (0.13 g, 0.28 mmol) in DCM (2.80 mL) and TFA (1.0 mL, 13.99 mmol) was stirred at 0° C. for 20 min before it was warmed to RT and stir for 1 h. The reaction mixture was concentrated and the residue was diluted with CHCl₃/IPA(3:2) (150 mL), added to a separatory funnel, and washed with saturated aq. NaHCO₃ (2×75 mL) before the organic layer was separated, dried over Na₂SO₄, and concentrated to give 2-(3-((1-amino-2-methylpropan-2-yl)amino)-2-methylquinoxalin-5-yl)-6,7-dihydro-1H-pyrrolo[3,2-c]pyridin-4(5H)-one (65 mg, 0.17 mmol, 63% yield) which was impure by NMR. This material was dissolved in MeOH (~20 mg/mL) and injected (2×1.0 mL) onto the Shimadzu preparatory LC (Phenomenex Gemini C18, 10 μm, 150×30 mm; 10-100% MeCN/water with 0.1% TFA); the pure fractions were combined, basicified with NaHCO₃ (saturated, aq.), extracted with CHCl₃/IPA(3:2), separated, dried over Na₂SO₄, and concentrated via rotary evaporation to give 2-(3-((1-amino-2-methylpropan-2-yl)amino)-2-methylquinoxalin-5-yl)-6,7-dihydro-1H-pyrrolo[3,2-c]pyridin-4(5H)-one (341) (19 mg, 0.05 mmol, 18% yield) as a yellow solid. ¹H NMR (400 MHz, CDCl₃) δ ppm 1.60 (s, 6H) 2.59 (s, 3H) 2.95 (s, 2H) 2.99 (t, J=6.85 Hz, 2H) 3.65 (td, J=6.85, 2.54 Hz, 2H) 5.33 (br. s., 1H) 6.19 (s, 1H) 7.10 (d, J=2.15 Hz, 1H) 7.36 (t, J=7.82 Hz, 1H) 7.65 (dd, J=8.02, 1.37 Hz, 1H) 7.92 (dd, J=7.63, 1.37 Hz, 1H) 12.64 (br. s., 1H). MS (ESI, pos. ion) m/z: 365.3 (M+1).

Example 342

2-(3-((1,1-dimethyl-2-((2-(methylsulfonyl)ethyl)amino)ethyl)amino)-2-methyl-5-quinoxalinyl)-1,5,6,7-tetrahydro-4H-pyrrolo[3,2-c]pyridin-4-one

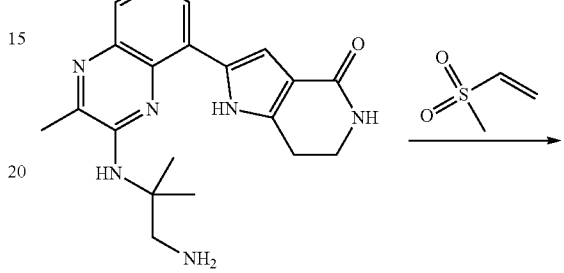

341

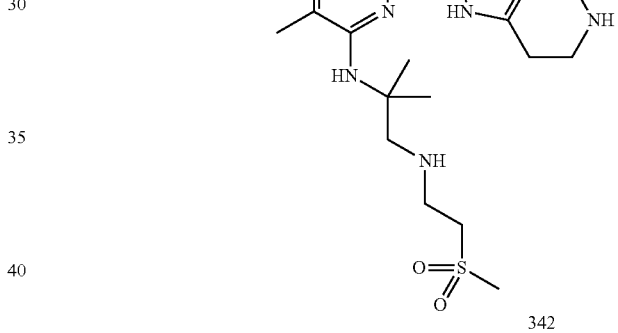

342

A solution of methyl vinyl sulfone (0.016 mL, 0.178 mmol) (Sigma-Aldrich) in THF (1.0 mL) was added to a mixture of 2-(3-((1-amino-2-methylpropan-2-yl)amino)-2-methylquinoxalin-5-yl)-6,7-dihydro-1H-pyrrolo[3,2-c]pyridin-4(5H)-one (341) (65 mg, 0.18 mmol) in 2-Propanol (2.00 mL); the reaction mixture was stirred at RT for 16 h when only a small amount of product was observed via lcms. More methyl vinyl sulfone (0.16 mL, 1.78 mmol) was added to the reaction mixture before it was heated in the microwave at 110° C. for 75 min when mostly product was observed via lcms. The crude product was adsorbed onto silica and was purified via automated flash chromatography (silica gel) with 1-6% of 2 M NH₃ in MeOH/DCM to give 2-(2-methyl-3-((2-methyl-1-((2-(methylsulfonyl)ethyl)amino)propan-2-yl)amino)quinoxalin-5-yl)-6,7-dihydro-1H-pyrrolo[3,2-c]pyridin-4(5H)-one (342, 58 mg, 0.12 mmol, 69% yield) as a yellow solid. ¹H NMR (400 MHz, CDCl₃) δ ppm 1.63 (s, 6H) 2.57 (s, 3H) 2.91 (s, 2H) 2.92 (s, 3H) 2.97 (t, J=6.94 Hz, 2H) 3.18-3.25 (m, 2H) 3.25-3.31 (m, 2H) 3.65 (td, J=6.85, 2.35 Hz, 2H) 5.52 (br. s., 1H) 5.92 (s, 1H) 7.09 (d, J=1.76 Hz, 1H) 7.36 (t, J=7.82 Hz, 1H) 7.64 (dd, J=8.12, 1.08 Hz, 1H) 7.91 (dd, J=7.63, 0.98 Hz, 1H) 12.49 (br. s., 1H). MS (ESI, pos. ion) m/z: 471.4 (M+1).

Example 343

2-(3-(tert-butylamino)-2-fluoro-5-quinoxalinyl)-1,5,6,7-tetrahydro-4H-pyrrolo[3,2-c]pyridin-4-one

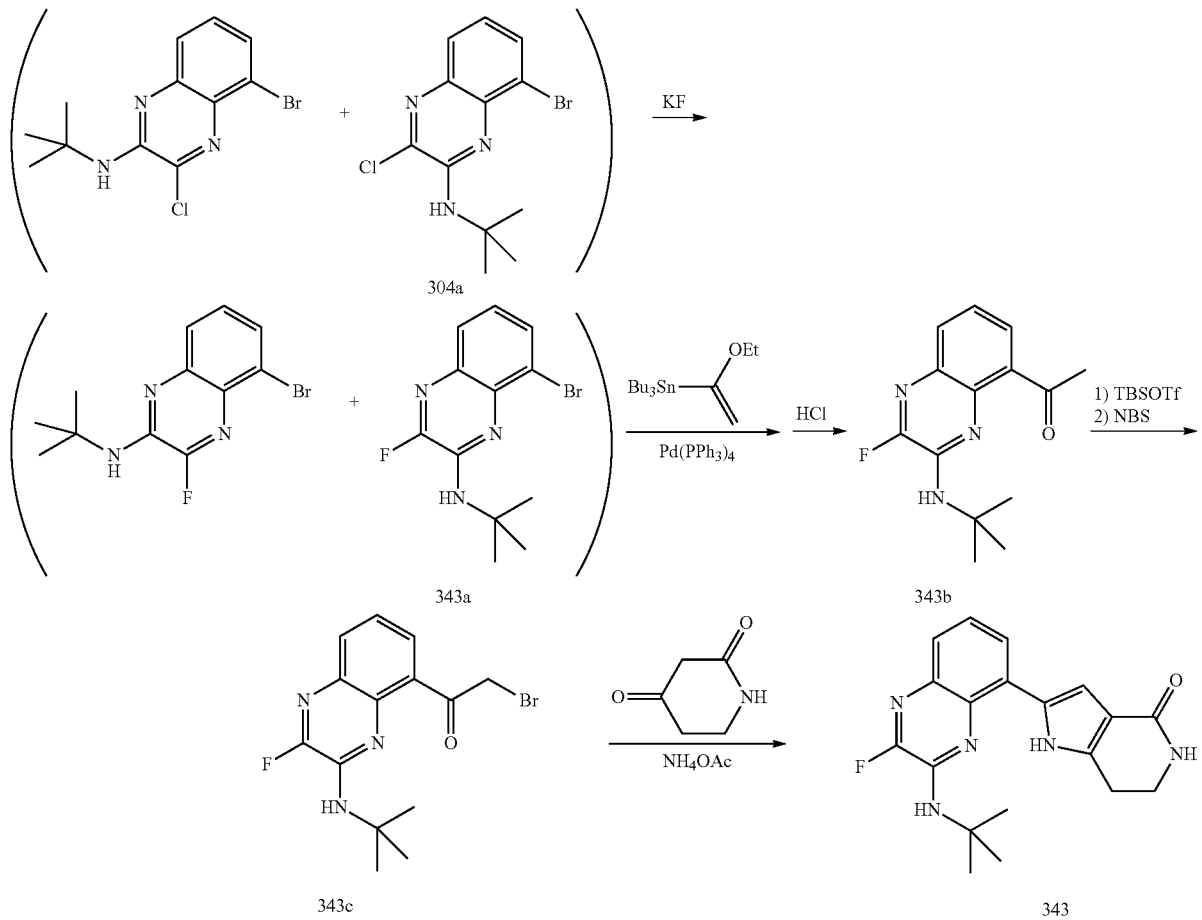

Preparation of 343a

A mixture of Intermediate 304a (as a ~2.5:1 mixture of 8-bromo-N-(tert-butyl)-3-chloroquinoxalin-2-amine and 5-bromo-N-(tert-butyl)-3-chloroquinoxalin-2-amine (407 mg, 0.6 mmol) and KF (113 mg, 1.94 mmol) in DMSO (1.3 mL) was heated to 90° C. for 24 h. The reaction mixture was diluted with DCM (100 mL), added to a separatory funnel, and washed with saturated aq. NaHCO$_3$ (2×75 mL) before the organic layer was separated, dried over Na$_2$SO$_4$, and concentrated to give an inseparable mixture (~2.5:1) of 8-bromo-N-(tert-butyl)-3-fluoroquinoxalin-2-amine/5-bromo-N-(tert-butyl)-3-fluoroquinoxalin-2-amine (343a) (124 mg, 0.41 mmol, 64% yield) as a yellow oil. $^1$H NMR (400 MHz, CDCl$_3$) δ ppm 1.57 (s, 9H) 1.63 (s, 18H) 5.22 (br. s., 0H) 5.25 (br. s., 1H) 7.20 (t, J=7.92 Hz, 1H) 7.37 (t, J=8.02 Hz, 1H) 7.61-7.65 (m, 2H) 7.67 (d, J=8.41 Hz, 1H) 7.83 (d, J=7.63 Hz, 1H). $^{19}$F NMR (376 MHz, CDCl$_3$) δ ppm −82.18 (s, 2F) −80.01 (s, 1F). MS (ESI, pos. ion) m/z: 298.0/300.0 (M+1).

Preparation of 1-(3-(tert-butylamino)-2-fluoroquinoxalin-5-yl)ethanone (343b)

A solution of (~1:2.5) 5-bromo-N-(tert-butyl)-3-fluoroquinoxalin-2-amine/8-bromo-N-(tert-butyl)-3-fluoroquinoxalin-2-amine (343a) (374 mg, 0.62 mmol), tributyl(1-ethoxyvinyl)stannane (0.32 ml, 0.94 mmol, Sigma-Aldrich), and Pd(PPh$_3$)$_4$ (72 mg, 0.06 mmol) in toluene (4.5 mL)/THF (1.80 mL) was stirred at reflux for 3 d. Concentrated hydrogen chloride (0.065 mL, 0.78 mmol) was added after cooling the reaction mixture to rt; TEA (0.22 mL, 1.57 mmol) was then added to neutralize the mixture. The crude product was adsorbed onto silica and was purified via automated flash chromatography (silica gel) with 15% EtOAc in hexanes to give 1-(3-(tert-butylamino)-2-fluoroquinoxalin-5-yl)ethanone (343b) (113 mg, 0.43 mmol, 69% yield) as a yellow solid. $^1$H NMR (400 MHz, CDCl$_3$) δ ppm 1.58 (s, 9H) 2.87 (s, 3H) 5.33 (br. s., 1H) 7.40 (t, J=7.73 Hz, 1H) 7.79-7.84 (m, 2H). $^{19}$F NMR (377 MHz, CDCl$_3$) δ ppm −80.42 (s, 1F). MS (ESI, pos. ion) m/z: 262.2 (M+1). The structure was confirmed via NOESY: nOe observed between 1.5 and 2.8 ppm.

Preparation of 2-bromo-1-(3-(tert-butylamino)-2-fluoroquinoxalin-5-yl)ethanone (343c)

A solution of 1-(3-(tert-butylamino)-2-fluoroquinoxalin-5-yl)ethanone (343b) (113 mg, 0.43 mmol), tert-butyldimethylsilyl trifluoromethanesulfonate (149 µL, 0.65 mmol), and TEA (181 µL, 1.29 mmol) in DCM (4.3 mL) was stirred at 0° C. for 30 min when silyl enol ether was observed via lcms. The reaction mixture was diluted with DCM (100 mL), added to a separatory funnel, and washed with saturated aq. NaHCO$_3$ (75 mL) before the organic layer was separated, dried over Na₂SO₄, and concentrated to give an oil. To a solution of the resulting oil in water (0.13 mL) and THF (4.3 mL) at RT was added NBS (92 mg, 0.52 mmol) and stirred for 1 h. The reaction mixture was diluted with DCM (100 mL), added to a separatory funnel, and washed with saturated aq. NaHCO₃ (75 mL) before the organic layer was separated, dried over Na₂SO₄, and concentrated. The crude product was adsorbed onto silica and was purified via automated flash chromatography (silica gel) with 0-15% EtOAc in hexanes to give 2-bromo-1-(3-(tert-butylamino)-2-fluoroquinoxalin-5-yl)ethanone (343c) (85 mg, 0.25 mmol, 58% yield) as a yellow oil. ¹H NMR (400 MHz, CDCl₃) δ ppm 1.58 (s, 9H) 4.94 (s, 2H) 5.41 (br. s., 1H) 7.44 (t, J=7.82 Hz, 1H) 7.87 (dd, J=8.02, 1.57 Hz, 1H) 7.92 (dd, J=7.43, 1.37 Hz, 1H). ¹⁹F NMR (377 MHz, CDCl₃) δ ppm −79.69 (s, 1F). MS (ESI, pos. ion) m/z: 340.2/342.2 (M+1).

Preparation of 2-(3-(tert-butylamino)-2-fluoroquinoxalin-5-yl)-6,7-dihydro-1H-pyrrolo[3,2-c]pyridin-4(5H)-one (343)

A solution of 2-bromo-1-(3-(tert-butylamino)-2-fluoroquinoxalin-5-yl)ethanone (343c) (85 mg, 0.25 mmol), piperidine-2,4-dione (Inogent, Hyderabad, India, 42 mg, 0.37 mmol), and NH₄OAc (96 mg, 1.25 mmol) in EtOH (2.5 mL) was stirred at 50° C. for 16 h. The reaction mixture was diluted with DCM (100 mL), added to a separatory funnel, and washed with saturated aq. NaHCO₃ (75 mL) before the organic layer was separated, dried over Na₂SO₄, and concentrated. The crude product was adsorbed onto silica and was purified via automated flash chromatography (silica gel) with 1-4% of 2 M NH₃ in MeOH/DCM to give 2-(3-(tert-butylamino)-2-fluoroquinoxalin-5-yl)-6,7-dihydro-1H-pyrrolo[3,2-c]pyridin-4(5H)-one (343, 20 mg, 23% yield) as a yellow solid. ¹H NMR (400 MHz, CDCl₃) δ ppm 1.67 (s, 9H) 2.98 (t, J=6.85 Hz, 2H) 3.67 (td, J=6.75, 2.15 Hz, 2H) 5.36 (d, J=2.15 Hz, 1H) 5.56 (br. s., 1H) 7.13 (s, 1H) 7.41 (t, J=7.63 Hz, 1H) 7.55 (d, J=8.02 Hz, 1H) 7.96 (d, J=7.63 Hz, 1H) 12.16 (br. s., 1H). ¹⁹F NMR (377 MHz, CDCl₃) δ ppm −80.63 (s, 1F). MS (ESI, pos. ion) m/z: 354.2 (M+1).

Example 344

2-(3-(tert-butylamino)-2-(methylamino)-5-quinoxalinyl)-1,5,6,7-tetrahydro-4H-pyrrolo[3,2-c]pyridin-4-one

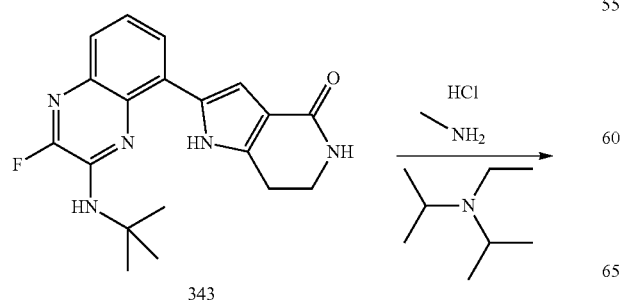

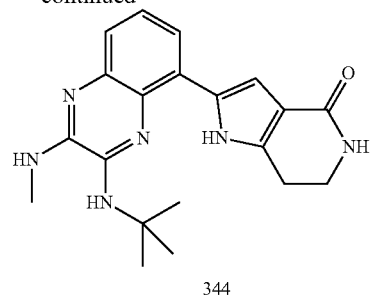

344

A solution of 2-(3-(tert-butylamino)-2-fluoroquinoxalin-5-yl)-6,7-dihydro-1H-pyrrolo[3,2-c]pyridin-4(5H)-one (343) (16 mg, 0.04 mmol), methanamine hydrochloride (15 mg, 0.22 mmol, Sigma-Aldrich), and DIEA (47.4 μL, 0.27 mmol) in DMSO (0.45 mL) was stirred at RT for 2 h. The reaction mixture was diluted with DCM (100 mL), added to a separatory funnel, and washed with saturated aq. NaHCO₃ (2×75 mL) before the organic layer was separated, dried over Na₂SO₄, and concentrated. The crude product was adsorbed onto silica and was purified via automated flash chromatography (silica gel) with 1-4% of 2 M NH₃ in MeOH/DCM to give 2-(3-(tert-butylamino)-2-(methylamino)quinoxalin-5-yl)-6,7-dihydro-1H-pyrrolo[3,2-c]pyridin-4 (5H)-one (344) (4 mg, 24% yield) as a beige solid. ¹H NMR (400 MHz, DMSO-d₆) δ ppm 1.55 (s, 9H) 2.85 (t, J=6.85 Hz, 2H) 2.95 (d, J=4.30 Hz, 3H) 3.42 (td, J=6.80, 2.45 Hz, 2H) 6.32 (s, 1H) 6.89 (d, J=2.15 Hz, 1H) 6.90 (br. s., 1H) 7.17 (t, J=7.63 Hz, 1H) 7.28 (dd, J=8.02, 1.37 Hz, 1H) 7.30-7.33 (m, 1H) 7.51 (dd, J=7.63, 1.37 Hz, 1H) 12.10 (br. s., 1H). MS (ESI, pos. ion) m/z: 365.3 (M+1).

Example 345

2-(3-(tert-butylamino)-2-chloro-5-quinoxalinyl)-1,5,6,7-tetrahydro-4H-pyrrolo[3,2-c]pyridin-4-one

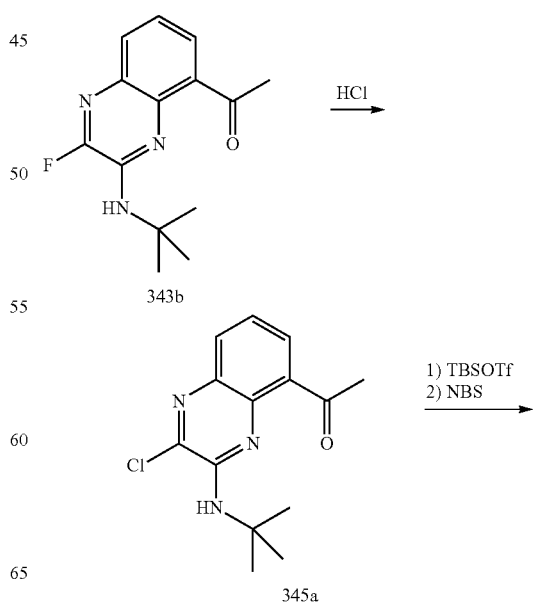

-continued

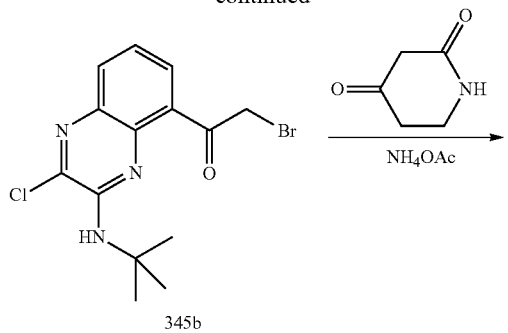

345b

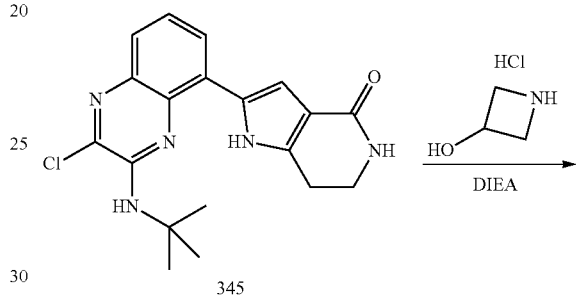

345

Preparation of 1-(3-(tert-butylamino)-2-chloroquinoxalin-5-yl)ethanone (345a)

A mixture of 1-(3-(tert-butylamino)-2-fluoroquinoxalin-5-yl)ethanone (343b) (300 mg, 1.14 mmol) in 4 M HCl in dioxane (2.87 mL, 11.48 mmol) was stirred at RT for 16 h under a drying tube. Lcms indicated the reaction was not completed. The reaction mixture was heated at 70° C. for 1.5 h. The reaction was quenched with saturated aq. NaHCO$_3$ (200 mL), diluted with DCM (100 mL), added to a separatory funnel, and extracted with DCM (3×100 mL) before the organic layer was separated, dried over Na$_2$SO$_4$, and concentrated to give 1-(3-(tert-butylamino)-2-chloroquinoxalin-5-yl)ethanone (345a, 285 mg, 1.02 mmol, 89% yield) as a yellow solid. $^1$H NMR (400 MHz, CDCl$_3$) δ ppm 1.57 (s, 9H) 2.86 (s, 3H) 5.73 (br. s., 1H) 7.39 (t, J=8.02 Hz, 1H) 7.83 (dd, J=7.43, 1.56 Hz, 1H) 7.89 (dd, J=8.22, 1.57 Hz, 1H). MS (ESI, pos. ion) m/z: 278.2 (M+1).

Preparation of 2-bromo-1-(3-(tert-butylamino)-2-chloroquinoxalin-5-yl)ethanone (345b)

This compound (215 mg, 59% yield) as a yellow oil was prepared according to the procedures described for intermediate 343c, using 1-(3-(tert-butylamino)-2-chloroquinoxalin-5-yl)ethanone (345a) (285 mg, 1.02 mmol) as the starting material. $^1$H NMR (400 MHz, CDCl$_3$) δ ppm 1.57 (s, 9H) 4.93 (s, 2H) 5.82 (br. s., 1H) 7.43 (t, J=7.82 Hz, 1H) 7.94 (d, J=7.63 Hz, 2H). MS (ESI, pos. ion) m/z: 356.0/358.0 (M+1).

Preparation of 2-(3-(tert-butylamino)-2-fluoroquinoxalin-5-yl)-6,7-dihydro-1H-pyrrolo[3,2-c]pyridin-4(5H)-one (345)

This compound (60 mg, 27% yield) as a yellow solid was prepared according to the procedures described for Example 343, using 2-bromo-1-(3-(tert-butylamino)-2-chloroquinoxalin-5-yl)ethanone (345b) (215 mg, 0.60 mmol), piperidine-2,4-dione (Inogent, Hyderabad, India) (0.10 g, 0.90 mmol) as the starting materials. $^1$H NMR (400 MHz, CDCl$_3$) δ ppm 1.67 (s, 9H) 2.99 (t, J=6.85 Hz, 2H) 3.67 (td, J=6.94, 2.54 Hz, 2H) 5.51 (br. s., 1H) 5.77 (s, 1H) 7.12 (d, J=2.15 Hz, 1H) 7.41 (t, J=7.82 Hz, 1H) 7.63 (dd, J=8.22, 1.37 Hz, 1H) 7.98 (dd, J=7.63, 1.37 Hz, 1H) 12.15 (br. s., 1H). MS (ESI, pos. ion) m/z: 370.1 (M+1).

Example 346

2-(3-(tert-butylamino)-2-(3-hydroxy-1-azetidinyl)-5-quinoxalinyl)-1,5,6,7-tetrahydro-4H-pyrrolo[3,2-c]pyridin-4-one

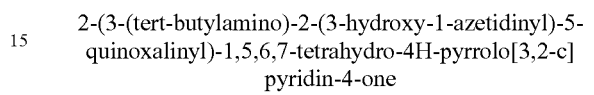

345

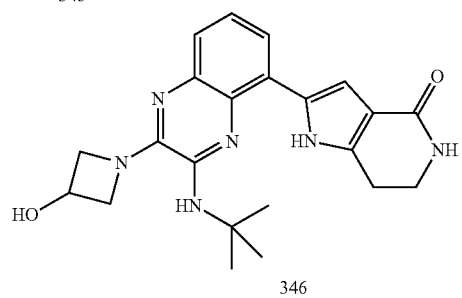

346

A solution of 2-(3-(tert-butylamino)-2-chloroquinoxalin-5-yl)-6,7-dihydro-1H-pyrrolo[3,2-c]pyridin-4(5H)-one (345) (28 mg, 0.07 mmol), azetidin-3-ol hydrochloride (41 mg, 0.37 mmol, Matrix Scientific, Columbia, S.C.), and N-ethyl-N-isopropylpropan-2-amine (81 pt, 0.45 mmol) in DMSO (0.75 mL) was stirred at 50° C. for 1 h. The reaction mixture was diluted with DCM (100 mL), added to a separatory funnel, and washed with saturated aq. NaHCO$_3$ (2×75 mL) before the organic layer was separated, dried over Na$_2$SO$_4$, and concentrated. The crude product was adsorbed onto silica and was purified via automated flash chromatography (silica gel) with 1-5% of 2 M NH$_3$ in MeOH/DCM to give 2-(3-(tert-butylamino)-2-(3-hydroxyazetidin-1-yl)quinoxalin-5-yl)-6,7-dihydro-1H-pyrrolo[3,2-c]pyridin-4(5H)-one (346) (19 mg, 61% yield) as a yellow solid. $^1$H NMR (400 MHz, DMSO-d$_6$) δ ppm 1.53 (s, 9H) 2.85 (t, J=6.94 Hz, 2H) 3.43 (td, J=6.75, 2.35 Hz, 2H) 3.94 (dd, J=9.00, 5.09 Hz, 2H) 4.41 (dd, J=8.80, 6.85 Hz, 2H) 4.57 (sxt, J=5.91 Hz, 1H) 5.64-5.71 (m, 2H) 6.95 (s, 1H) 6.96 (s, 1H) 7.24 (t, J=7.82 Hz, 1H) 7.36 (dd, J=7.92, 1.27 Hz, 1H) 7.61 (dd, J=7.43, 1.37 Hz, 1H) 12.00 (s, 1H). MS (ESI, pos. ion) m/z: 407.1 (M+1).

Example 347

2-(2-(1-azetidinyl)-3-(tert-butylamino)-5-quinoxalinyl)-1,5,6,7-tetrahydro-4H-pyrrolo[3,2-c]pyridin-4-one

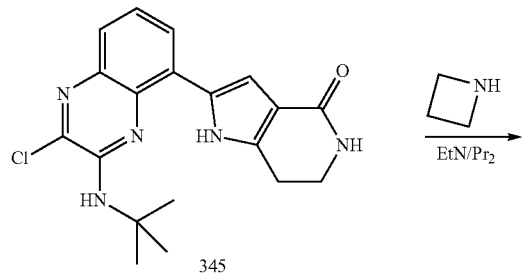

345

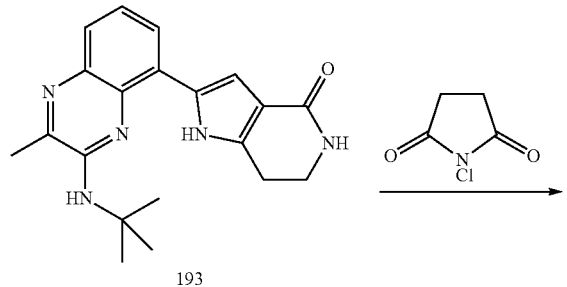

347

This compound (18 mg, 61% yield) as a yellow solid was prepared according to the procedures described for Example 346, using 2-(3-(tert-butylamino)-2-chloroquinoxalin-5-yl)-6,7-dihydro-1H-pyrrolo[3,2-c]pyridin-4(5H)-one (345) (28 mg, 0.076 mmol), azetidine (25.5 pt, 0.37 mmol, Matrix Scientific, Columbia, S.C.), and DIEA (26.4 µL, 0.15 mmol) in DMSO (0.75 mL) at 50° C. for 1 h. $^1$H NMR (400 MHz, DMSO-$d_6$) δ ppm 1.53 (s, 9H) 2.30 (quin, J=7.58 Hz, 2H) 2.85 (t, J=6.85 Hz, 2H) 3.43 (td, J=6.85, 2.35 Hz, 2H) 4.22 (t, J=7.63 Hz, 4H) 5.68 (s, 1H) 6.95 (s, 1H) 6.95 (s, 1H) 7.23 (t, J=7.82 Hz, 1H) 7.35 (dd, J=8.02, 1.37 Hz, 1H) 7.60 (dd, J=7.43, 1.37 Hz, 1H) 12.01 (br. s., 1H). MS (ESI, pos. ion) m/z: 391.2 (M+1).

Example 348

2-(3-(tert-butylamino)-2-methyl-5-quinoxalinyl)-3-chloro-1,5,6,7-tetrahydro-4H-pyrrolo[3,2-c]pyridin-4-one

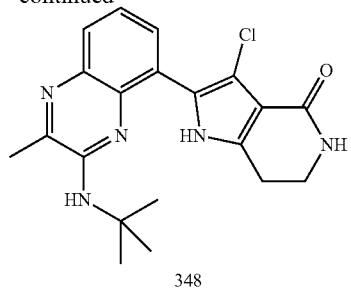

193

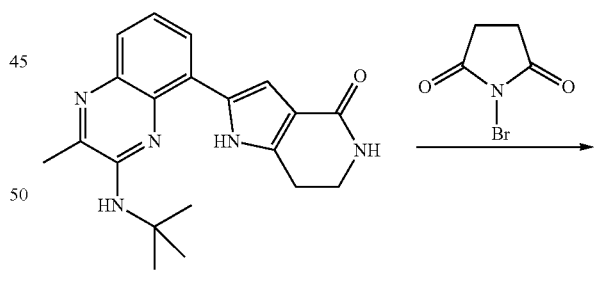

348

A solution of 2-(3-(tert-butylamino)-2-methylquinoxalin-5-yl)-6,7-dihydro-1H-pyrrolo[3,2-c]pyridin-4(5H)-one (193) (68 mg, 0.19 mmol) and 1-chloropyrrolidine-2,5-dione (39 mg, 0.29 mmol) in CHCl$_3$ (2 mL) was stirred at RT for 4 h. The reaction mixture was diluted with DCM (100 mL), added to a separatory funnel, and washed with saturated aq. NaHCO$_3$ (2×75 mL) before the organic layer was separated, dried over Na$_2$SO$_4$, and concentrated. The crude product was adsorbed onto silica and was purified via automated flash chromatography (silica gel) with 1-4% of 2 M NH$_3$ in MeOH/DCM to give impure product. The impure product was dissolved in MeOH (~20 mg/mL) and injected (2×1.0 mL) onto the Shimadzu preparatory LC (Phenomenex Gemini C18, 10 µm, 150×30 mm; 10-100% MeCN/water with 0.1% TFA); the pure fractions were combined, basicified with NaHCO$_3$ (saturated, aq.), extracted with DCM, separated, dried over Na$_2$SO$_4$, and concentrated via rotary evaporation to give 2-(3-(tert-butylamino)-2-methylquinoxalin-5-yl)-3-chloro-6,7-dihydro-1H-pyrrolo[3,2-c]pyridin-4(5H)-one (348) (12 mg, 0.03 mmol, 16% yield) as a yellow solid. $^1$H NMR (400 MHz, CDCl$_3$) δ ppm 1.62 (s, 9H) 2.56 (s, 3H) 2.96 (t, J=6.85 Hz, 2H) 3.63 (td, J=6.85, 2.74 Hz, 2H) 4.87 (s, 1H) 5.66 (br. s., 1H) 7.44 (t, J=7.92 Hz, 1H) 7.72 (dd, J=8.02, 1.37 Hz, 1H) 8.68 (dd, J=7.73, 1.27 Hz, 1H) 12.63 (br. s., 1H). MS (ESI, pos. ion) m/z: 384.0 (M+1).

Example 349

3-bromo-2-(3-(tert-butylamino)-2-methyl-5-quinoxalinyl)-1,5,6,7-tetrahydro-4H-pyrrolo[3,2-c]pyridin-4-one

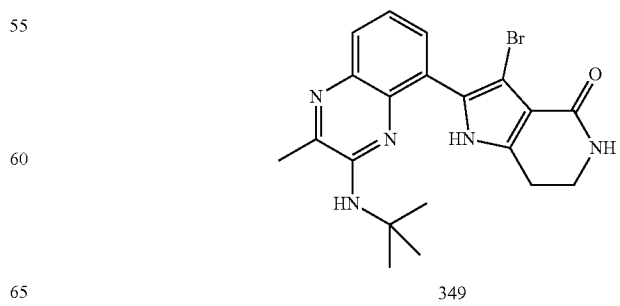

193

349

A solution of 2-(3-(tert-butylamino)-2-methylquinoxalin-5-yl)-6,7-dihydro-1H-pyrrolo[3,2-c]pyridin-4(5H)-one (193) (0.30 g, 0.86 mmol) and 1-bromopyrrolidine-2,5-dione (0.23 g, 1.28 mmol) in CHCl$_3$ (8.6 mL) was stirred at RT for 3 h. The reaction mixture was diluted with DCM (150 mL), added to a separatory funnel, and washed with saturated aq. NaHCO$_3$ (3×150 mL); the organic layer was separated, dried over Na$_2$SO$_4$, and concentrated. The crude product was directly injected onto the column and was purified via automated flash chromatography (silica gel) with 1-4% of 2 M NH$_3$ in MeOH/DCM to give 3-bromo-2-(3-(tert-butylamino)-2-methylquinoxalin-5-yl)-6,7-dihydro-1H-pyrrolo[3,2-c]pyridin-4(5H)-one (349) (228 mg, 0.53 mmol, 62% yield) as a yellow solid. $^1$H NMR (400 MHz, CDCl$_3$) δ ppm 1.60 (s, 9H) 2.55 (s, 3H) 2.97 (t, J=6.85 Hz, 2H) 3.61 (td, J=6.85, 2.74 Hz, 2H) 4.85 (s, 1H) 5.51 (br. s., 1H) 7.44 (t, J=7.92 Hz, 1H) 7.74 (dd, J=8.02, 1.37 Hz, 1H) 8.71 (dd, J=7.63, 1.37 Hz, 1H) 12.28 (br. s., 1H). MS (ESI, pos. ion) m/z: 428.0/430.1 (M+1).

Example 350

2-(3-(tert-butylamino)-2-methyl-5-quinoxalinyl)-3-methyl-1,5,6,7-tetrahydro-4H-pyrrolo[3,2-c]pyridin-4-one

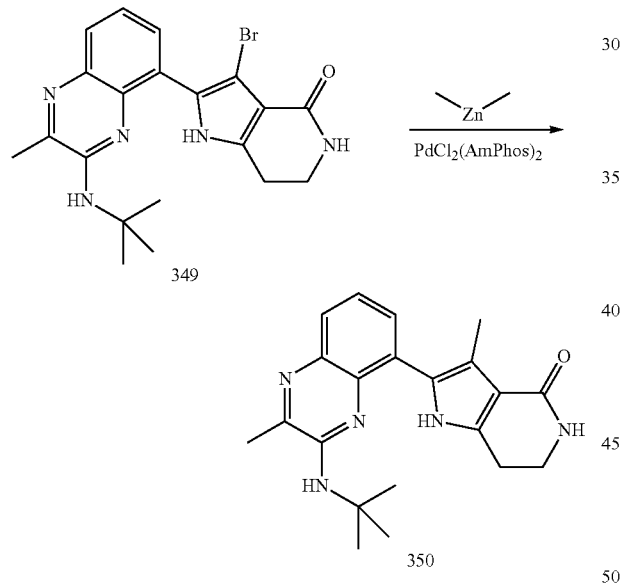

A mixture of 3-bromo-2-(3-(tert-butylamino)-2-methylquinoxalin-5-yl)-6,7-dihydro-1H-pyrrolo[3,2-c]pyridin-4(5H)-one (349) (61 mg, 0.14 mmol), dimethylzinc in hexanes (0.39 mL of 10% wt. in hexanes, 0.570 mmol, Strem Chemicals, Inc.), and (A-Phos)$_2$PdCl$_2$ (10 mg, 0.014 mmol) in dioxane (1.42 mL) was stirred at 80° C. for 2 h when product was observed via lcms. The reaction mixture was diluted with DCM (100 mL), added to a separatory funnel, and washed with saturated aq. NaHCO$_3$ (2×75 mL) before the organic layer was separated, dried over Na$_2$SO$_4$, and concentrated. The crude product was adsorbed onto silica and was purified via automated flash chromatography (silica gel) with 1-4% of 2 M NH$_3$ in MeOH/DCM to give impure 2-(3-(tert-butylamino)-2-methylquinoxalin-5-yl)-3-methyl-6,7-dihydro-1H-pyrrolo[3,2-c]pyridin-4(5H)-one contaminated with starting material. The impure product was purified via SFC [IC (3×15 cm, 5 μm), 60% 0.2% DEA in MeOH: EtOH: isopropanol (1:1:1) (NH$_4$OH)/CO$_2$, 100 bar; 65 mL/min, 220 nm; inj vol.: 1.5 mL, 3.5 mg/mL in MeOH] to give 2-(3-(tert-butylamino)-2-methylquinoxalin-5-yl)-3-methyl-6,7-dihydro-1H-pyrrolo[3,2-c]pyridin-4(5H)-one (350, 10 mg, 0.028 mmol, 19% yield) as a yellow solid. $^1$H NMR (400 MHz, CDCl$_3$) δ ppm 1.60 (s, 9H) 2.55 (s, 3H) 2.69 (s, 3H) 2.95 (t, J=6.85 Hz, 2H) 3.61 (td, J=6.85, 2.54 Hz, 2H) 4.79 (s, 1H) 5.18 (br. s., 1H) 7.42 (t, J=7.92 Hz, 1H) 7.68 (dd, J=8.12, 1.27 Hz, 1H) 7.85 (dd, J=7.53, 1.08 Hz, 1H) 11.62 (br. s., 1H). MS (ESI, pos. ion) m/z: 364.2 (M+1).

Example 351

N-tert-butyl-8-(4-methoxy-6,7-dihydro-1H-pyrrolo[3,2-c]pyridin-2-yl)-3-methyl-2-quinoxalinamine

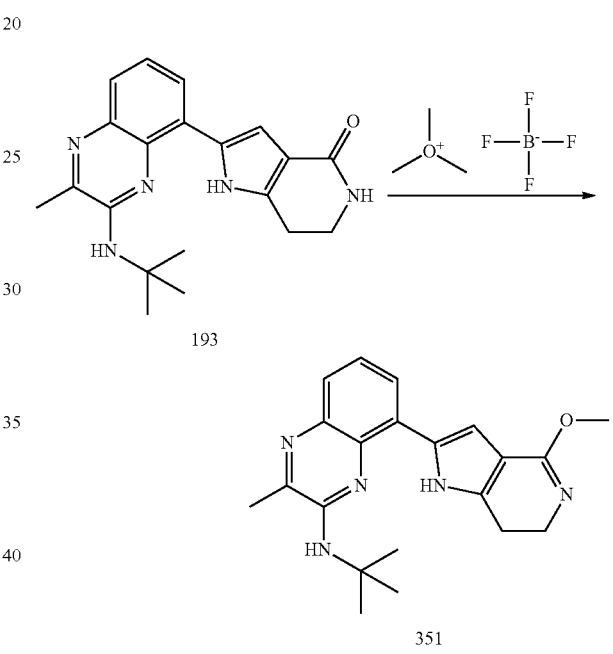

Trimethyloxonium tetrafluoroborate (239 mg, 1.617 mmol, Sigma-Aldrich) was added to a red slurry of 2-(3-(tert-butylamino)-2-methylquinoxalin-5-yl)-6,7-dihydro-1H-pyrrolo[3,2-c]pyridin-4(5H)-one (193, 113 mg, 0.32 mmol) in DCM (10 mL) and the resulting mixture was stirred at RT for 1 h when the solid had begun to stick to the side of the flask; MeOH (2 mL) was added to bring all the solid into solution and stir at RT for 16 h when a mixture of product and starting material was observed via lcms. The crude product was adsorbed onto silica and was purified via automated flash chromatography (silica gel) with 100% DCM to 4% 2 M NH$_3$ in MeOH/DCM to give N-(tert-butyl)-8-(4-methoxy-6,7-dihydro-1H-pyrrolo[3,2-c]pyridin-2-yl)-3-methylquinoxalin-2-amine (351, 16 mg, 14% yield) as a rust colored solid. $^1$H NMR (400 MHz, CDCl$_3$) δ ppm 1.66 (s, 9H) 2.55 (s, 3H) 2.82 (t, J=7.73 Hz, 2H) 3.84 (t, J=7.73 Hz, 2H) 3.88 (s, 3H) 4.84 (s, 1H) 6.80 (d, J=1.96 Hz, 1H) 7.36 (t, J=7.82 Hz, 1H) 7.63 (dd, J=8.12, 1.27 Hz, 1H) 7.91 (dd, J=7.63, 1.37 Hz, 1H) 12.54 (br. s., 1H). $^{13}$C NMR (101 MHz, CDCl$_3$) δ ppm 21.30, 21.51, 28.68, 46.23, 51.32, 52.37, 100.94, 110.83, 124.51, 124.72, 125.43, 126.11, 131.26, 135.55, 136.41, 136.91, 145.19, 148.40, 161.58. MS (ESI, pos. ion) m/z: 364.4 (M+1).

Example 352

(6R)-2-(3-(cyclopropylamino)-6-fluoro-2-methyl-5-quinoxalinyl)-6-((1R)-1-hydroxyethyl)-5,6-dihydropyrrolo[3,4-b]pyrrol-4(1H)-one

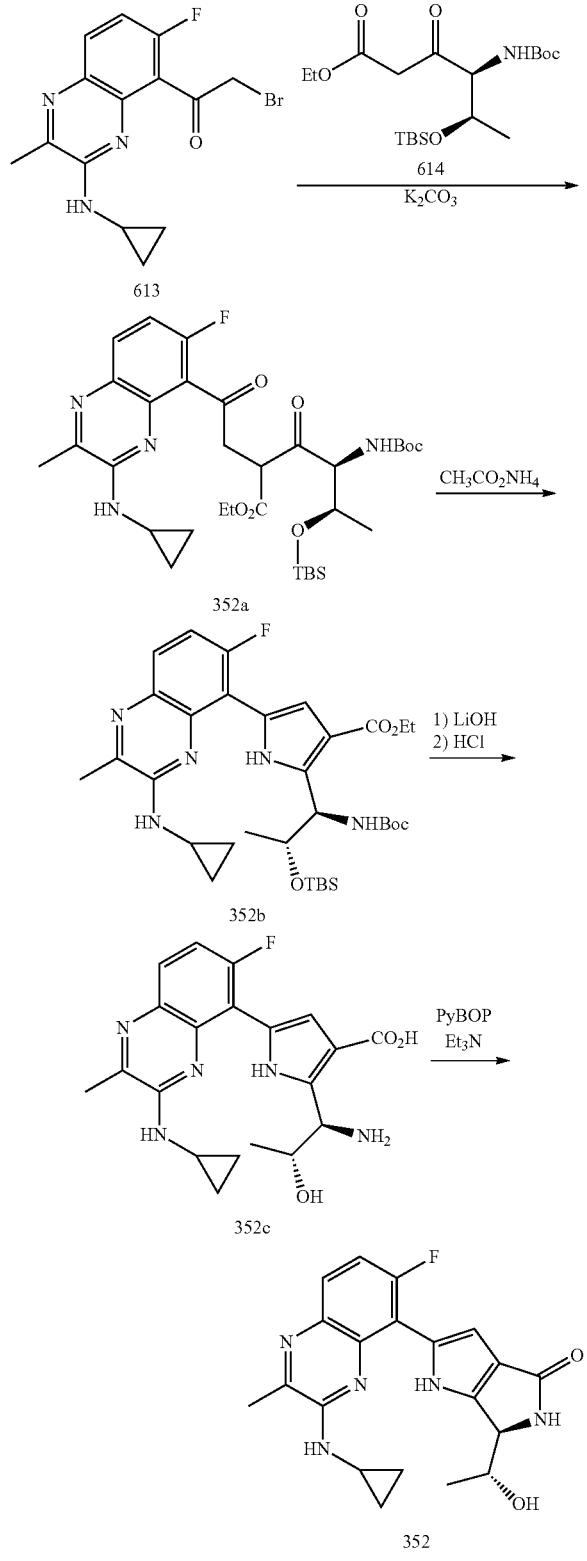

Preparation of (R)-2-(3-(cyclopropylamino)-6-fluoro-2-methylquinoxalin-5-yl)-6-((R)-1-hydroxyethyl)-5,6-dihydropyrrolo[3,4-b]pyrrol-4(1H)-one (352b)

A solution of 2-bromo-1-(3-(cyclopropylamino)-6-fluoro-2-methylquinoxalin-5-yl)ethanone (613) (566 mg, 1.674 mmol) and (4S,5R)-ethyl 4-((tert-butoxycarbonyl)amino)-5-((tert-butyldimethylsilyl)oxy)-3-oxohexanoate (614) (995 mg, 2.465 mmol) in DMF (9 mL) was cooled in an ice-water bath and treated with $K_2CO_3$ (509 mg, 3.68 mmol) The mixture was stirred for 16 h at RT then heated at 60° C. in an oil bath for 4 h. The mixture was extracted into $CHCl_3$ (3×100 mL) from saturated aq. $NaHCO_3$ (100 mL), dried ($Na_2SO_4$), concentrated, and purified by flash chromatography on silica gel (40 g) eluting with a gradient of 0-10% EtOAc in DCM to give (4S,5R)-ethyl 4-((tert-butoxycarbonyl)amino)-5-((tert-butyldimethylsilyl)oxy)-2-(2-(3-(cyclopropylamino)-6-fluoro-2-methylquinoxalin-5-yl)-2-oxoethyl)-3-oxohexanoate (352a) (247 mg, 0.374 mmol, 22% yield) as a yellow foam. LC-MS m/z 661.1, [M+H]. A solution of (4S,5R)-ethyl 4-((tert-butoxycarbonyl)amino)-5-((tert-butyldimethylsilyl)oxy)-2-(2-(3-(cyclopropylamino)-6-fluoro-2-methylquinoxalin-5-yl)-2-oxoethyl)-3-oxohexanoate (352a) (247 mg, 0.374 mmol) in EtOH (3.0 mL) and AcOH (1.5 mL) was treated with $NH_4OAc$ (Aldrich) (432 mg, 5.61 mmol). The resulting yellow solution was heated at 60° C. for 64 h. The mixture was concentrated and extracted into EtOAc (3×100 mL) from saturated aq. $NaHCO_3$ (150 mL). The organic extracts were dried ($Na_2SO_4$), concentrated, and purified by flash chromatography on silica gel (gradient: 0-15% EtOAc in DCM) to give the title compound (352b) as a yellow foam (184.5 mg). LC-MS m/z 642.2, [M+H]$^+$.

Preparation of (6R)-2-(3-(cyclopropylamino)-6-fluoro-2-methyl-5-quinoxalinyl)-6-((1R)-1-hydroxyethyl)-5,6-dihydropyrrol-4-b]pyrrol-4(1H)-one (352)

The yellow foam (352b) (184.5 mg) in 1,4-dioxane (6.0 mL) was treated with 1.0 M aq. LiOH (3.0 mL, 3.0 mmol). The mixture was heated at 100° C. for 16 h. The mixture was lyophilized to give a yellow solid containing m/z (ESI, +ve) 614.1 (M+H). The yellow solid was dissolved in 1 mL of dioxane and treated with a solution of 4 M HCl in 1,4-dioxane (5 mL) with a few drops of water added to aid solubility. The mixture was stirred at RT for 4 h, after which time bis-deprotection was observed by LC-MS. The mixture was lyophilized to give 2-((1R,2R)-1-amino-2-hydroxypropyl)-5-(3-(cyclopropylamino)-6-fluoro-2-methylquinoxalin-5-yl)-1H-pyrrole-3-carboxylic acid (352c) as a brown solid. A solution of the 2-((1R,2R)-1-amino-2-hydroxypropyl)-5-(3-(cyclopropylamino)-6-fluoro-2-methylquinoxalin-5-yl)-1H-pyrrole-3-carboxylic acid (352c) in DMF (3.0 mL) was treated with TEA (0.20 mL, 1.44 mmol) followed by PyBOP (NovaBiochem) (300 mg, 0.57 mmol). The mixture was stirred at RT for 16 h. The mixture was concentrated, dissolved in DMSO (5.0 mL), and purified by preparative HPLC (Gradient: 10-100% MeCN in $H_2O$, modified with 0.1% TFA) to give (R)-2-(3-(cyclopropylamino)-6-fluoro-2-methylquinoxalin-5-yl)-6-((R)-1-hydroxyethyl)-5,6-dihydropyrrolo[3,4-b]pyrrol-4(1H)-one bis(2,2,2-trifluoroacetate) (352) (54 mg, 0.089 mmol) as a red gum. LC-MS m/z 382.1, [M+H]$^+$; $^{19}$F NMR (DMSO-$d_6$; 376 MHz): δ −108.08 (s, 1F), −74.95 (s, 6F).

Examples 353 and 354

(6S)-2-(3-(cyclopropylamino)-6-fluoro-2-methyl-5-quinoxalinyl)-6-((1S)-1-hydroxyethyl)-5,6-dihydropyrrolo[3,4-b]pyrrol-4(1H)-one and (6R)-6-((benzyloxy)methyl)-2-(2-methyl-3-((1-methylcyclopropyl)amino)-5-quinoxalinyl)-5,6-dihydropyrrolo[3,4-b]pyrrol-4 (1H)-one|(6S)-6-((benzyloxy)methyl)-2-(2-methyl-3-((1-methylcyclopropyl)amino)-5-quinoxalinyl)-5,6-dihydropyrrolo[3,4-b]pyrrol-4 (1H)-one

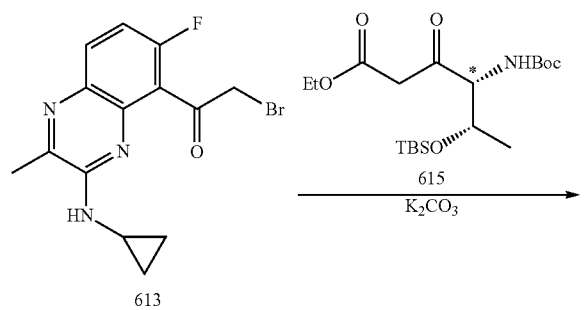

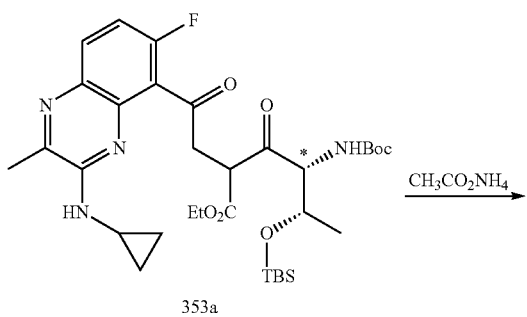

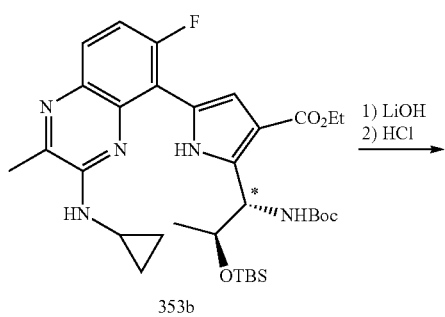

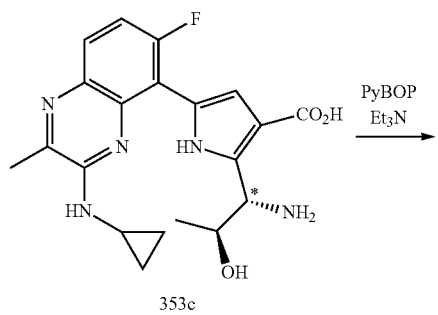

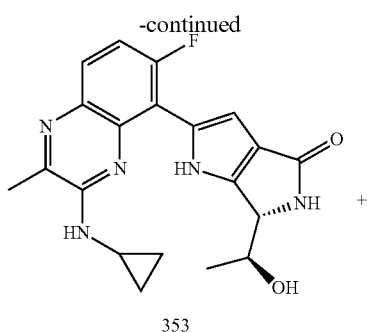

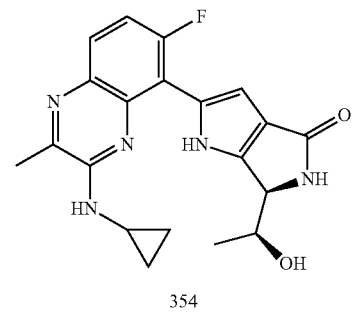

Preparation of ethyl 5-(3-(cyclopropylamino)-6-fluoro-2-methylquinoxalin-5-yl)-2-((5S,6S)-2,2,3,3,5,10,10-heptamethyl-8-oxo-4,9-dioxa-7-aza-3-silaundecan-6-yl)-1H-pyrrole-3-carboxylate (353b)

This compound (2.43 g, 73% yield) as a bright yellow crystalline solid was prepared according to the procedures described for Intermediate 352b, using 2-bromo-1-(3-(cyclopropylamino)-6-fluoro-2-methylquinoxalin-5-yl)ethanone (613) (1.82 g, 5.39 mmol) and (4R,5S)-ethyl 4-((tert-butoxycarbonyl)amino)-5-((tert-butyldimethylsilyl)oxy)-3-oxohexanoate (615) (2.61 g, 6.47 mmol) and $K_2CO_3$ (0.931 g, 6.73 mmol) in DMF (10 mL) as the strafing materials, followed by subsequent treatment of the resulting (4R,5S)-ethyl 4-((tert-butoxycarbonyl)amino)-5-((tert-butyldimethylsilyl)oxy)-2-(2-(3-(cyclopropylamino)-6-fluoro-2-methylquinoxalin-5-yl)-2-oxoethyl)-3-oxohexanoate (353a) (3.42 g, 96% yield, LC-MS m/z 661.1, [M+H]$^+$) with $NH_4OAc$ (5.98 g, 78 mmol) in 10 mL of EtOH and 5 mL of AcOH. $^{19}F$ NMR (DMSO-d$_6$; 376 MHz): δ −110.91 (s, 1F). LC-MS m/z 642.2, [M+H]$^+$.

Preparation of (S)-2-(3-(cyclopropylamino)-6-fluoro-2-methylquinoxalin-5-yl)-6-((S)-1-hydroxyethyl)-5,6-dihydropyrrolo[3,4-b]pyrrol-4(1H)-one (353) and (R)-2-(3-(cyclopropylamino)-6-fluoro-2-methylquinoxalin-5-yl)-6-((S)-1-hydroxyethyl)-5,6-dihydropyrrolo[3,4-b]pyrrol-4(1H)-one (354)

A solution of ethyl 5-(3-(cyclopropylamino)-6-fluoro-2-methylquinoxalin-5-yl)-2-((5S,6S)-2,2,3,3,5,10,10-heptamethyl-8-oxo-4,9-dioxa-7-aza-3-silaundecan-6-yl)-1H-pyrrole-3-carboxylate (353b) (2.43 g, 3.79 mmol) in 1,4-dioxane (40 mL) was treated with 1.0 M aq. LiOH (19 mL, 19 mmol). The resulting orange solution was stirred at RT for 16 h. The mixture was then heated at 85° C. for 6 h, and then at 65° C. for 64 h. The resulting suspension was concentrated to give a dark solid. Then solid was dissolved in a 4.0 M solution of HCl in 1,4-dioxane (20 mL). The resulting dark red solution was stirred at RT for 45 min. The mixture was concentrated and the dark red residue containing 354c was dissolved in a mixture of 1,4-dioxane (20 mL) and water (10 mL). TEA (1.2 mL, 8 mmol) was added and the mixture was lyophilized to give a brown solid. A solution of the brown solid in DMF (40 mL) was treated with TEA (2.64 mL, 18.94 mmol) followed by PyBOP (NovaBiochem) (3.94 g, 7.57 mmol). The mixture was stirred at RT for 1 h. The mixture was concentrated and water (100 mL) was added. A brown gum separated out. The mixture was stirred and heated at 100° C. for 1 h, and then cooled in an ice-water bath. Saturated aq. NaHCO$_3$ (5 mL) was added and the mixture was stirred for 15 min. The aq. layer was decanted from the flask (product adhered to the sides of the vessel), and the product was washed with water (10 mL). The product was dissolved in 1,4-dioxane (25 mL), filtered, and concentrated. The resulting gum was dissolved in DMSO (10 mL) and purified by preparative HPLC (Gradient: 10-100% MeCN in H$_2$O, modified with 0.1% TFA). The major product was concentrated, neutralized with 2 M NH$_3$ in MeOH, and lyophilized from 1,4-dioxane to give (S)-2-(3-(cyclopropylamino)-6-fluoro-2-methylquinoxalin-5-yl)-6-((S)-1-hydroxyethyl)-5,6-dihydropyrrolo[3,4-b]pyrrol-4(1H)-one (353) (342 mg) as a yellow solid. LC-MS m/z 382.0, [M+H]$^+$; $^{19}$F NMR (DMSO-d$_6$; 376 MHz): δ −108.03 (s, 1F). A slower eluting minor product was also isolated from the preparative HPLC. This product was concentrated, neutralized with 2 M NH$_3$ in MeOH, and lyophilized from 1,4-dioxane to give (R)-2-(3-(cyclopropylamino)-6-fluoro-2-methylquinoxalin-5-yl)-6-((S)-1-hydroxyethyl)-5,6-dihydropyrrolo[3,4-b]pyrrol-4(1H)-one (354) (29 mg) as a yellow solid. LC-MS m/z 382.0, [M+H]$^+$; $^{19}$F NMR (DMSO-d$_6$; 376 MHz): δ −108.79 (s, 1F).

Example 355

6-((benzyloxy)methyl)-2-(2-methyl-3-((1-methylcyclopropyl)amino)quinoxalin-5-yl)-5,6-dihydropyrrolo[3,4-b]pyrrol-4 (1H)-one

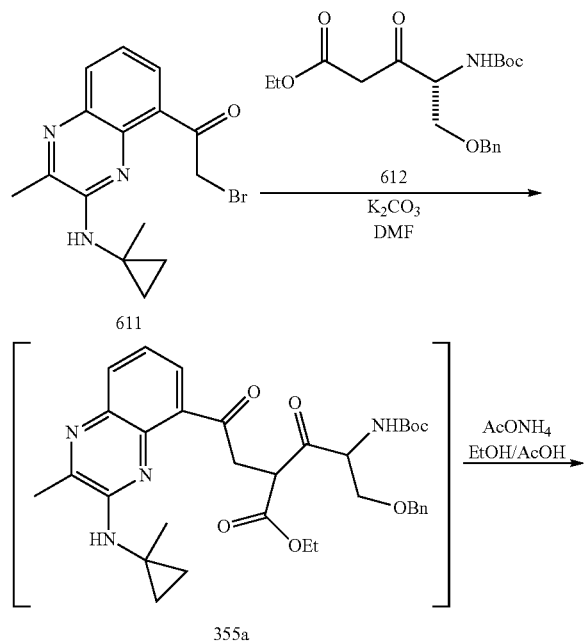

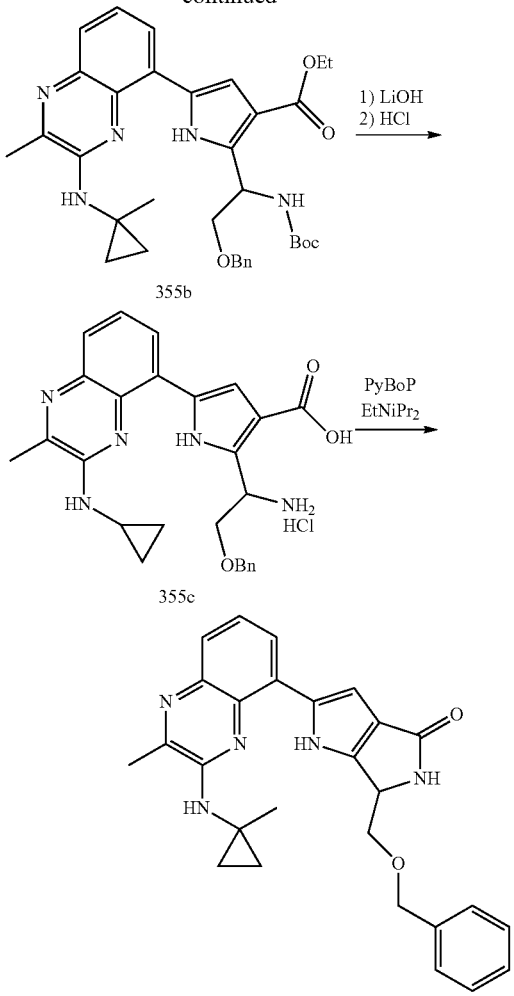

Preparation of ethyl 2-(((tert-butoxycarbonyl)amino) methyl)-5-(3-(tert-butylamino)-2-methylquinoxalin-5-yl)-1H-pyrrole-3-carboxylate (355b)

To a 50-mL round-bottomed flask was added (R)-ethyl 5-(benzyloxy)-4-((tert-butoxycarbonyl)amino)-3-oxopentanoate (612) (0.51 g, 1.19 mmol), K$_2$CO$_3$ (0.41 g, 2.97 mmol), 2-bromo-1-(2-methyl-3-((1-methylcyclopropyl)amino)quinoxalin-5-yl)ethanone (611) (0.63 g, 1.90 mmol), and DMF (4 mL). The reaction mixture was stirred at RT for 1 h. The reaction mixture was diluted with sat NH$_4$Cl (5 mL) and extracted with EtOAc (10 mL). The organic extract was washed with water (5 mL), dried over Na$_2$SO$_4$, and concentrated. Ethyl 5-(benzyloxy)-4-((tert-butoxycarbonyl)amino)-2-(2-(2-methyl-3-((1-methylcyclopropyl)amino)quinoxalin-5-yl)-2-oxoethyl)-3-oxopentanoate (355a) was obtained as a light yellow oil and used without further purification. m/z (ESI, +ve) 619.3 (M+H)$^+$. To a 15-mL glass tube was added ethyl 5-(benzyloxy)-4-((tert-butoxycarbonyl)amino)-2-(2-(2-methyl-3-((1-methylcyclopropyl)amino)quinoxalin-5-yl)-2-oxoethyl)-3-oxopentanoate (355a), crude from previous step, NH$_4$OAc (0.37 g, 4.75 mmol), EtOH (5 mL), and AcOH (1.5 mL). The tube was sealed and heated at 45° C. for 16 h. The reaction mixture was cooled to RT and was concentrated to half of its volume. The mixture was diluted with EtOAc (10 mL) and water (5 mL). The organic extract was washed with NaOH (1 N, 5 mL), water (5 mL), brine (5 mL), dried over $Na_2SO_4$, and concentrated. The crude material was absorbed onto a plug of silica gel and purified by chromatography through a Redi-Sep pre-packed silica gel column (40 g), eluting with a gradient of 10-30% EtOAc in hexanes to give ethyl 2-(2-(benzyloxy)-1-((tert-butoxycarbonyl)amino)ethyl)-5-(2-methyl-3-((1-methylcyclopropyl)amino)quinoxalin-5-yl)-1H-pyrrole-3-carboxylate (355b) (0.28 g, 40% yield) as a yellow solid. $^1$H NMR (400 MHz, DMSO-$d_6$) δ 11.75 (br. s., 1H), 8.06 (d, J=1.96 Hz, 1H), 7.92 (dd, J=1.17, 7.63 Hz, 1H), 7.62 (dd, J=1.17, 8.02 Hz, 1H), 7.49 (s, 1H), 7.39 (t, J=7.82 Hz, 1H), 7.24-7.31 (m, 5H), 7.12 (br. d, J=9.20 Hz, 1H), 5.61-5.72 (m, 1H), 4.44-4.58 (m, 2H), 4.23 (q, J=7.04 Hz, 2H), 3.62-3.67 (m, 2H), 2.49 (s, 3H), 1.58 (s, 3H), 1.41 (s, 9H), 1.29 (t, J=7.04 Hz, 3H), 0.97-1.02 (m, 2H), 0.84-0.89 (m, 2H). m/z (ESI, +ve) 600.2 (M+H)$^+$.

Preparation of 2-(1-amino-2-(benzyloxy)ethyl)-5-(2-methyl-3-((1-methylcyclopropyl)amino)quinoxalin-5-yl)-1H-pyrrole-3-carboxylic acid hydrochloride (355c)

A glass microwave reaction vessel was charged with ethyl 2-(2-(benzyloxy)-1-((tert-butoxycarbonyl)amino)ethyl)-5-(2-methyl-3-((1-methylcyclopropyl)amino)quinoxalin-5-yl)-1H-pyrrole-3-carboxylate (355b) (0.28 g, 0.47 mmol), LiOH hydrated (0.10 g, 2.38 mmol), dioxane (4 mL), and water (1 mL). The reaction mixture was stirred and heated in an Initiator microwave reactor (Personal Chemistry, Biotage AB, Inc., Uppsala, Sweden) at 110° C. for 4 h. The solvent was removed and the product used without further purification. The orange solid was suspended in HCl (4 mL, 4 N in dioxane) and the reaction mixture was stirred at RT for 1 h. The reaction mixture was concentrated to half of its volume and the orange solid obtained was filtered, washed with ether, and dried to give 2-(1-amino-2-(benzyloxy)ethyl)-5-(2-methyl-3-((1-methylcyclopropyl)amino)quinoxalin-5-yl)-1H-pyrrole-3-carboxylic acid hydrochloride (355c), which was used as crude material and based on theoretical yield.

Preparation 6-((benzyloxy)methyl)-2-(2-methyl-3-((1-methylcyclopropyl)amino)quinoxalin-5-yl)-5,6-dihydropyrrolo[3,4-b]pyrrol-4(1H)-one (355)

To a 50-mL round-bottomed flask was added 2-(1-amino-2-(benzyloxy)ethyl)-5-(2-methyl-3-((1-methylcyclopropyl)amino)quinoxalin-5-yl)-1H-pyrrole-3-carboxylic acid hydrochloride (355c) (0.24 g, 0.48 mmol), DCM (6 mL), DMF (6 mL), DIEA (0.25 mL, 1.43 mmol), and (benzotriazol-1-yloxy)tripyrrolidinophosphonium hexafluorophosphate (0.25 g, 0.48 mmol) (Sigma-Aldrich Chemical Company, Inc.). The reaction mixture was stirred at RT for 30 min, concentrated to half of its volume, and diluted with EtOAc (10 mL). The organic extract was washed with sat NaHCO$_3$ (5 mL), dried over Na$_2$SO$_4$, and concentrated. The crude material was absorbed onto a plug of silica gel and purified by chromatography through a Redi-Sep pre-packed silica gel column (12 g), eluted with a gradient of 0-3% MeOH in DCM to provide 6-((benzyloxy)methyl)-2-(2-methyl-3-((1-methylcyclopropyl)amino)quinoxalin-5-yl)-5,6-dihydropyrrolo[3,4-b]pyrrol-4(1H)-one (355) (124 mg, 57% yield, 50% ee) as a light yellow solid. $^1$H NMR (400 MHz, DMSO-d$_6$) δ 12.84 (s, 1H), 8.03 (dd, J=0.78, 7.43 Hz, 1H), 7.83 (s, 1H), 7.65 (s, 1H), 7.60 (dd, J=0.78, 8.02 Hz, 1H), 7.25-7.38 (m, 6H), 7.05 (s, 1H), 4.76 (t, J=5.67 Hz, 1H), 4.54 (s, 2H), 3.59-3.66 (m, 1H), 3.50-3.57 (m, 1H), 2.48 (s, 3H), 1.39 (s, 3H), 0.82-0.88 (m, 2H), 0.76-0.82 (m, 2H). m/z (ESI, +ve) 454.2 (M+H)$^+$.

Example 357

2-(2-Methyl-3-((1-methylcyclopropyl)amino)quinoxalin-5-yl)-5,6-dihydropyrrolo[3,4-b]pyrrol-4(1H)-one

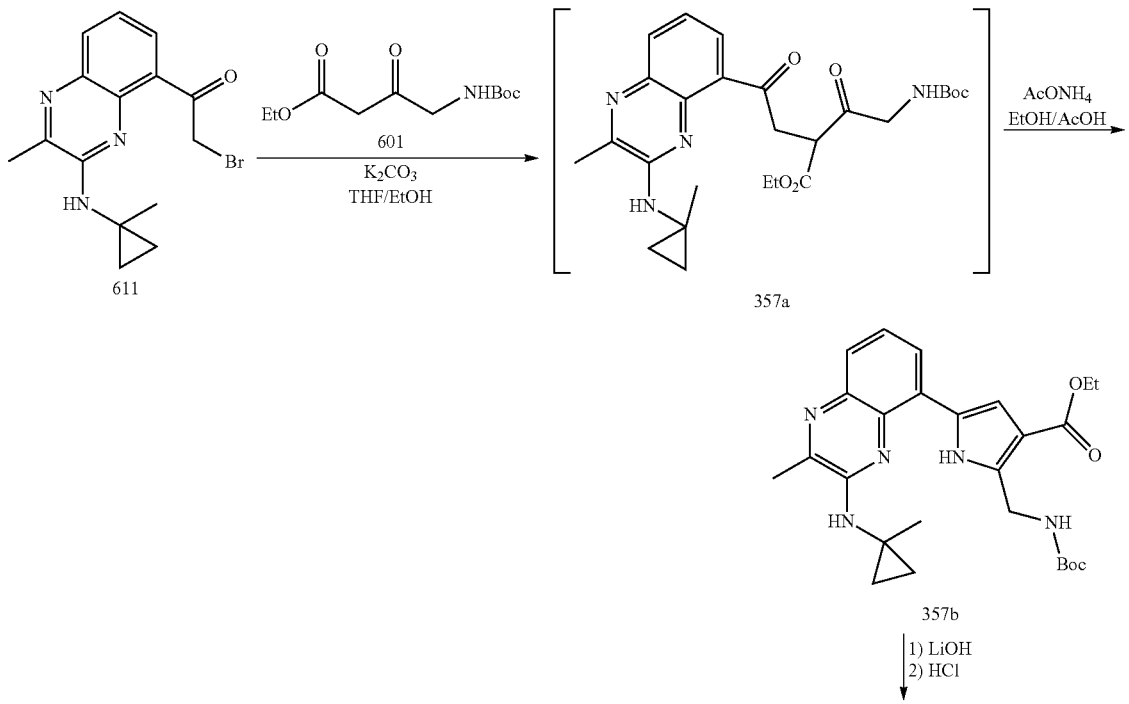

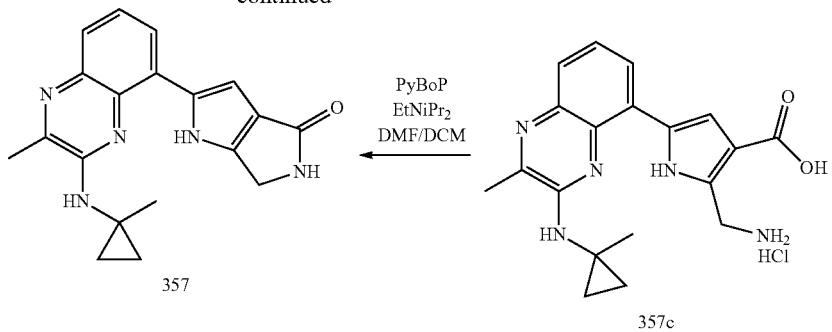

Preparation of ethyl 2-(((tert-butoxycarbonyl)amino) methyl)-5-(2-methyl-3-((1-methylcyclopropyl) amino)quinoxalin-5-yl)-1H-pyrrole-3-carboxylate (357b)

To a 25-mL round-bottomed flask was added ethyl 4-((tert-butoxycarbonyl)amino)-3-oxobutanoate (601) (0.60 g, 2.44 mmol), $K_2CO_3$ (0.56 g, 4.07 mmol), 2-bromo-1-(2-methyl-3-((1-methylcyclopropyl)amino)quinoxalin-5-yl)ethanone (611) (0.54 g, 1.63 mmol), THF (6 mL), and EtOH (6 mL). The reaction mixture was stirred at RT for 16 h and diluted with sat $NH_4Cl$ (5 mL) and extracted with EtOAc (10 mL). The organic extract was washed with water (5 mL), dried over $Na_2SO_4$ and concentrated. Ethyl 4-((tert-butoxycarbonyl)amino)-2-(2-(2-methyl-3-((1-methylcyclopropyl)amino) quinoxalin-5-yl)-2-oxoethyl)-3-oxobutanoate (357a) was obtained as a light yellow oil and used without further purification. m/z (ESI, +ve) 499.2 (M+H)$^+$. To a 15-mL glass tube was added ethyl 4-((tert-butoxycarbonyl)amino)-2-(2-(2-methyl-3-((1-methylcyclopropyl)amino)quinoxalin-5-yl)-2-oxoethyl)-3-oxobutanoate (357a), crude from previous step, $NH_4OAc$ (0.50 g, 6.51 mmol), EtOH (3 mL), and AcOH (1 mL). The tube was sealed and heated at 50° C. for 3 h. The reaction mixture was cooled to RT and was concentrated to half of its volume. The mixture was diluted with EtOAc (10 mL) and water (5 mL). The organic extract was washed with NaOH (1 N, 5 mL), water (5 mL), brine (5 mL), dried over $Na_2SO_4$, and concentrated. The crude material was absorbed onto a plug of silica gel and purified by chromatography through a Redi-Sep pre-packed silica gel column (24 g), eluting with a gradient of 10% to 30% EtOAc in hexanes to give ethyl 2-4(tert-butoxycarbonyl)amino)methyl)-5-(2-methyl-3-((1-methylcyclopropyl)amino)quinoxalin-5-yl)-1H-pyrrole-3-carboxylate (357b) (0.25 g, 32% yield) as a yellow solid. $^1$H NMR (400 MHz, DMSO-$d_6$) δ 12.24 (br. s., 1H), 7.97 (dd, J=1.17, 7.63 Hz, 1H), 7.54-7.63 (m, 3H), 7.34 (t, J=7.82 Hz, 1H), 6.94 (br. s., 1H), 4.51 (d, J=5.28 Hz, 2H), 4.22 (q, J=7.17 Hz, 2H), 2.48 (s, 3H), 1.56 (s, 3H), 1.38 (s, 9H), 1.29 (t, J=7.00 Hz, 3H), 0.91-0.94 (m, 2H), 0.84-0.89 (m, 2H). m/z (ESI, +ve) 480.4 (M+H)$^+$.

Preparation of 2-(aminomethyl)-5-(2-methyl-3-((1-methylcyclopropyl)amino)quinoxalin-5-yl)-1H-pyrrole-3-carboxylic acid hydrochloride (357c)

This compound was prepared according to the procedures described for Intermediate (334c), using ethyl 24(tert-butoxycarbonyl)amino)methyl)-5-(2-methyl-3-((1-methylcyclopropyl)amino)quinoxalin-5-yl)-1H-pyrrole-3-carboxylate (357b) (0.25 g, 0.53 mmol) as starting material. Crude material was used without further purification. Assumed theoretical conversion. m/z (ESI, +ve) 352.0 (M+H)$^+$.

Preparation 2-(2-methyl-3-((1-methylcyclopropyl) amino)quinoxalin-5-yl)-5,6-dihydropyrrolo[3,4-b] pyrrol-4(1H)-one (357)

This compound (87 mg, 50% yield) as a yellow solid was prepared according to the procedures described for Example 334, using 2-(aminomethyl)-5-(2-methyl-3-((1-methylcyclopropyl)amino)quinoxalin-5-yl)-1H-pyrrole-3-carboxylic acid hydrochloride (357c) (0.20 g, 0.53 mmol) as the starting material. $^1$H NMR (400 MHz, DMSO-$d_6$) δ 13.45 (s, 1H), 8.04 (dd, J=1.17, 7.63 Hz, 1H), 7.75 (s, 1H), 7.53-7.64 (m, 2H), 7.38 (t, J=7.82 Hz, 1H), 7.05 (d, J=1.37 Hz, 1H), 4.36 (s, 2H), 2.54 (s, 3H), 1.54 (s, 3H), 0.93-1.03 (m, 2H), 0.81-0.91 (m, 2H). m/z (ESI, +ve) 334.2 (M+H)$^+$.

Example 358

3-Chloro-2-(2-methyl-3-((1-methylcyclopropyl) amino)quinoxalin-5-yl)-5,6-dihydropyrrolo[3,4-b] pyrrol-4(1H)-one

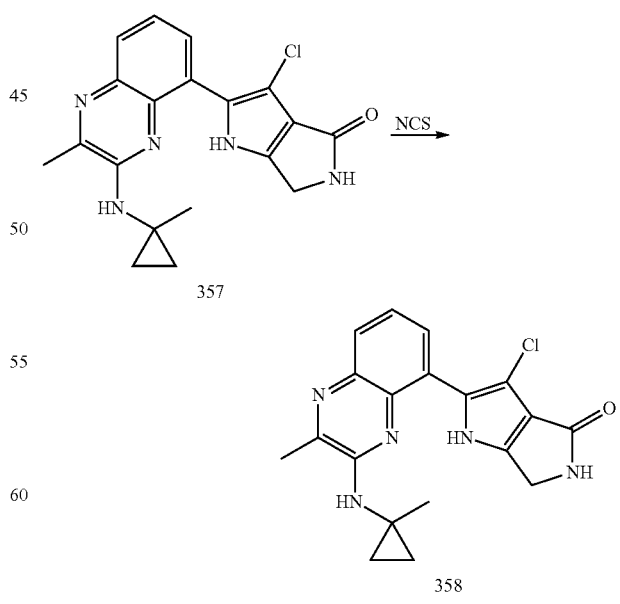

To a 25-mL round-bottomed flask was added 2-(2-methyl-3-((1-methylcyclopropyl)amino)quinoxalin-5-yl)-5,6-dihydropyrrolo[3,4-b]pyrrol-4(1H)-one (357) (68 mg, 0.20 mmol), N-chlorosuccinimide (33 mg, 0.24 mmol) (Alfa-Aesar, Ward Hill, Mass.), and CHCl$_3$ (3 mL). The reaction mixture was stirred at RT for 16 h and partitioned between water (5 mL) and EtOAc (5 mL). The organic extract was washed with brine (5 mL), dried over Na$_2$SO$_4$, and concentrated. The crude material was absorbed onto a plug of silica gel and purified by chromatography through a Redi-Sep pre-packed silica gel column (12 g), eluting with a gradient of 0-3% MeOH in DCM to provide 3-chloro-2-(2-methyl-3-((1-methylcyclopropyl)amino)quinoxalin-5-yl)-5,6-dihydropyrrolo[3,4-b]pyrrol-4(1H)-one (358) (9 mg, 12% yield) as a yellow solid. $^1$H NMR (400 MHz, DMSO-d$_6$) δ 13.75 (s, 1H), 8.40 (dd, J=1.27, 7.73 Hz, 1H), 7.75 (s, 2H), 7.70 (dd, J=1.27, 8.12 Hz, 1H), 7.44 (t, J=7.82 Hz, 1H), 4.32 (s, 2H), 2.51 (s, 3H), 1.45 (s, 3H), 0.90-0.95 (m, 2H), 0.73-0.79 (m, 2H). m/z (ESI, +ve) 368.1 (M+H)$^+$.

Example 360

6-(hydroxymethyl)-2-(2-methyl-3-((1-methylcyclopropyl)amino)quinoxalin-5-yl)-5,6-dihydropyrrolo[3,4-b]pyrrol-4 (1H)-one

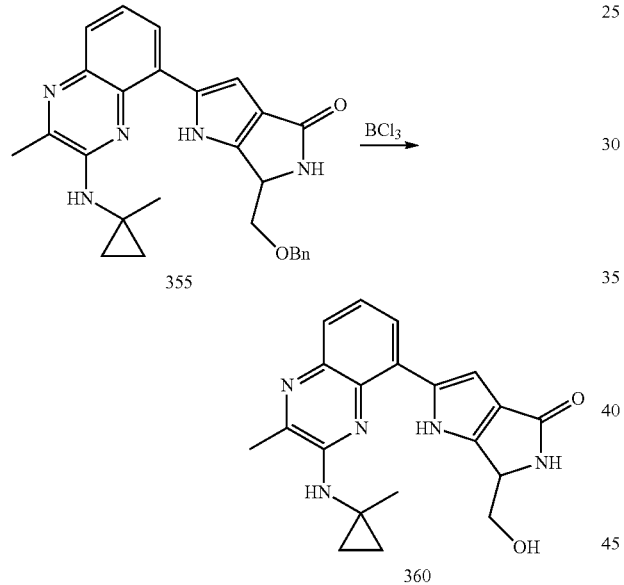

To a 25-mL round-bottomed flask was added 6-((benzyloxy)methyl)-2-(2-methyl-3-((1-methylcyclopropyl)amino) quinoxalin-5-yl)-5,6-dihydropyrrolo[3,4-b]pyrrol-4(1H)-one (355) (0.12 g, 0.27 mmol) and DCM (3 mL). The reaction mixture was cooled to −78° C. and under a N$_2$ atmosphere boron trichloride (0.54 mL, 0.54 mmol, 1 M in DCM) (Sigma-Aldrich Chemical Company, Inc.) was added dropwise. The reaction mixture was stirred at −78° C. for 30 min and at 0° C. for 30 min. The reaction was quenched by the addition of NaHCO$_3$ (100 mg in MeOH, 3 mL) and the solvent was removed under vacuum. The crude material was absorbed onto a plug of silica gel and purified by chromatography through a Redi-Sep pre-packed silica gel column (12 g), eluted with a gradient of 2-7% MeOH in DCM to provide 6-(hydroxymethyl)-2-(2-methyl-3-((1-methylcyclopropyl) amino)quinoxalin-5-yl)-5,6-dihydropyrrolo[3,4-b]pyrrol-4 (1H)-one (360) (70 mg, 71% yield) as a yellow solid. $^1$H NMR (400 MHz, DMSO-d$_6$) δ 12.80 (s, 1H), 8.05 (dd, J=1.17, 7.63 Hz, 1H), 7.68 (s, 1H), 7.63 (s, 1H), 7.61 (dd, J=1.17, 8.02 Hz, 1H), 7.37 (t, J=7.82 Hz, 1H), 7.03 (d, J=1.17 Hz, 1H), 5.20 (t, J=5.48 Hz, 1H), 4.54 (t, J=6.06 Hz, 1H), 3.66 (td, J=5.55, 10.61 Hz, 1H), 3.45-3.57 (m, 1H), 2.51 (s, 3H), 1.54 (s, 3H), 0.88-1.01 (m, 4H). m/z (ESI, +ve) 364.1 (M+H)$^+$.

Examples 361

(S)-6-(hydroxymethyl)-2-(2-methyl-3-((1-methylcyclopropyl)amino)quinoxalin-5-yl)-5,6-dihydropyrrolo[3,4-b]pyrrol-4 (1H)-one; and 362: (R)-6-(hydroxymethyl)-2-(2-methyl-3-((1-methylcyclopropyl) amino)quinoxalin-5-yl)-5,6-dihydropyrrolo[3,4-b] pyrrol-4 (1H)-one

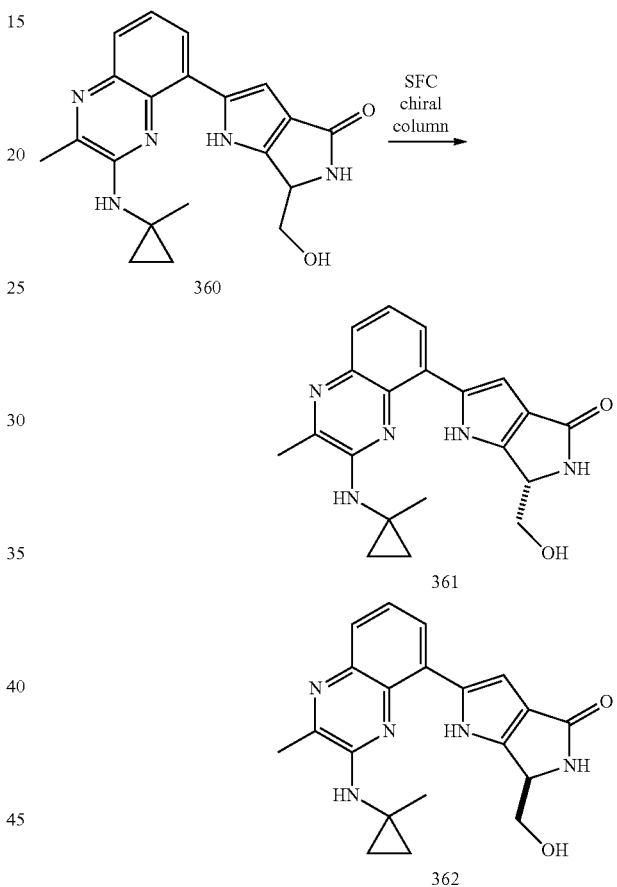

The individual enantiomers of Example 360 were obtained by chiral SFC (Column: Chiralcel OJH (250×20 mm, 5µ); Mobile Phase: 85:15 (A:B); A: Liquid CO$_2$; B: MeOH (20 mM NH$_3$); Flow Rate: 70 mL/min; Oven Temp: 40° C.; Inlet Pressure: 100 bar; Wavelength: 278 nm) to give Example 361 (first eluting product) and Example 362 (second eluting product). Example 361: (S)-6-(hydroxymethyl)-2-(2-methyl-3-((1-methylcyclopropyl)amino)quinoxalin-5-yl)-5,6-dihydropyrrolo[3,4-b]pyrrol-4(1H)-one (25 mg, >99% ee) as a yellow solid. $^1$H NMR (400 MHz, DMSO-d$_6$) δ 12.78 (br. s., 1H), 8.03 (dd, J=0.88, 7.53 Hz, 1H), 7.67 (s, 1H), 7.56-7.63 (m, 2H), 7.35 (t, J=7.82 Hz, 1H), 7.02 (d, J=0.98 Hz, 1H), 5.18 (t, J=5.38 Hz, 1H), 4.53 (t, J=6.26 Hz, 1H), 3.64 (td, J=5.43, 10.66 Hz, 1H), 3.49 (td, J=5.72, 10.86 Hz, 1H), 2.49 (s, 3H), 1.52 (s, 3H), 0.92-0.98 (m, 2H), 0.87-0.91 (m, 2H). m/z (ESI, +ve) 364.1 (M+H)$^+$. Example 362: (R)-6-(hydroxymethyl)-2-(2-methyl-3-((1-methylcyclopropyl)amino) quinoxalin-5-yl)-5,6-dihydropyrrolo[3,4-b]pyrrol-4(1H)-one (29 mg, >99% ee) as a yellow solid. $^1$H NMR (400 MHz, DMSO-d$_6$) δ 12.78 (br. s., 1H), 8.03 (d, J=7.04 Hz, 1H), 7.67 (s, 1H), 7.55-7.63 (m, 2H), 7.35 (t, J=7.82 Hz, 1H), 7.02 (s, 1H), 5.19 (br. s., 1H), 4.53 (t, J=6.16 Hz, 1H), 3.64 (dd, J=6.16, 10.27 Hz, 1H), 3.49 (dd, J=6.55, 10.27 Hz, 1H), 2.49 (s, 3H), 1.52 (s, 3H), 0.92-0.98 (m, 2H), 0.87-0.91 (m, 2H). m/z (ESI, +ve) 364.1 (M+H)$^+$.

Example 363

2-(3-(cyclopropylamino)-2-methylquinoxalin-5-yl)-5,6-dihydropyrrolo[3,4-b]pyrrol-4(1H)-one

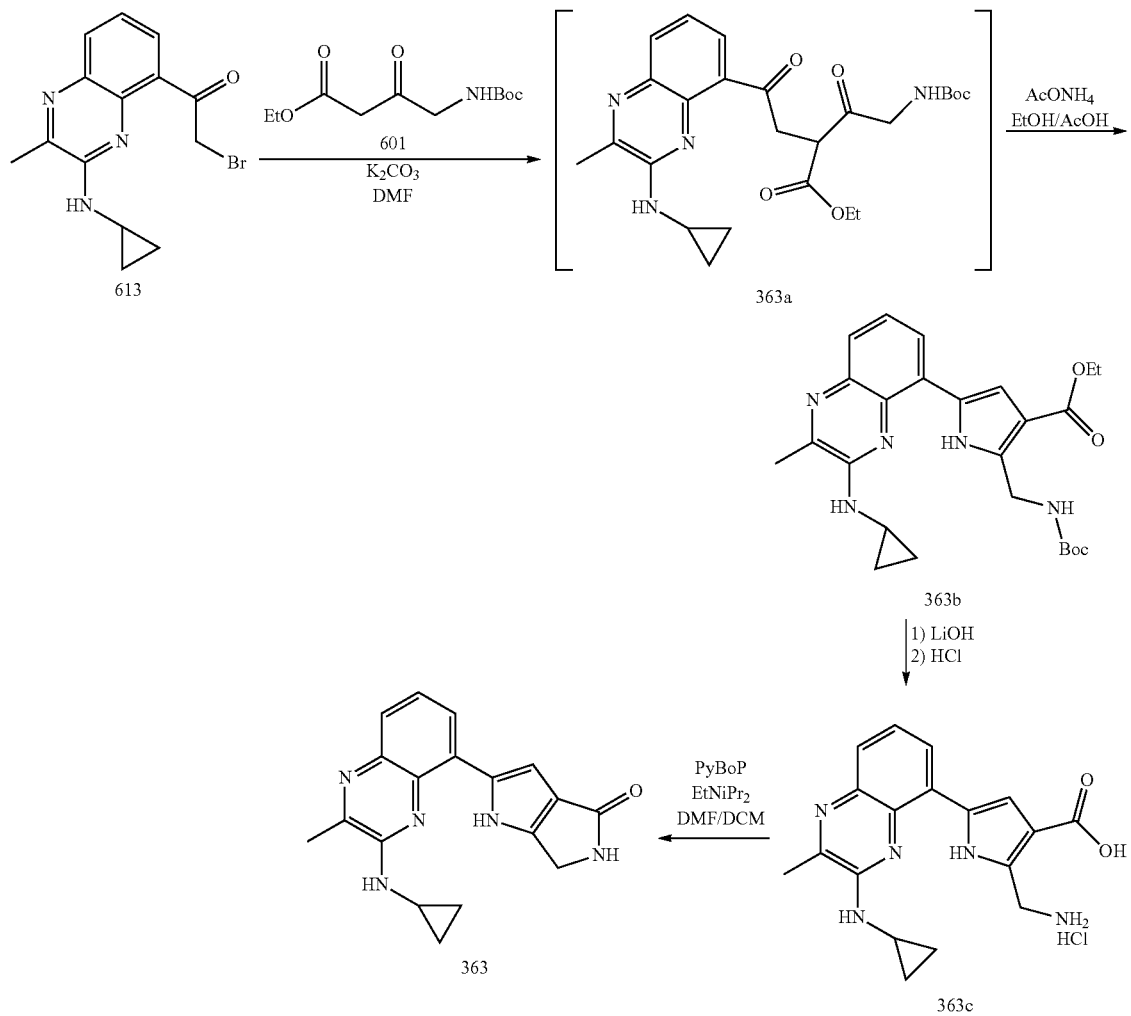

noxalin-5-yl)ethanone (613) (0.49 g, 1.53 mmol) in DMF (4 mL) as starting material, followed by subsequent treatment of ethyl 4-((tert-butoxycarbonyl)amino)-2-(2-(3-(cyclopropylamino)-2-methylquinoxalin-5-yl)-2-oxoethyl)-3-oxobutanoate (363a: m/z (ESI, +ve) 485.1 (M+H)$^+$) with NH$_4$OAc (0.36 g, 4.6 mmol) in EtOH (6 mL) and AcOH (1.5 mL). $^1$H NMR (400 MHz, DMSO-d$_6$) δ 12.56 (br. s., 1H), 7.60 (dd, J=0.98, 8.02 Hz, 1H), 7.54 (d, J=1.96 Hz, 1H), 7.31-7.39 (m, 2H), 7.06 (br. s., 1H), 4.50 (d, J=5.48 Hz, 2H), 4.22 (q, J=7.04 Hz, 2H), 3.03 (br. s., 1H), 2.49 (s, 3H), 1.38 (s, 9H), 1.30 (t, J=7.04 Hz, 3H), 0.96-1.02 (m, 2H), 0.62-0.69 (m, 2H). m/z (ESI, +ve) 466.2 (M+H)$^+$.

Preparation of ethyl 2-(((tert-butoxycarbonyl)amino)methyl)-5-(3-(cyclopropylamino)-2-methylquinoxalin-5-yl)-1H-pyrrole-3-carboxylate (363b)

This compound (0.25 g, 35% yield) as a yellow solid was prepared according to the procedures described for Intermediate 355b, using 4-((tert-butoxycarbonyl)amino)-3-oxobutanoate (601) (0.45 g, 1.84 mmol), K$_2$CO$_3$ (0.53 g, 3.83 mmol), 2-bromo-1-(3-(cyclopropylamino)-2-methylqui- Preparation of 2-(aminomethyl)-5-(3-(cyclopropylamino)-2-methylquinoxalin-5-yl)-1H-pyrrole-3-carboxylic acid hydrochloride (363c)

A glass microwave reaction vessel was charged with ethyl 2-4(tert-butoxycarbonyl)amino)methyl)-5-(3-(cyclopropylamino)-2-methylquinoxalin-5-yl)-1H-pyrrole-3-carboxylate (363b) (0.24 g, 0.52 mmol), LiOH hydrated (0.06 g, 1.56 mmol), dioxane (3 mL), and water (1 mL). The reaction mixture was stirred and heated in an Initiator microwave reactor (Personal Chemistry, Biotage AB, Inc., Uppsala, Sweden) at 110° C. for 2 h. The solvent was removed and the product used without further purification. The orange solid was suspended in HCl (4 mL, 4N in dioxane) and the reaction mixture was stirred at RT for 1.5 h. The mixture was concentrated to half of its volume and the orange solid obtained was filtered, washed with ether and dried to give 2-(aminomethyl)-5-(3-(cyclopropylamino)-2-methylquinoxalin-5-yl)-1H-pyrrole-3-carboxylic acid hydrochloride (363c), which was used as crude material and based on theoretical yield.

Preparation 2-(2-methyl-3-((1-methylcyclopropyl)amino)quinoxalin-5-yl)-5,6-dihydropyrrolo[3,4-b]pyrrol-4(1H)-one (363)

To a 25-mL round-bottomed flask was added 2-(aminomethyl)-5-(3-(cyclopropylamino)-2-methylquinoxalin-5-yl)-1H-pyrrole-3-carboxylic acid hydrochloride (363c) (0.19 g, 0.52 mmol), DCM (6 mL), DMF (6 mL), DIEA (0.27 mL, 1.57 mmol), and (benzotriazol-1-yloxy)tripyrrolidinophosphonium hexafluorophosphate (0.30 g, 0.58 mmol) (Sigma-Aldrich Chemical Company, Inc.). The reaction mixture was stirred at RT for 16 h, concentrated to half of its volume, and poured over water. The yellow solid obtained was filtered, washed with water, ether, and dried in a vacuum over at 50° C. for 16 h. 2-(2-Methyl-3-((1-methylcyclopropyl)amino)-quinoxalin-5-yl)-5,6-dihydropyrrolo[3,4-b]pyrrol-4(1H)-one (363) (0.13 g, 77% yield) was obtained a yellow solid. $^1$H NMR (400 MHz, DMSO-$d_6$) δ 13.16 (s, 1H), 8.01 (dd, J=0.68, 7.53 Hz, 1H), 7.63 (s, 1H), 7.61 (dd, J=0.78, 8.02 Hz, 1H), 7.53 (s, 1H), 7.36 (t, J=7.73 Hz, 1H), 7.04 (d, J=1.17 Hz, 1H), 4.31 (s, 2H), 2.89 (br. s, 1H), 2.52 (s, 3H), 0.87-0.94 (m, 2H), 0.67-0.74 (m, 2H). m/z (ESI, +ve) 320.1 (M+H)$^+$.

Example 364

6-((benzyloxy)methyl)-2-(2-methyl-3-((1-methylcyclopropyl)amino)quinoxalin-5-yl)-5,6-dihydropyrrolo[3,4-b]pyrrol-4(1H)-one

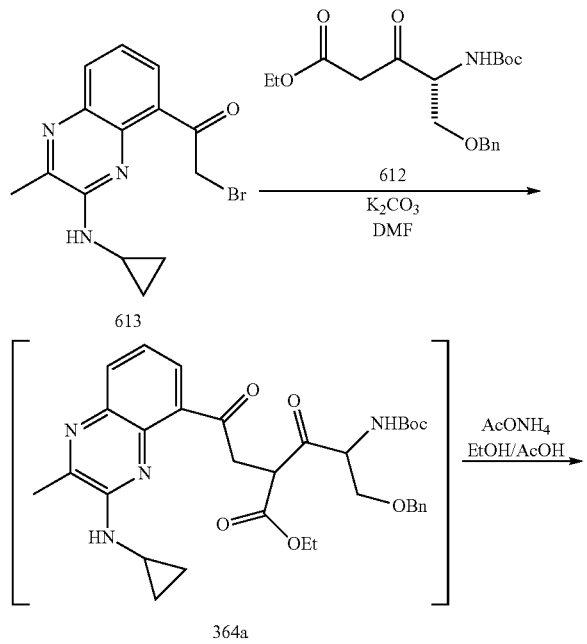

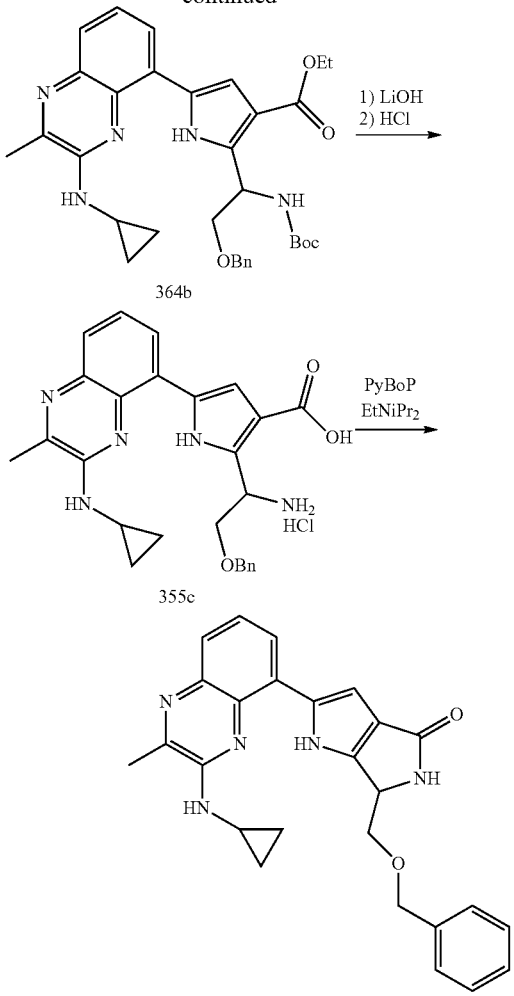

Preparation of ethyl 2-(2-(benzyloxy)-1-((tert-butoxycarbonyl)amino)ethyl)-5-(3-(cyclopropylamino)-2-methylquinoxalin-5-yl)-1H-pyrrole-3-carboxylate (364b)

To a 25-mL round-bottomed flask was added (R)-ethyl 5-(benzyloxy)-4-((tert-butoxycarbonyl)amino)-3-oxopentanoate (612) (0.78 g, 2.15 mmol), $K_2CO_3$ (0.67 g, 4.88 mmol), 2-bromo-1-(3-(cyclopropylamino)-2-methylquinoxalin-5-yl)ethanone (613) (0.62 g, 1.95 mmol), and DMF (4 mL). The reaction mixture was stirred at RT for 30 min. The reaction mixture was diluted with sat NH$_4$Cl (5 mL) and extracted with EtOAc (10 mL). The organic extract was washed with water (5 mL), dried over Na$_2$SO$_4$, and concentrated. Ethyl 5-(benzyloxy)-4-((tert-butoxycarbonyl)amino)-2-(2-(3-(cyclopropylamino)-2-methylquinoxalin-5-yl)-2-oxoethyl)-3-oxopentanoate (364a) was obtained as a yellow solid and used without further purification. m/z (ESI, +ve) 605.3 (M+H)$^+$. To a 20-mL glass tube was added ethyl 5-(benzyloxy)-4-((tert-butoxycarbonyl)amino)-2-(2-(3-(cyclopropylamino)-2-methylquinoxalin-5-yl)-2-oxoethyl)-3-oxopentanoate (364a), crude from previous step, NH$_4$OAc (0.45 g, 5.85 mmol), EtOH (6 mL), and AcOH (1.5 mL). The tube was sealed and heated at 60° C. for 5 h. The reaction mixture was cooled to RT and was concentrated to half of its volume. The mixture was diluted with EtOAc (10 mL) and water (5 mL). The organic extract was washed with NaOH (1 N, 5 mL), water (5 mL), brine (5 mL), dried over $Na_2SO_4$, and concentrated. The crude material was absorbed onto a plug of silica gel and purified by chromatography through a Redi-Sep pre-packed silica gel column (40 g), eluting with a gradient of 10-30% EtOAc in hexanes to give ethyl 2-(2-(benzyloxy)-1-((tert-butoxycarbonyl)amino)ethyl)-5-(3-(cyclopropylamino)-2-methylquinoxalin-5-yl)-1H-pyrrole-3-carboxylate (364b) (0.48 g, 42% yield) as a yellow solid. $^1$H NMR (400 MHz, DMSO-$d_6$) δ 12.56 (br. s., 1H), 7.60 (dd, J=0.98, 8.02 Hz, 1H), 7.54 (d, J=1.96 Hz, 1H), 7.31-7.39 (m, 2H), 7.06 (br. s., 1H), 4.50 (d, J=5.48 Hz, 2H), 4.22 (q, J=7.04 Hz, 2H), 3.03 (br. s., 1H), 2.49 (s, 3H) 1.38 (s, 9H), 1.30 (t, J=7.04 Hz, 3H), 0.96-1.02 (m, 2H), 0.62-0.69 (m, 2H). m/z (ESI, +ve) 586.2 (M+H)$^+$.

Preparation of 2-(1-amino-2-(benzyloxy)ethyl)-5-(3-(cyclopropylamino)-2-methylquinoxalin-5-yl)-1H-pyrrole-3-carboxylic acid hydrochloride (364c)

A glass microwave reaction vessel was charged with give ethyl 2-(2-(benzyloxy)-1-((tert-butoxycarbonyl)amino)ethyl)-5-(3-(cyclopropylamino)-2-methylquinoxalin-5-yl)-1H-pyrrole-3-carboxylate (364b) (0.48 g, 0.83 mmol), LiOH hydrated (0.14 g, 3.31 mmol), dioxane (5 mL), and water (3 mL). The reaction mixture was stirred and heated in an Initiator microwave reactor (Personal Chemistry, Biotage AB, Inc., Uppsala, Sweden) at 110° C. for 2 h. The solvent was removed and the product used without further purification. The orange solid was suspended in HCl (5 mL of 4 N in dioxane) and stirred at RT for 1.5 h. The mixture was concentrated to half of its volume and the orange solid obtained was filtered, washed with ether and dried to give 2-(1-amino-2-(benzyloxy)ethyl)-5-(3-(cyclopropylamino)-2-methylquinoxalin-5-yl)-1H-pyrrole-3-carboxylic acid hydrochloride (364c) which was used as crude material and based on theoretical yield.

Preparation 6-((benzyloxy)methyl)-2-(2-methyl-3-((1-methylcyclopropyl)amino)quinoxalin-5-yl)-5,6-dihydropyrrolo[3,4-b]pyrrol-4(1H)-one (364)

To a 50-mL round-bottomed flask was added 2-(1-amino-2-(benzyloxy)ethyl)-5-(3-(cyclopropylamino)-2-methylquinoxalin-5-yl)-1H-pyrrole-3-carboxylic acid hydrochloride (364c) (0.41 g, 0.83 mmol), DCM (8 mL), DMF (8 mL), DIEA (0.43 mL, 2.84 mmol), and (benzotriazol-1-yloxy) tripyrrolidinophosphonium hexafluorophosphate (0.52 g, 0.99 mmol) (Sigma-Aldrich Chemical Company, Inc.). The reaction mixture was stirred at RT for 30 min, concentrated to half of its volume, and diluted with EtOAc (10 mL). The organic extract was washed with sat $NaHCO_3$ (5 mL), dried over $Na_2SO_4$, and concentrated. The crude material was absorbed onto a plug of silica gel and purified by chromatography through a Redi-Sep pre-packed silica gel column (12 g), eluting with a gradient of 0-3% MeOH in DCM to provide 6-((benzyloxy)methyl)-2-(2-methyl-3-((1-methylcyclopropyl)amino)quinoxalin-5-yl)-5,6-dihydropyrrolo[3,4-b]pyrrol-4(1H)-one (364) (284 mg, 78% yield, 50% ee) as a light yellow solid. $^1$H NMR (400 MHz, DMSO-$d_6$) δ 13.12 (s, 1H), 8.04 (dd, J=1.17, 7.63 Hz, 1H), 7.70 (s, 1H), 7.56-7.64 (m, 2H), 7.36 (t, J=7.82 Hz, 1H), 7.25-7.33 (m, 5H), 7.01 (d, J=1.37 Hz, 1H), 4.71 (t, J=6.55 Hz, 1H), 4.44-4.58 (m, 2H), 3.62 (dd, J=5.97, 8.90 Hz, 1H), 3.40 (dd, J=7.43, 9.00 Hz, 1H), 2.51 (s, 3H), 1.20-1.29 (m, 1H), 0.90-1.03 (m, 1H), 0.64-0.76 (m, 2H), 0.46-0.57 (m, 1H). m/z (ESI, +ve) 440.2 (M+H)$^+$.

Example 365

6-(hydroxymethyl)-2-(2-methyl-3-((1-methylcyclopropyl)amino)quinoxalin-5-yl)-5,6-dihydropyrrolo[3,4-b]pyrrol-4 (1H)-one

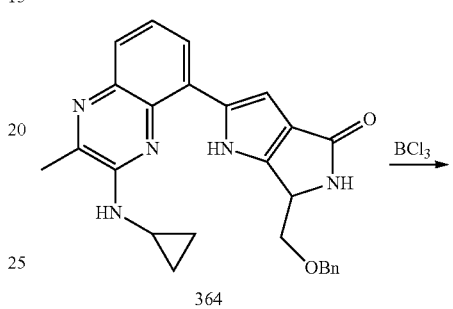

364

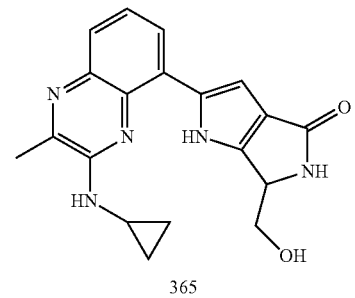

365

To a 50-mL round-bottomed flask was added 6-((benzyloxy)methyl)-2-(2-methyl-3-((1-methylcyclopropyl)amino) quinoxalin-5-yl)-5,6-dihydropyrrolo[3,4-b]pyrrol-4(1H)-one (364) (0.27 g, 0.63 mmol) and DCM (10 mL). The reaction mixture was cooled to −78° C. and under a $N_2$ atmosphere boron trichloride (1.25 mL, 1.25 mmol, 1M in DCM) (Sigma-Aldrich Chemical Company, Inc.) was added dropwise. The reaction mixture was stirred at −78° C. for 30 min and at 0° C. for 30 min. The reaction was quenched by the addition of $NaHCO_3$ (100 mg in MeOH, 3 mL) and the solvent was removed under vacuum. The crude material was absorbed onto a plug of silica gel and purified by chromatography through a Redi-Sep pre-packed silica gel column (12 g), eluting with a gradient of 2-8% MeOH in DCM to provide 6-(hydroxymethyl)-2-(2-methyl-3-((1-methylcyclopropyl) amino)quinoxalin-5-yl)-5,6-dihydropyrrolo[3,4-b]pyrrol-4 (1H)-one (365) (50% ee) as a yellow solid. $^1$H NMR (400 MHz, DMSO-$d_6$) δ 13.17 (s, 1H), 8.04 (dd, J=1.17, 7.63 Hz, 1H), 7.58-7.63 (m, 2H), 7.55 (s, 1H), 7.36 (t, J=7.82 Hz, 1H), 6.97 (d, J=1.17 Hz, 1H), 5.21 (t, J=5.28 Hz, 1H), 4.48 (dd, J=6.06, 8.02 Hz, 1H), 3.74 (td, J=5.21, 10.12 Hz, 1H), 3.20-3.28 (m, 1H), 2.92 (dt, J=2.93, 6.46 Hz, 1H), 2.51 (s, 3H), 1.00-1.13 (m, 1H), 0.86-0.96 (m, 1H), 0.75-0.85 (m, 1H), 0.44-0.55 (m, 1H). m/z (ESI, +ve) 350.3 (M+H)$^+$.

Examples 366

(S)-2-(3-(cyclopropylamino)-2-methylquinoxalin-5-yl)-6-(hydroxymethyl)-5,6-dihydropyrrolo[3,4-b]pyrrol-4(1H)-one; and 367: (R)-2-(3-(cyclopropylamino)-2-methylquinoxalin-5-yl)-6-(hydroxymethyl)-5,6-dihydropyrrolo[3,4-b]pyrrol-4(1H)-one

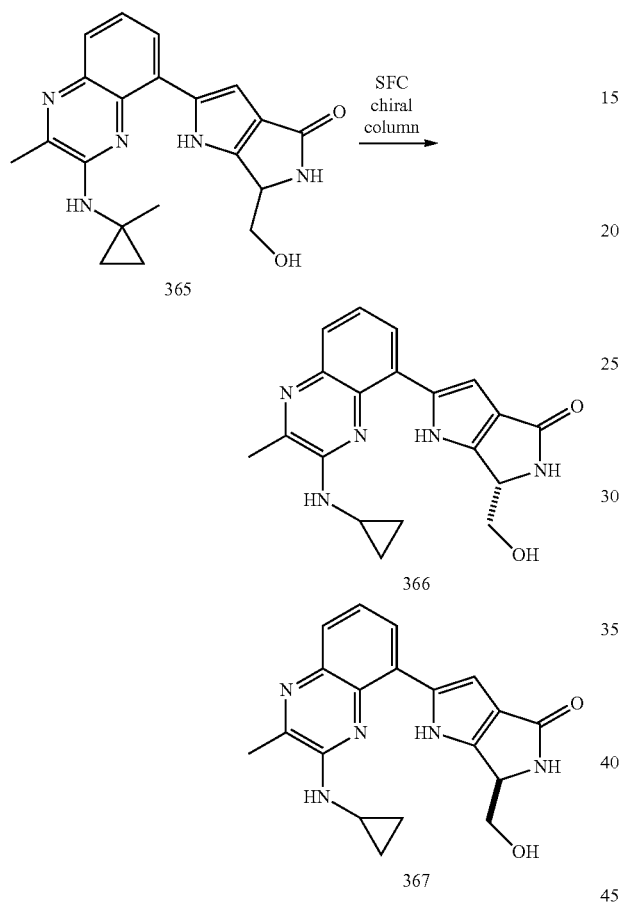

The individual enantiomers of Example 365 were obtained by chiral SFC (Column: Chiralcel OJH (250×20 mm, 5μ); Mobile Phase: 85:15 (A:B); A: Liquid $CO_2$; B: MeOH (20 mM $NH_3$); Flow Rate: 70 mL/min; Oven Temp: 40° C.; Inlet Pressure: 100 bar; Wavelength: 278 nm) to give Example 366 (first eluting product) and Example 367 (second eluting product). Example 366: (S)-2-(3-(cyclopropylamino)-2-methylquinoxalin-5-yl)-6-(hydroxymethyl)-5,6-dihydropyrrolo[3,4-b]pyrrol-4(1H)-one (23 mg, >99% ee) as a yellow solid. $^1$H NMR (400 MHz, DMSO-$d_6$) δ 13.17 (br. s., 1H), 8.04 (d, J=7.24 Hz, 1H), 7.56-7.67 (m, 3H), 7.37 (t, J=7.73 Hz, 1H), 6.97 (s, 1H), 5.21 (t, J=4.40 Hz, 1H), 4.48 (t, J=6.46 Hz, 1H), 3.70-3.78 (m, 1H), 2.91 (d, J=1.76 Hz, 1H), 2.51 (s, 3H), 1.00-1.13 (m, 1H), 0.86-0.96 (m, 1H), 0.75-0.85 (m, 1H), 0.44-0.55 (m, 1H). m/z (ESI, +ve) 350.3 (M+H)$^+$. Example 367: (R)-2-(3-(cyclopropylamino)-2-methylquinoxalin-5-yl)-6-(hydroxymethyl)-5,6-dihydropyrrolo[3,4-b]pyrrol-4(1H)-one (23 mg, >99% ee) as a yellow solid. $^1$H NMR (400 MHz, DMSO-$d_6$) δ 13.17 (br. s., 1H), 8.04 (d, J=7.24 Hz, 1H), 7.56-7.67 (m, 3H), 7.37 (t, J=7.73 Hz, 1H), 6.97 (s, 1H), 5.21 (t, J=4.40 Hz, 1H), 4.48 (t, J=6.46 Hz, 1H), 3.70-3.78 (m, 1H), 2.91 (d, J=1.76 Hz, 1H), 2.51 (s, 3H), 1.00-1.13 (m, 1H), 0.86-0.96 (m, 1H), 0.75-0.85 (m, 1H), 0.44-0.55 (m, 1H). m/z (ESI, +ve) 350.3 (M+H)$^+$.

Example 368

2-(3-(tert-butylamino)-2-methylpyrido[3,4-b]pyrazin-5-yl)-6,7-dihydro-1H-pyrrolo[3,2-c]pyridin-4(5H)-one

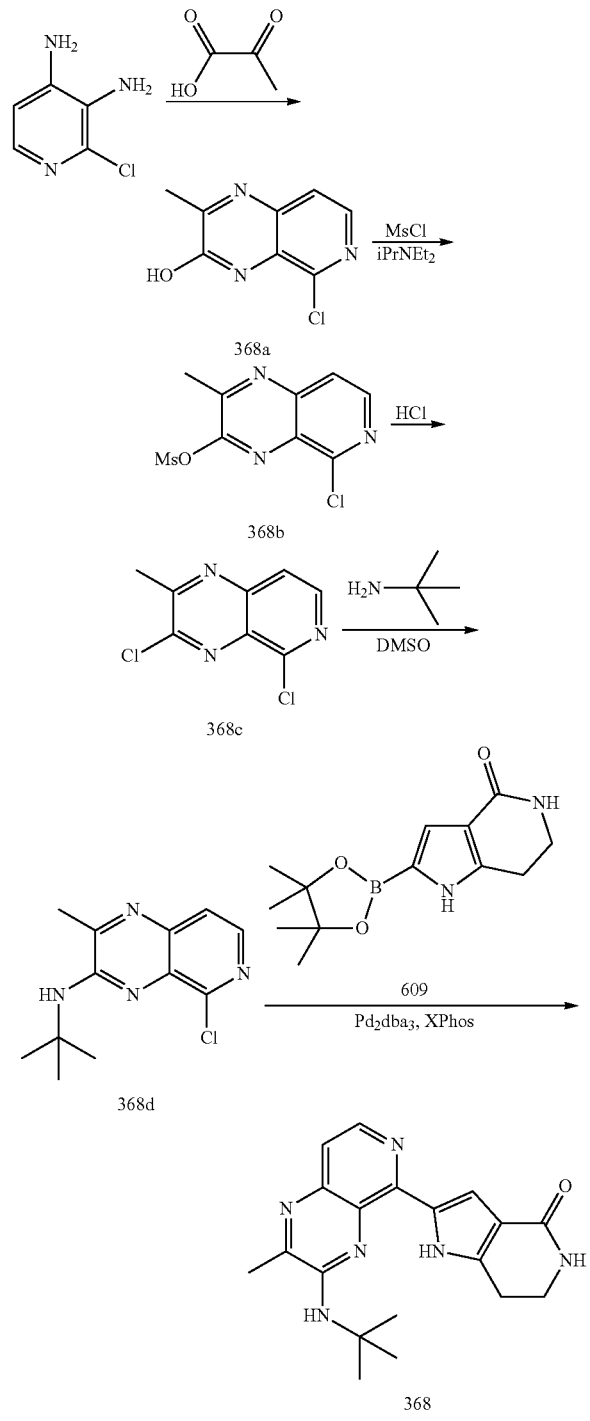

Preparation of 5-chloro-2-methylpyrido[3,4-b]pyrazin-3-ol (368a)

A mixture of 3,4-diamino-2-chloropyridine (2.1 g, 14.63 mmol) (Sigma Aldrich) and pyruvic acid (1.22 mL, 17.55 mmol) (Acros, New Jersey) in MeOH (40 mL) in a sealed glass tube was heated at 50° C. for 2 h. The mixture was cooled to RT and the solvent was removed in vacuo. The residue was triturated with ether and the suspension was filtered to give 1.88 g of crude product. MS (ESI, pos. ion) m/z: 196.1 (M+1).

Preparation of 5-chloro-2-methylpyrido[3,4-b]pyrazin-3-yl methanesulfonate (368b)

A solution of 5-chloro-2-methylpyrido[3,4-b]pyrazin-3-ol (1.88 g, 9.61 mmol) in DCM (30 mL) at 0° C. was treated with DIEA (3.34 mL, 19.22 mmol) followed by methanesulfonyl chloride (1.11 mL, 14.42 mmol) (Sigma Aldrich). The reaction mixture was warmed to RT and stiffed for 1 h. The mixture was diluted with DCM and washed with water. The organic layer was dried ($MgSO_4$), filtered and concentrated in vacuo. The residue was purified on a silica gel column (10-35% EtOAc in Hexanes) to give 5-chloro-2-methylpyrido[3,4-b]pyrazin-3-yl methanesulfonate (1.68 g, 6.14 mmol, 64% yield) as a brown solid. MS (ESI, pos. ion) m/z: 274.0 (M+1); $^1$H NMR (400 MHz, $CDCl_3$) δ ppm 8.59 (1H, d, J=5.7 Hz), 7.85 (1H, d, J=5.7 Hz), 3.83 (3H, s), 2.85 (3H, s).

Preparation of 3,5-dichloro-2-methylpyrido[3,4-b]pyrazine (368c)

A glass microwave reaction vessel was charged with 5-chloro-2-methylpyrido[3,4-b]pyrazin-3-yl methanesulfonate (160 mg, 0.585 mmol), 1,4-Dioxane (1 mL) and hydrogen chloride (4 M in 1,4-dioxane, 0.73 mL, 2.92 mmol) (Sigma Aldrich). The reaction mixture was stirred and heated in an oil bath at 70° C. for 1 h, then cooled to RT. The mixture was diluted with EtOAc (50 mL) and washed with sat. $NaHCO_3$. The organic layer was dried ($MgSO_4$), filtered and concentrated to give 3,5-dichloro-2-methylpyrido[3,4-b] pyrazine (62 mg, 0.290 mmol, 49% yield) as a brown solid. MS (ESI, pos. ion) m/z: 213.9 (M+1).

Preparation of N-(tert-butyl)-5-chloro-2-methylpyrido[3,4-b]pyrazin-3-amine (368d)

A glass microwave reaction vessel was charged with 3,5-dichloro-2-methylpyrido[3,4-b]pyrazine (110 mg, 0.51 mmol) and tert-butylamine (0.16 mL, 1.54 mmol) (Sigma Aldrich) in NMP (1.0 mL). The reaction mixture was stirred and heated in an Initiator microwave reactor (Personal Chemistry, Biotage AB, Inc., Upssala, Sweden) at 60° C. for 2 h. The mixture was diluted with water and extracted with DCM (30 mL×3). The combined organic layers was washed with water (30 mL×3) and dried ($MgSO_4$), filtered and concentrated. The residue was purified by silica gel chromatography (10-30% EtOAc in Hexanes) to give N-(tert-butyl)-5-chloro-2-methylpyrido[3,4-b]pyrazin-3-amine (15 mg, 0.060 mmol, 11% yield). MS (ESI, pos. ion) m/z: 251.1 (M+1).

Preparation of 2-(3-(tert-butylamino)-2-methylpyrido[3,4-b]pyrazin-5-yl)-6,7-dihydro-1H-pyrrolo[3,2-c]pyridin-4(5H)-one (368)

A glass microwave reaction vessel was charged with 2-(4,4,5,5-tetramethyl-1,3,2-dioxaborolan-2-yl)-6,7-dihydro-1H-pyrrolo[3,2-c]pyridin-4(5H)-one (609) (31 mg, 0.12 mmol) and N-(tert-butyl)-5-chloro-2-methylpyrido[3,4-b] pyrazin-3-amine (15 mg, 0.06 mmol) in 1,4-Dioxane (0.8 mL)/Water (0.2 mL) followed by Xphos (2.8 mg, 6.0 μmol) (Sigma Aldrich), $Pd_2dba_3$ (2.7 mg, 3.0 μmol) (Strem) and $K_2PO_4$ (38 mg, 0.18 mmol) (Sigma Aldrich). The reaction mixture was stirred and heated in an Initiator microwave reactor (Personal Chemistry, Biotage AB, Inc., Upssala, Sweden) at 100° C. for 1 h. The mixture was diluted with $CHCl_3$/iPrOH (4:1, 30 mL) and washed with water. The organic layer was dried ($MgSO_4$), filtered and concentrated. The residue was purified with prep-TLC (eluted with 8% MeOH in DCM) to give 2-(3-(tert-butylamino)-2-methylpyrido[3,4-b] pyrazin-5-yl)-6,7-dihydro-1H-pyrrolo[3,2-c]pyridin-4(5H)-one (5.0 mg, 0.014 mmol, 24% yield) as a light brown solid. MS (ESI, pos. ion) m/z: 351.1 (M+1); $^1$H NMR (400 MHz, MEOH-D4-$d_4$) δ ppm 8.33 (1H, d, J=5.5 Hz), 7.79 (1H, s), 7.45 (1H, d, J=5.5 Hz), 3.62 (2H, t, J=7.0 Hz), 3.01 (2H, t, J=7.0 Hz), 2.62 (3H, s), 1.70 (9H, s).

Example 369

2-(6-fluoro-2-methyl-3-((1-methylcyclopropyl)amino)quinoxalin-5-yl)-6,7-dihydro-1H-pyrrolo[3,2-c]pyridin-4(5H)-one 2,2,2-trifluoroacetate

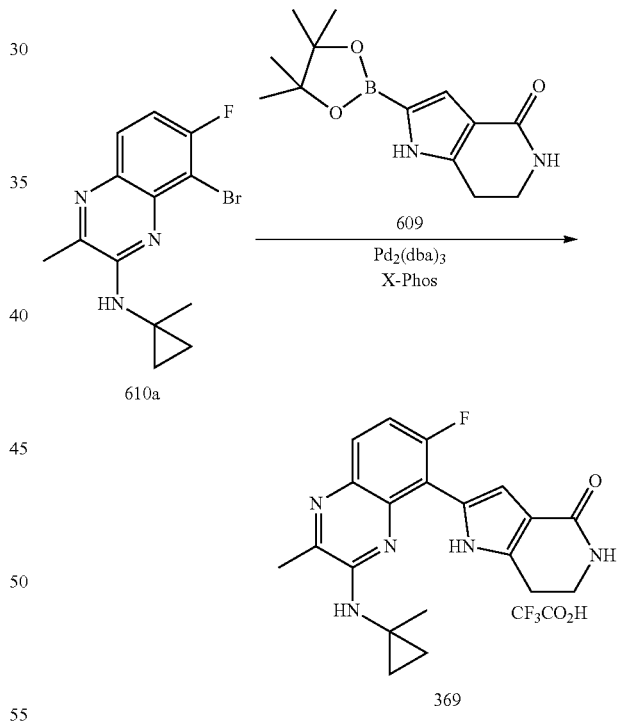

A glass microwave reaction vessel was charged with 2-bromo-6,7-dihydro-1H-pyrrolo[3,2-c]pyridin-4(5H)-one (608) (90 mg, 0.42 mmol) and $(BPin)_2$ (Aldrich Chemical Company) (213 mg, 0.84 mmol) in THF (2.0 mL) followed by $(Pd(dppf)Cl_2$ (Strem Chemicals) 917.09 mg, 0.02 mmol) and KOAc (164 mg, 1.67 mmol). The reaction mixture was stirred and heated in the microwave at 100° C. for 1 h. LC-MS indicated product (609) formation m/z (ESI, +ve ion) 263.1 $(M+H)^+$. The solvent was removed and the residue was filtered through a plug of basic alumina first washing with EtOAc (ca. 15 mL) and next washing with 5% MeOH in DCM (ca. 20 mL). The filtrate was concentrated to give the crude product (609), which was used in the next reaction without further purification. A glass microwave reaction vessel was charged with 2-(4,4,5,5-tetramethyl-1,3,2-dioxaborolan-2-yl)-6,7-dihydro-1H-pyrrolo[3,2-c]pyridin-4(5H)-one (609) (52.4 mg, 0.20 mmol), $K_2PO_4$ (127 mg, 0.600 mmol), $Pd_2dba_3$ (Strem Chemicals) (9.15 mg, 9.99 μmol), Xphos (Strem Chemicals,) (9.53 mg, 0.02 mmol) and 8-bromo-7-fluoro-3-methyl-N-(1-methylcyclopropyl)quinoxalin-2-amine (610a) (62 mg, 0.20 mmol) in 1,4-dioxane (1.50 mL) and water (0.56 mL). The reaction mixture was stirred and heated in an Initiator microwave reactor (Personal Chemistry, Biotage AB, Inc., Upssala, Sweden) at 110° C. for 30 min. The reaction mixture was treated with water and extracted with EtOAc (2×25 mL), washed with brine and concentrated. The residue was purified on the Gilson reverse phase HPLC (Silicycle Silichrome XT C18 column; 30×150 mm, 5 μm, 20-95% 0.1% TFA/$CH_3CN$ in 0.1% TFA/water) affording 2-(6-fluoro-2-methyl-3-((1-methylcyclopropyl)amino)quinoxalin-5-yl)-6,7-dihydro-1H-pyrrolo[3,2-c]pyridin-4(5H)-one 2,2,2-trifluoroacetate (42.9 mg, 0.089 mmol, 45% yield) as a rust-colored amorphous solid. $^1H$ NMR (400 MHz, MeOH-d4) δ ppm 7.63 (1H, dd, J=9.0, 5.7 Hz), 7.24-7.33 (2H, m), 3.65 (2H, t, J=6.9 Hz), 3.06 (2H, t, J=7.0 Hz), 2.53 (3H, s), 1.67 (3 H, s), 1.02-1.08 (2H, m), 0.96-1.02 (2H, m). $^{19}F$ NMR (376 MHz, MeOH-d4) δ ppm −109.22 (1F, s). m/z (ESI, +ve) 366.2 (M+H)$^+$.

Example 370

2-(6-fluoro-3-((1-hydroxy-2-methylpropan-2-yl)amino)-2-methylquinoxalin-5-yl)-6,7-dihydro-1H-pyrrolo[3,2-c]pyridin-4(5H)-one

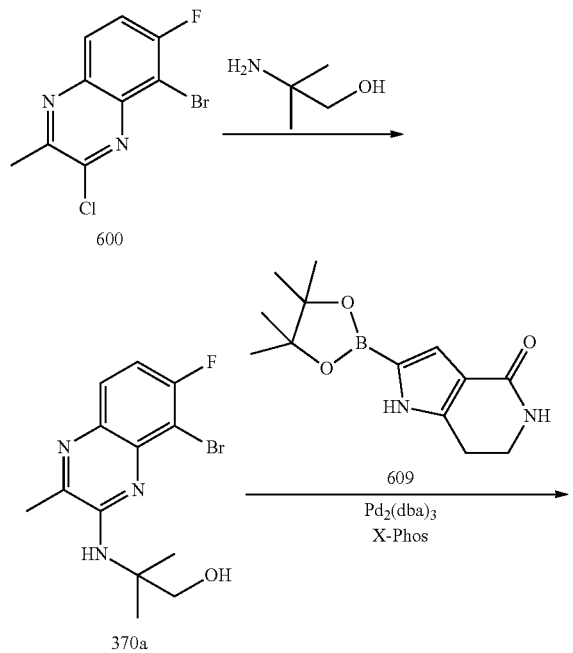

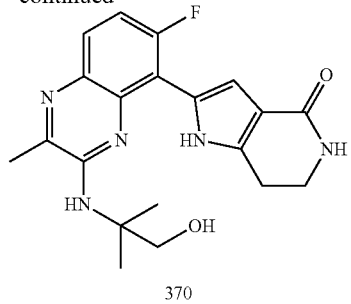

5-Bromo-3-chloro-6-fluoro-2-methylquinoxaline (600), (242 mg, 0.878 mmol) and 2-amino-2-methylpropan-1-ol (Aldrich Chemical Company) (0.42 mL, 4.39 mmol) in DMSO (4.0 mL) was stirred at 100° C. (17 h). The reaction mixture was treated with EtOAc (50 mL), and washed with saturated aq. $NaHCO_3$ (2×25 mL) and then with brine (1×25 mL). The organic layer was dried over $MgSO_4$, filtered and concentrated. The crude product was purified using an ISCO Combiflash Rf (25 g Thomson SingleStep column with a gradient of 0-80% EtOAc in hexanes) affording 2-((8-bromo-7-fluoro-3-methylquinoxalin-2-yl)amino)-2-methylpropan-1-ol (370a) (112 mg, 0.34 mmol, 39% yield) as a crystalline light purple solid. $^1H$ NMR (400 MHz, $CDCl_3$) δ ppm 7.75 (1H, dd, J=9.0, 5.7 Hz), 7.19 (1H, t, J=8.6 Hz), 5.42 (1H, br. s.), 5.07 (1H, br. s.), 3.85 (2H, d, J=4.1 Hz), 2.56 (3H, s), 1.56 (6H, s). $^{19}F$ NMR (376 MHz, $CDCl_3$) δ ppm −102.16 (1F, s). m/z (ESI, +ve ion) 328.0/330.0 (M+H)$^+$. A 20 mL glass microwave reaction vessel was charged with 6,7-dihydro-1H-pyrrolo[3,2-c]pyridin-4(5H)-one (607) (140 mg, 1.03 mmol), bis(1,5-cyclooctadiene)di-mu-methoxydiiridium(I) (Strem Chemicals,) (20.45 mg, 0.031 mmol), 4,4-di-tert-butyl-2,2-dipyridyl (Aldrich Chemical Company, 16.56 mg, 0.062 mmol), $(BPin)_2$ (Aldrich Chemical Company, 287 mg, 1.13 mmol) and purged with argon then treated with methyl tert-butyl ether (3.0 mL, 25.2 mmol) The reaction mixture was stirred at 50° C. for 1 h 15 min. The crude reaction mixture was passed through a pad of basic alumina (Aldrich, Brockmann I, standard grade ca. 150 mesh 58A) rinsing with DCM first (ca. 8 mL) then eluting with 5% MeOH in DCM (ca. 15 mL) affording crude boronic ester (609) as a dark brown oil. This material was concentrated and used in a subsequent Suzuki coupling without further purification. m/z (ESI, +ve) 263.5 (M+H)$^+$. A 5-mL glass microwave reaction vessel was charged with 2-(4,4,5,5-tetramethyl-1,3,2-dioxaborolan-2-yl)-6,7-dihydro-1H-pyrrolo[3,2-c]pyridin-4(5H)-one (609) (270 mg, 1.03 mmol), $K_2PO_4$ (217 mg, 1.02 mmol), $Pd_2dba_3$ (Strem Chemicals, 15.63 mg, 0.017 mmol), Xphos (Strem Chemicals 16.27 mg, 0.034 mmol) and 2-((8-bromo-7-fluoro-3-methylquinoxalin-2-yl)amino)-2-methylpropan-1-ol (370a) (112 mg, 0.34 mmol) in dioxane (2.0 mL) and water (0.66 mL). The reaction mixture was stirred and heated in a microwave reactor at 110° C. for 40 min. The reaction mixture was treated with water, extracted with EtOAc (2×25 mL), washed with brine and concentrated. The crude residue was purified on the ISCO Combiflash RF (25 g Thomson SingleStep column, using a gradient of 0-15% MeOH in DCM) affording 2-(6-fluoro-3-((1-hydroxy-2-methylpropan-2-yl)amino)-2-methylquinoxalin-5-yl)-6,7-dihydro-1H-pyrrolo[3,2-c]pyridin-4(5H)-one (83.1 mg, 0.22 mmol, 63% yield) as a light yellow amorphous solid after drying overnight under vacuum. $^1H$ NMR (400 MHz, DMSO-$d_6$) δ ppm 12.12 (1H, br. s.), 7.66 (1H, dd, J=9.0, 5.9 Hz), 7.32 (1H, dd, J=11.0, 9.0 Hz), 7.01 (1H, br. s.), 6.78 (1H, t, J=2.4 Hz), 5.99 (1H, s), 5.15 (1H, t, J=5.7 Hz), 3.61 (2H, d, J=5.3 Hz), 3.45 (2H, td, J=6.8, 2.3 Hz), 2.88 (2H, t, J=6.8 Hz), 1.45 (6H, s). $^{19}$F NMR (377 MHz, DMSO-d$_6$) δ ppm −111.08 (1F, s). m/z (ESI, +ve) 384.1 (M+H)$^+$.

Example 371

2-(3-(tert-butylamino)-6-fluoro-2-methylquinoxalin-5-yl)-1H-pyrrolo[3,2-c]pyridin-4(5H)-one 2,2,2-trifluoroacetate salt

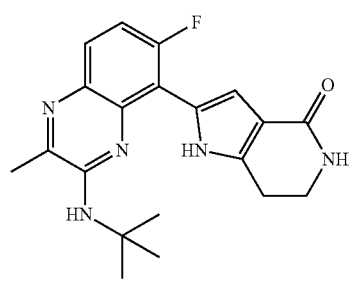

A brown solution of 2-(3-(tert-butylamino)-6-fluoro-2-methylquinoxalin-5-yl)-6,7-dihydro-1H-pyrrolo[3,2-c]pyridin-4(5H)-one (Example 286) (140 mg, 0.38 mmol) and DDQ (Fluka, 173 mg, 0.76 mmol) in dioxane (5.0 mL) was stirred at 60° C. for 2 h. The reaction mixture was diluted with DCM (20 mL), added to a separatory funnel, and quenched with saturated aq. NaHCO$_3$ (30 mL). The resulting suspension was filtered through a pad of celite and the filtrate was extracted with DCM (4×25 mL), dried over Na$_2$SO$_4$, and concentrated. The crude product purified on the Gilson reverse phase HPLC (Silicycle Silichrome XT C18 column; 30×150 mm, 5 u, 20-95% 0.1% TFA/CH$_3$CN in 0.1% TFA/water) affording 2-(3-(tert-butylamino)-6-fluoro-2-methylquinoxalin-5-yl)-1H-pyrrolo[3,2-c]pyridin-4(5H)-one 2,2,2-trifluoroacetate (11.5 mg, 0.024 mmol, 6% yield) as a yellow amorphous solid. $^1$H NMR (400 MHz, DMSO-d$_6$) δ ppm 12.18 (1H, s), 10.81 (1H, br. s.), 7.74 (1H, dd, J=8.9, 6.0 Hz), 7.31-7.39 (1H, m), 7.03 (1H, t, J=6.5 Hz), 6.98 (1H, s), 6.42 (1H, d, J=7.0 Hz), 6.18 (1H, s), 2.56 (3H, s), 1.49 (9H, s). $^{19}$F NMR (376 MHz, DMSO-d$_6$) δ ppm −110.70 (1F, s). m/z (ESI, +ve ion) 366.0 (M+H)$^+$.

Example 371

2-(3-(tert-butylamino)-2-(5-methyl-1,3,4-oxadiazol-2-yl)quinoxalin-5-yl)-6,7-dihydro-1H-pyrrolo[3,2-c]pyridin-4(5H)-one

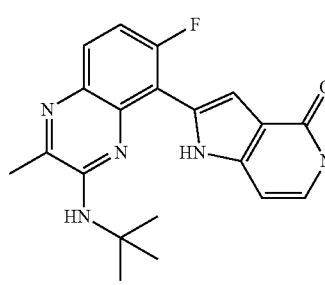

Preparation of 5-bromo-3-(tert-butylamino)quinoxaline-2-carboxylic acid (371a)

To a slurry of 5-bromo-3-(tert-butylamino)quinoxaline-2-carbaldehyde (306a) (250 mg, 0.81 mmol) in MeOH (0.4 mL) and NaOH 1.0 N (1.62 mL, 1.62 mmol) was added two drops H$_2$O$_2$ 30% in water (0.10 mL, 1.01 mmol) from a pasteur pipette. The reaction was stirred rapidly at RT and became a yellow/orange solution. Additional 0.05 mL 30% aq H₂O₂ was added. After 30 min, additional 0.05 mL 30% aq H₂O₂ was added. After 30 min, the reaction mixture was treated with ice, acidified to pH <2 with 1.0 N HCl, and diluted with 10 mL water. The orange suspension was filtered, rinsing with 10 mL of water to give 5-bromo-3-(tert-butylamino)quinoxaline-2-carboxylic acid (0.26 g, 0.80 mmol, 99% yield) as an orange solid. m/z (ESI, +ve ion) 324.0/326.0 (M+H)⁺.

Preparation of (8-bromo-N-(tert-butyl)-3-(5-methyl-1,3,4-oxadiazol-2-yl)quinoxalin-2-amine (371b)

Acetic hydrazide (33 mg, 0.44 mmol) and 5-bromo-3-(tert-butylamino)quinoxaline-2-carboxylic acid (371a) (130 mg, 0.40 mmol) were combined in EtOAc (4 mL) to give a yellow solution. TEA (0.17 mL, 1.20 mmol) was added followed by 1-propanephosphonic acid cyclic anhydride (Aldrich; 50 wt. % solution in EtOAc, 0.59 mL, 1.00 mmol). The reaction was sealed and heated in an oil bath at 90° C. for 16 h. The reaction mixture was cooled to RT, partitioned between saturated NaHCO₃ and EtOAc. The aq. layer was extracted with EtOAc and the combined organic layers were washed with brine, and the organic layer was dried over anhydrous Na₂SO₄, filtered, and concentrated in vacuo. The residue was adsorbed onto 1 g silica gel and purified by silica gel chromatography (12 g column) using a gradient of 0-20% EtOAc/hexanes to afford 8-bromo-N-(tert-butyl)-3-(5-methyl-1,3,4-oxadiazol-2-yl)quinoxalin-2-amine (67 mg, 0.18 mmol, 46% yield) as a yellow solid. m/z (ESI, +ve ion) 362.0/364.0 (M+H)⁺.

Preparation of Example 371

A 20-mL glass microwave reaction vessel was charged with 2-(4,4,5,5-tetramethyl-1,3,2-dioxaborolan-2-yl)-6,7-dihydro-1H-pyrrolo[3,2-c]pyridin-4(5H)-one (609) (96 mg, 0.36 mmol), K₂PO₄ (70 mg, 0.33 mmol), Pd₂dba₃ (Strem Chemicals) (5.06 mg, 5.52 µmol), Xphos (Strem Chemicals,) (5.26 mg, 0.011 mmol) and 8-bromo-N-(tert-butyl)-3-(5-methyl-1,3,4-oxadiazol-2-yl)quinoxalin-2-amine (371b) (40 mg, 0.11 mmol) in dioxane (2.0 mL) and water (0.66 mL). The reaction was stirred and heated in a microwave reactor at 110° C. for 40 min. The reaction mixture was treated with water, extracted with EtOAc (2×25 mL), washed with brine and concentrated. The crude residue was purified on the ISCO Combiflash RF (25 g Thomson SingleStep column, using a gradient of 0-15% MeOH in DCM) affording enriched product as a bright orange amorphous solid after drying under vacuum. The product was repurified on the Gilson reverse phase (Silicycle Silichrome XT C18 column; 30×150 mm, 5 u, 20-95% 0.1% TFA/CH₃CN in 0.1% TFA/water) affording 2-(3-(tert-butylamino)-2-(5-methyl-1,3,4-oxadiazol-2-yl)quinoxalin-5-yl)-6,7-dihydro-1H-pyrrolo[3,2-c]pyridin-4(5H)-one 2,2,2-trifluoroacetate (11 mg, 18% yield). ¹H NMR (400 MHz, DMSO-d₆) δ ppm 11.78 (1H, br. s.), 8.46 (1H, s), 7.99 (1H, dd, J=7.5, 1.3 Hz), 7.81 (1H, dd, J=8.1, 1.3 Hz), 7.51 (1H, t, J=7.8 Hz), 7.17 (1H, d, J=2.2 Hz), 6.99 (1H, br. s.), 2.88 (2H, t, J=6.8 Hz), 2.72 (3H, s), 1.62 (9H, s). ¹⁹F NMR (377 MHz, DMSO-d₆) δ ppm -74.19 (1F, s). m/z (ESI, +ve ion) 418.1 (M+H)⁺.

Example 373

2-(6-fluoro-3-(isopropylamino)-2-methylquinoxalin-5-yl)-6,7-dihydro-1H-pyrrolo[3,2-c]pyridin-4(5H)-one 2,2,2-trifluoroacetate

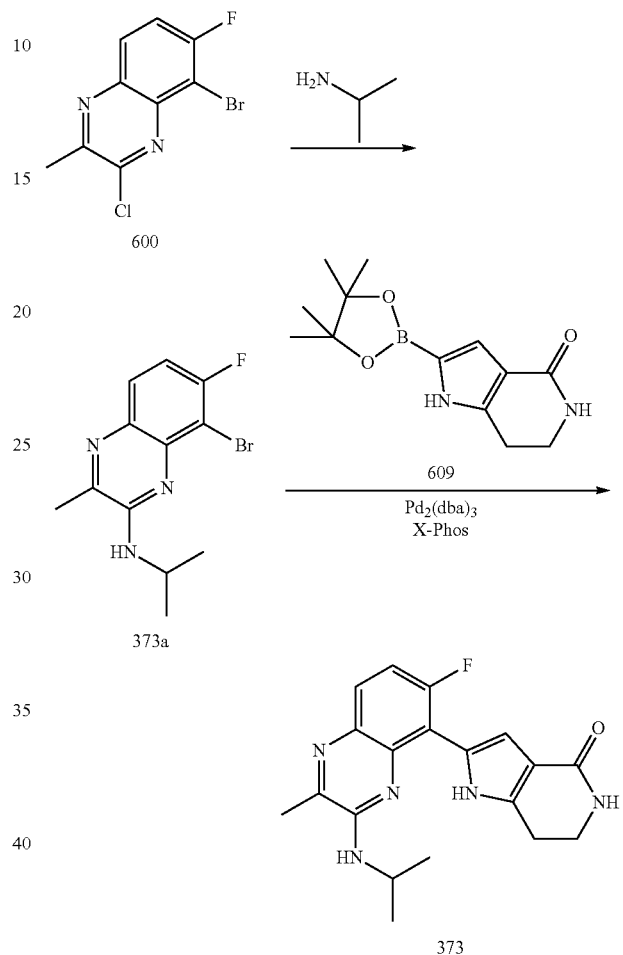

Preparation of 8-bromo-7-fluoro-N-isopropyl-3-methylquinoxalin-2-amine (373a)

This compound (594 mg, 1.99 mmol, 91% yield) as an orange crystalline solid was prepared according to the procedure described for Intermediate 605a, using 5-bromo-3-chloro-6-fluoro-2-methylquinoxaline (600) (600 mg, 2.17 mmol) and isopropylamine (0.94 mL, 10.9 mmol) in DMSO (5.0 mL) as the starting materials. ¹H NMR (400 MHz, CDCl₃) δ ppm 7.73 (1H, dd, J=9.0, 5.9 Hz), 7.15 (1H, t, J=8.6 Hz), 4.68-4.82 (1H, m), 4.52 (1H, dq, J=13.2, 6.5 Hz), 2.53 (3H, s), 1.39 (6H, d, J=6.5 Hz). ¹⁹F NMR (376 MHz, CDCl₃) δ ppm -103.43 (1F, s). m/z (ESI, +ve ion) 298.5/300.6 (M+H)⁺.

Preparation of Example 373

This compound (14 mg, 18% yield) as an orange-yellow amorphous solid was prepared according to the procedure described for Example 369, using 2-(4,4,5,5-tetramethyl-1,3, 2-dioxaborolan-2-yl)-6,7-dihydro-1H-pyrrolo[3,2-c]pyridin-4(5H)-one (609) (101 mg, 0.39 mmol), and 8-bromo-7-fluoro-N-isopropyl-3-methylquinoxalin-2-amine (373a) as the starting materials. $^1$H NMR (400 MHz, DMSO-$d_6$) δ ppm 12.63 (1H, br. s.), 7.62 (1H, dd, J=8.9, 5.8 Hz), 7.29 (1H, dd, J=11.5, 9.0 Hz), 7.09 (1H, d, J=7.0 Hz), 7.02 (1H, br. s.), 6.92 (1H, d, J=2.2 Hz), 4.25 (1H, dq, J=13.2, 6.6 Hz), 3.41-3.46 (2H, m), 2.91 (2H, t, J=6.8 Hz), 2.54 (3H, s), 1.37 (6H, d, J=6.5 Hz). $^{19}$F NMR (376 MHz, DMSO-$d_6$) δ ppm −110.18 (1F, s). m/z (ESI, +ve ion) 354.1 (M+H)$^+$.

Example 374

2-(2-(tert-butylamino)quinazolin-8-yl)-6,7-dihydro-1H-pyrrolo[3,2-c]pyridin-4(5H)-one

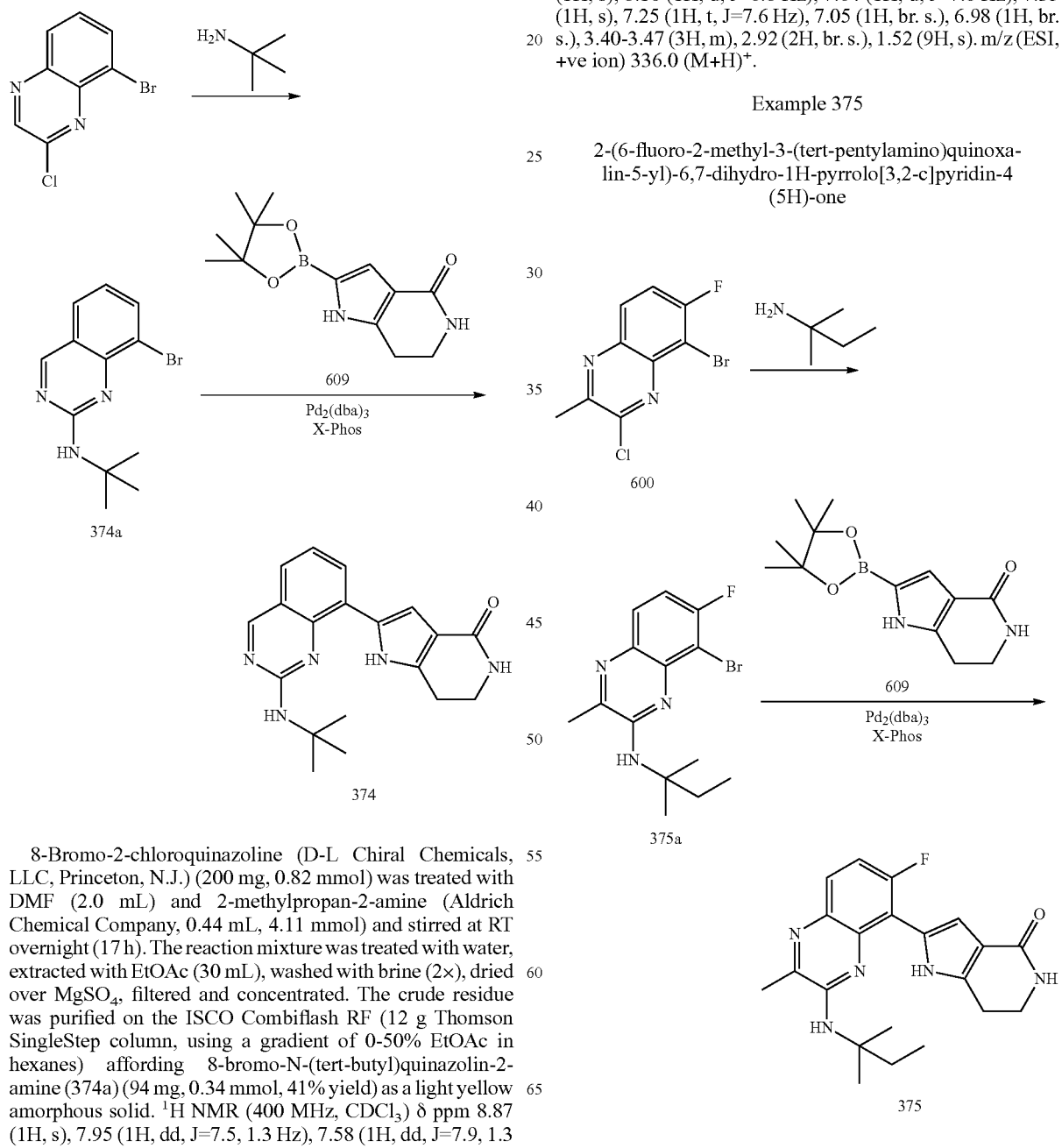

374

8-Bromo-2-chloroquinazoline (D-L Chiral Chemicals, LLC, Princeton, N.J.) (200 mg, 0.82 mmol) was treated with DMF (2.0 mL) and 2-methylpropan-2-amine (Aldrich Chemical Company, 0.44 mL, 4.11 mmol) and stirred at RT overnight (17 h). The reaction mixture was treated with water, extracted with EtOAc (30 mL), washed with brine (2×), dried over MgSO$_4$, filtered and concentrated. The crude residue was purified on the ISCO Combiflash RF (12 g Thomson SingleStep column, using a gradient of 0-50% EtOAc in hexanes) affording 8-bromo-N-(tert-butyl)quinazolin-2-amine (374a) (94 mg, 0.34 mmol, 41% yield) as a light yellow amorphous solid. $^1$H NMR (400 MHz, CDCl$_3$) δ ppm 8.87 (1H, s), 7.95 (1H, dd, J=7.5, 1.3 Hz), 7.58 (1H, dd, J=7.9, 1.3 Hz), 7.05 (1H, t, J=7.7 Hz), 5.43 (1H, br. s.), 1.54 (9H, s). m/z (ESI, +ve ion) 280.0/282.0 (M+H)$^+$. A 5-mL glass microwave reaction vessel was charged with 2-(4,4,5,5-tetramethyl-1,3,2-dioxaborolan-2-yl)-6,7-dihydro-1H-pyrrolo[3,2-c]pyridin-4(5H)-one (609) (120 mg, 0.46 mmol), K$_2$PO$_4$ (182 mg, 0.86 mmol), Pd$_2$dba$_3$ (Strem Chemicals, 13.07 mg, 0.014 mmol), Xphos (Strem Chemicals, 13.61 mg, 0.03 mmol) and 8-bromo-N-(tert-butyl)quinazolin-2-amine (374a) (80 mg, 0.29 mmol) in dioxane (2.5 mL) and water (0.80 mL). The reaction was stirred and heated in a heating block at 110° C. for 1 h. The reaction mixture was treated with water, extracted with EtOAc (30 mL), washed with brine and concentrated. The crude residue was purified on the ISCO Combiflash RF (25 g Thomson SingleStep column, using a gradient of 0-20% MeOH) affording 2-(2-(tert-butylamino)quinazolin-8-yl)-6,7-dihydro-1H-pyrrolo[3,2-c]pyridin-4(5H)-one (53.9 mg, 0.16 mmol, 56% yield) as a light yellow amorphous solid. $^1$H NMR (400 MHz, DMSO-$d_6$) δ ppm 12.37 (1H, br. s.), 9.17 (1H, s), 8.10 (1H, d, J=6.8 Hz), 7.64 (1H, d, J=7.0 Hz), 7.35 (1H, s), 7.25 (1H, t, J=7.6 Hz), 7.05 (1H, br. s.), 6.98 (1H, br. s.), 3.40-3.47 (3H, m), 2.92 (2H, br. s.), 1.52 (9H, s). m/z (ESI, +ve ion) 336.0 (M+H)$^+$.

Example 375

2-(6-fluoro-2-methyl-3-(tert-pentylamino)quinoxalin-5-yl)-6,7-dihydro-1H-pyrrolo[3,2-c]pyridin-4(5H)-one

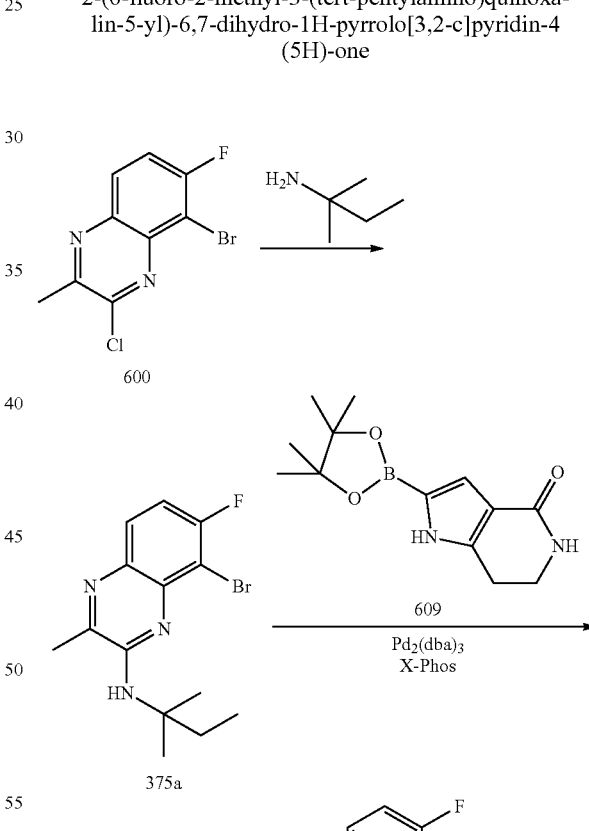

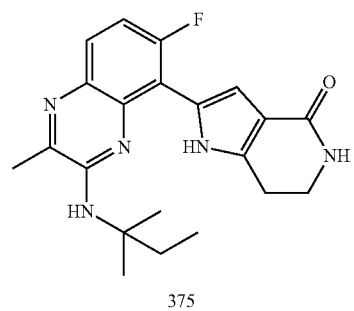

375

Preparation of 8-bromo-7-fluoro-3-methyl-N-(tert-pentyl)quinoxalin-2-amine (375a)

This compound (580 mg, 1.78 mmol, 81% yield) as an orange amorphous solid was prepared according to the procedure described for Intermediate 605a, using 5-bromo-3-chloro-6-fluoro-2-methylquinoxaline (600) (607 mg, 2.20 mmol) and tert-amylamine (Aldrich Chemical Company) (1.29 mL, 11.02 mmol) in DMSO (5.0 mL) as the starting materials. $^1$H NMR (400 MHz, CDCl$_3$) δ ppm 7.75 (1H, dd, J=9.0, 5.7 Hz), 7.15 (1H, t, J=8.7 Hz), 4.74 (1H, br. s.), 2.54 (3H, s), 2.09 (2H, q, J=7.4 Hz), 1.58 (6H, s), 0.88 (3H, t, J=7.5 Hz). $^{19}$F NMR (376 MHz, CDCl$_3$) δ ppm −103.39 (1F, s). m/z (ESI, +ve ion) 326.0/328.0.

Preparation of Example 375

This compound (314 mg, 0.82 mmol, 57% yield) as a yellow crystalline solid was prepared according to the procedure described for Example 370, using 2-(4,4,5,5-tetramethyl-1,3,2-dioxaborolan-2-yl)-6,7-dihydro-1H-pyrrolo[3,2-c]pyridin-4(5H)-one (609) (800 mg, 3.05 mmol), and 8-bromo-7-fluoro-3-methyl-N-(tert-pentyl)quinoxalin-2-amine (375a) (470 mg, 1.44 mmol) as the starting materials. $^1$H NMR (400 MHz, DMSO-d$_6$) δ ppm 11.94 (1H, br. s.), 7.64 (1H, dd, J=8.9, 6.0 Hz), 7.28 (1H, dd, J=11.0, 9.0 Hz), 6.95 (1H, br. s.), 6.71 (1H, t, J=2.5 Hz), 5.92 (1H, s), 3.38-3.47 (2H, m), 2.84 (2H, t, J=6.8 Hz), 2.55 (3H, s), 1.90 (2H, q, J=7.2 Hz), 1.43 (6H, s), 0.81 (3H, t, J=7.4 Hz). $^{19}$F NMR (377 MHz, DMSO-d$_6$) δ ppm −111.22 (1F, s). m/z (ESI, +ve ion) 382.1 (M+H)$^+$.

Example 376

2-(6-fluoro-2-methyl-3-((1-methylcyclobutyl)amino)quinoxalin-5-yl)-6,7-dihydro-1H-pyrrolo[3,2-c]pyridin-4(5H)-one

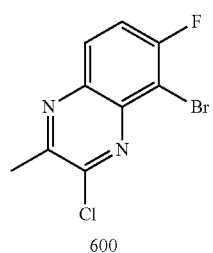

600

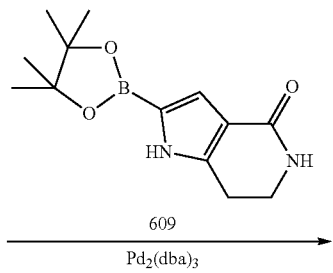

609
Pd$_2$(dba)$_3$
X-Phos

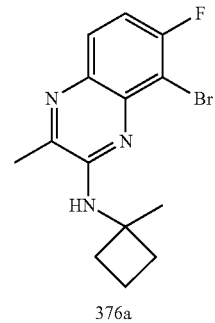

376a

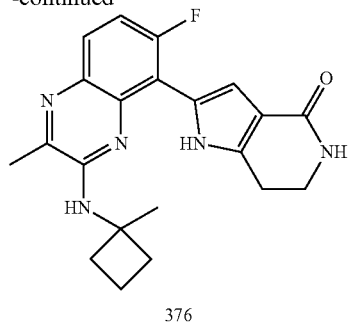

376

8-Bromo-7-fluoro-3-methyl-N-(1-methylcyclobutyl)quinoxalin-2-amine (376a) (620 mg, 1.91 mmol, 88% yield) as a light brown viscous oil was prepared according to the procedure described for Intermediate 605a, using 5-bromo-3-chloro-6-fluoro-2-methylquinoxaline (600) (600 mg, 2.18 mmol), TEA (0.76 mL, 5.44 mmol) and 1-methylcyclobutanamine hydrochloride (Matrix Scientific Columbia, S.C.) (500 mg, 4.11 mmol) in DMSO (5.0 mL) as the starting materials. $^1$H NMR (400 MHz, CDCl$_3$) δ ppm 7.71 (1H, dd, J=9.0, 5.7 Hz), 7.13 (1H, t, J=8.6 Hz), 5.01 (1H, br. s.), 2.51 (3H, s), 2.42-2.51 (2H, m), 2.30 (2H, dddd, J=9.8, 7.3, 4.6, 2.6 Hz), 1.90-2.01 (2H, m), 1.73 (3H, s). $^{19}$F NMR (377 MHz, CDCl$_3$) δ ppm −103.73 (1F, s). m/z (ESI, +ve ion) 324.0/326.0 (M+H)$^+$. 2-(6-Fluoro-2-methyl-3-((1-methylcyclobutyl)amino)quinoxalin-5-yl)-6,7-dihydro-1H-pyrrolo[3,2-c]pyridin-4(5H)-one (269 mg, 0.71 mmol, 42% yield) as an amorphous yellow solid was prepared according to the procedure described for Example 370, using 2-(4,4,5,5-tetramethyl-1,3,2-dioxaborolan-2-yl)-6,7-dihydro-1H-pyrrolo[3,2-c]pyridin-4(5H)-one (609) (800 mg, 3.05 mmol), and 8-bromo-7-fluoro-3-methyl-N-(1-methylcyclobutyl)quinoxalin-2-amine (376a) (549 mg, 1.70 mmol) as the starting materials. $^1$H NMR (400 MHz, DMSO-d$_6$) δ ppm 12.53 (1H, br. s.), 7.61 (1H, dd, J=9.0, 5.9 Hz), 7.29 (1H, dd, J=11.5, 9.0 Hz), 7.21 (1H, s), 7.05 (1H, br. s.), 6.85 (1H, dd, J=4.1, 2.0 Hz), 3.45 (2H, td, J=6.9, 2.4 Hz), 2.93 (2H, t, J=6.8 Hz), 2.54 (3H, s), 2.38-2.47 (2H, m), 2.13-2.24 (2H, m), 1.82-1.97 (2H, m), 1.66 (3H, s). $^{19}$F NMR (377 MHz, DMSO-d$_6$) δ ppm −109.90 (1F, s). m/z (ESI, +ve ion) 380.1 (M+H)$^+$.

Example 377

2-(2-(tert-butyl(methyl)amino)quinazolin-8-yl)-6,7-dihydro-1H-pyrrolo[3,2-c]pyridin-4(5H)-one

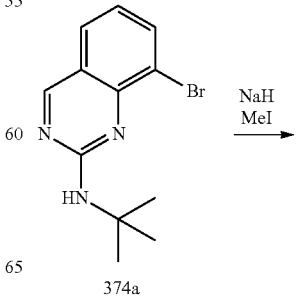

374a

NaH
MeI

539
-continued

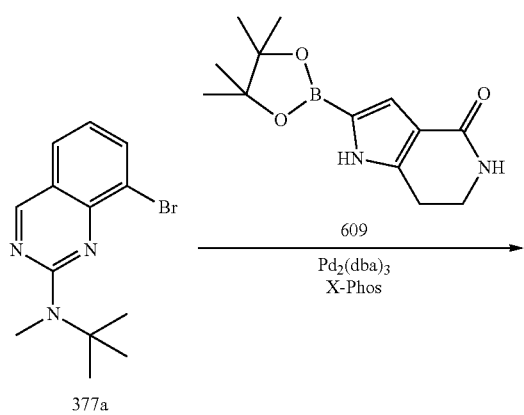

377a

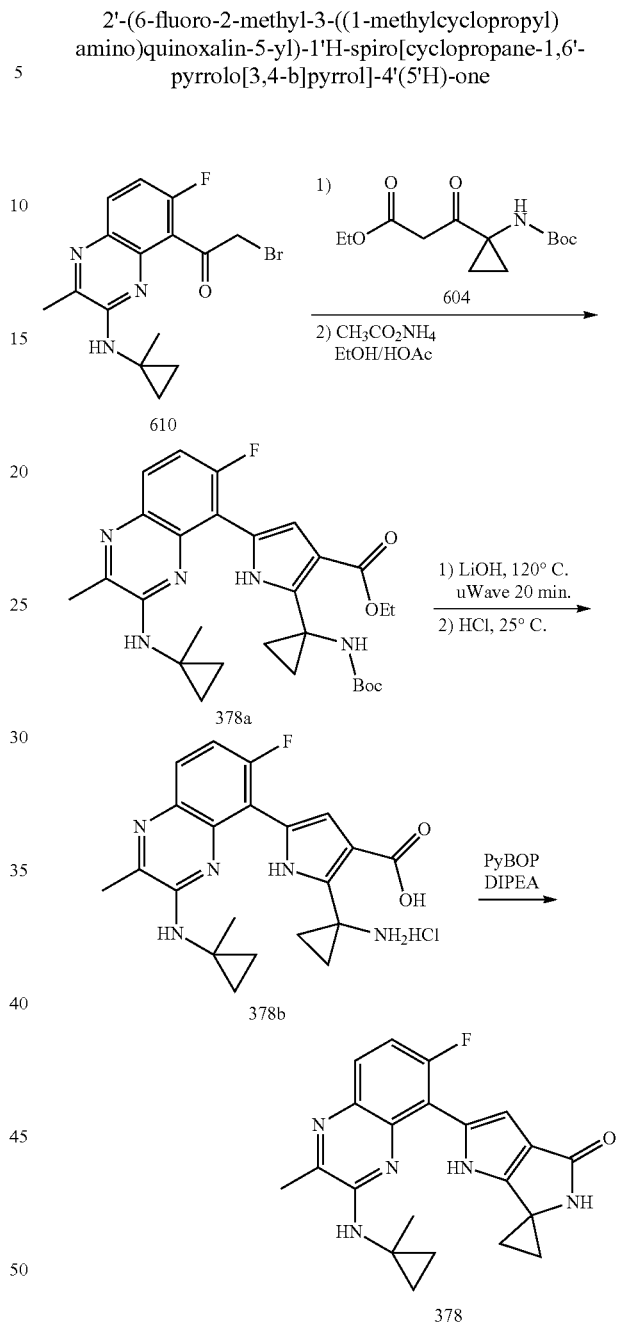

Preparation of 8-bromo-N-(tert-butyl)-N-methylquinazolin-2-amine (377a)

8-Bromo-N-(tert-butyl)quinazolin-2-amine (374a) (40 mg, 0.14 mmol) in THF (4 mL) at 0° C. was treated with NaH (60% dispersion in mineral oil, 8.6 mg, 0.21 mmol) and stirred at 0° C. for 30 min. MeI (10.71 µl, 0.17 mmol) was added and the solution was warmed to RT overnight (16 h). The reaction mixture was treated with brine and extracted with EtOAc (50 mL), dried over MgSO$_4$, filtered and concentrated. Purification on a silica gel column (0-50% EtOAc in hexanes) afforded the title compound (34 mg, 0.12 mmol, 82% yield) as yellow viscous oil. m/z (ESI, +ve ion) 294.0/296.0 (M+H)$^+$.

Preparation of Example 377

2-(2-(tert-butyl(methyl)amino)quinazolin-8-yl)-6,7-dihydro-1H-pyrrolo[3,2-c]pyridin-4(5H)-one (8 mg, 22% yield) as a yellow crystalline solid was prepared according to the procedure described for Example 370, using 2-(4,4,5,5-tetramethyl-1,3,2-dioxaborolan-2-yl)-6,7-dihydro-1H-pyrrolo [3,2-c]pyridin-4(5H)-one (609) (146 mg, 0.56 mmol), and 8-bromo-N-(tert-butyl)-N-methylquinazolin-2-amine (377a) (30 mg, 0.10 mmol) as the starting materials. $^1$H NMR (400 MHz, CDCl$_3$) δ ppm 12.87 (1H, br. s.), 9.04 (1H, s), 8.07 (1H, dd, J=7.5, 1.3 Hz), 7.52 (1H, dd, J=7.8, 1.2 Hz), 7.23-7.30 (1H, m), 7.11 (1H, d, J=2.0 Hz), 5.40 (1H, br. s.), 3.66 (2H, td, J=6.8, 2.5 Hz), 3.37 (3H, s), 2.98 (2H, t, J=6.8 Hz), 1.67 (9H, s). m/z (ESI, +ve ion) 350.1 (M+H)$^+$.

540

Example 378

2'-(6-fluoro-2-methyl-3-((1-methylcyclopropyl)amino)quinoxalin-5-yl)-1'H-spiro[cyclopropane-1,6'-pyrrolo[3,4-b]pyrrol]-4'(5'H)-one Ethyl 2-(1-((tert-butoxycarbonyl)amino)cyclopropyl)-5-(6-fluoro-2-methyl-3-((1-methylcyclopropyl)amino)quinoxalin-5-yl)-1H-pyrrole-3-carboxylate (378a) (455 mg, 0.87 mmol, 42% yield) as yellow foam was prepared according to the procedures described for Intermediate 283d, using 2-bromo-1-(6-fluoro-2-methyl-3-((1-methylcyclopropyl)amino)quinoxalin-5-yl)ethanone (610) (735 mg, 2.087 mmol), ethyl 3-(1-((tert-butoxycarbonyl)amino)cyclopropyl)-3-oxopropanoate (604) (849 mg, 3.13 mmol) as the starting materials, followed by the subsequent treatment of the resulting ethyl 2-(1-((tert-butoxycarbonyl)amino)cyclopropanecarbonyl)-4-(6-fluoro-2-methyl-3-((1-methylcyclopropyl)amino)quinoxalin-5-yl)-4-oxobutanoate (610 mg, 54% yield as a viscous yellow oil; m/z (ESI, +ve ion) 543.2 (M+H)⁺) with NH₄OAc (965 mg, 12.52 mmol) in EtOH (2.5 mL) and HOAc (2.5 mL). $^{19}$F NMR (376 MHz, CDCl₃) δ ppm −108.30 (1F, s). m/z (ESI, +ve ion) 524.3 (M+H)⁺. To a suspension of ethyl 2-(1-((tert-butoxycarbonyl)amino)cyclopropyl)-5-(6-fluoro-2-methyl-3-((1-methylcyclopropyl)amino)quinoxalin-5-yl)-1H-pyrrole-3-carboxylate (378a) (450 mg, 0.86 mmol) in dioxane (6 mL) and water (3.00 mL) was treated with LiOH monohydrate (144 mg, 3.44 mmol) and heated to 110° C. for 1.5 h. LC-MS indicated ca. 40% conversion to the carboxylic acid. The reaction mixture was treated with another 50 mg of LiOH·H₂O and heated again at 110° C. for another 2.5 h. The reaction mixture was transferred to a 250 mL RBF and the volatiles were removed under reduced pressure. The residue was treated with 4 M HCl in dioxane (12 mL) and stirred at RT for 1 h. The reaction mixture was concentrated to dryness on the rotovap affording 378b (m/z (ESI, +ve ion) 396.2 (M+H)⁺) as a bright orange solid, which was used in the subsequent step without further purification. To a solution of 1-(3-carboxy-5-(6-fluoro-2-methyl-3-((1-methylcyclopropyl)amino)quinoxalin-5-yl)-1H-pyrrol-2-yl)cyclopropanaminium chloride (371 mg, 0.859 mmol) was treated with DCM (15 mL) and DMF (15.00 mL) followed by DIEA (0.60 mL, 3.44 mmol) and (benzotriazol-1-yloxy)tripyrrolidinophosphonium hexafluorophosphate (581 mg, 1.117 mmol). The reaction mixture was then stirred at RT for 10 min. It was diluted with 200 mL of DCM, washed with 20 mL of sat. NaHCO₃ followed by 20 mL of brine. The organic solution was concentrated and the residue was purified a silica gel column (0-15% MeOH in DCM) affording the desired product, m/z (ESI, +ve ion) 378.2 (M+H)⁺, in about 95% pure. The material was washed with Et₂O (6×15 mL) to remove the residual tri(pyrrolidin-1-yl)phosphine oxide (about 5%) (m/z (ESI, +ve ion) 258.2 (M+H)⁺) to provide 2'-(6-fluoro-2-methyl-3-((1-methylcyclopropyl)amino)quinoxalin-5-yl)-1'H-spiro[cyclopropane-1,6'-pyrrolo[3,4-b]pyrrol]-4'(5'H)-one (378) (193 mg, 0.51 mmol, 60% yield) as a light yellow crystalline solid. $^1$H NMR (400 MHz, DMSO-d₆) δ ppm 12.52 (1H, s), 7.77 (1H, s), 7.81 (1H, s), 7.65 (1H, dd, J=8.9, 6.0 Hz), 7.34 (1H, dd, J=11.9, 9.0 Hz), 7.00 (1H, d, J=2.3 Hz), 2.48 (3H, s), 1.45-1.52 (5H, m), 1.31-1.37 (2H, m), 0.90-0.97 (2H, m), 0.69-0.75 (2H, m). $^{19}$F NMR (376 MHz, DMSO-d₆) δ ppm −108.46 (1F, s). m/z (ESI, +ve ion) 378.2 (M+H)⁺.

Examples 379

(R)-2-(6-fluoro-2-methyl-3-((1-methylcyclopropyl)amino)quinoxalin-5-yl)-6-methyl-5,6-dihydropyrrolo[3,4-b]pyrrol-4(1H)-one; and 380: (S)-2-(6-fluoro-2-methyl-3-((1-methylcyclopropyl)amino)quinoxalin-5-yl)-6-methyl-5,6-dihydropyrrolo[3,4-b]pyrrol-4(1H)-one

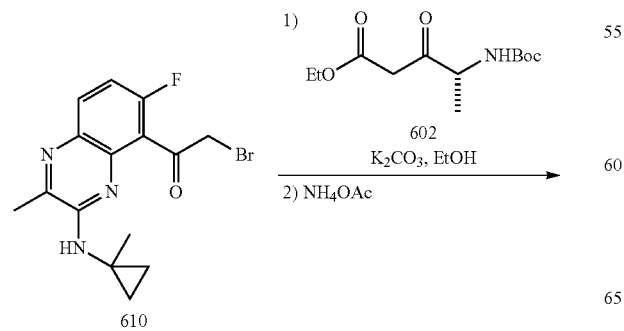

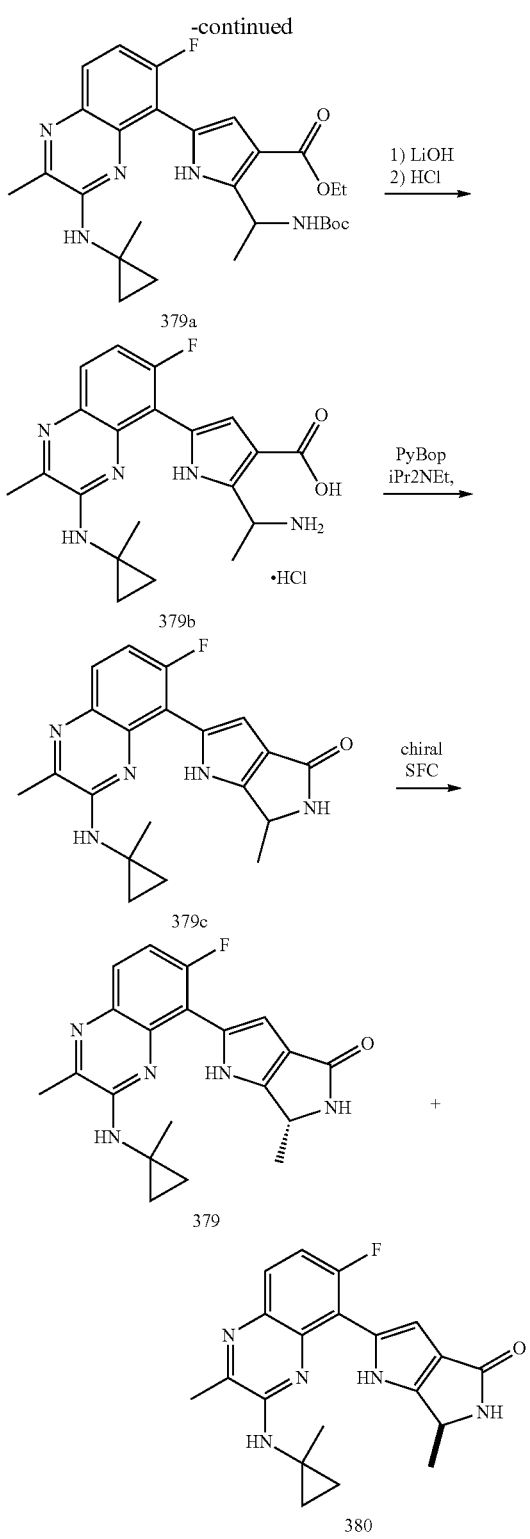

Preparation of ethyl 2-(1-((tert-butoxycarbonyl)amino)ethyl)-5-(6-fluoro-2-methyl-3-((1-methylcyclopropyl)amino)quinoxalin-5-yl)-1H-pyrrole-3-carboxylate (379a)

A mixture of 2-bromo-1-(6-fluoro-2-methyl-3-((1-methylcyclopropyl)amino)quinoxalin-5-yl)ethanone (610) (735 mg, 2.087 mmol), (R)-ethyl 4-((tert-butoxycarbonyl)amino)-3-oxopentanoate (602) (812 mg, 3.13 mmol) and $K_2CO_3$ (865 mg, 6.26 mmol) in EtOH (15 mL) was stirred at RT for 3 h, followed by 60° C. in an oil bath for 3 h. The reaction mixture was concentrated on the rotovap. Saturated $NH_4Cl$ (aq., 20 mL) and EtOAc (100 mL) was added and the layers were separated. The organic layer was dried over anhydrous $MgSO_4$, filtered and concentrated. The crude material was purified by silica gel chromatography (0-50% EtOAc in hexanes) affording 4-ethyl 4-((tert-butoxycarbonyl)amino)-2-(2-(6-fluoro-2-methyl-3-((1-methylcyclopropyl)amino)quinoxalin-5-yl)-2-oxoethyl)-3-oxopentanoate (300 mg) as a viscous yellow oil. m/z (ESI, +ve ion) 531.2 $(M+H)^+$. In a glass tube, the viscous yellow oil in EtOH (2.0 mL) and AcOH (2.0 mL) was treated with $NH_4OAc$ (643 mg, 8.35 mmol). The glass tube was sealed and heated at 60° C. overnight (16 h). The reaction mixture was cooled and concentrated. The residue was treated with EtOAc (50 mL) and 1 N NaOH (5 mL). The layers were separated and the organic layer was washed with brine (5 mL). The organic layer was dried over anhydrous $Na_2SO_4$, filtered and concentrated. The crude material was purified by silica gel chromatography (0-80% EtOAc in hexanes) affording ethyl 2-(1-((tert-butoxycarbonyl)amino)ethyl)-5-(6-fluoro-2-methyl-3-((1-methylcyclopropyl)amino)quinoxalin-5-yl)-1H-pyrrole-3-carboxylate (379a) (134 mg, 13% yield) as yellow crystalline solid. m/z (ESI, +ve ion) 512.3 $(M+H)^+$.

Preparation of 379b

Ethyl 2-(1-((tert-butoxycarbonyl)amino)ethyl)-5-(6-fluoro-2-methyl-3-((1-methylcyclopropyl)amino)quinoxalin-5-yl)-1H-pyrrole-3-carboxylate (379a) (130 mg, 0.25 mmol) in water (1.0 mL) and dioxane (2.0 mL) was treated with LiOH monohydrate (42.7 mg, 1.01 mmol), and heated to 110° C. in an oil bath for 2 h. The reaction mixture was treated with additional LiOH monohydrate (25 mg) and heated at 110° C. again for 30 min. The reaction mixture was concentrated to dryness. The remaining solid was treated with 4 M HCl in dioxane (4 mL) and stirred at RT for 1 h. The reaction mixture was concentrated to dryness affording a bright orange solid containing 1-(3-carboxy-5-(6-fluoro-2-methyl-3-((1-methylcyclopropyl)amino)quinoxalin-5-yl)-1H-pyrrolo-2-yl)ethanaminium chloride (379b, m/z (ESI, +ve ion) 384.1 $(M+H)^+$. It was used in the subsequent step without further purification.

Preparation of Examples 379 and 380

To a solution of 1-(3-carboxy-5-(6-fluoro-2-methyl-3((1-methylcyclopropyl)amino)quinoxalin-5-yl)-1H-pyrrol-2-yl)ethanaminium chloride (379b) (97 mg, 0.23 mmol) in DMF (5 mL) and DCM (5 mL) was added DIEA (0.16 mL, 0.92 mmol) followed by (benzotriazol-1-yloxy)tripyrrolidinophosphonium hexafluorophosphate (156 mg, 0.30 mmol). The mixture was stirred at RT for 25 min. The reaction mixture was diluted with EtOAc (50 mL) and washed with a saturated solution of $NaHCO_3$, and brine (3×50 mL), dried over $MgSO_4$, filtered and concentrated. The crude residue was purified on a silica gel column (0-15% MeOH in DCM) affording a mixture of 2-(6-fluoro-2-methyl-3-((1-methylcyclopropyl)amino)quinoxalin-5-yl)-6-methyl-5,6-dihydropyrrolo[3,4-b]pyrrol-4(1H)-one (379c, m/z (ESI, +ve ion) 366.2 $(M+H)^+$) and tri(pyrrolidin-1-yl)phosphine oxide (m/z (ESI, +ve ion) 258.2 $(M+H)^+$). The material was treated with DMSO (8 mL) and purified on the Gilson reverse phase HPLC (Gemini Phenomenex; 30×150 mm, 5 u, 20-95% 0.1% TFA/$CH_3CN$ in 0.1% TFA/water) affording 57 mg of pure 2-(6-fluoro-2-methyl-3-((1-methylcyclopropyl)amino)quinoxalin-5-yl)-6-methyl-5,6-dihydropyrrolo[3,4-b]pyrrol-4(1H)-one (379c, m/z (ESI, +ve ion) 366.2 $(M+H)^+$). 2-(6-Fluoro-2-methyl-3-((1-methylcyclopropyl)amino)quinoxalin-5-yl)-6-methyl-5,6-dihydropyrrolo[3,4-b]pyrrol-4(1H)-one (379c) (57 mg) was subjected to chiral purification using SFC (column: Chiralcel AD-H (250×21 mm, 5 u) with a mobile phase of 70:30 supercritical $CO_2$: 20 mM $NH_3$ in MeOH with a flow rate of 60 mL/min at 40° C., outlet pressure 100 bar affording 2 peaks. The first eluting peak: (R)-2-(6-fluoro-2-methyl-3-((1-methylcyclopropyl)amino)quinoxalin-5-yl)-6-methyl-5,6-dihydropyrrolo[3,4-b]pyrrol-4(1H)-one (379) (20 mg, 0.055 mmol, 24% yield) as a yellow amorphous solid. $^1$H NMR (400 MHz, DMSO-$d_6$) δ ppm 13.42 (1H, s), 7.87 (1H, s), 7.75 (1H, s), 7.64 (1H, dd, J=9.0, 5.7 Hz), 7.34 (1H, dd, J=12.0, 8.9 Hz), 6.87 (1H, d, J=3.1 Hz), 4.68 (1H, q, J=6.5 Hz), 1.53 (3H, s), 1.39 (3H, d, J=6.7 Hz), 0.91-1.02 (2H, m), 0.82-0.91 (2H, m). $^{19}$F NMR (377 MHz, DMSO-$d_6$) δ ppm −108.38 (1F, s). m/z (ESI, +ve ion) 366.2 $(M+H)^+$. The second eluting peak: (S)-2-(6-fluoro-2-methyl-3-((1-methylcyclopropyl)amino)quinoxalin-5-yl)-6-methyl-5,6-dihydropyrrolo[3,4-b]pyrrol-4(1H)-one (380) (20 mg, 0.055 mmol, 24% yield) as a yellow amorphous solid. $^1$H NMR (400 MHz, DMSO-$d_6$) δ ppm 13.44 (1H, s), 7.89 (1H, s), 7.77 (1H, s), 7.66 (1H, dd, J=8.9, 5.8 Hz), 7.36 (1H, dd, J=12.1, 9.0 Hz), 6.89 (1H, d, J=3.1 Hz), 4.71 (1H, q, J=6.9 Hz), 1.55 (3H, s), 1.41 (3H, d, J=6.5 Hz), 0.94-1.05 (2H, m), 0.84-0.94 (2H, m). $^{19}$F NMR (377 MHz, DMSO-$d_6$) δ ppm −108.36 (1F, s). m/z (ESI, +ve ion) 366.2 $(M+H)^+$.

Example 381

2'-(2-methyl-3-((2,2,2-trifluoroethyl)amino)quinoxalin-5-yl)-1'H-spiro[cyclopropane-1,6'-pyrrolo[3,4-b]pyrrol]-4'(5'H)-one

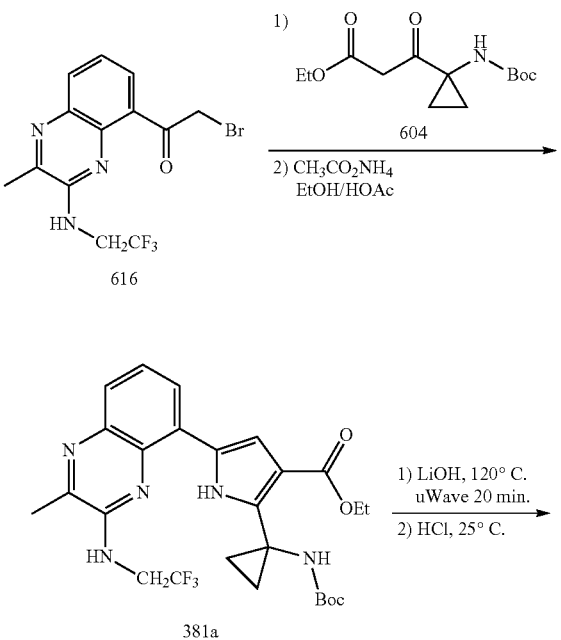

-continued

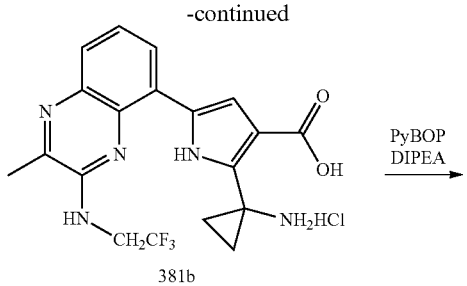

381b

Preparation of ethyl 2-(1-((tert-butoxycarbonyl)
amino)cyclopropyl)-5-(2-methyl-3-((2,2,2-trifluoro-
ethyl)amino)quinoxalin-5-yl)-1H-pyrrole-3-carboxy-
late (381a)

A mixture of 2-bromo-1-(2-methyl-3-((2,2,2-trifluoroet-hyl)amino)quinoxalin-5-yl)ethanone (616) (700 mg, 1.93 mmol), ethyl 3-(1-((tert-butoxycarbonyl)amino)cyclopropyl)-3-oxopropanoate (604, 629 mg, 2.32 mmol) and $K_2CO_3$ (668 mg, 4.83 mmol) in DMF (7.0 mL) was stirred at RT for 45 min. The reaction mixture was treated with a saturated solution of $NH_4Cl$ (aq.) and EtOAc was added and the layers were separated. The organic layer was washed with brine (25 mL), and dried over anhydrous $MgSO_4$, filtered and concentrated. The crude material was purified by chromatography on an ISCO Combiflash RF (40 g SingleStep column, eluted using a gradient of 0-90% EtOAc in hexanes) affording ethyl 2-(1-((tert-butoxycarbonyl)amino)cyclopropanecarbonyl)-4-(2-methyl-3-((2,2,2-trifluoroethyl)amino)quinoxalin-5-yl)-4-oxobutanoate (890 mg, 1.611 mmol, 83% yield) as a light orange viscous oil. m/z (ESI, +ve ion) 553.3 $(M+H)^+$. The light orange viscous oil was added to a sealed tube with EtOH (4 mL). AcOH (2 mL) and $NH_4OAc$ (1192 mg, 15.46 mmol) were added and the mixture was stirred at 60° C. for 12 h. The reaction mixture was concentrated. The residue was treated with EtOAc and water. The layers were separated and the organic layer was washed with brine. The organic layer was dried over anhydrous $MgSO_4$, filtered and concentrated. The crude material was purified by chromatography on an ISCO Combiflash RF (40 g Thomson SingleStep column, eluting with a gradient of 0-70% EtOAc in hexanes) to provide the title compound (970 mg, 1.81 mmol, 94% yield) as yellow crystalline solid. $^{19}F$ NMR (376 MHz, $CDCl_3$) δ ppm −71.24 (3F, s). m/z (ESI, +ve ion) 534.2 $(M+H)^+$.

Preparation 381b

A mixture of ethyl 2-(1-((tert-butoxycarbonyl)amino)cyclopropyl)-5-(2-methyl-3-((2,2,2-trifluoroethyl)amino)quinoxalin-5-yl)-1H-pyrrole-3-carboxylate (381a, 970 mg, 1.81 mmol) and LiOH monohydrate (381 mg, 9.09 mmol) in dioxane (8.0 mL) and water (4.00 mL) was heated at 110° C. for 5 h. It was concentrated to dryness and the remaining solid was treated with 4.0 M HCl solution in 1,4-dioxane (11.36 mL, 45.5 mmol) at RT and stirred for 30 min. The reaction mixture was concentrated to give 2-(1-aminocyclopropyl)-5-(2-methyl-3-((2,2,2-trifluoroethyl)amino)quinoxalin-5-yl)-1H-pyrrole-3-carboxylic acid hydrochloride (381b) as a red-orange solid. It was used in the subsequent step without further purification assuming quantitative yield. m/z (ESI, +ve ion) 406.1 $(M−35)^+$.

Preparation of Example 381

1-(3-carboxy-5-(2-methyl-3-((2,2,2-trifluoroethyl)amino)quinoxalin-5-yl)-1H-pyrrolo-2-yl)cyclopropanaminium chloride (381b, 800 mg, 1.81 mmol) was treated with DCM (15 mL) and DMF (15.00 mL) followed by DIEA (1.27 mL, 7.24 mmol) and (benzotriazol-1-yloxy)tripyrrolidinophosphonium hexafluorophosphate (1131 mg, 2.17 mmol). The reaction mixture was then stirred at RT for 15 min. It was diluted with EtOAc (100 mL) and washed with a saturated solution of $NaHCO_3$, and brine (3×50 mL), dried over $MgSO_4$, filtered and concentrated. The crude residue was purified by silica gel chromatography (0-20% MeOH in DCM) twice to give 2'-(2-methyl-3-((2,2,2-trifluoroethyl)amino)quinoxalin-5-yl)-1'H-spiro[cyclopropane-1,6'-pyrrolo[3,4-b]pyrrol]-4'(5'H)-one (381) (62 mg, 0.16 mmol, 9% yield) as a yellow crystalline solid. $^1H$ NMR (400 MHz, DMSO-$d_6$) δ ppm 11.60 (1H, s), 7.87 (1H, d, J=6.8 Hz), 7.72 (1H, t, J=6.3 Hz), 7.62-7.70 (2H, m), 7.44 (1H, t, J=7.8 Hz), 6.90-6.97 (1H, m), 4.31-4.45 (2H, m), 2.59 (3H, s), 1.36-1.45 (2H, m), 1.26 (2H, d, J=5.9 Hz). $^{19}F$ NMR (376 MHz, DMSO-$d_6$) δ ppm −69.21 (1F, s), −69.64 (1F, s), −71.10 (1F, s). m/z (ESI, +ve ion) 388.0 $(M+H)^+$.

Examples 382

(R)-2-(3-((2,2-difluoroethyl)amino)-2-methylquinoxalin-5-yl)-6-methyl-5,6-dihydropyrrolo[3,4-b]pyrrol-4(1H)-one; and 383: (S)-2-(3-((2,2-difluoroethyl)amino)-2-methylquinoxalin-5-yl)-6-methyl-5,6-dihydropyrrolo[3,4-b]pyrrol-4(1H)-one

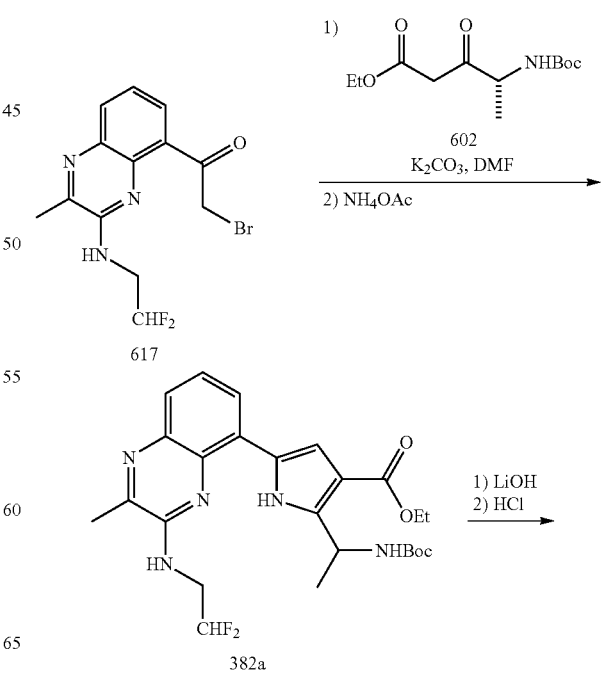

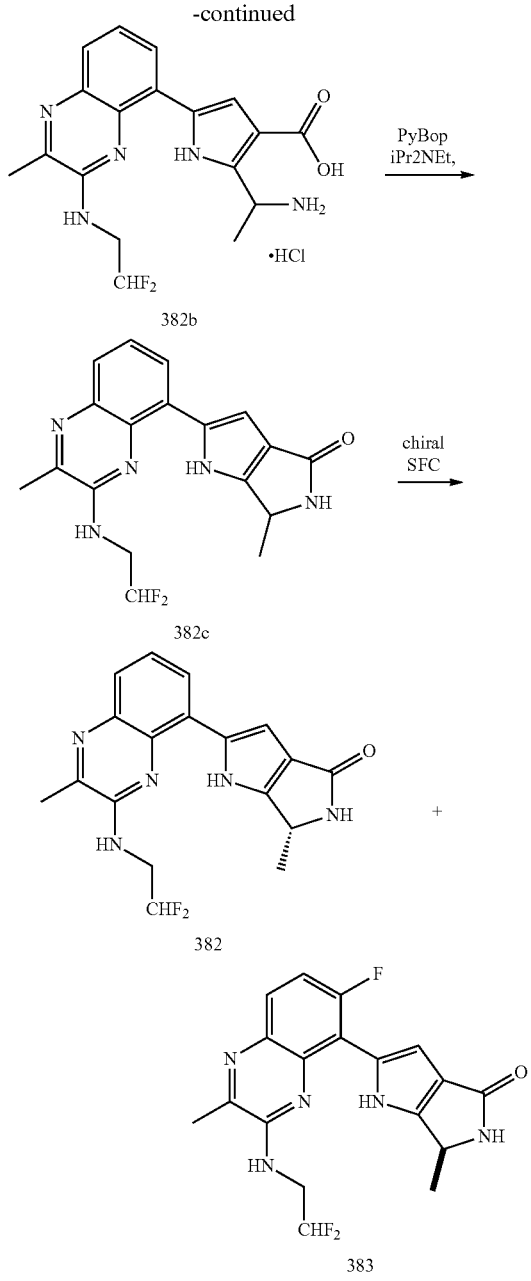

382b

382c

382

383

Preparation of ethyl 2-(1-((tert-butoxycarbonyl)amino)ethyl)-5-(3-((2,2-difluoroethyl)amino)-2-methylquinoxalin-5-yl)-1H-pyrrole-3-carboxylate (382a)

This compound (950 mg, 82% yield) as yellow crystalline solid was prepared according to the procedure described for Intermediate 293b, using 2-bromo-1-(3-((2,2-difluoroethyl)amino)-2-methylquinoxalin-5-yl)ethanone (617) (790 mg, 2.295 mmol), (R)-ethyl 4-((tert-butoxycarbonyl)amino)-3-oxopentanoate (602) (714 mg, 2.75 mmol) and $K_2CO_3$ (793 mg, 5.74 mmol) in DMF (7.0 mL) as the starting material, followed by the treatment of the resulting 4-ethyl 4-((tert-butoxycarbonyl)amino)-2-(2-(3-((2,2-difluoroethyl)amino)-2-methylquinoxalin-5-yl)-2-oxoethyl)-3-oxopentanoate (1.03 g, m/z (ESI, +ve ion) 523.1 (M+H)+) with $NH_4OAc$ (1.42 g, 18.36 mmol) in EtOH (6 mL) and AcOH (2 mL). $^{19}F$ NMR (376 MHz, $CDCl_3$) δ ppm −122.78 (1F, s), −123.02 (1F, s). m/z (ESI, +ve ion) 504.1 (M+H)+.

Preparation of 2-(1-((tert-butoxycarbonyl)amino)ethyl)-5-(3-((2,2-difluoroethyl)amino)-2-methylquinoxalin-5-yl)-1H-pyrrole-3-carboxylic acid (382b)

A glass microwave reaction vessel was charged with ethyl 2-(1-((tert-butoxycarbonyl)amino)ethyl)-5-(3-((2,2-difluoroethyl)amino)-2-methylquinoxalin-5-yl)-1H-pyrrole-3-carboxylate (950 mg, 1.887 mmol) and LiOH monohydrate (396 mg, 9.43 mmol) in dioxane (8.0 mL) and water (4.00 mL). The reaction mixture was stirred and heated in at 110° C. for 80 min. LC-MS indicated >87% conversion to the desired carboxylic acid m/z (ESI, +ve ion) 476.1 (M+H)+. The reaction mixture was transferred to a 250 mL RBF, using MeOH and concentrated to dryness affording 2-(1-((tert-butoxycarbonyl)amino)ethyl)-5-(3-((2,2-difluoroethyl)amino)-2-methylquinoxalin-5-yl)-1H-pyrrole-3-carboxylic acid as an orange solid. The orange solid was treated with 4.0 M HCl solution in 1,4-dioxane (11.79 mL, 47.2 mmol) at RT and stirred for 30 min. The reaction mixture was concentrated to give 2-(1-aminoethyl)-5-(3-((2,2-difluoroethyl)amino)-2-methylquinoxalin-5-yl)-1H-pyrrole-3-carboxylic acid hydrochloride (382b) as a red-orange solid. It was used in the subsequent step without further purification assuming quantitative yield. $^{19}F$ NMR (377 MHz, DMSO-$d_6$) δ ppm −120.68 (1F, s). (m/z (ESI, +ve ion) 376.1 (M+H)+).

Preparation of Examples 382 and 383

1-(3-Carboxy-5-(3-((2,2-difluoroethyl)amino)-2-methylquinoxalin-5-yl)-1H-pyrrol-2-yl)ethanaminium chloride (382b, 777 mg, 1.88 mmol) was treated with DCM (15 mL) and DMF (15.00 mL) followed by DIEA (1.32 mL, 7.55 mmol) and (benzotriazol-1-yloxy)tripyrrolidinophosphonium hexafluorophosphate (1.18 g, 2.26 mmol). The reaction mixture was then stirred at RT overnight. Additional (benzotriazol-1-yloxy)tripyrrolidinophosphonium hexafluorophosphate (1.00 g) was added along with DIEA (1.00 mL) and it was stirred for another 30 min. The reaction was judged to be complete by LC-MS. The reaction mixture was concentrated on the rotovap and the remaining solution treated with ice and water and the precipitate collected by filtration. The filtrate was back-extracted with EtOAc (50 mL) and $CHCl_3$/IPA 10:1 (2×50 mL), dried over $MgSO_4$, filtered and concentrated. The combined crude residue was purified on the ISCO Combiflash RF (40 g Thomson column, eluting with a gradient of 0-20% MeOH in DCM) affording the desired product (382c) as a light yellow crystalline solid after drying under vacuum. The compound (382c) was subjected to chiral purification using SFC (column: Chiralcel OD-H (Sepax) (150×21 mm, 5 u) with a mobile phase of 70:30 supercritical $CO_2$: 20 mM $NH_3$ in MeOH with a flow rate of 75 mL/min at 40° C., outlet pressure 100 bar, 5.6 mg/injection to afford 2 peaks. (R)-2-(3-((2,2-difluoroethyl)amino)-2-methylquinoxalin-5-yl)-6-methyl-5,6-dihydropyrrolo[3,4-b]pyrrol-4(1H)-one (382) (268 mg, 0.75 mmol, 40% yield) was isolated as a yellow fibrous solid as the second eluting peak. $^1H$ NMR (400 MHz, DMSO-$d_6$) δ ppm 11.89 (1H, s), 7.86 (1H, d, J=6.8 Hz), 7.67 (1H, d, J=7.4 Hz), 7.54-7.64 (2H, m), 7.41 (1H, t, J=7.7 Hz), 6.78-6.85 (1H, m), 4.53 (1H, q, J=6.6 Hz), 3.95-4.12 (1H, m), 3.79-3.95 (1H, m), 2.57 (3H, s), 1.39 (3H, d, J=6.5 Hz). $^{19}F$ NMR (376 MHz, DMSO-$d_6$) δ ppm −120.40 (2F, s). m/z (ESI, +ve ion) 358.1 (M+1)+. (S)-2-(34(2,2-difluoroethyl)amino)-2-methylquinoxalin-5-yl)-6-methyl-5,6-dihydropyrrolo[3,4-b]pyrrolo-4(1H)-one (383) (34 mg, 5% yield) was isolated as a yellow amorphous solid as the 1st eluting peak. $^1$H NMR (400 MHz, DMSO-$d_6$) δ ppm 11.89 (1H, s), 7.86 (1H, d, J=6.5 Hz), 7.67 (1H, d, J=7.2 Hz), 7.57-7.65 (2H, m), 7.41 (1H, t, J=7.8 Hz), 6.82 (1H, d, J=1.6 Hz), 4.58 (1H, s), 4.49-4.56 (1H, m), 3.97-4.11 (1H, m), 3.78-3.97 (1H, m), 2.57 (3H, s), 1.39 (3H, d, J=6.7 Hz). $^{19}$F NMR (376 MHz, DMSO-$d_6$) δ ppm −120.41 (1F, s). m/z (ESI, +ve ion) 358.1 (M+H)$^+$.

Example 401

2-(3-(2,6-dimethylphenyl)-5-quinoxalinyl)-1,5,6,7-tetrahydro-4H-pyrrolo[3,2-c]pyridin-4-one

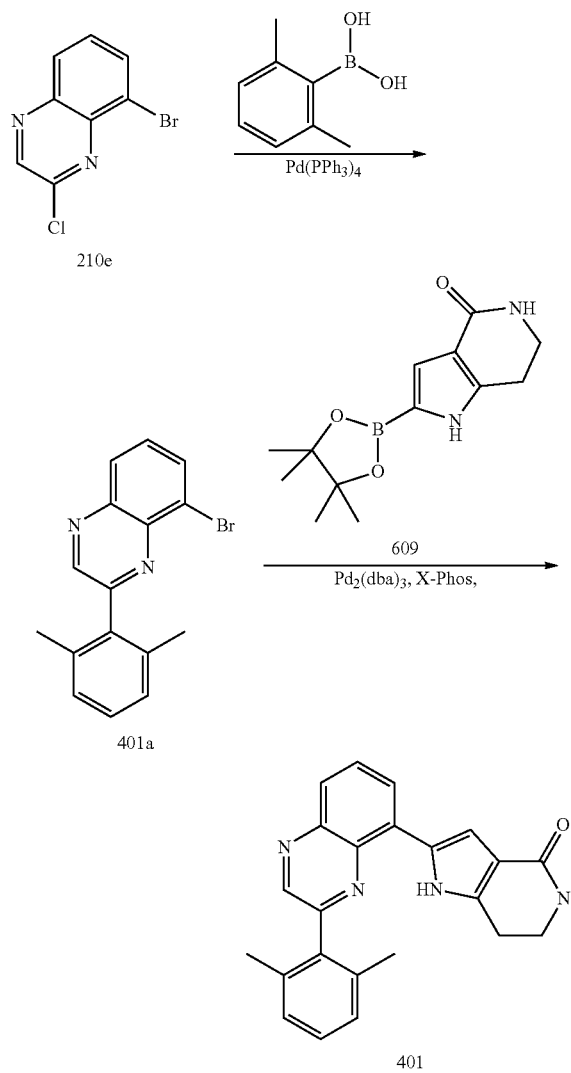

Preparation of 8-bromo-2-(2,6-dimethylphenyl)quinoxaline (401a)

Argon was bubbled into a mixture of 8-bromo-2-chloroquinoxaline (210e; 0.50 g, 2.05 mmol), Na$_2$CO$_3$ (1.09 g, 10.27 mmol), Pd(PPh$_3$)$_4$ (Strem; 0.119 g, 0.103 mmol), 2,6-dimethylbenzeneboronic acid (Aldrich; 0.31 g, 2.05 mmol) in 9 mL ACN and 3 mL water for 1 min. The reaction was sealed and heated to 80° C. overnight. The temperature was increased to 100° C. and the reaction was heated 8 h. The reaction was partitioned between water and DCM. The aqueous layer was extracted with DCM 3 times, and the combined organics were dried over anhydrous Na$_2$SO$_4$, filtered, and concentrated in vacuo. The material was treated with MeOH/DCM and adsorbed onto 2 g silica gel, dried, and purified by silica gel chromatography (40 g ISCO gold column) using 0-30% EtOAc/hexanes. The product-containing fractions were concentrated to afford 8-bromo-2-(2,6-dimethylphenyl)quinoxaline (0.08 g, 0.25 mmol, 12% yield) as an oil that solidifies very slowly to a white solid. $^1$H NMR (400 MHz, CDCl$_3$) δ ppm 8.83 (1H, s), 8.09-8.19 (2H, m), 7.67 (1H, dd, J=8.2, 7.6 Hz), 7.27-7.33 (1H, m), 7.16-7.23 (2H, m), 2.18 (6H, s). m/z (ESI, +ve) 313.0/315.0 (M+H)$^+$.

Preparation of 2-(3-(2,6-dimethylphenyl)-5-quinoxalinyl)-1,5,6,7-tetrahydro-4H-pyrrolo[3,2-c]pyridin-4-one (401)

Argon was bubbled into a mixture of potassium phosphate tribasic (0.28 g, 1.02 mmol), Xphos (Strem, 0.012 g, 0.026 mmol), Pd$_2$dba$_3$ (Strem; 0.012 g, 0.013 mmol), 2-(4,4,5,5-tetramethyl-1,3,2-dioxaborolan-2-yl)-6,7-dihydro-1H-pyrrolo[3,2-c]pyridin-4(5H)-one (609) (0.201 g, 0.766 mmol), 8-bromo-2-(2,6-dimethylphenyl)quinoxaline (401a; 0.08 g, 0.255 mmol) in 2 mL dioxane and 0.4 mL water for 2 min. The reaction was sealed and heated to 80° C. After 3 h, the reaction was cooled and 1.6 g silica gel was added, and the material dried in vacuo. The material was purified by silica gel chromatography (24 g ISCO gold column) using 0-50% 90/10 DCM/MeOH in DCM. The product-containing fractions were concentrated to afford 2-(3-(2,6-dimethylphenyl)quinoxalin-5-yl)-6,7-dihydro-1H-pyrrolo[3,2-c]pyridin-4(5H)-one (0.055 g, 0.149 mmol, 58% yield) as a yellow solid. $^1$H NMR (400 MHz, DMSO-$d_6$) δ ppm 11.77 (1H, br. s.), 8.97 (1H, s), 8.14 (1H, dd, J=7.3, 1.3 Hz), 7.95-8.02 (1H, m), 7.86-7.94 (1H, m), 7.31-7.39 (1H, m), 7.21-7.31 (3H, m), 6.98 (1H, s), 3.40 (2H, td, J=6.8, 2.3 Hz), 2.85 (2H, t, J=6.8 Hz), 2.10 (6H, s). m/z (ESI, +ve) 369.0 (M+H)$^+$.

Example 402

2-((1-methylethyl)amino)-8-(4-oxo-4,5,6,7-tetrahydro-1H-pyrrolo[3,2-c]pyridin-2-yl)-3-phenyl-4(3H)-quinazolinone

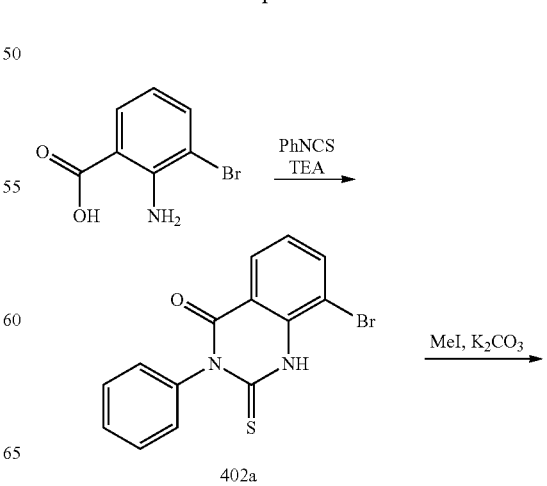

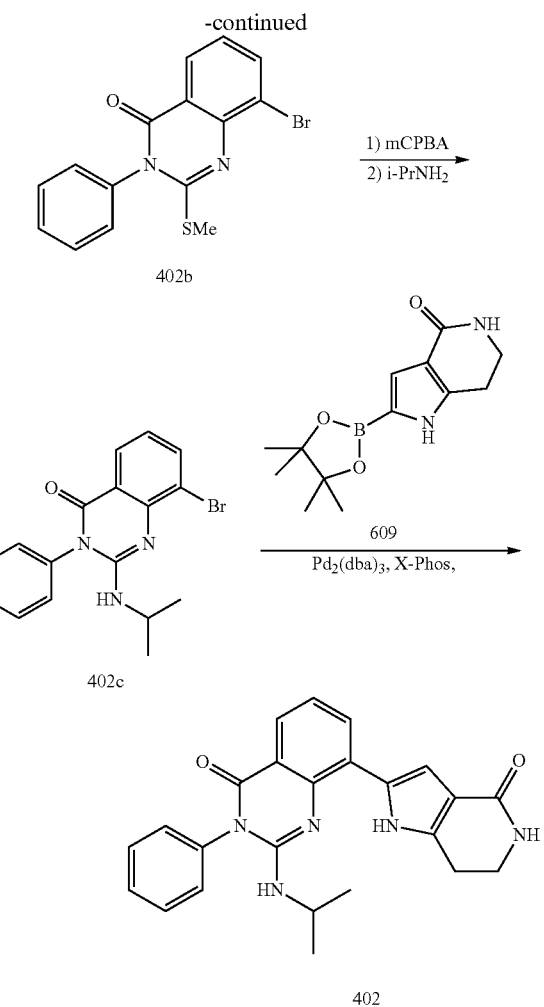

Preparation of 8-bromo-3-phenyl-2-thioxo-2,3-dihydroquinazolin-4(1H)-one (402a)

TEA (1.93 mL, 13.89 mmol), 2-amino-3-bromo-benzoic acid (Aldrich, 2.00 g, 9.26 mmol), phenyl isothiocyanate (Aldrich; 1.66 mL, 13.89 mmol) were combined in 30 mL t-BuOH, flask sealed, and heated to 100° C. overnight. The heterogeneous reaction was cooled to 40° C. and filtered, rinsing 3× Et$_2$O, and the solid was collected and dried in vacuo to give 8-bromo-3-phenyl-2-thioxo-2,3-dihydroquinazolin-4(1H)-one (3.0 g, 9.00 mmol, 97% yield) as an off-white solid. $^1$H NMR (400 MHz, DMSO-d$_6$) δ ppm 10.76 (1H, br. s.), 8.02 (1H, dd, J=7.8, 1.4 Hz), 7.94 (1H, dd, J=7.9, 1.3 Hz), 7.34-7.51 (3H, m), 7.14-7.26 (3H, m). m/z (ESI, +ve) 332.9/334.9 (M+H)$^+$.

Preparation of 8-bromo-2-(methylthio)-3-phenylquinazolin-4(3H)-one (402b)

A mixture of MeI (1.68 mL, 27.0 mmol), K$_2$CO$_3$ (2.49 g, 18.01 mmol), 8-bromo-3-phenyl-2-thioxo-2,3-dihydroquinazolin-4(1H)-one (402a; 3.00 g, 9.00 mmol) in 30 mL THF was fitted with a water cooled reflux condenser and heated to reflux (80° C. oil bath) overnight under N$_2$. Additional 1.5 equiv MeI was added and heating continued. After 2 h, water was added, and the reaction was partitioned between water and EtOAc. The aqueous layer was washed 1× brine, and the organics were dried over anhydrous Na$_2$SO$_4$, filtered, and concentrated in vacuo to give 8-bromo-2-(methylthio)-3-phenylquinazolin-4(3H)-one as an off-white solid. $^1$H NMR (400 MHz, DMSO-d$_6$) δ ppm 8.16 (1H, dd, J=7.8, 1.4 Hz), 8.07 (1H, dd, J=7.8, 1.4 Hz), 7.53-7.61 (3H, m), 7.44-7.51 (2H, m), 7.37 (1H, t, J=7.8 Hz), 2.56 (3H, s). m/z (ESI, +ve) 346.9/349.0 (M+H)$^+$.

Preparation of 8-bromo-2-(isopropylamino)-3-phenylquinazolin-4(3H)-one (402c)

To a solution of 8-bromo-2-(methylthio)-3-phenylquinazolin-4(3H)-one (402b, 1.76 g, 5.07 mmol) in 25 mL CHCl$_3$ at 0° C. was added 3-chloroperoxybenzoic acid (70-75% max.; Aldrich; 2.50 g, 10.14 mmol) in one portion. The ice bath was removed and the reaction stirred at RT for 30 min. A heterogeneous, white reaction resulted. The reaction was partitioned between sat'd NaHCO$_3$ and DCM. The aqueous layer was extracted with DCM 2 times, and the combined organics were dried over anhydrous Na$_2$SO$_4$, filtered, and concentrated in vacuo to give 2.1 g yellow solid. 0.442 g of the yellow solid was treated with isopropylamine (Aldrich; 2.87 mL, 33.4 mmol), the tube was sealed, and the reaction was heated to 80° C. for 1 h. The reaction was partitioned between saturated aqueous NaHCO$_3$ and DCM. The aqueous layer was extracted with DCM 2 times, and the combined organics were washed 1× sat'd aq. NaHCO$_3$, then dried over anhydrous Na$_2$SO$_4$, filtered, and concentrated in vacuo. The material was treated with DCM and purified by silica gel chromatography (40 g column) using 0-30% EtOAc/hexanes. The product-containing fractions were concentrated to afford 8-bromo-2-(isopropylamino)-3-phenylquinazolin-4(3H)-one (0.27 g, 0.75 mmol) as a white foam. $^1$H NMR (400 MHz, CDCl$_3$) δ ppm 8.09 (1H, dd, J=7.9, 1.5 Hz), 7.91 (1H, dd, J=7.6, 1.4 Hz), 7.52-7.67 (3H, m), 7.28-7.32 (2H, m), 7.01 (1H, t, J=7.8 Hz), 4.37 (1H, dq, J=13.3, 6.5 Hz), 3.95 (1H, d, J=6.5 Hz), 1.20 (6H, d, J=6.7 Hz). m/z (ESI, +ve) 358.0/360.0 (M+H)$^+$.

Preparation of 2-((1-methylethyl)amino)-8-(4-oxo-4,5,6,7-tetrahydro-1H-pyrrolo[3,2-c]pyridin-2-yl)-3-phenyl-4(3H)-quinazolinone (402)

Argon was bubbled into a mixture of potassium phosphate tribasic (0.26 g, 1.22 mmol), Xphos (Strem; 0.015 g, 0.030 mmol), Pd$_2$dba$_3$ (Strem; 0.014 g, 0.015 mmol), 2-(4,4,5,5-tetramethyl-1,3,2-dioxaborolan-2-yl)-6,7-dihydro-1H-pyrrolo[3,2-c]pyridin-4(5H)-one (609) (0.32 g, 1.22 mmol), 8-bromo-2-(isopropylamino)-3-phenylquinazolin-4(3H)-one (402c, 0.109 g, 0.304 mmol) in 2 mL dioxane and 0.4 mL water for 2 min. The reaction was sealed and heated to 80° C. After 2 h the reaction was concentrated onto 1.5 g silica gel and dried. The material was purified by silica gel chromatography (24 g column) using 0-100% 90/10 DCM/MeOH in DCM. The product-containing fractions were concentrated to afford 2-(isopropylamino)-8-(4-oxo-4,5,6,7-tetrahydro-1H-pyrrolo[3,2-c]pyridin-2-yl)-3-phenylquinazolin-4(3H)-one (55 mg, 0.133 mmol, 43.7% yield) as a light-yellow solid. $^1$H NMR (400 MHz, DMSO-d$_6$) δ ppm 12.15 (1H, br. s.), 8.03 (1H, dd, J=7.7, 1.5 Hz), 7.78 (1H, dd, J=7.7, 1.5 Hz), 7.52-7.66 (3H, m), 7.35-7.46 (2H, m), 7.17 (1H, t, J=7.7 Hz), 7.07 (1H, d, J=2.0 Hz), 6.94 (1H, s), 5.25 (1H, d, J=7.2 Hz), 4.13-4.28 (1H, m), 3.42 (2H, td, J=6.8, 2.3 Hz), 2.86 (2H, t, J=6.8 Hz), 1.20 (6H, d, J=6.5 Hz). m/z (ESI, +ve) 414.1 (M+H)+.

Example 403

2-((1-methylethyl)amino)-8-(4-oxo-4,5,6,7-tetrahydro-1H-pyrrolo[3,2-c]pyridin-2-yl)-3-(3-pyridinyl)-4(3H)-quinazolinone

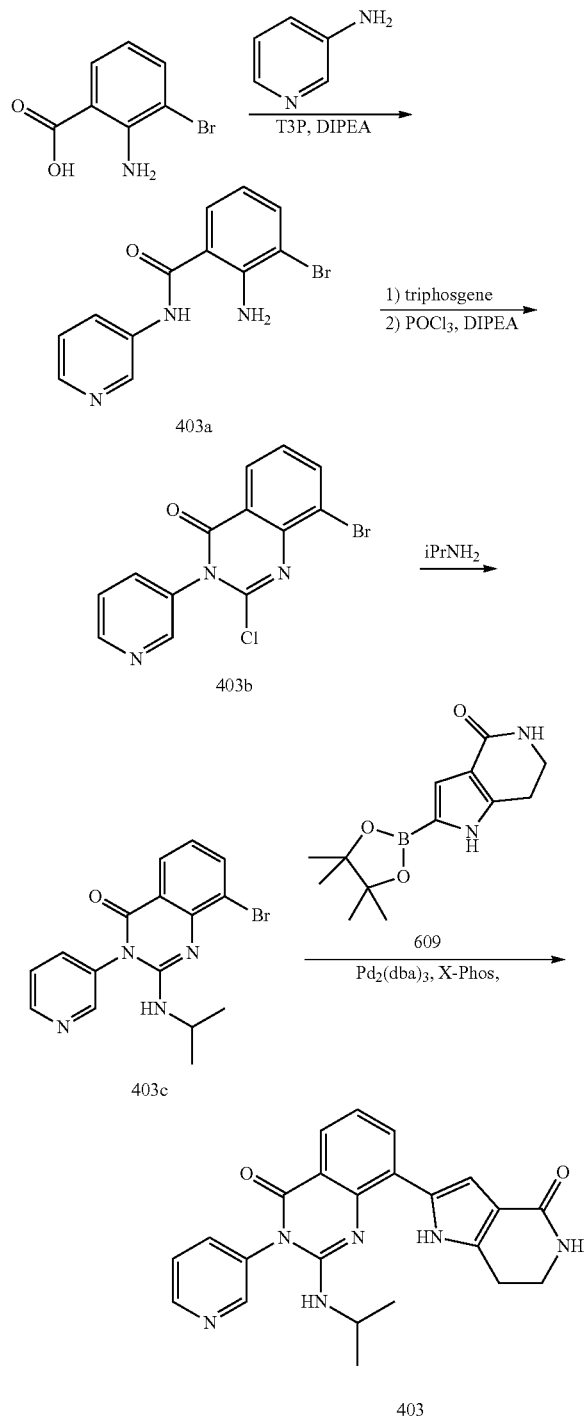

Preparation of 2-amino-3-bromo-N-(pyridin-3-yl)benzamide (403a)

To a solution of 2-amino-3-bromobenzoic acid (Aldrich; 2.00 g, 9.26 mmol) and 3-aminopyridine (Aldrich; 0.871 g, 9.26 mmol) in 10 mL EtOAc was added DIPEA (1.93 mL, 11.11 mmol) followed by 1-propanephosphonic acid cyclic anhydride (T3P) (50 wt. % solution in EtOAc; Matrix Scientific; 6.00 mL, 10.18 mmol). The reaction became warm and after 5 min a thick precipitate formed. The reaction was stirred overnight. The reaction was treated with sat'd aq. NaHCO$_3$ and EtOAc. The organic layer was washed 1× sat'd aq. NaHCO$_3$, 1× brine, dried over Na$_2$SO$_4$, filtered, and concentrated in vacuo to give 2-amino-3-bromo-N-(pyridin-3-yl)benzamide (2.13, 7.29 mmol, 79% yield) as a yellow solid used without further purification. $^1$H NMR (400 MHz, DMSO-d$_6$) δ ppm 10.37 (1H, s), 8.87 (1H, d, J=2.2 Hz), 8.31 (1H, dd, J=4.6, 1.5 Hz), 8.08-8.14 (1H, m), 7.71 (1H, dd, J=7.8, 1.4 Hz), 7.62 (1H, dd, J=7.8, 1.4 Hz), 7.39 (1H, dd, J=8.2, 4.7 Hz), 6.57-6.71 (1H, m), 6.36 (2H, s). m/z (ESI, +ve) 291.9/293.9 (M+H)+.

Preparation of 8-bromo-2-chloro-3-(pyridin-3-yl)quinazolin-4(3H)-one (403b)

Triphosgene (0.50 g, 1.69 mmol) was added to a suspension of 2-amino-3-bromo-N-(pyridin-3-yl)benzamide (403a, 1.50 g, 5.13 mmol) in 50 mL DCM. The reaction was fitted with a water-cooled reflux condenser and was heated to reflux under nitrogen overnight. The reaction was cooled and filtered, rinsing 2×DCM, and the solid collected and dried in vacuo to give 1.4 g of a yellow solid. This material was treated with POCl$_3$ (5.17 ml, 56.5 mmol), fitted with a water-cooled reflux condenser, and heated to reflux under nitrogen. After 1 h, additional POCl$_3$ (5.17 mL, 56.5 mmol) was added to promote stirring and refluxing continued. DIPEA (1.79 mL, 10.27 mmol) was added to give a dark brown solution. After 3 h the reaction was cooled, concentrated in vacuo and the brown syrup was poured onto ice and treated with 10 N NaOH until basic. The resulting cloudy mixture was extracted 2×DCM, then 1× EtOAc. Combined organics were dried over anhydrous Na$_2$SO$_4$, filtered, and concentrated in vacuo to give a brown oil. The material was treated with DCM and purified by silica gel chromatography (40 g column) using 0-40% EtOAc/hexanes. The product-containing fractions were concentrated to afford 8-bromo-2-chloro-3-(pyridin-3-yl)quinazolin-4(3H)-one (0.57 g, 1.69 mmol, 33% yield) as a light-yellow solid. $^1$H NMR (400 MHz, CDCl$_3$) δ ppm 8.80 (1H, d, J=3.9 Hz), 8.60 (1H, br. s.), 8.23 (1H, dd, J=8.0, 1.4 Hz), 8.11 (1H, dd, J=7.8, 1.4 Hz), 7.64-7.74 (1H, m), 7.55 (1H, dd, J=8.0, 4.9 Hz), 7.42 (1H, t, J=7.8 Hz). m/z (ESI, +ve) 335.9/337.9 (M+H)+.

Preparation of 8-bromo-2-(isopropylamino)-3-(pyridin-3-yl)quinazolin-4(3H)-one (403c)

A slurry of 8-bromo-2-chloro-3-(pyridin-3-yl)quinazolin-4(3H)-one (403b, 0.20 g, 0.594 mmol) and isopropylamine (2.04 mL, 23.77 mmol) was sealed and heated in an 80° C. oil bath for 1 h. The reaction was partitioned between sat'd aq. NaHCO$_3$ and DCM. The aqueous layer was extracted with DCM 2 times, and the combined organics were dried over anhydrous Na$_2$SO$_4$, filtered, and concentrated in vacuo to give 8-bromo-2-(isopropylamino)-3-(pyridin-3-yl)quinazolin-4(3H)-one (0.22 g, 0.612 mmol, 103% yield) as a light yellow foam. $^1$H NMR (400 MHz, CDCl$_3$) δ ppm 8.83 (1H, d, J=3.5 Hz), 8.60 (1H, br. s.), 8.08 (1H, dd, J=7.8, 1.6 Hz), 7.94

(1H, dd, J=7.7, 1.5 Hz), 7.66-7.75 (1H, m), 7.60 (1H, dd, J=8.0, 4.9 Hz), 7.04 (1H, t, J=7.8 Hz), 4.32-4.49 (1H, m), 3.80 (1H, d, J=6.3 Hz), 1.23 (6H, m). m/z (ESI, +ve) 359.0/361.0 (M+H)+.

Preparation of 2-((1-methylethyl)amino)-8-(4-oxo-4,5,6,7-tetrahydro-1H-pyrrolo[3,2-c]pyridin-2-yl)-3-(3-pyridinyl)-4(3H)-quinazolinone (403)

Argon was bubbled into a mixture of Xphos (Strem; 0.013 g, 0.028 mmol), potassium phosphate (0.236 g, 1.114 mmol), Pd₂dba₃ (Strem, 0.013 g, 0.014 mmol), 2-(4,4,5,5-tetramethyl-1,3,2-dioxaborolan-2-yl)-6,7-dihydro-1H-pyrrolo[3,2-c]pyridin-4(5H)-one (609; 0.292 g, 1.114 mmol), 8-bromo-2-(isopropylamino)-3-(pyridin-3-yl)quinazolin-4(3H)-one (403c, 0.100 g, 0.278 mmol) in 2 mL dioxane and 0.4 mL water for 1 min. The reaction was sealed and placed in an 80° C. oil bath. After 1 h, the reaction was cooled and adsorbed onto 1.5 g silica gel and dried. The material was purified by silica gel chromatography (24 g column) using 0-100% 90/10 DCM/MeOH in DCM. The product-containing fractions were combined and concentrated in vacuo to give 0.116 g solid. This material was sonicated in 2 mL MeOH and filtered, rinsing 2×2 mL MeOH, and the solid collected and dried in vacuo to give 2-(isopropylamino)-8-(4-oxo-4,5,6,7-tetrahydro-1H-pyrrolo[3,2-c]pyridin-2-yl)-3-(pyridin-3-yl)quinazolin-4(3H)-one (0.054 g, 0.130 mmol, 47% yield) as a yellow solid. ¹H NMR (400 MHz, DMSO-d₆) δ ppm 12.14 (1H, br. s.), 8.73 (1H, dd, J=4.8, 1.5 Hz), 8.60 (1H, d, J=2.0 Hz), 8.04 (1H, dd, J=7.6, 1.6 Hz), 7.82-7.92 (1H, m), 7.78 (1H, dd, J=7.8, 1.4 Hz), 7.64 (1H, dd, J=7.8, 5.1 Hz), 7.17 (1H, t, J=7.7 Hz), 7.09 (1H, d, J=2.2 Hz), 6.94 (1H, br. s.), 5.94 (1H, d, J=7.4 Hz), 4.16-4.33 (1H, m), 3.43 (2H, td, J=6.8, 2.3 Hz), 2.86 (2H, t, J=6.8 Hz), 1.21 (6H, d, J=3.3 Hz). m/z (ESI, +ve) 415.1 (M+H)+.

Example 404

2-(tert-butylamino)-8-(4-oxo-4,5,6,7-tetrahydro-1H-pyrrolo[3,2-c]pyridin-2-yl)-3-(3-pyridinyl)-4(3H)-quinazolinone

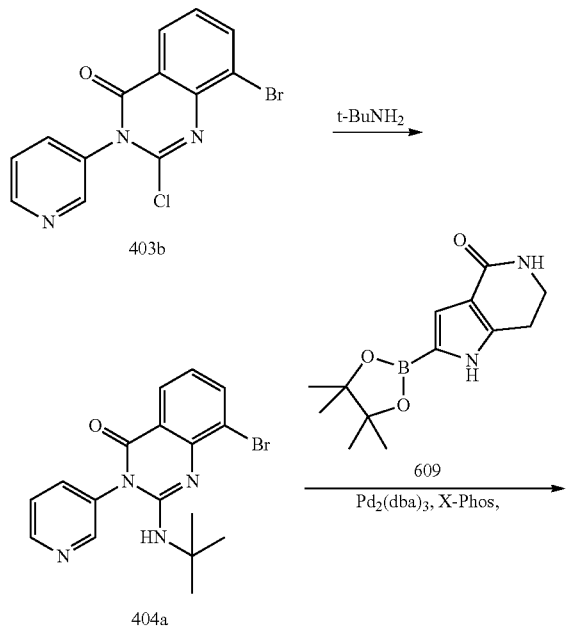

-continued

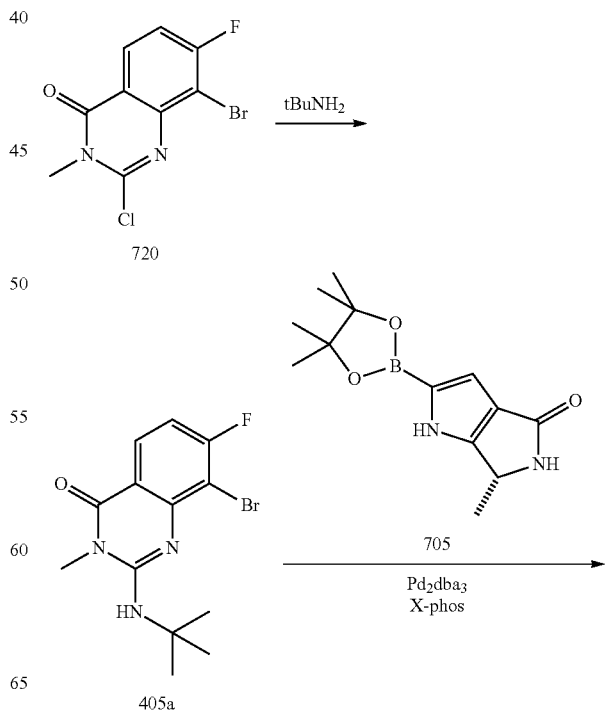

This compound was prepared according to the procedures described for Example 403. 8-Bromo-2-(tert-butylamino)-3-(pyridin-3-yl)quinazolin-4(3H)-one (404a): ¹H NMR (400 MHz, DMSO-d₆) δ ppm 8.72 (1H, dd, J=4.8, 1.5 Hz), 8.56-8.67 (1H, m), 7.99 (1H, dd, J=7.7, 1.5 Hz), 7.89-7.96 (2H, m), 7.64 (1H, ddd, J=8.1, 4.8, 0.8 Hz), 7.08 (1H, t, J=7.8 Hz), 4.74 (1H, s), 1.44 (9H, s). m/z (ESI, +ve) 373.0/375.0 (M+H)+. 2-(tert-Butylamino)-8-(4-oxo-4,5,6,7-tetrahydro-1H-pyrrolo[3,2-c]pyridin-2-yl)-3-(3-pyridinyl)-4(3H)-quinazolinone (404): ¹H NMR (400 MHz, DMSO-d₆) δ ppm 11.90 (1H, br. s.), 8.74 (1H, dd, J=4.8, 1.5 Hz), 8.64 (1H, d, J=2.0 Hz), 7.91-8.05 (2H, m), 7.84 (1H, dd, J=7.7, 1.5 Hz), 7.66 (1H, ddd, J=8.1, 4.8, 0.8 Hz), 7.22 (1H, t, J=7.7 Hz), 6.99 (1H, d, J=2.2 Hz), 6.94 (1H, br. s.), 4.62 (1H, s), 3.42 (2H, td, J=6.8, 2.5 Hz), 2.84 (2H, t, J=6.8 Hz), 1.40 (9H, s). m/z (ESI, +ve) 429.0 (M+H)+.

Example 405

2-(tert-butylamino)-7-fluoro-3-methyl-8-((6R)-6-methyl-4-oxo-1,4,5,6-tetrahydropyrrolo[3,4-b]pyrrol-2-yl)-4(3H)-quinazolinone

557

-continued

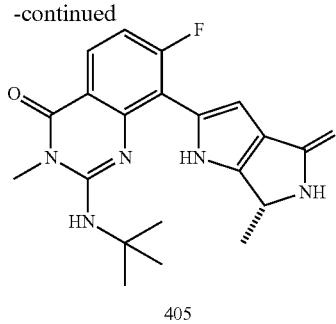

405

Preparation of 8-bromo-2-(tert-butylamino)-7-fluoro-3-methylquinazolin-4(3H)-one (405a)

A slurry mixture of 8-bromo-2-chloro-7-fluoro-3-methylquinazolin-4(3H)-one (720; 0.45 g, 1.54 mmol) in tert-butylamine (2.43 mL, 23.16 mmol) in a sealed glass tube was heated in an 80° C. oil bath for 1 h. The reaction was cooled to RT, diluted with water, and filtered, rinsing with 2× water and 2× diethyl ether. The solid was collected and dried in vacuo to give 0.364 g white solid. The aqueous filtrate was extracted 2×DCM, dried over anhydrous $Na_2SO_4$, filtered, and concentrated in vacuo to give additional 0.146 g white solid. Both materials were dissolved in DCM and adsorbed onto 2 g silica gel and dried. The material was purified by silica gel chromatography (24 g column) using 0-50% EtOAc/hexanes. The product-containing fractions were concentrated to afford 8-bromo-2-(tert-butylamino)-7-fluoro-3-methylquinazolin-4(3H)-one (0.47 g, 1.44 mmol, 94% yield) as a white solid. $^1$H NMR (400 MHz, $CDCl_3$) δ ppm 8.07 (1H, dd, J=8.8, 6.1 Hz), 6.91 (1H, t, J=8.4 Hz), 4.56 (1H, br. s.), 3.48 (3H, s), 1.60-1.70 (9H, s). MS (ESI, pos. ion) m/z: 328.0/330.0 (M+1).

Preparation of 2-(tert-butylamino)-7-fluoro-3-methyl-8-((6R)-6-methyl-4-oxo-1,4,5,6-tetrahydropyrrolo[3,4-b]pyrrol-2-yl)-4(3H)-quinazolinone (405)

Argon was bubbled into a mixture of tris $Pd_2dba_3$ (Strem; 0.014 g, 0.015 mmol), Xphos (Strem; 0.015 g, 0.030 mmol), (R)-6-methyl-2-(4,4,5,5-tetramethyl-1,3,2-dioxaborolan-2-yl)-5,6-dihydropyrrolo[3,4-b]pyrrolo-4(1H)-one (705; 0.160 g, 0.609 mmol), 8-bromo-2-(tert-butylamino)-7-fluoro-3-methylquinazolin-4(3H)-one (405a; 0.100 g, 0.305 mmol), potassium phosphate (Aldrich; 0.194 g, 0.914 mmol) in 2 mL dioxane and 0.4 mL water for 1 min. The reaction was sealed and heated to 80° C. for 2 h. The reaction was cooled and transferred to a RBF with some MeOH and adsorbed onto 1.5 g silica gel and dried in vacuo. The material was purified by silica gel chromatography (24 g column) using 0-100% 90/10 DCM/MeOH in DCM. The product-containing fractions were concentrated to afford (R)-2-(tert-butylamino)-7-fluoro-3-methyl-8-(6-methyl-4-oxo-1,4,5,6-tetrahydropyrrolo[3,4-b]pyrrol-2-yl)quinazolin-4(3H)-one (0.06 g, 0.15 mmol, 50% yield) as a off-white solid. $^1$H NMR (400 MHz, DMSO-$d_6$) δ ppm 11.76 (1H, s), 7.96 (1H, dd, J=8.8, 6.3 Hz), 7.58 (1H, s), 7.07 (1H, dd, J=10.0, 8.8 Hz), 6.35 (1H, t, J=1.8 Hz), 6.01 (1H, s), 4.50 (1H, q, J=6.7 Hz), 3.45 (3H, s), 1.38 (9H, s), 1.35 (3H, d, J=6.7 Hz). $^{19}$F NMR (377 MHz, DMSO-$d_6$) δ ppm −105.07 (s). m/z (ESI, +ve ion) 384.1 (M+H)$^+$.

558

Example 406

2-(tert-butylamino)-3-(1-methylethyl)-8-((6R)-6-methyl-4-oxo-1,4,5,6-tetrahydropyrrolo[3,4-b]pyrrol-2-yl)-4(3H)-quinazolinone

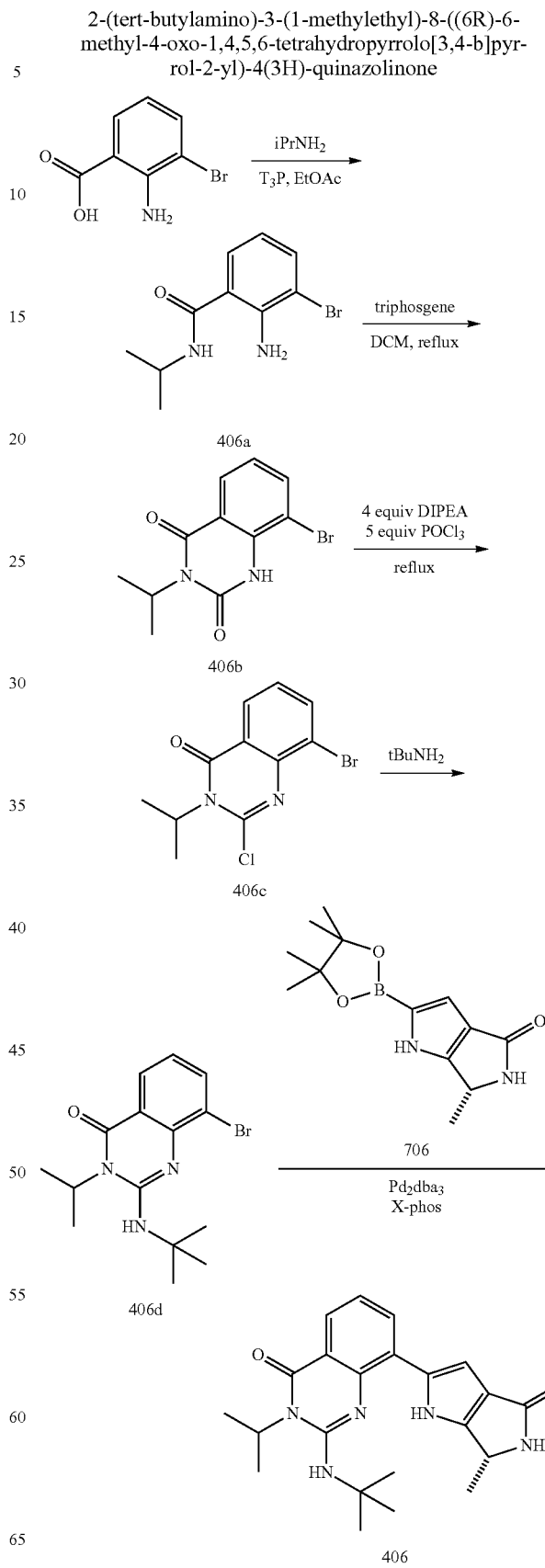

Preparation of 2-amino-3-bromo-N-isopropylbenzamide (406a)

To a slurry of 2-amino-3-bromobenzoic acid (Aldrich; 1.00 g, 4.63 mmol) in 10 mL EtOAc in an ice bath was added 1-propanephosphonic acid cyclic anhydride (50 wt % in EtOAc; Matrix Scientific; 3.00 mL, 5.09 mmol) followed by isopropylamine (1.19 mL, 13.89 mmol). The ice bath was removed and the solution stirred rapidly at RT. A precipitate formed. After 30 min, the reaction was judged complete. The reaction was partitioned between sat'd aq. NaHCO$_3$ and EtOAc. The organic layer was washed with sat'd aq. NaHCO$_3$ once, sat'd NaCl once, and the organics were dried over anhydrous Na$_2$SO$_4$, filtered, and concentrated in vacuo to give 2-amino-3-bromo-N-isopropylbenzamide (1.00 g, 3.89 mmol, 84% yield) as a white solid: $^1$H NMR (400 MHz, CDCl$_3$) δ ppm 7.51 (2H, dd, J=7.9, 1.5 Hz), 7.25 (1H, d, J=1.4 Hz), 6.53 (2H, t, J=7.8 Hz), 5.72-6.15 (3H, m), 4.15-4.33 (1H, m), 1.27 (7H, d, J=6.7 Hz). m/z (ESI, +ve) 257.0/259.0 (M+H)$^+$.

Preparation of 8-bromo-3-isopropylquinazoline-2,4(1H,3H)-dione (406b)

A slurry of 2-amino-3-bromo-N-isopropylbenzamide (406a, 1.00 g, 3.89 mmol) and tri-phosgene (Aldrich; 0.462 g, 1.556 mmol) in 50 mL DCM was fitted with a water cooled reflux condenser and drying tube and heated to reflux overnight. In the morning, complete conversion to desired product. The reaction was cooled and concentrated in vacuo to give 8-bromo-3-isopropylquinazoline-2,4(1H,3H)-dione (1.1 g, 3.89 mmol, 100% yield) as a white solid: $^1$H NMR (400 MHz, CDCl$_3$) δ ppm 8.02-8.25 (1H, m), 7.98 (1H, br. s.), 7.78 (1H, dd, J=7.8, 1.4 Hz), 7.11 (1H, t, J=7.9 Hz), 5.27 (1H, dt, J=13.9, 6.9 Hz), 1.56 (6H, s). m/z (ESI, +ve) 282.9/284.9 (M+H)$^+$.

Preparation of 8-bromo-2-chloro-3-isopropylquinazolin-4(3H)-one (406c)

A mixture of POCl$_3$ (1.79 mL, 19.60 mmol) and DIPEA (1.36 mL, 7.84 mmol) was heated to reflux for 2 h. The reaction reached 50% conversion. Additional DIPEA (Aldrich; 1.36 mL, 7.84 mmol) was added and the reaction stirred overnight. The reaction was judged complete. The reaction was cooled, treated with ice, and agitated. The slurry was poured onto ~20 mL 10 N NaOH in ice and stirred rapidly for 20 min. The precipitate (very fine) was collected by filtration rinsing with 3×20 mL water. The solid was dried in vacuo to give 8-bromo-2-chloro-3-isopropylquinazolin-4(3H)-one (0.978 g, 3.24 mmol, 83% yield) was a tan solid. $^1$H NMR (400 MHz, CDCl$_3$) δ ppm 8.18 (1H, dd, J=8.0, 1.4 Hz), 8.00 (1H, dd, J=7.8, 1.4 Hz), 7.33 (1H, t, J=7.9 Hz), 5.31 (1H, br. s.), 1.67 (6H, d, J=7.0 Hz). m/z (ESI, +ve) 301.0/302.9 (M+H)$^+$.

Preparation of 8-bromo-2-(tert-butylamino)-3-isopropylquinazolin-4(3H)-one (406d)

A slurry of 8-bromo-2-chloro-3-isopropylquinazolin-4(3H)-one (406c, 0.40 g, 1.326 mmol) and tert-butylamine (4.18 mL, 39.8 mmol) was heated in a sealed tube at 80° C. overnight. The reaction was treated with ice, water, and DCM. The cloudy aq. layer was extracted 4×DCM and 1× EtOAc. The combined organics were dried over anhydrous Na$_2$SO$_4$, filtered, and concentrated in vacuo. The material was treated with DCM and purified by silica gel chromatography (24 g column) using 0-40% EtOAc/hexanes. The product-containing fractions were concentrated to afford 8-bromo-2-(tert-butylamino)-3-isopropylquinazolin-4(3H)-one (0.39 g, 1.15 mmol, 87% yield) as an oil which slowly solidified. $^1$H NMR (400 MHz, CDCl$_3$) δ ppm 8.05 (1H, dd, J=7.9, 1.5 Hz), 7.83 (1H, dd, J=7.6, 1.4 Hz), 6.97 (1H, t, J=7.7 Hz), 5.55 (1H, br. s.), 4.68 (1H, br. s.), 1.63 (9H, s), 1.55 (6H, d, J=7.2 Hz). m/z (ESI, +ve) 338.0/340.0 (M+H)$^+$.

Preparation of 2-(tert-butylamino)-3-(1-methylethyl)-8-((6R)-6-methyl-4-oxo-1,4,5,6-tetrahydropyrrolo[3,4-b]pyrrol-2-yl)-4(3H)-quinazolinone (406)

Argon was bubbled into a mixture of Pd$_2$dba$_3$ (Strem, 7.45 mg, 8.13 μmol), Xphos (Strem; 7.75 mg, 0.016 mmol), (R)-6-methyl-2-(4,4,5,5-tetramethyl-1,3,2-dioxaborolan-2-yl)-5,6-dihydropyrrolo[3,4-b]pyrrol-4(1H)-one (705; 0.085 g, 0.325 mmol), 8-bromo-2-(tert-butylamino)-3-isopropylquinazolin-4(3H)-one (0.055 g, 0.163 mmol), potassium phosphate (0.10 g, 0.488 mmol) in 1 mL dioxane and 0.2 mL water for 1 min. The reaction was sealed and heated to 80° C. for 2 h. The reaction was cooled and transferred to a RBF with some MeOH and adsorbed onto 0.7 g silica gel and dried in vacuo. The material was purified by silica gel chromatography (12 g column) using 0-100% 90/10 DCM/MeOH in DCM. The product-containing fractions were concentrated to afford (R)-2-(tert-butylamino)-3-isopropyl-8-(6-methyl-4-oxo-1,4,5,6-tetrahydropyrrolo[3,4-b]pyrrol-2-yl)quinazolin-4(3H)-one (0.044 g, 0.112 mmol, 69% yield) as a light yellow solid. $^1$H NMR (400 MHz, DMSO-d$_6$) δ ppm 11.78 (1H, s), 7.84 (2H, ddd, J=14.9, 7.6, 1.6 Hz), 7.59 (1H, s), 7.15 (1H, t, J=7.7 Hz), 6.63 (1H, d, J=1.6 Hz), 5.72 (1H, s), 4.94 (1H, quin, J=6.7 Hz), 4.51 (1H, q, J=6.8 Hz), 3.17 (3H, s), 1.52 (6H, d, J=6.8 Hz), 1.48 (9H, s), 1.36 (3H, d, J=6.7 Hz). m/z (ESI, +ve ion) 394.1 (M+H)$^+$.

Example 407

2-(tert-butyl)methyl)amino)-8-((6R)-6-methyl-4-oxo-1,4,5,6-tetrahydropyrrolo[3,4-b]pyrrol-2-yl)-4(3H)-quinazolinone

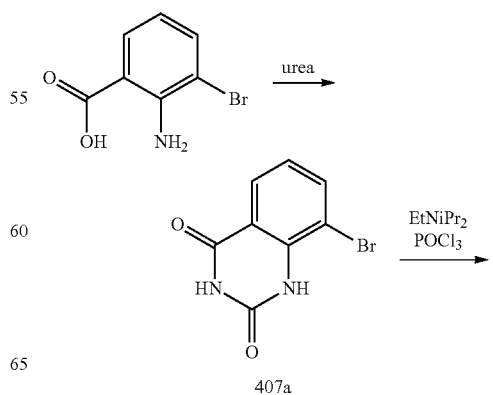

407a

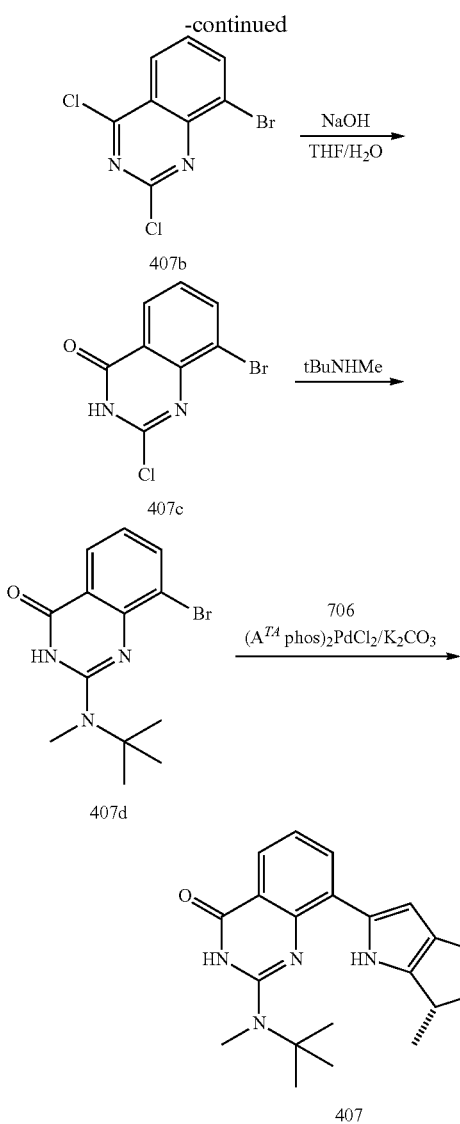

Preparation of
8-bromoquinazoline-2,4(1H,3H)-dione (407a)

Urea (Sigma; 3.78 g, 63.0 mmol) and 2-amino-3-bromobenzoic acid (Aldrich; 4.00 g, 18.52 mmol) were combined and heated, open to air, in a 170° C. oil bath. After 3 h, additional urea (Sigma; 3.78 g, 63.0 mmol) was added and stirring continued. After 5 h, the reaction was judged complete and cooled, treated with water, filtered, and the solid dried overnight in vacuo to give 4.7 g. The material was treated with water and stirred rapidly for 3 h to give a fine suspension. The solid was collected by filtration and dried in vacuo overnight, to give 8-bromoquinazoline-2,4(1H,3H)-dione (4.30 g, 17.84 mmol, 96% yield) as a light yellow solid. $^1$H NMR (400 MHz, DMSO-$d_6$) δ ppm 11.50 (1H, br. s.), 10.25 (1H, br. s.), 7.93 (2H, dq, J=7.8, 1.4 Hz), 7.13 (1H, t, J=7.8 Hz). m/z (ESI, +ve ion) 240.9/242.9 (M+H)$^+$.

Preparation of 8-bromo-2,4-dichloroquinazoline
(407b)

To a slurry of 8-bromoquinazoline-2,4-diol (407a, 4.30 g, 17.84 mmol) in POCl$_3$ (Aldrich; 8.17 mL, 89 mmol) was added DIPEA (15.52 mL, 89 mmol) in small ~2 mL portions. The reaction became hot and was cooled in an ice bath for the rest of DIPEA addition. The slurry was fitted with a water cooled reflux condenser and drying tube and heated to reflux. After 4 h, the reaction was nearly complete. The reaction was heated 1 h additional, cooled, and poured onto ice. While still cold the mixture was treated with 10 N NaOH until pH >10. The resulting very fine orange solid was collected by filtration. The solid was rinsed 2× water and dried in vacuo to give 8-bromo-2,4-dichloroquinazoline (4.30 g, 15.47 mmol, 87% yield) as an orange solid. $^1$H NMR (400 MHz, CDCl$_3$) δ ppm 8.25-8.31 (2H, m), 7.61 (1H, dd, J=8.2, 7.6 Hz). m/z (ESI, +ve ion) 276.9/278.9/280.9 (M+H)$^+$.

Preparation of 8-bromo-2-chloroquinazolin-4-ol
(407c)

To a biphasic mixture of NaOH 1 N aq. (10.79 mL, 10.79 mmol) and 11 mL THF was added 8-bromo-2,4-dichloroquinazoline (407b, 1.50 g, 5.40 mmol) in one portion. The reaction became dark red. After 20 min the reaction was checked by LC/MS and judged complete. The reaction was cooled in an ice/water bath and acidified with AcOH. The reaction was concentrated to ½ volume on rotovap (precipitate observed) and cooled in an ice/water bath. The slurry was filtered and the solid rinsed with 2× water. The orange solid was collected and dried in vacuo to give 8-bromo-2-chloroquinazolin-4-ol (1.10 g, 4.24 mmol, 79% yield) as an orange solid. $^1$H NMR (400 MHz, DMSO-$d_6$) δ ppm 13.49 (1H, br. s.), 8.15 (1H, dd, J=7.8, 1.4 Hz), 8.09 (1H, dd, J=7.9, 1.5 Hz), 7.45 (1H, t, J=7.8 Hz). m/z (ESI, +ve ion) 258.9/260.9 (M+H)$^+$.

Preparation of 8-bromo-2-(tert-butyl(methyl)amino)
quinazolin-4(3H)-one (407d)

A mixture of 8-bromo-2-chloroquinazolin-4-ol (407c, 0.20 g, 0.77 mmol) in N-methyl-tert-butylamine (Aldrich; 0.919 mL, 7.71 mmol) and 1 mL NMP was sealed and heated to 150° C. in an oil bath for 6 h. The reaction was heated for 3 days. The reaction was partitioned between sat'd aq. NH$_4$Cl and EtOAc. The organic layer was washed with sat'd aq. NH$_4$Cl once, sat'd aq. NaCl once, and the organics were dried over anhydrous Na$_2$SO$_4$, filtered, and concentrated in vacuo. The material was treated with 10% MeOH in DCM, adsorbed onto 1.5 g silica gel, and purified by silica gel chromatography (24 g column) using 0-50% EtOAc/hexanes. The product-containing fractions were concentrated to afford 8-bromo-2-(tert-butyl(methyl)amino)quinazolin-4(3H)-one (0.060 g, 0.19 mmol, 25% yield) as a yellow solid. $^1$H NMR (400 MHz, DMSO-$d_6$) δ ppm 11.36 (1H, br. s.), 7.76-8.03 (2H, m), 6.95-7.14 (1H, m), 2.97 (3H, s), 1.55 (9H, s). m/z (ESI, +ve ion) 310.0/312.0 (M+H)$^+$.

Preparation of 2-(tert-butyl(methyl)amino)-8-((6R)-6-methyl-4-oxo-1,4,5,6-tetrahydropyrrolo[3,4-b]pyrrol-2-yl)-4(3H)-quinazolinone (407)

Argon was bubbled into a mixture of 8-bromo-2-(tert-butyl(methyl)amino)quinazolin-4(3H)-one (407d, 0.060 g, 0.193 mmol), K$_2$CO$_3$ (Mallinkrodt; 0.107 g, 0.774 mmol), dichlorobis(p-dimethylaminophenylditbutylphosphine)palladium (ii) (Aldrich; 0.027 g, 0.039 mmol), (R)-6-methyl-2-(4,4,5,5-tetramethyl-1,3,2-dioxaborolan-2-yl)-5,6-dihydropyrrolo[3,4-b]pyrrol-4(1H)-one (706) (0.101 g, 0.387 mmol). The reaction was sealed and placed in a 100° C. oil bath for 30 min. The reaction was partitioned between sat'd aq. NH$_4$Cl and DCM. The aqueous layer was extracted with DCM twice and 5% IPA/CHCl$_3$ two times and the combined organics were dried over anhydrous Na$_2$SO$_4$, filtered, and concentrated in vacuo. This material was dissolved in DMSO, filtered, and purified by RPHPLC, Phenomenex Gemini 150×30 mm C$_{18}$ column, 10-70% ACN/H$_2$O with 0.1% TFA; product-containing fractions were treated with saturated aqueous NaHCO$_3$ and DCM. The aqueous layer was extracted 3×DCM and combined organics dried over Na$_2$SO$_4$, filtered, and concentrated in vacuo to give 20 mg yellow solid. The material was sonicated in 0.5 mL DCM and filtered, rinsing with 0.5 mL DCM to give (R)-2-(tert-butyl(methyl)amino)-8-(6-methyl-4-oxo-1,4,5,6-tetrahydropyrrolo[3,4-b]pyrrol-2-yl)quinazolin-4(3H)-one (0.011 g, 0.030 mmol, 15% yield) as a light yellow solid. $^1$H NMR (400 MHz, DMSO-d$_6$) δ ppm 11.97 (1H, br. s.), 11.39 (1H, br. s.), 7.90 (2H, dd, J=12.8, 7.5 Hz), 7.60 (1H, s), 7.22 (1H, t, J=7.7 Hz), 6.71 (1H, s), 4.46-4.59 (1H, m), 2.99 (3H, s), 1.45 (9H, s), 1.36 (3H, d, J=6.7 Hz). m/z (ESI, +ve ion) 366.0 (M+H)$^+$.

Example 408

2-(tert-butylamino)-8-((6R)-6-methyl-4-oxo-1,4,5,6-tetrahydropyrrolo[3,4-b]pyrrol-2-yl)-4(3H)-quinazolinone

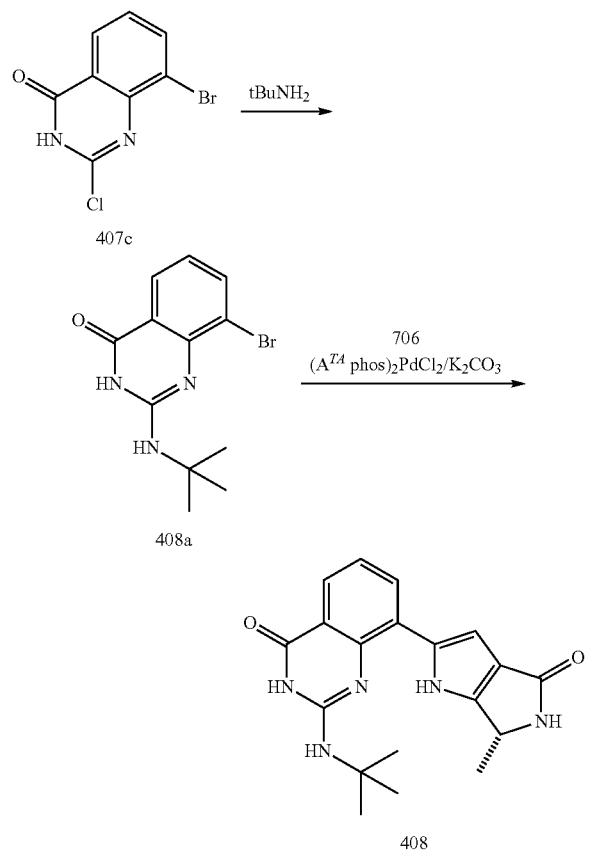

Preparation of 8-bromo-2-(tert-butylamino)quinazolin-4(3H)-one (408a)

A mixture of 8-bromo-2-chloroquinazolin-4-ol (407c, 0.20 g, 0.77 mmol) in 2-methylpropan-2-amine (1.62 mL, 15.42 mmol) was sealed and heated to 80° C. overnight. The reaction was transferred to a microwave vessel and heated to 170° C. for 30 min. The reaction was transferred to a flask with DCM/MeOH and concentrated in vacuo. The material was taken up in DCM/MeOH and adsorbed onto 1.3 g silica gel and dried in vacuo. The material was purified by silica gel chromatography (24 g column) using 0-100% EtOAc/hexanes. The product-containing fractions were concentrated to afford 8-bromo-2-(tert-butylamino)quinazolin-4(3H)-one (408a, 0.128 g, 0.432 mmol, 56% yield) as a yellow solid. $^1$H NMR (400 MHz, DMSO-d$_6$) δ ppm 10.59 (1H, s), 7.85-7.90 (2H, m), 7.00 (1H, t, J=7.7 Hz), 6.22 (1H, s), 1.48 (9H, s). m/z (ESI, +ve ion) 296.0/298.0 (M+H)$^+$.

Preparation of 2-(tert-butylamino)-8-((6R)-6-methyl-4-oxo-1,4,5,6-tetrahydro-pyrrolo[3,4-b]pyrrol-2-yl)-4(3H)-quinazolinone (408)

Argon was bubbled into a mixture of 8-bromo-2-(tert-butylamino)quinazolin-4(3H)-one (408a, 62 mg, 0.21 mmol), K$_2$CO$_3$ (0.116 g, 0.84 mmol), dichlorobis(p-dimethylaminophenylditbutylphosphine)palladium (ii) (Aldrich; 0.030 g, 0.042 mmol), (R)-6-methyl-2-(4,4,5,5-tetramethyl-1,3,2-dioxaborolan-2-yl)-5,6-dihydropyrrolo[3,4-b]pyrrol-4(1H)-one (706; 0.110 g, 0.419 mmol) and 2 mL dioxane and 0.4 mL water for 1 min. The reaction was sealed and placed in a 100° C. oil bath for 30 min. The reaction was cooled and partitioned between sat'd aq. NH$_4$Cl and DCM. The aqueous layer was extracted with 5% IPA/CHCl$_3$ three times and the combined organics were dried over anhydrous Na$_2$SO$_4$, filtered, and concentrated in vacuo. This material was dissolved in DMSO, filtered, and purified by RPHPLC, Phenomenex Gemini 150×30 mm C18 column, 10-70% ACN/H$_2$O with 0.1% TFA; product-containing fractions were treated with saturated aqueous NaHCO$_3$ and DCM. The aqueous layer was extracted 3×DCM and combined organics dried over Na$_2$SO$_4$, filtered, and concentrated in vacuo to give 21 mg as a tan solid. The material was sonicated in 0.5 mL DCM for 2 min, then filtered, rinsing 2×DCM. The solid was collected and dried in vacuo to give (R)-2-(tert-butylamino)-8-(6-methyl-4-oxo-1,4,5,6-tetrahydropyrrolo[3,4-b]pyrrol-2-yl)quinazolin-4(3H)-one (6 mg, 0.017 mmol, 8% yield) as a tan solid. $^1$H NMR (400 MHz, DMSO-d$_6$) δ ppm 12.21 (1H, br. s.), 10.63 (1H, s), 7.95 (1H, dd, J=7.6, 1.6 Hz), 7.82 (1H, dd, J=7.8, 1.6 Hz), 7.62 (1H, s), 7.16 (1H, t, J=7.7 Hz), 6.79 (1H, d, J=1.4 Hz), 6.30 (1H, s), 4.54 (1H, d, J=6.7 Hz), 1.47 (9H, s), 1.36 (3H, d, J=6.7 Hz). m/z (ESI, +ve ion) 352.1 (M+H)$^+$.

Example 409

2'-(3-(tert-butylamino)-2-methyl-5-quinoxalinyl)-2,3,5,6-tetrahydro-1'H-spiro[pyran-4,6'-pyrrolo[3,4-b]pyrrol]-4'(5'H)-one

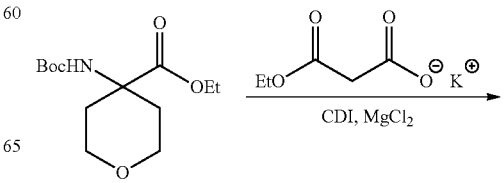

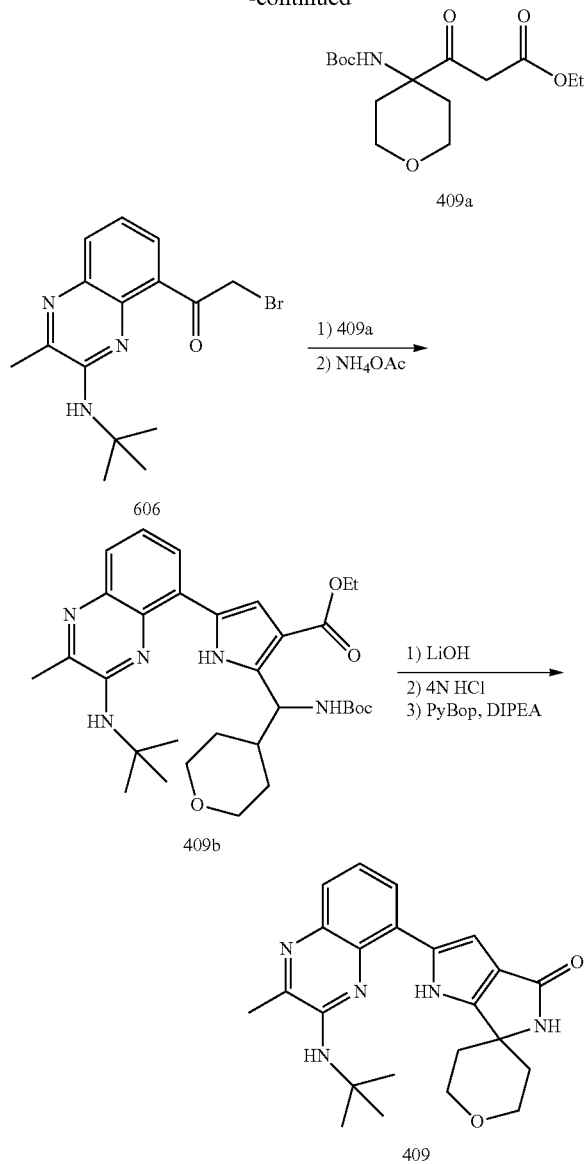

Preparation of ethyl 3-(4-(((tert-butoxycarbonyl)amino)tetrahydro-2H-pyran-4-yl)-3-oxopropanoate (409a)

A mixture of 4-(Boc-amino)tetrahyropyran-4-carboxylic acid (475 mg, 1.937 mmol, Alfa Aesar, Ward Hill, Mass.) and 1,1'-carbonyldiimidazole (471 mg, 2.90 mmol) was set stirring in THF (10.2 mL) at RT for 3 h. Magnesium chloride (369 mg, 3.87 mmol, Sigma Aldrich,) and ethyl potassium malonate (659 mg, 3.87 mmol, Sigma Aldrich,) were added sequentially, and the mixture was stirred at 50° C. for 16 h. The reaction mixture was cooled to RT, diluted with water, and extracted with EtOAc. The combined organics were washed with brine, dried over $Na_2SO_4$, filtered, and concentrated under reduced pressure. The crude mixture was taken up in DCM, adsorbed onto silica, and purified on 24 g $SiO_2$ (eluent: 0-100% EtOAc/hexanes, RediSep Gold). The product fractions were combined and concentrated in vacuo to give the product as a colorless oil (521 mg, 85%). m/z (ESI, +ve) 216.0 (M+H-Boc)[1].

Preparation of ethyl 2-(((tert-butoxycarbonyl)amino)(tetrahydro-2H-pyran-4-yl)methyl)-5-(3-(tert-butylamino)-2-methylquinoxalin-5-yl)-1H-pyrrole-3-carboxylate (409b)

A mixture of 2-bromo-1-(3-(tert-butylamino)-2-methylquinoxalin-5-yl)ethanone (250 mg, 0.744 mmol, 606), ethyl 3-(4-((tert-butoxy-carbonyl)amino)tetrahydro-2H-pyran-4-yl)-3-oxopropanoate (516 mg, 0.818 mmol, 409a), and $K_2CO_3$ (257 mg, 1.86 mmol) was set stirring at RT in DMF (0.9 mL)/THF (0.9 mL) for 3 h. The mixture was diluted with water and extracted with EtOAc. The organic partition was washed with brine, dried over $Na_2SO_4$, filtered, and concentrated to a yellow residue under reduced pressure. The crude material was purified on a silica gel column to give 366 mg of a yellow residue. The residue was taken up in EtOH (0.9 mL) and HOAc (0.6 mL) was added to encourage solublization of the material. An additional two volumes of EtOH and HOAc were added, and the mixture was set stirring with $NH_4OAc$ (287 mg, 3.72 mmol) in a sealed tube at 50° C. for 18 h. The material was cooled to RT and concentrated in vacuo to a yellow residue. It was diluted with 5 N NaOH (aq.) and extracted with EtOAc. The combined organics were dried over $Na_2SO_4$, filtered, and concentrated under reduced pressure. The residue was diluted with DCM, adsorbed onto silica, and purified on 24 g $SiO_2$ (0-100% EtOAc/hexanes, RediSep Gold) to give 280 mg of a yellow solid containing a mixture of the product and the uncyclized dione. m/z (ESI, +ve) 552.0 (M+H)$^+$.

Preparation of 2'-(3-(tert-butylamino)-2-methylquinoxalin-5-yl)-2,3,5,6-tetrahydro-1'H-spiro[pyran-4,6'-pyrrolo[3,4-b]pyrrol]-4'(5'H)-one (409)

The mixture of 409b and the uncyclized dione (280 mg, 0.508 mmol, 409b), LiOH hydrate (106 mg, 2.54 mmol), dioxane (2.1 mL), and water (2.1 mL) was sealed and heated to 110° C. for 1 h with microwave irradiation. The reaction was heated to 120° C. for an additional 1 h with microwave irradiation. The mixture was diluted with water and acidified to pH 2 with 5 N HCl (aq.). The mixture was extracted with 10% MeOH/DCM. The combined organics were dried over $Na_2SO_4$, filtered, and concentrated under reduced pressure to a red residue. The residue was taken up in 2 mL 1,4-dioxane and 4 N HCl in dioxane was added (4 mL). The solution was stirred at RT for 18 h. The material was adsorbed onto silica and purified on 12 g $SiO_2$ (eluent: 0-100% EtOAc/hexanes over 15 min then 5-10% MeOH/DCM over 20 min, RediSep). Fractions containing the major product were combined and concentrated under reduced pressure to give 54.7 mg of a yellow residue. The residue and DIPEA (0.135 mL, 0.775 mmol) in DCM (0.6 mL)/DMF (0.6 mL) was set stirring at 0° C. under nitrogen, and (benzotriazol-1-yloxy)tripyrrolidinophosphonium hexafluorophosphate (81 mg, 0.155 mmol) was added. The material was warmed to RT and stirred for an additional 3 h. It was concentrated under reduced pressure and purified by reverse-phase preparative HPLC using a Phenomenex Gemini column, 10 micron, C18, 100 Å, 150×30 mm, 0.1% TFA in $CH_3CN/H_2O$, gradient 10% to 95% over 8 min. The product fractions were concentrated in a Genevac EZ-2 Evaporator at 55° C. They were solublized with MeOH and applied to a MeOH-washed Si-carbonate cartridge (Silicycle). It was flushed with 2 M $NH_3$/MeOH to give a second yellow filtrate that was concentrated under reduced pressure to give the product (409; 7.4 mg, 14% yield for 3 steps) as a light-yellow solid. $^1$H NMR (400 MHz, $CDCl_3$) δ ppm: 12.02 (br. s., 1H), 7.96 (d, J=6.3 Hz, 1H), 7.70 (d, J=6.8 Hz, 1H), 7.39 (t, J=7.8 Hz, 1H), 7.22 (d, J=2.5 Hz, 1H), 5.96 (s, 1H), 4.88 (s, 1H), 4.36 (d, J=2.5 Hz, 2H), 3.97 (t, J=5.4 Hz, 2H), 2.63 (br. s., 2H), 2.57 (s, 3H), 1.62 (s, 9H), 1.26 (s, 2H). m/z (ESI, +ve) 407.0 (M+H)+.

Example 410

2-(3-(2-chloro-3-pyridinyl)-2-methyl-5-quinoxalinyl)-1,5,6,7-tetrahydro-4H-pyrrolo[3,2-c]pyridin-4-one

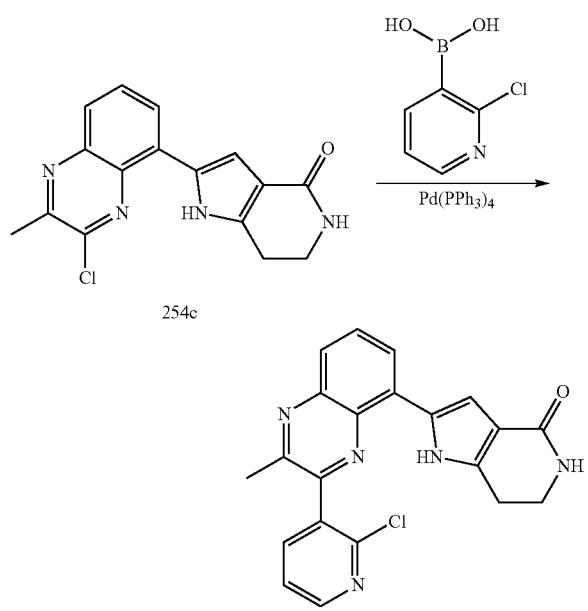

410

A mixture of Na₂CO₃ (102 mg, 0.959 mmol), Pd(Ph₃)₄ (18.47 mg, 0.016 mmol; Strem Chemicals), (2-chloropyridin-3-yl)boronic acid (75 mg, 0.480 mmol; Alfa Aesar, Ward Hil, Mass.), and 2-(3-chloro-2-methylquinoxalin-5-yl)-6,7-dihydro-1H-pyrrolo[3,2-c]pyridin-4(5H)-one (100 mg, 0.320 mmol, 254c) was added to a conical vessel, sealed, and evacuated and backfilled with nitrogen three times. 1,4-dioxane (2.4 mL) and water (0.8 mL) were added via syringe, and the reaction was heated to 100° C. overnight. The reaction was cooled to RT and concentrated under reduced pressure to a residue. The residue was taken up in 2 mL DMSO, filtered through a syringe filter, and purified by reverse-phase preparative HPLC using a Xbridge C18 column (150 mm×30 mm, 10 mm), 40 mL min with 0.1% TFA in CH₃CN/H₂O, gradient 25% to 75% over 12 min. The product fractions were concentrated in a Genevac EZ-2 evaporator. The resulting solids were taken up in MeOH and eluted through a Si-carbonate cartridge (Silicycle, pre-washed with MeOH). The eluent was concentrated under reduced pressure to give 2-(3-(2-chloro-3-pyridinyl)-2-methyl-5-quinoxalinyl)-1,5,6,7-tetrahydro-4H-pyrrolo[3,2-c]pyridin-4-one (5 mg, 4%). ¹H NMR (400 MHz, DMSO-d₆) δ ppm 11.72 (1H, s) 8.84-8.98 (1H, m) 8.79 (1H, d, J=4.89 Hz) 8.08 (1H, dd, J=5.97, 2.64 Hz) 7.89-7.95 (2H, m) 7.82 (1H, d, J=4.89 Hz) 7.16-7.23 (1H, m) 7.01 (1H, br. s.) 3.33-3.43 (2H, m) 2.83 (2H, t, J=6.94 Hz) 2.54 (3H, s) m/z (ESI, +ve) 390.8 (M+H)+.

Example 411

2-(3-(3-chloro-4-pyridinyl)-2-methyl-5-quinoxalinyl)-1,5,6,7-tetrahydro-4H-pyrrolo[3,2-c]pyridin-4-one

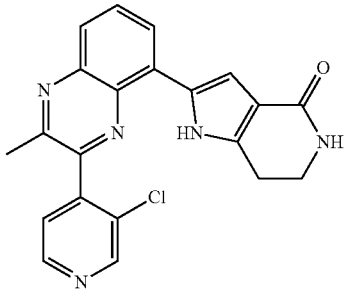

411

This compound was prepared according the procedures described for 410, using (3-chloropyridin-4-yl)boronic acid (75 mg, 0.480 mmol, Alfa Aesar, Ward Hill, Mass.) as the boronic acid. Purification by reverse-phase preparative HPLC using a Xbridge C18 column (150 mm×30 mm, 10 mm), 40 mL min with 0.1% TFA in CH₃CN/H₂O, gradient 25% to 75% over 12 min. The product fractions were concentrated in a Genevac EZ-2 evaporator. The resulting solids were taken up in MeOH and eluted through a Si-carbonate cartridge (Silicycle, pre-washed with MeOH). The eluent was concentrated under reduced pressure to give 2-(3-(3-chloro-4-pyridinyl)-2-methyl-5-quinoxalinyl)-1,5,6,7-tetrahydro-4H-pyrrolo[3,2-c]pyridin-4-one (5 mg, 4%). ¹H NMR (400 MHz, DMSO-d₆) δ ppm 11.72 (1H, s) 8.89-8.94 (1H, m) 8.77-8.81 (1H, m) 8.08 (1H, dd, J=5.97, 2.64 Hz) 7.91-7.94 (1H, m) 7.82 (1H, d, J=4.89 Hz) 7.18 (1H, d, J=2.35 Hz) 7.01 (1H, br. s.) 3.34-3.42 (3H, m) 2.83 (2H, t, J=6.94 Hz) 2.54 (3H, s) m/z (ESI, +ve) 390.0 (M+H)+.

Example 412

2-(3-(4-chloro-3-pyridinyl)-2-methyl-5-quinoxalinyl)-1,5,6,7-tetrahydro-4H-pyrrolo[3,2-c]pyridin-4-one

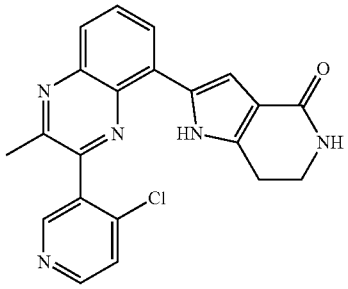

412

This compound was prepared according the procedures described for 410, using (4-chloropyridin-3-yl)boronic acid (75 mg, 0.480 mmol, Alfa Aesar, Ward Hill, Mass.) as the boronic acid. Purification by reverse-phase preparative HPLC using a Xbridge C18 column (150 mm×30 mm, 10 mm), 40 mL min with 0.1% TFA in CH₃CN/H₂O, gradient 25% to 75% over 12 min. The product fractions were concentrated in a Genevac EZ-2 evaporator. The resulting solids were taken up in MeOH and eluted through a Si-carbonate cartridge (Silicycle, pre-washed with MeOH). The eluent was concentrated under reduced pressure to give 2-(3-(4-chloro-3-pyridinyl)-2-methyl-5-quinoxalinyl)-1,5,6,7-tetrahydro-4H-pyrrolo[3,2-c]pyridin-4-one (4.9 mg, 4%). $^1$H NMR (400 MHz, DMSO-$d_6$) δ ppm 8.90 (1H, s) 8.75 (1H, d, J=5.48 Hz) 8.07 (1H, d, J=6.06 Hz) 7.89-7.93 (2H, m) 7.83 (1H, d, J=5.67 Hz) 7.18 (1H, s) 7.00 (1H, s) 3.37 (3H, br. s.) 2.82 (2H, t, J=6.85 Hz) 2.53-2.57 (3H, m). m/z (ESI, +ve) 390.9 (M+H)$^+$.

Example 413

2-(3-(4-amino-2-chlorophenyl)-2-methyl-5-quinoxalinyl)-1,5,6,7-tetrahydro-4H-pyrrolo[3,2-c]pyridin-4-one

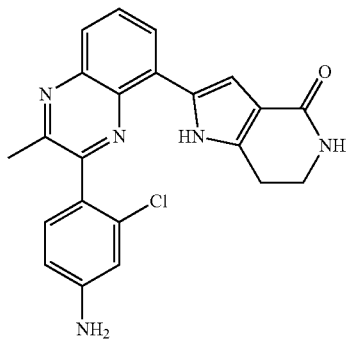

413

This compound was prepared according the procedures described for 410, using 3-chloro-4-(4,4,5,5-tetramethyl-1,3,2-dioxaborolan-2-yl)aniline (82 mg, 0.480 mmol, Combi-Blocks, San Diego, Calif.) as the boronate. Purification by reverse-phase preparative HPLC using a Xbridge $C_{18}$ column (150 mm×30 mm, 10 mm), 40 mL min with 0.1% TFA in CH$_3$CN/H$_2$O, gradient 25% to 75% over 12 min. The product fractions were concentrated in a Genevac EZ-2 evaporator. The resulting solids were taken up in MeOH and eluted through a Si-carbonate cartridge (Silicycle, pre-washed with MeOH). The eluent was concentrated under reduced pressure to give 2-(3-(4-amino-2-chlorophenyl)-2-methyl-5-quinoxalinyl)-1,5,6,7-tetrahydro-4H-pyrrolo[3,2-c]pyridin-4-one (5.6 mg, 4%). $^1$H NMR (400 MHz, DMSO-$d_6$) δ ppm 11.78 (1H, br. s.) 8.04 (1H, dd, J=7.14, 1.66 Hz) 7.76-7.89 (3H, m) 7.32 (1H, d, J=8.41 Hz) 7.20-7.27 (2H, m) 6.99 (1H, br. s.) 6.79 (1H, d, J=2.15 Hz) 6.69 (1H, dd, J=8.41, 2.15 Hz) 3.39 (2H, t, J=6.16 Hz) 2.83 (2H, t, J=6.85 Hz) 2.56 (3H, s). m/z (ESI, +ve) 404.9 (M+H)$^+$.

Example 414

2-(3-(2-chloro-6-fluorophenyl)-2-methyl-5-quinoxalinyl)-1,5,6,7-tetrahydro-4H-pyrrolo[3,2-c]pyridin-4-one

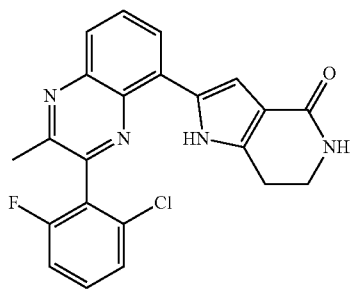

414

This compound was prepared according the procedures described for Example 410, using (2-chloro-6-fluorophenyl) boronic acid (84 mg, 0.480 mmol, Combi-Blocks, San Diego, Calif.) as the boronic acid. Purification by reverse-phase preparative HPLC using a Xbridge C18 column (150 mm×30 mm, 10 mm), 40 mL min with 0.1% TFA in CH$_3$CN/H$_2$O, gradient 25% to 75% over 12 min. The product fractions were concentrated in a Genevac EZ-2 evaporator. The resulting solids were taken up in MeOH and eluted through a Si-carbonate cartridge (Silicycle, pre-washed with MeOH). The eluent was concentrated under reduced pressure to give 2-(3-(2-chloro-6-fluorophenyl)-2-methyl-5-quinoxalinyl)-1,5,6,7-tetrahydro-4H-pyrrolo[3,2-c]pyridin-4-one (4.0 mg, 3%). $^1$H NMR (400 MHz, DMSO-$d_6$) δ ppm 11.78 (1H, br. s.) 8.10 (1H, dd, J=5.58, 3.03 Hz) 7.86-7.93 (2H, m) 7.66-7.73 (1H, m) 7.58-7.66 (1H, m) 7.47-7.57 (1H, m) 7.20 (1H, s) 6.93 (1H, br. s.) 3.36-3.40 (2H, m) 2.82 (2H, t, J=6.75 Hz) 2.52-2.52 (3H, m). m/z (ESI, +ve) 407.9 (M+H)$^+$.

Example 415

2-((1-methylethyl)amino)-8-(4-oxo-4,5,6,7-tetrahydro-1H-pyrrolo[3,2-c]pyridin-2-yl)-3-(2-pyridinyl)-4(3H)-quinazolinone

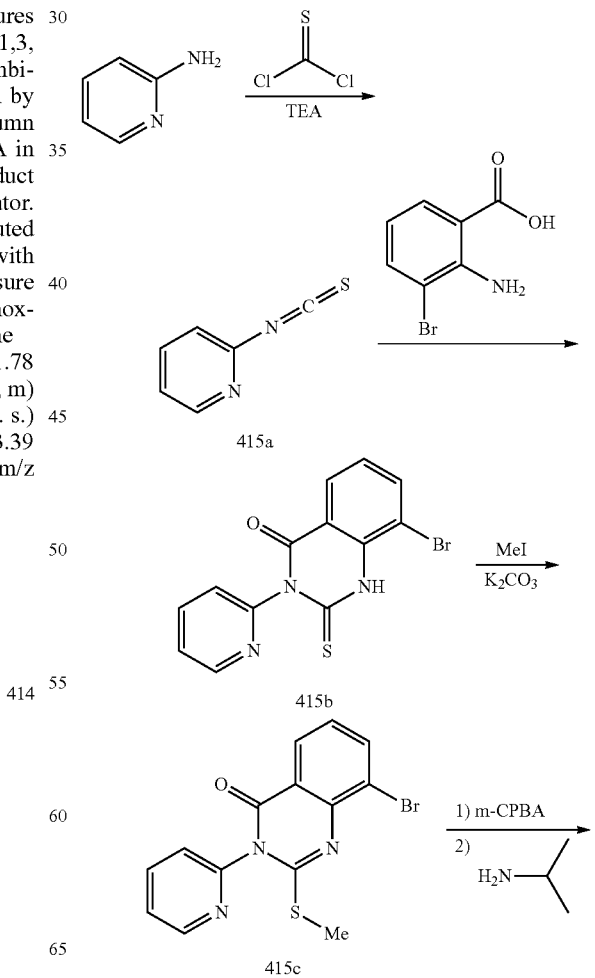

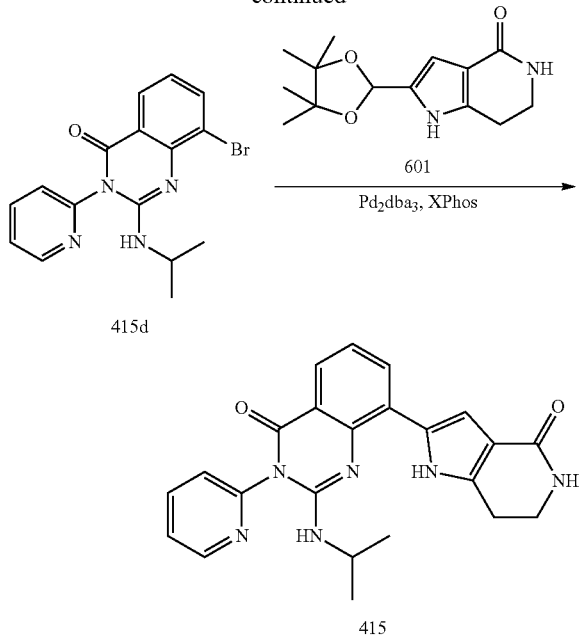

Preparation of 2-isothiocyanatopyridine (415a)

A solution of 2-aminopyridine (0.94 g, 9.99 mmol, Sigma Aldrich) and TEA (3.06 mL, 21.97 mmol) in THF (40.0 mL) was set stirring at 0° C. under nitrogen. A solution of thiophosgene (0.804 mL, 10.49 mmol, Fluka) in 2 mL THF was added dropwise over 5 minutes, and the reaction was stirred for 3 h at 0° C. Silica was added, and the reaction mixture was adsorbed under reduced pressure. It was purified on 16 g $SiO_2$ (eluent: 0-100% EtOAc/hexanes over 30 min, RediSep Gold). The product fractions containing the product by TLC (50% EtOAc/hexanes) were combined and concentrated under reduced pressure to give 2-isothiocyanatopyridine (852 mg, 63%). m/z (ESI, +ve) 137.0 (M+H)$^+$.

Preparation of 8-bromo-3-(pyridin-2-yl)-2-thioxo-2,3-dihydroquinazolin-4(1H)-one (415b)

A mixture of 2-amino-3-bromobenzoic acid (705 mg, 3.26 mmol, Sigma Aldrich) and 2-isothiocyanatopyridine (800 mg, 5.87 mmol, 415a) in EtOH (19.6 mL) was set stirring at RT, and TEA (0.68 mL, 4.90 mmol) was added dropwise. It was sealed and heated to 100° C. for 16 h. The mixture was concentrated under reduced pressure to a residue that was taken up in DCM. Silica was added, and the crude reaction was adsorbed. It was purified on 24 g $SiO_2$ (eluent: 0-100% EtOAc/hexanes over 30 min, RediSep Gold). The product fractions were combined and concentrated under reduced pressure to give a yellow-orange solid (311 mg, 29%). $^1$H NMR (400 MHz, DMSO-d$_6$) δ ppm 11.18 (1H, br. s.) 8.60 (1H, d, J=4.69 Hz) 8.39 (1H, d, J=4.11 Hz) 8.11 (1H, d, J=6.85 Hz) 7.83-7.93 (1H, m) 7.78 (1H, dd, J=7.82, 1.37 Hz) 7.44-7.53 (2H, m). m/z (ESI, +ve) 333.8 (M+H)$^+$.

Preparation of 8-bromo-2-(methylthio)-3-(pyridin-2-yl)quinazolin-4(3H)-one (415c)

A mixture of 8-bromo-3-(pyridin-2-yl)-2-thioxo-2,3-dihydroquinazolin-4(1H)-one (330 mg, 0.987 mmol, 415b), $K_2CO_3$ (59.6 mg, 0.987 mmol), and THF (9.9 mL) was set stirring under nitrogen at RT. MeI (61.3 pt, 0.987 mmol) was added, and the mixture was set stirring at 75° C. for 4 h. The reaction was cooled to RT and filtered, rinsing with chilled THF. The filtrate was concentrated under reduced pressure to give 310 mg of a waxy yellow-brown solid that contained the product. m/z (ESI, +ve) 349.7 (M+H)$^+$.

Preparation of 8-bromo-2-(isopropylamino)-3-(pyridin-2-yl)quinazolin-4(3H)-one (415d)

A mixture of 8-bromo-2-(methylthio)-3-(pyridin-2-yl)quinazolin-4(3H)-one (179 mg, 0.514 mmol, 415c) in DCM (5.1 mL) was set stirring and 3-chloroperoxybenzoic acid (127 mg, 0.565 mmol, 77% max.; Sigma Aldrich) was added. The mixture was stirred for 4 h to give a mixture of sulfone and sulfoxide. The reaction mixture was diluted with saturated aqueous $NaHCO_3$ and extracted with DCM. The combined organics were dried over $Na_2SO_4$, filtered, and concentrated under reduced pressure to give a yellow residue. The residue and isopropylamine (1.7 mL, 19.73 mmol) was set stirring at 80° C. for 30 min. The reaction was cooled to RT and diluted with water. The mixture was extracted with DCM and dried over $Na_2SO_4$. Silica was added, and the material was adsorbed under reduced pressure. It was purified on 12 g $SiO_2$ (eluent: 0-100% EtOAc/hexanes over 25 min, RediSep Gold). The product fractions were combined and concentrated under reduced pressure to give 8-bromo-2-(isopropylamino)-3-(pyridin-2-yl)quinazolin-4(3H)-one (71 mg, 30% for 2 steps). $^1$H NMR (400 MHz, DMSO-d$_6$) ppm 8.69 (1H, dd, J=4.79, 1.08 Hz) 8.08 (1H, td, J=7.73, 1.76 Hz) 7.97 (1H, dd, J=7.63, 1.37 Hz) 7.88 (1H, dd, J=7.92, 1.47 Hz) 7.55-7.63 (2H, m) 7.03 (1H, t, J=7.73 Hz) 5.90 (1H, d, J=7.63 Hz) 1.15 (6H, d, J=6.65 Hz). m/z (ESI, +ve) 360.8 (M+H)$^+$.

Preparation of 2-((1-methylethyl)amino)-8-(4-oxo-4,5,6,7-tetrahydro-1H-pyrrolo[3,2-c]pyridin-2-yl)-3-(2-pyridinyl)-4(3H)-quinazolinone (415)

A mixture of
Pd$_2$dba$_3$ (8.67 mg, 9.46 μmol, Strem Chemicals, MA), $K_3PO_4$ (161 mg, 0.757 mmol), XPhos (9.02 mg, 0.019 mmol, Strem Chemicals, MA), and 2-(4,4,5,5-tetramethyl-1,3,2-dioxaborolan-2-yl)-6,7-dihydro-1H-pyrrolo[3,2-c]pyridin-4 (5H)-one (248 mg, 0.946 mmol, 609) was sealed in a 5 mL conical microwave tube and evacuated and backfilled with nitrogen 3×. 8-Bromo-2-(isopropylamino)-3-(pyridin-2-yl)quinazolin-4(3H)-one (68 mg, 0.189 mmol, 415d) was added as a solution in 1,4-dioxane (0.7 mL). Water (0.2 mL) was added, and the mixture was stirred at 80° C. for 2 h. The material was cooled to RT and concentrated under reduced pressure. It was taken up in DMSO, filtered, and purified by reverse-phase preparative HPLC using an Xbridge column, 0.1% TFA in $CH_3CN/H_2O$, gradient 5% to 50% over 12 min. The product fractions were dried in a Genevac EZ-2 evaporator at 55° C. The material was solubilized in 1:1 MeOH: DCM, and the free base was generated using a Si-carbonate cartridge (Silicycle, pre-washed with MeOH). The filtrate was concentrated under reduced pressure to give 2-((1-methylethyl)amino)-8-(4-oxo-4,5,6,7-tetrahydro-1H-pyrrolo[3,2-c]pyridin-2-yl)-3-(2-pyridinyl)-4(3H)-quinazolinone as a pale yellow solid (6 mg, 7%). $^1$H NMR (DMSO-d$_6$) δ ppm 12.11 (1H, br. s.), 8.70 (1H, d, J=4.5 Hz), 8.06-8.12 (1H, m), 8.04 (1H, d, J=8.2 Hz), 7.78 (1H, d, J=7.0 Hz), 7.59-7.65 (2H, m), 7.18 (1H, t, J=7.7 Hz), 7.08 (1H, s), 6.97 (1H, br. s.), 5.84

(1H, d, J=7.4 Hz), 4.18-4.29 (1H, m), 4.11 (1H, br. s.), 3.14-3.19 (2H, m), 2.86 (2H, t, J=6.9 Hz), 1.18-1.25 (6H, m). m/z (ESI, +ve) 415.0 (M+H)+.

Example 416

2-(3-(tert-butylamino)-2-methylquinoxalin-5-yl)-7-methyl-1H-pyrrolo[2,3-d]pyridazin-4(5H)-one

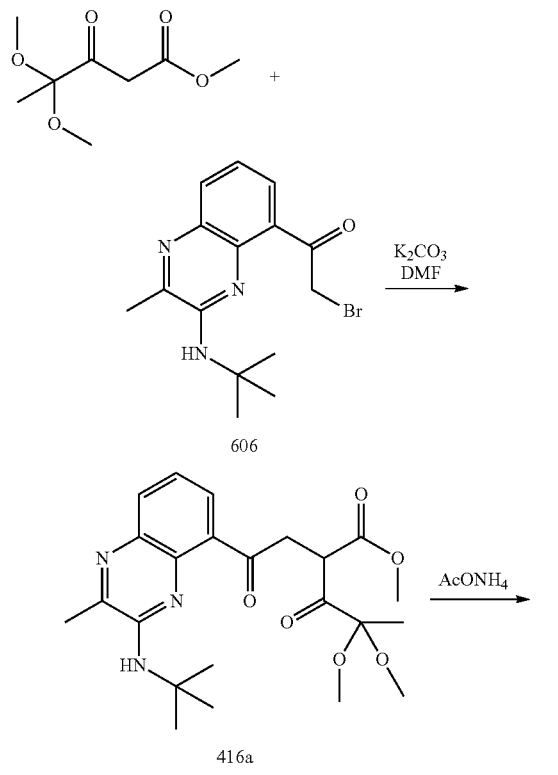

Preparation of methyl 2-(2-(3-(tert-butylamino)-2-methylquinoxalin-5-yl)-2-oxoethyl)-4,4-dimethoxy-3-oxopentanoate (416a)

A mixture of methyl 4,4-dimethoxy-3-oxovalerate (Sigma Aldrich, 0.127 ml, 0.744 mmol), K₂CO₃ (EMD Biosciences, 0.135 ml, 2.231 mmol), 2-bromo-1-(3-(tert-butylamino)-2-methylquinoxalin-5-yl)ethanone (606) (0.25 g, 0.744 mmol) in DMF (2.97 mL) was stirred at RT for 2 d. Reaction mixture was diluted with DCM and washed with alternating water and brine washes (2×) to remove DMF. The organic layer was concentrated and advanced to the next step. m/z (ESI, +ve) 446.1 (M+H).

Preparation of methyl 2-acetyl-5-(3-(tert-butylamino)-2-methylquinoxalin-5-yl)-1H-pyrrole-3-carboxylate (416b)

Methyl 2-(2-(3-(tert-butylamino)-2-methylquinoxalin-5-yl)-2-oxoethyl)-4,4-dimethoxy-3-oxopentanoate (416a) (0.331 g, 0.744 mmol), EtOH (1.69 mL), AcOH (0.169 mL), and NH₄OAc (Sigma Aldrich, 0.160 mL, 2.23 mmol) were mixed at RT and heated to 65° C. for 4 h. An additional 0.4 mL of AcOH and an additional aliquot of NH₄OAc were added and the resulting mixture was heated to 65° C. overnight. Reaction mixture was quenched with water, extracted with EtOAc. The organic layer was then washed with saturated NaHCO₃ solution. The organic layer was dried over MgSO₄, concentrated and advanced to next step. m/z (ESI, +ve) 381.2 (M+H).

Preparation of 2-(3-(tert-butylamino)-2-methylquinoxalin-5-yl)-7-methyl-1H-pyrrolo[2,3-d]pyridazin-4(5H)-one (416)

A mixture of methyl 2-acetyl-5-(3-(tert-butylamino)-2-methylquinoxalin-5-yl)-1H-pyrrole-3-carboxylate (416b) (0.141 g, 0.37 mmol), hydrazine monohydrate (Fluka, 0.020 mL, 0.408 mmol) in Ethanol (1.23 mL) was heated to 75° C. for 24 h. Reaction mixture was directly loaded on silica gel samplet and purified by Biotage (30-100% EtOAc:EtOH (3:1)/hexanes) to produce 2-(3-(tert-butylamino)-2-methylquinoxalin-5-yl)-7-methyl-1H-pyrrolo[2,3-d]pyridazin-4(5H)-one (416) (33 mg, 0.091 mmol, 24% yield) that solidified as yellow solid upon drying. ¹H NMR (300 MHz, MeOH) δ ppm 1.67 (s, 9H) 2.56-2.70 (m, 1H) 7.30-7.40 (m, 1H) 7.40-7.50 (m, 1H) 7.40-7.55 (m, 1H) 7.76-7.87 (m, 1H) 8.03-8.16 (m, 1H). m/z (ESI, +ve) 363.0 (M+H).

Example 417

5-(6-fluoro-2-methyl-3-((1-methylcyclopropyl)amino)quinoxalin-5-yl)-2-methyl-1H-pyrrole-3-carboxamide

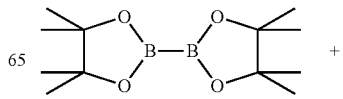

575

-continued

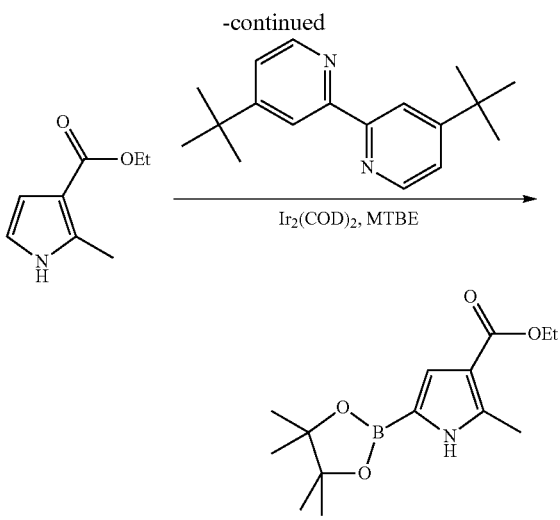

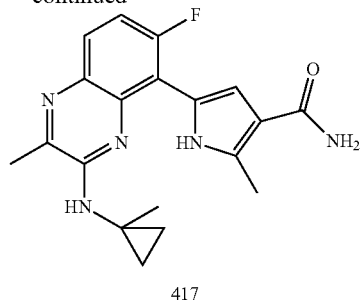

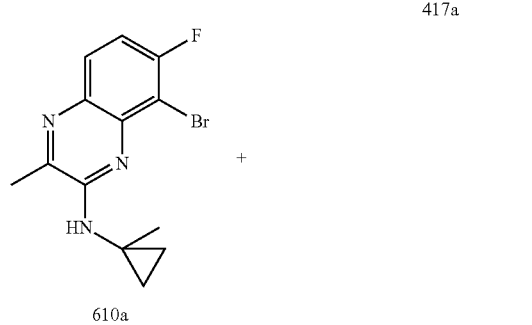

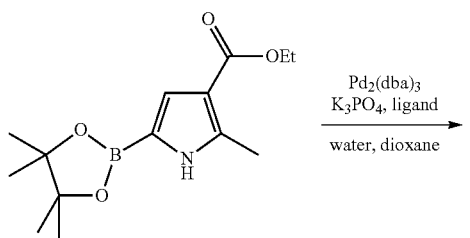

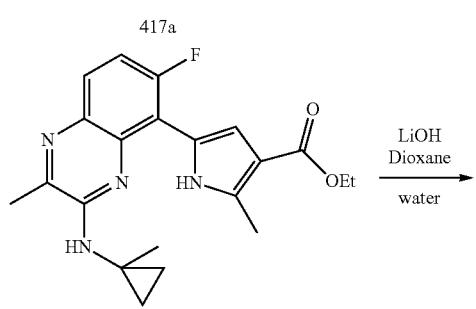

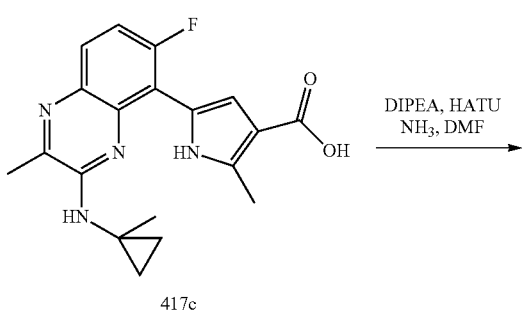

576

-continued

Preparation of ethyl 2-methyl-5-(4,4,5,5-tetramethyl-1,3,2-dioxaborolan-2-yl)-1H-pyrrole-3-carboxylate (417a)

A mixture of bis(pinacolato)diboron (Sigma Aldrich, 1.094 g, 4.31 mmol), methyl tert-butyl ether (Sigma Aldrich, 5.60 mL, 47.0 mmol), 4,4'-di-tert-butyl-2,2'-dipyridyl (0.063 g, 0.235 mmol), (Sigma Aldrich, 1,5-cyclooctadiene)(methoxy)-iridium(i) dimer (Strem Chemicals, 0.078 g, 0.118 mmol), 2-methyl-1h-pyrrole-3-carboxylic acid ethyl ester (Angene International Limited, 0.542 mL, 3.92 mmol) were combined under nitrogen and heated to 50° C. for 2 h. Reaction mixture was filtered over a large cake of alumina. Material was rinsed with 150 mL of DCM then rinsed with 200 mL of 10% MeOH/DCM. Filtrate was concentrated and advanced to next step directly. m/z (ESI, +ve) 280.1 (M+H).

Preparation of ethyl 5-(6-fluoro-2-methyl-3-((1-methyl-cyclopropyl)amino)quinoxalin-5-yl)-2-methyl-1H-pyrrole-3-carboxylate (417b)

A mixture of Xphos (Strem Chemicals, 0.169 g, 0.355 mmol), Pd$_2$dba$_3$ (Frontier Scientific, 0.162 g, 0.177 mmol), potassium phosphate tribasic monohydrate (Fluka, 2.450 g, 10.64 mmol), 8-bromo-7-fluoro-3-methyl-N-(1-methylcyclopropyl)quinoxalin-2-amine (610a) (0.880 g, 2.84 mmol), ethyl 2-methyl-5-(4,4,5,5-tetramethyl-1,3,2-dioxaborolan-2-yl)-1H-pyrrole-3-carboxylate (417a) (0.99 g, 3.55 mmol) in dioxane (10.32 mL) and water (3.87 mL) was microwaved to 110° C. for 30 min. Reaction mixture was separated into two biphasic layers. The organic layer was loaded onto a silica gel samplet. Purification by biotage (0-100% EtOAc/hexanes) produced ethyl 5-(6-fluoro-2-methyl-3-((1-methylcyclopropyl)amino)quinoxalin-5-yl)-2-methyl-1H-pyrrole-3-carboxylate (417b) (0.555 g, 1.451 mmol, 41% yield). m/z (ESI, +ve) 383.1 (M+H).

Preparation of 5-(6-fluoro-2-methyl-3-((1-methyl-cyclopropyl)amino)quinoxalin-5-yl)-2-methyl-1H-pyrrole-3-carboxylic acid (417c)

A mixture of ethyl 5-(6-fluoro-2-methyl-3-((1-methyl-cyclopropyl)amino)quinoxalin-5-yl)-2-methyl-1H-pyrrole-3-carboxylate (417b) (0.555 g, 1.451 mmol), LiOH monohydrate (Sigma Aldrich, 365 mg, 8.71 mmol) in water (9 mL) and dioxane (18.00 mL) was heated to 80° C. overnight. Reaction mixture was then heated to 105° C. for an additional 4 h. Mixture was cooled back to RT and quenched with 4 M HCl in 1,4-dioxane (Sigma Aldrich, 2.177 mL, 8.71 mmol). Volatile solvents were removed by rotovap. The residue was loaded onto a silica gel samplet. Purification by Biotage (0-100% EtOAc/hexanes) produced 5-(6-fluoro-2-methyl-3-

((1-methylcyclopropyl)amino)quinoxalin-5-yl)-2-methyl-1H-pyrrole-3-carboxylic acid (417c) (78 mg, 0.220 mmol, 15% yield). m/z (ESI, +ve) 355.0 (M+H).

Preparation of 5-(6-fluoro-2-methyl-3-((1-methylcyclopropyl)amino)quinoxalin-5-yl)-2-methyl-1H-pyrrole-3-carboxamide (417)

A mixture of 5-(6-fluoro-2-methyl-3-((1-methylcyclopropyl)amino)quinoxalin-5-yl)-2-methyl-1H-pyrrole-3-carboxylic acid (417c) (0.119 g, 0.336 mmol), 0-(~7-azabenzotriazol-1-yl)-n,'n,'n,'n'-tetramethyluronium-hexafluorophosphate (GenScript Corporation, 0.160 g, 0.420 mmol), DIPEA (0.146 mL, 0.839 mmol), in DMF (1.679 mL) was stirred at RT for 5 min before addition of ammonia (2.0 M solution in MeOH, Sigma Aldrich, 0.336 mL, 0.672 mmol). The resulting mixture was stirred at RT overnight. Reaction mixture was diluted with DCM and washed with water and brine to remove DMF. Purification by Biotage (0-100% EtOAc/hexanes then 30-100% EtOAc:EtOH(3:1)/hexanes) produced desired product. The residue was diluted with DCM and re-washed two times with alternating water and brine washes to remove DMF and provide 5-(6-fluoro-2-methyl-3-((1-methylcyclopropyl)amino)quinoxalin-5-yl)-2-methyl-1H-pyrrole-3-carboxamide (0.031 g, 0.88 mmol, 26% yield). $^1$H NMR (300 MHz, MeOH) δ ppm 0.84-0.94 (m, 4H) 1.56 (s, 3H) 2.38 (s, 3H) 2.55 (s, 3H) 7.01-7.17 (m, 2H) 7.25-7.35 (m, 1H) 7.37-7.47 (m, 1H) 12.84-13.00 (m, 1H). m/z (ESI, +ve) 354.0 (M+H).

Example 418

5-(3-(tert-butylamino)-2-methylquinoxalin-5-yl)-2-cyclopropyl-1H-pyrrole-3-carboxamide

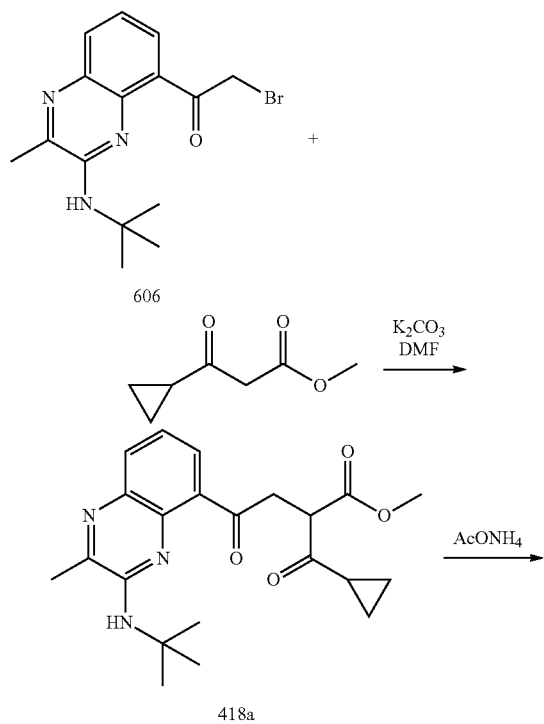

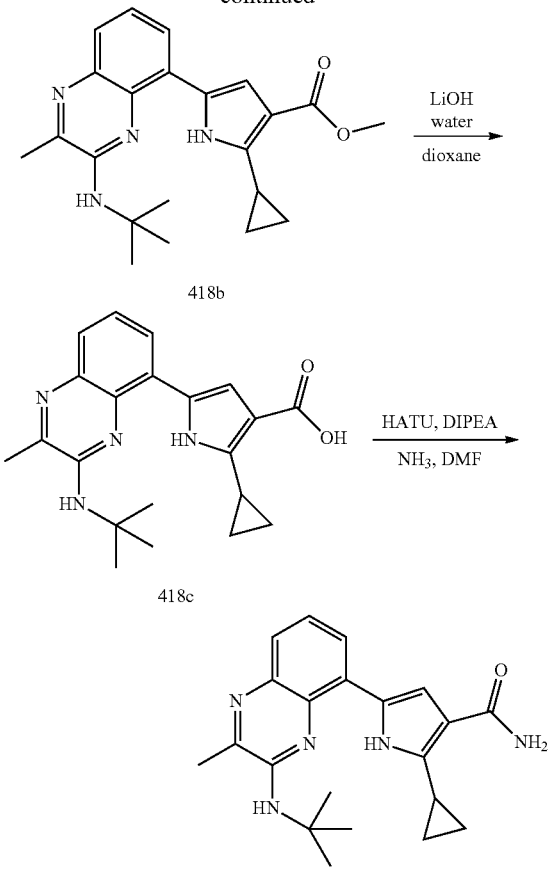

Preparation of methyl 4-(3-(tert-butylamino)-2-methylquinoxalin-5-yl)-2-(cyclopropanecarbonyl)-4-oxobutanoate (418a)

A mixture of 2-bromo-1-(3-(tert-butylamino)-2-methylquinoxalin-5-yl)ethanone (606) (0.27 g, 0.803 mmol), methyl 3-cyclopropyl-3-oxopropanoate (Accela ChemBio, 0.114 mL, 0.803 mmol), K$_2$CO$_3$ (EMD, 0.333 g, 2.409 mmol), in DMF (3.21 ml) was combined and stirred overnight at RT. Reaction mixture was diluted with DCM and water. The aqueous layer was acidified with 1 N HCl solution and back extracted with DCM. The organic layers were combined and washed with water and brine to remove DMF. Volatile solvents were removed by rotovap. The product methyl 4-(3-(tert-butylamino)-2-methylquinoxalin-5-yl)-2-(cyclopropanecarbonyl)-4-oxobutanoate (418a) was advanced to next step. m/z (ESI, +ve) 398.1 (M+H).

Preparation of methyl 5-(3-(tert-butylamino)-2-methylquinoxalin-5-yl)-2-cyclopropyl-1H-pyrrole-3-carboxylate (418b)

Methyl 4-(3-(tert-butylamino)-2-methylquinoxalin-5-yl)-2-(cyclopropanecarbonyl)-4-oxobutanoate (418a) (0.319 g, 0.803 mmol), Ethanol (1.338 mL), AcOH (0.669 mL), and NH$_4$OAc (Sigma Aldrich, 185 mg, 2.41 mmol) were mixed at RT and stirred overnight. An additional aliquot of NH$_4$OAc was added and the resulting mixture was heated to 60° C. for 6 h. Reaction mixture was diluted with EtOAc and washed with water. The organic layer was then washed with saturated NaHCO$_3$ solution to remove residual AcOH. The organic layer was dried over MgSO$_4$. Volatile solvents were removed by rotovap. Product methyl 5-(3-(tert-butylamino)-2-methylquinoxalin-5-yl)-2-cyclopropyl-1H-pyrrole-3-carboxylate (418b) was advanced to next step directly. m/z (ESI, +ve) 479.1 (M+H).

Preparation of 5-(3-(tert-butylamino)-2-methylquinoxalin-5-yl)-2-cyclopropyl-1H-pyrrole-3-carboxylic (418c)

A mixture of methyl 5-(3-(tert-butylamino)-2-methylquinoxalin-5-yl)-2-cyclopropyl-1H-pyrrole-3-carboxylate (418b) (0.304 g, 0.803 mmol), LiOH monohydrate (Sigma Aldrich, 202 mg, 4.82 mmol), in water (5 mL), dioxane (10.00 mL) was heated to 80° C. overnight. Reaction mixture was cooled to RT and then added HCl (4.0 M solution in 1,4-dioxane from Sigma Aldrich, 1.00 mL, 4.0 mmol). The resulting mixture was stirred at RT for 1 h before rotovap to remove all volatile solvents. The residue was loaded onto silica gel. Purification by Biotage (0-100% EtOAc:EtOH (3:1)/hexanes) produced 5-(3-(tert-butylamino)-2-methylquinoxalin-5-yl)-2-cyclopropyl-1H-pyrrole-3-carboxylic (418c) (0.102 g, 0.280 mmol, 35% yield). 1H NMR (300 MHz, DMSO-$d_6$) δ ppm 0.75-1.08 (m, 4H) 1.52 (br. s., 9H) 2.65-2.81 (m, 2H) 3.90-4.14 (m, 1H) 5.78-5.97 (m, 1H) 6.93-7.14 (m, 1H) 7.20-7.40 (m, 1H) 7.51-7.74 (m, 2H) 10.56-10.75 (m, 1H) 11.39-11.58 (m, 1H). m/z (ESI, +ve) 365.0 (M+H).

Preparation of 5-(3-(tert-butylamino)-2-methylquinoxalin-5-yl)-2-cyclopropyl-1H-pyrrole-3-carboxamide (418)

A mixture of 5-(3-(tert-butylamino)-2-methylquinoxalin-5-yl)-2-cyclopropyl-1H-pyrrole-3-carboxylic acid (418c) (0.15 g, 0.412 mmol), O-(-7-azabenzotriazol-1-yl)-n,'n,'n,'n'-tetramethyluronium-hexafluorophosphate (GenScript Corporation, 0.196 g, 0.514 mmol), DIPEA (Sigma Aldrich, 0.179 ml, 1.029 mmol), in DMF (2.058 mL) was stirred at RT for 5 min before addition of ammonia (2.0 M solution in MeOH, 0.412 mL, 0.823 mmol). Reaction mixture was stirred at RT overnight. Additional aliquots of HATU and DIPEA were added to the reaction mixture which was stirred at RT overnight. Reaction mixture was diluted with DCM and washed with water and brine to remove DMF. Purification by Biotage (0-10% MeOH/DCM) produced 5-(3-(tert-butylamino)-2-methylquinoxalin-5-yl)-2-cyclopropyl-1H-pyrrole-3-carboxamide (418) (0.028 g, 0.078 mmol, 19% yield). $^1$H NMR (300 MHz, MeOH-d4) δ ppm 0.82-0.92 (m, 2H) 0.98-1.08 (m, 2H) 1.65 (s, 9H) 2.30-2.45 (m, 1H) 2.57 (s, 3H) 6.93-6.99 (m, 1H) 7.26-7.39 (m, 1H) 7.56-7.65 (m, 1H) 7.75-7.85 (m, 1H). m/z (ESI, +ve) 364.1 (M+H).

Example 419

2-(tert-butylamino)-3-methyl-8-(4-oxo-1,4,5,6-tetrahydropyrrolo[3,4-b]pyrrol-2-yl)-4(3H)-quinazolinone

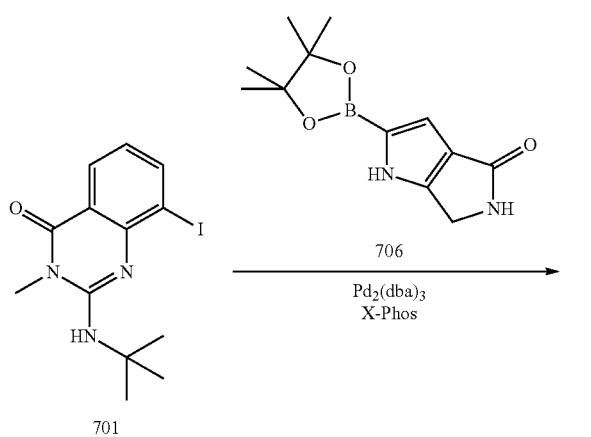

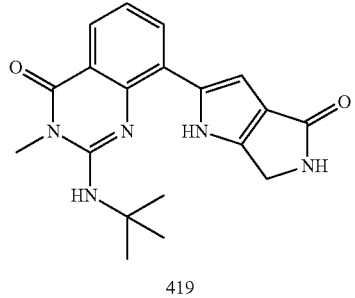

This compound (54 mg, 0.15 mmol, 19% yield) as a tan solid was prepared according to the procedures described for Example 287, using 2-(tert-butylamino)-8-iodo-3-methylquinazolin-4(3H)-one (701; 281 mg, 0.79 mmol), and 2-(4,4,5,5-tetramethyl-1,3,2-dioxaborolan-2-yl)-5,6-dihydropyrrolo[3,4-b]pyrrol-4(1H)-one (706; 477 mg, 1.35 mmol) as the starting materials. $^1$H NMR (400 MHz, DMSO-$d_6$) δ ppm 12.10 (s, 1H), 7.84-7.93 (m, 1H), 7.51 (s, 1H), 7.18 (t, J=7.73 Hz, 1H), 6.80 (d, J=1.56 Hz, 1H), 5.96 (s, 1H), 4.25 (d, J=0.59 Hz, 2H), 3.48 (s, 3H), 1.51 (s, 9H). m/z (ESI, +ve) 325.1 (M+H).

Example 420

4-(3-(tert-butylamino)-2-methyl-5-quinoxalinyl)-1H-pyrrole-2-carboxamide

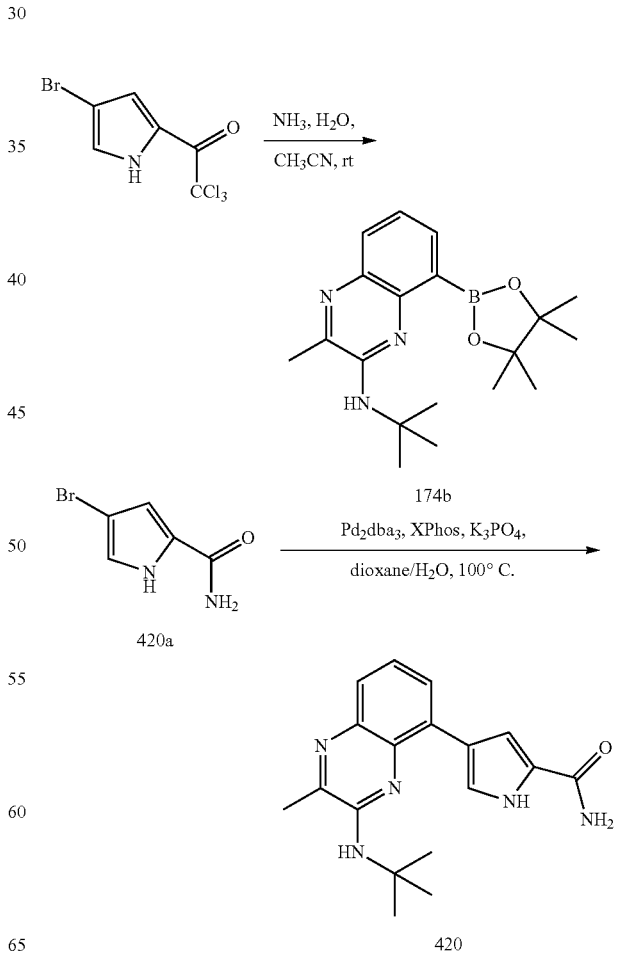

581

Preparation of 4-bromo-1H-pyrrole-2-carboxamide (420a)

A mixture of 1-(4-bromo-1H-pyrrol-2-yl)-2,2,2-trichloroethanone (CombiBlocks, Inc., San Diego, Calif.; 1.50 g, 5.15 mmol) and ammonia (30 wt. % in water; 4.0 mL, 55.5 mmol) in CH$_3$CN (62.5 mL) was stirred at 23° C. for 45 min. The reaction mixture was then concentrated in vacuo. Chromatographic purification of the residue (silica gel, 0-100% EtOAc/hexanes) furnished 4-bromo-1H-pyrrole-2-carboxamide (885 mg, 4.68 mmol, 91% yield) as a white solid. $^1$H NMR (400 MHz, DMSO-d$_6$) δ ppm 11.75 (1H, br. s.), 7.55 (1H, br. s.), 7.08 (1H, br. s.), 6.95 (1H, dd, J=2.8, 1.7 Hz), 6.84 (1H, dd, J=2.4, 1.7 Hz). $^{13}$C NMR (100 MHz, DMSO-d$_6$) δ ppm 161.1, 126.9, 121.2, 112.0, 94.8. m/z (ESL+ve) 188.9/190.9 (M+H)$^+$.

Preparation of 4-(3-(tert-butylamino)-2-methyl-5-quinoxalinyl)-1H-pyrrole-2-carboxamide (420)

A mixture of 4-bromo-1H-pyrrole-2-carboxamide (100 mg, 0.529 mmol), N-(tert-butyl)-3-methyl-8-(4,4,5,5-tetramethyl-1,3,2-dioxaborolan-2-yl)quinoxalin-2-amine (174b; 311 mg, 0.529 mmol), K$_3$PO$_4$ (337 mg, 1.587 mmol), XPhos (Strem Chemicals, Inc.; 25.2 mg, 0.053 mmol), and (Aldrich; 24.22 mg, 0.026 mmol) in a mixture of dioxane (4.0 mL) and water (1.0 mL) was stirred under argon at 100° C. for 16.5 h. The reaction mixture was then concentrated onto silica gel and chromatographically purified (silica gel, 0-100% EtOAc/hexanes) to provide 4-(3-(tert-butylamino)-2-methylquinoxalin-5-yl)-1H-pyrrole-2-carboxamide (86.7 mg, 0.268 mmol, 51% yield) as a light-yellow solid: $^1$H NMR (400 MHz, DMSO-d$_6$) δ ppm 11.53 (1H, br. s.), 7.78 (1H, dd, J=2.6, 1.5 Hz), 7.61 (1H, dd, J=7.3, 1.3 Hz), 7.54 (1H, dd, J=8.1, 1.5 Hz), 7.44 (1H, br. s.), 7.31 (1H, t, J=7.7 Hz), 7.22-7.26 (1H, m), 6.94 (1H, br. s.), 5.78 (1H, s), 2.53 (3H, s), 1.53 (9H, s). m/z (ESI, +ve) 324.0 (M+H)$^+$.

Example 421

6-(3-(tert-butylamino)-2-methylquinoxalin-5-yl)-1H-pyrrolo[1,2-c]imidazol-3(2H)-one

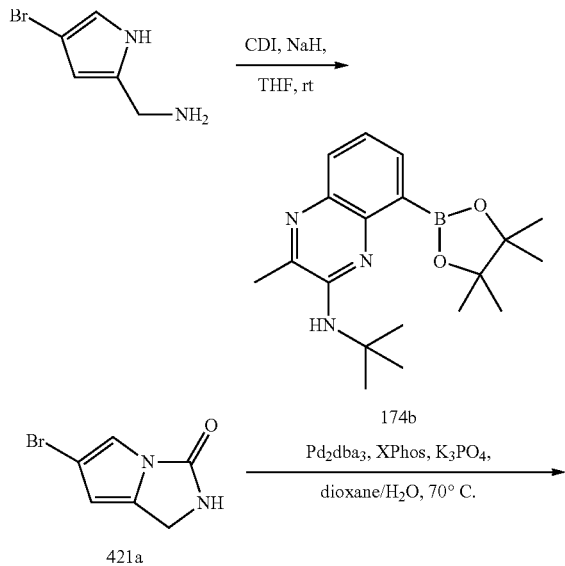

582

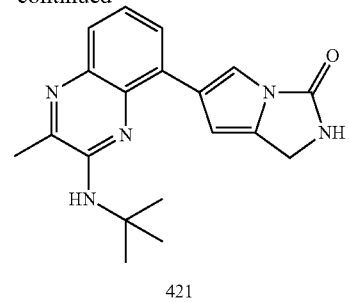

421

Preparation of 6-bromo-1H-pyrrolo[1,2-c]imidazol-3(2H)-one (421a)

A solution of (4-bromo-1H-pyrrol-2-yl)methanamine (Enamine, Ltd., Kiev, Ukraine; 57.7 mg, 0.330 mmol), di(1H-imidazol-1-yl)methanone (CDI; Aldrich; 58.8 mg, 0.363 mmol), and NaH (60% wt. in mineral oil; 15.8 mg, 0.396 mmol) in THF (3.0 mL) was stirred under argon at 23° C. for 15 min. The reaction mixture was subsequently concentrated onto silica gel and chromatographically purified (silica gel, 0-60% EtOAc/hexanes) to provide 6-bromo-1H-pyrrolo[1,2-c]imidazol-3(2H)-one (23.9 mg, 0.119 mmol, 36% yield) as an off-white solid. $^1$H NMR (400 MHz, DMSO-d$_6$) δ ppm 8.58 (1H, br. s.), 7.29 (1H, s), 6.16 (1H, d, J=1.2 Hz), 4.35 (2H, s). m/z (ESI, +ve) 200.9/202.9 (M+H)$^+$.

Preparation of 6-(3-(tert-butylamino)-2-methylquinoxalin-5-yl)-1H-pyrrolo[1,2-c]imidazol-3(2H)-one (421)

A mixture of 6-bromo-1H-pyrrolo[1,2-c]imidazol-3(2H)-one (20.5 mg, 0.102 mmol), N-(tert-butyl)-3-methyl-8-(4,4,5,5-tetramethyl-1,3,2-dioxaborolan-2-yl)quinoxalin-2-amine (Example 174b; 43.5 mg, 0.102 mmol), K$_3$PO$_4$ (64.9 mg, 0.306 mmol), Pd$_2$dba$_3$ (Aldrich; 4.67 mg, 5.10 µmol), and XPhos (Strem Chemicals, Inc. MA; 4.86 mg, 10.20 µmol) in a mixture of dioxane (1.0 mL) and water (0.25 mL) was stirred under argon at 70° C. for 70 min. The reaction mixture was subsequently concentrated onto silica gel and chromatographically purified (silica gel, 0-100% EtOAc/hexanes) to provide 6-(3-(tert-butylamino)-2-methyl-quinoxalin-5-yl)-1H-pyrrolo[1,2-c]imidazol-3(2H)-one (19.0 mg, 0.057 mmol, 56% yield) as a yellow solid. $^1$H NMR (400 MHz, CDCl$_3$) δ ppm 7.94 (1H, s), 7.79 (1H, br. s.), 7.70 (1H, d, J=7.4 Hz), 7.37 (1H, t, J=7.8 Hz), 6.56 (1H, d, J=1.2 Hz), 5.41 (1H, br. s.), 4.71 (1H, br. s.), 4.50 (2H, s), 2.57 (3H, s), 1.59 (9H, s). m/z (ESI, +ve) 336.0 (M+H)$^+$.

Example 422

6-(3-(tert-Butylamino)-2-methyl-5-quinoxalinyl)-1H-pyrrolo[1,2-c]imidazole-1,3(2H)-dione

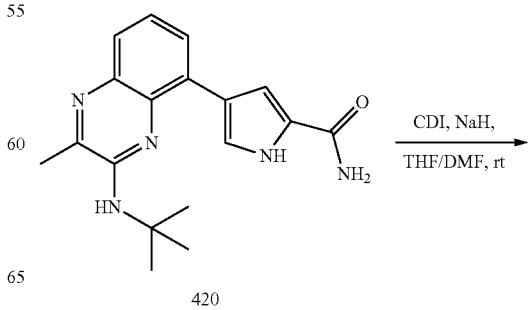

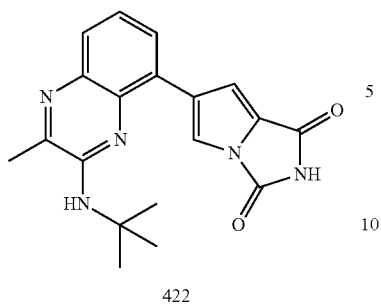

422

A solution of 4-(3-(tert-butylamino)-2-methylquinoxalin-5-yl)-1H-pyrrole-2-carboxamide (Example 420; 21.8 mg, 0.067 mmol), di(1H-imidazol-1-yl)methanone (CDI; Aldrich; 12.02 mg, 0.074 mmol), and NaH (60% w/w in mineral oil; 3.24 mg, 0.081 mmol) in a mixture of THF (1.0 mL) and DMF (0.10 mL) was stirred under argon at 23° C. for 1 h. Additional di(1H-imidazol-1-yl)methanone (12 mg, 0.074 mmol) was added, and the resulting mixture was stirred at 23° C. for 5 min. Additional di(1H-imidazol-1-yl)methanone (72 mg, 0.444 mmol) was added, and the resulting mixture was stirred at 23° C. for 5 min. The reaction mixture was subsequently concentrated onto silica gel and chromatographically purified (silica gel, 0-100% EtOAc/hexanes) to provide 6-(3-(tert-butylamino)-2-methylquinoxalin-5-yl)-1H-pyrrolo[1,2-c]imidazole-1,3(2H)-dione (11.9 mg, 0.034 mmol, 51% yield) as a light-yellow solid. $^1$H NMR (400 MHz, CDCl$_3$) δ ppm 8.06 (1H, s), 7.82 (1H, d, J=7.6 Hz), 7.66 (1H, dd, J=7.3, 1.3 Hz), 7.40 (1H, d, J=7.6 Hz), 7.32 (1H, d, J=0.7 Hz), 7.30 (0.5; H, br. s), 4.76 (1H, s), 4.05 (0.5; H, s), 2.56 (3H, s), 1.57 (9H, s). m/z (ESI, +ve) 350.0 (M+H)$^+$.

Example 423

2-(3-(tert-butylamino)-2-methylquinoxalin-5-yl)-1H-pyrrolo[2,3-d]pyridazin-4(5H)-one

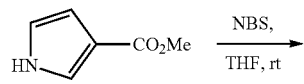

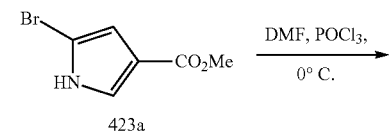

423a

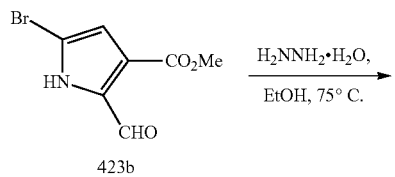

423b

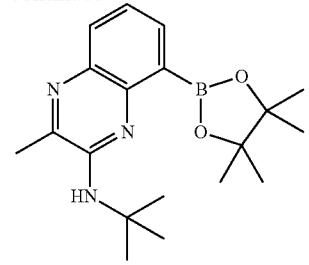

174b

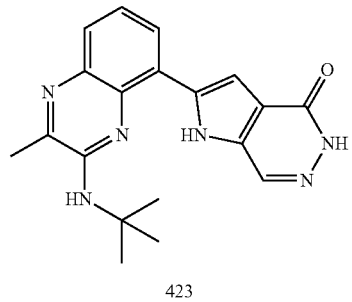

423

Preparation of 5-bromo-1H-pyrrole-3-carboxylate (423a)

NBS (Aldrich; 1.201 g, 6.75 mmol) was added in one portion to a solution of methyl 1H-pyrrole-3-carboxylate (Aldrich; 0.844 g, 6.75 mmol) in THF (10 mL), and the resulting solution was stirred at 23° C. for 1.5 h. THF was removed in vacuo, and the residue was taken up in DCM (50 mL) and washed with 10:1 water/sat. aq. NaHCO$_3$ (50 mL). The organic layer was separated, and the aq. layer was extracted with DCM (2×40 mL). The combined organic extracts were dried over Na$_2$SO$_4$, filtered, and concentrated onto silica gel. Chromatographic purification (silica gel, 0-50% EtOAc/hexanes) furnished methyl 5-bromo-1H-pyrrole-3-carboxylate (924.2 mg, 4.53 mmol, 67% yield) as a white solid. $^1$H NMR (400 MHz, CDCl$_3$) δ ppm 8.41 (1H, br. s.), 7.36 (1H, dd, J=2.9, 1.8 Hz), 6.60 (1H, dd, J=2.5, 1.8 Hz), 3.81 (3H, s). m/z (ESI, +ve) 203.9/205.9 (M+H)$^+$.

Preparation of methyl 5-bromo-2-formyl-1H-pyrrole-3-carboxylate (423b)

POCl$_3$ (Aldrich; 0.531 mL, 5.70 mmol) was added (dropwise, over 1 min) to DMF (1.32 mL, 17.10 mmol) under argon at 0° C., and the resulting solution was stirred at 0° C. for 15 min. This solution was then added (dropwise, over 1 min) to a dark-brown solution of methyl 5-bromo-1H-pyrrole-3-carboxylate (581 mg, 2.85 mmol) in ACN (6.0 mL) at 23° C., and the resulting solution was stirred under argon at 50° C. for 3 h. The reaction mixture was then poured into 10:1 water/sat. aq. NaHCO$_3$ (50 mL) and extracted with DCM (3×50 mL). The combined extracts were dried over Na$_2$SO$_4$, filtered, and concentrated onto silica gel. Chromatographic purification (silica gel, 0-30% EtOAc/hexanes) furnished methyl 5-bromo-2-formyl-1H-pyrrole-3-carboxylate (245 mg, 1.05 mmol, 37% yield) as a white solid. $^1$H NMR (400 MHz, CDCl$_3$) δ ppm 10.09 (1H, s), 9.56 (1H, br. s.), 6.72 (1H, d, J=2.7 Hz), 3.90 (3H, s). m/z (ESI, +ve) 231.9/234.1 (M+H)$^+$.

Preparation of 2-bromo-1H-pyrrolo[2,3-d]pyridazin-4(5H)-one (423c)

A solution of methyl 5-bromo-2-formyl-1H-pyrrole-3-carboxylate (245 mg, 1.056 mmol) and hydrazine hydrate (50-60 wt % in water; Aldrich; 0.14 mL, 1.58 mmol) in EtOH (5.0 mL) was stirred under argon at 75° C. for 1.5 h. Additional hydrazine hydrate (50-60 wt % in water; 0.33 mL, 3.70 mmol) was added, and the resulting mixture was stirred at 75° C. for 16 h. The reaction mixture was subsequently concentrated onto silica gel and chromatographic purified (silica gel, 0-100% EtOAc/hexanes, then 0-10% MeOH/DCM) to provide 2-bromo-1H-pyrrolo[2,3-d]pyridazin-4(5H)-one (89.3 mg, 0.417 mmol, 40% yield) as an off-white solid. $^1$H NMR (400 MHz, DMSO-d$_6$) δ ppm 12.69-13.17 (1H, m), 12.34 (1H, s), 8.06 (1H, d, J=0.6 Hz), 6.72 (1H, d, J=0.6 Hz) (2.5:1 mixture of pyridazinone tautomers; only major tautomer peaks reported). m/z (ESI, +ve) 213.8/215.9 (M+H)$^+$.

Preparation of 2-(3-(tert-Butylamino)-2-methylquinoxalin-5-yl)-1H-pyrrolo[2,3-d]pyridazin-4(5H)-one (423)

A mixture of 2-bromo-1H-pyrrolo[2,3-d]pyridazin-4(5H)-one (47.0 mg, 0.220 mmol), N-(tert-butyl)-3-methyl-8-(4,4,5,5-tetramethyl-1,3,2-dioxaborolan-2-yl)quinoxalin-2-amine (174b; 94 mg, 0.220 mmol), K$_3$PO$_4$ (140 mg, 0.659 mmol), Pd$_2$dba$_3$ (Aldrich; 10.05 mg, 10.98 μmol), and XPhos (Strem Chemicals, Inc., 10.47 mg, 0.022 mmol) in a mixture of dioxane (1.5 mL) and water (0.38 mL) was stirred under argon at 70° C. for 1.5 h. The reaction mixture was subsequently heated at 90° C. for 17 h. The reaction mixture was then concentrated onto silica gel and chromatographically purified (silica gel, 50-100% EtOAc/hexanes, then 0-10% MeOH/DCM) to provide 2-(3-(tert-butylamino)-2-methylquinoxalin-5-yl)-1H-pyrrolo[2,3-d]pyridazin-4(5H)-one (16.8 mg, 0.048 mmol, 22% yield) as a yellow solid. $^1$H NMR (400 MHz, DMSO-d$_6$) δ ppm 12.60 (1H, br. s.), 12.24 (1H, s), 8.16 (1H, d, J=0.4 Hz), 7.97 (1H, dd, J=7.4, 1.4 Hz), 7.75 (1H, dd, J=8.0, 1.4 Hz), 7.43 (1H, t, J=7.7 Hz), 7.38 (1H, s), 6.11 (1H, s), 2.58 (3H, s), 1.54 (9H, s). m/z (ESI, +ve) 349.0 (M+H)$^+$.

Example 424

2-(2-Methyl-3-phenylquinoxalin-5-yl)-6,7-dihydro-1H-pyrrolo[3,2-c]pyridin-4(5H)-one

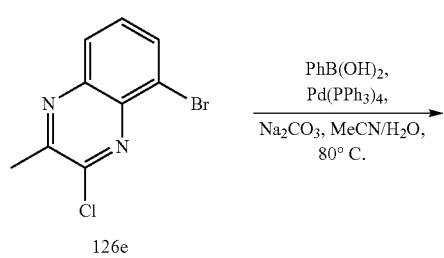

126e

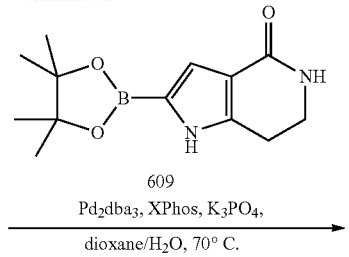

424a

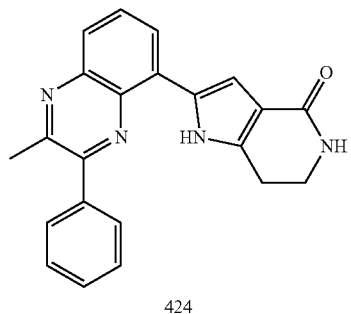

424

Preparation of 5-bromo-2-methyl-3-phenylquinoxaline (424a)

A suspension of 5-bromo-3-chloro-2-methylquinoxaline (126e; 327 mg, 1.270 mmol), phenylboronic acid (Aldrich; 155 mg, 1.270 mmol), Na$_2$CO$_3$ (673 mg, 6.35 mmol), and Pd(PPh$_3$)$_4$ (Strem Chemicals, Inc.; 73.4 mg, 0.063 mmol) in a mixture of CH$_3$CN (9.00 mL) and water (3 mL) was stirred under argon at 80° C. for 16 h. The reaction was cooled to RT and concentrated onto silica gel. Chromatographic purification (silica gel, 0-40% EtOAc/hexanes) furnished 5-bromo-2-methyl-3-phenylquinoxaline (340.0 mg, 1.136 mmol, 89% yield) as a peach-colored solid. $^1$H NMR (400 MHz, CDCl$_3$) δ ppm 8.03 (2H, d, J=7.8 Hz), 7.77 (2H, dd, J=7.9, 1.7 Hz), 7.60 (1H, d, J=7.8 Hz), 7.48-7.57 (3H, m), 2.85 (3H, s). m/z (ESI, +ve) 298.9/300.8 (M+H)$^+$.

Preparation of 2-(2-methyl-3-phenylquinoxalin-5-yl)-6,7-dihydro-1H-pyrrolo[3,2-c]pyridin-4(5H)-one (424)

A solution of 5-bromo-2-methyl-3-phenylquinoxaline (87.5 mg, 0.292 mmol), 2-(4,4,5,5-tetramethyl-1,3,2-dioxaborolan-2-yl)-6,7-dihydro-1H-pyrrolo[3,2-c]pyridin-4 (5H)-one (Example 609; 216 mg, 0.585 mmol), K$_3$PO$_4$ (186 mg, 0.877 mmol), XPhos (Strem Chemicals, Inc.; 13.94 mg, 0.029 mmol), and Pd$_2$dba$_3$ (Aldrich; 13.39 mg, 0.015 mmol) in a mixture of 1,4-dioxane (2.0 mL) and water (0.400 mL) was stirred under argon at 100° C. for 45 min. The reaction mixture was then concentrated onto silica gel and chromatographically purified (silica gel, 0-100% EtOAc/hexanes, then 0-10% MeOH/DCM) to provide 2-(2-methyl-3-phenylquinoxalin-5-yl)-6,7-dihydro-1H-pyrrolo[3,2-c]pyridin-4(5H)-one (32.8 mg, 0.093 mmol, 32% yield) as a yellow solid. $^1$H NMR (400 MHz, DMSO-d$_6$) δ ppm 11.81 (1H, br. s.), 8.06 (1H, dd, J=7.2, 1.4 Hz), 7.77-7.91 (4H, m), 7.53-7.64 (3H, m), 7.26 (1H, d, J=2.2 Hz), 7.00 (1H, s), 3.40 (2H, td, J=6.8, 2.4 Hz), 2.84 (2H, t, J=6.8 Hz), 2.75 (3H, s). m/z (ESI, +ve) 355.0 (M+H)$^+$.

Example 425

2-(3-Chloro-2-methylquinoxalin-5-yl)-6,7-dihydro-1H-pyrrolo[3,2-c]pyridin-4(5H)-one

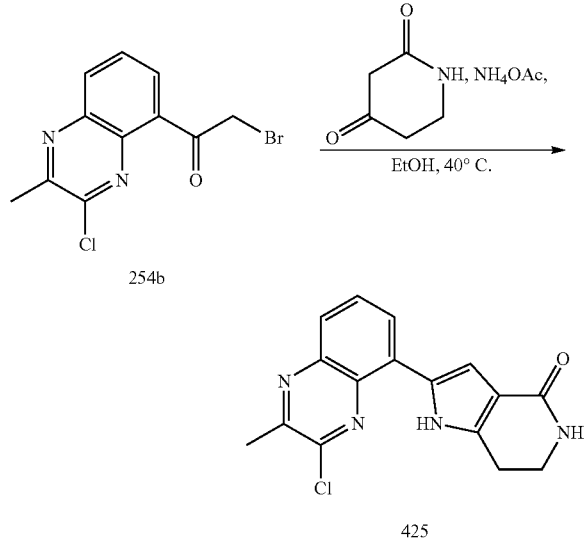

A suspension of 2-bromo-1-(3-chloro-2-methylquinoxalin-5-yl)ethanone (Example 254b; 2.00 g, 6.68 mmol), piperidine-2,4-dione (see J. Med. Chem. 2008, 51, 487-501; 1.510 g, 13.35 mmol), and NH$_4$OAc (4.12 g, 53.4 mmol) in EtOH (70 mL) was stirred under argon in a sealed flask at 40° C. for 20 h. The mixture was concentrated onto silica gel. Chromatographic purification (silica gel, 50-100% EtOAc/hexanes, then 0-10% MeOH/DCM) furnished 2-(3-chloro-2-methylquinoxalin-5-yl)-6,7-dihydro-1H-pyrrolo[3,2-c]pyridin-4(5H)-one (413 mg, 1.32 mmol, 20% yield) as an orange-brown solid: $^1$H NMR (400 MHz, DMSO-d$_6$) δ ppm 11.72 (1H, br. s.), 8.05 (1H, dd, J=6.6, 2.1 Hz), 7.79-7.91 (2H, m), 7.27 (1H, d, J=2.3 Hz), 7.01 (1H, br. s.), 3.43 (2H, td, J=6.8, 2.2 Hz), 2.89 (2H, t, J=6.8 Hz), 2.79 (3H, s). m/z (EST, +ve) 313.0 (M+H)$^+$.

Example 426

2-(2-Methyl-3-(o-tolyl)quinoxalin-5-yl)-6,7-dihydro-1H-pyrrolo[3,2-c]pyridin-4(5H)-one

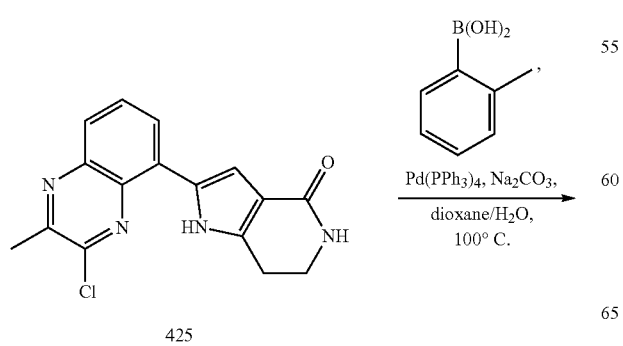

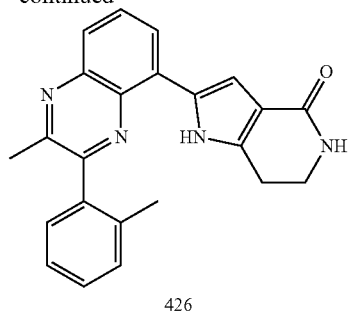

A solution of 2-(3-chloro-2-methylquinoxalin-5-yl)-6,7-dihydro-1H-pyrrolo[3,2-c]pyridin-4(5H)-one (Example 425; 50.3 mg, 0.161 mmol), o-tolylboronic acid (Aldrich; 32.8 mg, 0.241 mmol), Na$_2$CO$_3$ (51.1 mg, 0.482 mmol), and Pd(PPh$_3$)$_4$ (Strem Chemicals, Inc.; 9.29 mg, 8.04 µmol) in a mixture of 1,4-dioxane (1.5 mL) and water (0.500 mL) was stirred under argon at 100° C. for 45 min. The mixture was concentrated onto silica gel and chromatographically purified (silica gel, 50-100% EtOAc/hexanes, then 0-10% MeOH/DCM) to provide 2-(2-methyl-3-(o-tolyl)quinoxalin-5-yl)-6,7-dihydro-1H-pyrrolo[3,2-c]pyridin-4(5H)-one (54.6 mg, 0.148 mmol, 92% yield) as a brown solid. $^1$H NMR (400 MHz, CDCl$_3$) δ ppm 12.12 (1H, br. s.), 8.11 (1H, dd, J=7.4, 0.8 Hz), 7.90 (1H, dd, J=8.3, 0.9 Hz), 7.77 (1H, t, J=8.0 Hz), 7.31-7.49 (4H, m), 7.25 (1H, d, J=2.2 Hz), 5.38 (1H, br. s.), 3.58 (2H, td, J=6.7, 2.1 Hz), 2.85 (2H, t, J=6.8 Hz), 2.59 (3H, s), 2.21 (3H, s). m/z (ESI, +ve) 368.9 (M+H)$^+$.

Example 427

2-(3-(2-Chlorophenyl)-2-methylquinoxalin-5-yl)-6,7-dihydro-1H-pyrrolo[3,2-c]pyridin-4(5H)-one

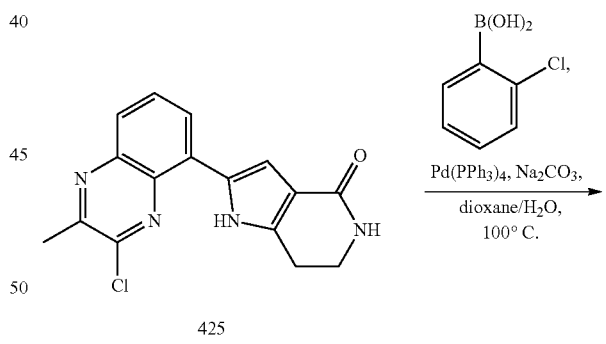

A solution of 2-(3-chloro-2-methylquinoxalin-5-yl)-6,7-dihydro-1H-pyrrolo[3,2-c]pyridin-4(5H)-one (Example 425;

38.4 mg, 0.123 mmol), (2-chlorophenyl)boronic acid (Aldrich; 28.8 mg, 0.184 mmol), Na$_2$CO$_3$ (39.0 mg, 0.368 mmol), and Pd(PPh$_3$)$_4$ (Strem Chemicals, Inc.; 7.09 mg, 6.14 μmol) in a mixture of 1,4-dioxane (1.5 mL) and water (0.500 mL) was stirred under argon at 100° C. for 20 min. The reaction mixture was then concentrated onto silica gel and chromatographically purified (silica gel, 50-100% EtOAc/hexanes, then 0-10% MeOH/DCM) to provide 2-(3-(2-chlorophenyl)-2-methylquinoxalin-5-yl)-6,7-dihydro-1H-pyrrolo[3,2-c]pyridin-4(5H)-one (40.3 mg, 0.104 mmol, 84% yield) as a brown solid. $^1$H NMR (400 MHz, CDCl$_3$) δ ppm 12.00 (1H, br. s.), 8.11 (1H, dd, J=7.6, 1.2 Hz), 7.92 (1H, dd, J=8.4, 1.2 Hz), 7.79 (1H, t, J=8.0 Hz), 7.59-7.64 (1H, m), 7.46-7.55 (3H, m), 7.24 (1H, d, J=2.2 Hz), 5.65 (1H, br. s.), 3.61 (2H, t, J=6.7 Hz), 2.89 (2H, td, J=6.7, 1.4 Hz), 2.67 (3H, s). m/z (ESI, +ve) 388.9 (M+H)$^+$.

Example 428

2-(3-(2-Fluorophenyl)-2-methylquinoxalin-5-yl)-6,7-dihydro-1H-pyrrolo[3,2-c]pyridin-4(5H)-one

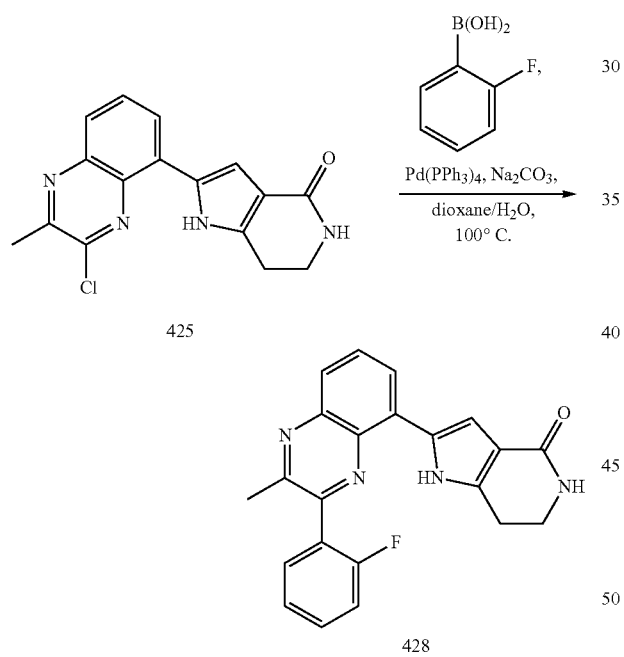

A solution of 2-(3-chloro-2-methylquinoxalin-5-yl)-6,7-dihydro-1H-pyrrolo[3,2-c]pyridin-4(5H)-one (Example 425; 36.7 mg, 0.117 mmol), (2-fluorophenyl)boronic acid (CombiBlocks, Inc., San Diego, Calif.; 24.63 mg, 0.176 mmol), Na$_2$CO$_3$ (37.3 mg, 0.352 mmol), and Pd(PPh$_3$)$_4$ (Strem Chemicals, Inc.; 6.78 mg, 5.87 μmol) in a mixture of 1,4-dioxane (1.5 mL) and water (0.500 mL) was stirred under argon at 100° C. for 20 min. The reaction mixture was then concentrated onto silica gel and chromatographically purified (silica gel, 50-100% EtOAc/hexanes, then 0-10% MeOH/DCM) to provide 2-(3-(2-fluorophenyl)-2-methylquinoxalin-5-yl)-6,7-dihydro-1H-pyrrolo[3,2-c]pyridin-4(5H)-one (39.8 mg, 0.107 mmol, 91% yield) as a brown solid. $^1$H NMR (400 MHz, CDCl$_3$) δ ppm 12.07 (1H, br. s.), 8.10 (1H, dd, J=7.4, 1.2 Hz), 7.90 (1H, dd, J=8.2, 1.2 Hz), 7.78 (1H, t, J=8.0 Hz), 7.50-7.62 (2H, m), 7.38 (1H, td, J=7.5, 1.0 Hz), 7.27-7.34 (1H, m), 7.25 (1H, br. s.), 5.39 (1H, br. s.), 3.61 (2H, td, J=6.8, 2.0 Hz), 2.89 (2H, t, J=6.9 Hz), 2.75 (3H, d, J=1.6 Hz). $^{19}$F NMR (377 MHz, CDCl$_3$) δ ppm −114.59 (1F, br. s.). m/z (ESI, +ve) 373.0 (M+H)$^+$.

Example 429

2-(2-Methyl-3-(pyridin-2-yl)quinoxalin-5-yl)-6,7-dihydro-1H-pyrrolo[3,2-c]pyridin-4(5H)-one

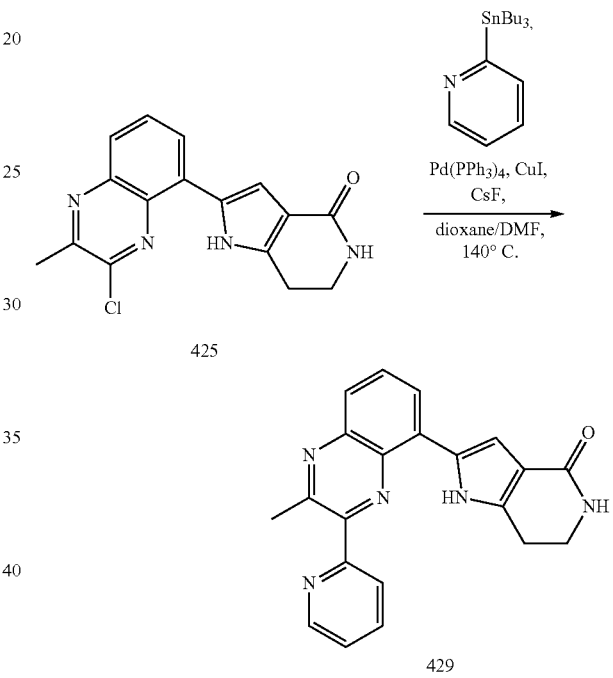

A solution of 2-(3-chloro-2-methylquinoxalin-5-yl)-6,7-dihydro-1H-pyrrolo[3,2-c]pyridin-4(5H)-one (Example 425; 38.0 mg, 0.122 mmol), 2-(tributylstannyl)pyridine (Aldrich; 0.043 mL, 0.134 mmol), CuI (2.314 mg, 0.012 mmol), cesium fluoride (36.9 mg, 0.243 mmol), and Pd(PPh$_3$)$_4$ (Strem Chemicals, Inc.; 7.02 mg, 6.08 μmol) in a mixture of 1,4-dioxane (2.0 mL) and DMF (2.0 mL) was stirred in a sealed tube under argon at 140° C. for 1 h. The reaction mixture was then concentrated onto silica gel and chromatographically purified (silica gel, 50-100% EtOAc/hexanes, then 0-10% MeOH/DCM) to provide 2-(2-methyl-3-(pyridin-2-yl)quinoxalin-5-yl)-6,7-dihydro-1H-pyrrolo[3,2-c]pyridin-4(5H)-one (31.2 mg, 0.088 mmol, 72% yield) as a brown solid. $^1$H NMR (400 MHz, CDCl$_3$) δ ppm 12.20 (1H, br. s.), 8.85 (1H, d, J=4.5 Hz), 8.09 (1H, dd, J=7.4, 1.0 Hz), 7.94-8.01 (1H, m), 7.90 (2H, d, J=8.2 Hz), 7.74-7.81 (1H, m), 7.50 (1H, ddd, J=7.3, 4.9, 1.1 Hz), 7.25 (1H, br. s.), 5.32 (1H, br. s.), 3.63 (2H, td, J=6.8, 2.1 Hz), 2.97 (3H, s), 2.94 (2H, t, J=6.8 Hz). m/z (ESI, +ve) 356.0 (M+H)$^+$.

Example 430

2-(2-Methyl-3-(3-methylpyridin-2-yl)quinoxalin-5-yl)-6,7-dihydro-1H-pyrrolo[3,2-c]pyridin-4(5H)-one

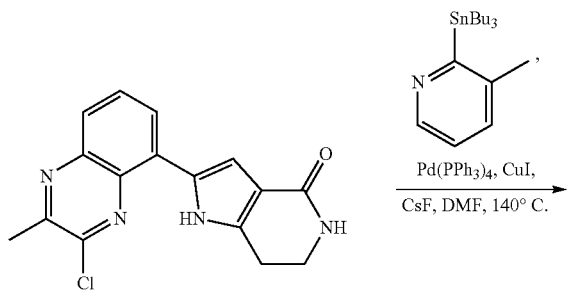

425

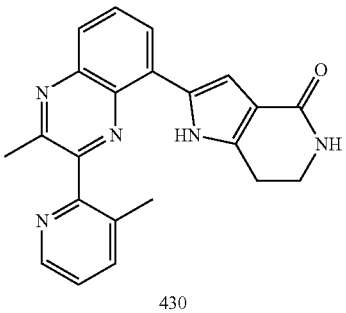

430

A solution of 2-(3-chloro-2-methylquinoxalin-5-yl)-6,7-dihydro-1H-pyrrolo[3,2-c]pyridin-4(5H)-one (Example 425; 33.7 mg, 0.108 mmol), 3-methyl-2-(tributylstannyl)pyridine (Indofine Chemical Company, Inc., Hillsborough, N.J.; 0.040 mL, 0.119 mmol), CuI (2.052 mg, 10.78 µmol), cesium fluoride (32.7 mg, 0.216 mmol), and Pd(PPh₃)₄ (Strem Chemicals, Inc.; 6.23 mg, 5.39 µmol) in DMF (2.0 mL) was stirred under argon in a microwave process vial at 140° C. for 30 min. The reaction mixture was then concentrated onto silica gel and chromatographically purified (silica gel, 50-100% EtOAc/hexanes, then 0-10% MeOH/DCM) to provide 2-(2-methyl-3-(3-methylpyridin-2-yl)quinoxalin-5-yl)-6,7-dihydro-1H-pyrrolo[3,2-c]pyridin-4(5H)-one (16.8 mg, 0.045 mmol, 42% yield) as a yellow-orange solid. ¹H NMR (400 MHz, CDCl₃) δ ppm 11.91 (1H, br. s.), 8.65 (1H, dd, J=4.5, 0.8 Hz), 8.10 (1H, dd, J=7.4, 1.2 Hz), 7.91 (1H, dd, J=8.2, 1.2 Hz), 7.74-7.82 (2H, m), 7.42 (1H, dd, J=7.8, 4.9 Hz), 7.23 (1H, d, J=2.2 Hz), 5.35 (1H, br. s.), 3.59 (2H, td, J=6.8, 1.9 Hz), 2.86 (2H, t, J=7.0 Hz), 2.64 (3H, s), 2.29 (3H, s). m/z (ESI, +ve) 370.0 (M+H)⁺.

Example 431

2-(3-(Furan-3-yl)-2-methylquinoxalin-5-yl)-6,7-dihydro-1H-pyrrolo[3,2-c]pyridin-4(5H)-one

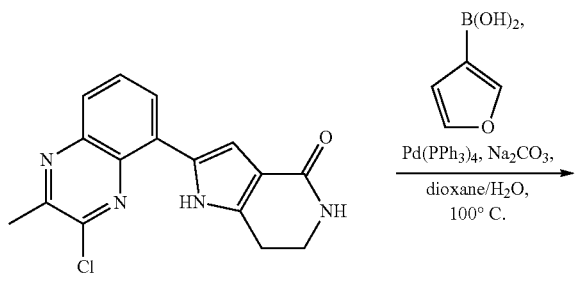

425

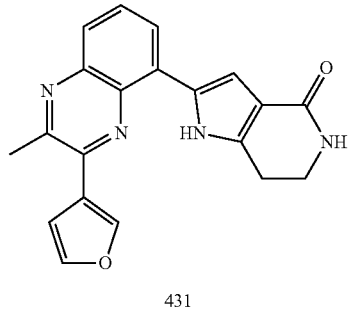

431

A solution of 2-(3-chloro-2-methylquinoxalin-5-yl)-6,7-dihydro-1H-pyrrolo[3,2-c]pyridin-4(5H)-one (Example 425; 37.7 mg, 0.121 mmol), furan-3-ylboronic acid (Boron Molecular, Research Triangle, N.C.; 20.23 mg, 0.181 mmol), Na₂CO₃ (38.3 mg, 0.362 mmol), and Pd(PPh₃)₄ (Strem Chemicals, Inc.; 6.96 mg, 6.03 µmol) in a mixture of 1,4-dioxane (1.5 mL) and water (0.500 mL) was stirred under argon at 100° C. for 20 min. The reaction mixture was then concentrated onto silica gel and chromatographically purified (silica gel, 50-100% EtOAc/hexanes, then 0-10% MeOH/DCM) to provide 2-(3-(furan-3-yl)-2-methylquinoxalin-5-yl)-6,7-dihydro-1H-pyrrolo[3,2-c]pyridin-4(5H)-one (37.0 mg, 0.107 mmol, 89% yield) as a yellow-orange solid. ¹H NMR (400 MHz, DMSO-d₆) δ ppm 11.81 (1H, br. s.), 8.52 (1H, s), 8.02 (1H, dd, J=7.2, 1.4 Hz), 7.95 (1H, t, J=1.7 Hz), 7.83 (1H, dd, J=8.2, 1.4 Hz), 7.74-7.80 (1H, m), 7.25 (1H, s), 7.24 (1H, dd, J=1.8, 0.8 Hz), 7.00 (1H, br. s.), 3.45 (2H, td, J=6.7, 2.3 Hz), 2.90-2.94 (2H, m), 2.90 (3H, s). m/z (ESI, +ve) 344.9 (M+H)⁺.

Example 432

2-(2-Methyl-3-(1-methyl-1H-imidazol-2-yl)quinoxalin-5-yl)-6,7-dihydro-1H-pyrrolo[3,2-c]pyridin-4(5H)-one

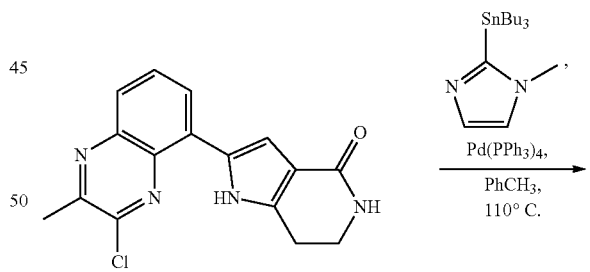

425

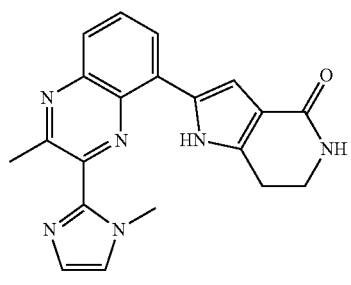

432

A solution of 2-(3-chloro-2-methylquinoxalin-5-yl)-6,7-dihydro-1H-pyrrolo[3,2-c]pyridin-4(5H)-one (Example 425; 34.1 mg, 0.109 mmol), 1-methyl-2-(tributylstannyl)-1H-imidazole (Indofine Chemical Company, Inc.; 0.042 mL, 0.131 mmol) and Pd(PPh₃)₄ (Strem Chemicals, Inc.; 12.60 mg, 10.90 μmol) in toluene (2.0 mL) was stirred under argon at 110° C. for 1 h. The reaction mixture was then cooled to RT and diluted with hexanes (10 mL). The precipitated solid was collected by vacuum filtration (fine glass frit), sequentially washed with hexanes (10 mL) and Et₂O (10 mL), and dried in vacuo to provide 2-(2-methyl-3-(1-methyl-1H-imidazol-2-yl)quinoxalin-5-yl)-6,7-dihydro-1H-pyrrolo[3,2-c]pyridin-4(5H)-one (34.7 mg, 0.097 mmol, 89% yield) as a brown solid. ¹H NMR (400 MHz, DMSO-d₆) δ ppm 11.70 (1H, br. s.), 7.97 (1H, dd, J=7.1, 1.3 Hz), 7.91 (1H, s), 7.85 (1H, dd, J=8.2, 1.2 Hz), 7.75-7.82 (1H, m), 7.66 (1H, d, J=0.6 Hz), 7.07 (1H, d, J=2.0 Hz), 6.98 (1H, br. s.), 3.79 (3H, s), 3.42 (2H, td, J=6.8, 2.2 Hz), 2.88 (2H, br. s.), 2.83-2.86 (3H, m). m/z (ESI, +ve) 359.0 (M+H)⁺.

Example 433

2-(2-Methyl-3-(2-methylfuran-3-yl)quinoxalin-5-yl)-6,7-dihydro-1H-pyrrolo[3,2-c]pyridin-4(5H)-one

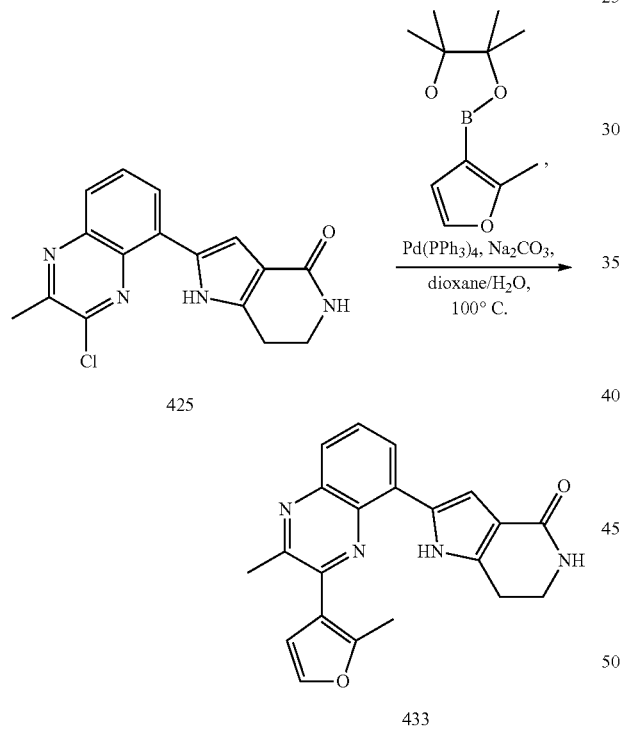

A solution of 2-(3-chloro-2-methylquinoxalin-5-yl)-6,7-dihydro-1H-pyrrolo[3,2-c]pyridin-4(5H)-one (Example 425; 36.5 mg, 0.117 mmol), 4,4,5,5-tetramethyl-2-(2-methylfuran-3-yl)-1,3,2-dioxaborolane (Maybridge, Tintagel, UK; 0.040 mL, 0.175 mmol), Na₂CO₃ (37.1 mg, 0.350 mmol), and Pd(PPh₃)₄ (Strem Chemicals, Inc.; 6.74 mg, 5.84 μmol) in a mixture of 1,4-dioxane (1.5 mL) and water (0.500 mL) was stirred under argon at 100° C. for 20 min. The reaction mixture was then concentrated onto silica gel and chromatographically purified (silica gel, 50-100% EtOAc/hexanes, then 0-10% MeOH/DCM) to provide 2-(2-methyl-3-(2-methylfuran-3-yl)quinoxalin-5-yl)-6,7-dihydro-1H-pyrrolo[3,2-c]pyridin-4(5H)-one (35.1 mg, 0.098 mmol, 84% yield) as a yellow-orange solid: ¹H NMR (400 MHz, DMSO-d₆) δ ppm 11.79 (1H, br. s.), 8.03 (1H, dd, J=7.3, 1.5 Hz), 7.83 (1H, dd, J=8.2, 1.2 Hz), 7.78 (1H, d, J=7.4 Hz), 7.74 (1H, d, J=2.0 Hz), 7.30 (1H, d, J=2.2 Hz), 7.00 (2H, d, J=1.8 Hz), 3.41 (2H, td, J=6.8, 2.4 Hz), 2.88 (2H, t, J=6.8 Hz), 2.75 (3H, s), 2.48 (3H, s). m/z (ESI, +ve) 359.0 (M+H)⁺.

Examples 434 and 435 tert-Butyl ((1s,3s)-3-((3-methyl-8-(4-oxo-4,5,6,7-tetrahydro-1H-pyrrolo[3,2-c]pyridin-2-yl)quinoxalin-2-yl)amino)cyclobutyl)carbamate and 2-(3-(((1s,3s)-3-Aminocyclobutyl)amino)-2-methylquinoxalin-5-yl)-6,7-dihydro-1H-pyrrolo[3,2-c]pyridin-4(5H)-one hydrochloride

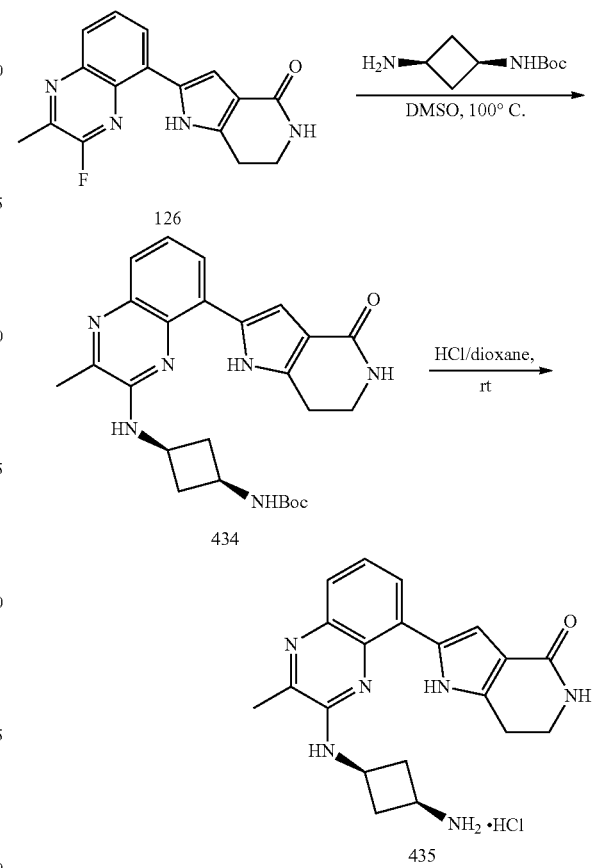

Preparation of tert-butyl ((1s,3s)-3-((3-methyl-8-(4-oxo-4,5,6,7-tetrahydro-1H-pyrrolo[3,2-c]pyridin-2-yl)quinoxalin-2-yl)amino)cyclobutyl)carbamate (434)

A solution of 2-(3-fluoro-2-methylquinoxalin-5-yl)-6,7-dihydro-1H-pyrrolo[3,2-c]pyridin-4(5H)-one (Example 126; 42.0 mg, 0.142 mmol) and tert-butyl ((1s,3s)-3-aminocyclobutyl)carbamate (see J. Org. Chem. 2010, 75, 5941-5952; 52.8 mg, 0.283 mmol) in DMSO (1.0 mL) was stirred under argon at 100° C. for 30 min. The reaction mixture was subsequently cooled to 23° C. and diluted with water (30 mL). The resulting mixture was extracted with 5% MeOH/DCM (2×30 mL), and the combined extracts were sequentially washed with water (30 mL), dried over Na₂SO₄, filtered, and concentrated onto silica gel. Chromatographic purification (50-100% EtOAc/Hexanes, then 0-10% MeOH/DCM) furnished tert-butyl ((1s,3s)-3-((3-methyl-8-(4-oxo-4,5,6,7-tetrahydro-1H-pyrrolo[3,2-c]pyridin-2-yl)quinoxalin-2-yl)amino)cyclobutyl)carbamate (41.5 mg, 0.090 mmol, 63% yield) as a yellow solid. $^1$H NMR (400 MHz, CDCl$_3$) δ ppm 12.60 (1H, br. s.), 7.95 (1H, d, J=7.0 Hz), 7.68 (1H, d, J=7.8 Hz), 7.42 (1H, t, J=7.8 Hz), 7.13 (1H, d, J=1.4 Hz), 5.65 (1H, br. s.), 5.18 (1H, br. s.), 4.82 (1H, d, J=6.7 Hz), 4.12-4.24 (1H, m), 4.04 (1H, br. s.), 3.63-3.73 (2H, m), 3.05-3.15 (2H, m), 3.02 (2H, t, J=7.0 Hz), 2.60 (3H, s), 2.09 (2H, s), 1.47 (9H, s). m/z (ESI, +ve) 463.0 (M+H)$^+$.

Preparation of 2-(3-(((1s,3s)-3-Aminocyclobutyl)amino)-2-methylquinoxalin-5-yl)-6,7-dihydro-1H-pyrrolo[3,2-c]pyridin-4(5H)-one hydrochloride (435)

A suspension of tert-butyl ((1s,3s)-3-((3-methyl-8-(4-oxo-4,5,6,7-tetrahydro-1H-pyrrolo[3,2-c]pyridin-2-yl)quinoxalin-2-yl)amino)cyclobutyl)carbamate (36.7 mg, 0.079 mmol) in 4.0 M HCl in 1,4-dioxane (Aldrich; 1.0 mL, 4.00 mmol) was stirred at 23° C. for 2 h. The reaction mixture was then diluted with Et$_2$O (5 mL) and vacuum filtered. The collected solid was washed with Et$_2$O (5×2 mL) and dried in vacuo to provide 2-(3-4(1s,3s)-3-amino cyclobutyl)amino)-2-methylquinoxalin-5-yl)-6,7-dihydro-1H-pyrrolo[3,2-c]pyridin-4(5H)-one hydrochloride (25.6 mg, 0.064 mmol, 81% yield) as a red-brown solid. $^1$H NMR (400 MHz, DMSO-d$_6$) δ ppm 12.07 (1H, br. s.), 8.26 (3H, br. s.), 7.88 (1H, d, J=7.2 Hz), 7.59 (1H, d, J=7.8 Hz), 7.52-7.58 (1H, m), 7.35 (1H, t, J=7.6 Hz), 7.13 (1H, s), 4.23-4.39 (1H, m), 3.50-3.63 (1H, m), 3.45 (2H, t, J=6.6 Hz), 2.94 (2H, t, J=6.7 Hz), 2.79-2.90 (2H, m), 2.58 (3H, s), 2.24-2.36 (2H, m). m/z (ESI, +ve) 363.0 (M+H)$^+$.

Examples 436 and 437: tert-Butyl ((1r,3s)-3-((3-methyl-8-(4-oxo-4,5,6,7-tetrahydro-1H-pyrrolo[3,2-c]pyridin-2-yl)quinoxalin-2-yl)amino)cyclobutyl)carbamate and 2-(3-(((1r,3s)-3-Aminocyclobutyl)amino)-2-methylquinoxalin-5-yl)-6,7-dihydro-1H-pyrrolo[3,2-c]pyridin-4(5H)-one hydrochloride

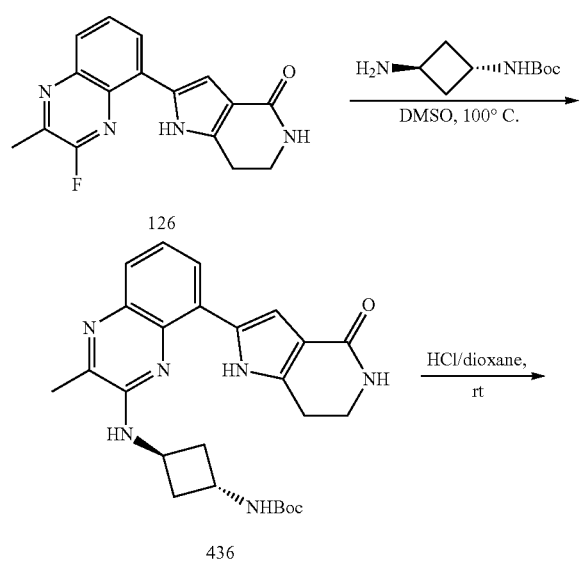

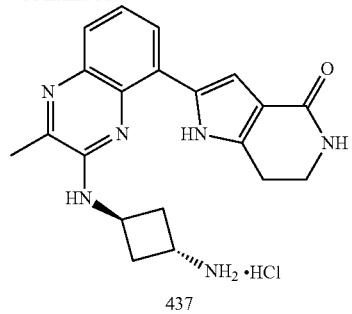

Preparation of tert-butyl ((1r,3s)-3-((3-methyl-8-(4-oxo-4,5,6,7-tetrahydro-1H-pyrrolo[3,2-c]pyridin-2-yl)quinoxalin-2-yl)amino)cyclobutyl)carbamate (436)

A solution of 2-(3-fluoro-2-methylquinoxalin-5-yl)-6,7-dihydro-1H-pyrrolo[3,2-c]pyridin-4(5H)-one (Example 126; 45.6 mg, 0.154 mmol) and tert-butyl ((1r,3s)-3-aminocyclobutyl)carbamate (see J. Org. Chem. 2010, 75, 5941-5952; 31.5 mg, 0.169 mmol) in DMSO (1.0 mL) was stirred under argon at 100° C. for 1 h. The reaction mixture was subsequently cooled to 23° C. and diluted with water (30 mL). The resulting mixture was extracted with 5% MeOH/DCM (2×30 mL), and the combined extracts were sequentially washed with water (2×30 mL) and then concentrated onto silica gel. Chromatographic purification (50-100% EtOAc/Hexanes, then 0-10% MeOH/DCM) furnished tert-butyl ((1r,3s)-3-((3-methyl-8-(4-oxo-4,5,6,7-tetrahydro-1H-pyrrolo[3,2-c]pyridin-2-yl)quinoxalin-2-yl)amino)cyclobutyl)carbamate (41.7 mg, 0.090 mmol, 59% yield) as a yellow solid. $^1$H NMR (400 MHz, CDCl$_3$) δ ppm 12.39 (1H, br. s.), 7.95 (1H, d, J=7.6 Hz), 7.69 (1H, dd, J=7.9, 1.1 Hz), 7.42 (1H, t, J=7.6 Hz), 7.15 (1H, d, J=1.8 Hz), 5.39 (1H, br. s.), 5.08 (1H, d, J=3.9 Hz), 4.87 (1H, br. s.), 4.50 (1H, br. s.), 4.40 (1H, br. s.), 3.67 (2H, td, J=6.9, 1.0 Hz), 3.04 (2H, t, J=6.7 Hz), 2.61 (3H, s), 2.48-2.66 (4H, m), 1.47 (9H, s). m/z (ESI, +ve) 463.0 (M+H)$^+$.

Preparation of 2-(3-(((1r,3r)-3-aminocyclobutyl)amino)-2-methylquinoxalin-5-yl)-6,7-dihydro-1H-pyrrolo[3,2-c]pyridin-4(5H)-one hydrochloride (437)

A suspension of tert-butyl ((1r,3s)-3-((3-methyl-8-(4-oxo-4,5,6,7-tetrahydro-1H-pyrrolo[3,2-c]pyridin-2-yl)quinoxalin-2-yl)amino)cyclobutyl)carbamate (36.0 mg, 0.078 mmol) in 4.0M HCl in 1,4-dioxane (Aldrich; 2.0 mL, 8.00 mmol) was stirred at 23° C. for 2.5 h. The reaction mixture was then diluted with Et$_2$O (10 mL) and vacuum filtered. The collected solid was washed with ethyl ether (5×2 mL) and dried in vacuo to provide 2-(3-(((1r,3r)-3-aminocyclobutyl)amino)-2-methylquinoxalin-5-yl)-6,7-dihydro-1H-pyrrolo[3,2-c]pyridin-4(5H)-one hydrochloride (30.5 mg, 0.076 mmol, 98% yield) as a red-orange solid. $^1$H NMR (400 MHz, DMSO-d$_6$) δ ppm 11.95 (1H, br. s.), 8.25 (3H, br. s.), 7.89 (1H, d, J=7.8 Hz), 7.59 (1H, d, J=8.0 Hz), 7.45 (1H, br. s.), 7.36 (1H, t, J=7.7 Hz), 7.18 (1H, br. s.), 7.03 (1H, br. s.), 4.65 (1H, br. s.), 3.84-3.95 (1H, m), 3.46 (2H, t, J=6.1 Hz), 2.99 (2H, t, J=6.5 Hz), 2.61-2.70 (2H, m), 2.59 (3H, br. s.), 2.40-2.48 (2H, obsc. m). m/z (ESI, +ve) 363.0 (M+H)$^+$.

Example 438

2-(3-(tert-Butylamino)-2-phenylquinoxalin-5-yl)-6,7-dihydro-1H-pyrrolo[3,2-c]pyridin-4(5H)-one

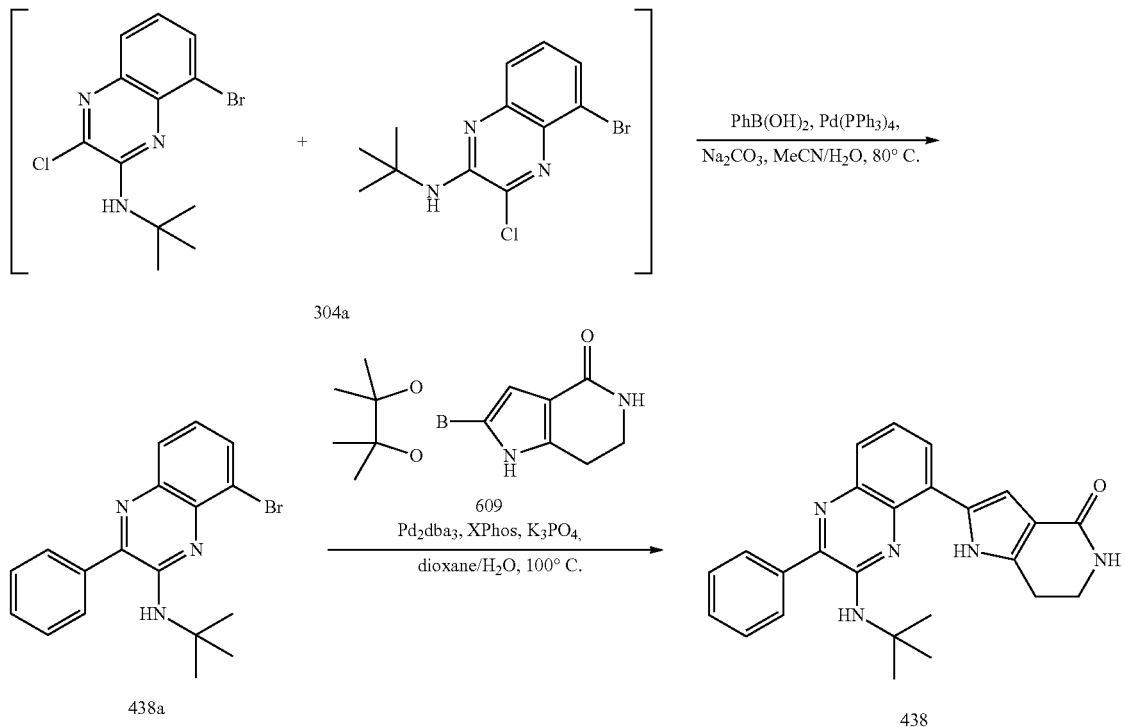

438a

438

Preparation of 8-bromo-N-(tert-butyl)-3-phenylquinoxalin-2-amine (438a)

A suspension of 8-bromo-N-(tert-butyl)-3-chloroquinoxalin-2-amine (Example 304a (~2.5:1 mixture with 5-bromo-N-(tert-butyl)-3-chloroquinoxalin-2-amine); 119.0 mg, 0.378 mmol), phenylboronic acid (Aldrich; 46.1 mg, 0.378 mmol), $Na_2CO_3$ (200 mg, 1.891 mmol), and $Pd(PPh_3)_4$ (Strem Chemicals, Inc.; 21.85 mg, 0.019 mmol) in a mixture of MeCN (3.0 mL) and water (1.000 mL) was stirred under argon at 80° C. for 17.5 h. The reaction mixture was cooled to RT and concentrated onto silica gel. Chromatographic purification (silica gel, 0-10% EtOAc/hexanes) furnished 8-bromo-N-(tert-butyl)-3-phenylquinoxalin-2-amine (83.0 mg, 0.233 mmol, 62% yield) as an off-white solid. $^1$H NMR (400 MHz, $CDCl_3$) δ ppm 7.85 (1H, dd, J=4.5, 1.2 Hz), 7.83 (1H, dd, J=5.1, 1.4 Hz), 7.67-7.72 (2H, m), 7.51-7.59 (3H, m), 7.20 (1H, t, J=7.8 Hz), 5.23 (1H, br. s.), 1.57 (9H, s). m/z (ESI, +ve) 355.9/358.0 (M+H)$^+$.

Preparation of 2-(3-(tert-Butylamino)-2-phenylquinoxalin-5-yl)-6,7-dihydro-1H-pyrrolo[3,2-c]pyridin-4(5H)-one (438)

A solution of 8-bromo-N-(tert-butyl)-3-phenylquinoxalin-2-amine (83.0 mg, 0.233 mmol), 2-(4,4,5,5-tetramethyl-1,3,2-dioxaborolan-2-yl)-6,7-dihydro-1H-pyrrolo[3,2-c]pyridin-4(5H)-one (Example 609; 172 mg, 0.466 mmol), $K_3PO_4$ (148 mg, 0.699 mmol), dicyclohexyl(2',4',6'-triisopropyl-[1,1'-biphenyl]-2-yl)phosphine (XPhos; Strem Chemicals, Inc.; 11.11 mg, 0.023 mmol), and $Pd_2dba_3$ (Aldrich; 10.67 mg, 0.012 mmol) in a mixture of 1,4-dioxane (2.0 mL) and water (0.400 mL) was stirred under argon at 100° C. for 1 h. The reaction mixture was then concentrated onto silica gel and chromatographically purified (silica gel, 50-100% EtOAc/hexanes, then 0-10% MeOH/DCM) to provide 2-(3-(tert-butylamino)-2-phenylquinoxalin-5-yl)-6,7-dihydro-1H-pyrrolo[3,2-c]pyridin-4(5H)-one (50.0 mg, 0.122 mmol, 52% yield) as a yellow solid. $^1$H NMR (400 MHz, $CDCl_3$) δ ppm 12.72 (1H, br. s.), 7.99 (1H, dd, J=7.6, 1.4 Hz), 7.77 (1H, dd, J=8.1, 1.3 Hz), 7.71 (2H, dd, J=7.8, 1.6 Hz), 7.53-7.62 (3H, m), 7.41 (1H, t, J=7.8 Hz), 7.13 (1H, d, J=2.2 Hz), 5.98-6.21 (1H, m), 5.36 (1H, s), 3.71 (2H, t, J=6.9 Hz), 3.03 (2H, t, J=7.0 Hz), 1.59 (9H, s). m/z (ESI, +ve) 412.0 (M+H)$^+$.

Example 439

2-(3-((cis-3-Hydroxycyclobutyl)amino)-2-methylquinoxalin-5-yl)-6,7-dihydro-1H-pyrrolo[3,2-c]pyridin-4(5H)-one

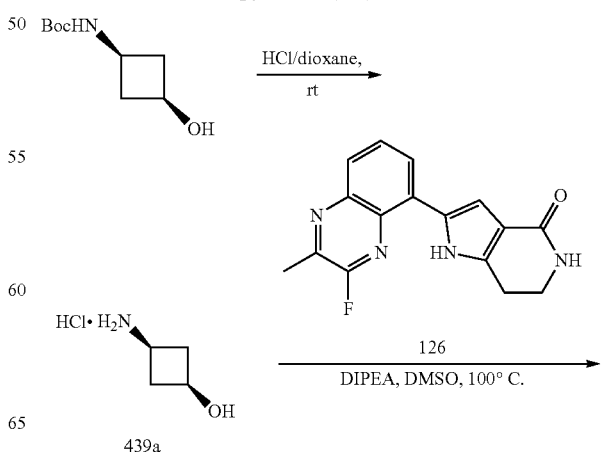

439a

-continued

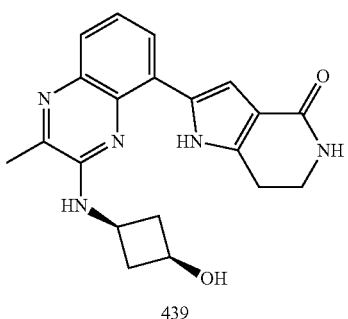

439

Preparation of cis-3-aminocyclobutanol hydrochloride (439a)

A suspension of tert-butyl (cis-3-hydroxycyclobutyl)carbamate (see J. Org. Chem. 2010, 75, 5941-5952; 70.0 mg, 0.374 mmol) and HCl (1.0M in Et$_2$O; Aldrich; 5.0 mL, 5.00 mmol) was stirred at 23° C. for 2.5 h. The reaction mixture was then concentrated in vacuo to provide cis-3-aminocyclobutanol hydrochloride (46.2 mg, 0.374 mmol, 100% yield) as a light-yellow, waxy solid, which was used directly in the subsequent step.

Preparation of 2-(3-((cis-3-Hydroxycyclobutyl)amino)-2-methylquinoxalin-5-yl)-6,7-dihydro-1H-pyrrolo[3,2-c]pyridin-4(5H)-one (439)

A solution of 2-(3-fluoro-2-methylquinoxalin-5-yl)-6,7-dihydro-1H-pyrrolo[3,2-c]pyridin-4(5H)-one (Example 126; 85.0 mg, 0.287 mmol), cis-3-aminocyclobutanol hydrochloride (46.2 mg, 0.374 mmol), and DIPEA (0.150 mL, 0.861 mmol) in DMSO (2.0 mL) was stirred under argon at 100° C. for 30 min. The reaction mixture was subsequently cooled to 23° C. and diluted with water (10 mL). The resulting mixture was extracted with 5% MeOH/DCM (2×30 mL), and the combined extracts were sequentially washed with water (2×10 mL) and then concentrated onto silica gel. Chromatographic purification (silica gel, 50-100% EtOAc/Hexanes, then 100% EtOAc, then 0-10% MeOH/DCM) provided 2-(3-((cis-3-hydroxycyclobutyl)amino)-2-methylquinoxalin-5-yl)-6,7-dihydro-1H-pyrrolo[3,2-c]pyridin-4(5H)-one (9.3 mg, 0.026 mmol, 11% yield) as a yellow solid. The combined aqueous layers from the aqueous workup were filtered through a fine glass frit, and the collected solid was sequentially washed with water (40 mL) and ether (30 mL), then dried in vacuo to provide additional 2-(3-((cis-3-hydroxycyclobutyl)amino)-2-methylquinoxalin-5-yl)-6,7-dihydro-1H-pyrrolo[3,2-c]pyridin-4(5H)-one (92.2 mg, 0.254 mmol, 88% yield) as a yellow solid: $^1$H NMR (400 MHz, DMSO-d$_6$) δ ppm 12.35 (1H, br. s.), 7.90 (1H, d, J=8.0 Hz), 7.56 (1H, d, J=7.6 Hz), 7.27-7.40 (2H, m), 7.09 (1H, br. s.), 6.95 (1H, br. s.), 5.18 (1H, d, J=6.3 Hz), 3.92-4.08 (1H, m), 3.41-3.50 (3H, m), 2.86-2.96 (2H, m), 2.74-2.86 (2H, m), 2.55 (3H, br. s.), 1.93-2.07 (2H, m). m/z (ESI, +ve) 364.0 (M+H)$^+$.

Examples 440 and 443

2-fluoroethyl ((1s,3s)-3-((3-methyl-8-(4-oxo-4,5,6,7-tetrahydro-1H-pyrrolo[3,2-c]pyridin-2-yl)quinoxalin-2-yl)amino)cyclobutyl)carbamate and 3-((1s,3s)-3-((3-methyl-8-(4-oxo-4,5,6,7-tetrahydro-1H-pyrrolo[3,2-c]pyridin-2-yl)quinoxalin-2-yl)amino)cyclobutyl)oxazolidin-2-one

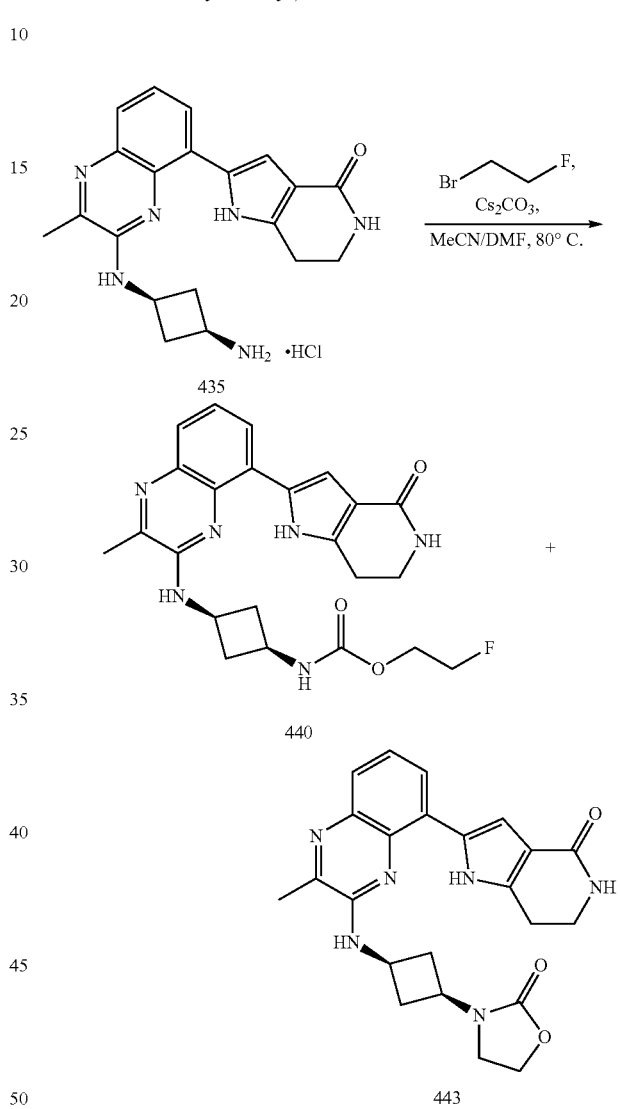

A suspension of 2-(3-((cis-3-aminocyclobutyl)amino)-2-methylquinoxalin-5-yl)-6,7-dihydro-1H-pyrrolo[3,2-c]pyridin-4(5H)-one hydrochloride (Example 435; 26.1 mg, 0.065 mmol), 1-bromo-2-fluoroethane (Alfa Aesar, Ward Hill, Mass.; 5.12 µl, 0.069 mmol), and cesium carbonate (74.6 mg, 0.229 mmol) in a mixture of MeCN (1.0 mL) and DMF (1.0 mL) was stirred in a sealed flask at 80° C. for 19 h. The reaction mixture was subsequently concentrated onto silica gel and chromatographically purified (silica gel, 50-100% (3:1 EtOAc/EtOH)/hexanes) to separately provide two products: A) 2-fluoroethyl ((1s,3s)-3-((3-methyl-8-(4-oxo-4,5,6,7-tetrahydro-1H-pyrrolo[3,2-c]pyridin-2-yl)quinoxalin-2-yl)amino)cyclobutyl)carbamate (Example 440; 7.4 mg, 0.016 mmol, 25% yield) as a yellow solid: $^1$H NMR (400 MHz, CDCl$_3$) δ ppm 12.54 (1H, br. s.), 7.95 (1H, dd, J=7.6, 1.4 Hz), 7.68 (1H, dd, J=8.0, 1.4 Hz), 7.42 (1H, t, J=7.8 Hz), 7.14 (1H, d, J=2.0 Hz), 5.33 (1H, br. s.), 5.17 (2H, br. s.), 4.60 (2H, dt, J=47.5, 4.1 Hz), 4.34 (2H, dt, J=28.5, 3.8 Hz), 4.16-4.25 (1H, m), 4.04-4.12 (1H, m), 3.65-3.71 (2H, m), 3.07-3.17 (2H, m), 3.02 (2H, t, J=6.8 Hz), 2.60 (3H, s), 2.04-2.13 (2H, m). $^{19}$F NMR (377 MHz, CDCl$_3$) δ ppm −224.84 (1F, s). m/z (ESI, +ve) 452.9 (M+H)$^+$. B) 3-((1s,3s)-3-((3-methyl-8-(4-oxo-4,5,6,7-tetrahydro-1H-pyrrolo[3,2-c]pyridin-2-yl)quinoxalin-2-yl)amino)cyclobutyl)oxazolidin-2-one (Example 443; 8.5 mg, 0.020 mmol, 30% yield) as a yellow solid: $^1$H NMR (400 MHz, CDCl$_3$) δ ppm 12.49 (1H, br. s.), 7.95 (1H, dd, J=7.6, 1.2 Hz), 7.69 (1H, dd, J=8.0, 1.2 Hz), 7.42 (1H, t, J=7.9 Hz), 7.14 (1H, d, J=2.0 Hz), 5.34 (1H, br. s.), 5.31 (1H, d, J=5.9 Hz), 4.34-4.42 (2H, m), 4.24 (2H, t, J=8.4 Hz), 3.69-3.76 (2H, m), 3.64-3.69 (2H, m), 2.99-3.05 (2H, m), 2.95-3.00 (2H, m), 2.61 (3H, s), 2.30-2.41 (2H, m). m/z (ESI, +ve) 433.0 (M+H)$^+$.

Example 441

2-(2-Methyl-3-((cis-3-((2-(methylsulfonyl)ethyl)amino)cyclobutyl)amino)quinoxalin-5-yl)-6,7-dihydro-1H-pyrrolo[3,2-c]pyridin-4(5H)-one

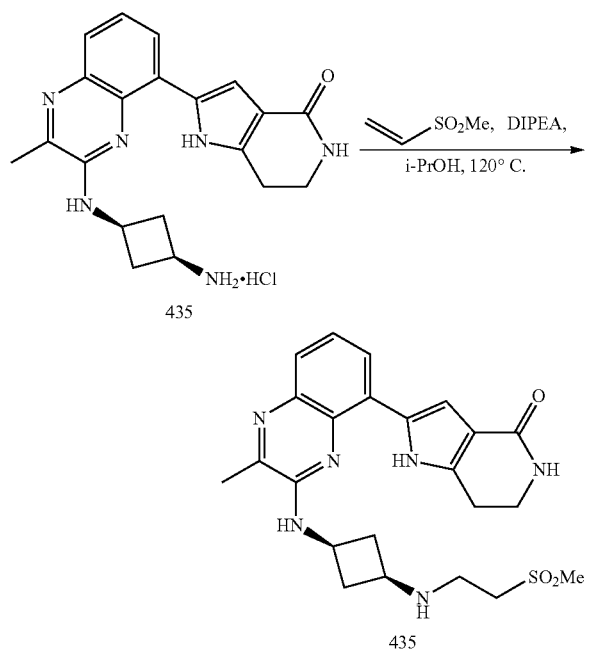

A suspension of 2-(3-((cis-3-aminocyclobutyl)amino)-2-methylquinoxalin-5-yl)-6,7-dihydro-1H-pyrrolo[3,2-c]pyridin-4(5H)-one hydrochloride (Example 435; 20.6 mg, 0.052 mmol), methylvinylsulfone (Aldrich; 0.018 mL, 0.207 mmol), and DIPEA (0.036 mL, 0.207 mmol) in IPA (1.0 mL) was heated in a sealed vial at 120° C. for 15 min. The reaction mixture was then concentrated onto silica gel and chromatographically purified (silica gel, 100% EtOAc, then 0-10% (2M NH$_3$ in MeOH)/DCM) to provide 2-(2-methyl-3-((cis-3-((2-(methylsulfonyl)ethyl)amino)cyclobutyl)amino)quinoxalin-5-yl)-6,7-dihydro-1H-pyrrolo[3,2-c]pyridin-4(5H)-one (20.5 mg, 0.044 mmol, 85% yield) as a yellow-orange solid. $^1$H NMR (400 MHz, DMSO-d$_6$) δ ppm 12.33 (1H, br. s.), 7.90 (1H, dd, J=7.5, 1.1 Hz), 7.56 (1H, dd, J=8.1, 1.1 Hz), 7.36 (1H, d, J=5.0.7 Hz), 7.32 (1H, t, J=7.8 Hz), 7.10 (1H, d, J=2.0 Hz), 6.95 (1H, s), 4.11-4.22 (1H, m), 3.46 (2H, td, J=6.8, 2.4 Hz), 3.28-3.30 (1H, m), 3.19-3.25 (2H, m), 3.05-3.15 (1H, m), 3.02 (3H, s), 2.92 (4H, t, J=6.7 Hz), 2.73-2.82 (2H, m), 2.55 (3H, s), 1.82-1.92 (2H, m). m/z (ESI, +ve) 469.0 (M+H)$^+$.

Example 442

2-(3-((trans-3-Hydroxycyclobutyl)amino)-2-methylquinoxalin-5-yl)-6,7-dihydro-1H-pyrrolo[3,2-c]pyridin-4(5H)-one

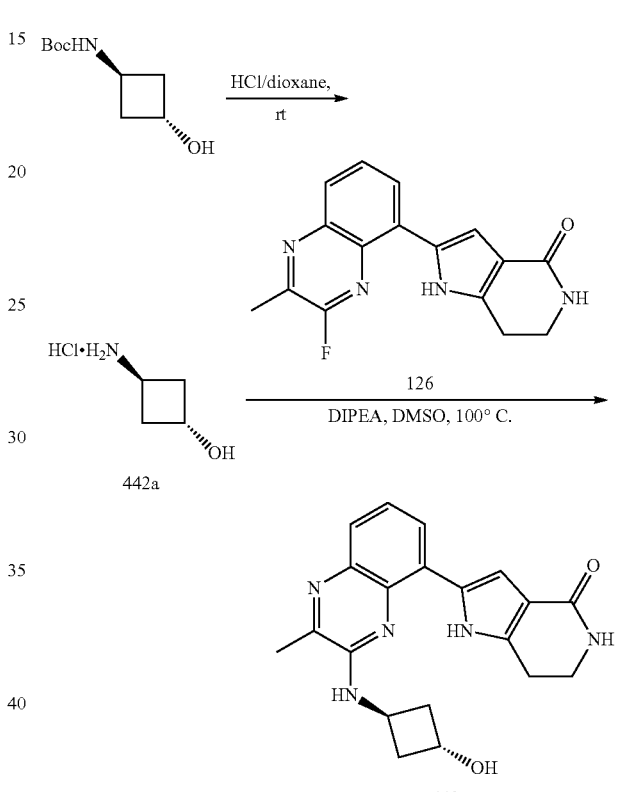

Preparation of trans-3-Aminocyclobutanol hydrochloride (442a)

A solution of tert-butyl (trans-3-hydroxycyclobutyl)carbamate (see J. Org. Chem. 2010, 75, 5941-5952; 66.3 mg, 0.354 mmol) and HCl (1.0M in Et$_2$O; Aldrich; 5.0 mL, 5.00 mmol) was stirred at 23° C. for 2.5 h. The reaction mixture was concentrated in vacuo to provide trans-3-aminocyclobutanol hydrochloride (43.8 mg, 0.354 mmol, 100% yield) as a waxy, white solid, which was used directly in the subsequent step.

Preparation of 2-(3-((trans-3-Hydroxycyclobutyl)amino)-2-methylquinoxalin-5-yl)-6,7-dihydro-1H-pyrrolo[3,2-c]pyridin-4(5H)-one (442)

A solution of 2-(3-fluoro-2-methylquinoxalin-5-yl)-6,7-dihydro-1H-pyrrolo[3,2-c]pyridin-4 (5M-one (Example 126; 60.3 mg, 0.204 mmol), trans-3-aminocyclobutanol hydrochloride (43.8 mg, 0.354 mmol), and DIPEA (0.124 mL, 0.712 mmol) in DMSO (2.0 mL) was stirred under argon at 100° C. for 1 h. Additional DIPEA (0.124 mL, 0.712 mmol) was added, and the resulting solution was stirred under argon at 100° C. for 4.5 h. The reaction mixture was subsequently purified by rpHPLC (Waters XBridge C18 column (150×30 mm, 10 μm), 40 mL/min, 5-95% $CH_3CN/H_2O$+0.1% TFA) to provide 2-(3-((trans-3-hydroxycyclobutyl)amino)-2-methylquinoxalin-5-yl)-6,7-dihydro-1H-pyrrolo[3,2-c]pyridin-4(5H)-one 2,2,2-trifluoroacetate (44.9 mg, 0.094 mmol, 46% yield) as a red solid. $^1$H NMR (400 MHz, DMSO-$d_6$) δ ppm 12.38 (1H, br. s.), 7.93 (1H, dd, J=7.5, 0.9 Hz), 7.56 (1H, dd, J=8.1, 0.9 Hz), 7.29-7.37 (2H, m), 7.05 (1H, d, J=2.0 Hz), 6.99 (1H, br. s.), 4.37-4.50 (1H, m), 4.14-4.23 (1H, m), 3.46 (2H, t, J=6.8 Hz), 2.97 (2H, t, J=6.8 Hz), 2.57 (3H, s), 2.41-2.46 (2H, m), 2.30-2.39 (2H, m). $^{19}$F NMR (376 MHz, DMSO-$d_6$) δ ppm −74.62 (3F, s). m/z (ESI, +ve) 364.0 $(M+H)^+$.

Example 444

2-(2-Methyl-3-4(1s,3s)-3-((2,2,2-trifluoroethyl) amino)cyclobutyl)amino)quinoxalin-5-yl)-6,7-dihydro-1H-pyrrolo[3,2-c]pyridin-4(5H)-one

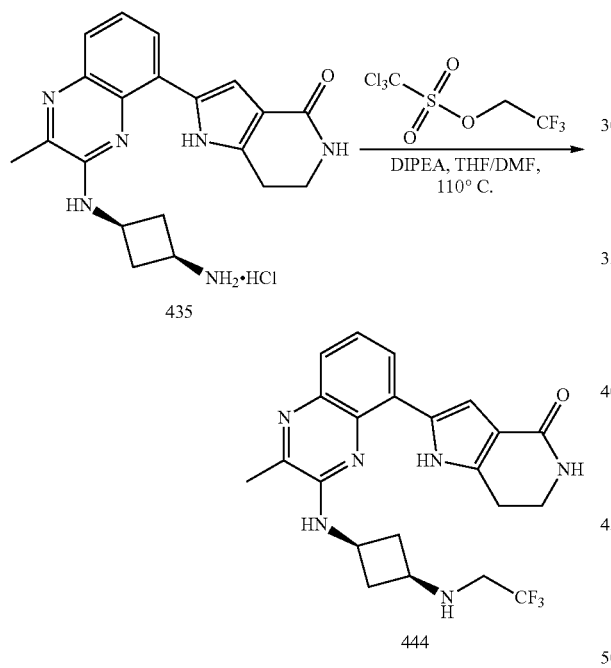

A solution of 2-(3-((cis-3-aminocyclobutyl)amino)-2-methylquinoxalin-5-yl)-6,7-dihydro-1H-pyrrolo[3,2-c]pyridin-4(5H)-one hydrochloride (Example 435; 27.4 mg, 0.069 mmol), 2,2,2-trifluoroethyl trichloromethanesulfonate (Oakwood Products, Inc., West Columbia, S.C.; 0.073 mL, 0.446 mmol), and DIPEA (0.120 mL, 0.686 mmol) in a mixture of THF (1.0 mL) and DMF (1.0 mL) was heated in a sealed flask at 110° C. for 30 min. The reaction mixture was then cooled to RT, concentrated onto silica gel, and chromatographically purified (silica gel, 10-100% (3:1 EtOAc-EtOH)/hexanes). The product-containing fractions were concentrated in vacuo, and the residue was taken up in 5% MeOH/DCM (40 mL), sequentially washed with half-saturated aqueous $NaHCO_3$ (30 mL) and water (30 mL), dried over $Na_2SO_4$, filtered and concentrated in vacuo to provide 2-(2-methyl-3-(1s,3s)-3-((2,2,2-trifluoroethyl)amino)cyclobutyl)amino)quinoxalin-5-yl)-6,7-dihydro-1H-pyrrolo[3,2-c]pyridin-4(5H)-one (11.8 mg, 0.027 mmol, 39% yield) as a yellow solid. $^1$H NMR (400 MHz, CDCl$_3$) δ ppm 12.57 (1H, br. s.), 7.94 (1H, dd, J=7.5, 1.1 Hz), 7.68 (1H, dd, J=8.1, 1.1 Hz), 7.41 (1H, t, J=7.8 Hz), 7.14 (1H, d, J=2.2 Hz), 5.31 (1H, br. s.), 5.16 (1H, d, J=4.7 Hz), 4.13-4.27 (1H, m), 3.68 (2H, td, J=6.9, 2.4 Hz), 3.32-3.43 (1H, m), 3.23 (2H, q, J=9.4 Hz), 3.01-3.08 (2H, m), 2.99 (2H, t, J=6.8 Hz), 2.59 (3H, s), 1.80-1.94 (2H, m). $^{19}$F NMR (376 MHz, CDCl$_3$) δ ppm −71.65 (3F, br. s.). m/z (ESI, +ve) 445.0 $(M+H)^+$.

Example 445

N-(3-methyl-8-(4-oxo-4,5,6,7-tetrahydro-1H-pyrrolo [3,2-c]pyridin-2-yl)quinoxalin-2-yl)acetamide

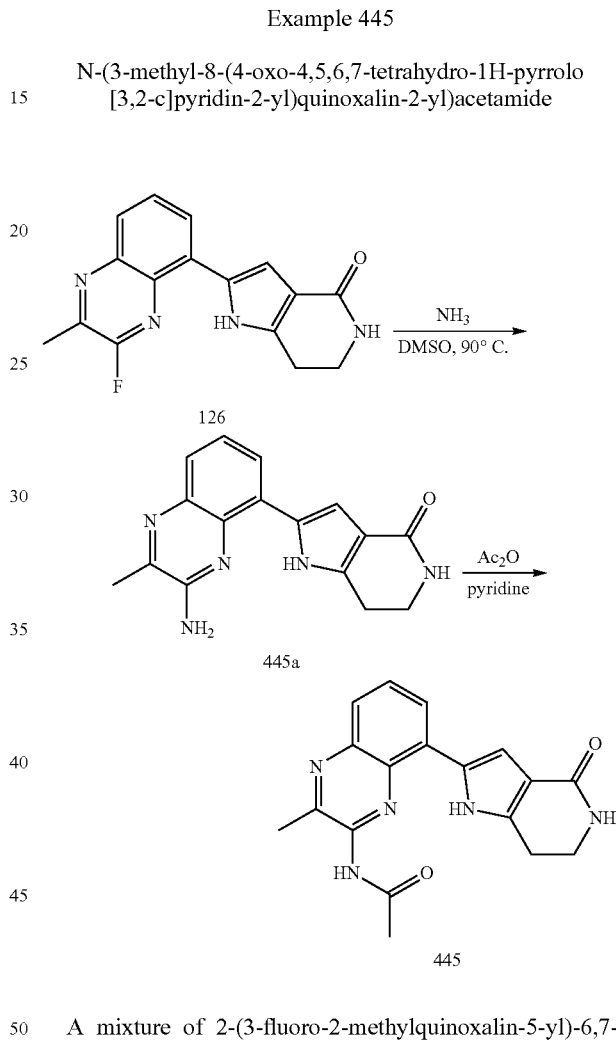

A mixture of 2-(3-fluoro-2-methylquinoxalin-5-yl)-6,7-dihydro-1H-pyrrolo[3,2-c]pyridin-4(5H)-one (126) (0.30 g, 1.01 mmol) and ammonia (4.05 mL, 8.10 mmol) in DMSO (5 mL) was heated at 90° C. in a sealed tube for 16 h. The reaction mixture was cooled to RT, treated with water, and extracted with DCM (3×). The extracts were dried over $Na_2SO_4$, concentrated. The residue was purified by silica gel chromatography (0-10% MeOH/DCM) to give 2-(3-amino-2-methylquinoxalin-5-yl)-6,7-dihydro-1H-pyrrolo[3,2-c] pyridin-4(5H)-one (445a, 235 mg, 79%). m/z (ESI, +ve) 294 $(M+H)^+$. A mixture of 2-(3-amino-2-methylquinoxalin-5-yl)-6,7-dihydro-1H-pyrrolo[3,2-c]pyridin-4(5H)-one (445a, 50 mg, 0.17 mmol) and $Ac_2O$ (0.016 mL, 0.17 mmol) in pyridine (2 mL) was heated at 50° C. for 16 h. It was concentrated under reduced pressure. The residue was purified by reverse phase HPLC. The pure fractions were combined and concentrated to dryness. The solid was dissolved in MeOH and neutralized by pass through Stratosphere SPE (PL-HCO3

MP-Resin) to give N-(3-methyl-8-(4-oxo-4,5,6,7-tetrahydro-1H-pyrrolo[3,2-c]pyridin-2-yl)quinoxalin-2-yl)acetamide as a tan solid (445) (10 mg, 17%). ¹H NMR (400 MHz, DMSO-d₆) δ ppm 13.21 (1H, br. s.), 10.22 (1H, s), 8.07-8.20 (1H, m), 7.71 (1H, dd, J=8.2, 1.2 Hz), 7.63 (1H, t, J=7.8 Hz), 7.09 (1H, d, J=2.3 Hz), 6.99 (1H, br. s.), 3.41-3.51 (2H, t, J=6.8 Hz), 2.94 (2H, t, J=6.8 Hz), 2.75 (3H, s), 2.36 (3H, s). m/z (ESI, +ve) 336 (M+H)⁺.

Example 446

N-(3-methyl-8-(4-oxo-4,5,6,7-tetrahydro-1H-pyrrolo[3,2-c]pyridin-2-yl)quinoxalin-2-yl)cyclopropanecarboxamide

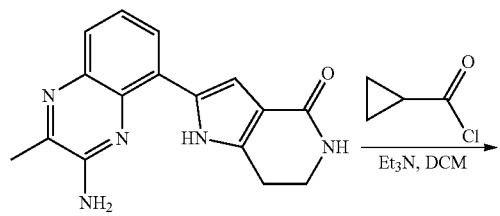

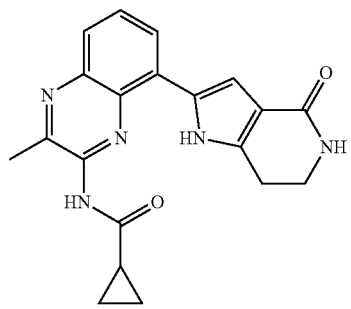

To a stirred mixture of 2-(3-amino-2-methylquinoxalin-5-yl)-6,7-dihydro-1H-pyrrolo[3,2-c]pyridin-4(5H)-one (445a, 79 mg, 0.269 mmol) and TEA (0.18 mL, 1.34 mmol) in DCM (3 mL) was added cyclopropane carbonyl chloride (0.037 mL, 0.404 mmol). After the addition, the mixture was stirred at RT 24 h, concentrated, and purified on a silica gel column (0-10% MeOH/DCM) to give the title compound (55 mg, 56%). ¹H NMR (400 MHz, DMSO-d₆) δ ppm 13.47 (1H, br. s.), 10.52 (1H, br. s.), 8.05 (1H, d, J=7.6 Hz), 7.64 (1H, d, J=8.0 Hz), 7.54 (1H, t, J=7.8 Hz), 7.03 (1H, d, J=2.0 Hz), 6.93 (1H, br. s.), 3.43 (2H, td, J=6.7, 2.3 Hz), 2.89 (2H, t, J=6.8 Hz), 2.74 (3H, s), 2.21 (1H, br. s.), 0.95-1.04 (2H, m), 0.90 (2H, d, J=7.2 Hz). m/z (ESI, +ve) 362 (M+H)⁺.

Example 447

1-(3-methyl-8-(4-oxo-4,5,6,7-tetrahydro-1H-pyrrolo[3,2-c]pyridin-2-yl)quinoxalin-2-yl)guanidine

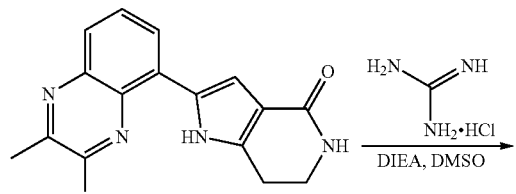

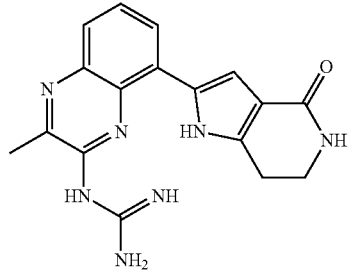

A mixture of 2-(3-fluoro-2-methylquinoxalin-5-yl)-6,7-dihydro-1H-pyrrolo[3,2-c]pyridin-4(5H)-one (445a, 10 mg, 0.33 mmol), DIEA (0.29 mL, 1.68 mmol), and guanidine hydrochloride (0.025 mL, 0.37 mmol) in DMSO (3 mL) was stirred at 70° C. for 24 h. The reaction mixture was cooled, H₂O was added, and extracted with DCM (3×). The extracts were dried over Na₂SO₄, concentrated and purified by reverse phase HPLC. The pure fractions were concentrated, dissolved in MeOH, and neutralized by Stratosphere SPE (PL-HCO3 MP-resin) to give the title compound (12 mg, 11%). ¹H NMR (400 MHz, DMSO-d₆) δ ppm 11.73 (1H, br. s.), 9.95 (1H, br. s.), 8.53-8.39 (3H, br. s.), 7.84 (1H, br. s.), 7.73 (1H, br. s.), 7.02 (1H, br. s.), 6.77 (1H, s), 3.38-3.52 (2H, t, J=6.8 Hz), 2.87 (2H, t, J=6.8 Hz), 2.73 (3H, s). m/z (ESI, +ve) 336 (M+H)⁺.

Example 448

2-(tert-butylamino)-3-methyl-8-(4-oxo-4,5,6,7-tetrahydro-1H-pyrrolo[3,2-c]pyridin-2-yl)-4(3H)-quinazolinone

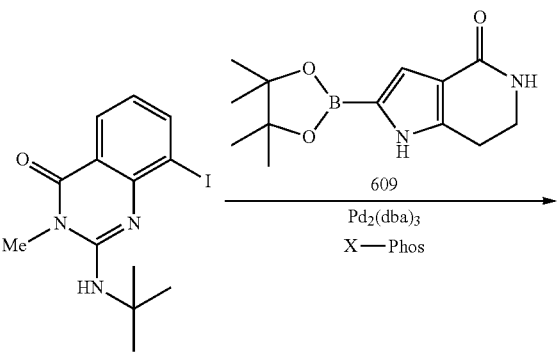

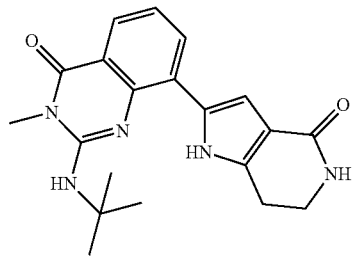

A mixture of Xphos (12 mg, 0.027 mmol), Pd₂dba₃ (12 mg, 0.013 mmol), K₃PO₄ (169 mg, 0.80 mmol), 2-(4,4,5,5-tetramethyl-1,3,2-dioxaborolan-2-yl)-6,7-dihydro-1H-pyrrolo[3,2-c]pyridin-4(5H)-one (609) (139 mg, 0.53 mmol) and 2-(tert-butylamino)-8-iodo-3-methylquinazolin-4(3H)-one (701) (95 mg, 0.27 mmol) in dioxane (2 mL), water (0.4 mL) in a sealed glass tube was heated in a Initiator microwave reactor (Personal Chemistry, Biotage AB, Inc.) at 105° C. for 30 min. It was partitioned between 15 mL of EtOAc and 2 mL of 0.5 N NaOH. The organic layer was separated and concentrated under reduced pressure. The crude material was purified on a silica gel column (eluted with a gradient of 1-10% MeOH in DCM) to afford 2-(tert-butylamino)-3-methyl-8-(4-oxo-4,5,6,7-tetrahydro-1H-pyrrolo[3,2-c]pyridin-2-yl)quinazolin-4(3H)-one (30 mg, 31% yield) as an off-white crystalline solid. $^1$H NMR (400 MHz, DMSO-$d_6$) δ ppm 12.00 (1H, br.), 7.94 (1H, dd, J=7.5, 1.5 Hz), 7.86 (1H, dd, J=7.8, 1.4 Hz), 7.18 (1H, t, J=7.6 Hz), 6.94 (2H, d, J=2.2 Hz), 5.98 (1H, s), 3.50 (3H, s), 3.44 (2H, m), 2.86 (2H, t, J=6.8 Hz), 1.56 (9H, s). m/z (ESI, +ve ion) 366.2 (M+H)$^+$.

Example 449

2-(tert-butylamino)-3-methyl-8-(1-oxo-1,2,3,4-tetrahydropyrrolo[1,2-a]pyrazin-7-yl)-4(3H)-quinazolinone Preparation of 2-(tert-butylamino)-8-(2-(2,4-dimethoxybenzyl)-1-oxo-1,2,3,4-tetrahydropyrrolo[1,2-a]pyrazin-7-yl)-3-methylquinazolin-4(3H)-one (449a)

A mixture of Pd(dppf)Cl$_2$ DCM adduct (4.0 mg), 2-(tert-butylamino)-8-iodo-3-methylquinazolin-4(3H)-one (701) (37 mg, 0.10 mmol), (BPin)$_2$ (39.5 mg, 0.155 mmol) and KOAc (22 mg, 0.22 mmol) in 0.5 mL of DMF was heated in a microwave at 110° C. for 40 min. It was diluted with 15 mL of EtOAc and filtered through a pad of Celite. The filtrate was washed with 2 mL of water followed by 2 mL of brine. The organic solution was dried over Na$_2$SO$_4$ and concentrated. The dark residue containing (2-(tert-butylamino)-3-methyl-4-oxo-3,4-dihydroquinazolin-8-yl)boronic acid (714) was used in next step without purification. m/z (ESI, +ve) 276.1 (M+H)$^+$. A 5 mL glass microwave reaction tube was charged with the crude (2-(tert-butylamino)-3-methyl-4-oxo-3,4-dihydroquinazolin-8-yl)boronic acid (714), dicyclohexyl(2',4',6'-triisopropyl-[1,1'-biphenyl]-2-yl)phosphine (2.86 mg, 6.00 µmol), Pd$_2$(dba)$_3$ (2.75 mg, 3.00 µmol), 7-bromo-2-(2,4-dimethoxybenzyl)-3,4-dihydropyrrolo[1,2-a]pyrazin-1(2H)-one (36.5 mg, 0.10 mmol) and K$_3$PO$_4$ (63 mg, 0.30 mmol). The tube was purged with argon, and the contents

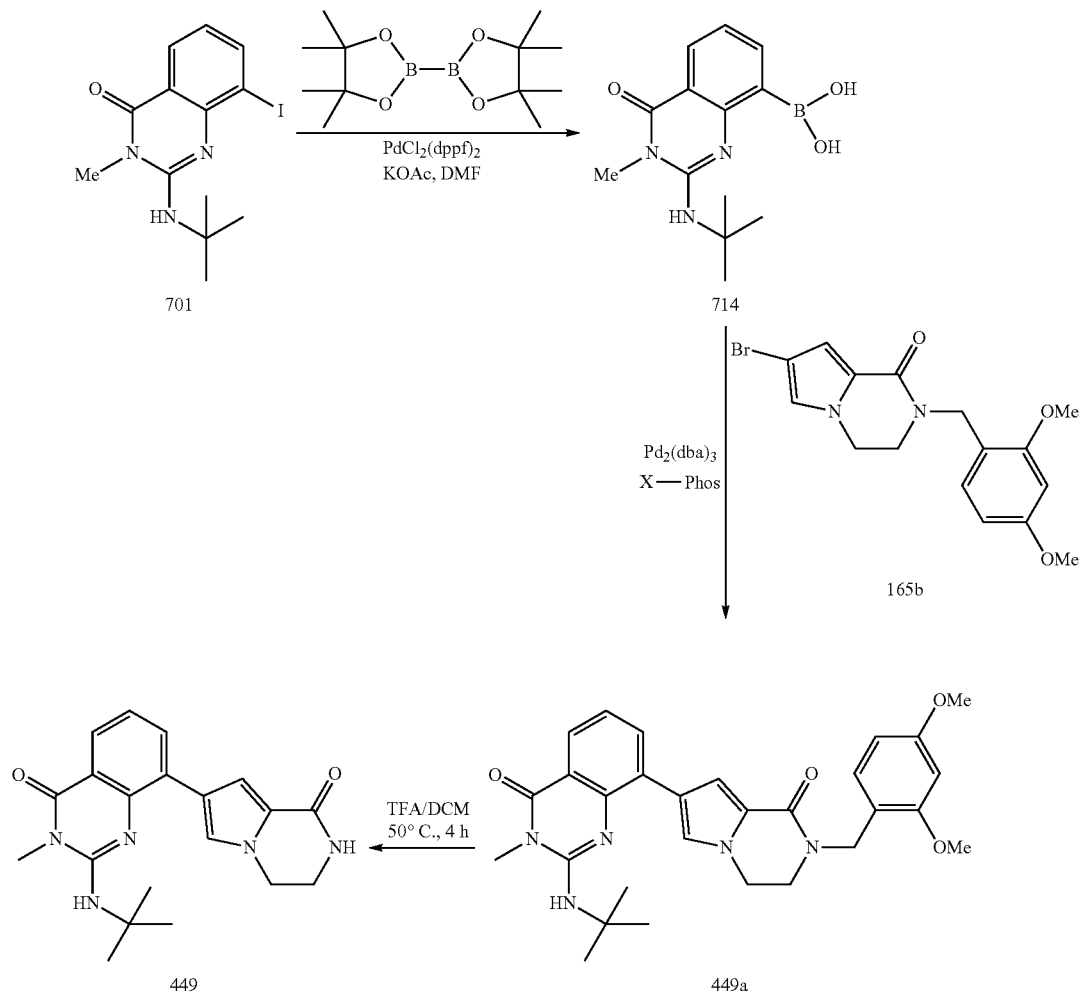

were suspended in Dioxane (2 mL) and Water (0.50 mL). The reaction mixture was heated in an Initiator microwave reactor (Personal Chemistry, Biotage AB, Inc.) at 130° C. for 45 min. Additional X-Phos (3 mg) and Pd$_2$(dba)3 (3 mg) were added and the resulting mixture was heated again in a microwave at 140° C. for 25 min. It was diluted with 10 mL of EtOAc, washed with 2 mL of 0.5 N NaOH followed by 2 mL of brine. The organic solution was concentrated and the residue was purified by silica gel chromatography (eluted with 40-65% EtOAc in Hexanes) to give 2-(tert-butylamino)-8-(2-(2,4-dimethoxybenzyl)-1-oxo-1,2,3,4-tetrahydropyrrolo[1,2-a]pyrazin-7-yl)-3-methylquinazolin-4(3H)-one (449a; 10 mg, 19% yield) as a brown amorphous solid. m/z (ESI, +ve) 516.2 (M+H)$^+$.

Preparation of 2-(tert-butylamino)-3-methyl-8-(1-oxo-1,2,3,4-tetrahydropyrrolo[1,2-a]pyrazin-7-yl)-4(3H)-quinazolinone (449)

A solution of 2-(tert-butylamino)-8-(2-(2,4-dimethoxybenzyl)-1-oxo-1,2,3,4-tetrahydropyrrolo[1,2-a]pyrazin-7-yl)-3-methylquinazolin-4(3H)-one (449a) (10 mg, 0.02 mmol) in 1 mL of DCM and 0.2 mL of TFA was heated in an oil bath at 50° C. for 4 h. The reaction mixture was concentrated under reduced pressure. The brown residue was partitioned between 25 mL of EtOAc and 3 mL of 0.5 N NaOH. The EtOAc layer was separated, washed with 5 mL of brine, and concentrated. The residue was purified on a silica gel column (1-5% MeOH in DCM) to afford 2-(tert-butylamino)-3-methyl-8-(1-oxo-1,2,3,4-tetrahydropyrrolo[1,2-a]pyrazin-7-yl)quinazolin-4(3H)-one (449) (5 mg, 70% yield) as an off white crystalline solid. $^1$H NMR (400 MHz, DMSO-d$_6$) δ ppm 7.77 (1H, dd, J=7.8, 1.6 Hz), 7.70 (1H, dd, J=7.4, 1.6 Hz), 7.64 (1H, d, J=1.6 Hz), 7.60 (1H, br.), 7.10 (1H, d, J=1.6 Hz), 7.06 (1H, t, J=7.6 Hz), 5.74 (1H, s), 4.06 (2H, m), 3.46 (2H, t, J=7.1 Hz), 3.39 (3H, s), 1.45 (9H, s). m/z (ESI, +ve) 366.2 (M+H)$^+$.

Example 450

2-(tert-butylamino)-3-methyl-8-((6R)-6-methyl-4-oxo-1,4,5,6-tetrahydropyrrolo[3,4-b]pyrrol-2-yl)-4(3H)-quinazolinone

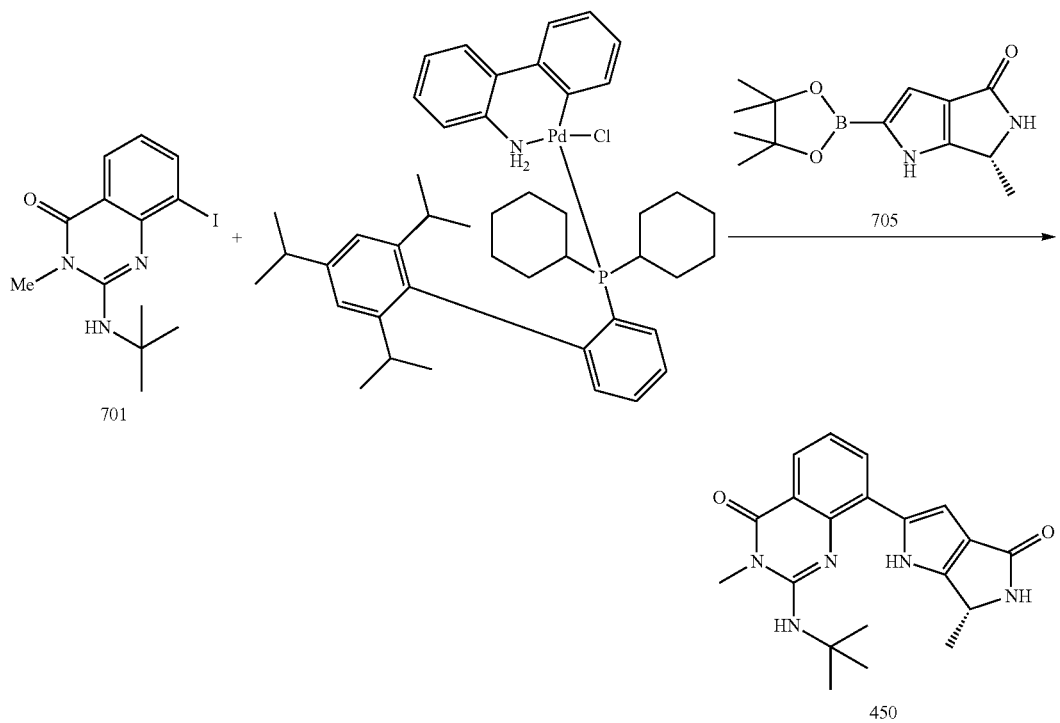

A sealable tube (75 mL) was charged with (R)-6-methyl-2-(4,4,5,5-tetramethyl-1,3,2-dioxaborolan-2-yl)-5,6-dihydropyrrolo[3,4-b]pyrrol-4(1H)-one (705) (2.00 g, 6.26 mmol), 2-(tert-butylamino)-8-iodo-3-methylquinazolin-4(3H)-one (701) (1.78 g, 5.01 mmol) and K$_3$PO$_4$ (3.98 g, 18.77 mmol) in 1,4-dioxane (16 mL)/water (4 mL). The mixture was bubbled with Argon for 3 min, then XPhos precatalyst II (Sigma-Aldrich; 0.24 g, 0.31 mmol) was added and the tube was sealed and heated in an oil bath at 45° C. for 90 min. The mixture was diluted with EtOAc (80 mL) and water (30 mL) and the layers were separated. The aqueous layer was extracted with EtOAc (100 mL×2). The combined organic layers were dried (MgSO$_4$), filtered and concentrated. The residue was purified on a silica gel column (1-10% MeOH in DCM) to give (R)-2-(tert-butylamino)-3-methyl-8-(6-methyl-4-oxo-1,4,5,6-tetrahydropyrrolo[3,4-b]pyrrol-2-yl)quinazolin-4(3H)-one (1.35 g, 3.69 mmol, 59% yield) as a light brown crystalline solid. $^1$H NMR (400 MHz, DMSO-d$_6$) δ ppm 11.95 (1H, br.), 7.91 (2H, m), 7.62 (1H, s), 7.19 (1H, t, J=7.6 Hz), 6.73 (1H, m), 5.96 (1H, s), 4.54 (1H, q, J=6.4 Hz), 3.49 (3H, s), 1.52 (9H, s), 1.38 (3H, d, J=6.7 Hz). m/z (ESI, +ve ion) 366.2 (M+H)$^+$.

Example 451

3-methyl-2-((1-methylcyclopropyl)amino)-8-((6R)-6-methyl-4-oxo-1,4,5,6-tetrahydropyrrolo[3,4-b]pyrrol-2-yl)-4(3H)-quinazolinone

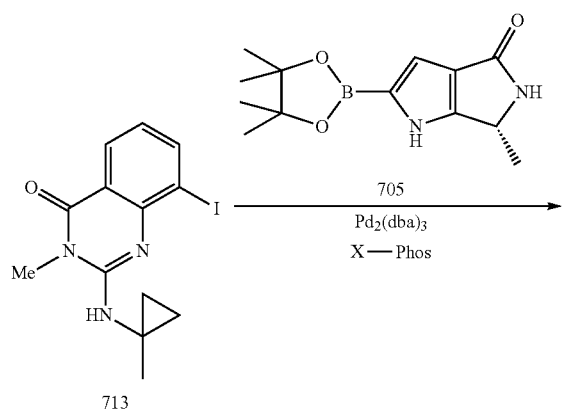

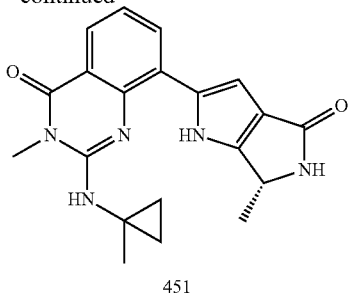

451

This compound (85 mg, 52% yield) as a brown solid was prepared according to the procedure described for Example 448, using 8-iodo-3-methyl-2-((1-methylcyclopropyl)amino)quinazolin-4(3H)-one (713) (160 mg, 0.45 mmol) and (R)-6-methyl-2-(4,4,5,5-tetramethyl-1,3,2-dioxaborolan-2-yl)-5,6-dihydropyrrolo[3,4-b]pyrrol-4(1H)-one (705) (130 mg, 0.50 mmol) as the starting materials. $^1$H NMR (400 MHz, DMSO-$d_6$) δ ppm 13.02 (1H, br.), 8.13 (1H, dd, J=7.6, 1.4 Hz), 7.83 (1H, dd, J=7.8, 1.4 Hz), 7.69 (2H, d, J=3.1 Hz), 7.18 (1H, t, J=7.7 Hz), 6.96 (1H, s), 4.64 (1H, q, J=6.6 Hz), 3.40 (3H, s), 1.56 (3H, s), 1.37 (3H, d, J=6.7 Hz), 1.01 (2H, m), 0.86 (2H, m). MS (ESI, pos. ion) m/z: 364.0 (M+1).

Examples 452 and 453

(6R)-6-methyl-2-(2-methyl-3-((1S)-2,2,2-trifluoro-1-methylethoxy)-5-quinoxalinyl)-5,6-dihydropyrrolo[3,4-b]pyrrol-4(1H)-one and (6R)-6-methyl-2-(2-methyl-3-((1R)-2,2,2-trifluoro-1-methylethoxy)-5-quinoxalinyl)-5,6-dihydropyrrolo[3,4-b]pyrrol-4(1H)-one

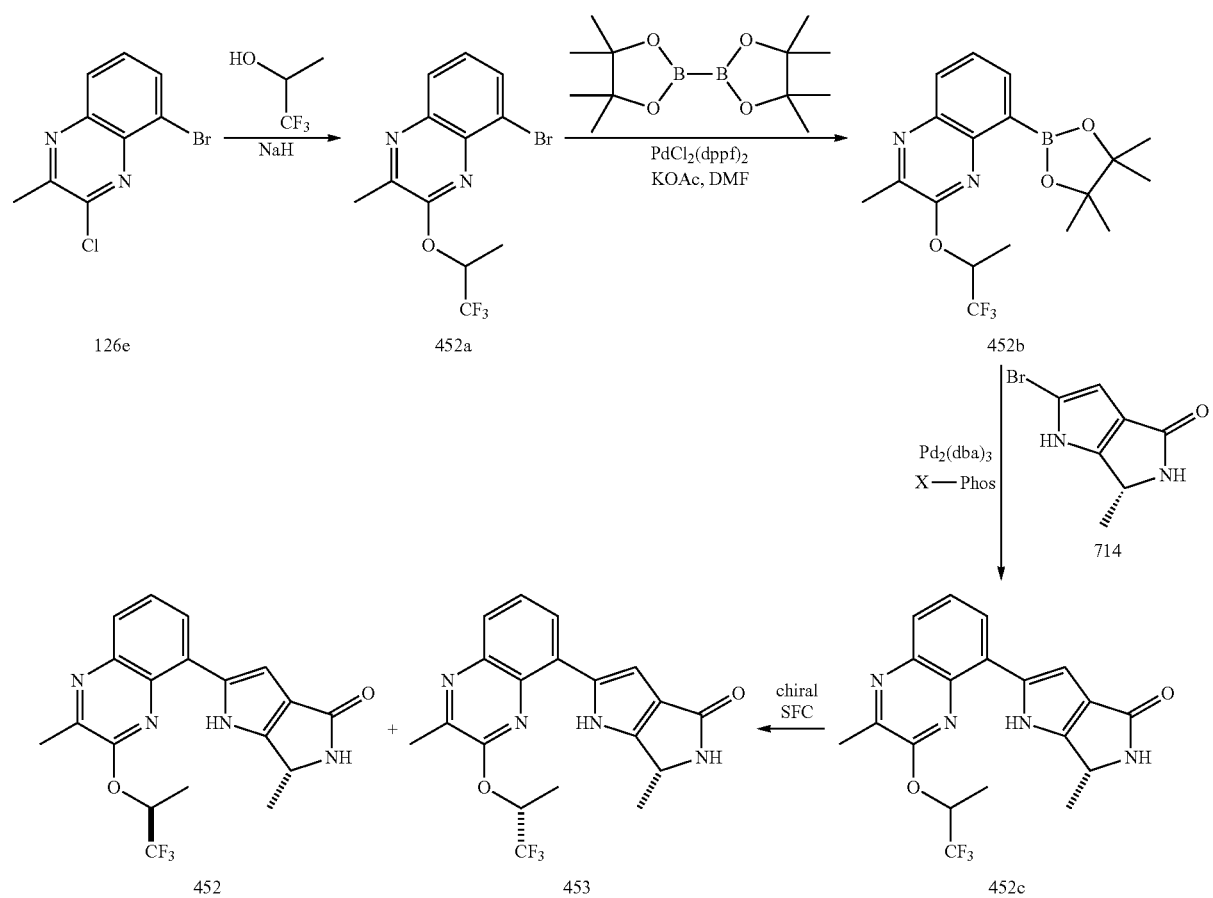

Preparation of 2-methyl-5-(4,4,5,5-tetramethyl-1,3,2-dioxaborolan-2-yl)-3-((1,1,1-trifluoropropan-2-yl)oxy)quinoxaline (452b)

To a suspension of 1,1,1,-trifluoro-2-propanol (0.85 mL, 9.38 mmol) and 5-bromo-3-chloro-2-methylquinoxaline (126e) (1.21 g, 4.69 mmol) in 5 mL of THF and 3 mL of DMF at 0° C. was added NaH (60% wt. in mineral oil) (0.31 g, 7.74 mmol). The resulting dark purple homogeneous solution was stirred at 0° C. for 5 min then RT for 1 h. It was quenched with 15 mL of sat. NH$_4$Cl aq. solution, and extracted with 2×75 mL of EtOAc. The organic extracts were concentrated and the residue was purified on a silica gel column (1-35% EtOAc in hexanes) to give 5-bromo-2-methyl-3-((1,1,1-trifluoropropan-2-yl)oxy)quinoxaline (452a) (1.39 g, 4.15 mmol, 88% yield) as an orange solid. $^1$H NMR (400 MHz, DMSO-d$_6$) δ ppm 8.09 (1H, m), 8.00 (1H, dd, J=8.2, 1.0 Hz), 7.60 (1H, t, J=7.9 Hz), 6.02 (1H, dt, J=13.4, 6.7 Hz), 2.62 (3H, s), 1.64 (3H, d, J=6.7 Hz). $^{19}$F NMR (376 MHz, DMSO-d$_6$) δ ppm −77.20 (1F, s). m/z (ESI, +ve) 335.0/337.0 (M+H)$^+$. A mixture of Pd(dppf)Cl$_2$ (51 mg, 0.06 mmol), (BPin)$_2$ (637 mg, 2.50 mmol), KOAc (492 mg, 5.01 mmol), 5-bromo-2-methyl-3-((1,1,1-trifluoropropan-2-yl)oxy)quinoxaline (452a) (420 mg, 1.25 mmol) in THF (5 mL) was heated in a microwave at 90° C. for 90 min. It was diluted with 50 mL of EtOAc and filtered through a pad of Celite. The filtrate was concentrated and the residue was purified on a silica gel column (25-75% EtOAc in hexanes) to give 2-methyl-5-(4,4,5,5-tetramethyl-1,3,2-dioxaborolan-2-yl)-3-((1,1,1-trifluoropropan-2-yl)oxy)quinoxaline (452b) (400 mg, 84% yield) as a brown solid. m/z (ESI, +ve) 383.0 (M+H)$^+$.

Preparation of 452 and 453

A mixture of Xphos (20 mg, 0.04 mmol)), Pd$_2$dba$_3$ (19 mg, 0.02 mmol), potassium phosphate tribasic monohydrate (369 mg, 1.60 mmol), 2-methyl-5-(4,4,5,5-tetramethyl-1,3,2-dioxaborolan-2-yl)-3-((1,1,1-trifluoropropan-2-yl)oxy)quinoxaline (266 mg, 0.69 mmol) and (R)-2-bromo-6-methyl-5,6-dihydropyrrolo[3,4-b]pyrrolo-4(1H)-one (714) (115 mg, 0.53 mmol) in dioxane (3 mL) and water (1 mL) in a sealed glass tube was heated in an Initiator microwave reactor (Personal Chemistry, Biotage AB, Inc.) at 105° C. for 35 min. It was partitioned between 45 mL of EtOAc and 5 mL of 1 N NaOH. The layers were separated. The organic layer was washed with 5 mL of brine, and concentrated under reduced pressure. The crude material was purified on a silica gel column (50-100% EtOAc in DCM) to give (6R)-6-methyl-2-(2-methyl-3-((1,1,1-trifluoropropan-2-yl)oxy)quinoxalin-5-yl)-5,6-dihydropyrrolo[3,4-b]pyrrolo-4(1H)-one (452c) (150 mg, 0.384 mmol, 72% yield) as a brown crystalline solid. m/z (ESI, +ve) 391.0 (M+H)$^+$. The individual diastereomer of 452c was obtained by chiral SFC (Column: Chiralcel OD-H (250×21 mm, 5µ); Mobile Phase: 80:20 (A:B); A: Liquid CO$_2$; B: MeOH (20 mM ammonia); Flow Rate: 70 mL/min; Oven Temp: 40° C.; Inlet Pressure: 100 bar; Wavelength: 266 nm) to give Example 452 (first eluting product) and Example 453 (second eluting product). Example 452: (6R)-6-methyl-2-(2-methyl-3-((1S)-2,2,2-trifluoro-1-methylethoxy)-5-quinoxalinyl)-5,6-dihydropyrrolo[3,4-b]pyrrolo-4(1H)-one (36 mg, 17% yield) as a yellow crystalline solid was obtained. $^1$H NMR (400 MHz, DMSO-d$_6$) δ ppm 11.74 (1H, br.), 7.96 (1H, dd, J=7.4, 1.2 Hz), 7.88 (1H, dd, J=8.1, 1.1 Hz), 7.62-7.77 (2H, m), 6.78 (1H, d, J=1.4 Hz), 6.14 (1H, dt, J=13.3, 6.7 Hz), 4.58 (1H, q, J=6.6 Hz), 2.62 (3H, s), 1.54 (3H, d, J=6.5 Hz), 1.42 (3H, d, J=6.5 Hz). $^{19}$F NMR (376 MHz, DMSO-d$_6$) δ ppm −77.30. m/z (ESI, +ve) 391.0 (M+H)$^+$. Example 453: (6R)-6-methyl-2-(2-methyl-3-((1R)-2,2,2-trifluoro-1-methylethoxy)-5-quinoxalinyl)-5,6-dihydropyrrolo[3,4-b]pyrrol-4(1H)-one (37 mg, 17% yield) as a brown crystalline solid was obtained. $^1$H NMR (400 MHz, DMSO-d$_6$) δ ppm 11.78 (1H, br.), 7.96 (1H, m), 7.88 (1H, dd, J=8.2, 1.2 Hz), 7.62-7.74 (2H, m), 6.84 (1H, br.), 6.11 (1H, m), 4.58 (1H, m), 2.63 (3H, s), 1.63 (3H, d, J=6.5 Hz), 1.41 (3H, d, J=6.5 Hz). $^{19}$F NMR (376 MHz, DMSO-d$_6$) δ ppm −77.12. m/z (ESI, +ve) 391.0 (M+H)$^+$.

Example 454

(R)-3-chloro-6-methyl-2-(2-methyl-3-((1-methylcyclopropyl)amino)quinoxalin-5-yl)-5,6-dihydropyrrolo[3,4-b]pyrrol-4 (1H)-one

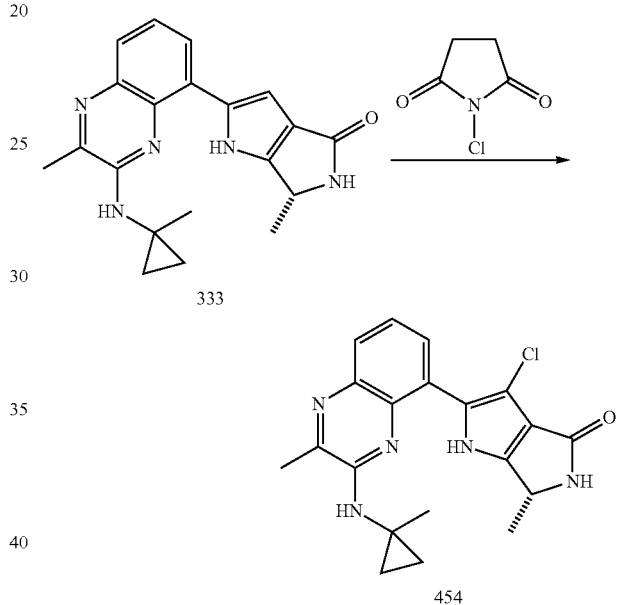

To a suspension of (R)-6-methyl-2-(2-methyl-3-((1-methylcyclopropyl)-amino)quinoxalin-5-yl)-5,6-dihydropyrrolo[3,4-b]pyrrol-4(1H)-one (333) (160 mg, 0.46 mmol) in 5 mL of CHCl$_3$ at RT was added n-chlorosuccinimide (73.8 mg, 0.55 mmol) and the mixture was stirred in an oil bath at 50° C. for 1.5 h. LCMS indicated 80% conversion. Additional n-chlorosuccinimide (21 mg, 1.55 mmol) was added and heating at 50° C. was continued for another 30 min. It was cooled to RT, treated with 5 mL of ice cold 0.5 N NaOH, and extracted with 25 mL of DCM followed by 25 mL of EtOAc. The combined organic extracts were concentrated and the residue was purified on a silica gel column (50% EtOAc in DCM followed by 5% MeOH in EtOAc) to give (R)-3-chloro-6-methyl-2-(2-methyl-3-((1-methylcyclopropyl)amino)quinoxalin-5-yl)-5,6-dihydropyrrolo[3,4-b]pyrrol-4(1H)-one (454) (145 mg, 82% yield) as a yellow crystalline solid. $^1$H NMR (400 MHz, DMSO-d$_6$) δ ppm 12.97 (1H, br.), 8.26 (1H, dd, J=7.6, 1.2 Hz), 7.84 (1H, s), 7.72 (1H, dd, J=8.0, 1.2 Hz), 7.64 (1H, s), 7.43 (1H, t, J=7.8 Hz), 4.61 (1H, q, J=6.7 Hz), 2.45 (3H, s), 1.45 (3H, s), 1.37 (3H, d, J=6.7 Hz), 0.89 (2H, m), 0.75 (2H, m). m/z (ESI, +ve) 382.0 (M+H)$^+$.

Example 455

(6R)-2-(3-(tert-butylamino)-2-methyl-5-quinoxalinyl)-3-chloro-6-methyl-5,6-dihydropyrrolo[3,4-b]pyrrol-4(1H)-one

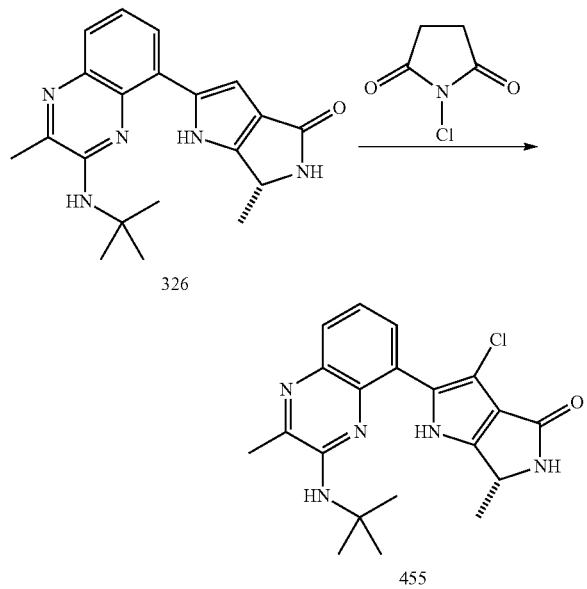

This compound (400 mg, 70% yield) as a yellow crystalline solid was prepared according the procedure described for Example 454, using (R)-2-(3-(tert-butylamino)-2-methylquinoxalin-5-yl)-6-methyl-5,6-dihydropyrrolo[3,4-b]pyrrol-4(1H)-one (326) (524 mg, 1.5 mmol) as the starting material. $^1$H NMR (400 MHz, DMSO-d$_6$) δ ppm 11.77 (1H, br.), 7.78 (2H, m), 7.63 (1H, d, J=7.2 Hz), 7.41 (1H, t, J=7.7 Hz), 5.97 (1H, br.), 4.46 (1H, d, J=6.7 Hz), 2.55 (3H, s), 1.34-1.44 (12H, m). m/z (ESI, +ve) 383.9 (M+H)$^+$.

Example 456

2'-(2-(tert-butylamino)-3-methyl-4-oxo-3,4-dihydro-8-quinazolinyl)-1'H-spiro[cyclopropane-1,6'-pyrrolo[3,4-b]pyrrol]-4'(5'H)-one

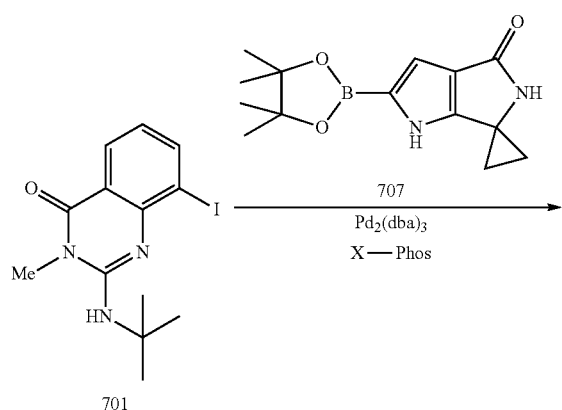

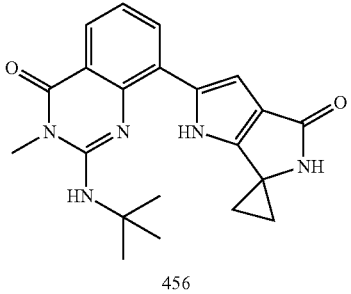

This compound (35 mg, 21% yield) as a brown solid was prepared according to the procedure described for Example 448, using 2-(tert-butylamino)-8-iodo-3-methylquinazolin-4(3H)-one (701) (157 mg, 0.44 mmol) and 2'-(4,4,5,5-tetramethyl-1,3,2-dioxaborolan-2-yl)-1'H-spiro[cyclopropane-1,6'-pyrrolo[3,4-b]pyrrol]-4'(5'H)-one (707) (157 mg, 0.57 mmol) as the starting materials. $^1$H NMR (400 MHz, DMSO-d$_6$) δ ppm 11.57 (1H, br.), 7.89 (2H, t, J=7.4 Hz), 7.67 (1H, s), 7.19 (1H, t, J=7.6 Hz), 6.81 (1H, s), 5.96 (1H, s), 3.49 (3H, s), 1.50 (9H, s), 1.41 (2H, m), 1.34 (2H, m). m/z (ESI, +ve) 378.0 (M+H)$^+$.

Example 457

2-(3-((1,1-dimethyl-2-(4-morpholinyl)ethyl)amino)-2-methyl-5-quinoxalinyl)-1,5,6,7-tetrahydro-4H-pyrrolo[3,2-c]pyridin-4-one

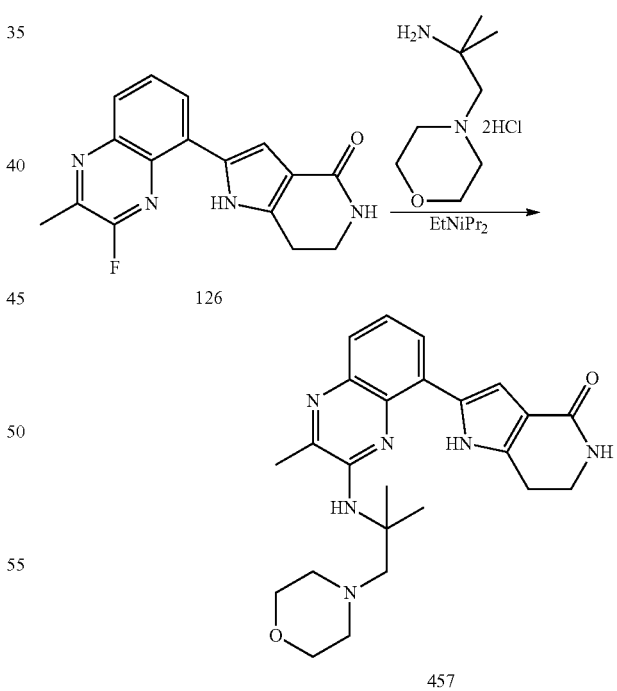

A mixture of 2-(3-fluoro-2-methylquinoxalin-5-yl)-6,7-dihydro-1H-pyrrolo[3,2-c]pyridin-4(5H)-one (40 mg, 0.13 mmol), 2-methyl-1-morpholinopropan-2-amine dihydrochloride [prepared according to the procedures reported in US 20060035903 A1 (2006)] (62 mg, 0.27 mmol) and DIPEA (0.14 mL, 0.81 mmol) in DMSO (2 mL) in a sealed glass tube was heated at 160° C. in a microwave for 45 min. It was diluted with 50 mL of EtOAc, washed with 5 mL of sat. NaHCO₃ followed by 5 mL of brine. The organic solution was concentrated and the residue was purified on a silica gel column (3% MeOH in DCM followed by 3-10% of 2 M NH₃ in MeOH in DCM) to provide the title compound (17 mg, 29% yield) as a yellow off white crystalline solid. ¹H NMR (400 MHz, DMSO-d₆) δ ppm 11.85 (1H, br.), 7.79 (1H, dd, J=7.4, 1.2 Hz), 7.60 (1H, dd, J=8.0, 1.2 Hz), 7.35 (1H, t, J=7.7 Hz), 7.02 (1H, s), 6.96 (1H, s), 6.32 (1H, s), 3.60 (4H, m), 3.44 (2H, td, J=6.9, 2.2 Hz), 3.30 (4H, m), 2.86 (2H, t, J=6.8 Hz), 2.70 (2H, s), 2.58 (3H, s), 1.55 (6H, s). m/z (ESI, +ve) 435.0 (M+H)⁺.

Example 458

2-(tert-butylamino)-3-(2-methoxyethyl)-8-(4-oxo-1,4,5,6-tetrahydropyrrolo[3,4-b]pyrrol-2-yl)-4(3H)-quinazolinone

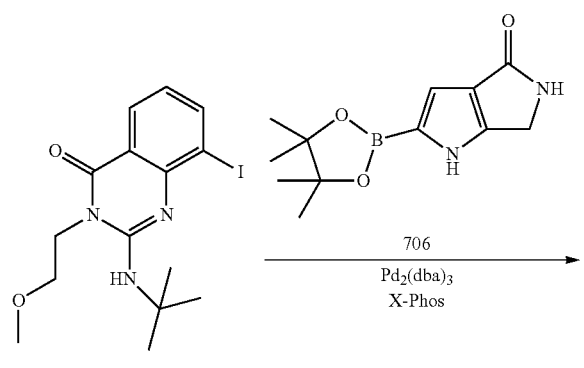

This compound (138 mg, 51% yield) as a brown solid was prepared according to the procedure described for Example 448, using 2-(tert-butylamino)-8-iodo-3-(2-methoxyethyl) quinazolin-4(3H)-one (715) (273 mg, 0.68 mmol) and 2-(4,4,5,5-tetramethyl-1,3,2-dioxaborolan-2-yl)-5,6-dihydropyrrolo[3,4-b]pyrrol-4(1H)-one (706) (219 mg, 0.88 mmol) as the starting materials. ¹H NMR (400 MHz, DMSO-d₆) δ ppm 12.09 (1H, br.), 7.90 (2H, m), 7.56 (1H, br.), 7.20 (1H, t, J=7.4 Hz), 6.83 (1H, s), 6.50 (1H, s), 4.27 (4H, m), 3.70 (2H, m), 3.35 (3H, s), 1.49 (9H, s). m/z (ESI, +ve) 395.9 (M+H)⁺.

Example 459

2-(tert-butylamino)-3-(2-methoxyethyl)-8-((6R)-6-methyl-4-oxo-1,4,5,6-tetrahydropyrrolo[3,4-b]pyrrol-2-yl)-4(3H)-quinazolinone

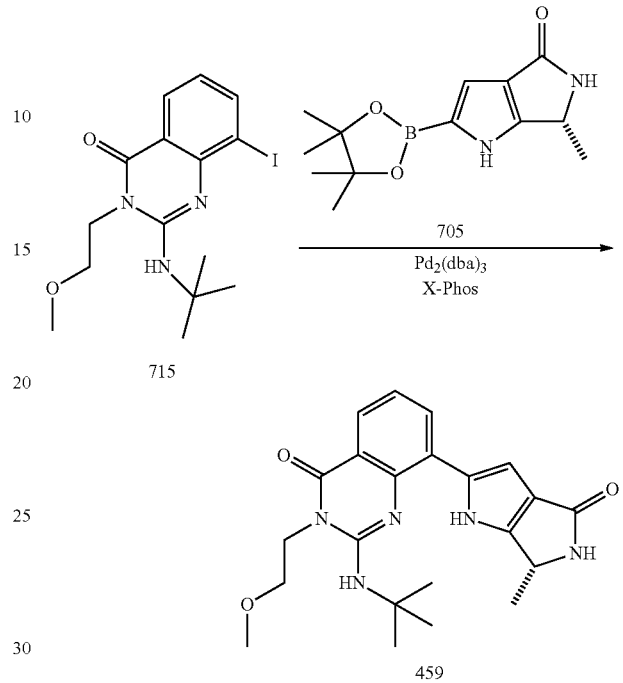

This compound (97 mg, 39% yield) as a brown solid was prepared according to the procedure described for Example 448, using 2-(tert-butylamino)-8-iodo-3-(2-methoxyethyl) quinazolin-4(3H)-one (715) (245 mg, 0.61 mmol) and (R)-6-methyl-2-(4,4,5,5-tetramethyl-1,3,2-dioxaborolan-2-yl)-5,6-dihydropyrrolo[3,4-b]pyrrol-4(1H)-one (705) (208 mg, 0.79 mmol) as the starting materials. ¹H NMR (400 MHz, DMSO-d₆) δ ppm 11.95 (1H, br.), 7.90 (2H, m), 7.66 (1H, s), 7.20 (1H, t, J=7.7 Hz), 6.74 (1H, s), 6.51 (1H, s), 4.55 (1H, q, J=6.7 Hz), 4.28 (2H, m), 3.71 (2H, t, J=4.5 Hz), 3.36 (3H, s), 1.49 (9H, s), 1.38 (3H, d, J=6.7 Hz). m/z (ESI, +ve) 410.0 (M+H)⁺.

Example 460

3-methyl-2-((1-methylcyclopropyl)oxy)-8-((6R)-6-methyl-4-oxo-1,4,5,6-tetrahydropyrrolo[3,4-b]pyrrol-2-yl)-4(3H)-quinazolinone

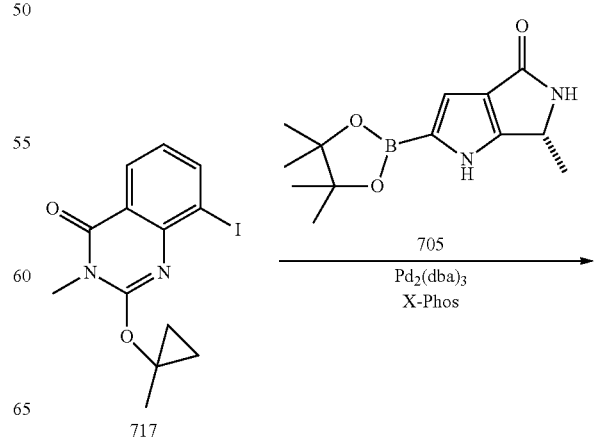

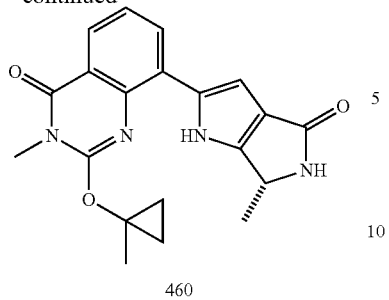

460

This compound (66 mg, 31% yield) as a brown solid was prepared according to the procedure described for Example 448, using 8-iodo-3-methyl-2-(1-methylcyclopropoxy)quinazolin-4(3H)-one (717) (210 mg, 0.59 mmol) and (R)-6-methyl-2-(4,4,5,5-tetramethyl-1,3,2-dioxaborolan-2-yl)-5,6-dihydropyrrolo[3,4-b]pyrrol-4(1H)-one (705) (201 mg, 0.76 mmol) as the starting materials. $^1$H NMR (400 MHz, DMSO-d$_6$) δ ppm 12.21 (1H, br.), 8.18 (1H, d, J=7.8 Hz), 7.94 (1H, d, J=7.6 Hz), 7.74 (1H, s), 7.41 (1H, t, J=7.7 Hz), 7.16 (1H, s), 4.65 (1H, d, J=6.5 Hz), 3.36 (3H, S), 1.78 (3H, s), 1.39 (3H, d, J=6.5 Hz), 1.25 (2H, m), 0.94 (2H, m). m/z (ESI, +ve) 365.0 (M+H)$^+$.

Example 461

(R)-2-(tert-butylamino)-3-cyclopropyl-7-fluoro-8-(6-methyl-4-oxo-1,4,5,6-tetrahydropyrrolo[3,4-b]pyrrol-2-yl)quinazolin-4(3H)-one

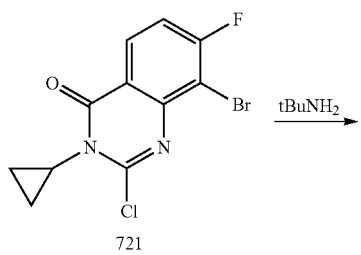

721

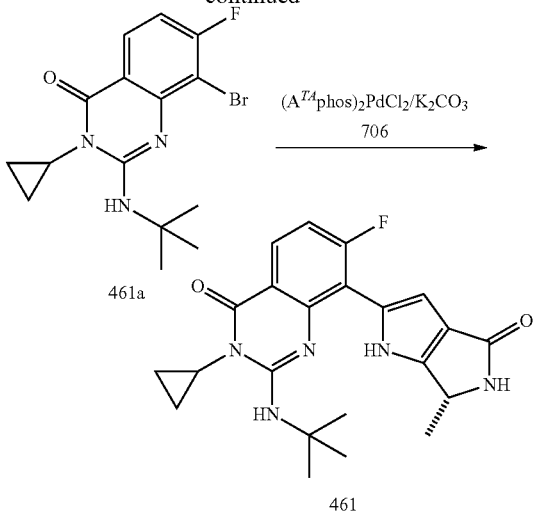

8-Bromo-2-(tert-butylamino)-3-cyclopropyl-7-fluoroquinazolin-4(3H)-one (461a, 288 mg, 85%) as a brown foam was prepared according to the procedures described for Intermediate 405a, starting from 8-bromo-2-chloro-3-cyclopropyl-7-fluoroquinazolin-4(3H)-one (721) (305 mg, 0.96 mmol). $^1$H NMR (400 MHz, DMSO-d$_6$) δ ppm 7.90 (1H, dd, J=8.7, 6.4 Hz), 7.04 (1H, t, J=8.7 Hz), 6.25 (1H, s), 2.76-2.88 (1H, m), 1.57 (9H, s), 1.18-1.27 (2H, m), 0.69-0.81 (2H, m). m/z (ESI, +ve ion) 354.0/356.0 (M+H)$^+$. (R)-2-(tert-butylamino)-3-cyclopropyl-7-fluoro-8-(6-methyl-4-oxo-1,4,5,6-tetrahydropyrrolo[3,4-b]pyrrol-2-yl)quinazolin-4(3H)-one (461) (171 mg, 51%) as a white solid was prepared according to the procedures described for Example 407, starting from 8-bromo-2-(tert-butylamino)-3-cyclopropyl-7-fluoroquinazolin-4(3H)-one (461a, 288 mg, 0.81 mmol). $^1$H NMR (400 MHz, DMSO-d$_6$) δ ppm 11.79 (1H, s), 7.90 (1H, dd, J=8.8, 6.5 Hz), 7.59 (1H, s), 7.04 (1H, dd, J=10.1, 8.9 Hz), 6.35 (1H, t, J=1.8 Hz), 6.15 (1H, s), 4.49 (1H, q, J=6.5 Hz), 2.76-2.88 (1H, m), 1.40 (9H, s), 1.34 (3H, d, J=6.5 Hz), 1.19-1.28 (2H, m), 0.70-0.78 (2H, m). $^{19}$F NMR (377 MHz, DMSO-d$_6$) δ ppm −105.25 (s). m/z (ESI, +ve ion) 410.1 (M+H)$^+$.

Examples 462

2-(3-(tert-butylamino)-2-methyl-5-quinoxalinyl)-6-(2-hydroxyethyl)-5,6-dihydropyrrolo[3,4-b]pyrrol-4(1H)-one

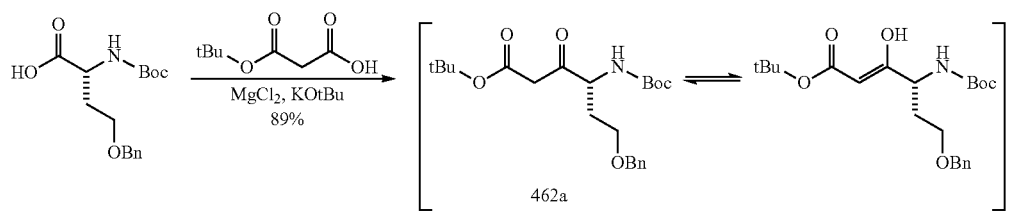

462a

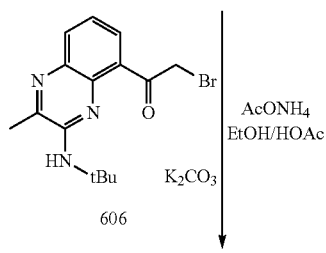

606

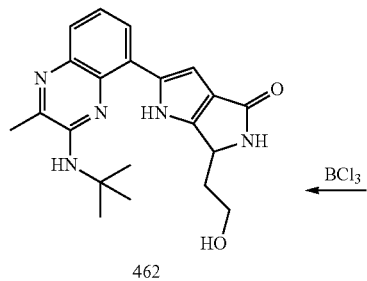 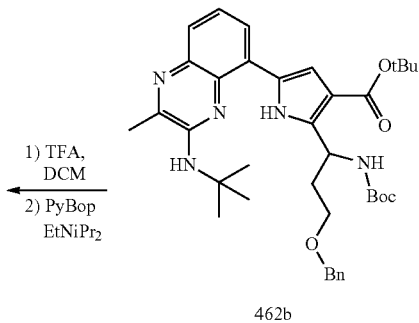

Preparation of Intermediate 462a

Flask A: To a clear solution of (R)-4-(benzyloxy)-2-((tert-butoxycarbonyl)amino)butanoic acid (Frontier Scientific; 2.25 g, 7.27 mmol) in 20 mL THF at RT under $N_2$ was added 1,1'-carbonyldiimidazole (1.77 g, 10.91 mmol) in one portion. Gas evolution observed. The reaction was stirred for 2 h. Flask B: To a cloudy mixture of mono-tert-butyl malonate (2.24 mL, 14.55 mmol) and magnesium chloride anhydrous (1.38 g, 14.55 mmol) in 50 mL THF in a 3 neck 500 mL RBF with temperature probe at 2° C. was added potassium tert-butoxide (1.0 M solution in THF, 14.55 mL, 14.55 mmol) slowly via addition funnel such that the temperature did not exceed 8° C. The resulting white suspension was stirred at RT for 2 h. Then the contents of Flask A was added and the reaction mixture placed in a 50° C. oil bath and stirred overnight. The reaction mixture was cooled to RT. The resulting white suspension was treated with 100 mL of EtOAc and washed sequentially with 25 mL of 1 M HCl, 10 mL of water, and 10 mL of brine, dried over anhydrous $MgSO_4$, filtered, and concentrated. Purification on a silica gel column (20-35% EtOAc in hexanes) gave a viscous oil containing a mixture (462a, 2.63 g, 6.45 mmol, 89% yield) of (R)-tert-butyl 6-(benzyloxy)-4-((tert-butoxycarbonyl)amino)-3-oxohexanoate and (R,Z)-tert-butyl 6-(benzyloxy)-4-((tert-butoxycarbonyl)amino)-3-hydroxyhex-2-enoate. ee % was not determined. m/z (ESI, +ve) 430.0 $(M+Na)^+$.

Preparation of Intermediate 462b tert-Butyl 2-(3-(benzyloxy)-1-((tert-butoxycarbonyl)amino)propyl)-5-(3-(tert-butylamino)-2-methylquinoxalin-5-yl)-1H-pyrrole-3-carboxylate (462b) (2.25 g, 61% yield) was prepared according to the procedures described for Intermediate 297b in Example 297, starting from 462a (2.55 g, 6.25 mmol) and 2-bromo-1-(3-(tert-butylamino)-2-methylquinoxalin-5-yl)ethanone (606) (1.91 g, 5.68 mmol). $^1$H NMR (400 MHz, DMSO-$d_6$) δ ppm 11.35 (1H, br.), 7.73 (1H, d, J=7.6 Hz), 7.60 (1H, m), 7.16-7.43 (7H, m), 6.96 (1H, d, J=10.0 Hz), 5.94 (1H, s), 5.50 (1H, d, J=8.6 Hz), 4.43 (2H, s), 3.44 (2H, t, J=6.3 Hz), 2.56 (3H, s), 1.99 (2H, m), 1.53 (9H, s), 1.56 (9H, s), 1.34-1.44 (9H, s). m/z (ESI, +ve) 644.2 $(M+H)^+$.

Preparation of Intermediate 462c

To a solution of tert-butyl 2-(3-(benzyloxy)-1-((tert-butoxycarbonyl)amino)propyl)-5-(3-(tert-butylamino)-2-methylquinoxalin-5-yl)-1H-pyrrole-3-carboxylate (1.28 g, 1.98 mmol) in 20 mL of DCM at RT was added TFA (5 mL) and the dark red solution was heated in an oil bath at 40° C. for 4 h. It was concentrated under reduced pressure. 5 mL of toluene was added to the residue and concentrated to dryness again. The brown amorphous solid was stirred in 15 mL of hexanes and the liquid was decanted. The brown residue was treated with 5 mL of DMF and 30 mL of DCM, cooled at 0° C., and added DIPEA (2.06 mL, 11.88 mmol) followed by (benzotriazol-1-yloxy)tripyrrolidinophosphonium hexafluorophosphate (1.28 g, 2.47 mmol). It was stirred at 0° C. for 10 min followed by RT for 15 min, then diluted with 50 mL of DCM. The mixture was washed sequentially with 5 mL of water, 5 mL of 0.5 N NaOH, and 5 mL of brine. The DCM solution was concentrated. The residue was purified on a silica gel column (50-100% EtOAc in DCM followed by 5% MeOH in DCM) to give 6-(2-(benzyloxy)ethyl)-2-(3-(tert-butylamino)-2-methylquinoxalin-5-yl)-5,6-dihydropyrrolo[3,4-b]pyrrol-4(1H)-one (0.65 g, 1.38 mmol, 70% yield) as a brown crystalline solid. m/z (ESI, +ve) 470.0 $(M+H)^+$.

Preparation of Example 462

To a solution of 6-(2-(benzyloxy)ethyl)-2-(3-(tert-butylamino)-2-methylquinoxalin-5-yl)-5,6-dihydropyrrolo[3,4-b]pyrrolo-4(1H)-one (462c) (110 mg, 0.23 mmol) in 5 mL of DCM at 0° C. was added boron trichloride (0.47 mL of 1.0 M solution in DCM, 0.47 mmol). The resulting rusty colored suspension was stirred at 0° C. for 5 min followed by RT for 30 min. It was quenched by the addition of 2 mL of MeOH dropwise followed by powder $NaHCO_3$ (79 mg, 0.94 mmol). Solvents were removed under vacuum. The residue was purified on a silica gel column (2-10% MeOH in DCM) to give 2-(3-(tert-butylamino)-2-methylquinoxalin-5-yl)-6-(2-hydroxyethyl)-5,6-dihydropyrrolo[3,4-b]pyrrol-4(1H)-one (462) (60 mg, 0.158 mmol, 67% yield) as a brown amorphous solid. $^1$H NMR (400 MHz, DMSO-$d_6$) δ ppm 11.88 (1H, br.), 7.82 (1H, d, J=7.4 Hz), 7.64 (1H, m), 7.37 (1H, t, J=7.7 Hz), 6.85 (1H, s), 6.02 (2H, br. s.), 4.58 (1H, dd, J=8.6, 3.9 Hz), 3.61 (2H, m), 2.58 (3H, s), 2.57 (1H, br.), 2.10 (1H, m), 1.67 (1H, m), 1.55 (9H, s). m/z (ESI, +ve) 380.0 $(M+H)^+$.

Example 463

6-(2-aminoethyl)-2-(3-(tert-butylamino)-2-methyl-5-quinoxalinyl)-5,6-dihydropyrrolo[3,4-b]pyrrol-4(1H)-one

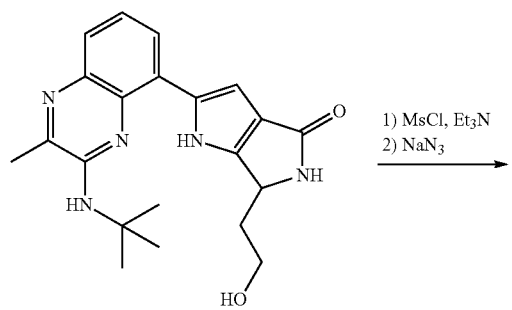

462

1) MsCl, Et₃N
2) NaN₃

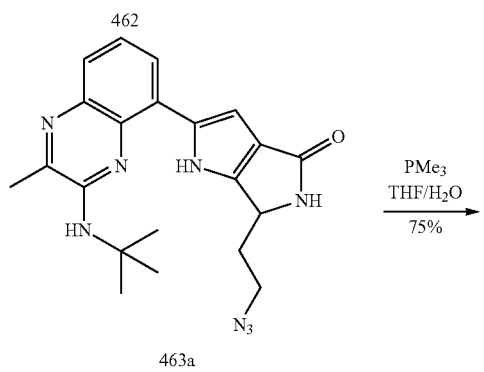

463a

PMe₃
THF/H₂O

75%

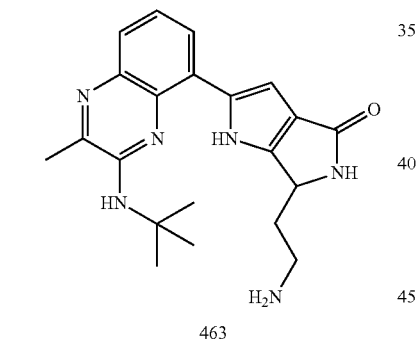

463

To a suspension of 2-(3-(tert-butylamino)-2-methylquinoxalin-5-yl)-6-(2-hydroxyethyl)-5,6-dihydropyrrolo[3,4-b]pyrrol-4(1H)-one (462) (149 mg, 0.39 mmol) in 5 mL of DCM at 0° C. was added TEA (0.27 mL, 1.96 mmol) followed by methanesulfonyl chloride (33.4 µL, 0.43 mmol). It was stirred at 0° C. for 30 min, diluted with 30 mL of DCM, washed sequentially with 5 mL of water, 5 mL of sat NaHCO3 and 5 mL of brine. The DCM solution was dried over Na₂SO₄ and concentrated. The brown residue was dissolved in 1 mL of DMF and treated with sodium azide (80 mg, 1.24 mmol). The mixture was heated in an oil bath at 70° C. for 45 min. It was diluted with EtOAc (50 mL) and filtered. The filtrate was washed with 2×5 mL of water. The EtOAc solution was concentrated and purified on a silica gel column (2-8% MeOH in DCM) to give 6-(2-azidoethyl)-2-(3-(tert-butylamino)-2-methylquinoxalin-5-yl)-5,6-dihydropyrrolo[3,4-b]pyrrol-4(1H)-one (463a, 97 mg, 0.24 mmol, 61% yield). m/z (ESI, +ve) 405 (M+H)⁺. To a solution of 6-(2-azidoethyl)-2-(3-(tert-butylamino)-2-methylquinoxalin-5-yl)-5,6-dihydropyrrolo[3,4-b]pyrrolo-4(1H)-one (463a, 97 mg, 0.24 mmol) in 3 mL of THF and water (43.2 µl, 2.39 mmol) at RT was added trimethylphosphine (0.36 mL of 1 M in THF, 0.36 mmol). It was stirred at RT for 30 min, then diluted with 50 mL of EtOAc, and washed with 5 mL of water. The organic layer was concentrated and the residue was purified on a silica gel column (5% MeOH in DCM followed by 5% of 2 M NH₃ in MeOH in DCM) to provide 6-(2-aminoethyl)-2-(3-(tert-butylamino)-2-methylquinoxalin-5-yl)-5,6-dihydropyrrolo[3,4-b]pyrrol-4(1H)-one (463) (68 mg, 0.18 mmol, 75% yield) as a brown amorphous solid. ¹H NMR (400 MHz, DMSO-d₆) δ ppm 7.81 (1H, dd, J=7.4, 1.4 Hz), 7.71 (1H, s), 7.57-7.67 (1H, m), 7.35 (1H, t, J=7.7 Hz), 6.84 (1H, s), 5.99 (1H, s), 4.57 (1H, dd, J=8.4, 4.1 Hz), 3.41 (3H, br.), 2.64-2.77 (2H, m), 2.56 (3H, s), 1.92 (1H, dd, J=13.3, 4.3 Hz), 1.57-1.65 (1H, m), 1.55 (9H, s). m/z 379.1 (ESI, +ve) (M+H)⁺.

Example 464

(R)-2-((1-fluoro-2-methylpropan-2-yl)amino)-3-methyl-8-(6-methyl-4-oxo-1,4,5,6-tetrahydropyrrolo[3,4-b]pyrrol-2-yl)quinazolin-4(3H)-one

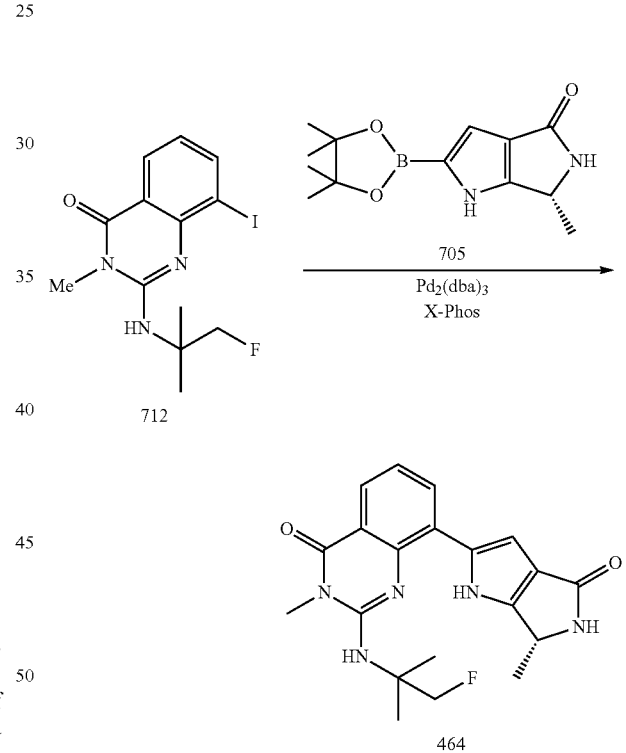

This compound (77 mg, 34% yield) as a brown solid was prepared according to the procedure described for Example 448, using 24(1-fluoro-2-methylpropan-2-yl)amino)-8-iodo-3-methylquinazolin-4(3H)-one (712) (221 mg, 0.59 mmol) and (R)-6-methyl-2-(4,4,5,5-tetramethyl-1,3,2-dioxaborolan-2-yl)-5,6-dihydropyrrolo[3,4-b]pyrrol-4(1H)-one (705) (193 mg, 0.74 mmol) as the starting materials. ¹H NMR (400 MHz, DMSO-d₆) δ ppm 11.63 (1H, br.), 7.94 (1H, d, J=7.4 Hz), 7.80 (1H, d, J=6.8 Hz), 7.60 (1H, br.), 7.22 (1H, t, J=7.1 Hz), 6.52 (1H, s), 6.02 (1H, s), 4.74 (1H, s), 4.62 (1H, s), 4.51 (1H, m), 3.51 (3H, s), 1.45 (6H, s), 1.38 (3H, d, J=5.9 Hz). m/z (ESI, +ve) 383.9 (M+H)⁺.

Example 465

3-methyl-2-((1-methylcyclobutyl)amino)-8-((6R)-6-methyl-4-oxo-1,4,5,6-tetrahydropyrrolo[3,4-b]pyrrol-2-yl)-4(3H)-quinazolinone

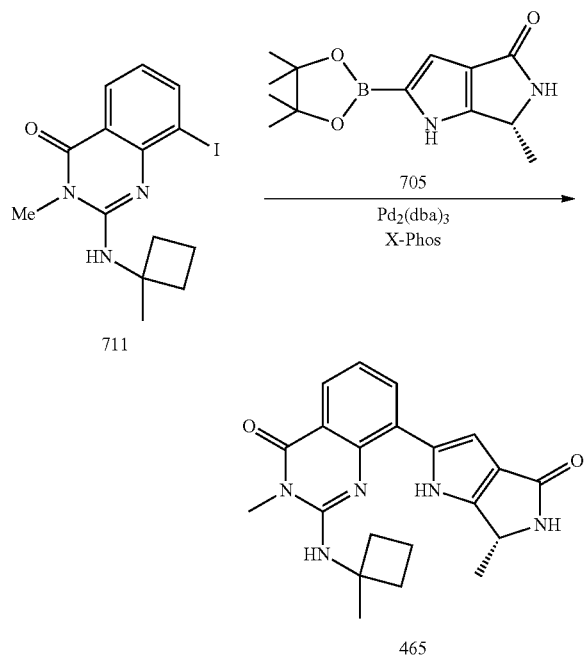

This compound (169 mg, 54% yield) as a brown solid was prepared according to the procedure described for Example 448, using 8-iodo-3-methyl-2-((1-methylcyclobutyl)amino)quinazolin-4(3H)-one (711) (303 mg, 0.82 mmol) and (R)-6-methyl-2-(4,4,5,5-tetramethyl-1,3,2-dioxaborolan-2-yl)-5,6-dihydropyrrolo[3,4-b]pyrrol-4(1H)-one (705) (215 mg, 0.82 mmol) as the starting materials. $^1$H NMR (400 MHz, DMSO-$d_6$) δ ppm 12.27 (1H, br.), 8.00 (1H, dd, J=7.6, 1.4 Hz), 7.85 (1H, dd, J=7.8, 1.4 Hz), 7.66 (1H, s), 7.15 (1H, t, J=7.7 Hz), 6.98 (1H, s), 6.81 (1H, s), 4.60 (1H, q, J=6.5 Hz), 3.41 (3H, s), 2.38 (2H, m), 2.14 (2H, m), 1.88 (2H, m), 1.67 (3H, s), 1.40 (3H, d, J=6.7 Hz). m/z (ESI, +ve) 378.2 (M+H)$^+$.

Example 466

2-(3-(tert-butylamino)-2-methyl-5-quinoxalinyl)-6,6-dimethyl-5,6-dihydropyrrolo[3,4-b]pyrrol-4(1H)-one

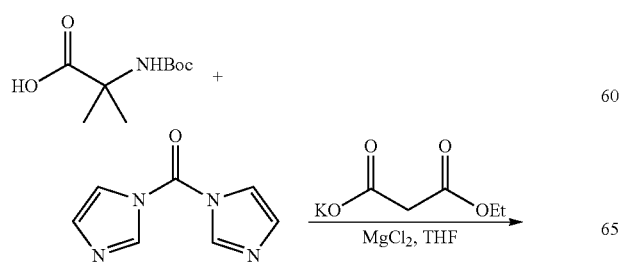

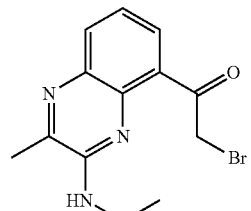

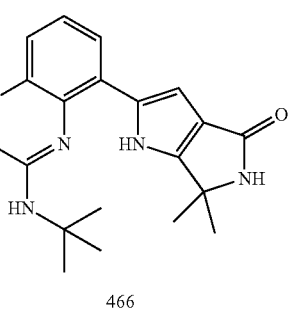

Preparation of ethyl 4-((tert-butoxycarbonyl)amino)-4-methyl-3-oxopentanoate (466a)

To a 1-liter, 3 neck, round-bottomed flask equipped with a mechanical stirrer and internal temperature probe was added Boc-Aib-OH (Bachem) (20 g, 98 mmol) and THF (500 mL). To the mixture at RT was added 1,1'-carbonyldiimidazole (Sigma-Aldrich) (23.9 g, 148 mmol) in portions. The solution was stirred for 2.5 h at RT. To the solution was added magnesium chloride (18.7 g, 197 mmol) and ethyl potassium malonate (Sigma-Aldrich) (33.5 g, 197 mmol). The solution was stirred at 50° C. for 17 h and then the solution was cooled to RT. The solution was diluted with EtOAc (400 mL) and filtered and the filter cake was washed with EtOAc. The filtrate was concentrated and the resulting material was diluted with EtOAc and hexanes. The solution was filtered and the filtrate was concentrated onto silica. Purification by silica gel chromatography (0-20% EtOAc/hexanes) afforded the title compound as a white solid (4.65 g, 17.0 mmol, 17% yield). m/z (ESI, +ve ion) 296.1 (M+Na)$^+$.

Preparation of ethyl 4-((tert-butoxycarbonyl)amino)-2-(2-(3-(tert-butylamino)-2-methyl-5-quinoxalinyl)-2-oxoethyl)-4-methyl-3-oxopentanoate (466b)

To a sealable vial was added 2-bromo-1-(3-(tert-butylamino)-2-methylquinoxalin-5-yl)ethanone (606) (1.0 g, 2.97 mmol), ethyl 4-((tert-butoxycarbonyl)amino)-4-methyl-3-oxopentanoate (466a) (0.98 g, 3.57 mmol), DMF (20 mL), and K$_2$CO$_3$ (1.03 g, 7.44 mmol). The solution was stirred at RT for 2 d. The solution was poured into sat NaHCO$_3$ (200 mL) and extracted with EtOAc (3×100 mL). The combined extracts were washed with H$_2$O (3×100 mL), brine (100 mL), dried (Na$_2$SO$_4$) and concentrated onto silica. Purification by silica gel chromatography (0 to 50% EtOAc/hexanes) afforded the title compound as a yellow solid (0.50 g, 0.95 mmol, 32% yield). m/z (ESI, +ve ion) 529.3 (M+H)$^+$. $^1$H NMR (400 MHz, DMSO-d$_6$) δ ppm 7.87 (dd, J=8.0, 1.6 Hz, 1H), 7.68 (dd, J=7.4, 1.6 Hz, 1H), 7.64 (br. s, 1H), 7.35 (t, J=7.7 Hz, 1H), 6.09 (br. s, 1H), 4.61 (dd, J=10.3, 2.8 Hz, 1H), 4.15 (dd, J=18.5, 10.5 Hz, 1H), 3.98-4.08 (m, 2H), 3.46 (dd, J=18.5, 3.4 Hz, 1H), 2.55 (s, 3H), 1.52 (s, 9H), 1.29 (s, 3H), 1.28 (s, 3H), 1.24 (s, 9H), 1.12 (t, J=7.0 Hz, 3H).

Preparation of ethyl 2-(1-((tert-butoxycarbonyl)amino)-1-methylethyl)-5-(3-(tert-butylamino)-2-methyl-5-quinoxalinyl)-1H-pyrrole-3-carboxylate (466c)

To a 250-mL, round-bottomed flask was added ethyl 4-((tert-butoxycarbonyl)amino)-2-(2-(3-(tert-butylamino)-2-methylquinoxalin-5-yl)-2-oxoethyl)-4-methyl-3-oxopentanoate (466b) (0.50 g, 0.95 mmol), EtOH (5 mL), AcOH (0.50 mL), and finally NH$_4$OAc (0.22 g, 2.84 mmol). The solution was stirred at RT for 17 h and additional AcOH (2 mL) and NH$_4$OAc (0.22 g, 2.84 mmol) was added. The solution was stirred at 50° C. for 2 d. The reaction mixture was partially concentrated and then was treated with sat NaHCO$_3$ (50 mL) and extracted with EtOAc (2×50 mL). The combined extracts were dried (Na$_2$SO$_4$) and concentrated onto silica. Purification by silica gel chromatography (Silicycle HP 40 g column, 0 to 50% EtOAc/hexanes) in which the product was isolated and purified again by silica gel chromatography (Silicycle HP 40 g column, (0 to 2.5% MeOH/CH$_2$Cl$_2$) afforded the title compound which was still impure (0.373 g). m/z (ESI, +ve ion) 510.2 (M+H)$^+$.

Preparation of 2-(3-(tert-butylamino)-2-methyl-5-quinoxalinyl)-6,6-dimethyl-5,6-dihydropyrrolo[3,4-b]pyrrol-4(1H)-one (466)

To a 10-20 mL Personal Chemistry microwave vial was added ethyl 2-(2-((tert-butoxycarbonyl)amino)propan-2-yl)-5-(3-(tert-butylamino)-2-methylquinoxalin-5-yl)-1H-pyrrole-3-carboxylate (466c) (0.37 g, 0.73 mmol), 1,4-dioxane (5 mL), water (5 mL), and finally LiOH monohydrate (Fluka Chemie) (0.154 g, 3.66 mmol). The mixture was stirred and heated at 110° C. for 1 h in the microwave. The solution was diluted with water (20 mL) and then lyophilized. The resulting solid was treated with 1,4-dioxane (4 mL) and then a solution of 4 M HCl in 1,4-dioxane (Sigma-Aldrich) (2.5 mL, 10.0 mmol). The reaction was stirred for 2 h at RT and then concentrated. The resulting material was dissolved in DCM (4 mL) and DMF (4.00 mL) and then treated with DIPEA (0.38 mL, 2.19 mmol) and ((1H-benzo[d][1,2,3]triazol-1-yl)oxy)tri(pyrrolidin-1-yl)phosphonium hexafluorophosphate (V) (PyBop, Matrix Innovation) (0.418 g, 0.803 mmol). The solution was stirred at RT for 1 h. The reaction mixture was treated with sat NaHCO$_3$ (50 mL) and extracted with EtOAc (3×50 mL). The combined extracts were washed with water (3×100 mL). The extracts were diluted with hexane (50 mL) and washed again with water (5×100 mL) and brine (50 mL) and then dried (Na$_2$SO$_4$) and concentrated onto silica. Purification by silica gel chromatography (40 g Silicycle HP column, 0 to 4.0% MeOH/CH$_2$Cl$_2$) followed by SFC purification (column: Princeton SFC Pyridine (250×21 mm, 5 micron), mobile phase: A: CO$_2$, B: MeOH (20 mM NH$_3$), flow rate: 70 mL/min, oven temp: 40° C., outlet pressure: 100 bar) afforded the title compound as a yellow solid (14 mg, 5%). m/z (ESI, +ve ion) 364.1 (M+H)$^+$. $^1$H NMR (400 MHz, DMSO-d$_6$) δ ppm 11.93 (br. s, 1H), 7.81 (dd, J=7.4, 1.4 Hz, 1H), 7.65 (s, 1H), 7.61 (dd, J=8.0, 1.4 Hz, 1H), 7.34 (t, J=7.7 Hz, 1H), 6.76 (d, J=1.6 Hz, 1H), 6.00 (s, 1H), 2.56 (s, 3H), 1.54 (s, 9H), 1.48 (s, 6H).

Example 467

5-(3-(tert-butylamino)-2-methylquinoxalin-5-yl)-1H-pyrazole-3-carboxamide

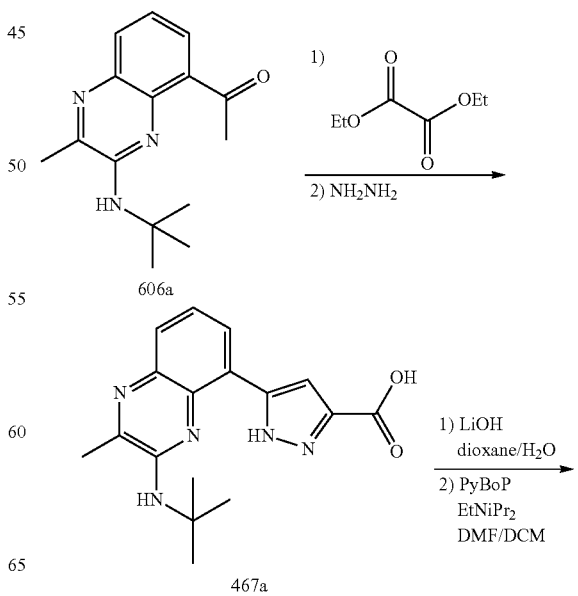

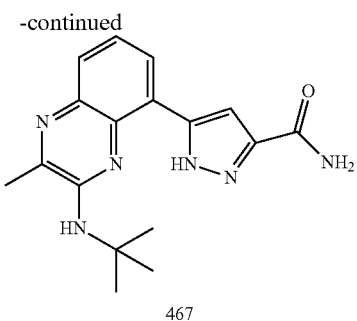

467

Preparation of ethyl 5-(3-(tert-butylamino)-2-methylquinoxalin-5-yl)-1H-pyrazole-3-carboxylate (467a)

To a 25-mL round-bottomed flask was added EtOH (4 mL) and sodium ethoxyde (1.01 g of 21% in EtOH, 3.11 mmol). The reaction mixture was cooled to −10° C. and added ethyl oxalate (0.21 mL, 1.55 mmol, Sigma-Aldrich) and 1-(3-(tert-butylamino)-2-methylquinoxalin-5-yl)ethanone (606a) (0.4 g, 1.55 mmol) slowly. The reaction mixture was warmed to RT and stirred at RT for 18 h. The reaction mixture was diluted with water (10 mL) and partially concentrated under vacuum. The reaction mixture was diluted with HCl (1 N, 5 mL) and extracted with EtOAc (15 mL). The organic extract was washed with brine (10 mL), dried over Na$_2$SO$_4$, and concentrated. The crude material was absorbed onto a plug of silica gel and purified by chromatography through a Redi-Sep pre-packed silica gel column (12 g), eluting with a gradient of 10% to 30% EtOAc in hexanes to give ethyl 4-(3-(tert-butylamino)-2-methylquinoxalin-5-yl)-2,4-dioxobutanoate as an orange oil (135 mg, 24% yield). m/z (ESI, +ve) 358.1 (M+H)$^+$. To a 15-mL glass tube was added ethyl 4-(3-(tert-butylamino)-2-methylquinoxalin-5-yl)-2,4-dioxobutanoate (135 mg, 0.38 mmol), hydrazine (12 μL, 0.38 mmol), and AcOH (2 mL). The tube was sealed and heated at 85° C. for 1 h. The reaction mixture was cooled to RT and the solvent was removed under vacuum. The mixture was diluted with EtOAc (10 mL) and NaOH (1 N, 5 mL). The organic extract was washed with water (5 mL), dried over Na$_2$SO$_4$, and concentrated. The crude material was absorbed onto a plug of silica gel and purified by chromatography through a Redi-Sep pre-packed silica gel column (12 g), eluting with a gradient of 30% to 40% EtOAc in hexanes to give ethyl 5-(3-(tert-butylamino)-2-methylquinoxalin-5-yl)-1H-pyrazole-3-carboxylate (467a) (102 mg, 76% yield) as a white solid. $^1$H NMR (400 MHz, DMSO-d$_6$) δ 7.82-7.97 (m, 1H), 7.74 (d, J=7.82 Hz, 1H), 7.51-7.60 (m, 1H), 7.40 (t, J=8.90 Hz, 1H), 6.00-6.07 (m, 1H), 4.31 (q, J=7.11 Hz, 2H), 2.56 (s, 3H), 1.53 (s, 9H), 1.33 (t, J=7.14 Hz, 3H). m/z (ESI, +ve) 354.0 (M+H)$^+$.

Preparation of 5-(3-(tert-butylamino)-2-methylquinoxalin-5-yl)-1H-pyrazole-3-carboxamide (467)

To a 10-mL reaction vial was added ethyl 5-(3-(tert-butylamino)-2-methylquinoxalin-5-yl)-1H-pyrazole-3-carboxylate (467a) (94 mg, 0.27 mmol), LiOH hydrated (56 mg, 1.33 mmol), dioxane (4 mL), and water (1 mL). The reaction mixture was heated at 50° C. for 1 h and at 100° C. for 2 h and then cooled to RT. The solvent was removed under vacuum and HCl (1N, 3 mL) was added, the yellow precipitate obtained was filtered off, washed with water, and dried. 5-(3-(tert-butylamino)-2-methylquinoxalin-5-yl)-1H-pyrazole-3-carboxylic acid (467b) was obtained as a yellow solid and used without further purification. To a 50-mL round-bottomed flask was added 5-(3-(tert-butylamino)-2-methylquinoxalin-5-yl)-1H-pyrazole-3-carboxylic acid (467b) (77 mg, 0.24 mmol), DCM (3 mL), DMF (1 mL), DIPEA (82 μL, 0.47 mmol), ammonia (0.95 mL, 0.47 mmol, 0.5 M in dioxane), and (benzotriazol-1-yloxy)tripyrrolidinophosphonium hexafluorophosphate (123 mg, 0.24 mmol) (Sigma-Aldrich). The reaction mixture was stirred at RT for 30 min, concentrated to half of its volume, and diluted with EtOAc (20 mL). The organic extract was washed with sat NaHCO$_3$ (10 mL), dried over Na$_2$SO$_4$, and concentrated. The crude material was absorbed onto a plug of silica gel and purified by chromatography through a Redi-Sep pre-packed silica gel column (12 g), eluting with a gradient of 30% to 40% EtOAc in hexanes to give 5-(3-(tert-butylamino)-2-methyl-quinoxalin-5-yl)-1H-pyrazole-3-carboxamide (467) (65 mg, 85% yield) as a light yellow solid. $^1$H NMR (400 MHz, DMSO-d$_6$) δ 13.38 (br. s, 1H), 7.85 (dd, J=1.08, 7.34 Hz, 1H), 7.76 (d, J=7.63 Hz, 1H), 7.53 (br. s., 1H), 7.41 (t, J=7.73 Hz, 1H), 7.30 (s, 1H), 7.18 (br. s, 1H), 6.06 (br. s., 1H), 2.58 (s, 3H), 1.52 (s, 9H). m/z (ESI, +ve) 325.1 (M+H)$^+$.

Example 468

(6R)-6-((benzyloxy)methyl)-2-(3-(tert-butylamino)-2-methyl-5-quinoxalinyl)-5,6-dihydropyrrolo[3,4-b]pyrrol-4(1H)-one and (6S)-6-((benzyloxy)methyl)-2-(3-(tert-butylamino)-2-methyl-5-quinoxalinyl)-5,6-dihydropyrrolo[3,4-b]pyrrol-4(1H)-one

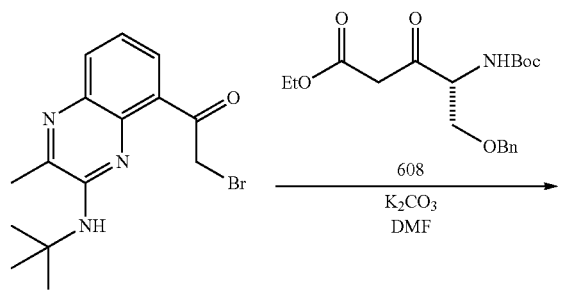

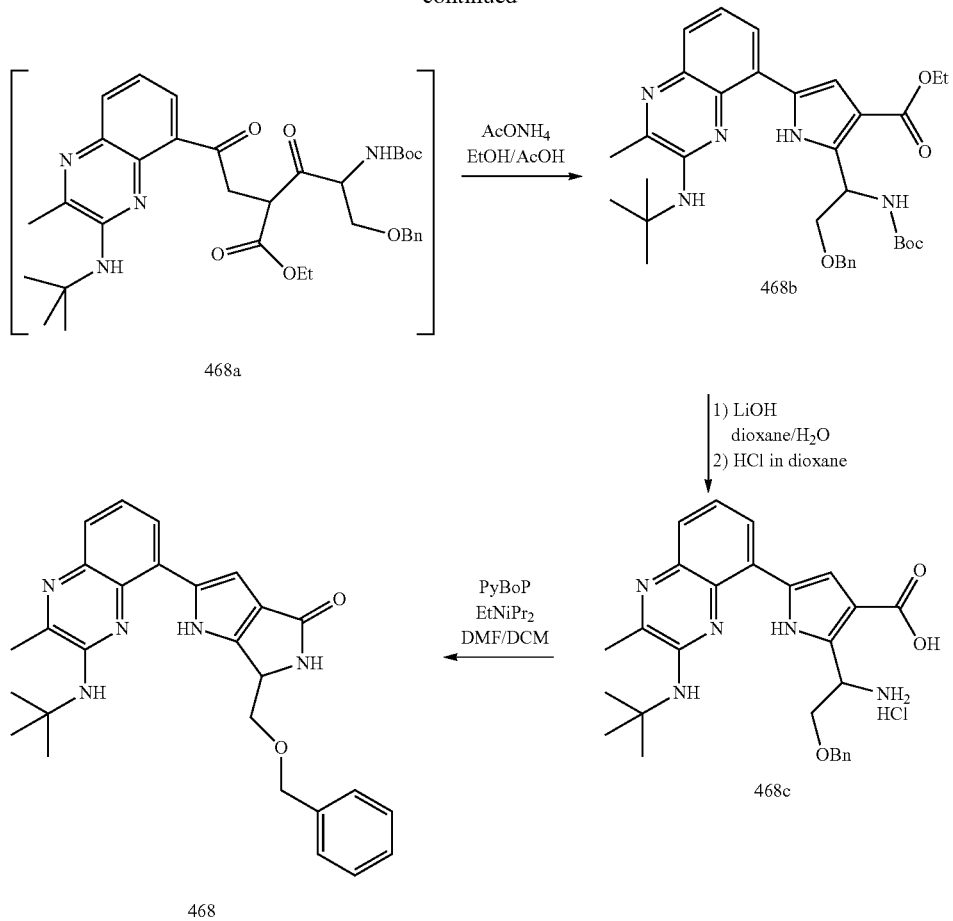

Preparation of ethyl 2-(2-(benzyloxy)-1-((tert-butoxycarbonyl)amino)ethyl)-5-(3-(tert-butylamino)-2-methylquinoxalin-5-yl)-1H-pyrrole-3-carboxylate (468b)

To a 50-mL round-bottomed flask was added (R)-ethyl 5-(benzyloxy)-4-((tert-butoxycarbonyl)amino)-3-oxopentanoate (608) (1.21 g, 3.31 mmol), $K_2CO_3$ (1.04 g, 7.52 mmol), 2-bromo-1-(3-(tert-butylamino)-2-methylquinoxalin-5-yl)ethanone (606) (1.01 g, 3.01 mmol), and DMF (8 mL). The reaction was stirred at RT for 4 h. The reaction mixture was diluted with sat. $NH_4Cl$ (20 mL) and extracted with EtOAc (30 mL). The organic extract was washed with water (10 mL), dried over $Na_2SO_4$, and concentrated. Ethyl 5-(benzyloxy)-4-((tert-butoxycarbonyl)amino)-2-(2-(3-(tert-butylamino)-2-methylquinoxalin-5-yl)-2-oxoethyl)-3-oxopentanoate (468a) was obtained as a light yellow oil and used without further purification. m/z (ESI, +ve) 621.3 $(M+H)^+$. To a 15-mL glass tube was added ethyl 5-(benzyloxy)-4-((tert-butoxycarbonyl)amino)-2-(2-(3-(tert-butylamino)-2-methylquinoxalin-5-yl)-2-oxoethyl)-3-oxopentanoate (468a), crude from previous step, $NH_4OAc$ (0.93 g, 12.0 mmol), EtOH (10 mL), and AcOH (3 mL). The tube was sealed and heated at 60° C. for 2 h. The reaction mixture was cooled to RT and was concentrated to half of its volume. The mixture was diluted with EtOAc (20 mL) and water (10 mL). The organic extract was washed with brine (10 mL), dried over $Na_2SO_4$, and concentrated. The crude material was absorbed onto a plug of silica gel and purified by chromatography through a Redi-Sep pre-packed silica gel column (40 g), eluting with a gradient of 10-30% EtOAc in hexanes to give ethyl 2-(2-(benzyloxy)-1-((tert-butoxycarbonyl)amino)ethyl)-5-(3-(tert-butylamino)-2-methylquinoxalin-5-yl)-1H-pyrrole-3-carboxylate (468b) (0.97 g, 53% yield) as a yellow solid. $^1H$ NMR (400 MHz, DMSO-$d_6$) δ 11.43 (br. s., 1H), 7.73 (dd, J=1.27, 7.53 Hz, 1H), 7.62 (dd, J=1.37, 8.02 Hz, 1H), 7.55 (d, J=2.35 Hz, 1H), 7.36 (t, J=7.73 Hz, 1H), 7.21-7.31 (m, 5H), 7.09 (br. d, J=10.17 Hz, 1H), 5.67-5.80 (m, 1H), 4.37-4.59 (m, 2H), 4.15-4.25 (m, 2H), 3.51-3.67 (m, 2H), 2.46 (s, 3H), 1.56 (s, 9H), 1.39 (s, 9H), 1.29 (t, J=7.14 Hz, 3H). m/z (ESI, +ve) 602.3 $(M+H)^+$.

Preparation of 2-(1-amino-2-(benzyloxy)ethyl)-5-(3-(tert-butylamino)-2-methylquinoxalin-5-yl)-1H-pyrrole-3-carboxylic acid hydrochloride (468c)

To a 50-mL round bottomed flask was added ethyl 2-(2-(benzyloxy)-1-((tert-butoxycarbonyl)amino)ethyl)-5-(3-(tert-butylamino)-2-methylquinoxalin-5-yl)-1H-pyrrole-3-carboxylate (468b) (0.97 g, 1.61 mmol), LiOH hydrated (0.34 g, 8.04 mmol), dioxane (10 mL), and water (10 mL). The reaction mixture was heated at 100° C. for 24 h and cooled to RT. The solvent was removed and the product used without further purification. The yellow solid obtained was suspended in HCl (10 mL, 4 N in dioxane) and the reaction mixture was stirred at RT for 2 h. The reaction mixture was concentrated under vacuum and the orange solid obtained was dried to give 2-(1-amino-2-(benzyloxy)ethyl)-5-(3-(tert-butylamino)-2-methylquinoxalin-5-yl)-1H-pyrrole-3-carboxylic acid hydrochloride (468c), which was used as crude material and based on theoretical yield.

Preparation of (6R)-6-((benzyloxy)methyl)-2-(3-(tert-butylamino)-2-methyl-5-quinoxalinyl)-5,6-dihydropyrrolo[3,4-b]pyrrol-4(1H)-one and (6S)-6-((benzyloxy)methyl)-2-(3-(tert-butylamino)-2-methyl-5-quinoxalinyl)-5,6-dihydropyrrolo[3,4-b]pyrrol-4(1H)-one (468)

To a 100-mL round-bottomed flask was added 2-(1-amino-2-(benzyloxy)ethyl)-5-(3-(tert-butylamino)-2-methylquinoxalin-5-yl)-1H-pyrrole-3-carboxylic acid hydrochloride (468c), (0.82 g, 1.61 mmol), DCM (6 mL), DMF (6 mL), DIPEA (1.12 mL, 6.44 mmol), and (benzotriazol-1-yloxy)tripyrrolidinophosphonium hexafluorophosphate (0.88 g, 1.69 mmol). The reaction mixture was stirred at RT for 1 h, concentrated to half of its volume, and diluted with EtOAc (20 mL). The organic extract was washed with sat NaHCO₃ (10 mL), dried over Na₂SO₄, and concentrated. The crude material was absorbed onto a plug of silica gel and purified by chromatography through a Redi-Sep pre-packed silica gel column (40 g), eluting with a gradient of 0-3% 2 M NH₃/MeOH in DCM to provide 6-((benzyloxy)methyl)-2-(3-(tert-butylamino)-2-methylquinoxalin-5-yl)-5,6-dihydropyrrolo[3,4-b]pyrrolo-4(1H)-one (468) (576 mg, 79% yield, 50% ee) as a yellow solid and as a mixture of enantiomers. ¹H NMR (400 MHz, DMSO-d₆) δ 11.93 (s, 1H), 7.79-7.91 (m, 2H), 7.63 (dd, J=1.08, 7.92 Hz, 1H), 7.27-7.42 (m, 6H), 6.87 (d, J=1.37 Hz, 1H), 5.99 (s, 1H), 4.69 (dd, J=4.21, 7.14 Hz, 1H), 4.58 (d, J=4.30 Hz, 2H), 3.77 (dd, J=4.30, 9.59 Hz, 1H), 3.47 (dd, J=7.43, 9.59 Hz, 1H), 2.57 (s, 3H), 1.47 (s, 9H). m/z (ESI, +ve) 456.0 (M+H)⁺.

Example 469

(R)-2-(3-(tert-butylamino)-2-methylquinoxalin-5-yl)-6-(hydroxymethyl)-5,6-dihydropyrrolo[3,4-b]pyrrol-4(1H)-one and (S)-2-(3-(tert-butylamino)-2-methylquinoxalin-5-yl)-6-(hydroxymethyl)-5,6-dihydropyrrolo[3,4-b]pyrrol-4(1H)-one

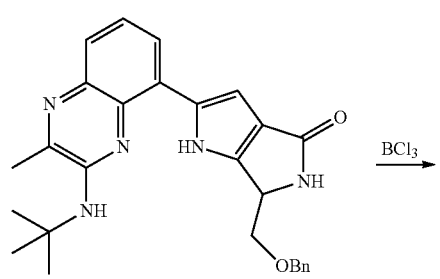

468

BCl₃ →

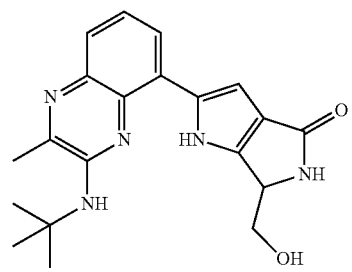

469

To a 100-mL round-bottomed flask was added (6R)-6-((benzyloxy)methyl)-2-(3-(tert-butylamino)-2-methyl-5-quinoxalinyl)-5,6-dihydropyrrolo[3,4-b]pyrrol-4(1H)-one and (6S)-6-((benzyloxy)methyl)-2-(3-(tert-butylamino)-2-methyl-5-quinoxalinyl)-5,6-dihydropyrrolo[3,4-b]pyrrol-4(1H)-one (468) (0.55 g, 1.20 mmol) and DCM (15 mL). The reaction mixture was cooled to 0° C. and under a nitrogen atmosphere boron trichloride (2.40 mL, 2.40 mmol, 1 M in DCM) (Sigma-Aldrich) was added dropwise. The reaction mixture was stirred at 0° C. for 30 min and at RT for 1 h. The reaction was quenched by the addition of NaHCO₃ (200 mg in MeOH, 5 mL) and the solvent was removed under vacuum. The crude material was absorbed onto a plug of silica gel and purified by chromatography through a Redi-Sep pre-packed silica gel column (12 g), eluting with a gradient of 0% to 4% 2M NH₃/MeOH in DCM to provide 2-(3-(tert-butylamino)-2-methylquinoxalin-5-yl)-6-(hydroxymethyl)-5,6-dihydropyrrolo[3,4-b]pyrrol-4(1H)-one (469) (0.25 g, 57% yield, 50% ee) as a yellow solid and as a mixture of enantiomers. ¹H NMR (400 MHz, DMSO-d₆) δ 11.91 (s, 1H), 7.86 (dd, J=1.37, 7.63 Hz, 1H), 7.63 (dd, J=1.37, 8.02 Hz, 1H), 7.58 (s, 1H), 7.36 (t, J=7.73 Hz, 1H), 6.88 (d, J=1.57 Hz, 1H), 6.02 (s, 1H), 5.09 (t, J=5.58 Hz, 1H), 4.48 (t, J=6.06 Hz, 1H), 3.66 (td, J=5.53, 10.86 Hz, 1H), 3.54 (td, J=6.16, 10.76 Hz, 1H), 2.56 (br. s., 3H), 1.56 (s, 9H). m/z (ESI, +ve) 366.0 (M+H)⁺.

Example 470

(R)-2-(3-(tert-butylamino)-2-methylquinoxalin-5-yl)-6-(hydroxymethyl)-1-methyl-5,6-dihydropyrrolo[3,4-b]pyrrol-4(1H)-one and (S)-2-(3-(tert-butylamino)-2-methylquinoxalin-5-yl)-6-(hydroxymethyl)-1-methyl-5,6-dihydropyrrolo[3,4-b]pyrrol-4(1H)-one

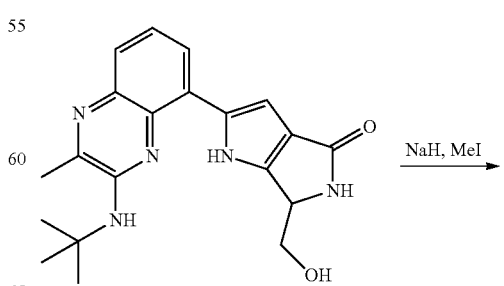

469

NaH, MeI →

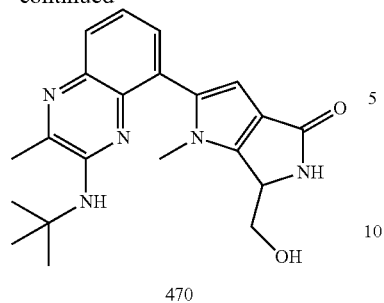

470

To a 25-mL round-bottomed flask was added (R)-2-(3-(tert-butylamino)-2-methylquinoxalin-5-yl)-6-(hydroxymethyl)-5,6-dihydropyrrolo[3,4-b]pyrrol-4(1H)-one and (S)-2-(3-(tert-butylamino)-2-methylquinoxalin-5-yl)-6-(hydroxymethyl)-5,6-dihydropyrrolo[3,4-b]pyrrol-4(1H)-one (469) (36 mg, 0.1 mmol), DMF (1 mL) and THF (1 mL). To the yellow suspension NaH (4 mg, 0.1 mmol, 60% in mineral oil) was added at RT. The reaction mixture was stirred at RT for 15 min and MeI (6 μt, 0.1 mmol) was added. The reaction mixture was stirred at RT for 1 h and the solvent was completely removed under vacuum. The crude material was absorbed onto a plug of silica gel and purified by chromatography through a Redi-Sep pre-packed silica gel column (12 g), eluting with a gradient of 3-8% MeOH in DCM to provide 2-(3-(tert-butylamino)-2-methylquinoxalin-5-yl)-6-(hydroxymethyl)-1-methyl-5,6-dihydropyrrolo[3,4-b]pyrrol-4(1H)-one (470) (28 mg, 75% yield, 50% ee) as a light yellow solid and a mixture of enantiomers. $^1$H NMR (400 MHz, DMSO-d$_6$) δ 7.78 (dd, J=1.47, 8.12 Hz, 1H), 7.43-7.51 (m, 2H), 7.33-7.39 (m, 1H), 6.10 (s, 1H), 5.88 (s, 1H), 5.15 (t, J=5.38 Hz, 1H), 4.46 (t, J=6.16 Hz, 1H), 3.59 (t, J=5.97 Hz, 2H), 3.32 (s, 3H), 2.52 (s, 3H), 1.29 (s, 9H). m/z (ESI, +ve) 380.1 (M+H)$^+$.

Example 471

2-(3-(tert-butylamino)-2-methylquinoxalin-5-yl)-6,7-dihydropyrazolo[1,5-a]pyrazin-4(5H)-one

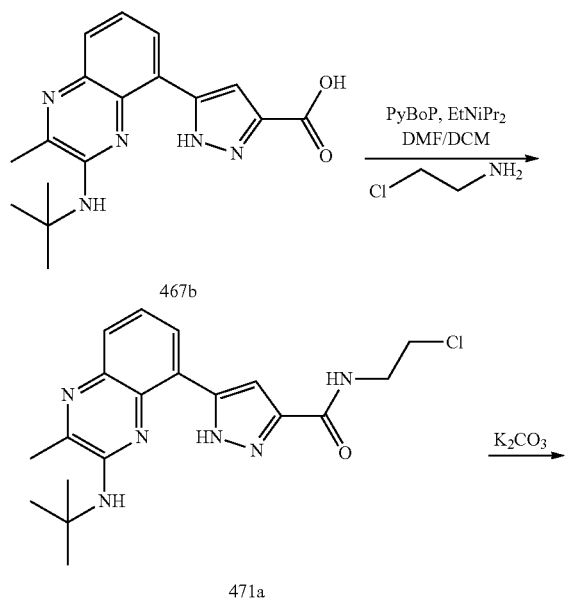

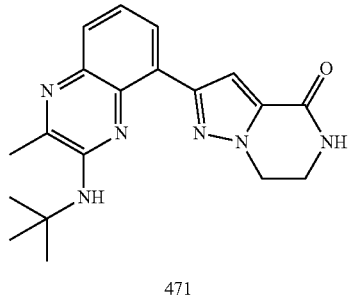

471

Preparation of 5-(3-(tert-butylamino)-2-methylquinoxalin-5-yl)-N-(2-chloroethyl)-1H-pyrazole-3-carboxamide (471a)

To a 50-mL round-bottomed flask was added 5-(3-(tert-butylamino)-2-methylquinoxalin-5-yl)-1H-pyrazole-3-carboxylic acid (467b) (69 mg, 0.21 mmol), DCM (4 mL), DMF (1 mL), DIPEA (0.15 mL, 0.85 mmol), 2-chloroethanamine hydrochloride (49 mg, 0.42 mmol) (Sigma-Aldrich), and (benzotriazol-1-yloxy)tripyrrolidinophosphonium hexafluorophosphate (110 mg, 0.21 mmol) (Sigma-Aldrich). The reaction mixture was stirred at RT for 16 h and the solvent was completely remover under vacuum. 5-(3-(tert-Butylamino)-2-methylquinoxalin-5-yl)-N-(2-chloroethyl)-1H-pyrazole-3-carboxamide (471a) was taken to next step without purification. m/z (ESI, +ve) 387.0 (M+H)$^+$.

Preparation of 2-(3-(tert-butylamino)-2-methylquinoxalin-5-yl)-6,7-dihydropyrazolo[1,5-a]pyrazin-4(5H)-one (471)

To a 10-mL reaction vial was added 5-(3-(tert-butylamino)-2-methylquinoxalin-5-yl)-N-(2-chloroethyl)-1H-pyrazole-3-carboxamide (471a) (82 mg, 0.21 mmol), K$_2$CO$_3$ (88 mg, 0.64 mmol), DMF (1 mL), and ACN (1 mL). The vial was closed and the reaction mixture was heated at 85° C. for 5 h. The reaction mixture was cooled to RT and partitioned between water (5 mL) and EtOAc (5 mL). The organic extract was taken and washed with brine (10 mL), dried over Na$_2$SO$_4$, and concentrated. The crude material was absorbed onto a plug of silica gel and purified by chromatography through a Redi-Sep pre-packed silica gel column (12 g), eluting with a gradient of 0-3% 2 M NH$_3$/MeOH in DCM to provide 2-(3-(tert-butylamino)-2-methylquinoxalin-5-yl)-6,7-dihydropyrazolo[1,5-a]pyrazin-4(5H)-one (471) (26 mg, 35% yield) as a white solid. $^1$H NMR (400 MHz, DMSO-d$_6$) δ 13.51 (s, 1H), 7.86 (dd, J=1.27, 7.34 Hz, 1H), 7.75 (dd, J=1.08, 7.92 Hz, 1H), 7.36-7.42 (m, 2H), 6.07 (s, 1H), 4.36 (t, J=9.49 Hz, 2H), 3.90-3.97 (m, 2H), 2.56 (s, 3H), 1.51 (s, 9H). m/z (ESI, +ve) 351.0 (M+H)$^+$.

Example 472

(S)-2-(tert-butylamino)-3-methyl-8-(6-methyl-4-oxo-1,4,5,6-tetrahydropyrrolo[3,4-b]pyrrol-2-yl)quinazolin-4(3H)-one

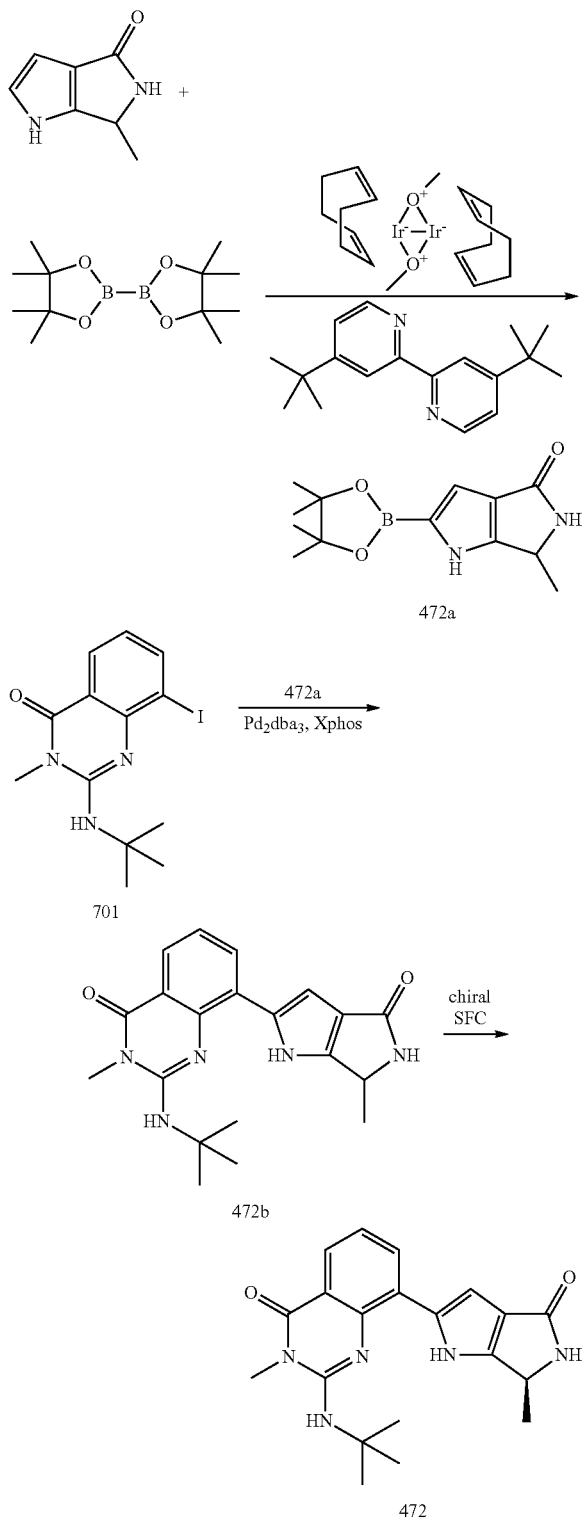

Preparation of 6-methyl-2-(4,4,5,5-tetramethyl-1,3,2-dioxaborolan-2-yl)-5,6-dihydropyrrolo[3,4-b]pyrrol-4(1H)-one (472a)

A sealable tube was charged with 6-methyl-5,6-dihydropyrrolo[3,4-b]pyrrol-4(1H)-one (280 mg, 2.05 mmol) and bis(pinacolato)diboron (574 mg, 2.26 mmol) in MTBE (3 mL) followed by (1,5-cyclooctadiene)(methoxy)-iridium(i) dimer (40.9 mg, 0.062 mmol) and 4,4'-di-tert-butyl-2,2'-dipyridyl (33.1 mg, 0.123 mmol). The suspension was purged with Ar for 3 min, then sealed and heated at 50° C. for 2 h. The mixture was cooled to RT and then filtered through a plug of aluminum oxide (activated, neutral, brockmann I) and washed with DCM (100 mL) then 10% MeOH in DCM (100 mL). The MeOH/DCM solution was concentrated to give the crude product, which was used in the next reaction without further purification. MS (ESI, pos. ion) m/z: 263.1 (M+1).

Preparation of 2-(tert-butylamino)-3-methyl-8-(6-methyl-4-oxo-1,4,5,6-tetrahydropyrrolo[3,4-b]pyrrol-2-yl)quinazolin-4(3H)-one (472b)

A glass microwave reaction vessel was charged with 6-methyl-2-(4,4,5,5-tetramethyl-1,3,2-dioxaborolan-2-yl)-5,6-dihydropyrrolo[3,4-b]pyrrol-4(1H)-one (472a, 500 mg, 1.91 mmol) and 2-(tert-butylamino)-8-iodo-3-methylquinazolin-4(3H)-one (701) (681 mg, 1.91 mmol) in 1,4-dioxane (6.0 mL)/water (1.5 mL) followed by $K_3PO_4$ (1215 mg, 5.72 mmol), Xphos (91 mg, 0.191 mmol, Sigma-Aldrich) and $Pd_2dba_3$ (87 mg, 0.095 mmol, Strem). The reaction mixture was stirred and heated in a Initiator microwave reactor (Personal Chemistry, Biotage AB, Inc.) at 105° C. for 45 min. The mixture was cooled to RT and EtOAc (50 mL) was added. The layers were separated and the aqueous layer was extracted with EtOAc (40 mL×2). The combined organic layers were dried ($MgSO_4$), filtered and concentrated. The reaction was repeated on a 1000 mg scale and the residues were combined and purified with silica gel chromatography (eluted with 1-4% MeOH in DCM) to give 2-(tert-butylamino)-3-methyl-8-(6-methyl-4-oxo-1,4,5,6-tetrahydropyrrolo[3,4-b]pyrrol-2-yl)quinazolin-4(3H)-one (472b, 740 mg, 36% yield) as a yellow solid. MS (ESI, pos. ion) m/z: 366 (M+1). This material was subjected to chiral SFC to give two eluents: the first eluent was Example 450 (530 mg); the second eluent was (S)-2-(tert-butylamino)-3-methyl-8-(6-methyl-4-oxo-1,4,5,6-tetrahydropyrrolo[3,4-b]pyrrol-2-yl)quinazolin-4(3H)-one (472) (110 mg) as a tan solid. The SFC conditions were: [AS-H (Sum, 21 mm×25 cm, S/N=1071) with 45% organic modifier: 55% carbon dioxide, organic modifier: MeOH with 20 mM ammonia. Flow rate=50 mL/min]. The analytical data for (S)-2-(tert-butylamino)-3-methyl-8-(6-methyl-4-oxo-1,4,5,6-tetrahydropyrrolo[3,4-b]pyrrol-2-yl)quinazolin-4(3H)-one (472) was: MS (ESI, pos. ion) m/z: 366.2 (M+1); $^1$H NMR (400 MHz, DMSO-$d_6$) δ ppm 11.94 (1H, br. s.), 7.79-7.97 (2H, m), 7.61 (1H, s), 7.18 (1H, t, J=7.7 Hz), 6.72 (1H, d, J=1.4 Hz), 5.95 (1H, s), 4.53 (1H, q, J=6.6 Hz), 3.48 (3H, s), 1.51 (9H, s), 1.37 (3H, d, J=6.7 Hz).

Example 473

2-((4-(bis(2-methoxyethyl)amino)-2-methylbutan-2-yl)amino)-3-methyl-8-(4-oxo-1,4,5,6-tetrahydropyr-rolo[3,4-b]pyrrol-2-yl)quinazolin-4(3H)-one

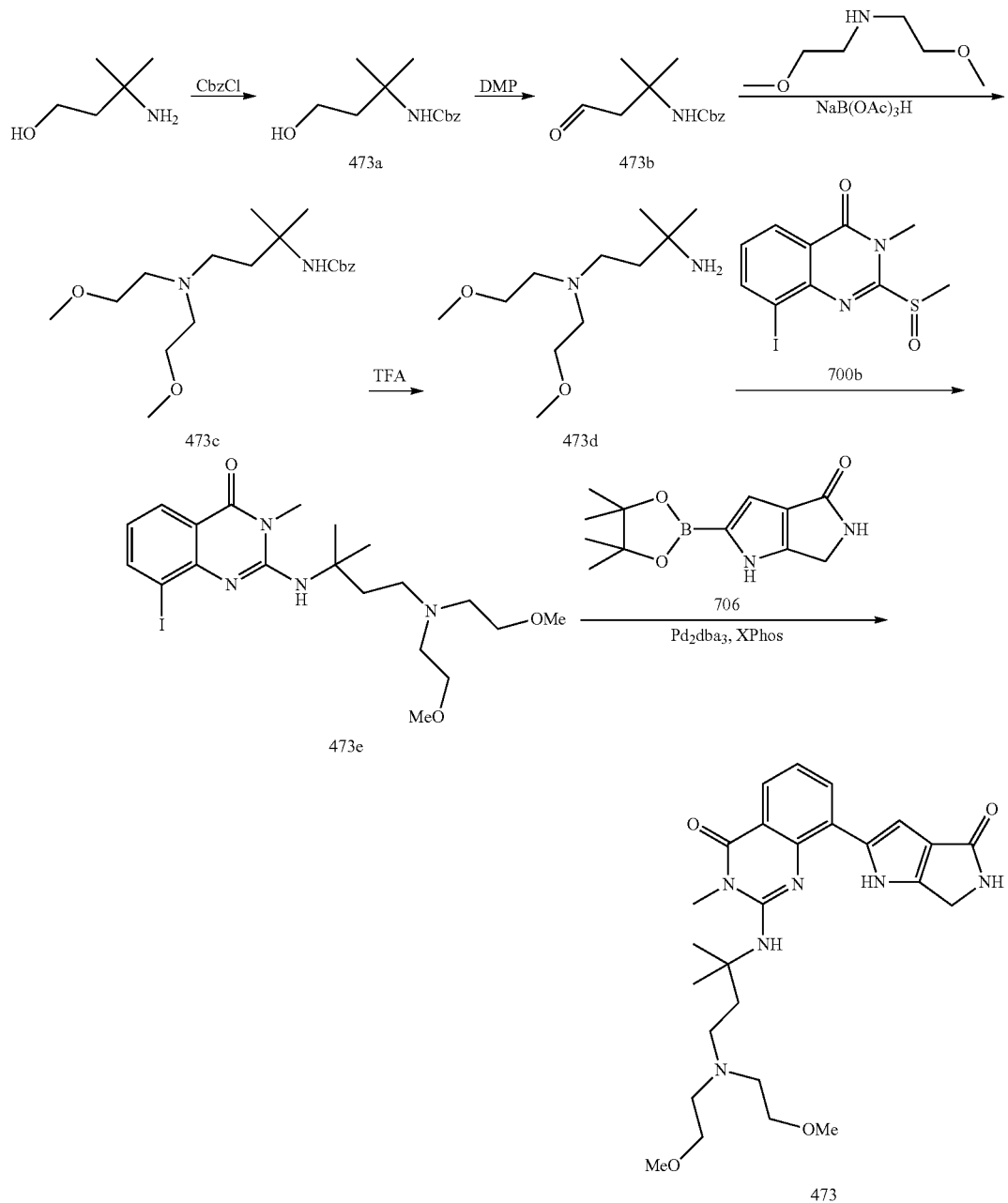

Preparation of benzyl(4-hydroxy-2-methylbutan-2-yl)carbamate (473a)

To a 150-mL round-bottomed flask was added 3-amino-3-methyl-butan-1-ol (2.18 mL, 19.39 mmol, Tyger Sci. Inc) and Na$_2$CO$_3$ (3.08 g, 29.1 mmol) (1 M in water) and the solution was cooled to 0° C. Benzyl chloroformate (3.03 mL, 21.33 mmol, Sigma-Aldrich) was added dropwise and the mixture was stirred at 0° C. for 2 h. The mixture was extracted with EtOAc (100 mL×3) and the combined organic layers were dried (MgSO$_4$), filtered and concentrated. The residue was purified with silica gel chromatography (eluted with 10-50% EtOAc in Hex) to give benzyl(4-hydroxy-2-methylbutan-2-yl)carbamate (3.33 g, 14.03 mmol, 72% yield) as a clear oil. MS (ESI, pos. ion) m/z: 238.1 (M+1).

Preparation of benzyl(2-methyl-4-oxobutan-2-yl)carbamate (473b)

To a 100-mL round-bottomed flask was added benzyl(4-hydroxy-2-methylbutan-2-yl)carbamate (1.60 g, 6.74 mmol) and dess-martinperiodinane (24.72 mL, 7.42 mmol) (0.3 M in DCM, Sigma-Aldrich) at 0° C. The reaction was stirred at 0° C. for 40 min, then diluted with DCM (100 mL). The mixture was washed with sat. NaHCO$_3$, and brine. The organic layer was dried (MgSO$_4$), filtered and concentrated. The residue was purified via silica gel chromatography (eluted with 10-60% EtOAc in Hex) to give benzyl(2-methyl-4-oxobutan-2-yl)carbamate (1.04 g, 4.42 mmol, 65% yield) as a colorless oil. MS (ESI, pos. ion) m/z: 236.1 (M+1).

Preparation of benzyl(4-(bis(2-methoxyethyl)amino)-2-methylbutan-2-yl)carbamate (473c)

To a 100-mL round-bottomed flask was added benzyl(2-methyl-4-oxobutan-2-yl)carbamate (1.04 g, 4.42 mmol) and bis(2-methoxyethyl)amine (0.776 mL, 5.30 mmol, Sigma-Aldrich) in 1,2-dichloroethane (20 mL) followed by AcOH (0.3 mL). The mixture was stirred at RT for 10 min, then sodium triacetoxyborohydride (1.124 g, 5.30 mmol, Sigma-Aldrich) was added portion wise. The reaction was stirred at RT for 1 h. Sat. NaHCO$_3$ (20 mL) was added slowly and the mixture was extracted with EtOAc (40 mL×3). The combined organic layers were dried (MgSO$_4$), filtered and concentrated in vacuo. The residue was purified with silica gel chromatography (eluted with 10-90% EtOAc in Hex) to give benzyl(4-(bis(2-methoxyethyl)amino)-2-methylbutan-2-yl)carbamate (1.03 g, 2.92 mmol, 66% yield) as a colorless oil. MS (ESI, pos. ion) m/z: 353.1 (M+1); $^1$H NMR (400 MHz, CDCl$_3$) δ ppm 7.27-7.40 (5H, m), 6.94 (1H, br. s.), 5.05 (2H, s), 3.45 (4H, t, J=5.8 Hz), 3.26 (6H, s), 2.64-2.73 (6H, m), 1.62 (2H, t, J=6.4 Hz), 1.36 (6H, s).

Preparation of N1,N1-bis(2-methoxyethyl)-3-methylbutane-1,3-diamine (473d)

A glass microwave reaction vessel was charged with benzyl(4-(bis(2-methoxyethyl)amino)-2-methylbutan-2-yl)carbamate (500 mg, 1.42 mmol) in TFA/DCM (1:1, 4 mL). The reaction mixture was stirred and heated in a Initiator microwave reactor (Personal Chemistry, Biotage AB, Inc.) at 85° C. for 7 h. The solvent was removed and the residue was filtered through a plug of Si-carbonate (0.59 mmol/g) and washed with DCM (300 mL, 5% MeOH in DCM (200 mL) and the filtrate was concentrated to give N1,N1-bis(2-methoxyethyl)-3-methylbutane-1,3-diamine (310 mg, 1.42 mmol, 100% yield) as an orange oil. $^1$H NMR (400 MHz, CDCl$_3$) δ ppm 3.47 (4H, t, J=6.1 Hz), 3.34 (6H, s), 2.71 (4H, t, J=6.1 Hz), 2.60-2.67 (2H, m), 1.50-1.59 (2H, m), 1.10 (6H, s).

Preparation of 2-((4-(bis(2-methoxyethyl)amino)-2-methylbutan-2-yl)amino)-8-iodo-3-methylquinazolin-4(3H)-one (473e)

A glass microwave reaction vessel was charged with N1,N1-bis(2-methoxyethyl)-3-methylbutane-1,3-diamine (50 mg, 0.229 mmol) and 8-iodo-3-methyl-2-(methylsulfinyl)quinazolin-4(3H)-one (700b; 80 mg, 0.229 mmol) in tBuOH (0.5 mL). The reaction mixture was stirred and heated in a Initiator microwave reactor (Personal Chemistry, Biotage AB, Inc.) at 120° C. for 45 min. Similarly another two batches (50 mg and 170 mg) were carried out. The three batches were combined and the solvent was removed. The residue was purified with silica gel chromatography (eluted with 0-5% MeOH in DCM) to give 2-((4-(bis(2-methoxyethyl)amino)-2-methylbutan-2-yl)amino)-8-iodo-3-methylquinazolin-4(3H)-one (210 mg, 0.42 mmol). MS (ESI, pos. ion) m/z: 503 (M+1).

Preparation of 2-((4-(bis(2-methoxyethyl)amino)-2-methylbutan-2-yl)amino)-3-methyl-8-(4-oxo-1,4,5,6-tetrahydropyrrolo[3,4-b]pyrrol-2-yl)quinazolin-4(3H)-one (473)

A glass microwave reaction vessel was charged with 2-((4-(bis(2-methoxyethyl)amino)-2-methylbutan-2-yl)amino)-8-iodo-3-methylquinazolin-4(3H)-one (473e; 210 mg, 0.42 mmol) and 2-(4,4,5,5-tetramethyl-1,3,2-dioxaborolan-2-yl)-5,6-dihydropyrrolo[3,4-b]pyrrolo-4(1H)-one (706, 114 mg, 0.46 mmol) in 1,4-dioxane (3.00 mL)/water (0.75 mL) followed by Pd$_2$dba$_3$ (19 mg, 0.021 mmol, Strem), Xphos (20 mg, 0.042 mmol, Sigma-Aldrich) and K$_3$PO$_4$ (266 mg, 1.25 mmol). The reaction mixture was stirred and heated in a Initiator microwave reactor (Personal Chemistry, Biotage AB, Inc.) at 95° C. for 30 min. The mixture was cooled to RT and extracted with EtOAc (30 mL×3). The combined organic layers were dried (MgSO$_4$), filtered and concentrated. The residue was purified with silica gel chromatography (eluted with 0-7% MeOH in DCM) to give 2-((4-(bis(2-methoxyethyl)amino)-2-methylbutan-2-yl)amino)-3-methyl-8-(4-oxo-1,4,5,6-tetrahydropyrrolo[3,4-b]pyrrol-2-yl)quinazolin-4(3H)-one (105 mg, 0.211 mmol, 50.6% yield) as a brown solid. MS (ESI, pos. ion) m/z: 503 (M+1); $^1$H NMR (400 MHz, DMSO-d$_6$) δ ppm 12.10 (1H, br. s.), 7.87 (2H, d, J=7.2 Hz), 7.62 (1H, s), 7.50 (1H, s), 7.15 (1H, t, J=7.7 Hz), 6.79 (1H, s), 4.25 (2H, s), 3.44 (3H, s), 3.38 (4H, t, J=5.5 Hz), 3.12 (6H, s), 2.64-2.71 (6H, m), 1.80 (2H, t, J=5.7 Hz), 1.54 (6H, s).

Example 474

2-(tert-butylamino)-3-(2-(2-methoxyethoxy)ethyl)-8-((6R)-6-methyl-4-oxo-1,4,5,6-tetrahydropyrrolo[3,4-b]pyrrol-2-yl)-4(3H)-quinazolinone

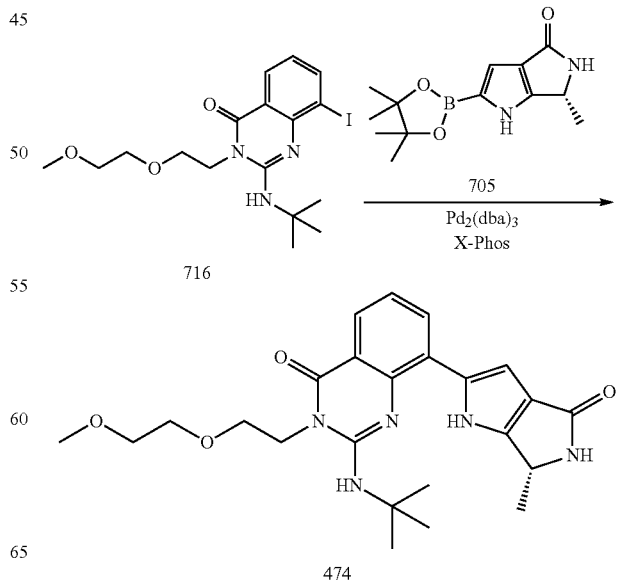

This compound (102 mg, 40% yield) as a tan amorphous solid was prepared according to the procedure described for Example 448, using 2-(tert-butylamino)-8-iodo-3-(2-(2-methoxyethoxyl)ethyl)quinazolin-4(3H)-one (716) (250 mg, 0.56 mmol) and (R)-6-methyl-2-(4,4,5,5-tetramethyl-1,3,2-dioxaborolan-2-yl)-5,6-dihydropyrrolo[3,4-b]pyrrol-4(1H)-one (705) (178 mg, 0.68 mmol) as the starting materials. $^1$H NMR (400 MHz, MeOH-$d_4$) δ ppm 7.99 (2H, dd, J=7.6, 1.8 Hz), 7.23 (1H, t, J=7.7 Hz), 6.75 (1H, s), 4.69 (1H, q, J=6.8 Hz), 4.27-4.38 (2H, m), 3.90 (2H, t, J=4.3 Hz), 3.67-3.74 (2H, m), 3.55-3.63 (2H, m), 1.60 (9H, s), 1.52 (3H, d, J=6.8 Hz), 1.22 (6H, s). m/z (ESI, +ve) 454.0 (M+H)$^+$.

Example 475

2-(tert-butylamino)-3-cyclopropyl-8-((6R)-6-methyl-4-oxo-1,4,5,6-tetrahydropyrrolo[3,4-b]pyrrol-2-yl)-4(3H)-quinazolinone

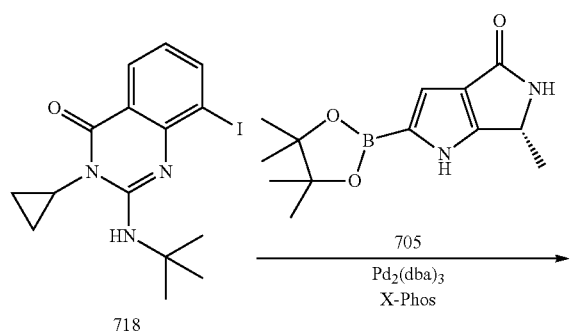

This compound (73 mg, 57% yield) as a tan amorphous solid was prepared according to the procedure described for Example 448, using 2-(tert-butylamino)-3-cyclopropyl-8-iodoquinazolin-4(3H)-one (718) (125 mg, 0.32 mmol) and (R)-6-methyl-2-(4,4,5,5-tetramethyl-1,3,2-dioxaborolan-2-yl)-5,6-dihydropyrrolo[3,4-b]pyrrol-4(1H)-one (705) (85 mg, 0.32 mmol) as the starting materials. $^1$H NMR (400 MHz, DMSO-$d_6$) δ ppm 11.99 (1H, br. s.), 7.89 (1H, d, J=7.4 Hz), 7.85 (1H, d, J=7.8 Hz), 7.65 (1H, s), 7.16 (1H, t, J=7.7 Hz), 6.74 (1H, s), 6.15 (1H, s), 4.48-4.59 (1H, m), 2.88 (1H, br. s.), 1.54 (9H, s), 1.38 (3H, d, J=6.5 Hz), 1.27 (2H, d, J=6.7 Hz), 0.78 (2H, br. s.). m/z (ESI, +ve) 392.0 (M+H)$^+$.

Examples 476 and 477

2-(3-(((1s,3s)-3-(Bis(2-fluoroethyl)amino)cyclobutyl)amino)-2-methylquinoxalin-5-yl)-6,7-dihydro-1H-pyrrolo[3,2-c]pyridin-4(5H)-one and 2-(3-(((1s,3s)-3-((2-Fluoroethyl)amino)cyclobutyl)amino)-2-methylquinoxalin-5-yl)-6,7-dihydro-1H-pyrrolo[3,2-c]pyridin-4(5H)-one

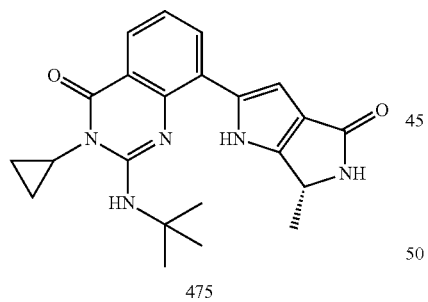

A suspension of 2-(3-((cis-3-aminocyclobutyl)amino)-2-methylquinoxalin-5-yl)-6,7-dihydro-1H-pyrrolo[3,2-c]pyridin-4(5H)-one hydrochloride (Example 435; 26.1 mg, 0.065 mmol), 1-bromo-2-fluoroethane (Alfa Aesar, Ward Hill, Mass.; 0.024 mL, 0.327 mmol), and DIPEA (0.068 mL, 0.393 mmol) in DMF (1.0 mL) was stirred in a sealed flask at 130° C. for 30 min. The reaction mixture was subsequently concentrated onto silica gel and chromatographically purified (silica gel, 0-10% MeOH/DCM). Product containing fractions of the separated products were subsequently separately combined, diluted with DCM (30 mL), sequentially washed with half-saturated brine (30 mL) and water (30 mL), dried over Na$_2$SO$_4$, filtered, and concentrated in vacuo to separately provide: 2-(3-(((1 s,3s)-3-(bis(2-fluoroethyl)amino)

cyclobutyl)amino)-2-methylquinoxalin-5-yl)-6,7-dihydro-1H-pyrrolo[3,2-c]pyridin-4(5H)-one (476; 6.7 mg, 0.015 mmol, 23% yield) as a yellow solid: $^1$H NMR (400 MHz, CDCl$_3$) δ ppm 12.57 (1H, br. s.), 7.94 (1H, dd, J=7.7, 0.7 Hz), 7.68 (1H, dd, J=7.9, 0.7 Hz), 7.41 (1H, t, J=7.8 Hz), 7.14 (1H, d, J=2.0 Hz), 5.27 (1H, br. s.), 4.61 (4H, d, J=46.0 Hz), 4.24 (1H, br. s.), 3.67 (2H, td, J=6.8, 2.6 Hz), 3.37 (1H, br. s.), 3.01-3.19 (2H, m), 2.99 (4H, t, J=6.8 Hz), 2.88-2.96 (2H, m), 2.60 (3H, s), 1.55-1.66 (2H, m). $^{19}$F NMR (377 MHz, CDCl$_3$) δ ppm −218.81 (2F, s). m/z (ESI, +ve) 455.0 (M+H)$^+$. 2-(3-(((1s,3s)-3-((2-fluoroethyl)amino)cyclobutyl)amino)-2-methylquinoxalin-5-yl)-6,7-dihydro-1H-pyrrolo[3,2-c]pyridin-4(5H)-one (477; 3.10 mg, 7.59 μmol, 12% yield) as a yellow solid. $^1$H NMR (400 MHz, CDCl$_3$) δ ppm 12.63 (1H, br. s.), 7.94 (1H, dd, J=7.6, 1.2 Hz), 7.68 (1H, dd, J=8.1, 1.1 Hz), 7.41 (1H, t, J=7.8 Hz), 7.14 (1H, d, J=2.2 Hz), 5.35 (1H, br. s.), 5.16 (1H, d, J=4.9 Hz), 4.56 (2H, dt, J=47.5, 4.7 Hz), 4.15-4.29 (1H, m), 3.68 (2H, td, J=6.8, 2.4 Hz), 3.32 (1H, quin, J=7.4 Hz), 2.93-3.09 (5H, m), 2.89 (2H, t, J=4.7 Hz), 2.59 (3H, s), 1.78-1.92 (2H, m). $^{19}$F NMR (376 MHz, CDCl$_3$) δ ppm −223.07 (1F, s). m/z (ESI, +ve) 409.0 (M+H)$^+$.

Example 478

2-(3-(((1s,3s)-3-((2,2-Difluoroethyl)amino)cyclobutyl)amino)-2-methylquinoxalin-5-yl)-6,7-dihydro-1H-pyrrolo[3,2-c]pyridin-4(5H)-one

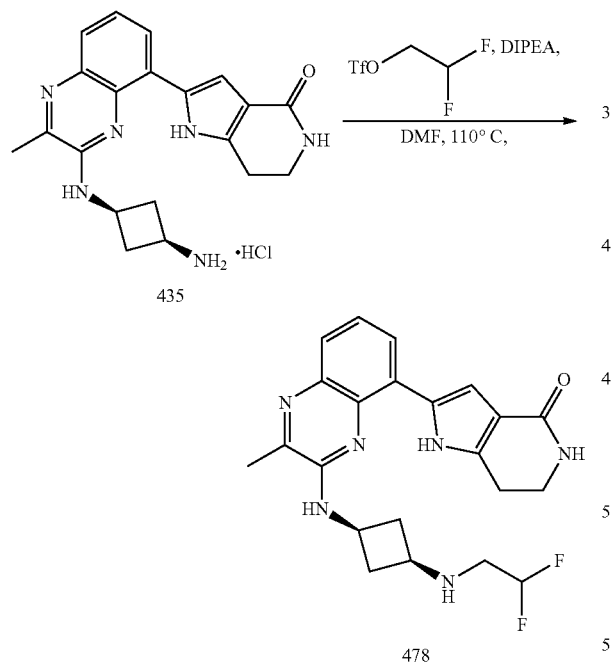

A mixture of 2-(3-((cis-3-aminocyclobutyl)amino)-2-methylquinoxalin-5-yl)-6,7-dihydro-1H-pyrrolo[3,2-c]pyridin-4(5H)-one hydrochloride (Example 435; 29.6 mg, 0.074 mmol), 2,2-difluoroethyl trifluoromethanesulfonate (SynQuest Labs, Inc., Alachua, Fla.; 0.015 mL, 0.111 mmol), and DIPEA (0.052 mL, 0.297 mmol) in DMF (1.0 mL) was stirred in a sealed flask at 110° C. for 30 min. The reaction mixture was then cooled to RT, concentrated onto silica gel, and chromatographically purified (silica gel, 0-10% MeOH/DCM) to provide a yellow solid (18.7 mg). This material was taken up in DCM (30 mL), sequentially washed with half-saturated brine (30 mL) and water (30 mL), dried over Na$_2$SO$_4$, filtered, and concentrated in vacuo to provide 2-(3-4(1s,3s)-3-(((2,2-difluoroethyl)amino)cyclobutyl)amino)-2-methylquinoxalin-5-yl)-6,7-dihydro-1H-pyrrolo[3,2-c]pyridin-4(5H)-one (12.3 mg, 0.029 mmol, 39% yield) as a yellow solid. $^1$H NMR (400 MHz, CDCl$_3$) δ ppm 12.59 (1H, br. s.), 7.95 (1H, dd, J=7.6, 1.0 Hz), 7.68 (1H, dd, J=8.0, 1.0 Hz), 7.41 (1H, t, J=7.8 Hz), 7.14 (1H, d, J=2.0 Hz), 5.86 (1H, tt, J=56.0, 4.0 Hz), 5.29 (1H, br. s.), 5.12 (1H, d, J=4.9 Hz), 4.15-4.26 (1H, m), 3.68 (2H, td, J=6.8, 2.5 Hz), 3.32 (1H, quin, J=7.7 Hz), 2.94-3.07 (6H, m), 2.59 (3H, s), 1.78-1.89 (2H, m). $^{19}$F NMR (376 MHz, CDCl$_3$) δ ppm −121.83 (2F, s). m/z (ESI, +ve) 427.1 (M+H)$^+$.

Example 479

2-(3-(((1s,3s)-3-(Dimethylamino)cyclobutyl)amino)-2-methylquinoxalin-5-yl)-6,7-dihydro-1H-pyrrolo[3,2-c]pyridin-4(5H)-one

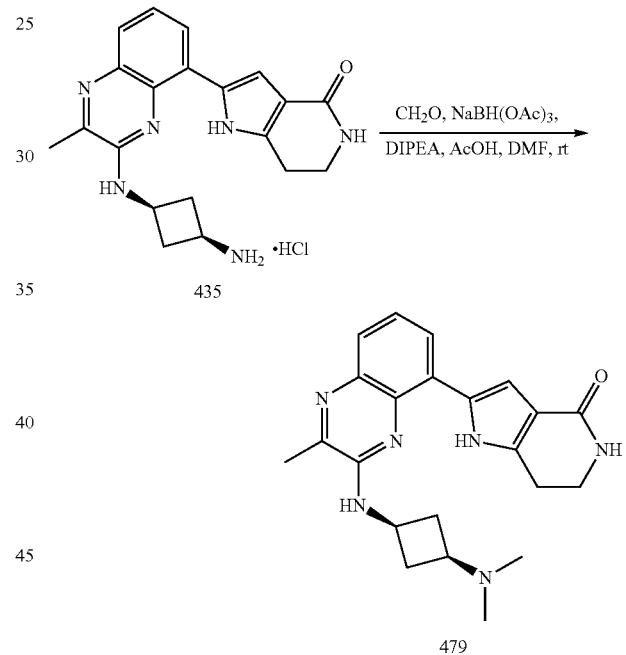

A solution of 2-(3-((cis-3-aminocyclobutyl)amino)-2-methylquinoxalin-5-yl)-6,7-dihydro-1H-pyrrolo[3,2-c]pyridin-4(5H)-one hydrochloride (Example 435; 32.3 mg, 0.081 mmol), DIPEA (0.014 mL, 0.081 mmol), AcOH (0.464 μl, 8.10 μmol), formaldehyde (37% w/w in water; 0.030 mL, 0.405 mmol), and sodium triacetoxyborohydride (24.03 mg, 0.113 mmol) in DMF (1.0 mL) was stirred at 23° C. for 30 min. Additional sodium triacetoxyborohydride (24.03 mg, 0.113 mmol) was added, and the resulting solution was stirred at 23° C. for 1 h. The reaction mixture was concentrated onto silica gel and chromatographically purified (silica gel, 0-10% (2M NH$_3$ in MeOH)/DCM) to provide a yellow solid. This material was taken up in MeOH (2.0 mL), HCl (conc. aq.; 0.014 mL, 0.170 mmol) was added, and the resulting solution was stirred at 65° C. for 2 d. The reaction mixture was then concentrated onto silica gel and chromatographically purified (silica gel, 0-10% (2M NH$_3$ in MeOH)/DCM), and product-containing fractions were concentrated in vacuo. The residue was taken up in DCM (30 mL), sequentially washed with half-saturated brine (30 mL) and water (30 mL), dried over Na$_2$SO$_4$, filtered, and concentrated in vacuo to provide 2-(3-(((1s,3s)-3-(dimethylamino)cyclobutyl)amino)-2-methylquinoxalin-5-yl)-6,7-dihydro-1H-pyrrolo[3,2-c]pyridin-4(5H)-one (12.7 mg, 0.033 mmol, 40% yield) as a yellow solid. $^1$H NMR (400 MHz, CDCl$_3$) δ ppm 12.61 (1H, br. s.), 7.94 (1H, dd, J=7.6, 1.2 Hz), 7.68 (1H, dd, J=8.0, 1.4 Hz), 7.41 (1H, t, J=7.8 Hz), 7.15 (1H, d, J=2.0 Hz), 5.26 (1H, br. s.), 4.21-4.33 (1H, m), 3.69 (2H, td, J=6.8, 2.4 Hz), 3.01 (2H, t, J=6.8 Hz), 2.84-2.95 (2H, m), 2.63-2.74 (1H, m), 2.59 (3H, s), 2.27 (6H, br. s.), 2.08 (2H, br. s.). m/z (ESI, +ve) 391.1 (M+H)$^+$.

Example 480

2-(2-Methyl-3-(((1s,3s)-3-morpholinocyclobutyl) amino)quinoxalin-5-yl)-6,7-dihydro-1H-pyrrolo[3,2-c]pyridin-4(5H)-one

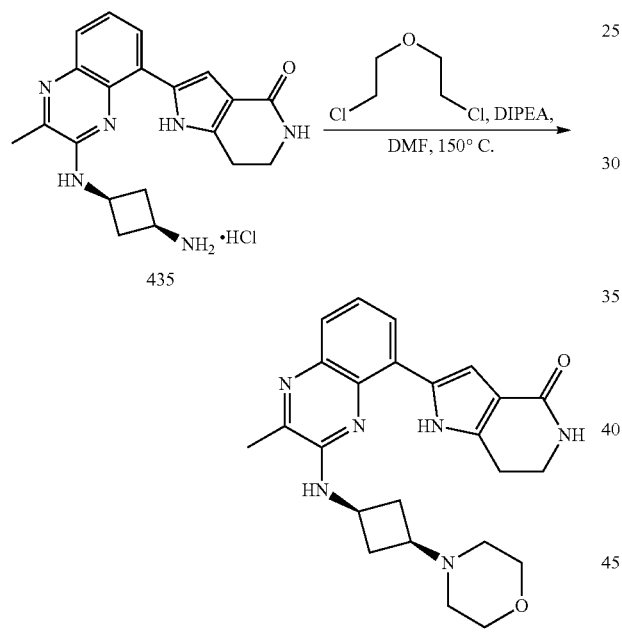

A suspension of 2-(3-((cis-3-aminocyclobutyl)amino)-2-methylquinoxalin-5-yl)-6,7-dihydro-1H-pyrrolo[3,2-c]pyridin-4(5H)-one hydrochloride (Example 435; 26.0 mg, 0.065 mmol), bis(2-chloroethyl) ether (Aldrich; 0.015 mL, 0.130 mmol), and DIPEA (0.068 mL, 0.391 mmol) in DMF (1.0 mL) was stirred in a sealed flask at 150° C. for 70 min. The reaction mixture was then concentrated onto silica gel and chromatographically purified (silica gel, 0-10% (2M NH$_3$ in MeOH)/DCM). Product-containing fractions were combined and diluted with DCM (20 mL), and the resulting mixture was sequentially washed with half-saturated brine (30 mL) and water (30 mL), dried over Na$_2$SO$_4$, filtered, and concentrated in vacuo to provide 2-(2-methyl-3-((1s,3s)-3-morpholinocyclobutyl)amino)quinoxalin-5-yl)-6,7-dihydro-1H-pyrrolo[3, 2-c]pyridin-4(5H)-one (5.8 mg, 0.013 mmol, 21% yield) as a yellow solid. $^1$H NMR (400 MHz, CDCl$_3$) δ ppm 12.63 (1H, br. s.), 7.95 (1H, dd, J=7.5, 1.3 Hz), 7.68 (1H, dd, J=8.1, 1.3 Hz), 7.41 (1H, t, J=7.8 Hz), 7.14 (1H, d, J=2.0 Hz), 5.25-5.33 (1H, m), 5.09 (1H, d, J=4.1 Hz), 4.22-4.32 (1H, m), 3.75 (4H, t, J=4.5 Hz), 3.70 (2H, m, J=6.8, 6.8, 2.5 Hz), 3.61-3.67 (1H, m), 3.00 (2H, t, J=6.8 Hz), 2.82-2.92 (2H, m), 2.57 (3H, s), 2.42 (4H, br. s.), 1.90-2.01 (2H, m). m/z (ESI, +ve) 433.1 (M+H)$^+$.

Example 481

(R)-2-(tert-butylamino)-3-ethyl-8-(6-methyl-4-oxo-1,4,5,6-tetrahydropyrrolo[3,4-b]pyrrol-2-yl)quinazolin-4(3H)-one

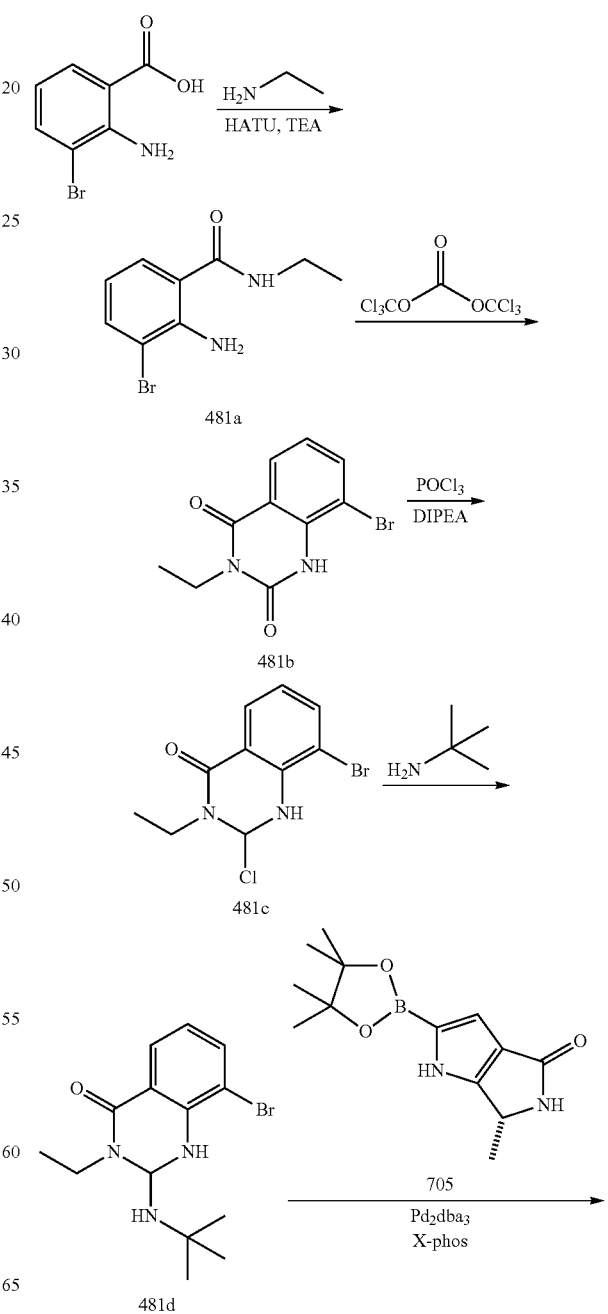

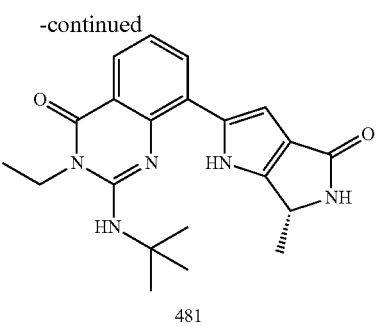

481

Preparation of 2-amino-3-bromo-N-ethylbenzamide (481a)

A mixture of 2-amino-3-bromo-benzoic acid (2 g, 9.26 mmol), HATU (3.84 g, 10.10 mmol, Sigma Aldrich), DMF (42.1 mL), 2.0 M ethylamine in MeOH (4.21 mL, 8.42 mmol, Sigma Aldrich), and TEA (1.8 mL, 12.62 mmol) was set stirring at RT for 18 h. It was diluted with water and extracted with EtOAc. The combined organics were dried over $Na_2SO_4$, filtered, and concentrated under reduced pressure. It was diluted with DCM, adsorbed onto silica, and purified on 40 g $SiO_2$ (eluent: 0-100% EtOAc/hexanes over 25 min, RediSep Gold). The product fractions were combined and concentrated to give the product as a yellow oil (2.5 g, 122%). $^1$H NMR (400 MHz, DMSO-$d_6$) δ ppm 8.39 (1H, br. s.) 7.47-7.54 (2H, m) 6.52 (1H, t, J=7.82 Hz) 6.44 (2H, br. s.) 3.19-3.29 (2H, m) 1.11 (3H, t, J=7.24 Hz). m/z (ESI, +ve) 242.9 (M+H)$^+$.

Preparation of 8-bromo-3-ethylquinazoline-2,4(1H,3H)-dione (481b)

A mixture of 2-amino-3-bromo-N-ethylbenzamide (2.0 g, 8.23 mmol, 481a), triphosgene (0.830 g, 2.80 mmol, Sigma Aldrich,), DCM (28.0 mL), and DIPEA (1.6 mL, 8.95 mmol) was set stirring at 60° C. with a condenser for 4 h. The mixture was concentrated under reduced pressure to a yellow residue. It was adsorbed onto silica and purified on 24 g $SiO_2$ (eluent: 0-100% EtOAc/hexanes over 25 min, RediSep Gold). The product fractions were combined and concentrated under reduced pressure to give the product as a white solid (736 mg, 98%). $^1$H NMR (400 MHz, DMSO-$d_6$) δ ppm 10.52 (1H, s) 7.95 (1H, dd, J=7.82, 1.37 Hz) 7.98 (1H, dd, J=7.82, 1.37 Hz) 7.15 (1H, t, J=7.82 Hz) 3.93 (2H, q, J=7.04 Hz) 1.15 (3H, t, J=7.04 Hz). m/z (ESI, +ve) 268.9 (M+H)$^+$.

Preparation of 8-bromo-2-chloro-3-ethylquinazolin-4(3H)-one (481c)

A mixture of 8-bromo-3-ethylquinazoline-2,4(1H,3H)-dione (736 mg, 2.74 mmol, 481b), $POCl_3$ (1.5 mL, 16.42 mmol, Sigma Aldrich), and DIPEA (0.9 mL, 5.47 mmol) was heated to reflux. Additional DIPEA (0.9 mL, 5.47 mmol) was added. It was stirred overnight at reflux. The mixture was cooled to RT and poured into rapidly stirred water at 0° C. It was basified to pH 10 with 10 N NaOH (aq.) to give an orange solution. The solution was extracted with DCM, dried over $Na_2SO_4$, filtered, and concentrated under reduced pressure to give a yellow orange solid (398 mg, 57%). m/z (ESI, +ve) 286.9 (M+H)$^+$.

Preparation of 8 8-bromo-2-(tert-butylamino)-3-ethylquinazolin-4(3H)-one (481d)

A mixture of tert-butylamine (1.1 mL, 10.43 mmol) and 8-bromo-2-chloro-3-ethylquinazolin-4(3H)-one (100 mg, 0.348 mmol, 481c) was sealed and set stirring for 3 h at 80° C. The reaction was cooled to RT, diluted with water, and extracted with DCM. The combined organics were dried over $Na_2SO_4$, filtered, and concentrated under reduced pressure giving a pale yellow solid. The material was taken up DCM, adsorbed onto silica, and purified on 4 g $SiO_2$ (eluent: 0-100% EtOAc/hexanes over 20 min, RediSep Gold). The product containing fractions were combined and concentrated under reduced pressure to a colorless residue (52 mg, 46%). m/z (ESI, +ve) 323.9 (M+H)$^+$.

Preparation of (R)-2-(tert-butylamino)-3-ethyl-8-(6-methyl-4-oxo-1,4,5,6-tetrahydropyrrolo[3,4-b]pyrrol-2-yl)quinazolin-4(3H)-one (481)

This compound (8.8 mg, 11% yield) as an off-white solid was prepared according to the procedure given in 405, using 8-bromo-3-ethylquinazoline-2,4(1H,3H)-dione (52 mg, 0.160 mmol, 481d) and (R)-6-methyl-2-(4,4,5,5-tetramethyl-1,3,2-dioxaborolan-2-yl)-5,6-dihydropyrrolo[3,4-b]pyrrol-4(1H)-one (84 mg, 0.321 mmol, 705) as the starting materials. $^1$H NMR (400 MHz, $CDCl_3$) δ ppm 12.41 (1H, br. s.) 8.02 (1H, d, J=8.41 Hz) 8.06 (1H, d, J=8.61 Hz) 7.23 (1H, br. s.) 6.84 (1H, s) 5.61 (1H, br. s.) 4.66 (1H, br. s.) 4.16 (1H, d, J=7.04 Hz) 3.50 (2H, s) 1.67 (9H, s) 1.54 (3H, d, J=6.46 Hz) 1.40 (3H, t, J=6.85 Hz). m/z (ESI, +ve) 380.0 (M+H)$^+$.

Example 482

2-(tert-butylamino)-8-((6R)-6-methyl-4-oxo-1,4,5,6-tetrahydropyrrolo[3,4-b]pyrrol-2-yl)-3-(3-pyridinyl)-4(3H)-quinazolinone

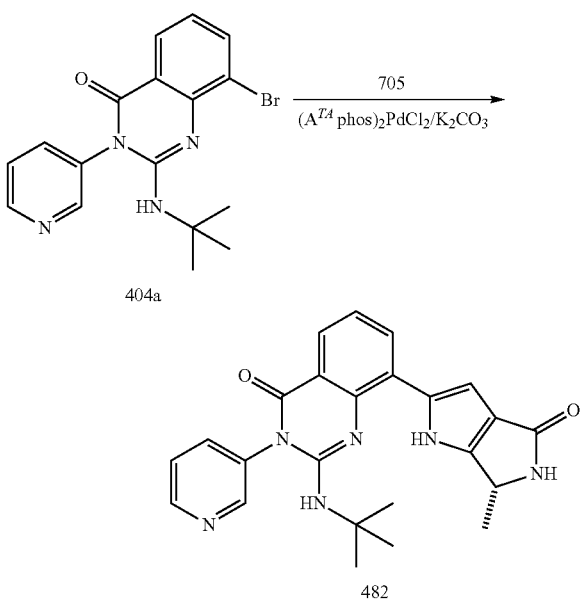

Argon was bubbled into a slurry of potassium carbonate (Mallinkrodt; 0.074 g, 0.536 mmol), dichlorobis(p-dimethylaminophenylditbutylphosphine)palladium(ii) (Aldrich; 4.74 mg, 6.70 μmol), (R)-6-methyl-2-(4,4,5,5-tetramethyl-1,3,2-dioxaborolan-2-yl)-5,6-dihydropyrrolo[3,4-b]pyrrol-4(1H)-one (705; 0.070 g, 0.268 mmol), 8-bromo-2-(tert-butylamino)-3-(pyridin-3-yl)quinazolin-4(3H)-one (404a; 0.050 g, 0.134 mmol) for 1 min. The reaction was sealed and heated to 80° C. for 30 min. The reaction was adsorbed onto 0.7 g silica gel and dried in vacuo. The material was treated with purified by silica gel chromatography (12 g column) using 0-100% (90/10 DCM/MeOH) in DCM. The product-containing fractions were concentrated to afford (R)-2-(tert-butylamino)-8-(6-methyl-4-oxo-1,4,5,6-tetrahydropyrrolo[3,4-b]pyrrol-2-yl)-3-(pyridin-3-yl)quinazolin-4(3H)-one (0.042 g, 0.098 mmol, 73% yield) as a yellow solid. $^1$H NMR (400 MHz, DMSO-$d_6$) δ ppm 11.91 (1H, s), 8.74 (1H, dd, J=4.9, 1.6 Hz), 8.64 (1H, d, J=2.2 Hz), 7.91-7.99 (2H, m), 7.89 (1H, dd, J=7.8, 1.6 Hz), 7.59-7.69 (2H, m), 7.24 (1H, t, J=7.6 Hz), 6.77 (1H, d, J=1.6 Hz), 4.61 (1H, s), 4.49-4.58 (1H, m), 1.31-1.41 (12H, m). m/z (ESI, +ve ion) 429.0 (M+H)$^+$.

Example 483

(6R)-2-(3-(((1S,3R)-3-aminocyclohexyl)amino)-2-methyl-5-quinoxalinyl)-6-methyl-5,6-dihydropyrrolo[3,4-b]pyrrol-4(1H)-one

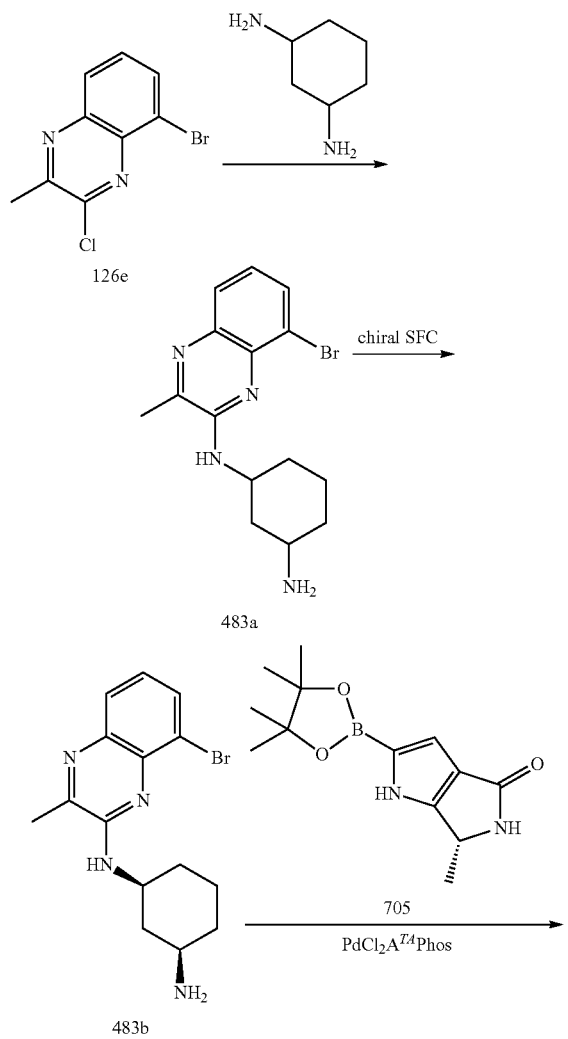

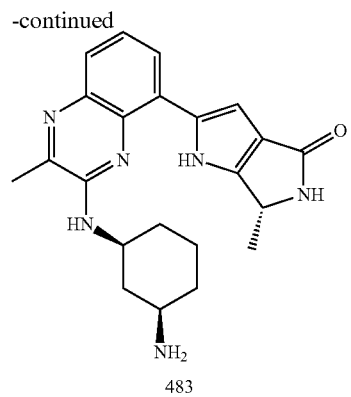

483

Preparation of (N1-(8-bromo-3-methylquinoxalin-2-yl)cyclohexane-1,3-diamine (483a)

A mixture of 5-bromo-3-chloro-2-methylquinoxaline (126e, 7.25 g, 28.2 mmol) and (rac)-1,3-cyclohexanediamine (TCI America, Inc., Portland, Oreg.; 23.69 m, 197 mmol) in DMSO (28.2 mL) was heated to 100° C. for 16 h. The reaction was cooled to RT and diluted with water. It was extracted with EtOAc (3×), dried over MgSO$_4$, filtered, and concentrated to give (N1-(8-bromo-3-methylquinoxalin-2-yl)cyclohexane-1,3-diamine (483a, 14.25 g, 151% yield) a dark orange-brown oil. MS (ESI, pos. ion) m/z: 335.0/337.0 (M+1). Separation of (1S,3R)—N1-(8-bromo-3-methylquinoxalin-2-yl)cyclohexane-1,3-diamine. The racemic mixture was separated using chiral SFC via two purifications. 1$^{st}$ Purification: Preparative SFC: AY-H (5 μm, 21 mm×25 cm) with 20% organic modifier: 80% carbon dioxide. Organic modifier: methanol with 0.2% diethylamine. F=70 ml/min, T=40° C., BPR=100 bar, P=179 bar, 256 nm. (N1-(8-bromo-3-methylquinoxalin-2-yl)cyclohexane-1,3-diamine (483a, 14.25 g) dissolved in methanol (250 mL, 60 mg/mL). 0.5 mL injection. Two peaks were collected. 2$^{nd}$ Purification: Preparative SFC: Repurification of peak 2. OJ-H (5 μm, 21 mm×25 cm, S/N=0131) with 20% organic modifier modifier: 80% carbon dioxide. Organic modifier: methanol with 0.2% diethylamine. F=70 mL/min, T=40° C., BPR=100 bar, P=172 bar, 256 nm. Peak 2 from the 1$^{st}$ purification was dissolved in methanol (60 mL). 0.6 mL injection. A single peak was collected to give (1S,3R)—N1-(8-bromo-3-methylquinoxalin-2-yl)cyclohexane-1,3-diamine (483b, 2.81 g, 30% recovery) as a light orange solid. $^1$H NMR (400 MHz, DMSO-$d_6$) δ ppm 7.80 (1H, d, J=7.63 Hz) 7.70 (1H, d, J=8.02 Hz) 7.15-7.26 (2H, m) 4.17 (1H, br. s.) 2.76 (1H, t, J=10.17 Hz) 2.52 (3H, br. s.) 2.08 (1H, d, J=12.13 Hz) 1.95 (1H, br. s.) 1.76 (2H, d, J=9.19 Hz) 1.26-1.41 (3H, m) 1.02-1.17 (1H, m). MS (ESI, pos. ion) m/z: 335.0/337.0 (M+1).

Preparation of (R)-2-(3-(((1S,3R)-3-aminocyclohexyl)amino)-2-methylquinoxalin-5-yl)-6-methyl-5,6-dihydropyrrolo[3,4-b]pyrrol-4(1H)-one (483)

A mixture of (1S,3R)—N1-(8-bromo-3-methylquinoxalin-2-yl)cyclohexane-1,3-diamine (483b, 1.62 g, 4.83 mmol), (R)-6-methyl-2-(4,4,5,5-tetramethyl-1,3,2-dioxaborolan-2-yl)-5,6-dihydropyrrolo[3,4-b]pyrrol-4(1H)-one (705, 2.53 g, 9.65 mmol), dichlorobis(p-dimethylaminophenylditbutylphosphine)palladium (II) (0.171 g, 0.24 mmol), and potassium phosphate (3.07 g, 14.48 mmol) in 1,4-dioxane (38.6 mL)/water (9.65 mL) was sparged with nitrogen for 3 min and was stirred at 80° C. for 45 min. The reaction mixture was diluted with water (200 mL), added to a separatory funnel, and extracted with 3:2 chloroform/IPA (5×100 mL); the combined organic layers were separated, dried over $Na_2SO_4$, and concentrated. The crude product in 10% MeOH/DCM was loaded onto the column and was purified via automated flash chromatography (silica gel) with 100% DCM to 50% 2 M ammonia in MeOH/DCM to give (R)-2-(3-4(1S,3R)-3-aminocyclohexyl)amino)-2-methylquinoxalin-5-yl)-6-methyl-5,6-dihydropyrrolo[3,4-b]pyrrol-4(1H)-one (483, 1.59 g, 4.07 mmol, 84% yield) as a brown amorphous solid. $^1$H NMR (400 MHz, DMSO-$d_6$) δ ppm 1.03-1.16 (m, 1H) 1.29-1.42 (m, 3H) 1.43 (d, J=6.65 Hz, 3H) 1.82 (d, J=11.15 Hz, 2H) 1.99-2.18 (m, 3H) 2.55 (s, 3H) 2.82 (t, J=10.27 Hz, 1H) 3.33 (br. s., 1H) 4.04-4.14 (m, 1H) 4.56 (q, J=6.52 Hz, 1H) 7.03 (s, 1H) 7.13 (br. s., 1H) 7.34 (t, J=7.82 Hz, 1H) 7.60 (dd, J=7.92, 1.08 Hz, 1H) 7.64 (s, 1H) 7.86-7.91 (m, 1H) 12.08 (br. s., 1H). MS (ESI, pos. ion) m/z: 391.1 (M+1).

Example 484

(6R)-2-(4-amino-2-(tert-butylamino)-8-quinazolinyl)-6-methyl-5,6-dihydropyrrolo[3,4-b]pyrrol-4(1H)-one

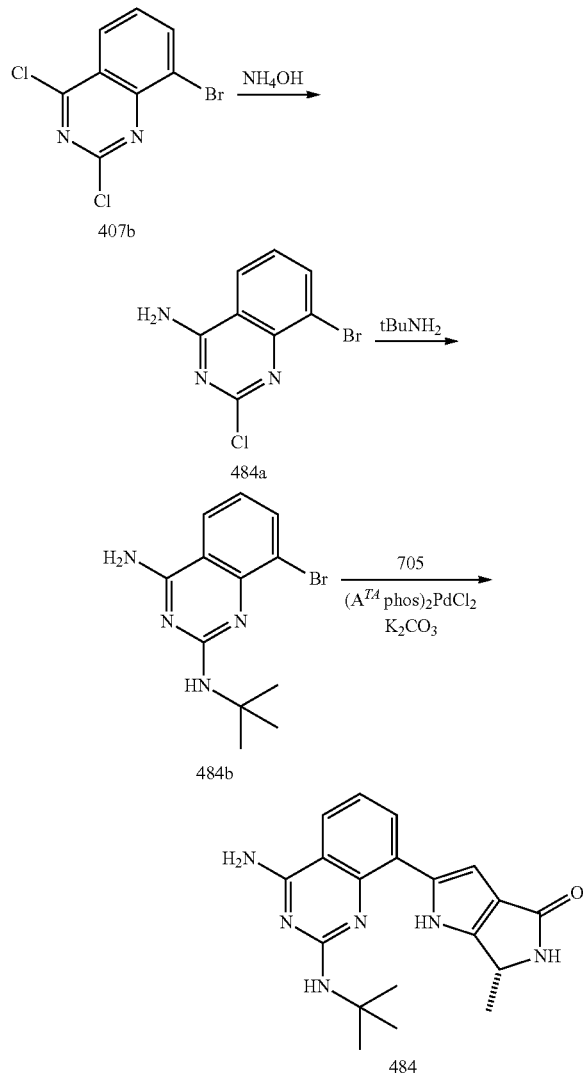

Preparation of 8-bromo-2-chloroquinazolin-4-amine (484a)

To a slurry of 8-bromo-2,4-dichloroquinazoline (407b; 0.50 g, 1.80 mmol) in 2 mL THF at 0° C. was added ammonium hydroxide, 28% ammonia in water (3.25 mL, 23.39 mmol). The reaction was sealed and the ice/water bath was removed. The heterogeneous reaction was stirred rapidly. In the morning starting material was still evident. 2 mL THF and 1 mL 28% ammonia in water were added and the reaction became homogeneous. After 1 h, reaction was checked and judged complete. The reaction was partitioned between water and DCM. The layers were separated and the aqueous layer was filtered through Celite and the filtrate was extracted 2×DCM and the combined organics were dried over anhydrous $Na_2SO_4$, filtered, and concentrated in vacuo to give 8-bromo-2-chloroquinazolin-4-amine (0.318 g, 1.23 mmol, 68% yield) as an orange solid. $^1$H NMR (400 MHz, DMSO-$d_6$) δ ppm 8.52 (2H, br. s.), 8.24 (1H, d, J=8.4 Hz), 8.14 (1H, d, J=7.6 Hz), 7.42 (1H, t, J=7.9 Hz). m/z (ESI, +ve ion) 257.9/259.9 (M+H)$^+$.

Preparation of (8-bromo-N2-(tert-butyl)quinazoline-2,4-diamine (484b)

A microwave vial was charged with 8-bromo-2-chloroquinazolin-4-amine (484a; 0.109 g, 0.422 mmol) and tert-butylamine (Aldrich; 1.33 mL, 12.65 mmol). The slurry was heated to 120° C. in a biotage initiator microwave for 30 min. 0.5 mL NMP was added to give a solution and the reaction was heated to 120° C. in a biotage initiator microwave for 30 min. The reaction was heated to 150° C. in a biotage initiator microwave for 30 min. The reaction was heated to 160° C. in a biotage initiator microwave for 30 min and then was heated to 170° C. in a biotage initiator microwave for 30 min. The reaction was partitioned between water and EtOAc. The organic layer was washed with water 2 times, saturated aqueous NaCl once, and the organics were dried over anhydrous $Na_2SO_4$, filtered, and concentrated in vacuo to give 8-bromo-N2-(tert-butyl)quinazoline-2,4-diamine (0.133 g, 0.451 mmol, quant. yield) as a brown foam: $^1$H NMR (400 MHz, CDCl$_3$) δ ppm 7.87 (1H, dd, J=7.5, 1.3 Hz), 7.48 (1H, d, J=7.8 Hz), 6.92 (1H, t, J=7.8 Hz), 5.27 (2H, br. s.), 5.02 (1H, br. s.), 1.55 (9H, s). m/z (ESI, +ve ion) 295.0/297.0 (M+H)$^+$.

Preparation of (6R)-2-(4-amino-2-(tert-butylamino)-8-quinazolinyl)-6-methyl-5,6-dihydropyrrolo[3,4-b]pyrrol-4(1H)-one (484)

Argon was bubbled into a slurry of potassium carbonate (Mallinkrodt; 0.140 g, 1.016 mmol), dichlorobis(p-dimethylaminophenylditbutylphosphine)palladium (ii) (Aldrich; 0.018 g, 0.025 mmol), (R)-6-methyl-2-(4,4,5,5-tetramethyl-1,3,2-dioxaborolan-2-yl)-5,6-dihydropyrrolo[3,4-b]pyrrol-4(1H)-one (705; 0.133 g, 0.51 mmol), 8-bromo-N2-(tert-butyl)quinazoline-2,4-diamine (484b; 0.075 g, 0.254 mmol) in 2 mL dioxane and 0.4 mL water for 1 min. The reaction was sealed and heated to 80° C. for 30 min. The reaction was adsorbed onto 1 g silica gel and dried in vacuo. The material was treated with purified by silica gel chromatography (12 g column) using 0-100% (90/10 (DCM/2.0 M NH$_3$/MeOH) in DCM). The product-containing fractions were concentrated to afford (R)-2-(4-amino-2-(tert-butylamino)quinazolin-8-yl)-6-methyl-5,6-dihydropyrrolo[3,4-b]pyrrol-4(1H)-one (0.044 g, 0.126 mmol, 49% yield) as an orange solid. $^1$H NMR (400 MHz, DMSO-$d_6$) δ ppm 13.13 (1H, s), 7.97 (1H, dd, J=7.6, 1.2 Hz), 7.83 (1H, d, J=8.0 Hz), 7.59 (1H, s), 7.32-7.47 (2H, m), 7.02 (1H, t, J=7.7 Hz), 6.76 (1H, d, J=1.2 Hz), 6.47 (1H, br. s.), 4.56 (1H, q, J=6.7 Hz), 1.49 (9H, s), 1.41 (3H, d, J=6.7 Hz). m/z (ESI, +ve ion) 351.0 (M+H)$^+$.

Example 485 rac-2-(tert-butylamino)-8-(6-(methoxymethyl)-4-oxo-1,4,5,6-tetrahydropyrrolo[3,4-b]pyrrol-2-yl)-3-methylquinazolin-4(31-1)-one

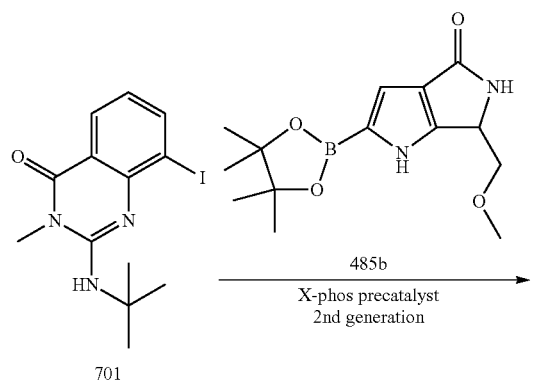

Preparation of 6-(methoxymethyl)-2-(4,4,5,5-tetramethyl-1,3,2-dioxaborolan-2-yl)-5,6-dihydropyrrolo[3,4-b]pyrrol-4(1H)-one (485b)

6-(Methoxymethyl)-5,6-dihydropyrrolo[3,4-b]pyrrolo-4(1H)-one (485a) was prepared in a manner similar to that described for Intermediate 702, starting from (R)-2-((tert-butoxycarbonyl)amino)-3-methoxypropanoic acid (prepared according to the procedure in WO 2012/051551). $^1$H NMR (400 MHz, DMSO-d$_6$) δ ppm 11.32 (br. s., 1H), 7.58 (s, 1H), 6.83 (d, J=2.74 Hz, 1H), 6.09 (d, J=2.74 Hz, 1H), 4.50 (ddd, J=6.75, 5.58, 1.37 Hz, 1H), 3.37-3.49 (m, 2H), 3.30 (s, 3H). m/z (ES, +ve) 167.0 (M+H)$^+$. 6-(Methoxymethyl)-2-(4,4,5,5-tetramethyl-1,3,2-dioxaborolan-2-yl)-5,6-dihydropyrrolo[3,4-b]pyrrol-4(1H)-one (485b) was prepared in a manner similar to that described for Intermediate 705, using 6-(methoxymethyl)-5,6-dihydropyrrolo[3,4-b]pyrrol-4(1H)-one (485a) as the starting material. $^1$H NMR (400 MHz, CDCl$_3$) δ ppm 6.93 (d, J=1.76 Hz, 1H), 5.85 (s, 1H), 4.56-4.65 (m, 1H), 3.55 (dd, J=8.61, 7.04 Hz, 1H), 3.40-3.47 (m, 4H), 1.30-1.36 (m, 12H). m/z (ES, +ve) 293.1 (M+H)$^+$.

Preparation of 2-(tert-butylamino)-8-(6-(methoxymethyl)-4-oxo-1,4,5,6-tetrahydropyrrolo[3,4-b]pyrrol-2-yl)-3-methylquinazolin-4(3H)-one A microwave tube was charged with 2-(tert-butylamino)-8-iodo-3-methylquinazolin-4(3H)-one (701; 316 mg, 0.89 mmol), 6-(methoxymethyl)-2-(4,4,5,5-tetramethyl-1,3,2-dioxaborolan-2-yl)-5,6-dihydropyrrolo[3,4-b]pyrrol-4(1H)-one (485b, 323 mg, 1.11 mmol), X-Phos precatalyst II (Sigma-Aldrich; 35 mg, 0.044 mmol) and K$_3$PO$_4$ (563 mg, 2.65 mmol). The tube was sealed and purged with argon for 5 minutes. 1,4-dioxane (2.6 mL) and water (0.65 mL) were added and Ar (g) was bubbled through the mixture for 5 min. The tube was heated at 45° C. in an oil bath for 90 min. The reaction mixture was cooled to RT and EtOAc and water were added. The layers were separated and the aqueous layer was extracted with EtOAc (2×). The combined organic layers were dried over anhydrous Na$_2$SO$_4$, filtered and concentrated. The crude material was absorbed onto a plug of silica gel and purified by silica gel chromatography (0-10% MeOH in CH$_2$Cl$_2$), to provide rac-2-(tert-butylamino)-8-(6-(methoxymethyl)-4-oxo-1,4,5,6-tetrahydropyrrolo[3,4-b]pyrrol-2-yl)-3-methylquinazolin-4(3H)-one (485) (160 mg, 0.41 mmol, 46% yield) as a tan solid. $^1$H NMR (400 MHz, CDCl$_3$) δ ppm 12.19 (br. s., 1H), 8.07 (dd, J=7.82, 1.76 Hz, 1H), 8.00 (dd, J=7.63, 1.76 Hz, 1H), 7.22 (t, J=7.73 Hz, 1H), 6.83 (d, J=1.57 Hz, 1H), 5.85 (s, 1H), 4.65-4.72 (m, 1H), 4.61 (s, 1H), 3.65 (dd, J=9.00, 5.48 Hz, 1H), 3.55 (s, 3H), 3.46 (t, J=8.61 Hz, 1H), 3.41 (s, 3H), 1.65 (s, 9H). m/z (ES, +ve) 396.0 (M+H)$^+$.

Example 493

2-(tert-butylamino)-8-((6R)-6-(methoxymethyl)-4-oxo-1,4,5,6-tetrahydropyrrolo[3,4-b]pyrrol-2-yl)-3-methyl-4(3H)-quinazolinone (first eluting enantiomer)

Example 494

2-(tert-butylamino)-8-46S)-6-(methoxymethyl)-4-oxo-1,4,5,6-tetrahydropyrrolo[3,4-b]pyrrol-2-yl)-3-methyl-4(3H)-quinazolinone (second eluting enantiomer)

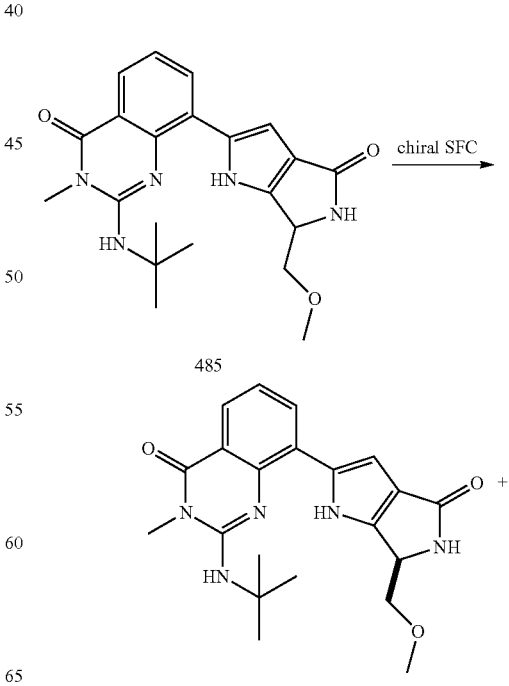

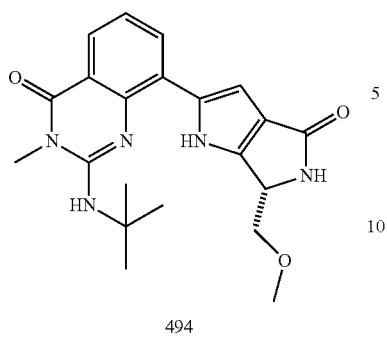

494

The mixture of enantiomers (485, 140 mg, 0.35 mmol) was separated by preparative chiral SFC (ChiralPak AS-H (Sepax) (21×150 mm, 5 μm); additive in supercritical fluid $CO_2$ was 45% MeOH with 20 mM $NH_3$; 70 mL/min; column temperature 40° C.; outlet pressure 100 bar) to give separated enantiomers. The enanantiomeric excess was determined by analytical chiral SFC (ChiralPak AS-H (Sepax) (4.6×150 mm, 5 μm); additive in supercritical fluid $CO_2$ was 50% MeOH with 20 mM $NH_3$; 4.0 mL/min; column temperature 40° C.; outlet pressure 100 bar). Example 493: (first eluting peak) (55 mg, 0.14 mmol, >99% ee) was isolated as an off white solid. $^1$H NMR (400 MHz, $CDCl_3$) δ ppm 12.19 (br. s., 1H), 8.07 (dd, J=7.82, 1.56 Hz, 1H), 8.00 (dd, J=7.63, 1.56 Hz, 1H), 7.22 (t, J=7.73 Hz, 1H), 6.84 (d, J=1.37 Hz, 1H), 5.83 (s, 1H), 4.68 (dd, J=7.73, 5.77 Hz, 1H), 4.61 (s, 1H), 3.65 (dd, J=8.90, 5.38 Hz, 1H), 3.55 (s, 3H), 3.43-3.48 (m, 1H), 3.41 (s, 3H), 1.65 (s, 9H). m/z (ES, +ve) 396.2 (M+H)$^+$. Example 494: (second eluting peak) (60 mg, 0.15 mmol, >98% ee) was isolated as an off white solid. m/z (ES, +ve) 396.0 (M+H)$^+$.

Example 486

N-((1R,3S)-3-((3-methyl-8-((6R)-6-methyl-4-oxo-1,4,5,6-tetrahydropyrrolo[3,4-b]pyrrol-2-yl)-2-quinoxalinyl)amino)cyclohexyl)acetamide

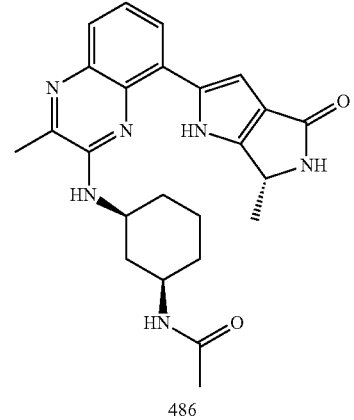

486

A mixture of (R)-2-(3-(((1S,3R)-3-aminocyclohexyl) amino)-2-methylquinoxalin-5-yl)-6-methyl-5,6-dihydropyrrolo[3,4-b]pyrrol-4(1H)-one (483) (29 mg, 0.074 mmol), acetic anhydride (35.0 μL, 0.37 mmol), and N-ethyl-N-isopropylpropan-2-amine (91 μL, 0.52 mmol) in DCM (743 μL) was stirred at RT for 30 min when mostly product was observed via LCMS. The reaction mixture was diluted with DCM (100 mL), added to a separatory funnel, and washed with saturated aqueous sodium bicarbonate (2×75 mL); the organic layer was separated, dried over $Na_2SO_4$, and concentrated. The crude product in DCM was loaded onto the column and was purified via automated flash chromatography (silica gel) with 100% DCM to 8% 2 M ammonia in MeOH/DCM to give N-((1R,3S)-3-((3-methyl-8-((R)-6-methyl-4-oxo-1,4,5,6-tetrahydropyrrolo[3,4-b]pyrrol-2-yl)quinoxalin-2-yl)amino)cyclohexyl)acetamide (486, 19 mg, 0.044 mmol, 59% yield) as a yellow solid. $^1$H NMR (400 MHz, DMSO-$d_6$) δ ppm 1.08-1.20 (m, 1H) 1.20-1.32 (m, 1H) 1.42 (d, J=6.65 Hz, 3H) 1.44-1.52 (m, 2H) 1.78 (s, 3H) 1.80-1.90 (m, 2H) 2.11 (br. s., 2H) 2.53 (s, 3H) 3.58-3.71 (m, 1H) 4.04-4.17 (m, 1H) 4.54 (q, J=6.59 Hz, 1H) 6.87 (d, J=7.63 Hz, 1H) 6.95 (d, J=1.57 Hz, 1H) 7.33 (t, J=7.82 Hz, 1H) 7.59 (dd, J=8.02, 1.37 Hz, 1H) 7.62 (s, 1H) 7.81-7.88 (m, 2H) 11.99 (s, 1H). MS (ESI, pos. ion) m/z: 433.1 (M+1).

Example 487

(6R)-6-methyl-2-(2-methyl-3-(((1S,3R)-3-((2,2,2-trifluoroethyl)amino)cyclohexyl)amino)-5-quinoxalinyl)-5,6-dihydropyrrolo[3,4-b]pyrrol-4(1H)-one

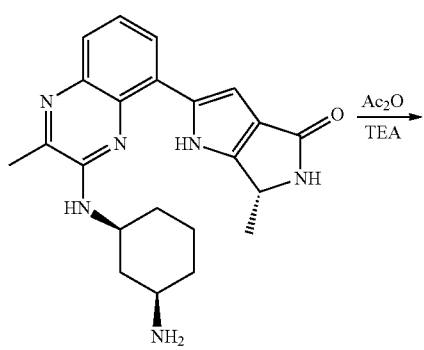

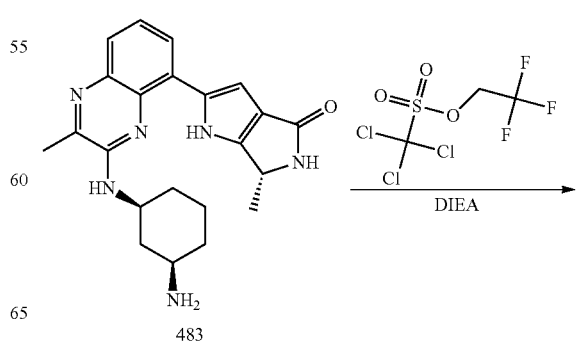

483

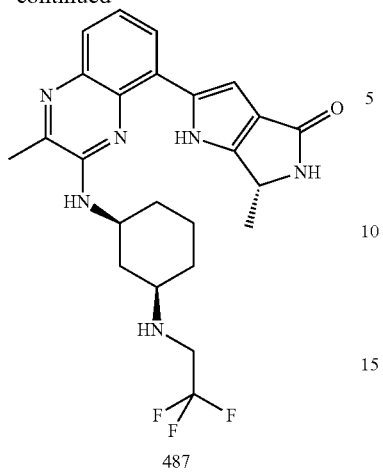

487

A mixture of 2-(((1S,3R)-3-aminocyclohexyl)amino)-3-methyl-8-((R)-6-methyl-4-oxo-1,4,5,6-tetrahydropyrrolo[3,4-b]pyrrol-2-yl)quinazolin-4(3H)-one (483, 107 mg, 0.263 mmol), 2,2,2-trifluoroethyl trichloromethanesulphonate (Oakwood Products, Inc., West Columbia, S.C., 370 mg, 1.316 mmol), and DIEA (0.230 mL, 1.316 mmol) in DMF (2.63 mL) was stirred at 110° C. for 1 h when product was observed via LCMS. The reaction mixture was diluted with saturated aqueous sodium bicarbonate (100 mL), added to a separatory funnel, and washed with DCM (3×75 mL); the organic layer was separated, dried over $Na_2SO_4$, and concentrated. The crude product was loaded onto the column and was purified via automated flash chromatography (silica gel) with 100% DCM to 6% 2 M ammonia in MeOH/DCM to give (R)-6-methyl-2-(2-methyl-3-(((1,3R)-3-((2,2,2-trifluoroethyl)amino)cyclohexyl)amino)quinoxalin-5-yl)-5,6-dihydropyrrolo[3,4-b]pyrrol-4(1H)-one (487, 42 mg, 0.089 mmol, 32% yield) as a yellow amorphous solid. $^1$H NMR (400 MHz, DMSO-$d_6$) δ ppm 0.98-1.11 (m, 1H) 1.25 (q, J=11.22 Hz, 1H) 1.30-1.38 (m, 2H) 1.41 (d, J=6.65 Hz, 3H) 1.77-1.86 (m, 1H) 1.92 (d, J=12.13 Hz, 1H) 2.00-2.08 (m, 1H) 2.23-2.38 (m, 2H) 2.53 (s, 3H) 2.60-2.70 (m, 1H) 3.20-3.29 (m, 2H) 3.97-4.10 (m, 1H) 4.49-4.58 (m, 1H) 6.91 (d, J=7.63 Hz, 1H) 7.06 (d, J=1.56 Hz, 1H) 7.33 (t, J=7.82 Hz, 1H) 7.59 (dd, J=8.02, 1.37 Hz, 1H) 7.61 (s, 1H) 7.85 (dd, J=7.53, 1.27 Hz, 1H) 11.99 (s, 1H). $^{19}$F NMR (377 MHz, DMSO-$d_6$) δ ppm −70.67 (s, 3F). MS (ESI, pos. ion) m/z: 473.1 (M+1).

Example 488

2-(ethyl (1-methylethyl)amino)-8-((06R)-6-methyl-4-oxo-1,4,5,6-tetrahydropyrrolo[3,4-b]pyrrol-2-yl)-4(3H)-quinazolinone

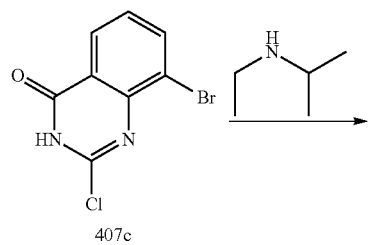

407c

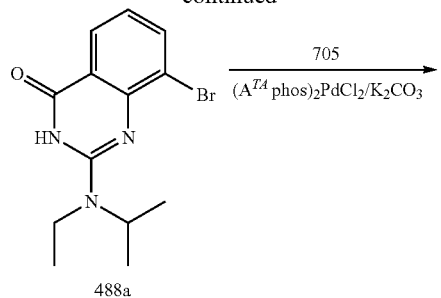

488a

488

Preparation of 8-bromo-2-(ethyl(isopropyl)amino)quinazolin-4-ol (488a)

A slurry of N-ethylisopropylamine (1.40 mL, 11.56 mmol) and 8-bromo-2-chloroquinazolin-4-ol (407c; 0.10 g, 0.385 mmol) was sealed in a microwave tube and heated to 170° C. for 30 min. The reaction was judged complete and clean. The reaction was partitioned between satd aq ammonium chloride and DCM. The aqueous layer was extracted with DCM 3 times, and the combined organics were dried over anhydrous $Na_2SO_4$, filtered, and concentrated in vacuo to give 8-bromo-2-(ethyl(isopropyl)amino)quinazolin-4-ol (0.116 g, 0.374 mmol, 97% yield) as a brown semi-solid. $^1$H NMR (400 MHz, DMSO-$d_6$) δ ppm 7.87 (2H, m), 6.96 (1H, t, J=7.7 Hz), 4.81 (1H, dt, J=13.4, 6.7 Hz), 3.51 (2H, q, J=7.0 Hz), 1.13-1.24 (9H, m). m/z (ESI, +ve ion) 310.0/312.0 (M+H)$^+$.

Preparation of 2-(ethyl(1-methylethyl)amino)-8-((6R)-6-methyl-4-oxo-1,4,5,6-tetrahydropyrrolo[3,4-b]pyrrol-2-yl)-4(3H)-quinazolinone (488)

Argon was bubbled into a slurry of potassium carbonate (Mallinkrodt; 0.068 ml, 1.122 mmol), 1,1-bis[(di-t-butyl-p-methylaminophenyl]palladium(ii) chloride (Aldrich; 0.013 g, 0.019 mmol), 8-bromo-2-(ethyl(isopropyl)amino)quinazolin-4-ol (488a; 0.116 g, 0.374 mmol), (R)-6-methyl-2-(4,4,5,5-tetramethyl-1,3,2-dioxaborolan-2-yl)-5,6-dihydropyrrolo[3,4-b]pyrrol-4(1H)-one (705; 0.147 g, 0.561 mmol) in 2 mL dioxane and 0.4 mL water for 1 min and the reaction was sealed and placed in an 80° C. oil bath for 1 h. The reaction was cooled and adsorbed onto 1 g silica gel and was purified by silica gel chromatography (24 g column) using 0-100% (90/10 DCM/MeOH in DCM). The product-containing fractions were concentrated to afford 0.044 g yellow solid. The material was sonicated in 1 mL MeOH and filtered, rinsing with 1 mL MeOH. The yellow solid was collected and dried in vacuo to give (R)-2-(ethyl(isopropyl)amino)-8-(6-methyl-4-oxo-1,4,5,6-tetrahydropyrrolo[3,4-b]pyrrol-2-yl)quinazolin-4(3H)-one (0.031 g, 0.085 mmol, 22% yield) as a yellow solid: $^1$H NMR (400 MHz, DMSO-$d_6$) δ ppm 12.17 (1H, br. s.), 11.23 (1H, s), 7.88-8.09 (1H, m), 7.82 (1H, dd, J=7.8, 1.4 Hz), 7.61 (1H, s), 7.13 (1H, t, J=7.7 Hz), 6.80 (1H, s), 4.70 (1H, dt, J=12.9, 6.5 Hz), 4.55 (1H, q, J=6.7 Hz), 3.57 (2H, qd, J=14.7, 7.4 Hz), 1.36 (3H, d, J=6.7 Hz), 1.12-1.30 (9H, m). m/z (ESI, +ve ion) 366.1 (M+H)$^+$.

Example 489

N-((1R,3S)-3-((3-methyl-8-((6R)-6-methyl-4-oxo-1,4,5,6-tetrahydropyrrolo[3,4-b]pyrrol-2-yl)-2-quinoxalinyl)amino)cyclohexyl)methanesulfonamide

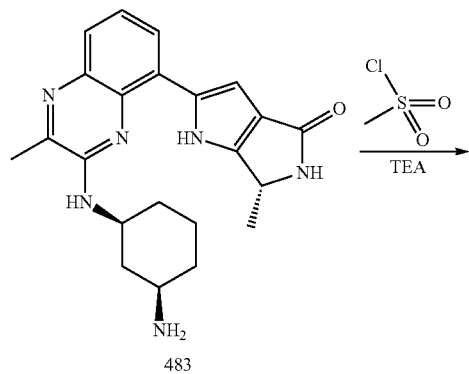

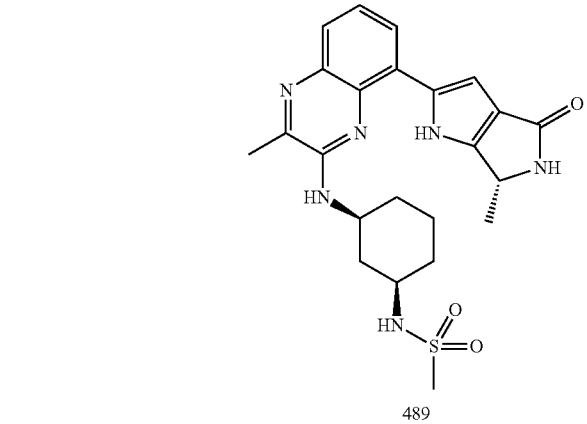

A mixture of (R)-2-(3-(((1S,3R)-3-aminocyclohexyl)amino)-2-methylquinoxalin-5-yl)-6-methyl-5,6-dihydropyrrolo[3,4-b]pyrrol-4(1H)-one (483, 52 mg, 0.133 mmol), methanesulfonyl chloride (41.4 μL, 0.533 mmol), and triethylamine (74.2 μL, 0.533 mmol) in DCM (1.33 mL) was stirred at 0° C. for 5 min; the reaction mixture was warmed to RT and stir for 1 h when product was observed via LCMS. The reaction mixture was diluted with DCM (100 mL), added to a separatory funnel, and washed with saturated aqueous NaHCO$_3$ (2×75 mL); the organic layer was separated, dried over Na$_2$SO$_4$, and concentrated. The crude product was loaded onto the column and was purified via automated flash chromatography (silica gel) with 0-5% 2 M ammonia in MeOH/DCM to give N-((1R,3S)-3-((3-methyl-8-((R)-6-methyl-4-oxo-1,4,5,6-tetrahydropyrrolo[3,4-b]pyrrol-2-yl)quinoxalin-2-yl)amino)cyclohexyl)methanesulfonamide (489, 6 mg, 0.013 mmol, 10% yield) as a yellow solid. $^1$H NMR (400 MHz, CDCl$_3$) δ ppm 1.24-1.36 (m, 2H) 1.37-1.51 (m, 2H) 1.59 (d, J=6.65 Hz, 3H) 1.99-2.06 (m, 1H) 2.16-2.23 (m, 1H) 2.39 (d, J=11.15 Hz, 1H) 2.52-2.57 (m, 1H) 2.59 (s, 3H) 3.00 (s, 3H) 3.48-3.59 (m, 1H) 3.99-4.10 (m, 1H) 4.54 (d, J=7.04 Hz, 1H) 4.68 (q, J=6.98 Hz, 1H) 4.97 (d, J=6.65 Hz, 1H) 5.68 (s, 1H) 6.92 (d, J=1.37 Hz, 1H) 7.42 (t, J=7.82 Hz, 1H) 7.69-7.74 (m, 1H) 7.91-7.97 (m, 1H) 12.29 (br. s., 1H). MS (ESI, pos. ion) m/z: 469.1 (M+1).

Example 490

(R)-3-cyclopropyl-7-fluoro-2-(isopropylamino)-8-(6-methyl-4-oxo-1,4,5,6-tetrahydropyrrolo[3,4-b]pyrrol-2-yl)quinazolin-4(3H)-one

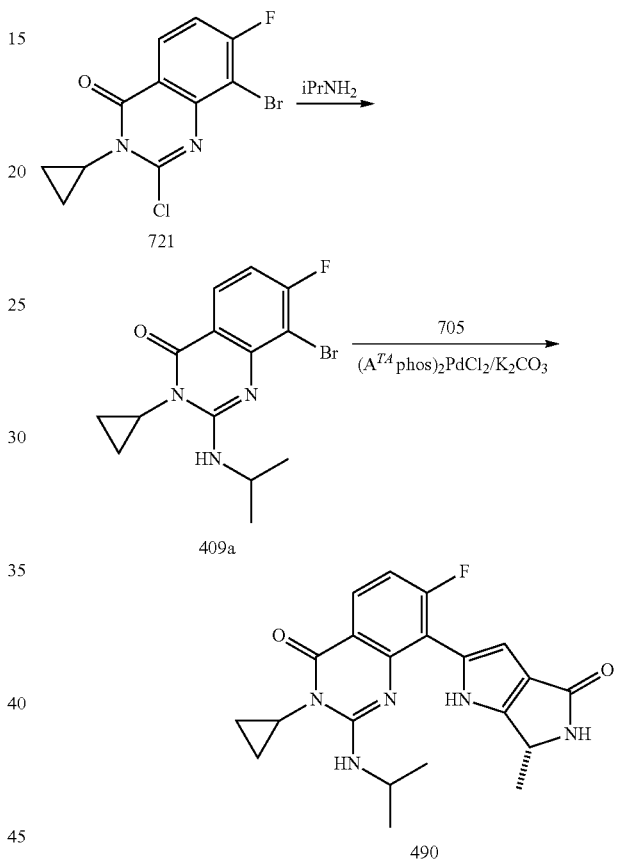

Preparation of 8-bromo-3-cyclopropyl-7-fluoro-2-(isopropylamino)quinazolin-4(3H)-one (490a)

A slurry of 8-bromo-2-chloro-3-cyclopropyl-7-fluoroquinazolin-4(3H)-one (721; 0.080 g, 0.252 mmol) in isopropylamine (Aldrich; 0.541 ml, 6.30 mmol) and 0.2 mL NMP was heated in a sealed tube in a biotage initiator microwave to 100° C. for 20 min. The reaction was partitioned between water and EtOAc. The organic layer was washed with water once, satd aq NaCl once, and the organics were dried over anhydrous Na$_2$SO$_4$, filtered, and concentrated in vacuo to give 8-bromo-3-cyclopropyl-7-fluoro-2-(isopropylamino)quinazolin-4(3H)-one (0.079 g, 0.232 mmol, 92% yield) as a brown solid: $^1$H NMR (400 MHz, DMSO-d$_6$) δ ppm 7.89 (1H, dd, J=8.8, 6.5 Hz), 7.01 (1H, t, J=8.7 Hz), 6.85 (1H, d, J=7.6 Hz), 4.41 (1H, dq, J=13.6, 6.7 Hz), 2.64-2.79 (1H, m), 1.30 (6H, d, J=6.7 Hz), 1.19-1.27 (2H, m), 0.71-0.79 (2H, m). m/z (ESI, +ve ion) 340.0/342.0 (M+H)$^+$.

Preparation of (R)-3-cyclopropyl-7-fluoro-2-(isopropylamino)-8-(6-methyl-4-oxo-1,4,5,6-tetrahydropyrrolo[3,4-b]pyrrol-2-yl)quinazolin-4(3H)-one (490)

Argon was bubbled into a slurry of potassium carbonate (Mallinkrodt; 0.056 ml, 0.929 mmol), 1,1-bis[(di-t-butyl-p-methylaminophenyl]palladium(ii) chloride (Aldrich; 8.22 mg, 0.012 mmol), 8-bromo-3-cyclopropyl-7-fluoro-2-(isopropylamino)quinazolin-4(3H)-one (0.079 g, 0.232 mmol), (R)-6-methyl-2-(4,4,5,5-tetramethyl-1,3,2-dioxaborolan-2-yl)-5,6-dihydropyrrolo[3,4-b]pyrrolo-4(1H)-one (705; 0.122 g, 0.464 mmol) in 2 mL dioxane and 0.4 mL water for 1 min and the reaction was sealed and placed in an 80° C. oil bath for 1 h. The reaction was cooled and adsorbed onto 1 g silica gel and the material was purified by silica gel chromatography (12 g column) using 0-100% (90/10 DCM/MeOH in DCM). The product-containing fractions were concentrated to afford 0.041 g of an off-white solid. The material was sonicated in 0.5 mL MeOH and filtered, rinsing 1× MeOH, and dried in vacuo to give (R)-3-cyclopropyl-7-fluoro-2-(isopropylamino)-8-(6-methyl-4-oxo-1,4,5,6-tetrahydropyrrolo[3,4-b]pyrrol-2-yl)quinazolin-4(3H)-one (0.026 g, 0.066 mmol, 28% yield) as a white solid. $^1$H NMR (400 MHz, DMSO-d$_6$) δ ppm 12.45 (1H, s), 7.83 (1H, dd, J=8.8, 6.3 Hz), 7.65 (1H, s), 7.03 (1H, dd, J=11.2, 8.8 Hz), 6.87 (1H, d, J=7.4 Hz), 6.60 (1H, d, J=2.5 Hz), 4.57 (1H, q, J=6.7 Hz), 4.23 (1H, dq, J=13.4, 6.7 Hz), 2.73-2.84 (1H, m), 1.32-1.39 (6H, m), 1.29 (3H, d, J=6.7 Hz), 1.22-1.28 (2H, m), 0.70-0.82 (2H, m). m/z (ESI, +ve ion) 396.0 (M+H)$^+$.

Example 491 tert-butyl((1R)-1-(hydroxymethyl)-2-(((1R,3S)-3-((3-methyl-8-((6R)-6-methyl-4-oxo-1,4,5,6-tetrahydropyrrolo[3,4-b]pyrrol-2-yl)-2-quinoxalinyl)amino)cyclohexyl)amino)-2-oxoethyl)carbamate

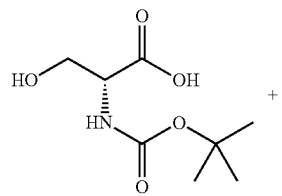

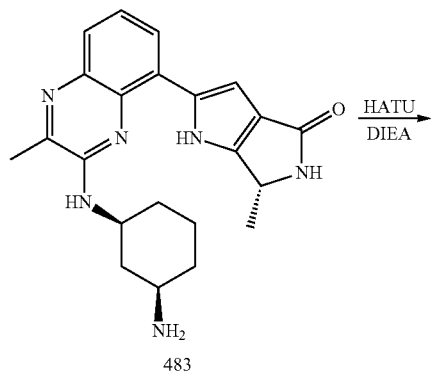
483

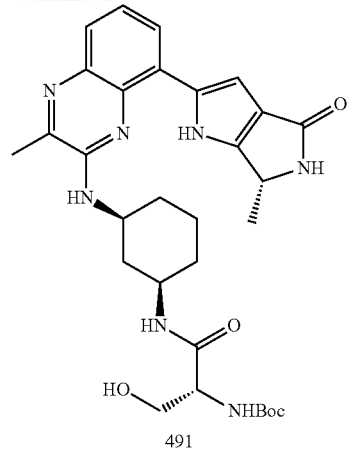
491

A solution of (R)-2-(3-(((1S,3R)-3-aminocyclohexyl)amino)-2-methylquinoxalin-5-yl)-6-methyl-5,6-dihydropyrrolo[3,4-b]pyrrol-4(1H)-one (483, 54 mg, 0.138 mmol), (R)-2-((tert-butoxycarbonyl)amino)-3-hydroxypropanoic acid (Sigma-Aldrich Co., 56.8 mg, 0.277 mmol), HATU (63 mg, 0.166 mmol), and DIEA (48 µL, 0.277 mmol) in DMF (1.383 mL) was stirred at RT for 1 h when mostly product was observed via LCMS. The reaction mixture was diluted with EtOAc (150 mL), added to a separatory funnel, and washed with saturated aqueous sodium bicarbonate (3×100 mL); the organic layer was separated, dried over Na$_2$SO$_4$, and concentrated. The crude product was loaded onto the column and was purified via automated flash chromatography (silica gel) with 100% DCM to 10% 2 M ammonia in MeOH/DCM to give tert-butyl((R)-3-hydroxy-1-(((1R,3S)-3-((3-methyl-84R)-6-methyl-4-oxo-1,4,5,6-tetrahydropyrrolo[3,4-b]pyrrol-2-yl)quinoxalin-2-yl)amino)cyclohexyl)amino)-1-oxopropan-2-yl)carbamate (491, 34 mg, 0.059 mmol, 43% yield) as a yellow solid. $^1$H NMR (400 MHz, MeOH-d4) δ ppm 1.29-1.36 (m, 1H) 1.46 (s, 9H) 1.52 (d, J=11.93 Hz, 1H) 1.58 (d, J=6.65 Hz, 3H) 1.90-2.00 (m, 1H) 2.00-2.07 (m, 1H) 2.25 (d, J=11.93 Hz, 1H) 2.35 (d, J=11.74 Hz, 1H) 2.52 (s, 3H) 3.37 (s, 2H) 3.73 (d, J=5.28 Hz, 2H) 3.88 (ddd, J=11.64, 7.92, 3.91 Hz, 1H) 4.00-4.17 (m, 2H) 4.67 (q, J=6.65 Hz, 1H) 6.83 (s, 1H) 7.33 (t, J=7.82 Hz, 1H) 7.58 (d, J=8.02 Hz, 1H) 7.83-7.90 (m, 1H). MS (ESI, pos. ion) m/z: 578.2 (M+1).

Example 492

(R)-3-cyclopropyl-8-(6-methyl-4-oxo-1,4,5,6-tetrahydropyrrolo[3,4-b]pyrrol-2-yl)-2-((1-methylcyclopropyl)amino)quinazolin-4(3H)-one

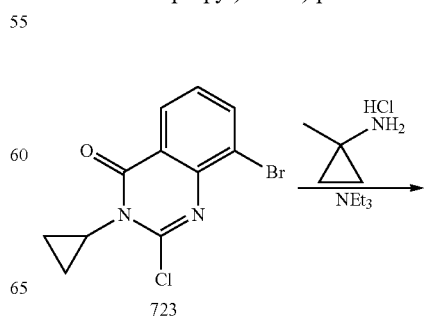
723

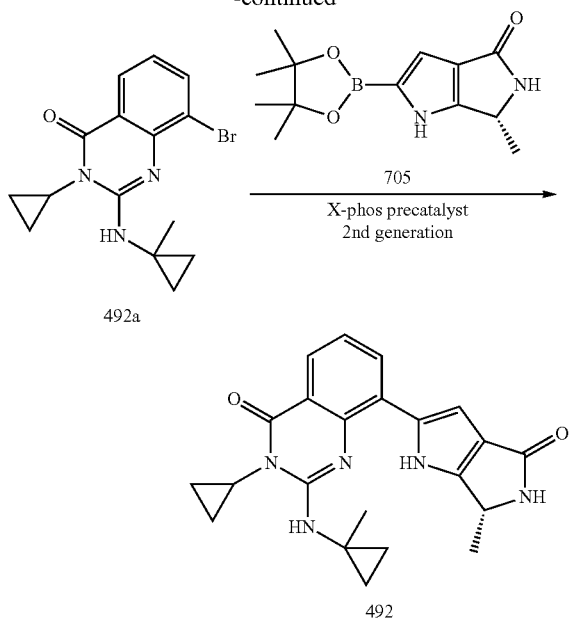

Preparation of 492a: 8-bromo-3-cyclopropyl-2-((1-methylcyclopropyl)amino)-quinazolin-4(3H)-one A glass microwave reaction vessel was charged with 8-bromo-2-chloro-3-cyclopropylquinazolin-4(3H)-one (723) (200 mg, 0.67 mmol), 1-methylcyclopropanamine hydrochloride (Small Molecules, Inc.; 126 mg, 1.17 mmol) and NEt$_3$ (0.46 mL, 3.34 mmol) in DMSO (0.5 mL). The tube was sealed and heated in an oil bath at 100° C. After 1 h, water and EtOAc were added and the layers were separated. The aqueous layer was extracted with EtOAc (2×). The combined organic layers were dried over anhydrous Na$_2$SO$_4$, filtered and concentrated. The crude material was absorbed onto a plug of silica gel and purified by silica gel chromatography (0-50% EtOAc in hexanes), to provide 8-bromo-3-cyclopropyl-2-((1-methylcyclopropyl)amino)-quinazolin-4(3H)-one (492a) (170 mg, 0.51 mmol, 76% yield) as a white solid. $^1$H NMR (400 MHz, CDCl$_3$) δ ppm 8.02 (dd, J=8.02, 1.56 Hz, 1H), 7.84 (dd, J=7.63, 1.57 Hz, 1H), 6.96 (t, J=7.73 Hz, 1H), 5.77 (s, 1H), 2.65 (tt, J=6.75, 4.11 Hz, 1H), 1.61 (s, 3H), 1.27-1.34 (m, 2H), 0.85-0.92 (m, 4H), 0.80-0.85 (m, 2H). m/z (ES, +ve) 334.0, 336.0 (M+H)$^+$.

Preparation of 492: (R)-3-cyclopropyl-8-(6-methyl-4-oxo-1,4,5,6-tetrahydropyrrolo[3,4-b]pyrrol-2-yl)-2-((1-methylcyclopropyl)amino)quinazolin-4(3H)-one A microwave tube was charged with 8-bromo-3-cyclopropyl-2-((1-methylcyclopropyl)amino)quinazolin-4(3H)-one (492a; 170 mg, 0.51 mmol), (R)-6-methyl-2-(4,4,5,5-tetramethyl-1,3,2-dioxaborolan-2-yl)-5,6-dihydropyrrolo[3,4-b]pyrrol-4(1H)-one (705; 167 mg, 0.64 mmol), X-Phos precatalyst II generation (Sigma-Aldrich; 20 mg, 0.025 mmol) and K$_3$PO$_4$ (Sigma-Aldrich; 324 mg, 1.53 mmol). The tube was sealed and purged with argon for 5 min. 1,4-Dioxane (1.4 mL) and water (0.35 mL) were added and Ar (g) was bubbled through the mixture for 5 min. The tube was sealed and heated in an oil bath at 45° C. for 90 min. The reaction was then cooled to RT and EtOAc and water were added. The layers were separated and the aqueous layer was extracted with EtOAc (2×). The combined organic layers were dried over anhydrous Na$_2$SO$_4$, filtered and concentrated. The crude material was absorbed onto a plug of silica gel and purified by silica gel chromatography (0-10% MeOH in CH$_2$Cl$_2$), to provide (R)-3-cyclopropyl-8-(6-methyl-4-oxo-1,4,5,6-tetrahydropyrrolo[3,4-b]pyrrol-2-yl)-2-((1-methylcyclopropyl)amino)quinazolin-4(1H)-one (492) (117 mg, 0.30 mmol, 59% yield) as a tan solid. $^1$H NMR (400 MHz, DMSO-d$_6$) δ ppm 13.01 (s, 1H), 8.09 (dd, J=7.63, 1.37 Hz, 1H), 7.77 (dd, J=7.73, 1.27 Hz, 1H), 7.68 (s, 1H), 7.59 (s, 1H), 7.13 (t, J=7.73 Hz, 1H), 6.93 (d, J=0.98 Hz, 1H), 4.63 (q, J=6.46 Hz, 1H), 2.67-2.74 (m, 1H), 1.55 (s, 3H), 1.36 (d, J=6.65 Hz, 3H), 1.19-1.27 (m, 2H), 0.99-1.04 (m, 2H), 0.83-0.88 (m, 2H), 0.73 (dd, J=3.91, 2.54 Hz, 2H). m/z (ES, +ve) 390.0 (M+H)$^+$.

Example 495

(R)-3-cyclopropyl-7-fluoro-8-(6-methyl-4-oxo-1,4,5,6-tetrahydropyrrolo[3,4-b]pyrrol-2-yl)-2-((1-methylcyclopropyl)amino)quinazolin

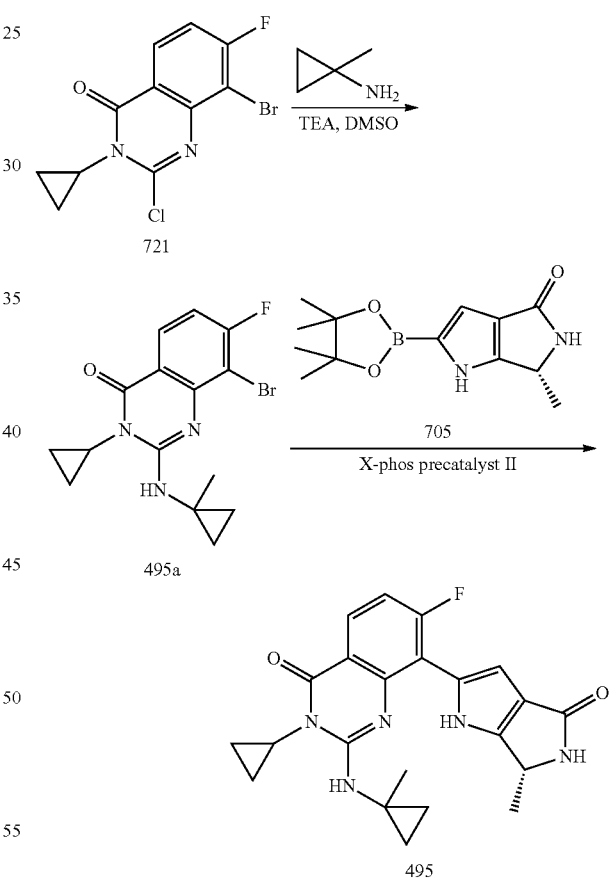

Preparation of 8-bromo-3-cyclopropyl-7-fluoro-2-((1-methylcyclopropyl)amino)quinazolin-4(3H)-one (495a)

A glass microwave reaction vessel was charged with 8-bromo-2-chloro-3-cyclopropyl-7-fluoroquinazolin-4(3H)-one (721) (125 mg, 0.394 mmol) and 1-methylcyclopropanamine hydrochloride (127 mg, 1.18 mmol, Small Molecules Inc.) in DMSO (1.0 mL) followed by triethylamine (0.16 mL, 1.18 mmol). The reaction mixture was stirred and heated in an Initiator microwave reactor (Personal Chemistry, Biotage AB, Inc., Upssala, Sweden) at 100° C. for 1 h. The mixture was diluted with water (20 mL) and extracted with DCM (30 mL×4). The combined organic layers were washed with water (15 mL), dried (MgSO$_4$), filtered and concentrated. The residue was triturated with hexanes and filtered to give the crude product 96 mg. MS (ESI, pos. ion) m/z: 352 (M+1); $^1$H NMR (400 MHz, CDCl$_3$) δ ppm 8.03 (1H, dd, J=8.8, 6.1 Hz), 6.90 (1H, t, J=8.4 Hz), 2.65-2.74 (1H, m), 1.61 (3H, s), 1.30-1.37 (2H, m), 0.83-0.96 (6H, m).

Preparation of (R)-3-cyclopropyl-7-fluoro-8-(6-methyl-4-oxo-1,4,5,6-tetrahydropyrrolo[3,4-b]pyrrol-2-yl)-2-((1-methylcyclopropyl)amino)quinazolin-4(3H)-one (495)

A glass microwave reaction vessel was charged with 8-bromo-3-cyclopropyl-7-fluoro-2-((1-methylcyclopropyl)amino)quinazolin-4(3H)-one (129 mg, 0.37 mmol) and (R)-6-methyl-2-(4,4,5,5-tetramethyl-1,3,2-dioxaborolan-2-yl)-5,6-dihydropyrrolo[3,4-b]pyrrolo-4(1H)-one (705) (144 mg, 0.44 mmol) in 1,4-dioxane (1.2 mL)/water (0.3 mL) followed by potassium phosphate (233 mg, 1.1 mmol) and XPhos precatalyst II (14.4 mg, 0.018 mmol, Sigma Aldrich). The reaction mixture was stirred and heated in an oil bath at 40° C. for 1 h. The mixture was diluted with EtOAc (30 mL)/water (15 mL). The layers were separated and the aqueous layer was extracted with EtOAc (30 mL×2). The combined organic layers were dried (MgSO$_4$), filtered and concentrated. The residue was purified with silica gel chromatography (eluted with 0-4% MeOH in DCM) and the isolated product was further triturated with ether (15 mL) and DCM (5 mL) and the suspension was filtered to give (R)-3-cyclopropyl-7-fluoro-8-(6-methyl-4-oxo-1,4,5,6-tetrahydropyrrolo[3,4-b]pyrrol-2-yl)-2-((1-methylcyclopropyl)amino)quinazolin-4(3H)-one (75 mg, 0.18 mmol, 50% yield) as an off-white solid. MS (ESI, pos. ion) m/z: 408 (M+1); $^1$H NMR (400 MHz, DMSO-d$_6$) δ ppm 13.39 (1H, s), 7.82 (1H, dd, J=8.8, 6.1 Hz), 7.74 (1H, s), 7.76 (1H, s), 7.08 (1H, dd, J=11.7, 8.8 Hz), 6.78 (1H, d, J=3.9 Hz), 4.66 (1H, q, J=6.7 Hz), 2.67-2.75 (1H, m), 1.54 (3H, s), 1.37 (3H, d, J=6.7 Hz), 1.17-1.28 (2H, m), 1.03 (2H, br. s.), 0.82-0.90 (2H, m), 0.68-0.78 (2H, m).

Example 496

(R)-3-cyclopropyl-8-(6-methyl-4-oxo-1,4,5,6-tetrahydropyrrolo[3,4-b]pyrrol-2-yl)-2-((1-methylcyclobutyl)amino)quinazolin-4(3H)-one

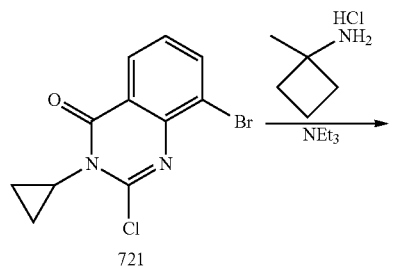

721

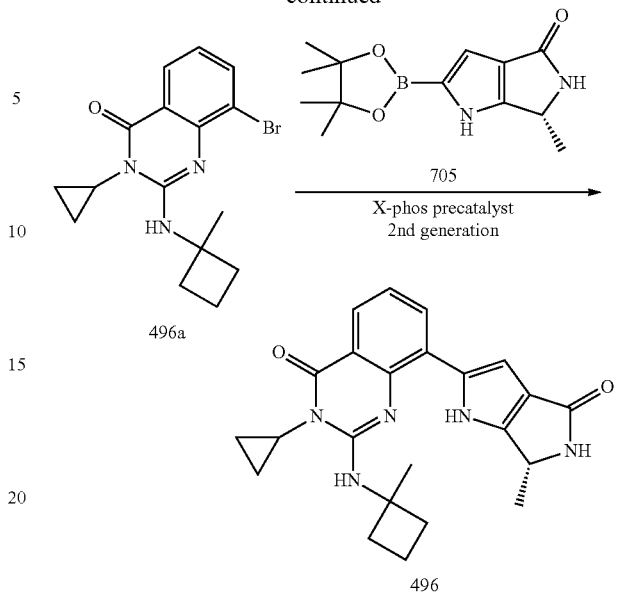

496a

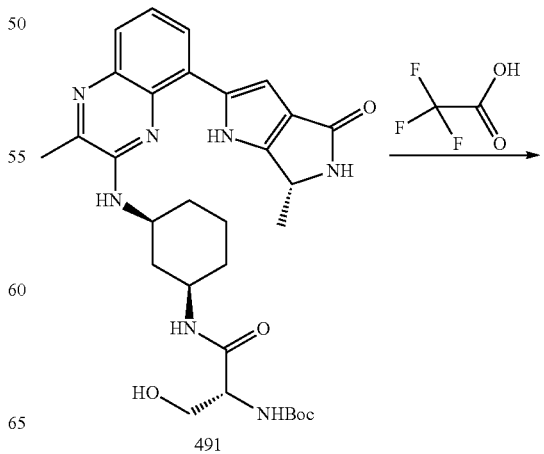

496

8-Bromo-3-cyclopropyl-2-((1-methylcyclobutyl)amino)quinazolin-4(3H)-one (496a) was made in a manner similar to that described for Intermediate 492a. $^1$H NMR (400 MHz, CDCl$_3$) δ ppm 8.01 (dd, J=7.82, 1.56 Hz, 1H), 7.80 (dd, J=7.63, 1.56 Hz, 1H), 6.93 (t, J=7.73 Hz, 1H), 5.53 (s, 1H), 2.64-2.73 (m, 1H), 2.40-2.52 (m, 2H), 2.28 (dddd, J=9.88, 7.78, 4.06, 2.54 Hz, 2H), 1.88-2.01 (m, 2H), 1.72 (s, 3H), 1.28-1.37 (m, 2H), 0.89-0.98 (m, 2H). m/z (ES, +ve) 348.0, 350.0 (M+H)$^+$.

(R)-3-Cyclopropyl-8-(6-methyl-4-oxo-1,4,5,6-tetrahydropyrrolo[3,4-b]pyrrol-2-yl)-2-((1-methylcyclobutyl)amino)quinazolin-4(3H)-one (496) (37 mg, 0.09 mmol, 26% yield) as a tan solid was made in a manner similar to that described for Example 492, starting from 8-bromo-3-cyclopropyl-2-((1-methylcyclobutyl)amino)quinazolin-4(3H)-one (496a; 125 mg, 0.36 mmol). $^1$H NMR (400 MHz, DMSO-d$_6$) δ ppm 12.27 (s, 1H), 7.97 (d, J=7.43 Hz, 1H), 7.80 (d, J=6.85 Hz, 1H), 7.65 (s, 1H), 7.12 (t, J=7.73 Hz, 1H), 6.94 (s, 1H), 6.80 (s, 1H), 4.59 (q, J=6.46 Hz, 1H), 2.76-2.85 (m, 1H), 2.39-2.47 (m, 2H), 2.13-2.26 (m, 2H), 1.88-1.98 (m, 2H), 1.66 (s, 3H), 1.40 (d, J=6.65 Hz, 3H), 1.23-1.30 (m, 2H), 0.76-0.85 (m, 2H). m/z (ES, +ve) 404.1 (M+H)$^+$.

Example 497

N-((1R,3S)-3-((3-methyl-8-((6R)-6-methyl-4-oxo-1,4,5,6-tetrahydropyrrolo[3,4-b]pyrrol-2-yl)-2-quinoxalinyl)amino)cyclohexyl)-D-serinamide

491

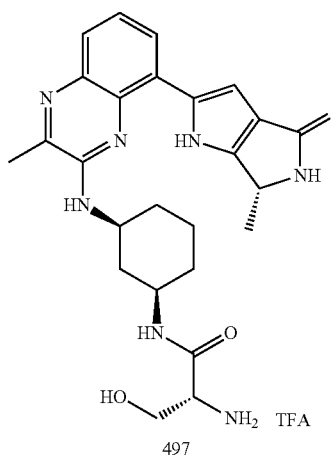

497

A solution of tert-butyl((R)-3-hydroxy-1-((((1R,3S)-3-((3-methyl-8-((R)-6-methyl-4-oxo-1,4,5,6-tetrahydropyrrolo[3,4-b]pyrrol-2-yl)quinoxalin-2-yl)amino)cyclohexyl)amino)-1-oxopropan-2-yl)carbamate (491, 34 mg, 0.059 mmol) and TFA (0.45 mL, 5.89 mmol) in DCM (0.29 mL) was stirred at 0° C. to RT for 15 min. It was concentrated under reduced pressure. The crude product was dissolved in methanol and injected (3×1 mL) onto the Shimadzu preparative LC (Phenomenex Gemini column, 10 micron, C18, 100 Å, 150×30 mm, 0.1% TFA in CH$_3$CN/H$_2$O, gradient 10% to 100% over 12 min) before the pure fractions were combined and concentrated via rotary evaporation to give (R)-2-amino-3-hydroxy-N-((1R,3S)-3-((3-methyl-8-((R)-6-methyl-4-oxo-1,4,5,6-tetrahydropyrrolo[3,4-b]pyrrol-2-yl)quinoxalin-2-yl)amino)cyclohexyl)propanamide 2,2,2-trifluoroacetate (497, 34 mg, 0.057 mmol, 98% yield) as a red oil. $^1$H NMR (400 MHz, DMSO-d$_6$) δ ppm 1.18-1.28 (m, 1H) 1.29-1.39 (m, 1H) 1.43-1.52 (m, 2H) 1.45 (d, J=6.65 Hz, 3H) 1.86 (d, J=10.56 Hz, 2H) 2.06-2.15 (m, 2H) 2.53 (s, 3H) 3.55-3.64 (m, 1H) 3.65-3.80 (m, 3H) 4.13-4.26 (m, 1H) 4.55 (q, J=6.85 Hz, 1H) 6.90 (d, J=8.02 Hz, 1H) 6.96 (d, J=1.37 Hz, 1H) 7.33 (t, J=7.73 Hz, 1H) 7.57-7.64 (m, 2H) 7.84 (d, J=7.43 Hz, 1H) 8.00-8.10 (m, 3H) 8.36 (d, J=7.82 Hz, 1H) 11.94 (s, 1H). MS (ESI, pos. ion) m/z: 478.1 (M+1).

Example 498

3-Cyclopropyl-7-fluoro-2-((1-methylcyclobutyl)amino)-8-((6R)-6-methyl-4-oxo-1,4,5,6-tetrahydropyrrolo[3,4-b]pyrrol-2-yl)-4(3H)-quinazolinone

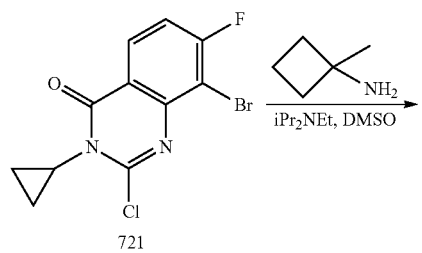

721

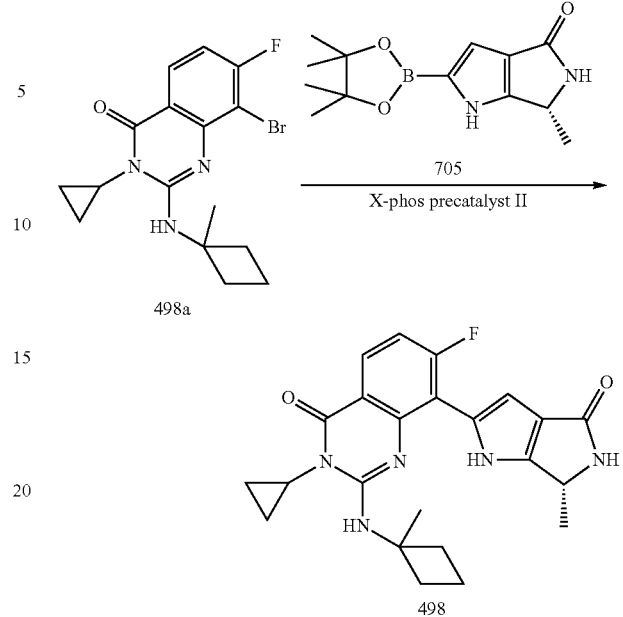

8-Bromo-3-cyclopropyl-7-fluoro-2-((1-methylcyclobutyl)amino)quinazolin-4(3H)-one (498a) was prepared according to the procedures described for Intermediate 495a, using 8-bromo-2-chloro-3-cyclopropyl-7-fluoroquinazolin-4(3H)-one (721) and 1-methylcyclobutanamine hydrochloride (Oakwood Chemical) as the starting materials. MS (ESI, pos. ion) m/z: 366.0/368.0 (M+1).

(R)-3-Cyclopropyl-7-fluoro-8-(6-methyl-4-oxo-1,4,5,6-tetrahydropyrrolo[3,4-b]pyrrol-2-yl)-2-((1-methylcyclopropyl)amino)quinazolin-4(3H)-one (78 mg, 50% yield) as a light yellow solid was prepared according to the procedure described for Example 495, using 8-bromo-3-cyclopropyl-7-fluoro-2-((1-methylcyclobutyl)amino)quinazolin-4(3H)-one (498a; 137 mg, 0.37 mmol) and boronic ester 705 (147 mg, 0.45 mmol) as starting material. MS (ESI, pos. ion) m/z: 422 (M+1); $^1$H NMR (400 MHz, DMSO-d$_6$) δ ppm 12.23 (1H, s), 7.86 (1H, dd, J=8.8, 6.3 Hz), 7.66 (1H, s), 6.98-7.14 (2H, m), 6.51 (1H, d, J=1.8 Hz), 4.57 (1H, q, J=6.6 Hz), 2.72-2.84 (1H, m), 2.35-2.44 (2H, m), 2.06 (2H, dt, J=12.3, 6.1 Hz), 1.78-1.91 (2H, m), 1.59 (3H, s), 1.39 (3H, d, J=6.7 Hz), 1.16-1.31 (2H, m), 0.75-0.83 (2H, m).

Example 499

(6R)-6-methyl-2-(2-((1-methylcyclopropyl)amino)-8-quinazolinyl)-5,6-dihydropyrrolo[3,4-b]pyrrol-4(1H)-one

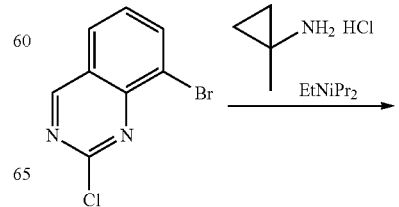

671

-continued

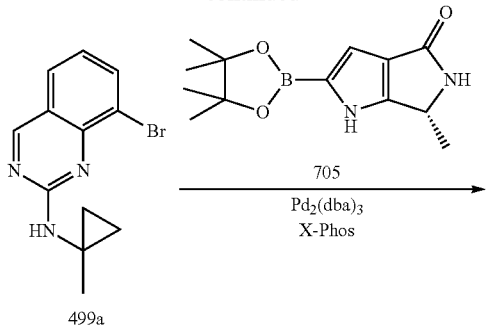

499a

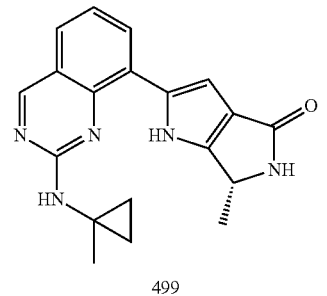

499

A mixture of 1-methylcyclopropanamine hydrochloride (Small Molecules Inc.; 0.32 g, 2.96 mmol), DIEA (1.37 mL, 7.89 mmol) and 8-bromo-2-chloroquinazoline (0.48 g, 1.97 mmol) in 5 mL of dioxane was heated in a microwave at 125° C. for 45 min. LCMS indicated the presence of starting material (8-bromo-2-chloroquinazoline). The reaction mixture was treated with 2 mL of DMF and heated in a microwave at 130° C. for 35 min. It was diluted with 50 mL of EtOAc, washed with 5 mL of water followed by 5 mL of brine. The organic layer was concentrated and the residue was stirred in 2 mL of ether and 10 mL of hexanes. The solid was filtered and dried to give 8-bromo-N-(1-methylcyclopropyl)quinazolin-2-amine (499a; 0.51 g, 1.83 mmol, 93% yield) in about 80% purity. This material was used in next step without further purification. $^1$H NMR (400 MHz, DMSO-$d_6$) δ ppm 9.12 (1H, br.), 8.05 (1H, dd, J=7.6, 1.2 Hz), 7.95 (1H, s), 7.83 (1H, d, J=7.4 Hz), 7.16 (1H, t, J=7.7 Hz), 1.51 (3H, s), 0.78 (2H, m), 0.65 (2H, m). MS (ESI, pos. ion) m/z: 278.1/280.1 (M+1).

A mixture of 2-(dicyclohexylphosphino)-2',4',6%-tri-isopropyl1,1'-biphenyl (30 mg, 0.063 mmol)), tris(dibenzylideneacetone)dipalladium (0) (29 mg, 0.031 mmol), potassium phosphate tribasic monohydrate (541 mg, 2.35 mmol), (R)-6-methyl-2-(4,4,5,5-tetramethyl-1,3,2-dioxaborolan-2-yl)-5,6-dihydropyrrolo[3,4-b]pyrrol-4(1H)-one (705) (308 mg, 1.18 mmol) and 8-bromo-N-(1-methylcyclopropyl)quinazolin-2-amine (499a; 218 mg, 0.78 mmol, about 80% pure) in dioxane (3 mL) and water (1 mL) in a sealed glass tube was heated in an Initiator microwave reactor (Personal Chemistry, Biotage AB, Inc.) at 100° C. for 40 min. The reaction mixture was partitioned between 75 mL of EtOAc and 5 mL of 0.5 N NaOH. The insoluble solid was filtered and discarded. The filtrate was transferred to a separatory funnel, the layers were separated. The organic layer was washed with 5 mL of water followed by 10 mL of brine. The organic solution was concentrated and the brown residue was purified on a silica gel column (2-8% MeOH in DCM) to give 90 mg of yellow solid that contained (6R)-6-methyl-2-(2-((1-methylcyclopropyl)amino)-8-quinazolinyl)-5,6-dihydropyrrolo[3,4-b]pyrrol-4(1H)-one (m/z (ESI, +ve ion) 334.0 (M+H)$^+$, about 90%) and

672

(R)-6-methyl-5,6-dihydropyrrolo[3,4-b]pyrrol-4(1H)-one (m/z (ESI, +ve ion) 137.0 (M+H)$^+$, about 10%). The yellow solid was stirred in 5 mL of water for 5 min, filtered, rinsed with 5 mL of water followed by 5 mL of ether, collected and dried in a vacuum oven at 40° C. for 18 h to provide (R)-6-methyl-5,6-dihydropyrrolo[3,4-b]pyrrol-4(1H)-one (499) (60 mg, 22% yield) as a yellow crystalline solid. $^1$H NMR (400 MHz, DMSO-$d_6$) δ ppm 13.22 (1H, br.), 9.17 (1H, s), 8.08-8.32 (2H, m), 7.62-7.83 (2H, m), 7.31 (1H, t, J=7.4 Hz), 7.05 (1H, br.), 4.66 (1H, d, J=6.5 Hz), 1.52 (3H, s), 1.39 (3H, d, J=6.1 Hz), 0.90 (2H, m), 0.82 (2H, m). m/z (ESI, +ve ion) 334.0 (M+H)$^+$.

Example 500

2-(tert-butylamino)-3-(3-hydroxypropyl)-8-((6R)-6-methyl-4-oxo-1,4,5,6-tetrahydropyrrolo[3,4-b]pyrrol-2-yl)-4(3H)-quinazolinone

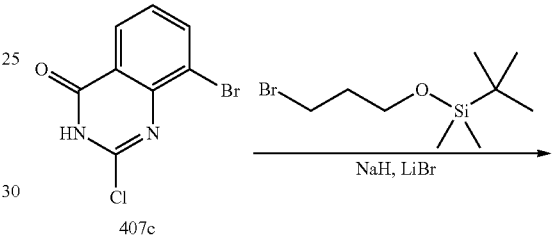

407c

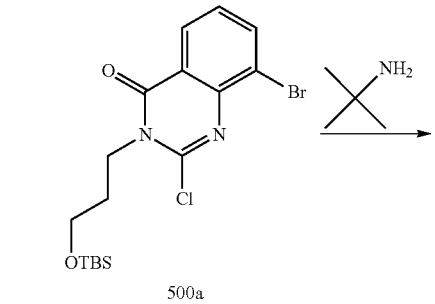

500a

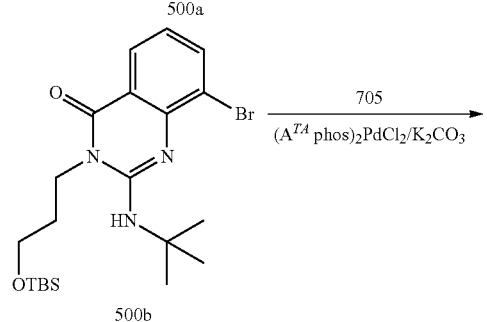

500b

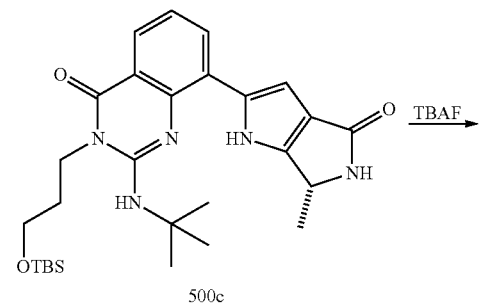

500c

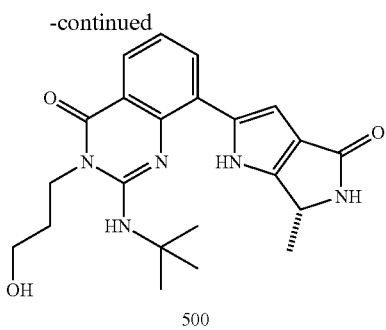

500

Preparation of 8-bromo-3-(3-((tert-butyldimethylsilyl)oxy)propyl)-2-chloroquinazolin-4(3H)-one (500a)

To a solution of 8-bromo-2-chloroquinazolin-4(3H)-one (407c; 0.110 g, 0.424 mmol) in 2 mL DME and 0.5 mL DMF in an ice/water bath was added sodium hydride (60% in mineral oil; Aldrich; 0.019 g, 0.466 mmol). After 10 min, lithium bromide (Aldrich; 0.074 g, 0.848 mmol) was added and the reaction was warmed to RT. After 15 min, (3-bromopropoxy)-tert-butyldimethylsilane (0.108 mL, 0.466 mmol) was added. After 30 min, the reaction was placed in a 60° C. oil bath and heated over the weekend. The reaction was partitioned between water and EtOAc. The aq layer was extracted 2× EtOAc and The combined organic layers were washed with water 2 times, satd aq NaCl once, and the organics were dried over anhydrous $Na_2SO_4$, filtered, and concentrated in vacuo. The material was treated with DCM and purified by silica gel chromatography using 0-20% EtOAc/hexane. The product-containing fractions were concentrated to afford 8-bromo-3-(3-((tert-butyldimethylsilyl)oxy)propyl)-2-chloroquinazolin-4(3H)-one (0.080 g, 0.185 mmol, 43% yield) as a yellow oil. $^1$H NMR (400 MHz, $CDCl_3$) δ ppm 8.21 (1H, dd, J=7.9, 1.3 Hz), 8.02 (1H, dd, J=7.8, 1.4 Hz), 7.34 (1H, t, J=7.8 Hz), 4.38-4.50 (2H, m), 3.78 (2H, t, J=5.8 Hz), 1.96-2.05 (2H, m), 0.89 (9H, s), 0.03-0.08 (6H, m). m/z (ESI, +ve ion) 431.0/433.0/435.0 (M+H)$^+$.

Preparation of 8-bromo-2-(tert-butylamino)-3-(3-((tert-butyldimethylsilyl)oxy)propyl)quinazolin-4(3H)-one (500b)

A solution of 8-bromo-3-(3-((tert-butyldimethylsilyl)oxy)propyl)-2-chloroquinazolin-4(3H)-one (500a; 0.080 g, 0.185 mmol) in tert-butylamine (Aldrich; 0.584 mL, 5.56 mmol) was sealed and heated in a biotage initiator microwave at 100° C. for 30 min, 130° C. for 30 min, and 150° C. for 60 min. The reaction was partitioned between satd aq sodium bicarbonate and DCM. The aqueous layer was extracted with DCM 3 times, and the combined organics were dried over anhydrous $Na_2SO_4$, filtered, and concentrated in vacuo to give 8-bromo-2-(tert-butylamino)-3-(3-((tert-butyldimethylsilyl)oxy)propyl)quinazolin-4(3H)-one (0.077 g, 0.164 mmol, 89% yield) as a yellow oil. $^1$H NMR (400 MHz, $CDCl_3$) δ ppm 8.05 (1H, dd, J=8.0, 1.4 Hz), 7.85 (1H, dd, J=7.6, 1.4 Hz), 6.97 (1H, t, J=7.8 Hz), 5.24 (1H, s), 4.10 (2H, t, J=7.1 Hz), 3.75 (2H, t, J=5.4 Hz), 1.85-1.99 (2H, m), 1.62 (9H, s), 0.95 (9H, s), 0.12 (6H, br. s.). m/z (ESI, +ve ion) 468.0/470.0 (M+H)$^+$.

Preparation of (R)-2-(tert-butylamino)-3-(3-((tert-butyldimethylsilyl)oxy)propyl)-8-(6-methyl-4-oxo-1,4,5,6-tetrahydropyrrolo[3,4-b]pyrrol-2-yl)quinazolin-4(3H)-one (500c)

Potassium carbonate (Mallinkrodt; 0.091 g, 0.657 mmol), 1,1-bis[(di-t-butyl-p-methylaminophenyl]palladium(ii) chloride (Aldrich; 5.82 mg, 8.22 μmol), (R)-6-methyl-2-(4,4,5,5-tetramethyl-1,3,2-dioxaborolan-2-yl)-5,6-dihydropyrrolo[3,4-b]pyrrol-4(1H)-one (705; 0.086 g, 0.329 mmol), 8-bromo-2-(tert-butylamino)-3-(3-((tert-butyldimethylsilyl)oxy)propyl)quinazolin-4(3H)-one (500b; 0.077 g, 0.164 mmol) were combined in 2 mL dioxane and 0.4 mL water. Argon was bubbled into the reaction for 1 min. The reaction was sealed and heated to 80° C. for 1 h. The reaction was adsorbed onto 1 g silica gel and The material was and purified by silica gel chromatography (12 g column) using 0-100% EtOAc/hexanes. The product-containing fractions were concentrated to afford (R)-2-(tert-butylamino)-3-(3-((tert-butyldimethylsilyl)oxy)propyl)-8-(6-methyl-4-oxo-1,4,5,6-tetrahydropyrrolo[3,4-b]pyrrol-2-yl)quinazolin-4(3H)-one (0.047 g, 0.090 mmol, 54.6% yield) as a light-yellow solid: $^1$H NMR (400 MHz, $CDCl_3$) δ ppm 12.52 (1H, br. s.), 7.88-8.23 (2H, m), 7.22 (1H, t, J=7.7 Hz), 6.84 (1H, d, J=1.2 Hz), 5.89 (1H, br. s.), 5.31 (1H, s), 4.68 (1H, q, J=6.7 Hz), 4.18 (2H, t, J=7.1 Hz), 3.79 (2H, t, J=5.3 Hz), 1.92-2.02 (2H, m), 1.65 (9H, s), 1.54 (3H, d, J=6.8 Hz), 0.96 (9H, s), 0.15 (6H, s). m/z (ESI, +ve ion) 524.2 (M+H)$^+$.

Preparation of 2-(tert-butylamino)-3-(3-hydroxypropyl)-8-((6R)-6-methyl-4-oxo-1,4,5,6-tetrahydropyrrolo[3,4-b]pyrrol-2-yl)-4(3H)-quinazolinone (500)

To a slurry of (R)-2-(tert-butylamino)-3-(3-((tert-butyldimethylsilyl)oxy)propyl)-8-(6-methyl-4-oxo-1,4,5,6-tetrahydropyrrolo[3,4-b]pyrrol-2-yl)quinazolin-4(3H)-one (500c; 0.047 g, 0.090 mmol) in 0.7 mL THF was added TBAF 1.0 M in THF (0.18 mL, 0.179 mmol). The reaction became a yellow solution. After 30 min, the reaction was adsorbed onto 0.7 g silica gel and purified by silica gel chromatography (12 g column) using 0-100% 90/10 DCM/MeOH in DCM. The product-containing fractions were concentrated to afford (R)-2-(tert-butylamino)-3-(3-hydroxypropyl)-8-(6-methyl-4-oxo-1,4,5,6-tetrahydropyrrolo[3,4-b]pyrrol-2-yl)quinazolin-4(3H)-one (0.033 g, 0.081 mmol, 90% yield) as a white solid: $^1$H NMR (400 MHz, DMSO-$d_6$) δ ppm 11.91 (1H, br. s.), 7.88 (2H, d, J=7.8 Hz), 7.61 (1H, s), 7.17 (1H, t, J=7.7 Hz), 6.70 (1H, s), 6.61 (1H, s), 5.31 (1H, br. s.), 4.53 (1H, q, J=6.6 Hz), 4.09 (2H, t, J=6.3 Hz), 3.47 (2H, t, J=5.5 Hz), 1.83 (2H, quin, J=5.9 Hz), 1.49 (9H, s), 1.37 (3H, d, J=6.7 Hz). m/z (ESI, +ve ion) 410.1 (M+H)$^+$.

Example 501

2-(tert-butylamino)-8-((6R)-6-methyl-4-oxo-1,4,5,6-tetrahydropyrrolo[3,4-b]pyrrol-2-yl)-3-(2,2,2-trifluoroethyl)-4(3H)-quinazolinone

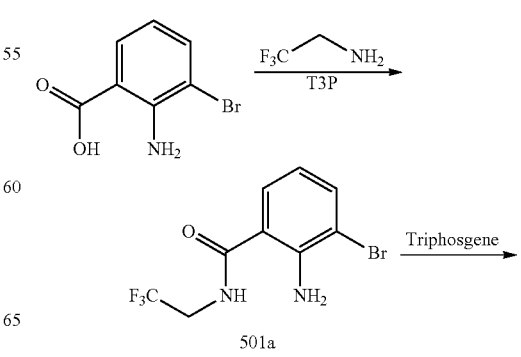

501a

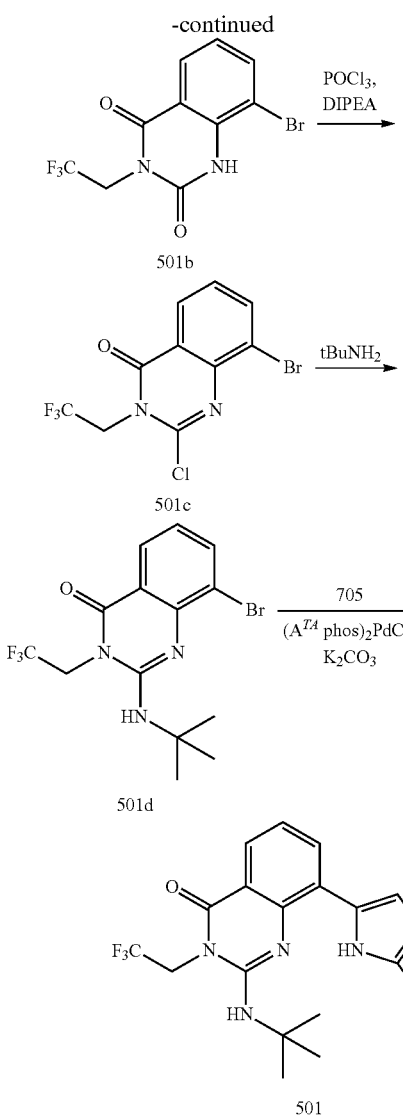

mmol, Sigma Aldrich). $^1$H NMR (400 MHz, DMSO-d$_6$) δ ppm 8.23 (1H, dd, J=7.82, 1.37 Hz) 8.16 (1H, dd, J=7.82, 1.37 Hz) 7.53 (1H, t, J=7.92 Hz) 5.11 (2H, q, J=8.74 Hz). m/z (ESI, +ve) 342.8/344.8 (M+H)$^+$.

8-Bromo-2-(tert-butylamino)-3-(2,2,2-trifluoroethyl) quinazolin-4(3H)-one (501d, 505 mg, 86%) as an off-white solid was prepared according to the procedures described for 408 using 8-bromo-2-chloro-3-(2,2,2-trifluoroethyl) quinazolin-4(3H)-one (534 mg, 1.562 mmol, 501c), tert-butylamine (4.9 mL, 46.9 mmol), and NMP (0.5 mL). $^1$H NMR (400 MHz, DMSO-d$_6$) δ ppm 7.87-8.00 (2H, m) 7.06 (1H, t, J=7.73 Hz) 6.44 (1H, s) 5.22 (2H, q, J=9.00 Hz) 1.55 (9H, s). m/z (ESI, +ve) 379.9/381.0 (M+H)$^+$.

2-(tert-Butylamino)-8-((6R)-6-methyl-4-oxo-1,4,5,6-tetrahydropyrrolo[3,4-b]pyrrol-2-yl)-3-(2,2,2-trifluoroethyl)-4 (3H)-quinazolinone (501) as a yellow solid (32 mg, 26%) was prepared according the procedures described for 408, using 1,1-bis[(di-t-butyl-p-methylaminophenyl]palladium(II) chloride (9.8 mg, 0.014 mmol, Sigma Aldrich), K$_2$CO$_3$ (153 mg, 1.111 mmol, Sigma Aldrich), (R)-6-methyl-2-(4,4,5,5-tetramethyl-1,3,2-dioxaborolan-2-yl)-5,6-dihydropyrrolo[3,4-b]pyrrol-4(1H)-one (146 mg, 0.555 mmol, 706), and 8-bromo-2-(tert-butylamino)-3-(2,2,2-trifluoroethyl) quinazolin-4(3H)-one (105 mg, 0.278 mmol, 501d). $^1$H NMR (400 MHz, DMSO-d$_6$) δ ppm 11.68 (1H, s) 7.89-7.96 (1H, m) 7.83-7.88 (1H, m) 7.59 (1H, s) 7.21 (1H, t, J=7.73 Hz) 6.62 (1H, d, J=1.37 Hz) 6.28 (1H, s) 5.28 (2H, q, J=8.93 Hz) 4.50 (1H, d, J=6.26 Hz) 1.45 (9H, s) 1.36 (3H, d, J=6.65 Hz). m/z (ESI, +ve) 434.0 (M+H)$^+$.

Example 502

7-fluoro-3-methyl-2-((1-methylcyclobutyl)amino)-8-((6R)-6-methyl-4-oxo-1,4,5,6-tetrahydropyrrolo[3,4-b]pyrrol-2-yl)-4(3H)-quinazolinone

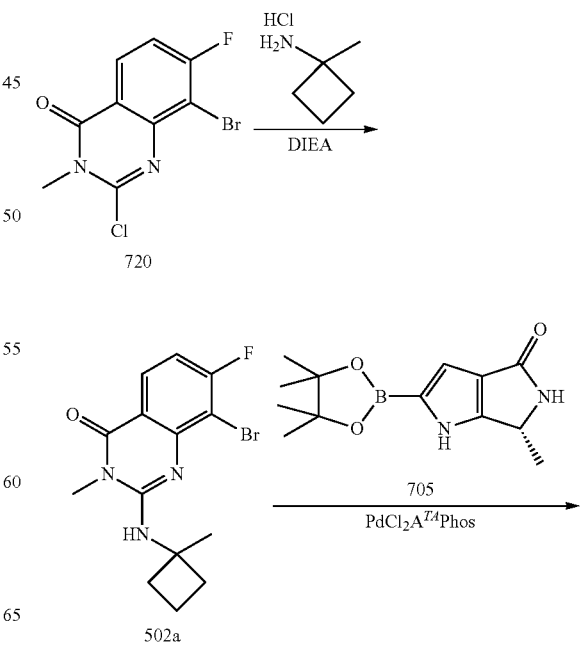

2-Amino-3-bromo-N-(2,2,2-trifluoroethyl)benzamide (501a) (1.67 g, 81%) was prepared according to the procedures described for 720 using (2-amino-3-bromo-benzoic acid (1.5 g, 6.94 mmol, Sigma Aldrich), 2,2,2-trifluoroethylamine hydrochloride (1.1 g, 8.33 mmol, TCI), and DIEA (2.9 mL, 16.66 mmol, Sigma Aldrich) as the reagents. $^1$H NMR (400 MHz, DMSO-d$_6$) δ ppm 9.00 (1H, t, J=6.16 Hz) 7.52-7.63 (2H, m) 6.57 (1H, t, J=7.82 Hz) 6.48 (1H, s) 4.05 (2H, qd, J=9.75, 6.36 Hz). m/z (ESI, +ve) 298.9/300.9 (M+H)$^+$.

8-Bromo-3-(2,2,2-trifluoroethyl)quinazoline-2,4(1H, 3H)-dione (501b, 1.53 g, 88%) was prepared according to the procedures described for 720 using 2-amino-3-bromo-N-(2,2,2-trifluoroethyl)benzamide (1.6 g, 5.39 mmol, 501a) and tri-phosgene (0.5 g, 1.777 mmol, Sigma Aldrich) as the reagents. $^1$H NMR (400 MHz, DMSO-d$_6$) δ ppm 10.86 (1H, s) 8.01 (2H, d, J=7.82 Hz) 7.20 (1H, t, J=7.82 Hz) 4.73 (2H, q, J=9.19 Hz). m/z (ESI, +ve) 322.9/324.9 (M+H)$^+$.

8-Bromo-2-chloro-3-(2,2,2-trifluoroethyl)quinazolin-4 (3H)-one (501c) as an off-white solid (1.22 g, 76%) was prepared according to the procedures described for 720 using 8-bromo-3-(2,2,2-trifluoroethyl)quinazoline-2,4(1H,3H)-dione (1.51 g, 4.67 mmol, 501b), phosphorus oxychloride (2.1 mL, 23.37 mmol, Sigma Aldrich), and DIEA (3.3 mL, 18.70

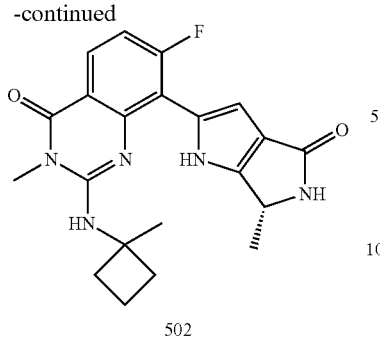

502

Preparation of 8-bromo-7-fluoro-3-methyl-2-((1-methylcyclobutyl)amino)-quinazolin-4(3H)-one (502a)

A solution of 8-bromo-2-chloro-7-fluoro-3-methylquinazolin-4(3H)-one (720, 239 mg, 0.820 mmol), 1-methylcyclobutanamine hydrochloride (Oakwood Products, Inc., West Columbia, S.C., 199 mg, 1.640 mmol), and N-ethyl-N-isopropylpropan-2-amine (314 µL, 1.804 mmol) in DMSO (8.2 mL) was stirred at 80° C. for 1 h. The reaction mixture was diluted with EtOAc (100 mL), added to a separatory funnel, and washed with saturated aqueous NaHCO$_3$ (3×100 mL); the organic layer was separated, dried over Na$_2$SO$_4$, and concentrated. The crude product was loaded onto the column and was purified via automated flash chromatography (silica gel) with 0-40% EtOAc in hexanes to give 8-bromo-7-fluoro-3-methyl-2-((1-methylcyclobutyl)amino)quinazolin-4(3H)-one (502a, 0.120 g, 0.353 mmol, 43% yield) as a brown amorphous solid. $^1$H NMR (400 MHz, CDCl$_3$) δ ppm 1.74 (s, 3H) 1.89-2.00 (m, 2H) 2.26-2.36 (m, 2H) 2.38-2.49 (m, 2H) 3.46 (s, 3H) 4.72 (br. s., 1H) 6.90 (t, J=8.51 Hz, 1H) 8.06 (dd, J=8.80, 6.06 Hz, 1H). $^{19}$F NMR (377 MHz, CDCl$_3$) δ ppm −96.60 (s, 1F). MS (ESI, pos. ion) m/z: 340.0/341.9 (M+1).

Preparation of 7-fluoro-3-methyl-2-((1-methylcyclobutyl)amino)-8-((6R)-6-methyl-4-oxo-1,4,5,6-tetrahydropyrrolo[3,4-b]pyrrol-2-yl)-4(3H)-quinazolinone (502)

A mixture of 8-bromo-7-fluoro-3-methyl-2-((1-methylcyclobutyl)amino)quinazolin-4(3H)-one (502a, 120 mg, 0.353 mmol), (R)-6-methyl-2-(4,4,5,5-tetramethyl-1,3,2-dioxaborolan-2-yl)-5,6-dihydropyrrolo[3,4-b]pyrrol-4(1H)-one (705, 237 mg, 0.705 mmol), bis(di-tert-butyl(4-dimethylaminophenyl)phosphine)-dichloropalladium (II) (12.49 mg, 0.018 mmol), and potassium phosphate (225 mg, 1.058 mmol) in 1,4-dioxane (2.82 mL)/water (0.70 mL) was sparged with nitrogen for 3 min at RT; the red reaction mixture was then heated to 80° C. for 45 min. The reaction mixture was diluted with EtOAc (100 mL), added to a separatory funnel, and washed with saturated aqueous NaHCO$_3$ (2×100 mL); the organic layer was separated, dried over Na$_2$SO$_4$, and concentrated. The crude product was loaded onto the column and was purified via automated flash chromatography (silica gel) with 0-5% 2 M ammonia in MeOH/DCM to give (R)-7-fluoro-3-methyl-8-(6-methyl-4-oxo-1,4,5,6-tetrahydropyrrolo[3,4-b]pyrrol-2-yl)-2-((1-methylcyclobutyl)amino)quinazolin-4(3H)-one (502, 24 mg, 0.061 mmol, 17% yield) as an off-white solid. $^1$H NMR (400 MHz, CDCl$_3$) δ ppm 1.58 (s, 3H) 1.78 (s, 3H) 1.98-2.15 (m, 2H) 2.27-2.42 (m, 3H) 2.42-2.52 (m, 1H) 3.56 (s, 3H) 4.69 (q, J=6.65 Hz, 1H) 5.08 (s, 1H) 6.01 (s, 1H) 7.00 (dd, J=11.54, 8.80 Hz, 1H) 7.08 (d, J=4.11 Hz, 1H) 8.01 (dd, J=8.80, 6.06 Hz, 1H) 12.76 (br. s., 1H). $^{19}$F NMR (376 MHz, CDCl$_3$) δ ppm −99.57 (s, 1F). MS (ESI, pos. ion) m/z: 369.0 (M+1).

Example 503

(R)-2-(tert-butylamino)-8-(6-(2-hydroxyethyl)-4-oxo-1,4,5,6-tetrahydropyrrolo[3,4-b]pyrrol-2-yl)-3-methylquinazolin-4(3H)-one

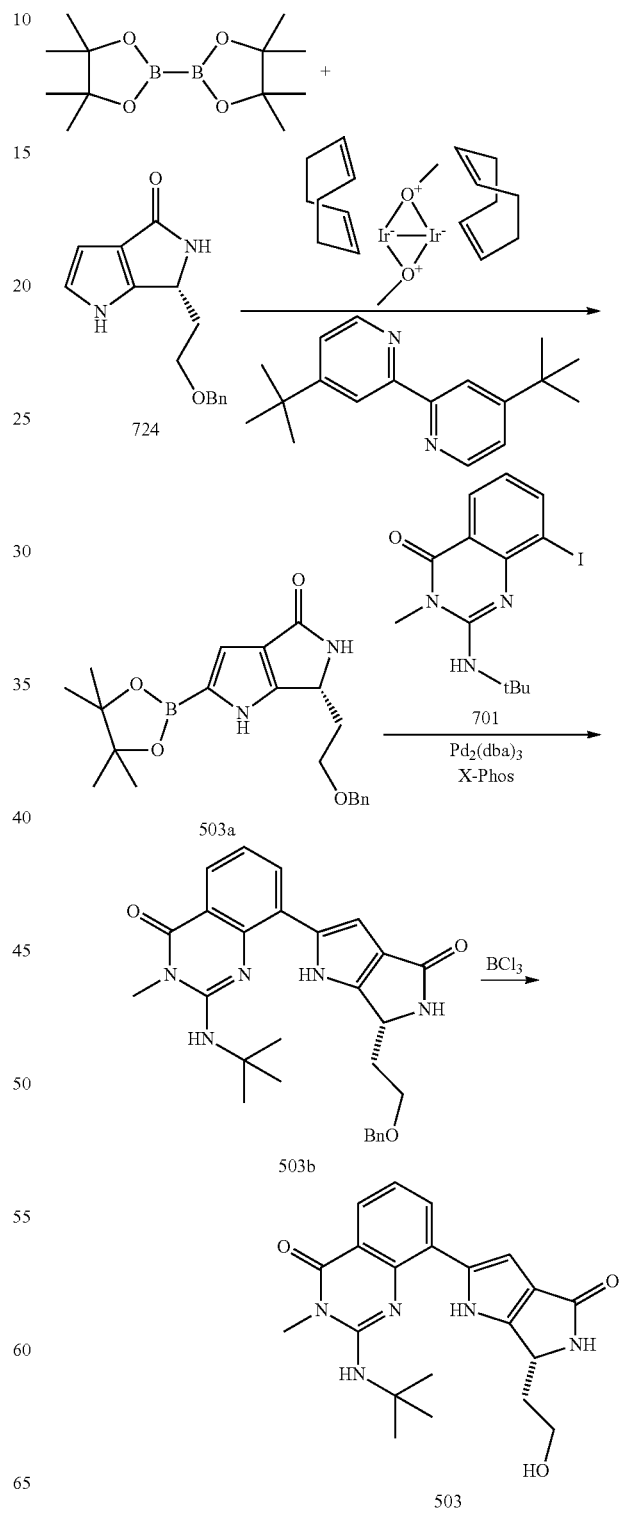

Preparation of (R)-6-(2-(benzyloxy)ethyl)-2-(4,4,5, 5-tetramethyl-1,3,2-dioxaborolan-2-yl)-5,6-dihydropyrrolo[3,4-b]pyrrol-4(1H)-one (503a)

A mixture of (R)-6-(2-(benzyloxy)ethyl)-5,6-dihydropyrrolo[3,4-b]pyrrol-4(1H)-one (724) (780 mg, 3.04 mmol), bis(1,5-cyclooctadiene)di-mu-methoxydiiridium(I) (Strem Chemicals, Newburyport, Mass., 60.5 mg, 0.091 mmol), 4,4-di-tert-butyl-2,2-dipyridyl (Sigma Aldrich, 49.0 mg, 0.183 mmol), bis(pinacolato)diboron (Sigma Aldrich, 850 mg, 3.35 mmol) in methyl tert-butyl ether (7.0 mL, 58.8 mmol) in a glass tube was purged with argon for 5 min. The glass tube was sealed and the reaction mixture was stirred at 50° C. for 2 h 45 min. The reaction mixture was filtered through a large pad of aluminum oxide (activated, neutral, Brockmann I, standard grade ca. 150 mesh, 58A). It was first rinsed with DCM and the desired boronic ester was eluted with 10% MeOH in DCM (ca. 50 mL) affording crude boronic ester (503a) as a dark brown oil. This material was used in a subsequent Suzuki coupling without further purification. m/z (ESI, +ve) 383.2 (M+1)⁺.

Preparation of (R)-8-(6-(2-(benzyloxy)ethyl)-4-oxo-1,4,5,6-tetrahydropyrrolo[3,4-b]pyrrol-2-yl)-2-(tert-butylamino)-3-methylquinazolin-4(3H)-one (503b)

A mixture of 2-(dicyclohexylphosphino)-2',4',6%-tri-isopropyl1,1'-biphenyl(Strem Chemicals, Newburyport, Mass., 110 mg, 0.23 mmol), tris(dibenzylideneacetone)dipalladium (0) (Strem Chemicals, Newburyport, Mass., 105 mg, 0.115 mmol), potassium phosphate tribasic (1.83 g, 8.63 mmol), (R)-6-(2-(benzyloxy)ethyl)-2-(4,4,5,5-tetramethyl-1,3,2-dioxaborolan-2-yl)-5,6-dihydropyrrolo[3,4-b]pyrrol-4(1H)-one (503a, 1.10 g, 2.88 mmol) and 2-(tert-butylamino)-8-iodo-3-methylquinazolin-4(3H)-one (701) (830 mg, 2.32 mmol) in 1,4-dioxane (12 mL), water (3.60 mL) in a sealed glass tube was heated in a heating block at 80° C. for 2 h. The reaction mixture was treated with 1 N NaOH and extracted with EtOAc (2×50 mL), washed with brine and dried over MgSO₄, filtered and concentrated. The crude reaction mixture was chromatographed on an ISCO Combiflash RF (40 g Thomson SingleStep column, using a gradient of 20-100% EtOAc in hexanes then 0-10% MeOH in DCM) affording (R)-8-(6-(2-(benzyloxy)ethyl)-4-oxo-1,4,5,6-tetrahydropyrrolo[3,4-b]pyrrol-2-yl)-2-(tert-butylamino)-3-methylquinazolin-4(3H)-one (503b, 555 mg, 1.14 mmol, 40% yield) as a dark brown oil. ¹H NMR (400 MHz, MeOH-d4) δ ppm 8.01 (1H, dd, J=7.9, 1.5 Hz), 7.89 (1H, dd, J=7.5, 1.5 Hz), 7.19-7.28 (3H, m), 7.08-7.17 (3H, m), 6.69 (1H, s), 4.75 (1H, dd, J=6.7, 5.1 Hz), 4.45 (2H, q, J=11.3 Hz), 3.70-3.77 (1H, m), 3.62-3.70 (1H, m), 3.55 (3H, s), 2.19-2.31 (1H, m), 1.98-2.09 (1H, m), 1.54 (9H, s). m/z (ESI, +ve) 486.0 (M+1)'.

Preparation of (R)-2-(tert-butylamino)-8-(6-(2-hydroxyethyl)-4-oxo-1,4,5,6-tetrahydropyrrolo[3,4-b]pyrrol-2-yl)-3-methylquinazolin-4(3H)-one (503)

To a solution of (R)-8-(6-(2-(benzyloxy)ethyl)-4-oxo-1,4,5,6-tetrahydropyrrolo[3,4-b]pyrrol-2-yl)-2-(tert-butylamino)-3-methylquinazolin-4(3H)-one (503b, 555 mg, 1.14 mmol) in DCM (30 mL) at 0° C. was added boron trichloride (1.0 M in DCM, 1.71 mL, 1.71 mmol) slowly dropwise. The resulting tan suspension was stirred at 0° C. for 5 min, then RT for 15 min. LC-MS indicated only unreacted starting material. The reaction mixture was treated with additional BCl₃ solution (0.5 mL) at RT and stirred 10 min. LC-MS indicated product formation. The reaction was cooled to 0° C. in an ice bath and treated with MeOH (ca. 3 mL) and ca. 500 mg of powdered NaHCO₃ and stirred for 5 min. The reaction mixture was then treated with silica gel and purified on an ISCO Combiflash RF (40 g Silicycle column, using a gradient of 0-20% MeOH in DCM) affording (R)-2-(tert-butylamino)-8-(6-(2-hydroxyethyl)-4-oxo-1,4,5,6-tetrahydropyrrolo[3,4-b]pyrrolo-2-yl)-3-methylquinazolin-4(3H)-one (503) (233 mg, 0.589 mmol, 51.5% yield) as a white solid. ¹H NMR (400 MHz, DMSO-d₆) δ ppm 11.81 (1H, s), 7.88 (2H, dd, J=7.6, 2.5 Hz), 7.66 (1H, br. s.), 7.18 (1H, t, J=7.7 Hz), 6.72 (1H, d, J=1.4 Hz), 5.93 (1H, s), 4.54 (1H, dd, J=8.8, 3.9 Hz), 3.52-3.83 (6H, m), 1.95-2.09 (1H, m), 1.55-1.67 (1H, m), 1.45-1.54 (9H, s). m/z (ESI, +ve) 396.0 (M+1)⁺.

Example 504

(R)-8-(6-(2-aminoethyl)-4-oxo-1,4,5,6-tetrahydropyrrolo[3,4-b]pyrrol-2-yl)-2-(tert-butylamino)-3-methylquinazolin-4(3H)-one

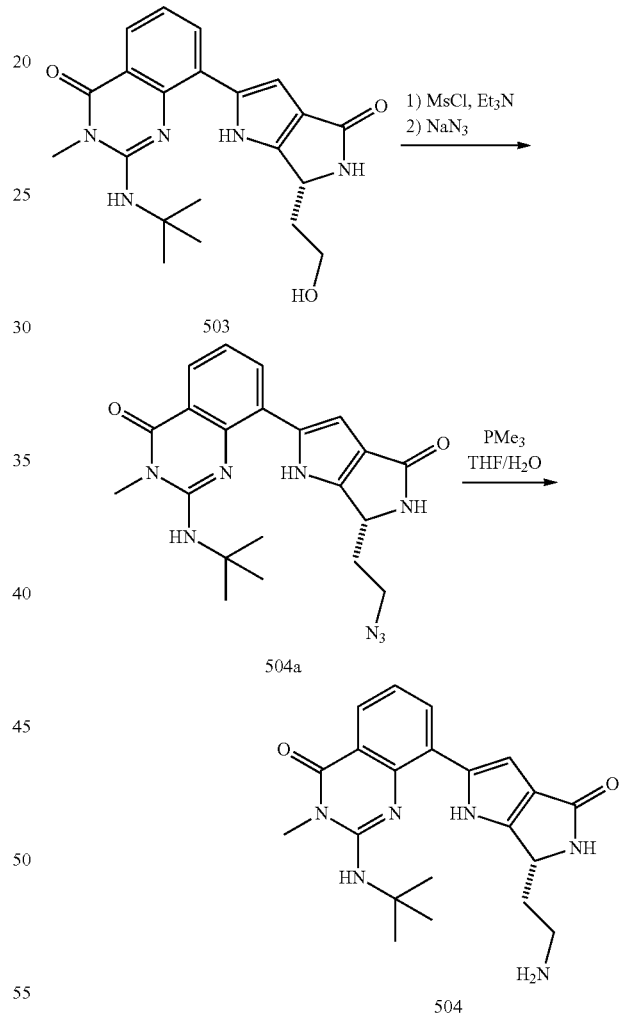

Preparation of (R)-8-(6-(2-azidoethyl)-4-oxo-1,4,5, 6-tetrahydropyrrolo[3,4-b]pyrrol-2-yl)-2-(tert-butylamino)-3-methylquinazolin-4(3H)-one (504a)

To a suspension of (R)-2-(tert-butylamino)-8-(6-(2-hydroxyethyl)-4-oxo-1,4,5,6-tetrahydropyrrolo[3,4-b]pyrrol-2-yl)-3-methylquinazolin-4(3H)-one (503) (233 mg, 0.589 mmol) in DCM (10 mL) at 0° C. was added triethylamine (0.41 mL, 2.95 mmol) followed by methanesulfonyl chloride (0.050 mL, 0.648 mmol). After 30 min at 0° C., LC-MS indicated formation of the desired product in ca. 20%. The reaction mixture was treated with additional MsCl (0.05 mL), triethylamine (0.2 mL) and DCM (10 mL) and stirred at RT for 30 min. LC-MS indicated ca. 30% conversion to the desired mesylate. Additional MsCl (0.15 mL) was added and the reaction was stirred at RT for 2 h. LC-MS indicated ca. 52% conversion to the desired mesylate. The reaction mixture was diluted with DCM (30 mL), washed sequentially with sat'd NaHCO$_3$ (15 mL) and brine (20 mL). The DCM solution was dried over Na$_2$SO$_4$ and concentrated affording a mixture of mesylate and unreacted alcohol in a ratio of 63:37 favoring the mesylate. m/z (ESI, +ve) 473.9 (M+1)$^+$. The brown residue was dissolved in DMF (5 mL) and treated with sodium azide (320 mg, 4.92 mmol) and heated in a heating block at 65° C. for 15 min. This resulted in complete conversion to the desired azide. The reaction mixture was diluted with EtOAc (50 mL) and washed with brine (2×25 mL). The EtOAc solution was dried over MgSO$_4$, filtered and concentrated and purified on an ISCO Combiflash RF (24 g Redisep column, using a gradient of 0-5% MeOH in DCM) affording (R)-8-(6-(2-azidoethyl)-4-oxo-1,4,5,6-tetrahydropyrrolo[3,4-b]pyrrol-2-yl)-2-(tert-butylamino)-3-methylquinazolin-4(3H)-one (504a, 205.7 mg, 0.489 mmol, 83% yield) as a light yellow solid that crystallized upon standing. $^1$H NMR analysis indicated that this compound was contaminated with residual DMF. m/z (ESI, +ve) 421.0 (M+1)'.

Preparation of (R)-8-(6-(2-aminoethyl)-4-oxo-1,4,5,6-tetrahydropyrrolo[3,4-b]pyrrol-2-yl)-2-(tert-butylamino)-3-methylquinazolin-4(3H)-one (504)

To a solution of (R)-8-(6-(2-azidoethyl)-4-oxo-1,4,5,6-tetrahydropyrrolo[3,4-b]pyrrol-2-yl)-2-(tert-butylamino)-3-methylquinazolin-4(3H)-one (504a, 200 mg, 0.476 mmol) in THF (7 mL) at RT was added trimethylphosphine (1.0 M in THF, 0.71 mL, 0.71 mmol) followed by 3 drops of water. It was stirred at RT for 30 min then the reaction mixture was concentrated and the crude residue was purified on the ISCO Combiflash RF (24 g Redisep column, using a gradient of 0-20% 2M NH$_3$/MeOH in DCM) affording (R)-8-(6-(2-aminoethyl)-4-oxo-1,4,5,6-tetrahydropyrrolo[3,4-b]pyrrol-2-yl)-2-(tert-butylamino)-3-methylquinazolin-4(3H)-one (504, 65 mg, 0.166 mmol, 35% yield) as a light yellow amorphous solid after drying under vacuum. $^1$H NMR (400 MHz, MeOH-d4) δ ppm 8.00 (1H, dd, J=8.0, 1.4 Hz), 7.93 (1H, dd, J=7.5, 1.5 Hz), 7.21 (1H, t, J=7.7 Hz), 6.75 (1H, s), 4.73 (1H, dd, J=7.6, 4.1 Hz), 3.56 (3H, s), 2.74-2.93 (2H, m), 2.12-2.26 (1H, m), 1.85-1.98 (1H, m), 1.57-1.67 (9H, s). m/z (ESI, +ve) 395.0 (M+1)$^+$.

Example 505

(R)-2-(tert-butylamino)-8-(6-ethyl-4-oxo-1,4,5,6-tetrahydropyrrolo[3,4-b]pyrrol-2-yl)-3-methylquinazolin-4(3H)-one

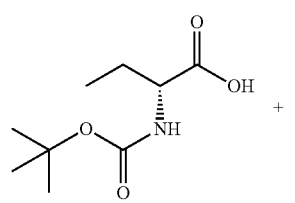

+

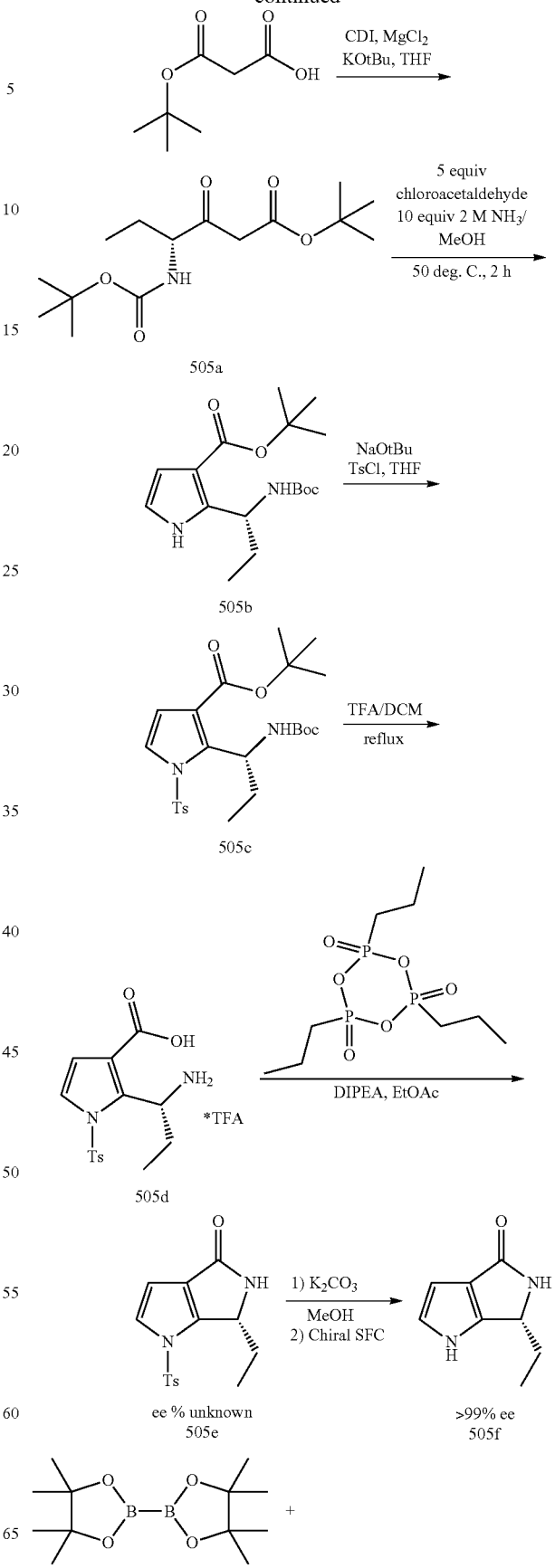

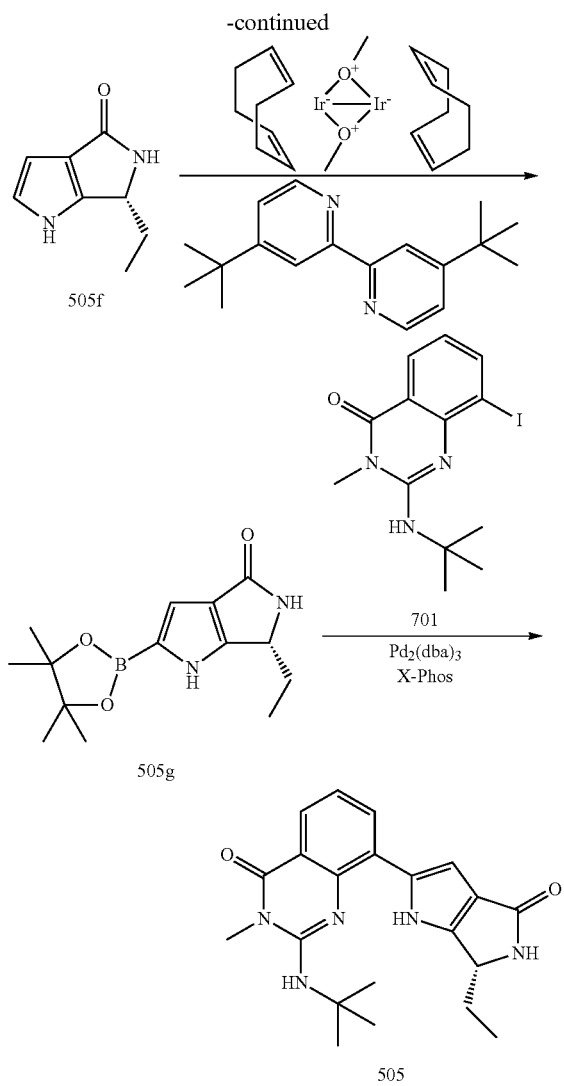

Preparation of (R)-tert-butyl-4-((tert-butoxycarbonyl)amino)-3-oxohexanoate (505a)

Flask B: To a clear solution of Boc-D-abu-oh (Bachem, 5.00 g, 24.60 mmol) in THF (40 mL) at RT under nitrogen was added 1,1'-carbonyldiimidazole (4.19 g, 25.8 mmol) in one portion. Gas evolution observed and the reaction was stirred for 2.5 h at RT. Flask A: To a mixture of mono-tert-butyl malonate (4.17 mL, 27.1 mmol) and anhydrous magnesium chloride (2.58 g, 27.1 mmol) in THF (100 mL) in a 500 mL 3-necked round-bottomed flask in an ice bath was added potassium tert-butoxide (1.0 M in THF, 27.1 mL, 27.1 mmol) slowly dropwise via addition funnel such that the temperature did not exceed 8° C. The resulting white suspension (milk-like) was stirred at RT for 2 h 30 min then the contents of flask B was added to flask A and the reaction mixture was heated at 50° C. overnight (16 h). The reaction mixture was treated with 1N HCl (15 mL) to pH=7 and then treated with Et$_2$O (60 mL) and water (45 mL). The organic layer was separated, and washed brine (30 mL), dried over anhydrous MgSO$_4$, filtered, and concentrated in vacuo to afford (R)-tert-butyl 4-((tert-butoxycarbonyl)amino)-3-oxohexanoate (505a) as a viscous light yellow oil. m/z (ESI, +ve) 324.2 (M+Na)$^+$.

Preparation of (R)-tert-butyl 2-(1-((tert-butoxycarbonyl)amino)propyl)-1H-pyrrole-3-carboxylate (505b)

(R)-tert-butyl 4-((tert-butoxycarbonyl)amino)-3-oxohexanoate (505a, 7.41 g, 24.59 mmol) was treated with ammonia (2M in MeOH, 123 mL, 246 mmol) and ammonium acetate (14.21 g, 184 mmol) at RT. The resulting mixture was stirred for at 50° C. for 30 min, then treated with chloroacetaldehyde (50 wt % in water, 15.82 mL, 123 mmol) and stirred at 50° C. for 2 h. The reaction mixture was then stirred at RT overnight. The reaction mixture was concentrated to remove most of MeOH and partitioned between sat'd NaHCO$_3$ (100 mL) and EtOAc (100 mL). The aqueous layer was extracted with EtOAc (2×50 mL), and the combined organics were washed with water and brine, dried over anhydrous MgSO$_4$, filtered, and concentrated in vacuo to give a brown residue. It was purified on an ISCO Combiflash RF (160 g Thomson SingleStep column, 0-10% EtOAc in DCM) affording (R)-tert-butyl 2-(1-((tert-butoxycarbonyl)amino)propyl)-1H-pyrrole-3-carboxylate (505b, 4.58 g, 14.12 mmol, 57.4% yield) as a light yellow viscous oil. m/z (ESI, +ve) 347.1 (M+Na)$^+$

Preparation of (R)-tert-butyl 2-(1-((tert-butoxycarbonyl)amino)propyl)-1-tosyl-1H-pyrrole-3-carboxylate (505c)

(R)-tert-butyl 2-(1-((tert-butoxycarbonyl)amino)propyl)-1H-pyrrole-3-carboxylate (505b, 4.58 g, 14.12 mmol) was dissolved in THF (40 mL) under nitrogen and cooled in an ice bath. Sodium tert-butoxide (1M in THF, 14.12 mL, 14.12 mmol) was added and the mixture stirred for 5 min. Toluene-4-sulfonyl chloride (2.69 g, 14.12 mmol) was added to the solution and the mixture was stirred at 0° C. for 30 min. Water (50 mL), and EtOAc (50 mL) were added to the reaction mixture and the organic layer was washed with brine and dried over MgSO$_4$, filtered and concentrated affording crude (R)-tert-butyl 2-(1-aminopropyl)-1-tosyl-1H-pyrrole-3-carboxylate (505c) as an orange viscous oil. m/z (ESI, +ve) 501.2 (M+Na)$^+$.

Preparation of (R)-2-(1-aminopropyl)-1-tosyl-1H-pyrrole-3-carboxylic acid compound with 2,2,2-trifluoroacetic acid (1:1) (505d)

An orange solution of (R)-tert-butyl 2-(1-((tert-butoxycarbonyl)amino)propyl)-1-tosyl-1H-pyrrole-3-carboxylate (505c, 6.19 g, 12.93 mmol) in DCM (15 mL) was treated with TFA (15 mL, 202 mmol) and heated at 40° C. for 4 h. The TFA and DCM was removed in vacuo affording (R)-2-(1-aminopropyl)-1-tosyl-1H-pyrrole-3-carboxylic acid compound with TFA (1:1) as a viscous orange oil (505d) which was used the next step without further purification. m/z (ESI, +ve) 323.1 (M+1)'.

Preparation of (R)-6-ethyl-1-tosyl-5,6-dihydropyrrolo[3,4-b]pyrrol-4(1H)-one (505e)

To a solution of (R)-2-(1-aminopropyl)-1-tosyl-1H-pyrrole-3-carboxylic acid compound with TFA (1:1) (505d, 5.64 g, 12.92 mmol) and DIEA (6.74 mL, 38.8 mmol) in EtOAc (50 mL) was added 1-propanephosphonic acid cyclic anhydride (50 wt. % in EtOAc, 7.69 mL, 12.92 mmol) dropwise via syringe. After 20 min, the reaction was judged complete by LCMS. The reaction was partitioned between sat'd NaHCO$_3$ and EtOAc. The organic layer was washed with sat'd NaHCO$_3$ once, sat'd NaCl once, and the organics were dried over anhydrous MgSO$_4$, filtered, and concentrated in vacuo to give (R)-6-ethyl-1-tosyl-5,6-dihydropyrrolo[3,4-b]pyrrol-4(1H)-one (505e, 3.49 g, 11.47 mmol, 89% yield) as an orange-brown foam. m/z (ESI, +ve) 305.1 (M+1)$^+$.

Preparation of (R)-6-ethyl-5,6-dihydropyrrolo[3,4-b]pyrrol-4(1H)-one (505f)

To a solution of (R)-6-ethyl-1-tosyl-5,6-dihydropyrrolo[3,4-b]pyrrol-4(1H)-one (505e, 3.49 g, 11.47 mmol) in MeOH (50 mL) in an ice bath was added potassium carbonate (3.17 g, 22.93 mmol) in one portion. The resulting white suspension was stirred in an ice bath for 1 h and at RT for 1 h. The suspension was filtered through a pad of Celite washing with MeOH. 10 g silica gel was added to the filtrate and concentrated in vacuo. It was purified on the ISCO Combiflash RF (40 g Grace Reveleris column, using a gradient of 0-20% 2 M NH$_3$/MeOH in DCM) affording (R)-6-ethyl-5,6-dihydropyrrolo[3,4-b]pyrrol-4(1H)-one (966 mg, 6.43 mmol, 56% yield) as a tan solid. m/z (ESI, +ve) 151.1 (M+1)$^+$. The material was further purified by chiral SFC (mobile phase CO$_2$/15% MeOH (20 mM NH$_3$), chiral column AS (250×30 mm), wave length 245 nm, flow rate 120 mL/min) The second eluting peak was collected and concentrated in vacuo to give (R)-6-ethyl-5,6-dihydropyrrolo[3,4-b]pyrrolo-4(1H)-one (505f, 450 mg, 3.00 mmol, 26% yield) as an off-white crystalline solid. $^1$H NMR (400 MHz, DMSO-d$_6$) δ ppm 11.31 (1H, br. s.), 7.55 (1H, s), 6.83 (1H, t, J=2.3 Hz), 6.07 (1H, dd, J=2.7, 1.6 Hz), 4.31 (1H, t, J=5.9 Hz), 1.50-1.74 (2H, m), 0.85 (3H, t, J=7.4 Hz). m/z (ESI, +ve) 151.1 (M+1)$^+$.

Preparation of (R)-6-ethyl-2-(4,4,5,5-tetramethyl-1,3,2-dioxaborolan-2-yl)-5,6-dihydropyrrolo[3,4-b]pyrrol-4(1H)-one (505g)

A mixture of (R)-6-ethyl-5,6-dihydropyrrolo[3,4-b]pyrrol-4(1H)-one (505f, 250 mg, 1.665 mmol), bis(1,5-cyclooctadiene)di-mu-methoxydiiridium(I) (Strem Chemicals, 33.1 mg, 0.050 mmol), 4,4-di-tert-butyl-2,2-dipyridyl (Sigma Aldrich, 26.8 mg, 0.10 mmol), bis(pinacolato)diboron (Sigma Aldrich, 465 mg, 1.83 mmol) in methyl tert-butyl ether (7.0 mL, 58.8 mmol) in a glass tube was purged with argon for 5 min. The glass tube was sealed and the reaction mixture was stirred at 50° C. for 2 h 15 min. After 10 min, the solution gelled so an additional 4.0 mL of TBME was added and the pressure in the vial was released. The reaction mixture was filtered through a large pad of aluminum oxide (activated, neutral, Brockmann I, standard grade ca. 150 mesh, 58A). It was first rinsed with DCM and the desired boronic ester (505g) was eluted with 10% MeOH in DCM (ca. 50 mL) affording crude boronic ester as a dark brown oil. This material was used in a subsequent Suzuki coupling without further purification. m/z (ESI, +ve) 277.0 (M+1)$^+$.

Preparation of (R)-2-(tert-butylamino)-8-(6-ethyl-4-oxo-1,4,5,6-tetrahydropyrrolo[3,4-b]pyrrol-2-yl)-3-methylquinazolin-4(3H)-one (505)

A mixture of 2-(dicyclohexylphosphino)-2',4',6%-tri-isopropyl1,1'-biphenyl (Strem Chemicals, 16.02 mg, 0.034 mmol), tris(dibenzylideneacetone)dipalladium (0) (Strem Chemicals, 15.38 mg, 0.017 mmol), potassium phosphate tribasic (Sigma Aldrich, 267 mg, 1.260 mmol), (R)-6-ethyl-2-(4,4,5,5-tetramethyl-1,3,2-dioxaborolan-2-yl)-5,6-dihydropyrrolo[3,4-b]pyrrol-4(1H)-one (505g, 232 mg, 0.840 mmol) and 2-(tert-butylamino)-8-iodo-3-methylquinazolin-4(3H)-one (Intermediate 701, 150 mg, 0.420 mmol) in 1,4-dioxane (4 mL), water (1.20 mL) in a sealed glass tube was heated at 80° C. for 1.5 h. The reaction mixture was treated with 1N NaOH and extracted with EtOAc (2×50 mL), washed with brine and dried over MgSO$_4$, filtered and concentrated. The crude reaction mixture was chromatographed on an ISCO Combiflash RF (40 g Thomson SingleStep column, using a gradient of 0-10% MeOH in DCM) affording a dark brown oil. It was suspended in Et$_2$O with sonication and filtered and washed with Et$_2$O and dried in the vacuum oven at 34° C. for 2 h affording (R)-2-(tert-butylamino)-8-(6-ethyl-4-oxo-1,4,5,6-tetrahydropyrrolo[3,4-b]pyrrol-2-yl)-3-methylquinazolin-4(3H)-one (505, 83.8 mg, 0.221 mmol, 52.6% yield) as a tan amorphous solid. $^1$H NMR (400 MHz, DMSO-d$_6$) δ ppm 11.83 (1H, br. s.), 7.89 (2H, d, J=7.2 Hz), 7.65 (1H, br. s.), 7.18 (1H, br. s.), 6.71 (1H, br. s.), 5.94 (1H, br. s.), 4.45 (1H, br. s.), 3.48 (3H, br. s.), 1.84 (1H, br. s.), 1.61 (1H, br. s.), 1.50 (9H, br. s.), 0.85 (3H, br. s.). m/z (ESI, +ve) 380.0 (M+1)$^+$.

Example 506

(rac)-2-(((cis)-3-aminocyclohexyl)amino)-3-methyl-8-((6R)-6-methyl-4-oxo-1,4,5,6-tetrahydropyrrolo[3,4-b]pyrrol-2-yl)-4(3H)-quinazolinone, 2-(((1S,3R)-3-aminocyclohexyl)amino)-3-methyl-8-((6R)-6-methyl-4-oxo-1,4,5,6-tetrahydropyrrolo[3,4-b]pyrrol-2-yl)-4(3H)-quinazolinone

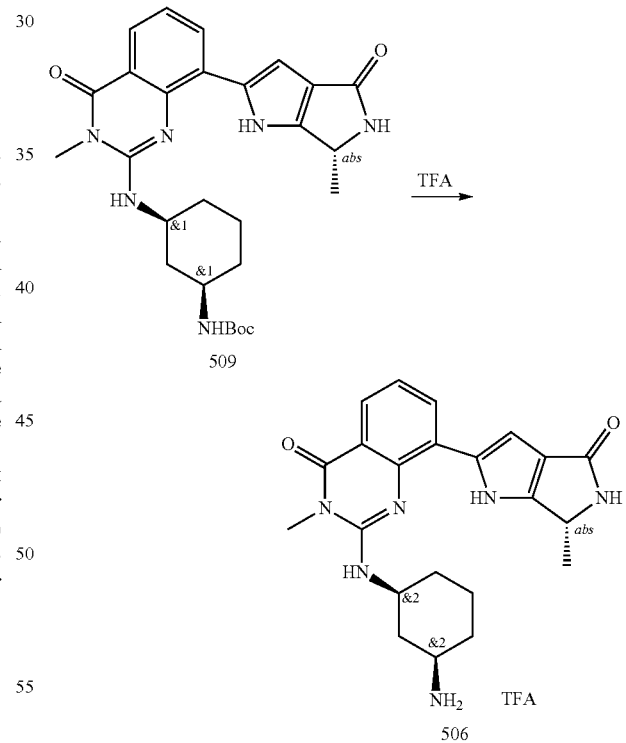

A solution of (rac)-tert-butyl ((cis)-3-((3-methyl-8-((R)-6-methyl-4-oxo-1,4,5,6-tetrahydropyrrolo[3,4-b]pyrrol-2-yl)-4-oxo-3,4-dihydroquinazolin-2-yl)amino)cyclohexyl)carbamate (509, see below) (47 mg, 0.093 mmol) and TFA (71.5 pt, 0.928 mmol) in DCM (928 pt) was stirred at RT for 1.5 h when mostly product was observed via LCMS. The reaction mixture was concentrated to give (rac)-2-(((cis)-3-aminocyclohexyl)amino)-3-methyl-8-((R)-6-methyl-4-oxo-1,4,5,6-tetrahydropyrrolo[3,4-b]pyrrol-2-yl)quinazolin-4(3H)-one TFA salt (506, 48 mg, 0.092 mmol, 99% yield) as an off-white solid and a 2.6:1 ratio of diastereomers via LCMS and 1.3:1 via $^1$H NMR. $^1$H NMR (400 MHz, DMSO-$d_6$) δ ppm 1.21-1.33 (m, 1H) 1.33-1.46 (m, 5H) 1.46-1.56 (m, 1H) 1.89 (d, J=12.72 Hz, 1H) 1.98 (d, J=11.74 Hz, 1H) 2.06 (d, J=10.56 Hz, 1H) 2.30-2.39 (m, 1H) 3.05-3.17 (m, 1H) 3.45 (s, 3H) 4.01-4.15 (m, 1H) 4.50-4.61 (m, 1H) 6.93-7.01 (m, 1H) 7.06 (d, J=4.11 Hz, 1H) 7.17 (t, J=7.63 Hz, 1H) 7.62 (s, 0.42H) 7.66 (s, 0.58; H) 7.84 (d, J=7.63 Hz, 1H) 7.88-8.00 (m, 3H) 11.78 (s, 0.42; H) 11.91 (s, 0.58; H). $^{19}$F NMR (376 MHz, DMSO-$d_6$) δ ppm −73.81 (s, 3F). MS (ESI, pos. ion) m/z: 407.1 (M+1).

Example 507

(R)-2-(tert-Butylamino)-3-cyclobutyl-8-(6-methyl-4-oxo-1,4,5,6-tetrahydropyrrolo[3,4-b]pyrrol-2-yl)quinazolin-4(3H)-one

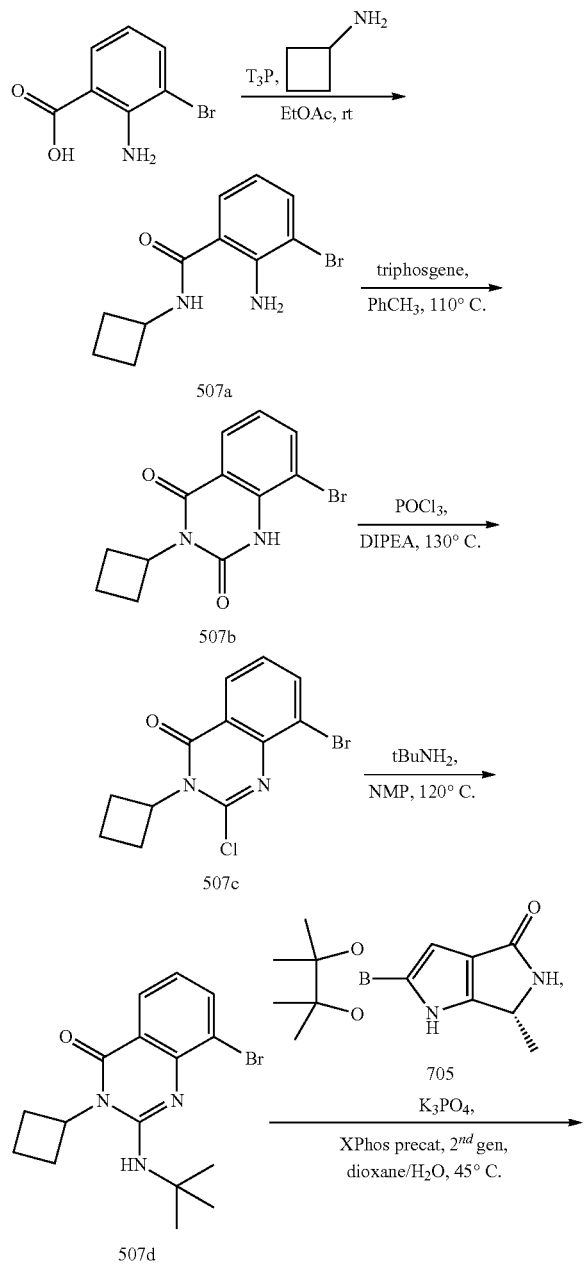

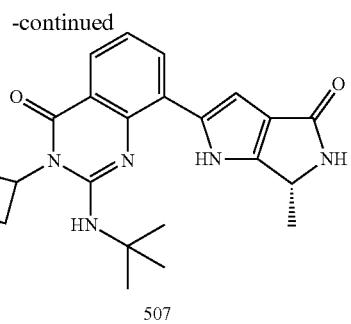

Preparation of 2-Amino-3-bromo-N-cyclobutylbenzamide (507a)

Propylphosphonic anhydride solution (T3P; Alfa Aesar, Ward Hill, Mass.; ≥50 wt % in EtOAc; 6.06 mL, 10.18 mmol) was added (dropwise, over 1 min) to a suspension of 2-amino-3-bromobenzoic acid (Aldrich; 2.00 g, 9.26 mmol) and cyclobutylamine (Aldrich; 2.37 mL, 27.8 mmol) in EtOAc (20 mL) at 0° C. The resulting solution was warmed to 23° C. and stirred for 1.5 h Additional propylphosphonic anhydride solution (≥50 wt % in EtOAc; 1.21 mL, 2.04 mmol) and cyclobutylamine (0.790 mL, 9.27 mmol) were sequentially added, and the resulting mixture was stirred at 23° C. for 3 h. The reaction mixture was then partitioned between EtOAc (100 mL) and saturated aqueous NaHCO$_3$ (100 mL). The organic layer was separated, sequentially washed with saturated aqueous NaHCO$_3$ (2×50 mL), and brine (50 mL), dried over Na$_2$SO$_4$, filtered, and concentrated in vacuo to give 2-amino-3-bromo-N-cyclobutylbenzamide (2.127 g, 7.90 mmol, 85% yield) as a light-yellow solid: $^1$H NMR (400 MHz, CDCl$_3$) δ ppm 7.50 (1H, dd, J=7.8, 1.2 Hz), 7.27 (1H, d, J=7.8 Hz), 6.52 (1H, t, J=7.8 Hz), 6.12 (2H, br. s.), 5.81-6.06 (1H, m), 4.53 (1H, sxt, J=8.0 Hz), 2.35-2.53 (2H, m), 1.90-1.98 (2H, m), 1.74-1.82 (2H, m). m/z (ESI, +ve) 268.9/271.0 (M+H)$^+$.

Preparation of 8-Bromo-3-cyclobutylquinazoline-2,4(1H,3H)-dione (507b)

A mixture of 2-amino-3-bromo-N-cyclobutylbenzamide (2.127 g, 7.90 mmol) and triphosgene (0.797 g, 2.69 mmol) in DCM (80 mL) was heated at reflux (using a water-cooled reflux condenser) for 17 h. The reaction mixture was then concentrated in vacuo, and the residue was taken up in toluene (80 mL) and heated at 110° C. for 1.5 h. Additional triphosgene (0.040 g, 014 mmol) was added, and the resulting solution was stirred at 110° C. for 45 min. The reaction mixture was then cooled to RT and concentrated in vacuo to give crude 8-bromo-3-cyclobutylquinazoline-2,4(1H,3H)-dione (2.59 g, 8.78 mmol) as a light-yellow solid. m/z (ESI, +ve) 295.0/297.0 (M+H)$^+$. This material was used directly in the subsequent transformation.

Preparation of 8-Bromo-2-chloro-3-cyclobutylquinazolin-4(3H)-one (507c)

A solution of 8-bromo-3-cyclobutylquinazoline-2,4(1H,3H)-dione (2.33 g, 7.89 mmol), phosphorous oxychloride (Acros Organics, Geel, Belgium; 3.68 ml, 39.5 mmol), and DIPEA (5.50 ml, 31.6 mmol) was heated over a 130° C. oil bath for 5 h. The reaction mixture was then cooled to RT and poured onto ice, and the resulting mixture was diluted with water (250 mL) to provide a brown suspension. 10N aqueous NaOH was added to the vigorously stirred suspension (maintaining the reaction mixture at 0° C.) until a pH of 10 was achieved. The precipitated solid was collected by vacuum filtration, washed with water (3×20 mL), and dried in vacuo to provide 8-bromo-2-chloro-3-cyclobutylquinazolin-4(3H)-one (1.888 g, 6.02 mmol, 76% yield) as a tan solid: $^1$H NMR (400 MHz, CDCl$_3$) δ ppm 8.16 (1H, dd, J=8.0, 1.4 Hz), 7.99 (1H, dd, J=7.8, 1.4 Hz), 7.32 (1H, t, J=7.8 Hz), 5.22 (1H, quin, J=8.8 Hz), 2.89-3.05 (2H, m), 2.43-2.56 (2H, m), 1.98 (1H, q, J=10.7 Hz), 1.74-1.90 (1H, m). m/z (ESI, +ve) 313.0/314.9/316.9 (M+H)$^+$.

Preparation of 8-Bromo-2-(tert-butylamino)-3-cyclobutylquinazolin-4(3H)-one (507d)

A solution of 8-bromo-2-chloro-3-cyclobutylquinazolin-4(3H)-one (294.7 mg, 0.94 mmol), tert-butylamine (Aldrich; 1.5 mL, 14.27 mmol), and NMP (0.5 mL) was heated in a sealed microwave vial at 120° C. for 30 min. The reaction mixture was then partitioned between EtOAc (60 mL) and water (40 mL). The organic layer was separated and sequentially washed water (40 mL) and brine (40 mL), then dried over Na$_2$SO$_4$, filtered, and concentrated in vacuo to give 8-bromo-2-(tert-butylamino)-3-cyclobutylquinazolin-4(3H)-one (266 mg, 0.759 mmol, 81% yield) as a tan solid. $^1$H NMR (400 MHz, DMSO-d$_6$) δ ppm 7.87 (1H, dd, J=7.6, 1.2 Hz), 7.84 (1H, dd, J=7.8, 1.4 Hz), 6.98 (1H, t, J=7.8 Hz), 5.88 (1H, s), 4.47-4.60 (1H, m), 2.54-2.64 (2H, m), 2.06-2.20 (2H, m), 1.56-1.66 (2H, m), 1.52 (9H, s). m/z (ESI, +ve) 349.9/352.0 (M+H)$^+$.

Preparation of (R)-2-(tert-Butylamino)-3-cyclobutyl-8-(6-methyl-4-oxo-1,4,5,6-tetrahydropyrrolo[3,4-b]pyrrol-2-yl)quinazolin-4(3H)-one (507)

A solution of 8-bromo-2-(tert-butylamino)-3-cyclobutylquinazolin-4(3H)-one (254.1 mg, 0.725 mmol), (R)-6-methyl-2-(4,4,5,5-tetramethyl-1,3,2-dioxaborolan-2-yl)-5,6-dihydropyrrolo[3,4-b]pyrrol-4(1H)-one (Example 705; 238 mg, 0.907 mmol), potassium phosphate (462 mg, 2.176 mmol), and chloro(2-dicyclohexylphosphino-2',4',6'-triisopropyl-1,1'-biphenyl)[2-(2'-amino-1,1'-biphenyl)]palladium (II) (XPhos precatalyst, 2nd generation; Aldrich; 28.6 mg, 0.036 mmol) in a mixture of 1,4-dioxane (3.0 mL) and water (0.750 mL) was stirred under argon at 45° C. for 1 h. The reaction mixture was then concentrated onto silica gel and chromatographically purified (silica gel, 50-100% EtOAc/hexanes, then 0-10% MeOH/DCM) to provide (R)-2-(tert-butylamino)-3-cyclobutyl-8-(6-methyl-4-oxo-1,4,5,6-tetrahydropyrrolo[3,4-b]pyrrol-2-yl)quinazolin-4(3H)-one (206.3 mg, 0.509 mmol, 70% yield) as a white solid: $^1$H NMR (400 MHz, DMSO-d$_6$) δ ppm 11.95 (1H, s), 7.87 (1H, dd, J=7.7, 0.9 Hz), 7.80 (1H, dd, J=7.7, 0.9 Hz), 7.61 (1H, s), 7.13 (1H, t, J=7.7 Hz), 6.72 (1H, s), 5.81 (1H, s), 4.48-4.64 (2H, m), 2.63 (2H, td, J=11.3, 5.0 Hz), 2.01-2.18 (2H, m), 1.56-1.70 (2H, m), 1.48 (9H, s), 1.36 (3H, d, J=6.7 Hz). m/z (ESI, +ve) 406.0 (M+H)$^+$.

Example 508

(R)-2-(tert-butylamino)-8-(6-methyl-4-oxo-1,4,5,6-tetrahydropyrrolo[3,4-b]pyrrol-2-yl)-3-(3-(methylsulfonyl)propyl)quinazolin-4(3H)-one

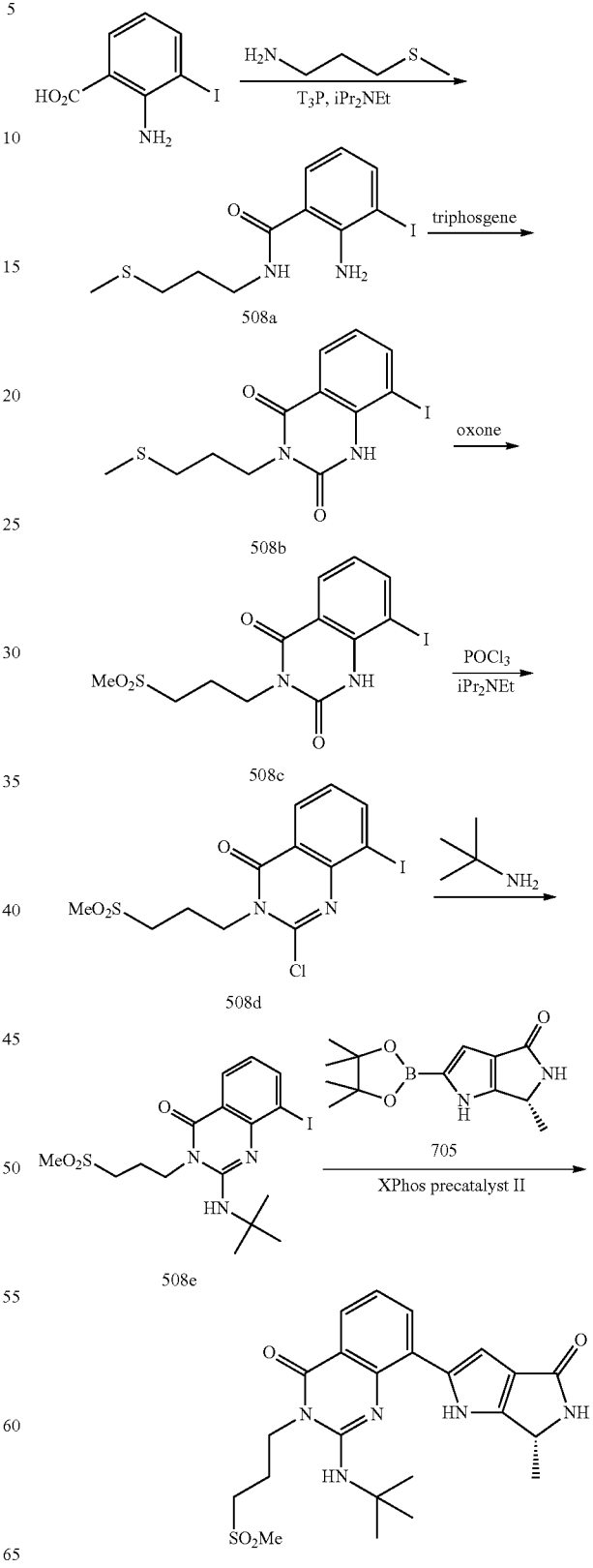

Preparation of 2-amino-3-iodo-N-(3-(methylthio) propyl)benzamide (508a)

To a 100-mL round-bottomed flask was added 2-amino-3-iodobenzoic acid (1.50 g, 5.70 mmol, Bosche Scientific) and 3-(methylthio)propylamine (0.72 mL, 6.84 mmol, Acros) in EtOAc (15 mL) followed by DIEA (1.19 mL, 6.84 mmol) and 1-propanephosphonic acid cyclic anhydride (3.99 mL, 6.27 mmol, 50% in EtOAc, Sigma Aldrich). The reaction was stirred at RT for 4 h, and then quenched with sat. NaHCO$_3$. The layers were separated and the organic layer was washed with sat. NaHCO$_3$, brine, then dried (MgSO$_4$), filtered and concentrated to give the crude product. MS (ESI, pos. ion) m/z: 350.9 (M+1); $^1$H NMR (400 MHz, CDCl$_3$) δ ppm 7.74 (1H, dd, J=7.6, 1.4 Hz), 7.30 (1H, dd, J=7.8, 1.4 Hz), 6.41 (1H, t, J=7.8 Hz), 6.32 (1H, br. s.), 3.54 (2H, q, J=6.7 Hz), 2.61 (2H, t, J=6.9 Hz), 2.09-2.17 (3H, m), 1.92 (2H, quin, J=6.8 Hz)

Preparation of 8-iodo-3-(3-(methylthio)propyl) quinazoline-2,4(1H,3H)-dione (508b)

To a 100 mL round-bottomed flask was added 2-amino-3-iodo-N-(3-(methylthio)propyl)benzamide (1.25 g, 3.57 mmol) and triphosgene (0.185 mL, 1.25 mmol, Sigma Aldrich) in DCM (20 mL). The reaction was heated to reflux for 15 h, and then cooled to RT. The solvent was removed to give the crude product 1.5 g. MS (ESI, pos. ion) m/z: 376.9 (M+1).

Preparation of 8-iodo-3-(3-(methylsulfonyl)propyl) quinazoline-2,4(1H,3H)-dione (508c)

To a 150 mL round-bottomed flask was added 8-iodo-3-(3-(methylthio)propyl)quinazoline-2,4(1H,3H)-dione (1.34 g, 3.56 mmol) in MeOH (15 mL) and oxone monopersulfate (3.28 g, 5.34 mmol, Sigma Aldrich) in water (15 mL) was added. The mixture was stirred at RT for 24 h. Another 0.5 equiv. of oxone was added and the mixture was stirred at 35° C. for 24 h. The mixture was diluted with water (30 mL) and extracted with DCM (60 mL×3). The combined organic layers were dried (MgSO$_4$), filtered and concentrated to give the crude product (1.09 g). MS (ESI, pos. ion) m/z: 408.8 (M+1).

Preparation of 2-chloro-8-iodo-3-(3-(methylsulfonyl) propyl)quinazolin-4(3H)-one (508d)

A pressure vessel was charged with 8-iodo-3-(3-(methylsulfonyl)propyl)-quinazoline-2,4(1H,3H)-dione (1.09 g, 2.67 mmol), DIEA (1.858 mL, 10.68 mmol) and phosphorus oxychloride (1.222 mL, 13.35 mmol). The tube was sealed and heated in an oil bath at 120° C. for 3 h, then cooled to RT. The solvent was removed in vacuo and the residue was poured into ice/water (50 mL) and 1 M NaOH was added until pH 10. The suspension was filtered and the solid was dried to give the crude product. MS (ESI, pos. ion) m/z: 426.8 (M+1).

Preparation of 2-(tert-butylamino)-8-iodo-3-(3-(methylsulfonyl)propyl)quinazolin-4(3H)-one (508e)

A glass microwave reaction vessel was charged with 2-chloro-8-iodo-3-(3-(methylsulfonyl)propyl)quinazolin-4 (3H)-one (50 mg, 0.117 mmol) and tert-butylamine (0.123 mL, 1.172 mmol) in DMSO (0.5 mL). The reaction mixture was stirred and heated in an Initiator microwave reactor (Personal Chemistry, Biotage AB, Inc., Upssala, Sweden) at 100° C. for 1 h. The reaction was repeated on 150 mg scale. The reaction mixture were combined and diluted with water (20 mL). The mixture was extracted with CHCl$_3$/iPrOH (4:1, 40 mL×3) and the combined organic layers were washed with water, dried (MgSO$_4$), filtered and concentrated. The residue was purified with silica gel chromatography (eluted with 10-70% EtOAc in Hexanes) to give 2-(tert-butylamino)-8-iodo-3-(3-(methylsulfonyl)propyl)quinazolin-4(3H)-one (108 mg, 50% yield) as a yellow solid. MS (ESI, pos. ion) m/z: 464 (M+1).

Preparation of (R)-2-(tert-butylamino)-8-(6-methyl-4-oxo-1,4,5,6-tetrahydropyrrolo[3,4-b]pyrrol-2-yl)-3-(3-(methylsulfonyl)propyl)quinazolin-4(3H)-one (508)

A glass microwave reaction vessel was charged with 2-(tert-butylamino)-8-iodo-3-(3-(methylsulfonyl)propyl) quinazolin-4(3H)-one (105 mg, 0.227 mmol) and (R)-6-methyl-2-(4,4,5,5-tetramethyl-1,3,2-dioxaborolan-2-yl)-5,6-dihydropyrrolo[3,4-b]pyrrol-4(1H)-one (705) (89 mg, 0.272 mmol) in 1,4-dioxane (1.0 mL)/water (0.2 mL) followed by potassium phosphate (0.056 mL, 0.680 mmol) and XPhos precatalyst II (8.92 mg, 0.011 mmol, Sigma Aldrich, St. Louis, Mo.). The reaction mixture was stirred and heated in an oil bath at 45° C. for 2 h, then another 0.3 equiv. of boronic ester 705 was added and the reaction was stirred at RT overnight. More boronic ester 705 (0.3 equiv) was added and the reaction was stirred at 45° C. for 1 h. The mixture was cooled to RT and diluted with water (15 mL). The suspension was filtered and the solid was purified with silica gel chromatography (eluted with 1-4% MeOH in DCM) to give (R)-2-(tert-butylamino)-8-(6-methyl-4-oxo-1,4,5,6-tetrahydropyrrolo [3,4-b]pyrrol-2-yl)-3-(3-(methylsulfonyl)propyl)quinazolin-4(3H)-one (85 mg, 0.180 mmol, 80% yield) as a yellow solid. MS (ESI, pos. ion) m/z: 472 (M+1); $^1$H NMR (400 MHz, DMSO-d$_6$) δ ppm 11.83 (1H, s), 7.83-7.93 (2H, m), 7.60 (1H, s), 7.19 (1H, t, J=7.6 Hz), 6.68 (1H, d, J=1.4 Hz), 5.95 (1H, s), 4.52 (1H, q, J=6.6 Hz), 4.28 (2H, t, J=7.2 Hz), 3.21 (2H, t, J=7.5 Hz), 3.02 (3H, s), 2.00-2.10 (2H, m), 1.50 (9H, s), 1.36 (3H, d, J=6.7 Hz).

Example 509

(rac)-tert-butyl ((cis)-3-((3-methyl-8-((R)-6-methyl-4-oxo-1,4,5,6-tetrahydropyrrolo[3,4-b]pyrrol-2-yl)-4-oxo-3,4-dihydroquinazolin-2-yl)amino)cyclohexyl)carbamate

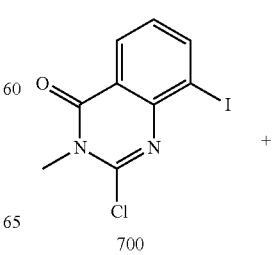

700

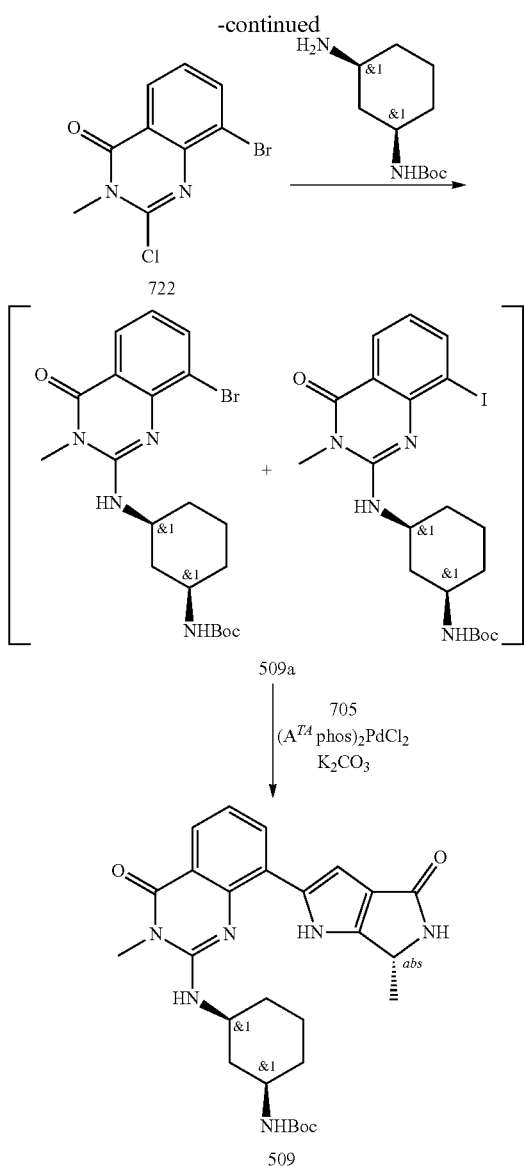

Preparation of (rac)-tert-butyl ((cis)-3-((8-bromo-3-methyl-4-oxo-3,4-dihydroquinazolin-2-yl)amino)cyclohexyl)carbamate/(rac)-tert-butyl and ((cis)-3-((8-iodo-3-methyl-4-oxo-3,4-dihydroquinazolin-2-yl)amino)cyclohexyl)carbamate (509a)

A solution of 2-chloro-8-iodo-3-methylquinazolin-4(3H)-one (700, 0.663 g, 2.07 mmol), 8-bromo-2-chloro-3-methylquinazolin-4(3H)-one (722, 0.71 g, 2.60 mmol), (rac)-tert-butyl ((1R,3S)-3-aminocyclohexyl)carbamate (Small Molecules, Inc., Hoboken, N.J., 1 g, 4.67 mmol), and N-ethyl-N-isopropylpropan-2-amine (1.22 mL, 7.00 mmol) in DMSO (9.33 mL) was heated to 80° C. for 16 h. The reaction mixture was diluted with EtOAc (150 mL), added to a separatory funnel, and washed with saturated aqueous sodium bicarbonate (4×150 mL); the organic layer was separated, dried over $Na_2SO_4$, and concentrated. The crude product was adsorbed onto silica and was purified via automated flash chromatography (silica gel) with 0-80% EtOAc in hexanes to give a mixture of (rac)-tert-butyl ((cis)-3-((8-bromo-3-methyl-4-oxo-3,4-dihydroquinazolin-2-yl)amino)cyclohexyl)carbamate/(rac)-tert-butyl and ((cis)-3-((8-iodo-3-methyl-4-oxo-3,4-dihydroquinazolin-2-yl)amino)cyclohexyl)carbamate (509a, 1.49 g, 2.99 mmol, 64% yield) as an off-white solid. MS (ESI, pos. ion) m/z: 451.0/453.0 & 499.0 (M+1).

Preparation of (rac)-tert-butyl ((cis)-3-((3-methyl-8-((R)-6-methyl-4-oxo-1,4,5,6-tetrahydropyrrolo[3,4-b]pyrrol-2-yl)-4-oxo-3,4-dihydroquinazolin-2-yl)amino)cyclohexyl)carbamate (509)

A mixture of (rac)-tert-butyl ((1R,3S)-3-((8-bromo-3-methyl-4-oxo-3,4-dihydroquinazolin-2-yl)amino)cyclohexyl)carbamate and (rac)-tert-butyl ((1R,3S)-3-((8-iodo-3-methyl-4-oxo-3,4-dihydroquinazolin-2-yl)amino)cyclohexyl)carbamate (509a, 1.49 g, 3.30 mmol), (R)-6-methyl-2-(4,4,5,5-tetramethyl-1,3,2-dioxaborolan-2-yl)-5,6-dihydropyrrolo[3,4-b]pyrrol-4(1H)-one (705, 1.331 g, 3.96 mmol), bis(di-tert-butyl(4-dimethylaminophenyl)phosphine)-dichloropalladium (II) (0.117 g, 0.165 mmol), and potassium phosphate (2.102 g, 9.90 mmol) in 1,4-dioxane (26.4 mL)/water (6.60 mL) was sparged with nitrogen for 3 min at RT; the red reaction mixture was then heated to 80° C. for 1 h. More (R)-6-methyl-2-(4,4,5,5-tetramethyl-1,3,2-dioxaborolan-2-yl)-5,6-dihydropyrrolo[3,4-b]pyrrol-4(1H)-one (0.33 g) was added, and the reaction mixture was stirred at 80° C. for 16 h. The reaction mixture was diluted with EtOAc (150 mL), added to a separatory funnel, and washed with saturated aqueous $NaHCO_3$ (3×100 mL); the aqueous layer was extracted with EtOAc (4×100); the organic layers were separated, dried over $Na_2SO_4$, and concentrated. The crude product was loaded onto the column and was purified via automated flash chromatography (silica gel) with 0-8% 2 M ammonia in MeOH/DCM to give (rac)-tert-butyl ((cis)-3-((3-methyl-8-((R)-6-methyl-4-oxo-1,4,5,6-tetrahydropyrrolo[3,4-b]pyrrol-2-yl)-4-oxo-3,4-dihydroquinazolin-2-yl)amino)cyclohexyl)carbamate (509, 0.59 g, 0.582 mmol, 17% yield) as a light yellow solid. $^1H$ NMR (400 MHz, DMSO-$d_6$) δ ppm 1.05-1.34 (m, 3H) 1.37 (s, 9H) 1.40 (d, J=6.65 Hz, 3H) 1.42-1.54 (m, 2H) 1.73-1.89 (m, 2H) 1.99-2.20 (m, 2H) 3.44 (s, 3H) 3.92-4.11 (m, 1H) 4.48-4.59 (m, 0.5; H) 4.60-4.74 (m, 0.5; H) 6.79-6.99 (m, 3H) 7.15 (t, J=7.73 Hz, 1H) 7.63 (d, J=4.30 Hz, 1H) 7.82 (d, J=7.04 Hz, 1H) 7.97 (dd, J=11.54, 7.82 Hz, 1H) 11.99 (br. s., 0.4; H) 12.09 (br. s., 0.6; H). MS (ESI, pos. ion) m/z: 507.2 (M+1).

Example 510

(R)-7-fluoro-3-methyl-8-(6-methyl-4-oxo-1,4,5,6-tetrahydropyrrolo[3,4-b]pyrrol-2-yl)-2-((1-methylcyclopropyl)amino)quinazolin-4(3H)-one

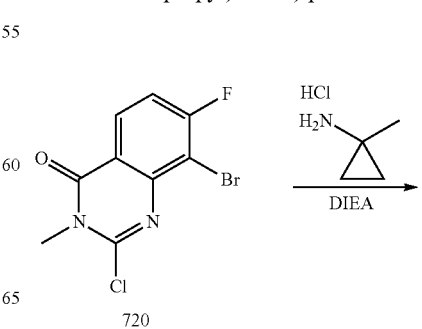

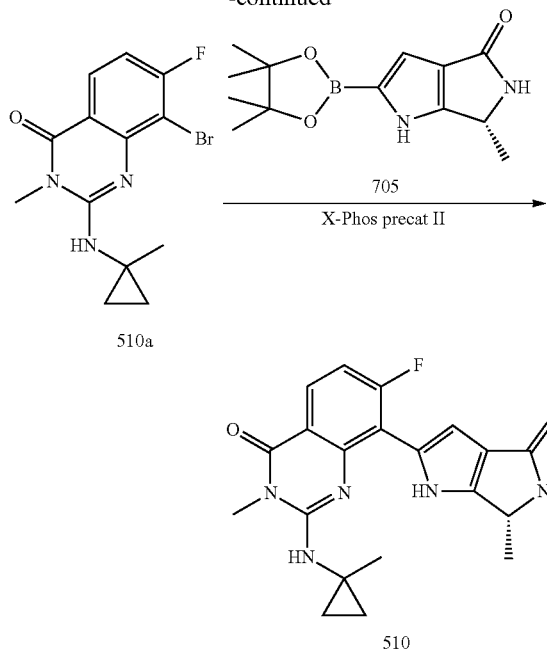

Preparation of 8-bromo-7-fluoro-3-methyl-2-((1-methylcyclopropyl)amino)quinazolin-4(3H)-one (510a)

A brown solution of 8-bromo-2-chloro-7-fluoro-3-methylquinazolin-4(3H)-one (720, 180 mg, 0.617 mmol), 1-methylcyclopropanamine hydrochloride (Small Molecules, Inc., 133 mg, 1.235 mmol), and N-ethyl-N-isopropylpropan-2-amine (237 µL, 1.358 mmol) in DMSO (6.2 mL) was stirred at 80° C. for 1 h when product was observed via LCMS. The reaction mixture was diluted with EtOAc (100 mL), added to a separatory funnel, and washed with saturated aqueous NaHCO$_3$ (2×75 mL); the organic layer was separated, dried over Na$_2$SO$_4$, and concentrated. The crude product was adsorbed onto silica and was purified via automated flash chromatography (silica gel) with 0-100% EtOAc in hexanes to give 8-bromo-7-fluoro-3-methyl-2-((1-methylcyclopropyl)amino)quinazolin-4(3H)-one (510a, 88 mg, 0.270 mmol, 43% yield) as a brown oil. $^1$H NMR (400 MHz, CDCl$_3$) δ ppm 0.80-0.87 (m, 2H) 0.87-0.93 (m, 2H) 1.61 (s, 3H) 3.42 (s, 3H) 5.12 (br. s., 1H) 6.92 (t, J=8.51 Hz, 1H) 8.06 (dd, J=8.80, 6.06 Hz, 1H). $^{19}$F NMR (376 MHz, CDCl$_3$) δ ppm −96.48 (s, 1F). MS (ESI, pos. ion) m/z: 326.0/328.0 (M+1).

Preparation of (R)-7-fluoro-3-methyl-8-(6-methyl-4-oxo-1,4,5,6-tetrahydropyrrolo[3,4-b]pyrrol-2-yl)-2-((1-methylcyclopropyl)amino)quinazolin-4(3H)-one (510)

A mixture of 8-bromo-7-fluoro-3-methyl-2-((1-methylcyclopropyl)amino)quinazolin-4(3H)-one (510a, 88 mg, 0.270 mmol), (R)-6-methyl-2-(4,4,5,5-tetramethyl-1,3,2-dioxaborolan-2-yl)-5,6-dihydropyrrolo[3,4-b]pyrrol-4(1H)-one (705, 109 mg, 0.324 mmol), X-Phos precatalyst II (10.61 mg, 0.013 mmol), and potassium phosphate (172 mg, 0.809 mmol) in 1,4-dioxane (2.2 mL)/water (0.54 mL) was sparged with nitrogen for 3 min at RT; the red solution was then heated to 40° C. for 1 h when starting bromide and product were observed via LCMS. More (R)-6-methyl-2-(4,4,5,5-tetramethyl-1,3,2-dioxaborolan-2-yl)-5,6-dihydropyrrolo[3,4-b]pyrrol-4(1H)-one (120 mg) was added, and the red solution was stirred for another 1 h at 40° C. when more product was observed via LCMS. The reaction mixture was diluted with EtOAc (100 mL), added to a separatory funnel, and washed with saturated aqueous sodium bicarbonate (2×75 mL); the organic layer was separated, dried over Na$_2$SO$_4$, and concentrated. The crude product was adsorbed onto silica and was purified via automated flash chromatography (silica gel) with 0-6% 2 M ammonia in MeOH/DCM to give (R)-7-fluoro-3-methyl-8-(6-methyl-4-oxo-1,4,5,6-tetrahydropyrrolo[3,4-b]pyrrol-2-yl)-2-((1-methylcyclopropyl)amino)quinazolin-4(3H)-one (510, 15 mg, 0.039 mmol, 14% yield) as an off-white solid. $^1$H NMR (400 MHz, DMSO-d$_6$) δ ppm 0.83-0.89 (m, 2H) 0.96-1.05 (m, 2H) 1.38 (d, J=6.65 Hz, 3H) 1.54 (s, 3H) 3.38 (s, 3H) 4.66 (q, J=6.39 Hz, 1H) 6.80 (d, J=3.91 Hz, 1H) 7.11 (dd, J=11.93, 8.80 Hz, 1H) 7.75 (s, 1H) 7.84 (s, 1H) 7.85-7.90 (m, 1H) 13.39 (s, 1H). $^{19}$F NMR (376 MHz, DMSO-d$_6$) δ ppm −102.44 (s, 1F). MS (ESI, pos. ion) m/z: 382.1 (M+1).

Example 511

(R)-2-(tert-butylamino)-3-cyclopropyl-8-(6-ethyl-4-oxo-1,4,5,6-tetrahydropyrrolo[3,4-b]pyrrol-2-yl)quinazolin-4(3H)-one

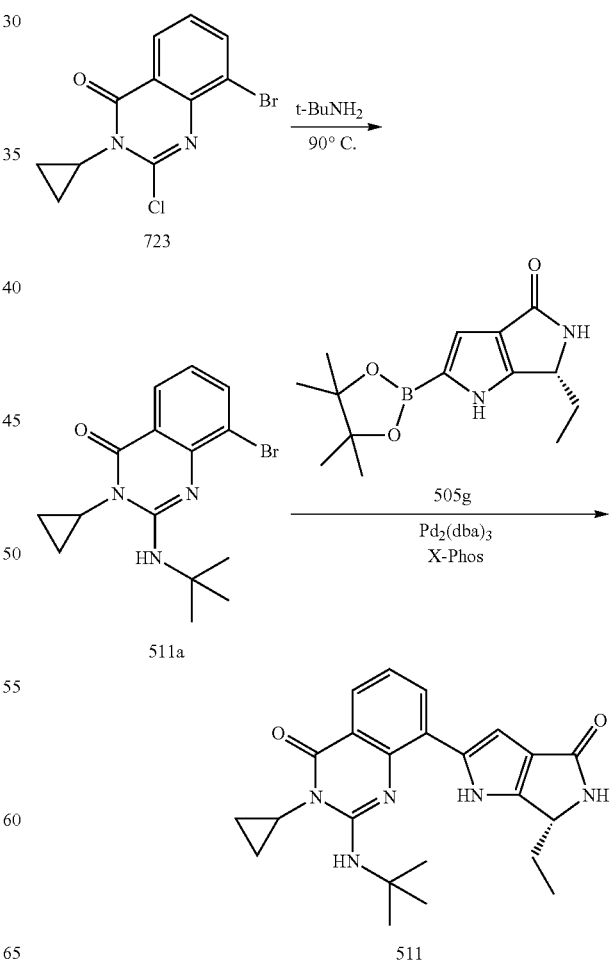

Preparation of 8-bromo-2-(tert-butylamino)-3-cyclopropylquinazolin-4(3H)-one (511a)

8-bromo-2-chloro-3-cyclopropylquinazolin-4(3H)-one (723) (213 mg, 0.711 mmol) was treated with tert-butylamine (0.90 mL, 8.56 mmol) and heated at 90° C. in a sealed tube for 24 h. The reaction mixture was concentrated to remove the excess t-BuNH$_2$ and the crude residue was chromatographed on an ISCO Combiflash RF (12 g Redisep column, using a gradient of 0-5% MeOH in DCM) affording 8-bromo-2-(tert-butylamino)-3-cyclopropylquinazolin-4(3H)-one (224 mg, 0.66 mmol, 94% yield) as an off-white crystalline solid. $^1$H NMR (400 MHz, CDCl$_3$) δ ppm 8.02 (1H, dd, J=8.0, 1.4 Hz), 7.82 (1H, dd, J=7.7, 1.5 Hz), 6.94 (1H, t, J=7.7 Hz), 5.42 (1H, s), 2.62-2.71 (1H, m), 1.61 (9H, s), 1.28-1.35 (2H, m), 0.87-0.95 (2H, m). m/z (ESI, +ve) 335.9/337.9 (M+1)$^+$.

Preparation of (R)-2-(tert-butylamino)-3-cyclopropyl-8-(6-ethyl-4-oxo-1,4,5,6-tetrahydropyrrolo[3,4-b]pyrrol-2-yl)quinazolin-4(3H)-one (511)

A mixture of 2-(dicyclohexylphosphino)-2',4',6',-tri-isopropyl1,1'-biphenyl (Strem Chemicals, Newburyport, Mass., 25.0 mg, 0.052 mmol), tris(dibenzylideneacetone)dipalladium (0) (Strem Chemicals, 24.0 mg, 0.026 mmol), potassium phosphate tribasic (Sigma Aldrich, 417 mg, 1.96 mmol), (R)-6-ethyl-2-(4,4,5,5-tetramethyl-1,3,2-dioxaborolan-2-yl)-5,6-dihydropyrrolo[3,4-b]pyrrolo-4(1H)-one (505g, 97 mg, 0.351 mmol) and 8-bromo-2-(tert-butylamino)-3-cyclopropylquinazolin-4(3H)-one (511a, 220 mg, 0.654 mmol) in 1,4-dioxane (6 mL), water (1.80 mL) in a sealed glass tube was heated at 80° C. for 1 h. The reaction mixture was treated with 1N NaOH and extracted with EtOAc (2×50 mL), washed with brine and dried over MgSO$_4$, filtered and concentrated. The crude reaction mixture was chromatographed on an ISCO Combiflash RF (40 g Thomson SingleStep column, using a gradient of 0-10% MeOH in DCM) affording a light orange oil. It was treated with Et$_2$O and sonicated affording a suspension which was filtered and washed with Et$_2$O and dried in the vacuum oven at 34° C. overnight affording (R)-2-(tert-butylamino)-3-cyclopropyl-8-(6-ethyl-4-oxo-1,4,5,6-tetrahydropyrrolo[3,4-b]pyrrol-2-yl)quinazolin-4(3H)-one (511) (19 mg, 0.047 mmol, 7% yield) as a tan amorphous solid. $^1$H NMR (400 MHz, DMSO-d$_6$) δ ppm 11.86 (1H, s), 7.84 (1H, d, J=7.8 Hz), 7.86 (1H, d, J=7.4 Hz), 7.64 (1H, s), 7.14 (1H, t, J=7.6 Hz), 6.68-6.74 (1H, m), 6.11 (1H, s), 4.45 (1H, t, J=5.4 Hz), 2.86 (1H, dt, J=6.9, 3.2 Hz), 1.78-1.91 (1H, m), 1.61 (1H, dt, J=13.9, 6.9 Hz), 1.51 (9H, s), 1.25 (3H, d, J=7.2 Hz), 0.84 (2H, t, J=7.3 Hz), 0.73-0.80 (2H, m). m/z (ESI, +ve) 406.0 (M+1)$^+$.

Example 512

(R)-2-(tert-Butylamino)-3-ethyl-7-fluoro-8-(6-methyl-4-oxo-1,4,5,6-tetrahydropyrrolo[3,4-b]pyrrol-2-yl)quinazolin-4(3H)-one

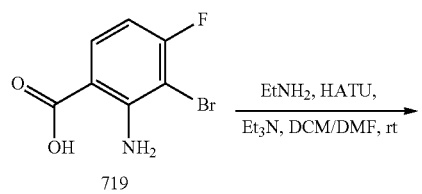

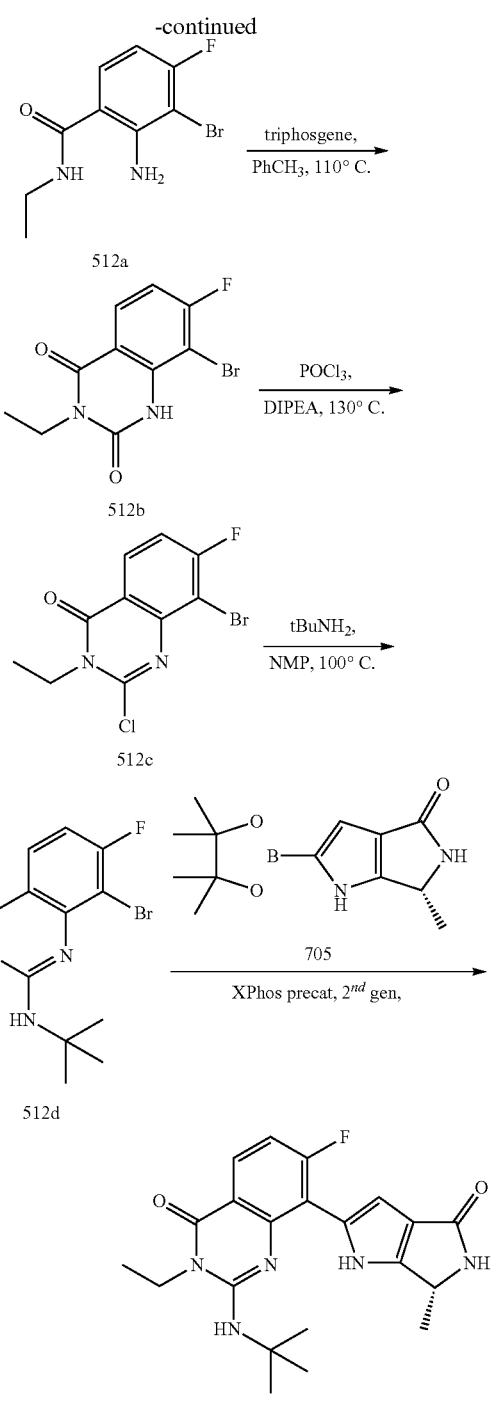

Preparation of 2-Amino-3-bromo-N-ethyl-4-fluorobenzamide (512a)

2-(3H-[1,2,3]triazolo[4,5-b]pyridin-3-yl)-1,1,3,3-tetramethylisouronium hexafluorophosphate(V) (HATU; Aldrich; 5.36 g, 14.10 mmol) was added to a mixture of 2-amino-3-bromo-4-fluorobenzoic acid (Example 719; 3.00 g, 12.82 mmol), ethylamine (2.0 M in MeOH; Aldrich; 7.05 mL, 14.10 mmol), and TEA (2.68 mL, 19.23 mmol) in a mixture of DMF (10 mL) and DCM (10.00 mL), and the resulting solution was stirred at 23° C. for 17 h. The reaction mixture was then diluted with DCM (100 mL), and the resulting solution was sequentially washed with water (2×80 mL), 0.5 N aqueous NaOH (50 mL), and brine (50 mL), then concentrated in vacuo. The residue was chromatographically purified (silica gel, 0-60% EtOAc/hexanes) to yield 2-amino-3-bromo-N-ethyl-4-fluorobenzamide (2.59 g, 9.92 mmol, 77% yield) as an off-white solid. $^1$H NMR (400 MHz, DMSO-d$_6$) δ ppm 8.39 (1H, t, J=4.5 Hz), 7.59 (1H, dd, J=8.8, 6.3 Hz), 6.86 (2H, br. s.), 6.57 (1H, t, J=8.5 Hz), 3.20-3.29 (2H, m), 1.11 (3H, t, J=7.2 Hz). $^{19}$F NMR (376 MHz, DMSO-d$_6$) δ ppm −101.26 (1F, s). m/z (ESI, +ve) 260.9/262.9 (M+H)$^+$.

Preparation of 8-Bromo-3-ethyl-7-fluoroquinazoline-2,4(1H,3H)-dione (512b)

A solution of 2-amino-3-bromo-N-ethyl-4-fluorobenzamide (512a, 2.00 g, 7.66 mmol) and triphosgene (Aldrich; 0.796 g, 2.68 mmol) in toluene (80 mL) was heated at 110° C. for 18 h (water-cooled reflux condenser attached to flask). The reaction mixture was then cooled to RT and concentrated in vacuo to give 8-bromo-3-ethyl-7-fluoroquinazoline-2,4 (1H,3H)-dione (2.238 g, 7.80 mmol) as a light-yellow solid: m/z (ESI, +ve) 286.9/288.8 (M+H)$^+$. This material was used directly in the subsequent transformation.

Preparation of 8-Bromo-2-chloro-3-ethyl-7-fluoro-quinazolin-4(3H)-one (512c)

A solution of 8-bromo-3-ethyl-7-fluoroquinazoline-2,4 (1H,3H)-dione (512b, 2.20 g, 7.66 mmol), phosphorous oxychloride (Acros Organics, Geel, Belgium; 3.57 mL, 38.3 mmol), and DIPEA (5.34 mL, 30.6 mmol) was heated over a 130° C. oil bath for 4.5 h. The reaction mixture was then cooled to RT and poured onto ice, and the resulting mixture was diluted with water (250 mL) to provide a brown suspension. 10 N aqueous NaOH was added to the vigorously stirred suspension (maintaining the reaction mixture at 0° C.) until a pH of 10 was achieved. The precipitated solid was collected by vacuum filtration, washed with water (3×20 mL), and dried in vacuo to provide 8-bromo-2-chloro-3-ethyl-7-fluoroquinazolin-4(3H)-one (2.301 g, 7.53 mmol, 98% yield) as a tan solid. $^1$H NMR (400 MHz, CDCl$_3$) δ ppm 8.22 (1H, dd, J=8.9, 5.8 Hz), 7.23-7.29 (1H, m), 4.37 (2H, q, J=7.1 Hz), 1.41 (3H, t, J=7.0 Hz). $^{19}$F NMR (376 MHz, CDCl$_3$) δ ppm −93.38 (1F, s). m/z (ESI, +ve) 304.7/306.8/308.7 (M+H)$^+$.

Preparation of 8-Bromo-2-(tert-butylamino)-3-ethyl-7-fluoroquinazolin-4(3H)-one (512d)

A solution of 8-bromo-2-chloro-3-ethyl-7-fluoroquinazolin-4(3H)-one (512c, 197 mg, 0.645 mmol), tert-butylamine (Aldrich; 1.5 mL, 14.27 mmol), and NMP (0.5 mL) was heated in a sealed microwave vial at 100° C. for 30 min. The reaction mixture was then partitioned between EtOAc (60 mL) and water (40 mL). The organic layer was separated and sequentially washed water (40 mL) and brine (40 mL), then dried over Na$_2$SO$_4$, filtered, and concentrated in vacuo to give as a yellow solid. The combined aqueous layers were subsequently extracted with DCM (2×30 mL), and the combined organic extracts were then sequentially washed with water (2×40 mL) and brine (40 mL), dried over Na$_2$SO$_4$, filtered, and concentrated in vacuo to provide a yellow solid. Combination of the two batches of isolated solids afforded 8-bromo-2-(tert-butylamino)-3-ethyl-7-fluoroquinazolin-4(3H)-one (204.3 mg, 0.597 mmol, 93% yield) as a light-yellow solid. $^1$H NMR (400 MHz, CDCl$_3$) δ ppm 8.05 (1H, dd, J=8.8, 6.1 Hz), 6.89 (1H, t, J=8.5 Hz), 4.56 (1H, br. s.), 4.05 (2H, q, J=7.2 Hz), 1.62 (9H, s), 1.33 (3H, t, J=7.2 Hz). $^{19}$F NMR (376 MHz, CDCl$_3$) δ ppm −96.81 (1F, s). m/z (ESI, +ve) 341.9/343.9 (M+H)$^+$.

Preparation of (R)-2-(tert-Butylamino)-3-ethyl-7-fluoro-8-(6-methyl-4-oxo-1,4,5,6-tetrahydropyrrolo[3,4-b]pyrrol-2-yl)quinazolin-4(3H)-one (512)

A solution of 8-bromo-2-(tert-butylamino)-3-ethyl-7-fluoroquinazolin-4(3H)-one (204.3 mg, 0.597 mmol), (R)-6-methyl-2-(4,4,5,5-tetramethyl-1,3,2-dioxaborolan-2-yl)-5,6-dihydropyrrolo[3,4-b]pyrrolo-4(1H)-one (Example 705; 196 mg, 0.746 mmol), potassium phosphate (380 mg, 1.791 mmol), and chloro(2-dicyclohexylphosphino-2',4',6'-triisopropyl-1,1'-biphenyl)[2-(2'-amino-1,1'-biphenyl)]palladium (II) (XPhos precatalyst, 2nd generation; Aldrich; 23.52 mg, 0.030 mmol) in a mixture of 1,4-dioxane (2.5 mL) and water (0.625 mL) was stirred under argon at 45° C. for 1 h. The reaction mixture was then concentrated onto silica gel and chromatographically purified (silica gel, 50-100% EtOAc/hexanes, then 0-10% MeOH/DCM) to provide (R)-2-(tert-butylamino)-3-ethyl-7-fluoro-8-(6-methyl-4-oxo-1,4,5,6-tetrahydropyrrolo[3,4-b]pyrrol-2-yl)quinazolin-4(3H)-one (154.6 mg, 0.389 mmol, 65% yield) as an off-white solid. $^1$H NMR (400 MHz, DMSO-d$_6$) δ ppm 11.67 (1H, s), 7.95 (1H, dd, J=8.8, 6.5 Hz), 7.57 (1H, s), 7.07 (1H, t, J=9.4 Hz), 6.30 (1H, s), 6.01 (1H, s), 4.48 (1H, q, J=6.7 Hz), 4.18 (2H, q, J=7.0 Hz), 1.36 (9H, s), 1.34 (3H, d, J=6.7 Hz), 1.15 (3H, t, J=7.0 Hz). $^{19}$F NMR (376 MHz, DMSO-d$_6$) δ ppm −105.18 (1F, s). m/z (ESI, +ve) 398.0 (M+H)$^+$.

Example 513

(R)-3-Ethyl-7-fluoro-8-(6-methyl-4-oxo-1,4,5,6-tetrahydropyrrolo[3,4-b]pyrrol-2-yl)-2-((1-methylcyclopropyl)amino)quinazolin-4(3H)-one

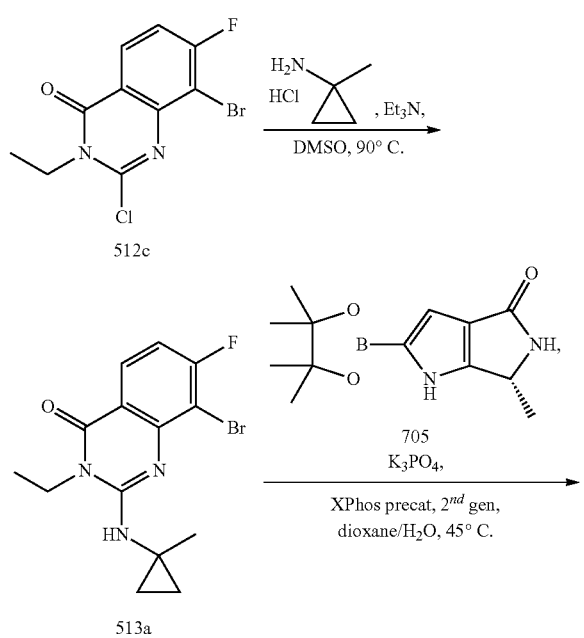

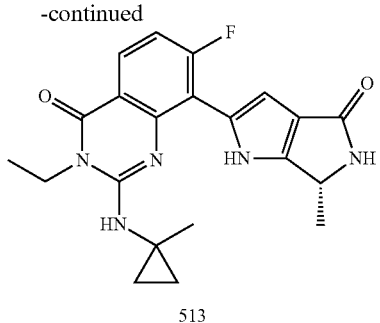

513

Preparation of 8-bromo-3-ethyl-7-fluoro-2-((1-methylcyclopropyl)amino)quinazolin-4(3H)-one (513a)

A solution of 8-bromo-2-chloro-3-ethyl-7-fluoroquinazolin-4(3H)-one (512c; 200 mg, 0.655 mmol), 1-methylcyclopropanamine hydrochloride (Small Molecules, Inc.; 211 mg, 1.964 mmol), and TEA (0.274 mL, 1.964 mmol) in DMSO (1.5 mL) was heated in a sealed microwave vial at 90° C. for 30 min. The reaction mixture was then partitioned between DCM (60 mL) and water (40 mL). The organic layer was separated and sequentially washed with water (2×40 mL) and brine (40 mL), then dried over $Na_2SO_4$, filtered, and concentrated in vacuo to give 8-bromo-3-ethyl-7-fluoro-2-((1-methylcyclopropyl)amino)quinazolin-4(3H)-one (181.1 mg, 0.532 mmol, 81% yield) as a light-yellow solid. $^1$H NMR (400 MHz, $CDCl_3$) δ ppm 8.06 (1H, dd, J=8.8, 6.1 Hz), 6.93 (1H, t, J=8.5 Hz), 4.84-5.23 (1H, m), 4.02 (2H, q, J=6.4 Hz), 1.61 (3H, s), 1.30 (3H, t, J=7.2 Hz), 0.91 (2H, br. s.), 0.81-0.88 (2H, m). $^{19}$F NMR (376 MHz, $CDCl_3$) δ ppm −96.57 (1F, br. s.). m/z (ESI, +ve) 339.8/341.9 (M+H)$^+$.

Preparation of (R)-3-Ethyl-7-fluoro-8-(6-methyl-4-oxo-1,4,5,6-tetrahydropyrrolo[3,4-b]pyrrol-2-yl)-2-((1-methylcyclopropyl)amino)quinazolin-4(3H)-one (513)

A solution of 8-bromo-3-ethyl-7-fluoro-2-(1-methylcyclopropyl)amino)quinazolin-4(3H)-one (513a, 181.1 mg, 0.53 mmol), (R)-6-methyl-2-(4,4,5,5-tetramethyl-1,3,2-dioxaborolan-2-yl)-5,6-dihydropyrrolo[3,4-b]pyrrol-4(1H)-one (Example 705; 174 mg, 0.665 mmol), potassium phosphate (339 mg, 1.597 mmol), and chloro(2-dicyclohexylphosphino-2',4',6'-triisopropyl-1,1'-biphenyl)[2-(2'-amino-1,1'-biphenyl)]palladium(II) (XPhos precatalyst, 2nd generation; Aldrich; 20.97 mg, 0.027 mmol) in a mixture of 1,4-dioxane (2.2 mL) and water (0.55 mL) was stirred under argon at 45° C. for 1.5 h. The reaction mixture was then concentrated onto silica gel and chromatographically purified (silica gel, 50-100% EtOAc/hexanes, then 0-10% MeOH/DCM). The isolated product was suspended in MeOH (2 mL), collected by vacuum filtration, washed with ethyl ether (5 mL), and dried in vacuo to provide (R)-3-ethyl-7-fluoro-8-(6-methyl-4-oxo-1,4,5,6-tetrahydropyrrolo[3,4-b]pyrrol-2-yl)-2-((1-methylcyclopropyl)amino)quinazolin-4(3H)-one (148.2 mg, 0.375 mmol, 70% yield) as a white solid: $^1$H NMR (400 MHz, DMSO-$d_6$) δ ppm 13.32 (1H, s), 7.90 (1H, s), 7.86 (1H, m, J=8.8, 6.3 Hz), 7.74 (1H, s), 7.11 (1H, dd, J=11.9, 8.8 Hz), 6.79 (1H, d, J=3.7 Hz), 4.66 (1H, q, J=6.3 Hz), 4.06 (2H, q, J=6.5 Hz), 1.54 (3H, s), 1.37 (3H, d, J=6.5 Hz), 1.15 (3H, t, J=6.9 Hz), 0.95-1.05 (2H, m), 0.86 (2H, d, J=2.0 Hz). $^{19}$F NMR (376 MHz, DMSO-$d_6$) δ ppm −102.43 (1F, s). m/z (ESI, +ve) 395.9 (M+H)$^+$.

Example 514

(R)-2-(tert-butylamino)-8-(6-methyl-4-oxo-1,4,5,6-tetrahydropyrrolo[3,4-b]pyrrol-2-yl)-3-(tetrahydro-2H-pyran-4-yl)quinazolin-4(3H)-one

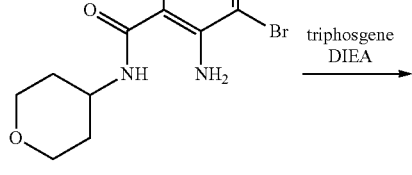

515a

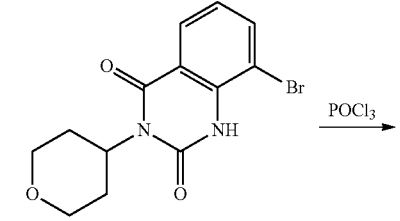

515b

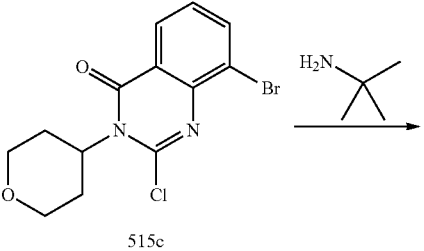

515c

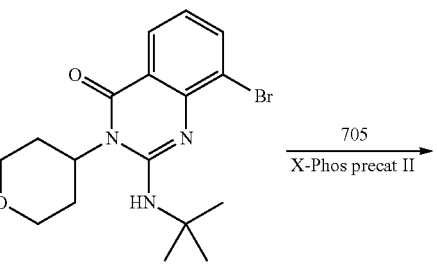

515d

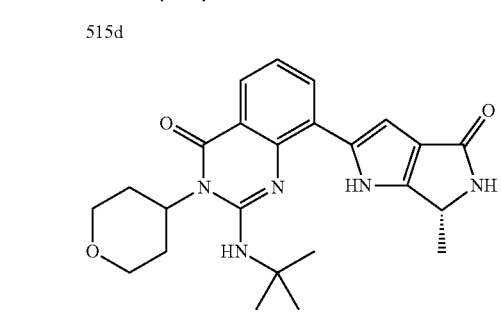

515

Preparation of 2-amino-3-bromo-N-(tetrahydro-2H-pyran-4-yl)benzamide (515a)

A yellow mixture of 2-amino-3-bromobenzoic acid (Oakwood Products, Inc., West Columbia, S.C., 2.125 g, 9.83 mmol), 2,4,6-tripropyl-1,3,5,2,4,6-trioxatriphosphinane 2,4,6-trioxide (6.37 mL, 10.82 mmol), tetrahydro-2H-pyran-4-amine hydrochloride (Combi-Blocks, Inc., San Diego, Calif., 4.06 g, 29.5 mmol), and DIEA (5.15 mL, 29.5 mmol) was stirred at 0° C. for 5 min; the reaction mixture was then warmed to RT and stir for 30 min when product was observed via LCMS. The reaction mixture was diluted with EtOAc (150 mL), added to a separatory funnel, and washed with saturated aqueous $NaHCO_3$ (4×100 mL); the organic layer was separated, dried over $Na_2SO_4$, and concentrated to give 2-amino-3-bromo-N-(tetrahydro-2H-pyran-4-yl)benzamide (515a, 1.54 g, 5.15 mmol, 52% yield) as an off-white solid. $^1$H NMR (400 MHz, $CDCl_3$) δ ppm 1.49-1.63 (m, 2H) 2.00 (dd, J=12.52, 2.15 Hz, 2H) 3.53 (td, J=11.69, 2.05 Hz, 2H) 3.95-4.05 (m, 2H) 4.10-4.21 (m, 1H) 5.87 (d, J=7.24 Hz, 1H) 6.06 (br. s., 2H) 6.54 (t, J=7.92 Hz, 1H) 7.25-7.30 (m, 1H) 7.51 (dd, J=7.82, 1.17 Hz, 1H). MS (ESI, pos. ion) m/z: 299.0/301.0 (M+1).

Preparation of 8-bromo-3-(tetrahydro-2H-pyran-4-yl)quinazoline-2,4(1H,3H)-dione (515b)

A solution of 2-amino-3-bromo-N-(tetrahydro-2H-pyran-4-yl)benzamide (515a, 1.54 g, 5.15 mmol), bis(trichloromethyl) carbonate (0.764 g, 2.57 mmol), and triethylamine (3.59 mL, 25.7 mmol) in DCM (51.5 mL) was refluxed for 16 h. Toluene (50 mL) was added to the clear solution; this mixture was partially concentrated to remove the DCM. More bis(trichloromethyl) carbonate (0.764 g, 2.57 mmol) was added, and the yellow solution was heated to 90° C. for 1 h. The reaction mixture was concentrated to give 8-bromo-3-(tetrahydro-2H-pyran-4-yl)quinazoline-2,4(1H,3H)-dione (515b) as a light yellow solid. $^1$H NMR (400 MHz, $CDCl_3$) δ ppm 1.56-1.62 (m, 2H) 2.87 (qd, J=12.39, 4.69 Hz, 2H) 3.52 (td, J=12.03, 1.76 Hz, 2H) 4.10 (dd, J=11.54, 4.69 Hz, 2H) 5.11 (tt, J=12.18, 3.96 Hz, 1H) 7.11 (t, J=8.02 Hz, 1H) 7.79 (dd, J=7.82, 1.17 Hz, 1H) 8.09 (s, 1H) 8.11 (s, 1H). MS (ESI, pos. ion) m/z: 325.0/326.9 (M+1).

Preparation of 8-bromo-2-chloro-3-(tetrahydro-2H-pyran-4-yl)quinazolin-4(3H)-one (515c)

A mixture of 8-bromo-3-(tetrahydro-2H-pyran-4-yl)quinazoline-2,4(1H,3H)-dione (515b, 1.67 g, 5.14 mmol), phosphoryl trichloride (4.70 mL, 51.4 mmol), and N-ethyl-N-isopropylpropan-2-amine (3.58 mL, 20.54 mmol) was stirred at 90° C. for 20 h. The reaction mixture was concentrated to give a brown oil. Ice was added until the mixture began to stir, and $NaHCO_3$ was added to the mixture; a brown solid which formed was filtered and washed with water. The solid was dissolved in DCM, placed in a separatory funnel, separated, dried over $Na_2SO_4$, and concentrated to give 8-bromo-2-chloro-3-(tetrahydro-2H-pyran-4-yl)quinazolin-4(3H)-one (515c, 1.60 g, 4.66 mmol, 91% yield over two steps) as a brown solid. $^1$H NMR (400 MHz, $CDCl_3$) δ ppm 1.70 (dd, J=12.23, 2.25 Hz, 2H) 3.00 (qd, J=12.36, 4.79 Hz, 2H) 3.51 (td, J=11.93, 1.76 Hz, 2H) 4.14 (dd, J=11.54, 4.69 Hz, 2H) 5.05-5.19 (m, 1H) 7.33 (t, J=7.92 Hz, 1H) 8.00 (dd, J=7.73, 1.27 Hz, 1H) 8.18 (dd, J=8.02, 1.37 Hz, 1H). MS (ESI, pos. ion) m/z: 343.0/344.9 (M+1).

Preparation of 8-bromo-2-(tert-butylamino)-3-(tetrahydro-2H-pyran-4-yl)quinazolin-4(3H)-one (515 (1)

A solution of 8-bromo-2-chloro-3-(tetrahydro-2H-pyran-4-yl)quinazolin-4(3H)-one (515c, 0.51 g, 1.484 mmol) and 2-methylpropan-2-amine (Sigma-Aldrich Co., 3.12 mL, 29.7 mmol) in NMP (7.42 mL) was stirred at 100° C. for 16 h. The reaction mixture was diluted with EtOAc (100 mL), added to a separatory funnel, and washed with water (3×100 mL); the organic layer was separated, dried over $Na_2SO_4$, and concentrated. The crude product was adsorbed onto silica and was purified via automated flash chromatography (silica gel) with 100% hexanes to 60% EtOAc in hexanes to give 8-bromo-2-(tert-butylamino)-3-(tetrahydro-2H-pyran-4-yl)quinazolin-4(3H)-one (515d, 70 mg, 0.184 mmol, 12.40% yield) as a light yellow solid. $^1$H NMR (400 MHz, $CDCl_3$) δ ppm 1.63 (s, 9H) 1.77 (dd, J=12.52, 2.54 Hz, 2H) 2.41 (qd, J=12.52, 4.69 Hz, 2H) 3.58 (td, J=11.74, 1.96 Hz, 2H) 4.14 (dd, J=12.23, 4.21 Hz, 2H) 4.70 (s, 1H) 5.48 (t, J=12.72 Hz, 1H) 6.97 (t, J=7.82 Hz, 1H) 7.83 (dd, J=7.63, 1.37 Hz, 1H) 8.04 (dd, J=8.02, 1.37 Hz, 1H). MS (ESI, pos. ion) m/z: 380.2/382.2 (M+1).

Preparation of (R)-2-(tert-butylamino)-8-(6-methyl-4-oxo-1,4,5,6-tetrahydropyrrolo[3,4-b]pyrrol-2-yl)-3-(tetrahydro-2H-pyran-4-yl)quinazolin-4(3H)-one (515)

A mixture of 8-bromo-2-(tert-butylamino)-3-(tetrahydro-2H-pyran-4-yl)quinazolin-4(3H)-one (515d, 70 mg, 0.184 mmol), (R)-6-methyl-2-(4,4,5,5-tetramethyl-1,3,2-dioxaborolan-2-yl)-5,6-dihydropyrrolo[3,4-b]pyrrol-4(1H)-one (705, 93 mg, 0.276 mmol), X-Phos precatalyst II (7.24 mg, 9.20 μmol), and potassium phosphate (117 mg, 0.552 mmol) in 1,4-dioxane (1.5 mL)/water (0.4 mL) was sparged with nitrogen for 3 min at RT; the reaction mixture was stirred at 40° C. for 1.5 h. The reaction mixture was diluted with EtOAc (100 mL), added to a separatory funnel, and washed with saturated aqueous $NaHCO_3$ (3×75 mL); the organic layer was separated, dried over $Na_2SO_4$, and concentrated. The crude product was loaded onto the column and was purified via automated flash chromatography (silica gel) with 0-6% 2 M ammonia in MeOH/DCM to give (R)-2-(tert-butylamino)-8-(6-methyl-4-oxo-1,4,5,6-tetrahydropyrrolo[3,4-b]pyrrol-2-yl)-3-(tetrahydro-2H-pyran-4-yl)quinazolin-4(3H)-one (515, 10 mg, 0.023 mmol, 12% yield) as an off-white solid. $^1$H NMR (400 MHz, $CDCl_3$) δ ppm 1.52 (d, J=6.65 Hz, 3H) 1.65 (s, 9H) 1.85 (d, J=11.15 Hz, 2H) 2.33-2.48 (m, 2H) 3.61 (t, J=11.54 Hz, 2H) 4.17 (dd, J=11.74, 4.50 Hz, 2H) 4.65 (q, J=6.72 Hz, 1H) 4.88 (s, 1H) 5.59-5.68 (m, 1H) 5.70 (s, 1H) 6.82 (d, J=1.17 Hz, 1H) 7.21 (t, J=7.73 Hz, 1H) 8.00 (dd, J=7.73, 1.47 Hz, 1H) 8.04 (dd, J=7.83, 1.37 Hz, 1H) 12.27 (br. s., 1H). MS (ESI, pos. ion) m/z: 436.1 (M+1).

Example 515

(R)-2-(tert-butylamino)-8-(6-methyl-4-oxo-1,4,5,6-tetrahydropyrrolo[3,4-b]pyrrol-2-yl)-3-(2-(methylsulfonyl)ethyl)quinazolin-4(3H)-one

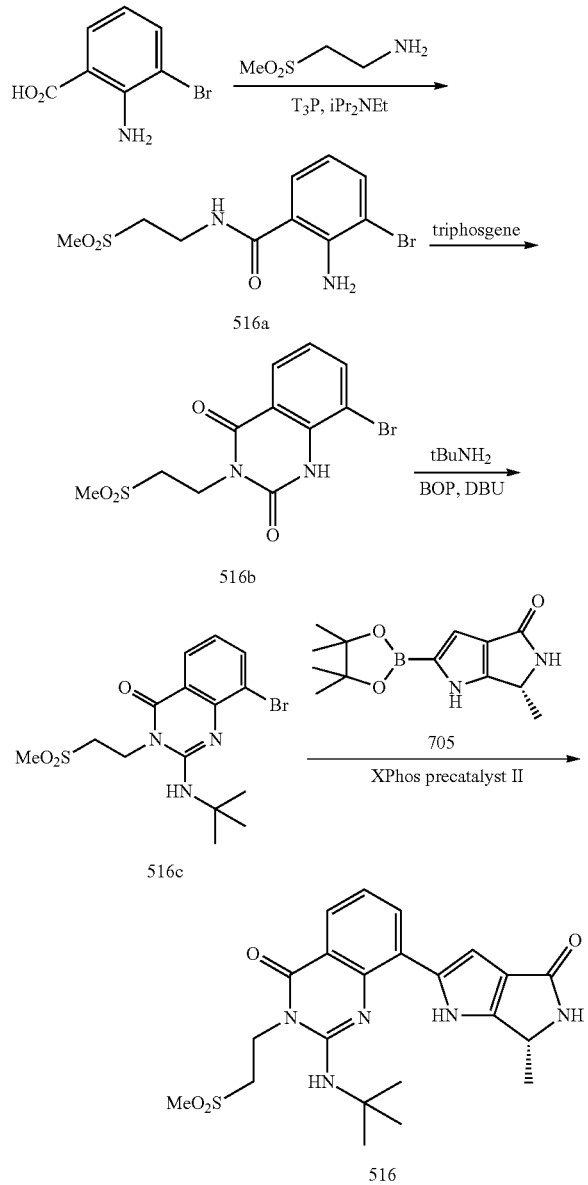

Preparation of 2-amino-3-bromo-N-(2-(methylsulfonyl)ethyl)benzamide (516a)

To a 100-mL round-bottomed flask was added 2-amino-3-bromobenzoic acid (0.8 g, 3.70 mmol) and 2-(methylsulfonyl)ethanamine hydrochloride (0.709 g, 4.44 mmol, ChemBridge Inc.) in EtOAc (15 mL) followed by DIEA (1.61 mL, 9.26 mmol) and T3P (2.59 mL, 4.07 mmol, Sigma Aldrich). The mixture was stirred at RT for 2 h, then quenched with sat. $NaHCO_3$. EtOAc (100 mL) was added and the layers were separated. The organic layer was washed with sat. $NaHCO_3$ (20 mL), brine (15 mL), then dried ($MgSO_4$), filtered and concentrated to give the crude product 485 mg. MS (ESI, pos. ion) m/z: 321 (M+1).

Preparation of 8-bromo-3-(2-(methylsulfonyl)ethyl)quinazoline-2,4(1H,3H)-dione (516b)

A glass microwave reaction vessel was charged with 2-amino-3-bromo-N-(2-(methylsulfonyl)ethyl)benzamide (480 mg, 1.494 mmol) and triphosgene (0.078 mL, 0.523 mmol, Fluka) in 1,4-dioxane (6 mL). The reaction mixture was stirred and heated in an Initiator microwave reactor (Personal Chemistry, Biotage AB, Inc., Upssala, Sweden) at 100° C. for 45 min. The mixture was cooled to RT and the solvent was removed to give the crude product 600 mg. MS (ESI, pos. ion) m/z: 347 (M+1).

Preparation of 8-bromo-2-(tert-butylamino)-3-(2-(methylsulfonyl)ethyl)quinazolin-4(3H)-one (516c)

A glass microwave reaction vessel was charged with 8-bromo-3-(2-(methylsulfonyl)ethyl)quinazoline-2,4(1H,3H)-dione (200 mg, 0.576 mmol) and (benzotriazol-1-yloxy)tris(dimethylamino)phosphonium hexafluorophosphate (382 mg, 0.864 mmol, Sigma Aldrich) in DMF (2 mL) followed by 1,8-diazabicyclo-[5.4.0]undec-7-ene (0.172 mL, 1.152 mmol, Sigma Aldrich). The reaction mixture was stirred for 5 min. tert-butylamine (0.30 mL, 2.88 mmol) was added. The reaction was stirred at 40° C. for 4 h. The mixture was diluted with EtOAc (30 mL) and washed with water, brine, dried ($MgSO_4$), filtered and concentrated. The residue was purified with silica gel chromatography (eluted with 0-10% EtOAc in DCM) to give 8-bromo-2-(tert-butylamino)-3-(2-(methylsulfonyl)ethyl)quinazolin-4(3H)-one (516c; 90 mg, 0.224 mmol, 39% yield) as a yellow solid. MS (ESI, pos. ion) m/z: 402 (M+1).

Preparation of (R)-2-(tert-butylamino)-8-(6-methyl-4-oxo-1,4,5,6-tetrahydropyrrolo[3,4-b]pyrrol-2-yl)-3-(2-(methylsulfonyl)ethyl)quinazolin-4(3H)-one (516)

A glass microwave reaction vessel was charged with 8-bromo-2-(tert-butylamino)-3-(2-(methylsulfonyl)ethyl)quinazolin-4(3H)-one (516c; 88 mg, 0.219 mmol) and (R)-6-methyl-2-(4,4,5,5-tetramethyl-1,3,2-dioxaborolan-2-yl)-5,6-dihydropyrrolo[3,4-b]pyrrol-4(1H)-one (705) (86 mg, 0.262 mmol) in 1,4-dioxane (1.0 mL)/water (0.2 mL) followed by potassium phosphate (0.054 mL, 0.656 mmol) and XPhos precatalyst II (8.6 mg, 10.94 μmol, Sigma Aldrich). The reaction mixture was stirred and heated in an oil bath at 45° C. for 6 h, then cooled to RT. The mixture was diluted with water (25 mL) and the suspension was filtered and the solid was further purified with silica gel chromatography (eluted with 0-4% MeOH in DCM) to give (R)-2-(tert-butylamino)-8-(6-methyl-4-oxo-1,4,5,6-tetrahydropyrrolo[3,4-b]pyrrol-2-yl)-3-(2-(methylsulfonyl)ethyl)quinazolin-4(3H)-one (72 mg, 0.157 mmol, 72% yield) as a light yellow solid. MS (ESI, pos. ion) m/z: 458 (M+1); $^1$H NMR (400 MHz, DMSO-$d_6$) δ ppm 11.86 (1H, s), 7.89 (2H, d, J=7.8 Hz), 7.61 (1H, s), 7.20 (1H, t, J=7.7 Hz), 6.71 (1H, d, J=1.4 Hz), 6.09 (1H, s), 4.47-4.62 (3H, m), 3.56 (2H, t, J=6.7 Hz), 3.12 (3H, s), 1.49 (9H, s), 1.37 (3H, d, J=6.7 Hz).

Biological Activity
Pim-1 and Pim-2
Cloning and Expression:

Full-length human cDNAs encoding Pim-1 (MGC ID 3913552) or Pim-2 (IMAGE ID 5092935) were purchased from Invitrogen, Carlsbad, Calif. These cDNAs were used as templates in PCR reactions to produce full-length DNA clones of the PIMs. Oligonucleotide PCR primers for Pim-1 were 5'-tggctgatcaatgctcttgtccaaaatc-3' (SEQ ID NO: 1) and 5'-attagaattctatttgctgggccccggc-3' (SEQ ID NO: 2). Oligonucleotide PCR primers for Pim-2 were 5'-tgcaggatccatgt-tgaccaagcctctac-3' (SEQ ID NO: 3) and 5'-acgtgaattctatccct-gtgacatggcc-3' (SEQ ID NO: 4). PCR products were digested with BclI and EcoRI for Pim-1 and BamHI and EcoRI for Pim-2 and ligated into a modified baculovirus transfer vector (pFastBac1) cleaved with BamHI and EcoRI. For bacterial expression, the same cleaved PCR products encoding Pim-1 or Pim-2 were ligated into a modified *E. coli* expression vector pET28(a) cleaved with BamHI and EcoRI. Amino-terminal hexahistidine tags followed by a thrombin cleavage site were previously added to the vectors using standard methods of molecular biology.

Recombinant baculoviruses expressing Pim-1 or Pim-2 were made using standard methods (Fastbac manual, Invitrogen, Carlsbad, Calif.). Infection of Sf9 cells was done at an m.o.i. of greater than 5 for 24-48 h. Cells were harvested by centrifugation and frozen at −80 C. For *E. coli* expression, cells carrying pET28-His6-Th-Pim-1 or pET28-His6-Th-Pim-2 were picked from a single colony and grown o/n in LB media. The o/n culture was used to inoculate a 2 liter flask with 500 mL media. This was grown o/n and used to inoculate 15-20 liters of Terrific Broth in a New Brunswick Scientific fermentor. The *E. coli* were grown at 37° C. to and OD600 >1.6. The temperature was dropped to 18° C. and o/n expression was induced with 0.5 mM IPTG. Cells were harvested by centrifugation and frozen at −80° C.

Purification

The frozen cell pellets were thawed by stirring in chilled lysis buffer (0.05 M HEPES, pH 8.0, 0.25 M NaCl, 0.01 M 2-mercaptoethanol, 10%(w/v) glycerol, 0.5% (v/v) protease inhibitor cocktail (Sigma P-8340) at a ratio of 1 L/200 g cells until homogeneous. The thawed suspension was applied to a microfluidizer at 10,000 PSI to disrupt the cells and the whole lysates were clarified by centrifugation at 50,000×g for 90 min, 4° C. Imidazole was added to the clarified lysate to a final concentration of 2.5 mM and the lysate was mixed with 10 mL of Talon resin (Clontech) and the slurry rocked gently overnight at 4° C. The slurry was centrifuged at 1,000×g for 5 min, the supernatant decanted, and the resin suspended in 40 mL of lysis wash buffer (lysis buffer at 0.75 M NaCl). This step was repeated 3× and the resin was transferred to a 2.5 cm glass column. Ten column volumes of wash buffer (0.05 M HEPES, pH 8.0, 0.1 M NaCl, 0.01 M 2-mercaptoethanol, 10%(w/v) glycerol) were applied to the resin followed by 10 column volumes of elution buffer (0.05 M HEPES, pH 8.0, 0.25 M NaCl, 0.01 M 2-mercaptoethanol, 10%(w/v) glycerol, 0.1 M imidazole). Fractions were analyzed by SDS-PAGE and those containing the protein of interest were pooled and concentrated. The concentrated protein was applied to an Amersham Superdex 75 (XK 26/60) column equilibrated in 0.025 M Tris-HCl, pH 7.5, 0.1 M NaCl, 0.01 M 2-mercaptoethanol, 10% (w/v) glycerol. The protein eluted at a retention time indicative of it being monomeric and fractions were analyzed by SDS-PAGE. Fractions containing the monomeric protein of interest were pooled, concentrated to ~2 mg/mL, and stored at −80° C.

Pim Enzyme Assays

The assay for the determination of Pim activity is based on the formation of phosphorylated biotinylated-BAD peptide at the Serine 112 residue (S112) and employs HTRF® (homogeneous time resolved fluorescence) technology to detect the product in a 96-well plate format. The phosphorylation of biotinylated-BAD (S112) peptide by full length recombinant Pim-1, Pim-2, or Pim-3 protein was detected with streptavidin:Allophycocyanin (APC) conjugate and a europium (Eu) labeled antibody directed against phosphorylated-BAD (S112). Excitation of Eu by a high energy laser light (337 nm) leads to a transfer of energy to the APC molecule, and results in an emission at 665 nm. The fluorescence is directly proportional to the amount of phosphorylated BAD peptide present in the reaction. Compounds were prepared in DMSO by conducting 3-fold serial dilutions to give a 10-point dosing curve having a high dose of 1 uM. A reference compound was included on each assay plate in order to validate that plate; on one plate of every assay run, two additional reference compounds were included. The final buffer conditions were as follows: 60 mM Hepes, pH 7.0, 0.05% BSA, 2 mM DTT. Incubations were carried out at RT (22° C.) for 2 h for Pim-1, 1 hour and 30 min for Pim-3, and 45 min for Pim-2. The reaction was stopped by the addition of 3 mM EDTA, and fluorescence was measured by an HTRF® Rubystar microplate reader. For each plate, percent of control (POC) values were calculated for each well. Values for the IC50 IP were estimated using a standard 4-parameter logistic model.

Pim-Mn Enzyme Assays

The assay for the determination of Pim activity is based on the formation of phosphorylated biotinylated-BAD peptide at the Serine 112 residue (S112) and employs HTRF® (homogeneous time resolved fluorescence) technology to detect the product in a 384-well plate format. The phosphorylation of biotinylated-BAD (S112) peptide by full length recombinant Pim-1, Pim-2, or Pim-3 protein was detected with streptavidin:Allophycocyanin (APC) conjugate and a europium (Eu) labeled antibody directed against phosphorylated-BAD (S112). Excitation of Eu by a high energy laser light (337 nm) leads to a transfer of energy to the APC molecule, and results in an emission at 665 nm. The fluorescence is directly proportional to the amount of phosphorylated BAD peptide present in the reaction. Compounds were prepared in DMSO by conducting 3-fold serial dilutions to give a 22-point dosing curve having a high dose of 1 µM. A reference compound was included on each assay plate [Costar 3658] in order to validate that plate; on one plate of every assay run, two additional reference compounds were included. The Reaction Buffer consisted of 45 mM Hepes, pH 7.0, 15 mM NaCl, and 1 mM MgCl. The quench/detection buffer consisted of 50 mM Tris, 100 mM NaCl, 0.05% BSA, 0.1% Tween and 3 mM EDTA. Biotinylated BAD peptide (Biopeptide), 10 mM ATP (Sigma), Labeled p-BAD (S112) mAb (Cell Signalling and Perkin Elmer) [with 0.05% BSA and 2 mM DTT added] streptavidin:Allophycocyanin [Perkin Elmer]. Final concentrations either Pim-1 enzyme [5 pM], or Pim-2 enzyme [0.5 pM], DMSO [1%], BLC BAD (S112) [0.5 µM], ATP [1.5 µM], streptavidin:Allophycocyanin [0.002 mg/mL] and biotinylated-BAD (S112) mAb [100 pM]. Initial incubations were carried out at RT (22° C.) for 30 min for both Pim-1 and for Pim-2. Pim enzyme is added to compound in buffer, and plates are incubated of 30 min. Biotinylated BAD and ATP are added and plates are incubated for 1 h. A mixture of labeled p-BAD (S112) mAb and quench/detection buffer are added and incubated for 2 h. Fluorescence was measured by an HTRF® Envision microplate reader. For each plate, percent of control (POC) values were calculated for each well. Values for the IC50 IP were estimated using a standard 3 or 4-parameter logistic model.

Pim U2OS Cell Assay

The cell lines used in the assay were generated by the stable transfection of either Pim-1 or Pim-2 into the U2OS human osteogenic sarcoma line. The assay for determination of the Pim activity in the engineered U2OS cell lines measures levels of phospho-BAD normalized against total BAD protein levels. It was conducted as follows:

The adherent cells were dissociated from the flasks using non-enzymatic cell dissociation solution (Sigma # C5914). Cells were then plated out to 96-well plates at an initial density of 40,000 cells/well in 100 uL of complete growth medium (McCoy's 5A-Invitrogen #16600-082, 10% FBS-Gibco #10099-141, Geneticin/G418 at 500 ug/mL-Invitrogen #10131-027). The cells were then incubated overnight at 37° C., 5% $CO_2$. Compounds were initially diluted in DMSO by conducting 3-fold serial dilutions to give a 10-point dosing curve having a high dose of 31.6 uM. In addition to the 10-point dosing curve of the test compound, DMSO alone was run as the high control. This dilution in DMSO was then diluted again into cell growth medium. Aliquots (12 uL) of the compound diluted in growth medium were then transferred to the appropriate wells of the 96-well plates containing cells to yield a final DMSO concentration of 0.3%. The cell plates were then incubated with compound for 29 min at 37° C., 5% $CO_2$. After a 29 minute incubation, the cell plates had the compound-containing medium removed, and were washed with 150 uL of PBS (Gibco #14040). Following the wash, the cell plates were placed on ice and given 50 uL of ice-cold complete lysis buffer (MSD kit components, Protease Inhibitor Cocktail Tablets—Roche #04 693 116 001). The cell plates containing lysis buffer were then immediately stored at −70° C. These prepared lysates were then assayed for phospho and total BAD according to the manufacturer's protocols (Meso Scale Diagnostics, Cat# K15103C-3 & # K15103D-3). The plates were read on the MSD Sector Imager 6000, and results were calculated according to the assay protocols:

((% Phosphoprotein=((2×Phospho signal)/(Phospho signal+Total signal))×100)).

Pim KMS-12 Cell Assay

The KMS-12-BM myeloma cell line was used to determine the in vitro cellular inhibition of Pim kinases. Disruption of Pim signaling by Pim inhibitors was determined by measuring the levels of phospho-BAD (S112) and total BAD. This cellular assay was conducted as follows: The suspension cells were plated out onto 96-well, V-bottom plates at an initial density of 80,000 cells/well in 100 uL of complete growth medium (RPM/Medium 1640—Invitrogen #11875, 20% Heat inactivated FBS—Hyclone #SH 30070.03HI, 1× L-glutamine—Invitrogen #25030). The cells were then incubated overnight at 37° C., 5% $CO_2$. Compounds were initially diluted in DMSO by conducting 3-fold serial dilutions to give a 10-point dosing curve having a high dose of 31.6 uM. In addition to the 10-point dosing curve of the test compound, DMSO alone was run as a control. This dilution in DMSO was then diluted again into cell growth medium. Aliquots (11.1 uL) of the compound diluted in growth medium were then transferred to the appropriate wells of the 96-well plates containing cells to yield a final DMSO concentration of 0.3%. The cell plates were then incubated with compound for 1 hour and 50 minutes at 37° C., 5% $CO_2$. After the 1 hour and 50 min incubation, the cell plates were spun at 1000 RPM for 10 minutes and the compound-containing medium was removed. The cell plates were placed on ice and given 50 uL of ice-cold complete lysis buffer (MSD kit components, Protease Inhibitor Cocktail Tablets—Roche #04 693 116 001) supplemented with 0.5% Membrane Blocking Agent (Amersham Biosciences # RPN2125). The cell plates containing lysis buffer were then immediately stored at −70° C. These prepared lysates were then assayed for phospho-(S112) and total-BAD according to the manufacturer's protocol (Meso Scale Diagnostics, Cat # K15103D-3). The plates were read on the MSD Sector Imager 6000, and results were calculated according to the assay protocol:

((% Phosphoprotein=((2×Phospho signal)/(Phospho signal+Total signal))×100)).

KMS12 #2

The flow cytometry assay for determination of the Pim activity in the engineered KMS-12-BM cell lines (DSMZ cat# ACC 551) measures levels of phospho-BAD normalized against total BAD protein levels. It was conducted as follows:

Protocol:

Compounds are initially diluted in DMSO by conducting 2-fold serial dilutions to give a 22-point dosing curve having a high dose of 30 μM. Exponentially growing KMS-12-BM cells (50 between 0.5 and 1.5×10^6/ml, DSMZ) in Assay Media (RPMI/20% heat inactivated FBS/1× NaPyruvate/1× NEAA/1×PSG (pen/strep glutamine)) are added to a 384-well plate containing 200 nL of compound. The cell plates are then incubated with compound for 110 min at 37° C., 5% $CO_2$. BD Phosflow Lyse/Fix (BD Biosciences) is diluted to 2× with Assay Media. 50 μL of the diluted BD Phosflow Lyse/Fix is added to each well. The cell plates are incubated for 15 min at RT. The plates are spun for 15 sec at 2K RPM then aspirated. Staining Media (1×PBS with 0.5% FBS) is added (80 The plates again are spun for 15 sec at 2K RPM then aspirated. BD Perm/Wash Buffer (1×, 50 BD Biosciences) is added. The cell plates are then incubated for >30 min at RT in the dark. The plates are spun for 15 sec at 2K RPM then aspirated. Staining Media (1×PBS with 0.5% FBS) is added (80 The plates are spun for 15 sec at 2K RPM then aspirated and additional Staining Media (1×PBS with 0.5% FBS) is added (80 The plates are spun for 15 sec at 2K RPM then aspirated. Rabbit anti-human pBAD Ser112 Ab (Cell Signaling) is diluted in Staining Media (1:120). The diluted p BAD Ab (10 μL) is added to each well. The cell plates are incubated for >1 hr at RT. The plates are spun for 15 sec at 2K RPM then aspirated. Staining Media (1×PBS with 0.5% FBS) is added (80 μL). Goat Anti Rabbit Alexa-647 (Invitrogen) is diluted in Staining Media (1:4000). The diluted Goat Anti Rabbit Alexa-647 (70 μL) is added to each well. The cell plates are then incubated for >30 min at RT in the dark. The plates are spun for 15 sec at 2K RPM then aspirated. Staining Media (1×PBS with 0.5% FBS) is added (80 μL). The plates are spun for 15 sec at 2K RPM then aspirated and additional Staining Media (1×PBS with 0.5% FBS) is added (80 μL). The plates are spun for 15 sec at 2K RPM then aspirated. Staining Media (1×PBS with 0.5% FBS) is added (30 μL). The plates are read on a BD LSRII, and results were calculated according to the assay protocols ((% Phosphoprotein=((2×Phospho signal)/(Phospho signal+Total signal))×100)).

TABLE 2

IC$_{50}$ Activity of compounds of the Invention

| Ex# | Pim-1 IC50 IP (µM) | Pim-2 IC50 IP (µM) | Pim-1-Mn IC50 IP (µM) | Pim-2-Mn IC50 IP (µM) | KMS-12-BM IC50 IP (µM) |
|---|---|---|---|---|---|
| 1 | .315 | .636 | | | |
| 2 | .0016 | .008 | | | .708 |
| 3 | .0128 | .037 | | | 6.1 |
| 4 | .0021 | .0068 | | | 2.34 |
| 5 | .0049 | .0115 | | | 5.7 |
| 6 | .0012 | .0046 | | | 1.17 |
| 7 | .0010 | .0052 | | | 2.74 |
| 8 | .0028 | .0127 | | | 1.28 |
| 9 | .0046 | .0086 | | | 6.35 |
| 10 | .0121 | .0211 | | | 7.49 |
| 11 | .0061 | .0103 | | | 7 |
| 12 | .0020 | .011 | | | NA |
| 13 | .0008 | .0028 | | | NA |
| 14 | .0011 | .0060 | | | 2.34 |
| 15 | .004 | .0204 | | | 3.23 |
| 16 | .0027 | .0135 | | | 3.85 |
| 17 | .034 | .0802 | | | |
| 18 | .0155 | .0449 | | | NA |
| 19 | .133 | .908 | | | |
| 20 | .0385 | .0984 | | | |
| 21 | .0028 | .0216 | | | 4.92 |
| 22 | .0609 | .248 | | | |
| 23 | .0141 | .0536 | | | NA |
| 24 | .0007 | .0024 | | | 1.41 |
| 25 | .0024 | .0297 | | | 4.56 |
| 27 | .153 | .366 | | | |
| 28 | .0149 | .061 | | | NA |
| 29 | .0005 | .0024 | | | .737 |
| 30 | .0041 | .0237 | | | 5.89 |
| 31 | .37 | NA | | | |
| 32 | .0003 | .0006 | | | 1.39 |
| 33 | .0063 | .0353 | | | 4.1 |
| 34 | .0184 | .0733 | | | NA |
| 36 | | | .0020 | .0018 | .209 |
| 37 | .0059 | .0139 | | | 5.53 |
| 38 | .0003 | .0007 | | | 1.29 |
| 39 | .0063 | .0046 | | | 5.38 |
| 40 | .0018 | .0143 | | | NA |
| 41 | .0136 | .068 | | | NA |
| 42 | .0036 | .0091 | | | 3.46 |
| 43 | .0179 | .0478 | | | NA |
| 44 | .0072 | .0292 | | | 13.1 |
| 45 | .0015 | .0077 | | | 1.45 |
| 46 | .0581 | .125 | | | |
| 47 | | | .0132 | .0349 | N/A |
| 48 | | | .0262 | .116 | |
| 49 | | | .0472 | .144 | |
| 50 | | | .0137 | .0244 | |
| 51 | | | .191 | .22 | |
| 52 | | | .149 | .403 | |
| 53 | | | .0006 | .0024 | |
| 54 | | | .0013 | .0029 | |
| 55 | | | .0007 | .0030 | |
| 56 | | | .0227 | .0383 | |
| 57 | | | .0242 | .0543 | |
| 58 | | | .06 | .18 | |
| 59 | | | .019 | .0257 | |
| 60 | | | .3 | .191 | |
| 61 | | | .0061 | .0264 | N/A |
| 62 | | | .0062 | .0227 | 2.61 |
| 63 | | | .0043 | .0054 | .513 |
| 64 | | | .0259 | .0345 | N/A |
| 65 | | | .0578 | .0728 | |
| 66 | | | .0027 | .0007 | .215 |
| 67 | | | .0004 | .0006 | .167 |
| 68 | | | .0045 | .0061 | .445 |
| 69 | | | .0034 | .0017 | .223 |
| 70 | | | .0043 | .0063 | 2.91 |
| 71 | | | .0064 | .0061 | .474 |
| 72 | | | .0031 | .0019 | .713 |
| 73 | | | .0012 | .0018 | .107 |
| 74 | | | .0221 | .0205 | |
| 75 | | | .0006 | .0012 | .892 |
| 76 | | | .0081 | .027 | 6.13 |
| 77 | | | .0016 | .0038 | .494 |
| 78 | .0036 | .019 | | | 5.5 |
| 79 | .0548 | .204 | | | |
| 80 | .0074 | .0305 | | | 14.4 |
| 81 | .0060 | .0956 | | | NA |
| 82 | .0070 | .0572 | | | 4.62 |
| 83 | .0020 | .015 | | | 2.91 |
| 84 | .0206 | .115 | | | 12.2 |
| 85 | .0044 | .0226 | | | .953 |
| 86 | .0495 | .143 | | | |
| 87 | .0038 | .0147 | | | 1.78 |
| 88 | .0421 | .166 | | | |
| 89 | .0466 | .34 | | | |
| 90 | .34 | NA | | | |
| 91 | .0106 | .0461 | | | NA |
| 92 | .0165 | .062 | | | 12.2 |
| 93 | NA | NA | | | |
| 94 | .269 | NA | | | |
| 95 | .222 | NA | | | |
| 96 | .283 | NA | | | |
| 97 | .227 | NA | | | |
| 98 | NA | NA | | | |
| 99 | | | .0011 | .0070 | .723 |
| 100 | | | .00134 | .000961 | .144 |
| 101 | .0198 | .0809 | | | NA |
| 102 | .0076 | .0739 | | | 10.4 |
| 103 | .0081 | .0181 | | | 7.73 |
| 104 | .0093 | .0090 | | | 5.23 |
| 105 | .0008 | .0012 | | | .407 |
| 106 | .0045 | .0105 | | | 8.44 |
| 107 | .0052 | .0322 | | | 15.6 |
| 108 | .0015 | .0134 | | | 6.74 |
| 109 | .0041 | .0158 | | | 8.81 |
| 110 | .0011 | .0029 | | | 1.13 |
| 111 | .019 | .181 | | | NA |
| 112 | .029 | .182 | | | |
| 113 | .0047 | .0081 | | | NA |
| 114 | .0041 | .0089 | | | 4.18 |
| 115 | .0587 | .122 | | | |
| 116 | .0076 | .0178 | | | 7.54 |
| 117 | .0006 | .0009 | | | 3.15 |
| 118 | .0032 | .0161 | | | 5.21 |
| 119 | .0394 | .206 | | | |
| 120 | .0006 | .0046 | | | 2.21 |
| 121 | .0006 | .0226 | | | NA |
| 122 | .0001 | .0003 | | | .348 |
| 123 | .0010 | .012 | | | 2.51 |
| 124 | .0064 | .141 | | | NA |
| 125 | .0418 | NA | .0211 | .278 | |
| 126 | N/A | >1.0 | | | |
| 127 | .0171 | .0126 | | | .427 |
| 128 | .204 | .222 | | | N/A |
| 129 | .0993 | .227 | | | N/A |
| 130 | .0058 | .0055 | | | .371 |
| 131 | .0050 | .0026 | .0016 | .0008 | .142 |
| 132 | .0053 | .0049 | | | .143 |
| 133 | .0934 | .0998 | | | |
| 134 | .0089 | .0139 | | | N/A |
| 135 | .0076 | .0047 | | | .217 |
| 136 | .0495 | .154 | | | |
| 137 | .0967 | .0741 | | | |
| 138 | .0348 | .0301 | | | |
| 139 | .0176 | .016 | .0242 | .0197 | |
| 140 | .0008 | .0002 | .0003 | <.0001 | 1.235 |
| 141 | .0037 | .0093 | .0013 | .0035 | N/A |
| 142 | .0019 | .0053 | .0007 | .0014 | 2.26 |
| 143 | .0007 | .0008 | .0003 | .0004 | .44 |
| 144 | .0020 | .0016 | .0008 | .0006 | .0678 |
| 145 | .0142 | .0089 | .0087 | .0046 | .971 |
| 146 | .0089 | .0079 | .0065 | .0030 | .481 |
| 147 | .0029 | .0014 | .0019 | .0006 | .176 |
| 148 | | | .0080 | .0087 | .42 |
| 149 | | | .02 | .033 | |
| 150 | | | .0020 | .0059 | |

TABLE 2-continued

IC$_{50}$ Activity of compounds of the Invention

| Ex# | Pim-1 IC50 IP (μM) | Pim-2 IC50 IP (μM) | Pim-1-Mn IC50 IP (μM) | Pim-2-Mn IC50 IP (μM) | KMS-12-BM IC50 IP (μM) |
|---|---|---|---|---|---|
| 151 | | | .0182 | .0123 | |
| 152 | | | .0542 | .0447 | |
| 155 | | | .0007 | .0015 | .292 |
| 156 | | | .526 | .758 | |
| 157 | | | .0009 | .0006 | |
| 158 | | | .0010 | .0018 | |
| 159 | | | .0031 | .0017 | |
| 160 | | | .0010 | .0005 | |
| 161 | | | .0008 | .0007 | |
| 164 | .243 | NA | | | |
| 165 | .0067 | .0179 | | | 3.85 |
| 166 | .0011 | .0022 | | | 4.31 |
| 167 | .671 | .667 | | | |
| 168 | .608 | NA | | | |
| 173 | | | .0013 | .0014 | .181 |
| 174 | | | .0059 | .0035 | .336 |
| 175 | .0009 | .0032 | | | 1.51 |
| 176 | .0026 | .0047 | | | 3.58 |
| 177 | .0124 | .0184 | | | 4.66 |
| 180 | .0019 | .0028 | | | .39 |
| 183 | .0015 | .0016 | | | .165 |
| 186 | .0022 | .0043 | | | 1.49 |
| 187 | .0019 | .0043 | | | 1.28 |
| 188 | .0028 | .0044 | | | 1.01 |
| 189 | .0286 | .0718 | | | NA |
| 190 | .0362 | .0176 | | | .966 |
| 191 | .0093 | .0066 | | | .376 |
| 192 | .0075 | .0049 | | | .27 |
| 193 | .0011 | .0013 | | | .0762 |
| 194 | .0037 | .0020 | | | .0628 |
| 195 | .0509 | .177 | | | |
| 196 | .0238 | .0114 | | | .585 |
| 197 | .0072 | .0057 | | | .511 |
| 198 | .0068 | .0087 | .0036 | .0028 | .307 |
| 199 | .0282 | .05 | .0145 | .0262 | |
| 200 | .11 | .0857 | .0536 | .0418 | |
| 201 | .0030 | .0028 | .0025 | .0017 | .136 |
| 202 | | | .0003 | .0003 | .0413 |
| 203 | | | .0012 | .0056 | .232 |
| 204 | | | .0026 | .0035 | .445 |
| 205 | | | .0049 | .0045 | 1.14 |
| 206 | | | .0027 | .0040 | |
| 208 | | | .0027 | .0021 | .366 |
| 209 | | | .00383 | .0040 | .268 |
| 210 | | | .0002 | .0003 | .0601 |
| 211 | | | .0002 | .0003 | .0497 |
| 212 | | | .0013 | .0023 | .538 |
| 213 | | | .0016 | .0032 | .227 |
| 214 | | | .0047 | .058 | 9.87 |
| 215 | | | .0006 | .0007 | .153 |
| 216 | | | .0003 | .0008 | .225 |
| 217 | | | .0020 | .0053 | .933 |
| 218 | | | .036 | .0174 | 1.09 |
| 219 | | | .0078 | .0041 | .346 |
| 220 | | | .0001 | .0001 | .0863 |
| 221 | | | .0031 | .0043 | .75 |
| 222 | | | .0035 | .0021 | .397 |
| 223 | | | .0004 | .0008 | |
| 224 | | | .0042 | .0028 | |
| 225 | .0159 | .0437 | | | NA |
| 226 | .0253 | .0381 | | | |
| 227 | .0009 | .0039 | | | .539 |
| 228 | .003 | .0009 | | | 1.61 |
| 229 | .092 | .092 | .0909 | | |
| 231 | .0081 | .0919 | | | NA |
| 232 | .0233 | .0529 | | | |
| 233 | .0446 | .0164 | .025 | .0069 | .621 |
| 235 | | | .0095 | .0145 | |
| 236 | .0342 | .0402 | | | NA |
| 237 | .0147 | .0342 | | | 6.58 |
| 238 | .0007 | .0040 | | | 1.28 |
| 239 | .0007 | .0028 | | | 1.85 |
| 240 | | | .0875 | .0096 | |
| 241 | | | .0437 | .0684 | |
| 242 | | | .129 | .137 | |
| 243 | | | .853 | 1.05 | |
| 244 | .0069 | .0179 | | | NA |
| 245 | .0129 | .0236 | | | NA |
| 246 | .0011 | .0017 | .00034 | .0004 | .746 |
| 248 | .0018 | .0007 | .0004 | .0001 | .758 |
| 250 | .0010 | .0019 | | | 2.82 |
| 251 | .0083 | .0135 | | | NA |
| 254 | | | .00267 | .00224 | |
| 255 | | | .0283 | .0272 | |
| 256 | | | .00497 | .00432 | |
| 258 | | | .000694 | .000338 | |
| 260 | | | .0016 | .00123 | .243 |
| 261 | | | .00122 | .00129 | .252 |
| 262 | | | .0189 | .021 | |
| 263 | | | .0051 | .0058 | .907 |
| 264 | | | 1.12 | 1.69 | |
| 265 | | | .0252 | .0119 | N/A |
| 266 | | | .0031 | .0020 | N/A |
| 269 | | | .0445 | .0653 | |
| 270 | | | .0022 | .0014 | .215 |
| 271 | | | .0013 | .0020 | .418 |
| 272 | | | .0069 | .0078 | 1.53 |
| 273 | | | .039 | .0191 | |
| 274 | | | .0444 | .0395 | |
| 276 | | | .0018 | .0050 | 1.22 |
| 277 | | | .0010 | .0004 | .169 |
| 278 | | | .0031 | .0105 | N/A |
| 279 | | | .0010 | .0010 | .252 |
| 280 | | | .838 | .706 | N/A |
| 281 | | | .0067 | .0028 | .533 |
| 282 | | | .0053 | .0118 | 3.44 |
| 283 | | | .0033 | .0008 | .199 |
| 284 | | | .0012 | | |
| 285 | | | | | |
| 286 | | | .0004 | .0049 | .143 |

TABLE 3

IC$_{50}$ Activity of compounds of the Invention

| Ex# | Pim-1 IC50 IP (μM) | Pim-2 IC50 IP (μM) | Pim-1-Mn IC50 IP (μM) | Pim-2-Mn IC50 IP (μM) | KMS-12-Flow IC50 IP (μM) |
|---|---|---|---|---|---|
| 283 | | | 0.000303 | 0.000278 | 0.0752 |
| 284 | | | 0.0000282 | 0.0000378 | 0.0186 |
| 285 | | | 0.000534 | 0.000902 | 0.0518 |
| 286 | | | 0.000289 | 0.000305 | 0.0282 |
| 287 | | | 0.00178 | 0.00164 | 0.0758 |
| 288 | | | 0.00585 | 0.00396 | 597 |
| 289 | | | 0.00269 | 0.00337 | 235 |
| 290 | | | 0.0397 | 0.0358 | 4.19 |
| 291 | | | 0.099 | 0.0652 | 7.92 |
| 292 | | | 0.00161 | 0.00254 | 0.657 |
| 293 | | | 0.00637 | 0.00602 | 0.41 |
| 294 | | | 0.00123 | 0.00223 | 0.165 |
| 295 | | | 0.000562 | 0.00052 | 0.041 |
| 296 | | | 0.000508 | 0.000501 | 0.0362 |
| 297 | | | 0.000116 | 0.000109 | 0.0284 |
| 298 | | | 0.000181 | 0.000201 | 0.0571 |
| 299 | | | 0.007 | 0.009 | >40 |
| 300 | | | 0.009 | 0.012 | >10 |
| 301 | | | 0.00125 | 0.00191 | 0.341 |
| 302 | | | 0.00184 | 0.00145 | 0.0712 |
| 303 | | | 0.000839 | 0.00147 | 0.572 |
| 304 | | | 0.000791 | 0.000429 | 0.0876 |
| 305 | | | 0.00263 | 0.00814 | 1.64 |
| 306 | | | 0.00212 | 0.00226 | 0.558 |
| 307 | | | 0.00163 | 0.00145 | 0.59 |
| 308 | | | 0.00105 | 0.00127 | 0.177 |

TABLE 3-continued

IC$_{50}$ Activity of compounds of the Invention

| Ex# | Pim-1 IC50 IP (μM) | Pim-2 IC50 IP (μM) | Pim-1-Mn IC50 IP (μM) | Pim-2-Mn IC50 IP (μM) | KMS-12-Flow IC50 IP (μM) |
|---|---|---|---|---|---|
| 309 | | | 0.00355 | 0.00376 | 1.16 |
| 310 | | | 0.004 | 0.003 | 0.344 |
| 311 | | | 0.00198 | 0.00195 | 0.151 |
| 312 | | | 0.000271 | 0.000195 | 0.123 |
| 314 | | | 0.00948 | 0.00858 | 6.73 |
| 315 | | | 0.0352 | 0.0454 | 0.895 |
| 316 | | | 0.036 | 0.075 | 21.5 |
| 317 | | | 0.00994 | 0.0147 | 1.36 |
| 318 | | | 0.0341 | 0.0267 | >40.0 |
| 320 | | | 0.176 | 0.272 | >40.0 [2] |
| 321 | | | 0.0986 | 0.156 | >40.0 [2] |
| 322 | | | 0.0946 | 0.163 | >40.0 [2] |
| 323 | | | 0.0838 | 0.0627 | >20.0 [2] |
| 324 | | | 0.000139 | 0.000223 | 0.0917 |
| 325 | | | 0.000293 | 0.000242 | 0.0688 |
| 326 | | | 0.000618 | 0.000559 | 0.0316 |
| 327 | | | 0.0021 | 0.00202 | 0.0986 |
| 328 | | | 0.000195 | 0.000201 | 0.046 |
| 329 | | | 0.000334 | 0.00039 | 0.0262 |
| 330 | | | 0.000724 | 0.00117 | 0.0856 |
| 331 | | | 0.00167 | 0.00112 | 0.13 |
| 332 | | | 0.00327 | 0.00276 | >40 |
| 333 | | | 0.000185 | 0.000183 | 0.00842 |
| 334 | | | 0.00118 | 0.000882 | 0.0438 |
| 335 | | | 0.00122 | 0.000996 | 0.0993 |
| 336 | | | 0.00282 | 0.00132 | 0.145 |
| 337 | | | 0.0719 | 0.0546 | 6.92 |
| 338 | | | 0.232 | 0.0986 | 14.3 |
| 339 | | | 0.0508 | 0.0618 | 2.52 |
| 340 | | | 0.000434 | 0.00111 | 0.595 |
| 341 | | | 0.00685 | 0.0107 | 7.83 |
| 342 | | | 0.0281 | 0.0204 | 11.5 |
| 343 | | | 0.00233 | 0.00278 | 1.77 |
| 344 | | | 0.00119 | 0.00561 | 0.202 |
| 345 | | | 0.001 | 0.00225 | 2.73 |
| 346 | | | 0.00407 | 0.0108 | 1.12 |
| 347 | | | 0.00455 | 0.0105 | 3.66 |
| 348 | | | 0.000455 | 0.000454 | 0.19 |
| 349 | | | 0.000625 | 0.000874 | 1 |
| 350 | | | 0.00231 | 0.00338 | 1.51 |
| 351 | | | 0.00923 | 0.0089 | 2.35 |
| 352 | | | 0.00159 | 0.00245 | 0.188 |
| 353 | | | 0.00226 | 0.0023 | 0.109 |
| 354 | | | 0.00708 | 0.0164 | 2.31 |
| 355 | | | 0.00179 | 0.00186 | 2.43 |
| 357 | | | 0.000463 | 0.00057 | 0.015 |
| 358 | | | 0.0000339 | 0.0000783 | 0.0496 |
| 360 | | | 0.00142 | 0.00137 | 0.0884 |
| 361 | | | 0.000414 | 0.00053 | 0.0671 |
| 362 | | | 0.00173 | 0.00182 | 0.251 |
| 363 | | | 0.000345 | 0.000297 | 0.142 |
| 364 | | | 0.00166 | 0.00218 | 0.391 |
| 365 | | | 0.000331 | 0.000212 | 0.184 |
| 366 | | | 0.000192 | 0.000177 | 0.0794 |
| 367 | | | 0.00381 | 0.00368 | 0.429 |
| 368 | | | 0.0308 | 0.0337 | 13.3 |
| 369 | | | 0.000184 | 0.000162 | 0.0115 |
| 370 | | | 0.000992 | 0.000272 | 0.143 |
| 371 | | | 0.000246 | 0.0000667 | 0.148 |
| 372 | | | 0.00394 | 0.0748 | >40.0 [2] |
| 373 | | | 0.0018 | 0.00163 | 0.0943 |
| 374 | | | 0.00254 | 0.00362 | 0.769 |
| 375 | | | 0.000259 | 0.000275 | 0.119 |
| 376 | | | 0.000191 | 0.000136 | 0.0376 |
| 377 | | | 0.00243 | 0.00332 | 1.63 |
| 378 | | | 0.0000295 | 0.0000354 | 0.0161 |
| 379 | | | 0.0000376 | 0.0000484 | 0.0113 |
| 380 | | | 0.000249 | 0.000385 | 0.0347 |
| 381 | | | 0.0016 | 0.00136 | 0.215 |
| 382 | | | 0.000258 | 0.000246 | 0.0825 |
| 383 | | | 0.0037 | 0.00457 | 0.445 |

TABLE 4

IC$_{50}$ Activity of compounds of the Invention

| Example # | Pim-1-Mn IC50 IP (μM) | Pim-2-Mn IC50 IP (μM) | KMS-12-Flow IC50 IP (μM) |
|---|---|---|---|
| 401 | 0.0195 | 0.0349 | 18.5 |
| 402 | 0.00591 | 0.00587 | 0.59 |
| 403 | 0.0115 | 0.0164 | >40 |
| 404 | 0.0015 | 0.0026 | 0.659 |
| 405 | 0.000012 | 0.000012 | 0.028 |
| 406 | 0.00007 | 0.000012 | 0.03 |
| 407 | 0.00018 | 0.0004 | 0.144 |
| 408 | 0.0001 | 0.00024 | 0.047 |
| 409 | 0.0317 | 0.0626 | 5.76 |
| 410 | 0.0985 | 0.187 | 21.7 |
| 411 | 0.0665 | 0.239 | >40 |
| 412 | 0.0507 | 0.0656 | 21.8 |
| 413 | 0.0103 | 0.0334 | >40 |
| 414 | 0.00604 | 0.0226 | 5.86 |
| 415 | 0.0109 | 0.0294 | 5.86 |
| 416 | 0.00763 | 0.0158 | 2.95 |
| 417 | 0.00291 | 0.00356 | 0.279 |
| 418 | 0.00352 | 0.00779 | 3.15 |
| 419 | 0.000249 | 0.000193 | 0.0483 |
| 420 | 0.0265 | 0.0348 | 9.12 |
| 421 | 0.086 | 0.189 | 21.2 |
| 422 | 0.0123 | 0.0371 | 2.61 |
| 423 | 0.00544 | 0.00371 | 0.378 |
| 424 | 0.0824 | 0.0821 | >40.0 |
| 425 | 0.392 | 0.521 | >40 |
| 426 | 0.0523 | 0.127 | >40 |
| 427 | 0.0233 | 0.082 | >40 |
| 428 | 0.0399 | 0.0474 | >40.0 |
| 429 | 0.212 | 0.167 | 8.73 |
| 430 | 0.2 | 0.257 | 24.8 |
| 431 | 0.0673 | 0.0619 | 5.06 |
| 432 | 0.413 | 0.244 | >40 |
| 433 | 0.0309 | 0.0409 | 8.4 |
| 434 | 0.0181 | 0.0172 | 1.31 |
| 435 | 0.000347 | 0.000301 | 3 |
| 436 | 0.0041 | 0.0082 | |
| 437 | 0.0005 | 0.0004 | |
| 438 | 0.0031 | 0.012 | |
| 439 | 0.0025 | 0.0014 | |
| 440 | | | |
| 441 | 0.0007 | 0.0013 | >40 |
| 442 | 0.0034 | 0.00173 | 0.527 |
| 443 | | | >40.0 |
| 444 | | | 0.471 |
| 445 | 0.0279 | 0.0201 | >40 |
| 446 | 0.145 | 0.131 | >40.0 |
| 447 | 0.133 | 0.139 | 2.63 |
| 448 | 0.000178 | 0.000169 | 0.0308 |
| 449 | 0.00774 | 0.00405 | 0.429 |
| 450 | 0.000779 | 0.000826 | 0.031 |
| 451 | 0.000238 | 0.000364 | 0.0113 |
| 452 | 0.0216 | 0.0325 | 3.19 |
| 453 | 0.0375 | 0.258 | >40.0 |
| 454 | 0.000255 | 0.000599 | 50 |
| 455 | 0.000849 | 0.00143 | 110 |
| 456 | 0.00018 | 0.000407 | 0.0294 |
| 457 | 0.0357 | 0.134 | 3.49 |
| 458 | 0.000325 | 0.000218 | 0.0546 |
| 459 | 0.000199 | 0.000193 | 0.076 |
| 460 | 0.000554 | 0.00101 | 0.094 |
| 460 | | | |
| 461 | | | |
| 462 | 0.00051 | 0.00047 | 0.122 |
| 463 | | | 0.009 |
| 464 | | | |
| 465 | 0.000074 | 0.00013 | 0.035 |
| 466 | 0.00228 | 0.00193 | 0.0755 |
| 467 | 0.0216 | 0.0089 | 3.88 |
| 468 | 0.0054 | 0.00794 | 3.39 |
| 469 | 0.00232 | 0.00216 | 0.119 |
| 470 | 0.0103 | 0.0078 | 1.28 |
| 471 | 0.164 | 0.593 | 15.5 |
| 472 | 0.000548 | 0.000864 | 0.0758 |
| 473 | 0.0114 | 0.036 | 12.4 |

TABLE 4-continued

IC$_{50}$ Activity of compounds of the Invention

| Example # | Pim-1-Mn IC50 IP (µM) | Pim-2-Mn IC50 IP (µM) | KMS-12-Flow IC50 IP (µM) |
|---|---|---|---|
| 474 | 0.00134 | 0.000917 | 0.121 |
| 475 | 0.0000586 | 0.000076 | 0.028 |
| 476 | 0.002 | 0.012 | |
| 477 | 0.001 | 0.001 | |
| 478 | 0.002 | 0.002 | |
| 479 | 0.002 | 0.004 | |
| 480 | 0.006 | 0.006 | |
| 481 | 0.000082 | 0.000077 | 0.02 |
| 482 | 0.000718 | 0.00277 | |
| 483 | 0.0000598 | 0.0000358 | |
| 484 | 0.00398 | 0.00766 | |
| 485 | 0.00101 | 0.00312 | |
| 486 | 0.00173 | 0.00238 | |
| 487 | 0.000501 | 0.000267 | |
| 488 | 0.00139 | 0.00154 | |
| 489 | 0.004 | 0.002 | |
| 490 | 0.0001 | 0.0002 | |
| 491 | 0.02 | 0.01 | |
| 492 | 0.0001 | 0.0001 | |
| 493 | 0.005 | 0.005 | |
| 494 | 0.001 | 0.002 | |
| 495 | 0.000046 | 0.00006 | |
| 496 | 0.0002 | 0.0002 | |
| 497 | 0.00028 | 0.00016 | |
| 498 | 0.00007 | 0.0001 | |
| 499 | 0.001 | 0.0016 | |
| 500 | 0.00012 | 0.00011 | |
| 501 | 0.00016 | 0.00019 | |
| 502 | 0.0001 | 0.0002 | |
| 503 | 0.0004 | 0.0005 | |
| 504 | 0.00004 | 0.00002 | |
| 505 | 0.0008 | 0.0008 | |
| 506 | 0.0002 | 0.0001 | |
| 507 | 0.0003 | 0.0006 | |
| 508 | 0.0009 | 0.0003 | |
| 509 | 0.014 | 0.015 | |
| 510 | 0.000065 | 0.0001 | |
| 511 | 0.001 | 0.0007 | |
| 512 | 0.000029 | 0.0000741 | |
| 513 | 0.000013 | 0.0000378 | |
| 514 | 0.000287 | 0.000671 | |
| 515 | | | |

The compounds of the present invention may be administered orally, parentally, by inhalation spray, rectally, or topically in dosage unit formulations containing conventional pharmaceutically acceptable carriers, adjuvants, and vehicles.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment.

The dosage regimen for using these compounds diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aq. or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic NaCl solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maxim/ze the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$)alkyloxy) ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, dimethylformamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention. While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition. The foregoing is merely illustrative of the invention and is not intended to limit the invention to the disclosed compounds. Variations and changes which are obvious to one skilled in the art are intended to be within the scope and nature of the invention which are defined in the appended claims. From the foregoing description, one skilled in the art can easily ascertain the essential characteristics of this invention, and without departing from the spirit and scope thereof, can make various changes and modifications of the invention to adapt it to various usages and conditions.

What is claimed:

1. A compound of Formula 11d

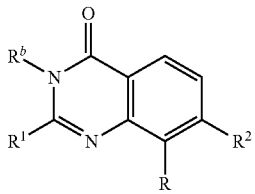

wherein R is

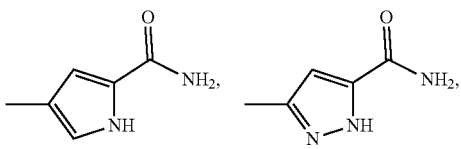

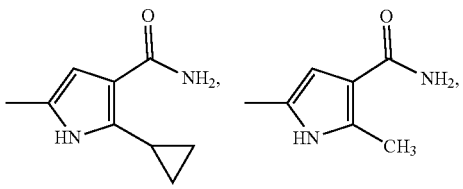

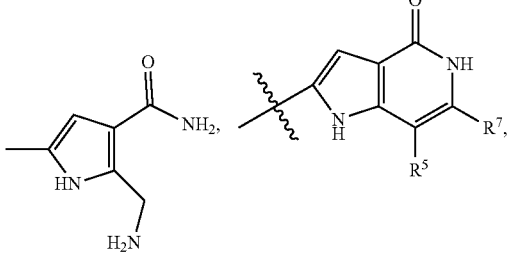

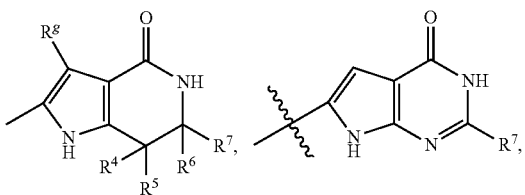

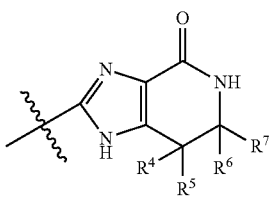

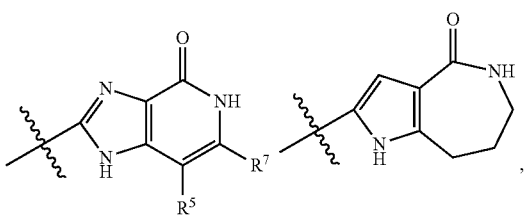

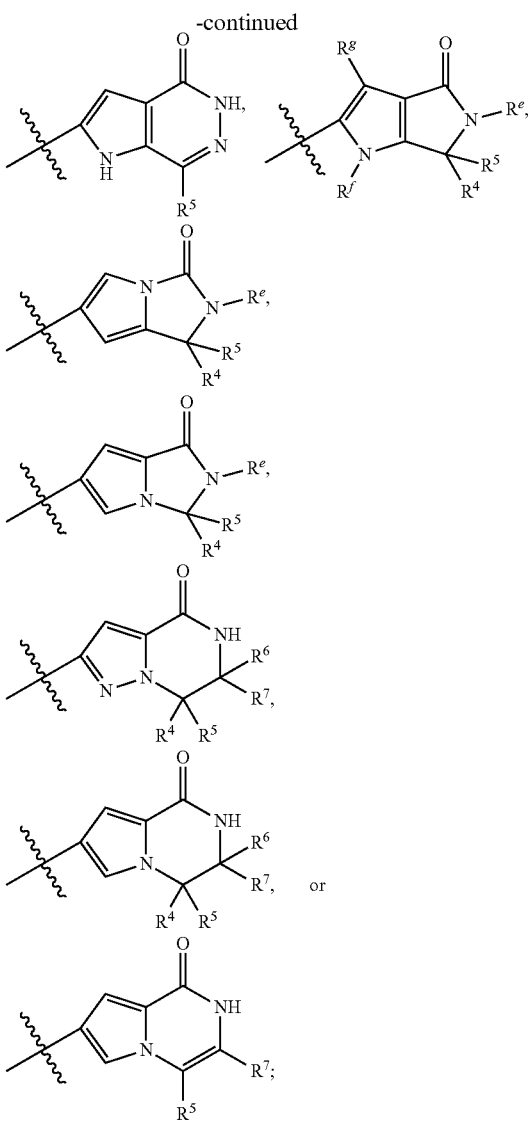

wherein $R^1$ is H, halo, $C_{1-6}$ alkyl, amino, $C_{1-6}$ alkylamino, $C_{2-6}$ alkenylamino, $C_{1-6}$ haloalkylamino, $C_{1-6}$ alkylsulfonyl-$C_{1-6}$ alkylamino, aminocarbonyl-$C_{1-6}$ alkylamino, amino-$C_{1-6}$ alkylamino, hydroxy-$C_{1-6}$ alkylamino, $C_{1-6}$ alkylsulfonylamino, carboxy-$C_{1-6}$ alkylamino, $C_{1-6}$ alkoxycarbonyl-$C_{1-6}$ alkylamino, $C_{1-6}$ alkoxy-$C_{1-6}$ alkylamino, $C_{1-6}$ alkoxycarbonylamino-$C_{1-6}$ alkylamino, $C_{1-6}$ alkoxy-$C_{1-6}$ alkoxy-$C_{1-6}$ alkylamino, $C_{1-6}$ alkoxy-$C_{1-6}$ alkylamino-$C_{1-6}$ alkylamino, $C_{1-6}$ alkylsulfonyl-$C_{1-6}$ alkylamino-$C_{1-6}$ alkylamino, substituted or unsubstituted $C_{3-6}$ cycloalkylamino, substituted or unsubstituted $C_{3-6}$ cycloalkyl-$C_{1-6}$ alkylamino, substituted or unsubstituted phenylamino, substituted or unsubstituted phenyl-$C_{1-3}$ alkylamino, substituted or unsubstituted 3-7-membered heterocyclylamino, substituted or unsubstituted 3-7-membered heterocyclyl-$C_{1-6}$ alkylamino, guanidinyl, —CONHR$^b$, —NHC=OR$^b$, —OR$^b$, —S(=O)$_n$R$^b$, —COR$^c$, unsubstituted or substituted aryl, unsubstituted or substituted aryl-$C_{1-6}$ alkyl, unsubstituted or substituted aryl-$C_{2-4}$ alkenyl, unsubstituted or substituted $C_{3-6}$ cycloalkyl, unsubstituted or substituted $C_{3-6}$ cycloalkyl-$C_{1-6}$ alkyl, unsubstituted or substituted 3-7-membered heterocyclyl-$C_{1-6}$ alkyl or substituted or unsubstituted 3-7-membered heterocyclyl;

wherein n is 0, 1 or 2;

wherein $R^b$ is H, $C_{1-6}$ alkyl, $C_{1-6}$ haloalkyl, $C_{1-6}$ aminoalkyl, $C_{1-6}$ alkoxy-$C_{1-6}$ alkyl, $C_{1-6}$ hydroxyalkyl, $C_{1-6}$ alksulfonyl-$C_{1-6}$ alkyl, $C_{2-6}$ alkenyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^c$ is H, $C_{1-6}$ alkyl, $C_{1-6}$ alkoxy, $C_{1-6}$ alkoxy-$C_{1-6}$ alkyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl;

wherein $R^e$ is H or Boc;

wherein $R^f$ is H or methyl;

wherein $R^g$ is H, fluoro or chloro;

wherein $R^2$ is H or fluoro;

wherein $R^4$ is H or methyl;

wherein $R^5$ is H, $C_{1-4}$ alkyl, $C_{3-6}$ cycloalkyl, $C_{1-4}$ aminoalkyl, $C_{1-4}$ hydroxyalkyl, $C_{1-4}$ alkoxy-$C_{1-4}$ alkyl, benzyloxy-$C_{14}$ alkyl, $C_{2-4}$ alkynyl, $C_{3-6}$ cycloalkyl or benzyl; or wherein $R^4$ and $R^5$ together form $C_{3-6}$ cycloalkyl or 4-6 membered saturated heterocyclyl;

wherein $R^6$ is H; and wherein $R^7$ is H, or $C_{1-3}$ alkyl; or a pharmaceutically acceptable salt thereof.

2. The compound of claim 1, wherein R is

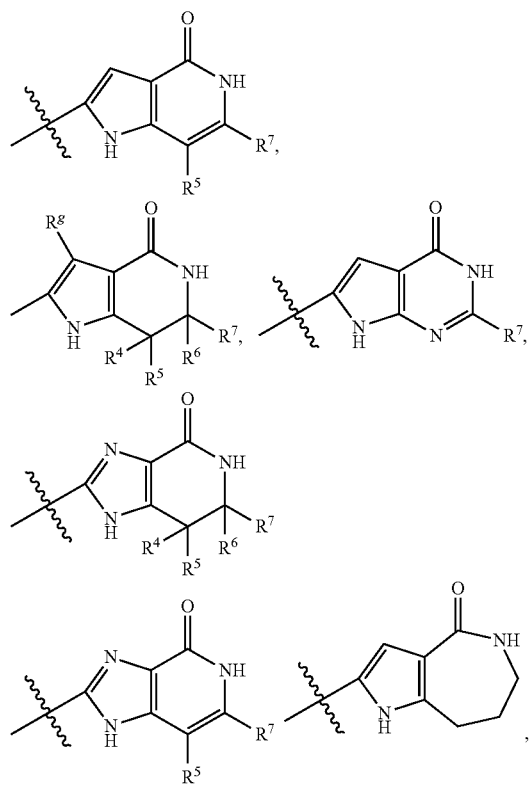

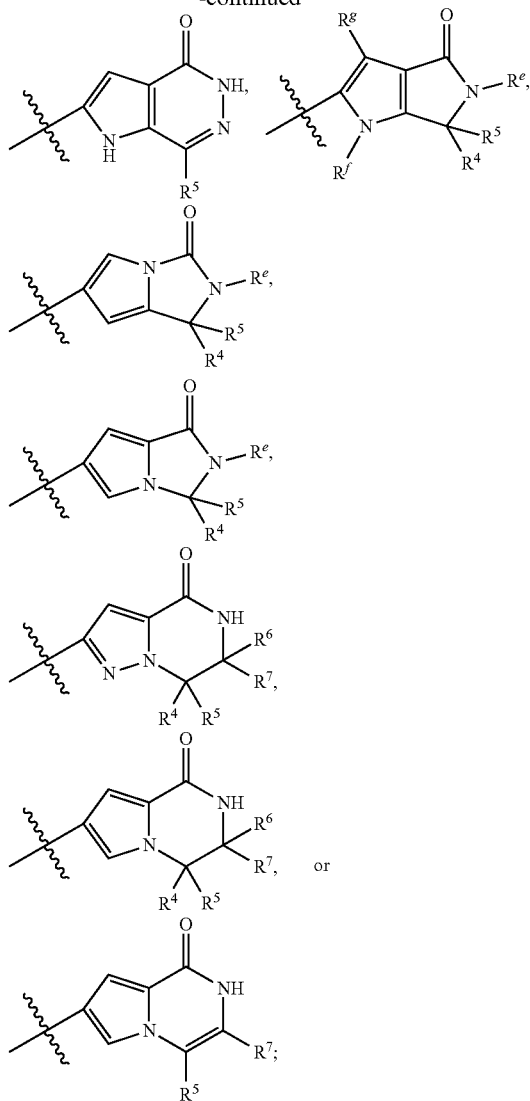

wherein $R^5$ is H, $C_{1-4}$ alkyl, $C_{1-4}$ hydroxyalkyl, benzyloxy-$C_{1-4}$ alkyl, $C_{2-4}$ alkynyl, or benzyl; or
wherein $R^4$ and $R^5$ together form $C_{3-6}$ cycloalkyl or 4-6 membered heterocyclyl;
or a pharmaceutically acceptable salt thereof.

3. The compound of claim 1, or a pharmaceutically acceptable salt thereof, wherein R is

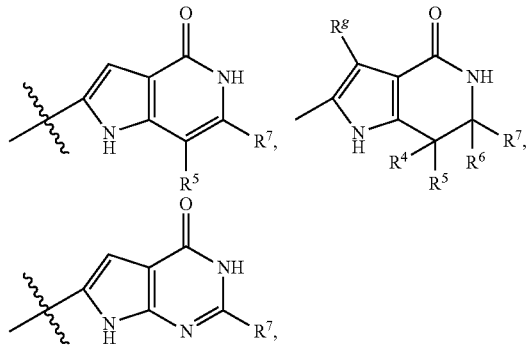

727

-continued

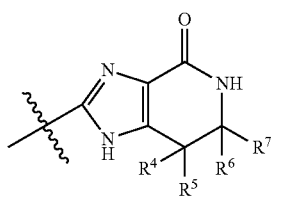

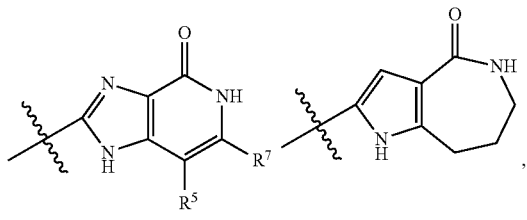

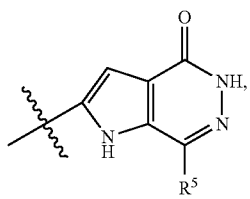

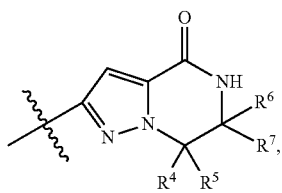

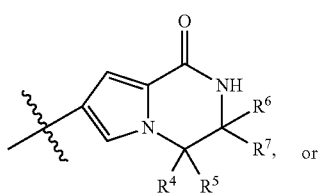

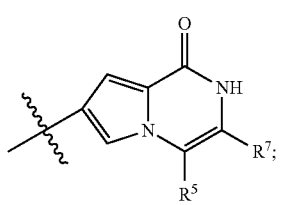

$R^5$ is H, methyl, ethyl, 2-methylpropyl, hydroxyethyl, aminoethyl, cyclopropyl, butynyl, benzyloxymethyl, or benzyl; $R^7$ is H, or methyl; and wherein $R^g$ is H, or chloro; provided $R^5$ is H if $R^7$ is methyl; further provided $R^7$ is H if $R^5$ is methyl, ethyl, or 2-methylpropyl.

4. The compound of claim 1, wherein R is

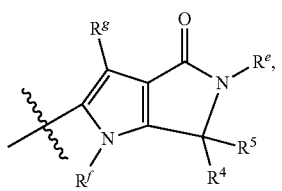

728

-continued

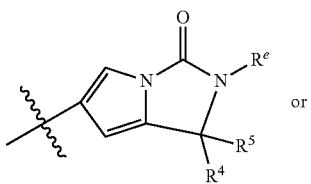

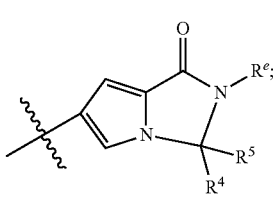

wherein $R^g$ is H, or chloro; and $R^5$ is H, ethyl, 2-methylpropyl, hydroxyethyl, butynyl, benzyl, aminoethyl, benzyloxymethyl, hydroxymethyl, cyclopropyl or methyl; or a pharmaceutically acceptable salt thereof.

5. The compound of claim 1, wherein R is

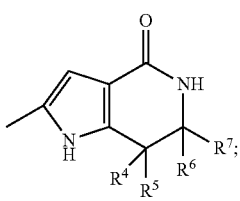

$R^4$ is H; $R^5$ is H; and $R^7$ is H; or a pharmaceutically acceptable salt thereof.

6. The compound of claim 1, wherein R is

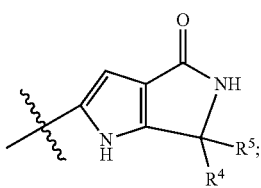

$R^4$ is H; $R^5$ is H, aminoethyl, hydroxyethyl, benzyloxymethyl, hydroxymethyl, cyclopropyl or methyl; or wherein $R^4$ and $R^5$ together form cyclopropyl; or a pharmaceutically acceptable salt thereof.

7. The compound of claim 1, wherein R is selected from

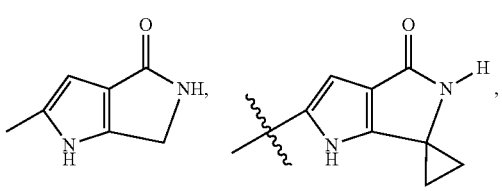

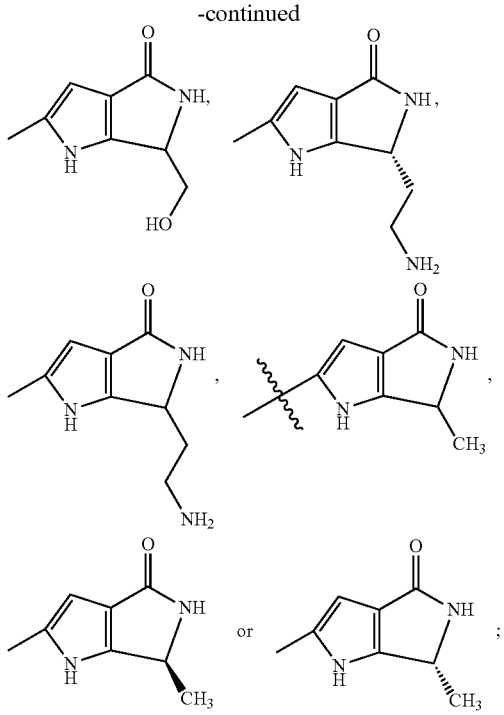

or a pharmaceutically acceptable salt thereof.

8. The compound of claim 1, wherein R¹ is H, chloro, fluoro, 2,2-dimethylpropyl, amino, methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-ethyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, (2-amino-1,1-dimethylethyl)amino, (2-(tert-butoxycarbonylamino)-1,1-dimethylethyl)amino, 2,2,2-trifluoroethylamino, 2,2-difluoroethylamino, (1,1-dimethyl-3-(methylsulfonyl)propyl)amino, (1,1-dimethyl-2-(methylsulfonyl)-ethyl) amino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy-2-methylpropylamino, 3-hydroxy-1,1-dimethylpropylamino, 2-trifluoromethyl-2-methylethylamino, 2-(trifluoromethyl)ethylamino, methylsulfonyl-(1,1-dimethylethyl)amino, methylsulfonylamino, 2-methyl-3-((1R)-1-(2-pyridinyl)ethyl)amino, 2-methyl-3-((1R)-1-(2-pyrazinyl) ethyl)amino, 2-methyl-3-((1R)-1-(4-pyrimidinyl)ethyl) amino, (1-methylcyclopropyl)methylamino, 2-methoxyethoxy-1,1-dimethylethylamino, guanidinyl, ethoxy, isopropoxy, 3-amino-3-methylbutoxy, 2-(trifluoromethyl)ethoxy, 1-(trifluoromethyl)ethoxy, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methylcyclopentylamino, 3-aminocyclopentylamino, cyclohexylamino, 1-methylcyclohexylamino, 3-aminocyclohexylamino, 3-methylcarbonylaminocyclohexylamino, 3-(2,2,2-trifluoroethylamino)cyclohexylamino, 3-methylsulfonylaminocyclohexylamino, 3-(tert-butyl carboxyamino-1-(hydroxyethyl)-carbonylamino)cyclohexylamino, 3-(amino-1-(hydroxyethyl)-carbonylamino)cyclohexylamino, 3-(tert-butylcarboxyamino)-cyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, 2-methyl-1-imidazolyl, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-yl amino, 2-pyridylamino, 3-pyridylamino, 4-pyridylamino, 5-pyrimidinylamino, benzylamino, 1-phenylethylamino, cyclopropylethylamino, 3-oxetanylmethylamino, 3-methyl-3-oxetanylmethylamino, 1-(4-pyrimidinyl)ethyl, 1-(2-pyridyl)ethyl, 1-(2-pyrazinyl) ethyl, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, methoxyethylaminocarbonyl, phenyl, 2,6-difluorophenyl, 2-fluoro-4-methylsulfonylphenyl, 3-aminocarbonyl-6-methylphenyl, 4-amino-2-fluorophenyl, 3-chloro-6-methoxyphenyl, 1-pyrrolidinyl, 2,2-dimethyl-1-pyrrolidinyl, 3-methylsulfonyl-1-azetidinyl, 2-methyl-2-imidazolyl, 1-azetidinyl, 2,2-dimethyl-1-azetidinyl, 4-morpholinyl, 3-tetrahydrofuryl, 3,3-dimethyl-4-morpholinyl, 2,2-dimethylpiperidin-1-yl, 2,2-dimethyl-1-piperazinyl, 1-methyl-4-pyrazolyl, or 2-amino-6-fluoro-5-pyridyl; or a pharmaceutically acceptable salt thereof.

9. The compound of claim 1, wherein R¹ is methylamino, dimethylamino, ethylamino, propylamino, isopropylamino, 1,1-dimethylpropylamino, 1,2-dimethylpropylamino, 2,2-dimethylpropylamino, tert-butylamino, butylamino, isobutylamino, N-methyl-N-isopropylamino, N-methyl-N-tert-butylamino, N-ethyl-N-tert-butylamino, 1-aminocarbonylethylamino, 1-aminocarbonyl-1-methylethylamino, 2-amino-2-methylpropylamino, (2-amino-1,1-dimethylethyl)amino, (2 (tert-butoxycarbonylamino)-1,1-dimethylethyl)amino, 2,2,2-trifluoroethylamino, 2,2-difluoroethylamino, (1,1-dimethyl-3-(methylsulfonyl)propyl)amino, (1,1-dimethyl-2-(methylsulfonyl)-ethyl) amino, 2-methyl-2-propen-1-ylamino, 1-methoxycarbonyl-1-ethylamino, 1-methoxycarbonyl-1-methylethylamino, 2-methoxy-1,1-dimethylethylamino, 1-carboxyl-1-methylethylamino, 2-hydroxy-1,1-dimethylethylamino, 2-hydroxy- 2-methylpropylamino, 3-hydroxy-1,1-dimethylpropylamino, 2-trifluoromethyl-2-methylethylamino, 2-(trifluoromethyl)ethylamino, methylsulfonyl-(1,1-dimethylethyl)amino, methylsulfonylamino, 2-methyl-3-((1R)-1-(2-pyridinyl)ethyl)amino, 2-methyl-3-((1R)-1-(2-pyrazinyl)ethyl)amino, 2-methyl-3-((1R)-1-(4-pyrimidinyl)ethyl)amino, (1-methylcyclopropyl)methylamino, 2-methoxyethoxy-1,1-dimethylethylamino, guanidinyl, cyclopropylamino, 1-methylcyclopropylamino, 1-cyanocyclopropylamino, 1-hydroxymethylcyclopropylamino, cyclobutylamino, 1-methylcyclobutylamino, 1-hydroxymethylcyclobutylamino, 2-aminocyclobutylamino, 2-methylcarbonylaminocyclobutylamino, 2-hydroxycyclobutylamino, 3,3-difluorocyclobutylamino, cyclopentylamino, 1-methyl-cyclopentylamino, 3-aminocyclopentylamino, cyclohexylamino, 1-methylcyclohexylamino, 3-aminocyclohexylamino, 4-hydroxycyclohexylamino, 3-hydroxycyclohexylamino, 2-hydroxycyclohexylamino, cycloheptylamino, phenylamino, 3-aminophenylamino, 4-bromophenylamino, 2-fluorophenylamino, 3-fluorophenylamino, 2-chlorophenylamino, 3-chlorophenylamino, 4-chlorophenylamino, 2-chloro-6-fluorophenylamino, 2,4-difluorophenylamino, 2,6-difluorophenylamino, 3-methylphenylamino, 2,6-dimethylphenylamino, N-methyl-N-phenylamino, N-ethyl-N-phenylamino, N-ethyl-N-pyrid-3-ylamino, 2-methyl-1-imidazolyl, piperidin-3-ylamino, 1-BOC-azetidin-3-ylamino, 1-methylcarbonyl-3-azetidinylamino, 1-methyl-3-azetidinylamino, azetidin-3-ylamino, 1-BOC-piperidin-4-ylamino, 1-BOC-piperidin-3-ylamino, 1-BOC-3-pyrrolidinylamino, 3-pyrrolidinylamino, 1-methylcarbonyl-3-pyrrolidinylamino, 1-methylcarbonyl-piperidin-4-ylamino, 1-methylcarbonyl-piperidin-3-ylamino, 1-methyl-2-oxo-piperidin-5-ylamino, 2-oxo-piperidin-5-ylamino, 2-oxo-piperidin-3-ylamino, 3-oxetanylamino, 3-methyl-3-oxetanylamino, 3-tetrahydropyranylamino, 4-tetrahydropyranylamino, 4-methyl-4-tetrahydropyranylamino, 1,1-dioxidotetrahydrothien-3-yl amino, 2-pyridylamino, 3-pyridylamino, 4-pyridylamino, 5-pyrimidinylamino, benzylamino, 1-phenylethylamino, cyclopropylethylamino, 3-oxetanylmethylamino, or 3-methyl-3-oxetanylmethylamino; or a pharmaceutically acceptable salt thereof.

10. The compound of claim 1, wherein $R^1$ is H, chloro, fluoro, 2,2-dimethylpropyl, amino, ethoxy, isopropoxy, 3-amino-3-methylbutoxy, 2-(trifluoromethyl)ethoxy, 1-(trifluoromethyl)ethoxy, 1-(4-pyrimidinyl)ethyl, 1-(2-pyridyl)ethyl, 1-(2-pyrazinyl)ethyl, 2,2-dimethylpropoxy, 3-amino-3-methylbutoxy, 2-(trifluoromethyl)ethoxy, cyclobutyloxy, cyclopentyloxy, phenyloxy, 2-chlorophenyloxy, 3-chlorophenyloxy, 4-chlorophenyloxy, 2-fluorophenyloxy, 3-fluorophenyloxy, 2-chloro-6-fluorophenyloxy, 2,4-difluorophenyloxy, 2,6-difluorophenyloxy, 3-hydroxyphenyloxy, 2,6-dimethylphenyloxy, 3-methylphenyloxy, 3-piperidinyloxy, 4-piperidinyloxy, 3-pyridyloxy, benzyloxy, phenylthio, tert-butylthio, methylthio, benzyl, 1-phenylethyl, 1-phenylethenyl, 1-phenylcyclopropyl, 4-morpholinylcarbonyl, 4-methylpiperazin-1-ylcarbonyl, 1-pyrrolindinylcarbonyl, 4-tetrahydropyranylaminocarbonyl, cyclopropylaminocarbonyl, phenylaminocarbonyl, or methoxyethylaminocarbonyl; or a pharmaceutically acceptable salt thereof.

11. The compound of claim 1, wherein $R^1$ is an unsubstituted or substituted ring selected from phenyl, pyrrolidinyl, azetidinyl, morpholinyl, tetrahydrofuryl, piperidinyl, piperazinyl, pyrazolyl, and pyridyl; or a pharmaceutically acceptable salt thereof.

12. The compound of claim 1, wherein $R^2$ is H; or a pharmaceutically acceptable salt thereof.

13. The compound of claim 1, wherein $R^4$ is H; and $R^5$ is H; or a pharmaceutically acceptable salt thereof.

14. The compound of claim 1, wherein $R^7$ is H; or a pharmaceutically acceptable salt thereof.

15. The compound of claim 1, wherein $R^4$ is H; and $R^5$ is H, methyl, benzyloxymethyl, hydroxymethyl or hydroxyethyl; or a pharmaceutically acceptable salt thereof.

16. The compound of claim 1, wherein $R^4$ and $R^5$ together form cyclopropyl; or a pharmaceutically acceptable salt thereof.

17. The compound of claim 1, wherein $R^5$ is H, $C_{1-2}$ alkyl, $C_{3-4}$ cycloalkyl $C_{1-2}$ aminoalkyl, $C_{1-2}$ hydroxyalkyl, benzyloxy-$C_{1-2}$ alkyl, $C_{2-4}$ alkynyl, or benzyl; or wherein $R^4$ and $R^5$ together form $C_{3-4}$ cycloalkyl; and $R^7$ is H, or $C_{1-2}$ alkyl; or a pharmaceutically acceptable salt thereof.

18. The compound of claim 1, wherein $R^b$ is H, $C_{1-6}$ alkyl, $C_{1-2}$ haloalkyl, $C_{1-4}$ aminoalkyl, $C_{1-3}$ alkoxy-$C_{1-3}$ alkyl, $C_{1-3}$ alkoxy-$C_{1-3}$ alkyl, $C_{1-3}$ alksulfonyl-$C_{14}$ alkyl, $C_{2-4}$ alkenyl, unsubstituted or substituted $C_{3-6}$ cycloalkyl, unsubstituted or substituted phenyl, unsubstituted or substituted phenyl-$C_{1-2}$-alkyl or unsubstituted or substituted 5-6 membered heterocyclyl; or a pharmaceutically acceptable salt thereof.

19. The compound of claim 1, wherein $R^b$ is an unsubstituted or substituted ring selected from cyclopropyl, cyclobutyl, cyclopentyl, phenyl, pyridyl, piperidinyl, morpholinyl, piperazinyl, pyrrolindinyl, tetrahydrofuryl and tetrahydropyranyl; or a pharmaceutically acceptable salt thereof.

20. A composition comprising a therapeutically effective amount of the compound of claim 1 or a pharmaceutically acceptable salt thereof, together with a pharmaceutically acceptable carrier.

* * * * *

```
                        SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Oligonucleotide PCR primer

<400> SEQUENCE: 1
tggctgatca atgctcttgt ccaaaatc                                          28

<210> SEQ ID NO 2
<211> LENGTH: 28
<212> TYPE: DNA
<213> ORGANISM: Artificial Sequence
<220> FEATURE:
<223> OTHER INFORMATION: Oligonucleotide PCR primer

<400> SEQUENCE: 2
attagaattc tatttgctgg gccccggc                                          28

<210> SEQ ID NO 3
<211> LENGTH: 29
<212> TYPE: DNA
<213> ORGANISM: Artificial Sequence
<220> FEATURE:
<223> OTHER INFORMATION: Oligonucleotide PCR primer

<400> SEQUENCE: 3
tgcaggatcc atgttgacca agcctctac                                         29

<210> SEQ ID NO 4
<211> LENGTH: 28
<212> TYPE: DNA
<213> ORGANISM: Artificial Sequence
<220> FEATURE:
<223> OTHER INFORMATION: Oligonucleotide PCR primer

<400> SEQUENCE: 4
acgtgaattc tatccctgtg acatggcc                                          28
```